(12) United States Patent
Guo et al.

(10) Patent No.: US 8,334,295 B2
(45) Date of Patent: Dec. 18, 2012

(54) PYRIMIDINE DERIVATIVES AS HIV REVERSE TRANSCRIPTASE INHIBITORS

(75) Inventors: Hongyan Guo, San Mateo, CA (US); Choung U. Kim, San Carlos, CA (US); Ill Y. Lee, Daejeon (KR); Michael L. Mitchell, Hayward, CA (US); Gerry Rhodes, Los Altos, CA (US); Jong C. Son, Daejeon (KR); Lianhong Xu, Palo Alto, CA (US)

(73) Assignee: Korea Research Institute of Chemical Technology, Daejeon (KR)

( * ) Notice: Subject to any disclaimer, the term of this patent is extended or adjusted under 35 U.S.C. 154(b) by 208 days.

(21) Appl. No.: 12/215,450

(22) Filed: Jun. 26, 2008

(65) Prior Publication Data

US 2011/0076276 A1  Mar. 31, 2011

Related U.S. Application Data

(60) Provisional application No. 60/959,676, filed on Jul. 16, 2007, provisional application No. 60/937,756, filed on Jun. 29, 2007.

(51) Int. Cl.
*A61K 31/505* (2006.01)
(52) U.S. Cl. .......................... 514/274; 544/309
(58) Field of Classification Search .................. 514/274; 544/309
See application file for complete search history.

(56) References Cited

U.S. PATENT DOCUMENTS

| | | | |
|---|---|---|---|
| 4,518,685 A | 5/1985 | Yagihara et al. |
| 4,656,209 A | 4/1987 | Wehner et al. |
| 5,112,835 A | 5/1992 | Miyasaka et al. |
| 5,162,326 A | 11/1992 | Naka et al. |
| 5,188,928 A | 2/1993 | Karino et al. |
| 5,219,869 A | 6/1993 | Shiokawa et al. |
| 5,227,284 A | 7/1993 | Matushita et al. |
| 5,266,453 A | 11/1993 | Matushita et al. |
| 5,318,972 A | 6/1994 | Miyasaka et al. |
| 5,461,060 A | 10/1995 | Miyasaka et al. |
| 5,604,209 A | 2/1997 | Ubasawa et al. |
| 5,643,744 A | 7/1997 | Nitta et al. |
| 5,747,500 A | 5/1998 | Son et al. |
| 5,859,100 A | 1/1999 | Wehner et al. |
| 5,889,013 A | 3/1999 | Kim et al. |
| 5,922,727 A | 7/1999 | Cho et al. |
| 5,998,411 A | 12/1999 | Vig et al. |
| 6,136,815 A | 10/2000 | Son et al. |
| 6,174,941 B1 | 1/2001 | Wehner et al. |
| 6,174,998 B1 | 1/2001 | Muhlegger et al. |
| 6,177,437 B1 | 1/2001 | Wright |
| 6,372,725 B1 | 4/2002 | Zilch et al. |
| 6,713,486 B1 | 3/2004 | Son et al. |
| 6,911,450 B1 | 6/2005 | Tronchet |
| 7,250,421 B2 | 7/2007 | Nair et al. |
| 2005/0215568 A1 | 9/2005 | Howell et al. |
| 2005/0239054 A1 | 10/2005 | Arimilli et al. |
| 2006/0223834 A1 | 10/2006 | Nair et al. |
| 2008/0070920 A1 | 3/2008 | Guo et al. |
| 2009/0163712 A1 * | 6/2009 | Guo et al. .................... 544/243 |

FOREIGN PATENT DOCUMENTS

| | | |
|---|---|---|
| CN | 101016265 | 8/2007 |
| FR | 2779721 | 12/1999 |
| FR | 2779722 | 12/1999 |
| JP | 3264579 | 11/1991 |
| JP | 05289238 | 11/1993 |
| JP | 06135943 | 5/1994 |
| JP | 08003143 | 1/1996 |
| JP | 09020792 | 1/1997 |
| JP | 10130244 | 5/1998 |
| JP | 10130245 | 5/1998 |
| JP | 10168068 | 6/1998 |
| JP | 11102047 | 4/1999 |
| JP | 2001114767 | 4/2001 |
| JP | 2002284686 | 10/2002 |
| JP | 2005212143 | 8/2005 |
| MX | PA03011298 | 6/2005 |
| WO | WO-8910701 | 11/1989 |
| WO | WO-9200964 | 1/1992 |
| WO | WO-9302044 | 2/1993 |
| WO | WO-9316091 | 8/1993 |
| WO | WO-9316092 | 8/1993 |
| WO | WO-9833505 | 8/1998 |
| WO | 00/51990 A1 | 8/2000 |
| WO | WO-0061563 | 10/2000 |
| WO | WO-0061564 | 10/2000 |
| WO | WO-0123363 | 4/2001 |
| WO | WO-0179203 | 10/2001 |
| WO | WO-0183459 | 11/2001 |
| WO | WO-03029226 | 4/2003 |
| WO | WO-03057677 | 7/2003 |
| WO | WO-03064511 | 8/2003 |
| WO | WO-03091264 | 11/2003 |
| WO | WO-2005026184 | 3/2005 |
| WO | WO-2006070292 | 7/2006 |
| WO | WO-2006089221 | 8/2006 |
| WO | WO-2007104834 | 9/2007 |
| WO | WO-2007106450 | 9/2007 |

OTHER PUBLICATIONS

Office Action for European Patent No. 08779769.2, dated Jan. 19, 2012.

* cited by examiner

*Primary Examiner* — Douglas M Willis
(74) *Attorney, Agent, or Firm* — Edwards Wildman Palmer LLP

(57) ABSTRACT

The invention is related to compounds of Formula (I):

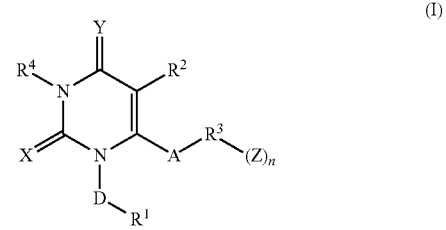

or a pharmaceutically acceptable salt, solvate, ester, and/or phosphonate thereof, compositions containing such compounds, and therapeutic methods that include the administration of such compounds.

2 Claims, No Drawings

PYRIMIDINE DERIVATIVES AS HIV REVERSE TRANSCRIPTASE INHIBITORS

CROSS-REFERENCE TO RELATED APPLICATION

The present application claims the benefit of U.S. Provisional Application No. 60/959,676, filed Jul. 16, 2007, and U.S. Provisional Application No. 60/937,756, filed Jun. 29, 2007, both of which are herein incorporated by reference in their entirety for all purposes.

FIELD OF THE INVENTION

This invention relates to novel HIV reverse transcriptase (RT) inhibitors, pharmaceutical compositions thereof, processes for making the novel HIV reverse transcriptase, and methods for inhibiting and treating an HIV infection.

BACKGROUND OF THE INVENTION

In recent years, inhibitors of HIV reverse transcriptase (RT) have become an important class of therapeutic agents for inhibition and treatment of HIV infection in humans. Compounds that inhibit the enzymatic functions of HIV reverse transcriptase inhibit replication of HIV in infected cells. Such compounds are useful in the prevention or treatment of HIV infection in humans, as demonstrated by known RT inhibitors such as zidovudine, didanosine, zalcitabine, stavudine, lamivudine, emtricitabine, abacavir, tenofovir, nevirapine, delavirdine and efavirenz, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is believed to be due to mutations in the RT gene. Thus, to be effective, new HIV RT inhibitors must be effective not only against wild-type strains of HIV, but must also demonstrate efficacy against the newly emerging mutant strains that are resistant to the commercially available RT inhibitors. Accordingly, there continues to be a need for new HIV RT inhibitors, for example, those targeting the HIV RT in both wild type and mutant strains of HIV.

SUMMARY OF THE INVENTION

Accordingly, in one embodiment, the present application provides novel HIV RT inhibitor compounds of Formula (I):

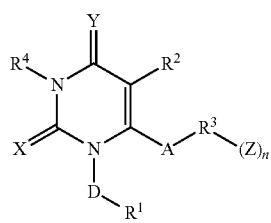

(I)

or a pharmaceutically acceptable salt, solvate, and/or ester thereof, wherein:
X and Y are independently O or S;
A is a covalent bond, —O—, —S—, —NR$^5$—, —C(O)—, —C(S)—, —C(NR$^8$)—, or —C(R$^6$)$_2$—;
D is a covalent bond, alkylene, alkenylene, or alkynylene;
R$^1$ is H, halo, alkyl, haloalkyl, cycloalkyl, substituted cycloalkyl, heterocyclyl, substituted heterocyclyl, —OH, alkoxy, thioalky, silyloxy, alkenyl, substituted alkenyl, alkynyl, substituted alkynyl, CN, —C(O)—N(R$^7$)$_2$, —O—C(O)—N(R$^7$)$_2$, —N(R$^7$)—C(O)—N(R$^7$)$_2$, —C(O)—Oalkyl, —C(O)—OH, —O—C(O)—Oalkyl, —N(R$^7$)—C(O)—Oalkyl, silyloxy, —O-alkylene-OH, —O-alkylene-O-acyl, or —S(O)$_2$—N(R$^7$)$_2$;
R$^2$ is halogen, nitro, cyano, alkyl, haloalkyl, substituted alkyl, hydroxyalkyl, alkoxyalkyl, alkenyl, substituted alkenyl, alkynyl, or substituted alkynyl, alkoxycarbonyl, —N(R$^7$)$_2$, alkylcarbamoyl, dialkylcarbamoyl, cycloalkyl, substituted cycloalkyl, arylalkyl, or substituted arylalkyl;
R$^3$ is aryl or heteroaryl;
R$^4$ is H, alkyl, substituted alkyl, cycloalkyl, substituted cycloalkyl, hydroxyalkyl, alkoxyalkyl, arylalkyl, or substituted arylalkyl;
R$^5$ is H, alkyl, substituted alkyl, arylalkyl, substituted arylalkyl, —OH, acyl, substituted acyl;
each R$^6$ is independently H, alkyl, cycloalkyl, substituted cycloalkyl, hydroxyl, alkoxy, cyano, or halo;
each R$^7$ is independently H, alkyl, aryl, substituted aryl, arylalkyl, substituted arylalkyl, cycloalkyl, substituted cycloalkyl, heteroaryl, or substituted heteroaryl;
R$^8$ is H; alkyl, aryl, substituted aryl, OH, or alkoxy;
each Z is independently selected from the group consisting of halo, nitro, hydroxyl, amino, acetamido, trifluoroacetamido, azido, cyano, formyl, alkyl, substituted alkyl, alkylcarbamoyl, dialkylcarbamoyl, alkenyl, substituted alkenyl, alkynyl, substituted alkynyl, alkoxy, substituted alkoxy, alkoxycarbonyl, cycloalkyl, substituted cycloalkyl, cycloalkenyl, substituted cycloalkenyl, heterocyclyl, substituted heterocyclyl, aryl, substituted aryl, oxide; and
n is an integer of from 0 to 4;
with the following provisos:
(a) when X and Y are both O, R$^4$ is H, A is —O—, —S—, —C(O)—, —CH(OH)— or —CH$_2$—, R$^3$ is phenyl, and D is —CH$_2$—,
   then R$^1$ is not alkoxy;
(b) when X and Y are both 0, A is —S—, —O—, or —C(O)—, R$^3$ is phenyl, n is 2, each Z is alkyl, D is —CH$_2$—, R$^2$ is alkyl, and R$^4$ is H,
   then R$^1$ is not unsubstituted cycloalkyl, unsubstituted heterocycloalkyl, or unsubstituted heteroaryl;
(c) when X and Y are both 0, A is —C(O)—, —O—, or —NH—, D is —CH$_2$—, R$^2$ is alkyl, R$^3$ is phenyl, n is 2, R$^4$ is H,
   then R$^1$ is not a substituted or unsubstituted heteroaryl selected from the group consisting of pyridyl, pyrimidyl and pyridazyl;
(d) when X and Y are both O, n is 0 or 2, each Z is alkyl, A-R$^3$ is benzyl, benzoyl, thiophenyl, or phenoxyl, R$^4$ is H, and R$^2$ is ethyl or isopropyl, then D is not alkenylene or alkynylene and -D-R$^1$ is not alkyl, hydroxyalkyl or -alkylene-C(O)—Oalkyl;
(e) only one of R$^4$ and -D-R$^1$ is H.

In another embodiment, the present application provides a method for treating HIV infections which comprises administering to a patient in need of such treatment a therapeutically effective amount of at least one compound of Formula (I), or a pharmaceutically acceptable salt, solvate, and/or ester thereof.

In another embodiment, the present application provides a method for treating HIV infection which comprises administering to a patient in need of such treatment a therapeutically effective combination of (a) one or more compounds of Formula (I) and (b) another therapeutic agent (e.g., one or more compounds selected from HIV reverse transcriptase inhibitor and HIV protease inhibitors).

In another embodiment, the present invention provides a method of treating HIV infection which comprises administering to a patient in need thereof a therapeutically effective amount of: (a) a compound of Formula (I); and, (b) at least one compound selected from the group HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR$^4$ inhibitors, gp120 inhibitors, G6PD and NADH-oxidase inhibitors, CCR$^5$ inhibitors, other drugs for treating HIV, and mixtures thereof.

In another embodiment, the present invention provides a kit or container comprising a compound of Formula (I) in an amount effective for use as a standard or reagent in a test or assay for determining the ability of a potential pharmaceutical compound to inhibit HIV RT and/or HIV growth.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended the invention to those claims. On the contrary, the invention is intended to cover all alternatives, modifications, and equivalents, which may be included within the scope of the present invention as defined by the claims.

Unless stated otherwise, the following terms and phrases as used herein are intended to have the following meanings:

When trade names are used herein, applicants intend to independently include the tradename product and the active pharmaceutical ingredient(s) of the tradename product.

In accordance with a convention used in the art,

is used in structural formulas herein to depict the bond that is the point of attachment of the moiety or substituent to the core or backbone structure.

As used herein, "a compound of the invention" or "a compound of Formula (I)" means a compound of Formula (I) or a pharmaceutically acceptable salt, solvate, ester, or physiologically functional derivative thereof. Compounds of the invention also include tautomeric forms thereof, e.g., tautomeric "enols" as described herein. Similarly, with respect to isolatable intermediates such as for example, compounds of formula (4), the phrase "a compound of formula (number)" means a compound of that formula and pharmaceutically acceptable salts, solvates, esters and physiologically functional derivatives thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl).

Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, sp$^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH$ (CH$_3$)—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Amino" refers to —NR$_2$, where each "R" is independently selected from H, alkyl, substituted alkyl, aryl, substituted aryl, arylalkyl, substituted arylalkyl, etc., wherein the terms alkyl, substituted alkyl, aryl, substituted aryl, arylalkyl, and substituted arylalkyl are as defined and described herein. Typical amino groups include, but are not limited to —NH$_2$, —N(CH$_3$)$_2$, —NH(CH$_3$), —N(CH$_2$CH$_3$)$_2$, —NH(CH$_2$CH$_3$), —NH (substituted or unsubstituted benzyl), —NH (substituted or unsubstituted phenyl), and the like.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, substituted or unsubstituted naphthalene, substituted or unsubstituted anthracene, substituted or unsubstituted biphenyl, and the like.

"Arylalkyl" refers to an acyclic alkyl radical in which one of the hydrogen atoms bonded to a carbon atom, typically a terminal or spa carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like (each of which can be substituted or unsubstituted). The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Cycloalkyl" refers to a saturated mono-cyclic or polycyclic ring containing only carbon atoms in the ring. A cycloalkyl can have 3 to 7 carbon atoms as a monocycle, 7 to 12 carbon atoms as a bicyclic cycloalkyl, and up to about 20 carbon atoms as a polycycle. Monocyclic cycloalkyls have 3 to 6 ring atoms, still more typically 5 or 6 ring atoms. Bicyclic cycloalkyls have 7 to 12 ring atoms, e.g., arranged as a bicyclo [4,5], [5,5], [5,6] or [6,6] system, or 9 or 10 ring atoms arranged as a bicyclo[5,6] or [6,6] system, or spiro-fused rings. Non-limiting examples of monocyclic cycloalkyls include cyclopropyl, cyclobutyl, cyclopentyl, and cyclohexyl (each of which can be substituted or unsubstituted).

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, heterocyclyl, etc., for example, "substituted alkyl", "substituted alkylene", "substituted aryl", "substituted arylalkyl", "substituted heterocyclyl", and "substituted carbocyclyl" (e.g., substituted cycloalkyl) means alkyl, alkylene, aryl, arylalkyl, heterocyclyl, carbocyclyl (e.g., cycloalkyl) respectively, in which one or more hydrogen atoms are each independently replaced with a non-hydrogen substituent. Typical substituents include, but are not limited to, —X, —R, —O$^-$, =O, —OR, —SR, —S$^-$, —NR$_2$, —N$^+$R$_3$, =NR, —CX$_3$, —CN, —OCN, —SCN, —N=C=O, —NCS, —NO, —NO$_2$, =N$_2$, —N$_3$, —NHC(=O)R, —C(S)R, —C(=O)NRR, —S(=O)$_2$O$^-$, —S(=O)$_2$OH, —S(=O)$_2$R, —OS(=O)$_2$OR, —S(O)$_2$NR, —S(=O)R, —OP(=O)(OR)$_2$, —N(=O)(OR)$_2$, —N(=O)(O$^-$)$_2$, —N(=O)(OH)$_2$, —N(O)(OR)(O$^-$), —C(=O)R, alkylene-C(=O)R, —C(=O)X, alkylene-C(=O)X, —C(S)R, —C(O)OR, alkylene-C(O)OR, —C(O)O$^-$, alkylene-C(O)O$^-$, —C(S)OR, —C(O)SR, —C(S)SR, —C(O)NRR, alkylene-C(O)NRR, —C(S)NRR, —C(=NR)NRR, where each X is independently a halogen: F, Cl, Br, or I; and each R is independently H, alkyl, aryl, arylalkyl, a heterocycle, a carbocycle, or a protecting group or prodrug moiety. Alkylene, alkenylene, and alkynylene groups may also be similarly substituted.

Those skilled in the art will recognize that when moieties such as "alkyl", "aryl", "heterocyclyl", etc. are substituted with one or more substituents, they could alternatively be referred to as "alkylene", "arylene", "heterocyclylene", etc., moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula (I) should be selected in order to provide a compound which is sufficiently stable to provide a pharmaceutically useful compound which can be formulated into an acceptably stable pharmaceutical composition. Compounds of Formula (I) which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl, and the like (each of which can be substituted or unsubstituted).

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl (each of which can be substituted or unsubstituted).

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline (each of which can be substituted or unsubstituted). Still more typically, nitrogen bonded heterocycles include 1-aziridyl, 1-azetedyl, 1-pyrrolyl, 1-imidazolyl, 1-pyrazolyl, and 1-piperidinyl (each of which can be substituted or unsubstituted).

"Heterocyclylalkyl" refers to an acyclic alkyl radical in which one of the hydrogen atoms bonded to a carbon atom, typically a terminal or spa carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 2 to 20 carbon atoms, e.g., the alkyl portion of the arylalkyl group is 1 to 6 carbon atoms and the heterocyclyl moiety is 1 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc. (each of which can be substituted or unsubstituted).

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 3 to 20 carbon atoms, e.g., the alkenyl portion of the heterocyclyl alkenyl group is 2 to 6 carbon atoms and the heterocyclyl moiety is 1 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 3 to 20 carbon atoms, e.g., the alkynyl portion of the heterocyclyl alkynyl group is 2 to 6 carbon atoms and the heterocyclyl moiety is 1 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc. (each of which can be substituted or unsubstituted).

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl (each of which can be substituted or unsubstituted).

"Acyl" refers to a —C(O)-alkyl, —C(O)-carbocycle (substituted or unsubstituted), —C(O)-heterocycle (substituted or unsubstituted), wherein the alkyl, carbocycle, or heterocycle portion thereof is as defined herein. Non-limiting examples of "acyl" include —C(O)CH$_3$, —C(O)CH$_2$CH$_3$, —C(O)CH(CH$_3$)$_2$, —C(O)C(CH$_3$)$_3$, —C(O)-phenyl (substituted or unsubstituted), —C(O)-cyclopropyl (substituted or unsubstituted), —C(O)-cyclobutyl (substituted or unsubstituted), —C(O)-cyclopentyl (substituted or unsubstituted), —C(O)-cyclohexyl (substituted or unsubstituted), —C(O)-pyridyl (substituted or unsubstituted), etc.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)— thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

"Silyloxy" refers to a —O—SiR$_3$ group, where R includes alkyl, aryl (substituted or unsubstituted), and heteroaryl (substituted or unsubstituted), or combinations thereof. Non-limiting examples of silyloxy groups include —O—Si(CH$_3$)$_3$, —O—Si(CH$_3$)$_2$tBu, —O—Si(tBu)$_2$CH$_3$, —O—Si(tBu)$_3$, —O—Si(CH$_3$)$_2$-phenyl, —O—Si(phenyl)$_2$CH$_3$, —O—Si(phenyl)$_3$.

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. As defined herein, "phosphonate" and "phosphonate group" include molecules with phosphonic acid, phosphonic monoester, phosphonic diester, phosphonamidate, phosphondiamidate, and phosphonthioate functional groups.

"Linker" or "link" refers to a chemical moiety comprising a covalent bond or a chain or group of atoms that covalently attaches a phosphonate or phosphinate group to a drug. Linkers which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

"Optionally substituted" refers to a particular moiety of the compound of Formula (I) (e.g., an optionally substituted aryl group) refers to a moiety having 0, 1, 2, or more substituents.

"Ester thereof" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. Esters can also include esters—as described above—of "tautomeric enols", e.g. as shown below:

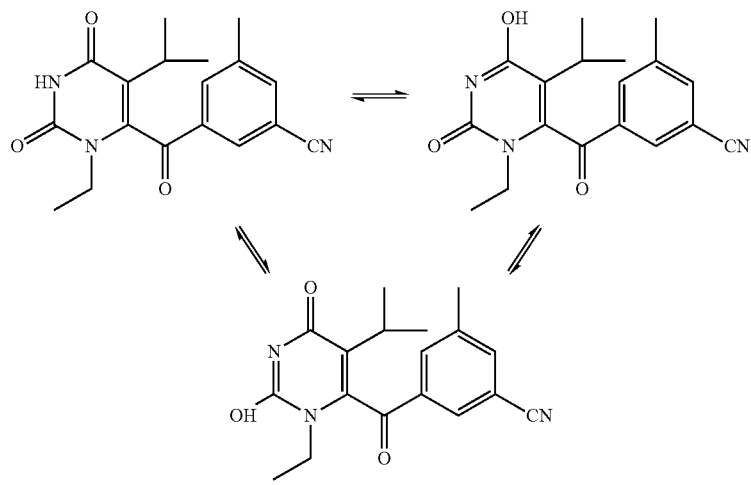

The term "ester thereof" includes but is not limited to pharmaceutically acceptable esters thereof.

"Salt thereof" means any acid and/or base addition salt of a compound according to the invention; preferably a pharmaceutically acceptable salt thereof.

"Pharmaceutically acceptable salt" means a salt of a compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the compound of formula (I) or (II), the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

"Treatment" or "treating" means the administration of a compound or composition according to the present invention to alleviate or eliminate symptoms of the HIV disease and/or to reduce viral load in a patient. The term "treatment" or "treating" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

"Chiral" refers to molecules which have the property of non-superimposability of the mirror image partner, while the term "achiral" refers to molecules which are superimposable on their mirror image partner.

"Stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. N. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphoric acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula (I)

In one embodiment, the present application provides compounds according to Formula (I), as described herein.

In each of the embodiments of the compounds of Formula (I), the following provisos apply, unless otherwise stated, or unless they would clearly not be applicable (e.g., for embodiments in which one or more of X and Y is not O):

(a) when X and Y are both O, $R^4$ is H, A is —O—, —S—, —C(O)—, —CH(OH)— or —CH$_2$—, $R^3$ is phenyl, and D is —CH$_2$—,
then $R^1$ is not alkoxy;

(b) when X and Y are both O, A is —S—, —O—, or —C(O)—, $R^3$ is phenyl, n is 2, each Z is alkyl, D is —CH$_2$—, $R^2$ is alkyl, and $R^4$ is H,
then $R^1$ is not unsubstituted cycloalkyl, unsubstituted heterocycloalkyl, or unsubstituted heteroaryl;

(c) when X and Y are both O, A is —C(O)—, —O—, or —NH—, D is —CH$_2$—, $R^2$ is alkyl, $R^3$ is phenyl, n is 2, $R^4$ is H,
then $R^1$ is not a substituted or unsubstituted heteroaryl selected from the group consisting of pyridyl, pyrimidyl and pyridazyl;

(d) when X and Y are both O, n is 0 or 2, each Z is alkyl, A-$R^3$ is benzyl, benzoyl, thiophenyl, or phenoxyl, $R^4$ is H, and $R^2$ is ethyl or isopropyl,
then D is not alkenylene or alkynylene and -D-$R^1$ is not alkyl, hydroxyalkyl or -alkylene-C(O)—Oalkyl;

(e) only one of $R^4$ and -D-$R^1$ is H.

For example, proviso (a) excludes compounds of the following structure:

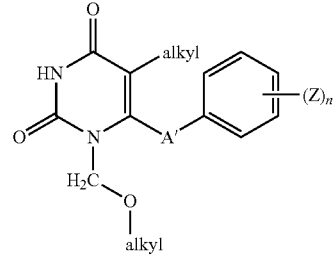

wherein A' is —O—, —S—, —C(O)—, —CH(OH)— or —CH$_2$—, and alkyl, and Z and n are as defined herein. Compounds excluded include those specific compounds disclosed in, for example, U.S. Pat. No. 6,911,450, U.S. Pat. No. 5,112,835, U.S. Pat. No. 5,461,060, U.S. Pat. No. 5,318,972, U.S. Pat. No. 5,604,209, U.S. Pat. No. 6,136,815, CN 101016265, WO 03/057677, JP 2001-114767, JP 8-3143, FR 2779721, etc. (each of which is herein incorporated by reference in their entirety for all purposes).

For example, proviso (b) excludes compounds of the following structure:

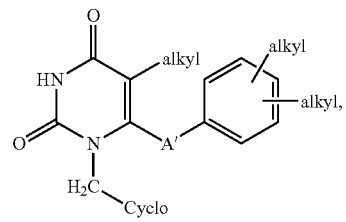

wherein A' is —S—, —O—, or —C(O)—, "cyclo" is unsubstituted cycloalkyl, unsubstituted heterocycloalkyl, or unsubstituted heteroaryl, and alkyl is as defined herein. In some embodiments, "cyclo" can include substituted cycloalkyl, heterocycloalkyl, or heteroaryl. Compounds excluded include, for example those specific compounds disclosed in WO 00/61563, WO 00/61564, WO 2007/091857, U.S. Pat. No. 5,922,727, etc. (each of which is herein incorporated by reference in their entirety for all purposes).

For example, proviso (c) excludes compounds of the following structure:

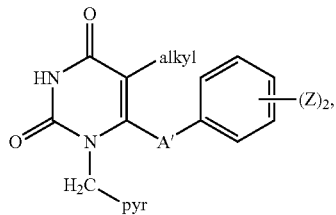

wherein A' is —C(O)—, —O—, or —NH—, Z and alkyl are as defined herein, and "pyr" is substituted or unsubstituted pyridyl, pyrimidyl, or pyridazyl. Compounds excluded include, for example, those specific compounds disclosed in WO 2008/016522 (herein incorporated by reference in its entirety for all purposes).

For example, proviso (d) excludes compounds of the following structures:

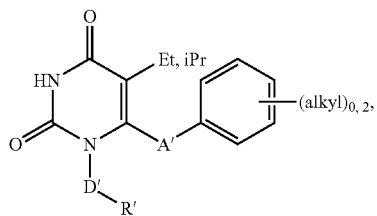

wherein A' is —CH$_2$—, —O—, —S—, or —C(O)—, and D' is alkenylene or alkynylene; or wherein A' is —CH$_2$—, —O—, —S—, or —C(O)—, and D'-R' is alkyl, hydroxyalkyl, or -alkylene-C(O)—Oalkyl; and alkyl, alkylene, alkenylene, and alkynylene are as defined herein. Compounds excluded include, for example, those specific compounds disclosed in U.S. Pat. No. 5,747,500 and KR 1996-014106 (each of which is herein incorporated by reference in its entirety for all purposes).

For example, proviso (e) requires that only one of R$^4$ or D-R$^1$ can be H. In other words, the compounds of Formula (I) have one of the following structures:

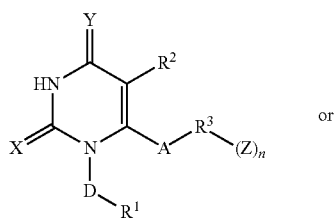

or

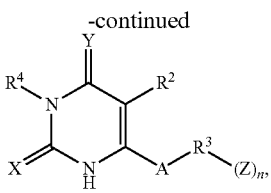

wherein R$^1$, R$^2$, R$^3$, R$^4$, A, X, Y, Z, and n are as defined or described herein.

In another embodiment of the compounds of Formula (I), A is —C(R$^6$)$_2$—.

In another embodiment of the compounds of Formula (I), A is —CH$_2$—.

In another embodiment of the compounds of Formula (I), A is —C(halo)$_2$-.

In another embodiment of the compounds of Formula (I), A is —CF$_2$—.

In another embodiment of the compounds of Formula (I), A is —CCl$_2$—.

In another embodiment of the compounds of Formula (I), A is —CHF—.

In another embodiment of the compounds of Formula (I), A is —CHCl—.

In another embodiment of the compounds of Formula (I), A is —CHOH—.

In another embodiment of the compounds of Formula (I), A is —CH(O-alkyl)-, wherein alkyl includes any alkyl moiety described and defined herein.

In another embodiment of the compounds of Formula (I), A is —C(O)—.

In another embodiment of the compounds of Formula (I), A is —O—.

In another embodiment of the compounds of Formula (I), A is —S—.

In another embodiment of the compounds of Formula (I), A is —NR$^5$—.

In another embodiment of the compounds of Formula (I), A is —NH—.

In another embodiment of the compounds of Formula (I), A is —N(alkyl)-, wherein alkyl includes any alkyl moiety described and defined herein.

In another embodiment of the compounds of Formula (I), A is —N(arylalkyl)-, wherein the arylalkyl moiety includes any arylalkyl moiety described and defined herein, which may be substituted or unsubstituted.

In another embodiment of the compounds of Formula (I), A is —N(benzyl)-, wherein the benzyl moiety may be substituted or unsubstituted.

In another embodiment of the compounds of Formula (I), A is —N(phenylalkyl)-, wherein the phenylalkyl moiety may be substituted or unsubstituted.

In another embodiment of the compounds of Formula (I), A is —N(phenethyl)-, wherein the phenethyl moiety may be substituted or unsubstituted.

In another embodiment of the compounds of Formula (I), A is —N(phenylpropyl)-, wherein the phenylpropyl moiety may be substituted or unsubstituted.

In another embodiment of the compounds of Formula (I), A is —C(NR$^8$)— wherein R$^8$ is as defined herein.

In another embodiment of the compounds of Formula (I), A is —C(NH)—.

In another embodiment of the compounds of Formula (I), A is —C(Nalkyl)-.

In another embodiment of the compounds of Formula (I), A is —C(NCH$_3$)—.

In another embodiment of the compounds of Formula (I), A is —C(NCH$_2$CH$_3$)—.

In another embodiment of the compounds of Formula (I), A is —C(NC(CH$_3$)$_3$)—.

In another embodiment of the compounds of Formula (I), A is —C(Nphenyl)-.

In another embodiment of the compounds of Formula (I), A is —C(Nphenyl)-, wherein the phenyl moiety is substituted.

In another embodiment of the compounds of Formula (I), A is —C(NOH)—.

In another embodiment of the compounds of Formula (I), A is —C(N-Oalkyl)-.

In another embodiment of the compounds of Formula (I), A is —C(N-Oalkyl)-, wherein said alkyl moiety includes any alkyl described herein.

In another embodiment of the compounds of Formula (I), A is a covalent bond.

In another embodiment of the compounds of Formula (I), A is —CH(CN)—.

In another embodiment of the compounds of Formula (I), R$^3$ is aryl, wherein said aryl may be any aryl described or defined herein.

In another embodiment of the compounds of Formula (I), R$^3$ is phenyl.

In another embodiment of the compounds of Formula (I), R$^3$ is naphthyl.

In another embodiment of the compounds of Formula (I), R$^3$ is heteroaryl, wherein said heteroaryl may be any heteroaryl described or defined herein.

In another embodiment of the compounds of Formula (I), R$^3$ is pyridyl.

In another embodiment of the compounds of Formula (I), R$^3$ is 2-pyridyl.

In another embodiment of the compounds of Formula (I), R$^3$ is 3-pyridyl.

In another embodiment of the compounds of Formula (I), R$^3$ is 4-pyridyl.

In another embodiment of the compounds of Formula (I), R$^3$ is pyrroyl.

In another embodiment of the compounds of Formula (I), R$^3$ is 1-pyrroyl.

In another embodiment of the compounds of Formula (I), R$^3$ is 2-pyrroyl.

In another embodiment of the compounds of Formula (I), R$^3$ is 3-pyrroyl.

In another embodiment of the compounds of Formula (I), R$^3$ is furanyl.

In another embodiment of the compounds of Formula (I), R$^3$ is 2-furanyl.

In another embodiment of the compounds of Formula (I), R$^3$ is 3-furanyl.

In another embodiment of the compounds of Formula (I), R$^3$ is thiophenyl.

In another embodiment of the compounds of Formula (I), R$^3$ is 2-thiophenyl.

In another embodiment of the compounds of Formula (I), R$^3$ is 3-thiophenyl.

In another embodiment of the compounds of Formula (I), R$^3$ is pyrazolyl.

In another embodiment of the compounds of Formula (I), R$^3$ is imidazolyl.

In another embodiment of the compounds of Formula (I), R$^3$ is oxazolyl.

In another embodiment of the compounds of Formula (I), R$^3$ is isoxazolyl.

In another embodiment of the compounds of Formula (I), R$^3$ is thiazolyl.

In another embodiment of the compounds of Formula (I), R$^3$ is pyridazinyl.

In another embodiment of the compounds of Formula (I), R$^3$ is pyrimidinyl.

In another embodiment of the compounds of Formula (I), R$^3$ is pyrazinyl.

In another embodiment of the compounds of Formula (I), R$^3$ is quinolinyl.

In another embodiment of the compounds of Formula (I), R$^3$ is benzoimidazolyl.

In another embodiment of the compounds of Formula (I), R$^3$ is indazolyl.

In another embodiment of the compounds of Formula (I), R$^3$ is indolyl.

In another embodiment of the compounds of Formula (I), Z is halo.

In another embodiment of the compounds of Formula (I), Z is Cl.

In another embodiment of the compounds of Formula (I), Z is F.

In another embodiment of the compounds of Formula (I), Z is independently F or Cl.

In another embodiment of the compounds of Formula (I), Z is nitro.

In another embodiment of the compounds of Formula (I), Z is hydroxyl.

In another embodiment of the compounds of Formula (I), Z is amino.

In another embodiment of the compounds of Formula (I), Z is acetamido.

In another embodiment of the compounds of Formula (I), Z is trifluoroacetamido.

In another embodiment of the compounds of Formula (I), Z is azido.

In another embodiment of the compounds of Formula (I), Z is cyano.

In another embodiment of the compounds of Formula (I), Z is formyl.

In another embodiment of the compounds of Formula (I), Z is alkylcarbamoyl.

In another embodiment of the compounds of Formula (I), Z is dialkylcarbamoyl.

In another embodiment of the compounds of Formula (I), Z is alkyl.

In another embodiment of the compounds of Formula (I), Z is —CH$_3$.

In another embodiment of the compounds of Formula (I), Z is —CH$_2$CH$_3$.

In another embodiment of the compounds of Formula (I), Z is i-propyl.

In another embodiment of the compounds of Formula (I), Z is t-butyl.

In another embodiment of the compounds of Formula (I), Z is alkenyl.

In another embodiment of the compounds of Formula (I), Z is allyl.

In another embodiment of the compounds of Formula (I), Z is substituted alkenyl.

In another embodiment of the compounds of Formula (I), Z is —CH=CH—CN.

In another embodiment of the compounds of Formula (I), Z is alkynyl.

In another embodiment of the compounds of Formula (I), Z is alkoxy.

In another embodiment of the compounds of Formula (I), Z is methoxy.

In another embodiment of the compounds of Formula (I), Z is ethoxy.
In another embodiment of the compounds of Formula (I), Z is substituted alkoxy.
In another embodiment of the compounds of Formula (I), Z is trifluoromethoxy.
In another embodiment of the compounds of Formula (I), Z is methoxyethoxy.
In another embodiment of the compounds of Formula (I), Z is ethoxymethoxy.
In another embodiment of the compounds of Formula (I), Z is alkoxycarbonyl.
In another embodiment of the compounds of Formula (I), Z is —C(O)—OCH$_3$.
In another embodiment of the compounds of Formula (I), Z is —C(O)—OC(CH$_3$)$_3$.
In another embodiment of the compounds of Formula (I), Z is —C(O)—OCH$_2$CH$_3$.
In another embodiment of the compounds of Formula (I), Z is substituted or unsubstituted cycloalkyl.
In another embodiment of the compounds of Formula (I), Z is substituted or unsubstituted cyclopropyl.
In another embodiment of the compounds of Formula (I), Z is substituted or unsubstituted butyl.
In another embodiment of the compounds of Formula (I), Z is substituted or unsubstituted cyclopentyl.
In another embodiment of the compounds of Formula (I), Z is substituted or unsubstituted cyclohexyl.
In another embodiment of the compounds of Formula (I), Z is substituted or unsubstituted cycloalkenyl.
In another embodiment of the compounds of Formula (I), Z is substituted or unsubstituted cyclopropenyl.
In another embodiment of the compounds of Formula (I), Z is substituted or unsubstituted cyclobutenyl.
In another embodiment of the compounds of Formula (I), Z is substituted or unsubstituted cyclopentenyl.
In another embodiment of the compounds of Formula (I), Z is substituted or unsubstituted cyclohexenyl.
In another embodiment of the compounds of Formula (I), Z is substituted or unsubstituted heterocyclyl.
In another embodiment of the compounds of Formula (I), Z is substituted or unsubstituted heteroaryl.
In another embodiment of the compounds of Formula (I), Z is substituted or unsubstituted aryl.
In another embodiment of the compounds of Formula (I), when $R^3$ is a substituted or unsubstituted N-containing heteroaryl, Z is oxide, whereby $R^3$—Z is an N-oxide of a N-containing substituted or unsubstituted heteroaryl.
In any of the previous embodiments of the compounds of Formula (I) in which Z is specifically or generically defined, n is at least 1, and $R^3$ may optionally be substituted with other groups Z not specifically defined. For example, in an embodiment wherein Z is halo, $R^3$ may optionally include at least one additional group Z which is not halo. Alternatively, $R^3$ can include more than one of the Z groups specifically or generically defined in the embodiment. Thus, if Z is halo, the embodiment includes $R^3$ mono-, di-, tri-substituted, etc., with halo.
In another embodiment of the compounds of Formula (I), n is 2.
In another embodiment of the compounds of Formula (I), n is 2 and Z is selected from the group consisting of halo, alkyl, cyano, —CH$_2$—CH$_2$—CN, and —CH=CH—CN.
In another embodiment of the compounds of Formula (I), n is 2 and Z is alkyl and/or cyano.
In another embodiment of the compounds of Formula (I), n is 2 and Z is alkyl and/or halo.
In another embodiment of the compounds of Formula (I), n is 2 and Z is alkyl and/or Cl.
In another embodiment of the compounds of Formula (I), n is 2 and Z is alkyl and/or F.
In another embodiment of the compounds of Formula (I), n is 2 and Z is halo and/or cyano.
In another embodiment of the compounds of Formula (I), n is 2 and Z is Cl and/or cyano.
In another embodiment of the compounds of Formula (I), n is 2 and Z is F and/or cyano.
In another embodiment of the compounds of Formula (I), n is 2 and Z is alkyl.
In another embodiment of the compounds of Formula (I), n is 2 and Z is halo.
In another embodiment of the compounds of Formula (I), n is 2 and Z is Cl.
In another embodiment of the compounds of Formula (I), n is 2 and Z is F.
In another embodiment of the compounds of Formula (I), n is 2 and Z is Cl and F.
In another embodiment of the compounds of Formula (I), D is a covalent bond.
In another embodiment of the compounds of Formula (I), D is alkylene.
In another embodiment of the compounds of Formula (I), D is —CH$_2$—.
In another embodiment of the compounds of Formula (I), D is —CH$_2$CH$_2$—.
In another embodiment of the compounds of Formula (I), D is —CH$_2$CH$_2$CH$_2$—.
In another embodiment of the compounds of Formula (I), D is —CH(CH$_3$)—.
In another embodiment of the compounds of Formula (I), D is —C(CH$_3$)$_2$—.
In another embodiment of the compounds of Formula (I), D is —CH$_2$-cyclopropylene-CH$_2$—.
In another embodiment of the compounds of Formula (I), D is alkenylene.
In another embodiment of the compounds of Formula (I), D is —CH=CH—.
In another embodiment of the compounds of Formula (I), D is —CH$_2$CH=CH—.
In another embodiment of the compounds of Formula (I), D is —CH=CHCH$_2$—.
In another embodiment of the compounds of Formula (I), D is —CH$_2$CH=CHCH$_2$—.
In another embodiment of the compounds of Formula (I), D is —CH=CHCH$_2$CH$_2$—.
In another embodiment of the compounds of Formula (I), D is —CH$_2$CH$_2$CH=CH—.
In another embodiment of the compounds of Formula (I), D is —CH$_2$CH=CHCH$_2$—.
In another embodiment of the compounds of Formula (I), D is —(CH$_3$)C=CH—.
In another embodiment of the compounds of Formula (I), D is —CH$_2$CH=C(CH$_3$)—.
In another embodiment of the compounds of Formula (I), D is —(CH$_3$)C=CHCH$_2$—.
In another embodiment of the compounds of Formula (I), D is —CH$_2$C(CH$_3$)=CHCH$_2$—.
In another embodiment of the compounds of Formula (I), D is —C(CH$_3$)=CHCH$_2$CH$_2$—.
In another embodiment of the compounds of Formula (I), D is —CH$_2$CH$_2$C(CH$_3$)=CH—.
In another embodiment of the compounds of Formula (I), D is —CH$_2$C(CH$_3$)=CHCH$_2$—.

In another embodiment of the compounds of Formula (I), D is —CH=C(CH$_3$)—.

In another embodiment of the compounds of Formula (I), D is —CH$_2$CH=C(CH$_3$)—.

In another embodiment of the compounds of Formula (I), D is —CH=C(CH$_3$)CH$_2$—.

In another embodiment of the compounds of Formula (I), D is —CH$_2$CH=C(CH$_3$)CH$_2$—.

In another embodiment of the compounds of Formula (I), D is —CH=C(CH$_3$)CH$_2$CH$_2$—.

In another embodiment of the compounds of Formula (I), D is —CH$_2$CH$_2$CH=C(CH$_3$)—.

In another embodiment of the compounds of Formula (I), D is —CH$_2$CH=C(CH$_3$)CH$_2$—.

In another embodiment of the compounds of Formula (I), D is alkynylene.

In another embodiment of the compounds of Formula (I), D is —C≡C—.

In another embodiment of the compounds of Formula (I), D is —CH$_2$C≡C—.

In another embodiment of the compounds of Formula (I), D is —CH$_2$CH$_2$C≡C—.

In another embodiment of the compounds of Formula (I), D is —C≡CCH$_2$—.

In another embodiment of the compounds of Formula (I), D is —C≡CCH$_2$CH$_2$—.

In another embodiment of the compounds of Formula (I), D is —CH$_2$C≡CCH$_2$—.

In another embodiment of the compounds of Formula (I), D is —CH$_2$CH$_2$C≡CCH$_2$—.

In another embodiment of the compounds of Formula (I), D is —CH$_2$C≡CCH$_2$CH$_2$—.

In another embodiment of the compounds of Formula (I), R$^1$ is H, provided that D is not a covalent bond.

In another embodiment of the compounds of Formula (I), R$^1$ is alkyl, wherein said alkyl can include any alkyl defined and described herein.

In another embodiment of the compounds of Formula (I), R$^1$ is —CH$_3$.

In another embodiment of the compounds of Formula (I), R$^1$ is —CH$_2$CH$_3$.

In another embodiment of the compounds of Formula (I), R$^1$ is i-propyl.

In another embodiment of the compounds of Formula (I), R$^1$ is t-butyl.

In another embodiment of the compounds of Formula (I), R$^1$ is halo.

In another embodiment of the compounds of Formula (I), R$^1$ is Cl.

In another embodiment of the compounds of Formula (I), R$^1$ is F.

In another embodiment of the compounds of Formula (I), R$^1$ is substituted or unsubstituted cycloalkyl.

In another embodiment of the compounds of Formula (I), R$^1$ is substituted or unsubstituted cyclopropyl.

In another embodiment of the compounds of Formula (I), R$^1$ is substituted or unsubstituted cyclobutyl.

In another embodiment of the compounds of Formula (I), R$^1$ is substituted or unsubstituted cyclopentyl.

In another embodiment of the compounds of Formula (I), R$^1$ is substituted or unsubstituted cyclohexyl.

In another embodiment of the compounds of Formula (I), R$^1$ is hydroxyl.

In another embodiment of the compounds of Formula (I), R$^1$ is alkoxy.

In another embodiment of the compounds of Formula (I), R$^1$ is methoxy.

In another embodiment of the compounds of Formula (I), R$^1$ is ethoxy.

In another embodiment of the compounds of Formula (I), R$^1$ is butoxy.

In another embodiment of the compounds of Formula (I), R$^1$ is isopropoxy.

In another embodiment of the compounds of Formula (I), R$^1$ is t-butoxy.

In another embodiment of the compounds of Formula (I), R$^1$ is alkenyl.

In another embodiment of the compounds of Formula (I), R$^1$ is allyl.

In another embodiment of the compounds of Formula (I), R$^1$ is alkynyl.

In another embodiment of the compounds of Formula (I), R$^1$ is propargyl.

In another embodiment of the compounds of Formula (I), R$^1$ is cyano.

In another embodiment of the compounds of Formula (I), R$^1$ is —C(O)—N(R$^7$)$_2$.

In another embodiment of the compounds of Formula (I), R$^1$ is —C(O)—N(R$^7$)$_2$, wherein R$^7$ is as defined herein.

In another embodiment of the compounds of Formula (I), R$^1$ is —C(O)—NH$_2$.

In another embodiment of the compounds of Formula (I), R$^1$ is —O—C(O)—N(R$^7$)$_2$.

In another embodiment of the compounds of Formula (I), R$^1$ is —O—C(O)—N(R$^7$)$_2$, wherein R$^7$ is as defined herein.

In another embodiment of the compounds of Formula (I), R$^1$ is —O—C(O)—NH$_2$.

In another embodiment of the compounds of Formula (I), R$^1$ is heterocyclyl.

In another embodiment of the compounds of Formula (I), R$^1$ is substituted heterocyclyl.

In another embodiment of the compounds of Formula (I), R$^1$ is tetrahydrofuranyl.

In another embodiment of the compounds of Formula (I), R$^1$ is oxetanyl.

In another embodiment of the compounds of Formula (I), R$^1$ is —C(O)—Oalkyl.

In another embodiment of the compounds of Formula (I), R$^1$ is —C(O)—Oalkyl, wherein the alkyl moiety includes any alkyl defined or described herein.

In another embodiment of the compounds of Formula (I), R$^1$ is —C(O)—OH.

In another embodiment of the compounds of Formula (I), R$^1$ is silyloxy.

In another embodiment of the compounds of Formula (I), R$^1$ is —OSi(alkyl)$_3$.

In another embodiment of the compounds of Formula (I), R$^1$ is substituted or unsubstituted —OSi(alkyl)$_2$aryl.

In another embodiment of the compounds of Formula (I), R$^1$ is substituted or unsubstituted —OSi(aryl)$_2$alkyl.

In another embodiment of the compounds of Formula (I), R$^1$ is substituted or unsubstituted —OSi(aryl)$_3$.

In another embodiment of the compounds of Formula (I), R$^1$ is —O-alkylene-OH, wherein said alkylene is any alkylene defined or described herein.

In another embodiment of the compounds of Formula (I), R$^1$ is —O-alkylene-O-acyl, wherein said alkylene is any alkylene defined or described herein, and acyl is as defined herein.

In another embodiment of the compounds of Formula (I), R$^1$ is —S(O)$_2$—N(R$^7$)$_2$, wherein R$^7$ is as defined herein.

In another embodiment of the compounds of Formula (I), R$^2$ is halo.

In another embodiment of the compounds of Formula (I), R$^2$ is Cl.

In another embodiment of the compounds of Formula (I), $R^2$ is F.

In another embodiment of the compounds of Formula (I), $R^2$ is nitro.

In another embodiment of the compounds of Formula (I), $R^2$ is cyano.

In another embodiment of the compounds of Formula (I), $R^2$ is alkyl.

In another embodiment of the compounds of Formula (I), $R^2$ is —$CH_3$.

In another embodiment of the compounds of Formula (I), $R^2$ is —$CH_2CH_3$.

In another embodiment of the compounds of Formula (I), $R^2$ is —$CH_2CH_2CH_3$.

In another embodiment of the compounds of Formula (I), $R^2$ is isopropyl.

In another embodiment of the compounds of Formula (I), $R^2$ is butyl.

In another embodiment of the compounds of Formula (I), $R^2$ is t-butyl.

In another embodiment of the compounds of Formula (I), $R^2$ is substituted alkyl.

In another embodiment of the compounds of Formula (I), $R^2$ is alkoxyalkyl.

In another embodiment of the compounds of Formula (I), $R^2$ is methoxyethyl.

In another embodiment of the compounds of Formula (I), $R^2$ is ethoxyethyl.

In another embodiment of the compounds of Formula (I), $R^2$ is ethoxymethyl.

In another embodiment of the compounds of Formula (I), $R^2$ is hydroxyalkyl.

In another embodiment of the compounds of Formula (I), $R^2$ is alkenyl.

In another embodiment of the compounds of Formula (I), $R^2$ is allyl.

In another embodiment of the compounds of Formula (I), $R^2$ is substituted alkenyl.

In another embodiment of the compounds of Formula (I), $R^2$ is halo substituted alkenyl.

In another embodiment of the compounds of Formula (I), $R^2$ is alkynyl.

In another embodiment of the compounds of Formula (I), $R^2$ is propargyl.

In another embodiment of the compounds of Formula (I), $R^2$ is substituted alkynyl.

In another embodiment of the compounds of Formula (I), $R^2$ is alkoxycarbonyl.

In another embodiment of the compounds of Formula (I), $R^2$ is —C(O)—O—$CH_3$.

In another embodiment of the compounds of Formula (I), $R^2$ is —C(O)—O—$CH_2CH_3$.

In another embodiment of the compounds of Formula (I), $R^2$ is —C(O)—O—$C(CH_3)_3$.

In another embodiment of the compounds of Formula (I), $R^2$ is —C(O)—O—$CH(CH_3)_2$.

In another embodiment of the compounds of Formula (I), $R^2$ is —$N(R^7)_2$, wherein $R^7$ is as defined herein.

In another embodiment of the compounds of Formula (I), $R^2$ is alkylcarbamoyl.

In another embodiment of the compounds of Formula (I), $R^2$ is —O—C(O)—NH—$CH_3$.

In another embodiment of the compounds of Formula (I), $R^2$ is dialkylcarbamoyl.

In another embodiment of the compounds of Formula (I), $R^2$ is —O—C(O)—$N(CH_3)_2$.

In another embodiment of the compounds of Formula (I), $R^2$ is cycloalkyl.

In another embodiment of the compounds of Formula (I), $R^2$ is cyclopropyl.

In another embodiment of the compounds of Formula (I), $R^2$ is cyclobutyl.

In another embodiment of the compounds of Formula (I), $R^2$ is cyclopentyl.

In another embodiment of the compounds of Formula (I), $R^2$ is cyclohexyl.

In another embodiment of the compounds of Formula (I), $R^2$ is substituted cycloalkyl.

In another embodiment of the compounds of Formula (I), $R^2$ is substituted cyclopropyl.

In another embodiment of the compounds of Formula (I), $R^2$ is substituted cyclobutyl.

In another embodiment of the compounds of Formula (I), $R^2$ is substituted cyclopentyl.

In another embodiment of the compounds of Formula (I), $R^2$ is substituted cyclohexyl.

In another embodiment of the compounds of Formula (I), $R^2$ is arylalkyl.

In another embodiment of the compounds of Formula (I), $R^2$ is benzyl.

In another embodiment of the compounds of Formula (I), $R^2$ is phenethyl.

In another embodiment of the compounds of Formula (I), $R^2$ is substituted arylalkyl.

In another embodiment of the compounds of Formula (I), $R^2$ is substituted benzyl.

In another embodiment of the compounds of Formula (I), $R^2$ is substituted phenethyl.

In another embodiment of the compounds of Formula (I), $R^3$ is aryl.

In another embodiment of the compounds of Formula (I), $R^3$ is phenyl.

In another embodiment of the compounds of Formula (I), $R^3$ is heteroaryl.

In another embodiment of the compounds of Formula (I), $R^3$ is a monocyclic heteroaryl.

In another embodiment of the compounds of Formula (I), $R^3$ is a bicyclic heteroaryl.

In another embodiment of the compounds of Formula (I), $R^3$ is selected from the group consisting of In another embodiment of the compounds of Formula (I), $R^3$—$(Z)_n$ is selected from the group consisting of

[chemical structures: a chloro-cyano-indolyl group; a quinolinyl group; an imidazolyl group; a pyrazolyl group; a benzimidazolyl group; an indazolyl group; and an indolyl group]

In another embodiment of the compounds of Formula (I), $R^4$ is H.
In another embodiment of the compounds of Formula (I), $R^4$ is alkyl.
In another embodiment of the compounds of Formula (I), $R^4$ is methyl.
In another embodiment of the compounds of Formula (I), $R^4$ is ethyl.
In another embodiment of the compounds of Formula (I), $R^4$ is isopropyl.
In another embodiment of the compounds of Formula (I), $R^4$ is propyl.
In another embodiment of the compounds of Formula (I), $R^4$ is butyl.
In another embodiment of the compounds of Formula (I), $R^4$ is sec-butyl.
In another embodiment of the compounds of Formula (I), $R^4$ is t-butyl.
In another embodiment of the compounds of Formula (I), $R^4$ is pentyl.
In another embodiment of the compounds of Formula (I), $R^4$ is hexyl.
In another embodiment of the compounds of Formula (I), $R^4$ is substituted alkyl.
In another embodiment of the compounds of Formula (I), $R^4$ is haloalkyl.
In another embodiment of the compounds of Formula (I), $R^4$ is cycloalkyl.
In another embodiment of the compounds of Formula (I), $R^4$ is cyclopropyl.
In another embodiment of the compounds of Formula (I), $R^4$ is cyclobutyl.
In another embodiment of the compounds of Formula (I), $R^4$ is cyclopentyl.
In another embodiment of the compounds of Formula (I), $R^4$ is cyclohexyl.
In another embodiment of the compounds of Formula (I), $R^4$ is substituted cycloalkyl.
In another embodiment of the compounds of Formula (I), $R^4$ is substituted cycloalkyl.
In another embodiment of the compounds of Formula (I), $R^4$ is substituted cyclopropyl.
In another embodiment of the compounds of Formula (I), $R^4$ is substituted cyclobutyl.
In another embodiment of the compounds of Formula (I), $R^4$ is substituted cyclopentyl.
In another embodiment of the compounds of Formula (I), $R^4$ is substituted cyclohexyl.
In another embodiment of the compounds of Formula (I), $R^4$ is hydroxyalkyl.
In another embodiment of the compounds of Formula (I), $R^4$ is hydroxymethyl.
In another embodiment of the compounds of Formula (I), $R^4$ is hydroxyethyl.
In another embodiment of the compounds of Formula (I), $R^4$ is hydroxypropyl.
In another embodiment of the compounds of Formula (I), $R^4$ is hydroxybutyl.
In another embodiment of the compounds of Formula (I), $R^4$ is alkoxyalkyl.
In another embodiment of the compounds of Formula (I), $R^4$ is methoxyethyl.
In another embodiment of the compounds of Formula (I), $R^4$ is ethoxymethyl.
In another embodiment of the compounds of Formula (I), $R^4$ is ethoxyethyl.
In another embodiment of the compounds of Formula (I), $R^4$ is t-butoxyethyl.
In another embodiment of the compounds of Formula (I), $R^4$ is arylalkyl.
In another embodiment of the compounds of Formula (I), $R^4$ is benzyl.
In another embodiment of the compounds of Formula (I), $R^4$ is phenethyl.
In another embodiment of the compounds of Formula (I), $R^4$ is substituted arylalkyl.
In another embodiment of the compounds of Formula (I), $R^4$ is substituted benzyl.
In another embodiment of the compounds of Formula (I), $R^4$ is substituted phenethyl.
In another embodiment of the compounds of Formula (I), A is —C(O)— and $R^2$ is alkyl.
In another embodiment of the compounds of Formula (I), A is —C(O)— and $R^2$ is methyl.
In another embodiment of the compounds of Formula (I), A is —C(O)— and $R^2$ is ethyl.
In another embodiment of the compounds of Formula (I), A is —C(O)— and $R^2$ is propyl.
In another embodiment of the compounds of Formula (I), A is —C(O)— and $R^2$ is isopropyl.
In another embodiment of the compounds of Formula (I), A is —C(O)— and $R^2$ is butyl.
In another embodiment of the compounds of Formula (I), A is —C(O)— and $R^2$ is t-butyl.
In another embodiment of the compounds of Formula (I), A is a covalent bond and $R^2$ is alkyl.
In another embodiment of the compounds of Formula (I), A is a covalent bond and $R^2$ is methyl.
In another embodiment of the compounds of Formula (I), A is a covalent bond and $R^2$ is ethyl.
In another embodiment of the compounds of Formula (I), A is a covalent bond and $R^2$ is propyl.
In another embodiment of the compounds of Formula (I), A is a covalent bond and $R^2$ is isopropyl.
In another embodiment of the compounds of Formula (I), A is a covalent bond and $R^2$ is butyl.
In another embodiment of the compounds of Formula (I), A is a covalent bond and $R^2$ is t-butyl.

In another embodiment of the compounds of Formula (I), A is —C(O)— and $R^3$ is phenyl.

In another embodiment of the compounds of Formula (I), A is —C(O)—, $R^3$ is phenyl, and n is 2.

In another embodiment of the compounds of Formula (I), A is —C(O)—, $R^3$ is phenyl, n is 2, and each Z is alkyl.

In another embodiment of the compounds of Formula (I), A is —C(O)—, $R^3$ is phenyl, n is 2, and each Z is methyl.

In another embodiment of the compounds of Formula (I), A is —C(O)—, $R^3$ is phenyl, n is 2, one Z is alkyl, and the other Z is cyano.

In another embodiment of the compounds of Formula (I), A is —C(O)—, $R^3$ is phenyl, n is 2, one Z is methyl, and the other Z is cyano.

In another embodiment of the compounds of Formula (I), A is —C(O)—, $R^3$ is phenyl, n is 2, one Z is ethyl, and the other Z is cyano.

In another embodiment of the compounds of Formula (I), A is —C(O)—, $R^3$ is phenyl, n is 2, one Z is propyl, and the other Z is cyano.

In another embodiment of the compounds of Formula (I), A is —C(O)— and $R^3$—$Z_n$ is 3,5-disubstituted phenyl.

In another embodiment of the compounds of Formula (I), A is —C(O)—, $R^3$—$Z_n$ is 3,5-disubstituted phenyl, and $R^2$ is alkyl.

In another embodiment of the compounds of Formula (I), A is —C(O)—, $R^3$—$Z_n$ is 3,5-disubstituted phenyl, and $R^2$ is methyl.

In another embodiment of the compounds of Formula (I), A is —C(O)—, $R^3$—$Z_n$ is 3,5-disubstituted phenyl, and $R^2$ is ethyl.

In another embodiment of the compounds of Formula (I), A is —C(O)—, $R^3$—$Z_n$ is 3,5-disubstituted phenyl, and $R^2$ is propyl.

In another embodiment of the compounds of Formula (I), A is —C(O)—, $R^3$—$Z_n$ is 3,5-disubstituted phenyl, and $R^2$ is isopropyl.

In another embodiment of the compounds of Formula (I), A is —C(O)—, $R^3$—$Z_n$ is 3,5-disubstituted phenyl, and $R^2$ is butyl.

In another embodiment of the compounds of Formula (I), A is —C(O)—, $R^3$—$Z_n$ is 3,5-disubstituted phenyl, and $R^2$ is t-butyl.

In another embodiment of the compounds of Formula (I), A is a covalentcovalent bond and $R^3$ is aryl or heteroaryl.

In another embodiment of the compounds of Formula (I), A is a covalentcovalent bond, $R^3$ is aryl or heteroaryl, and n is 2.

In another embodiment of the compounds of Formula (I), A is a covalentcovalent bond, $R^3$ is aryl or heteroaryl, n is 2, and each Z is alkyl.

In another embodiment of the compounds of Formula (I), A is a covalentcovalent bond, $R^3$ is aryl or heteroaryl, n is 2, and each Z is methyl.

In another embodiment of the compounds of Formula (I), A is a covalentcovalent bond, $R^3$ is aryl or heteroaryl, n is 2, one Z is alkyl, and the other Z is cyano.

In another embodiment of the compounds of Formula (I), A is a covalentcovalent bond, $R^3$ is aryl or heteroaryl, n is 2, one Z is methyl, and the other Z is cyano.

In another embodiment of the compounds of Formula (I), A is a covalentcovalent bond, $R^3$ is aryl or heteroaryl, n is 2, one Z is ethyl, and the other Z is cyano.

In another embodiment of the compounds of Formula (I), A is a covalent bond, $R^3$ is aryl or heteroaryl, n is 2, one Z is propyl, and the other Z is cyano.

In another embodiment of the compounds of Formula (I), A is a covalent bond and $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl.

In another embodiment of the compounds of Formula (I), A is a covalent bond, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, and each Z is independently alkyl, cyano, or halo.

In another embodiment of the compounds of Formula (I), A is a covalent bond, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, n is 2, and each Z is independently alkyl, cyano, or halo.

In another embodiment of the compounds of Formula (I), A is —C(O)— and $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, and $R^4$ is H.

In another embodiment of the compounds of Formula (I), A is —C(O)—, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, each Z is independently alkyl, cyano, or halo, and $R^4$ is H.

In another embodiment of the compounds of Formula (I), A is —C(O)—, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, n is 2, each Z is independently alkyl, cyano, or halo, and $R^4$ is H.

In another embodiment of the compounds of Formula (I), A is —O— and $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, and $R^4$ is H.

In another embodiment of the compounds of Formula (I), A is —O—, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, each Z is independently alkyl, cyano, or halo, and $R^4$ is H.

In another embodiment of the compounds of Formula (I), A is —O—, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, n is 2, each Z is independently alkyl, cyano, or halo, and $R^4$ is H.

In another embodiment of the compounds of Formula (I), A is —$NR^5$— and $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, and $R^4$ is H.

In another embodiment of the compounds of Formula (I), A is —$NR^5$—, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, each Z is independently alkyl, cyano, or halo, and $R^4$ is H.

In another embodiment of the compounds of Formula (I), A is $-NR^5-$, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, n is 2, each Z is independently alkyl, cyano, or halo, and $R^4$ is H.

In another embodiment of the compounds of Formula (I), A is $-S-$ and $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, and $R^4$ is H.

In another embodiment of the compounds of Formula (I), A is $-S-$, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, each Z is independently alkyl, cyano, or halo, and $R^4$ is H.

In another embodiment of the compounds of Formula (I), A is $-S-$, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, n is 2, each Z is independently alkyl, cyano, or halo, and $R^4$ is H.

In another embodiment of the compounds of Formula (I), A is $-C(O)-$ $R^2$ is alkyl, and $R^4$ is H.

In another embodiment of the compounds of Formula (I), A is $-C(O)-$, $R^2$ is methyl, and $R^4$ is H.

In another embodiment of the compounds of Formula (I), A is $-C(O)-$ and $R^2$ is ethyl, and $R^4$ is H.

In another embodiment of the compounds of Formula (I), A is $-C(O)-$, $R^2$ is propyl, and $R^4$ is H.

In another embodiment of the compounds of Formula (I), A is $-C(O)-$, $R^2$ is isopropyl, and $R^4$ is H.

In another embodiment of the compounds of Formula (I), A is $-C(O)-$, $R^2$ is butyl, and $R^4$ is H.

In another embodiment of the compounds of Formula (I), A is $-C(O)-$, $R^2$ is t-butyl, and $R^4$ is H.

In another embodiment of the compounds of Formula (I), A is a covalent bond, $R^2$ is alkyl, and $R^4$ is H.

In another embodiment of the compounds of Formula (I), A is a covalent bond, $R^2$ is methyl, and $R^4$ is H.

In another embodiment of the compounds of Formula (I), A is a covalent bond, $R^2$ is ethyl, and $R^4$ is H.

In another embodiment of the compounds of Formula (I), A is a covalent bond, $R^2$ is propyl, and $R^4$ is H.

In another embodiment of the compounds of Formula (I), A is a covalent bond, $R^2$ is isopropyl, and $R^4$ is H.

In another embodiment of the compounds of Formula (I), A is a covalent bond, $R^2$ is butyl, and $R^4$ is H.

In another embodiment of the compounds of Formula (I), A is a covalent bond, $R^2$ is t-butyl, and $R^4$ is H.

In another embodiment of the compounds of Formula (I), A is $-C(O)-$, $R^3$ is phenyl, and $R^4$ is H.

In another embodiment of the compounds of Formula (I), A is $-C(O)-$, $R^3$ is phenyl, n is 2, and $R^4$ is H.

In another embodiment of the compounds of Formula (I), A is $-C(O)-$, $R^3$ is phenyl, n is 2, each Z is alkyl, and $R^4$ is H.

In another embodiment of the compounds of Formula (I), A is $-C(O)-$, $R^3$ is phenyl, n is 2, each Z is methyl, and $R^4$ is H.

In another embodiment of the compounds of Formula (I), A is $-C(O)-$, $R^3$ is phenyl, n is 2, one Z is alkyl, the other Z is cyano, and $R^4$ is H.

In another embodiment of the compounds of Formula (I), A is $-C(O)-$, $R^3$ is phenyl, n is 2, one Z is methyl, the other Z is cyano, and $R^4$ is H.

In another embodiment of the compounds of Formula (I), A is $-C(O)-$, $R^3$ is phenyl, n is 2, one Z is ethyl, the other Z is cyano, and $R^4$ is H.

In another embodiment of the compounds of Formula (I), A is $-C(O)-$, $R^3$ is phenyl, n is 2, one Z is propyl, the other Z is cyano, and $R^4$ is H.

In another embodiment of the compounds of Formula (I), A is $-C(O)-$, $R^3-Z_n$ is 3,5-disubstituted phenyl, and $R^4$ is H.

In another embodiment of the compounds of Formula (I), A is $-C(O)-$, $R^3-Z_n$ is 3,5-disubstituted phenyl, $R^2$ is alkyl, and $R^4$ is H.

In another embodiment of the compounds of Formula (I), A is $-C(O)-$, $R^3-Z_n$ is 3,5-disubstituted phenyl, $R^2$ is methyl, and $R^4$ is H.

In another embodiment of the compounds of Formula (I), A is $-C(O)-$, $R^3-Z_n$ is 3,5-disubstituted phenyl, $R^2$ is ethyl, and $R^4$ is H.

In another embodiment of the compounds of Formula (I), A is $-C(O)-$, $R^3-Z_n$ is 3,5-disubstituted phenyl, $R^2$ is propyl, and $R^4$ is H.

In another embodiment of the compounds of Formula (I), A is $-C(O)-$, $R^3-Z_n$ is 3,5-disubstituted phenyl, $R^2$ is isopropyl, and $R^4$ is H.

In another embodiment of the compounds of Formula (I), A is $-C(O)-$, $R^3-Z_n$ is 3,5-disubstituted phenyl, $R^2$ is butyl, and $R^4$ is H.

In another embodiment of the compounds of Formula (I), A is $-C(O)-$, $R^3-Z_n$ is 3,5-disubstituted phenyl, $R^2$ is t-butyl, and $R^4$ is H.

In another embodiment of the compounds of Formula (I), A is a covalent bond, $R^3$ is aryl or heteroaryl, and $R^4$ is H.

In another embodiment of the compounds of Formula (I), A is a covalent bond, $R^3$ is aryl or heteroaryl, n is 2, and $R^4$ is H.

In another embodiment of the compounds of Formula (I), A is a covalent bond, $R^3$ is aryl or heteroaryl, n is 2, each Z is alkyl, and $R^4$ is H.

In another embodiment of the compounds of Formula (I), A is a covalent bond, $R^3$ is aryl or heteroaryl, n is 2, each Z is methyl, and $R^4$ is H.

In another embodiment of the compounds of Formula (I), A is a covalent bond, $R^3$ is aryl or heteroaryl, n is 2, one Z is alkyl, the other Z is cyano, and $R^4$ is H.

In another embodiment of the compounds of Formula (I), A is a covalent bond, $R^3$ is aryl or heteroaryl, n is 2, one Z is methyl, the other Z is cyano, and $R^4$ is H.

In another embodiment of the compounds of Formula (I), A is a covalent bond, $R^3$ is aryl or heteroaryl, n is 2, one Z is ethyl, and the other Z is cyano, and $R^4$ is H.

In another embodiment of the compounds of Formula (I), A is a covalent bond, $R^3$ is aryl or heteroaryl, n is 2, one Z is propyl, the other Z is cyano, and $R^4$ is H.

In another embodiment of the compounds of Formula (I), A is a covalent bond and $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, and $R^4$ is H.

In another embodiment of the compounds of Formula (I), A is a covalent bond, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, each Z is independently alkyl, cyano, or halo, and $R^4$ is H.

In another embodiment of the compounds of Formula (I), A is a covalent bond, $R^3$ is selected from the group consisting of phenyl, naphthyl, pyridyl, pyrroyl, furanyl, thiophenyl, pyrazolyl, imidazolyl, oxazolyl, isoxazolyl, thiazolyl, pyridazinyl, pyrimidinyl, pyrazinyl, quinolinyl, benzoimidazolyl, indazolyl, and indolyl, n is 2, each Z is independently alkyl, cyano, or halo, and $R^4$ is H.

In another embodiment of the compounds of Formula (I), A is —O— and $R^2$ is alkyl.

In another embodiment of the compounds of Formula (I), A is —O— and $R^2$ is methyl.

In another embodiment of the compounds of Formula (I), A is —O— and $R^2$ is ethyl.

In another embodiment of the compounds of Formula (I), A is —O— and $R^2$ is propyl.

In another embodiment of the compounds of Formula (I), A is —O— and $R^2$ is isopropyl.

In another embodiment of the compounds of Formula (I), A is —O— and $R^2$ is butyl.

In another embodiment of the compounds of Formula (I), A is —O— and $R^2$ is t-butyl.

In another embodiment of the compounds of Formula (I), A is —O— and $R^3$ is phenyl.

In another embodiment of the compounds of Formula (I), A is —O—, $R^3$ is phenyl, and n is 2.

In another embodiment of the compounds of Formula (I), A is —O—, $R^3$ is phenyl, n is 2, and each Z is alkyl.

In another embodiment of the compounds of Formula (I), A is —O—, $R^3$ is phenyl, n is 2, and each Z is methyl.

In another embodiment of the compounds of Formula (I), A is —O—, $R^3$ is phenyl, n is 2, one Z is alkyl, and the other Z is cyano.

In another embodiment of the compounds of Formula (I), A is —O—, $R^3$ is phenyl, n is 2, one Z is methyl, and the other Z is cyano.

In another embodiment of the compounds of Formula (I), A is —O—, $R^3$ is phenyl, n is 2, one Z is ethyl, and the other Z is cyano.

In another embodiment of the compounds of Formula (I), A is —O—, $R^3$ is phenyl, n is 2, one Z is propyl, and the other Z is cyano.

In another embodiment of the compounds of Formula (I), A is —O— and $R^3$—$Z_n$ is 3,5-disubstituted phenyl.

In another embodiment of the compounds of Formula (I), A is —O—, $R^3$—$Z_n$ is 3,5-disubstituted phenyl, and $R^2$ is alkyl.

In another embodiment of the compounds of Formula (I), A is —O—, $R^3$—$Z_n$ is 3,5-disubstituted phenyl, and $R^2$ is methyl.

In another embodiment of the compounds of Formula (I), A is —O—, $R^3$—$Z_n$ is 3,5-disubstituted phenyl, and $R^2$ is ethyl.

In another embodiment of the compounds of Formula (I), A is —O—, $R^3$—$Z_n$ is 3,5-disubstituted phenyl, and $R^2$ is propyl.

In another embodiment of the compounds of Formula (I), A is —O—, $R^3$—$Z_n$ is 3,5-disubstituted phenyl, and $R^2$ is isopropyl.

In another embodiment of the compounds of Formula (I), A is —O—, $R^3$—$Z_n$ is 3,5-disubstituted phenyl, and $R^2$ is butyl.

In another embodiment of the compounds of Formula (I), A is —O—, $R^3$—$Z_n$ is 3,5-disubstituted phenyl, and $R^2$ is t-butyl.

In another embodiment of the compounds of Formula (I), A is —O—$R^2$ is alkyl, and $R^4$ is H.

In another embodiment of the compounds of Formula (I), A is —O—, $R^2$ is methyl, and $R^4$ is H.

In another embodiment of the compounds of Formula (I), A is —O— and $R^2$ is ethyl, and $R^4$ is H.

In another embodiment of the compounds of Formula (I), A is —O—, $R^2$ is propyl, and $R^4$ is H.

In another embodiment of the compounds of Formula (I), A is —O—, $R^2$ is isopropyl, and $R^4$ is H.

In another embodiment of the compounds of Formula (I), A is —O—, $R^2$ is butyl, and $R^4$ is H.

In another embodiment of the compounds of Formula (I), A is —O—, $R^2$ is t-butyl, and $R^4$ is H.

In another embodiment of the compounds of Formula (I), A is —O—, $R^3$ is phenyl, and $R^4$ is H.

In another embodiment of the compounds of Formula (I), A is —O—, $R^3$ is phenyl, n is 2, and $R^4$ is H.

In another embodiment of the compounds of Formula (I), A is —O—, $R^3$ is phenyl, n is 2, each Z is alkyl, and $R^4$ is H.

In another embodiment of the compounds of Formula (I), A is —O—, $R^3$ is phenyl, n is 2, each Z is methyl, and $R^4$ is H.

In another embodiment of the compounds of Formula (I), A is —O—, $R^3$ is phenyl, n is 2, one Z is alkyl, the other Z is cyano, and $R^4$ is H.

In another embodiment of the compounds of Formula (I), A is —O—, $R^3$ is phenyl, n is 2, one Z is methyl, the other Z is cyano, and $R^4$ is H.

In another embodiment of the compounds of Formula (I), A is —O—, $R^3$ is phenyl, n is 2, one Z is ethyl, the other Z is cyano, and $R^4$ is H.

In another embodiment of the compounds of Formula (I), A is —O—, $R^3$ is phenyl, n is 2, one Z is propyl, the other Z is cyano, and $R^4$ is H.

In another embodiment of the compounds of Formula (I), A is —O—, $R^3$—$Z_n$ is 3,5-disubstituted phenyl, and $R^4$ is H.

In another embodiment of the compounds of Formula (I), A is —O—, $R^3$—$Z_n$ is 3,5-disubstituted phenyl, $R^2$ is alkyl, and $R^4$ is H.

In another embodiment of the compounds of Formula (I), A is —O—, $R^3$—$Z_n$ is 3,5-disubstituted phenyl, $R^2$ is methyl, and $R^4$ is H.

In another embodiment of the compounds of Formula (I), A is —O—, $R^3$—$Z_n$ is 3,5-disubstituted phenyl, $R^2$ is ethyl, and $R^4$ is H.

In another embodiment of the compounds of Formula (I), A is —O—, $R^3$—$Z_n$ is 3,5-disubstituted phenyl, $R^2$ is propyl, and $R^4$ is H.

In another embodiment of the compounds of Formula (I), A is —O—, $R^3$—$Z_n$ is 3,5-disubstituted phenyl, $R^2$ is isopropyl, and $R^4$ is H.

In another embodiment of the compounds of Formula (I), A is —O—, $R^3$—$Z_n$ is 3,5-disubstituted phenyl, $R^2$ is butyl, and $R^4$ is H.

In another embodiment of the compounds of Formula (I), A is —O—, $R^3$—$Z_n$ is 3,5-disubstituted phenyl, $R^2$ is t-butyl, and $R^4$ is H.

In another embodiment of the compounds of Formula (I), A is —NH— and $R^2$ is alkyl.

In another embodiment of the compounds of Formula (I), A is —NH— and $R^2$ is methyl.

In another embodiment of the compounds of Formula (I), A is —NH— and $R^2$ is ethyl.

In another embodiment of the compounds of Formula (I), A is —NH— and $R^2$ is propyl.

In another embodiment of the compounds of Formula (I), A is —NH— and $R^2$ is isopropyl.

In another embodiment of the compounds of Formula (I), A is —NH— and $R^2$ is butyl.

In another embodiment of the compounds of Formula (I), A is —NH— and $R^2$ is t-butyl.

In another embodiment of the compounds of Formula (I), A is —NH— and $R^3$ is phenyl.

In another embodiment of the compounds of Formula (I), A is —NH—, $R^3$ is phenyl, and n is 2.

In another embodiment of the compounds of Formula (I), A is —NH—, $R^3$ is phenyl, n is 2, and each Z is alkyl.

In another embodiment of the compounds of Formula (I), A is —NH—, $R^3$ is phenyl, n is 2, and each Z is methyl.

In another embodiment of the compounds of Formula (I), A is —NH—, $R^3$ is phenyl, n is 2, one Z is alkyl, and the other Z is cyano.

In another embodiment of the compounds of Formula (I), A is —NH—, $R^3$ is phenyl, n is 2, one Z is methyl, and the other Z is cyano.

In another embodiment of the compounds of Formula (I), A is —NH—, $R^3$ is phenyl, n is 2, one Z is ethyl, and the other Z is cyano.

In another embodiment of the compounds of Formula (I), A is —NH—, $R^3$ is phenyl, n is 2, one Z is propyl, and the other Z is cyano.

In another embodiment of the compounds of Formula (I), A is —NH— and $R^3$—$Z_n$ is 3,5-disubstituted phenyl.

In another embodiment of the compounds of Formula (I), A is —NH—, $R^3$—$Z_n$ is 3,5-disubstituted phenyl, and $R^2$ is alkyl.

In another embodiment of the compounds of Formula (I), A is —NH—, $R^3$—$Z_n$ is 3,5-disubstituted phenyl, and $R^2$ is methyl.

In another embodiment of the compounds of Formula (I), A is —NH—, $R^3$—$Z_n$ is 3,5-disubstituted phenyl, and $R^2$ is ethyl.

In another embodiment of the compounds of Formula (I), A is —NH—, $R^3$—$Z_n$ is 3,5-disubstituted phenyl, and $R^2$ is propyl.

In another embodiment of the compounds of Formula (I), A is —NH—, $R^3$—$Z_n$ is 3,5-disubstituted phenyl, and $R^2$ is isopropyl.

In another embodiment of the compounds of Formula (I), A is —NH—, $R^3$—$Z_n$ is 3,5-disubstituted phenyl, and $R^2$ is butyl.

In another embodiment of the compounds of Formula (I), A is —NH—, $R^3$—$Z_n$ is 3,5-disubstituted phenyl, and $R^2$ is t-butyl.

In another embodiment of the compounds of Formula (I), A is —NH—$R^2$ is alkyl, and $R^4$ is H.

In another embodiment of the compounds of Formula (I), A is —NH—, $R^2$ is methyl, and $R^4$ is H.

In another embodiment of the compounds of Formula (I), A is —NH— and $R^2$ is ethyl, and $R^4$ is H.

In another embodiment of the compounds of Formula (I), A is —NH—, $R^2$ is propyl, and $R^4$ is H.

In another embodiment of the compounds of Formula (I), A is —NH—, $R^2$ is isopropyl, and $R^4$ is H.

In another embodiment of the compounds of Formula (I), A is —NH—, $R^2$ is butyl, and $R^4$ is H.

In another embodiment of the compounds of Formula (I), A is —NH—, $R^2$ is t-butyl, and $R^4$ is H.

In another embodiment of the compounds of Formula (I), A is —NH—, $R^3$ is phenyl, and $R^4$ is H.

In another embodiment of the compounds of Formula (I), A is —NH—, $R^3$ is phenyl, n is 2, and $R^4$ is H.

In another embodiment of the compounds of Formula (I), A is —NH—, $R^3$ is phenyl, n is 2, each Z is alkyl, and $R^4$ is H.

In another embodiment of the compounds of Formula (I), A is —NH—, $R^3$ is phenyl, n is 2, each Z is methyl, and $R^4$ is H.

In another embodiment of the compounds of Formula (I), A is —NH—, $R^3$ is phenyl, n is 2, one Z is alkyl, the other Z is cyano, and $R^4$ is H.

In another embodiment of the compounds of Formula (I), A is —NH—, $R^3$ is phenyl, n is 2, one Z is methyl, the other Z is cyano, and $R^4$ is H.

In another embodiment of the compounds of Formula (I), A is —NH—, $R^3$ is phenyl, n is 2, one Z is ethyl, the other Z is cyano, and $R^4$ is H.

In another embodiment of the compounds of Formula (I), A is —NH—, $R^3$ is phenyl, n is 2, one Z is propyl, the other Z is cyano, and $R^4$ is H.

In another embodiment of the compounds of Formula (I), A is —NH—, $R^3$—$Z_n$ is 3,5-disubstituted phenyl, and $R^4$ is H.

In another embodiment of the compounds of Formula (I), A is —NH—, $R^3$—$Z_n$ is 3,5-disubstituted phenyl, $R^2$ is alkyl, and $R^4$ is H.

In another embodiment of the compounds of Formula (I), A is —NH—, $R^3$—$Z_n$ is 3,5-disubstituted phenyl, $R^2$ is methyl, and $R^4$ is H.

In another embodiment of the compounds of Formula (I), A is —NH—, $R^3$—$Z_n$ is 3,5-disubstituted phenyl, $R^2$ is ethyl, and $R^4$ is H.

In another embodiment of the compounds of Formula (I), A is —NH—, $R^3$—$Z_n$ is 3,5-disubstituted phenyl, $R^2$ is propyl, and $R^4$ is H.

In another embodiment of the compounds of Formula (I), A is —NH—, $R^3$—$Z_n$ is 3,5-disubstituted phenyl, $R^2$ is isopropyl, and $R^4$ is H.

In another embodiment of the compounds of Formula (I), A is —NH—, $R^3$—$Z_n$ is 3,5-disubstituted phenyl, $R^2$ is butyl, and $R^4$ is H.

In another embodiment of the compounds of Formula (I), A is —NH—, $R^3$—$Z_n$ is 3,5-disubstituted phenyl, $R^2$ is t-butyl, and $R^4$ is H.

In another embodiment of the compounds of Formula (I), A is —$CF_2$— and $R^2$ is alkyl.

In another embodiment of the compounds of Formula (I), A is —$CF_2$— and $R^2$ is methyl.

In another embodiment of the compounds of Formula (I), A is —$CF_2$— and $R^2$ is ethyl.

In another embodiment of the compounds of Formula (I), A is —$CF_2$— and $R^2$ is propyl.

In another embodiment of the compounds of Formula (I), A is —$CF_2$— and $R^2$ is isopropyl.

In another embodiment of the compounds of Formula (I), A is —$CF_2$— and $R^2$ is butyl.

In another embodiment of the compounds of Formula (I), A is —$CF_2$— and $R^2$ is t-butyl.

In another embodiment of the compounds of Formula (I), A is —$CF_2$— and $R^3$ is phenyl.

In another embodiment of the compounds of Formula (I), A is —$CF_2$—, $R^3$ is phenyl, and n is 2.

In another embodiment of the compounds of Formula (I), A is —$CF_2$—, $R^3$ is phenyl, n is 2, and each Z is alkyl.

In another embodiment of the compounds of Formula (I), A is —$CF_2$—, $R^3$ is phenyl, n is 2, and each Z is methyl.

In another embodiment of the compounds of Formula (I), A is —$CF_2$—, $R^3$ is phenyl, n is 2, one Z is alkyl, and the other Z is cyano.

In another embodiment of the compounds of Formula (I), A is —$CF_2$—, $R^3$ is phenyl, n is 2, one Z is methyl, and the other Z is cyano.

In another embodiment of the compounds of Formula (I), A is —$CF_2$—, $R^3$ is phenyl, n is 2, one Z is ethyl, and the other Z is cyano.

In another embodiment of the compounds of Formula (I), A is —$CF_2$—, $R^3$ is phenyl, n is 2, one Z is propyl, and the other Z is cyano.

In another embodiment of the compounds of Formula (I), A is —$CF_2$— and $R^3$—$Z_n$ is 3,5-disubstituted phenyl.

In another embodiment of the compounds of Formula (I), A is —$CF_2$—, $R^3$—$Z_n$ is 3,5-disubstituted phenyl, and $R^2$ is alkyl.

In another embodiment of the compounds of Formula (I), A is —$CF_2$—, $R^3$—$Z_n$ is 3,5-disubstituted phenyl, and $R^2$ is methyl.

In another embodiment of the compounds of Formula (I), A is —$CF_2$—, $R^3$—$Z_n$ is 3,5-disubstituted phenyl, and $R^2$ is ethyl.

In another embodiment of the compounds of Formula (I), A is —$CF_2$—, $R^3$—$Z_n$ is 3,5-disubstituted phenyl, and $R^2$ is propyl.

In another embodiment of the compounds of Formula (I), A is —$CF_2$—, $R^3$—$Z_n$ is 3,5-disubstituted phenyl, and $R^2$ is isopropyl.

In another embodiment of the compounds of Formula (I), A is —$CF_2$—, $R^3$—$Z_n$ is 3,5-disubstituted phenyl, and $R^2$ is butyl.

In another embodiment of the compounds of Formula (I), A is —$CF_2$—, $R^3$—$Z_n$ is 3,5-disubstituted phenyl, and $R^2$ is t-butyl.

In another embodiment of the compounds of Formula (I), A is —$CF_2$—$R^2$ is alkyl, and $R^4$ is H.

In another embodiment of the compounds of Formula (I), A is —$CF_2$—, $R^2$ is methyl, and $R^4$ is H.

In another embodiment of the compounds of Formula (I), A is —$CF_2$— and $R^2$ is ethyl, and $R^4$ is H.

In another embodiment of the compounds of Formula (I), A is —$CF_2$—, $R^2$ is propyl, and $R^4$ is H.

In another embodiment of the compounds of Formula (I), A is —$CF_2$—, $R^2$ is isopropyl, and $R^4$ is H.

In another embodiment of the compounds of Formula (I), A is —$CF_2$—, $R^2$ is butyl, and $R^4$ is H.

In another embodiment of the compounds of Formula (I), A is —$CF_2$—, $R^2$ is t-butyl, and $R^4$ is H.

In another embodiment of the compounds of Formula (I), A is —$CF_2$—, $R^3$ is phenyl, and $R^4$ is H.

In another embodiment of the compounds of Formula (I), A is —$CF_2$—, $R^3$ is phenyl, n is 2, and $R^4$ is H.

In another embodiment of the compounds of Formula (I), A is —$CF_2$—, $R^3$ is phenyl, n is 2, each Z is alkyl, and $R^4$ is H.

In another embodiment of the compounds of Formula (I), A is —$CF_2$—, $R^3$ is phenyl, n is 2, each Z is methyl, and $R^4$ is H.

In another embodiment of the compounds of Formula (I), A is —$CF_2$—, $R^3$ is phenyl, n is 2, one Z is alkyl, the other Z is cyano, and $R^4$ is H.

In another embodiment of the compounds of Formula (I), A is —$CF_2$—, $R^3$ is phenyl, n is 2, one Z is methyl, the other Z is cyano, and $R^4$ is H.

In another embodiment of the compounds of Formula (I), A is —$CF_2$—, $R^3$ is phenyl, n is 2, one Z is ethyl, the other Z is cyano, and $R^4$ is H.

In another embodiment of the compounds of Formula (I), A is —$CF_2$—, $R^3$ is phenyl, n is 2, one Z is propyl, the other Z is cyano, and $R^4$ is H.

In another embodiment of the compounds of Formula (I), A is —$CF_2$—, $R^3$—$Z_n$ is 3,5-disubstituted phenyl, and $R^4$ is H.

In another embodiment of the compounds of Formula (I), A is —$CF_2$—, $R^3$—$Z_n$ is 3,5-disubstituted phenyl, $R^2$ is alkyl, and $R^4$ is H.

In another embodiment of the compounds of Formula (I), A is —$CF_2$—, $R^3$—$Z_n$ is 3,5-disubstituted phenyl, $R^2$ is methyl, and $R^4$ is H.

In another embodiment of the compounds of Formula (I), A is —$CF_2$—, $R^3$—$Z_n$ is 3,5-disubstituted phenyl, $R^2$ is ethyl, and $R^4$ is H.

In another embodiment of the compounds of Formula (I), A is —$CF_2$—, $R^3$—$Z_n$ is 3,5-disubstituted phenyl, $R^2$ is propyl, and $R^4$ is H.

In another embodiment of the compounds of Formula (I), A is —$CF_2$—, $R^3$—$Z_n$ is 3,5-disubstituted phenyl, $R^2$ is isopropyl, and $R^4$ is H.

In another embodiment of the compounds of Formula (I), A is —$CF_2$—, $R^3$—$Z_n$ is 3,5-disubstituted phenyl, $R^2$ is butyl, and $R^4$ is H.

In another embodiment of the compounds of Formula (I), A is —$CF_2$—, $R^3$—$Z_n$ is 3,5-disubstituted phenyl, $R^2$ is t-butyl, and $R^4$ is H.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is H.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is alkyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is haloalkyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is cycloalkylalkyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is hydroxyalkyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is cyanoalkyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is -alkylene-C(O)—N($R^7$)$_2$.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is alkoxyalkyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is alkynyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is -alkynylene-cyclopropyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is hydroxyalkynyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is alkenyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is haloalkenyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is substituted or unsubstituted heterocyclylalkyl.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is —$CH_2$-cyclopropylene-$CH_2$—C(O)—$OCH_3$.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is —$CH_2$-cyclopropylene-$CH_2$—C(O)—OH.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is —$CH_2$-cyclopropylene-$CH_2$—C(O)—NH(PMB).

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is -alkylene-C(O)—N($R^7$)$_2$.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is —$CH_2$-cyclopropylene-$CH_2$—C(O)—$NH_2$.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is —$CH_2$—$CH_2$—O—C(O)—$OCH_3$.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is -alkylene-C(O)—N($R^7$)$_2$.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is -alkenylene-C(O)—$OR^7$.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is -alkenylene-C(O)—N($R^7$)$_2$.

In another embodiment of the compounds of Formula (I), A is —C(O), $R^3$—$Z_n$ is 3,5-disubstituted phenyl, $R^2$ is alkyl, $R^4$ is H, X and Y are both O, and -D-$R^1$ is —$CH_2$—CH═CH—C(O)—$NH_2$.

In another embodiment of the compounds of Formula (I), A is a covalent bond, $R^3$ is aryl or heteroaryl, $R^2$ is alkyl, $R^4$ is H, X and Y are both O, and -D-$R^1$ is H.

In another embodiment of the compounds of Formula (I), A is a covalent bond, $R^3$ is aryl or heteroaryl, Z is alkyl, cyano, or halo, $R^2$ is alkyl, $R^4$ is H, X and Y are both O, and -D-$R^1$ is H.

In another embodiment of the compounds of Formula (I), A is a covalent bond, $R^3$ is aryl or heteroaryl, Z is alkyl, cyano, or halo, n is 2, $R^2$ is alkyl, $R^4$ is H, X and Y are both O, and -D-R' is H.

In another embodiment of the compounds of Formula (I), A is a covalent bond, $R^3$ is aryl or heteroaryl, $R^2$ is alkyl, $R^4$ is H, X and Y are both O, and -D-$R^1$ is alkyl.

In another embodiment of the compounds of Formula (I), A is a covalent bond, $R^3$ is aryl or heteroaryl, $R^2$ is alkyl, $R^4$ is H, X and Y are both O, and -D-$R^1$ is alkyl.

In another embodiment of the compounds of Formula (I), A is a covalent bond, $R^3$ is aryl or heteroaryl, Z is alkyl, cyano, or halo, $R^2$ is alkyl, $R^4$ is H, X and Y are both O, and -D-$R^1$ is alkyl.

In another embodiment of the compounds of Formula (I), A is a covalent bond, $R^3$ is aryl or heteroaryl, $R^2$ is alkyl, $R^4$ is H, X and Y are both O, and -D-$R^1$ is haloalkyl.

In another embodiment of the compounds of Formula (I), A is a covalent bond, $R^3$ is aryl or heteroaryl, Z is alky, cyano, or halo, $R^2$ is alkyl, $R^4$ is H, X and Y are both O, and -D-$R^1$ is haloalkyl.

In another embodiment of the compounds of Formula (I), A is a covalent bond, $R^3$ is aryl or heteroaryl, Z is alky, cyano, or halo, n is 2, $R^2$ is alkyl, $R^4$ is H, X and Y are both O, and -D-$R^1$ is haloalkyl.

In another embodiment of the compounds of Formula (I), D is alkylene, alkenylene, or alkynylene.

In yet another embodiment, the compounds of Formula (I) have the following structure of Formula (Ia):

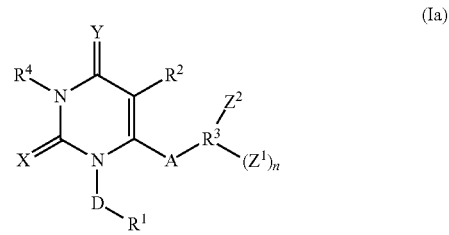

(Ia)

wherein X, Y, A, D, $R^2$, $R^3$, $R^4$, W, $R^6$, and $R^7$ are as defined above for Formula (I), and each $Z^1$ is independently selected from the group consisting of halo, nitro, hydroxyl, amino, acetamido, trifluoroacetamido, azido, cyano, formyl, alkyl, substituted alkyl, alkylcarbamoyl, dialkylcarbamoyl, alkenyl, substituted alkenyl, alkynyl, substituted alkynyl, alkoxy, substituted alkoxy, alkoxycarbonyl, cycloalkyl, substituted cycloalkyl, cycloalkenyl, substituted cycloalkenyl, heterocyclyl, substituted heterocyclyl, aryl, substituted aryl, oxide; and $Z^2$ is selected from the group consisting of halo, nitro, hydroxyl, amino, acetamido, trifluoroacetamido, azido, cyano, formyl, alkylcarbamoyl, dialkylcarbamoyl, alkenyl, substituted alkenyl, alkynyl, substituted alkynyl, alkoxy, substituted alkoxy, alkoxycarbonyl, cycloalkyl, substituted cycloalkyl, cycloalkenyl, substituted cycloalkenyl, heterocyclyl, substituted heterocyclyl, aryl, substituted aryl, oxide; n is an integer of from 0 to 3; and only one of $R^4$ and -D-$R^1$ is H.

In yet another embodiment, the compounds of Formula (I), or pharmaceutically acceptable salts, solvates, and/or esters thereof, have a structure selected from:

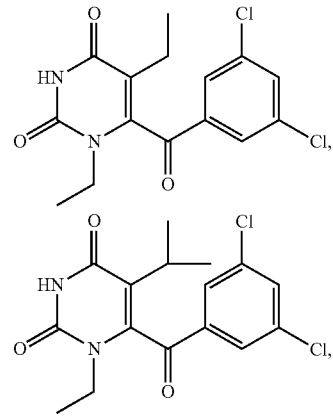

-continued
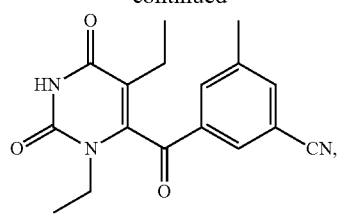
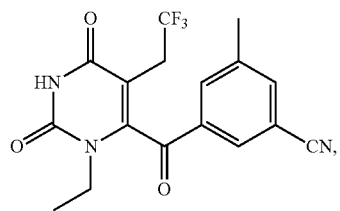
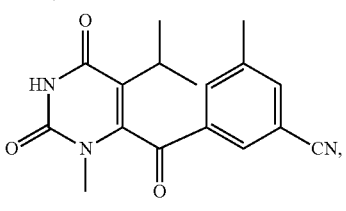
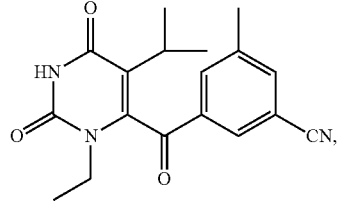
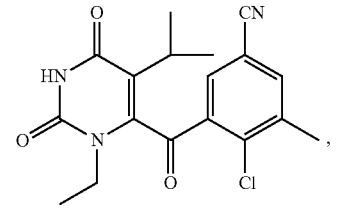
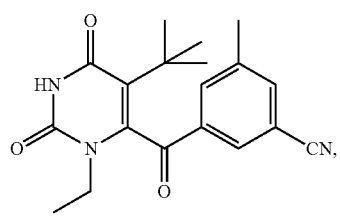
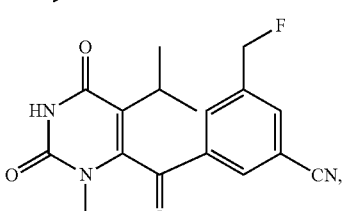
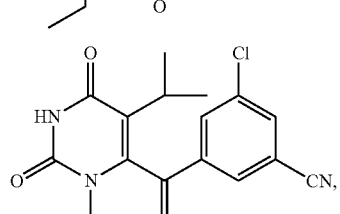
-continued
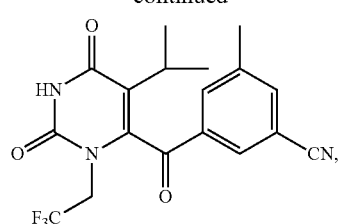
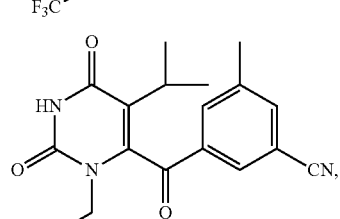
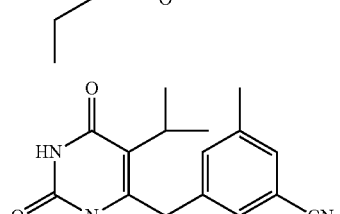
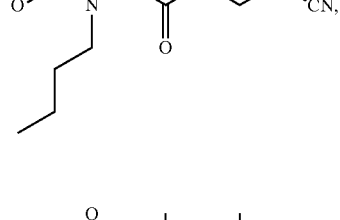
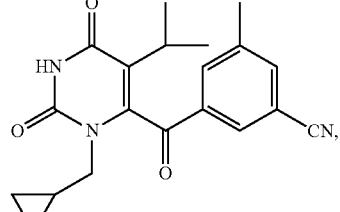
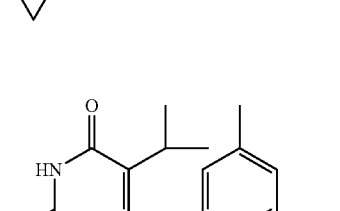
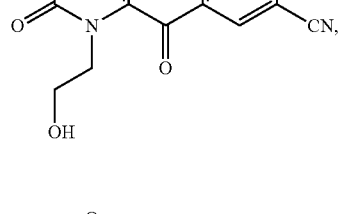
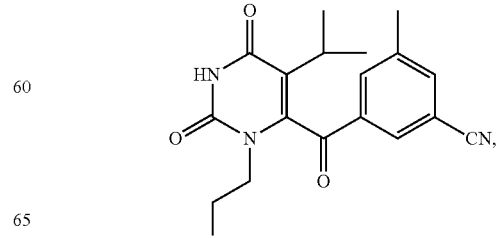

-continued
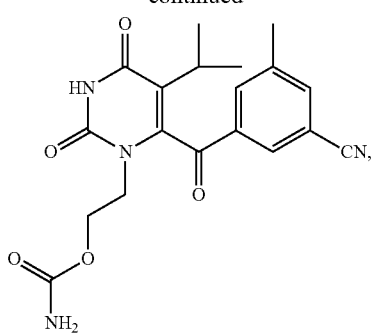
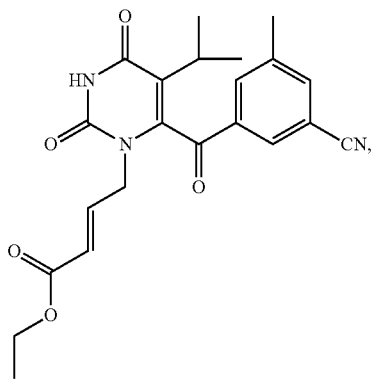
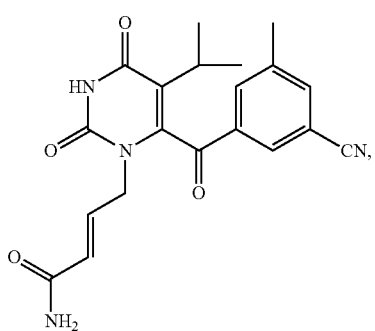
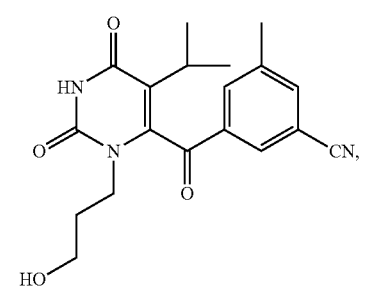
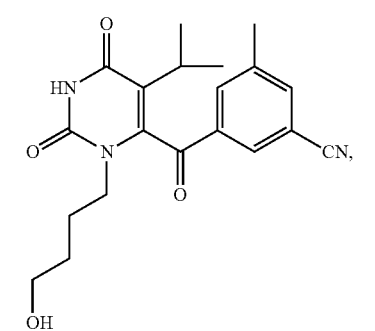
-continued
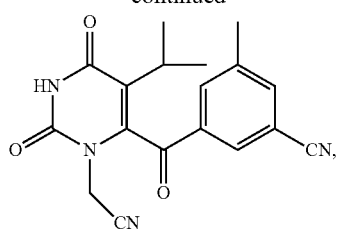
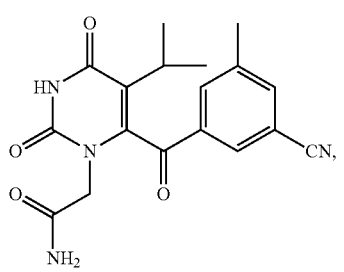
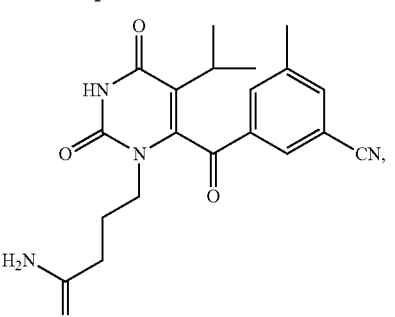
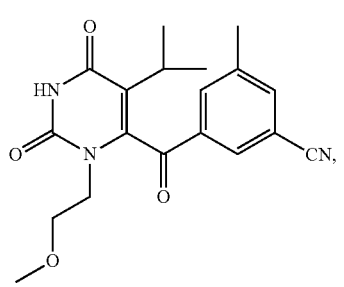
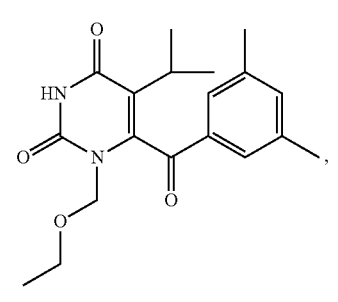
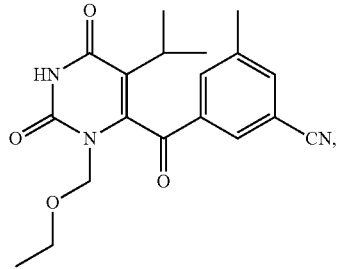

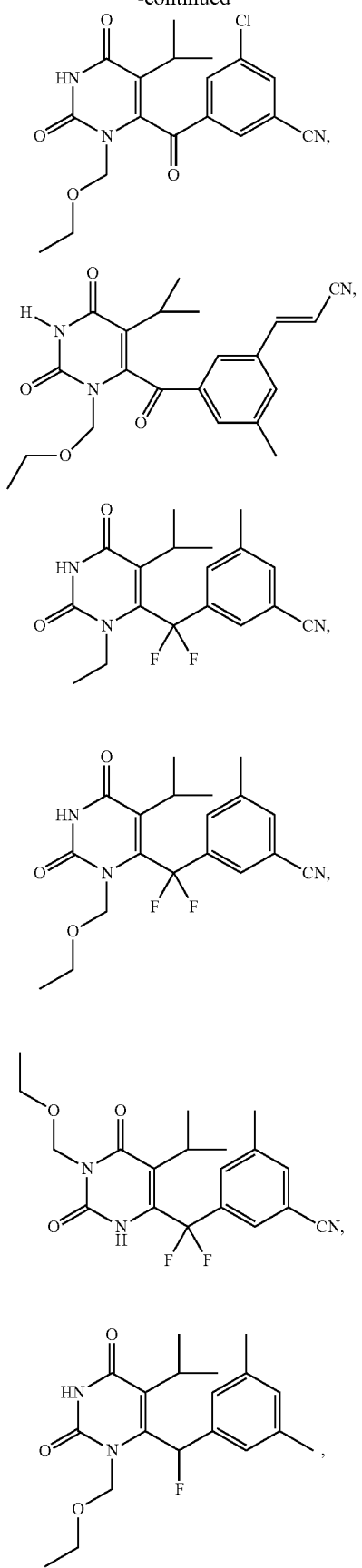
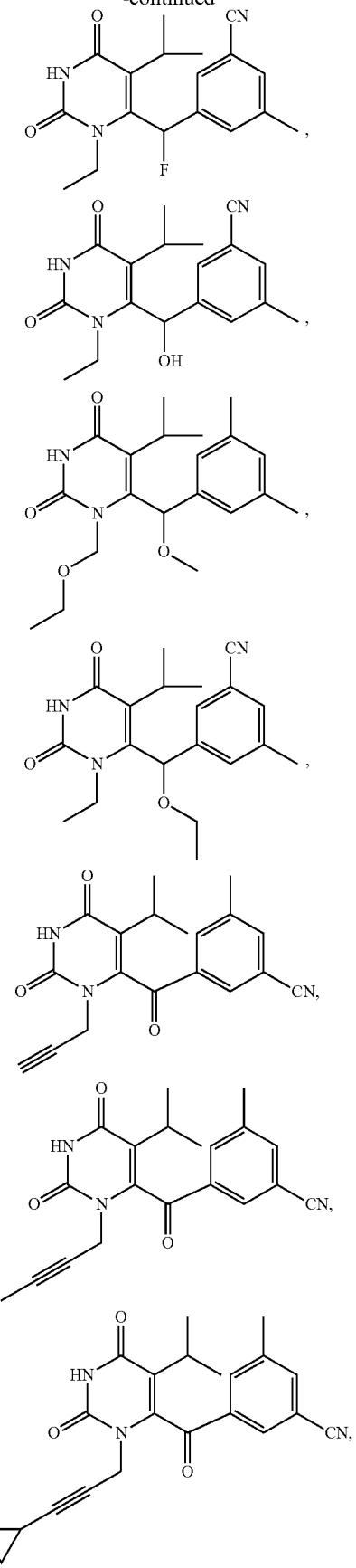

45
-continued
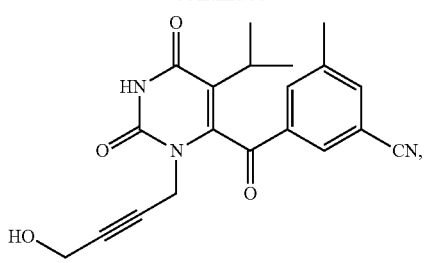
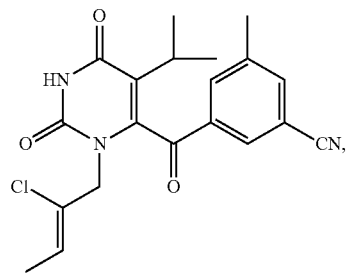
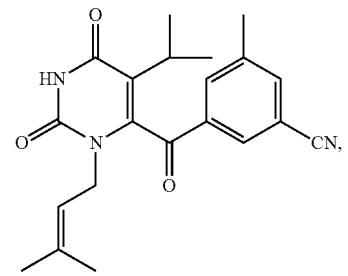
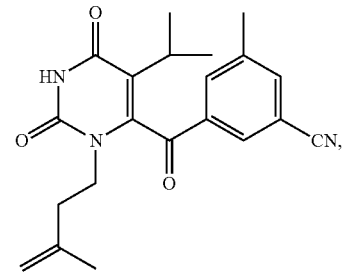
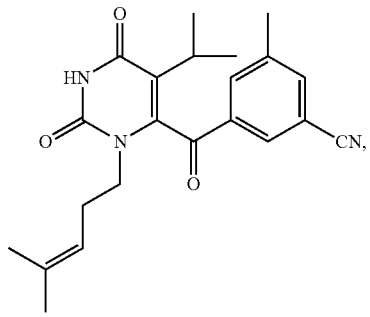
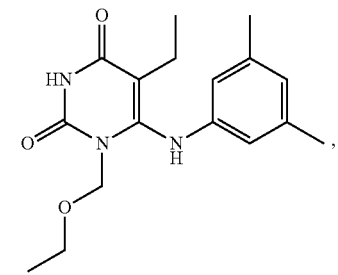
46
-continued
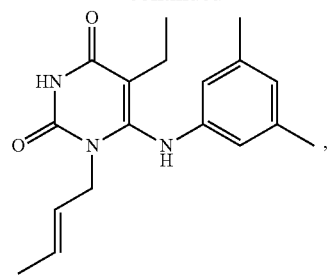
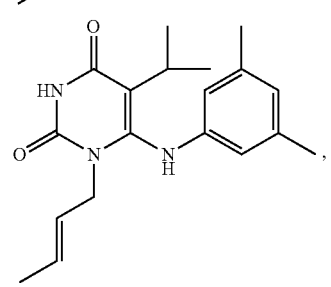
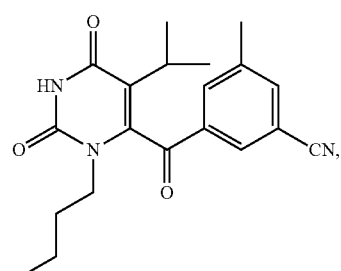
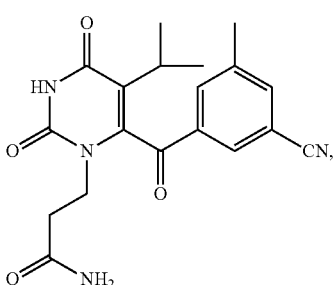
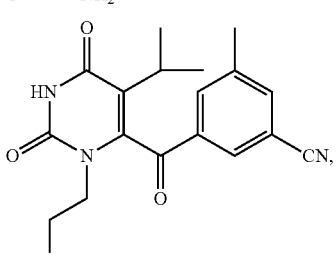
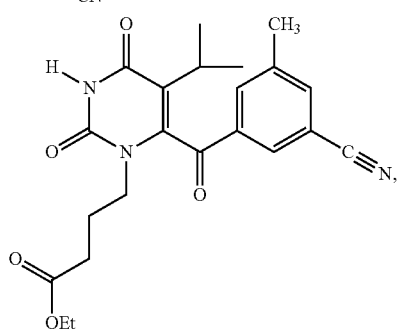

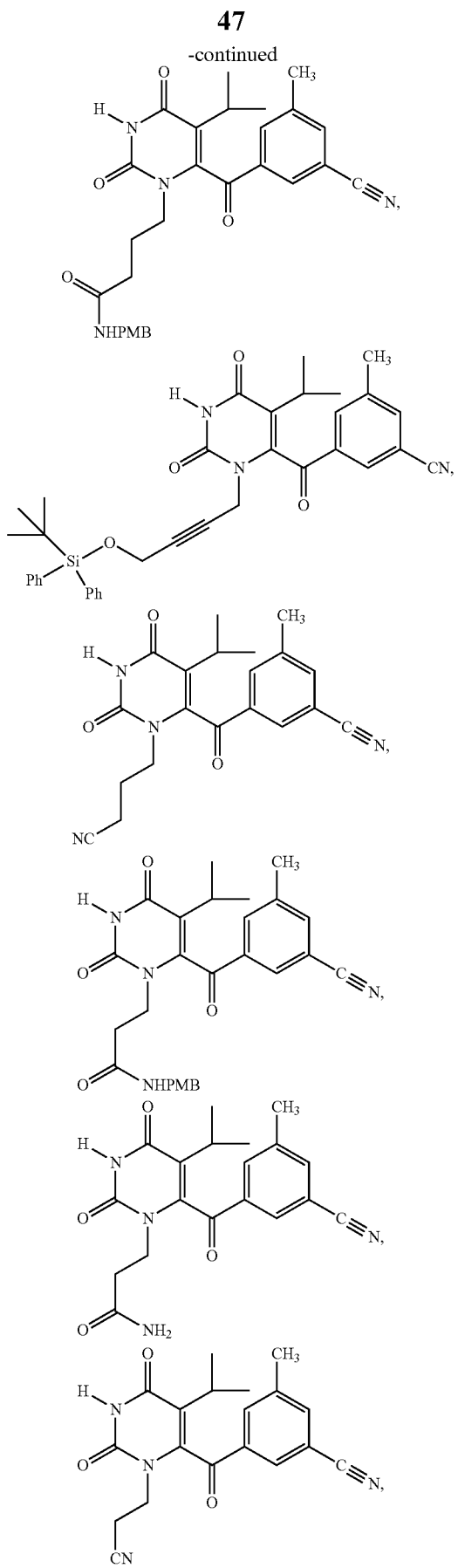
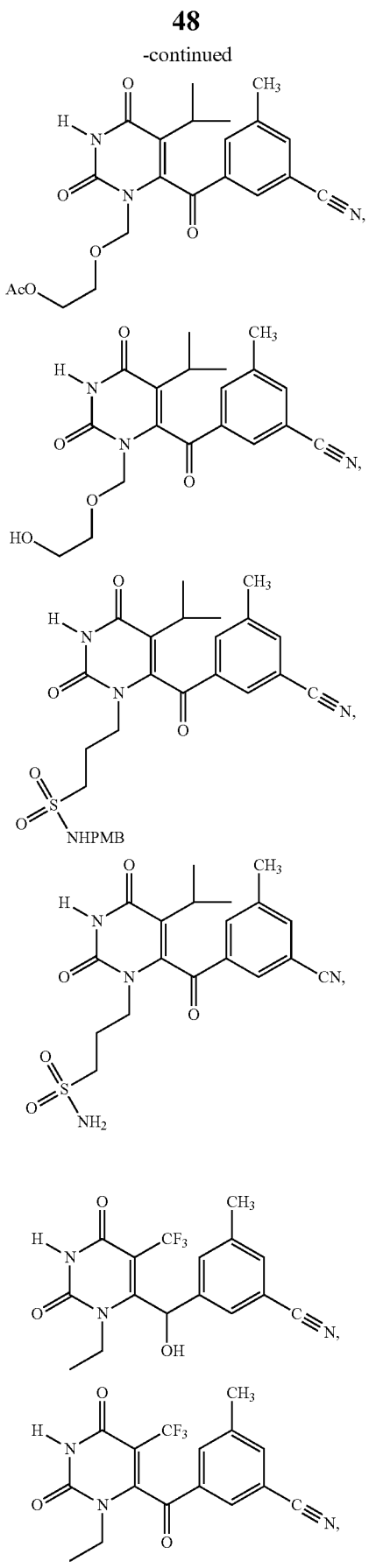

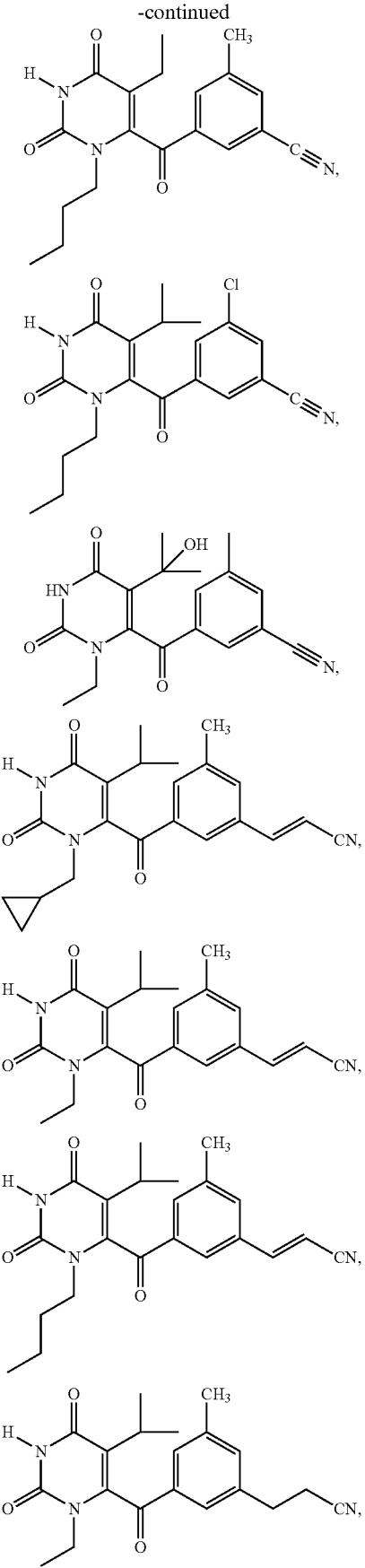

-continued
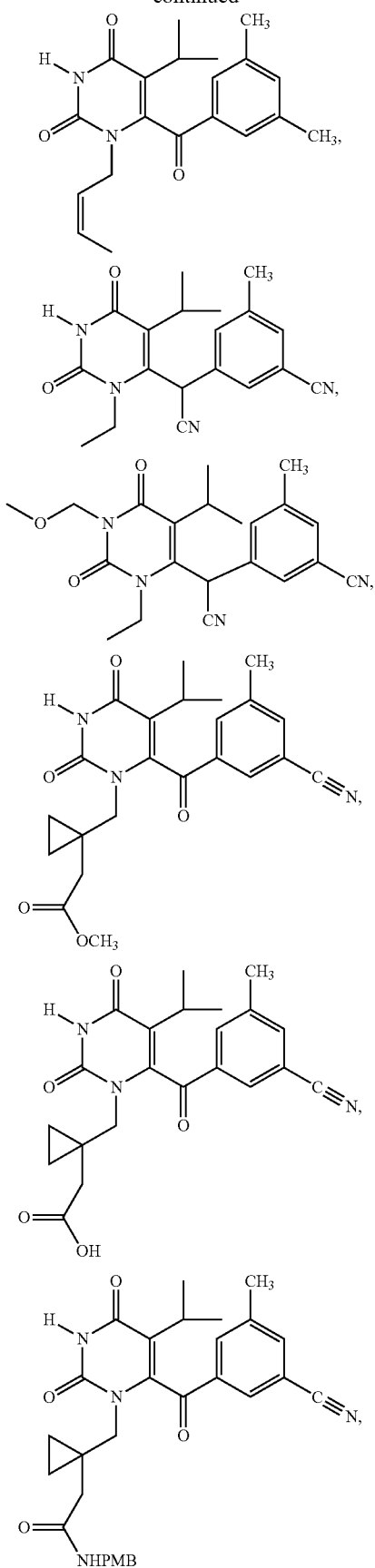
-continued
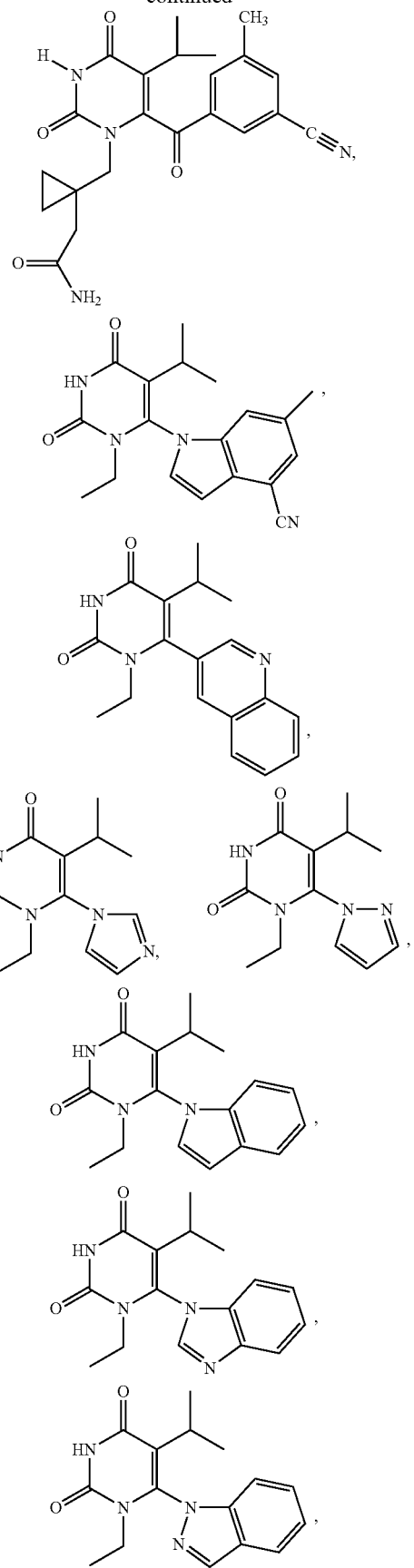

-continued

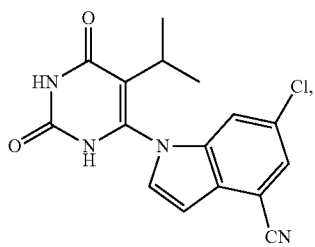

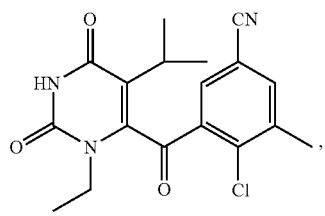

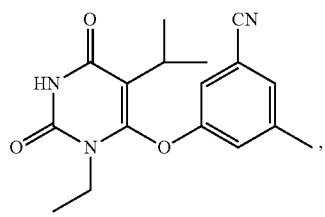

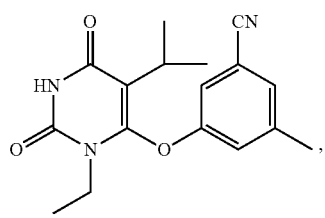

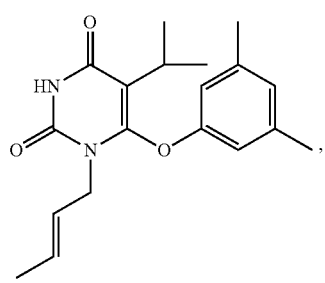

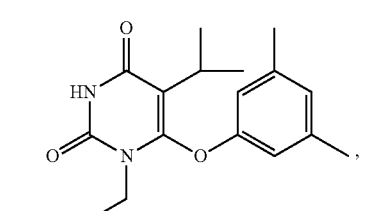

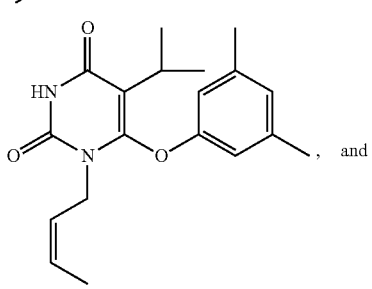, and

-continued

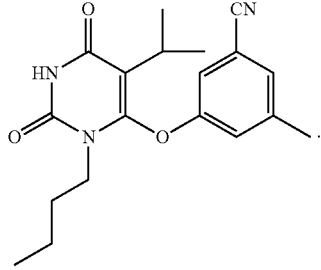

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, as defined above, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl n-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day, typically, from about 0.01 to about 10 mg/kg body weight per day, more typically, from about 0.01 to about 5 mg/kg body weight per day, even more typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In another embodiment, the present application provides a pharmaceutical composition comprising a therapeutically effective amount of a compound of Formula (I), or a pharmaceutically acceptable salt, solvate, and/or ester thereof, and a pharmaceutically acceptable carrier.

In another embodiment, the present application provides a pharmaceutical composition comprising a therapeutically effective amount of a compound of Formula (I), or a pharmaceutically acceptable salt, solvate, and/or ester thereof, in combination with at least one additional active therapeutic agent and a pharmaceutically acceptable carrier.

HIV Combination Therapy

In one embodiment, non-limiting examples of suitable combinations include combinations of one or more compounds of the present invention with one or more HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, and other drugs for treating HIV, and combinations of any of the above.

More specifically, one or more compounds of the present invention may be combined with one or more compounds selected from the group consisting of 1) HIV protease inhibitors, e.g., amprenavir (Agenerase), atazanavir (Reyataz), fosamprenavir (Lexiva), indinavir (Crixivan), lopinavir, ritonavir (norvir), nelfinavir (Viracept), saquinavir (Invirase), tipranavir (Aptivus), brecanavir, darunavir (Prezista), TMC-126, TMC-114, mozenavir (DMP-450), JE-2147 (AG1776), L-756423, RO0334649, KNI-272, DPC-681, DPC-684, DG17, GS-8374, MK-8122 (PPL-100), DG35, and AG 1859, SPI-256, TMC 52390, PL-337, SM-322377, SM-309515, GRL-02031, CRS-074, CRS-075, KB-98, and A-790742, 2) HIV non-nucleoside inhibitors of reverse transcriptase, e.g., capravirine, emivirine, delaviridine (Rescriptor), efavirenz (Sustiva), nevirapine (Viramune), (+)-calanolide A, calanolide B, etravirine (Intelence), GW5634, DPC-083, DPC-961, DPC-963, MIV-150, MIV-160, MIV-170, dapivirine (TMC-120), rilpivirine (TMC-278), BILR 355 BS, VRX 840773, UK-453061, and RDEA806, RDEA 427, RDEA 640, IDX 899, ANX-201 (Thiovir), R-1206, LOC-dd, IQP-0410 (SJ-3366), YM-215389, YM-228855, CMX-052, and CMX-182, 3) HIV nucleoside inhibitors of reverse transcriptase, e.g., zidovudine (Retrovir), emtricitabine (Emtriva), didanosine (Videx), stavudine (Zerit), zalcitabine (Hivid), lamivudine (Epivir), abacavir (Ziagen), amdoxovir, elvucitabine (ACH 126443), alovudine (MIV-310), MIV-210, racivir (racemic FTC, PSI-5004), D-d4FC, phosphazide, fozivudine tidoxil, apricitibine (AVX754, SPD-754), GS-7340, KP-1461, AVX756, OBP-601, dioxolane thymine, TMC-254072, INK-20, PPI-801, PPI-802, MIV-410, 4'-Ed4T, B-108, and fosalvudine tidoxil (HDP 99.0003), 4) HIV nucleotide inhibitors of reverse transcriptase, e.g., tenofovir disoproxil fumarate (Viread), and adefovir dipivoxil, 5) HIV integrase inhibitors, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, raltegravir (Isentress, MK-0518), elvitegravir (GS-9137), BMS-538158, GSK364735C, BMS-707035, MK-2048, GSK-349572 (S-349572), GSK-265744 (S-265744), GSK-247303 (S-247303), S-1360 (GW810871), 1,5-DCQA, INH-001, INT-349, V-165, RIN-25, BFX-1001, BFX-1002, BFX-1003, RSC-1838, BCH-33040, and BA 011, 6) gp41 inhibitors, e.g., enfuvirtide (Fuzeon), sifuvirtide, MPI-451936, FB006M, A-329029, and TRI-1144, 7) CXCR4 inhibitors, e.g., AMD-070, KRH-3955 (CS-3955), AMD-9370, AMD-3451, RPI-MN, MSX-122, and POL-2438, 8) entry inhibitors, e.g., SP01A, PA-161, SPC3, TNX-355, DES6, SP-10, SP-03, CT-319, and CT-326, 9) gp120 inhibitors, e.g., BMS-488043 and its prodrugs, BlockAide/CR, KPC-2, and MNLP62, 10) G6PD and NADH-oxidase inhibitors, e.g., immunitin, 11) CCR5 inhibitors, e.g., aplaviroc, nifeviroc, vicriviroc (SCH-417690), maraviroc (Selzentry), PRO-140, PRO-542, INCB15050, INCB9471, PF-232798, SCH-532706, GSK-706769, TAK-652, TAK-220, ESN-196, RO-1752, ZM-688523, AMD-887, YM-370749, NIBR-1282, SCH-350634, ZM-688523, and CCR5 mAb004, 12) CCR8 inhibitors, e.g., ZK-756326, 13) RNase H inhibitors, e.g., ODN-93, and ODN-112, 14) maturation inhibitors, e.g., bevirimat (PA-457), PA-040, MPC-9055 (vicecon, MPI-49839), ACH-100703, ACH-100706

15) pharmacokinetic enhancers, e.g., BAS-100, SPI-452, PF-4194477, TMC-41629, and roxythromycin, and 16) other drugs for treating HIV, e.g., REP 9, SP-01A, TNX-355, DES6, ODN-93, ODN-112, VGV-1, Ampligen, HRG214, Cytolin, VGX-410, VGX-820, KD-247, AMZ 0026, CYT 99007, A-221 HIV, HPH-116, DEBIO-025, BAY 50-4798, MDX010 (ipilimumab), PBS 119, BIT-225, UBT-8147, ITI-367, AFX-400, BL-1050, GRN-139951, GRN-140665, AX-38679, RGB-340638, PPI-367, and ALG 889.

In another embodiment, the present application provides a combination pharmaceutical agent comprising: a first pharmaceutical composition comprising a compound of Formula (I), or a pharmaceutically acceptable salt, solvate, and/or ester thereof; and a second pharmaceutical composition comprising at least one additional active agent selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, and other drugs for treating HIV, and combinations of any of the above.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of Formula (I) can be administered alone, e.g., without other active therapeutic ingredients or agents. In another embodiment, the compounds of Formula (I) are used in combination with other active therapeutic ingredients or agents. Preferably, the other active therapeutic ingredients or agents are HIV protease inhibitors, other HIV reverse transcriptase inhibitors, HIV entry/fusion inhibitors, HIV integrase inhibitors, HIV budding/maturation inhibitors, or combinations thereof.

Combinations of the compounds of Formula (I) are typically selected based on the condition to be treated, cross-reactivities of ingredients and pharmaco-properties of the combination. For example, when treating an infection (e.g., HIV or HCV), the compositions of the invention are combined with anti-infective agents (such as those described herein).

Non-limiting examples of suitable anti-infective agents suitable for combining with the compounds of Formula (I) include HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, and other drugs for treating HIV, and combinations thereof. More specifically, one or more compounds of the present invention may be combined with one or more compounds selected from the group consisting of 1) HIV protease inhibitors, e.g., amprenavir (Agenerase), atazanavir (Reyataz), fosamprenavir (Lexiva), indinavir (Crixivan), lopinavir, ritonavir (norvir), nelfinavir (Viracept), saquinavir (Invirase), tipranavir (Aptivus), brecanavir, darunavir (Prezista), TMC-126, TMC-114, mozenavir (DMP-450), JE-2147 (AG1776), L-756423, RO0334649, KNI-272, DPC-681, DPC-684, DG17, GS-8374, MK-8122 (PPL-100), DG35, and AG 1859, SPI-256, TMC 52390, PL-337, SM-322377, SM-309515, GRL-02031, CRS-074, CRS-075, KB-98, and A-790742; 2) HIV non-nucleoside inhibitors of reverse transcriptase, e.g., capravirine, emivirine, delaviridine (Rescriptor), efavirenz (Sustiva), nevirapine (Viramune), (+)-calanolide A, calanolide B, etravirine (Intelence), GW5634, DPC-083, DPC-961, DPC-963, MIV-150, MIV-160, MIV-170, dapivirine (TMC-120), rilpivirine (TMC-278), BILR 355 BS, VRX 840773, UK-453061, and RDEA806, RDEA 427, RDEA 640, IDX 899, ANX-201 (Thiovir), R-1206, LOC-dd, IQP-0410 (SJ-3366), YM-215389, YM-228855, CMX-052, and CMX-182; 3) HIV nucleoside inhibitors of reverse transcriptase, e.g., zidovudine (Retrovir), emtricitabine (Emtriva), didanosine (Videx), stavudine (Zerit), zalcitabine (Hivid), lamivudine (Epivir), abacavir (Ziagen), amdoxovir, elvucitabine (ACH 126443), alovudine (MIV-310), MIV-210, racivir (racemic FTC, PSI-5004), D-d4FC, phosphazide, fozivudine tidoxil, apricitibine (AVX754, SPD-754), GS-7340, KP-1461, AVX756, OBP-601, dioxolane thymine, TMC-254072, INK-20, PPI-801, PPI-802, MW-410, 4'-Ed4T, B-108, and fosalvudine tidoxil (HDP 99.0003); 4) HIV nucleotide inhibitors of reverse transcriptase, e.g., tenofovir disoproxil fumarate (Viread), and adefovir dipivoxil; 5) HIV integrase inhibitors, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, raltegravir (Isentress, MK-0518), elvitegravir (GS-9137), BMS-538158, GSK364735C, BMS-707035, MK-2048, GSK-349572 (S-349572), GSK-265744 (S-265744), GSK-247303 (S-247303), S-1360 (GW810871), 1,5-DCQA, INH-001, INT-349, V-165, RIN-25, BFX-1001, BFX-1002, BFX-1003, RSC-1838, BCH-33040, and BA 011; 6) gp41 inhibitors, e.g., enfuvirtide (Fuzeon), sifuvirtide, MPI-451936, FB006M, A-329029, and TRI-1144; 7) CXCR4 inhibitors, e.g., AMD-070, KRH-3955 (CS-3955), AMD-9370, AMD-3451, RPI-MN, MSX-122, and POL-2438; 8) entry inhibitors, e.g., SP01A, PA-161, SPC3, TNX-355, DES6, SP-10, SP-03, CT-319, and CT-326; 9) gp120 inhibitors, e.g., BMS-488043 and its prodrugs, BlockAide/CR, KPC-2, and MNLP62; 10) G6PD and NADH-oxidase inhibitors, e.g., immunitin; 11) CCR5 inhibitors, e.g., aplaviroc, nifeviroc, vicriviroc (SCH-417690), maraviroc (Selzentry), PRO-140, PRO-542, INCB15050, INCB9471, PF-232798, SCH-532706, GSK-706769, TAK-652, TAK-220, ESN-196, RO-1752, ZM-688523, AMD-887, YM-370749, NIBR-1282, SCH-350634, ZM-688523, and CCR5 mAb004; 12) CCR8 inhibitors, e.g., ZK-756326; 13) RNase H inhibitors, e.g., ODN-93, and ODN-112; 14) maturation inhibitors, e.g., bevirimat (PA-457), PA-040, MPC-9055 (vicecon, MPI-49839), ACH-100703, ACH-100706; 15) pharmacokinetic enhancers, e.g., BAS-100, SPI-452, PF-4194477, TMC-41629, and roxythromycin; other drugs for treating HIV, e.g., REP 9, SP-01A, TNX-355, DES6, ODN-93, ODN-112, VGV-1, Ampligen, HRG214, Cytolin, VGX-410, VGX-820, KD-247, AMZ 0026, CYT 99007, A-221 HIV, HPH-116, DEBIO-025, BAY 50-4798, MDX010 (ipilimumab), PBS 119, BIT-225, UBT-8147, ITI-367, AFX-400, BL-1050, GRN-139951, GRN-140665, AX-38679, RGB-340638, PPI-367, and ALG 889.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In another embodiment, the present invention provides a method for inhibiting HIV RT comprising administering a therapeutically effective amount of a compound of Formula (I), or a pharmaceutically acceptable salt, solvate, or ester thereof, to a patient in need of such treatment.

In another embodiment, the present invention provides a method for treating or preventing a HIV infection comprising: administering a therapeutically effective amount of a compound of Formula (I), or a pharmaceutically acceptable salt, solvate, and/or ester thereof, to a patient in need of such treatment.

In another embodiment, the present invention provides a method, further comprising co-administering a therapeutic amount of at least one additional active agent selected from the group consisting of one or more HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, and other drugs for treating HIV, and combinations thereof.

In another embodiment, the present invention provides a method for treating AIDS or AIDS Related Complex (ARC) comprising administering a therapeutically effective amount of a compound of Formula (I), or a pharmaceutically acceptable salt, solvate, and/or ester thereof, to a patient in need of such treatment.

In another embodiment, the present invention provides a method of co-administering a therapeutic amount of compound of Formula (I) and at least one additional active agent selected from the group consisting of one or more HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, and other drugs for treating HIV, and combinations thereof.

In another embodiment, the present invention provides a method of inhibiting the replication of a retrovirus comprising contacting said retrovirus with a compound of Formula (I), or a pharmaceutically acceptable salt, solvate, and/or ester thereof. The replication of a retrovirus can be inhibited in vitro or in vivo (e.g., in a patient infected with a retrovirus).

In another embodiment, the present invention provides a method of inhibiting the replication of a retrovirus comprising contacting the retrovirus with a compound of Formula (I) and at least one additional active agent selected from the group consisting of one or more HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, and other drugs for treating HIV, and combinations thereof.

In another embodiment, the present application provides for the use of a compound of Formulae I or II for the preparation of a medicament for treating or preventing an HIV infection in a patient.

In another embodiment, the present application provides for the use of a compound of Formulae I or II for the preparation of a medicament for treating AIDS or AIDS Related Complex (ARC) in a patient.

In another embodiment, the present application provides for the use of a compound of Formula I for the preparation of a medicament for inhibiting the replication of a retrovirus in a patient.

In still yet another embodiment, the compounds of Formula I are named below in tabular format (Table 7) as compounds of general Formula II:

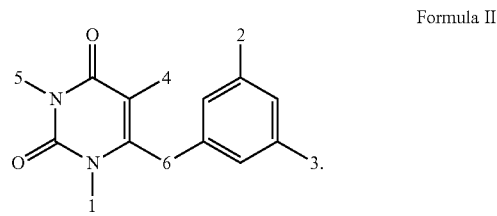

Formula II

Tables 1-6, respectively, show the structures of the "1", "2", "3", "4", "5", and "6" moieties. Each substituent "1", "2", "3", "4", "5", and "6" in Tables 1-6 is represented by a "code" comprising a number and a letter. Each structure of a compound of Formula II can be designated in tabular form by combining the "code" representing each structural moiety using the following syntax: 1.2.3.4.5.6. Thus, for example, 1a.2a.3a.4a.5a.6a represents the following structure:

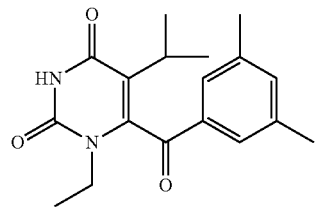

TABLE 1

"1" Structures

| Code | "1" Structure |
| --- | --- |
| 1a | —CH$_2$CH$_3$ |
| 1b | —CH$_2$CH$_2$CH$_2$CH$_3$ |
| 1c | (cyclopropylmethyl) |
| 1d | —CH$_2$—O—CH$_2$CH$_3$ |
| 1e | (oxetanylmethyl) |

TABLE 1-continued

"1" Structures

| Code | "1" Structure |
|---|---|
| 1f |  |

TABLE 2

"2" Structures

| Code | "2" Structure |
|---|---|
| 2a | —CH$_3$ |
| 2b | —CN |
| 2c | Cl |
| 2d | —CH$_2$F |
| 2e | —NH$_2$ |
| 2f | 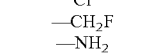 |

TABLE 3

"3" Structures

| Code | "3" Structure |
|---|---|
| 3a | —CH$_3$ |
| 3b | —CN |
| 3c | Cl |
| 3d | —CH$_2$F |
| 3e | —NH$_2$ |
| 3f | (CN-vinyl structure) |

TABLE 4

"4" Structures

| Code | "4" Structure |
|---|---|
| 4a | —CH(CH$_3$)$_2$ |
| 4b | —CH$_2$CH$_3$ |
| 4c | —CH$_2$CH$_2$F |
| 4d | —C(CH$_3$)$_3$ |
| 4e | —C(CH$_3$)$_2$OH |
| 4f | —CH(CH$_3$)CH$_2$OH |

TABLE 5

"5" Structures

| Code | "5" Structure |
|---|---|
| 5a | H |
| 5b | —CH$_2$NH$_2$ |
| 5c | —CH$_2$OH |
| 5d | —CH$_2$CH$_2$OH |
| 5e | —CH$_2$CH$_2$CH$_2$OH |
| 5f | —O—CH$_3$ |

TABLE 6

"6" Structures

| Code | "6" Structure |
|---|---|
| 6a | —C(O)— |
| 6b | —O— |
| 6c | —S— |
| 6d | —CHF— |
| 6e | —CH$_2$— |
| 6f | —CF$_2$— |

TABLE 7

List of Compounds of Formula (II)

1a.2a.3a.4a.5a.6a, 1a.2a.3a.4a.5a.6b, 1a.2a.3a.4a.5a.6c, 1a.2a.3a.4a.5a.6d,
1a.2a.3a.4a.5a.6e, 1a.2a.3a.4a.5a.6f, 1a.2a.3a.4a.5b.6a, 1a.2a.3a.4a.5b.6b,
1a.2a.3a.4a.5b.6c, 1a.2a.3a.4a.5b.6d, 1a.2a.3a.4a.5b.6e, 1a.2a.3a.4a.5b.6f,
1a.2a.3a.4a.5c.6a, 1a.2a.3a.4a.5c.6b, 1a.2a.3a.4a.5c.6c, 1a.2a.3a.4a.5c.6d,
1a.2a.3a.4a.5c.6e, 1a.2a.3a.4a.5c.6f, 1a.2a.3a.4a.5d.6a, 1a.2a.3a.4a.5d.6b,
1a.2a.3a.4a.5d.6c, 1a.2a.3a.4a.5d.6d, 1a.2a.3a.4a.5d.6e, 1a.2a.3a.4a.5d.6f,
1a.2a.3a.4a.5e.6a, 1a.2a.3a.4a.5e.6b, 1a.2a.3a.4a.5e.6c, 1a.2a.3a.4a.5e.6d,
1a.2a.3a.4a.5e.6e, 1a.2a.3a.4a.5e.6f, 1a.2a.3a.4a.5f.6a, 1a.2a.3a.4a.5f.6b, 1a.2a.3a.4a.5f.6c,
1a.2a.3a.4a.5f.6d, 1a.2a.3a.4a.5f.6e, 1a.2a.3a.4a.5f.6f, 1a.2a.3a.4b.5a.6a,
1a.2a.3a.4b.5a.6b, 1a.2a.3a.4b.5a.6c, 1a.2a.3a.4b.5a.6d, 1a.2a.3a.4b.5a.6e,
1a.2a.3a.4b.5a.6f, 1a.2a.3a.4b.5b.6a, 1a.2a.3a.4b.5b.6b, 1a.2a.3a.4b.5b.6c,
1a.2a.3a.4b.5b.6d, 1a.2a.3a.4b.5b.6e, 1a.2a.3a.4b.5b.6f, 1a.2a.3a.4b.5c.6a,
1a.2a.3a.4b.5c.6b, 1a.2a.3a.4b.5c.6c, 1a.2a.3a.4b.5c.6d, 1a.2a.3a.4b.5c.6e,
1a.2a.3a.4b.5c.6f, 1a.2a.3a.4b.5d.6a, 1a.2a.3a.4b.5d.6b, 1a.2a.3a.4b.5d.6c,
1a.2a.3a.4b.5d.6d, 1a.2a.3a.4b.5d.6e, 1a.2a.3a.4b.5d.6f, 1a.2a.3a.4b.5e.6a,
1a.2a.3a.4b.5e.6b, 1a.2a.3a.4b.5e.6c, 1a.2a.3a.4b.5e.6d, 1a.2a.3a.4b.5e.6e,
1a.2a.3a.4b.5e.6f, 1a.2a.3a.4b.5f.6a, 1a.2a.3a.4b.5f.6b, 1a.2a.3a.4b.5f.6c,
1a.2a.3a.4b.5f.6d, 1a.2a.3a.4b.5f.6e, 1a.2a.3a.4b.5f.6f, 1a.2a.3a.4c.5a.6a,
1a.2a.3a.4c.5a.6b, 1a.2a.3a.4c.5a.6c, 1a.2a.3a.4c.5a.6d, 1a.2a.3a.4c.5a.6e,
1a.2a.3a.4c.5a.6f, 1a.2a.3a.4c.5b.6a, 1a.2a.3a.4c.5b.6b, 1a.2a.3a.4c.5b.6c,
1a.2a.3a.4c.5b.6d, 1a.2a.3a.4c.5b.6e, 1a.2a.3a.4c.5b.6f, 1a.2a.3a.4c.5c.6a,
1a.2a.3a.4c.5c.6b, 1a.2a.3a.4c.5c.6c, 1a.2a.3a.4c.5c.6d, 1a.2a.3a.4c.5c.6e, 1a.2a.3a.4c.5c.6f,
1a.2a.3a.4c.5d.6a, 1a.2a.3a.4c.5d.6b, 1a.2a.3a.4c.5d.6c, 1a.2a.3a.4c.5d.6d,
1a.2a.3a.4c.5d.6e, 1a.2a.3a.4c.5d.6f, 1a.2a.3a.4c.5e.6a, 1a.2a.3a.4c.5e.6b,
1a.2a.3a.4c.5e.6c, 1a.2a.3a.4c.5e.6d, 1a.2a.3a.4c.5e.6e, 1a.2a.3a.4c.5e.6f, 1a.2a.3a.4c.5f.6a,
1a.2a.3a.4c.5f.6b, 1a.2a.3a.4c.5f.6c, 1a.2a.3a.4c.5f.6d, 1a.2a.3a.4c.5f.6e, 1a.2a.3a.4c.5f.6f,

TABLE 7-continued

List of Compounds of Formula (II)

| | | | | |
|---|---|---|---|---|
| 1a.2a.3a.4d.5a.6a, | 1a.2a.3a.4d.5a.6b, | 1a.2a.3a.4d.5a.6c, | 1a.2a.3a.4d.5a.6d, | |
| 1a.2a.3a.4d.5a.6e, | 1a.2a.3a.4d.5a.6f, | 1a.2a.3a.4d.5b.6a, | 1a.2a.3a.4d.5b.6b, | |
| 1a.2a.3a.4d.5b.6c, | 1a.2a.3a.4d.5b.6d, | 1a.2a.3a.4d.5b.6e, | 1a.2a.3a.4d.5b.6f, | |
| 1a.2a.3a.4d.5c.6a, | 1a.2a.3a.4d.5c.6b, | 1a.2a.3a.4d.5c.6c, | 1a.2a.3a.4d.5c.6d, | |
| 1a.2a.3a.4d.5c.6e, | 1a.2a.3a.4d.5c.6f, | 1a.2a.3a.4d.5d.6a, | 1a.2a.3a.4d.5d.6b, | |
| 1a.2a.3a.4d.5d.6c, | 1a.2a.3a.4d.5d.6d, | 1a.2a.3a.4d.5d.6e, | 1a.2a.3a.4d.5d.6f, | |
| 1a.2a.3a.4d.5e.6a, | 1a.2a.3a.4d.5e.6b, | 1a.2a.3a.4d.5e.6c, | 1a.2a.3a.4d.5e.6d, | |
| 1a.2a.3a.4d.5e.6e, | 1a.2a.3a.4d.5e.6f, | 1a.2a.3a.4d.5f.6a, | 1a.2a.3a.4d.5f.6b, | |
| 1a.2a.3a.4d.5f.6c, | 1a.2a.3a.4d.5f.6d, | 1a.2a.3a.4d.5f.6e, | 1a.2a.3a.4d.5f.6f, | |
| 1a.2a.3a.4e.5a.6a, | 1a.2a.3a.4e.5a.6b, | 1a.2a.3a.4e.5a.6c, | 1a.2a.3a.4e.5a.6d, | |
| 1a.2a.3a.4e.5a.6e, | 1a.2a.3a.4e.5a.6f, | 1a.2a.3a.4e.5b.6a, | 1a.2a.3a.4e.5b.6b, | |
| 1a.2a.3a.4e.5b.6c, | 1a.2a.3a.4e.5b.6d, | 1a.2a.3a.4e.5b.6e, | 1a.2a.3a.4e.5b.6f, | |
| 1a.2a.3a.4e.5c.6a, | 1a.2a.3a.4e.5c.6b, | 1a.2a.3a.4e.5c.6c, | 1a.2a.3a.4e.5c.6d, | |
| 1a.2a.3a.4e.5c.6e, | 1a.2a.3a.4e.5c.6f, | 1a.2a.3a.4e.5d.6a, | 1a.2a.3a.4e.5d.6b, | |
| 1a.2a.3a.4e.5d.6c, | 1a.2a.3a.4e.5d.6d, | 1a.2a.3a.4e.5d.6e, | 1a.2a.3a.4e.5d.6f, | |
| 1a.2a.3a.4e.5e.6a, | 1a.2a.3a.4e.5e.6b, | 1a.2a.3a.4e.5e.6c, | 1a.2a.3a.4e.5e.6d, | |
| 1a.2a.3a.4e.5e.6e, | 1a.2a.3a.4e.5e.6f, | 1a.2a.3a.4e.5f.6a, | 1a.2a.3a.4e.5f.6b, | 1a.2a.3a.4e.5f.6c, |
| 1a.2a.3a.4e.5f.6d, | 1a.2a.3a.4e.5f.6e, | 1a.2a.3a.4e.5f.6f, | 1a.2a.3a.4f.5a.6a, | 1a.2a.3a.4f.5a.6b, |
| 1a.2a.3a.4f.5a.6c, | 1a.2a.3a.4f.5a.6d, | 1a.2a.3a.4f.5a.6e, | 1a.2a.3a.4f.5a.6f, | 1a.2a.3a.4f.5b.6a, |
| 1a.2a.3a.4f.5b.6b, | 1a.2a.3a.4f.5b.6c, | 1a.2a.3a.4f.5b.6d, | 1a.2a.3a.4f.5b.6e, | 1a.2a.3a.4f.5b.6f, |
| 1a.2a.3a.4f.5c.6a, | 1a.2a.3a.4f.5c.6b, | 1a.2a.3a.4f.5c.6c, | 1a.2a.3a.4f.5c.6d, | 1a.2a.3a.4f.5c.6e, |
| 1a.2a.3a.4f.5c.6f, | 1a.2a.3a.4f.5d.6a, | 1a.2a.3a.4f.5d.6b, | 1a.2a.3a.4f.5d.6c, | |
| 1a.2a.3a.4f.5d.6d, | 1a.2a.3a.4f.5d.6e, | 1a.2a.3a.4f.5d.6f, | 1a.2a.3a.4f.5e.6a, | |
| 1a.2a.3a.4f.5e.6b, | 1a.2a.3a.4f.5e.6c, | 1a.2a.3a.4f.5e.6d, | 1a.2a.3a.4f.5e.6e, | 1a.2a.3a.4f.5e.6f, |
| 1a.2a.3a.4f.5f.6a, | 1a.2a.3a.4f.5f.6b, | 1a.2a.3a.4f.5f.6c, | 1a.2a.3a.4f.5f.6d, | 1a.2a.3a.4f.5f.6e, |
| 1a.2a.3a.4f.5f.6f, | 1a.2a.3b.4a.5a.6a, | 1a.2a.3b.4a.5a.6b, | 1a.2a.3b.4a.5a.6c, | |
| 1a.2a.3b.4a.5a.6d, | 1a.2a.3b.4a.5a.6e, | 1a.2a.3b.4a.5a.6f, | 1a.2a.3b.4a.5b.6a, | |
| 1a.2a.3b.4a.5b.6b, | 1a.2a.3b.4a.5b.6c, | 1a.2a.3b.4a.5b.6d, | 1a.2a.3b.4a.5b.6e, | |
| 1a.2a.3b.4a.5b.6f, | 1a.2a.3b.4a.5c.6a, | 1a.2a.3b.4a.5c.6b, | 1a.2a.3b.4a.5c.6c, | |
| 1a.2a.3b.4a.5c.6d, | 1a.2a.3b.4a.5c.6e, | 1a.2a.3b.4a.5c.6f, | 1a.2a.3b.4a.5d.6a, | |
| 1a.2a.3b.4a.5d.6b, | 1a.2a.3b.4a.5d.6c, | 1a.2a.3b.4a.5d.6d, | 1a.2a.3b.4a.5d.6e, | |
| 1a.2a.3b.4a.5d.6f, | 1a.2a.3b.4a.5e.6a, | 1a.2a.3b.4a.5e.6b, | 1a.2a.3b.4a.5e.6c, | |
| 1a.2a.3b.4a.5e.6d, | 1a.2a.3b.4a.5e.6e, | 1a.2a.3b.4a.5e.6f, | 1a.2a.3b.4a.5f.6a, | |
| 1a.2a.3b.4a.5f.6b, | 1a.2a.3b.4a.5f.6c, | 1a.2a.3b.4a.5f.6d, | 1a.2a.3b.4a.5f.6e, | 1a.2a.3b.4a.5f.6f, |
| 1a.2a.3b.4b.5a.6a, | 1a.2a.3b.4b.5a.6b, | 1a.2a.3b.4b.5a.6c, | 1a.2a.3b.4b.5a.6d, | |
| 1a.2a.3b.4b.5a.6e, | 1a.2a.3b.4b.5a.6f, | 1a.2a.3b.4b.5b.6a, | 1a.2a.3b.4b.5b.6b, | |
| 1a.2a.3b.4b.5b.6c, | 1a.2a.3b.4b.5b.6d, | 1a.2a.3b.4b.5b.6e, | 1a.2a.3b.4b.5b.6f, | |
| 1a.2a.3b.4b.5c.6a, | 1a.2a.3b.4b.5c.6b, | 1a.2a.3b.4b.5c.6c, | 1a.2a.3b.4b.5c.6d, | |
| 1a.2a.3b.4b.5c.6e, | 1a.2a.3b.4b.5c.6f, | 1a.2a.3b.4b.5d.6a, | 1a.2a.3b.4b.5d.6b, | |
| 1a.2a.3b.4b.5d.6c, | 1a.2a.3b.4b.5d.6d, | 1a.2a.3b.4b.5d.6e, | 1a.2a.3b.4b.5d.6f, | |
| 1a.2a.3b.4b.5e.6a, | 1a.2a.3b.4b.5e.6b, | 1a.2a.3b.4b.5e.6c, | 1a.2a.3b.4b.5e.6d, | |
| 1a.2a.3b.4b.5e.6e, | 1a.2a.3b.4b.5e.6f, | 1a.2a.3b.4b.5f.6a, | 1a.2a.3b.4b.5f.6b, | |
| 1a.2a.3b.4b.5f.6c, | 1a.2a.3b.4b.5f.6d, | 1a.2a.3b.4b.5f.6e, | 1a.2a.3b.4b.5f.6f, | |
| 1a.2a.3b.4c.5a.6a, | 1a.2a.3b.4c.5a.6b, | 1a.2a.3b.4c.5a.6c, | 1a.2a.3b.4c.5a.6d, | |
| 1a.2a.3b.4c.5a.6e, | 1a.2a.3b.4c.5a.6f, | 1a.2a.3b.4c.5b.6a, | 1a.2a.3b.4c.5b.6b, | |
| 1a.2a.3b.4c.5b.6c, | 1a.2a.3b.4c.5b.6d, | 1a.2a.3b.4c.5b.6e, | 1a.2a.3b.4c.5b.6f, | |
| 1a.2a.3b.4c.5c.6a, | 1a.2a.3b.4c.5c.6b, | 1a.2a.3b.4c.5c.6c, | 1a.2a.3b.4c.5c.6d, | |
| 1a.2a.3b.4c.5c.6e, | 1a.2a.3b.4c.5c.6f, | 1a.2a.3b.4c.5d.6a, | 1a.2a.3b.4c.5d.6b, | |
| 1a.2a.3b.4c.5d.6c, | 1a.2a.3b.4c.5d.6d, | 1a.2a.3b.4c.5d.6e, | 1a.2a.3b.4c.5d.6f, | |
| 1a.2a.3b.4c.5e.6a, | 1a.2a.3b.4c.5e.6b, | 1a.2a.3b.4c.5e.6c, | 1a.2a.3b.4c.5e.6d, | |
| 1a.2a.3b.4c.5e.6e, | 1a.2a.3b.4c.5e.6f, | 1a.2a.3b.4c.5f.6a, | 1a.2a.3b.4c.5f.6b, | 1a.2a.3b.4c.5f.6c, |
| 1a.2a.3b.4c.5f.6d, | 1a.2a.3b.4c.5f.6e, | 1a.2a.3b.4c.5f.6f, | 1a.2a.3b.4d.5a.6a, | |
| 1a.2a.3b.4d.5a.6b, | 1a.2a.3b.4d.5a.6c, | 1a.2a.3b.4d.5a.6d, | 1a.2a.3b.4d.5a.6e, | |
| 1a.2a.3b.4d.5a.6f, | 1a.2a.3b.4d.5b.6a, | 1a.2a.3b.4d.5b.6b, | 1a.2a.3b.4d.5b.6c, | |
| 1a.2a.3b.4d.5b.6d, | 1a.2a.3b.4d.5b.6e, | 1a.2a.3b.4d.5b.6f, | 1a.2a.3b.4d.5c.6a, | |
| 1a.2a.3b.4d.5c.6b, | 1a.2a.3b.4d.5c.6c, | 1a.2a.3b.4d.5c.6d, | 1a.2a.3b.4d.5c.6e, | |
| 1a.2a.3b.4d.5c.6f, | 1a.2a.3b.4d.5d.6a, | 1a.2a.3b.4d.5d.6b, | 1a.2a.3b.4d.5d.6c, | |
| 1a.2a.3b.4d.5d.6d, | 1a.2a.3b.4d.5d.6e, | 1a.2a.3b.4d.5d.6f, | 1a.2a.3b.4d.5e.6a, | |
| 1a.2a.3b.4d.5e.6b, | 1a.2a.3b.4d.5e.6c, | 1a.2a.3b.4d.5e.6d, | 1a.2a.3b.4d.5e.6e, | |
| 1a.2a.3b.4d.5e.6f, | 1a.2a.3b.4d.5f.6a, | 1a.2a.3b.4d.5f.6b, | 1a.2a.3b.4d.5f.6c, | |
| 1a.2a.3b.4d.5f.6d, | 1a.2a.3b.4d.5f.6e, | 1a.2a.3b.4d.5f.6f, | 1a.2a.3b.4e.5a.6a, | |
| 1a.2a.3b.4e.5a.6b, | 1a.2a.3b.4e.5a.6c, | 1a.2a.3b.4e.5a.6d, | 1a.2a.3b.4e.5a.6e, | |
| 1a.2a.3b.4e.5a.6f, | 1a.2a.3b.4e.5b.6a, | 1a.2a.3b.4e.5b.6b, | 1a.2a.3b.4e.5b.6c, | |
| 1a.2a.3b.4e.5b.6d, | 1a.2a.3b.4e.5b.6e, | 1a.2a.3b.4e.5b.6f, | 1a.2a.3b.4e.5c.6a, | |
| 1a.2a.3b.4e.5c.6b, | 1a.2a.3b.4e.5c.6c, | 1a.2a.3b.4e.5c.6d, | 1a.2a.3b.4e.5c.6e, | |
| 1a.2a.3b.4e.5c.6f, | 1a.2a.3b.4e.5d.6a, | 1a.2a.3b.4e.5d.6b, | 1a.2a.3b.4e.5d.6c, | |
| 1a.2a.3b.4e.5d.6d, | 1a.2a.3b.4e.5d.6e, | 1a.2a.3b.4e.5d.6f, | 1a.2a.3b.4e.5e.6a, | |
| 1a.2a.3b.4e.5e.6b, | 1a.2a.3b.4e.5e.6c, | 1a.2a.3b.4e.5e.6d, | 1a.2a.3b.4e.5e.6e, | |
| 1a.2a.3b.4e.5e.6f, | 1a.2a.3b.4e.5f.6a, | 1a.2a.3b.4e.5f.6b, | 1a.2a.3b.4e.5f.6c, | |
| 1a.2a.3b.4e.5f.6d, | 1a.2a.3b.4e.5f.6e, | 1a.2a.3b.4e.5f.6f, | 1a.2a.3b.4f.5a.6a, | 1a.2a.3b.4f.5a.6b, |
| 1a.2a.3b.4f.5a.6c, | 1a.2a.3b.4f.5a.6d, | 1a.2a.3b.4f.5a.6e, | 1a.2a.3b.4f.5a.6f, | 1a.2a.3b.4f.5b.6a, |
| 1a.2a.3b.4f.5b.6b, | 1a.2a.3b.4f.5b.6c, | 1a.2a.3b.4f.5b.6d, | 1a.2a.3b.4f.5b.6e, | |
| 1a.2a.3b.4f.5b.6f, | 1a.2a.3b.4f.5c.6a, | 1a.2a.3b.4f.5c.6b, | 1a.2a.3b.4f.5c.6c, | 1a.2a.3b.4f.5c.6d, |
| 1a.2a.3b.4f.5c.6e, | 1a.2a.3b.4f.5c.6f, | 1a.2a.3b.4f.5d.6a, | 1a.2a.3b.4f.5d.6b, | |
| 1a.2a.3b.4f.5d.6c, | 1a.2a.3b.4f.5d.6d, | 1a.2a.3b.4f.5d.6e, | 1a.2a.3b.4f.5d.6f, | |
| 1a.2a.3b.4f.5e.6a, | 1a.2a.3b.4f.5e.6b, | 1a.2a.3b.4f.5e.6c, | 1a.2a.3b.4f.5e.6d, | |
| 1a.2a.3b.4f.5e.6e, | 1a.2a.3b.4f.5e.6f, | 1a.2a.3b.4f.5f.6a, | 1a.2a.3b.4f.5f.6b, | 1a.2a.3b.4f.5f.6c, |
| 1a.2a.3b.4f.5f.6d, | 1a.2a.3b.4f.5f.6e, | 1a.2a.3b.4f.5f.6f, | 1a.2a.3c.4a.5a.6a, | 1a.2a.3c.4a.5a.6b, |

TABLE 7-continued

List of Compounds of Formula (II)

| | | | | |
|---|---|---|---|---|
| 1a.2a.3c.4a.5a.6c, | 1a.2a.3c.4a.5a.6d, | 1a.2a.3c.4a.5a.6e, | 1a.2a.3c.4a.5a.6f, | |
| 1a.2a.3c.4a.5b.6a, | 1a.2a.3c.4a.5b.6b, | 1a.2a.3c.4a.5b.6c, | 1a.2a.3c.4a.5b.6d, | |
| 1a.2a.3c.4a.5b.6e, | 1a.2a.3c.4a.5b.6f, | 1a.2a.3c.4a.5c.6a, | 1a.2a.3c.4a.5c.6b, | |
| 1a.2a.3c.4a.5c.6c, | 1a.2a.3c.4a.5c.6d, | 1a.2a.3c.4a.5c.6e, | 1a.2a.3c.4a.5c.6f, | |
| 1a.2a.3c.4a.5d.6a, | 1a.2a.3c.4a.5d.6b, | 1a.2a.3c.4a.5d.6c, | 1a.2a.3c.4a.5d.6d, | |
| 1a.2a.3c.4a.5d.6e, | 1a.2a.3c.4a.5d.6f, | 1a.2a.3c.4a.5e.6a, | 1a.2a.3c.4a.5e.6b, | |
| 1a.2a.3c.4a.5e.6c, | 1a.2a.3c.4a.5e.6d, | 1a.2a.3c.4a.5e.6e, | 1a.2a.3c.4a.5e.6f, | 1a.2a.3c.4a.5f.6a, |
| 1a.2a.3c.4a.5f.6b, | 1a.2a.3c.4a.5f.6c, | 1a.2a.3c.4a.5f.6d, | 1a.2a.3c.4a.5f.6e, | 1a.2a.3c.4a.5f.6f, |
| 1a.2a.3c.4b.5a.6a, | 1a.2a.3c.4b.5a.6b, | 1a.2a.3c.4b.5a.6c, | 1a.2a.3c.4b.5a.6d, | |
| 1a.2a.3c.4b.5a.6e, | 1a.2a.3c.4b.5a.6f, | 1a.2a.3c.4b.5b.6a, | 1a.2a.3c.4b.5b.6b, | |
| 1a.2a.3c.4b.5b.6c, | 1a.2a.3c.4b.5b.6d, | 1a.2a.3c.4b.5b.6e, | 1a.2a.3c.4b.5b.6f, | |
| 1a.2a.3c.4b.5c.6a, | 1a.2a.3c.4b.5c.6b, | 1a.2a.3c.4b.5c.6c, | 1a.2a.3c.4b.5c.6d, | |
| 1a.2a.3c.4b.5c.6e, | 1a.2a.3c.4b.5c.6f, | 1a.2a.3c.4b.5d.6a, | 1a.2a.3c.4b.5d.6b, | |
| 1a.2a.3c.4b.5d.6c, | 1a.2a.3c.4b.5d.6d, | 1a.2a.3c.4b.5d.6e, | 1a.2a.3c.4b.5d.6f, | |
| 1a.2a.3c.4b.5e.6a, | 1a.2a.3c.4b.5e.6b, | 1a.2a.3c.4b.5e.6c, | 1a.2a.3c.4b.5e.6d, | |
| 1a.2a.3c.4b.5e.6e, | 1a.2a.3c.4b.5e.6f, | 1a.2a.3c.4b.5f.6a, | 1a.2a.3c.4b.5f.6b, | 1a.2a.3c.4b.5f.6c, |
| 1a.2a.3c.4b.5f.6d, | 1a.2a.3c.4b.5f.6e, | 1a.2a.3c.4b.5f.6f, | 1a.2a.3c.4c.5a.6a, | 1a.2a.3c.4c.5a.6b, |
| 1a.2a.3c.4c.5a.6c, | 1a.2a.3c.4c.5a.6d, | 1a.2a.3c.4c.5a.6e, | 1a.2a.3c.4c.5a.6f, | 1a.2a.3c.4c.5b.6a, |
| 1a.2a.3c.4c.5b.6b, | 1a.2a.3c.4c.5b.6c, | 1a.2a.3c.4c.5b.6d, | 1a.2a.3c.4c.5b.6e, | |
| 1a.2a.3c.4c.5b.6f, | 1a.2a.3c.4c.5c.6a, | 1a.2a.3c.4c.5c.6b, | 1a.2a.3c.4c.5c.6c, | 1a.2a.3c.4c.5c.6d, |
| 1a.2a.3c.4c.5c.6e, | 1a.2a.3c.4c.5c.6f, | 1a.2a.3c.4c.5d.6a, | 1a.2a.3c.4c.5d.6b, | |
| 1a.2a.3c.4c.5d.6c, | 1a.2a.3c.4c.5d.6d, | 1a.2a.3c.4c.5d.6e, | 1a.2a.3c.4c.5d.6f, | |
| 1a.2a.3c.4c.5e.6a, | 1a.2a.3c.4c.5e.6b, | 1a.2a.3c.4c.5e.6c, | 1a.2a.3c.4c.5e.6d, | |
| 1a.2a.3c.4c.5e.6e, | 1a.2a.3c.4c.5e.6f, | 1a.2a.3c.4c.5f.6a, | 1a.2a.3c.4c.5f.6b, | 1a.2a.3c.4c.5f.6c, |
| 1a.2a.3c.4c.5f.6d, | 1a.2a.3c.4c.5f.6e, | 1a.2a.3c.4c.5f.6f, | 1a.2a.3c.4d.5a.6a, | 1a.2a.3c.4d.5a.6b, |
| 1a.2a.3c.4d.5a.6c, | 1a.2a.3c.4d.5a.6d, | 1a.2a.3c.4d.5a.6e, | 1a.2a.3c.4d.5a.6f, | |
| 1a.2a.3c.4d.5b.6a, | 1a.2a.3c.4d.5b.6b, | 1a.2a.3c.4d.5b.6c, | 1a.2a.3c.4d.5b.6d, | |
| 1a.2a.3c.4d.5b.6e, | 1a.2a.3c.4d.5b.6f, | 1a.2a.3c.4d.5c.6a, | 1a.2a.3c.4d.5c.6b, | |
| 1a.2a.3c.4d.5c.6c, | 1a.2a.3c.4d.5c.6d, | 1a.2a.3c.4d.5c.6e, | 1a.2a.3c.4d.5c.6f, | |
| 1a.2a.3c.4d.5d.6a, | 1a.2a.3c.4d.5d.6b, | 1a.2a.3c.4d.5d.6c, | 1a.2a.3c.4d.5d.6d, | |
| 1a.2a.3c.4d.5d.6e, | 1a.2a.3c.4d.5d.6f, | 1a.2a.3c.4d.5e.6a, | 1a.2a.3c.4d.5e.6b, | |
| 1a.2a.3c.4d.5e.6c, | 1a.2a.3c.4d.5e.6d, | 1a.2a.3c.4d.5e.6e, | 1a.2a.3c.4d.5e.6f, | |
| 1a.2a.3c.4d.5f.6a, | 1a.2a.3c.4d.5f.6b, | 1a.2a.3c.4d.5f.6c, | 1a.2a.3c.4d.5f.6d, | |
| 1a.2a.3c.4d.5f.6e, | 1a.2a.3c.4d.5f.6f, | 1a.2a.3c.4e.5a.6a, | 1a.2a.3c.4e.5a.6b, | 1a.2a.3c.4e.5a.6c, |
| 1a.2a.3c.4e.5a.6d, | 1a.2a.3c.4e.5a.6e, | 1a.2a.3c.4e.5a.6f, | 1a.2a.3c.4e.5b.6a, | |
| 1a.2a.3c.4e.5b.6b, | 1a.2a.3c.4e.5b.6c, | 1a.2a.3c.4e.5b.6d, | 1a.2a.3c.4e.5b.6e, | |
| 1a.2a.3c.4e.5b.6f, | 1a.2a.3c.4e.5c.6a, | 1a.2a.3c.4e.5c.6b, | 1a.2a.3c.4e.5c.6c, | |
| 1a.2a.3c.4e.5c.6d, | 1a.2a.3c.4e.5c.6e, | 1a.2a.3c.4e.5c.6f, | 1a.2a.3c.4e.5d.6a, | |
| 1a.2a.3c.4e.5d.6b, | 1a.2a.3c.4e.5d.6c, | 1a.2a.3c.4e.5d.6d, | 1a.2a.3c.4e.5d.6e, | |
| 1a.2a.3c.4e.5d.6f, | 1a.2a.3c.4e.5e.6a, | 1a.2a.3c.4e.5e.6b, | 1a.2a.3c.4e.5e.6c, | |
| 1a.2a.3c.4e.5e.6d, | 1a.2a.3c.4e.5e.6e, | 1a.2a.3c.4e.5e.6f, | 1a.2a.3c.4e.5f.6a, | 1a.2a.3c.4e.5f.6b, |
| 1a.2a.3c.4e.5f.6c, | 1a.2a.3c.4e.5f.6d, | 1a.2a.3c.4e.5f.6e, | 1a.2a.3c.4e.5f.6f, | 1a.2a.3c.4f.5a.6a, |
| 1a.2a.3c.4f.5a.6b, | 1a.2a.3c.4f.5a.6c, | 1a.2a.3c.4f.5a.6d, | 1a.2a.3c.4f.5a.6e, | 1a.2a.3c.4f.5a.6f, |
| 1a.2a.3c.4f.5b.6a, | 1a.2a.3c.4f.5b.6b, | 1a.2a.3c.4f.5b.6c, | 1a.2a.3c.4f.5b.6d, | 1a.2a.3c.4f.5b.6e, |
| 1a.2a.3c.4f.5b.6f, | 1a.2a.3c.4f.5c.6a, | 1a.2a.3c.4f.5c.6b, | 1a.2a.3c.4f.5c.6c, | 1a.2a.3c.4f.5c.6d, |
| 1a.2a.3c.4f.5c.6e, | 1a.2a.3c.4f.5c.6f, | 1a.2a.3c.4f.5d.6a, | 1a.2a.3c.4f.5d.6b, | 1a.2a.3c.4f.5d.6c, |
| 1a.2a.3c.4f.5d.6d, | 1a.2a.3c.4f.5d.6e, | 1a.2a.3c.4f.5d.6f, | 1a.2a.3c.4f.5e.6a, | 1a.2a.3c.4f.5e.6b, |
| 1a.2a.3c.4f.5e.6c, | 1a.2a.3c.4f.5e.6d, | 1a.2a.3c.4f.5e.6e, | 1a.2a.3c.4f.5e.6f, | 1a.2a.3c.4f.5f.6a, |
| 1a.2a.3c.4f.5f.6b, | 1a.2a.3c.4f.5f.6c, | 1a.2a.3c.4f.5f.6d, | 1a.2a.3c.4f.5f.6e, | 1a.2a.3c.4f.5f.6f, |
| 1a.2a.3d.4a.5a.6a, | 1a.2a.3d.4a.5a.6b, | 1a.2a.3d.4a.5a.6c, | 1a.2a.3d.4a.5a.6d, | |
| 1a.2a.3d.4a.5a.6e, | 1a.2a.3d.4a.5a.6f, | 1a.2a.3d.4a.5b.6a, | 1a.2a.3d.4a.5b.6b, | |
| 1a.2a.3d.4a.5b.6c, | 1a.2a.3d.4a.5b.6d, | 1a.2a.3d.4a.5b.6e, | 1a.2a.3d.4a.5b.6f, | |
| 1a.2a.3d.4a.5c.6a, | 1a.2a.3d.4a.5c.6b, | 1a.2a.3d.4a.5c.6c, | 1a.2a.3d.4a.5c.6d, | |
| 1a.2a.3d.4a.5c.6e, | 1a.2a.3d.4a.5c.6f, | 1a.2a.3d.4a.5d.6a, | 1a.2a.3d.4a.5d.6b, | |
| 1a.2a.3d.4a.5d.6c, | 1a.2a.3d.4a.5d.6d, | 1a.2a.3d.4a.5d.6e, | 1a.2a.3d.4a.5d.6f, | |
| 1a.2a.3d.4a.5e.6a, | 1a.2a.3d.4a.5e.6b, | 1a.2a.3d.4a.5e.6c, | 1a.2a.3d.4a.5e.6d, | |
| 1a.2a.3d.4a.5e.6e, | 1a.2a.3d.4a.5e.6f, | 1a.2a.3d.4a.5f.6a, | 1a.2a.3d.4a.5f.6b, | |
| 1a.2a.3d.4a.5f.6c, | 1a.2a.3d.4a.5f.6d, | 1a.2a.3d.4a.5f.6e, | 1a.2a.3d.4a.5f.6f, | |
| 1a.2a.3d.4b.5a.6a, | 1a.2a.3d.4b.5a.6b, | 1a.2a.3d.4b.5a.6c, | 1a.2a.3d.4b.5a.6d, | |
| 1a.2a.3d.4b.5a.6e, | 1a.2a.3d.4b.5a.6f, | 1a.2a.3d.4b.5b.6a, | 1a.2a.3d.4b.5b.6b, | |
| 1a.2a.3d.4b.5b.6c, | 1a.2a.3d.4b.5b.6d, | 1a.2a.3d.4b.5b.6e, | 1a.2a.3d.4b.5b.6f, | |
| 1a.2a.3d.4b.5c.6a, | 1a.2a.3d.4b.5c.6b, | 1a.2a.3d.4b.5c.6c, | 1a.2a.3d.4b.5c.6d, | |
| 1a.2a.3d.4b.5c.6e, | 1a.2a.3d.4b.5c.6f, | 1a.2a.3d.4b.5d.6a, | 1a.2a.3d.4b.5d.6b, | |
| 1a.2a.3d.4b.5d.6c, | 1a.2a.3d.4b.5d.6d, | 1a.2a.3d.4b.5d.6e, | 1a.2a.3d.4b.5d.6f, | |
| 1a.2a.3d.4b.5e.6a, | 1a.2a.3d.4b.5e.6b, | 1a.2a.3d.4b.5e.6c, | 1a.2a.3d.4b.5e.6d, | |
| 1a.2a.3d.4b.5e.6e, | 1a.2a.3d.4b.5e.6f, | 1a.2a.3d.4b.5f.6a, | 1a.2a.3d.4b.5f.6b, | |
| 1a.2a.3d.4b.5f.6c, | 1a.2a.3d.4b.5f.6d, | 1a.2a.3d.4b.5f.6e, | 1a.2a.3d.4b.5f.6f, | |
| 1a.2a.3d.4c.5a.6a, | 1a.2a.3d.4c.5a.6b, | 1a.2a.3d.4c.5a.6c, | 1a.2a.3d.4c.5a.6d, | |
| 1a.2a.3d.4c.5a.6e, | 1a.2a.3d.4c.5a.6f, | 1a.2a.3d.4c.5b.6a, | 1a.2a.3d.4c.5b.6b, | |
| 1a.2a.3d.4c.5b.6c, | 1a.2a.3d.4c.5b.6d, | 1a.2a.3d.4c.5b.6e, | 1a.2a.3d.4c.5b.6f, | |
| 1a.2a.3d.4c.5c.6a, | 1a.2a.3d.4c.5c.6b, | 1a.2a.3d.4c.5c.6c, | 1a.2a.3d.4c.5c.6d, | |
| 1a.2a.3d.4c.5c.6e, | 1a.2a.3d.4c.5c.6f, | 1a.2a.3d.4c.5d.6a, | 1a.2a.3d.4c.5d.6b, | |
| 1a.2a.3d.4c.5d.6c, | 1a.2a.3d.4c.5d.6d, | 1a.2a.3d.4c.5d.6e, | 1a.2a.3d.4c.5d.6f, | |
| 1a.2a.3d.4c.5e.6a, | 1a.2a.3d.4c.5e.6b, | 1a.2a.3d.4c.5e.6c, | 1a.2a.3d.4c.5e.6d, | |
| 1a.2a.3d.4c.5e.6e, | 1a.2a.3d.4c.5e.6f, | 1a.2a.3d.4c.5f.6a, | 1a.2a.3d.4c.5f.6b, | |
| 1a.2a.3d.4c.5f.6c, | 1a.2a.3d.4c.5f.6d, | 1a.2a.3d.4c.5f.6e, | 1a.2a.3d.4c.5f.6f, | |
| 1a.2a.3d.4d.5a.6a, | 1a.2a.3d.4d.5a.6b, | 1a.2a.3d.4d.5a.6c, | 1a.2a.3d.4d.5a.6d, | |
| 1a.2a.3d.4d.5a.6e, | 1a.2a.3d.4d.5a.6f, | 1a.2a.3d.4d.5b.6a, | 1a.2a.3d.4d.5b.6b, | |

TABLE 7-continued

List of Compounds of Formula (II)

| | | | | |
|---|---|---|---|---|
| 1a.2a.3d.4d.5b.6c, | 1a.2a.3d.4d.5b.6d, | 1a.2a.3d.4d.5b.6e, | 1a.2a.3d.4d.5b.6f, | |
| 1a.2a.3d.4d.5c.6a, | 1a.2a.3d.4d.5c.6b, | 1a.2a.3d.4d.5c.6c, | 1a.2a.3d.4d.5c.6d, | |
| 1a.2a.3d.4d.5c.6e, | 1a.2a.3d.4d.5c.6f, | 1a.2a.3d.4d.5d.6a, | 1a.2a.3d.4d.5d.6b, | |
| 1a.2a.3d.4d.5d.6c, | 1a.2a.3d.4d.5d.6d, | 1a.2a.3d.4d.5d.6e, | 1a.2a.3d.4d.5d.6f, | |
| 1a.2a.3d.4d.5e.6a, | 1a.2a.3d.4d.5e.6b, | 1a.2a.3d.4d.5e.6c, | 1a.2a.3d.4d.5e.6d, | |
| 1a.2a.3d.4d.5e.6e, | 1a.2a.3d.4d.5e.6f, | 1a.2a.3d.4d.5f.6a, | 1a.2a.3d.4d.5f.6b, | |
| 1a.2a.3d.4d.5f.6c, | 1a.2a.3d.4d.5f.6d, | 1a.2a.3d.4d.5f.6e, | 1a.2a.3d.4d.5f.6f, | |
| 1a.2a.3d.4e.5a.6a, | 1a.2a.3d.4e.5a.6b, | 1a.2a.3d.4e.5a.6c, | 1a.2a.3d.4e.5a.6d, | |
| 1a.2a.3d.4e.5a.6e, | 1a.2a.3d.4e.5a.6f, | 1a.2a.3d.4e.5b.6a, | 1a.2a.3d.4e.5b.6b, | |
| 1a.2a.3d.4e.5b.6c, | 1a.2a.3d.4e.5b.6d, | 1a.2a.3d.4e.5b.6e, | 1a.2a.3d.4e.5b.6f, | |
| 1a.2a.3d.4e.5c.6a, | 1a.2a.3d.4e.5c.6b, | 1a.2a.3d.4e.5c.6c, | 1a.2a.3d.4e.5c.6d, | |
| 1a.2a.3d.4e.5c.6e, | 1a.2a.3d.4e.5c.6f, | 1a.2a.3d.4e.5d.6a, | 1a.2a.3d.4e.5d.6b, | |
| 1a.2a.3d.4e.5d.6c, | 1a.2a.3d.4e.5d.6d, | 1a.2a.3d.4e.5d.6e, | 1a.2a.3d.4e.5d.6f, | |
| 1a.2a.3d.4e.5e.6a, | 1a.2a.3d.4e.5e.6b, | 1a.2a.3d.4e.5e.6c, | 1a.2a.3d.4e.5e.6d, | |
| 1a.2a.3d.4e.5e.6e, | 1a.2a.3d.4e.5e.6f, | 1a.2a.3d.4e.5f.6a, | 1a.2a.3d.4e.5f.6b, | |
| 1a.2a.3d.4e.5f.6c, | 1a.2a.3d.4e.5f.6d, | 1a.2a.3d.4e.5f.6e, | 1a.2a.3d.4e.5f.6f, | |
| 1a.2a.3d.4f.5a.6a, | 1a.2a.3d.4f.5a.6b, | 1a.2a.3d.4f.5a.6c, | 1a.2,a.3d.4f.5a.6d, | |
| 1a.2a.3d.4f.5a.6e, | 1a.2a.3d.4f.5a.6f, | 1a.2a.3d.4f.5b.6a, | 1a.2a.3d.4f.5b.6b, | |
| 1a.2a.3d.4f.5b.6c, | 1a.2a.3d.4f.5b.6d, | 1a.2a.3d.4f.5b.6e, | 1a.2a.3d.4f.5b.6f, | |
| 1a.2a.3d.4f.5c.6a, | 1a.2a.3d.4f.5c.6b, | 1a.2a.3d.4f.5c.6c, | 1a.2a.3d.4f.5c.6d, | |
| 1a.2a.3d.4f.5c.6e, | 1a.2a.3d.4f.5c.6f, | 1a.2a.3d.4f.5d.6a, | 1a.2a.3d.4f.5d.6b, | |
| 1a.2a.3d.4f.5d.6c, | 1a.2a.3d.4f.5d.6d, | 1a.2a.3d.4f.5d.6e, | 1a.2a.3d.4f.5d.6f, | |
| 1a.2a.3d.4f.5e.6a, | 1a.2a.3d.4f.5e.6b, | 1a.2a.3d.4f.5e.6c, | 1a.2a.3d.4f.5e.6d, | |
| 1a.2a.3d.4f.5e.6e, | 1a.2a.3d.4f.5e.6f, | 1a.2a.3d.4f.5f.6a, | 1a.2a.3d.4f.5f.6b, | 1a.2a.3d.4f.5f.6c, |
| 1a.2a.3d.4f.5f.6d, | 1a.2a.3d.4f.5f.6e, | 1a.2a.3d.4f.5f.6f, | 1a.2a.3e.4a.5a.6a, | 1a.2a.3e.4a.5a.6b, |
| 1a.2a.3e.4a.5a.6c, | 1a.2a.3e.4a.5a.6d, | 1a.2a.3e.4a.5a.6e, | 1a.2a.3e.4a.5a.6f, | |
| 1a.2a.3e.4a.5b.6a, | 1a.2a.3e.4a.5b.6b, | 1a.2a.3e.4a.5b.6c, | 1a.2a.3e.4a.5b.6d, | |
| 1a.2a.3e.4a.5b.6e, | 1a.2a.3e.4a.5b.6f, | 1a.2a.3e.4a.5c.6a, | 1a.2a.3e.4a.5c.6b, | |
| 1a.2a.3e.4a.5c.6c, | 1a.2a.3e.4a.5c.6d, | 1a.2a.3e.4a.5c.6e, | 1a.2a.3e.4a.5c.6f, | |
| 1a.2a.3e.4a.5d.6a, | 1a.2a.3e.4a.5d.6b, | 1a.2a.3e.4a.5d.6c, | 1a.2a.3e.4a.5d.6d, | |
| 1a.2a.3e.4a.5d.6e, | 1a.2a.3e.4a.5d.6f, | 1a.2a.3e.4a.5e.6a, | 1a.2a.3e.4a.5e.6b, | |
| 1a.2a.3e.4a.5e.6c, | 1a.2a.3e.4a.5e.6d, | 1a.2a.3e.4a.5e.6e, | 1a.2a.3e.4a.5e.6f, | |
| 1a.2a.3e.4a.5f.6a, | 1a.2a.3e.4a.5f.6b, | 1a.2a.3e.4a.5f.6c, | 1a.2a.3e.4a.5f.6d, | 1a.2a.3e.4a.5f.6e, |
| 1a.2a.3e.4a.5f.6f, | 1a.2a.3e.4b.5a.6a, | 1a.2a.3e.4b.5a.6b, | 1a.2a.3e.4b.5a.6c, | |
| 1a.2a.3e.4b.5a.6d, | 1a.2a.3e.4b.5a.6e, | 1a.2a.3e.4b.5a.6f, | 1a.2a.3e.4b.5b.6a, | |
| 1a.2a.3e.4b.5b.6b, | 1a.2a.3e.4b.5b.6c, | 1a.2a.3e.4b.5b.6d, | 1a.2a.3e.4b.5b.6e, | |
| 1a.2a.3e.4b.5b.6f, | 1a.2a.3e.4b.5c.6a, | 1a.2a.3e.4b.5c.6b, | 1a.2a.3e.4b.5c.6c, | |
| 1a.2a.3e.4b.5c.6d, | 1a.2a.3e.4b.5c.6e, | 1a.2a.3e.4b.5c.6f, | 1a.2a.3e.4b.5d.6a, | |
| 1a.2a.3e.4b.5d.6b, | 1a.2a.3e.4b.5d.6c, | 1a.2a.3e.4b.5d.6d, | 1a.2a.3e.4b.5d.6e, | |
| 1a.2a.3e.4b.5d.6f, | 1a.2a.3e.4b.5e.6a, | 1a.2a.3e.4b.5e.6b, | 1a.2a.3e.4b.5e.6c, | |
| 1a.2a.3e.4b.5e.6d, | 1a.2a.3e.4b.5e.6e, | 1a.2a.3e.4b.5e.6f, | 1a.2a.3e.4b.5f.6a, | |
| 1a.2a.3e.4b.5f.6b, | 1a.2a.3e.4b.5f.6c, | 1a.2a.3e.4b.5f.6d, | 1a.2a.3e.4b.5f.6e, | 1a.2a.3e.4b.5f.6f, |
| 1a.2a.3e.4c.5a.6a, | 1a.2a.3e.4c.5a.6b, | 1a.2a.3e.4c.5a.6c, | 1a.2a.3e.4c.5a.6d, | |
| 1a.2a.3e.4c.5a.6e, | 1a.2a.3e.4c.5a.6f, | 1a.2a.3e.4c.5b.6a, | 1a.2a.3e.4c.5b.6b, | |
| 1a.2a.3e.4c.5b.6c, | 1a.2a.3e.4c.5b.6d, | 1a.2a.3e.4c.5b.6e, | 1a.2a.3e.4c.5b.6f, | |
| 1a.2a.3e.4c.5c.6a, | 1a.2a.3e.4c.5c.6b, | 1a.2a.3e.4c.5c.6c, | 1a.2a.3e.4c.5c.6d, | |
| 1a.2a.3e.4c.5c.6e, | 1a.2a.3e.4c.5c.6f, | 1a.2a.3e.4c.5d.6a, | 1a.2a.3e.4c.5d.6b, | |
| 1a.2a.3e.4c.5d.6c, | 1a.2a.3e.4c.5d.6d, | 1a.2a.3e.4c.5d.6e, | 1a.2a.3e.4c.5d.6f, | |
| 1a.2a.3e.4c.5e.6a, | 1a.2a.3e.4c.5e.6b, | 1a.2a.3e.4c.5e.6c, | 1a.2a.3e.4c.5e.6d, | |
| 1a.2a.3e.4c.5e.6e, | 1a.2a.3e.4c.5e.6f, | 1a.2a.3e.4c.5f.6a, | 1a.2a.3e.4c.5f.6b, | 1a.2a.3e.4c.5f.6c, |
| 1a.2a.3e.4c.5f.6d, | 1a.2a.3e.4c.5f.6e, | 1a.2a.3e.4c.5f.6f, | 1a.2a.3e.4d.5a.6a, | |
| 1a.2a.3e.4d.5a.6b, | 1a.2a.3e.4d.5a.6c, | 1a.2a.3e.4d.5a.6d, | 1a.2a.3e.4d.5a.6e, | |
| 1a.2a.3e.4d.5a.6f, | 1a.2a.3e.4d.5b.6a, | 1a.2a.3e.4d.5b.6b, | 1a.2a.3e.4d.5b.6c, | |
| 1a.2a.3e.4d.5b.6d, | 1a.2a.3e.4d.5b.6e, | 1a.2a.3e.4d.5b.6f, | 1a.2a.3e.4d.5c.6a, | |
| 1a.2a.3e.4d.5c.6b, | 1a.2a.3e.4d.5c.6c, | 1a.2a.3e.4d.5c.6d, | 1a.2a.3e.4d.5c.6e, | |
| 1a.2a.3e.4d.5c.6f, | 1a.2a.3e.4d.5d.6a, | 1a.2a.3e.4d.5d.6b, | 1a.2a.3e.4d.5d.6c, | |
| 1a.2a.3e.4d.5d.6d, | 1a.2a.3e.4d.5d.6e, | 1a.2a.3e.4d.5d.6f, | 1a.2a.3e.4d.5e.6a, | |
| 1a.2a.3e.4d.5e.6b, | 1a.2a.3e.4d.5e.6c, | 1a.2a.3e.4d.5e.6d, | 1a.2a.3e.4d.5e.6e, | |
| 1a.2a.3e.4d.5e.6f, | 1a.2a.3e.4d.5f.6a, | 1a.2a.3e.4d.5f.6b, | 1a.2a.3e.4d.5f.6c, | |
| 1a.2a.3e.4d.5f.6d, | 1a.2a.3e.4d.5f.6e, | 1a.2a.3e.4d.5f.6f, | 1a.2a.3e.4e.5a.6a, | |
| 1a.2a.3e.4e.5a.6b, | 1a.2a.3e.4e.5a.6c, | 1a.2a.3e.4e.5a.6d, | 1a.2a.3e.4e.5a.6e, | |
| 1a.2a.3e.4e.5a.6f, | 1a.2a.3e.4e.5b.6a, | 1a.2a.3e.4e.5b.6b, | 1a.2a.3e.4e.5b.6c, | |
| 1a.2a.3e.4e.5b.6d, | 1a.2a.3e.4e.5b.6e, | 1a.2a.3e.4e.5b.6f, | 1a.2a.3e.4e.5c.6a, | |
| 1a.2a.3e.4e.5c.6b, | 1a.2a.3e.4e.5c.6c, | 1a.2a.3e.4e.5c.6d, | 1a.2a.3e.4e.5c.6e, | |
| 1a.2a.3e.4e.5c.6f, | 1a.2a.3e.4e.5d.6a, | 1a.2a.3e.4e.5d.6b, | 1a.2a.3e.4e.5d.6c, | |
| 1a.2a.3e.4e.5d.6d, | 1a.2a.3e.4e.5d.6e, | 1a.2a.3e.4e.5d.6f, | 1a.2a.3e.4e.5e.6a, | |
| 1a.2a.3e.4e.5e.6b, | 1a.2a.3e.4e.5e.6c, | 1a.2a.3e.4e.5e.6d, | 1a.2a.3e.4e.5e.6e, | |
| 1a.2a.3e.4e.5e.6f, | 1a.2a.3e.4e.5f.6a, | 1a.2a.3e.4e.5f.6b, | 1a.2a.3e.4e.5f.6c, | 1a.2a.3e.4e.5f.6d, |
| 1a.2a.3e.4e.5f.6e, | 1a.2a.3e.4e.5f.6f, | 1a.2a.3e.4f.5a.6a, | 1a.2a.3e.4f.5a.6b, | 1a.2a.3e.4f.5a.6c, |
| 1a.2a.3e.4f.5a.6d, | 1a.2a.3e.4f.5a.6e, | 1a.2a.3e.4f.5a.6f, | 1a.2a.3e.4f.5b.6a, | 1a.2a.3e.4f.5b.6b, |
| 1a.2a.3e.4f.5b.6c, | 1a.2a.3e.4f.5b.6d, | 1a.2a.3e.4f.5b.6e, | 1a.2a.3e.4f.5b.6f, | 1a.2a.3e.4f.5c.6a, |
| 1a.2a.3e.4f.5c.6b, | 1a.2a.3e.4f.5c.6c, | 1a.2a.3e.4f.5c.6d, | 1a.2a.3e.4f.5c.6e, | 1a.2a.3e.4f.5c.6f, |
| 1a.2a.3e.4f.5d.6a, | 1a.2a.3e.4f.5d.6b, | 1a.2a.3e.4f.5d.6c, | 1a.2a.3e.4f.5d.6d, | |
| 1a.2a.3e.4f.5d.6e, | 1a.2a.3e.4f.5d.6f, | 1a.2a.3e.4f.5e.6a, | 1a.2a.3e.4f.5e.6b, | 1a.2a.3e.4f.5e.6c, |
| 1a.2a.3e.4f.5e.6d, | 1a.2a.3e.4f.5e.6e, | 1a.2a.3e.4f.5e.6f, | 1a.2a.3e.4f.5f.6a, | 1a.2a.3e.4f.5f.6b, |
| 1a.2a.3e.4f.5f.6c, | 1a.2a.3e.4f.5f.6d, | 1a.2a.3e.4f.5f.6e, | 1a.2a.3e.4f.5f.6f, | 1a.2a.3f.4a.5a.6a, |
| 1a.2a.3f.4a.5a.6b, | 1a.2a.3f.4a.5a.6c, | 1a.2a.3f.4a.5a.6d, | 1a.2a.3f.4a.5a.6e, | 1a.2a.3f.4a.5a.6f, |
| 1a.2a.3f.4a.5b.6a, | 1a.2a.3f.4a.5b.6b, | 1a.2a.3f.4a.5b.6c, | 1a.2a.3f.4a.5b.6d, | |

TABLE 7-continued

List of Compounds of Formula (II)

| | | | | |
|---|---|---|---|---|
| 1a.2a.3f.4a.5b.6e, | 1a.2a.3f.4a.5b.6f, | 1a.2a.3f.4a.5c.6a, | 1a.2a.3f.4a.5c.6b, | 1a.2a.3f.4a.5c.6c, |
| 1a.2a.3f.4a.5c.6d, | 1a.2a.3f.4a.5c.6e, | 1a.2a.3f.4a.5c.6f, | 1a.2a.3f.4a.5d.6a, | 1a.2a.3f.4a.5d.6b, |
| 1a.2a.3f.4a.5d.6c, | 1a.2a.3f.4a.5d.6d, | 1a.2a.3f.4a.5d.6e, | 1a.2a.3f.4a.5d.6f, | |
| 1a.2a.3f.4a.5e.6a, | 1a.2a.3f.4a.5e.6b, | 1a.2a.3f.4a.5e.6c, | 1a.2a.3f.4a.5e.6d, | 1a.2a.3f.4a.5e.6e, |
| 1a.2a.3f.4a.5e.6f, | 1a.2a.3f.4a.5f.6a, | 1a.2a.3f.4a.5f.6b, | 1a.2a.3f.4a.5f.6c, | 1a.2a.3f.4a.5f.6d, |
| 1a.2a.3f.4a.5f.6e, | 1a.2a.3f.4a.5f.6f, | 1a.2a.3f.4b.5a.6a, | 1a.2a.3f.4b.5a.6b, | 1a.2a.3f.4b.5a.6c, |
| 1a.2a.3f.4b.5a.6d, | 1a.2a.3f.4b.5a.6e, | 1a.2a.3f.4b.5a.6f, | 1a.2a.3f.4b.5b.6a, | |
| 1a.2a.3f.4b.5b.6b, | 1a.2a.3f.4b.5b.6c, | 1a.2a.3f.4b.5b.6d, | 1a.2a.3f.4b.5b.6e, | |
| 1a.2a.3f.4b.5b.6f, | 1a.2a.3f.4b.5c.6a, | 1a.2a.3f.4b.5c.6b, | 1a.2a.3f.4b.5c.6c, | 1a.2a.3f.4b.5c.6d, |
| 1a.2a.3f.4b.5c.6e, | 1a.2a.3f.4b.5c.6f, | 1a.2a.3f.4b.5d.6a, | 1a.2a.3f.4b.5d.6b, | |
| 1a.2a.3f.4b.5d.6c, | 1a.2a.3f.4b.5d.6d, | 1a.2a.3f.4b.5d.6e, | 1a.2a.3f.4b.5d.6f, | |
| 1a.2a.3f.4b.5e.6a, | 1a.2a.3f.4b.5e.6b, | 1a.2a.3f.4b.5e.6c, | 1a.2a.3f.4b.5e.6d, | |
| 1a.2a.3f.4b.5e.6e, | 1a.2a.3f.4b.5e.6f, | 1a.2a.3f.4b.5f.6a, | 1a.2a.3f.4b.5f.6b, | 1a.2a.3f.4b.5f.6c, |
| 1a.2a.3f.4b.5f.6d, | 1a.2a.3f.4b.5f.6e, | 1a.2a.3f.4b.5f.6f, | 1a.2a.3f.4c.5a.6a, | 1a.2a.3f.4c.5a.6b, |
| 1a.2a.3f.4c.5a.6c, | 1a.2a.3f.4c.5a.6d, | 1a.2a.3f.4c.5a.6e, | 1a.2a.3f.4c.5a.6f, | 1a.2a.3f.4c.5b.6a, |
| 1a.2a.3f.4c.5b.6b, | 1a.2a.3f.4c.5b.6c, | 1a.2a.3f.4c.5b.6d, | 1a.2a.3f.4c.5b.6e, | 1a.2a.3f.4c.5b.6f, |
| 1a.2a.3f.4c.5c.6a, | 1a.2a.3f.4c.5c.6b, | 1a.2a.3f.4c.5c.6c, | 1a.2a.3f.4c.5c.6d, | 1a.2a.3f.4c.5c.6e, |
| 1a.2a.3f.4c.5c.6f, | 1a.2a.3f.4c.5d.6a, | 1a.2a.3f.4c.5d.6b, | 1a.2a.3f.4c.5d.6c, | 1a.2a.3f.4c.5d.6d, |
| 1a.2a.3f.4c.5d.6e, | 1a.2a.3f.4c.5d.6f, | 1a.2a.3f.4c.5e.6a, | 1a.2a.3f.4c.5e.6b, | 1a.2a.3f.4c.5e.6c, |
| 1a.2a.3f.4c.5e.6d, | 1a.2a.3f.4c.5e.6e, | 1a.2a.3f.4c.5e.6f, | 1a.2a.3f.4c.5f.6a, | 1a.2a.3f.4c.5f.6b, |
| 1a.2a.3f.4c.5f.6c, | 1a.2a.3f.4c.5f.6d, | 1a.2a.3f.4c.5f.6e, | 1a.2a.3f.4c.5f.6f, | 1a.2a.3f.4d.5a.6a, |
| 1a.2a.3f.4d.5a.6b, | 1a.2a.3f.4d.5a.6c, | 1a.2a.3f.4d.5a.6d, | 1a.2a.3f.4d.5a.6e, | |
| 1a.2a.3f.4d.5a.6f, | 1a.2a.3f.4d.5b.6a, | 1a.2a.3f.4d.5b.6b, | 1a.2a.3f.4d.5b.6c, | |
| 1a.2a.3f.4d.5b.6d, | 1a.2a.3f.4d.5b.6e, | 1a.2a.3f.4d.5b.6f, | 1a.2a.3f.4d.5c.6a, | |
| 1a.2a.3f.4d.5c.6b, | 1a.2a.3f.4d.5c.6c, | 1a.2a.3f.4d.5c.6d, | 1a.2a.3f.4d.5c.6e, | 1a.2a.3f.4d.5c.6f, |
| 1a.2a.3f.4d.5d.6a, | 1a.2a.3f.4d.5d.6b, | 1a.2a.3f.4d.5d.6c, | 1a.2a.3f.4d.5d.6d, | |
| 1a.2a.3f.4d.5d.6e, | 1a.2a.3f.4d.5d.6f, | 1a.2a.3f.4d.5e.6a, | 1a.2a.3f.4d.5e.6b, | |
| 1a.2a.3f.4d.5e.6c, | 1a.2a.3f.4d.5e.6d, | 1a.2a.3f.4d.5e.6e, | 1a.2a.3f.4d.5e.6f, | 1a.2a.3f.4d.5f.6a, |
| 1a.2a.3f.4d.5f.6b, | 1a.2a.3f.4d.5f.6c, | 1a.2a.3f.4d.5f.6d, | 1a.2a.3f.4d.5f.6e, | 1a.2a.3f.4d.5f.6f, |
| 1a.2a.3f.4e.5a.6a, | 1a.2a.3f.4e.5a.6b, | 1a.2a.3f.4e.5a.6c, | 1a.2a.3f.4e.5a.6d, | 1a.2a.3f.4e.5a.6e, |
| 1a.2a.3f.4e.5a.6f, | 1a.2a.3f.4e.5b.6a, | 1a.2a.3f.4e.5b.6b, | 1a.2a.3f.4e.5b.6c, | 1a.2a.3f.4e.5b.6d, |
| 1a.2a.3f.4e.5b.6e, | 1a.2a.3f.4e.5b.6f, | 1a.2a.3f.4e.5c.6a, | 1a.2a.3f.4e.5c.6b, | 1a.2a.3f.4e.5c.6c, |
| 1a.2a.3f.4e.5c.6d, | 1a.2a.3f.4e.5c.6e, | 1a.2a.3f.4e.5c.6f, | 1a.2a.3f.4e.5d.6a, | 1a.2a.3f.4e.5d.6b, |
| 1a.2a.3f.4e.5d.6c, | 1a.2a.3f.4e.5d.6d, | 1a.2a.3f.4e.5d.6e, | 1a.2a.3f.4e.5d.6f, | 1a.2a.3f.4e.5e.6a, |
| 1a.2a.3f.4e.5e.6b, | 1a.2a.3f.4e.5e.6c, | 1a.2a.3f.4e.5e.6d, | 1a.2a.3f.4e.5e.6e, | 1a.2a.3f.4e.5e.6f, |
| 1a.2a.3f.4e.5f.6a, | 1a.2a.3f.4e.5f.6b, | 1a.2a.3f.4e.5f.6c, | 1a.2a.3f.4e.5f.6d, | 1a.2a.3f.4e.5f.6e, |
| 1a.2a.3f.4e.5f.6f, | 1a.2a.3f.4f.5a.6a, | 1a.2a.3f.4f.5a.6b, | 1a.2a.3f.4f.5a.6c, | 1a.2a.3f.4f.5a.6d, |
| 1a.2a.3f.4f.5a.6e, | 1a.2a.3f.4f.5a.6f, | 1a.2a.3f.4f.5b.6a, | 1a.2a.3f.4f.5b.6b, | 1a.2a.3f.4f.5b.6c, |
| 1a.2a.3f.4f.5b.6d, | 1a.2a.3f.4f.5b.6e, | 1a.2a.3f.4f.5b.6f, | 1a.2a.3f.4f.5c.6a, | 1a.2a.3f.4f.5c.6b, |
| 1a.2a.3f.4f.5c.6c, | 1a.2a.3f.4f.5c.6d, | 1a.2a.3f.4f.5c.6e, | 1a.2a.3f.4f.5c.6f, | 1a.2a.3f.4f.5d.6a, |
| 1a.2a.3f.4f.5d.6b, | 1a.2a.3f.4f.5d.6c, | 1a.2a.3f.4f.5d.6d, | 1a.2a.3f.4f.5d.6e, | 1a.2a.3f.4f.5d.6f, |
| 1a.2a.3f.4f.5e.6a, | 1a.2a.3f.4f.5e.6b, | 1a.2a.3f.4f.5e.6c, | 1a.2a.3f.4f.5e.6d, | 1a.2a.3f.4f.5e.6e, |
| 1a.2a.3f.4f.5e.6f, | 1a.2a.3f.4f.5f.6a, | 1a.2a.3f.4f.5f.6b, | 1a.2a.3f.4f.5f.6c, | 1a.2a.3f.4f.5f.6d, |
| 1a.2a.3f.4f.5f.6e, | 1a.2a.3f.4f.5f.6f, | 1a.2b.3a.4a.5a.6a, | 1a.2b.3a.4a.5a.6b, | 1a.2b.3a.4a.5a.6c, |
| 1a.2b.3a.4a.5a.6d, | 1a.2b.3a.4a.5a.6e, | 1a.2b.3a.4a.5a.6f, | 1a.2b.3a.4a.5b.6a, | |
| 1a.2b.3a.4a.5b.6b, | 1a.2b.3a.4a.5b.6c, | 1a.2b.3a.4a.5b.6d, | 1a.2b.3a.4a.5b.6e, | |
| 1a.2b.3a.4a.5b.6f, | 1a.2b.3a.4a.5c.6a, | 1a.2b.3a.4a.5c.6b, | 1a.2b.3a.4a.5c.6c, | |
| 1a.2b.3a.4a.5c.6d, | 1a.2b.3a.4a.5c.6e, | 1a.2b.3a.4a.5c.6f, | 1a.2b.3a.4a.5d.6a, | |
| 1a.2b.3a.4a.5d.6b, | 1a.2b.3a.4a.5d.6c, | 1a.2b.3a.4a.5d.6d, | 1a.2b.3a.4a.5d.6e, | |
| 1a.2b.3a.4a.5d.6f, | 1a.2b.3a.4a.5e.6a, | 1a.2b.3a.4a.5e.6b, | 1a.2b.3a.4a.5e.6c, | |
| 1a.2b.3a.4a.5e.6d, | 1a.2b.3a.4a.5e.6e, | 1a.2b.3a.4a.5e.6f, | 1a.2b.3a.4a.5f.6a, | |
| 1a.2b.3a.4a.5f.6b, | 1a.2b.3a.4a.5f.6c, | 1a.2b.3a.4a.5f.6d, | 1a.2b.3a.4a.5f.6e, | 1a.2b.3a.4a.5f.6f, |
| 1a.2b.3a.4b.5a.6a, | 1a.2b.3a.4b.5a.6b, | 1a.2b.3a.4b.5a.6c, | 1a.2b.3a.4b.5a.6d, | |
| 1a.2b.3a.4b.5a.6e, | 1a.2b.3a.4b.5a.6f, | 1a.2b.3a.4b.5b.6a, | 1a.2b.3a.4b.5b.6b, | |
| 1a.2b.3a.4b.5b.6c, | 1a.2b.3a.4b.5b.6d, | 1a.2b.3a.4b.5b.6e, | 1a.2b.3a.4b.5b.6f, | |
| 1a.2b.3a.4b.5c.6a, | 1a.2b.3a.4b.5c.6b, | 1a.2b.3a.4b.5c.6c, | 1a.2b.3a.4b.5c.6d, | |
| 1a.2b.3a.4b.5c.6e, | 1a.2b.3a.4b.5c.6f, | 1a.2b.3a.4b.5d.6a, | 1a.2b.3a.4b.5d.6b, | |
| 1a.2b.3a.4b.5d.6c, | 1a.2b.3a.4b.5d.6d, | 1a.2b.3a.4b.5d.6e, | 1a.2b.3a.4b.5d.6f, | |
| 1a.2b.3a.4b.5e.6a, | 1a.2b.3a.4b.5e.6b, | 1a.2b.3a.4b.5e.6c, | 1a.2b.3a.4b.5e.6d, | |
| 1a.2b.3a.4b.5e.6e, | 1a.2b.3a.4b.5e.6f, | 1a.2b.3a.4b.5f.6a, | 1a.2b.3a.4b.5f.6b, | |
| 1a.2b.3a.4b.5f.6c, | 1a.2b.3a.4b.5f.6d, | 1a.2b.3a.4b.5f.6e, | 1a.2b.3a.4b.5f.6f, | |
| 1a.2b.3a.4c.5a.6a, | 1a.2b.3a.4c.5a.6b, | 1a.2b.3a.4c.5a.6c, | 1a.2b.3a.4c.5a.6d, | |
| 1a.2b.3a.4c.5a.6e, | 1a.2b.3a.4c.5a.6f, | 1a.2b.3a.4c.5b.6a, | 1a.2b.3a.4c.5b.6b, | |
| 1a.2b.3a.4c.5b.6c, | 1a.2b.3a.4c.5b.6d, | 1a.2b.3a.4c.5b.6e, | 1a.2b.3a.4c.5b.6f, | |
| 1a.2b.3a.4c.5c.6a, | 1a.2b.3a.4c.5c.6b, | 1a.2b.3a.4c.5c.6c, | 1a.2b.3a.4c.5c.6d, | |
| 1a.2b.3a.4c.5c.6e, | 1a.2b.3a.4c.5c.6f, | 1a.2b.3a.4c.5d.6a, | 1a.2b.3a.4c.5d.6b, | |
| 1a.2b.3a.4c.5d.6c, | 1a.2b.3a.4c.5d.6d, | 1a.2b.3a.4c.5d.6e, | 1a.2b.3a.4c.5d.6f, | |
| 1a.2b.3a.4c.5e.6a, | 1a.2b.3a.4c.5e.6b, | 1a.2b.3a.4c.5e.6c, | 1a.2b.3a.4c.5e.6d, | |
| 1a.2b.3a.4c.5e.6e, | 1a.2b.3a.4c.5e.6f, | 1a.2b.3a.4c.5f.6a, | 1a.2b.3a.4c.5f.6b, | 1a.2b.3a.4c.5f.6c, |
| 1a.2b.3a.4c.5f.6d, | 1a.2b.3a.4c.5f.6e, | 1a.2b.3a.4c.5f.6f, | 1a.2b.3a.4d.5a.6a, | |
| 1a.2b.3a.4d.5a.6b, | 1a.2b.3a.4d.5a.6c, | 1a.2b.3a.4d.5a.6d, | 1a.2b.3a.4d.5a.6e, | |
| 1a.2b.3a.4d.5a.6f, | 1a.2b.3a.4d.5b.6a, | 1a.2b.3a.4d.5b.6b, | 1a.2b.3a.4d.5b.6c, | |
| 1a.2b.3a.4d.5b.6d, | 1a.2b.3a.4d.5b.6e, | 1a.2b.3a.4d.5b.6f, | 1a.2b.3a.4d.5c.6a, | |
| 1a.2b.3a.4d.5c.6b, | 1a.2b.3a.4d.5c.6c, | 1a.2b.3a.4d.5c.6d, | 1a.2b.3a.4d.5c.6e, | |
| 1a.2b.3a.4d.5c.6f, | 1a.2b.3a.4d.5d.6a, | 1a.2b.3a.4d.5d.6b, | 1a.2b.3a.4d.5d.6c, | |
| 1a.2b.3a.4d.5d.6d, | 1a.2b.3a.4d.5d.6e, | 1a.2b.3a.4d.5d.6f, | 1a.2b.3a.4d.5e.6a, | |
| 1a.2b.3a.4d.5e.6b, | 1a.2b.3a.4d.5e.6c, | 1a.2b.3a.4d.5e.6d, | 1a.2b.3a.4d.5e.6e, | |
| 1a.2b.3a.4d.5e.6f, | 1a.2b.3a.4d.5f.6a, | 1a.2b.3a.4d.5f.6b, | 1a.2b.3a.4d.5f.6c, | |

TABLE 7-continued

List of Compounds of Formula (II)

| | | | | |
|---|---|---|---|---|
| 1a.2b.3a.4d.5f.6d, | 1a.2b.3a.4d.5f.6e, | 1a.2b.3a.4d.5f.6f, | 1a.2b.3a.4e.5a.6a, | |
| 1a.2b.3a.4e.5a.6b, | 1a.2b.3a.4e.5a.6c, | 1a.2b.3a.4e.5a.6d, | 1a.2b.3a.4e.5a.6e, | |
| 1a.2b.3a.4e.5a.6f, | 1a.2b.3a.4e.5b.6a, | 1a.2b.3a.4e.5b.6b, | 1a.2b.3a.4e.5b.6c, | |
| 1a.2b.3a.4e.5b.6d, | 1a.2b.3a.4e.5b.6e, | 1a.2b.3a.4e.5b.6f, | 1a.2b.3a.4e.5c.6a, | |
| 1a.2b.3a.4e.5c.6b, | 1a.2b.3a.4e.5c.6c, | 1a.2b.3a.4e.5c.6d, | 1a.2b.3a.4e.5c.6e, | |
| 1a.2b.3a.4e.5c.6f, | 1a.2b.3a.4e.5d.6a, | 1a.2b.3a.4e.5d.6b, | 1a.2b.3a.4e.5d.6c, | |
| 1a.2b.3a.4e.5d.6d, | 1a.2b.3a.4e.5d.6e, | 1a.2b.3a.4e.5d.6f, | 1a.2b.3a.4e.5e.6a, | |
| 1a.2b.3a.4e.5e.6b, | 1a.2b.3a.4e.5e.6c, | 1a.2b.3a.4e.5e.6d, | 1a.2b.3a.4e.5e.6e, | |
| 1a.2b.3a.4e.5e.6f, | 1a.2b.3a.4e.5f.6a, | 1a.2b.3a.4e.5f.6b, | 1a.2b.3a.4e.5f.6c, | |
| 1a.2b.3a.4e.5f.6d, | 1a.2b.3a.4e.5f.6e, | 1a.2b.3a.4e.5f.6f, | 1a.2b.3a.4f.5a.6a, | 1a.2b.3a.4f.5a.6b, |
| 1a.2b.3a.4f.5a.6c, | 1a.2b.3a.4f.5a.6d, | 1a.2b.3a.4f.5a.6e, | 1a.2b.3a.4f.5a.6f, | 1a.2b.3a.4f.5b.6a, |
| 1a.2b.3a.4f.5b.6b, | 1a.2b.3a.4f.5b.6c, | 1a.2b.3a.4f.5b.6d, | 1a.2b.3a.4f.5b.6e, | |
| 1a.2b.3a.4f.5b.6f, | 1a.2b.3a.4f.5c.6a, | 1a.2b.3a.4f.5c.6b, | 1a.2b.3a.4f.5c.6c, | 1a.2b.3a.4f.5c.6d, |
| 1a.2b.3a.4f.5c.6e, | 1a.2b.3a.4f.5c.6f, | 1a.2b.3a.4f.5d.6a, | 1a.2b.3a.4f.5d.6b, | |
| 1a.2b.3a.4f.5d.6c, | 1a.2b.3a.4f.5d.6d, | 1a.2b.3a.4f.5d.6e, | 1a.2b.3a.4f.5d.6f, | |
| 1a.2b.3a.4f.5e.6a, | 1a.2b.3a.4f.5e.6b, | 1a.2b.3a.4f.5e.6c, | 1a.2b.3a.4f.5e.6d, | |
| 1a.2b.3a.4f.5e.6e, | 1a.2b.3a.4f.5e.6f, | 1a.2b.3a.4f.5f.6a, | 1a.2b.3a.4f.5f.6b, | 1a.2b.3a.4f.5f.6c, |
| 1a.2b.3a.4f.5f.6d, | 1a.2b.3a.4f.5f.6e, | 1a.2b.3a.4f.5f.6f, | 1a.2b.3b.4a.5a.6a, | 1a.2b.3b.4a.5a.6b, |
| 1a.2b.3b.4a.5a.6c, | 1a.2b.3b.4a.5a.6d, | 1a.2b.3b.4a.5a.6e, | 1a.2b.3b.4a.5a.6f, | |
| 1a.2b.3b.4a.5b.6a, | 1a.2b.3b.4a.5b.6b, | 1a.2b.3b.4a.5b.6c, | 1a.2b.3b.4a.5b.6d, | |
| 1a.2b.3b.4a.5b.6e, | 1a.2b.3b.4a.5b.6f, | 1a.2b.3b.4a.5c.6a, | 1a.2b.3b.4a.5c.6b, | |
| 1a.2b.3b.4a.5c.6c, | 1a.2b.3b.4a.5c.6d, | 1a.2b.3b.4a.5c.6e, | 1a.2b.3b.4a.5c.6f, | |
| 1a.2b.3b.4a.5d.6a, | 1a.2b.3b.4a.5d.6b, | 1a.2b.3b.4a.5d.6c, | 1a.2b.3b.4a.5d.6d, | |
| 1a.2b.3b.4a.5d.6e, | 1a.2b.3b.4a.5d.6f, | 1a.2b.3b.4a.5e.6a, | 1a.2b.3b.4a.5e.6b, | |
| 1a.2b.3b.4a.5e.6c, | 1a.2b.3b.4a.5e.6d, | 1a.2b.3b.4a.5e.6e, | 1a.2b.3b.4a.5e.6f, | |
| 1a.2b.3b.4a.5f.6a, | 1a.2b.3b.4a.5f.6b, | 1a.2b.3b.4a.5f.6c, | 1a.2b.3b.4a.5f.6d, | |
| 1a.2b.3b.4a.5f.6e, | 1a.2b.3b.4a.5f.6f, | 1a.2b.3b.4b.5a.6a, | 1a.2b.3b.4b.5a.6b, | |
| 1a.2b.3b.4b.5a.6c, | 1a.2b.3b.4b.5a.6d, | 1a.2b.3b.4b.5a.6e, | 1a.2b.3b.4b.5a.6f, | |
| 1a.2b.3b.4b.5b.6a, | 1a.2b.3b.4b.5b.6b, | 1a.2b.3b.4b.5b.6c, | 1a.2b.3b.4b.5b.6d, | |
| 1a.2b.3b.4b.5b.6e, | 1a.2b.3b.4b.5b.6f, | 1a.2b.3b.4b.5c.6a, | 1a.2b.3b.4b.5c.6b, | |
| 1a.2b.3b.4b.5c.6c, | 1a.2b.3b.4b.5c.6d, | 1a.2b.3b.4b.5c.6e, | 1a.2b.3b.4b.5c.6f, | |
| 1a.2b.3b.4b.5d.6a, | 1a.2b.3b.4b.5d.6b, | 1a.2b.3b.4b.5d.6c, | 1a.2b.3b.4b.5d.6d, | |
| 1a.2b.3b.4b.5d.6e, | 1a.2b.3b.4b.5d.6f, | 1a.2b.3b.4b.5e.6a, | 1a.2b.3b.4b.5e.6b, | |
| 1a.2b.3b.4b.5e.6c, | 1a.2b.3b.4b.5e.6d, | 1a.2b.3b.4b.5e.6e, | 1a.2b.3b.4b.5e.6f, | |
| 1a.2b.3b.4b.5f.6a, | 1a.2b.3b.4b.5f.6b, | 1a.2b.3b.4b.5f.6c, | 1a.2b.3b.4b.5f.6d, | |
| 1a.2b.3b.4b.5f.6e, | 1a.2b.3b.4b.5f.6f, | 1a.2b.3b.4c.5a.6a, | 1a.2b.3b.4c.5a.6b, | |
| 1a.2b.3b.4c.5a.6c, | 1a.2b.3b.4c.5a.6d, | 1a.2b.3b.4c.5a.6e, | 1a.2b.3b.4c.5a.6f, | |
| 1a.2b.3b.4c.5b.6a, | 1a.2b.3b.4c.5b.6b, | 1a.2b.3b.4c.5b.6c, | 1a.2b.3b.4c.5b.6d, | |
| 1a.2b.3b.4c.5b.6e, | 1a.2b.3b.4c.5b.6f, | 1a.2b.3b.4c.5c.6a, | 1a.2b.3b.4c.5c.6b, | |
| 1a.2b.3b.4c.5c.6c, | 1a.2b.3b.4c.5c.6d, | 1a.2b.3b.4c.5c.6e, | 1a.2b.3b.4c.5c.6f, | |
| 1a.2b.3b.4c.5d.6a, | 1a.2b.3b.4c.5d.6b, | 1a.2b.3b.4c.5d.6c, | 1a.2b.3b.4c.5d.6d, | |
| 1a.2b.3b.4c.5d.6e, | 1a.2b.3b.4c.5d.6f, | 1a.2b.3b.4c.5e.6a, | 1a.2b.3b.4c.5e.6b, | |
| 1a.2b.3b.4c.5e.6c, | 1a.2b.3b.4c.5e.6d, | 1a.2b.3b.4c.5e.6e, | 1a.2b.3b.4c.5e.6f, | |
| 1a.2b.3b.4c.5f.6a, | 1a.2b.3b.4c.5f.6b, | 1a.2b.3b.4c.5f.6c, | 1a.2b.3b.4c.5f.6d, | |
| 1a.2b.3b.4c.5f.6e, | 1a.2b.3b.4c.5f.6f, | 1a.2b.3b.4d.5a.6a, | 1a.2b.3b.4d.5a.6b, | |
| 1a.2b.3b.4d.5a.6c, | 1a.2b.3b.4d.5a.6d, | 1a.2b.3b.4d.5a.6e, | 1a.2b.3b.4d.5a.6f, | |
| 1a.2b.3b.4d.5b.6a, | 1a.2b.3b.4d.5b.6b, | 1a.2b.3b.4d.5b.6c, | 1a.2b.3b.4d.5b.6d, | |
| 1a.2b.3b.4d.5b.6e, | 1a.2b.3b.4d.5b.6f, | 1a.2b.3b.4d.5c.6a, | 1a.2b.3b.4d.5c.6b, | |
| 1a.2b.3b.4d.5c.6c, | 1a.2b.3b.4d.5c.6d, | 1a.2b.3b.4d.5c.6e, | 1a.2b.3b.4d.5c.6f, | |
| 1a.2b.3b.4d.5d.6a, | 1a.2b.3b.4d.5d.6b, | 1a.2b.3b.4d.5d.6c, | 1a.2b.3b.4d.5d.6d, | |
| 1a.2b.3b.4d.5d.6e, | 1a.2b.3b.4d.5d.6f, | 1a.2b.3b.4d.5e.6a, | 1a.2b.3b.4d.5e.6b, | |
| 1a.2b.3b.4d.5e.6c, | 1a.2b.3b.4d.5e.6d, | 1a.2b.3b.4d.5e.6e, | 1a.2b.3b.4d.5e.6f, | |
| 1a.2b.3b.4d.5f.6a, | 1a.2b.3b.4d.5f.6b, | 1a.2b.3b.4d.5f.6c, | 1a.2b.3b.4d.5f.6d, | |
| 1a.2b.3b.4d.5f.6e, | 1a.2b.3b.4d.5f.6f, | 1a.2b.3b.4e.5a.6a, | 1a.2b.3b.4e.5a.6b, | |
| 1a.2b.3b.4e.5a.6c, | 1a.2b.3b.4e.5a.6d, | 1a.2b.3b.4e.5a.6e, | 1a.2b.3b.4e.5a.6f, | |
| 1a.2b.3b.4e.5b.6a, | 1a.2b.3b.4e.5b.6b, | 1a.2b.3b.4e.5b.6c, | 1a.2b.3b.4e.5b.6d, | |
| 1a.2b.3b.4e.5b.6e, | 1a.2b.3b.4e.5b.6f, | 1a.2b.3b.4e.5c.6a, | 1a.2b.3b.4e.5c.6b, | |
| 1a.2b.3b.4e.5c.6c, | 1a.2b.3b.4e.5c.6d, | 1a.2b.3b.4e.5c.6e, | 1a.2b.3b.4e.5c.6f, | |
| 1a.2b.3b.4e.5d.6a, | 1a.2b.3b.4e.5d.6b, | 1a.2b.3b.4e.5d.6c, | 1a.2b.3b.4e.5d.6d, | |
| 1a.2b.3b.4e.5d.6e, | 1a.2b.3b.4e.5d.6f, | 1a.2b.3b.4e.5e.6a, | 1a.2b.3b.4e.5e.6b, | |
| 1a.2b.3b.4e.5e.6c, | 1a.2b.3b.4e.5e.6d, | 1a.2b.3b.4e.5e.6e, | 1a.2b.3b.4e.5e.6f, | |
| 1a.2b.3b.4e.5f.6a, | 1a.2b.3b.4e.5f.6b, | 1a.2b.3b.4e.5f.6c, | 1a.2b.3b.4e.5f.6d, | |
| 1a.2b.3b.4e.5f.6e, | 1a.2b.3b.4e.5f.6f, | 1a.2b.3b.4f.5a.6a, | 1a.2b.3b.4f.5a.6b, | |
| 1a.2b.3b.4f.5a.6c, | 1a.2b.3b.4f.5a.6d, | 1a.2b.3b.4f.5a.6e, | 1a.2b.3b.4f.5a.6f, | |
| 1a.2b.3b.4f.5b.6a, | 1a.2b.3b.4f.5b.6b, | 1a.2b.3b.4f.5b.6c, | 1a.2b.3b.4f.5b.6d, | |
| 1a.2b.3b.4f.5b.6e, | 1a.2b.3b.4f.5b.6f, | 1a.2b.3b.4f.5c.6a, | 1a.2b.3b.4f.5c.6b, | |
| 1a.2b.3b.4f.5c.6c, | 1a.2b.3b.4f.5c.6d, | 1a.2b.3b.4f.5c.6e, | 1a.2b.3b.4f.5c.6f, | |
| 1a.2b.3b.4f.5d.6a, | 1a.2b.3b.4f.5d.6b, | 1a.2b.3b.4f.5d.6c, | 1a.2b.3b.4f.5d.6d, | |
| 1a.2b.3b.4f.5d.6e, | 1a.2b.3b.4f.5d.6f, | 1a.2b.3b.4f.5e.6a, | 1a.2b.3b.4f.5e.6b, | |
| 1a.2b.3b.4f.5e.6c, | 1a.2b.3b.4f.5e.6d, | 1a.2b.3b.4f.5e.6e, | 1a.2b.3b.4f.5e.6f, | 1a.2b.3b.4f.5f.6a, |
| 1a.2b.3b.4f.5f.6b, | 1a.2b.3b.4f.5f.6c, | 1a.2b.3b.4f.5f.6d, | 1a.2b.3b.4f.5f.6e, | 1a.2b.3b.4f.5f.6f, |
| 1a.2b.3c.4a.5a.6a, | 1a.2b.3c.4a.5a.6b, | 1a.2b.3c.4a.5a.6c, | 1a.2b.3c.4a.5a.6d, | |
| 1a.2b.3c.4a.5a.6e, | 1a.2b.3c.4a.5a.6f, | 1a.2b.3c.4a.5b.6a, | 1a.2b.3c.4a.5b.6b, | |
| 1a.2b.3c.4a.5b.6c, | 1a.2b.3c.4a.5b.6d, | 1a.2b.3c.4a.5b.6e, | 1a.2b.3c.4a.5b.6f, | |
| 1a.2b.3c.4a.5c.6a, | 1a.2b.3c.4a.5c.6b, | 1a.2b.3c.4a.5c.6c, | 1a.2b.3c.4a.5c.6d, | |
| 1a.2b.3c.4a.5c.6e, | 1a.2b.3c.4a.5c.6f, | 1a.2b.3c.4a.5d.6a, | 1a.2b.3c.4a.5d.6b, | |
| 1a.2b.3c.4a.5d.6c, | 1a.2b.3c.4a.5d.6d, | 1a.2b.3c.4a.5d.6e, | 1a.2b.3c.4a.5d.6f, | |
| 1a.2b.3c.4a.5e.6a, | 1a.2b.3c.4a.5e.6b, | 1a.2b.3c.4a.5e.6c, | 1a.2b.3c.4a.5e.6d, | |

TABLE 7-continued

List of Compounds of Formula (II)

| | | | | |
|---|---|---|---|---|
| 1a.2b.3c.4a.5e.6e, | 1a.2b.3c.4a.5e.6f, | 1a.2b.3c.4a.5f.6a, | 1a.2b.3c.4a.5f.6b, | 1a.2b.3c.4a.5f.6c, |
| 1a.2b.3c.4a.5f.6d, | 1a.2b.3c.4a.5f.6e, | 1a.2b.3c.4a.5f.6f, | 1a.2b.3c.4b.5a.6a, | |
| 1a.2b.3c.4b.5a.6b, | 1a.2b.3c.4b.5a.6c, | 1a.2b.3c.4b.5a.6d, | 1a.2b.3c.4b.5a.6e, | |
| 1a.2b.3c.4b.5a.6f, | 1a.2b.3c.4b.5b.6a, | 1a.2b.3c.4b.5b.6b, | 1a.2b.3c.4b.5b.6c, | |
| 1a.2b.3c.4b.5b.6d, | 1a.2b.3c.4b.5b.6e, | 1a.2b.3c.4b.5b.6f, | 1a.2b.3c.4b.5c.6a, | |
| 1a.2b.3c.4b.5c.6b, | 1a.2b.3c.4b.5c.6c, | 1a.2b.3c.4b.5c.6d, | 1a.2b.3c.4b.5c.6e, | |
| 1a.2b.3c.4b.5c.6f, | 1a.2b.3c.4b.5d.6a, | 1a.2b.3c.4b.5d.6b, | 1a.2b.3c.4b.5d.6c, | |
| 1a.2b.3c.4b.5d.6d, | 1a.2b.3c.4b.5d.6e, | 1a.2b.3c.4b.5d.6f, | 1a.2b.3c.4b.5e.6a, | |
| 1a.2b.3c.4b.5e.6b, | 1a.2b.3c.4b.5e.6c, | 1a.2b.3c.4b.5e.6d, | 1a.2b.3c.4b.5e.6e, | |
| 1a.2b.3c.4b.5e.6f, | 1a.2b.3c.4b.5f.6a, | 1a.2b.3c.4b.5f.6b, | 1a.2b.3c.4b.5f.6c, | |
| 1a.2b.3c.4b.5f.6d, | 1a.2b.3c.4b.5f.6e, | 1a.2b.3c.4b.5f.6f, | 1a.2b.3c.4c.5a.6a, | |
| 1a.2b.3c.4c.5a.6b, | 1a.2b.3c.4c.5a.6c, | 1a.2b.3c.4c.5a.6d, | 1a.2b.3c.4c.5a.6e, | |
| 1a.2b.3c.4c.5a.6f, | 1a.2b.3c.4c.5b.6a, | 1a.2b.3c.4c.5b.6b, | 1a.2b.3c.4c.5b.6c, | |
| 1a.2b.3c.4c.5b.6d, | 1a.2b.3c.4c.5b.6e, | 1a.2b.3c.4c.5b.6f, | 1a.2b.3c.4c.5c.6a, | |
| 1a.2b.3c.4c.5c.6b, | 1a.2b.3c.4c.5c.6c, | 1a.2b.3c.4c.5c.6d, | 1a.2b.3c.4c.5c.6e, | 1a.2b.3c.4c.5c.6f, |
| 1a.2b.3c.4c.5d.6a, | 1a.2b.3c.4c.5d.6b, | 1a.2b.3c.4c.5d.6c, | 1a.2b.3c.4c.5d.6d, | |
| 1a.2b.3c.4c.5d.6e, | 1a.2b.3c.4c.5d.6f, | 1a.2b.3c.4c.5e.6a, | 1a.2b.3c.4c.5e.6b, | |
| 1a.2b.3c.4c.5e.6c, | 1a.2b.3c.4c.5e.6d, | 1a.2b.3c.4c.5e.6e, | 1a.2b.3c.4c.5e.6f, | 1a.2b.3c.4c.5f.6a, |
| 1a.2b.3c.4c.5f.6b, | 1a.2b.3c.4c.5f.6c, | 1a.2b.3c.4c.5f.6d, | 1a.2b.3c.4c.5f.6e, | 1a.2b.3c.4c.5f.6f, |
| 1a.2b.3c.4d.5a.6a, | 1a.2b.3c.4d.5a.6b, | 1a.2b.3c.4d.5a.6c, | 1a.2b.3c.4d.5a.6d, | |
| 1a.2b.3c.4d.5a.6e, | 1a.2b.3c.4d.5a.6f, | 1a.2b.3c.4d.5b.6a, | 1a.2b.3c.4d.5b.6b, | |
| 1a.2b.3c.4d.5b.6c, | 1a.2b.3c.4d.5b.6d, | 1a.2b.3c.4d.5b.6e, | 1a.2b.3c.4d.5b.6f, | |
| 1a.2b.3c.4d.5c.6a, | 1a.2b.3c.4d.5c.6b, | 1a.2b.3c.4d.5c.6c, | 1a.2b.3c.4d.5c.6d, | |
| 1a.2b.3c.4d.5c.6e, | 1a.2b.3c.4d.5c.6f, | 1a.2b.3c.4d.5d.6a, | 1a.2b.3c.4d.5d.6b, | |
| 1a.2b.3c.4d.5d.6c, | 1a.2b.3c.4d.5d.6d, | 1a.2b.3c.4d.5d.6e, | 1a.2b.3c.4d.5d.6f, | |
| 1a.2b.3c.4d.5e.6a, | 1a.2b.3c.4d.5e.6b, | 1a.2b.3c.4d.5e.6c, | 1a.2b.3c.4d.5e.6d, | |
| 1a.2b.3c.4d.5e.6e, | 1a.2b.3c.4d.5e.6f, | 1a.2b.3c.4d.5f.6a, | 1a.2b.3c.4d.5f.6b, | |
| 1a.2b.3c.4d.5f.6c, | 1a.2b.3c.4d.5f.6d, | 1a.2b.3c.4d.5f.6e, | 1a.2b.3c.4d.5f.6f, | |
| 1a.2b.3c.4e.5a.6a, | 1a.2b.3c.4e.5a.6b, | 1a.2b.3c.4e.5a.6c, | 1a.2b.3c.4e.5a.6d, | |
| 1a.2b.3c.4e.5a.6e, | 1a.2b.3c.4e.5a.6f, | 1a.2b.3c.4e.5b.6a, | 1a.2b.3c.4e.5b.6b, | |
| 1a.2b.3c.4e.5b.6c, | 1a.2b.3c.4e.5b.6d, | 1a.2b.3c.4e.5b.6e, | 1a.2b.3c.4e.5b.6f, | |
| 1a.2b.3c.4e.5c.6a, | 1a.2b.3c.4e.5c.6b, | 1a.2b.3c.4e.5c.6c, | 1a.2b.3c.4e.5c.6d, | |
| 1a.2b.3c.4e.5c.6e, | 1a.2b.3c.4e.5c.6f, | 1a.2b.3c.4e.5d.6a, | 1a.2b.3c.4e.5d.6b, | |
| 1a.2b.3c.4e.5d.6c, | 1a.2b.3c.4e.5d.6d, | 1a.2b.3c.4e.5d.6e, | 1a.2b.3c.4e.5d.6f, | |
| 1a.2b.3c.4e.5e.6a, | 1a.2b.3c.4e.5e.6b, | 1a.2b.3c.4e.5e.6c, | 1a.2b.3c.4e.5e.6d, | |
| 1a.2b.3c.4e.5e.6e, | 1a.2b.3c.4e.5e.6f, | 1a.2b.3c.4e.5f.6a, | 1a.2b.3c.4e.5f.6b, | 1a.2b.3c.4e.5f.6c, |
| 1a.2b.3c.4e.5f.6d, | 1a.2b.3c.4e.5f.6e, | 1a.2b.3c.4e.5f.6f, | 1a.2b.3c.4f.5a.6a, | 1a.2b.3c.4f.5a.6b, |
| 1a.2b.3c.4f.5a.6c, | 1a.2b.3c.4f.5a.6d, | 1a.2b.3c.4f.5a.6e, | 1a.2b.3c.4f.5a.6f, | 1a.2b.3c.4f.5b.6a, |
| 1a.2b.3c.4f.5b.6b, | 1a.2b.3c.4f.5b.6c, | 1a.2b.3c.4f.5b.6d, | 1a.2b.3c.4f.5b.6e, | 1a.2b.3c.4f.5b.6f, |
| 1a.2b.3c.4f.5c.6a, | 1a.2b.3c.4f.5c.6b, | 1a.2b.3c.4f.5c.6c, | 1a.2b.3c.4f.5c.6d, | 1a.2b.3c.4f.5c.6e, |
| 1a.2b.3c.4f.5c.6f, | 1a.2b.3c.4f.5d.6a, | 1a.2b.3c.4f.5d.6b, | 1a.2b.3c.4f.5d.6c, | |
| 1a.2b.3c.4f.5d.6d, | 1a.2b.3c.4f.5d.6e, | 1a.2b.3c.4f.5d.6f, | 1a.2b.3c.4f.5e.6a, | |
| 1a.2b.3c.4f.5e.6b, | 1a.2b.3c.4f.5e.6c, | 1a.2b.3c.4f.5e.6d, | 1a.2b.3c.4f.5e.6e, | 1a.2b.3c.4f.5e.6f, |
| 1a.2b.3c.4f.5f.6a, | 1a.2b.3c.4f.5f.6b, | 1a.2b.3c.4f.5f.6c, | 1a.2b.3c.4f.5f.6d, | 1a.2b.3c.4f.5f.6e, |
| 1a.2b.3c.4f.5f.6f, | 1a.2b.3d.4a.5a.6a, | 1a.2b.3d.4a.5a.6b, | 1a.2b.3d.4a.5a.6c, | |
| 1a.2b.3d.4a.5a.6d, | 1a.2b.3d.4a.5a.6e, | 1a.2b.3d.4a.5a.6f, | 1a.2b.3d.4a.5b.6a, | |
| 1a.2b.3d.4a.5b.6b, | 1a.2b.3d.4a.5b.6c, | 1a.2b.3d.4a.5b.6d, | 1a.2b.3d.4a.5b.6e, | |
| 1a.2b.3d.4a.5b.6f, | 1a.2b.3d.4a.5c.6a, | 1a.2b.3d.4a.5c.6b, | 1a.2b.3d.4a.5c.6c, | |
| 1a.2b.3d.4a.5c.6d, | 1a.2b.3d.4a.5c.6e, | 1a.2b.3d.4a.5c.6f, | 1a.2b.3d.4a.5d.6a, | |
| 1a.2b.3d.4a.5d.6b, | 1a.2b.3d.4a.5d.6c, | 1a.2b.3d.4a.5d.6d, | 1a.2b.3d.4a.5d.6e, | |
| 1a.2b.3d.4a.5d.6f, | 1a.2b.3d.4a.5e.6a, | 1a.2b.3d.4a.5e.6b, | 1a.2b.3d.4a.5e.6c, | |
| 1a.2b.3d.4a.5e.6d, | 1a.2b.3d.4a.5e.6e, | 1a.2b.3d.4a.5e.6f, | 1a.2b.3d.4a.5f.6a, | |
| 1a.2b.3d.4a.5f.6b, | 1a.2b.3d.4a.5f.6c, | 1a.2b.3d.4a.5f.6d, | 1a.2b.3d.4a.5f.6e, | |
| 1a.2b.3d.4a.5f.6f, | 1a.2b.3d.4b.5a.6a, | 1a.2b.3d.4b.5a.6b, | 1a.2b.3d.4b.5a.6c, | |
| 1a.2b.3d.4b.5a.6d, | 1a.2b.3d.4b.5a.6e, | 1a.2b.3d.4b.5a.6f, | 1a.2b.3d.4b.5b.6a, | |
| 1a.2b.3d.4b.5b.6b, | 1a.2b.3d.4b.5b.6c, | 1a.2b.3d.4b.5b.6d, | 1a.2b.3d.4b.5b.6e, | |
| 1a.2b.3d.4b.5b.6f, | 1a.2b.3d.4b.5c.6a, | 1a.2b.3d.4b.5c.6b, | 1a.2b.3d.4b.5c.6c, | |
| 1a.2b.3d.4b.5c.6d, | 1a.2b.3d.4b.5c.6e, | 1a.2b.3d.4b.5c.6f, | 1a.2b.3d.4b.5d.6a, | |
| 1a.2b.3d.4b.5d.6b, | 1a.2b.3d.4b.5d.6c, | 1a.2b.3d.4b.5d.6d, | 1a.2b.3d.4b.5d.6e, | |
| 1a.2b.3d.4b.5d.6f, | 1a.2b.3d.4b.5e.6a, | 1a.2b.3d.4b.5e.6b, | 1a.2b.3d.4b.5e.6c, | |
| 1a.2b.3d.4b.5e.6d, | 1a.2b.3d.4b.5e.6e, | 1a.2b.3d.4b.5e.6f, | 1a.2b.3d.4b.5f.6a, | |
| 1a.2b.3d.4b.5f.6b, | 1a.2b.3d.4b.5f.6c, | 1a.2b.3d.4b.5f.6d, | 1a.2b.3d.4b.5f.6e, | |
| 1a.2b.3d.4b.5f.6f, | 1a.2b.3d.4c.5a.6a, | 1a.2b.3d.4c.5a.6b, | 1a.2b.3d.4c.5a.6c, | |
| 1a.2b.3d.4c.5a.6d, | 1a.2b.3d.4c.5a.6e, | 1a.2b.3d.4c.5a.6f, | 1a.2b.3d.4c.5b.6a, | |
| 1a.2b.3d.4c.5b.6b, | 1a.2b.3d.4c.5b.6c, | 1a.2b.3d.4c.5b.6d, | 1a.2b.3d.4c.5b.6e, | |
| 1a.2b.3d.4c.5b.6f, | 1a.2b.3d.4c.5c.6a, | 1a.2b.3d.4c.5c.6b, | 1a.2b.3d.4c.5c.6c, | |
| 1a.2b.3d.4c.5c.6d, | 1a.2b.3d.4c.5c.6e, | 1a.2b.3d.4c.5c.6f, | 1a.2b.3d.4c.5d.6a, | |
| 1a.2b.3d.4c.5d.6b, | 1a.2b.3d.4c.5d.6c, | 1a.2b.3d.4c.5d.6d, | 1a.2b.3d.4c.5d.6e, | |
| 1a.2b.3d.4c.5d.6f, | 1a.2b.3d.4c.5e.6a, | 1a.2b.3d.4c.5e.6b, | 1a.2b.3d.4c.5e.6c, | |
| 1a.2b.3d.4c.5e.6d, | 1a.2b.3d.4c.5e.6e, | 1a.2b.3d.4c.5e.6f, | 1a.2b.3d.4c.5f.6a, | |
| 1a.2b.3d.4c.5f.6b, | 1a.2b.3d.4c.5f.6c, | 1a.2b.3d.4c.5f.6d, | 1a.2b.3d.4c.5f.6e, | |
| 1a.2b.3d.4c.5f.6f, | 1a.2b.3d.4d.5a.6a, | 1a.2b.3d.4d.5a.6b, | 1a.2b.3d.4d.5a.6c, | |
| 1a.2b.3d.4d.5a.6d, | 1a.2b.3d.4d.5a.6e, | 1a.2b.3d.4d.5a.6f, | 1a.2b.3d.4d.5b.6a, | |
| 1a.2b.3d.4d.5b.6b, | 1a.2b.3d.4d.5b.6c, | 1a.2b.3d.4d.5b.6d, | 1a.2b.3d.4d.5b.6e, | |
| 1a.2b.3d.4d.5b.6f, | 1a.2b.3d.4d.5c.6a, | 1a.2b.3d.4d.5c.6b, | 1a.2b.3d.4d.5c.6c, | |
| 1a.2b.3d.4d.5c.6d, | 1a.2b.3d.4d.5c.6e, | 1a.2b.3d.4d.5c.6f, | 1a.2b.3d.4d.5d.6a, | |
| 1a.2b.3d.4d.5d.6b, | 1a.2b.3d.4d.5d.6c, | 1a.2b.3d.4d.5d.6d, | 1a.2b.3d.4d.5d.6e, | |
| 1a.2b.3d.4d.5d.6f, | 1a.2b.3d.4d.5e.6a, | 1a.2b.3d.4d.5e.6b, | 1a.2b.3d.4d.5e.6c, | |

TABLE 7-continued

List of Compounds of Formula (II)

| | | | | |
|---|---|---|---|---|
| 1a.2b.3d.4d.5e.6d, | 1a.2b.3d.4d.5e.6e, | 1a.2b.3d.4d.5e.6f, | 1a.2b.3d.4d.5f.6a, | |
| 1a.2b.3d.4d.5f.6b, | 1a.2b.3d.4d.5f.6c, | 1a.2b.3d.4d.5f.6d, | 1a.2b.3d.4d.5f.6e, | |
| 1a.2b.3d.4d.5f.6f, | 1a.2b.3d.4e.5a.6a, | 1a.2b.3d.4e.5a.6b, | 1a.2b.3d.4e.5a.6c, | |
| 1a.2b.3d.4e.5a.6d, | 1a.2b.3d.4e.5a.6e, | 1a.2b.3d.4e.5a.6f, | 1a.2b.3d.4e.5b.6a, | |
| 1a.2b.3d.4e.5b.6b, | 1a.2b.3d.4e.5b.6c, | 1a.2b.3d.4e.5b.6d, | 1a.2b.3d.4e.5b.6e, | |
| 1a.2b.3d.4e.5b.6f, | 1a.2b.3d.4e.5c.6a, | 1a.2b.3d.4e.5c.6b, | 1a.2b.3d.4e.5c.6c, | |
| 1a.2b.3d.4e.5c.6d, | 1a.2b.3d.4e.5c.6e, | 1a.2b.3d.4e.5c.6f, | 1a.2b.3d.4e.5d.6a, | |
| 1a.2b.3d.4e.5d.6b, | 1a.2b.3d.4e.5d.6c, | 1a.2b.3d.4e.5d.6d, | 1a.2b.3d.4e.5d.6e, | |
| 1a.2b.3d.4e.5d.6f, | 1a.2b.3d.4e.5e.6a, | 1a.2b.3d.4e.5e.6b, | 1a.2b.3d.4e.5e.6c, | |
| 1a.2b.3d.4e.5e.6d, | 1a.2b.3d.4e.5e.6e, | 1a.2b.3d.4e.5e.6f, | 1a.2b.3d.4e.5f.6a, | |
| 1a.2b.3d.4e.5f.6b, | 1a.2b.3d.4e.5f.6c, | 1a.2b.3d.4e.5f.6d, | 1a.2b.3d.4e.5f.6e, | |
| 1a.2b.3d.4e.5f.6f, | 1a.2b.3d.4f.5a.6a, | 1a.2b.3d.4f.5a.6b, | 1a.2b.3d.4f.5a.6c, | |
| 1a.2b.3d.4f.5a.6d, | 1a.2b.3d.4f.5a.6e, | 1a.2b.3d.4f.5a.6f, | 1a.2b.3d.4f.5b.6a, | |
| 1a.2b.3d.4f.5b.6b, | 1a.2b.3d.4f.5b.6c, | 1a.2b.3d.4f.5b.6d, | 1a.2b.3d.4f.5b.6e, | |
| 1a.2b.3d.4f.5b.6f, | 1a.2b.3d.4f.5c.6a, | 1a.2b.3d.4f.5c.6b, | 1a.2b.3d.4f.5c.6c, | |
| 1a.2b.3d.4f.5c.6d, | 1a.2b.3d.4f.5c.6e, | 1a.2b.3d.4f.5c.6f, | 1a.2b.3d.4f.5d.6a, | |
| 1a.2b.3d.4f.5d.6b, | 1a.2b.3d.4f.5d.6c, | 1a.2b.3d.4f.5d.6d, | 1a.2b.3d.4f.5d.6e, | |
| 1a.2b.3d.4f.5d.6f, | 1a.2b.3d.4f.5e.6a, | 1a.2b.3d.4f.5e.6b, | 1a.2b.3d.4f.5e.6c, | |
| 1a.2b.3d.4f.5e.6d, | 1a.2b.3d.4f.5e.6e, | 1a.2b.3d.4f.5e.6f, | 1a.2b.3d.4f.5f.6a, | |
| 1a.2b.3d.4f.5f.6b, | 1a.2b.3d.4f.5f.6c, | 1a.2b.3d.4f.5f.6d, | 1a.2b.3d.4f.5f.6e, | 1a.2b.3d.4f.5f.6f, |
| 1a.2b.3e.4a.5a.6a, | 1a.2b.3e.4a.5a.6b, | 1a.2b.3e.4a.5a.6c, | 1a.2b.3e.4a.5a.6d, | |
| 1a.2b.3e.4a.5a.6e, | 1a.2b.3e.4a.5a.6f, | 1a.2b.3e.4a.5b.6a, | 1a.2b.3e.4a.5b.6b, | |
| 1a.2b.3e.4a.5b.6c, | 1a.2b.3e.4a.5b.6d, | 1a.2b.3e.4a.5b.6e, | 1a.2b.3e.4a.5b.6f, | |
| 1a.2b.3e.4a.5c.6a, | 1a.2b.3e.4a.5c.6b, | 1a.2b.3e.4a.5c.6c, | 1a.2b.3e.4a.5c.6d, | |
| 1a.2b.3e.4a.5c.6e, | 1a.2b.3e.4a.5c.6f, | 1a.2b.3e.4a.5d.6a, | 1a.2b.3e.4a.5d.6b, | |
| 1a.2b.3e.4a.5d.6c, | 1a.2b.3e.4a.5d.6d, | 1a.2b.3e.4a.5d.6e, | 1a.2b.3e.4a.5d.6f, | |
| 1a.2b.3e.4a.5e.6a, | 1a.2b.3e.4a.5e.6b, | 1a.2b.3e.4a.5e.6c, | 1a.2b.3e.4a.5e.6d, | |
| 1a.2b.3e.4a.5e.6e, | 1a.2b.3e.4a.5e.6f, | 1a.2b.3e.4a.5f.6a, | 1a.2b.3e.4a.5f.6b, | |
| 1a.2b.3e.4a.5f.6c, | 1a.2b.3e.4a.5f.6d, | 1a.2b.3e.4a.5f.6e, | 1a.2b.3e.4a.5f.6f, | |
| 1a.2b.3e.4b.5a.6a, | 1a.2b.3e.4b.5a.6b, | 1a.2b.3e.4b.5a.6c, | 1a.2b.3e.4b.5a.6d, | |
| 1a.2b.3e.4b.5a.6e, | 1a.2b.3e.4b.5a.6f, | 1a.2b.3e.4b.5b.6a, | 1a.2b.3e.4b.5b.6b, | |
| 1a.2b.3e.4b.5b.6c, | 1a.2b.3e.4b.5b.6d, | 1a.2b.3e.4b.5b.6e, | 1a.2b.3e.4b.5b.6f, | |
| 1a.2b.3e.4b.5c.6a, | 1a.2b.3e.4b.5c.6b, | 1a.2b.3e.4b.5c.6c, | 1a.2b.3e.4b.5c.6d, | |
| 1a.2b.3e.4b.5c.6e, | 1a.2b.3e.4b.5c.6f, | 1a.2b.3e.4b.5d.6a, | 1a.2b.3e.4b.5d.6b, | |
| 1a.2b.3e.4b.5d.6c, | 1a.2b.3e.4b.5d.6d, | 1a.2b.3e.4b.5d.6e, | 1a.2b.3e.4b.5d.6f, | |
| 1a.2b.3e.4b.5e.6a, | 1a.2b.3e.4b.5e.6b, | 1a.2b.3e.4b.5e.6c, | 1a.2b.3e.4b.5e.6d, | |
| 1a.2b.3e.4b.5e.6e, | 1a.2b.3e.4b.5e.6f, | 1a.2b.3e.4b.5f.6a, | 1a.2b.3e.4b.5f.6b, | |
| 1a.2b.3e.4b.5f.6c, | 1a.2b.3e.4b.5f.6d, | 1a.2b.3e.4b.5f.6e, | 1a.2b.3e.4b.5f.6f, | |
| 1a.2b.3e.4c.5a.6a, | 1a.2b.3e.4c.5a.6b, | 1a.2b.3e.4c.5a.6c, | 1a.2b.3e.4c.5a.6d, | |
| 1a.2b.3e.4c.5a.6e, | 1a.2b.3e.4c.5a.6f, | 1a.2b.3e.4c.5b.6a, | 1a.2b.3e.4c.5b.6b, | |
| 1a.2b.3e.4c.5b.6c, | 1a.2b.3e.4c.5b.6d, | 1a.2b.3e.4c.5b.6e, | 1a.2b.3e.4c.5b.6f, | |
| 1a.2b.3e.4c.5c.6a, | 1a.2b.3e.4c.5c.6b, | 1a.2b.3e.4c.5c.6c, | 1a.2b.3e.4c.5c.6d, | |
| 1a.2b.3e.4c.5c.6e, | 1a.2b.3e.4c.5c.6f, | 1a.2b.3e.4c.5d.6a, | 1a.2b.3e.4c.5d.6b, | |
| 1a.2b.3e.4c.5d.6c, | 1a.2b.3e.4c.5d.6d, | 1a.2b.3e.4c.5d.6e, | 1a.2b.3e.4c.5d.6f, | |
| 1a.2b.3e.4c.5e.6a, | 1a.2b.3e.4c.5e.6b, | 1a.2b.3e.4c.5e.6c, | 1a.2b.3e.4c.5e.6d, | |
| 1a.2b.3e.4c.5e.6e, | 1a.2b.3e.4c.5e.6f, | 1a.2b.3e.4c.5f.6a, | 1a.2b.3e.4c.5f.6b, | 1a.2b.3e.4c.5f.6c, |
| 1a.2b.3e.4c.5f.6d, | 1a.2b.3e.4c.5f.6e, | 1a.2b.3e.4c.5f.6f, | 1a.2b.3e.4d.5a.6a, | |
| 1a.2b.3e.4d.5a.6b, | 1a.2b.3e.4d.5a.6c, | 1a.2b.3e.4d.5a.6d, | 1a.2b.3e.4d.5a.6e, | |
| 1a.2b.3e.4d.5a.6f, | 1a.2b.3e.4d.5b.6a, | 1a.2b.3e.4d.5b.6b, | 1a.2b.3e.4d.5b.6c, | |
| 1a.2b.3e.4d.5b.6d, | 1a.2b.3e.4d.5b.6e, | 1a.2b.3e.4d.5b.6f, | 1a.2b.3e.4d.5c.6a, | |
| 1a.2b.3e.4d.5c.6b, | 1a.2b.3e.4d.5c.6c, | 1a.2b.3e.4d.5c.6d, | 1a.2b.3e.4d.5c.6e, | |
| 1a.2b.3e.4d.5c.6f, | 1a.2b.3e.4d.5d.6a, | 1a.2b.3e.4d.5d.6b, | 1a.2b.3e.4d.5d.6c, | |
| 1a.2b.3e.4d.5d.6d, | 1a.2b.3e.4d.5d.6e, | 1a.2b.3e.4d.5d.6f, | 1a.2b.3e.4d.5e.6a, | |
| 1a.2b.3e.4d.5e.6b, | 1a.2b.3e.4d.5e.6c, | 1a.2b.3e.4d.5e.6d, | 1a.2b.3e.4d.5e.6e, | |
| 1a.2b.3e.4d.5e.6f, | 1a.2b.3e.4d.5f.6a, | 1a.2b.3e.4d.5f.6b, | 1a.2b.3e.4d.5f.6c, | |
| 1a.2b.3e.4d.5f.6d, | 1a.2b.3e.4d.5f.6e, | 1a.2b.3e.4d.5f.6f, | 1a.2b.3e.4e.5a.6a, | |
| 1a.2b.3e.4e.5a.6b, | 1a.2b.3e.4e.5a.6c, | 1a.2b.3e.4e.5a.6d, | 1a.2b.3e.4e.5a.6e, | |
| 1a.2b.3e.4e.5a.6f, | 1a.2b.3e.4e.5b.6a, | 1a.2b.3e.4e.5b.6b, | 1a.2b.3e.4e.5b.6c, | |
| 1a.2b.3e.4e.5b.6d, | 1a.2b.3e.4e.5b.6e, | 1a.2b.3e.4e.5b.6f, | 1a.2b.3e.4e.5c.6a, | |
| 1a.2b.3e.4e.5c.6b, | 1a.2b.3e.4e.5c.6c, | 1a.2b.3e.4e.5c.6d, | 1a.2b.3e.4e.5c.6e, | |
| 1a.2b.3e.4e.5c.6f, | 1a.2b.3e.4e.5d.6a, | 1a.2b.3e.4e.5d.6b, | 1a.2b.3e.4e.5d.6c, | |
| 1a.2b.3e.4e.5d.6d, | 1a.2b.3e.4e.5d.6e, | 1a.2b.3e.4e.5d.6f, | 1a.2b.3e.4e.5e.6a, | |
| 1a.2b.3e.4e.5e.6b, | 1a.2b.3e.4e.5e.6c, | 1a.2b.3e.4e.5e.6d, | 1a.2b.3e.4e.5e.6e, | |
| 1a.2b.3e.4e.5e.6f, | 1a.2b.3e.4e.5f.6a, | 1a.2b.3e.4e.5f.6b, | 1a.2b.3e.4e.5f.6c, | 1a.2b.3e.4e.5f.6d, |
| 1a.2b.3e.4e.5f.6e, | 1a.2b.3e.4e.5f.6f, | 1a.2b.3e.4f.5a.6a, | 1a.2b.3e.4f.5a.6b, | 1a.2b.3e.4f.5a.6c, |
| 1a.2b.3e.4f.5a.6d, | 1a.2b.3e.4f.5a.6e, | 1a.2b.3e.4f.5a.6f, | 1a.2b.3e.4f.5b.6a, | |
| 1a.2b.3e.4f.5b.6b, | 1a.2b.3e.4f.5b.6c, | 1a.2b.3e.4f.5b.6d, | 1a.2b.3e.4f.5b.6e, | |
| 1a.2b.3e.4f.5b.6f, | 1a.2b.3e.4f.5c.6a, | 1a.2b.3e.4f.5c.6b, | 1a.2b.3e.4f.5c.6c, | 1a.2b.3e.4f.5c.6d, |
| 1a.2b.3e.4f.5c.6e, | 1a.2b.3e.4f.5c.6f, | 1a.2b.3e.4f.5d.6a, | 1a.2b.3e.4f.5d.6b, | 1a.2b.3e.4f.5d.6c, |
| 1a.2b.3e.4f.5d.6d, | 1a.2b.3e.4f.5d.6e, | 1a.2b.3e.4f.5d.6f, | 1a.2b.3e.4f.5e.6a, | |
| 1a.2b.3e.4f.5e.6b, | 1a.2b.3e.4f.5e.6c, | 1a.2b.3e.4f.5e.6d, | 1a.2b.3e.4f.5e.6e, | 1a.2b.3e.4f.5e.6f, |
| 1a.2b.3e.4f.5f.6a, | 1a.2b.3e.4f.5f.6b, | 1a.2b.3e.4f.5f.6c, | 1a.2b.3e.4f.5f.6d, | 1a.2b.3e.4f.5f.6e, |
| 1a.2b.3e.4f.5f.6f, | 1a.2b.3f.4a.5a.6a, | 1a.2b.3f.4a.5a.6b, | 1a.2b.3f.4a.5a.6c, | 1a.2b.3f.4a.5a.6d, |
| 1a.2b.3f.4a.5a.6e, | 1a.2b.3f.4a.5a.6f, | 1a.2b.3f.4a.5b.6a, | 1a.2b.3f.4a.5b.6b, | |
| 1a.2b.3f.4a.5b.6c, | 1a.2b.3f.4a.5b.6d, | 1a.2b.3f.4a.5b.6e, | 1a.2b.3f.4a.5b.6f, | |
| 1a.2b.3f.4a.5c.6a, | 1a.2b.3f.4a.5c.6b, | 1a.2b.3f.4a.5c.6c, | 1a.2b.3f.4a.5c.6d, | 1a.2b.3f.4a.5c.6e, |
| 1a.2b.3f.4a.5c.6f, | 1a.2b.3f.4a.5d.6a, | 1a.2b.3f.4a.5d.6b, | 1a.2b.3f.4a.5d.6c, | |
| 1a.2b.3f.4a.5d.6d, | 1a.2b.3f.4a.5d.6e, | 1a.2b.3f.4a.5d.6f, | 1a.2b.3f.4a.5e.6a, | |

TABLE 7-continued

List of Compounds of Formula (II)

| | | | | |
|---|---|---|---|---|
| 1a.2b.3f.4a.5e.6b, | 1a.2b.3f.4a.5e.6c, | 1a.2b.3f.4a.5e.6d, | 1a.2b.3f.4a.5e.6e, | 1a.2b.3f.4a.5e.6f, |
| 1a.2b.3f.4a.5f.6a, | 1a.2b.3f.4a.5f.6b, | 1a.2b.3f.4a.5f.6c, | 1a.2b.3f.4a.5f.6d, | 1a.2b.3f.4a.5f.6e, |
| 1a.2b.3f.4a.5f.6f, | 1a.2b.3f.4b.5a.6a, | 1a.2b.3f.4b.5a.6b, | 1a.2b.3f.4b.5a.6c, | |
| 1a.2b.3f.4b.5a.6d, | 1a.2b.3f.4b.5a.6e, | 1a.2b.3f.4b.5a.6f, | 1a.2b.3f.4b.5b.6a, | |
| 1a.2b.3f.4b.5b.6b, | 1a.2b.3f.4b.5b.6c, | 1a.2b.3f.4b.5b.6d, | 1a.2b.3f.4b.5b.6e, | |
| 1a.2b.3f.4b.5b.6f, | 1a.2b.3f.4b.5c.6a, | 1a.2b.3f.4b.5c.6b, | 1a.2b.3f.4b.5c.6c, | |
| 1a.2b.3f.4b.5c.6d, | 1a.2b.3f.4b.5c.6e, | 1a.2b.3f.4b.5c.6f, | 1a.2b.3f.4b.5d.6a, | |
| 1a.2b.3f.4b.5d.6b, | 1a.2b.3f.4b.5d.6c, | 1a.2b.3f.4b.5d.6d, | 1a.2b.3f.4b.5d.6e, | |
| 1a.2b.3f.4b.5d.6f, | 1a.2b.3f.4b.5e.6a, | 1a.2b.3f.4b.5e.6b, | 1a.2b.3f.4b.5e.6c, | |
| 1a.2b.3f.4b.5e.6d, | 1a.2b.3f.4b.5e.6e, | 1a.2b.3f.4b.5e.6f, | 1a.2b.3f.4b.5f.6a, | 1a.2b.3f.4b.5f.6b, |
| 1a.2b.3f.4b.5f.6c, | 1a.2b.3f.4b.5f.6d, | 1a.2b.3f.4b.5f.6e, | 1a.2b.3f.4b.5f.6f, | 1a.2b.3f.4c.5a.6a, |
| 1a.2b.3f.4c.5a.6b, | 1a.2b.3f.4c.5a.6c, | 1a.2b.3f.4c.5a.6d, | 1a.2b.3f.4c.5a.6e, | 1a.2b.3f.4c.5a.6f, |
| 1a.2b.3f.4c.5b.6a, | 1a.2b.3f.4c.5b.6b, | 1a.2b.3f.4c.5b.6c, | 1a.2b.3f.4c.5b.6d, | |
| 1a.2b.3f.4c.5b.6e, | 1a.2b.3f.4c.5b.6f, | 1a.2b.3f.4c.5c.6a, | 1a.2b.3f.4c.5c.6b, | 1a.2b.3f.4c.5c.6c, |
| 1a.2b.3f.4c.5c.6d, | 1a.2b.3f.4c.5c.6e, | 1a.2b.3f.4c.5c.6f, | 1a.2b.3f.4c.5d.6a, | 1a.2b.3f.4c.5d.6b, |
| 1a.2b.3f.4c.5d.6c, | 1a.2b.3f.4c.5d.6d, | 1a.2b.3f.4c.5d.6e, | 1a.2b.3f.4c.5d.6f, | |
| 1a.2b.3f.4c.5e.6a, | 1a.2b.3f.4c.5e.6b, | 1a.2b.3f.4c.5e.6c, | 1a.2b.3f.4c.5e.6d, | 1a.2b.3f.4c.5e.6e, |
| 1a.2b.3f.4c.5e.6f, | 1a.2b.3f.4c.5f.6a, | 1a.2b.3f.4c.5f.6b, | 1a.2b.3f.4c.5f.6c, | 1a.2b.3f.4c.5f.6d, |
| 1a.2b.3f.4c.5f.6e, | 1a.2b.3f.4c.5f.6f, | 1a.2b.3f.4d.5a.6a, | 1a.2b.3f.4d.5a.6b, | 1a.2b.3f.4d.5a.6c, |
| 1a.2b.3f.4d.5a.6d, | 1a.2b.3f.4d.5a.6e, | 1a.2b.3f.4d.5a.6f, | 1a.2b.3f.4d.5b.6a, | |
| 1a.2b.3f.4d.5b.6b, | 1a.2b.3f.4d.b.6c, | 1a.2b.3f.4d.5b.6d, | 1a.2b.3f.4d.5b.6e, | |
| 1a.2b.3f.4d.5b.6f, | 1a.2b.3f.4d.5c.6a, | 1a.2b.3f.4d.5c.6b, | 1a.2b.3f.4d.5c.6c, | |
| 1a.2b.3f.4d.5c.6d, | 1a.2b.3f.4d.5c.6e, | 1a.2b.3f.4d.5c.6f, | 1a.2b.3f.4d.5d.6a, | |
| 1a.2b.3f.4d.5d.6b, | 1a.2b.3f.4d.5d.6c, | 1a.2b.3f.4d.5d.6d, | 1a.2b.3f.4d.5d.6e, | |
| 1a.2b.3f.4d.5d.6f, | 1a.2b.3f.4d.5e.6a, | 1a.2b.3f.4d.5e.6b, | 1a.2b.3f.4d.5e.6c, | |
| 1a.2b.3f.4d.5e.6d, | 1a.2b.3f.4d.5e.6e, | 1a.2b.3f.4d.5e.6f, | 1a.2b.3f.4d.5f.6a, | |
| 1a.2b.3f.4d.5f.6b, | 1a.2b.3f.4d.5f.6c, | 1a.2b.3f.4d.5f.6d, | 1a.2b.3f.4d.5f.6e, | 1a.2b.3f.4d.5f.6f, |
| 1a.2b.3f.4e.5a.6a, | 1a.2b.3f.4e.5a.6b, | 1a.2b.3f.4e.5a.6c, | 1a.2b.3f.4e.5a.6d, | |
| 1a.2b.3f.4e.5a.6e, | 1a.2b.3f.4e.5a.6f, | 1a.2b.3f.4e.5b.6a, | 1a.2b.3f.4e.5b.6b, | 1a.2b.3f.4e.5b.6c, |
| 1a.2b.3f.4e.5b.6d, | 1a.2b.3f.4e.5b.6e, | 1a.2b.3f.4e.5b.6f, | 1a.2b.3f.4e.5c.6a, | 1a.2b.3f.4e.5c.6b, |
| 1a.2b.3f.4e.5c.6c, | 1a.2b.3f.4e.5c.6d, | 1a.2b.3f.4e.5c.6e, | 1a.2b.3f.4e.5c.6f, | 1a.2b.3f.4e.5d.6a, |
| 1a.2b.3f.4e.5d.6b, | 1a.2b.3f.4e.5d.6c, | 1a.2b.3f.4e.5d.6d, | 1a.2b.3f.4e.5d.6e, | |
| 1a.2b.3f.4e.5d.6f, | 1a.2b.3f.4e.5e.6a, | 1a.2b.3f.4e.5e.6b, | 1a.2b.3f.4e.5e.6c, | 1a.2b.3f.4e.5e.6d, |
| 1a.2b.3f.4e.5e.6e, | 1a.2b.3f.4e.5e.6f, | 1a.2b.3f.4e.5f.6a, | 1a.2b.3f.4e.5f.6b, | 1a.2b.3f.4e.5f.6c, |
| 1a.2b.3f.4e.5f.6d, | 1a.2b.3f.4e.5f.6e, | 1a.2b.3f.4e.5f.6f, | 1a.2b.3f.4f.5a.6a, | 1a.2b.3f.4f.5a.6b, |
| 1a.2b.3f.4f.5a.6c, | 1a.2b.3f.4f.5a.6d, | 1a.2b.3f.4f.5a.6e, | 1a.2b.3f.4f.5a.6f, | 1a.2b.3f.4f.5b.6a, |
| 1a.2b.3f.4f.5b.6b, | 1a.2b.3f.4f.5b.6c, | 1a.2b.3f.4f.5b.6d, | 1a.2b.3f.4f.5b.6e, | 1a.2b.3f.4f.5b.6f, |
| 1a.2b.3f.4f.5c.6a, | 1a.2b.3f.4f.5c.6b, | 1a.2b.3f.4f.5c.6c, | 1a.2b.3f.4f.5c.6d, | 1a.2b.3f.4f.5c.6e, |
| 1a.2b.3f.4f.5c.6f, | 1a.2b.3f.4f.5d.6a, | 1a.2b.3f.4f.5d.6b, | 1a.2b.3f.4f.5d.6c, | 1a.2b.3f.4f.5d.6d, |
| 1a.2b.3f.4f.5d.6e, | 1a.2b.3f.4f.5d.6f, | 1a.2b.3f.4f.5e.6a, | 1a.2b.3f.4f.5e.6b, | 1a.2b.3f.4f.5e.6c, |
| 1a.2b.3f.4f.5e.6d, | 1a.2b.3f.4f.5e.6e, | 1a.2b.3f.4f.5e.6f, | 1a.2b.3f.4f.5f.6a, | 1a.2b.3f.4f.5f.6b, |
| 1a.2b.3f.4f.5f.6c, | 1a.2b.3f.4f.5f.6d, | 1a.2b.3f.4f.5f.6e, | 1a.2b.3f.4f.5f.6f, | 1a.2c.3a.4a.5a.6a, |
| 1a.2c.3a.4a.5a.6b, | 1a.2c.3a.4a.5a.6c, | 1a.2c.3a.4a.5a.6d, | 1a.2c.3a.4a.5a.6e, | |
| 1a.2c.3a.4a.5a.6f, | 1a.2c.3a.4a.5b.6a, | 1a.2c.3a.4a.5b.6b, | 1a.2c.3a.4a.5b.6c, | |
| 1a.2c.3a.4a.5b.6d, | 1a.2c.3a.4a.5b.6e, | 1a.2c.3a.4a.5b.6f, | 1a.2c.3a.4a.5c.6a, | |
| 1a.2c.3a.4a.5c.6b, | 1a.2c.3a.4a.5c.6c, | 1a.2c.3a.4a.5c.6d, | 1a.2c.3a.4a.5c.6e, | 1a.2c.3a.4a.5c.6f, |
| 1a.2c.3a.4a.5d.6a, | 1a.2c.3a.4a.5d.6b, | 1a.2c.3a.4a.5d.6c, | 1a.2c.3a.4a.5d.6d, | |
| 1a.2c.3a.4a.5d.6e, | 1a.2c.3a.4a.5d.6f, | 1a.2c.3a.4a.5e.6a, | 1a.2c.3a.4a.5e.6b, | |
| 1a.2c.3a.4a.5e.6c, | 1a.2c.3a.4a.5e.6d, | 1a.2c.3a.4a.5e.6e, | 1a.2c.3a.4a.5e.6f, | 1a.2c.3a.4a.5f.6a, |
| 1a.2c.3a.4a.5f.6b, | 1a.2c.3a.4a.5f.6c, | 1a.2c.3a.4a.5f.6d, | 1a.2c.3a.4a.5f.6e, | 1a.2c.3a.4a.5f.6f, |
| 1a.2c.3a.4b.5a.6a, | 1a.2c.3a.4b.5a.6b, | 1a.2c.3a.4b.5a.6c, | 1a.2c.3a.4b.5a.6d, | |
| 1a.2c.3a.4b.5a.6e, | 1a.2c.3a.4b.5a.6f, | 1a.2c.3a.4b.5b.6a, | 1a.2c.3a.4b.5b.6b, | |
| 1a.2c.3a.4b.5b.6c, | 1a.2c.3a.4b.5b.6d, | 1a.2c.3a.4b.5b.6e, | 1a.2c.3a.4b.5b.6f, | |
| 1a.2c.3a.4b.5c.6a, | 1a.2c.3a.4b.5c.6b, | 1a.2c.3a.4b.5c.6c, | 1a.2c.3a.4b.5c.6d, | |
| 1a.2c.3a.4b.5c.6e, | 1a.2c.3a.4b.5c.6f, | 1a.2c.3a.4b.5d.6a, | 1a.2c.3a.4b.5d.6b, | |
| 1a.2c.3a.4b.5d.6c, | 1a.2c.3a.4b.5d.6d, | 1a.2c.3a.4b.5d.6e, | 1a.2c.3a.4b.5d.6f, | |
| 1a.2c.3a.4b.5e.6a, | 1a.2c.3a.4b.5e.6b, | 1a.2c.3a.4b.5e.6c, | 1a.2c.3a.4b.5e.6d, | |
| 1a.2c.3a.4b.5e.6e, | 1a.2c.3a.4b.5e.6f, | 1a.2c.3a.4b.5f.6a, | 1a.2c.3a.4b.5f.6b, | 1a.2c.3a.4b.5f.6c, |
| 1a.2c.3a.4b.5f.6d, | 1a.2c.3a.4b.5f.6e, | 1a.2c.3a.4b.5f.6f, | 1a.2c.3a.4c.5a.6a, | 1a.2c.3a.4c.5a.6b, |
| 1a.2c.3a.4c.5a.6c, | 1a.2c.3a.4c.5a.6d, | 1a.2c.3a.4c.5a.6e, | 1a.2c.3a.4c.5a.6f, | 1a.2c.3a.4c.5b.6a, |
| 1a.2c.3a.4c.5b.6b, | 1a.2c.3a.4c.5b.6c, | 1a.2c.3a.4c.5b.6d, | 1a.2c.3a.4c.5b.6e, | |
| 1a.2c.3a.4c.5b.6f, | 1a.2c.3a.4c.5c.6a, | 1a.2c.3a.4c.5c.6b, | 1a.2c.3a.4c.5c.6c, | 1a.2c.3a.4c.5c.6d, |
| 1a.2c.3a.4c.5c.6e, | 1a.2c.3a.4c.5c.6f, | 1a.2c.3a.4c.5d.6a, | 1a.2c.3a.4c.5d.6b, | |
| 1a.2c.3a.4c.5d.6c, | 1a.2c.3a.4c.5d.6d, | 1a.2c.3a.4c.5d.6e, | 1a.2c.3a.4c.5d.6f, | |
| 1a.2c.3a.4c.5e.6a, | 1a.2c.3a.4c.5e.6b, | 1a.2c.3a.4c.5e.6c, | 1a.2c.3a.4c.5e.6d, | |
| 1a.2c.3a.4c.5e.6e, | 1a.2c.3a.4c.5e.6f, | 1a.2c.3a.4c.5f.6a, | 1a.2c.3a.4c.5f.6b, | 1a.2c.3a.4c.5f.6c, |
| 1a.2c.3a.4c.5f.6d, | 1a.2c.3a.4c.5f.6e, | 1a.2c.3a.4c.5f.6f, | 1a.2c.3a.4d.5a.6a, | 1a.2c.3a.4d.5a.6b, |
| 1a.2c.3a.4d.5a.6c, | 1a.2c.3a.4d.5a.6d, | 1a.2c.3a.4d.5a.6e, | 1a.2c.3a.4d.5a.6f, | |
| 1a.2c.3a.4d.5b.6a, | 1a.2c.3a.4d.5b.6b, | 1a.2c.3a.4d.5b.6c, | 1a.2c.3a.4d.5b.6d, | |
| 1a.2c.3a.4d.5b.6e, | 1a.2c.3a.4d.5b.6f, | 1a.2c.3a.4d.5c.6a, | 1a.2c.3a.4d.5c.6b, | |
| 1a.2c.3a.4d.5c.6c, | 1a.2c.3a.4d.5c.6d, | 1a.2c.3a.4d.5c.6e, | 1a.2c.3a.4d.5c.6f, | |
| 1a.2c.3a.4d.5d.6a, | 1a.2c.3a.4d.5d.6b, | 1a.2c.3a.4d.5d.6c, | 1a.2c.3a.4d.5d.6d, | |
| 1a.2c.3a.4d.5d.6e, | 1a.2c.3a.4d.5d.6f, | 1a.2c.3a.4d.5e.6a, | 1a.2c.3a.4d.5e.6b, | |
| 1a.2c.3a.4d.5e.6c, | 1a.2c.3a.4d.5e.6d, | 1a.2c.3a.4d.5e.6e, | 1a.2c.3a.4d.5e.6f, | |
| 1a.2c.3a.4d.5f.6a, | 1a.2c.3a.4d.5f.6b, | 1a.2c.3a.4d.5f.6c, | 1a.2c.3a.4d.5f.6d, | |
| 1a.2c.3a.4d.5f.6e, | 1a.2c.3a.4d.5f.6f, | 1a.2c.3a.4e.5a.6a, | 1a.2c.3a.4e.5a.6b, | 1a.2c.3a.4e.5a.6c, |
| 1a.2c.3a.4e.5a.6d, | 1a.2c.3a.4e.5a.6e, | 1a.2c.3a.4e.5a.6f, | 1a.2c.3a.4e.5b.6a, | |
| 1a.2c.3a.4e.5b.6b, | 1a.2c.3a.4e.5b.6c, | 1a.2c.3a.4e.5b.6d, | 1a.2c.3a.4e.5b.6e, | |

TABLE 7-continued

List of Compounds of Formula (II)

| | | | | |
|---|---|---|---|---|
| 1a.2c.3a.4e.5b.6f, | 1a.2c.3a.4e.5c.6a, | 1a.2c.3a.4e.5c.6b, | 1a.2c.3a.4e.5c.6c, | |
| 1a.2c.3a.4e.5c.6d, | 1a.2c.3a.4e.5c.6e, | 1a.2c.3a.4e.5c.6f, | 1a.2c.3a.4e.5d.6a, | |
| 1a.2c.3a.4e.5d.6b, | 1a.2c.3a.4e.5d.6c, | 1a.2c.3a.4e.5d.6d, | 1a.2c.3a.4e.5d.6e, | |
| 1a.2c.3a.4e.5d.6f, | 1a.2c.3a.4e.5e.6a, | 1a.2c.3a.4e.5e.6b, | 1a.2c.3a.4e.5e.6c, | |
| 1a.2c.3a.4e.5e.6d, | 1a.2c.3a.4e.5e.6e, | 1a.2c.3a.4e.5e.6f, | 1a.2c.3a.4e.5f.6a, | 1a.2c.3a.4e.5f.6b, |
| 1a.2c.3a.4e.5f.6c, | 1a.2c.3a.4e.5f.6d, | 1a.2c.3a.4e.5f.6e, | 1a.2c.3a.4e.5f.6f, | 1a.2c.3a.4f.5a.6a, |
| 1a.2c.3a.4f.5a.6b, | 1a.2c.3a.4f.5a.6c, | 1a.2c.3a.4f.5a.6d, | 1a.2c.3a.4f.5a.6e, | 1a.2c.3a.4f.5a.6f, |
| 1a.2c.3a.4f.5b.6a, | 1a.2c.3a.4f.5b.6b, | 1a.2c.3a.4f.5b.6c, | 1a.2c.3a.4f.5b.6d, | 1a.2c.3a.4f.5b.6e, |
| 1a.2c.3a.4f.5b.6f, | 1a.2c.3a.4f.5c.6a, | 1a.2c.3a.4f.5c.6b, | 1a.2c.3a.4f.5c.6c, | 1a.2c.3a.4f.5c.6d, |
| 1a.2c.3a.4f.5c.6e, | 1a.2c.3a.4f.5c.6f, | 1a.2c.3a.4f.5d.6a, | 1a.2c.3a.4f.5d.6b, | 1a.2c.3a.4f.5d.6c, |
| 1a.2c.3a.4f.5d.6d, | 1a.2c.3a.4f.5d.6e, | 1a.2c.3a.4f.5d.6f, | 1a.2c.3a.4f.5e.6a, | 1a.2c.3a.4f.5e.6b, |
| 1a.2c.3a.4f.5e.6c, | 1a.2c.3a.4f.5e.6d, | 1a.2c.3a.4f.5e.6e, | 1a.2c.3a.4f.5e.6f, | 1a.2c.3a.4f.5f.6a, |
| 1a.2c.3a.4f.5f.6b, | 1a.2c.3a.4f.5f.6c, | 1a.2c.3a.4f.5f.6d, | 1a.2c.3a.4f.5f.6e, | 1a.2c.3a.4f.5f.6f, |
| 1a.2c.3b.4a.5a.6a, | 1a.2c.3b.4a.5a.6b, | 1a.2c.3b.4a.5a.6c, | 1a.2c.3b.4a.5a.6d, | |
| 1a.2c.3b.4a.5a.6e, | 1a.2c.3b.4a.5a.6f, | 1a.2c.3b.4a.5b.6a, | 1a.2c.3b.4a.5b.6b, | |
| 1a.2c.3b.4a.5b.6c, | 1a.2c.3b.4a.5b.6d, | 1a.2c.3b.4a.5b.6e, | 1a.2c.3b.4a.5b.6f, | |
| 1a.2c.3b.4a.5c.6a, | 1a.2c.3b.4a.5c.6b, | 1a.2c.3b.4a.5c.6c, | 1a.2c.3b.4a.5c.6d, | |
| 1a.2c.3b.4a.5c.6e, | 1a.2c.3b.4a.5c.6f, | 1a.2c.3b.4a.5d.6a, | 1a.2c.3b.4a.5d.6b, | |
| 1a.2c.3b.4a.5d.6c, | 1a.2c.3b.4a.5d.6d, | 1a.2c.3b.4a.5d.6e, | 1a.2c.3b.4a.5d.6f, | |
| 1a.2c.3b.4a.5e.6a, | 1a.2c.3b.4a.5e.6b, | 1a.2c.3b.4a.5e.6c, | 1a.2c.3b.4a.5e.6d, | |
| 1a.2c.3b.4a.5e.6e, | 1a.2c.3b.4a.5e.6f, | 1a.2c.3b.4a.5f.6a, | 1a.2c.3b.4a.5f.6b, | 1a.2c.3b.4a.5f.6c, |
| 1a.2c.3b.4a.5f.6d, | 1a.2c.3b.4a.5f.6e, | 1a.2c.3b.4a.5f.6f, | 1a.2c.3b.4b.5a.6a, | |
| 1a.2c.3b.4b.5a.6b, | 1a.2c.3b.4b.5a.6c, | 1a.2c.3b.4b.5a.6d, | 1a.2c.3b.4b.5a.6e, | |
| 1a.2c.3b.4b.5a.6f, | 1a.2c.3b.4b.5b.6a, | 1a.2c.3b.4b.5b.6b, | 1a.2c.3b.4b.5b.6c, | |
| 1a.2c.3b.4b.5b.6d, | 1a.2c.3b.4b.5b.6e, | 1a.2c.3b.4b.5b.6f, | 1a.2c.3b.4b.5c.6a, | |
| 1a.2c.3b.4b.5c.6b, | 1a.2c.3b.4b.5c.6c, | 1a.2c.3b.4b.5c.6d, | 1a.2c.3b.4b.5c.6e, | |
| 1a.2c.3b.4b.5c.6f, | 1a.2c.3b.4b.5d.6a, | 1a.2c.3b.4b.5d.6b, | 1a.2c.3b.4b.5d.6c, | |
| 1a.2c.3b.4b.5d.6d, | 1a.2c.3b.4b.5d.6e, | 1a.2c.3b.4b.5d.6f, | 1a.2c.3b.4b.5e.6a, | |
| 1a.2c.3b.4b.5e.6b, | 1a.2c.3b.4b.5e.6c, | 1a.2c.3b.4b.5e.6d, | 1a.2c.3b.4b.5e.6e, | |
| 1a.2c.3b.4b.5e.6f, | 1a.2c.3b.4b.5f.6a, | 1a.2c.3b.4b.5f.6b, | 1a.2c.3b.4b.5f.6c, | |
| 1a.2c.3b.4b.5f.6d, | 1a.2c.3b.4b.5f.6e, | 1a.2c.3b.4b.5f.6f, | 1a.2c.3b.4c.5a.6a, | |
| 1a.2c.3b.4c.5a.6b, | 1a.2c.3b.4c.5a.6c, | 1a.2c.3b.4c.5a.6d, | 1a.2c.3b.4c.5a.6e, | |
| 1a.2c.3b.4c.5a.6f, | 1a.2c.3b.4c.5b.6a, | 1a.2c.3b.4c.5b.6b, | 1a.2c.3b.4c.5b.6c, | |
| 1a.2c.3b.4c.5b.6d, | 1a.2c.3b.4c.5b.6e, | 1a.2c.3b.4c.5b.6f, | 1a.2c.3b.4c.5c.6a, | |
| 1a.2c.3b.4c.5c.6b, | 1a.2c.3b.4c.5c.6c, | 1a.2c.3b.4c.5c.6d, | 1a.2c.3b.4c.5c.6e, | 1a.2c.3b.4c.5c.6f, |
| 1a.2c.3b.4c.5d.6a, | 1a.2c.3b.4c.5d.6b, | 1a.2c.3b.4c.5d.6c, | 1a.2c.3b.4c.5d.6d, | |
| 1a.2c.3b.4c.5d.6e, | 1a.2c.3b.4c.5d.6f, | 1a.2c.3b.4c.5e.6a, | 1a.2c.3b.4c.5e.6b, | |
| 1a.2c.3b.4c.5e.6c, | 1a.2c.3b.4c.5e.6d, | 1a.2c.3b.4c.5e.6e, | 1a.2c.3b.4c.5e.6f, | 1a.2c.3b.4c.5f.6a, |
| 1a.2c.3b.4c.5f.6b, | 1a.2c.3b.4c.5f.6c, | 1a.2c.3b.4c.5f.6d, | 1a.2c.3b.4c.5f.6e, | 1a.2c.3b.4c.5f.6f, |
| 1a.2c.3b.4d.5a.6a, | 1a.2c.3b.4d.5a.6b, | 1a.2c.3b.4d.5a.6c, | 1a.2c.3b.4d.5a.6d, | |
| 1a.2c.3b.4d.5a.6e, | 1a.2c.3b.4d.5a.6f, | 1a.2c.3b.4d.5b.6a, | 1a.2c.3b.4d.5b.6b, | |
| 1a.2c.3b.4d.5b.6c, | 1a.2c.3b.4d.5b.6d, | 1a.2c.3b.4d.5b.6e, | 1a.2c.3b.4d.5b.6f, | |
| 1a.2c.3b.4d.5c.6a, | 1a.2c.3b.4d.5c.6b, | 1a.2c.3b.4d.5c.6c, | 1a.2c.3b.4d.5c.6d, | |
| 1a.2c.3b.4d.5c.6e, | 1a.2c.3b.4d.5c.6f, | 1a.2c.3b.4d.5d.6a, | 1a.2c.3b.4d.5d.6b, | |
| 1a.2c.3b.4d.5d.6c, | 1a.2c.3b.4d.5d.6d, | 1a.2c.3b.4d.5d.6e, | 1a.2c.3b.4d.5d.6f, | |
| 1a.2c.3b.4d.5e.6a, | 1a.2c.3b.4d.5e.6b, | 1a.2c.3b.4d.5e.6c, | 1a.2c.3b.4d.5e.6d, | |
| 1a.2c.3b.4d.5e.6e, | 1a.2c.3b.4d.5e.6f, | 1a.2c.3b.4d.5f.6a, | 1a.2c.3b.4d.5f.6b, | |
| 1a.2c.3b.4d.5f.6c, | 1a.2c.3b.4d.5f.6d, | 1a.2c.3b.4d.5f.6e, | 1a.2c.3b.4d.5f.6f, | |
| 1a.2c.3b.4e.5a.6a, | 1a.2c.3b.4e.5a.6b, | 1a.2c.3b.4e.5a.6c, | 1a.2c.3b.4e.5a.6d, | |
| 1a.2c.3b.4e.5a.6e, | 1a.2c.3b.4e.5a.6f, | 1a.2c.3b.4e.5b.6a, | 1a.2c.3b.4e.5b.6b, | |
| 1a.2c.3b.4e.5b.6c, | 1a.2c.3b.4e.5b.6d, | 1a.2c.3b.4e.5b.6e, | 1a.2c.3b.4e.5b.6f, | |
| 1a.2c.3b.4e.5c.6a, | 1a.2c.3b.4e.5c.6b, | 1a.2c.3b.4e.5c.6c, | 1a.2c.3b.4e.5c.6d, | |
| 1a.2c.3b.4e.5c.6e, | 1a.2c.3b.4e.5c.6f, | 1a.2c.3b.4e.5d.6a, | 1a.2c.3b.4e.5d.6b, | |
| 1a.2c.3b.4e.5d.6c, | 1a.2c.3b.4e.5d.6d, | 1a.2c.3b.4e.5d.6e, | 1a.2c.3b.4e.5d.6f, | |
| 1a.2c.3b.4e.5e.6a, | 1a.2c.3b.4e.5e.6b, | 1a.2c.3b.4e.5e.6c, | 1a.2c.3b.4e.5e.6d, | |
| 1a.2c.3b.4e.5e.6e, | 1a.2c.3b.4e.5e.6f, | 1a.2c.3b.4e.5f.6a, | 1a.2c.3b.4e.5f.6b, | 1a.2c.3b.4e.5f.6c, |
| 1a.2c.3b.4e.5f.6d, | 1a.2c.3b.4e.5f.6e, | 1a.2c.3b.4e.5f.6f, | 1a.2c.3b.4f.5a.6a, | 1a.2c.3b.4f.5a.6b, |
| 1a.2c.3b.4f.5a.6c, | 1a.2c.3b.4f.5a.6d, | 1a.2c.3b.4f.5a.6e, | 1a.2c.3b.4f.5a.6f, | 1a.2c.3b.4f.5b.6a, |
| 1a.2c.3b.4f.5b.6b, | 1a.2c.3b.4f.5b.6c, | 1a.2c.3b.4f.5b.6d, | 1a.2c.3b.4f.5b.6e, | 1a.2c.3b.4f.5b.6f, |
| 1a.2c.3b.4f.5c.6a, | 1a.2c.3b.4f.5c.6b, | 1a.2c.3b.4f.5c.6c, | 1a.2c.3b.4f.5c.6d, | 1a.2c.3b.4f.5c.6e, |
| 1a.2c.3b.4f.5c.6f, | 1a.2c.3b.4f.5d.6a, | 1a.2c.3b.4f.5d.6b, | 1a.2c.3b.4f.5d.6c, | |
| 1a.2c.3b.4f.5d.6d, | 1a.2c.3b.4f.5d.6e, | 1a.2c.3b.4f.5d.6f, | 1a.2c.3b.4f.5e.6a, | |
| 1a.2c.3b.4f.5e.6b, | 1a.2c.3b.4f.5e.6c, | 1a.2c.3b.4f.5e.6d, | 1a.2c.3b.4f.5e.6e, | 1a.2c.3b.4f.5e.6f, |
| 1a.2c.3b.4f.5f.6a, | 1a.2c.3b.4f.5f.6b, | 1a.2c.3b.4f.5f.6c, | 1a.2c.3b.4f.5f.6d, | 1a.2c.3b.4f.5f.6e, |
| 1a.2c.3b.4f.5f.6f, | 1a.2c.3c.4a.5a.6a, | 1a.2c.3c.4a.5a.6b, | 1a.2c.3c.4a.5a.6c, | 1a.2c.3c.4a.5a.6d, |
| 1a.2c.3c.4a.5a.6e, | 1a.2c.3c.4a.5a.6f, | 1a.2c.3c.4a.5b.6a, | 1a.2c.3c.4a.5b.6b, | |
| 1a.2c.3c.4a.5b.6c, | 1a.2c.3c.4a.5b.6d, | 1a.2c.3c.4a.5b.6e, | 1a.2c.3c.4a.5b.6f, | |
| 1a.2c.3c.4a.5c.6a, | 1a.2c.3c.4a.5c.6b, | 1a.2c.3c.4a.5c.6c, | 1a.2c.3c.4a.5c.6d, | 1a.2c.3c.4a.5c.6e, |
| 1a.2c.3c.4a.5c.6f, | 1a.2c.3c.4a.5d.6a, | 1a.2c.3c.4a.5d.6b, | 1a.2c.3c.4a.5d.6c, | |
| 1a.2c.3c.4a.5d.6d, | 1a.2c.3c.4a.5d.6e, | 1a.2c.3c.4a.5d.6f, | 1a.2c.3c.4a.5e.6a, | |
| 1a.2c.3c.4a.5e.6b, | 1a.2c.3c.4a.5e.6c, | 1a.2c.3c.4a.5e.6d, | 1a.2c.3c.4a.5e.6e, | 1a.2c.3c.4a.5e.6f, |
| 1a.2c.3c.4a.5f.6a, | 1a.2c.3c.4a.5f.6b, | 1a.2c.3c.4a.5f.6c, | 1a.2c.3c.4a.5f.6d, | 1a.2c.3c.4a.5f.6e, |
| 1a.2c.3c.4a.5f.6f, | 1a.2c.3c.4b.5a.6a, | 1a.2c.3c.4b.5a.6b, | 1a.2c.3c.4b.5a.6c, | |
| 1a.2c.3c.4b.5a.6d, | 1a.2c.3c.4b.5a.6e, | 1a.2c.3c.4b.5a.6f, | 1a.2c.3c.4b.5b.6a, | |
| 1a.2c.3c.4b.5b.6b, | 1a.2c.3c.4b.5b.6c, | 1a.2c.3c.4b.5b.6d, | 1a.2c.3c.4b.5b.6e, | |
| 1a.2c.3c.4b.5b.6f, | 1a.2c.3c.4b.5c.6a, | 1a.2c.3c.4b.5c.6b, | 1a.2c.3c.4b.5c.6c, | |
| 1a.2c.3c.4b.5c.6d, | 1a.2c.3c.4b.5c.6e, | 1a.2c.3c.4b.5c.6f, | 1a.2c.3c.4b.5d.6a, | |
| 1a.2c.3c.4b.5d.6b, | 1a.2c.3c.4b.5d.6c, | 1a.2c.3c.4b.5d.6d, | 1a.2c.3c.4b.5d.6e, | |

TABLE 7-continued

List of Compounds of Formula (II)

| | | | | |
|---|---|---|---|---|
| 1a.2c.3c.4b.5d.6f, | 1a.2c.3c.4b.5e.6a, | 1a.2c.3c.4b.5e.6b, | 1a.2c.3c.4b.5e.6c, | |
| 1a.2c.3c.4b.5e.6d, | 1a.2c.3c.4b.5e.6e, | 1a.2c.3c.4b.5e.6f, | 1a.2c.3c.4b.5f.6a, | 1a.2c.3c.4b.5f.6b, |
| 1a.2c.3c.4b.5f.6c, | 1a.2c.3c.4b.5f.6d, | 1a.2c.3c.4b.5f.6e, | 1a.2c.3c.4b.5f.6f, | 1a.2c.3c.4c.5a.6a, |
| 1a.2c.3c.4c.5a.6b, | 1a.2c.3c.4c.5a.6c, | 1a.2c.3c.4c.5a.6d, | 1a.2c.3c.4c.5a.6e, | 1a.2c.3c.4c.5a.6f, |
| 1a.2c.3c.4c.5b.6a, | 1a.2c.3c.4c.5b.6b, | 1a.2c.3c.4c.5b.6c, | 1a.2c.3c.4c.5b.6d, | |
| 1a.2c.3c.4c.5b.6e, | 1a.2c.3c.4c.5b.6f, | 1a.2c.3c.4c.5c.6a, | 1a.2c.3c.4c.5c.6b, | 1a.2c.3c.4c.5c.6c, |
| 1a.2c.3c.4c.5c.6d, | 1a.2c.3c.4c.5c.6e, | 1a.2c.3c.4c.5c.6f, | 1a.2c.3c.4c.5d.6a, | 1a.2c.3c.4c.5d.6b, |
| 1a.2c.3c.4c.5d.6c, | 1a.2c.3c.4c.5d.6d, | 1a.2c.3c.4c.5d.6e, | 1a.2c.3c.4c.5d.6f, | |
| 1a.2c.3c.4c.5e.6a, | 1a.2c.3c.4c.5e.6b, | 1a.2c.3c.4c.5e.6c, | 1a.2c.3c.4c.5e.6d, | 1a.2c.3c.4c.5e.6e, |
| 1a.2c.3c.4c.5e.6f, | 1a.2c.3c.4c.5f.6a, | 1a.2c.3c.4c.5f.6b, | 1a.2c.3c.4c.5f.6c, | 1a.2c.3c.4c.5f.6d, |
| 1a.2c.3c.4c.5f.6e, | 1a.2c.3c.4c.5f.6f, | 1a.2c.3c.4d.5a.6a, | 1a.2c.3c.4d.5a.6b, | 1a.2c.3c.4d.5a.6c, |
| 1a.2c.3c.4d.5a.6d, | 1a.2c.3c.4d.5a.6e, | 1a.2c.3c.4d.5a.6f, | 1a.2c.3c.4d.5b.6a, | |
| 1a.2c.3c.4d.5b.6b, | 1a.2c.3c.4d.5b.6c, | 1a.2c.3c.4d.5b.6d, | 1a.2c.3c.4d.5b.6e, | |
| 1a.2c.3c.4d.5b.6f, | 1a.2c.3c.4d.5c.6a, | 1a.2c.3c.4d.5c.6b, | 1a.2c.3c.4d.5c.6c, | |
| 1a.2c.3c.4d.5c.6d, | 1a.2c.3c.4d.5c.6e, | 1a.2c.3c.4d.5c.6f, | 1a.2c.3c.4d.5d.6a, | |
| 1a.2c.3c.4d.5d.6b, | 1a.2c.3c.4d.5d.6c, | 1a.2c.3c.4d.5d.6d, | 1a.2c.3c.4d.5d.6e, | |
| 1a.2c.3c.4d.5d.6f, | 1a.2c.3c.4d.5e.6a, | 1a.2c.3c.4d.5e.6b, | 1a.2c.3c.4d.5e.6c, | |
| 1a.2c.3c.4d.5e.6d, | 1a.2c.3c.4d.5e.6e, | 1a.2c.3c.4d.5e.6f, | 1a.2c.3c.4d.5f.6a, | |
| 1a.2c.3c.4d.5f.6b, | 1a.2c.3c.4d.5f.6c, | 1a.2c.3c.4d.5f.6d, | 1a.2c.3c.4d.5f.6e, | 1a.2c.3c.4d.5f.6f, |
| 1a.2c.3c.4e.5a.6a, | 1a.2c.3c.4e.5a.6b, | 1a.2c.3c.4e.5a.6c, | 1a.2c.3c.4e.5a.6d, | |
| 1a.2c.3c.4e.5a.6e, | 1a.2c.3c.4e.5a.6f, | 1a.2c.3c.4e.5b.6a, | 1a.2c.3c.4e.5b.6b, | 1a.2c.3c.4e.5b.6c, |
| 1a.2c.3c.4e.5b.6d, | 1a.2c.3c.4e.5b.6e, | 1a.2c.3c.4e.5b.6f, | 1a.2c.3c.4e.5c.6a, | 1a.2c.3c.4e.5c.6b, |
| 1a.2c.3c.4e.5c.6c, | 1a.2c.3c.4e.5c.6d, | 1a.2c.3c.4e.5c.6e, | 1a.2c.3c.4e.5c.6f, | 1a.2c.3c.4e.5d.6a, |
| 1a.2c.3c.4e.5d.6b, | 1a.2c.3c.4e.5d.6c, | 1a.2c.3c.4e.5d.6d, | 1a.2c.3c.4e.5d.6e, | |
| 1a.2c.3c.4e.5d.6f, | 1a.2c.3c.4e.5e.6a, | 1a.2c.3c.4e.5e.6b, | 1a.2c.3c.4e.5e.6c, | 1a.2c.3c.4e.5e.6d, |
| 1a.2c.3c.4e.5e.6e, | 1a.2c.3c.4e.5e.6f, | 1a.2c.3c.4e.5f.6a, | 1a.2c.3c.4e.5f.6b, | 1a.2c.3c.4e.5f.6c, |
| 1a.2c.3c.4e.5f.6d, | 1a.2c.3c.4e.5f.6e, | 1a.2c.3c.4e.5f.6f, | 1a.2c.3c.4f.5a.6a, | 1a.2c.3c.4f.5a.6b, |
| 1a.2c.3c.4f.5a.6c, | 1a.2c.3c.4f.5a.6d, | 1a.2c.3c.4f.5a.6e, | 1a.2c.3c.4f.5a.6f, | 1a.2c.3c.4f.5b.6a, |
| 1a.2c.3c.4f.5b.6b, | 1a.2c.3c.4f.5b.6c, | 1a.2c.3c.4f.5b.6d, | 1a.2c.3c.4f.5b.6e, | 1a.2c.3c.4f.5b.6f, |
| 1a.2c.3c.4f.5c.6a, | 1a.2c.3c.4f.5c.6b, | 1a.2c.3c.4f.5c.6c, | 1a.2c.3c.4f.5c.6d, | 1a.2c.3c.4f.5c.6e, |
| 1a.2c.3c.4f.5c.6f, | 1a.2c.3c.4f.5d.6a, | 1a.2c.3c.4f.5d.6b, | 1a.2c.3c.4f.5d.6c, | 1a.2c.3c.4f.5d.6d, |
| 1a.2c.3c.4f.5d.6e, | 1a.2c.3c.4f.5d.6f, | 1a.2c.3c.4f.5e.6a, | 1a.2c.3c.4f.5e.6b, | 1a.2c.3c.4f.5e.6c, |
| 1a.2c.3c.4f.5e.6d, | 1a.2c.3c.4f.5e.6e, | 1a.2c.3c.4f.5e.6f, | 1a.2c.3c.4f.5f.6a, | 1a.2c.3c.4f.5f.6b, |
| 1a.2c.3c.4f.5f.6c, | 1a.2c.3c.4f.5f.6d, | 1a.2c.3c.4f.5f.6e, | 1a.2c.3c.4f.5f.6f, | 1a.2c.3d.4a.5a.6a, |
| 1a.2c.3d.4a.5a.6b, | 1a.2c.3d.4a.5a.6c, | 1a.2c.3d.4a.5a.6d, | 1a.2c.3d.4a.5a.6e, | |
| 1a.2c.3d.4a.5a.6f, | 1a.2c.3d.4a.5b.6a, | 1a.2c.3d.4a.5b.6b, | 1a.2c.3d.4a.5b.6c, | |
| 1a.2c.3d.4a.5b.6d, | 1a.2c.3d.4a.5b.6e, | 1a.2c.3d.4a.5b.6f, | 1a.2c.3d.4a.5c.6a, | |
| 1a.2c.3d.4a.5c.6b, | 1a.2c.3d.4a.5c.6c, | 1a.2c.3d.4a.5c.6d, | 1a.2c.3d.4a.5c.6e, | |
| 1a.2c.3d.4a.5c.6f, | 1a.2c.3d.4a.5d.6a, | 1a.2c.3d.4a.5d.6b, | 1a.2c.3d.4a.5d.6c, | |
| 1a.2c.3d.4a.5d.6d, | 1a.2c.3d.4a.5d.6e, | 1a.2c.3d.4a.5d.6f, | 1a.2c.3d.4a.5e.6a, | |
| 1a.2c.3d.4a.5e.6b, | 1a.2c.3d.4a.5e.6c, | 1a.2c.3d.4a.5e.6d, | 1a.2c.3d.4a.5e.6e, | |
| 1a.2c.3d.4a.5e.6f, | 1a.2c.3d.4a.5f.6a, | 1a.2c.3d.4a.5f.6b, | 1a.2c.3d.4a.5f.6c, | |
| 1a.2c.3d.4a.5f.6d, | 1a.2c.3d.4a.5f.6e, | 1a.2c.3d.4a.5f.6f, | 1a.2c.3d.4b.5a.6a, | |
| 1a.2c.3d.4b.5a.6b, | 1a.2c.3d.4b.5a.6c, | 1a.2c.3d.4b.5a.6d, | 1a.2c.3d.4b.5a.6e, | |
| 1a.2c.3d.4b.5a.6f, | 1a.2c.3d.4b.5b.6a, | 1a.2c.3d.4b.5b.6b, | 1a.2c.3d.4b.5b.6c, | |
| 1a.2c.3d.4b.5b.6d, | 1a.2c.3d.4b.5b.6e, | 1a.2c.3d.4b.5b.6f, | 1a.2c.3d.4b.5c.6a, | |
| 1a.2c.3d.4b.5c.6b, | 1a.2c.3d.4b.5c.6c, | 1a.2c.3d.4b.5c.6d, | 1a.2c.3d.4b.5c.6e, | |
| 1a.2c.3d.4b.5c.6f, | 1a.2c.3d.4b.5d.6a, | 1a.2c.3d.4b.5d.6b, | 1a.2c.3d.4b.5d.6c, | |
| 1a.2c.3d.4b.5d.6d, | 1a.2c.3d.4b.5d.6e, | 1a.2c.3d.4b.5d.6f, | 1a.2c.3d.4b.5e.6a, | |
| 1a.2c.3d.4b.5e.6b, | 1a.2c.3d.4b.5e.6c, | 1a.2c.3d.4b.5e.6d, | 1a.2c.3d.4b.5e.6e, | |
| 1a.2c.3d.4b.5e.6f, | 1a.2c.3d.4b.5f.6a, | 1a.2c.3d.4b.5f.6b, | 1a.2c.3d.4b.5f.6c, | |
| 1a.2c.3d.4b.5f.6d, | 1a.2c.3d.4b.5f.6e, | 1a.2c.3d.4b.5f.6f, | 1a.2c.3d.4c.5a.6a, | |
| 1a.2c.3d.4c.5a.6b, | 1a.2c.3d.4c.5a.6c, | 1a.2c.3d.4c.5a.6d, | 1a.2c.3d.4c.5a.6e, | |
| 1a.2c.3d.4c.5a.6f, | 1a.2c.3d.4c.5b.6a, | 1a.2c.3d.4c.5b.6b, | 1a.2c.3d.4c.5b.6c, | |
| 1a.2c.3d.4c.5b.6d, | 1a.2c.3d.4c.5b.6e, | 1a.2c.3d.4c.5b.6f, | 1a.2c.3d.4c.5c.6a, | |
| 1a.2c.3d.4c.5c.6b, | 1a.2c.3d.4c.5c.6c, | 1a.2c.3d.4c.5c.6d, | 1a.2c.3d.4c.5c.6e, | |
| 1a.2c.3d.4c.5c.6f, | 1a.2c.3d.4c.5d.6a, | 1a.2c.3d.4c.5d.6b, | 1a.2c.3d.4c.5d.6c, | |
| 1a.2c.3d.4c.5d.6d, | 1a.2c.3d.4c.5d.6e, | 1a.2c.3d.4c.5d.6f, | 1a.2c.3d.4c.5e.6a, | |
| 1a.2c.3d.4c.5e.6b, | 1a.2c.3d.4c.5e.6c, | 1a.2c.3d.4c.5e.6d, | 1a.2c.3d.4c.5e.6e, | |
| 1a.2c.3d.4c.5e.6f, | 1a.2c.3d.4c.5f.6a, | 1a.2c.3d.4c.5f.6b, | 1a.2c.3d.4c.5f.6c, | 1a.2c.3d.4c.5f.6d, |
| 1a.2c.3d.4c.5f.6e, | 1a.2c.3d.4c.5f.6f, | 1a.2c.3d.4d.5a.6a, | 1a.2c.3d.4d.5a.6b, | |
| 1a.2c.3d.4d.5a.6c, | 1a.2c.3d.4d.5a.6d, | 1a.2c.3d.4d.5a.6e, | 1a.2c.3d.4d.5a.6f, | |
| 1a.2c.3d.4d.5b.6a, | 1a.2c.3d.4d.5b.6b, | 1a.2c.3d.4d.5b.6c, | 1a.2c.3d.4d.5b.6d, | |
| 1a.2c.3d.4d.5b.6e, | 1a.2c.3d.4d.5b.6f, | 1a.2c.3d.4d.5c.6a, | 1a.2c.3d.4d.5c.6b, | |
| 1a.2c.3d.4d.5c.6c, | 1a.2c.3d.4d.5c.6d, | 1a.2c.3d.4d.5c.6e, | 1a.2c.3d.4d.5c.6f, | |
| 1a.2c.3d.4d.5d.6a, | 1a.2c.3d.4d.5d.6b, | 1a.2c.3d.4d.5d.6c, | 1a.2c.3d.4d.5d.6d, | |
| 1a.2c.3d.4d.5d.6e, | 1a.2c.3d.4d.5d.6f, | 1a.2c.3d.4d.5e.6a, | 1a.2c.3d.4d.5e.6b, | |
| 1a.2c.3d.4d.5e.6c, | 1a.2c.3d.4d.5e.6d, | 1a.2c.3d.4d.5e.6e, | 1a.2c.3d.4d.5e.6f, | |
| 1a.2c.3d.4d.5f.6a, | 1a.2c.3d.4d.5f.6b, | 1a.2c.3d.4d.5f.6c, | 1a.2c.3d.4d.5f.6d, | |
| 1a.2c.3d.4d.5f.6e, | 1a.2c.3d.4d.5f.6f, | 1a.2c.3d.4e.5a.6a, | 1a.2c.3d.4e.5a.6b, | |
| 1a.2c.3d.4e.5a.6c, | 1a.2c.3d.4e.5a.6d, | 1a.2c.3d.4e.5a.6e, | 1a.2c.3d.4e.5a.6f, | |
| 1a.2c.3d.4e.5b.6a, | 1a.2c.3d.4e.5b.6b, | 1a.2c.3d.4e.5b.6c, | 1a.2c.3d.4e.5b.6d, | |
| 1a.2c.3d.4e.5b.6e, | 1a.2c.3d.4e.5b.6f, | 1a.2c.3d.4e.5c.6a, | 1a.2c.3d.4e.5c.6b, | |
| 1a.2c.3d.4e.5c.6c, | 1a.2c.3d.4e.5c.6d, | 1a.2c.3d.4e.5c.6e, | 1a.2c.3d.4e.5c.6f, | |
| 1a.2c.3d.4e.5d.6a, | 1a.2c.3d.4e.5d.6b, | 1a.2c.3d.4e.5d.6c, | 1a.2c.3d.4e.5d.6d, | |
| 1a.2c.3d.4e.5d.6e, | 1a.2c.3d.4e.5d.6f, | 1a.2c.3d.4e.5e.6a, | 1a.2c.3d.4e.5e.6b, | |
| 1a.2c.3d.4e.5e.6c, | 1a.2c.3d.4e.5e.6d, | 1a.2c.3d.4e.5e.6e, | 1a.2c.3d.4e.5e.6f, | |
| 1a.2c.3d.4e.5f.6a, | 1a.2c.3d.4e.5f.6b, | 1a.2c.3d.4e.5f.6c, | 1a.2c.3d.4e.5f.6d, | |

TABLE 7-continued

List of Compounds of Formula (II)

| | | | | |
|---|---|---|---|---|
| 1a.2c.3d.4e.5f.6e, | 1a.2c.3d.4e.5f.6f, | 1a.2c.3d.4f.5a.6a, | 1a.2c.3d.4f.5a.6b, | 1a.2c.3d.4f.5a.6c, |
| 1a.2c.3d.4f.5a.6d, | 1a.2c.3d.4f.5a.6e, | 1a.2c.3d.4f.5a.6f, | 1a.2c.3d.4f.5b.6a, | |
| 1a.2c.3d.4f.5b.6b, | 1a.2c.3d.4f.5b.6c, | 1a.2c.3d.4f.5b.6d, | 1a.2c.3d.4f.5b.6e, | |
| 1a.2c.3d.4f.5b.6f, | 1a.2c.3d.4f.5c.6a, | 1a.2c.3d.4f.5c.6b, | 1a.2c.3d.4f.5c.6c, | 1a.2c.3d.4f.5c.6d, |
| 1a.2c.3d.4f.5c.6e, | 1a.2c.3d.4f.5c.6f, | 1a.2c.3d.4f.5d.6a, | 1a.2c.3d.4f.5d.6b, | |
| 1a.2c.3d.4f.5d.6c, | 1a.2c.3d.4f.5d.6d, | 1a.2c.3d.4f.5d.6e, | 1a.2c.3d.4f.5d.6f, | |
| 1a.2c.3d.4f.5e.6a, | 1a.2c.3d.4f.5e.6b, | 1a.2c.3d.4f.5e.6c, | 1a.2c.3d.4f.5e.6d, | |
| 1a.2c.3d.4f.5e.6e, | 1a.2c.3d.4f.5e.6f, | 1a.2c.3d.4f.5f.6a, | 1a.2c.3d.4f.5f.6b, | 1a.2c.3d.4f.5f.6c, |
| 1a.2c.3d.4f.5f.6d, | 1a.2c.3d.4f.5f.6e, | 1a.2c.3d.4f.5f.6f, | 1a.2c.3e.4a.5a.6a, | 1a.2c.3e.4a.5a.6b, |
| 1a.2c.3e.4a.5a.6c, | 1a.2c.3e.4a.5a.6d, | 1a.2c.3e.4a.5a.6e, | 1a.2c.3e.4a.5a.6f, | |
| 1a.2c.3e.4a.5b.6a, | 1a.2c.3e.4a.5b.6b, | 1a.2c.3e.4a.5b.6c, | 1a.2c.3e.4a.5b.6d, | |
| 1a.2c.3e.4a.5b.6e, | 1a.2c.3e.4a.5b.6f, | 1a.2c.3e.4a.5c.6a, | 1a.2c.3e.4a.5c.6b, | 1a.2c.3e.4a.5c.6c, |
| 1a.2c.3e.4a.5c.6d, | 1a.2c.3e.4a.5c.6e, | 1a.2c.3e.4a.5c.6f, | 1a.2c.3e.4a.5d.6a, | |
| 1a.2c.3e.4a.5d.6b, | 1a.2c.3e.4a.5d.6c, | 1a.2c.3e.4a.5d.6d, | 1a.2c.3e.4a.5d.6e, | |
| 1a.2c.3e.4a.5d.6f, | 1a.2c.3e.4a.5e.6a, | 1a.2c.3e.4a.5e.6b, | 1a.2c.3e.4a.5e.6c, | |
| 1a.2c.3e.4a.5e.6d, | 1a.2c.3e.4a.5e.6e, | 1a.2c.3e.4a.5e.6f, | 1a.2c.3e.4a.5f.6a, | 1a.2c.3e.4a.5f.6b, |
| 1a.2c.3e.4a.5f.6c, | 1a.2c.3e.4a.5f.6d, | 1a.2c.3e.4a.5f.6e, | 1a.2c.3e.4a.5f.6f, | 1a.2c.3e.4b.5a.6a, |
| 1a.2c.3e.4b.5a.6b, | 1a.2c.3e.4b.5a.6c, | 1a.2c.3e.4b.5a.6d, | 1a.2c.3e.4b.5a.6e, | |
| 1a.2c.3e.4b.5a.6f, | 1a.2c.3e.4b.5b.6a, | 1a.2c.3e.4b.5b.6b, | 1a.2c.3e.4b.5b.6c, | |
| 1a.2c.3e.4b.5b.6d, | 1a.2c.3e.4b.5b.6e, | 1a.2c.3e.4b.5b.6f, | 1a.2c.3e.4b.5c.6a, | |
| 1a.2c.3e.4b.5c.6b, | 1a.2c.3e.4b.5c.6c, | 1a.2c.3e.4b.5c.6d, | 1a.2c.3e.4b.5c.6e, | |
| 1a.2c.3e.4b.5c.6f, | 1a.2c.3e.4b.5d.6a, | 1a.2c.3e.4b.5d.6b, | 1a.2c.3e.4b.5d.6c, | |
| 1a.2c.3e.4b.5d.6d, | 1a.2c.3e.4b.5d.6e, | 1a.2c.3e.4b.5d.6f, | 1a.2c.3e.4b.5e.6a, | |
| 1a.2c.3e.4b.5e.6b, | 1a.2c.3e.4b.5e.6c, | 1a.2c.3e.4b.5e.6d, | 1a.2c.3e.4b.5e.6e, | |
| 1a.2c.3e.4b.5e.6f, | 1a.2c.3e.4b.5f.6a, | 1a.2c.3e.4b.5f.6b, | 1a.2c.3e.4b.5f.6c, | 1a.2c.3e.4b.5f.6d, |
| 1a.2c.3e.4b.5f.6e, | 1a.2c.3e.4b.5f.6f, | 1a.2c.3e.4c.5a.6a, | 1a.2c.3e.4c.5a.6b, | 1a.2c.3e.4c.5a.6c, |
| 1a.2c.3e.4c.5a.6d, | 1a.2c.3e.4c.5a.6e, | 1a.2c.3e.4c.5a.6f, | 1a.2c.3e.4c.5b.6a, | |
| 1a.2c.3e.4c.5b.6b, | 1a.2c.3e.4c.5b.6c, | 1a.2c.3e.4c.5b.6d, | 1a.2c.3e.4c.5b.6e, | |
| 1a.2c.3e.4c.5b.6f, | 1a.2c.3e.4c.5c.6a, | 1a.2c.3e.4c.5c.6b, | 1a.2c.3e.4c.5c.6c, | 1a.2c.3e.4c.5c.6d, |
| 1a.2c.3e.4c.5c.6e, | 1a.2c.3e.4c.5c.6f, | 1a.2c.3e.4c.5d.6a, | 1a.2c.3e.4c.5d.6b, | 1a.2c.3e.4c.5d.6c, |
| 1a.2c.3e.4c.5d.6d, | 1a.2c.3e.4c.5d.6e, | 1a.2c.3e.4c.5d.6f, | 1a.2c.3e.4c.5e.6a, | |
| 1a.2c.3e.4c.5e.6b, | 1a.2c.3e.4c.5e.6c, | 1a.2c.3e.4c.5e.6d, | 1a.2c.3e.4c.5e.6e, | 1a.2c.3e.4c.5e.6f, |
| 1a.2c.3e.4c.5f.6a, | 1a.2c.3e.4c.5f.6b, | 1a.2c.3e.4c.5f.6c, | 1a.2c.3e.4c.5f.6d, | 1a.2c.3e.4c.5f.6e, |
| 1a.2c.3e.4c.5f.6f, | 1a.2c.3e.4d.5a.6a, | 1a.2c.3e.4d.5a.6b, | 1a.2c.3e.4d.5a.6c, | |
| 1a.2c.3e.4d.5a.6d, | 1a.2c.3e.4d.5a.6e, | 1a.2c.3e.4d.5a.6f, | 1a.2c.3e.4d.5b.6a, | |
| 1a.2c.3e.4d.5b.6b, | 1a.2c.3e.4d.5b.6c, | 1a.2c.3e.4d.5b.6d, | 1a.2c.3e.4d.5b.6e, | |
| 1a.2c.3e.4d.5b.6f, | 1a.2c.3e.4d.5c.6a, | 1a.2c.3e.4d.5c.6b, | 1a.2c.3e.4d.5c.6c, | |
| 1a.2c.3e.4d.5c.6d, | 1a.2c.3e.4d.5c.6e, | 1a.2c.3e.4d.5c.6f, | 1a.2c.3e.4d.5d.6a, | |
| 1a.2c.3e.4d.5d.6b, | 1a.2c.3e.4d.5d.6c, | 1a.2c.3e.4d.5d.6d, | 1a.2c.3e.4d.5d.6e, | |
| 1a.2c.3e.4d.5d.6f, | 1a.2c.3e.4d.5e.6a, | 1a.2c.3e.4d.5e.6b, | 1a.2c.3e.4d.5e.6c, | |
| 1a.2c.3e.4d.5e.6d, | 1a.2c.3e.4d.5e.6e, | 1a.2c.3e.4d.5e.6f, | 1a.2c.3e.4d.5f.6a, | |
| 1a.2c.3e.4d.5f.6b, | 1a.2c.3e.4d.5f.6c, | 1a.2c.3e.4d.5f.6d, | 1a.2c.3e.4d.5f.6e, | 1a.2c.3e.4d.5f.6f, |
| 1a.2c.3e.4e.5a.6a, | 1a.2c.3e.4e.5a.6b, | 1a.2c.3e.4e.5a.6c, | 1a.2c.3e.4e.5a.6d, | |
| 1a.2c.3e.4e.5a.6e, | 1a.2c.3e.4e.5a.6f, | 1a.2c.3e.4e.5b.6a, | 1a.2c.3e.4e.5b.6b, | |
| 1a.2c.3e.4e.5b.6c, | 1a.2c.3e.4e.5b.6d, | 1a.2c.3e.4e.5b.6e, | 1a.2c.3e.4e.5b.6f, | |
| 1a.2c.3e.4e.5c.6a, | 1a.2c.3e.4e.5c.6b, | 1a.2c.3e.4e.5c.6c, | 1a.2c.3e.4e.5c.6d, | 1a.2c.3e.4e.5c.6e, |
| 1a.2c.3e.4e.5c.6f, | 1a.2c.3e.4e.5d.6a, | 1a.2c.3e.4e.5d.6b, | 1a.2c.3e.4e.5d.6c, | |
| 1a.2c.3e.4e.5d.6d, | 1a.2c.3e.4e.5d.6e, | 1a.2c.3e.4e.5d.6f, | 1a.2c.3e.4e.5e.6a, | |
| 1a.2c.3e.4e.5e.6b, | 1a.2c.3e.4e.5e.6c, | 1a.2c.3e.4e.5e.6d, | 1a.2c.3e.4e.5e.6e, | 1a.2c.3e.4e.5e.6f, |
| 1a.2c.3e.4e.5f.6a, | 1a.2c.3e.4e.5f.6b, | 1a.2c.3e.4e.5f.6c, | 1a.2c.3e.4e.5f.6d, | 1a.2c.3e.4e.5f.6e, |
| 1a.2c.3e.4e.5f.6f, | 1a.2c.3e.4f.5a.6a, | 1a.2c.3e.4f.5a.6b, | 1a.2c.3e.4f.5a.6c, | 1a.2c.3e.4f.5a.6d, |
| 1a.2c.3e.4f.5a.6e, | 1a.2c.3e.4f.5a.6f, | 1a.2c.3e.4f.5b.6a, | 1a.2c.3e.4f.5b.6b, | 1a.2c.3e.4f.5b.6c, |
| 1a.2c.3e.4f.5b.6d, | 1a.2c.3e.4f.5b.6e, | 1a.2c.3e.4f.5b.6f, | 1a.2c.3e.4f.5c.6a, | 1a.2c.3e.4f.5c.6b, |
| 1a.2c.3e.4f.5c.6c, | 1a.2c.3e.4f.5c.6d, | 1a.2c.3e.4f.5c.6e, | 1a.2c.3e.4f.5c.6f, | 1a.2c.3e.4f.5d.6a, |
| 1a.2c.3e.4f.5d.6b, | 1a.2c.3e.4f.5d.6c, | 1a.2c.3e.4f.5d.6d, | 1a.2c.3e.4f.5d.6e, | 1a.2c.3e.4f.5d.6f, |
| 1a.2c.3e.4f.5e.6a, | 1a.2c.3e.4f.5e.6b, | 1a.2c.3e.4f.5e.6c, | 1a.2c.3e.4f.5e.6d, | 1a.2c.3e.4f.5e.6e, |
| 1a.2c.3e.4f.5e.6f, | 1a.2c.3e.4f.5f.6a, | 1a.2c.3e.4f.5f.6b, | 1a.2c.3e.4f.5f.6c, | 1a.2c.3e.4f.5f.6d, |
| 1a.2c.3e.4f.5f.6e, | 1a.2c.3e.4f.5f.6f, | 1a.2c.3f.4a.5a.6a, | 1a.2c.3f.4a.5a.6b, | 1a.2c.3f.4a.5a.6c, |
| 1a.2c.3f.4a.5a.6d, | 1a.2c.3f.4a.5a.6e, | 1a.2c.3f.4a.5a.6f, | 1a.2c.3f.4a.5b.6a, | 1a.2c.3f.4a.5b.6b, |
| 1a.2c.3f.4a.5b.6c, | 1a.2c.3f.4a.5b.6d, | 1a.2c.3f.4a.5b.6e, | 1a.2c.3f.4a.5b.6f, | 1a.2c.3f.4a.5c.6a, |
| 1a.2c.3f.4a.5c.6b, | 1a.2c.3f.4a.5c.6c, | 1a.2c.3f.4a.5c.6d, | 1a.2c.3f.4a.5c.6e, | 1a.2c.3f.4a.5c.6f, |
| 1a.2c.3f.4a.5d.6a, | 1a.2c.3f.4a.5d.6b, | 1a.2c.3f.4a.5d.6c, | 1a.2c.3f.4a.5d.6d, | |
| 1a.2c.3f.4a.5d.6e, | 1a.2c.3f.4a.5d.6f, | 1a.2c.3f.4a.5e.6a, | 1a.2c.3f.4a.5e.6b, | 1a.2c.3f.4a.5e.6c, |
| 1a.2c.3f.4a.5e.6d, | 1a.2c.3f.4a.5e.6e, | 1a.2c.3f.4a.5e.6f, | 1a.2c.3f.4a.5f.6a, | 1a.2c.3f.4a.5f.6b, |
| 1a.2c.3f.4a.5f.6c, | 1a.2c.3f.4a.5f.6d, | 1a.2c.3f.4a.5f.6e, | 1a.2c.3f.4a.5f.6f, | 1a.2c.3f.4b.5a.6a, |
| 1a.2c.3f.4b.5a.6b, | 1a.2c.3f.4b.5a.6c, | 1a.2c.3f.4b.5a.6d, | 1a.2c.3f.4b.5a.6e, | 1a.2c.3f.4b.5a.6f, |
| 1a.2c.3f.4b.5b.6a, | 1a.2c.3f.4b.5b.6b, | 1a.2c.3f.4b.5b.6c, | 1a.2c.3f.4b.5b.6d, | |
| 1a.2c.3f.4b.5b.6e, | 1a.2c.3f.4b.5b.6f, | 1a.2c.3f.4b.5c.6a, | 1a.2c.3f.4b.5c.6b, | 1a.2c.3f.4b.5c.6c, |
| 1a.2c.3f.4b.5c.6d, | 1a.2c.3f.4b.5c.6e, | 1a.2c.3f.4b.5c.6f, | 1a.2c.3f.4b.5d.6a, | 1a.2c.3f.4b.5d.6b, |
| 1a.2c.3f.4b.5d.6c, | 1a.2c.3f.4b.5d.6d, | 1a.2c.3f.4b.5d.6e, | 1a.2c.3f.4b.5d.6f, | |
| 1a.2c.3f.4b.5e.6a, | 1a.2c.3f.4b.5e.6b, | 1a.2c.3f.4b.5e.6c, | 1a.2c.3f.4b.5e.6d, | 1a.2c.3f.4b.5e.6e, |
| 1a.2c.3f.4b.5e.6f, | 1a.2c.3f.4b.5f.6a, | 1a.2c.3f.4b.5f.6b, | 1a.2c.3f.4b.5f.6c, | 1a.2c.3f.4b.5f.6d, |
| 1a.2c.3f.4b.5f.6e, | 1a.2c.3f.4b.5f.6f, | 1a.2c.3f.4c.5a.6a, | 1a.2c.3f.4c.5a.6b, | 1a.2c.3f.4c.5a.6c, |
| 1a.2c.3f.4c.5a.6d, | 1a.2c.3f.4c.5a.6e, | 1a.2c.3f.4c.5a.6f, | 1a.2c.3f.4c.5b.6a, | 1a.2c.3f.4c.5b.6b, |
| 1a.2c.3f.4c.5b.6c, | 1a.2c.3f.4c.5b.6d, | 1a.2c.3f.4c.5b.6e, | 1a.2c.3f.4c.5b.6f, | 1a.2c.3f.4c.5c.6a, |
| 1a.2c.3f.4c.5c.6b, | 1a.2c.3f.4c.5c.6c, | 1a.2c.3f.4c.5c.6d, | 1a.2c.3f.4c.5c.6e, | 1a.2c.3f.4c.5c.6f, |
| 1a.2c.3f.4c.5d.6a, | 1a.2c.3f.4c.5d.6b, | 1a.2c.3f.4c.5d.6c, | 1a.2c.3f.4c.5d.6d, | 1a.2c.3f.4c.5d.6e, |
| 1a.2c.3f.4c.5d.6f, | 1a.2c.3f.4c.5e.6a, | 1a.2c.3f.4c.5e.6b, | 1a.2c.3f.4c.5e.6c, | 1a.2c.3f.4c.5e.6d, |

TABLE 7-continued

List of Compounds of Formula (II)

| | | | | |
|---|---|---|---|---|
| 1a.2c.3f.4c.5e.6e, | 1a.2c.3f.4c.5e.6f, | 1a.2c.3f.4c.5f.6a, | 1a.2c.3f.4c.5f.6b, | 1a.2c.3f.4c.5f.6c, |
| 1a.2c.3f.4c.5f.6d, | 1a.2c.3f.4c.5f.6e, | 1a.2c.3f.4c.5f.6f, | 1a.2c.3f.4d.5a.6a, | 1a.2c.3f.4d.5a.6b, |
| 1a.2c.3f.4d.5a.6c, | 1a.2c.3f.4d.5a.6d, | 1a.2c.3f.4d.5a.6e, | 1a.2c.3f.4d.5a.6f, | 1a.2c.3f.4d.5b.6a, |
| 1a.2c.3f.4d.5b.6b, | 1a.2c.3f.4d.5b.6c, | 1a.2c.3f.4d.5b.6d, | 1a.2c.3f.4d.5b.6e, | |
| 1a.2c.3f.4d.5b.6f, | 1a.2c.3f.4d.5c.6a, | 1a.2c.3f.4d.5c.6b, | 1a.2c.3f.4d.5c.6c, | 1a.2c.3f.4d.5c.6d, |
| 1a.2c.3f.4d.5c.6e, | 1a.2c.3f.4d.5c.6f, | 1a.2c.3f.4d.5d.6a, | 1a.2c.3f.4d.5d.6b, | |
| 1a.2c.3f.4d.5d.6c, | 1a.2c.3f.4d.5d.6d, | 1a.2c.3f.4d.5d.6e, | 1a.2c.3f.4d.5d.6f, | |
| 1a.2c.3f.4d.5e.6a, | 1a.2c.3f.4d.5e.6b, | 1a.2c.3f.4d.5e.6c, | 1a.2c.3f.4d.5e.6d, | |
| 1a.2c.3f.4d.5e.6e, | 1a.2c.3f.4d.5e.6f, | 1a.2c.3f.4d.5f.6a, | 1a.2c.3f.4d.5f.6b, | 1a.2c.3f.4d.5f.6c, |
| 1a.2c.3f.4d.5f.6d, | 1a.2c.3f.4d.5f.6e, | 1a.2c.3f.4d.5f.6f, | 1a.2c.3f.4e.5a.6a, | 1a.2c.3f.4e.5a.6b, |
| 1a.2c.3f.4e.5a.6c, | 1a.2c.3f.4e.5a.6d, | 1a.2c.3f.4e.5a.6e, | 1a.2c.3f.4e.5a.6f, | 1a.2c.3f.4e.5b.6a, |
| 1a.2c.3f.4e.5b.6b, | 1a.2c.3f.4e.5b.6c, | 1a.2c.3f.4e.5b.6d, | 1a.2c.3f.4e.5b.6e, | 1a.2c.3f.4e.5b.6f, |
| 1a.2c.3f.4e.5c.6a, | 1a.2c.3f.4e.5c.6b, | 1a.2c.3f.4e.5c.6c, | 1a.2c.3f.4e.5c.6d, | 1a.2c.3f.4e.5c.6e, |
| 1a.2c.3f.4e.5c.6f, | 1a.2c.3f.4e.5d.6a, | 1a.2c.3f.4e.5d.6b, | 1a.2c.3f.4e.5d.6c, | 1a.2c.3f.4e.5d.6d, |
| 1a.2c.3f.4e.5d.6e, | 1a.2c.3f.4e.5d.6f, | 1a.2c.3f.4e.5e.6a, | 1a.2c.3f.4e.5e.6b, | 1a.2c.3f.4e.5e.6c, |
| 1a.2c.3f.4e.5e.6d, | 1a.2c.3f.4e.5e.6e, | 1a.2c.3f.4e.5e.6f, | 1a.2c.3f.4e.5f.6a, | 1a.2c.3f.4e.5f.6b, |
| 1a.2c.3f.4e.5f.6c, | 1a.2c.3f.4e.5f.6d, | 1a.2c.3f.4e.5f.6e, | 1a.2c.3f.4e.5f.6f, | 1a.2c.3f.4f.5a.6a, |
| 1a.2c.3f.4f.5a.6b, | 1a.2c.3f.4f.5a.6c, | 1a.2c.3f.4f.5a.6d, | 1a.2c.3f.4f.5a.6e, | 1a.2c.3f.4f.5a.6f, |
| 1a.2c.3f.4f.5b.6a, | 1a.2c.3f.4f.5b.6b, | 1a.2c.3f.4f.5b.6c, | 1a.2c.3f.4f.5b.6d, | 1a.2c.3f.4f.5b.6e, |
| 1a.2c.3f.4f.5b.6f, | 1a.2c.3f.4f.5c.6a, | 1a.2c.3f.4f.5c.6b, | 1a.2c.3f.4f.5c.6c, | 1a.2c.3f.4f.5c.6d, |
| 1a.2c.3f.4f.5c.6e, | 1a.2c.3f.4f.5c.6f, | 1a.2c.3f.4f.5d.6a, | 1a.2c.3f.4f.5d.6b, | 1a.2c.3f.4f.5d.6c, |
| 1a.2c.3f.4f.5d.6d, | 1a.2c.3f.4f.5d.6e, | 1a.2c.3f.4f.5d.6f, | 1a.2c.3f.4f.5e.6a, | 1a.2c.3f.4f.5e.6b, |
| 1a.2c.3f.4f.5e.6c, | 1a.2c.3f.4f.5e.6d, | 1a.2c.3f.4f.5e.6e, | 1a.2c.3f.4f.5e.6f, | 1a.2c.3f.4f.5f.6a, |
| 1a.2c.3f.4f.5f.6b, | 1a.2c.3f.4f.5f.6c, | 1a.2c.3f.4f.5f.6d, | 1a.2c.3f.4f.5f.6e, | 1a.2c.3f.4f.5f.6f, |
| 1a.2d.3a.4a.5a.6a, | 1a.2d.3a.4a.5a.6b, | 1a.2d.3a.4a.5a.6c, | 1a.2d.3a.4a.5a.6d, | |
| 1a.2d.3a.4a.5a.6e, | 1a.2d.3a.4a.5a.6f, | 1a.2d.3a.4a.5b.6a, | 1a.2d.3a.4a.5b.6b, | |
| 1a.2d.3a.4a.5b.6c, | 1a.2d.3a.4a.5b.6d, | 1a.2d.3a.4a.5b.6e, | 1a.2d.3a.4a.5b.6f, | |
| 1a.2d.3a.4a.5c.6a, | 1a.2d.3a.4a.5c.6b, | 1a.2d.3a.4a.5c.6c, | 1a.2d.3a.4a.5c.6d, | |
| 1a.2d.3a.4a.5c.6e, | 1a.2d.3a.4a.5c.6f, | 1a.2d.3a.4a.5d.6a, | 1a.2d.3a.4a.5d.6b, | |
| 1a.2d.3a.4a.5d.6c, | 1a.2d.3a.4a.5d.6d, | 1a.2d.3a.4a.5d.6e, | 1a.2d.3a.4a.5d.6f, | |
| 1a.2d.3a.4a.5e.6a, | 1a.2d.3a.4a.5e.6b, | 1a.2d.3a.4a.5e.6c, | 1a.2d.3a.4a.5e.6d, | |
| 1a.2d.3a.4a.5e.6e, | 1a.2d.3a.4a.5e.6f, | 1a.2d.3a.4a.5f.6a, | 1a.2d.3a.4a.5f.6b, | |
| 1a.2d.3a.4a.5f.6c, | 1a.2d.3a.4a.5f.6d, | 1a.2d.3a.4a.5f.6e, | 1a.2d.3a.4a.5f.6f, | |
| 1a.2d.3a.4b.5a.6a, | 1a.2d.3a.4b.5a.6b, | 1a.2d.3a.4b.5a.6c, | 1a.2d.3a.4b.5a.6d, | |
| 1a.2d.3a.4b.5a.6e, | 1a.2d.3a.4b.5a.6f, | 1a.2d.3a.4b.5b.6a, | 1a.2d.3a.4b.5b.6b, | |
| 1a.2d.3a.4b.5b.6c, | 1a.2d.3a.4b.5b.6d, | 1a.2d.3a.4b.5b.6e, | 1a.2d.3a.4b.5b.6f, | |
| 1a.2d.3a.4b.5c.6a, | 1a.2d.3a.4b.5c.6b, | 1a.2d.3a.4b.5c.6c, | 1a.2d.3a.4b.5c.6d, | |
| 1a.2d.3a.4b.5c.6e, | 1a.2d.3a.4b.5c.6f, | 1a.2d.3a.4b.5d.6a, | 1a.2d.3a.4b.5d.6b, | |
| 1a.2d.3a.4b.5d.6c, | 1a.2d.3a.4b.5d.6d, | 1a.2d.3a.4b.5d.6e, | 1a.2d.3a.4b.5d.6f, | |
| 1a.2d.3a.4b.5e.6a, | 1a.2d.3a.4b.5e.6b, | 1a.2d.3a.4b.5e.6c, | 1a.2d.3a.4b.5e.6d, | |
| 1a.2d.3a.4b.5e.6e, | 1a.2d.3a.4b.5e.6f, | 1a.2d.3a.4b.5f.6a, | 1a.2d.3a.4b.5f.6b, | |
| 1a.2d.3a.4b.5f.6c, | 1a.2d.3a.4b.5f.6d, | 1a.2d.3a.4b.5f.6e, | 1a.2d.3a.4b.5f.6f, | |
| 1a.2d.3a.4c.5a.6a, | 1a.2d.3a.4c.5a.6b, | 1a.2d.3a.4c.5a.6c, | 1a.2d.3a.4c.5a.6d, | |
| 1a.2d.3a.4c.5a.6e, | 1a.2d.3a.4c.5a.6f, | 1a.2d.3a.4c.5b.6a, | 1a.2d.3a.4c.5b.6b, | |
| 1a.2d.3a.4c.5b.6c, | 1a.2d.3a.4c.5b.6d, | 1a.2d.3a.4c.5b.6e, | 1a.2d.3a.4c.5b.6f, | |
| 1a.2d.3a.4c.5c.6a, | 1a.2d.3a.4c.5c.6b, | 1a.2d.3a.4c.5c.6c, | 1a.2d.3a.4c.5c.6d, | |
| 1a.2d.3a.4c.5c.6e, | 1a.2d.3a.4c.5c.6f, | 1a.2d.3a.4c.5d.6a, | 1a.2d.3a.4c.5d.6b, | |
| 1a.2d.3a.4c.5d.6c, | 1a.2d.3a.4c.5d.6d, | 1a.2d.3a.4c.5d.6e, | 1a.2d.3a.4c.5d.6f, | |
| 1a.2d.3a.4c.5e.6a, | 1a.2d.3a.4c.5e.6b, | 1a.2d.3a.4c.5e.6c, | 1a.2d.3a.4c.5e.6d, | |
| 1a.2d.3a.4c.5e.6e, | 1a.2d.3a.4c.5e.6f, | 1a.2d.3a.4c.5f.6a, | 1a.2d.3a.4c.5f.6b, | |
| 1a.2d.3a.4c.5f.6c, | 1a.2d.3a.4c.5f.6d, | 1a.2d.3a.4c.5f.6e, | 1a.2d.3a.4c.5f.6f, | |
| 1a.2d.3a.4d.5a.6a, | 1a.2d.3a.4d.5a.6b, | 1a.2d.3a.4d.5a.6c, | 1a.2d.3a.4d.5a.6d, | |
| 1a.2d.3a.4d.5a.6e, | 1a.2d.3a.4d.5a.6f, | 1a.2d.3a.4d.5b.6a, | 1a.2d.3a.4d.5b.6b, | |
| 1a.2d.3a.4d.5b.6c, | 1a.2d.3a.4d.5b.6d, | 1a.2d.3a.4d.5b.6e, | 1a.2d.3a.4d.5b.6f, | |
| 1a.2d.3a.4d.5c.6a, | 1a.2d.3a.4d.5c.6b, | 1a.2d.3a.4d.5c.6c, | 1a.2d.3a.4d.5c.6d, | |
| 1a.2d.3a.4d.5c.6e, | 1a.2d.3a.4d.5c.6f, | 1a.2d.3a.4d.5d.6a, | 1a.2d.3a.4d.5d.6b, | |
| 1a.2d.3a.4d.5d.6c, | 1a.2d.3a.4d.5d.6d, | 1a.2d.3a.4d.5d.6e, | 1a.2d.3a.4d.5d.6f, | |
| 1a.2d.3a.4d.5e.6a, | 1a.2d.3a.4d.5e.6b, | 1a.2d.3a.4d.5e.6c, | 1a.2d.3a.4d.5e.6d, | |
| 1a.2d.3a.4d.5e.6e, | 1a.2d.3a.4d.5e.6f, | 1a.2d.3a.4d.5f.6a, | 1a.2d.3a.4d.5f.6b, | |
| 1a.2d.3a.4d.5f.6c, | 1a.2d.3a.4d.5f.6d, | 1a.2d.3a.4d.5f.6e, | 1a.2d.3a.4d.5f.6f, | |
| 1a.2d.3a.4e.5a.6a, | 1a.2d.3a.4e.5a.6b, | 1a.2d.3a.4e.5a.6c, | 1a.2d.3a.4e.5a.6d, | |
| 1a.2d.3a.4e.5a.6e, | 1a.2d.3a.4e.5a.6f, | 1a.2d.3a.4e.5b.6a, | 1a.2d.3a.4e.5b.6b, | |
| 1a.2d.3a.4e.5b.6c, | 1a.2d.3a.4e.5b.6d, | 1a.2d.3a.4e.5b.6e, | 1a.2d.3a.4e.5b.6f, | |
| 1a.2d.3a.4e.5c.6a, | 1a.2d.3a.4e.5c.6b, | 1a.2d.3a.4e.5c.6c, | 1a.2d.3a.4e.5c.6d, | |
| 1a.2d.3a.4e.5c.6e, | 1a.2d.3a.4e.5c.6f, | 1a.2d.3a.4e.5d.6a, | 1a.2d.3a.4e.5d.6b, | |
| 1a.2d.3a.4e.5d.6c, | 1a.2d.3a.4e.5d.6d, | 1a.2d.3a.4e.5d.6e, | 1a.2d.3a.4e.5d.6f, | |
| 1a.2d.3a.4e.5e.6a, | 1a.2d.3a.4e.5e.6b, | 1a.2d.3a.4e.5e.6c, | 1a.2d.3a.4e.5e.6d, | |
| 1a.2d.3a.4e.5e.6e, | 1a.2d.3a.4e.5e.6f, | 1a.2d.3a.4e.5f.6a, | 1a.2d.3a.4e.5f.6b, | |
| 1a.2d.3a.4e.5f.6c, | 1a.2d.3a.4e.5f.6d, | 1a.2d.3a.4e.5f.6e, | 1a.2d.3a.4e.5f.6f, | |
| 1a.2d.3a.4f.5a.6a, | 1a.2d.3a.4f.5a.6b, | 1a.2d.3a.4f.5a.6c, | 1a.2d.3a.4f.5a.6d, | |
| 1a.2d.3a.4f.5a.6e, | 1a.2d.3a.4f.5a.6f, | 1a.2d.3a.4f.5b.6a, | 1a.2d.3a.4f.5b.6b, | |
| 1a.2d.3a.4f.5b.6c, | 1a.2d.3a.4f.5b.6d, | 1a.2d.3a.4f.5b.6e, | 1a.2d.3a.4f.5b.6f, | |
| 1a.2d.3a.4f.5c.6a, | 1a.2d.3a.4f.5c.6b, | 1a.2d.3a.4f.5c.6c, | 1a.2d.3a.4f.5c.6d, | |
| 1a.2d.3a.4f.5c.6e, | 1a.2d.3a.4f.5c.6f, | 1a.2d.3a.4f.5d.6a, | 1a.2d.3a.4f.5d.6b, | |
| 1a.2d.3a.4f.5d.6c, | 1a.2d.3a.4f.5d.6d, | 1a.2d.3a.4f.5d.6e, | 1a.2d.3a.4f.5d.6f, | |
| 1a.2d.3a.4f.5e.6a, | 1a.2d.3a.4f.5e.6b, | 1a.2d.3a.4f.5e.6c, | 1a.2d.3a.4f.5e.6d, | |
| 1a.2d.3a.4f.5e.6e, | 1a.2d.3a.4f.5e.6f, | 1a.2d.3a.4f.5f.6a, | 1a.2d.3a.4f.5f.6b, | 1a.2d.3a.4f.5f.6c, |
| 1a.2d.3a.4f.5f.6d, | 1a.2d.3a.4f.5f.6e, | 1a.2d.3a.4f.5f.6f, | 1a.2d.3b.4a.5a.6a, | |

TABLE 7-continued

List of Compounds of Formula (II)

| | | | | |
|---|---|---|---|---|
| 1a.2d.3b.4a.5a.6b, | 1a.2d.3b.4a.5a.6c, | 1a.2d.3b.4a.5a.6d, | 1a.2d.3b.4a.5a.6e, | |
| 1a.2d.3b.4a.5a.6f, | 1a.2d.3b.4a.5b.6a, | 1a.2d.3b.4a.5b.6b, | 1a.2d.3b.4a.5b.6c, | |
| 1a.2d.3b.4a.5b.6d, | 1a.2d.3b.4a.5b.6e, | 1a.2d.3b.4a.5b.6f, | 1a.2d.3b.4a.5c.6a, | |
| 1a.2d.3b.4a.5c.6b, | 1a.2d.3b.4a.5c.6c, | 1a.2d.3b.4a.5c.6d, | 1a.2d.3b.4a.5c.6e, | |
| 1a.2d.3b.4a.5c.6f, | 1a.2d.3b.4a.5d.6a, | 1a.2d.3b.4a.5d.6b, | 1a.2d.3b.4a.5d.6c, | |
| 1a.2d.3b.4a.5d.6d, | 1a.2d.3b.4a.5d.6e, | 1a.2d.3b.4a.5d.6f, | 1a.2d.3b.4a.5e.6a, | |
| 1a.2d.3b.4a.5e.6b, | 1a.2d.3b.4a.5e.6c, | 1a.2d.3b.4a.5e.6d, | 1a.2d.3b.4a.5e.6e, | |
| 1a.2d.3b.4a.5e.6f, | 1a.2d.3b.4a.5f.6a, | 1a.2d.3b.4a.5f.6b, | 1a.2d.3b.4a.5f.6c, | |
| 1a.2d.3b.4a.5f.6d, | 1a.2d.3b.4a.5f.6e, | 1a.2d.3b.4a.5f.6f, | 1a.2d.3b.4b.5a.6a, | |
| 1a.2d.3b.4b.5a.6b, | 1a.2d.3b.4b.5a.6c, | 1a.2d.3b.4b.5a.6d, | 1a.2d.3b.4b.5a.6e, | |
| 1a.2d.3b.4b.5a.6f, | 1a.2d.3b.4b.5b.6a, | 1a.2d.3b.4b.5b.6b, | 1a.2d.3b.4b.5b.6c, | |
| 1a.2d.3b.4b.5b.6d, | 1a.2d.3b.4b.5b.6e, | 1a.2d.3b.4b.5b.6f, | 1a.2d.3b.4b.5c.6a, | |
| 1a.2d.3b.4b.5c.6b, | 1a.2d.3b.4b.5c.6c, | 1a.2d.3b.4b.5c.6d, | 1a.2d.3b.4b.5c.6e, | |
| 1a.2d.3b.4b.5c.6f, | 1a.2d.3b.4b.5d.6a, | 1a.2d.3b.4b.5d.6b, | 1a.2d.3b.4b.5d.6c, | |
| 1a.2d.3b.4b.5d.6d, | 1a.2d.3b.4b.5d.6e, | 1a.2d.3b.4b.5d.6f, | 1a.2d.3b.4b.5e.6a, | |
| 1a.2d.3b.4b.5e.6b, | 1a.2d.3b.4b.5e.6c, | 1a.2d.3b.4b.5e.6d, | 1a.2d.3b.4b.5e.6e, | |
| 1a.2d.3b.4b.5e.6f, | 1a.2d.3b.4b.5f.6a, | 1a.2d.3b.4b.5f.6b, | 1a.2d.3b.4b.5f.6c, | |
| 1a.2d.3b.4b.5f.6d, | 1a.2d.3b.4b.5f.6e, | 1a.2d.3b.4b.5f.6f, | 1a.2d.3b.4c.5a.6a, | |
| 1a.2d.3b.4c.5a.6b, | 1a.2d.3b.4c.5a.6c, | 1a.2d.3b.4c.5a.6d, | 1a.2d.3b.4c.5a.6e, | |
| 1a.2d.3b.4c.5a.6f, | 1a.2d.3b.4c.5b.6a, | 1a.2d.3b.4c.5b.6b, | 1a.2d.3b.4c.5b.6c, | |
| 1a.2d.3b.4c.5b.6d, | 1a.2d.3b.4c.5b.6e, | 1a.2d.3b.4c.5b.6f, | 1a.2d.3b.4c.5c.6a, | |
| 1a.2d.3b.4c.5c.6b, | 1a.2d.3b.4c.5c.6c, | 1a.2d.3b.4c.5c.6d, | 1a.2d.3b.4c.5c.6e, | |
| 1a.2d.3b.4c.5c.6f, | 1a.2d.3b.4c.5d.6a, | 1a.2d.3b.4c.5d.6b, | 1a.2d.3b.4c.5d.6c, | |
| 1a.2d.3b.4c.5d.6d, | 1a.2d.3b.4c.5d.6e, | 1a.2d.3b.4c.5d.6f, | 1a.2d.3b.4c.5e.6a, | |
| 1a.2d.3b.4c.5e.6b, | 1a.2d.3b.4c.5e.6c, | 1a.2d.3b.4c.5e.6d, | 1a.2d.3b.4c.5e.6e, | |
| 1a.2d.3b.4c.5e.6f, | 1a.2d.3b.4c.5f.6a, | 1a.2d.3b.4c.5f.6b, | 1a.2d.3b.4c.5f.6c, | |
| 1a.2d.3b.4c.5f.6d, | 1a.2d.3b.4c.5f.6e, | 1a.2d.3b.4c.5f.6f, | 1a.2d.3b.4d.5a.6a, | |
| 1a.2d.3b.4d.5a.6b, | 1a.2d.3b.4d.5a.6c, | 1a.2d.3b.4d.5a.6d, | 1a.2d.3b.4d.5a.6e, | |
| 1a.2d.3b.4d.5a.6f, | 1a.2d.3b.4d.5b.6a, | 1a.2d.3b.4d.5b.6b, | 1a.2d.3b.4d.5b.6c, | |
| 1a.2d.3b.4d.5b.6d, | 1a.2d.3b.4d.5b.6e, | 1a.2d.3b.4d.5b.6f, | 1a.2d.3b.4d.5c.6a, | |
| 1a.2d.3b.4d.5c.6b, | 1a.2d.3b.4d.5c.6c, | 1a.2d.3b.4d.5c.6d, | 1a.2d.3b.4d.5c.6e, | |
| 1a.2d.3b.4d.5c.6f, | 1a.2d.3b.4d.5d.6a, | 1a.2d.3b.4d.5d.6b, | 1a.2d.3b.4d.5d.6c, | |
| 1a.2d.3b.4d.5d.6d, | 1a.2d.3b.4d.5d.6e, | 1a.2d.3b.4d.5d.6f, | 1a.2d.3b.4d.5e.6a, | |
| 1a.2d.3b.4d.5e.6b, | 1a.2d.3b.4d.5e.6c, | 1a.2d.3b.4d.5e.6d, | 1a.2d.3b.4d.5e.6e, | |
| 1a.2d.3b.4d.5e.6f, | 1a.2d.3b.4d.5f.6a, | 1a.2d.3b.4d.5f.6b, | 1a.2d.3b.4d.5f.6c, | |
| 1a.2d.3b.4d.5f.6d, | 1a.2d.3b.4d.5f.6e, | 1a.2d.3b.4d.5f.6f, | 1a.2d.3b.4e.5a.6a, | |
| 1a.2d.3b.4e.5a.6b, | 1a.2d.3b.4e.5a.6c, | 1a.2d.3b.4e.5a.6d, | 1a.2d.3b.4e.5a.6e, | |
| 1a.2d.3b.4e.5a.6f, | 1a.2d.3b.4e.5b.6a, | 1a.2d.3b.4e.5b.6b, | 1a.2d.3b.4e.5b.6c, | |
| 1a.2d.3b.4e.5b.6d, | 1a.2d.3b.4e.5b.6e, | 1a.2d.3b.4e.5b.6f, | 1a.2d.3b.4e.5c.6a, | |
| 1a.2d.3b.4e.5c.6b, | 1a.2d.3b.4e.5c.6c, | 1a.2d.3b.4e.5c.6d, | 1a.2d.3b.4e.5c.6e, | |
| 1a.2d.3b.4e.5c.6f, | 1a.2d.3b.4e.5d.6a, | 1a.2d.3b.4e.5d.6b, | 1a.2d.3b.4e.5d.6c, | |
| 1a.2d.3b.4e.5d.6d, | 1a.2d.3b.4e.5d.6e, | 1a.2d.3b.4e.5d.6f, | 1a.2d.3b.4e.5e.6a, | |
| 1a.2d.3b.4e.5e.6b, | 1a.2d.3b.4e.5e.6c, | 1a.2d.3b.4e.5e.6d, | 1a.2d.3b.4e.5e.6e, | |
| 1a.2d.3b.4e.5e.6f, | 1a.2d.3b.4e.5f.6a, | 1a.2d.3b.4e.5f.6b, | 1a.2d.3b.4e.5f.6c, | |
| 1a.2d.3b.4e.5f.6d, | 1a.2d.3b.4e.5f.6e, | 1a.2d.3b.4e.5f.6f, | 1a.2d.3b.4f.5a.6a, | |
| 1a.2d.3b.4f.5a.6b, | 1a.2d.3b.4f.5a.6c, | 1a.2d.3b.4f.5a.6d, | 1a.2d.313.4f.5a.6e, | |
| 1a.2d.3b.4f.5a.6f, | 1a.2d.3b.4f.5b.6a, | 1a.2d.3b.4f.5b.6b, | 1a.2d.3b.4f.5b.6c, | |
| 1a.2d.3b.4f.5b.6d, | 1a.2d.3b.4f.5b.6e, | 1a.2d.3b.4f.5b.6f, | 1a.2d.3b.4f.5c.6a, | |
| 1a.2d.3b.4f.5c.6b, | 1a.2d.3b.4f.5c.6c, | 1a.2d.3b.4f.5c.6d, | 1a.2d.3b.4f.5c.6e, | |
| 1a.2d.3b.4f.5c.6f, | 1a.2d.3b.4f.5d.6a, | 1a.2d.3b.4f.5d.6b, | 1a.2d.3b.4f.5d.6c, | |
| 1a.2d.3b.4f.5d.6d, | 1a.2d.3b.4f.5d.6e, | 1a.2d.3b.4f.5d.6f, | 1a.2d.3b.4f.5e.6a, | |
| 1a.2d.3b.4f.5e.6b, | 1a.2d.3b.4f.5e.6c, | 1a.2d.3b.4f.5e.6d, | 1a.2d.3b.4f.5e.6e, | |
| 1a.2d.3b.4f.5e.6f, | 1a.2d.3b.4f.5f.6a, | 1a.2d.3b.4f.5f.6b, | 1a.2d.3b.4f.5f.6c, | 1a.2d.3b.4f.5f.6d, |
| 1a.2d.3b.4f.5f.6e, | 1a.2d.3b.4f.5f.6f, | 1a.2d.3c.4a.5a.6a, | 1a.2d.3c.4a.5a.6b, | |
| 1a.2d.3c.4a.5a.6c, | 1a.2d.3c.4a.5a.6d, | 1a.2d.3c.4a.5a.6e, | 1a.2d.3c.4a.5a.6f, | |
| 1a.2d.3c.4a.5b.6a, | 1a.2d.3c.4a.5b.6b, | 1a.2d.3c.4a.5b.6c, | 1a.2d.3c.4a.5b.6d, | |
| 1a.2d.3c.4a.5b.6e, | 1a.2d.3c.4a.5b.6f, | 1a.2d.3c.4a.5c.6a, | 1a.2d.3c.4a.5c.6b, | |
| 1a.2d.3c.4a.5c.6c, | 1a.2d.3c.4a.5c.6d, | 1a.2d.3c.4a.5c.6e, | 1a.2d.3c.4a.5c.6f, | |
| 1a.2d.3c.4a.5d.6a, | 1a.2d.3c.4a.5d.6b, | 1a.2d.3c.4a.5d.6c, | 1a.2d.3c.4a.5d.6d, | |
| 1a.2d.3c.4a.5d.6e, | 1a.2d.3c.4a.5d.6f, | 1a.2d.3c.4a.5e.6a, | 1a.2d.3c.4a.5e.6b, | |
| 1a.2d.3c.4a.5e.6c, | 1a.2d.3c.4a.5e.6d, | 1a.2d.3c.4a.5e.6e, | 1a.2d.3c.4a.5e.6f, | |
| 1a.2d.3c.4a.5f.6a, | 1a.2d.3c.4a.5f.6b, | 1a.2d.3c.4a.5f.6c, | 1a.2d.3c.4a.5f.6d, | |
| 1a.2d.3c.4a.5f.6e, | 1a.2d.3c.4a.5f.6f, | 1a.2d.3c.4b.5a.6a, | 1a.2d.3c.4b.5a.6b, | |
| 1a.2d.3c.4b.5a.6c, | 1a.2d.3c.4b.5a.6d, | 1a.2d.3c.4b.5a.6e, | 1a.2d.3c.4b.5a.6f, | |
| 1a.2d.3c.4b.5b.6a, | 1a.2d.3c.4b.5b.6b, | 1a.2d.3c.4b.5b.6c, | 1a.2d.3c.4b.5b.6d, | |
| 1a.2d.3c.4b.5b.6e, | 1a.2d.3c.4b.5b.6f, | 1a.2d.3c.4b.5c.6a, | 1a.2d.3c.4b.5c.6b, | |
| 1a.2d.3c.4b.5c.6c, | 1a.2d.3c.4b.5c.6d, | 1a.2d.3c.4b.5c.6e, | 1a.2d.3c.4b.5c.6f, | |
| 1a.2d.3c.4b.5d.6a, | 1a.2d.3c.4b.5d.6b, | 1a.2d.3c.4b.5d.6c, | 1a.2d.3c.4b.5d.6d, | |
| 1a.2d.3c.4b.5d.6e, | 1a.2d.3c.4b.5d.6f, | 1a.2d.3c.4b.5e.6a, | 1a.2d.3c.4b.5e.6b, | |
| 1a.2d.3c.4b.5e.6c, | 1a.2d.3c.4b.5e.6d, | 1a.2d.3c.4b.5e.6e, | 1a.2d.3c.4b.5e.6f, | |
| 1a.2d.3c.4b.5f.6a, | 1a.2d.3c.4b.5f.6b, | 1a.2d.3c.4b.5f.6c, | 1a.2d.3c.4b.5f.6d, | |
| 1a.2d.3c.4b.5f.6e, | 1a.2d.3c.4b.5f.6f, | 1a.2d.3c.4c.5a.6a, | 1a.2d.3c.4c.5a.6b, | |
| 1a.2d.3c.4c.5a.6c, | 1a.2d.3c.4c.5a.6d, | 1a.2d.3c.4c.5a.6e, | 1a.2d.3c.4c.5a.6f, | |
| 1a.2d.3c.4c.5b.6a, | 1a.2d.3c.4c.5b.6b, | 1a.2d.3c.4c.5b.6c, | 1a.2d.3c.4c.5b.6d, | |
| 1a.2d.3c.4c.5b.6e, | 1a.2d.3c.4c.5b.6f, | 1a.2d.3c.4c.5c.6a, | 1a.2d.3c.4c.5c.6b, | |
| 1a.2d.3c.4c.5c.6c, | 1a.2d.3c.4c.5c.6d, | 1a.2d.3c.4c.5c.6e, | 1a.2d.3c.4c.5c.6f, | |
| 1a.2d.3c.4c.5d.6a, | 1a.2d.3c.4c.5d.6b, | 1a.2d.3c.4c.5d.6c, | 1a.2d.3c.4c.5d.6d, | |
| 1a.2d.3c.4c.5d.6e, | 1a.2d.3c.4c.5d.6f, | 1a.2d.3c.4c.5e.6a, | 1a.2d.3c.4c.5e.6b, | |

TABLE 7-continued

List of Compounds of Formula (II)

| | | | | |
|---|---|---|---|---|
| 1a.2d.3c.4c.5e.6c, | 1a.2d.3c.4c.5e.6d, | 1a.2d.3c.4c.5e.6e, | 1a.2d.3c.4c.5e.6f, | |
| 1a.2d.3c.4c.5f.6a, | 1a.2d.3c.4c.5f.6b, | 1a.2d.3c.4c.5f.6c, | 1a.2d.3c.4c.5f.6d, | 1a.2d.3c.4c.5f.6e, |
| 1a.2d.3c.4c.5f.6f, | 1a.2d.3c.4d.5a.6a, | 1a.2d.3c.4d.5a.6b, | 1a.2d.3c.4d.5a.6c, | |
| 1a.2d.3c.4d.5a.6d, | 1a.2d.3c.4d.5a.6e, | 1a.2d.3c.4d.5a.6f, | 1a.2d.3c.4d.5b.6a, | |
| 1a.2d.3c.4d.5b.6b, | 1a.2d.3c.4d.5b.6c, | 1a.2d.3c.4d.5b.6d, | 1a.2d.3c.4d.5b.6e, | |
| 1a.2d.3c.4d.5b.6f, | 1a.2d.3c.4d.5c.6a, | 1a.2d.3c.4d.5c.6b, | 1a.2d.3c.4d.5c.6c, | |
| 1a.2d.3c.4d.5c.6d, | 1a.2d.3c.4d.5c.6e, | 1a.2d.3c.4d.5c.6f, | 1a.2d.3c.4d.5d.6a, | |
| 1a.2d.3c.4d.5d.6b, | 1a.2d.3c.4d.5d.6c, | 1a.2d.3c.4d.5d.6d, | 1a.2d.3c.4d.5d.6e, | |
| 1a.2d.3c.4d.5d.6f, | 1a.2d.3c.4d.5e.6a, | 1a.2d.3c.4d.5e.6b, | 1a.2d.3c.4d.5e.6c, | |
| 1a.2d.3c.4d.5e.6d, | 1a.2d.3c.4d.5e.6e, | 1a.2d.3c.4d.5e.6f, | 1a.2d.3c.4d.5f.6a, | |
| 1a.2d.3c.4d.5f.6b, | 1a.2d.3c.4d.5f.6c, | 1a.2d.3c.4d.5f.6d, | 1a.2d.3c.4d.5f.6e, | |
| 1a.2d.3c.4d.5f.6f, | 1a.2d.3c.4e.5a.6a, | 1a.2d.3c.4e.5a.6b, | 1a.2d.3c.4e.5a.6c, | |
| 1a.2d.3c.4e.5a.6d, | 1a.2d.3c.4e.5a.6e, | 1a.2d.3c.4e.5a.6f, | 1a.2d.3c.4e.5b.6a, | |
| 1a.2d.3c.4e.5b.6b, | 1a.2d.3c.4e.5b.6c, | 1a.2d.3c.4e.5b.6d, | 1a.2d.3c.4e.5b.6e, | |
| 1a.2d.3c.4e.5b.6f, | 1a.2d.3c.4e.5c.6a, | 1a.2d.3c.4e.5c.6b, | 1a.2d.3c.4e.5c.6c, | |
| 1a.2d.3c.4e.5c.6d, | 1a.2d.3c.4e.5c.6e, | 1a.2d.3c.4e.5c.6f, | 1a.2d.3c.4e.5d.6a, | |
| 1a.2d.3c.4e.5d.6b, | 1a.2d.3c.4e.5d.6c, | 1a.2d.3c.4e.5d.6d, | 1a.2d.3c.4e.5d.6e, | |
| 1a.2d.3c.4e.5d.6f, | 1a.2d.3c.4e.5e.6a, | 1a.2d.3c.4e.5e.6b, | 1a.2d.3c.4e.5e.6c, | |
| 1a.2d.3c.4e.5e.6d, | 1a.2d.3c.4e.5e.6e, | 1a.2d.3c.4e.5e.6f, | 1a.2d.3c.4e.5f.6a, | |
| 1a.2d.3c.4e.5f.6b, | 1a.2d.3c.4e.5f.6c, | 1a.2d.3c.4e.5f.6d, | 1a.2d.3c.4e.5f.6e, | 1a.2d.3c.4e.5f.6f, |
| 1a.2d.3c.4f.5a.6a, | 1a.2d.3c.4f.5a.6b, | 1a.2d.3c.4f.5a.6c, | 1a.2d.3c.4f.5a.6d, | |
| 1a.2d.3c.4f.5a.6e, | 1a.2d.3c.4f.5a.6f, | 1a.2d.3c.4f.5b.6a, | 1a.2d.3c.4f.5b.6b, | |
| 1a.2d.3c.4f.5b.6c, | 1a.2d.3c.4f.5b.6d, | 1a.2d.3c.4f.5b.6e, | 1a.2d.3c.4f.5b.6f, | |
| 1a.2d.3c.4f.5c.6a, | 1a.2d.3c.4f.5c.6b, | 1a.2d.3c.4f.5c.6c, | 1a.2d.3c.4f.5c.6d, | 1a.2d.3c.4f.5c.6e, |
| 1a.2d.3c.4f.5c.6f, | 1a.2d.3c.4f.5d.6a, | 1a.2d.3c.4f.5d.6b, | 1a.2d.3c.4f.5d.6c, | |
| 1a.2d.3c.4f.5d.6d, | 1a.2d.3c.4f.5d.6e, | 1a.2d.3c.4f.5d.6f, | 1a.2d.3c.4f.5e.6a, | |
| 1a.2d.3c.4f.5e.6b, | 1a.2d.3c.4f.5e.6c, | 1a.2d.3c.4f.5e.6d, | 1a.2d.3c.4f.5e.6e, | 1a.2d.3c.4f.5e.6f, |
| 1a.2d.3c.4f.5f.6a, | 1a.2d.3c.4f.5f.6b, | 1a.2d.3c.4f.5f.6c, | 1a.2d.3c.4f.5f.6d, | 1a.2d.3c.4f.5f.6e, |
| 1a.2d.3c.4f.5f.6f, | 1a.2d.3d.4a.5a.6a, | 1a.2d.3d.4a.5a.6b, | 1a.2d.3d.4a.5a.6c, | |
| 1a.2d.3d.4a.5a.6d, | 1a.2d.3d.4a.5a.6e, | 1a.2d.3d.4a.5a.6f, | 1a.2d.3d.4a.5b.6a, | |
| 1a.2d.3d.4a.5b.6b, | 1a.2d.3d.4a.5b.6c, | 1a.2d.3d.4a.5b.6d, | 1a.2d.3d.4a.5b.6e, | |
| 1a.2d.3d.4a.5b.6f, | 1a.2d.3d.4a.5c.6a, | 1a.2d.3d.4a.5c.6b, | 1a.2d.3d.4a.5c.6c, | |
| 1a.2d.3d.4a.5c.6d, | 1a.2d.3d.4a.5c.6e, | 1a.2d.3d.4a.5c.6f, | 1a.2d.3d.4a.5d.6a, | |
| 1a.2d.3d.4a.5d.6b, | 1a.2d.3d.4a.5d.6c, | 1a.2d.3d.4a.5d.6d, | 1a.2d.3d.4a.5d.6e, | |
| 1a.2d.3d.4a.5d.6f, | 1a.2d.3d.4a.5e.6a, | 1a.2d.3d.4a.5e.6b, | 1a.2d.3d.4a.5e.6c, | |
| 1a.2d.3d.4a.5e.6d, | 1a.2d.3d.4a.5e.6e, | 1a.2d.3d.4a.5e.6f, | 1a.2d.3d.4a.5f.6a, | |
| 1a.2d.3d.4a.5f.6b, | 1a.2d.3d.4a.5f.6c, | 1a.2d.3d.4a.5f.6d, | 1a.2d.3d.4a.5f.6e, | |
| 1a.2d.3d.4a.5f.6f, | 1a.2d.3d.4b.5a.6a, | 1a.2d.3d.4b.5a.6b, | 1a.2d.3d.4b.5a.6c, | |
| 1a.2d.3d.4b.5a.6d, | 1a.2d.3d.4b.5a.6e, | 1a.2d.3d.4b.5a.6f, | 1a.2d.3d.4b.5b.6a, | |
| 1a.2d.3d.4b.5b.6b, | 1a.2d.3d.4b.5b.6c, | 1a.2d.3d.4b.5b.6d, | 1a.2d.3d.4b.5b.6e, | |
| 1a.2d.3d.4b.5b.6f, | 1a.2d.3d.4b.5c.6a, | 1a.2d.3d.4b.5c.6b, | 1a.2d.3d.4b.5c.6c, | |
| 1a.2d.3d.4b.5c.6d, | 1a.2d.3d.4b.5c.6e, | 1a.2d.3d.4b.5c.6f, | 1a.2d.3d.4b.5d.6a, | |
| 1a.2d.3d.4b.5d.6b, | 1a.2d.3d.4b.5d.6c, | 1a.2d.3d.4b.5d.6d, | 1a.2d.3d.4b.5d.6e, | |
| 1a.2d.3d.4b.5d.6f, | 1a.2d.3d.4b.5e.6a, | 1a.2d.3d.4b.5e.6b, | 1a.2d.3d.4b.5e.6c, | |
| 1a.2d.3d.4b.5e.6d, | 1a.2d.3d.4b.5e.6e, | 1a.2d.3d.4b.5e.6f, | 1a.2d.3d.4b.5f.6a, | |
| 1a.2d.3d.4b.5f.6b, | 1a.2d.3d.4b.5f.6c, | 1a.2d.3d.4b.5f.6d, | 1a.2d.3d.4b.5f.6e, | |
| 1a.2d.3d.4b.5f.6f, | 1a.2d.3d.4c.5a.6a, | 1a.2d.3d.4c.5a.6b, | 1a.2d.3d.4c.5a.6c, | |
| 1a.2d.3d.4c.5a.6d, | 1a.2d.3d.4c.5a.6e, | 1a.2d.3d.4c.5a.6f, | 1a.2d.3d.4c.5b.6a, | |
| 1a.2d.3d.4c.5b.6b, | 1a.2d.3d.4c.5b.6c, | 1a.2d.3d.4c.5b.6d, | 1a.2d.3d.4c.5b.6e, | |
| 1a.2d.3d.4c.5b.6f, | 1a.2d.3d.4c.5c.6a, | 1a.2d.3d.4c.5c.6b, | 1a.2d.3d.4c.5c.6c, | |
| 1a.2d.3d.4c.5c.6d, | 1a.2d.3d.4c.5c.6e, | 1a.2d.3d.4c.5c.6f, | 1a.2d.3d.4c.5d.6a, | |
| 1a.2d.3d.4c.5d.6b, | 1a.2d.3d.4c.5d.6c, | 1a.2d.3d.4c.5d.6d, | 1a.2d.3d.4c.5d.6e, | |
| 1a.2d.3d.4c.5d.6f, | 1a.2d.3d.4c.5e.6a, | 1a.2d.3d.4c.5e.6b, | 1a.2d.3d.4c.5e.6c, | |
| 1a.2d.3d.4c.5e.6d, | 1a.2d.3d.4c.5e.6e, | 1a.2d.3d.4c.5e.6f, | 1a.2d.3d.4c.5f.6a, | |
| 1a.2d.3d.4c.5f.6b, | 1a.2d.3d.4c.5f.6c, | 1a.2d.3d.4c.5f.6d, | 1a.2d.3d.4c.5f.6e, | |
| 1a.2d.3d.4c.5f.6f, | 1a.2d.3d.4d.5a.6a, | 1a.2d.3d.4d.5a.6b, | 1a.2d.3d.4d.5a.6c, | |
| 1a.2d.3d.4d.5a.6d, | 1a.2d.3d.4d.5a.6e, | 1a.2d.3d.4d.5a.6f, | 1a.2d.3d.4d.5b.6a, | |
| 1a.2d.3d.4d.5b.6b, | 1a.2d.3d.4d.5b.6c, | 1a.2d.3d.4d.5b.6d, | 1a.2d.3d.4d.5b.6e, | |
| 1a.2d.3d.4d.5b.6f, | 1a.2d.3d.4d.5c.6a, | 1a.2d.3d.4d.5c.6b, | 1a.2d.3d.4d.5c.6c, | |
| 1a.2d.3d.4d.5c.6d, | 1a.2d.3d.4d.5c.6e, | 1a.2d.3d.4d.5c.6f, | 1a.2d.3d.4d.5d.6a, | |
| 1a.2d.3d.4d.5d.6b, | 1a.2d.3d.4d.5d.6c, | 1a.2d.3d.4d.5d.6d, | 1a.2d.3d.4d.5d.6e, | |
| 1a.2d.3d.4d.5d.6f, | 1a.2d.3d.4d.5e.6a, | 1a.2d.3d.4d.5e.6b, | 1a.2d.3d.4d.5e.6c, | |
| 1a.2d.3d.4d.5e.6d, | 1a.2d.3d.4d.5e.6e, | 1a.2d.3d.4d.5e.6f, | 1a.2d.3d.4d.5f.6a, | |
| 1a.2d.3d.4d.5f.6b, | 1a.2d.3d.4d.5f.6c, | 1a.2d.3d.4d.5f.6d, | 1a.2d.3d.4d.5f.6e, | |
| 1a.2d.3d.4d.5f.6f, | 1a.2d.3d.4e.5a.6a, | 1a.2d.3d.4e.5a.6b, | 1a.2d.3d.4e.5a.6c, | |
| 1a.2d.3d.4e.5a.6d, | 1a.2d.3d.4e.5a.6e, | 1a.2d.3d.4e.5a.6f, | 1a.2d.3d.4e.5b.6a, | |
| 1a.2d.3d.4e.5b.6b, | 1a.2d.3d.4e.5b.6c, | 1a.2d.3d.4e.5b.6d, | 1a.2d.3d.4e.5b.6e, | |
| 1a.2d.3d.4e.5b.6f, | 1a.2d.3d.4e.5c.6a, | 1a.2d.3d.4e.5c.6b, | 1a.2d.3d.4e.5c.6c, | |
| 1a.2d.3d.4e.5c.6d, | 1a.2d.3d.4e.5c.6e, | 1a.2d.3d.4e.5c.6f, | 1a.2d.3d.4e.5d.6a, | |
| 1a.2d.3d.4e.5d.6b, | 1a.2d.3d.4e.5d.6c, | 1a.2d.3d.4e.5d.6d, | 1a.2d.3d.4e.5d.6e, | |
| 1a.2d.3d.4e.5d.6f, | 1a.2d.3d.4e.5e.6a, | 1a.2d.3d.4e.5e.6b, | 1a.2d.3d.4e.5e.6c, | |
| 1a.2d.3d.4e.5e.6d, | 1a.2d.3d.4e.5e.6e, | 1a.2d.3d.4e.5e.6f, | 1a.2d.3d.4e.5f.6a, | |
| 1a.2d.3d.4e.5f.6b, | 1a.2d.3d.4e.5f.6c, | 1a.2d.3d.4e.5f.6d, | 1a.2d.3d.4e.5f.6e, | |
| 1a.2d.3d.4e.5f.6f, | 1a.2d.3d.4f.5a.6a, | 1a.2d.3d.4f.5a.6b, | 1a.2d.3d.4f.5a.6c, | |
| 1a.2d.3d.4f.5a.6d, | 1a.2d.3d.4f.5a.6e, | 1a.2d.3d.4f.5a.6f, | 1a.2d.3d.4f.5b.6a, | |
| 1a.2d.3d.4f.5b.6b, | 1a.2d.3d.4f.5b.6c, | 1a.2d.3d.4f.5b.6d, | 1a.2d.3d.4f.5b.6e, | |
| 1a.2d.3d.4f.5b.6f, | 1a.2d.3d.4f.5c.6a, | 1a.2d.3d.4f.5c.6b, | 1a.2d.3d.4f.5c.6c, | |
| 1a.2d.3d.4f.5c.6d, | 1a.2d.3d.4f.5c.6e, | 1a.2d.3d.4f.5c.6f, | 1a.2d.3d.4f.5d.6a, | |

TABLE 7-continued

List of Compounds of Formula (II)

| | | | | |
|---|---|---|---|---|
| 1a.2d.3d.4f.5d.6b, | 1a.2d.3d.4f.5d.6c, | 1a.2d.3d.4f.5d.6d, | 1a.2d.3d.4f.5d.6e, | |
| 1a.2d.3d.4f.5d.6f, | 1a.2d.3d.4f.5e.6a, | 1a.2d.3d.4f.5e.6b, | 1a.2d.3d.4f.5e.6c, | |
| 1a.2d.3d.4f.5e.6d, | 1a.2d.3d.4f.5e.6e, | 1a.2d.3d.4f.5e.6f, | 1a.2d.3d.4f.5f.6a, | |
| 1a.2d.3d.4f.5f.6b, | 1a.2d.3d.4f.5f.6c, | 1a.2d.3d.4f.5f.6d, | 1a.2d.3d.4f.5f.6e, | 1a.2d.3d.4f.5f.6f |
| 1a.2d.3e.4a.5a.6a, | 1a.2d.3e.4a.5a.6b, | 1a.2d.3e.4a.5a.6c, | 1a.2d.3e.4a.5a.6d, | |
| 1a.2d.3e.4a.5a.6e, | 1a.2d.3e.4a.5a.6f, | 1a.2d.3e.4a.5b.6a, | 1a.2d.3e.4a.5b.6b, | |
| 1a.2d.3e.4a.5b.6c, | 1a.2d.3e.4a.5b.6d, | 1a.2d.3e.4a.5b.6e, | 1a.2d.3e.4a.5b.6f, | |
| 1a.2d.3e.4a.5c.6a, | 1a.2d.3e.4a.5c.6b, | 1a.2d.3e.4a.5c.6c, | 1a.2d.3e.4a.5c.6d, | |
| 1a.2d.3e.4a.5c.6e, | 1a.2d.3e.4a.5c.6f, | 1a.2d.3e.4a.5d.6a, | 1a.2d.3e.4a.5d.6b, | |
| 1a.2d.3e.4a.5d.6c, | 1a.2d.3e.4a.5d.6d, | 1a.2d.3e.4a.5d.6e, | 1a.2d.3e.4a.5d.6f, | |
| 1a.2d.3e.4a.5e.6a, | 1a.2d.3e.4a.5e.6b, | 1a.2d.3e.4a.5e.6c, | 1a.2d.3e.4a.5e.6d, | |
| 1a.2d.3e.4a.5e.6e, | 1a.2d.3e.4a.5e.6f, | 1a.2d.3e.4a.5f.6a, | 1a.2d.3e.4a.5f.6b, | |
| 1a.2d.3e.4a.5f.6c, | 1a.2d.3e.4a.5f.6d, | 1a.2d.3e.4a.5f.6e, | 1a.2d.3e.4a.5f.6f, | |
| 1a.2d.3e.4b.5a.6a, | 1a.2d.3e.4b.5a.6b, | 1a.2d.3e.4b.5a.6c, | 1a.2d.3e.4b.5a.6d, | |
| 1a.2d.3e.4b.5a.6e, | 1a.2d.3e.4b.5a.6f, | 1a.2d.3e.4b.5b.6a, | 1a.2d.3e.4b.5b.6b, | |
| 1a.2d.3e.4b.5b.6c, | 1a.2d.3e.4b.5b.6d, | 1a.2d.3e.4b.5b.6e, | 1a.2d.3e.4b.5b.6f, | |
| 1a.2d.3e.4b.5c.6a, | 1a.2d.3e.4b.5c.6b, | 1a.2d.3e.4b.5c.6c, | 1a.2d.3e.4b.5c.6d, | |
| 1a.2d.3e.4b.5c.6e, | 1a.2d.3e.4b.5c.6f, | 1a.2d.3e.4b.5d.6a, | 1a.2d.3e.4b.5d.6b, | |
| 1a.2d.3e.4b.5d.6c, | 1a.2d.3e.4b.5d.6d, | 1a.2d.3e.4b.5d.6e, | 1a.2d.3e.4b.5d.6f, | |
| 1a.2d.3e.4b.5e.6a, | 1a.2d.3e.4b.5e.6b, | 1a.2d.3e.4b.5e.6c, | 1a.2d.3e.4b.5e.6d, | |
| 1a.2d.3e.4b.5e.6e, | 1a.2d.3e.4b.5e.6f, | 1a.2d.3e.4b.5f.6a, | 1a.2d.3e.4b.5f.6b, | |
| 1a.2d.3e.4b.5f.6c, | 1a.2d.3e.4b.5f.6d, | 1a.2d.3e.4b.5f.6e, | 1a.2d.3e.4b.5f.6f, | |
| 1a.2d.3e.4c.5a.6a, | 1a.2d.3e.4c.5a.6b, | 1a.2d.3e.4c.5a.6c, | 1a.2d.3e.4c.5a.6d, | |
| 1a.2d.3e.4c.5a.6e, | 1a.2d.3e.4c.5a.6f, | 1a.2d.3e.4c.5b.6a, | 1a.2d.3e.4c.5b.6b, | |
| 1a.2d.3e.4c.5b.6c, | 1a.2d.3e.4c.5b.6d, | 1a.2d.3e.4c.5b.6e, | 1a.2d.3e.4c.5b.6f, | |
| 1a.2d.3e.4c.5c.6a, | 1a.2d.3e.4c.5c.6b, | 1a.2d.3e.4c.5c.6c, | 1a.2d.3e.4c.5c.6d, | |
| 1a.2d.3e.4c.5c.6e, | 1a.2d.3e.4c.5c.6f, | 1a.2d.3e.4c.5d.6a, | 1a.2d.3e.4c.5d.6b, | |
| 1a.2d.3e.4c.5d.6c, | 1a.2d.3e.4c.5d.6d, | 1a.2d.3e.4c.5d.6e, | 1a.2d.3e.4c.5d.6f, | |
| 1a.2d.3e.4c.5e.6a, | 1a.2d.3e.4c.5e.6b, | 1a.2d.3e.4c.5e.6c, | 1a.2d.3e.4c.5e.6d, | |
| 1a.2d.3e.4c.5e.6e, | 1a.2d.3e.4c.5e.6f, | 1a.2d.3e.4c.5f.6a, | 1a.2d.3e.4c.5f.6b, | |
| 1a.2d.3e.4c.5f.6c, | 1a.2d.3e.4c.5f.6d, | 1a.2d.3e.4c.5f.6e, | 1a.2d.3e.4c.5f.6f, | |
| 1a.2d.3e.4d.5a.6a, | 1a.2d.3e.4d.5a.6b, | 1a.2d.3e.4d.5a.6c, | 1a.2d.3e.4d.5a.6d, | |
| 1a.2d.3e.4d.5a.6e, | 1a.2d.3e.4d.5a.6f, | 1a.2d.3e.4d.5b.6a, | 1a.2d.3e.4d.5b.6b, | |
| 1a.2d.3e.4d.5b.6c, | 1a.2d.3e.4d.5b.6d, | 1a.2d.3e.4d.5b.6e, | 1a.2d.3e.4d.5b.6f, | |
| 1a.2d.3e.4d.5c.6a, | 1a.2d.3e.4d.5c.6b, | 1a.2d.3e.4d.5c.6c, | 1a.2d.3e.4d.5c.6d, | |
| 1a.2d.3e.4d.5c.6e, | 1a.2d.3e.4d.5c.6f, | 1a.2d.3e.4d.5d.6a, | 1a.2d.3e.4d.5d.6b, | |
| 1a.2d.3e.4d.5d.6c, | 1a.2d.3e.4d.5d.6d, | 1a.2d.3e.4d.5d.6e, | 1a.2d.3e.4d.5d.6f, | |
| 1a.2d.3e.4d.5e.6a, | 1a.2d.3e.4d.5e.6b, | 1a.2d.3e.4d.5e.6c, | 1a.2d.3e.4d.5e.6d, | |
| 1a.2d.3e.4d.5e.6e, | 1a.2d.3e.4d.5e.6f, | 1a.2d.3e.4d.5f.6a, | 1a.2d.3e.4d.5f.6b, | |
| 1a.2d.3e.4d.5f.6c, | 1a.2d.3e.4d.5f.6d, | 1a.2d.3e.4d.5f.6e, | 1a.2d.3e.4d.5f.6f, | |
| 1a.2d.3e.4e.5a.6a, | 1a.2d.3e.4e.5a.6b, | 1a.2d.3e.4e.5a.6c, | 1a.2d.3e.4e.5a.6d, | |
| 1a.2d.3e.4e.5a.6e, | 1a.2d.3e.4e.5a.6f, | 1a.2d.3e.4e.5b.6a, | 1a.2d.3e.4e.5b.6b, | |
| 1a.2d.3e.4e.5b.6c, | 1a.2d.3e.4e.5b.6d, | 1a.2d.3e.4e.5b.6e, | 1a.2d.3e.4e.5b.6f, | |
| 1a.2d.3e.4e.5c.6a, | 1a.2d.3e.4e.5c.6b, | 1a.2d.3e.4e.5c.6c, | 1a.2d.3e.4e.5c.6d, | |
| 1a.2d.3e.4e.5c.6e, | 1a.2d.3e.4e.5c.6f, | 1a.2d.3e.4e.5d.6a, | 1a.2d.3e.4e.5d.6b, | |
| 1a.2d.3e.4e.5d.6c, | 1a.2d.3e.4e.5d.6d, | 1a.2d.3e.4e.5d.6e, | 1a.2d.3e.4e.5d.6f, | |
| 1a.2d.3e.4e.5e.6a, | 1a.2d.3e.4e.5e.6b, | 1a.2d.3e.4e.5e.6c, | 1a.2d.3e.4e.5e.6d, | |
| 1a.2d.3e.4e.5e.6e, | 1a.2d.3e.4e.5e.6f, | 1a.2d.3e.4e.5f.6a, | 1a.2d.3e.4e.5f.6b, | |
| 1a.2d.3e.4e.5f.6c, | 1a.2d.3e.4e.5f.6d, | 1a.2d.3e.4e.5f.6e, | 1a.2d.3e.4e.5f.6f, | |
| 1a.2d.3e.4f.5a.6a, | 1a.2d.3e.4f.5a.6b, | 1a.2d.3e.4f.5a.6c, | 1a.2d.3e.4f.5a.6d, | |
| 1a.2d.3e.4f.5a.6e, | 1a.2d.3e.4f.5a.6f, | 1a.2d.3e.4f.5b.6a, | 1a.2d.3e.4f.5b.6b, | |
| 1a.2d.3e.4f.5b.6c, | 1a.2d.3e.4f.5b.6d, | 1a.2d.3e.4f.5b.6e, | 1a.2d.3e.4f.5b.6f, | |
| 1a.2d.3e.4f.5c.6a, | 1a.2d.3e.4f.5c.6b, | 1a.2d.3e.4f.5c.6c, | 1a.2d.3e.4f.5c.6d, | |
| 1a.2d.3e.4f.5c.6e, | 1a.2d.3e.4f.5c.6f, | 1a.2d.3e.4f.5d.6a, | 1a.2d.3e.4f.5d.6b, | |
| 1a.2d.3e.4f.5d.6c, | 1a.2d.3e.4f.5d.6d, | 1a.2d.3e.4f.5d.6e, | 1a.2d.3e.4f.5d.6f, | |
| 1a.2d.3e.4f.5e.6a, | 1a.2d.3e.4f.5e.6b, | 1a.2d.3e.4f.5e.6c, | 1a.2d.3e.4f.5e.6d, | |
| 1a.2d.3e.4f.5e.6e, | 1a.2d.3e.4f.5e.6f, | 1a.2d.3e.4f.5f.6a, | 1a.2d.3e.4f.5f.6b, | 1a.2d.3e.4f.5f.6c, |
| 1a.2d.3e.4f.5f.6d, | 1a.2d.3e.4f.5f.6e, | 1a.2d.3e.4f.5f.6f, | 1a.2d.3f.4a.5a.6a, | 1a.2d.3f.4a.5a.6b, |
| 1a.2d.3f.4a.5a.6c, | 1a.2d.3f.4a.5a.6d, | 1a.2d.3f.4a.5a.6e, | 1a.2d.3f.4a.5a.6f, | |
| 1a.2d.3f.4a.5b.6a, | 1a.2d.3f.4a.5b.6b, | 1a.2d.3f.4a.5b.6c, | 1a.2d.3f.4a.5b.6d, | |
| 1a.2d.3f.4a.5b.6e, | 1a.2d.3f.4a.5b.6f, | 1a.2d.3f.4a.5c.6a, | 1a.2d.3f.4a.5c.6b, | |
| 1a.2d.3f.4a.5c.6c, | 1a.2d.3f.4a.5c.6d, | 1a.2d.3f.4a.5c.6e, | 1a.2d.3f.4a.5c.6f, | |
| 1a.2d.3f.4a.5d.6a, | 1a.2d.3f.4a.5d.6b, | 1a.2d.3f.4a.5d.6c, | 1a.2d.3f.4a.5d.6d, | |
| 1a.2d.3f.4a.5d.6e, | 1a.2d.3f.4a.5d.6f, | 1a.2d.3f.4a.5e.6a, | 1a.2d.3f.4a.5e.6b, | |
| 1a.2d.3f.4a.5e.6c, | 1a.2d.3f.4a.5e.6d, | 1a.2d.3f.4a.5e.6e, | 1a.2d.3f.4a.5e.6f, | 1a.2d.3f.4a.5f.6a, |
| 1a.2d.3f.4a.5f.6b, | 1a.2d.3f.4a.5f.6c, | 1a.2d.3f.4a.5f.6d, | 1a.2d.3f.4a.5f.6e, | 1a.2d.3f.4a.5f.6f, |
| 1a.2d.3f.4b.5a.6a, | 1a.2d.3f.4b.5a.6b, | 1a.2d.3f.4b.5a.6c, | 1a.2d.3f.4b.5a.6d, | |
| 1a.2d.3f.4b.5a.6e, | 1a.2d.3f.4b.5a.6f, | 1a.2d.3f.4b.5b.6a, | 1a.2d.3f.4b.5b.6b, | |
| 1a.2d.3f.4b.5b.6c, | 1a.2d.3f.4b.5b.6d, | 1a.2d.3f.4b.5b.6e, | 1a.2d.3f.4b.5b.6f, | |
| 1a.2d.3f.4b.5c.6a, | 1a.2d.3f.4b.5c.6b, | 1a.2d.3f.4b.5c.6c, | 1a.2d.3f.4b.5c.6d, | |
| 1a.2d.3f.4b.5c.6e, | 1a.2d.3f.4b.5c.6f, | 1a.2d.3f.4b.5d.6a, | 1a.2d.3f.4b.5d.6b, | |
| 1a.2d.3f.4b.5d.6c, | 1a.2d.3f.4b.5d.6d, | 1a.2d.3f.4b.5d.6e, | 1a.2d.3f.4b.5d.6f, | |
| 1a.2d.3f.4b.5e.6a, | 1a.2d.3f.4b.5e.6b, | 1a.2d.3f.4b.5e.6c, | 1a.2d.3f.4b.5e.6d, | |
| 1a.2d.3f.4b.5e.6e, | 1a.2d.3f.4b.5e.6f, | 1a.2d.3f.4b.5f.6a, | 1a.2d.3f.4b.5f.6b, | 1a.2d.3f.4b.5f.6c, |
| 1a.2d.3f.4b.5f.6d, | 1a.2d.3f.4b.5f.6e, | 1a.2d.3f.4b.5f.6f, | 1a.2d.3f.4c.5a.6a, | 1a.2d.3f.4c.5a.6b, |
| 1a.2d.3f.4c.5a.6c, | 1a.2d.3f.4c.5a.6d, | 1a.2d.3f.4c.5a.6e, | 1a.2d.3f.4c.5a.6f, | 1a.2d.3f.4c.5b.6a, |
| 1a.2d.3f.4c.5b.6b, | 1a.2d.3f.4c.5b.6c, | 1a.2d.3f.4c.5b.6d, | 1a.2d.3f.4c.5b.6e, | |
| 1a.2d.3f.4c.5b.6f, | 1a.2d.3f.4c.5c.6a, | 1a.2d.3f.4c.5c.6b, | 1a.2d.3f.4c.5c.6c, | 1a.2d.3f.4c.5c.6d, |

TABLE 7-continued

List of Compounds of Formula (II)

| | | | | |
|---|---|---|---|---|
| 1a.2d.3f.4c.5c.6e, | 1a.2d.3f.4c.5c.6f, | 1a.2d.3f.4c.5d.6a, | 1a.2d.3f.4c.5d.6b, | |
| 1a.2d.3f.4c.5d.6c, | 1a.2d.3f.4c.5d.6d, | 1a.2d.3f.4c.5d.6e, | 1a.2d.3f.4c.5d.6f, | |
| 1a.2d.3f.4c.5e.6a, | 1a.2d.3f.4c.5e.6b, | 1a.2d.3f.4c.5e.6c, | 1a.2d.3f.4c.5e.6d, | |
| 1a.2d.3f.4c.5e.6e, | 1a.2d.3f.4c.5e.6f, | 1a.2d.3f.4c.5f.6a, | 1a.2d.3f.4c.5f.6b, | 1a.2d.3f.4c.5f.6c, |
| 1a.2d.3f.4c.5f.6d, | 1a.2d.3f.4c.5f.6e, | 1a.2d.3f.4c.5f.6f, | 1a.2d.3f.4d.5a.6a, | 1a.2d.3f.4d.5a.6b, |
| 1a.2d.3f.4d.5a.6c, | 1a.2d.3f.4d.5a.6d, | 1a.2d.3f.4d.5a.6e, | 1a.2d.3f.4d.5a.6f, | |
| 1a.2d.3f.4d.5b.6a, | 1a.2d.3f.4d.5b.6b, | 1a.2d.3f.4d.5b.6c, | 1a.2d.3f.4d.5b.6d, | |
| 1a.2d.3f.4d.5b.6e, | 1a.2d.3f.4d.5b.6f, | 1a.2d.3f.4d.5c.6a, | 1a.2d.3f.4d.5c.6b, | |
| 1a.2d.3f.4d.5c.6c, | 1a.2d.3f.4d.5c.6d, | 1a.2d.3f.4d.5c.6e, | 1a.2d.3f.4d.5c.6f, | |
| 1a.2d.3f.4d.5d.6a, | 1a.2d.3f.4d.5d.6b, | 1a.2d.3f.4d.5d.6c, | 1a.2d.3f.4d.5d.6d, | |
| 1a.2d.3f.4d.5d.6e, | 1a.2d.3f.4d.5d.6f, | 1a.2d.3f.4d.5e.6a, | 1a.2d.3f.4d.5e.6b, | |
| 1a.2d.3f.4d.5e.6c, | 1a.2d.3f.4d.5e.6d, | 1a.2d.3f.4d.5e.6e, | 1a.2d.3f.4d.5e.6f, | |
| 1a.2d.3f.4d.5f.6a, | 1a.2d.3f.4d.5f.6b, | 1a.2d.3f.4d.5f.6c, | 1a.2d.3f.4d.5f.6d, | |
| 1a.2d.3f.4d.5f.6e, | 1a.2d.3f.4d.5f.6f, | 1a.2d.3f.4e.5a.6a, | 1a.2d.3f.4e.5a.6b, | 1a.2d.3f.4e.5a.6c, |
| 1a.2d.3f.4e.5a.6d, | 1a.2d.3f.4e.5a.6e, | 1a.2d.3f.4e.5a.6f, | 1a.2d.3f.4e.5b.6a, | |
| 1a.2d.3f.4e.5b.6b, | 1a.2d.3f.4e.5b.6c, | 1a.2d.3f.4e.5b.6d, | 1a.2d.3f.4e.5b.6e, | |
| 1a.2d.3f.4e.5b.6f, | 1a.2d.3f.4e.5c.6a, | 1a.2d.3f.4e.5c.6b, | 1a.2d.3f.4e.5c.6c, | |
| 1a.2d.3f.4e.5c.6d, | 1a.2d.3f.4e.5c.6e, | 1a.2d.3f.4e.5c.6f, | 1a.2d.3f.4e.5d.6a, | |
| 1a.2d.3f.4e.5d.6b, | 1a.2d.3f.4e.5d.6c, | 1a.2d.3f.4e.5d.6d, | 1a.2d.3f.4e.5d.6e, | |
| 1a.2d.3f.4e.5d.6f, | 1a.2d.3f.4e.5e.6a, | 1a.2d.3f.4e.5e.6b, | 1a.2d.3f.4e.5e.6c, | |
| 1a.2d.3f.4e.5e.6d, | 1a.2d.3f.4e.5e.6e, | 1a.2d.3f.4e.5e.6f, | 1a.2d.3f.4e.5f.6a, | 1a.2d.3f.4e.5f.6b, |
| 1a.2d.3f.4e.5f.6c, | 1a.2d.3f.4e.5f.6d, | 1a.2d.3f.4e.5f.6e, | 1a.2d.3f.4e.5f.6f, | 1a.2d.3f.4f.5a.6a, |
| 1a.2d.3f.4f.5a.6b, | 1a.2d.3f.4f.5a.6c, | 1a.2d.3f.4f.5a.6d, | 1a.2d.3f.4f.5a.6e, | 1a.2d.3f.4f.5a.6f, |
| 1a.2d.3f.4f.5b.6a, | 1a.2d.3f.4f.5b.6b, | 1a.2d.3f.4f.5b.6c, | 1a.2d.3f.4f.5b.6d, | 1a.2d.3f.4f.5b.6e, |
| 1a.2d.3f.4f.5b.6f, | 1a.2d.3f.4f.5c.6a, | 1a.2d.3f.4f.5c.6b, | 1a.2d.3f.4f.5c.6c, | 1a.2d.3f.4f.5c.6d, |
| 1a.2d.3f.4f.5c.6e, | 1a.2d.3f.4f.5c.6f, | 1a.2d.3f.4f.5d.6a, | 1a.2d.3f.4f.5d.6b, | 1a.2d.3f.4f.5d.6c, |
| 1a.2d.3f.4f.5d.6d, | 1a.2d.3f.4f.5d.6e, | 1a.2d.3f.4f.5d.6f, | 1a.2d.3f.4f.5e.6a, | 1a.2d.3f.4f.5e.6b, |
| 1a.2d.3f.4f.5e.6c, | 1a.2d.3f.4f.5e.6d, | 1a.2d.3f.4f.5e.6e, | 1a.2d.3f.4f.5e.6f, | 1a.2d.3f.4f.5f.6a, |
| 1a.2d.3f.4f.5f.6b, | 1a.2d.3f.4f.5f.6c, | 1a.2d.3f.4f.5f.6d, | 1a.2d.3f.4f.5f.6e, | 1a.2d.3f.4f.5f.6f, |
| 1a.2e.3a.4a.5a.6a, | 1a.2e.3a.4a.5a.6b, | 1a.2e.3a.4a.5a.6c, | 1a.2e.3a.4a.5a.6d, | |
| 1a.2e.3a.4a.5a.6e, | 1a.2e.3a.4a.5a.6f, | 1a.2e.3a.4a.5b.6a, | 1a.2e.3a.4a.5b.6b, | |
| 1a.2e.3a.4a.5b.6c, | 1a.2e.3a.4a.5b.6d, | 1a.2e.3a.4a.5b.6e, | 1a.2e.3a.4a.5b.6f, | |
| 1a.2e.3a.4a.5c.6a, | 1a.2e.3a.4a.5c.6b, | 1a.2e.3a.4a.5c.6c, | 1a.2e.3a.4a.5c.6d, | |
| 1a.2e.3a.4a.5c.6e, | 1a.2e.3a.4a.5c.6f, | 1a.2e.3a.4a.5d.6a, | 1a.2e.3a.4a.5d.6b, | |
| 1a.2e.3a.4a.5d.6c, | 1a.2e.3a.4a.5d.6d, | 1a.2e.3a.4a.5d.6e, | 1a.2e.3a.4a.5d.6f, | |
| 1a.2e.3a.4a.5e.6a, | 1a.2e.3a.4a.5e.6b, | 1a.2e.3a.4a.5e.6c, | 1a.2e.3a.4a.5e.6d, | |
| 1a.2e.3a.4a.5e.6e, | 1a.2e.3a.4a.5e.6f, | 1a.2e.3a.4a.5f.6a, | 1a.2e.3a.4a.5f.6b, | 1a.2e.3a.4a.5f.6c, |
| 1a.2e.3a.4a.5f.6d, | 1a.2e.3a.4a.5f.6e, | 1a.2e.3a.4a.5f.6f, | 1a.2e.3a.4b.5a.6a, | |
| 1a.2e.3a.4b.5a.6b, | 1a.2e.3a.4b.5a.6c, | 1a.2e.3a.4b.5a.6d, | 1a.2e.3a.4b.5a.6e, | |
| 1a.2e.3a.4b.5a.6f, | 1a.2e.3a.4b.5b.6a, | 1a.2e.3a.4b.5b.6b, | 1a.2e.3a.4b.5b.6c, | |
| 1a.2e.3a.4b.5b.6d, | 1a.2e.3a.4b.5b.6e, | 1a.2e.3a.4b.5b.6f, | 1a.2e.3a.4b.5c.6a, | |
| 1a.2e.3a.4b.5c.6b, | 1a.2e.3a.4b.5c.6c, | 1a.2e.3a.4b.5c.6d, | 1a.2e.3a.4b.5c.6e, | |
| 1a.2e.3a.4b.5c.6f, | 1a.2e.3a.4b.5d.6a, | 1a.2e.3a.4b.5d.6b, | 1a.2e.3a.4b.5d.6c, | |
| 1a.2e.3a.4b.5d.6d, | 1a.2e.3a.4b.5d.6e, | 1a.2e.3a.4b.5d.6f, | 1a.2e.3a.4b.5e.6a, | |
| 1a.2e.3a.4b.5e.6b, | 1a.2e.3a.4b.5e.6c, | 1a.2e.3a.4b.5e.6d, | 1a.2e.3a.4b.5e.6e, | |
| 1a.2e.3a.4b.5e.6f, | 1a.2e.3a.4b.5f.6a, | 1a.2e.3a.4b.5f.6b, | 1a.2e.3a.4b.5f.6c, | |
| 1a.2e.3a.4b.5f.6d, | 1a.2e.3a.4b.5f.6e, | 1a.2e.3a.4b.5f.6f, | 1a.2e.3a.4c.5a.6a, | |
| 1a.2e.3a.4c.5a.6b, | 1a.2e.3a.4c.5a.6c, | 1a.2e.3a.4c.5a.6d, | 1a.2e.3a.4c.5a.6e, | |
| 1a.2e.3a.4c.5a.6f, | 1a.2e.3a.4c.5b.6a, | 1a.2e.3a.4c.5b.6b, | 1a.2e.3a.4c.5b.6c, | |
| 1a.2e.3a.4c.5b.6d, | 1a.2e.3a.4c.5b.6e, | 1a.2e.3a.4c.5b.6f, | 1a.2e.3a.4c.5c.6a, | |
| 1a.2e.3a.4c.5c.6b, | 1a.2e.3a.4c.5c.6c, | 1a.2e.3a.4c.5c.6d, | 1a.2e.3a.4c.5c.6e, | 1a.2e.3a.4c.5c.6f, |
| 1a.2e.3a.4c.5d.6a, | 1a.2e.3a.4c.5d.6b, | 1a.2e.3a.4c.5d.6c, | 1a.2e.3a.4c.5d.6d, | |
| 1a.2e.3a.4c.5d.6e, | 1a.2e.3a.4c.5d.6f, | 1a.2e.3a.4c.5e.6a, | 1a.2e.3a.4c.5e.6b, | |
| 1a.2e.3a.4c.5e.6c, | 1a.2e.3a.4c.5e.6d, | 1a.2e.3a.4c.5e.6e, | 1a.2e.3a.4c.5e.6f, | 1a.2e.3a.4c.5f.6a, |
| 1a.2e.3a.4c.5f.6b, | 1a.2e.3a.4c.5f.6c, | 1a.2e.3a.4c.5f.6d, | 1a.2e.3a.4c.5f.6e, | 1a.2e.3a.4c.5f.6f, |
| 1a.2e.3a.4d.5a.6a, | 1a.2e.3a.4d.5a.6b, | 1a.2e.3a.4d.5a.6c, | 1a.2e.3a.4d.5a.6d, | |
| 1a.2e.3a.4d.5a.6e, | 1a.2e.3a.4d.5a.6f, | 1a.2e.3a.4d.5b.6a, | 1a.2e.3a.4d.5b.6b, | |
| 1a.2e.3a.4d.5b.6c, | 1a.2e.3a.4d.5b.6d, | 1a.2e.3a.4d.5b.6e, | 1a.2e.3a.4d.5b.6f, | |
| 1a.2e.3a.4d.5c.6a, | 1a.2e.3a.4d.5c.6b, | 1a.2e.3a.4d.5c.6c, | 1a.2e.3a.4d.5c.6d, | |
| 1a.2e.3a.4d.5c.6e, | 1a.2e.3a.4d.5c.6f, | 1a.2e.3a.4d.5d.6a, | 1a.2e.3a.4d.5d.6b, | |
| 1a.2e.3a.4d.5d.6c, | 1a.2e.3a.4d.5d.6d, | 1a.2e.3a.4d.5d.6e, | 1a.2e.3a.4d.5d.6f, | |
| 1a.2e.3a.4d.5e.6a, | 1a.2e.3a.4d.5e.6b, | 1a.2e.3a.4d.5e.6c, | 1a.2e.3a.4d.5e.6d, | |
| 1a.2e.3a.4d.5e.6e, | 1a.2e.3a.4d.5e.6f, | 1a.2e.3a.4d.5f.6a, | 1a.2e.3a.4d.5f.6b, | |
| 1a.2e.3a.4d.5f.6c, | 1a.2e.3a.4d.5f.6d, | 1a.2e.3a.4d.5f.6e, | 1a.2e.3a.4d.5f.6f, | |
| 1a.2e.3a.4e.5a.6a, | 1a.2e.3a.4e.5a.6b, | 1a.2e.3a.4e.5a.6c, | 1a.2e.3a.4e.5a.6d, | |
| 1a.2e.3a.4e.5a.6e, | 1a.2e.3a.4e.5a.6f, | 1a.2e.3a.4e.5b.6a, | 1a.2e.3a.4e.5b.6b, | |
| 1a.2e.3a.4e.5b.6c, | 1a.2e.3a.4e.5b.6d, | 1a.2e.3a.4e.5b.6e, | 1a.2e.3a.4e.5b.6f, | |
| 1a.2e.3a.4e.5c.6a, | 1a.2e.3a.4e.5c.6b, | 1a.2e.3a.4e.5c.6c, | 1a.2e.3a.4e.5c.6d, | |
| 1a.2e.3a.4e.5c.6e, | 1a.2e.3a.4e.5c.6f, | 1a.2e.3a.4e.5d.6a, | 1a.2e.3a.4e.5d.6b, | |
| 1a.2e.3a.4e.5d.6c, | 1a.2e.3a.4e.5d.6d, | 1a.2e.3a.4e.5d.6e, | 1a.2e.3a.4e.5d.6f, | |
| 1a.2e.3a.4e.5e.6a, | 1a.2e.3a.4e.5e.6b, | 1a.2e.3a.4e.5e.6c, | 1a.2e.3a.4e.5e.6d, | |
| 1a.2e.3a.4e.5e.6e, | 1a.2e.3a.4e.5e.6f, | 1a.2e.3a.4e.5f.6a, | 1a.2e.3a.4e.5f.6b, | 1a.2e.3a.4e.5f.6c, |
| 1a.2e.3a.4e.5f.6d, | 1a.2e.3a.4e.5f.6e, | 1a.2e.3a.4e.5f.6f, | 1a.2e.3a.4f.5a.6a, | 1a.2e.3a.4f.5a.6b, |
| 1a.2e.3a.4f.5a.6c, | 1a.2e.3a.4f.5a.6d, | 1a.2e.3a.4f.5a.6e, | 1a.2e.3a.4f.5a.6f, | 1a.2e.3a.4f.5b.6a, |
| 1a.2e.3a.4f.5b.6b, | 1a.2e.3a.4f.5b.6c, | 1a.2e.3a.4f.5b.6d, | 1a.2e.3a.4f.5b.6e, | 1a.2e.3a.4f.5b.6f, |
| 1a.2e.3a.4f.5c.6a, | 1a.2e.3a.4f.5c.6b, | 1a.2e.3a.4f.5c.6c, | 1a.2e.3a.4f.5c.6d, | 1a.2e.3a.4f.5c.6e, |
| 1a.2e.3a.4f.5c.6f, | 1a.2e.3a.4f.5d.6a, | 1a.2e.3a.4f.5d.6b, | 1a.2e.3a.4f.5d.6c, | |
| 1a.2e.3a.4f.5d.6d, | 1a.2e.3a.4f.5d.6e, | 1a.2e.3a.4f.5d.6f, | 1a.2e.3a.4f.5e.6a, | 1a.2e.3a.4f.5e.6b, |

TABLE 7-continued

List of Compounds of Formula (II)

| | | | | |
|---|---|---|---|---|
| 1a.2e.3a.4f.5e.6c, | 1a.2e.3a.4f.5e.6d, | 1a.2e.3a.4f.5e.6e, | 1a.2e.3a.4f.5e.6f, | 1a.2e.3a.4f.5f.6a, |
| 1a.2e.3a.4f.5f.6b, | 1a.2e.3a.4f.5f.6c, | 1a.2e.3a.4f.5f.6d, | 1a.2e.3a.4f.5f.6e, | 1a.2e.3a.4f.5f.6f, |
| 1a.2e.3b.4a.5a.6a, | 1a.2e.3b.4a.5a.6b, | 1a.2e.3b.4a.5a.6c, | 1a.2e.3b.4a.5a.6d, | |
| 1a.2e.3b.4a.5a.6e, | 1a.2e.3b.4a.5a.6f, | 1a.2e.3b.4a.5b.6a, | 1a.2e.3b.4a.5b.6b, | |
| 1a.2e.3b.4a.5b.6c, | 1a.2e.3b.4a.5b.6d, | 1a.2e.3b.4a.5b.6e, | 1a.2e.3b.4a.5b.6f, | |
| 1a.2e.3b.4a.5c.6a, | 1a.2e.3b.4a.5c.6b, | 1a.2e.3b.4a.5c.6c, | 1a.2e.3b.4a.5c.6d, | |
| 1a.2e.3b.4a.5c.6e, | 1a.2e.3b.4a.5c.6f, | 1a.2e.3b.4a.5d.6a, | 1a.2e.3b.4a.5d.6b, | |
| 1a.2e.3b.4a.5d.6c, | 1a.2e.3b.4a.5d.6d, | 1a.2e.3b.4a.5d.6e, | 1a.2e.3b.4a.5d.6f, | |
| 1a.2e.3b.4a.5e.6a, | 1a.2e.3b.4a.5e.6b, | 1a.2e.3b.4a.5e.6c, | 1a.2e.3b.4a.5e.6d, | |
| 1a.2e.3b.4a.5e.6e, | 1a.2e.3b.4a.5e.6f, | 1a.2e.3b.4a.5f.6a, | 1a.2e.3b.4a.5f.6b, | |
| 1a.2e.3b.4a.5f.6c, | 1a.2e.3b.4a.5f.6d, | 1a.2e.3b.4a.5f.6e, | 1a.2e.3b.4a.5f.6f, | |
| 1a.2e.3b.4b.5a.6a, | 1a.2e.3b.4b.5a.6b, | 1a.2e.3b.4b.5a.6c, | 1a.2e.3b.4b.5a.6d, | |
| 1a.2e.3b.4b.5a.6e, | 1a.2e.3b.4b.5a.6f, | 1a.2e.3b.4b.5b.6a, | 1a.2e.3b.4b.5b.6b, | |
| 1a.2e.3b.4b.5b.6c, | 1a.2e.3b.4b.5b.6d, | 1a.2e.3b.4b.5b.6e, | 1a.2e.3b.4b.5b.6f, | |
| 1a.2e.3b.4b.5c.6a, | 1a.2e.3b.4b.5c.6b, | 1a.2e.3b.4b.5c.6c, | 1a.2e.3b.4b.5c.6d, | |
| 1a.2e.3b.4b.5c.6e, | 1a.2e.3b.4b.5c.6f, | 1a.2e.3b.4b.5d.6a, | 1a.2e.3b.4b.5d.6b, | |
| 1a.2e.3b.4b.5d.6c, | 1a.2e.3b.4b.5d.6d, | 1a.2e.3b.4b.5d.6e, | 1a.2e.3b.4b.5d.6f, | |
| 1a.2e.3b.4b.5e.6a, | 1a.2e.3b.4b.5e.6b, | 1a.2e.3b.4b.5e.6c, | 1a.2e.3b.4b.5e.6d, | |
| 1a.2e.3b.4b.5e.6e, | 1a.2e.3b.4b.5e.6f, | 1a.2e.3b.4b.5f.6a, | 1a.2e.3b.4b.5f.6b, | |
| 1a.2e.3b.4b.5f.6c, | 1a.2e.3b.4b.5f.6d, | 1a.2e.3b.4b.5f.6e, | 1a.2e.3b.4b.5f.6f, | |
| 1a.2e.3b.4c.5a.6a, | 1a.2e.3b.4c.5a.6b, | 1a.2e.3b.4c.5a.6c, | 1a.2e.3b.4c.5a.6d, | |
| 1a.2e.3b.4c.5a.6e, | 1a.2e.3b.4c.5a.6f, | 1a.2e.3b.4c.5b.6a, | 1a.2e.3b.4c.5b.6b, | |
| 1a.2e.3b.4c.5b.6c, | 1a.2e.3b.4c.5b.6d, | 1a.2e.3b.4c.5b.6e, | 1a.2e.3b.4c.5b.6f, | |
| 1a.2e.3b.4c.5c.6a, | 1a.2e.3b.4c.5c.6b, | 1a.2e.3b.4c.5c.6c, | 1a.2e.3b.4c.5c.6d, | |
| 1a.2e.3b.4c.5c.6e, | 1a.2e.3b.4c.5c.6f, | 1a.2e.3b.4c.5d.6a, | 1a.2e.3b.4c.5d.6b, | |
| 1a.2e.3b.4c.5d.6c, | 1a.2e.3b.4c.5d.6d, | 1a.2e.3b.4c.5d.6e, | 1a.2e.3b.4c.5d.6f, | |
| 1a.2e.3b.4c.5e.6a, | 1a.2e.3b.4c.5e.6b, | 1a.2e.3b.4c.5e.6c, | 1a.2e.3b.4c.5e.6d, | |
| 1a.2e.3b.4c.5e.6e, | 1a.2e.3b.4c.5e.6f, | 1a.2e.3b.4c.5f.6a, | 1a.2e.3b.4c.5f.6b, | 1a.2e.3b.4c.5f.6c, |
| 1a.2e.3b.4c.5f.6d, | 1a.2e.3b.4c.5f.6e, | 1a.2e.3b.4c.5f.6f, | 1a.2e.3b.4d.5a.6a, | |
| 1a.2e.3b.4d.5a.6b, | 1a.2e.3b.4d.5a.6c, | 1a.2e.3b.4d.5a.6d, | 1a.2e.3b.4d.5a.6e, | |
| 1a.2e.3b.4d.5a.6f, | 1a.2e.3b.4d.5b.6a, | 1a.2e.3b.4d.5b.6b, | 1a.2e.3b.4d.5b.6c, | |
| 1a.2e.3b.4d.5b.6d, | 1a.2e.3b.4d.5b.6e, | 1a.2e.3b.4d.5b.6f, | 1a.2e.3b.4d.5c.6a, | |
| 1a.2e.3b.4d.5c.6b, | 1a.2e.3b.4d.5c.6c, | 1a.2e.3b.4d.5c.6d, | 1a.2e.3b.4d.5c.6e, | |
| 1a.2e.3b.4d.5c.6f, | 1a.2e.3b.4d.5d.6a, | 1a.2e.3b.4d.5d.6b, | 1a.2e.3b.4d.5d.6c, | |
| 1a.2e.3b.4d.5d.6d, | 1a.2e.3b.4d.5d.6e, | 1a.2e.3b.4d.5d.6f, | 1a.2e.3b.4d.5e.6a, | |
| 1a.2e.3b.4d.5e.6b, | 1a.2e.3b.4d.5e.6c, | 1a.2e.3b.4d.5e.6d, | 1a.2e.3b.4d.5e.6e, | |
| 1a.2e.3b.4d.5e.6f, | 1a.2e.3b.4d.5f.6a, | 1a.2e.3b.4d.5f.6b, | 1a.2e.3b.4d.5f.6c, | |
| 1a.2e.3b.4d.5f.6d, | 1a.2e.3b.4d.5f.6e, | 1a.2e.3b.4d.5f.6f, | 1a.2e.3b.4e.5a.6a, | |
| 1a.2e.3b.4e.5a.6b, | 1a.2e.3b.4e.5a.6c, | 1a.2e.3b.4e.5a.6d, | 1a.2e.3b.4e.5a.6e, | |
| 1a.2e.3b.4e.5a.6f, | 1a.2e.3b.4e.5b.6a, | 1a.2e.3b.4e.5b.6b, | 1a.2e.3b.4e.5b.6c, | |
| 1a.2e.3b.4e.5b.6d, | 1a.2e.3b.4e.5b.6e, | 1a.2e.3b.4e.5b.6f, | 1a.2e.3b.4e.5c.6a, | |
| 1a.2e.3b.4e.5c.6b, | 1a.2e.3b.4e.5c.6c, | 1a.2e.3b.4e.5c.6d, | 1a.2e.3b.4e.5c.6e, | |
| 1a.2e.3b.4e.5c.6f, | 1a.2e.3b.4e.5d.6a, | 1a.2e.3b.4e.5d.6b, | 1a.2e.3b.4e.5d.6c, | |
| 1a.2e.3b.4e.5d.6d, | 1a.2e.3b.4e.5d.6e, | 1a.2e.3b.4e.5d.6f, | 1a.2e.3b.4e.5e.6a, | |
| 1a.2e.3b.4e.5e.6b, | 1a.2e.3b.4e.5e.6c, | 1a.2e.3b.4e.5e.6d, | 1a.2e.3b.4e.5e.6e, | |
| 1a.2e.3b.4e.5e.6f, | 1a.2e.3b.4e.5f.6a, | 1a.2e.3b.4e.5f.6b, | 1a.2e.3b.4e.5f.6c, | 1a.2e.3b.4e.5f.6d, |
| 1a.2e.3b.4e.5f.6e, | 1a.2e.3b.4e.5f.6f, | 1a.2e.3b.4f.5a.6a, | 1a.2e.3b.4f.5a.6b, | 1a.2e.3b.4f.5a.6c, |
| 1a.2e.3b.4f.5a.6d, | 1a.2e.3b.4f.5a.6e, | 1a.2e.3b.4f.5a.6f, | 1a.2e.3b.4f.5b.6a, | |
| 1a.2e.3b.4f.5b.6b, | 1a.2e.3b.4f.5b.6c, | 1a.2e.3b.4f.5b.6d, | 1a.2e.3b.4f.5b.6e, | |
| 1a.2e.3b.4f.5b.6f, | 1a.2e.3b.4f.5c.6a, | 1a.2e.3b.4f.5c.6b, | 1a.2e.3b.4f.5c.6c, | 1a.2e.3b.4f.5c.6d, |
| 1a.2e.3b.4f.5c.6e, | 1a.2e.3b.4f.5c.6f, | 1a.2e.3b.4f.5d.6a, | 1a.2e.3b.4f.5d.6b, | 1a.2e.3b.4f.5d.6c, |
| 1a.2e.3b.4f.5d.6d, | 1a.2e.3b.4f.5d.6e, | 1a.2e.3b.4f.5d.6f, | 1a.2e.3b.4f.5e.6a, | |
| 1a.2e.3b.4f.5e.6b, | 1a.2e.3b.4f.5e.6c, | 1a.2e.3b.4f.5e.6d, | 1a.2e.3b.4f.5e.6e, | 1a.2e.3b.4f.5e.6f, |
| 1a.2e.3b.4f.5f.6a, | 1a.2e.3b.4f.5f.6b, | 1a.2e.3b.4f.5f.6c, | 1a.2e.3b.4f.5f.6d, | 1a.2e.3b.4f.5f.6e, |
| 1a.2e.3b.4f.5f.6f, | 1a.2e.3c.4a.5a.6a, | 1a.2e.3c.4a.5a.6b, | 1a.2e.3c.4a.5a.6c, | 1a.2e.3c.4a.5a.6d, |
| 1a.2e.3c.4a.5a.6e, | 1a.2e.3c.4a.5a.6f, | 1a.2e.3c.4a.5b.6a, | 1a.2e.3c.4a.5b.6b, | |
| 1a.2e.3c.4a.5b.6c, | 1a.2e.3c.4a.5b.6d, | 1a.2e.3c.4a.5b.6e, | 1a.2e.3c.4a.5b.6f, | |
| 1a.2e.3c.4a.5c.6a, | 1a.2e.3c.4a.5c.6b, | 1a.2e.3c.4a.5c.6c, | 1a.2e.3c.4a.5c.6d, | |
| 1a.2e.3c.4a.5c.6e, | 1a.2e.3c.4a.5c.6f, | 1a.2e.3c.4a.5d.6a, | 1a.2e.3c.4a.5d.6b, | |
| 1a.2e.3c.4a.5d.6c, | 1a.2e.3c.4a.5d.6d, | 1a.2e.3c.4a.5d.6e, | 1a.2e.3c.4a.5d.6f, | |
| 1a.2e.3c.4a.5e.6a, | 1a.2e.3c.4a.5e.6b, | 1a.2e.3c.4a.5e.6c, | 1a.2e.3c.4a.5e.6d, | |
| 1a.2e.3c.4a.5e.6e, | 1a.2e.3c.4a.5e.6f, | 1a.2e.3c.4a.5f.6a, | 1a.2e.3c.4a.5f.6b, | 1a.2e.3c.4a.5f.6c, |
| 1a.2e.3c.4a.5f.6d, | 1a.2e.3c.4a.5f.6e, | 1a.2e.3c.4a.5f.6f, | 1a.2e.3c.4b.5a.6a, | 1a.2e.3c.4b.5a.6b, |
| 1a.2e.3c.4b.5a.6c, | 1a.2e.3c.4b.5a.6d, | 1a.2e.3c.4b.5a.6e, | 1a.2e.3c.4b.5a.6f, | |
| 1a.2e.3c.4b.5b.6a, | 1a.2e.3c.4b.5b.6b, | 1a.2e.3c.4b.5b.6c, | 1a.2e.3c.4b.5b.6d, | |
| 1a.2e.3c.4b.5b.6e, | 1a.2e.3c.4b.5b.6f, | 1a.2e.3c.4b.5c.6a, | 1a.2e.3c.4b.5c.6b, | |
| 1a.2e.3c.4b.5c.6c, | 1a.2e.3c.4b.5c.6d, | 1a.2e.3c.4b.5c.6e, | 1a.2e.3c.4b.5c.6f, | |
| 1a.2e.3c.4b.5d.6a, | 1a.2e.3c.4b.5d.6b, | 1a.2e.3c.4b.5d.6c, | 1a.2e.3c.4b.5d.6d, | |
| 1a.2e.3c.4b.5d.6e, | 1a.2e.3c.4b.5d.6f, | 1a.2e.3c.4b.5e.6a, | 1a.2e.3c.4b.5e.6b, | |
| 1a.2e.3c.4b.5e.6c, | 1a.2e.3c.4b.5e.6d, | 1a.2e.3c.4b.5e.6e, | 1a.2e.3c.4b.5e.6f, | |
| 1a.2e.3c.4b.5f.6a, | 1a.2e.3c.4b.5f.6b, | 1a.2e.3c.4b.5f.6c, | 1a.2e.3c.4b.5f.6d, | 1a.2e.3c.4b.5f.6e, |
| 1a.2e.3c.4b.5f.6f, | 1a.2e.3c.4c.5a.6a, | 1a.2e.3c.4c.5a.6b, | 1a.2e.3c.4c.5a.6c, | 1a.2e.3c.4c.5a.6d, |
| 1a.2e.3c.4c.5a.6e, | 1a.2e.3c.4c.5a.6f, | 1a.2e.3c.4c.5b.6a, | 1a.2e.3c.4c.5b.6b, | 1a.2e.3c.4c.5b.6c, |
| 1a.2e.3c.4c.5b.6d, | 1a.2e.3c.4c.5b.6e, | 1a.2e.3c.4c.5b.6f, | 1a.2e.3c.4c.5c.6a, | 1a.2e.3c.4c.5c.6b, |
| 1a.2e.3c.4c.5c.6c, | 1a.2e.3c.4c.5c.6d, | 1a.2e.3c.4c.5c.6e, | 1a.2e.3c.4c.5c.6f, | 1a.2e.3c.4c.5d.6a, |
| 1a.2e.3c.4c.5d.6b, | 1a.2e.3c.4c.5d.6c, | 1a.2e.3c.4c.5d.6d, | 1a.2e.3c.4c.5d.6e, | |
| 1a.2e.3c.4c.5d.6f, | 1a.2e.3c.4c.5e.6a, | 1a.2e.3c.4c.5e.6b, | 1a.2e.3c.4c.5e.6c, | 1a.2e.3c.4c.5e.6d, |
| 1a.2e.3c.4c.5e.6e, | 1a.2e.3c.4c.5e.6f, | 1a.2e.3c.4c.5f.6a, | 1a.2e.3c.4c.5f.6b, | 1a.2e.3c.4c.5f.6c, |

TABLE 7-continued

List of Compounds of Formula (II)

| | | | | |
|---|---|---|---|---|
| 1a.2e.3c.4c.5f.6d, | 1a.2e.3c.4c.5f.6e, | 1a.2e.3c.4c.5f.6f, | 1a.2e.3c.4d.5a.6a, | 1a.2e.3c.4d.5a.6b, |
| 1a.2e.3c.4d.5a.6c, | 1a.2e.3c.4d.5a.6d, | 1a.2e.3c.4d.5a.6e, | 1a.2e.3c.4d.5a.6f, | |
| 1a.2e.3c.4d.5b.6a, | 1a.2e.3c.4d.5b.6b, | 1a.2e.3c.4d.5b.6c, | 1a.2e.3c.4d.5b.6d, | |
| 1a.2e.3c.4d.5b.6e, | 1a.2e.3c.4d.5b.6f, | 1a.2e.3c.4d.5c.6a, | 1a.2e.3c.4d.5c.6b, | |
| 1a.2e.3c.4d.5c.6c, | 1a.2e.3c.4d.5c.6d, | 1a.2e.3c.4d.5c.6e, | 1a.2e.3c.4d.5c.6f, | |
| 1a.2e.3c.4d.5d.6a, | 1a.2e.3c.4d.5d.6b, | 1a.2e.3c.4d.5d.6c, | 1a.2e.3c.4d.5d.6d, | |
| 1a.2e.3c.4d.5d.6e, | 1a.2e.3c.4d.5d.6f, | 1a.2e.3c.4d.5e.6a, | 1a.2e.3c.4d.5e.6b, | |
| 1a.2e.3c.4d.5e.6c, | 1a.2e.3c.4d.5e.6d, | 1a.2e.3c.4d.5e.6e, | 1a.2e.3c.4d.5e.6f, | |
| 1a.2e.3c.4d.5f.6a, | 1a.2e.3c.4d.5f.6b, | 1a.2e.3c.4d.5f.6c, | 1a.2e.3c.4d.5f.6d, | |
| 1a.2e.3c.4d.5f.6e, | 1a.2e.3c.4d.5f.6f, | 1a.2e.3c.4e.5a.6a, | 1a.2e.3c.4e.5a.6b, | 1a.2e.3c.4e.5a.6c, |
| 1a.2e.3c.4e.5a.6d, | 1a.2e.3c.4e.5a.6e, | 1a.2e.3c.4e.5a.6f, | 1a.2e.3c.4e.5b.6a, | |
| 1a.2e.3c.4e.5b.6b, | 1a.2e.3c.4e.5b.6c, | 1a.2e.3c.4e.5b.6d, | 1a.2e.3c.4e.5b.6e, | |
| 1a.2e.3c.4e.5b.6f, | 1a.2e.3c.4e.5c.6a, | 1a.2e.3c.4e.5c.6b, | 1a.2e.3c.4e.5c.6c, | 1a.2e.3c.4e.5c.6d, |
| 1a.2e.3c.4e.5c.6e, | 1a.2e.3c.4e.5c.6f, | 1a.2e.3c.4e.5d.6a, | 1a.2e.3c.4e.5d.6b, | |
| 1a.2e.3c.4e.5d.6c, | 1a.2e.3c.4e.5d.6d, | 1a.2e.3c.4e.5d.6e, | 1a.2e.3c.4e.5d.6f, | |
| 1a.2e.3c.4e.5e.6a, | 1a.2e.3c.4e.5e.6b, | 1a.2e.3c.4e.5e.6c, | 1a.2e.3c.4e.5e.6d, | |
| 1a.2e.3c.4e.5e.6e, | 1a.2e.3c.4e.5e.6f, | 1a.2e.3c.4e.5f.6a, | 1a.2e.3c.4e.5f.6b, | 1a.2e.3c.4e.5f.6c, |
| 1a.2e.3c.4e.5f.6d, | 1a.2e.3c.4e.5f.6e, | 1a.2e.3c.4e.5f.6f, | 1a.2e.3c.4f.5a.6a, | 1a.2e.3c.4f.5a.6b, |
| 1a.2e.3c.4f.5a.6c, | 1a.2e.3c.4f.5a.6d, | 1a.2e.3c.4f.5a.6e, | 1a.2e.3c.4f.5a.6f, | 1a.2e.3c.4f.5b.6a, |
| 1a.2e.3c.4f.5b.6b, | 1a.2e.3c.4f.5b.6c, | 1a.2e.3c.4f.5b.6d, | 1a.2e.3c.4f.5b.6e, | 1a.2e.3c.4f.5b.6f, |
| 1a.2e.3c.4f.5c.6a, | 1a.2e.3c.4f.5c.6b, | 1a.2e.3c.4f.5c.6c, | 1a.2e.3c.4f.5c.6d, | 1a.2e.3c.4f.5c.6e, |
| 1a.2e.3c.4f.5c.6f, | 1a.2e.3c.4f.5d.6a, | 1a.2e.3c.4f.5d.6b, | 1a.2e.3c.4f.5d.6c, | 1a.2e.3c.4f.5d.6d, |
| 1a.2e.3c.4f.5d.6e, | 1a.2e.3c.4f.5d.6f, | 1a.2e.3c.4f.5e.6a, | 1a.2e.3c.4f.5e.6b, | 1a.2e.3c.4f.5e.6c, |
| 1a.2e.3c.4f.5e.6d, | 1a.2e.3c.4f.5e.6e, | 1a.2e.3c.4f.5e.6f, | 1a.2e.3c.4f.5f.6a, | 1a.2e.3c.4f.5f.6b, |
| 1a.2e.3c.4f.5f.6c, | 1a.2e.3c.4f.5f.6d, | 1a.2e.3c.4f.5f.6e, | 1a.2e.3c.4f.5f.6f, | 1a.2e.3d.4a.5a.6a, |
| 1a.2e.3d.4a.5a.6b, | 1a.2e.3d.4a.5a.6c, | 1a.2e.3d.4a.5a.6d, | 1a.2e.3d.4a.5a.6e, | |
| 1a.2e.3d.4a.5a.6f, | 1a.2e.3d.4a.5b.6a, | 1a.2e.3d.4a.5b.6b, | 1a.2e.3d.4a.5b.6c, | |
| 1a.2e.3d.4a.5b.6d, | 1a.2e.3d.4a.5b.6e, | 1a.2e.3d.4a.5b.6f, | 1a.2e.3d.4a.5c.6a, | |
| 1a.2e.3d.4a.5c.6b, | 1a.2e.3d.4a.5c.6c, | 1a.2e.3d.4a.5c.6d, | 1a.2e.3d.4a.5c.6e, | |
| 1a.2e.3d.4a.5c.6f, | 1a.2e.3d.4a.5d.6a, | 1a.2e.3d.4a.5d.6b, | 1a.2e.3d.4a.5d.6c, | |
| 1a.2e.3d.4a.5d.6d, | 1a.2e.3d.4a.5d.6e, | 1a.2e.3d.4a.5d.6f, | 1a.2e.3d.4a.5e.6a, | |
| 1a.2e.3d.4a.5e.6b, | 1a.2e.3d.4a.5e.6c, | 1a.2e.3d.4a.5e.6d, | 1a.2e.3d.4a.5e.6e, | |
| 1a.2e.3d.4a.5e.6f, | 1a.2e.3d.4a.5f.6a, | 1a.2e.3d.4a.5f.6b, | 1a.2e.3d.4a.5f.6c, | |
| 1a.2e.3d.4a.5f.6d, | 1a.2e.3d.4a.5f.6e, | 1a.2e.3d.4a.5f.6f, | 1a.2e.3d.4b.5a.6a, | |
| 1a.2e.3d.4b.5a.6b, | 1a.2e.3d.4b.5a.6c, | 1a.2e.3d.4b.5a.6d, | 1a.2e.3d.4b.5a.6e, | |
| 1a.2e.3d.4b.5a.6f, | 1a.2e.3d.4b.5b.6a, | 1a.2e.3d.4b.5b.6b, | 1a.2e.3d.4b.5b.6c, | |
| 1a.2e.3d.4b.5b.6d, | 1a.2e.3d.4b.5b.6e, | 1a.2e.3d.4b.5b.6f, | 1a.2e.3d.4b.5c.6a, | |
| 1a.2e.3d.4b.5c.6b, | 1a.2e.3d.4b.5c.6c, | 1a.2e.3d.4b.5c.6d, | 1a.2e.3d.4b.5c.6e, | |
| 1a.2e.3d.4b.5c.6f, | 1a.2e.3d.4b.5d.6a, | 1a.2e.3d.4b.5d.6b, | 1a.2e.3d.4b.5d.6c, | |
| 1a.2e.3d.4b.5d.6d, | 1a.2e.3d.4b.5d.6e, | 1a.2e.3d.4b.5d.6f, | 1a.2e.3d.4b.5e.6a, | |
| 1a.2e.3d.4b.5e.6b, | 1a.2e.3d.4b.5e.6c, | 1a.2e.3d.4b.5e.6d, | 1a.2e.3d.4b.5e.6e, | |
| 1a.2e.3d.4b.5e.6f, | 1a.2e.3d.4b.5f.6a, | 1a.2e.3d.4b.5f.6b, | 1a.2e.3d.4b.5f.6c, | |
| 1a.2e.3d.4b.5f.6d, | 1a.2e.3d.4b.5f.6e, | 1a.2e.3d.4b.5f.6f, | 1a.2e.3d.4c.5a.6a, | |
| 1a.2e.3d.4c.5a.6b, | 1a.2e.3d.4c.5a.6c, | 1a.2e.3d.4c.5a.6d, | 1a.2e.3d.4c.5a.6e, | |
| 1a.2e.3d.4c.5a.6f, | 1a.2e.3d.4c.5b.6a, | 1a.2e.3d.4c.5b.6b, | 1a.2e.3d.4c.5b.6c, | |
| 1a.2e.3d.4c.5b.6d, | 1a.2e.3d.4c.5b.6e, | 1a.2e.3d.4c.5b.6f, | 1a.2e.3d.4c.5c.6a, | |
| 1a.2e.3d.4c.5c.6b, | 1a.2e.3d.4c.5c.6c, | 1a.2e.3d.4c.5c.6d, | 1a.2e.3d.4c.5c.6e, | |
| 1a.2e.3d.4c.5c.6f, | 1a.2e.3d.4c.5d.6a, | 1a.2e.3d.4c.5d.6b, | 1a.2e.3d.4c.5d.6c, | |
| 1a.2e.3d.4c.5d.6d, | 1a.2e.3d.4c.5d.6e, | 1a.2e.3d.4c.5d.6f, | 1a.2e.3d.4c.5e.6a, | |
| 1a.2e.3d.4c.5e.6b, | 1a.2e.3d.4c.5e.6c, | 1a.2e.3d.4c.5e.6d, | 1a.2e.3d.4c.5e.6e, | |
| 1a.2e.3d.4c.5e.6f, | 1a.2e.3d.4c.5f.6a, | 1a.2e.3d.4c.5f.6b, | 1a.2e.3d.4c.5f.6c, | |
| 1a.2e.3d.4c.5f.6d, | 1a.2e.3d.4c.5f.6e, | 1a.2e.3d.4c.5f.6f, | 1a.2e.3d.4d.5a.6a, | |
| 1a.2e.3d.4d.5a.6b, | 1a.2e.3d.4d.5a.6c, | 1a.2e.3d.4d.5a.6d, | 1a.2e.3d.4d.5a.6e, | |
| 1a.2e.3d.4d.5a.6f, | 1a.2e.3d.4d.5b.6a, | 1a.2e.3d.4d.5b.6b, | 1a.2e.3d.4d.5b.6c, | |
| 1a.2e.3d.4d.5b.6d, | 1a.2e.3d.4d.5b.6e, | 1a.2e.3d.4d.5b.6f, | 1a.2e.3d.4d.5c.6a, | |
| 1a.2e.3d.4d.5c.6b, | 1a.2e.3d.4d.5c.6c, | 1a.2e.3d.4d.5c.6d, | 1a.2e.3d.4d.5c.6e, | |
| 1a.2e.3d.4d.5c.6f, | 1a.2e.3d.4d.5d.6a, | 1a.2e.3d.4d.5d.6b, | 1a.2e.3d.4d.5d.6c, | |
| 1a.2e.3d.4d.5d.6d, | 1a.2e.3d.4d.5d.6e, | 1a.2e.3d.4d.5d.6f, | 1a.2e.3d.4d.5e.6a, | |
| 1a.2e.3d.4d.5e.6b, | 1a.2e.3d.4d.5e.6c, | 1a.2e.3d.4d.5e.6d, | 1a.2e.3d.4d.5e.6e, | |
| 1a.2e.3d.4d.5e.6f, | 1a.2e.3d.4d.5f.6a, | 1a.2e.3d.4d.5f.6b, | 1a.2e.3d.4d.5f.6c, | |
| 1a.2e.3d.4d.5f.6d, | 1a.2e.3d.4d.5f.6e, | 1a.2e.3d.4d.5f.6f, | 1a.2e.3d.4e.5a.6a, | |
| 1a.2e.3d.4e.5a.6b, | 1a.2e.3d.4e.5a.6c, | 1a.2e.3d.4e.5a.6d, | 1a.2e.3d.4e.5a.6e, | |
| 1a.2e.3d.4e.5a.6f, | 1a.2e.3d.4e.5b.6a, | 1a.2e.3d.4e.5b.6b, | 1a.2e.3d.4e.5b.6c, | |
| 1a.2e.3d.4e.5b.6d, | 1a.2e.3d.4e.5b.6e, | 1a.2e.3d.4e.5b.6f, | 1a.2e.3d.4e.5c.6a, | |
| 1a.2e.3d.4e.5c.6b, | 1a.2e.3d.4e.5c.6c, | 1a.2e.3d.4e.5c.6d, | 1a.2e.3d.4e.5c.6e, | |
| 1a.2e.3d.4e.5c.6f, | 1a.2e.3d.4e.5d.6a, | 1a.2e.3d.4e.5d.6b, | 1a.2e.3d.4e.5d.6c, | |
| 1a.2e.3d.4e.5d.6d, | 1a.2e.3d.4e.5d.6e, | 1a.2e.3d.4e.5d.6f, | 1a.2e.3d.4e.5e.6a, | |
| 1a.2e.3d.4e.5e.6b, | 1a.2e.3d.4e.5e.6c, | 1a.2e.3d.4e.5e.6d, | 1a.2e.3d.4e.5e.6e, | |
| 1a.2e.3d.4e.5e.6f, | 1a.2e.3d.4e.5f.6a, | 1a.2e.3d.4e.5f.6b, | 1a.2e.3d.4e.5f.6c, | |
| 1a.2e.3d.4e.5f.6d, | 1a.2e.3d.4e.5f.6e, | 1a.2e.3d.4e.5f.6f, | 1a.2e.3d.4f.5a.6a, | |
| 1a.2e.3d.4f.5a.6b, | 1a.2e.3d.4f.5a.6c, | 1a.2e.3d.4f.5a.6d, | 1a.2e.3d.4f.5a.6e, | |
| 1a.2e.3d.4f.5a.6f, | 1a.2e.3d.4f.5b.6a, | 1a.2e.3d.4f.5b.6b, | 1a.2e.3d.4f.5b.6c, | |
| 1a.2e.3d.4f.5b.6d, | 1a.2e.3d.4f.5b.6e, | 1a.2e.3d.4f.5b.6f, | 1a.2e.3d.4f.5c.6a, | |
| 1a.2e.3d.4f.5c.6b, | 1a.2e.3d.4f.5c.6c, | 1a.2e.3d.4f.5c.6d, | 1a.2e.3d.4f.5c.6e, | 1a.2e.3d.4f.5c.6f, |
| 1a.2e.3d.4f.5d.6a, | 1a.2e.3d.4f.5d.6b, | 1a.2e.3d.4f.5d.6c, | 1a.2e.3d.4f.5d.6d, | |
| 1a.2e.3d.4f.5d.6e, | 1a.2e.3d.4f.5d.6f, | 1a.2e.3d.4f.5e.6a, | 1a.2e.3d.4f.5e.6b, | |
| 1a.2e.3d.4f.5e.6c, | 1a.2e.3d.4f.5e.6d, | 1a.2e.3d.4f.5e.6e, | 1a.2e.3d.4f.5e.6f, | 1a.2e.3d.4f.5f.6a, |
| 1a.2e.3d.4f.5f.6b, | 1a.2e.3d.4f.5f.6c, | 1a.2e.3d.4f.5f.6d, | 1a.2e.3d.4f.5f.6e, | 1a.2e.3d.4f.5f.6f, |

TABLE 7-continued

List of Compounds of Formula (II)

| | | | | |
|---|---|---|---|---|
| 1a.2e.3e.4a.5a.6a, | 1a.2e.3e.4a.5a.6b, | 1a.2e.3e.4a.5a.6c, | 1a.2e.3e.4a.5a.6d, | |
| 1a.2e.3e.4a.5a.6e, | 1a.2e.3e.4a.5a.6f, | 1a.2e.3e.4a.5b.6a, | 1a.2e.3e.4a.5b.6b, | |
| 1a.2e.3e.4a.5b.6c, | 1a.2e.3e.4a.5b.6d, | 1a.2e.3e.4a.5b.6e, | 1a.2e.3e.4a.5b.6f, | |
| 1a.2e.3e.4a.5c.6a, | 1a.2e.3e.4a.5c.6b, | 1a.2e.3e.4a.5c.6c, | 1a.2e.3e.4a.5c.6d, | |
| 1a.2e.3e.4a.5c.6e, | 1a.2e.3e.4a.5c.6f, | 1a.2e.3e.4a.5d.6a, | 1a.2e.3e.4a.5d.6b, | |
| 1a.2e.3e.4a.5d.6c, | 1a.2e.3e.4a.5d.6d, | 1a.2e.3e.4a.5d.6e, | 1a.2e.3e.4a.5d.6f, | |
| 1a.2e.3e.4a.5e.6a, | 1a.2e.3e.4a.5e.6b, | 1a.2e.3e.4a.5e.6c, | 1a.2e.3e.4a.5e.6d, | |
| 1a.2e.3e.4a.5e.6e, | 1a.2e.3e.4a.5e.6f, | 1a.2e.3e.4a.5f.6a, | 1a.2e.3e.4a.5f.6b, | 1a.2e.3e.4a.5f.6c, |
| 1a.2e.3e.4a.5f.6d, | 1a.2e.3e.4a.5f.6e, | 1a.2e.3e.4a.5f.6f, | 1a.2e.3e.4b.5a.6a, | |
| 1a.2e.3e.4b.5a.6b, | 1a.2e.3e.4b.5a.6c, | 1a.2e.3e.4b.5a.6d, | 1a.2e.3e.4b.5a.6e, | |
| 1a.2e.3e.4b.5a.6f, | 1a.2e.3e.4b.5b.6a, | 1a.2e.3e.4b.5b.6b, | 1a.2e.3e.4b.5b.6c, | |
| 1a.2e.3e.4b.5b.6d, | 1a.2e.3e.4b.5b.6e, | 1a.2e.3e.4b.5b.6f, | 1a.2e.3e.4b.5c.6a, | |
| 1a.2e.3e.4b.5c.6b, | 1a.2e.3e.4b.5c.6c, | 1a.2e.3e.4b.5c.6d, | 1a.2e.3e.4b.5c.6e, | |
| 1a.2e.3e.4b.5c.6f, | 1a.2e.3e.4b.5d.6a, | 1a.2e.3e.4b.5d.6b, | 1a.2e.3e.4b.5d.6c, | |
| 1a.2e.3e.4b.5d.6d, | 1a.2e.3e.4b.5d.6e, | 1a.2e.3e.4b.5d.6f, | 1a.2e.3e.4b.5e.6a, | |
| 1a.2e.3e.4b.5e.6b, | 1a.2e.3e.4b.5e.6c, | 1a.2e.3e.4b.5e.6d, | 1a.2e.3e.4b.5e.6e, | |
| 1a.2e.3e.4b.5e.6f, | 1a.2e.3e.4b.5f.6a, | 1a.2e.3e.4b.5f.6b, | 1a.2e.3e.4b.5f.6c, | 1a.2e.3e.4b.5f.6d, |
| 1a.2e.3e.4b.5f.6e, | 1a.2e.3e.4b.5f.6f, | 1a.2e.3e.4c.5a.6a, | 1a.2e.3e.4c.5a.6b, | 1a.2e.3e.4c.5a.6c, |
| 1a.2e.3e.4c.5a.6d, | 1a.2e.3e.4c.5a.6e, | 1a.2e.3e.4c.5a.6f, | 1a.2e.3e.4c.5b.6a, | |
| 1a.2e.3e.4c.5b.6b, | 1a.2e.3e.4c.5b.6c, | 1a.2e.3e.4c.5b.6d, | 1a.2e.3e.4c.5b.6e, | |
| 1a.2e.3e.4c.5b.6f, | 1a.2e.3e.4c.5c.6a, | 1a.2e.3e.4c.5c.6b, | 1a.2e.3e.4c.5c.6c, | 1a.2e.3e.4c.5c.6d, |
| 1a.2e.3e.4c.5c.6e, | 1a.2e.3e.4c.5c.6f, | 1a.2e.3e.4c.5d.6a, | 1a.2e.3e.4c.5d.6b, | |
| 1a.2e.3e.4c.5d.6c, | 1a.2e.3e.4c.5d.6d, | 1a.2e.3e.4c.5d.6e, | 1a.2e.3e.4c.5d.6f, | |
| 1a.2e.3e.4c.5e.6a, | 1a.2e.3e.4c.5e.6b, | 1a.2e.3e.4c.5e.6c, | 1a.2e.3e.4c.5e.6d, | |
| 1a.2e.3e.4c.5e.6e, | 1a.2e.3e.4c.5e.6f, | 1a.2e.3e.4c.5f.6a, | 1a.2e.3e.4c.5f.6b, | 1a.2e.3e.4c.5f.6c, |
| 1a.2e.3e.4c.5f.6d, | 1a.2e.3e.4c.5f.6e, | 1a.2e.3e.4c.5f.6f, | 1a.2e.3e.4d.5a.6a, | 1a.2e.3e.4d.5a.6b, |
| 1a.2e.3e.4d.5a.6c, | 1a.2e.3e.4d.5a.6d, | 1a.2e.3e.4d.5a.6e, | 1a.2e.3e.4d.5a.6f, | |
| 1a.2e.3e.4d.5b.6a, | 1a.2e.3e.4d.5b.6b, | 1a.2e.3e.4d.5b.6c, | 1a.2e.3e.4d.5b.6d, | |
| 1a.2e.3e.4d.5b.6e, | 1a.2e.3e.4d.5b.6f, | 1a.2e.3e.4d.5c.6a, | 1a.2e.3e.4d.5c.6b, | |
| 1a.2e.3e.4d.5c.6c, | 1a.2e.3e.4d.5c.6d, | 1a.2e.3e.4d.5c.6e, | 1a.2e.3e.4d.5c.6f, | |
| 1a.2e.3e.4d.5d.6a, | 1a.2e.3e.4d.5d.6b, | 1a.2e.3e.4d.5d.6c, | 1a.2e.3e.4d.5d.6d, | |
| 1a.2e.3e.4d.5d.6e, | 1a.2e.3e.4d.5d.6f, | 1a.2e.3e.4d.5e.6a, | 1a.2e.3e.4d.5e.6b, | |
| 1a.2e.3e.4d.5e.6c, | 1a.2e.3e.4d.5e.6d, | 1a.2e.3e.4d.5e.6e, | 1a.2e.3e.4d.5e.6f, | |
| 1a.2e.3e.4d.5f.6a, | 1a.2e.3e.4d.5f.6b, | 1a.2e.3e.4d.5f.6c, | 1a.2e.3e.4d.5f.6d, | |
| 1a.2e.3e.4d.5f.6e, | 1a.2e.3e.4d.5f.6f, | 1a.2e.3e.4e.5a.6a, | 1a.2e.3e.4e.5a.6b, | |
| 1a.2e.3e.4e.5a.6c, | 1a.2e.3e.4e.5a.6d, | 1a.2e.3e.4e.5a.6e, | 1a.2e.3e.4e.5a.6f, | |
| 1a.2e.3e.4e.5b.6a, | 1a.2e.3e.4e.5b.6b, | 1a.2e.3e.4e.5b.6c, | 1a.2e.3e.4e.5b.6d, | |
| 1a.2e.3e.4e.5b.6e, | 1a.2e.3e.4e.5b.6f, | 1a.2e.3e.4e.5c.6a, | 1a.2e.3e.4e.5c.6b, | |
| 1a.2e.3e.4e.5c.6c, | 1a.2e.3e.4e.5c.6d, | 1a.2e.3e.4e.5c.6e, | 1a.2e.3e.4e.5c.6f, | |
| 1a.2e.3e.4e.5d.6a, | 1a.2e.3e.4e.5d.6b, | 1a.2e.3e.4e.5d.6c, | 1a.2e.3e.4e.5d.6d, | |
| 1a.2e.3e.4e.5d.6e, | 1a.2e.3e.4e.5d.6f, | 1a.2e.3e.4e.5e.6a, | 1a.2e.3e.4e.5e.6b, | |
| 1a.2e.3e.4e.5e.6c, | 1a.2e.3e.4e.5e.6d, | 1a.2e.3e.4e.5e.6e, | 1a.2e.3e.4e.5e.6f, | 1a.2e.3e.4e.5f.6a, |
| 1a.2e.3e.4e.5f.6b, | 1a.2e.3e.4e.5f.6c, | 1a.2e.3e.4e.5f.6d, | 1a.2e.3e.4e.5f.6e, | 1a.2e.3e.4e.5f.6f, |
| 1a.2e.3e.4f.5a.6a, | 1a.2e.3e.4f.5a.6b, | 1a.2e.3e.4f.5a.6c, | 1a.2e.3e.4f.5a.6d, | 1a.2e.3e.4f.5a.6e, |
| 1a.2e.3e.4f.5a.6f, | 1a.2e.3e.4f.5b.6a, | 1a.2e.3e.4f.5b.6b, | 1a.2e.3e.4f.5b.6c, | 1a.2e.3e.4f.5b.6d, |
| 1a.2e.3e.4f.5b.6e, | 1a.2e.3e.4f.5b.6f, | 1a.2e.3e.4f.5c.6a, | 1a.2e.3e.4f.5c.6b, | 1a.2e.3e.4f.5c.6c, |
| 1a.2e.3e.4f.5c.6d, | 1a.2e.3e.4f.5c.6e, | 1a.2e.3e.4f.5c.6f, | 1a.2e.3e.4f.5d.6a, | 1a.2e.3e.4f.5d.6b, |
| 1a.2e.3e.4f.5d.6c, | 1a.2e.3e.4f.5d.6d, | 1a.2e.3e.4f.5d.6e, | 1a.2e.3e.4f.5d.6f, | 1a.2e.3e.4f.5e.6a, |
| 1a.2e.3e.4f.5e.6b, | 1a.2e.3e.4f.5e.6c, | 1a.2e.3e.4f.5e.6d, | 1a.2e.3e.4f.5e.6e, | 1a.2e.3e.4f.5e.6f, |
| 1a.2e.3e.4f.5f.6a, | 1a.2e.3e.4f.5f.6b, | 1a.2e.3e.4f.5f.6c, | 1a.2e.3e.4f.5f.6d, | 1a.2e.3e.4f.5f.6e, |
| 1a.2e.3e.4f.5f.6f, | 1a.2e.3f.4a.5a.6a, | 1a.2e.3f.4a.5a.6b, | 1a.2e.3f.4a.5a.6c, | 1a.2e.3f.4a.5a.6d, |
| 1a.2e.3f.4a.5a.6e, | 1a.2e.3f.4a.5a.6f, | 1a.2e.3f.4a.5b.6a, | 1a.2e.3f.4a.5b.6b, | 1a.2e.3f.4a.5b.6c, |
| 1a.2e.3f.4a.5b.6d, | 1a.2e.3f.4a.5b.6e, | 1a.2e.3f.4a.5b.6f, | 1a.2e.3f.4a.5c.6a, | 1a.2e.3f.4a.5c.6b, |
| 1a.2e.3f.4a.5c.6c, | 1a.2e.3f.4a.5c.6d, | 1a.2e.3f.4a.5c.6e, | 1a.2e.3f.4a.5c.6f, | 1a.2e.3f.4a.5d.6a, |
| 1a.2e.3f.4a.5d.6b, | 1a.2e.3f.4a.5d.6c, | 1a.2e.3f.4a.5d.6d, | 1a.2e.3f.4a.5d.6e, | |
| 1a.2e.3f.4a.5d.6f, | 1a.2e.3f.4a.5e.6a, | 1a.2e.3f.4a.5e.6b, | 1a.2e.3f.4a.5e.6c, | 1a.2e.3f.4a.5e.6d, |
| 1a.2e.3f.4a.5e.6e, | 1a.2e.3f.4a.5e.6f, | 1a.2e.3f.4a.5f.6a, | 1a.2e.3f.4a.5f.6b, | 1a.2e.3f.4a.5f.6c, |
| 1a.2e.3f.4a.5f.6d, | 1a.2e.3f.4a.5f.6e, | 1a.2e.3f.4a.5f.6f, | 1a.2e.3f.4b.5a.6a, | 1a.2e.3f.4b.5a.6b, |
| 1a.2e.3f.4b.5a.6c, | 1a.2e.3f.4b.5a.6d, | 1a.2e.3f.4b.5a.6e, | 1a.2e.3f.4b.5a.6f, | 1a.2e.3f.4b.5b.6a, |
| 1a.2e.3f.4b.5b.6b, | 1a.2e.3f.4b.5b.6c, | 1a.2e.3f.4b.5b.6d, | 1a.2e.3f.4b.5b.6e, | |
| 1a.2e.3f.4b.5b.6f, | 1a.2e.3f.4b.5c.6a, | 1a.2e.3f.4b.5c.6b, | 1a.2e.3f.4b.5c.6c, | 1a.2e.3f.4b.5c.6d, |
| 1a.2e.3f.4b.5c.6e, | 1a.2e.3f.4b.5c.6f, | 1a.2e.3f.4b.5d.6a, | 1a.2e.3f.4b.5d.6b, | 1a.2e.3f.4b.5d.6c, |
| 1a.2e.3f.4b.5d.6d, | 1a.2e.3f.4b.5d.6e, | 1a.2e.3f.4b.5d.6f, | 1a.2e.3f.4b.5e.6a, | |
| 1a.2e.3f.4b.5e.6b, | 1a.2e.3f.4b.5e.6c, | 1a.2e.3f.4b.5e.6d, | 1a.2e.3f.4b.5e.6e, | 1a.2e.3f.4b.5e.6f, |
| 1a.2e.3f.4b.5f.6a, | 1a.2e.3f.4b.5f.6b, | 1a.2e.3f.4b.5f.6c, | 1a.2e.3f.4b.5f.6d, | 1a.2e.3f.4b.5f.6e, |
| 1a.2e.3f.4b.5f.6f, | 1a.2e.3f.4c.5a.6a, | 1a.2e.3f.4c.5a.6b, | 1a.2e.3f.4c.5a.6c, | 1a.2e.3f.4c.5a.6d, |
| 1a.2e.3f.4c.5a.6e, | 1a.2e.3f.4c.5a.6f, | 1a.2e.3f.4c.5b.6a, | 1a.2e.3f.4c.5b.6b, | 1a.2e.3f.4c.5b.6c, |
| 1a.2e.3f.4c.5b.6d, | 1a.2e.3f.4c.5b.6e, | 1a.2e.3f.4c.5b.6f, | 1a.2e.3f.4c.5c.6a, | 1a.2e.3f.4c.5c.6b, |
| 1a.2e.3f.4c.5c.6c, | 1a.2e.3f.4c.5c.6d, | 1a.2e.3f.4c.5c.6e, | 1a.2e.3f.4c.5c.6f, | 1a.2e.3f.4c.5d.6a, |
| 1a.2e.3f.4c.5d.6b, | 1a.2e.3f.4c.5d.6c, | 1a.2e.3f.4c.5d.6d, | 1a.2e.3f.4c.5d.6e, | 1a.2e.3f.4c.5d.6f, |
| 1a.2e.3f.4c.5e.6a, | 1a.2e.3f.4c.5e.6b, | 1a.2e.3f.4c.5e.6c, | 1a.2e.3f.4c.5e.6d, | 1a.2e.3f.4c.5e.6e, |
| 1a.2e.3f.4c.5e.6f, | 1a.2e.3f.4c.5f.6a, | 1a.2e.3f.4c.5f.6b, | 1a.2e.3f.4c.5f.6c, | 1a.2e.3f.4c.5f.6d, |
| 1a.2e.3f.4c.5f.6e, | 1a.2e.3f.4c.5f.6f, | 1a.2e.3f.4d.5a.6a, | 1a.2e.3f.4d.5a.6b, | 1a.2e.3f.4d.5a.6c, |
| 1a.2e.3f.4d.5a.6d, | 1a.2e.3f.4d.5a.6e, | 1a.2e.3f.4d.5a.6f, | 1a.2e.3f.4d.5b.6a, | |
| 1a.2e.3f.4d.5b.6b, | 1a.2e.3f.4d.5b.6c, | 1a.2e.3f.4d.5b.6d, | 1a.2e.3f.4d.5b.6e, | |
| 1a.2e.3f.4d.5b.6f, | 1a.2e.3f.4d.5c.6a, | 1a.2e.3f.4d.5c.6b, | 1a.2e.3f.4d.5c.6c, | |
| 1a.2e.3f.4d.5c.6d, | 1a.2e.3f.4d.5c.6e, | 1a.2e.3f.4d.5c.6f, | 1a.2e.3f.4d.5d.6a, | |
| 1a.2e.3f.4d.5d.6b, | 1a.2e.3f.4d.5d.6c, | 1a.2e.3f.4d.5d.6d, | 1a.2e.3f.4d.5d.6e, | |

TABLE 7-continued

List of Compounds of Formula (II)

| | | | | |
|---|---|---|---|---|
| 1a.2e.3f.4d.5d.6f, | 1a.2e.3f.4d.5d.6a, | 1a.2e.3f.4d.5e.6b, | 1a.2e.3f.4d.5e.6c, | |
| 1a.2e.3f.4d.5e.6d, | 1a.2e.3f.4d.5e.6e, | 1a.2e.3f.4d.5e.6f, | 1a.2e.3f.4d.5f.6a, | 1a.2e.3f.4d.5f.6b, |
| 1a.2e.3f.4d.5f.6c, | 1a.2e.3f.4d.5f.6d, | 1a.2e.3f.4d.5f.6e, | 1a.2e.3f.4d.5f.6f, | 1a.2e.3f.4e.5a.6a, |
| 1a.2e.3f.4e.5a.6b, | 1a.2e.3f.4e.5a.6c, | 1a.2e.3f.4e.5a.6d, | 1a.2e.3f.4e.5a.6e, | 1a.2e.3f.4e.5a.6f, |
| 1a.2e.3f.4e.5b.6a, | 1a.2e.3f.4e.5b.6b, | 1a.2e.3f.4e.5b.6c, | 1a.2e.3f.4e.5b.6d, | 1a.2e.3f.4e.5b.6e, |
| 1a.2e.3f.4e.5b.6f, | 1a.2e.3f.4e.5c.6a, | 1a.2e.3f.4e.5c.6b, | 1a.2e.3f.4e.5c.6c, | 1a.2e.3f.4e.5c.6d, |
| 1a.2e.3f.4e.5c.6e, | 1a.2e.3f.4e.5c.6f, | 1a.2e.3f.4e.5d.6a, | 1a.2e.3f.4e.5d.6b, | 1a.2e.3f.4e.5d.6c, |
| 1a.2e.3f.4e.5d.6d, | 1a.2e.3f.4e.5d.6e, | 1a.2e.3f.4e.5d.6f, | 1a.2e.3f.4e.5e.6a, | 1a.2e.3f.4e.5e.6b, |
| 1a.2e.3f.4e.5e.6c, | 1a.2e.3f.4e.5e.6d, | 1a.2e.3f.4e.5e.6e, | 1a.2e.3f.4e.5e.6f, | 1a.2e.3f.4e.5f.6a, |
| 1a.2e.3f.4e.5f.6b, | 1a.2e.3f.4e.5f.6c, | 1a.2e.3f.4e.5f.6d, | 1a.2e.3f.4e.5f.6e, | 1a.2e.3f.4e.5f.6f, |
| 1a.2e.3f.4f.5a.6a, | 1a.2e.3f.4f.5a.6b, | 1a.2e.3f.4f.5a.6c, | 1a.2e.3f.4f.5a.6d, | 1a.2e.3f.4f.5a.6e, |
| 1a.2e.3f.4f.5a.6f, | 1a.2e.3f.4f.5b.6a, | 1a.2e.3f.4f.5b.6b, | 1a.2e.3f.4f.5b.6c, | 1a.2e.3f.4f.5b.6d, |
| 1a.2e.3f.4f.5b.6e, | 1a.2e.3f.4f.5b.6f, | 1a.2e.3f.4f.5c.6a, | 1a.2e.3f.4f.5c.6b, | 1a.2e.3f.4f.5c.6c, |
| 1a.2e.3f.4f.5c.6d, | 1a.2e.3f.4f.5c.6e, | 1a.2e.3f.4f.5c.6f, | 1a.2e.3f.4f.5d.6a, | 1a.2e.3f.4f.5d.6b, |
| 1a.2e.3f.4f.5d.6c, | 1a.2e.3f.4f.5d.6d, | 1a.2e.3f.4f.5d.6e, | 1a.2e.3f.4f.5d.6f, | 1a.2e.3f.4f.5e.6a, |
| 1a.2e.3f.4f.5e.6b, | 1a.2e.3f.4f.5e.6c, | 1a.2e.3f.4f.5e.6d, | 1a.2e.3f.4f.5e.6e, | 1a.2e.3f.4f.5e.6f, |
| 1a.2e.3f.4f.5f.6a, | 1a.2e.3f.4f.5f.6b, | 1a.2e.3f.4f.5f.6c, | 1a.2e.3f.4f.5f.6d, | 1a.2e.3f.4f.5f.6e, |
| 1a.2e.3f.4f.5f.6f, | 1a.2f.3a.4a.5a.6a, | 1a.2f.3a.4a.5a.6b, | 1a.2f.3a.4a.5a.6c, | 1a.2f.3a.4a.5a.6d, |
| 1a.2f.3a.4a.5a.6e, | 1a.2f.3a.4a.5a.6f, | 1a.2f.3a.4a.5b.6a, | 1a.2f.3a.4a.5b.6b, | 1a.2f.3a.4a.5b.6c, |
| 1a.2f.3a.4a.5b.6d, | 1a.2f.3a.4a.5b.6e, | 1a.2f.3a.4a.5b.6f, | 1a.2f.3a.4a.5c.6a, | 1a.2f.3a.4a.5c.6b, |
| 1a.2f.3a.4a.5c.6c, | 1a.2f.3a.4a.5c.6d, | 1a.2f.3a.4a.5c.6e, | 1a.2f.3a.4a.5c.6f, | 1a.2f.3a.4a.5d.6a, |
| 1a.2f.3a.4a.5d.6b, | 1a.2f.3a.4a.5d.6c, | 1a.2f.3a.4a.5d.6d, | 1a.2f.3a.4a.5d.6e, | |
| 1a.2f.3a.4a.5d.6f, | 1a.2f.3a.4a.5e.6a, | 1a.2f.3a.4a.5e.6b, | 1a.2f.3a.4a.5e.6c, | 1a.2f.3a.4a.5e.6d, |
| 1a.2f.3a.4a.5e.6e, | 1a.2f.3a.4a.5e.6f, | 1a.2f.3a.4a.5f.6a, | 1a.2f.3a.4a.5f.6b, | 1a.2f.3a.4a.5f.6c, |
| 1a.2f.3a.4a.5f.6d, | 1a.2f.3a.4a.5f.6e, | 1a.2f.3a.4a.5f.6f, | 1a.2f.3a.4b.5a.6a, | 1a.2f.3a.4b.5a.6b, |
| 1a.2f.3a.4b.5a.6c, | 1a.2f.3a.4b.5a.6d, | 1a.2f.3a.4b.5a.6e, | 1a.2f.3a.4b.5a.6f, | 1a.2f.3a.4b.5b.6a, |
| 1a.2f.3a.4b.5b.6b, | 1a.2f.3a.4b.5b.6c, | 1a.2f.3a.4b.5b.6d, | 1a.2f.3a.4b.5b.6e, | |
| 1a.2f.3a.4b.5b.6f, | 1a.2f.3a.4b.5c.6a, | 1a.2f.3a.4b.5c.6b, | 1a.2f.3a.4b.5c.6c, | 1a.2f.3a.4b.5c.6d, |
| 1a.2f.3a.4b.5c.6e, | 1a.2f.3a.4b.5c.6f, | 1a.2f.3a.4b.5d.6a, | 1a.2f.3a.4b.5d.6b, | |
| 1a.2f.3a.4b.5d.6c, | 1a.2f.3a.4b.5d.6d, | 1a.2f.3a.4b.5d.6e, | 1a.2f.3a.4b.5d.6f, | |
| 1a.2f.3a.4b.5e.6a, | 1a.2f.3a.4b.5e.6b, | 1a.2f.3a.4b.5e.6c, | 1a.2f.3a.4b.5e.6d, | |
| 1a.2f.3a.4b.5e.6e, | 1a.2f.3a.4b.5e.6f, | 1a.2f.3a.4b.5f.6a, | 1a.2f.3a.4b.5f.6b, | 1a.2f.3a.4b.5f.6c, |
| 1a.2f.3a.4b.5f.6d, | 1a.2f.3a.4b.5f.6e, | 1a.2f.3a.4b.5f.6f, | 1a.2f.3a.4c.5a.6a, | 1a.2f.3a.4c.5a.6b, |
| 1a.2f.3a.4c.5a.6c, | 1a.2f.3a.4c.5a.6d, | 1a.2f.3a.4c.5a.6e, | 1a.2f.3a.4c.5a.6f, | 1a.2f.3a.4c.5b.6a, |
| 1a.2f.3a.4c.5b.6b, | 1a.2f.3a.4c.5b.6c, | 1a.2f.3a.4c.5b.6d, | 1a.2f.3a.4c.5b.6e, | 1a.2f.3a.4c.5b.6f, |
| 1a.2f.3a.4c.5c.6a, | 1a.2f.3a.4c.5c.6b, | 1a.2f.3a.4c.5c.6c, | 1a.2f.3a.4c.5c.6d, | 1a.2f.3a.4c.5c.6e, |
| 1a.2f.3a.4c.5c.6f, | 1a.2f.3a.4c.5d.6a, | 1a.2f.3a.4c.5d.6b, | 1a.2f.3a.4c.5d.6c, | 1a.2f.3a.4c.5d.6d, |
| 1a.2f.3a.4c.5d.6e, | 1a.2f.3a.4c.5d.6f, | 1a.2f.3a.4c.5e.6a, | 1a.2f.3a.4c.5e.6b, | 1a.2f.3a.4c.5e.6c, |
| 1a.2f.3a.4c.5e.6d, | 1a.2f.3a.4c.5e.6e, | 1a.2f.3a.4c.5e.6f, | 1a.2f.3a.4c.5f.6a, | 1a.2f.3a.4c.5f.6b, |
| 1a.2f.3a.4c.5f.6c, | 1a.2f.3a.4c.5f.6d, | 1a.2f.3a.4c.5f.6e, | 1a.2f.3a.4c.5f.6f, | 1a.2f.3a.4d.5a.6a, |
| 1a.2f.3a.4d.5a.6b, | 1a.2f.3a.4d.5a.6c, | 1a.2f.3a.4d.5a.6d, | 1a.2f.3a.4d.5a.6e, | |
| 1a.2f.3a.4d.5a.6f, | 1a.2f.3a.4d.5b.6a, | 1a.2f.3a.4d.5b.6b, | 1a.2f.3a.4d.5b.6c, | |
| 1a.2f.3a.4d.5b.6d, | 1a.2f.3a.4d.5b.6e, | 1a.2f.3a.4d.5b.6f, | 1a.2f.3a.4d.5c.6a, | |
| 1a.2f.3a.4d.5c.6b, | 1a.2f.3a.4d.5c.6c, | 1a.2f.3a.4d.5c.6d, | 1a.2f.3a.4d.5c.6e, | 1a.2f.3a.4d.5c.6f, |
| 1a.2f.3a.4d.5d.6a, | 1a.2f.3a.4d.5d.6b, | 1a.2f.3a.4d.5d.6c, | 1a.2f.3a.4d.5d.6d, | |
| 1a.2f.3a.4d.5d.6e, | 1a.2f.3a.4d.5d.6f, | 1a.2f.3a.4d.5e.6a, | 1a.2f.3a.4d.5e.6b, | |
| 1a.2f.3a.4d.5e.6c, | 1a.2f.3a.4d.5e.6d, | 1a.2f.3a.4d.5e.6e, | 1a.2f.3a.4d.5e.6f, | 1a.2f.3a.4d.5f.6a, |
| 1a.2f.3a.4d.5f.6b, | 1a.2f.3a.4d.5f.6c, | 1a.2f.3a.4d.5f.6d, | 1a.2f.3a.4d.5f.6e, | 1a.2f.3a.4d.5f.6f, |
| 1a.2f.3a.4e.5a.6a, | 1a.2f.3a.4e.5a.6b, | 1a.2f.3a.4e.5a.6c, | 1a.2f.3a.4e.5a.6d, | 1a.2f.3a.4e.5a.6e, |
| 1a.2f.3a.4e.5a.6f, | 1a.2f.3a.4e.5b.6a, | 1a.2f.3a.4e.5b.6b, | 1a.2f.3a.4e.5b.6c, | 1a.2f.3a.4e.5b.6d, |
| 1a.2f.3a.4e.5b.6e, | 1a.2f.3a.4e.5b.6f, | 1a.2f.3a.4e.5c.6a, | 1a.2f.3a.4e.5c.6b, | 1a.2f.3a.4e.5c.6c, |
| 1a.2f.3a.4e.5c.6d, | 1a.2f.3a.4e.5c.6e, | 1a.2f.3a.4e.5c.6f, | 1a.2f.3a.4e.5d.6a, | 1a.2f.3a.4e.5d.6b, |
| 1a.2f.3a.4e.5d.6c, | 1a.2f.3a.4e.5d.6d, | 1a.2f.3a.4e.5d.6e, | 1a.2f.3a.4e.5d.6f, | 1a.2f.3a.4e.5e.6a, |
| 1a.2f.3a.4e.5e.6b, | 1a.2f.3a.4e.5e.6c, | 1a.2f.3a.4e.5e.6d, | 1a.2f.3a.4e.5e.6e, | 1a.2f.3a.4e.5e.6f, |
| 1a.2f.3a.4e.5f.6a, | 1a.2f.3a.4e.5f.6b, | 1a.2f.3a.4e.5f.6c, | 1a.2f.3a.4e.5f.6d, | 1a.2f.3a.4e.5f.6e, |
| 1a.2f.3a.4e.5f.6f, | 1a.2f.3a.4f.5a.6a, | 1a.2f.3a.4f.5a.6b, | 1a.2f.3a.4f.5a.6c, | 1a.2f.3a.4f.5a.6d, |
| 1a.2f.3a.4f.5a.6e, | 1a.2f.3a.4f.5a.6f, | 1a.2f.3a.4f.5b.6a, | 1a.2f.3a.4f.5b.6b, | 1a.2f.3a.4f.5b.6c, |
| 1a.2f.3a.4f.5b.6d, | 1a.2f.3a.4f.5b.6e, | 1a.2f.3a.4f.5b.6f, | 1a.2f.3a.4f.5c.6a, | 1a.2f.3a.4f.5c.6b, |
| 1a.2f.3a.4f.5c.6c, | 1a.2f.3a.4f.5c.6d, | 1a.2f.3a.4f.5c.6e, | 1a.2f.3a.4f.5c.6f, | 1a.2f.3a.4f.5d.6a, |
| 1a.2f.3a.4f.5d.6b, | 1a.2f.3a.4f.5d.6c, | 1a.2f.3a.4f.5d.6d, | 1a.2f.3a.4f.5d.6e, | 1a.2f.3a.4f.5d.6f, |
| 1a.2f.3a.4f.5e.6a, | 1a.2f.3a.4f.5e.6b, | 1a.2f.3a.4f.5e.6c, | 1a.2f.3a.4f.5e.6d, | 1a.2f.3a.4f.5e.6e, |
| 1a.2f.3a.4f.5e.6f, | 1a.2f.3a.4f.5f.6a, | 1a.2f.3a.4f.5f.6b, | 1a.2f.3a.4f.5f.6c, | 1a.2f.3a.4f.5f.6d, |
| 1a.2f.3a.4f.5f.6e, | 1a.2f.3a.4f.5f.6f, | 1a.2f.3b.4a.5a.6a, | 1a.2f.3b.4a.5a.6b, | 1a.2f.3b.4a.5a.6c, |
| 1a.2f.3b.4a.5a.6d, | 1a.2f.3b.4a.5a.6e, | 1a.2f.3b.4a.5a.6f, | 1a.2f.3b.4a.5b.6a, | |
| 1a.2f.3b.4a.5b.6b, | 1a.2f.3b.4a.5b.6c, | 1a.2f.3b.4a.5b.6d, | 1a.2f.3b.4a.5b.6e, | |
| 1a.2f.3b.4a.5b.6f, | 1a.2f.3b.4a.5c.6a, | 1a.2f.3b.4a.5c.6b, | 1a.2f.3b.4a.5c.6c, | 1a.2f.3b.4a.5c.6d, |
| 1a.2f.3b.4a.5c.6e, | 1a.2f.3b.4a.5c.6f, | 1a.2f.3b.4a.5d.6a, | 1a.2f.3b.4a.5d.6b, | |
| 1a.2f.3b.4a.5d.6c, | 1a.2f.3b.4a.5d.6d, | 1a.2f.3b.4a.5d.6e, | 1a.2f.3b.4a.5d.6f, | |
| 1a.2f.3b.4a.5e.6a, | 1a.2f.3b.4a.5e.6b, | 1a.2f.3b.4a.5e.6c, | 1a.2f.3b.4a.5e.6d, | |
| 1a.2f.3b.4a.5e.6e, | 1a.2f.3b.4a.5e.6f, | 1a.2f.3b.4a.5f.6a, | 1a.2f.3b.4a.5f.6b, | 1a.2f.3b.4a.5f.6c, |
| 1a.2f.3b.4a.5f.6d, | 1a.2f.3b.4a.5f.6e, | 1a.2f.3b.4a.5f.6f, | 1a.2f.3b.4b.5a.6a, | 1a.2f.3b.4b.5a.6b, |
| 1a.2f.3b.4b.5a.6c, | 1a.2f.3b.4b.5a.6d, | 1a.2f.3b.4b.5a.6e, | 1a.2f.3b.4b.5a.6f, | |
| 1a.2f.3b.4b.5b.6a, | 1a.2f.3b.4b.5b.6b, | 1a.2f.3b.4b.5b.6c, | 1a.2f.3b.4b.5b.6d, | |
| 1a.2f.3b.4b.5b.6e, | 1a.2f.3b.4b.5b.6f, | 1a.2f.3b.4b.5c.6a, | 1a.2f.3b.4b.5c.6b, | |
| 1a.2f.3b.4b.5c.6c, | 1a.2f.3b.4b.5c.6d, | 1a.2f.3b.4b.5c.6e, | 1a.2f.3b.4b.5c.6f, | |
| 1a.2f.3b.4b.5d.6a, | 1a.2f.3b.4b.5d.6b, | 1a.2f.3b.4b.5d.6c, | 1a.2f.3b.4b.5d.6d, | |
| 1a.2f.3b.4b.5d.6e, | 1a.2f.3b.4b.5d.6f, | 1a.2f.3b.4b.5e.6a, | 1a.2f.3b.4b.5e.6b, | |
| 1a.2f.3b.4b.5e.6c, | 1a.2f.3b.4b.5e.6d, | 1a.2f.3b.4b.5e.6e, | 1a.2f.3b.4b.5e.6f, | 1a.2f.3b.4b.5f.6a, |

TABLE 7-continued

List of Compounds of Formula (II)

| | | | | |
|---|---|---|---|---|
| 1a.2f.3b.4b.5f.6b, | 1a.2f.3b.4b.5f.6c, | 1a.2f.3b.4b.5f.6d, | 1a.2f.3b.4b.5f.6e, | 1a.2f.3b.4b.5f.6f, |
| 1a.2f.3b.4c.5a.6a, | 1a.2f.3b.4c.5a.6b, | 1a.2f.3b.4c.5a.6c, | 1a.2f.3b.4c.5a.6d, | 1a.2f.3b.4c.5a.6e, |
| 1a.2f.3b.4c.5a.6f, | 1a.2f.3b.4c.5b.6a, | 1a.2f.3b.4c.5b.6b, | 1a.2f.3b.4c.5b.6c, | 1a.2f.3b.4c.5b.6d, |
| 1a.2f.3b.4c.5b.6e, | 1a.2f.3b.4c.5b.6f, | 1a.2f.3b.4c.5c.6a, | 1a.2f.3b.4c.5c.6b, | 1a.2f.3b.4c.5c.6c, |
| 1a.2f.3b.4c.5c.6d, | 1a.2f.3b.4c.5c.6e, | 1a.2f.3b.4c.5c.6f, | 1a.2f.3b.4c.5d.6a, | 1a.2f.3b.4c.5d.6b, |
| 1a.2f.3b.4c.5d.6c, | 1a.2f.3b.4c.5d.6d, | 1a.2f.3b.4c.5d.6e, | 1a.2f.3b.4c.5d.6f, | |
| 1a.2f.3b.4c.5e.6a, | 1a.2f.3b.4c.5e.6b, | 1a.2f.3b.4c.5e.6c, | 1a.2f.3b.4c.5e.6d, | 1a.2f.3b.4c.5e.6e, |
| 1a.2f.3b.4c.5e.6f, | 1a.2f.3b.4c.5f.6a, | 1a.2f.3b.4c.5f.6b, | 1a.2f.3b.4c.5f.6c, | 1a.2f.3b.4c.5f.6d, |
| 1a.2f.3b.4c.5f.6e, | 1a.2f.3b.4c.5f.6f, | 1a.2f.3b.4d.5a.6a, | 1a.2f.3b.4d.5a.6b, | 1a.2f.3b.4d.5a.6c, |
| 1a.2f.3b.4d.5a.6d, | 1a.2f.3b.4d.5a.6e, | 1a.2f.3b.4d.5a.6f, | 1a.2f.3b.4d.5b.6a, | |
| 1a.2f.3b.4d.5b.6b, | 1a.2f.3b.4d.5b.6c, | 1a.2f.3b.4d.5b.6d, | 1a.2f.3b.4d.5b.6e, | |
| 1a.2f.3b.4d.5b.6f, | 1a.2f.3b.4d.5c.6a, | 1a.2f.3b.4d.5c.6b, | 1a.2f.3b.4d.5c.6c, | |
| 1a.2f.3b.4d.5c.6d, | 1a.2f.3b.4d.5c.6e, | 1a.2f.3b.4d.5c.6f, | 1a.2f.3b.4d.5d.6a, | |
| 1a.2f.3b.4d.5d.6b, | 1a.2f.3b.4d.5d.6c, | 1a.2f.3b.4d.5d.6d, | 1a.2f.3b.4d.5d.6e, | |
| 1a.2f.3b.4d.5d.6f, | 1a.2f.3b.4d.5e.6a, | 1a.2f.3b.4d.5e.6b, | 1a.2f.3b.4d.5e.6c, | |
| 1a.2f.3b.4d.5e.6d, | 1a.2f.3b.4d.5e.6e, | 1a.2f.3b.4d.5e.6f, | 1a.2f.3b.4d.5f.6a, | |
| 1a.2f.3b.4d.5f.6b, | 1a.2f.3b.4d.5f.6c, | 1a.2f.3b.4d.5f.6d, | 1a.2f.3b.4d.5f.6e, | 1a.2f.3b.4d.5f.6f, |
| 1a.2f.3b.4e.5a.6a, | 1a.2f.3b.4e.5a.6b, | 1a.2f.3b.4e.5a.6c, | 1a.2f.3b.4e.5a.6d, | |
| 1a.2f.3b.4e.5a.6e, | 1a.2f.3b.4e.5a.6f, | 1a.2f.3b.4e.5b.6a, | 1a.2f.3b.4e.5b.6b, | 1a.2f.3b.4e.5b.6c, |
| 1a.2f.3b.4e.5b.6d, | 1a.2f.3b.4e.5b.6e, | 1a.2f.3b.4e.5b.6f, | 1a.2f.3b.4e.5c.6a, | 1a.2f.3b.4e.5c.6b, |
| 1a.2f.3b.4e.5c.6c, | 1a.2f.3b.4e.5c.6d, | 1a.2f.3b.4e.5c.6e, | 1a.2f.3b.4e.5c.6f, | 1a.2f.3b.4e.5d.6a, |
| 1a.2f.3b.4e.5d.6b, | 1a.2f.3b.4e.5d.6c, | 1a.2f.3b.4e.5d.6d, | 1a.2f.3b.4e.5d.6e, | |
| 1a.2f.3b.4e.5d.6f, | 1a.2f.3b.4e.5e.6a, | 1a.2f.3b.4e.5e.6b, | 1a.2f.3b.4e.5e.6c, | 1a.2f.3b.4e.5e.6d, |
| 1a.2f.3b.4e.5e.6e, | 1a.2f.3b.4e.5e.6f, | 1a.2f.3b.4e.5f.6a, | 1a.2f.3b.4e.5f.6b, | 1a.2f.3b.4e.5f.6c, |
| 1a.2f.3b.4e.5f.6d, | 1a.2f.3b.4e.5f.6e, | 1a.2f.3b.4e.5f.6f, | 1a.2f.3b.4f.5a.6a, | 1a.2f.3b.4f.5a.6b, |
| 1a.2f.3b.4f.5a.6c, | 1a.2f.3b.4f.5a.6d, | 1a.2f.3b.4f.5a.6e, | 1a.2f.3b.4f.5a.6f, | 1a.2f.3b.4f.5b.6a, |
| 1a.2f.3b.4f.5b.6b, | 1a.2f.3b.4f.5b.6c, | 1a.2f.3b.4f.5b.6d, | 1a.2f.3b.4f.5b.6e, | 1a.2f.3b.4f.5b.6f, |
| 1a.2f.3b.4f.5c.6a, | 1a.2f.3b.4f.5c.6b, | 1a.2f.3b.4f.5c.6c, | 1a.2f.3b.4f.5c.6d, | 1a.2f.3b.4f.5c.6e, |
| 1a.2f.3b.4f.5c.6f, | 1a.2f.3b.4f.5d.6a, | 1a.2f.3b.4f.5d.6b, | 1a.2f.3b.4f.5d.6c, | 1a.2f.3b.4f.5d.6d, |
| 1a.2f.3b.4f.5d.6e, | 1a.2f.3b.4f.5d.6f, | 1a.2f.3b.4f.5e.6a, | 1a.2f.3b.4f.5e.6b, | 1a.2f.3b.4f.5e.6c, |
| 1a.2f.3b.4f.5e.6d, | 1a.2f.3b.4f.5e.6e, | 1a.2f.3b.4f.5e.6f, | 1a.2f.3b.4f.5f.6a, | 1a.2f.3b.4f.5f.6b, |
| 1a.2f.3b.4f.5f.6c, | 1a.2f.3b.4f.5f.6d, | 1a.2f.3b.4f.5f.6e, | 1a.2f.3b.4f.5f.6f, | 1a.2f.3c.4a.5a.6a, |
| 1a.2f.3c.4a.5a.6b, | 1a.2f.3c.4a.5a.6c, | 1a.2f.3c.4a.5a.6d, | 1a.2f.3c.4a.5a.6e, | 1a.2f.3c.4a.5a.6f, |
| 1a.2f.3c.4a.5b.6a, | 1a.2f.3c.4a.5b.6b, | 1a.2f.3c.4a.5b.6c, | 1a.2f.3c.4a.5b.6d, | 1a.2f.3c.4a.5b.6e, |
| 1a.2f.3c.4a.5b.6f, | 1a.2f.3c.4a.5c.6a, | 1a.2f.3c.4a.5c.6b, | 1a.2f.3c.4a.5c.6c, | 1a.2f.3c.4a.5c.6d, |
| 1a.2f.3c.4a.5c.6e, | 1a.2f.3c.4a.5c.6f, | 1a.2f.3c.4a.5d.6a, | 1a.2f.3c.4a.5d.6b, | 1a.2f.3c.4a.5d.6c, |
| 1a.2f.3c.4a.5d.6d, | 1a.2f.3c.4a.5d.6e, | 1a.2f.3c.4a.5d.6f, | 1a.2f.3c.4a.5e.6a, | 1a.2f.3c.4a.5e.6b, |
| 1a.2f.3c.4a.5e.6c, | 1a.2f.3c.4a.5e.6d, | 1a.2f.3c.4a.5e.6e, | 1a.2f.3c.4a.5e.6f, | 1a.2f.3c.4a.5f.6a, |
| 1a.2f.3c.4a.5f.6b, | 1a.2f.3c.4a.5f.6c, | 1a.2f.3c.4a.5f.6d, | 1a.2f.3c.4a.5f.6e, | 1a.2f.3c.4a.5f.6f, |
| 1a.2f.3c.4b.5a.6a, | 1a.2f.3c.4b.5a.6b, | 1a.2f.3c.4b.5a.6c, | 1a.2f.3c.4b.5a.6d, | 1a.2f.3c.4b.5a.6e, |
| 1a.2f.3c.4b.5a.6f, | 1a.2f.3c.4b.5b.6a, | 1a.2f.3c.4b.5b.6b, | 1a.2f.3c.4b.5b.6c, | 1a.2f.3c.4b.5b.6d, |
| 1a.2f.3c.4b.5b.6e, | 1a.2f.3c.4b.5b.6f, | 1a.2f.3c.4b.5c.6a, | 1a.2f.3c.4b.5c.6b, | 1a.2f.3c.4b.5c.6c, |
| 1a.2f.3c.4b.5c.6d, | 1a.2f.3c.4b.5c.6e, | 1a.2f.3c.4b.5c.6f, | 1a.2f.3c.4b.5d.6a, | 1a.2f.3c.4b.5d.6b, |
| 1a.2f.3c.4b.5d.6c, | 1a.2f.3c.4b.5d.6d, | 1a.2f.3c.4b.5d.6e, | 1a.2f.3c.4b.5d.6f, | |
| 1a.2f.3c.4b.5e.6a, | 1a.2f.3c.4b.5e.6b, | 1a.2f.3c.4b.5e.6c, | 1a.2f.3c.4b.5e.6d, | 1a.2f.3c.4b.5e.6e, |
| 1a.2f.3c.4b.5e.6f, | 1a.2f.3c.4b.5f.6a, | 1a.2f.3c.4b.5f.6b, | 1a.2f.3c.4b.5f.6c, | 1a.2f.3c.4b.5f.6d, |
| 1a.2f.3c.4b.5f.6e, | 1a.2f.3c.4b.5f.6f, | 1a.2f.3c.4c.5a.6a, | 1a.2f.3c.4c.5a.6b, | 1a.2f.3c.4c.5a.6c, |
| 1a.2f.3c.4c.5a.6d, | 1a.2f.3c.4c.5a.6e, | 1a.2f.3c.4c.5a.6f, | 1a.2f.3c.4c.5b.6a, | 1a.2f.3c.4c.5b.6b, |
| 1a.2f.3c.4c.5b.6c, | 1a.2f.3c.4c.5b.6d, | 1a.2f.3c.4c.5b.6e, | 1a.2f.3c.4c.5b.6f, | 1a.2f.3c.4c.5c.6a, |
| 1a.2f.3c.4c.5c.6b, | 1a.2f.3c.4c.5c.6c, | 1a.2f.3c.4c.5c.6d, | 1a.2f.3c.4c.5c.6e, | 1a.2f.3c.4c.5c.6f, |
| 1a.2f.3c.4c.5d.6a, | 1a.2f.3c.4c.5d.6b, | 1a.2f.3c.4c.5d.6c, | 1a.2f.3c.4c.5d.6d, | 1a.2f.3c.4c.5d.6e, |
| 1a.2f.3c.4c.5d.6f, | 1a.2f.3c.4c.5e.6a, | 1a.2f.3c.4c.5e.6b, | 1a.2f.3c.4c.5e.6c, | 1a.2f.3c.4c.5e.6d, |
| 1a.2f.3c.4c.5e.6e, | 1a.2f.3c.4c.5e.6f, | 1a.2f.3c.4c.5f.6a, | 1a.2f.3c.4c.5f.6b, | 1a.2f.3c.4c.5f.6c, |
| 1a.2f.3c.4c.5f.6d, | 1a.2f.3c.4c.5f.6e, | 1a.2f.3c.4c.5f.6f, | 1a.2f.3c.4d.5a.6a, | 1a.2f.3c.4d.5a.6b, |
| 1a.2f.3c.4d.5a.6c, | 1a.2f.3c.4d.5a.6d, | 1a.2f.3c.4d.5a.6e, | 1a.2f.3c.4d.5a.6f, | 1a.2f.3c.4d.5b.6a, |
| 1a.2f.3c.4d.5b.6b, | 1a.2f.3c.4d.5b.6c, | 1a.2f.3c.4d.5b.6d, | 1a.2f.3c.4d.5b.6e, | |
| 1a.2f.3c.4d.5b.6f, | 1a.2f.3c.4d.5c.6a, | 1a.2f.3c.4d.5c.6b, | 1a.2f.3c.4d.5c.6c, | 1a.2f.3c.4d.5c.6d, |
| 1a.2f.3c.4d.5c.6e, | 1a.2f.3c.4d.5c.6f, | 1a.2f.3c.4d.5d.6a, | 1a.2f.3c.4d.5d.6b, | |
| 1a.2f.3c.4d.5d.6c, | 1a.2f.3c.4d.5d.6d, | 1a.2f.3c.4d.5d.6e, | 1a.2f.3c.4d.5d.6f, | |
| 1a.2f.3c.4d.5e.6a, | 1a.2f.3c.4d.5e.6b, | 1a.2f.3c.4d.5e.6c, | 1a.2f.3c.4d.5e.6d, | |
| 1a.2f.3c.4d.5e.6e, | 1a.2f.3c.4d.5e.6f, | 1a.2f.3c.4d.5f.6a, | 1a.2f.3c.4d.5f.6b, | 1a.2f.3c.4d.5f.6c, |
| 1a.2f.3c.4d.5f.6d, | 1a.2f.3c.4d.5f.6e, | 1a.2f.3c.4d.5f.6f, | 1a.2f.3c.4e.5a.6a, | 1a.2f.3c.4e.5a.6b, |
| 1a.2f.3c.4e.5a.6c, | 1a.2f.3c.4e.5a.6d, | 1a.2f.3c.4e.5a.6e, | 1a.2f.3c.4e.5a.6f, | 1a:2f.3c.4e.5b.6a, |
| 1a.2f.3c.4e.5b.6b, | 1a.2f.3c.4e.5b.6c, | 1a.2f.3c.4e.5b.6d, | 1a.2f.3c.4e.5b.6e, | 1a.2f.3c.4e.5b.6f, |
| 1a.2f.3c.4e.5c.6a, | 1a.2f.3c.4e.5c.6b, | 1a.2f.3c.4e.5c.6c, | 1a.2f.3c.4e.5c.6d, | 1a.2f.3c.4e.5c.6e, |
| 1a.2f.3c.4e.5c.6f, | 1a.2f.3c.4e.5d.6a, | 1a.2f.3c.4e.5d.6b, | 1a.2f.3c.4e.5d.6c, | 1a.2f.3c.4e.5d.6d, |
| 1a.2f.3c.4e.5d.6e, | 1a.2f.3c.4e.5d.6f, | 1a.2f.3c.4e.5e.6a, | 1a.2f.3c.4e.5e.6b, | 1a.2f.3c.4e.5e.6c, |
| 1a.2f.3c.4e.5e.6d, | 1a.2f.3c.4e.5e.6e, | 1a.2f.3c.4e.5e.6f, | 1a.2f.3c.4e.5f.6a, | 1a.2f.3c.4e.5f.6b, |
| 1a.2f.3c.4e.5f.6c, | 1a.2f.3c.4e.5f.6d, | 1a.2f.3c.4e.5f.6e, | 1a.2f.3c.4e.5f.6f, | 1a.2f.3c.4f.5a.6a, |
| 1a.2f.3c.4f.5a.6b, | 1a.2f.3c.4f.5a.6c, | 1a.2f.3c.4f.5a.6d, | 1a.2f.3c.4f.5a.6e, | 1a.2f.3c.4f.5a.6f, |
| 1a.2f.3c.4f.5b.6a, | 1a.2f.3c.4f.5b.6b, | 1a.2f.3c.4f.5b.6c, | 1a.2f.3c.4f.5b.6d, | 1a.2f.3c.4f.5b.6e, |
| 1a.2f.3c.4f.5b.6f, | 1a.2f.3c.4f.5c.6a, | 1a.2f.3c.4f.5c.6b, | 1a.2f.3c.4f.5c.6c, | 1a.2f.3c.4f.5c.6d, |
| 1a.2f.3c.4f.5c.6e, | 1a.2f.3c.4f.5c.6f, | 1a.2f.3c.4f.5d.6a, | 1a.2f.3c.4f.5d.6b, | 1a.2f.3c.4f.5d.6c, |
| 1a.2f.3c.4f.5d.6d, | 1a.2f.3c.4f.5d.6e, | 1a.2f.3c.4f.5d.6f, | 1a.2f.3c.4f.5e.6a, | 1a.2f.3c.4f.5e.6b, |
| 1a.2f.3c.4f.5e.6c, | 1a.2f.3c.4f.5e.6d, | 1a.2f.3c.4f.5e.6e, | 1a.2f.3c.4f.5e.6f, | 1a.2f.3c.4f.5f.6a, |
| 1a.2f.3c.4f.5f.6b, | 1a.2f.3c.4f.5f.6c, | 1a.2f.3c.4f.5f.6d, | 1a.2f.3c.4f.5f.6e, | 1a.2f.3c.4f.5f.6f, |
| 1a.2f.3d.4a.5a.6a, | 1a.2f.3d.4a.5a.6b, | 1a.2f.3d.4a.5a.6c, | 1a.2f.3d.4a.5a.6d, | |
| 1a.2f.3d.4a.5a.6e, | 1a.2f.3d.4a.5a.6f, | 1a.2f.3d.4a.5b.6a, | 1a.2f.3d.4a.5b.6b, | |

TABLE 7-continued

List of Compounds of Formula (II)

| | | | | |
|---|---|---|---|---|
| 1a.2f.3d.4a.5b.6c, | 1a.2f.3d.4a.5b.6d, | 1a.2f.3d.4a.5b.6e, | 1a.2f.3d.4a.5b.6f, | |
| 1a.2f.3d.4a.5c.6a, | 1a.2f.3d.4a.5c.6b, | 1a.2f.3d.4a.5c.6c, | 1a.2f.3d.4a.5c.6d, | |
| 1a.2f.3d.4a.5c.6e, | 1a.2f.3d.4a.5c.6f, | 1a.2f.3d.4a.5d.6a, | 1a.2f.3d.4a.5d.6b, | |
| 1a.2f.3d.4a.5d.6c, | 1a.2f.3d.4a.5d.6d, | 1a.2f.3d.4a.5d.6e, | 1a.2f.3d.4a.5d.6f, | |
| 1a.2f.3d.4a.5e.6a, | 1a.2f.3d.4a.5e.6b, | 1a.2f.3d.4a.5e.6c, | 1a.2f.3d.4a.5e.6d, | |
| 1a.2f.3d.4a.5e.6e, | 1a.2f.3d.4a.5e.6f, | 1a.2f.3d.4a.5f.6a, | 1a.2f.3d.4a.5f.6b, | 1a.2f.3d.4a.5f.6c, |
| 1a.2f.3d.4a.5f.6d, | 1a.2f.3d.4a.5f.6e, | 1a.2f.3d.4a.5f.6f, | 1a.2f.3d.4b.5a.6a, | 1a.2f.3d.4b.5a.6b, |
| 1a.2f.3d.4b.5a.6c, | 1a.2f.3d.4b.5a.6d, | 1a.2f.3d.4b.5a.6e, | 1a.2f.3d.4b.5a.6f, | |
| 1a.2f.3d.4b.5b.6a, | 1a.2f.3d.4b.5b.6b, | 1a.2f.3d.4b.5b.6c, | 1a.2f.3d.4b.5b.6d, | |
| 1a.2f.3d.4b.5b.6e, | 1a.2f.3d.4b.5b.6f, | 1a.2f.3d.4b.5c.6a, | 1a.2f.3d.4b.5c.6b, | |
| 1a.2f.3d.4b.5c.6c, | 1a.2f.3d.4b.5c.6d, | 1a.2f.3d.4b.5c.6e, | 1a.2f.3d.4b.5c.6f, | |
| 1a.2f.3d.4b.5d.6a, | 1a.2f.3d.4b.5d.6b, | 1a.2f.3d.4b.5d.6c, | 1a.2f.3d.4b.5d.6d, | |
| 1a.2f.3d.4b.5d.6e, | 1a.2f.3d.4b.5d.6f, | 1a.2f.3d.4b.5e.6a, | 1a.2f.3d.4b.5e.6b, | |
| 1a.2f.3d.4b.5e.6c, | 1a.2f.3d.4b.5e.6d, | 1a.2f.3d.4b.5e.6e, | 1a.2f.3d.4b.5e.6f, | |
| 1a.2f.3d.4b.5f.6a, | 1a.2f.3d.4b.5f.6b, | 1a.2f.3d.4b.5f.6c, | 1a.2f.3d.4b.5f.6d, | 1a.2f.3d.4b.5f.6e, |
| 1a.2f.3d.4b.5f.6f, | 1a.2f.3d.4c.5a.6a, | 1a.2f.3d.4c.5a.6b, | 1a.2f.3d.4c.5a.6C, | 1a.2f.3d.4c.5a.6d, |
| 1a.2f.3d.4c.5a.6e, | 1a.2f.3d.4c.5a.6f, | 1a.2f.3d.4c.5b.6a, | 1a.2f.3d.4c.5b.6b, | |
| 1a.2f.3d.4c.5b.6c, | 1a.2f.3d.4c.5b.6d, | 1a.2f.3d.4c.5b.6e, | 1a.2f.3d.4c.5b.6f, | |
| 1a.2f.3d.4c.5c.6a, | 1a.2f.3d.4c.5c.6b, | 1a.2f.3d.4c.5c.6c, | 1a.2f.3d.4c.5c.6d, | 1a.2f.3d.4c.5c.6e, |
| 1a.2f.3d.4c.5c.6f, | 1a.2f.3d.4c.5d.6a, | 1a.2f.3d.4c.5d.6b, | 1a.2f.3d.4c.5d.6c, | |
| 1a.2f.3d.4c.5d.6d, | 1a.2f.3d.4c.5d.6e, | 1a.2f.3d.4c.5d.6f, | 1a.2f.3d.4c.5e.6a, | |
| 1a.2f.3d.4c.5e.6b, | 1a.2f.3d.4c.5e.6c, | 1a.2f.3d.4c.5e.6d, | 1a.2f.3d.4c.5e.6e, | 1a.2f.3d.4c.5e.6f, |
| 1a.2f.3d.4c.5f.6a, | 1a.2f.3d.4c.5f.6b, | 1a.2f.3d.4c.5f.6c, | 1a.2f.3d.4c.5f.6d, | 1a.2f.3d.4c.5f.6e, |
| 1a.2f.3d.4c.5f.6f, | 1a.2f.3d.4d.5a.6a, | 1a.2f.3d.4d.5a.6b, | 1a.2f.3d.4d.5a.6c, | |
| 1a.2f.3d.4d.5a.6d, | 1a.2f.3d.4d.5a.6e, | 1a.2f.3d.4d.5a.6f, | 1a.2f.3d.4d.5b.6a, | |
| 1a.2f.3d.4d.5b.6b, | 1a.2f.3d.4d.5b.6c, | 1a.2f.3d.4d.5b.6d, | 1a.2f.3d.4d.5b.6e, | |
| 1a.2f.3d.4d.5b.6f, | 1a.2f.3d.4d.5c.6a, | 1a.2f.3d.4d.5c.6b, | 1a.2f.3d.4d.5c.6c, | |
| 1a.2f.3d.4d.5c.6d, | 1a.2f.3d.4d.5c.6e, | 1a.2f.3d.4d.5c.6f, | 1a.2f.3d.4d.5d.6a, | |
| 1a.2f.3d.4d.5d.6b, | 1a.2f.3d.4d.5d.6c, | 1a.2f.3d.4d.5d.6d, | 1a.2f.3d.4d.5d.6e, | |
| 1a.2f.3d.4d.5d.6f, | 1a.2f.3d.4d.5e.6a, | 1a.2f.3d.4d.5e.6b, | 1a.2f.3d.4d.5e.6c, | |
| 1a.2f.3d.4d.5e.6d, | 1a.2f.3d.4d.5e.6e, | 1a.2f.3d.4d.5e.6f, | 1a.2f.3d.4d.5f.6a, | |
| 1a.2f.3d.4d.5f.6b, | 1a.2f.3d.4d.5f.6c, | 1a.2f.3d.4d.5f.6d, | 1a.2f.3d.4d.5f.6e, | 1a.2f.3d.4d.5f.6f, |
| 1a.2f.3d.4e.5a.6a, | 1a.2f.3d.4e.5a.6b, | 1a.2f.3d.4e.5a.6c, | 1a.2f.3d.4e.5a.6d, | |
| 1a.2f.3d.4e.5a.6e, | 1a.2f.3d.4e.5a.6f, | 1a.2f.3d.4e.5b.6a, | 1a.2f.3d.4e.5b.6b, | |
| 1a.2f.3d.4e.5b.6c, | 1a.2f.3d.4e.5b.6d, | 1a.2f.3d.4e.5b.6e, | 1a.2f.3d.4e.5b.6f, | |
| 1a.2f.3d.4e.5c.6a, | 1a.2f.3d.4e.5c.6b, | 1a.2f.3d.4e.5c.6c, | 1a.2f.3d.4e.5c.6d, | |
| 1a.2f.3d.4e.5c.6e, | 1a.2f.3d.4e.5c.6f, | 1a.2f.3d.4e.5d.6a, | 1a.2f.3d.4e.5d.6b, | |
| 1a.2f.3d.4e.5d.6c, | 1a.2f.3d.4e.5d.6d, | 1a.2f.3d.4e.5d.6e, | 1a.2f.3d.4e.5d.6f, | |
| 1a.2f.3d.4e.5e.6a, | 1a.2f.3d.4e.5e.6b, | 1a.2f.3d.4e.5e.6c, | 1a.2f.3d.4e.5e.6d, | |
| 1a.2f.3d.4e.5e.6e, | 1a.2f.3d.4e.5e.6f, | 1a.2f.3d.4e.5f.6a, | 1a.2f.3d.4e.5f.6b, | 1a.2f.3d.4e.5f.6c, |
| 1a.2f.3d.4e.5f.6d, | 1a.2f.3d.4e.5f.6e, | 1a.2f.3d.4e.5f.6f, | 1a.2f.3d.4f.5a.6a, | 1a.2f.3d.4f.5a.6b, |
| 1a.2f.3d.4f.5a.6c, | 1a.2f.3d.4f.5a.6d, | 1a.2f.3d.4f.5a.6e, | 1a.2f.3d.4f.5a.6f, | 1a.2f.3d.4f.5b.6a, |
| 1a.2f.3d.4f.5b.6b, | 1a.2f.3d.4f.5b.6c, | 1a.2f.3d.4f.5b.6d, | 1a.2f.3d.4f.5b.6e, | 1a.2f.3d.4f.5b.6f, |
| 1a.2f.3d.4f.5c.6a, | 1a.2f.3d.4f.5c.6b, | 1a.2f.3d.4f.5c.6c, | 1a.2f.3d.4f.5c.6d, | 1a.2f.3d.4f.5c.6e, |
| 1a.2f.3d.4f.5c.6f, | 1a.2f.3d.4f.5d.6a, | 1a.2f.3d.4f.5d.6b, | 1a.2f.3d.4f.5d.6c, | 1a.2f.3d.4f.5d.6d, |
| 1a.2f.3d.4f.5d.6e, | 1a.2f.3d.4f.5d.6f, | 1a.2f.3d.4f.5e.6a, | 1a.2f.3d.4f.5e.6b, | 1a.2f.3d.4f.5e.6c, |
| 1a.2f.3d.4f.5e.6d, | 1a.2f.3d.4f.5e.6e, | 1a.2f.3d.4f.5e.6f, | 1a.2f.3d.4f.5f.6a, | 1a.2f.3d.4f.5f.6b, |
| 1a.2f.3d.4f.5f.6c, | 1a.2f.3d.4f.5f.6d, | 1a.2f.3d.4f.5f.6e, | 1a.2f.3d.4f.5f.6f, | 1a.2f.3e.4a.5a.6a, |
| 1a.2f.3e.4a.5a.6b, | 1a.2f.3e.4a.5a.6c, | 1a.2f.3e.4a.5a.6d, | 1a.2f.3e.4a.5a.6e, | 1a.2f.3e.4a.5a.6f, |
| 1a.2f.3e.4a.5b.6a, | 1a.2f.3e.4a.5b.6b, | 1a.2f.3e.4a.5b.6c, | 1a.2f.3e.4a.5b.6d, | |
| 1a.2f.3e.4a.5b.6e, | 1a.2f.3e.4a.5b.6f, | 1a.2f.3e.4a.5c.6a, | 1a.2f.3e.4a.5c.6b, | 1a.2f.3e.4a.5c.6c, |
| 1a.2f.3e.4a.5c.6d, | 1a.2f.3e.4a.5c.6e, | 1a.2f.3e.4a.5c.6f, | 1a.2f.3e.4a.5d.6a, | 1a.2f.3e.4a.5d.6b, |
| 1a.2f.3e.4a.5d.6c, | 1a.2f.3e.4a.5d.6d, | 1a.2f.3e.4a.5d.6e, | 1a.2f.3e.4a.5d.6f, | 1a.2f.3e.4a.5e.6a, |
| 1a.2f.3e.4a.5e.6b, | 1a.2f.3e.4a.5e.6c, | 1a.2f.3e.4a.5e.6d, | 1a.2f.3e.4a.5e.6e, | 1a.2f.3e.4a.5e.6f, |
| 1a.2f.3e.4a.5f.6a, | 1a.2f.3e.4a.5f.6b, | 1a.2f.3e.4a.5f.6c, | 1a.2f.3e.4a.5f.6d, | 1a.2f.3e.4a.5f.6e, |
| 1a.2f.3e.4a.5f.6f, | 1a.2f.3e.4b.5a.6a, | 1a.2f.3e.4b.5a.6b, | 1a.2f.3e.4b.5a.6c, | 1a.2f.3e.4b.5a.6d, |
| 1a.2f.3e.4b.5a.6e, | 1a.2f.3e.4b.5a.6f, | 1a.2f.3e.4b.5b.6a, | 1a.2f.3e.4b.5b.6b, | 1a.2f.3e.4b.5b.6c, |
| 1a.2f.3e.4b.5b.6d, | 1a.2f.3e.4b.5b.6e, | 1a.2f.3e.4b.5b.6f, | 1a.2f.3e.4b.5c.6a, | 1a.2f.3e.4b.5c.6b, |
| 1a.2f.3e.4b.5c.6c, | 1a.2f.3e.4b.5c.6d, | 1a.2f.3e.4b.5c.6e, | 1a.2f.3e.4b.5c.6f, | 1a.2f.3e.4b.5d.6a, |
| 1a.2f.3e.4b.5d.6b, | 1a.2f.3e.4b.5d.6c, | 1a.2f.3e.4b.5d.6d, | 1a.2f.3e.4b.5d.6e, | |
| 1a.2f.3e.4b.5d.6f, | 1a.2f.3e.4b.5e.6a, | 1a.2f.3e.4b.5e.6b, | 1a.2f.3e.4b.5e.6c, | 1a.2f.3e.4b.5e.6d, |
| 1a.2f.3e.4b.5e.6e, | 1a.2f.3e.4b.5e.6f, | 1a.2f.3e.4b.5f.6a, | 1a.2f.3e.4b.5f.6b, | 1a.2f.3e.4b.5f.6c, |
| 1a.2f.3e.4b.5f.6d, | 1a.2f.3e.4b.5f.6e, | 1a.2f.3e.4b.5f.6f, | 1a.2f.3e.4c.5a.6a, | 1a.2f.3e.4c.5a.6b, |
| 1a.2f.3e.4c.5a.6c, | 1a.2f.3e.4c.5a.6d, | 1a.2f.3e.4c.5a.6e, | 1a.2f.3e.4c.5a.6f, | 1a.2f.3e.4c.5b.6a, |
| 1a.2f.3e.4c.5b.6b, | 1a.2f.3e.4c.5b.6c, | 1a.2f.3e.4c.5b.6d, | 1a.2f.3e.4c.5b.6e, | 1a.2f.3e.4c.5b.6f, |
| 1a.2f.3e.4c.5c.6a, | 1a.2f.3e.4c.5c.6b, | 1a.2f.3e.4c.5c.6c, | 1a.2f.3e.4c.5c.6d, | 1a.2f.3e.4c.5c.6e, |
| 1a.2f.3e.4c.5c.6f, | 1a.2f.3e.4c.5d.6a, | 1a.2f.3e.4c.5d.6b, | 1a.2f.3e.4c.5d.6c, | 1a.2f.3e.4c.5d.6d, |
| 1a.2f.3e.4c.5d.6e, | 1a.2f.3e.4c.5d.6f, | 1a.2f.3e.4c.5e.6a, | 1a.2f.3e.4c.5e.6b, | 1a.2f.3e.4c.5e.6c, |
| 1a.2f.3e.4c.5e.6d, | 1a.2f.3e.4c.5e.6e, | 1a.2f.3e.4c.5e.6f, | 1a.2f.3e.4c.5f.6a, | 1a.2f.3e.4c.5f.6b, |
| 1a.2f.3e.4c.5f.6c, | 1a.2f.3e.4c.5f.6d, | 1a.2f.3e.4c.5f.6e, | 1a.2f.3e.4c.5f.6f, | 1a.2f.3e.4d.5a.6a, |
| 1a.2f.3e.4d.5a.6b, | 1a.2f.3e.4d.5a.6c, | 1a.2f.3e.4d.5a.6d, | 1a.2f.3e.4d.5a.6e, | |
| 1a.2f.3e.4d.5a.6f, | 1a.2f.3e.4d.5b.6a, | 1a.2f.3e.4d.5b.6b, | 1a.2f.3e.4d.5b.6c, | |
| 1a.2f.3e.4d.5b.6d, | 1a.2f.3e.4d.5b.6e, | 1a.2f.3e.4d.5b.6f, | 1a.2f.3e.4d.5c.6a, | |
| 1a.2f.3e.4d.5c.6b, | 1a.2f.3e.4d.5c.6c, | 1a.2f.3e.4d.5c.6d, | 1a.2f.3e.4d.5c.6e, | 1a.2f.3e.4d.5c.6f, |
| 1a.2f.3e.4d.5d.6a, | 1a.2f.3e.4d.5d.6b, | 1a.2f.3e.4d.5d.6c, | 1a.2f.3e.4d.5d.6d, | |
| 1a.2f.3e.4d.5d.6e, | 1a.2f.3e.4d.5d.6f, | 1a.2f.3e.4d.5e.6a, | 1a.2f.3e.4d.5e.6b, | |
| 1a.2f.3e.4d.5e.6c, | 1a.2f.3e.4d.5e.6d, | 1a.2f.3e.4d.5e.6e, | 1a.2f.3e.4d.5e.6f, | 1a.2f.3e.4d.5f.6a, |
| 1a.2f.3e.4d.5f.6b, | 1a.2f.3e.4d.5f.6c, | 1a.2f.3e.4d.5f.6d, | 1a.2f.3e.4d.5f.6e, | 1a.2f.3e.4d.5f.6f, |

TABLE 7-continued

List of Compounds of Formula (II)

| | | | | |
|---|---|---|---|---|
| 1a.2f.3e.4e.5a.6a, | 1a.2f.3e.4e.5a.6b, | 1a.2f.3e.4e.5a.6c, | 1a.2f.3e.4e.5a.6d, | 1a.2f.3e.4e.5a.6e, |
| 1a.2f.3e.4e.5a.6f, | 1a.2f.3e.4e.5b.6a, | 1a.2f.3e.4e.5b.6b, | 1a.2f.3e.4e.5b.6c, | 1a.2f.3e.4e.5b.6d, |
| 1a.2f.3e.4e.5b.6e, | 1a.2f.3e.4e.5b.6f, | 1a.2f.3e.4e.5c.6a, | 1a.2f.3e.4e.5c.6b, | 1a.2f.3e.4e.5c.6c, |
| 1a.2f.3e.4e.5c.6d, | 1a.2f.3e.4e.5c.6e, | 1a.2f.3e.4e.5c.6f, | 1a.2f.3e.4e.5d.6a, | 1a.2f.3e.4e.5d.6b, |
| 1a.2f.3e.4e.5d.6c, | 1a.2f.3e.4e.5d.6d, | 1a.2f.3e.4e.5d.6e, | 1a.2f.3e.4e.5d.6f, | 1a.2f.3e.4e.5e.6a, |
| 1a.2f.3e.4e.5e.6b, | 1a.2f.3e.4e.5e.6c, | 1a.2f.3e.4e.5e.6d, | 1a.2f.3e.4e.5e.6e, | 1a.2f.3e.4e.5e.6f, |
| 1a.2f.3e.4e.5f.6a, | 1a.2f.3e.4e.5f.6b, | 1a.2f.3e.4e.5f.6c, | 1a.2f.3e.4e.5f.6d, | 1a.2f.3e.4e.5f.6e, |
| 1a.2f.3e.4e.5f.6f, | 1a.2f.3e.4f.5a.6a, | 1a.2f.3e.4f.5a.6b, | 1a.2f.3e.4f.5a.6c, | 1a.2f.3e.4f.5a.6d, |
| 1a.2f.3e.4f.5a.6e, | 1a.2f.3e.4f.5a.6f, | 1a.2f.3e.4f.5b.6a, | 1a.2f.3e.4f.5b.6b, | 1a.2f.3e.4f.5b.6c, |
| 1a.2f.3e.4f.5b.6d, | 1a.2f.3e.4f.5b.6e, | 1a.2f.3e.4f.5b.6f, | 1a.2f.3e.4f.5c.6a, | 1a.2f.3e.4f.5c.6b, |
| 1a.2f.3e.4f.5c.6c, | 1a.2f.3e.4f.5c.6d, | 1a.2f.3e.4f.5c.6e, | 1a.2f.3e.4f.5c.6f, | 1a.2f.3e.4f.5d.6a, |
| 1a.2f.3e.4f.5d.6b, | 1a.2f.3e.4f.5d.6c, | 1a.2f.3e.4f.5d.6d, | 1a.2f.3e.4f.5d.6e, | 1a.2f.3e.4f.5d.6f, |
| 1a.2f.3e.4f.5e.6a, | 1a.2f.3e.4f.5e.6b, | 1a.2f.3e.4f.5e.6c, | 1a.2f.3e.4f.5e.6d, | 1a.2f.3e.4f.5e.6e, |
| 1a.2f.3e.4f.5e.6f, | 1a.2f.3e.4f.5f.6a, | 1a.2f.3e.4f.5f.6b, | 1a.2f.3e.4f.5f.6c, | 1a.2f.3e.4f.5f.6d, |
| 1a.2f.3e.4f.5f.6e, | 1a.2f.3e.4f.5f.6f, | 1a.2f.3f.4a.5a.6a, | 1a.2f.3f.4a.5a.6b, | 1a.2f.3f.4a.5a.6c, |
| 1a.2f.3f.4a.5a.6d, | 1a.2f.3f.4a.5a.6e, | 1a.2f.3f.4a.5a.6f, | 1a.2f.3f.4a.5b.6a, | 1a.2f.3f.4a.5b.6b, |
| 1a.2f.3f.4a.5b.6c, | 1a.2f.3f.4a.5b.6d, | 1a.2f.3f.4a.5b.6e, | 1a.2f.3f.4a.5b.6f, | 1a.2f.314a.5c.6a, |
| 1a.2f.3f.4a.5c.6b, | 1a.2f.3f.4a.5c.6c, | 1a.2f.3f.4a.5c.6d, | 1a.2f.3f.4a.5c.6e, | 1a.2f.3f.4a.5c.6f, |
| 1a.2f.3f.4a.5d.6a, | 1a.2f.3f.4a.5d.6b, | 1a.2f.3f.4a.5d.6c, | 1a.2f.3f.4a.5d.6d, | 1a.2f.3f.4a.5d.6e, |
| 1a.2f.3f.4a.5d.6f, | 1a.2f.3f.4a.5e.6a, | 1a.2f.3f.4a.5e.6b, | 1a.2f.3f.4a.5e.6c, | 1a.2f.3f.4a.5e.6d, |
| 1a.2f.3f.4a.5e.6e, | 1a.2f.3f.4a.5e.6f, | 1a.2f.3f.4a.5f.6a, | 1a.2f.3f.4a.5f.6b, | 1a.2f.3f.4a.5f.6c, |
| 1a.2f.3f.4a.5f.6d, | 1a.2f.3f.4a.5f.6e, | 1a.2f.3f.4a.5f.6f, | 1a.2f.3f.4b.5a.6a, | 1a.2f.3f.4b.5a.6b, |
| 1a.2f.3f.4b.5a.6c, | 1a.2f.3f.4b.5a.6d, | 1a.2f.3f.4b.5a.6e, | 1a.2f.3f.4b.5a.6f, | 1a.2f.3f.4b.5b.6a, |
| 1a.2f.3f.4b.5b.6b, | 1a.2f.3f.4b.5b.6c, | 1a.2f.3f.4b.5b.6d, | 1a.2f.3f.4b.5b.6e, | 1a.2f.3f.4b.5b.6f, |
| 1a.2f.3f.4b.5c.6a, | 1a.2f.3f.4b.5c.6b, | 1a.2f.3f.4b.5c.6c, | 1a.2f.3f.4b.5c.6d, | 1a.2f.3f.4b.5c.6e, |
| 1a.2f.3f.4b.5c.6f, | 1a.2f.3f.4b.5d.6a, | 1a.2f.3f.4b.5d.6b, | 1a.2f.3f.4b.5d.6c, | 1a.2f.3f.4b.5d.6d, |
| 1a.2f.3f.4b.5d.6e, | 1a.2f.3f.4b.5d.6f, | 1a.2f.3f.4b.5e.6a, | 1a.2f.3f.4b.5e.6b, | 1a.2f.3f.4b.5e.6c, |
| 1a.2f.3f.4b.5e.6d, | 1a.2f.3f.4b.5e.6e, | 1a.2f.3f.4b.5e.6f, | 1a.2f.3f.4b.5f.6a, | 1a.2f.3f.4b.5f.6b, |
| 1a.2f.3f.4b.5f.6c, | 1a.2f.3f.4b.5f.6d, | 1a.2f.3f.4b.5f.6e, | 1a.2f.3f.4b.5f.6f, | 1a.2f.3f.4c.5a.6a, |
| 1a.2f.3f.4c.5a.6b, | 1a.2f.3f.4c.5a.6c, | 1a.2f.3f.4c.5a.6d, | 1a.2f.3f.4c.5a.6e, | 1a.2f.3f.4c.5a.6f, |
| 1a.2f.3f.4c.5b.6a, | 1a.2f.3f.4c.5b.6b, | 1a.2f.3f.4c.5b.6c, | 1a.2f.3f.4c.5b.6d, | 1a.2f.3f.4c.5b.6e, |
| 1a.2f.3f.4c.5b.6f, | 1a.2f.3f.4c.5c.6a, | 1a.2f.3f.4c.5c.6b, | 1a.2f.3f.4c.5c.6c, | 1a.2f.3f.4c.5c.6d, |
| 1a.2f.3f.4c.5c.6e, | 1a.2f.3f.4c.5c.6f, | 1a.2f.3f.4c.5d.6a, | 1a.2f.3f.4c.5d.6b, | 1a.2f.3f.4c.5d.6c, |
| 1a.2f.3f.4c.5d.6d, | 1a.2f.3f.4c.5d.6e, | 1a.2f.3f.4c.5d.6f, | 1a.2f.3f.4c.5e.6a, | 1a.2f.3f.4c.5e.6b, |
| 1a.2f.3f.4c.5e.6c, | 1a.2f.3f.4c.5e.6d, | 1a.2f.3f.4c.5e.6e, | 1a.2f.3f.4c.5e.6f, | 1a.2f.3f.4c.5f.6a, |
| 1a.2f.3f.4c.5f.6b, | 1a.2f.3f.4c.5f.6c, | 1a.2f.3f.4c.5f.6d, | 1a.2f.3f.4c.5f.6e, | 1a.2f.3f.4c.5f.6f, |
| 1a.2f.3f.4d.5a.6a, | 1a.2f.3f.4d.5a.6b, | 1a.2f.3f.4d.5a.6c, | 1a.2f.3f.4d.5a.6d, | 1a.2f.3f.4d.5a.6e, |
| 1a.2f.3f.4d.5a.6f, | 1a.2f.3f.4d.5b.6a, | 1a.2f.3f.4d.5b.6b, | 1a.2f.3f.4d.5b.6c, | 1a.2f.3f.4d.5b.6d, |
| 1a.2f.3f.4d.5b.6e, | 1a.2f.3f.4d.5b.6f, | 1a.2f.3f.4d.5c.6a, | 1a.2f.3f.4d.5c.6b, | 1a.2f.3f.4d.5c.6c, |
| 1a.2f.3f.4d.5c.6d, | 1a.2f.3f.4d.5c.6e, | 1a.2f.3f.4d.5c.6f, | 1a.2f.3f.4d.5d.6a, | 1a.2f.3f.4d.5d.6b, |
| 1a.2f.3f.4d.5d.6c, | 1a.2f.3f.4d.5d.6d, | 1a.2f.3f.4d.5d.6e, | 1a.2f.3f.4d.5d.6f, | 1a.2f.3f.4d.5e.6a, |
| 1a.2f.3f.4d.5e.6b, | 1a.2f.3f.4d.5e.6c, | 1a.2f.3f.4d.5e.6d, | 1a.2f.3f.4d.5e.6e, | 1a.2f.3f.4d.5e.6f, |
| 1a.2f.3f.4d.5f.6a, | 1a.2f.3f.4d.5f.6b, | 1a.2f.3f.4d.5f.6c, | 1a.2f.3f.4d.5f.6d, | 1a.2f.3f.4d.5f.6e, |
| 1a.2f.3f.4d.5f.6f, | 1a.2f.3f.4e.5a.6a, | 1a.2f.3f.4e.5a.6b, | 1a.2f.3f.4e.5a.6c, | 1a.2f.3f.4e.5a.6d, |
| 1a.2f.3f.4e.5a.6e, | 1a.2f.3f.4e.5a.6f, | 1a.2f.3f.4e.5b.6a, | 1a.2f.3f.4e.5b.6b, | 1a.2f.3f.4e.5b.6c, |
| 1a.2f.3f.4e.5b.6d, | 1a.2f.3f.4e.5b.6e, | 1a.2f.3f.4e.5b.6f, | 1a.2f.3f.4e.5c.6a, | 1a.2f.3f.4e.5c.6b, |
| 1a.2f.3f.4e.5c.6c, | 1a.2f.3f.4e.5c.6d, | 1a.2f.3f.4e.5c.6e, | 1a.2f.3f.4e.5c.6f, | 1a.2f.3f.4e.5d.6a, |
| 1a.2f.3f.4e.5d.6b, | 1a.2f.3f.4e.5d.6c, | 1a.2f.3f.4e.5d.6d, | 1a.2f.3f.4e.5d.6e, | 1a.2f.3f.4e.5d.6f, |
| 1a.2f.3f.4e.5e.6a, | 1a.2f.3f.4e.5e.6b, | 1a.2f.3f.4e.5e.6c, | 1a.2f.3f.4e.5e.6d, | 1a.2f.3f.4e.5e.6e, |
| 1a.2f.3f.4e.5e.6f, | 1a.2f.3f.4e.5f.6a, | 1a.2f.3f.4e.5f.6b, | 1a.2f.3f.4e.5f.6c, | 1a.2f.3f.4e.5f.6d, |
| 1a.2f.3f.4e.5f.6e, | 1a.2f.3f.4e.5f.6f, | 1a.2f.3f.4f.5a.6a, | 1a.2f.3f.4f.5a.6b, | 1a.2f.3f.4f.5a.6c, |
| 1a.2f.3f.4f.5a.6d, | 1a.2f.3f.4f.5a.6e, | 1a.2f.3f.4f.5a.6f, | 1a.2f.3f.4f.5b.6a, | 1a.2f.3f.4f.5b.6b, |
| 1a.2f.3f.4f.5b.6c, | 1a.2f.3f.4f.5b.6d, | 1a.2f.3f.4f.5b.6e, | 1a.2f.3f.4f.5b.6f, | 1a.2f.3f.4f.5c.6a, |
| 1a.2f.3f.4f.5c.6b, | 1a.2f.3f.4f.5c.6c, | 1a.2f.3f.4f.5c.6d, | 1a.2f.3f.4f.5c.6e, | 1a.2f.3f.4f.5c.6f, |
| 1a.2f.3f.4f.5d.6a, | 1a.2f.3f.4f.5d.6b, | 1a.2f.3f.4f.5d.6c, | 1a.2f.3f.4f.5d.6d, | 1a.2f.3f.4f.5d.6e, |
| 1a.2f.3f.4f.5d.6f, | 1a.2f.3f.4f.5e.6a, | 1a.2f.3f.4f.5e.6b, | 1a.2f.3f.4f.5e.6c, | 1a.2f.3f.4f.5e.6d, |
| 1a.2f.3f.4f.5e.6e, | 1a.2f.3f.4f.5e.6f, | 1a.2f.3f.4f.5f.6a, | 1a.2f.3f.4f.5f.6b, | 1a.2f.3f.4f.5f.6c, |
| 1a.2f.3f.4f.5f.6d, | 1a.2f.3f.4f.5f.6e, | 1a.2f.3f.4f.5f.6f, | 1b.2a.3a.4a.5a.6a, | 1b.2a.3a.4a.5a.6b, |
| 1b.2a.3a.4a.5a.6c, | 1b.2a.3a.4a.5a.6d, | 1b.2a.3a.4a.5a.6e, | 1b.2a.3a.4a.5a.6f, | |
| 1b.2a.3a.4a.5b.6a, | 1b.2a.3a.4a.5b.6b, | 1b.2a.3a.4a.5b.6c, | 1b.2a.3a.4a.5b.6d, | |
| 1b.2a.3a.4a.5b.6e, | 1b.2a.3a.4a.5b.6f, | 1b.2a.3a.4a.5c.6a, | 1b.2a.3a.4a.5c.6b, | |
| 1b.2a.3a.4a.5c.6c, | 1b.2a.3a.4a.5c.6d, | 1b.2a.3a.4a.5c.6e, | 1b.2a.3a.4a.5c.6f, | |
| 1b.2a.3a.4a.5d.6a, | 1b.2a.3a.4a.5d.6b, | 1b.2a.3a.4a.5d.6c, | 1b.2a.3a.4a.5d.6d, | |
| 1b.2a.3a.4a.5d.6e, | 1b.2a.3a.4a.5d.6f, | 1b.2a.3a.4a.5e.6a, | 1b.2a.3a.4a.5e.6b, | |
| 1b.2a.3a.4a.5e.6c, | 1b.2a.3a.4a.5e.6d, | 1b.2a.3a.4a.5e.6e, | 1b.2a.3a.4a.5e.6f, | |
| 1b.2a.3a.4a.5f.6a, | 1b.2a.3a.4a.5f.6b, | 1b.2a.3a.4a.5f.6c, | 1b.2a.3a.4a.5f.6d, | |
| 1b.2a.3a.4a.5f.6e, | 1b.2a.3a.4a.5f.6f, | 1b.2a.3a.4b.5a.6a, | 1b.2a.3a.4b.5a.6b, | |
| 1b.2a.3a.4b.5a.6c, | 1b.2a.3a.4b.5a.6d, | 1b.2a.3a.4b.5a.6e, | 1b.2a.3a.4b.5a.6f, | |
| 1b.2a.3a.4b.5b.6a, | 1b.2a.3a.4b.5b.6b, | 1b.2a.3a.4b.5b.6c, | 1b.2a.3a.4b.5b.6d, | |
| 1b.2a.3a.4b.5b.6e, | 1b.2a.3a.4b.5b.6f, | 1b.2a.3a.4b.5c.6a, | 1b.2a.3a.4b.5c.6b, | |
| 1b.2a.3a.4b.5c.6c, | 1b.2a.3a.4b.5c.6d, | 1b.2a.3a.4b.5c.6e, | 1b.2a.3a.4b.5c.6f, | |
| 1b.2a.3a.4b.5d.6a, | 1b.2a.3a.4b.5d.6b, | 1b.2a.3a.4b.5d.6c, | 1b.2a.3a.4b.5d.6d, | |
| 1b.2a.3a.4b.5d.6e, | 1b.2a.3a.4b.5d.6f, | 1b.2a.3a.4b.5e.6a, | 1b.2a.3a.4b.5e.6b, | |
| 1b.2a.3a.4b.5e.6c, | 1b.2a.3a.4b.5e.6d, | 1b.2a.3a.4b.5e.6e, | 1b.2a.3a.4b.5e.6f, | |
| 1b.2a.3a.4b.5f.6a, | 1b.2a.3a.4b.5f.6b, | 1b.2a.3a.4b.5f.6c, | 1b.2a.3a.4b.5f.6d, | |
| 1b.2a.3a.4b.5f.6e, | 1b.2a.3a.4b.5f.6f, | 1b.2a.3a.4c.5a.6a, | 1b.2a.3a.4c.5a.6b, | |
| 1b.2a.3a.4c.5a.6c, | 1b.2a.3a.4c.5a.6d, | 1b.2a.3a.4c.5a.6e, | 1b.2a.3a.4c.5a.6f, | |
| 1b.2a.3a.4c.5b.6a, | 1b.2a.3a.4c.5b.6b, | 1b.2a.3a.4c.5b.6c, | 1b.2a.3a.4c.5b.6d, | |

TABLE 7-continued

List of Compounds of Formula (II)

| | | | | |
|---|---|---|---|---|
| 1b.2a.3a.4c.5b.6e, | 1b.2a.3a.4c.5b.6f, | 1b.2a.3a.4c.5c.6a, | 1b.2a.3a.4c.5c.6b, | |
| 1b.2a.3a.4c.5c.6c, | 1b.2a.3a.4c.5c.6d, | 1b.2a.3a.4c.5c.6e, | 1b.2a.3a.4c.5c.6f, | |
| 1b.2a.3a.4c.5d.6a, | 1b.2a.3a.4c.5d.6b, | 1b.2a.3a.4c.5d.6c, | 1b.2a.3a.4c.5d.6d, | |
| 1b.2a.3a.4c.5d.6e, | 1b.2a.3a.4c.5d.6f, | 1b.2a.3a.4c.5e.6a, | 1b.2a.3a.4c.5e.6b, | |
| 1b.2a.3a.4c.5e.6c, | 1b.2a.3a.4c.5e.6d, | 1b.2a.3a.4c.5e.6e, | 1b.2a.3a.4c.5e.6f, | |
| 1b.2a.3a.4c.5f.6a, | 1b.2a.3a.4c.5f.6b, | 1b.2a.3a.4c.5f.6c, | 1b.2a.3a.4c.5f.6d, | 1b.2a.3a.4c.5f.6e, |
| 1b.2a.3a.4c.5f.6f, | 1b.2a.3a.4d.5a.6a, | 1b.2a.3a.4d.5a.6b, | 1b.2a.3a.4d.5a.6c, | |
| 1b.2a.3a.4d.5a.6d, | 1b.2a.3a.4d.5a.6e, | 1b.2a.3a.4d.5a.6f, | 1b.2a.3a.4d.5b.6a, | |
| 1b.2a.3a.4d.5b.6b, | 1b.2a.3a.4d.5b.6c, | 1b.2a.3a.4d.5b.6d, | 1b.2a.3a.4d.5b.6e, | |
| 1b.2a.3a.4d.5b.6f, | 1b.2a.3a.4d.5c.6a, | 1b.2a.3a.4d.5c.6b, | 1b.2a.3a.4d.5c.6c, | |
| 1b.2a.3a.4d.5c.6d, | 1b.2a.3a.4d.5c.6e, | 1b.2a.3a.4d.5c.6f, | 1b.2a.3a.4d.5d.6a, | |
| 1b.2a.3a.4d.5d.6b, | 1b.2a.3a.4d.5d.6c, | 1b.2a.3a.4d.5d.6d, | 1b.2a.3a.4d.5d.6e, | |
| 1b.2a.3a.4d.5d.6f, | 1b.2a.3a.4d.5e.6a, | 1b.2a.3a.4d.5e.6b, | 1b.2a.3a.4d.5e.6c, | |
| 1b.2a.3a.4d.5e.6d, | 1b.2a.3a.4d.5e.6e, | 1b.2a.3a.4d.5e.6f, | 1b.2a.3a.4d.5f.6a, | |
| 1b.2a.3a.4d.5f.6b, | 1b.2a.3a.4d.5f.6c, | 1b.2a.3a.4d.5f.6d, | 1b.2a.3a.4d.5f.6e, | |
| 1b.2a.3a.4d.5f.6f, | 1b.2a.3a.4e.5a.6a, | 1b.2a.3a.4e.5a.6b, | 1b.2a.3a.4e.5a.6c, | |
| 1b.2a.3a.4e.5a.6d, | 1b.2a.3a.4e.5a.6e, | 1b.2a.3a.4e.5a.6f, | 1b.2a.3a.4e.5b.6a, | |
| 1b.2a.3a.4e.5b.6b, | 1b.2a.3a.4e.5b.6c, | 1b.2a.3a.4e.5b.6d, | 1b.2a.3a.4e.5b.6e, | |
| 1b.2a.3a.4e.5b.6f, | 1b.2a.3a.4e.5c.6a, | 1b.2a.3a.4e.5c.6b, | 1b.2a.3a.4e.5c.6c, | |
| 1b.2a.3a.4e.5c.6d, | 1b.2a.3a.4e.5c.6e, | 1b.2a.3a.4e.5c.6f, | 1b.2a.3a.4e.5d.6a, | |
| 1b.2a.3a.4e.5d.6b, | 1b.2a.3a.4e.5d.6c, | 1b.2a.3a.4e.5d.6d, | 1b.2a.3a.4e.5d.6e, | |
| 1b.2a.3a.4e.5d.6f, | 1b.2a.3a.4e.5e.6a, | 1b.2a.3a.4e.5e.6b, | 1b.2a.3a.4e.5e.6c, | |
| 1b.2a.3a.4e.5e.6d, | 1b.2a.3a.4e.5e.6e, | 1b.2a.3a.4e.5e.6f, | 1b.2a.3a.4e.5f.6a, | |
| 1b.2a.3a.4e.5f.6b, | 1b.2a.3a.4e.5f.6c, | 1b.2a.3a.4e.5f.6d, | 1b.2a.3a.4e.5f.6e, | 1b.2a.3a.4e.5f.6f, |
| 1b.2a.3a.4f.5a.6a, | 1b.2a.3a.4f.5a.6b, | 1b.2a.3a.4f.5a.6c, | 1b.2a.3a.4f.5a.6d, | |
| 1b.2a.3a.4f.5a.6e, | 1b.2a.3a.4f.5a.6f, | 1b.2a.3a.4f.5b.6a, | 1b.2a.3a.4f.5b.6b, | |
| 1b.2a.3a.4f.5b.6c, | 1b.2a.3a.4f.5b.6d, | 1b.2a.3a.4f.5b.6e, | 1b.2a.3a.4f.5b.6f, | |
| 1b.2a.3a.4f.5c.6a, | 1b.2a.3a.4f.5c.6b, | 1b.2a.3a.4f.5c.6c, | 1b.2a.3a.4f.5c.6d, | 1b.2a.3a.4f.5c.6e, |
| 1b.2a.3a.4f.5c.6f, | 1b.2a.3a.4f.5d.6a, | 1b.2a.3a.4f.5d.6b, | 1b.2a.3a.4f.5d.6c, | |
| 1b.2a.3a.4f.5d.6d, | 1b.2a.3a.4f.5d.6e, | 1b.2a.3a.4f.5d.6f, | 1b.2a.3a.4f.5e.6a, | |
| 1b.2a.3a.4f.5e.6b, | 1b.2a.3a.4f.5e.6c, | 1b.2a.3a.4f.5e.6d, | 1b.2a.3a.4f.5e.6e, | 1b.2a.3a.4f.5e.6f, |
| 1b.2a.3a.4f.5f.6a, | 1b.2a.3a.4f.5f.6b, | 1b.2a.3a.4f.5f.6c, | 1b.2a.3a.4f.5f.6d, | 1b.2a.3a.4f.5f.6e, |
| 1b.2a.3a.4f.5f.6f, | 1b.2a.3b.4a.5a.6a, | 1b.2a.3b.4a.5a.6b, | 1b.2a.3b.4a.5a.6c, | |
| 1b.2a.3b.4a.5a.6d, | 1b.2a.3b.4a.5a.6e, | 1b.2a.3b.4a.5a.6f, | 1b.2a.3b.4a.5b.6a, | |
| 1b.2a.3b.4a.5b.6b, | 1b.2a.3b.4a.5b.6c, | 1b.2a.3b.4a.5b.6d, | 1b.2a.3b.4a.5b.6e, | |
| 1b.2a.3b.4a.5b.6f, | 1b.2a.3b.4a.5c.6a, | 1b.2a.3b.4a.5c.6b, | 1b.2a.3b.4a.5c.6c, | |
| 1b.2a.3b.4a.5c.6d, | 1b.2a.3b.4a.5c.6e, | 1b.2a.3b.4a.5c.6f, | 1b.2a.3b.4a.5d.6a, | |
| 1b.2a.3b.4a.5d.6b, | 1b.2a.3b.4a.5d.6c, | 1b.2a.3b.4a.5d.6d, | 1b.2a.3b.4a.5d.6e, | |
| 1b.2a.3b.4a.5d.6f, | 1b.2a.3b.4a.5e.6a, | 1b.2a.3b.4a.5e.6b, | 1b.2a.3b.4a.5e.6c, | |
| 1b.2a.3b.4a.5e.6d, | 1b.2a.3b.4a.5e.6e, | 1b.2a.3b.4a.5e.6f, | 1b.2a.3b.4a.5f.6a, | |
| 1b.2a.3b.4a.5f.6b, | 1b.2a.3b.4a.5f.6c, | 1b.2a.3b.4a.5f.6d, | 1b.2a.3b.4a.5f.6e, | |
| 1b.2a.3b.4a.5f.6f, | 1b.2a.3b.4b.5a.6a, | 1b.2a.3b.4b.5a.6b, | 1b.2a.3b.4b.5a.6c, | |
| 1b.2a.3b.4b.5a.6d, | 1b.2a.3b.4b.5a.6e, | 1b.2a.3b.4b.5a.6f, | 1b.2a.3b.4b.5b.6a, | |
| 1b.2a.3b.4b.5b.6b, | 1b.2a.3b.4b.5b.6c, | 1b.2a.3b.4b.5b.6d, | 1b.2a.3b.4b.5b.6e, | |
| 1b.2a.3b.4b.5b.6f, | 1b.2a.3b.4b.5c.6a, | 1b.2a.3b.4b.5c.6b, | 1b.2a.3b.4b.5c.6c, | |
| 1b.2a.3b.4b.5c.6d, | 1b.2a.3b.4b.5c.6e, | 1b.2a.3b.4b.5c.6f, | 1b.2a.3b.4b.5d.6a, | |
| 1b.2a.3b.4b.5d.6b, | 1b.2a.3b.4b.5d.6c, | 1b.2a.3b.4b.5d.6d, | 1b.2a.3b.4b.5d.6e, | |
| 1b.2a.3b.4b.5d.6f, | 1b.2a.3b.4b.5e.6a, | 1b.2a.3b.4b.5e.6b, | 1b.2a.3b.4b.5e.6c, | |
| 1b.2a.3b.4b.5e.6d, | 1b.2a.3b.4b.5e.6e, | 1b.2a.3b.4b.5e.6f, | 1b.2a.3b.4b.5f.6a, | |
| 1b.2a.3b.4b.5f.6b, | 1b.2a.3b.4b.5f.6c, | 1b.2a.3b.4b.5f.6d, | 1b.2a.3b.4b.5f.6e, | |
| 1b.2a.3b.4b.5f.6f, | 1b.2a.3b.4c.5a.6a, | 1b.2a.3b.4c.5a.6b, | 1b.2a.3b.4c.5a.6c, | |
| 1b.2a.3b.4c.5a.6d, | 1b.2a.3b.4c.5a.6e, | 1b.2a.3b.4c.5a.6f, | 1b.2a.3b.4c.5b.6a, | |
| 1b.2a.3b.4c.5b.6b, | 1b.2a.3b.4c.5b.6c, | 1b.2a.3b.4c.5b.6d, | 1b.2a.3b.4c.5b.6e, | |
| 1b.2a.3b.4c.5b.6f, | 1b.2a.3b.4c.5c.6a, | 1b.2a.3b.4c.5c.6b, | 1b.2a.3b.4c.5c.6c, | |
| 1b.2a.3b.4c.5c.6d, | 1b.2a.3b.4c.5c.6e, | 1b.2a.3b.4c.5c.6f, | 1b.2a.3b.4c.5d.6a, | |
| 1b.2a.3b.4c.5d.6b, | 1b.2a.3b.4c.5d.6c, | 1b.2a.3b.4c.5d.6d, | 1b.2a.3b.4c.5d.6e, | |
| 1b.2a.3b.4c.5d.6f, | 1b.2a.3b.4c.5e.6a, | 1b.2a.3b.4c.5e.6b, | 1b.2a.3b.4c.5e.6c, | |
| 1b.2a.3b.4c.5e.6d, | 1b.2a.3b.4c.5e.6e, | 1b.2a.3b.4c.5e.6f, | 1b.2a.3b.4c.5f.6a, | |
| 1b.2a.3b.4c.5f.6b, | 1b.2a.3b.4c.5f.6c, | 1b.2a.3b.4c.5f.6d, | 1b.2a.3b.4c.5f.6e, | 1b.2a.3b.4c.5f.6f, |
| 1b.2a.3b.4d.5a.6a, | 1b.2a.3b.4d.5a.6b, | 1b.2a.3b.4d.5a.6c, | 1b.2a.3b.4d.5a.6d, | |
| 1b.2a.3b.4d.5a.6e, | 1b.2a.3b.4d.5a.6f, | 1b.2a.3b.4d.5b.6a, | 1b.2a.3b.4d.5b.6b, | |
| 1b.2a.3b.4d.5b.6c, | 1b.2a.3b.4d.5b.6d, | 1b.2a.3b.4d.5b.6e, | 1b.2a.3b.4d.5b.6f, | |
| 1b.2a.3b.4d.5c.6a, | 1b.2a.3b.4d.5c.6b, | 1b.2a.3b.4d.5c.6c, | 1b.2a.3b.4d.5c.6d, | |
| 1b.2a.3b.4d.5c.6e, | 1b.2a.3b.4d.5c.6f, | 1b.2a.3b.4d.5d.6a, | 1b.2a.3b.4d.5d.6b, | |
| 1b.2a.3b.4d.5d.6c, | 1b.2a.3b.4d.5d.6d, | 1b.2a.3b.4d.5d.6e, | 1b.2a.3b.4d.5d.6f, | |
| 1b.2a.3b.4d.5e.6a, | 1b.2a.3b.4d.5e.6b, | 1b.2a.3b.4d.5e.6c, | 1b.2a.3b.4d.5e.6d, | |
| 1b.2a.3b.4d.5e.6e, | 1b.2a.3b.4d.5e.6f, | 1b.2a.3b.4d.5f.6a, | 1b.2a.3b.4d.5f.6b, | |
| 1b.2a.3b.4d.5f.6c, | 1b.2a.3b.4d.5f.6d, | 1b.2a.3b.4d.5f.6e, | 1b.2a.3b.4d.5f.6f, | |
| 1b.2a.3b.4e.5a.6a, | 1b.2a.3b.4e.5a.6b, | 1b.2a.3b.4e.5a.6c, | 1b.2a.3b.4e.5a.6d, | |
| 1b.2a.3b.4e.5a.6e, | 1b.2a.3b.4e.5a.6f, | 1b.2a.3b.4e.5b.6a, | 1b.2a.3b.4e.5b.6b, | |
| 1b.2a.3b.4e.5b.6c, | 1b.2a.3b.4e.5b.6d, | 1b.2a.3b.4e.5b.6e, | 1b.2a.3b.4e.5b.6f, | |
| 1b.2a.3b.4e.5c.6a, | 1b.2a.3b.4e.5c.6b, | 1b.2a.3b.4e.5c.6c, | 1b.2a.3b.4e.5c.6d, | |
| 1b.2a.3b.4e.5c.6e, | 1b.2a.3b.4e.5c.6f, | 1b.2a.3b.4e.5d.6a, | 1b.2a.3b.4e.5d.6b, | |
| 1b.2a.3b.4e.5d.6c, | 1b.2a.3b.4e.5d.6d, | 1b.2a.3b.4e.5d.6e, | 1b.2a.3b.4e.5d.6f, | |
| 1b.2a.3b.4e.5e.6a, | 1b.2a.3b.4e.5e.6b, | 1b.2a.3b.4e.5e.6c, | 1b.2a.3b.4e.5e.6d, | |
| 1b.2a.3b.4e.5e.6e, | 1b.2a.3b.4e.5e.6f, | 1b.2a.3b.4e.5f.6a, | 1b.2a.3b.4e.5f.6b, | |
| 1b.2a.3b.4e.5f.6c, | 1b.2a.3b.4e.5f.6d, | 1b.2a.3b.4e.5f.6e, | 1b.2a.3b.4e.5f.6f, | |
| 1b.2a.3b.4f.5a.6a, | 1b.2a.3b.4f.5a.6b, | 1b.2a.3b.4f.5a.6c, | 1b.2a.3b.4f.5a.6d, | |

TABLE 7-continued

List of Compounds of Formula (II)

| | | | | |
|---|---|---|---|---|
| 1b.2a.3b.4f.5a.6e, | 1b.2a.3b.4f.5a.6f, | 1b.2a.3b.4f.5b.6a, | 1b.2a.3b.4f.5b.6b, | |
| 1b.2a.3b.4f.5b.6c, | 1b.2a.3b.4f.5b.6d, | 1b.2a.3b.4f.5b.6e, | 1b.2a.3b.4f.5b.6f, | |
| 1b.2a.3b.4f.5c.6a, | 1b.2a.3b.4f.5c.6b, | 1b.2a.3b.4f.5c.6c, | 1b.2a.3b.4f.5c.6d, | |
| 1b.2a.3b.4f.5c.6e, | 1b.2a.3b.4f.5c.6f, | 1b.2a.3b.4f.5d.6a, | 1b.2a.3b.4f.5d.6b, | |
| 1b.2a.3b.4f.5d.6c, | 1b.2a.3b.4f.5d.6d, | 1b.2a.3b.4f.5d.6e, | 1b.2a.3b.4f.5d.6f, | |
| 1b.2a.3b.4f.5e.6a, | 1b.2a.3b.4f.5e.6b, | 1b.2a.3b.4f.5e.6c, | 1b.2a.3b.4f.5e.6d, | |
| 1b.2a.3b.4f.5e.6e, | 1b.2a.3b.4f.5e.6f, | 1b.2a.3b.4f.5f.6a, | 1b.2a.3b.4f.5f.6b, | 1b.2a.3b.4f.5f.6c, |
| 1b.2a.3b.4f.5f.6d, | 1b.2a.3b.4f.5f.6e, | 1b.2a.3b.4f.5f.6f, | 1b.2a.3c.4a.5a.6a, | 1b.2a.3c.4a.5a.6b, |
| 1b.2a.3c.4a.5a.6c, | 1b.2a.3c.4a.5a.6d, | 1b.2a.3c.4a.5a.6e, | 1b.2a.3c.4a.5a.6f, | |
| 1b.2a.3c.4a.5b.6a, | 1b.2a.3c.4a.5b.6b, | 1b.2a.3c.4a.5b.6c, | 1b.2a.3c.4a.5b.6d, | |
| 1b.2a.3c.4a.5b.6e, | 1b.2a.3c.4a.5b.6f, | 1b.2a.3c.4a.5c.6a, | 1b.2a.3c.4a.5c.6b, | |
| 1b.2a.3c.4a.5c.6c, | 1b.2a.3c.4a.5c.6d, | 1b.2a.3c.4a.5c.6e, | 1b.2a.3c.4a.5c.6f, | |
| 1b.2a.3c.4a.5d.6a, | 1b.2a.3c.4a.5d.6b, | 1b.2a.3c.4a.5d.6c, | 1b.2a.3c.4a.5d.6d, | |
| 1b.2a.3c.4a.5d.6e, | 1b.2a.3c.4a.5d.6f, | 1b.2a.3c.4a.5e.6a, | 1b.2a.3c.4a.5e.6b, | |
| 1b.2a.3c.4a.5e.6c, | 1b.2a.3c.4a.5e.6d, | 1b.2a.3c.4a.5e.6e, | 1b.2a.3c.4a.5e.6f, | |
| 1b.2a.3c.4a.5f.6a, | 1b.2a.3c.4a.5f.6b, | 1b.2a.3c.4a.5f.6c, | 1b.2a.3c.4a.5f.6d, | 1b.2a.3c.4a.5f.6e, |
| 1b.2a.3c.4a.5f.6f, | 1b.2a.3c.4b.5a.6a, | 1b.2a.3c.4b.5a.6b, | 1b.2a.3c.4b.5a.6c, | |
| 1b.2a.3c.4b.5a.6d, | 1b.2a.3c.4b.5a.6e, | 1b.2a.3c.4b.5a.6f, | 1b.2a.3c.4b.5b.6a, | |
| 1b.2a.3c.4b.5b.6b, | 1b.2a.3c.4b.5b.6c, | 1b.2a.3c.4b.5b.6d, | 1b.2a.3c.4b.5b.6e, | |
| 1b.2a.3c.4b.5b.6f, | 1b.2a.3c.4b.5c.6a, | 1b.2a.3c.4b.5c.6b, | 1b.2a.3c.4b.5c.6c, | |
| 1b.2a.3c.4b.5c.6d, | 1b.2a.3c.4b.5c.6e, | 1b.2a.3c.4b.5c.6f, | 1b.2a.3c.4b.5d.6a, | |
| 1b.2a.3c.4b.5d.6b, | 1b.2a.3c.4b.5d.6c, | 1b.2a.3c.4b.5d.6d, | 1b.2a.3c.4b.5d.6e, | |
| 1b.2a.3c.4b.5d.6f, | 1b.2a.3c.4b.5e.6a, | 1b.2a.3c.4b.5e.6b, | 1b.2a.3c.4b.5e.6c, | |
| 1b.2a.3c.4b.5e.6d, | 1b.2a.3c.4b.5e.6e, | 1b.2a.3c.4b.5e.6f, | 1b.2a.3c.4b.5f.6a, | |
| 1b.2a.3c.4b.5f.6b, | 1b.2a.3c.4b.5f.6c, | 1b.2a.3c.4b.5f.6d, | 1b.2a.3c.4b.5f.6e, | 1b.2a.3c.4b.5f.6f, |
| 1b.2a.3c.4c.5a.6a, | 1b.2a.3c.4c.5a.6b, | 1b.2a.3c.4c.5a.6c, | 1b.2a.3c.4c.5a.6d, | |
| 1b.2a.3c.4c.5a.6e, | 1b.2a.3c.4c.5a.6f, | 1b.2a.3c.4c.5b.6a, | 1b.2a.3c.4c.5b.6b, | |
| 1b.2a.3c.4c.5b.6c, | 1b.2a.3c.4c.5b.6d, | 1b.2a.3c.4c.5b.6e, | 1b.2a.3c.4c.5b.6f, | |
| 1b.2a.3c.4c.5c.6a, | 1b.2a.3c.4c.5c.6b, | 1b.2a.3c.4c.5c.6c, | 1b.2a.3c.4c.5c.6d, | |
| 1b.2a.3c.4c.5c.6e, | 1b.2a.3c.4c.5c.6f, | 1b.2a.3c.4c.5d.6a, | 1b.2a.3c.4c.5d.6b, | |
| 1b.2a.3c.4c.5d.6c, | 1b.2a.3c.4c.5d.6d, | 1b.2a.3c.4c.5d.6e, | 1b.2a.3c.4c.5d.6f, | |
| 1b.2a.3c.4c.5e.6a, | 1b.2a.3c.4c.5e.6b, | 1b.2a.3c.4c.5e.6c, | 1b.2a.3c.4c.5e.6d, | |
| 1b.2a.3c.4c.5e.6e, | 1b.2a.3c.4c.5e.6f, | 1b.2a.3c.4c.5f.6a, | 1b.2a.3c.4c.5f.6b, | 1b.2a.3c.4c.5f.6c, |
| 1b.2a.3c.4c.5f.6d, | 1b.2a.3c.4c.5f.6e, | 1b.2a.3c.4c.5f.6f, | 1b.2a.3c.4d.5a.6a, | |
| 1b.2a.3c.4d.5a.6b, | 1b.2a.3c.4d.5a.6c, | 1b.2a.3c.4d.5a.6d, | 1b.2a.3c.4d.5a.6e, | |
| 1b.2a.3c.4d.5a.6f, | 1b.2a.3c.4d.5b.6a, | 1b.2a.3c.4d.5b.6b, | 1b.2a.3c.4d.5b.6c, | |
| 1b.2a.3c.4d.5b.6d, | 1b.2a.3c.4d.5b.6e, | 1b.2a.3c.4d.5b.6f, | 1b.2a.3c.4d.5c.6a, | |
| 1b.2a.3c.4d.5c.6b, | 1b.2a.3c.4d.5c.6c, | 1b.2a.3c.4d.5c.6d, | 1b.2a.3c.4d.5c.6e, | |
| 1b.2a.3c.4d.5c.6f, | 1b.2a.3c.4d.5d.6a, | 1b.2a.3c.4d.5d.6b, | 1b.2a.3c.4d.5d.6c, | |
| 1b.2a.3c.4d.5d.6d, | 1b.2a.3c.4d.5d.6e, | 1b.2a.3c.4d.5d.6f, | 1b.2a.3c.4d.5e.6a, | |
| 1b.2a.3c.4d.5e.6b, | 1b.2a.3c.4d.5e.6c, | 1b.2a.3c.4d.5e.6d, | 1b.2a.3c.4d.5e.6e, | |
| 1b.2a.3c.4d.5e.6f, | 1b.2a.3c.4d.5f.6a, | 1b.2a.3c.4d.5f.6b, | 1b.2a.3c.4d.5f.6c, | |
| 1b.2a.3c.4d.5f.6d, | 1b.2a.3c.4d.5f.6e, | 1b.2a.3c.4d.5f.6f, | 1b.2a.3c.4e.5a.6a, | |
| 1b.2a.3c.4e.5a.6b, | 1b.2a.3c.4e.5a.6c, | 1b.2a.3c.4e.5a.6d, | 1b.2a.3c.4e.5a.6e, | |
| 1b.2a.3c.4e.5a.6f, | 1b.2a.3c.4e.5b.6a, | 1b.2a.3c.4e.5b.6b, | 1b.2a.3c.4e.5b.6c, | |
| 1b.2a.3c.4e.5b.6d, | 1b.2a.3c.4e.5b.6e, | 1b.2a.3c.4e.5b.6f, | 1b.2a.3c.4e.5c.6a, | |
| 1b.2a.3c.4e.5c.6b, | 1b.2a.3c.4e.5c.6c, | 1b.2a.3c.4e.5c.6d, | 1b.2a.3c.4e.5c.6e, | |
| 1b.2a.3c.4e.5c.6f, | 1b.2a.3c.4e.5d.6a, | 1b.2a.3c.4e.5d.6b, | 1b.2a.3c.4e.5d.6c, | |
| 1b.2a.3c.4e.5d.6d, | 1b.2a.3c.4e.5d.6e, | 1b.2a.3c.4e.5d.6f, | 1b.2a.3c.4e.5e.6a, | |
| 1b.2a.3c.4e.5e.6b, | 1b.2a.3c.4e.5e.6c, | 1b.2a.3c.4e.5e.6d, | 1b.2a.3c.4e.5e.6e, | |
| 1b.2a.3c.4e.5e.6f, | 1b.2a.3c.4e.5f.6a, | 1b.2a.3c.4e.5f.6b, | 1b.2a.3c.4e.5f.6c, | 1b.2a.3c.4e.5f.6d, |
| 1b.2a.3c.4e.5f.6e, | 1b.2a.3c.4e.5f.6f, | 1b.2a.3c.4f.5a.6a, | 1b.2a.3c.4f.5a.6b, | 1b.2a.3c.4f.5a.6c, |
| 1b.2a.3c.4f.5a.6d, | 1b.2a.3c.4f.5a.6e, | 1b.2a.3c.4f.5a.6f, | 1b.2a.3c.4f.5b.6a, | 1b.2a.3c.4f.5b.6b, |
| 1b.2a.3c.4f.5b.6c, | 1b.2a.3c.4f.5b.6d, | 1b.2a.3c.4f.5b.6e, | 1b.2a.3c.4f.5b.6f, | 1b.2a.3c.4f.5c.6a, |
| 1b.2a.3c.4f.5c.6b, | 1b.2a.3c.4f.5c.6c, | 1b.2a.3c.4f.5c.6d, | 1b.2a.3c.4f.5c.6e, | 1b.2a.3c.4f.5c.6f, |
| 1b.2a.3c.4f.5d.6a, | 1b.2a.3c.4f.5d.6b, | 1b.2a.3c.4f.5d.6c, | 1b.2a.3c.4f.5d.6d, | |
| 1b.2a.3c.4f.5d.6e, | 1b.2a.3c.4f.5d.6f, | 1b.2a.3c.4f.5e.6a, | 1b.2a.3c.4f.5e.6b, | 1b.2a.3c.4f.5e.6c, |
| 1b.2a.3c.4f.5e.6d, | 1b.2a.3c.4f.5e.6e, | 1b.2a.3c.4f.5e.6f, | 1b.2a.3c.4f.5f.6a, | 1b.2a.3c.4f.5f.6b, |
| 1b.2a.3c.4f.5f.6c, | 1b.2a.3c.4f.5f.6d, | 1b.2a.3c.4f.5f.6e, | 1b.2a.3c.4f.5f.6f, | 1b.2a.3d.4a.5a.6a, |
| 1b.2a.3d.4a.5a.6b, | 1b.2a.3d.4a.5a.6c, | 1b.2a.3d.4a.5a.6d, | 1b.2a.3d.4a.5a.6e, | |
| 1b.2a.3d.4a.5a.6f, | 1b.2a.3d.4a.5b.6a, | 1b.2a.3d.4a.5b.6b, | 1b.2a.3d.4a.5b.6c, | |
| 1b.2a.3d.4a.5b.6d, | 1b.2a.3d.4a.5b.6e, | 1b.2a.3d.4a.5b.6f, | 1b.2a.3d.4a.5c.6a, | |
| 1b.2a.3d.4a.5c.6b, | 1b.2a.3d.4a.5c.6c, | 1b.2a.3d.4a.5c.6d, | 1b.2a.3d.4a.5c.6e, | |
| 1b.2a.3d.4a.5c.6f, | 1b.2a.3d.4a.5d.6a, | 1b.2a.3d.4a.5d.6b, | 1b.2a.3d.4a.5d.6c, | |
| 1b.2a.3d.4a.5d.6d, | 1b.2a.3d.4a.5d.6e, | 1b.2a.3d.4a.5d.6f, | 1b.2a.3d.4a.5e.6a, | |
| 1b.2a.3d.4a.5e.6b, | 1b.2a.3d.4a.5e.6c, | 1b.2a.3d.4a.5e.6d, | 1b.2a.3d.4a.5e.6e, | |
| 1b.2a.3d.4a.5e.6f, | 1b.2a.3d.4a.5f.6a, | 1b.2a.3d.4a.5f.6b, | 1b.2a.3d.4a.5f.6c, | |
| 1b.2a.3d.4a.5f.6d, | 1b.2a.3d.4a.5f.6e, | 1b.2a.3d.4a.5f.6f, | 1b.2a.3d.4b.5a.6a, | |
| 1b.2a.3d.4b.5a.6b, | 1b.2a.3d.4b.5a.6c, | 1b.2a.3d.4b.5a.6d, | 1b.2a.3d.4b.5a.6e, | |
| 1b.2a.3d.4b.5a.6f, | 1b.2a.3d.4b.5b.6a, | 1b.2a.3d.4b.5b.6b, | 1b.2a.3d.4b.5b.6c, | |
| 1b.2a.3d.4b.5b.6d, | 1b.2a.3d.4b.5b.6e, | 1b.2a.3d.4b.5b.6f, | 1b.2a.3d.4b.5c.6a, | |
| 1b.2a.3d.4b.5c.6b, | 1b.2a.3d.4b.5c.6c, | 1b.2a.3d.4b.5c.6d, | 1b.2a.3d.4b.5c.6e, | |
| 1b.2a.3d.4b.5c.6f, | 1b.2a.3d.4b.5d.6a, | 1b.2a.3d.4b.5d.6b, | 1b.2a.3d.4b.5d.6c, | |
| 1b.2a.3d.4b.5d.6d, | 1b.2a.3d.4b.5d.6e, | 1b.2a.3d.4b.5d.6f, | 1b.2a.3d.4b.5e.6a, | |
| 1b.2a.3d.4b.5e.6b, | 1b.2a.3d.4b.5e.6c, | 1b.2a.3d.4b.5e.6d, | 1b.2a.3d.4b.5e.6e, | |
| 1b.2a.3d.4b.5e.6f, | 1b.2a.3d.4b.5f.6a, | 1b.2a.3d.4b.5f.6b, | 1b.2a.3d.4b.5f.6c, | |
| 1b.2a.3d.4b.5f.6d, | 1b.2a.3d.4b.5f.6e, | 1b.2a.3d.4b.5f.6f, | 1b.2a.3d.4c.5a.6a, | |
| 1b.2a.3d.4c.5a.6b, | 1b.2a.3d.4c.5a.6c, | 1b.2a.3d.4c.5a.6d, | 1b.2a.3d.4c.5a.6e, | |

TABLE 7-continued

List of Compounds of Formula (II)

| | | | | |
|---|---|---|---|---|
| 1b.2a.3d.4c.5a.6f, | 1b.2a.3d.4c.5b.6a, | 1b.2a.3d.4c.5b.6b, | 1b.2a.3d.4c.5b.6c, | |
| 1b.2a.3d.4c.5b.6d, | 1b.2a.3d.4c.5b.6e, | 1b.2a.3d.4c.5b.6f, | 1b.2a.3d.4c.5c.6a, | |
| 1b.2a.3d.4c.5c.6b, | 1b.2a.3d.4c.5c.6c, | 1b.2a.3d.4c.5c.6d, | 1b.2a.3d.4c.5c.6e, | |
| 1b.2a.3d.4c.5c.6f, | 1b.2a.3d.4c.5d.6a, | 1b.2a.3d.4c.5d.6b, | 1b.2a.3d.4c.5d.6c, | |
| 1b.2a.3d.4c.5d.6d, | 1b.2a.3d.4c.5d.6e, | 1b.2a.3d.4c.5d.6f, | 1b.2a.3d.4c.5e.6a, | |
| 1b.2a.3d.4c.5e.6b, | 1b.2a.3d.4c.5e.6c, | 1b.2a.3d.4c.5e.6d, | 1b.2a.3d.4c.5e.6e, | |
| 1b.2a.3d.4c.5e.6f, | 1b.2a.3d.4c.5f.6a, | 1b.2a.3d.4c.5f.6b, | 1b.2a.3d.4c.5f.6c, | |
| 1b.2a.3d.4c.5f.6d, | 1b.2a.3d.4c.5f.6e, | 1b.2a.3d.4c.5f.6f, | 1b.2a.3d.4d.5a.6a, | |
| 1b.2a.3d.4d.5a.6b, | 1b.2a.3d.4d.5a.6c, | 1b.2a.3d.4d.5a.6d, | 1b.2a.3d.4d.5a.6e, | |
| 1b.2a.3d.4d.5a.6f, | 1b.2a.3d.4d.5b.6a, | 1b.2a.3d.4d.5b.6b, | 1b.2a.3d.4d.5b.6c, | |
| 1b.2a.3d.4d.5b.6d, | 1b.2a.3d.4d.5b.6e, | 1b.2a.3d.4d.5b.6f, | 1b.2a.3d.4d.5c.6a, | |
| 1b.2a.3d.4d.5c.6b, | 1b.2a.3d.4d.5c.6c, | 1b.2a.3d.4d.5c.6d, | 1b.2a.3d.4d.5c.6e, | |
| 1b.2a.3d.4d.5c.6f, | 1b.2a.3d.4d.5d.6a, | 1b.2a.3d.4d.5d.6b, | 1b.2a.3d.4d.5d.6c, | |
| 1b.2a.3d.4d.5d.6d, | 1b.2a.3d.4d.5d.6e, | 1b.2a.3d.4d.5d.6f, | 1b.2a.3d.4d.5e.6a, | |
| 1b.2a.3d.4d.5e.6b, | 1b.2a.3d.4d.5e.6c, | 1b.2a.3d.4d.5e.6d, | 1b.2a.3d.4d.5e.6e, | |
| 1b.2a.3d.4d.5e.6f, | 1b.2a.3d.4d.5f.6a, | 1b.2a.3d.4d.5f.6b, | 1b.2a.3d.4d.5f.6c, | |
| 1b.2a.3d.4d.5f.6d, | 1b.2a.3d.4d.5f.6e, | 1b.2a.3d.4d.5f.6f, | 1b.2a.3d.4e.5a.6a, | |
| 1b.2a.3d.4e.5a.6b, | 1b.2a.3d.4e.5a.6c, | 1b.2a.3d.4e.5a.6d, | 1b.2a.3d.4e.5a.6e, | |
| 1b.2a.3d.4e.5a.6f, | 1b.2a.3d.4e.5b.6a, | 1b.2a.3d.4e.5b.6b, | 1b.2a.3d.4e.5b.6c, | |
| 1b.2a.3d.4e.5b.6d, | 1b.2a.3d.4e.5b.6e, | 1b.2a.3d.4e.5b.6f, | 1b.2a.3d.4e.5c.6a, | |
| 1b.2a.3d.4e.5c.6b, | 1b.2a.3d.4e.5c.6c, | 1b.2a.3d.4e.5c.6d, | 1b.2a.3d.4e.5c.6e, | |
| 1b.2a.3d.4e.5c.6f, | 1b.2a.3d.4e.5d.6a, | 1b.2a.3d.4e.5d.6b, | 1b.2a.3d.4e.5d.6c, | |
| 1b.2a.3d.4e.5d.6d, | 1b.2a.3d.4e.5d.6e, | 1b.2a.3d.4e.5d.6f, | 1b.2a.3d.4e.5e.6a, | |
| 1b.2a.3d.4e.5e.6b, | 1b.2a.3d.4e.5e.6c, | 1b.2a.3d.4e.5e.6d, | 1b.2a.3d.4e.5e.6e, | |
| 1b.2a.3d.4e.5e.6f, | 1b.2a.3d.4e.5f.6a, | 1b.2a.3d.4e.5f.6b, | 1b.2a.3d.4e.5f.6c, | |
| 1b.2a.3d.4e.5f.6d, | 1b.2a.3d.4e.5f.6e, | 1b.2a.3d.4e.5f.6f, | 1b.2a.3d.4f.5a.6a, | |
| 1b.2a.3d.4f.5a.6b, | 1b.2a.3d.4f.5a.6c, | 1b.2a.3d.4f.5a.6d, | 1b.2a.3d.4f.5a.6e, | |
| 1b.2a.3d.4f.5a.6f, | 1b.2a.3d.4f.5b.6a, | 1b.2a.3d.4f.5b.6b, | 1b.2a.3d.4f.5b.6c, | |
| 1b.2a.3d.4f.5b.6d, | 1b.2a.3d.4f.5b.6e, | 1b.2a.3d.4f.5b.6f, | 1b.2a.3d.4f.5c.6a, | |
| 1b.2a.3d.4f.5c.6b, | 1b.2a.3d.4f.5c.6c, | 1b.2a.3d.4f.5c.6d, | 1b.2a.3d.4f.5c.6e, | |
| 1b.2a.3d.4f.5c.6f, | 1b.2a.3d.4f.5d.6a, | 1b.2a.3d.4f.5d.6b, | 1b.2a.3d.4f.5d.6c, | |
| 1b.2a.3d.4f.5d.6d, | 1b.2a.3d.4f.5d.6e, | 1b.2a.3d.4f.5d.6f, | 1b.2a.3d.4f.5e.6a, | |
| 1b.2a.3d.4f.5e.6b, | 1b.2a.3d.4f.5e.6c, | 1b.2a.3d.4f.5e.6d, | 1b.2a.3d.4f.5e.6e, | |
| 1b.2a.3d.4f.5e.6f, | 1b.2a.3d.4f.5f.6a, | 1b.2a.3d.4f.5f.6b, | 1b.2a.3d.4f.5f.6c, | 1b.2a.3d.4f.5f.6d, |
| 1b.2a.3d.4f.5f.6e, | 1b.2a.3d.4f.5f.6f, | 1b.2a.3e.4a.5a.6a, | 1b.2a.3e.4a.5a.6b, | |
| 1b.2a.3e.4a.5a.6c, | 1b.2a.3e.4a.5a.6d, | 1b.2a.3e.4a.5a.6e, | 1b.2a.3e.4a.5a.6f, | |
| 1b.2a.3e.4a.5b.6a, | 1b.2a.3e.4a.5b.6b, | 1b.2a.3e.4a.5b.6c, | 1b.2a.3e.4a.5b.6d, | |
| 1b.2a.3e.4a.5b.6e, | 1b.2a.3e.4a.5b.6f, | 1b.2a.3e.4a.5c.6a, | 1b.2a.3e.4a.5c.6b, | |
| 1b.2a.3e.4a.5c.6c, | 1b.2a.3e.4a.5c.6d, | 1b.2a.3e.4a.5c.6e, | 1b.2a.3e.4a.5c.6f, | |
| 1b.2a.3e.4a.5d.6a, | 1b.2a.3e.4a.5d.6b, | 1b.2a.3e.4a.5d.6c, | 1b.2a.3e.4a.5d.6d, | |
| 1b.2a.3e.4a.5d.6e, | 1b.2a.3e.4a.5d.6f, | 1b.2a.3e.4a.5e.6a, | 1b.2a.3e.4a.5e.6b, | |
| 1b.2a.3e.4a.5e.6c, | 1b.2a.3e.4a.5e.6d, | 1b.2a.3e.4a.5e.6e, | 1b.2a.3e.4a.5e.6f, | |
| 1b.2a.3e.4a.5f.6a, | 1b.2a.3e.4a.5f.6b, | 1b.2a.3e.4a.5f.6c, | 1b.2a.3e.4a.5f.6d, | |
| 1b.2a.3e.4a.5f.6e, | 1b.2a.3e.4a.5f.6f, | 1b.2a.3e.4b.5a.6a, | 1b.2a.3e.4b.5a.6b, | |
| 1b.2a.3e.4b.5a.6c, | 1b.2a.3e.4b.5a.6d, | 1b.2a.3e.4b.5a.6e, | 1b.2a.3e.4b.5a.6f, | |
| 1b.2a.3e.4b.5b.6a, | 1b.2a.3e.4b.5b.6b, | 1b.2a.3e.4b.5b.6c, | 1b.2a.3e.4b.5b.6d, | |
| 1b.2a.3e.4b.5b.6e, | 1b.2a.3e.4b.5b.6f, | 1b.2a.3e.4b.5c.6a, | 1b.2a.3e.4b.5c.6b, | |
| 1b.2a.3e.4b.5c.6c, | 1b.2a.3e.4b.5c.6d, | 1b.2a.3e.4b.5c.6e, | 1b.2a.3e.4b.5c.6f, | |
| 1b.2a.3e.4b.5d.6a, | 1b.2a.3e.4b.5d.6b, | 1b.2a.3e.4b.5d.6c, | 1b.2a.3e.4b.5d.6d, | |
| 1b.2a.3e.4b.5d.6e, | 1b.2a.3e.4b.5d.6f, | 1b.2a.3e.4b.5e.6a, | 1b.2a.3e.4b.5e.6b, | |
| 1b.2a.3e.4b.5e.6c, | 1b.2a.3e.4b.5e.6d, | 1b.2a.3e.4b.5e.6e, | 1b.2a.3e.4b.5e.6f, | |
| 1b.2a.3e.4b.5f.6a, | 1b.2a.3e.4b.5f.6b, | 1b.2a.3e.4b.5f.6c, | 1b.2a.3e.4b.5f.6d, | |
| 1b.2a.3e.4b.5f.6e, | 1b.2a.3e.4b.5f.6f, | 1b.2a.3e.4c.5a.6a, | 1b.2a.3e.4c.5a.6b, | |
| 1b.2a.3e.4c.5a.6c, | 1b.2a.3e.4c.5a.6d, | 1b.2a.3e.4c.5a.6e, | 1b.2a.3e.4c.5a.6f, | |
| 1b.2a.3e.4c.5b.6a, | 1b.2a.3e.4c.5b.6b, | 1b.2a.3e.4c.5b.6c, | 1b.2a.3e.4c.5b.6d, | |
| 1b.2a.3e.4c.5b.6e, | 1b.2a.3e.4c.5b.6f, | 1b.2a.3e.4c.5c.6a, | 1b.2a.3e.4c.5c.6b, | |
| 1b.2a.3e.4c.5c.6c, | 1b.2a.3e.4c.5c.6d, | 1b.2a.3e.4c.5c.6e, | 1b.2a.3e.4c.5c.6f, | |
| 1b.2a.3e.4c.5d.6a, | 1b.2a.3e.4c.5d.6b, | 1b.2a.3e.4c.5d.6c, | 1b.2a.3e.4c.5d.6d, | |
| 1b.2a.3e.4c.5d.6e, | 1b.2a.3e.4c.5d.6f, | 1b.2a.3e.4c.5e.6a, | 1b.2a.3e.4c.5e.6b, | |
| 1b.2a.3e.4c.5e.6c, | 1b.2a.3e.4c.5e.6d, | 1b.2a.3e.4c.5e.6e, | 1b.2a.3e.4c.5e.6f, | |
| 1b.2a.3e.4c.5f.6a, | 1b.2a.3e.4c.5f.6b, | 1b.2a.3e.4c.5f.6c, | 1b.2a.3e.4c.5f.6d, | 1b.2a.3e.4c.5f.6e, |
| 1b.2a.3e.4c.5f.6f, | 1b.2a.3e.4d.5a.6a, | 1b.2a.3e.4d.5a.6b, | 1b.2a.3e.4d.5a.6c, | |
| 1b.2a.3e.4d.5a.6d, | 1b.2a.3e.4d.5a.6e, | 1b.2a.3e.4d.5a.6f, | 1b.2a.3e.4d.5b.6a, | |
| 1b.2a.3e.4d.5b.6b, | 1b.2a.3e.4d.5b.6c, | 1b.2a.3e.4d.5b.6d, | 1b.2a.3e.4d.5b.6e, | |
| 1b.2a.3e.4d.5b.6f, | 1b.2a.3e.4d.5c.6a, | 1b.2a.3e.4d.5c.6b, | 1b.2a.3e.4d.5c.6c, | |
| 1b.2a.3e.4d.5c.6d, | 1b.2a.3e.4d.5c.6e, | 1b.2a.3e.4d.5c.6f, | 1b.2a.3e.4d.5d.6a, | |
| 1b.2a.3e.4d.5d.6b, | 1b.2a.3e.4d.5d.6c, | 1b.2a.3e.4d.5d.6d, | 1b.2a.3e.4d.5d.6e, | |
| 1b.2a.3e.4d.5d.6f, | 1b.2a.3e.4d.5e.6a, | 1b.2a.3e.4d.5e.6b, | 1b.2a.3e.4d.5e.6c, | |
| 1b.2a.3e.4d.5e.6d, | 1b.2a.3e.4d.5e.6e, | 1b.2a.3e.4d.5e.6f, | 1b.2a.3e.4d.5f.6a, | |
| 1b.2a.3e.4d.5f.6b, | 1b.2a.3e.4d.5f.6c, | 1b.2a.3e.4d.5f.6d, | 1b.2a.3e.4d.5f.6e, | |
| 1b.2a.3e.4d.5f.6f, | 1b.2a.3e.4e.5a.6a, | 1b.2a.3e.4e.5a.6b, | 1b.2a.3e.4e.5a.6c, | |
| 1b.2a.3e.4e.5a.6d, | 1b.2a.3e.4e.5a.6e, | 1b.2a.3e.4e.5a.6f, | 1b.2a.3e.4e.5b.6a, | |
| 1b.2a.3e.4e.5b.6b, | 1b.2a.3e.4e.5b.6c, | 1b.2a.3e.4e.5b.6d, | 1b.2a.3e.4e.5b.6e, | |
| 1b.2a.3e.4e.5b.6f, | 1b.2a.3e.4e.5c.6a, | 1b.2a.3e.4e.5c.6b, | 1b.2a.3e.4e.5c.6c, | |
| 1b.2a.3e.4e.5c.6d, | 1b.2a.3e.4e.5c.6e, | 1b.2a.3e.4e.5c.6f, | 1b.2a.3e.4e.5d.6a, | |
| 1b.2a.3e.4e.5d.6b, | 1b.2a.3e.4e.5d.6c, | 1b.2a.3e.4e.5d.6d, | 1b.2a.3e.4e.5d.6e, | |
| 1b.2a.3e.4e.5d.6f, | 1b.2a.3e.4e.5e.6a, | 1b.2a.3e.4e.5e.6b, | 1b.2a.3e.4e.5e.6c, | |
| 1b.2a.3e.4e.5e.6d, | 1b.2a.3e.4e.5e.6e, | 1b.2a.3e.4e.5e.6f, | 1b.2a.3e.4e.5f.6a, | |

TABLE 7-continued

List of Compounds of Formula (II)

| | | | | |
|---|---|---|---|---|
| 1b.2a.3e.4e.5f.6b, | 1b.2a.3e.4e.5f.6c, | 1b.2a.3e.4e.5f.6d, | 1b.2a.3e.4e.5f.6e, | 1b.2a.3e.4e.5f.6f, |
| 1b.2a.3e.4f.5a.6a, | 1b.2a.3e.4f.5a.6b, | 1b.2a.3e.4f.5a.6c, | 1b.2a.3e.4f.5a.6d, | |
| 1b.2a.3e.4f.5a.6e, | 1b.2a.3e.4f.5a.6f, | 1b.2a.3e.4f.5b.6a, | 1b.2a.3e.4f.5b.6b, | 1b.2a.3e.4f.5b.6c, |
| 1b.2a.3e.4f.5b.6d, | 1b.2a.3e.4f.5b.6e, | 1b.2a.3e.4f.5b.6f, | 1b.2a.3e.4f.5c.6a, | 1b.2a.3e.4f.5c.6b, |
| 1b.2a.3e.4f.5c.6c, | 1b.2a.3e.4f.5c.6d, | 1b.2a.3e.4f.5c.6e, | 1b.2a.3e.4f.5c.6f, | 1b.2a.3e.4f.5d.6a, |
| 1b.2a.3e.4f.5d.6b, | 1b.2a.3e.4f.5d.6c, | 1b.2a.3e.4f.5d.6d, | 1b.2a.3e.4f.5d.6e, | |
| 1b.2a.3e.4f.5d.6f, | 1b.2a.3e.4f.5e.6a, | 1b.2a.3e.4f.5e.6b, | 1b.2a.3e.4f.5e.6c, | 1b.2a.3e.4f.5e.6d, |
| 1b.2a.3e.4f.5e.6e, | 1b.2a.3e.4f.5e.6f, | 1b.2a.3e.4f.5f.6a, | 1b.2a.3e.4f.5f.6b, | 1b.2a.3e.4f.5f.6c, |
| 1b.2a.3e.4f.5f.6d, | 1b.2a.3e.4f.5f.6e, | 1b.2a.3e.4f.5f.6f, | 1b.2a.3f.4a.5a.6a, | 1b.2a.3f.4a.5a.6b, |
| 1b.2a.3f.4a.5a.6c, | 1b.2a.3f.4a.5a.6d, | 1b.2a.3f.4a.5a.6e, | 1b.2a.3f.4a.5a.6f, | 1b.2a.3f.4a.5b.6a, |
| 1b.2a.3f.4a.5b.6b, | 1b.2a.3f.4a.5b.6c, | 1b.2a.3f.4a.5b.6d, | 1b.2a.3f.4a.5b.6e, | |
| 1b.2a.3f.4a.5b.6f, | 1b.2a.3f.4a.5c.6a, | 1b.2a.3f.4a.5c.6b, | 1b.2a.3f.4a.5c.6c, | 1b.2a.3f.4a.5c.6d, |
| 1b.2a.3f.4a.5c.6e, | 1b.2a.3f.4a.5c.6f, | 1b.2a.3f.4a.5d.6a, | 1b.2a.3f.4a.5d.6b, | |
| 1b.2a.3f.4a.5d.6c, | 1b.2a.3f.4a.5d.6d, | 1b.2a.3f.4a.5d.6e, | 1b.2a.3f.4a.5d.6f, | |
| 1b.2a.3f.4a.5e.6a, | 1b.2a.3f.4a.5e.6b, | 1b.2a.3f.4a.5e.6c, | 1b.2a.3f.4a.5e.6d, | |
| 1b.2a.3f.4a.5e.6e, | 1b.2a.3f.4a.5e.6f, | 1b.2a.3f.4a.5f.6a, | 1b.2a.3f.4a.5f.6b, | 1b.2a.3f.4a.5f.6c, |
| 1b.2a.3f.4a.5f.6d, | 1b.2a.3f.4a.5f.6e, | 1b.2a.3f.4a.5f.6f, | 1b.2a.3f.4b.5a.6a, | 1b.2a.3f.4b.5a.6b, |
| 1b.2a.3f.4b.5a.6c, | 1b.2a.3f.4b.5a.6d, | 1b.2a.3f.4b.5a.6e, | 1b.2a.3f.4b.5a.6f, | |
| 1b.2a.3f.4b.5b.6a, | 1b.2a.3f.4b.5b.6b, | 1b.2a.3f.4b.5b.6c, | 1b.2a.3f.4b.5b.6d, | |
| 1b.2a.3f.4b.5b.6e, | 1b.2a.3f.4b.5b.6f, | 1b.2a.3f.4b.5c.6a, | 1b.2a.3f.4b.5c.6b, | |
| 1b.2a.3f.4b.5c.6c, | 1b.2a.3f.4b.5c.6d, | 1b.2a.3f.4b.5c.6e, | 1b.2a.3f.4b.5c.6f, | |
| 1b.2a.3f.4b.5d.6a, | 1b.2a.3f.4b.5d.6b, | 1b.2a.3f.4b.5d.6c, | 1b.2a.3f.4b.5d.6d, | |
| 1b.2a.3f.4b.5d.6e, | 1b.2a.3f.4b.5d.6f, | 1b.2a.3f.4b.5e.6a, | 1b.2a.3f.4b.5e.6b, | |
| 1b.2a.3f.4b.5e.6c, | 1b.2a.3f.4b.5e.6d, | 1b.2a.3f.4b.5e.6e, | 1b.2a.3f.4b.5e.6f, | 1b.2a.3f.4b.5f.6a, |
| 1b.2a.3f.4b.5f.6b, | 1b.2a.3f.4b.5f.6c, | 1b.2a.3f.4b.5f.6d, | 1b.2a.3f.4b.5f.6e, | 1b.2a.3f.4b.5f.6f, |
| 1b.2a.3f.4c.5a.6a, | 1b.2a.3f.4c.5a.6b, | 1b.2a.3f.4c.5a.6c, | 1b.2a.3f.4c.5a.6d, | 1b.2a.3f.4c.5a.6e, |
| 1b.2a.3f.4c.5a.6f, | 1b.2a.3f.4c.5b.6a, | 1b.2a.3f.4c.5b.6b, | 1b.2a.3f.4c.5b.6c, | 1b.2a.3f.4c.5b.6d, |
| 1b.2a.3f.4c.5b.6e, | 1b.2a.3f.4c.5b.6f, | 1b.2a.3f.4c.5c.6a, | 1b.2a.3f.4c.5c.6b, | 1b.2a.3f.4c.5c.6c, |
| 1b.2a.3f.4c.5c.6d, | 1b.2a.3f.4c.5c.6e, | 1b.2a.3f.4c.5c.6f, | 1b.2a.3f.4c.5d.6a, | 1b.2a.3f.4c.5d.6b, |
| 1b.2a.3f.4c.5d.6c, | 1b.2a.3f.4c.5d.6d, | 1b.2a.3f.4c.5d.6e, | 1b.2a.3f.4c.5d.6f, | |
| 1b.2a.3f.4c.5e.6a, | 1b.2a.3f.4c.5e.6b, | 1b.2a.3f.4c.5e.6c, | 1b.2a.3f.4c.5e.6d, | 1b.2a.3f.4c.5e.6e, |
| 1b.2a.3f.4c.5e.6f, | 1b.2a.3f.4c.5f.6a, | 1b.2a.3f.4c.5f.6b, | 1b.2a.3f.4c.5f.6c, | 1b.2a.3f.4c.5f.6d, |
| 1b.2a.3f.4c.5f.6e, | 1b.2a.3f.4c.5f.6f, | 1b.2a.3f.4d.5a.6a, | 1b.2a.3f.4d.5a.6b, | 1b.2a.3f.4d.5a.6c, |
| 1b.2a.3f.4d.5a.6d, | 1b.2a.3f.4d.5a.6e, | 1b.2a.3f.4d.5a.6f, | 1b.2a.3f.4d.5b.6a, | |
| 1b.2a.3f.4d.5b.6b, | 1b.2a.3f.4d.5b.6c, | 1b.2a.3f.4d.5b.6d, | 1b.2a.3f.4d.5b.6e, | |
| 1b.2a.3f.4d.5b.6f, | 1b.2a.3f.4d.5c.6a, | 1b.2a.3f.4d.5c.6b, | 1b.2a.3f.4d.5c.6c, | |
| 1b.2a.3f.4d.5c.6d, | 1b.2a.3f.4d.5c.6e, | 1b.2a.3f.4d.5c.6f, | 1b.2a.3f.4d.5d.6a, | |
| 1b.2a.3f.4d.5d.6b, | 1b.2a.3f.4d.5d.6c, | 1b.2a.3f.4d.5d.6d, | 1b.2a.3f.4d.5d.6e, | |
| 1b.2a.3f.4d.5d.6f, | 1b.2a.3f.4d.5e.6a, | 1b.2a.3f.4d.5e.6b, | 1b.2a.3f.4d.5e.6c, | |
| 1b.2a.3f.4d.5e.6d, | 1b.2a.3f.4d.5e.6e, | 1b.2a.3f.4d.5e.6f, | 1b.2a.3f.4d.5f.6a, | |
| 1b.2a.3f.4d.5f.6b, | 1b.2a.3f.4d.5f.6c, | 1b.2a.3f.4d.5f.6d, | 1b.2a.3f.4d.5f.6e, | 1b.2a.3f.4d.5f.6f, |
| 1b.2a.3f.4e.5a.6a, | 1b.2a.3f.4e.5a.6b, | 1b.2a.3f.4e.5a.6c, | 1b.2a.3f.4e.5a.6d, | |
| 1b.2a.3f.4e.5a.6e, | 1b.2a.3f.4e.5a.6f, | 1b.2a.3f.4e.5b.6a, | 1b.2a.3f.4e.5b.6b, | 1b.2a.3f.4e.5b.6c, |
| 1b.2a.3f.4e.5b.6d, | 1b.2a.3f.4e.5b.6e, | 1b.2a.3f.4e.5b.6f, | 1b.2a.3f.4e.5c.6a, | 1b.2a.3f.4e.5c.6b, |
| 1b.2a.3f.4e.5c.6c, | 1b.2a.3f.4e.5c.6d, | 1b.2a.3f.4e.5c.6e, | 1b.2a.3f.4e.5c.6f, | 1b.2a.3f.4e.5d.6a, |
| 1b.2a.3f.4e.5d.6b, | 1b.2a.3f.4e.5d.6c, | 1b.2a.3f.4e.5d.6d, | 1b.2a.3f.4e.5d.6e, | |
| 1b.2a.3f.4e.5d.6f, | 1b.2a.3f.4e.5e.6a, | 1b.2a.3f.4e.5e.6b, | 1b.2a.3f.4e.5e.6c, | 1b.2a.3f.4e.5e.6d, |
| 1b.2a.3f.4e.5e.6e, | 1b.2a.3f.4e.5e.6f, | 1b.2a.3f.4e.5f.6a, | 1b.2a.3f.4e.5f.6b, | 1b.2a.3f.4e.5f.6c, |
| 1b.2a.3f.4e.5f.6d, | 1b.2a.3f.4e.5f.6e, | 1b.2a.3f.4e.5f.6f, | 1b.2a.3f.4f.5a.6a, | 1b.2a.3f.4f.5a.6b, |
| 1b.2a.3f.4f.5a.6c, | 1b.2a.3f.4f.5a.6d, | 1b.2a.3f.4f.5a.6e, | 1b.2a.3f.4f.5a.6f, | 1b.2a.3f.4f.5b.6a, |
| 1b.2a.3f.4f.5b.6b, | 1b.2a.3f.4f.5b.6c, | 1b.2a.3f.4f.5b.6d, | 1b.2a.3f.4f.5b.6e, | 1b.2a.3f.4f.5b.6f, |
| 1b.2a.3f.4f.5c.6a, | 1b.2a.3f.4f.5c.6b, | 1b.2a.3f.4f.5c.6c, | 1b.2a.3f.4f.5c.6d, | 1b.2a.3f.4f.5c.6e, |
| 1b.2a.3f.4f.5c.6f, | 1b.2a.3f.4f.5d.6a, | 1b.2a.3f.4f.5d.6b, | 1b.2a.3f.4f.5d.6c, | 1b.2a.3f.4f.5d.6d, |
| 1b.2a.3f.4f.5d.6e, | 1b.2a.3f.4f.5d.6f, | 1b.2a.3f.4f.5e.6a, | 1b.2a.3f.4f.5e.6b, | 1b.2a.3f.4f.5e.6c, |
| 1b.2a.3f.4f.5e.6d, | 1b.2a.3f.4f.5e.6e, | 1b.2a.3f.4f.5e.6f, | 1b.2a.3f.4f.5f.6a, | 1b.2a.3f.4f.5f.6b, |
| 1b.2a.3f.4f.5f.6c, | 1b.2a.3f.4f.5f.6d, | 1b.2a.3f.4f.5f.6e, | 1b.2a.3f.4f.5f.6f, | 1b.2b.3a.4a.5a.6a, |
| 1b.2b.3a.4a.5a.6b, | 1b.2b.3a.4a.5a.6c, | 1b.2b.3a.4a.5a.6d, | 1b.2b.3a.4a.5a.6e, | |
| 1b.2b.3a.4a.5a.6f, | 1b.2b.3a.4a.5b.6a, | 1b.2b.3a.4a.5b.6b, | 1b.2b.3a.4a.5b.6c, | |
| 1b.2b.3a.4a.5b.6d, | 1b.2b.3a.4a.5b.6e, | 1b.2b.3a.4a.5b.6f, | 1b.2b.3a.4a.5c.6a, | |
| 1b.2b.3a.4a.5c.6b, | 1b.2b.3a.4a.5c.6c, | 1b.2b.3a.4a.5c.6d, | 1b.2b.3a.4a.5c.6e, | |
| 1b.2b.3a.4a.5c.6f, | 1b.2b.3a.4a.5d.6a, | 1b.2b.3a.4a.5d.6b, | 1b.2b.3a.4a.5d.6c, | |
| 1b.2b.3a.4a.5d.6d, | 1b.2b.3a.4a.5d.6e, | 1b.2b.3a.4a.5d.6f, | 1b.2b.3a.4a.5e.6a, | |
| 1b.2b.3a.4a.5e.6b, | 1b.2b.3a.4a.5e.6c, | 1b.2b.3a.4a.5e.6d, | 1b.2b.3a.4a.5e.6e, | |
| 1b.2b.3a.4a.5e.6f, | 1b.2b.3a.4a.5f.6a, | 1b.2b.3a.4a.5f.6b, | 1b.2b.3a.4a.5f.6c, | |
| 1b.2b.3a.4a.5f.6d, | 1b.2b.3a.4a.5f.6e, | 1b.2b.3a.4a.5f.6f, | 1b.2b.3a.4b.5a.6a, | |
| 1b.2b.3a.4b.5a.6b, | 1b.2b.3a.4b.5a.6c, | 1b.2b.3a.4b.5a.6d, | 1b.2b.3a.4b.5a.6e, | |
| 1b.2b.3a.4b.5a.6f, | 1b.2b.3a.4b.5b.6a, | 1b.2b.3a.4b.5b.6b, | 1b.2b.3a.4b.5b.6c, | |
| 1b.2b.3a.4b.5b.6d, | 1b.2b.3a.4b.5b.6e, | 1b.2b.3a.4b.5b.6f, | 1b.2b.3a.4b.5c.6a, | |
| 1b.2b.3a.4b.5c.6b, | 1b.2b.3a.4b.5c.6c, | 1b.2b.3a.4b.5c.6d, | 1b.2b.3a.4b.5c.6e, | |
| 1b.2b.3a.4b.5c.6f, | 1b.2b.3a.4b.5d.6a, | 1b.2b.3a.4b.5d.6b, | 1b.2b.3a.4b.5d.6c, | |
| 1b.2b.3a.4b.5d.6d, | 1b.2b.3a.4b.5d.6e, | 1b.2b.3a.4b.5d.6f, | 1b.2b.3a.4b.5e.6a, | |
| 1b.2b.3a.4b.5e.6b, | 1b.2b.3a.4b.5e.6c, | 1b.2b.3a.4b.5e.6d, | 1b.2b.3a.4b.5e.6e, | |
| 1b.2b.3a.4b.5e.6f, | 1b.2b.3a.4b.5f.6a, | 1b.2b.3a.4b.5f.6b, | 1b.2b.3a.4b.5f.6c, | |
| 1b.2b.3a.4b.5f.6d, | 1b.2b.3a.4b.5f.6e, | 1b.2b.3a.4b.5f.6f, | 1b.2b.3a.4c.5a.6a, | |
| 1b.2b.3a.4c.5a.6b, | 1b.2b.3a.4c.5a.6c, | 1b.2b.3a.4c.5a.6d, | 1b.2b.3a.4c.5a.6e, | |
| 1b.2b.3a.4c.5a.6f, | 1b.2b.3a.4c.5b.6a, | 1b.2b.3a.4c.5b.6b, | 1b.2b.3a.4c.5b.6c, | |
| 1b.2b.3a.4c.5b.6d, | 1b.2b.3a.4c.5b.6e, | 1b.2b.3a.4c.5b.6f, | 1b.2b.3a.4c.5c.6a, | |
| 1b.2b.3a.4c.5c.6b, | 1b.2b.3a.4c.5c.6c, | 1b.2b.3a.4c.5c.6d, | 1b.2b.3a.4c.5c.6e, | |

TABLE 7-continued

List of Compounds of Formula (II)

| | | | |
|---|---|---|---|
| 1b.2b.3a.4c.5c.6f, | 1b.2b.3a.4c.5d.6a, | 1b.2b.3a.4c.5d.6b, | 1b.2b.3a.4c.5d.6c, |
| 1b.2b.3a.4c.5d.6d, | 1b.2b.3a.4c.5d.6e, | 1b.2b.3a.4c.5d.6f, | 1b.2b.3a.4c.5e.6a, |
| 1b.2b.3a.4c.5e.6b, | 1b.2b.3a.4c.5e.6c, | 1b.2b.3a.4c.5e.6d, | 1b.2b.3a.4c.5e.6e, |
| 1b.2b.3a.4c.5e.6f, | 1b.2b.3a.4c.5f.6a, | 1b.2b.3a.4c.5f.6b, | 1b.2b.3a.4c.5f.6c, |
| 1b.2b.3a.4c.5f.6d, | 1b.2b.3a.4c.5f.6e, | 1b.2b.3a.4c.5f.6f, | 1b.2b.3a.4d.5a.6a, |
| 1b.2b.3a.4d.5a.6b, | 1b.2b.3a.4d.5a.6c, | 1b.2b.3a.4d.5a.6d, | 1b.2b.3a.4d.5a.6e, |
| 1b.2b.3a.4d.5a.6f, | 1b.2b.3a.4d.5b.6a, | 1b.2b.3a.4d.5b.6b, | 1b.2b.3a.4d.5b.6c, |
| 1b.2b.3a.4d.5b.6d, | 1b.2b.3a.4d.5b.6e, | 1b.2b.3a.4d.5b.6f, | 1b.2b.3a.4d.5c.6a, |
| 1b.2b.3a.4d.5c.6b, | 1b.2b.3a.4d.5c.6c, | 1b.2b.3a.4d.5c.6d, | 1b.2b.3a.4d.5c.6e, |
| 1b.2b.3a.4d.5c.6f, | 1b.2b.3a.4d.5d.6a, | 1b.2b.3a.4d.5d.6b, | 1b.2b.3a.4d.5d.6c, |
| 1b.2b.3a.4d.5d.6d, | 1b.2b.3a.4d.5d.6e, | 1b.2b.3a.4d.5d.6f, | 1b.2b.3a.4d.5e.6a, |
| 1b.2b.3a.4d.5e.6b, | 1b.2b.3a.4d.5e.6c, | 1b.2b.3a.4d.5e.6d, | 1b.2b.3a.4d.5e.6e, |
| 1b.2b.3a.4d.5e.6f, | 1b.2b.3a.4d.5f.6a, | 1b.2b.3a.4d.5f.6b, | 1b.2b.3a.4d.5f.6c, |
| 1b.2b.3a.4d.5f.6d, | 1b.2b.3a.4d.5f.6e, | 1b.2b.3a.4d.5f.6f, | 1b.2b.3a.4e.5a.6a, |
| 1b.2b.3a.4e.5a.6b, | 1b.2b.3a.4e.5a.6c, | 1b.2b.3a.4e.5a.6d, | 1b.2b.3a.4e.5a.6e, |
| 1b.2b.3a.4e.5a.6f, | 1b.2b.3a.4e.5b.6a, | 1b.2b.3a.4e.5b.6b, | 1b.2b.3a.4e.5b.6c, |
| 1b.2b.3a.4e.5b.6d, | 1b.2b.3a.4e.5b.6e, | 1b.2b.3a.4e.5b.6f, | 1b.2b.3a.4e.5c.6a, |
| 1b.2b.3a.4e.5c.6b, | 1b.2b.3a.4e.5c.6c, | 1b.2b.3a.4e.5c.6d, | 1b.2b.3a.4e.5c.6e, |
| 1b.2b.3a.4e.5c.6f, | 1b.2b.3a.4e.5d.6a, | 1b.2b.3a.4e.5d.6b, | 1b.2b.3a.4e.5d.6c, |
| 1b.2b.3a.4e.5d.6d, | 1b.2b.3a.4e.5d.6e, | 1b.2b.3a.4e.5d.6f, | 1b.2b.3a.4e.5e.6a, |
| 1b.2b.3a.4e.5e.6b, | 1b.2b.3a.4e.5e.6c, | 1b.2b.3a.4e.5e.6d, | 1b.2b.3a.4e.5e.6e, |
| 1b.2b.3a.4e.5e.6f, | 1b.2b.3a.4e.5f.6a, | 1b.2b.3a.4e.5f.6b, | 1b.2b.3a.4e.5f.6c, |
| 1b.2b.3a.4e.5f.6d, | 1b.2b.3a.4e.5f.6e, | 1b.2b.3a.4e.5f.6f, | 1b.2b.3a.4f.5a.6a, |
| 1b.2b.3a.4f.5a.6b, | 1b.2b.3a.4f.5a.6c, | 1b.2b.3a.4f.5a.6d, | 1b.2b.3a.4f.5a.6e, |
| 1b.2b.3a.4f.5a.6f, | 1b.2b.3a.4f.5b.6a, | 1b.2b.3a.4f.5b.6b, | 1b.2b.3a.4f.5b.6c, |
| 1b.2b.3a.4f.5b.6d, | 1b.2b.3a.4f.5b.6e, | 1b.2b.3a.4f.5b.6f, | 1b.2b.3a.4f.5c.6a, |
| 1b.2b.3a.4f.5c.6b, | 1b.2b.3a.4f.5c.6c, | 1b.2b.3a.4f.5c.6d, | 1b.2b.3a.4f.5c.6e, | 1b.2b.3a.4f.5c.6f, |
| 1b.2b.3a.4f.5d.6a, | 1b.2b.3a.4f.5d.6b, | 1b.2b.3a.4f.5d.6c, | 1b.2b.3a.4f.5d.6d, |
| 1b.2b.3a.4f.5d.6e, | 1b.2b.3a.4f.5d.6f, | 1b.2b.3a.4f.5e.6a, | 1b.2b.3a.4f.5e.6b, |
| 1b.2b.3a.4f.5e.6c, | 1b.2b.3a.4f.5e.6d, | 1b.2b.3a.4f.5e.6e, | 1b.2b.3a.4f.5e.6f, | 1b.2b.3a.4f.5f.6a, |
| 1b.2b.3a.4f.5f.6b, | 1b.2b.3a.4f.5f.6c, | 1b.2b.3a.4f.5f.6d, | 1b.2b.3a.4f.5f.6e, | 1b.2b.3a.4f.5f.6f, |
| 1b.2b.3b.4a.5a.6a, | 1b.2b.3b.4a.5a.6b, | 1b.2b.3b.4a.5a.6c, | 1b.2b.3b.4a.5a.6d, |
| 1b.2b.3b.4a.5a.6e, | 1b.2b.3b.4a.5a.6f, | 1b.2b.3b.4a.5b.6a, | 1b.2b.3b.4a.5b.6b, |
| 1b.2b.3b.4a.5b.6c, | 1b.2b.3b.4a.5b.6d, | 1b.2b.3b.4a.5b.6e, | 1b.2b.3b.4a.5b.6f, |
| 1b.2b.3b.4a.5c.6a, | 1b.2b.3b.4a.5c.6b, | 1b.2b.3b.4a.5c.6c, | 1b.2b.3b.4a.5c.6d, |
| 1b.2b.3b.4a.5c.6e, | 1b.2b.3b.4a.5c.6f, | 1b.2b.3b.4a.5d.6a, | 1b.2b.3b.4a.5d.6b, |
| 1b.2b.3b.4a.5d.6c, | 1b.2b.3b.4a.5d.6d, | 1b.2b.3b.4a.5d.6e, | 1b.2b.3b.4a.5d.6f, |
| 1b.2b.3b.4a.5e.6a, | 1b.2b.3b.4a.5e.6b, | 1b.2b.3b.4a.5e.6c, | 1b.2b.3b.4a.5e.6d, |
| 1b.2b.3b.4a.5e.6e, | 1b.2b.3b.4a.5e.6f, | 1b.2b.3b.4a.5f.6a, | 1b.2b.3b.4a.5f.6b, |
| 1b.2b.3b.4a.5f.6c, | 1b.2b.3b.4a.5f.6d, | 1b.2b.3b.4a.5f.6e, | 1b.2b.3b.4a.5f.6f, |
| 1b.2b.3b.4b.5a.6a, | 1b.2b.3b.4b.5a.6b, | 1b.2b.3b.4b.5a.6c, | 1b.2b.3b.4b.5a.6d, |
| 1b.2b.3b.4b.5a.6e, | 1b.2b.3b.4b.5a.6f, | 1b.2b.3b.4b.5b.6a, | 1b.2b.3b.4b.5b.6b, |
| 1b.2b.3b.4b.5b.6c, | 1b.2b.3b.4b.5b.6d, | 1b.2b.3b.4b.5b.6e, | 1b.2b.3b.4b.5b.6f, |
| 1b.2b.3b.4b.5c.6a, | 1b.2b.3b.4b.5c.6b, | 1b.2b.3b.4b.5c.6c, | 1b.2b.3b.4b.5c.6d, |
| 1b.2b.3b.4b.5c.6e, | 1b.2b.3b.4b.5c.6f, | 1b.2b.3b.4b.5d.6a, | 1b.2b.3b.4b.5d.6b, |
| 1b.2b.3b.4b.5d.6c, | 1b.2b.3b.4b.5d.6d, | 1b.2b.3b.4b.5d.6e, | 1b.2b.3b.4b.5d.6f, |
| 1b.2b.3b.4b.5e.6a, | 1b.2b.3b.4b.5e.6b, | 1b.2b.3b.4b.5e.6c, | 1b.2b.3b.4b.5e.6d, |
| 1b.2b.3b.4b.5e.6e, | 1b.2b.3b.4b.5e.6f, | 1b.2b.3b.4b.5f.6a, | 1b.2b.3b.4b.5f.6b, |
| 1b.2b.3b.4b.5f.6c, | 1b.2b.3b.4b.5f.6d, | 1b.2b.3b.4b.5f.6e, | 1b.2b.3b.4b.5f.6f, |
| 1b.2b.3b.4c.5a.6a, | 1b.2b.3b.4c.5a.6b, | 1b.2b.3b.4c.5a.6c, | 1b.2b.3b.4c.5a.6d, |
| 1b.2b.3b.4c.5a.6e, | 1b.2b.3b.4c.5a.6f, | 1b.2b.3b.4c.5b.6a, | 1b.2b.3b.4c.5b.6b, |
| 1b.2b.3b.4c.5b.6c, | 1b.2b.3b.4c.5b.6d, | 1b.2b.3b.4c.5b.6e, | 1b.2b.3b.4c.5b.6f, |
| 1b.2b.3b.4c.5c.6a, | 1b.2b.3b.4c.5c.6b, | 1b.2b.3b.4c.5c.6c, | 1b.2b.3b.4c.5c.6d, |
| 1b.2b.3b.4c.5c.6e, | 1b.2b.3b.4c.5c.6f, | 1b.2b.3b.4c.5d.6a, | 1b.2b.3b.4c.5d.6b, |
| 1b.2b.3b.4c.5d.6c, | 1b.2b.3b.4c.5d.6d, | 1b.2b.3b.4c.5d.6e, | 1b.2b.3b.4c.5d.6f, |
| 1b.2b.3b.4c.5e.6a, | 1b.2b.3b.4c.5e.6b, | 1b.2b.3b.4c.5e.6c, | 1b.2b.3b.4c.5e.6d, |
| 1b.2b.3b.4c.5e.6e, | 1b.2b.3b.4c.5e.6f, | 1b.2b.3b.4c.5f.6a, | 1b.2b.3b.4c.5f.6b, |
| 1b.2b.3b.4c.5f.6c, | 1b.2b.3b.4c.5f.6d, | 1b.2b.3b.4c.5f.6e, | 1b.2b.3b.4c.5f.6f, |
| 1b.2b.3b.4d.5a.6a, | 1b.2b.3b.4d.5a.6b, | 1b.2b.3b.4d.5a.6c, | 1b.2b.3b.4d.5a.6d, |
| 1b.2b.3b.4d.5a.6e, | 1b.2b.3b.4d.5a.6f, | 1b.2b.3b.4d.5b.6a, | 1b.2b.3b.4d.5b.6b, |
| 1b.2b.3b.4d.5b.6c, | 1b.2b.3b.4d.5b.6d, | 1b.2b.3b.4d.5b.6e, | 1b.2b.3b.4d.5b.6f, |
| 1b.2b.3b.4d.5c.6a, | 1b.2b.3b.4d.5c.6b, | 1b.2b.3b.4d.5c.6c, | 1b.2b.3b.4d.5c.6d, |
| 1b.2b.3b.4d.5c.6e, | 1b.2b.3b.4d.5c.6f, | 1b.2b.3b.4d.5d.6a, | 1b.2b.3b.4d.5d.6b, |
| 1b.2b.3b.4d.5d.6c, | 1b.2b.3b.4d.5d.6d, | 1b.2b.3b.4d.5d.6e, | 1b.2b.3b.4d.5d.6f, |
| 1b.2b.3b.4d.5e.6a, | 1b.2b.3b.4d.5e.6b, | 1b.2b.3b.4d.5e.6c, | 1b.2b.3b.4d.5e.6d, |
| 1b.2b.3b.4d.5e.6e, | 1b.2b.3b.4d.5e.6f, | 1b.2b.3b.4d.5f.6a, | 1b.2b.3b.4d.5f.6b, |
| 1b.2b.3b.4d.5f.6c, | 1b.2b.3b.4d.5f.6d, | 1b.2b.3b.4d.5f.6e, | 1b.2b.3b.4d.5f.6f, |
| 1b.2b.3b.4e.5a.6a, | 1b.2b.3b.4e.5a.6b, | 1b.2b.3b.4e.5a.6c, | 1b.2b.3b.4e.5a.6d, |
| 1b.2b.3b.4e.5a.6e, | 1b.2b.3b.4e.5a.6f, | 1b.2b.3b.4e.5b.6a, | 1b.2b.3b.4e.5b.6b, |
| 1b.2b.3b.4e.5b.6c, | 1b.2b.3b.4e.5b.6d, | 1b.2b.3b.4e.5b.6e, | 1b.2b.3b.4e.5b.6f, |
| 1b.2b.3b.4e.5c.6a, | 1b.2b.3b.4e.5c.6b, | 1b.2b.3b.4e.5c.6c, | 1b.2b.3b.4e.5c.6d, |
| 1b.2b.3b.4e.5c.6e, | 1b.2b.3b.4e.5c.6f, | 1b.2b.3b.4e.5d.6a, | 1b.2b.3b.4e.5d.6b, |
| 1b.2b.3b.4e.5d.6c, | 1b.2b.3b.4e.5d.6d, | 1b.2b.3b.4e.5d.6e, | 1b.2b.3b.4e.5d.6f, |
| 1b.2b.3b.4e.5e.6a, | 1b.2b.3b.4e.5e.6b, | 1b.2b.3b.4e.5e.6c, | 1b.2b.3b.4e.5e.6d, |
| 1b.2b.3b.4e.5e.6e, | 1b.2b.3b.4e.5e.6f, | 1b.2b.3b.4e.5f.6a, | 1b.2b.3b.4e.5f.6b, |
| 1b.2b.3b.4e.5f.6c, | 1b.2b.3b.4e.5f.6d, | 1b.2b.3b.4e.5f.6e, | 1b.2b.3b.4e.5f.6f, |
| 1b.2b.3b.4f.5a.6a, | 1b.2b.3b.4f.5a.6b, | 1b.2b.3b.4f.5a.6c, | 1b.2b.3b.4f.5a.6d, |
| 1b.2b.3b.4f.5a.6e, | 1b.2b.3b.4f.5a.6f, | 1b.2b.3b.4f.5b.6a, | 1b.2b.3b.4f.5b.6b, |

TABLE 7-continued

List of Compounds of Formula (II)

| | | | | |
|---|---|---|---|---|
| 1b.2b.3b.4f.5b.6c, | 1b.2b.3b.4f.5b.6d, | 1b.2b.3b.4f.5b.6e, | 1b.2b.3b.4f.5b.6f, | |
| 1b.2b.3b.4f.5c.6a, | 1b.2b.3b.4f.5c.6b, | 1b.2b.3b.4f.5c.6c, | 1b.2b.3b.4f.5c.6d, | |
| 1b.2b.3b.4f.5c.6e, | 1b.2b.3b.4f.5c.6f, | 1b.2b.3b.4f.5d.6a, | 1b.2b.3b.4f.5d.6b, | |
| 1b.2b.3b.4f.5d.6c, | 1b.2b.3b.4f.5d.6d, | 1b.2b.3b.4f.5d.6e, | 1b.2b.3b.4f.5d.6f, | |
| 1b.2b.3b.4f.5e.6a, | 1b.2b.3b.4f.5e.6b, | 1b.2b.3b.4f.5e.6c, | 1b.2b.3b.4f.5e.6d, | |
| 1b.2b.3b.4f.5e.6e, | 1b.2b.3b.4f.5e.6f, | 1b.2b.3b.4f.5f.6a, | 1b.2b.3b.4f.5f.6b, | 1b.2b.3b.4f.5f.6c, |
| 1b.2b.3b.4f.5f.6d, | 1b.2b.3b.4f.5f.6e, | 1b.2b.3b.4f.5f.6f, | 1b.2b.3c.4a.5a.6a, | |
| 1b.2b.3c.4a.5a.6b, | 1b.2b.3c.4a.5a.6c, | 1b.2b.3c.4a.5a.6d, | 1b.2b.3c.4a.5a.6e, | |
| 1b.2b.3c.4a.5a.6f, | 1b.2b.3c.4a.5b.6a, | 1b.2b.3c.4a.5b.6b, | 1b.2b.3c.4a.5b.6c, | |
| 1b.2b.3c.4a.5b.6d, | 1b.2b.3c.4a.5b.6e, | 1b.2b.3c.4a.5b.6f, | 1b.2b.3c.4a.5c.6a, | |
| 1b.2b.3c.4a.5c.6b, | 1b.2b.3c.4a.5c.6c, | 1b.2b.3c.4a.5c.6d, | 1b.2b.3c.4a.5c.6e, | |
| 1b.2b.3c.4a.5c.6f, | 1b.2b.3c.4a.5d.6a, | 1b.2b.3c.4a.5d.6b, | 1b.2b.3c.4a.5d.6c, | |
| 1b.2b.3c.4a.5d.6d, | 1b.2b.3c.4a.5d.6e, | 1b.2b.3c.4a.5d.6f, | 1b.2b.3c.4a.5e.6a, | |
| 1b.2b.3c.4a.5e.6b, | 1b.2b.3c.4a.5e.6c, | 1b.2b.3c.4a.5e.6d, | 1b.2b.3c.4a.5e.6e, | |
| 1b.2b.3c.4a.5e.6f, | 1b.2b.3c.4a.5f.6a, | 1b.2b.3c.4a.5f.6b, | 1b.2b.3c.4a.5f.6c, | |
| 1b.2b.3c.4a.5f.6d, | 1b.2b.3c.4a.5f.6e, | 1b.2b.3c.4a.5f.6f, | 1b.2b.3c.4b.5a.6a, | |
| 1b.2b.3c.4b.5a.6b, | 1b.2b.3c.4b.5a.6c, | 1b.2b.3c.4b.5a.6d, | 1b.2b.3c.4b.5a.6e, | |
| 1b.2b.3c.4b.5a.6f, | 1b.2b.3c.4b.5b.6a, | 1b.2b.3c.4b.5b.6b, | 1b.2b.3c.4b.5b.6c, | |
| 1b.2b.3c.4b.5b.6d, | 1b.2b.3c.4b.5b.6e, | 1b.2b.3c.4b.5b.6f, | 1b.2b.3c.4b.5c.6a, | |
| 1b.2b.3c.4b.5c.6b, | 1b.2b.3c.4b.5c.6c, | 1b.2b.3c.4b.5c.6d, | 1b.2b.3c.4b.5c.6e, | |
| 1b.2b.3c.4b.5c.6f, | 1b.2b.3c.4b.5d.6a, | 1b.2b.3c.4b.5d.6b, | 1b.2b.3c.4b.5d.6c, | |
| 1b.2b.3c.4b.5d.6d, | 1b.2b.3c.4b.5d.6e, | 1b.2b.3c.4b.5d.6f, | 1b.2b.3c.4b.5e.6a, | |
| 1b.2b.3c.4b.5e.6b, | 1b.2b.3c.4b.5e.6c, | 1b.2b.3c.4b.5e.6d, | 1b.2b.3c.4b.5e.6e, | |
| 1b.2b.3c.4b.5e.6f, | 1b.2b.3c.4b.5f.6a, | 1b.2b.3c.4b.5f.6b, | 1b.2b.3c.4b.5f.6c, | |
| 1b.2b.3c.4b.5f.6d, | 1b.2b.3c.4b.5f.6e, | 1b.2b.3c.4b.5f.6f, | 1b.2b.3c.4c.5a.6a, | |
| 1b.2b.3c.4c.5a.6b, | 1b.2b.3c.4c.5a.6c, | 1b.2b.3c.4c.5a.6d, | 1b.2b.3c.4c.5a.6e, | |
| 1b.2b.3c.4c.5a.6f, | 1b.2b.3c.4c.5b.6a, | 1b.2b.3c.4c.5b.6b, | 1b.2b.3c.4c.5b.6c, | |
| 1b.2b.3c.4c.5b.6d, | 1b.2b.3c.4c.5b.6e, | 1b.2b.3c.4c.5b.6f, | 1b.2b.3c.4c.5c.6a, | |
| 1b.2b.3c.4c.5c.6b, | 1b.2b.3c.4c.5c.6c, | 1b.2b.3c.4c.5c.6d, | 1b.2b.3c.4c.5c.6e, | |
| 1b.2b.3c.4c.5c.6f, | 1b.2b.3c.4c.5d.6a, | 1b.2b.3c.4c.5d.6b, | 1b.2b.3c.4c.5d.6c, | |
| 1b.2b.3c.4c.5d.6d, | 1b.2b.3c.4c.5d.6e, | 1b.2b.3c.4c.5d.6f, | 1b.2b.3c.4c.5e.6a, | |
| 1b.2b.3c.4c.5e.6b, | 1b.2b.3c.4c.5e.6c, | 1b.2b.3c.4c.5e.6d, | 1b.2b.3c.4c.5e.6e, | |
| 1b.2b.3c.4c.5e.6f, | 1b.2b.3c.4c.5f.6a, | 1b.2b.3c.4c.5f.6b, | 1b.2b.3c.4c.5f.6c, | 1b.2b.3c.4c.5f.6d, |
| 1b.2b.3c.4c.5f.6e, | 1b.2b.3c.4c.5f.6f, | 1b.2b.3c.4d.5a.6a, | 1b.2b.3c.4d.5a.6b, | |
| 1b.2b.3c.4d.5a.6c, | 1b.2b.3c.4d.5a.6d, | 1b.2b.3c.4d.5a.6e, | 1b.2b.3c.4d.5a.6f, | |
| 1b.2b.3c.4d.5b.6a, | 1b.2b.3c.4d.5b.6b, | 1b.2b.3c.4d.5b.6c, | 1b.2b.3c.4d.5b.6d, | |
| 1b.2b.3c.4d.5b.6e, | 1b.2b.3c.4d.5b.6f, | 1b.2b.3c.4d.5c.6a, | 1b.2b.3c.4d.5c.6b, | |
| 1b.2b.3c.4d.5c.6c, | 1b.2b.3c.4d.5c.6d, | 1b.2b.3c.4d.5c.6e, | 1b.2b.3c.4d.5c.6f, | |
| 1b.2b.3c.4d.5d.6a, | 1b.2b.3c.4d.5d.6b, | 1b.2b.3c.4d.5d.6c, | 1b.2b.3c.4d.5d.6d, | |
| 1b.2b.3c.4d.5d.6e, | 1b.2b.3c.4d.5d.6f, | 1b.2b.3c.4d.5e.6a, | 1b.2b.3c.4d.5e.6b, | |
| 1b.2b.3c.4d.5e.6c, | 1b.2b.3c.4d.5e.6d, | 1b.2b.3c.4d.5e.6e, | 1b.2b.3c.4d.5e.6f, | |
| 1b.2b.3c.4d.5f.6a, | 1b.2b.3c.4d.5f.6b, | 1b.2b.3c.4d.5f.6c, | 1b.2b.3c.4d.5f.6d, | |
| 1b.2b.3c.4d.5f.6e, | 1b.2b.3c.4d.5f.6f, | 1b.2b.3c.4e.5a.6a, | 1b.2b.3c.4e.5a.6b, | |
| 1b.2b.3c.4e.5a.6c, | 1b.2b.3c.4e.5a.6d, | 1b.2b.3c.4e.5a.6e, | 1b.2b.3c.4e.5a.6f, | |
| 1b.2b.3c.4e.5b.6a, | 1b.2b.3c.4e.5b.6b, | 1b.2b.3c.4e.5b.6c, | 1b.2b.3c.4e.5b.6d, | |
| 1b.2b.3c.4e.5b.6e, | 1b.2b.3c.4e.5b.6f, | 1b.2b.3c.4e.5c.6a, | 1b.2b.3c.4e.5c.6b, | |
| 1b.2b.3c.4e.5c.6c, | 1b.2b.3c.4e.5c.6d, | 1b.2b.3c.4e.5c.6e, | 1b.2b.3c.4e.5c.6f, | |
| 1b.2b.3c.4e.5d.6a, | 1b.2b.3c.4e.5d.6b, | 1b.2b.3c.4e.5d.6c, | 1b.2b.3c.4e.5d.6d, | |
| 1b.2b.3c.4e.5d.6e, | 1b.2b.3c.4e.5d.6f, | 1b.2b.3c.4e.5e.6a, | 1b.2b.3c.4e.5e.6b, | |
| 1b.2b.3c.4e.5e.6c, | 1b.2b.3c.4e.5e.6d, | 1b.2b.3c.4e.5e.6e, | 1b.2b.3c.4e.5e.6f, | |
| 1b.2b.3c.4e.5f.6a, | 1b.2b.3c.4e.5f.6b, | 1b.2b.3c.4e.5f.6c, | 1b.2b.3c.4e.5f.6d, | |
| 1b.2b.3c.4e.5f.6e, | 1b.2b.3c.4e.5f.6f, | 1b.2b.3c.4f.5a.6a, | 1b.2b.3c.4f.5a.6b, | 1b.2b.3c.4f.5a.6c, |
| 1b.2b.3c.4f.5a.6d, | 1b.2b.3c.4f.5a.6e, | 1b.2b.3c.4f.5a.6f, | 1b.2b.3c.4f.5b.6a, | |
| 1b.2b.3c.4f.5b.6b, | 1b.2b.3c.4f.5b.6c, | 1b.2b.3c.4f.5b.6d, | 1b.2b.3c.4f.5b.6e, | |
| 1b.2b.3c.4f.5b.6f, | 1b.2b.3c.4f.5c.6a, | 1b.2b.3c.4f.5c.6b, | 1b.2b.3c.4f.5c.6c, | 1b.2b.3c.4f.5c.6d, |
| 1b.2b.3c.4f.5c.6e, | 1b.2b.3c.4f.5c.6f, | 1b.2b.3c.4f.5d.6a, | 1b.2b.3c.4f.5d.6b, | |
| 1b.2b.3c.4f.5d.6c, | 1b.2b.3c.4f.5d.6d, | 1b.2b.3c.4f.5d.6e, | 1b.2b.3c.4f.5d.6f, | |
| 1b.2b.3c.4f.5e.6a, | 1b.2b.3c.4f.5e.6b, | 1b.2b.3c.4f.5e.6c, | 1b.2b.3c.4f.5e.6d, | |
| 1b.2b.3c.4f.5e.6e, | 1b.2b.3c.4f.5e.6f, | 1b.2b.3c.4f.5f.6a, | 1b.2b.3c.4f.5f.6b, | 1b.2b.3c.4f.5f.6c, |
| 1b.2b.3c.4f.5f.6d, | 1b.2b.3c.4f.5f.6e, | 1b.2b.3c.4f.5f.6f, | 1b.2b.3d.4a.5a.6a, | |
| 1b.2b.3d.4a.5a.6b, | 1b.2b.3d.4a.5a.6c, | 1b.2b.3d.4a.5a.6d, | 1b.2b.3d.4a.5a.6e, | |
| 1b.2b.3d.4a.5a.6f, | 1b.2b.3d.4a.5b.6a, | 1b.2b.3d.4a.5b.6b, | 1b.2b.3d.4a.5b.6c, | |
| 1b.2b.3d.4a.5b.6d, | 1b.2b.3d.4a.5b.6e, | 1b.2b.3d.4a.5b.6f, | 1b.2b.3d.4a.5c.6a, | |
| 1b.2b.3d.4a.5c.6b, | 1b.2b.3d.4a.5c.6c, | 1b.2b.3d.4a.5c.6d, | 1b.2b.3d.4a.5c.6e, | |
| 1b.2b.3d.4a.5c.6f, | 1b.2b.3d.4a.5d.6a, | 1b.2b.3d.4a.5d.6b, | 1b.2b.3d.4a.5d.6c, | |
| 1b.2b.3d.4a.5d.6d, | 1b.2b.3d.4a.5d.6e, | 1b.2b.3d.4a.5d.6f, | 1b.2b.3d.4a.5e.6a, | |
| 1b.2b.3d.4a.5e.6b, | 1b.2b.3d.4a.5e.6c, | 1b.2b.3d.4a.5e.6d, | 1b.2b.3d.4a.5e.6e, | |
| 1b.2b.3d.4a.5e.6f, | 1b.2b.3d.4a.5f.6a, | 1b.2b.3d.4a.5f.6b, | 1b.2b.3d.4a.5f.6c, | |
| 1b.2b.3d.4a.5f.6d, | 1b.2b.3d.4a.5f.6e, | 1b.2b.3d.4a.5f.6f, | 1b.2b.3d.4b.5a.6a, | |
| 1b.2b.3d.4b.5a.6b, | 1b.2b.3d.4b.5a.6c, | 1b.2b.3d.4b.5a.6d, | 1b.2b.3d.4b.5a.6e, | |
| 1b.2b.3d.4b.5a.6f, | 1b.2b.3d.4b.5b.6a, | 1b.2b.3d.4b.5b.6b, | 1b.2b.3d.4b.5b.6c, | |
| 1b.2b.3d.4b.5b.6d, | 1b.2b.3d.4b.5b.6e, | 1b.2b.3d.4b.5b.6f, | 1b.2b.3d.4b.5c.6a, | |
| 1b.2b.3d.4b.5c.6b, | 1b.2b.3d.4b.5c.6c, | 1b.2b.3d.4b.5c.6d, | 1b.2b.3d.4b.5c.6e, | |
| 1b.2b.3d.4b.5c.6f, | 1b.2b.3d.4b.5d.6a, | 1b.2b.3d.4b.5d.6b, | 1b.2b.3d.4b.5d.6c, | |
| 1b.2b.3d.4b.5d.6d, | 1b.2b.3d.4b.5d.6e, | 1b.2b.3d.4b.5d.6f, | 1b.2b.3d.4b.5e.6a, | |
| 1b.2b.3d.4b.5e.6b, | 1b.2b.3d.4b.5e.6c, | 1b.2b.3d.4b.5e.6d, | 1b.2b.3d.4b.5e.6e, | |
| 1b.2b.3d.4b.5e.6f, | 1b.2b.3d.4b.5f.6a, | 1b.2b.3d.4b.5f.6b, | 1b.2b.3d.4b.5f.6c, | |
| 1b.2b.3d.4b.5f.6d, | 1b.2b.3d.4b.5f.6e, | 1b.2b.3d.4b.5f.6f, | 1b.2b.3d.4c.5a.6a, | |

TABLE 7-continued

List of Compounds of Formula (II)

| | | | |
|---|---|---|---|
| 1b.2b.3d.4c.5a.6b, | 1b.2b.3d.4c.5a.6c, | 1b.2b.3d.4c.5a.6d, | 1b.2b.3d.4c.5a.6e, |
| 1b.2b.3d.4c.5a.6f, | 1b.2b.3d.4c.5b.6a, | 1b.2b.3d.4c.5b.6b, | 1b.2b.3d.4c.5b.6c, |
| 1b.2b.3d.4c.5b.6d, | 1b.2b.3d.4c.5b.6e, | 1b.2b.3d.4c.5b.6f, | 1b.2b.3d.4c.5c.6a, |
| 1b.2b.3d.4c.5c.6b, | 1b.2b.3d.4c.5c.6c, | 1b.2b.3d.4c.5c.6d, | 1b.2b.3d.4c.5c.6e, |
| 1b.2b.3d.4c.5c.6f, | 1b.2b.3d.4c.5d.6a, | 1b.2b.3d.4c.5d.6b, | 1b.2b.3d.4c.5d.6c, |
| 1b.2b.3d.4c.5d.6d, | 1b.2b.3d.4c.5d.6e, | 1b.2b.3d.4c.5d.6f, | 1b.2b.3d.4c.5e.6a, |
| 1b.2b.3d.4c.5e.6b, | 1b.2b.3d.4c.5e.6c, | 1b.2b.3d.4c.5e.6d, | 1b.2b.3d.4c.5e.6e, |
| 1b.2b.3d.4c.5e.6f, | 1b.2b.3d.4c.5f.6a, | 1b.2b.3d.4c.5f.6b, | 1b.2b.3d.4c.5f.6c, |
| 1b.2b.3d.4c.5f.6d, | 1b.2b.3d.4c.5f.6e, | 1b.2b.3d.4c.5f.6f, | 1b.2b.3d.4d.5a.6a, |
| 1b.2b.3d.4d.5a.6b, | 1b.2b.3d.4d.5a.6c, | 1b.2b.3d.4d.5a.6d, | 1b.2b.3d.4d.5a.6e, |
| 1b.2b.3d.4d.5a.6f, | 1b.2b.3d.4d.5b.6a, | 1b.2b.3d.4d.5b.6b, | 1b.2b.3d.4d.5b.6c, |
| 1b.2b.3d.4d.5b.6d, | 1b.2b.3d.4d.5b.6e, | 1b.2b.3d.4d.5b.6f, | 1b.2b.3d.4d.5c.6a, |
| 1b.2b.3d.4d.5c.6b, | 1b.2b.3d.4d.5c.6c, | 1b.2b.3d.4d.5c.6d, | 1b.2b.3d.4d.5c.6e, |
| 1b.2b.3d.4d.5c.6f, | 1b.2b.3d.4d.5d.6a, | 1b.2b.3d.4d.5d.6b, | 1b.2b.3d.4d.5d.6c, |
| 1b.2b.3d.4d.5d.6d, | 1b.2b.3d.4d.5d.6e, | 1b.2b.3d.4d.5d.6f, | 1b.2b.3d.4d.5e.6a, |
| 1b.2b.3d.4d.5e.6b, | 1b.2b.3d.4d.5e.6c, | 1b.2b.3d.4d.5e.6d, | 1b.2b.3d.4d.5e.6e, |
| 1b.2b.3d.4d.5e.6f, | 1b.2b.3d.4d.5f.6a, | 1b.2b.3d.4d.5f.6b, | 1b.2b.3d.4d.5f.6c, |
| 1b.2b.3d.4d.5f.6d, | 1b.2b.3d.4d.5f.6e, | 1b.2b.3d.4d.5f.6f, | 1b.2b.3d.4e.5a.6a, |
| 1b.2b.3d.4e.5a.6b, | 1b.2b.3d.4e.5a.6c, | 1b.2b.3d.4e.5a.6d, | 1b.2b.3d.4e.5a.6e, |
| 1b.2b.3d.4e.5a.6f, | 1b.2b.3d.4e.5b.6a, | 1b.2b.3d.4e.5b.6b, | 1b.2b.3d.4e.5b.6c, |
| 1b.2b.3d.4e.5b.6d, | 1b.2b.3d.4e.5b.6e, | 1b.2b.3d.4e.5b.6f, | 1b.2b.3d.4e.5c.6a, |
| 1b.2b.3d.4e.5c.6b, | 1b.2b.3d.4e.5c.6c, | 1b.2b.3d.4e.5c.6d, | 1b.2b.3d.4e.5c.6e, |
| 1b.2b.3d.4e.5c.6f, | 1b.2b.3d.4e.5d.6a, | 1b.2b.3d.4e.5d.6b, | 1b.2b.3d.4e.5d.6c, |
| 1b.2b.3d.4e.5d.6d, | 1b.2b.3d.4e.5d.6e, | 1b.2b.3d.4e.5d.6f, | 1b.2b.3d.4e.5e.6a, |
| 1b.2b.3d.4e.5e.6b, | 1b.2b.3d.4e.5e.6c, | 1b.2b.3d.4e.5e.6d, | 1b.2b.3d.4e.5e.6e, |
| 1b.2b.3d.4e.5e.6f, | 1b.2b.3d.4e.5f.6a, | 1b.2b.3d.4e.5f.6b, | 1b.2b.3d.4e.5f.6c, |
| 1b.2b.3d.4e.5f.6d, | 1b.2b.3d.4e.5f.6e, | 1b.2b.3d.4e.5f.6f, | 1b.2b.3d.4f.5a.6a, |
| 1b.2b.3d.4f.5a.6b, | 1b.2b.3d.4f.5a.6c, | 1b.2b.3d.4f.5a.6d, | 1b.2b.3d.4f.5a.6e, |
| 1b.2b.3d.4f.5a.6f, | 1b.2b.3d.4f.5b.6a, | 1b.2b.3d.4f.5b.6b, | 1b.2b.3d.4f.5b.6c, |
| 1b.2b.3d.4f.5b.6d, | 1b.2b.3d.4f.5b.6e, | 1b.2b.3d.4f.5b.6f, | 1b.2b.3d.4f.5c.6a, |
| 1b.2b.3d.4f.5c.6b, | 1b.2b.3d.4f.5c.6c, | 1b.2b.3d.4f.5c.6d, | 1b.2b.3d.4f.5c.6e, |
| 1b.2b.3d.4f.5c.6f, | 1b.2b.3d.4f.5d.6a, | 1b.2b.3d.4f.5d.6b, | 1b.2b.3d.4f.5d.6c, |
| 1b.2b.3d.4f.5d.6d, | 1b.2b.3d.4f.5d.6e, | 1b.2b.3d.4f.5d.6f, | 1b.2b.3d.4f.5e.6a, |
| 1b.2b.3d.4f.5e.6b, | 1b.2b.3d.4f.5e.6c, | 1b.2b.3d.4f.5e.6d, | 1b.2b.3d.4f.5e.6e, |
| 1b.2b.3d.4f.5e.6f, | 1b.2b.3d.4f.5f.6a, | 1b.2b.3d.4f.5f.6b, | 1b.2b.3d.4f.5f.6c, |
| 1b.2b.3d.4f.5f.6d, | 1b.2b.3d.4f.5f.6e, | 1b.2b.3d.4f.5f.6f, | 1b.2b.3e.4a.5a.6a, |
| 1b.2b.3e.4a.5a.6b, | 1b.2b.3e.4a.5a.6c, | 1b.2b.3e.4a.5a.6d, | 1b.2b.3e.4a.5a.6e, |
| 1b.2b.3e.4a.5a.6f, | 1b.2b.3e.4a.5b.6a, | 1b.2b.3e.4a.5b.6b, | 1b.2b.3e.4a.5b.6c, |
| 1b.2b.3e.4a.5b.6d, | 1b.2b.3e.4a.5b.6e, | 1b.2b.3e.4a.5b.6f, | 1b.2b.3e.4a.5c.6a, |
| 1b.2b.3e.4a.5c.6b, | 1b.2b.3e.4a.5c.6c, | 1b.2b.3e.4a.5c.6d, | 1b.2b.3e.4a.5c.6e, |
| 1b.2b.3e.4a.5c.6f, | 1b.2b.3e.4a.5d.6a, | 1b.2b.3e.4a.5d.6b, | 1b.2b.3e.4a.5d.6c, |
| 1b.2b.3e.4a.5d.6d, | 1b.2b.3e.4a.5d.6e, | 1b.2b.3e.4a.5d.6f, | 1b.2b.3e.4a.5e.6a, |
| 1b.2b.3e.4a.5e.6b, | 1b.2b.3e.4a.5e.6c, | 1b.2b.3e.4a.5e.6d, | 1b.2b.3e.4a.5e.6e, |
| 1b.2b.3e.4a.5e.6f, | 1b.2b.3e.4a.5f.6a, | 1b.2b.3e.4a.5f.6b, | 1b.2b.3e.4a.5f.6c, |
| 1b.2b.3e.4a.5f.6d, | 1b.2b.3e.4a.5f.6e, | 1b.2b.3e.4a.5f.6f, | 1b.2b.3e.4b.5a.6a, |
| 1b.2b.3e.4b.5a.6b, | 1b.2b.3e.4b.5a.6c, | 1b.2b.3e.4b.5a.6d, | 1b.2b.3e.4b.5a.6e, |
| 1b.2b.3e.4b.5a.6f, | 1b.2b.3e.4b.5b.6a, | 1b.2b.3e.4b.5b.6b, | 1b.2b.3e.4b.5b.6c, |
| 1b.2b.3e.4b.5b.6d, | 1b.2b.3e.4b.5b.6e, | 1b.2b.3e.4b.5b.6f, | 1b.2b.3e.4b.5c.6a, |
| 1b.2b.3e.4b.5c.6b, | 1b.2b.3e.4b.5c.6c, | 1b.2b.3e.4b.5c.6d, | 1b.2b.3e.4b.5c.6e, |
| 1b.2b.3e.4b.5c.6f, | 1b.2b.3e.4b.5d.6a, | 1b.2b.3e.4b.5d.6b, | 1b.2b.3e.4b.5d.6c, |
| 1b.2b.3e.4b.5d.6d, | 1b.2b.3e.4b.5d.6e, | 1b.2b.3e.4b.5d.6f, | 1b.2b.3e.4b.5e.6a, |
| 1b.2b.3e.4b.5e.6b, | 1b.2b.3e.4b.5e.6c, | 1b.2b.3e.4b.5e.6d, | 1b.2b.3e.4b.5e.6e, |
| 1b.2b.3e.4b.5e.6f, | 1b.2b.3e.4b.5f.6a, | 1b.2b.3e.4b.5f.6b, | 1b.2b.3e.4b.5f.6c, |
| 1b.2b.3e.4b.5f.6d, | 1b.2b.3e.4b.5f.6e, | 1b.2b.3e.4b.5f.6f, | 1b.2b.3e.4c.5a.6a, |
| 1b.2b.3e.4c.5a.6b, | 1b.2b.3e.4c.5a.6c, | 1b.2b.3e.4c.5a.6d, | 1b.2b.3e.4c.5a.6e, |
| 1b.2b.3e.4c.5a.6f, | 1b.2b.3e.4c.5b.6a, | 1b.2b.3e.4c.5b.6b, | 1b.2b.3e.4c.5b.6c, |
| 1b.2b.3e.4c.5b.6d, | 1b.2b.3e.4c.5b.6e, | 1b.2b.3e.4c.5b.6f, | 1b.2b.3e.4c.5c.6a, |
| 1b.2b.3e.4c.5c.6b, | 1b.2b.3e.4c.5c.6c, | 1b.2b.3e.4c.5c.6d, | 1b.2b.3e.4c.5c.6e, |
| 1b.2b.3e.4c.5c.6f, | 1b.2b.3e.4c.5d.6a, | 1b.2b.3e.4c.5d.6b, | 1b.2b.3e.4c.5d.6c, |
| 1b.2b.3e.4c.5d.6d, | 1b.2b.3e.4c.5d.6e, | 1b.2b.3e.4c.5d.6f, | 1b.2b.3e.4c.5e.6a, |
| 1b.2b.3e.4c.5e.6b, | 1b.2b.3e.4c.5e.6c, | 1b.2b.3e.4c.5e.6d, | 1b.2b.3e.4c.5e.6e, |
| 1b.2b.3e.4c.5e.6f, | 1b.2b.3e.4c.5f.6a, | 1b.2b.3e.4c.5f.6b, | 1b.2b.3e.4c.5f.6c, |
| 1b.2b.3e.4c.5f.6d, | 1b.2b.3e.4c.5f.6e, | 1b.2b.3e.4c.5f.6f, | 1b.2b.3e.4d.5a.6a, |
| 1b.2b.3e.4d.5a.6b, | 1b.2b.3e.4d.5a.6c, | 1b.2b.3e.4d.5a.6d, | 1b.2b.3e.4d.5a.6e, |
| 1b.2b.3e.4d.5a.6f, | 1b.2b.3e.4d.5b.6a, | 1b.2b.3e.4d.5b.6b, | 1b.2b.3e.4d.5b.6c, |
| 1b.2b.3e.4d.5b.6d, | 1b.2b.3e.4d.5b.6e, | 1b.2b.3e.4d.5b.6f, | 1b.2b.3e.4d.5c.6a, |
| 1b.2b.3e.4d.5c.6b, | 1b.2b.3e.4d.5c.6c, | 1b.2b.3e.4d.5c.6d, | 1b.2b.3e.4d.5c.6e, |
| 1b.2b.3e.4d.5c.6f, | 1b.2b.3e.4d.5d.6a, | 1b.2b.3e.4d.5d.6b, | 1b.2b.3e.4d.5d.6c, |
| 1b.2b.3e.4d.5d.6d, | 1b.2b.3e.4d.5d.6e, | 1b.2b.3e.4d.5d.6f, | 1b.2b.3e.4d.5e.6a, |
| 1b.2b.3e.4d.5e.6b, | 1b.2b.3e.4d.5e.6c, | 1b.2b.3e.4d.5e.6d, | 1b.2b.3e.4d.5e.6e, |
| 1b.2b.3e.4d.5e.6f, | 1b.2b.3e.4d.5f.6a, | 1b.2b.3e.4d.5f.6b, | 1b.2b.3e.4d.5f.6c, |
| 1b.2b.3e.4d.5f.6d, | 1b.2b.3e.4d.5f.6e, | 1b.2b.3e.4d.5f.6f, | 1b.2b.3e.4e.5a.6a, |
| 1b.2b.3e.4e.5a.6b, | 1b.2b.3e.4e.5a.6c, | 1b.2b.3e.4e.5a.6d, | 1b.2b.3e.4e.5a.6e, |
| 1b.2b.3e.4e.5a.6f, | 1b.2b.3e.4e.5b.6a, | 1b.2b.3e.4e.5b.6b, | 1b.2b.3e.4e.5b.6c, |
| 1b.2b.3e.4e.5b.6d, | 1b.2b.3e.4e.5b.6e, | 1b.2b.3e.4e.5b.6f, | 1b.2b.3e.4e.5c.6a, |
| 1b.2b.3e.4e.5c.6b, | 1b.2b.3e.4e.5c.6c, | 1b.2b.3e.4e.5c.6d, | 1b.2b.3e.4e.5c.6e, |
| 1b.2b.3e.4e.5c.6f, | 1b.2b.3e.4e.5d.6a, | 1b.2b.3e.4e.5d.6b, | 1b.2b.3e.4e.5d.6c, |
| 1b.2b.3e.4e.5d.6d, | 1b.2b.3e.4e.5d.6e, | 1b.2b.3e.4e.5d.6f, | 1b.2b.3e.4e.5e.6a, |

TABLE 7-continued

List of Compounds of Formula (II)

| | | | | |
|---|---|---|---|---|
| 1b.2b.3e.4e.5e.6b, | 1b.2b.3e.4e.5e.6c, | 1b.2b.3e.4e.5e.6d, | 1b.2b.3e.4e.5e.6e, | |
| 1b.2b.3e.4e.5e.6f, | 1b.2b.3e.4e.5f.6a, | 1b.2b.3e.4e.5f.6b, | 1b.2b.3e.4e.5f.6c, | |
| 1b.2b.3e.4e.5f.6d, | 1b.2b.3e.4e.5f.6e, | 1b.2b.3e.4e.5f.6f, | 1b.2b.3e.4f.5a.6a, | |
| 1b.2b.3e.4f.5a.6b, | 1b.2b.3e.4f.5a.6c, | 1b.2b.3e.4f.5a.6d, | 1b.2b.3e.4f.5a.6e, | |
| 1b.2b.3e.4f.5a.6f, | 1b.2b.3e.4f.5b.6a, | 1b.2b.3e.4f.5b.6b, | 1b.2b.3e.4f.5b.6c, | |
| 1b.2b.3e.4f.5b.6d, | 1b.2b.3e.4f.5b.6e, | 1b.2b.3e.4f.5b.6f, | 1b.2b.3e.4f.5c.6a, | |
| 1b.2b.3e.4f.5c.6b, | 1b.2b.3e.4f.5c.6c, | 1b.2b.3e.4f.5c.6d, | 1b.2b.3e.4f.5c.6e, | 1b.2b.3e.4f.5c.6f, |
| 1b.2b.3e.4f.5d.6a, | 1b.2b.3e.4f.5d.6b, | 1b.2b.3e.4f.5d.6c, | 1b.2b.3e.4f.5d.6d, | |
| 1b.2b.3e.4f.5d.6e, | 1b.2b.3e.4f.5d.6f, | 1b.2b.3e.4f.5e.6a, | 1b.2b.3e.4f.5e.6b, | |
| 1b.2b.3e.4f.5e.6c, | 1b.2b.3e.4f.5e.6d, | 1b.2b.3e.4f.5e.6e, | 1b.2b.3e.4f.5e.6f, | 1b.2b.3e.4f.5f.6a, |
| 1b.2b.3e.4f.5f.6b, | 1b.2b.3e.4f.5f.6c, | 1b.2b.3e.4f.5f.6d, | 1b.2b.3e.4f.5f.6e, | 1b.2b.3e.4f.5f.6f, |
| 1b.2b.3f.4a.5a.6a, | 1b.2b.3f.4a.5a.6b, | 1b.2b.3f.4a.5a.6c, | 1b.2b.3f.4a.5a.6d, | |
| 1b.2b.3f.4a.5a.6e, | 1b.2b.3f.4a.5a.6f, | 1b.2b.3f.4a.5b.6a, | 1b.2b.3f.4a.5b.6b, | |
| 1b.2b.3f.4a.5b.6c, | 1b.2b.3f.4a.5b.6d, | 1b.2b.3f.4a.5b.6e, | 1b.2b.3f.4a.5b.6f, | |
| 1b.2b.3f.4a.5c.6a, | 1b.2b.3f.4a.5c.6b, | 1b.2b.3f.4a.5c.6c, | 1b.2b.3f.4a.5c.6d, | |
| 1b.2b.3f.4a.5c.6e, | 1b.2b.3f.4a.5c.6f, | 1b.2b.3f.4a.5d.6a, | 1b.2b.3f.4a.5d.6b, | |
| 1b.2b.3f.4a.5d.6c, | 1b.2b.3f.4a.5d.6d, | 1b.2b.3f.4a.5d.6e, | 1b.2b.3f.4a.5d.6f, | |
| 1b.2b.3f.4a.5e.6a, | 1b.2b.3f.4a.5e.6b, | 1b.2b.3f.4a.5e.6c, | 1b.2b.3f.4a.5e.6d, | |
| 1b.2b.3f.4a.5e.6e, | 1b.2b.3f.4a.5e.6f, | 1b.2b.3f.4a.5f.6a, | 1b.2b.3f.4a.5f.6b, | 1b.2b.3f.4a.5f.6c, |
| 1b.2b.3f.4a.5f.6d, | 1b.2b.3f.4a.5f.6e, | 1b.2b.3f.4a.5f.6f, | 1b.2b.3f.4b.5a.6a, | 1b.2b.3f.4b.5a.6b, |
| 1b.2b.3f.4b.5a.6c, | 1b.2b.3f.4b.5a.6d, | 1b.2b.3f.4b.5a.6e, | 1b.2b.3f.4b.5a.6f, | |
| 1b.2b.3f.4b.5b.6a, | 1b.2b.3f.4b.5b.6b, | 1b.2b.3f.4b.5b.6c, | 1b.2b.3f.4b.5b.6d, | |
| 1b.2b.3f.4b.5b.6e, | 1b.2b.3f.4b.5b.6f, | 1b.2b.3f.4b.5c.6a, | 1b.2b.3f.4b.5c.6b, | |
| 1b.2b.3f.4b.5c.6c, | 1b.2b.3f.4b.5c.6d, | 1b.2b.3f.4b.5c.6e, | 1b.2b.3f.4b.5c.6f, | |
| 1b.2b.3f.4b.5d.6a, | 1b.2b.3f.4b.5d.6b, | 1b.2b.3f.4b.5d.6c, | 1b.2b.3f.4b.5d.6d, | |
| 1b.2b.3f.4b.5d.6e, | 1b.2b.3f.4b.5d.6f, | 1b.2b.3f.4b.5e.6a, | 1b.2b.3f.4b.5e.6b, | |
| 1b.2b.3f.4b.5e.6c, | 1b.2b.3f.4b.5e.6d, | 1b.2b.3f.4b.5e.6e, | 1b.2b.3f.4b.5e.6f, | |
| 1b.2b.3f.4b.5f.6a, | 1b.2b.3f.4b.5f.6b, | 1b.2b.3f.4b.5f.6c, | 1b.2b.3f.4b.5f.6d, | 1b.2b.3f.4b.5f.6e, |
| 1b.2b.3f.4b.5f.6f, | 1b.2b.3f.4c.5a.6a, | 1b.2b.3f.4c.5a.6b, | 1b.2b.3f.4c.5a.6c, | 1b.2b.3f.4c.5a.6d, |
| 1b.2b.3f.4c.5a.6e, | 1b.2b.3f.4c.5a.6f, | 1b.2b.3f.4c.5b.6a, | 1b.2b.3f.4c.5b.6b, | |
| 1b.2b.3f.4c.5b.6c, | 1b.2b.3f.4c.5b.6d, | 1b.2b.3f.4c.5b.6e, | 1b.2b.3f.4c.5b.6f, | |
| 1b.2b.3f.4c.5c.6a, | 1b.2b.3f.4c.5c.6b, | 1b.2b.3f.4c.5c.6c, | 1b.2b.3f.4c.5c.6d, | 1b.2b.3f.4c.5c.6e, |
| 1b.2b.3f.4c.5c.6f, | 1b.2b.3f.4c.5d.6a, | 1b.2b.3f.4c.5d.6b, | 1b.2b.3f.4c.5d.6c, | |
| 1b.2b.3f.4c.5d.6d, | 1b.2b.3f.4c.5d.6e, | 1b.2b.3f.4c.5d.6f, | 1b.2b.3f.4c.5e.6a, | |
| 1b.2b.3f.4c.5e.6b, | 1b.2b.3f.4c.5e.6c, | 1b.2b.3f.4c.5e.6d, | 1b.2b.3f.4c.5e.6e, | 1b.2b.3f.4c.5e.6f, |
| 1b.2b.3f.4c.5f.6a, | 1b.2b.3f.4c.5f.6b, | 1b.2b.3f.4c.5f.6c, | 1b.2b.3f.4c.5f.6d, | 1b.2b.3f.4c.5f.6e, |
| 1b.2b.3f.4c.5f.6f, | 1b.2b.3f.4d.5a.6a, | 1b.2b.3f.4d.5a.6b, | 1b.2b.3f.4d.5a.6c, | |
| 1b.2b.3f.4d.5a.6d, | 1b.2b.3f.4d.5a.6e, | 1b.2b.3f.4d.5a.6f, | 1b.2b.3f.4d.5b.6a, | |
| 1b.2b.3f.4d.5b.6b, | 1b.2b.3f.4d.5b.6c, | 1b.2b.3f.4d.5b.6d, | 1b.2b.3f.4d.5b.6e, | |
| 1b.2b.3f.4d.5b.6f, | 1b.2b.3f.4d.5c.6a, | 1b.2b.3f.4d.5c.6b, | 1b.2b.3f.4d.5c.6c, | |
| 1b.2b.3f.4d.5c.6d, | 1b.2b.3f.4d.5c.6e, | 1b.2b.3f.4d.5c.6f, | 1b.2b.3f.4d.5d.6a, | |
| 1b.2b.3f.4d.5d.6b, | 1b.2b.3f.4d.5d.6c, | 1b.2b.3f.4d.5d.6d, | 1b.2b.3f.4d.5d.6e, | |
| 1b.2b.3f.4d.5d.6f, | 1b.2b.3f.4d.5e.6a, | 1b.2b.3f.4d.5e.6b, | 1b.2b.3f.4d.5e.6c, | |
| 1b.2b.3f.4d.5e.6d, | 1b.2b.3f.4d.5e.6e, | 1b.2b.3f.4d.5e.6f, | 1b.2b.3f.4d.5f.6a, | |
| 1b.2b.3f.4d.5f.6b, | 1b.2b.3f.4d.5f.6c, | 1b.2b.3f.4d.5f.6d, | 1b.2b.3f.4d.5f.6e, | 1b.2b.3f.4d.5f.6f, |
| 1b.2b.3f.4e.5a.6a, | 1b.2b.3f.4e.5a.6b, | 1b.2b.3f.4e.5a.6c, | 1b.2b.3f.4e.5a.6d, | |
| 1b.2b.3f.4e.5a.6e, | 1b.2b.3f.4e.5a.6f, | 1b.2b.3f.4e.5b.6a, | 1b.2b.3f.4e.5b.6b, | |
| 1b.2b.3f.4e.5b.6c, | 1b.2b.3f.4e.5b.6d, | 1b.2b.3f.4e.5b.6e, | 1b.2b.3f.4e.5b.6f, | |
| 1b.2b.3f.4e.5c.6a, | 1b.2b.3f.4e.5c.6b, | 1b.2b.3f.4e.5c.6c, | 1b.2b.3f.4e.5c.6d, | |
| 1b.2b.3f.4e.5c.6e, | 1b.2b.3f.4e.5c.6f, | 1b.2b.3f.4e.5d.6a, | 1b.2b.3f.4e.5d.6b, | |
| 1b.2b.3f.4e.5d.6c, | 1b.2b.3f.4e.5d.6d, | 1b.2b.3f.4e.5d.6e, | 1b.2b.3f.4e.5d.6f, | |
| 1b.2b.3f.4e.5e.6a, | 1b.2b.3f.4e.5e.6b, | 1b.2b.3f.4e.5e.6c, | 1b.2b.3f.4e.5e.6d, | |
| 1b.2b.3f.4e.5e.6e, | 1b.2b.3f.4e.5e.6f, | 1b.2b.3f.4e.5f.6a, | 1b.2b.3f.4e.5f.6b, | 1b.2b.3f.4e.5f.6c, |
| 1b.2b.3f.4e.5f.6d, | 1b.2b.3f.4e.5f.6e, | 1b.2b.3f.4e.5f.6f, | 1b.2b.3f.4f.5a.6a, | 1b.2b.3f.4f.5a.6b, |
| 1b.2b.3f.4f.5a.6c, | 1b.2b.3f.4f.5a.6d, | 1b.2b.3f.4f.5a.6e, | 1b.2b.3f.4f.5a.6f, | 1b.2b.3f.4f.5b.6a, |
| 1b.2b.3f.4f.5b.6b, | 1b.2b.3f.4f.5b.6c, | 1b.2b.3f.4f.5b.6d, | 1b.2b.3f.4f.5b.6e, | 1b.2b.3f.4f.5b.6f, |
| 1b.2b.3f.4f.5c.6a, | 1b.2b.3f.4f.5c.6b, | 1b.2b.3f.4f.5c.6c, | 1b.2b.3f.4f.5c.6d, | 1b.2b.3f.4f.5c.6e, |
| 1b.2b.3f.4f.5c.6f, | 1b.2b.3f.4f.5d.6a, | 1b.2b.3f.4f.5d.6b, | 1b.2b.3f.4f.5d.6c, | 1b.2b.3f.4f.5d.6d, |
| 1b.2b.3f.4f.5d.6e, | 1b.2b.3f.4f.5d.6f, | 1b.2b.3f.4f.5e.6a, | 1b.2b.3f.4f.5e.6b, | 1b.2b.3f.4f.5e.6c, |
| 1b.2b.3f.4f.5e.6d, | 1b.2b.3f.4f.5e.6e, | 1b.2b.3f.4f.5e.6f, | 1b.2b.3f.4f.5f.6a, | 1b.2b.3f.4f.5f.6b, |
| 1b.2b.3f.4f.5f.6c, | 1b.2b.3f.4f.5f.6d, | 1b.2b.3f.4f.5f.6e, | 1b.2b.3f.4f.5f.6f, | 1b.2c.3a.4a.5a.6a, |
| 1b.2c.3a.4a.5a.6b, | 1b.2c.3a.4a.5a.6c, | 1b.2c.3a.4a.5a.6d, | 1b.2c.3a.4a.5a.6e, | |
| 1b.2c.3a.4a.5a.6f, | 1b.2c.3a.4a.5b.6a, | 1b.2c.3a.4a.5b.6b, | 1b.2c.3a.4a.5b.6c, | |
| 1b.2c.3a.4a.5b.6d, | 1b.2c.3a.4a.5b.6e, | 1b.2c.3a.4a.5b.6f, | 1b.2c.3a.4a.5c.6a, | |
| 1b.2c.3a.4a.5c.6b, | 1b.2c.3a.4a.5c.6c, | 1b.2c.3a.4a.5c.6d, | 1b.2c.3a.4a.5c.6e, | |
| 1b.2c.3a.4a.5c.6f, | 1b.2c.3a.4a.5d.6a, | 1b.2c.3a.4a.5d.6b, | 1b.2c.3a.4a.5d.6c, | |
| 1b.2c.3a.4a.5d.6d, | 1b.2c.3a.4a.5d.6e, | 1b.2c.3a.4a.5d.6f, | 1b.2c.3a.4a.5e.6a, | |
| 1b.2c.3a.4a.5e.6b, | 1b.2c.3a.4a.5e.6c, | 1b.2c.3a.4a.5e.6d, | 1b.2c.3a.4a.5e.6e, | |
| 1b.2c.3a.4a.5e.6f, | 1b.2c.3a.4a.5f.6a, | 1b.2c.3a.4a.5f.6b, | 1b.2c.3a.4a.5f.6c, | 1b.2c.3a.4a.5f.6d, |
| 1b.2c.3a.4a.5f.6e, | 1b.2c.3a.4a.5f.6f, | 1b.2c.3a.4b.5a.6a, | 1b.2c.3a.4b.5a.6b, | |
| 1b.2c.3a.4b.5a.6c, | 1b.2c.3a.4b.5a.6d, | 1b.2c.3a.4b.5a.6e, | 1b.2c.3a.4b.5a.6f, | |
| 1b.2c.3a.4b.5b.6a, | 1b.2c.3a.4b.5b.6b, | 1b.2c.3a.4b.5b.6c, | 1b.2c.3a.4b.5b.6d, | |
| 1b.2c.3a.4b.5b.6e, | 1b.2c.3a.4b.5b.6f, | 1b.2c.3a.4b.5c.6a, | 1b.2c.3a.4b.5c.6b, | |
| 1b.2c.3a.4b.5c.6c, | 1b.2c.3a.4b.5c.6d, | 1b.2c.3a.4b.5c.6e, | 1b.2c.3a.4b.5c.6f, | |
| 1b.2c.3a.4b.5d.6a, | 1b.2c.3a.4b.5d.6b, | 1b.2c.3a.4b.5d.6c, | 1b.2c.3a.4b.5d.6d, | |
| 1b.2c.3a.4b.5d.6e, | 1b.2c.3a.4b.5d.6f, | 1b.2c.3a.4b.5e.6a, | 1b.2c.3a.4b.5e.6b, | |
| 1b.2c.3a.4b.5e.6c, | 1b.2c.3a.4b.5e.6d, | 1b.2c.3a.4b.5e.6e, | 1b.2c.3a.4b.5e.6f, | |
| 1b.2c.3a.4b.5f.6a, | 1b.2c.3a.4b.5f.6b, | 1b.2c.3a.4b.5f.6c, | 1b.2c.3a.4b.5f.6d, | |

TABLE 7-continued

List of Compounds of Formula (II)

| | | | | |
|---|---|---|---|---|
| 1b.2c.3a.4b.5f.6e, | 1b.2c.3a.4b.5f.6f, | 1b.2c.3a.4c.5a.6a, | 1b.2c.3a.4c.5a.6b, | |
| 1b.2c.3a.4c.5a.6c, | 1b.2c.3a.4c.5a.6d, | 1b.2c.3a.4c.5a.6e, | 1b.2c.3a.4c.5a.6f, | |
| 1b.2c.3a.4c.5b.6a, | 1b.2c.3a.4c.5b.6b, | 1b.2c.3a.4c.5b.6c, | 1b.2c.3a.4c.5b.6d, | |
| 1b.2c.3a.4c.5b.6e, | 1b.2c.3a.4c.5b.6f, | 1b.2c.3a.4c.5c.6a, | 1b.2c.3a.4c.5c.6b, | |
| 1b.2c.3a.4c.5c.6c, | 1b.2c.3a.4c.5c.6d, | 1b.2c.3a.4c.5c.6e, | 1b.2c.3a.4c.5c.6f, | |
| 1b.2c.3a.4c.5d.6a, | 1b.2c.3a.4c.5d.6b, | 1b.2c.3a.4c.5d.6c, | 1b.2c.3a.4c.5d.6d, | |
| 1b.2c.3a.4c.5d.6e, | 1b.2c.3a.4c.5d.6f, | 1b.2c.3a.4c.5e.6a, | 1b.2c.3a.4c.5e.6b, | |
| 1b.2c.3a.4c.5e.6c, | 1b.2c.3a.4c.5e.6d, | 1b.2c.3a.4c.5e.6e, | 1b.2c.3a.4c.5e.6f, | 1b.2c.3a.4c.5f.6a, |
| 1b.2c.3a.4c.5f.6b, | 1b.2c.3a.4c.5f.6c, | 1b.2c.3a.4c.5f.6d, | 1b.2c.3a.4c.5f.6e, | 1b.2c.3a.4c.5f.6f, |
| 1b.2c.3a.4d.5a.6a, | 1b.2c.3a.4d.5a.6b, | 1b.2c.3a.4d.5a.6c, | 1b.2c.3a.4d.5a.6d, | |
| 1b.2c.3a.4d.5a.6e, | 1b.2c.3a.4d.5a.6f, | 1b.2c.3a.4d.5b.6a, | 1b.2c.3a.4d.5b.6b, | |
| 1b.2c.3a.4d.5b.6c, | 1b.2c.3a.4d.5b.6d, | 1b.2c.3a.4d.5b.6e, | 1b.2c.3a.4d.5b.6f, | |
| 1b.2c.3a.4d.5c.6a, | 1b.2c.3a.4d.5c.6b, | 1b.2c.3a.4d.5c.6c, | 1b.2c.3a.4d.5c.6d, | |
| 1b.2c.3a.4d.5c.6e, | 1b.2c.3a.4d.5c.6f, | 1b.2c.3a.4d.5d.6a, | 1b.2c.3a.4d.5d.6b, | |
| 1b.2c.3a.4d.5d.6c, | 1b.2c.3a.4d.5d.6d, | 1b.2c.3a.4d.5d.6e, | 1b.2c.3a.4d.5d.6f, | |
| 1b.2c.3a.4d.5e.6a, | 1b.2c.3a.4d.5e.6b, | 1b.2c.3a.4d.5e.6c, | 1b.2c.3a.4d.5e.6d, | |
| 1b.2c.3a.4d.5e.6e, | 1b.2c.3a.4d.5e.6f, | 1b.2c.3a.4d.5f.6a, | 1b.2c.3a.4d.5f.6b, | |
| 1b.2c.3a.4d.5f.6c, | 1b.2c.3a.4d.5f.6d, | 1b.2c.3a.4d.5f.6e, | 1b.2c.3a.4d.5f.6f, | |
| 1b.2c.3a.4e.5a.6a, | 1b.2c.3a.4e.5a.6b, | 1b.2c.3a.4e.5a.6c, | 1b.2c.3a.4e.5a.6d, | |
| 1b.2c.3a.4e.5a.6e, | 1b.2c.3a.4e.5a.6f, | 1b.2c.3a.4e.5b.6a, | 1b.2c.3a.4e.5b.6b, | |
| 1b.2c.3a.4e.5b.6c, | 1b.2c.3a.4e.5b.6d, | 1b.2c.3a.4e.5b.6e, | 1b.2c.3a.4e.5b.6f, | |
| 1b.2c.3a.4e.5c.6a, | 1b.2c.3a.4e.5c.6b, | 1b.2c.3a.4e.5c.6c, | 1b.2c.3a.4e.5c.6d, | |
| 1b.2c.3a.4e.5c.6e, | 1b.2c.3a.4e.5c.6f, | 1b.2c.3a.4e.5d.6a, | 1b.2c.3a.4e.5d.6b, | |
| 1b.2c.3a.4e.5d.6c, | 1b.2c.3a.4e.5d.6d, | 1b.2c.3a.4e.5d.6e, | 1b.2c.3a.4e.5d.6f, | |
| 1b.2c.3a.4e.5e.6a, | 1b.2c.3a.4e.5e.6b, | 1b.2c.3a.4e.5e.6c, | 1b.2c.3a.4e.5e.6d, | |
| 1b.2c.3a.4e.5e.6e, | 1b.2c.3a.4e.5e.6f, | 1b.2c.3a.4e.5f.6a, | 1b.2c.3a.4e.5f.6b, | 1b.2c.3a.4e.5f.6c, |
| 1b.2c.3a.4e.5f.6d, | 1b.2c.3a.4e.5f.6e, | 1b.2c.3a.4e.5f.6f, | 1b.2c.3a.4f.5a.6a, | 1b.2c.3a.4f.5a.6b, |
| 1b.2c.3a.4f.5a.6c, | 1b.2c.3a.4f.5a.6d, | 1b.2c.3a.4f.5a.6e, | 1b.2c.3a.4f.5a.6f, | 1b.2c.3a.4f.5b.6a, |
| 1b.2c.3a.4f.5b.6b, | 1b.2c.3a.4f.5b.6c, | 1b.2c.3a.4f.5b.6d, | 1b.2c.3a.4f.5b.6e, | 1b.2c.3a.4f.5b.6f, |
| 1b.2c.3a.4f.5c.6a, | 1b.2c.3a.4f.5c.6b, | 1b.2c.3a.4f.5c.6c, | 1b.2c.3a.4f.5c.6d, | 1b.2c.3a.4f.5c.6e, |
| 1b.2c.3a.4f.5c.6f, | 1b.2c.3a.4f.5d.6a, | 1b.2c.3a.4f.5d.6b, | 1b.2c.3a.4f.5d.6c, | |
| 1b.2c.3a.4f.5d.6d, | 1b.2c.3a.4f.5d.6e, | 1b.2c.3a.4f.5d.6f, | 1b.2c.3a.4f.5e.6a, | |
| 1b.2c.3a.4f.5e.6b, | 1b.2c.3a.4f.5e.6c, | 1b.2c.3a.4f.5e.6d, | 1b.2c.3a.4f.5e.6e, | 1b.2c.3a.4f.5e.6f, |
| 1b.2c.3a.4f.5f.6a, | 1b.2c.3a.4f.5f.6b, | 1b.2c.3a.4f.5f.6c, | 1b.2c.3a.4f.5f.6d, | 1b.2c.3a.4f.5f.6e, |
| 1b.2c.3a.4f.5f.6f, | 1b.2c.3b.4a.5a.6a, | 1b.2c.3b.4a.5a.6b, | 1b.2c.3b.4a.5a.6c, | |
| 1b.2c.3b.4a.5a.6d, | 1b.2c.3b.4a.5a.6e, | 1b.2c.3b.4a.5a.6f, | 1b.2c.3b.4a.5b.6a, | |
| 1b.2c.3b.4a.5b.6b, | 1b.2c.3b.4a.5b.6c, | 1b.2c.3b.4a.5b.6d, | 1b.2c.3b.4a.5b.6e, | |
| 1b.2c.3b.4a.5b.6f, | 1b.2c.3b.4a.5c.6a, | 1b.2c.3b.4a.5c.6b, | 1b.2c.3b.4a.5c.6c, | |
| 1b.2c.3b.4a.5c.6d, | 1b.2c.3b.4a.5c.6e, | 1b.2c.3b.4a.5c.6f, | 1b.2c.3b.4a.5d.6a, | |
| 1b.2c.3b.4a.5d.6b, | 1b.2c.3b.4a.5d.6c, | 1b.2c.3b.4a.5d.6d, | 1b.2c.3b.4a.5d.6e, | |
| 1b.2c.3b.4a.5d.6f, | 1b.2c.3b.4a.5e.6a, | 1b.2c.3b.4a.5e.6b, | 1b.2c.3b.4a.5e.6c, | |
| 1b.2c.3b.4a.5e.6d, | 1b.2c.3b.4a.5e.6e, | 1b.2c.3b.4a.5e.6f, | 1b.2c.3b.4a.5f.6a, | |
| 1b.2c.3b.4a.5f.6b, | 1b.2c.3b.4a.5f.6c, | 1b.2c.3b.4a.5f.6d, | 1b.2c.3b.4a.5f.6e, | 1b.2c.3b.4a.5f.6f, |
| 1b.2c.3b.4b.5a.6a, | 1b.2c.3b.4b.5a.6b, | 1b.2c.3b.4b.5a.6c, | 1b.2c.3b.4b.5a.6d, | |
| 1b.2c.3b.4b.5a.6e, | 1b.2c.3b.4b.5a.6f, | 1b.2c.3b.4b.5b.6a, | 1b.2c.3b.4b.5b.6b, | |
| 1b.2c.3b.4b.5b.6c, | 1b.2c.3b.4b.5b.6d, | 1b.2c.3b.4b.5b.6e, | 1b.2c.3b.4b.5b.6f, | |
| 1b.2c.3b.4b.5c.6a, | 1b.2c.3b.4b.5c.6b, | 1b.2c.3b.4b.5c.6c, | 1b.2c.3b.4b.5c.6d, | |
| 1b.2c.3b.4b.5c.6e, | 1b.2c.3b.4b.5c.6f, | 1b.2c.3b.4b.5d.6a, | 1b.2c.3b.4b.5d.6b, | |
| 1b.2c.3b.4b.5d.6c, | 1b.2c.3b.4b.5d.6d, | 1b.2c.3b.4b.5d.6e, | 1b.2c.3b.4b.5d.6f, | |
| 1b.2c.3b.4b.5e.6a, | 1b.2c.3b.4b.5e.6b, | 1b.2c.3b.4b.5e.6c, | 1b.2c.3b.4b.5e.6d, | |
| 1b.2c.3b.4b.5e.6e, | 1b.2c.3b.4b.5e.6f, | 1b.2c.3b.4b.5f.6a, | 1b.2c.3b.4b.5f.6b, | |
| 1b.2c.3b.4b.5f.6c, | 1b.2c.3b.4b.5f.6d, | 1b.2c.3b.4b.5f.6e, | 1b.2c.3b.4b.5f.6f, | |
| 1b.2c.3b.4c.5a.6a, | 1b.2c.3b.4c.5a.6b, | 1b.2c.3b.4c.5a.6c, | 1b.2c.3b.4c.5a.6d, | |
| 1b.2c.3b.4c.5a.6e, | 1b.2c.3b.4c.5a.6f, | 1b.2c.3b.4c.5b.6a, | 1b.2c.3b.4c.5b.6b, | |
| 1b.2c.3b.4c.5b.6c, | 1b.2c.3b.4c.5b.6d, | 1b.2c.3b.4c.5b.6e, | 1b.2c.3b.4c.5b.6f, | |
| 1b.2c.3b.4c.5c.6a, | 1b.2c.3b.4c.5c.6b, | 1b.2c.3b.4c.5c.6c, | 1b.2c.3b.4c.5c.6d, | |
| 1b.2c.3b.4c.5c.6e, | 1b.2c.3b.4c.5c.6f, | 1b.2c.3b.4c.5d.6a, | 1b.2c.3b.4c.5d.6b, | |
| 1b.2c.3b.4c.5d.6c, | 1b.2c.3b.4c.5d.6d, | 1b.2c.3b.4c.5d.6e, | 1b.2c.3b.4c.5d.6f, | |
| 1b.2c.3b.4c.5e.6a, | 1b.2c.3b.4c.5e.6b, | 1b.2c.3b.4c.5e.6c, | 1b.2c.3b.4c.5e.6d, | |
| 1b.2c.3b.4c.5e.6e, | 1b.2c.3b.4c.5e.6f, | 1b.2c.3b.4c.5f.6a, | 1b.2c.3b.4c.5f.6b, | 1b.2c.3b.4c.516c, |
| 1b.2c.3b.4c.5f.6d, | 1b.2c.3b.4c.5f.6e, | 1b.2c.3b.4c.5f.6f, | 1b.2c.3b.4d.5a.6a, | |
| 1b.2c.3b.4d.5a.6b, | 1b.2c.3b.4d.5a.6c, | 1b.2c.3b.4d.5a.6d, | 1b.2c.3b.4d.5a.6e, | |
| 1b.2c.3b.4d.5a.6f, | 1b.2c.3b.4d.5b.6a, | 1b.2c.3b.4d.5b.6b, | 1b.2c.3b.4d.5b.6c, | |
| 1b.2c.3b.4d.5b.6d, | 1b.2c.3b.4d.5b.6e, | 1b.2c.3b.4d.5b.6f, | 1b.2c.3b.4d.5c.6a, | |
| 1b.2c.3b.4d.5c.6b, | 1b.2c.3b.4d.5c.6c, | 1b.2c.3b.4d.5c.6d, | 1b.2c.3b.4d.5c.6e, | |
| 1b.2c.3b.4d.5c.6f, | 1b.2c.3b.4d.5d.6a, | 1b.2c.3b.4d.5d.6b, | 1b.2c.3b.4d.5d.6c, | |
| 1b.2c.3b.4d.5d.6d, | 1b.2c.3b.4d.5d.6e, | 1b.2c.3b.4d.5d.6f, | 1b.2c.3b.4d.5e.6a, | |
| 1b.2c.3b.4d.5e.6b, | 1b.2c.3b.4d.5e.6c, | 1b.2c.3b.4d.5e.6d, | 1b.2c.3b.4d.5e.6e, | |
| 1b.2c.3b.4d.5e.6f, | 1b.2c.3b.4d.5f.6a, | 1b.2c.3b.4d.5f.6b, | 1b.2c.3b.4d.5f.6c, | |
| 1b.2c.3b.4d.5f.6d, | 1b.2c.3b.4d.5f.6e, | 1b.2c.3b.4d.5f.6f, | 1b.2c.3b.4e.5a.6a, | |
| 1b.2c.3b.4e.5a.6b, | 1b.2c.3b.4e.5a.6c, | 1b.2c.3b.4e.5a.6d, | 1b.2c.3b.4e.5a.6e, | |
| 1b.2c.3b.4e.5a.6f, | 1b.2c.3b.4e.5b.6a, | 1b.2c.3b.4e.5b.6b, | 1b.2c.3b.4e.5b.6c, | |
| 1b.2c.3b.4e.5b.6d, | 1b.2c.3b.4e.5b.6e, | 1b.2c.3b.4e.5b.6f, | 1b.2c.3b.4e.5c.6a, | |
| 1b.2c.3b.4e.5c.6b, | 1b.2c.3b.4e.5c.6c, | 1b.2c.3b.4e.5c.6d, | 1b.2c.3b.4e.5c.6e, | |
| 1b.2c.3b.4e.5c.6f, | 1b.2c.3b.4e.5d.6a, | 1b.2c.3b.4e.5d.6b, | 1b.2c.3b.4e.5d.6c, | |
| s1b.2c.3b.4e.5d.6d, | 1b.2c.3b.4e.5d.6e, | 1b.2c.3b.4e.5d.6f, | 1b.2c.3b.4e.5e.6a, | |
| 1b.2c.3b.4e.5e.6b, | 1b.2c.3b.4e.5e.6c, | 1b.2c.3b.4e.5e.6d, | 1b.2c.3b.4e.5e.6e, | |
| 1b.2c.3b.4e.5e.6f, | 1b.2c.3b.4e.5f.6a, | 1b.2c.3b.4e.5f.6b, | 1b.2c.3b.4e.5f.6c, | |

TABLE 7-continued

List of Compounds of Formula (II)

| | | | | |
|---|---|---|---|---|
| 1b.2c.3b.4e.5f.6d, | 1b.2c.3b.4e.5f.6e, | 1b.2c.3b.4e.5f.6f, | 1b.2c.3b.4f.5a.6a, | 1b.2c.3b.4f.5a.6b, |
| 1b.2c.3b.4f.5a.6c, | 1b.2c.3b.4f.5a.6d, | 1b.2c.3b.4f.5a.6e, | 1b.2c.3b.4f.5a.6f, | 1b.2c.3b.4f.5b.6a, |
| 1b.2c.3b.4f.5b.6b, | 1b.2c.3b.4f.5b.6c, | 113.2c.3b.4f.5b.6d, | 1b.2c.3b.4f.5b.6e, | |
| 1b.2c.3b.4f.5b.6f, | 1b.2c.3b.4f.5c.6a, | 1b.2c.3b.4f.5c.6b, | 1b.2c.3b.4f.5c.6c, | 1b.2c.3b.4f.5c.6d, |
| 1b.2c.3b.4f.5c.6e, | 1b.2c.3b.4f.5c.6f, | 1b.2c.3b.4f.5d.6a, | 1b.2c.3b.4f.5d.6b, | |
| 1b.2c.3b.4f.5d.6c, | 1b.2c.3b.4f.5d.6d, | 1b.2c.3b.4f.5d.6e, | 1b.2c.3b.4f.5d.6f, | |
| 1b.2c.3b.4f.5e.6a, | 1b.2c.3b.4f.5e.6b, | 1b.2c.3b.4f.5e.6c, | 1b.2c.3b.4f.5e.6d, | |
| 1b.2c.3b.4f.5e.6e, | 1b.2c.3b.4f.5e.6f, | 1b.2c.3b.4f.5f.6a, | 1b.2c.3b.4f.5f.6b, | 1b.2c.3b.4f.5f.6c, |
| 1b.2c.3b.4f.5f.6d, | 1b.2c.3b.4f.5f.6e, | 1b.2c.3b.4f.5f.6f, | 1b.2c.3c.4a.5a.6a, | 1b.2c.3c.4a.5a.6b, |
| 1b.2c.3c.4a.5a.6c, | 1b.2c.3c.4a.5a.6d, | 1b.2c.3c.4a.5a.6e, | 1b.2c.3c.4a.5a.6f, | |
| 1b.2c.3c.4a.5b.6a, | 1b.2c.3c.4a.5b.6b, | 1b.2c.3c.4a.5b.6c, | 1b.2c.3c.4a.5b.6d, | |
| 1b.2c.3c.4a.5b.6e, | 1b.2c.3c.4a.5b.6f, | 1b.2c.3c.4a.5c.6a, | 1b.2c.3c.4a.5c.6b, | |
| 1b.2c.3c.4a.5c.6c, | 1b.2c.3c.4a.5c.6d, | 1b.2c.3c.4a.5c.6e, | 1b.2c.3c.4a.5c.6f, | |
| 1b.2c.3c.4a.5d.6a, | 1b.2c.3c.4a.5d.6b, | 1b.2c.3c.4a.5d.6c, | 1b.2c.3c.4a.5d.6d, | |
| 1b.2c.3c.4a.5d.6e, | 1b.2c.3c.4a.5d.6f, | 1b.2c.3c.4a.5e.6a, | 1b.2c.3c.4a.5e.6b, | |
| 1b.2c.3c.4a.5e.6c, | 1b.2c.3c.4a.5e.6d, | 1b.2c.3c.4a.5e.6e, | 1b.2c.3c.4a.5e.6f, | 1b.2c.3c.4a.5f.6a, |
| 1b.2c.3c.4a.5f.6b, | 1b.2c.3c.4a.5f.6c, | 1b.2c.3c.4a.5f.6d, | 1b.2c.3c.4a.5f.6e, | 1b.2c.3c.4a.5f.6f, |
| 1b.2c.3c.4b.5a.6a, | 1b.2c.3c.4b.5a.6b, | 1b.2c.3c.4b.5a.6c, | 1b.2c.3c.4b.5a.6d, | |
| 1b.2c.3c.4b.5a.6e, | 1b.2c.3c.4b.5a.6f, | 1b.2c.3c.4b.5b.6a, | 1b.2c.3c.4b.5b.6b, | |
| 1b.2c.3c.4b.5b.6c, | 1b.2c.3c.4b.5b.6d, | 1b.2c.3c.4b.5b.6e, | 1b.2c.3c.4b.5b.6f, | |
| 1b.2c.3c.4b.5c.6a, | 1b.2c.3c.4b.5c.6b, | 1b.2c.3c.4b.5c.6c, | 1b.2c.3c.4b.5c.6d,, | |
| 1b.2c.3c.4b.5c.6e, | 1b.2c.3c.4b.5c.6f, | 1b.2c.3c.4b.5d.6a, | 1b.2c.3c.4b.5d.6b, | |
| 1b.2c.3c.4b.5d.6c, | 1b.2c.3c.4b.5d.6d, | 1b.2c.3c.4b.5d.6e, | 1b.2c.3c.4b.5d.6f, | |
| 1b.2c.3c.4b.5e.6a, | 1b.2c.3c.4b.5e.6b, | 1b.2c.3c.4b.5e.6c, | 1b.2c.3c.4b.5e.6d, | |
| 1b.2c.3c.4b.5e.6e, | 1b.2c.3c.4b.5e.6f, | 1b.2c.3c.4b.5f.6a, | 1b.2c.3c.4b.5f.6b, | 1b.2c.3c.4b.5f.6c, |
| 1b.2c.3c.4b.5f.6d, | 1b.2c.3c.4b.5f.6e, | 1b.2c.3c.4b.5f.6f, | 1b.2c.3c.4c.5a.6a, | 1b.2c.3c.4c.5a.6b, |
| 1b.2c.3c.4c.5a.6c, | 1b.2c.3c.4c.5a.6d, | 1b.2c.3c.4c.5a.6e, | 1b.2c.3c.4c.5a.6f, | 1b.2c.3c.4c.5b.6a, |
| 1b.2c.3c.4c.5b.6b, | 1b.2c.3c.4c.5b.6c, | 1b.2c.3c.4c.5b.6d, | 1b.2c.3c.4c.5b.6e, | |
| 1b.2c.3c.4c.5b.6f, | 1b.2c.3c.4c.5c.6a, | 1b.2c.3c.4c.5c.6b, | 1b.2c.3c.4c.5c.6c, | 1b.2c.3c.4c.5c.6d, |
| 1b.2c.3c.4c.5c.6e, | 1b.2c.3c.4c.5c.6f, | 1b.2c.3c.4c.5d.6a, | 1b.2c.3c.4c.5d.6b, | |
| 1b.2c.3c.4c.5d.6c, | 1b.2c.3c.4c.5d.6d, | 1b.2c.3c.4c.5d.6e, | 1b.2c.3c.4c.5d.6f, | |
| 1b.2c.3c.4c.5e.6a, | 1b.2c.3c.4c.5e.6b, | 1b.2c.3c.4c.5e.6c, | 1b.2c.3c.4c.5e.6d, | |
| 1b.2c.3c.4c.5e.6e, | 1b.2c.3c.4c.5e.6f, | 1b.2c.3c.4c.5f.6a, | 1b.2c.3c.4c.5f.6b, | 1b.2c.3c.4c.5f.6c, |
| 1b.2c.3c.4c.5f.6d, | 1b.2c.3c.4c.5f.6e, | 1b.2c.3c.4c.5f.6f, | 1b.2c.3c.4d.5a.6a, | 1b.2c.3c.4d.5a.6b, |
| 1b.2c.3c.4d.5a.6c, | 1b.2c.3c.4d.5a.6d, | 1b.2c.3c.4d.5a.6e, | 1b.2c.3c.4d.5a.6f, | |
| 1b.2c.3c.4d.5b.6a, | 1b.2c.3c.4d.5b.6b, | 1b.2c.3c.4d.5b.6c, | 1b.2c.3c.4d.5b.6d, | |
| 1b.2c.3c.4d.5b.6e, | 1b.2c.3c.4d.5b.6f, | 1b.2c.3c.4d.5c.6a, | 1b.2c.3c.4d.5c.6b, | |
| 1b.2c.3c.4d.5c.6c, | 1b.2c.3c.4d.5c.6d, | 1b.2c.3c.4d.5c.6e, | 1b.2c.3c.4d.5c.6f, | |
| 1b.2c.3c.4d.5d.6a, | 1b.2c.3c.4d.5d.6b, | 1b.2c.3c.4d.5d.6c, | 1b.2c.3c.4d.5d.6d, | |
| 1b.2c.3c.4d.5d.6e, | 1b.2c.3c.4d.5d.6f, | 1b.2c.3c.4d.5e.6a, | 1b.2c.3c.4d.5e.6b, | |
| 1b.2c.3c.4d.5e.6c, | 1b.2c.3c.4d.5e.6d, | 1b.2c.3c.4d.5e.6e, | 1b.2c.3c.4d.5e.6f, | |
| 1b.2c.3c.4d.5f.6a, | 1b.2c.3c.4d.5f.6b, | 1b.2c.3c.4d.5f.6c, | 1b.2c.3c.4d.5f.6d, | |
| 1b.2c.3c.4d.5f.6e, | 1b.2c.3c.4d.5f.6f, | 1b.2c.3c.4e.5a.6a, | 1b.2c.3c.4e.5a.6b, | 1b.2c.3c.4e.5a.6c, |
| 1b.2c.3c.4e.5a.6d, | 1b.2c.3c.4e.5a.6e, | 1b.2c.3c.4e.5a.6f, | 1b.2c.3c.4e.5b.6a, | |
| 1b.2c.3c.4e.5b.6b, | 1b.2c.3c.4e.5b.6c, | 1b.2c.3c.4e.5b.6d, | 1b.2c.3c.4e.5b.6e, | |
| 1b.2c.3c.4e.5b.6f, | 1b.2c.3c.4e.5c.6a, | 1b.2c.3c.4e.5c.6b, | 1b.2c.3c.4e.5c.6c, | 1b.2c.3c.4e.5c.6d, |
| 1b.2c.3c.4e.5c.6e, | 1b.2c.3c.4e.5c.6f, | 1b.2c.3c.4e.5d.6a, | 1b.2c.3c.4e.5d.6b, | |
| 1b.2c.3c.4e.5d.6c, | 1b.2c.3c.4e.5d.6d, | 1b.2c.3c.4e.5d.6e, | 1b.2c.3c.4e.5d.6f, | |
| 1b.2c.3c.4e.5e.6a, | 1b.2c.3c.4e.5e.6b, | 1b.2c.3c.4e.5e.6c, | 1b.2c.3c.4e.5e.6d, | |
| 1b.2c.3c.4e.5e.6e, | 1b.2c.3c.4e.5e.6f, | 1b.2c.3c.4e.5f.6a, | 1b.2c.3c.4e.5f.6b, | 1b.2c.3c.4e.5f.6c, |
| 1b.2c.3c.4e.5f.6d, | 1b.2c.3c.4e.5f.6e, | 1b.2c.3c.4e.5f.6f, | 1b.2c.3c.4f.5a.6a, | 1b.2c.3c.4f.5a.6b, |
| 1b.2c.3c.4f.5a.6c, | 1b.2c.3c.4f.5a.6d, | 1b.2c.3c.4f.5a.6e, | 1b.2c.3c.4f.5a.6f, | 1b.2c.3c.4f.5b.6a, |
| 1b.2c.3c.4f.5b.6b, | 1b.2c.3c.4f.5b.6c, | 1b.2c.3c.4f.5b.6d, | 1b.2c.3c.4f.5b.6e, | 1b.2c.3c.4f.5b.6f, |
| 1b.2c.3c.4f.5c.6a, | 1b.2c.3c.4f.5c.6b, | 1b.2c.3c.4f.5c.6c, | 1b.2c.3c.4f.5c.6d, | 1b.2c.3c.4f.5c.6e, |
| 1b.2c.3c.4f.5c.6f, | 1b.2c.3c.4f.5d.6a, | 1b.2c.3c.4f.5d.6b, | 1b.2c.3c.4f.5d.6c, | 1b.2c.3c.4f.5d.6d, |
| 1b.2c.3c.4f.5d.6e, | 1b.2c.3c.4f.5d.6f, | 1b.2c.3c.4f.5e.6a, | 1b.2c.3c.4f.5e.6b, | 1b.2c.3c.4f.5e.6c, |
| 1b.2c.3c.4f.5e.6d, | 1b.2c.3c.4f.5e.6e, | 1b.2c.3c.4f.5e.6f, | 1b.2c.3c.4f.5f.6a, | 1b.2c.3c.4f.5f.6b, |
| 1b.2c.3c.4f.5f.6c, | 1b.2c.3c.4f.5f.6d, | 1b.2c.3c.4f.5f.6e, | 1b.2c.3c.4f.5f.6f, | 1b.2c.3d.4a.5a.6a, |
| 1b.2c.3d.4a.5a.6b, | 1b.2c.3d.4a.5a.6c, | 1b.2c.3d.4a.5a.6d, | 1b.2c.3d.4a.5a.6e, | |
| 1b.2c.3d.4a.5a.6f, | 1b.2c.3d.4a.5b.6a, | 1b.2c.3d.4a.5b.6b, | 1b.2c.3d.4a.5b.6c, | |
| 1b.2c.3d.4a.5b.6d, | 1b.2c.3d.4a.5b.6e, | 1b.2c.3d.4a.5b.6f, | 1b.2c.3d.4a.5c.6a, | |
| 1b.2c.3d.4a.5c.6b, | 1b.2c.3d.4a.5c.6c, | 1b.2c.3d.4a.5c.6d, | 1b.2c.3d.4a.5c.6e, | |
| 1b.2c.3d.4a.5c.6f, | 1b.2c.3d.4a.5d.6a, | 1b.2c.3d.4a.5d.6b, | 1b.2c.3d.4a.5d.6c, | |
| 1b.2c.3d.4a.5d.6d, | 1b.2c.3d.4a.5d.6e, | 1b.2c.3d.4a.5d.6f, | 1b.2c.3d.4a.5e.6a, | |
| 1b.2c.3d.4a.5e.6b, | 1b.2c.3d.4a.5e.6c, | 1b.2c.3d.4a.5e.6d, | 1b.2c.3d.4a.5e.6e, | |
| 1b.2c.3d.4a.5e.6f, | 1b.2c.3d.4a.5f.6a, | 1b.2c.3d.4a.5f.6b, | 1b.2c.3d.4a.5f.6c, | |
| 1b.2c.3d.4a.5f.6d, | 1b.2c.3d.4a.5f.6e, | 1b.2c.3d.4a.5f.6f, | 1b.2c.3d.4b.5a.6a, | |
| 1b.2c.3d.4b.5a.6b, | 1b.2c.3d.4b.5a.6c, | 1b.2c.3d.4b.5a.6d, | 1b.2c.3d.4b.5a.6e, | |
| 1b.2c.3d.4b.5a.6f, | 1b.2c.3d.4b.5b.6a, | 1b.2c.3d.4b.5b.6b, | 1b.2c.3d.4b.5b.6c, | |
| 1b.2c.3d.4b.5b.6d, | 1b.2c.3d.4b.5b.6e, | 1b.2c.3d.4b.5b.6f, | 1b.2c.3d.4b.5c.6a, | |
| 1b.2c.3d.4b.5c.6b, | 1b.2c.3d.4b.5c.6c, | 1b.2c.3d.4b.5c.6d, | 1b.2c.3d.4b.5c.6e, | |
| 1b.2c.3d.4b.5c.6f, | 1b.2c.3d.4b.5d.6a, | 1b.2c.3d.4b.5d.6b, | 1b.2c.3d.4b.5d.6c, | |
| 1b.2c.3d.4b.5d.6d, | 1b.2c.3d.4b.5d.6e, | 1b.2c.3d.4b.5d.6f, | 1b.2c.3d.4b.5e.6a, | |
| 1b.2c.3d.4b.5e.6b, | 1b.2c.3d.4b.5e.6c, | 1b.2c.3d.4b.5e.6d, | 1b.2c.3d.4b.5e.6e, | |
| 1b.2c.3d.4b.5e.6f, | 1b.2c.3d.4b.5f.6a, | 1b.2c.3d.4b.5f.6b, | 1b.2c.3d.4b.5f.6c, | |
| 1b.2c.3d.4b.5f.6d, | 1b.2c.3d.4b.5f.6e, | 1b.2c.3d.4b.5f.6f, | 1b.2c.3d.4c.5a.6a, | |
| 1b.2c.3d.4c.5a.6b, | 1b.2c.3d.4c.5a.6c, | 1b.2c.3d.4c.5a.6d, | 1b.2c.3d.4c.5a.6e, | |
| 1b.2c.3d.4c.5a.6f, | 1b.2c.3d.4c.5b.6a, | 1b.2c.3d.4c.5b.6b, | 1b.2c.3d.4c.5b.6c, | |

TABLE 7-continued

List of Compounds of Formula (II)

| | | | | |
|---|---|---|---|---|
| 1b.2c.3d.4c.5b.6d, | 1b.2c.3d.4c.5b.6e, | 1b.2c.3d.4c.5b.6f, | 1b.2c.3d.4c.5c.6a, | |
| 1b.2c.3d.4c.5c.6b, | 1b.2c.3d.4c.5c.6c, | 1b.2c.3d.4c.5c.6d, | 1b.2c.3d.4c.5c.6e, | |
| 1b.2c.3d.4c.5c.6f, | 1b.2c.3d.4c.5d.6a, | 1b.2c.3d.4c.5d.6b, | 1b.2c.3d.4c.5d.6c, | |
| 1b.2c.3d.4c.5d.6d, | .1b.2c.3d.4c.5d.6e, | 1b.2c.3d.4c.5d.6f, | 1b.2c.3d.4c.5e.6a, | |
| 1b.2c.3d.4c.5e.6b, | 1b.2c.3d.4c.5e.6c, | 1b.2c.3d.4c.5e.6d, | 1b.2c.3d.4c.5e.6e, | |
| 1b.2c.3d.4c.5e.6f, | 1b.2c.3d.4c.5f.6a, | 1b.2c.3d.4c.5f.6b, | 1b.2c.3d.4c.5f.6c, | |
| 1b.2c.3d.4c.5f.6d, | 1b.2c.3d.4c.5f.6e, | 1b.2c.3d.4c.5f.6f, | 1b.2c.3d.4d.5a.6a, | |
| 1b.2c.3d.4d.5a.6b, | 1b.2c.3d.4d.5a.6c, | 1b.2c.3d.4d.5a.6d, | 1b.2c.3d.4d.5a.6e, | |
| 1b.2c.3d.4d.5a.6f, | 1b.2c.3d.4d.5b.6a, | 1b.2c.3d.4d.5b.6b, | 1b.2c.3d.4d.5b.6c, | |
| 1b.2c.3d.4d.5b.6d, | 1b.2c.3d.4d.5b.6e, | 1b.2c.3d.4d.5b.6f, | 1b.2c.3d.4d.5c.6a, | |
| 1b.2c.3d.4d.5c.6b, | 1b.2c.3d.4d.5c.6c, | 1b.2c.3d.4d.5c.6d, | 1b.2c.3d.4d.5c.6e, | |
| 1b.2c.3d.4d.5c.6f, | 1b.2c.3d.4d.5d.6a, | 1b.2c.3d.4d.5d.6b, | 1b.2c.3d.4d.5d.6c, | |
| 1b.2c.3d.4d.5d.6d, | 1b.2c.3d.4d.5d.6e, | 1b.2c.3d.4d.5d.6f, | 1b.2c.3d.4d.5e.6a, | |
| 1b.2c.3d.4d.5e.6b, | 1b.2c.3d.4d.5e.6c, | 1b.2c.3d.4d.5e.6d, | 1b.2c.3d.4d.5e.6e, | |
| 1b.2c.3d.4d.5e.6f, | 1b.2c.3d.4d.5f.6a, | 1b.2c.3d.4d.5f.6b, | 1b.2c.3d.4d.5f.6c, | |
| 1b.2c.3d.4d.5f.6d, | 1b.2c.3d.4d.5f.6e, | 1b.2c.3d.4d.5f.6f, | 1b.2c.3d.4e.5a.6a, | |
| 1b.2c.3d.4e.5a.6b, | 1b.2c.3d.4e.5a.6c, | 1b.2c.3d.4e.5a.6d, | 1b.2c.3d.4e.5a.6e, | |
| 1b.2c.3d.4e.5a.6f, | 1b.2c.3d.4e.5b.6a, | 1b.2c.3d.4e.5b.6b, | 1b.2c.3d.4e.5b.6c, | |
| 1b.2c.3d.4e.5b.6d, | 1b.2c.3d.4e.5b.6e, | 1b.2c.3d.4e.5b.6f, | 1b.2c.3d.4e.5c.6a, | |
| 1b.2c.3d.4e.5c.6b, | 1b.2c.3d.4e.5c.6c, | 1b.2c.3d.4e.5c.6d, | 1b.2c.3d.4e.5c.6e, | |
| 1b.2c.3d.4e.5c.6f, | 1b.2c.3d.4e.5d.6a, | 1b.2c.3d.4e.5d.6b, | 1b.2c.3d.4e.5d.6c, | |
| 1b.2c.3d.4e.5d.6d, | 1b.2c.3d.4e.5d.6e, | 1b.2c.3d.4e.5d.6f, | 1b.2c.3d.4e.5e.6a, | |
| 1b.2c.3d.4e.5e.6b, | 1b.2c.3d.4e.5e.6c, | 1b.2c.3d.4e.5e.6d, | 1b.2c.3d.4e.5e.6e, | |
| 1b.2c.3d.4e.5e.6f, | 1b.2c.3d.4e.5f.6a, | 1b.2c.3d.4e.5f.6b, | 1b.2c.3d.4e.5f.6c, | |
| 1b.2c.3d.4e.5f.6d, | 1b.2c.3d.4e.5f.6e, | 1b.2c.3d.4e.5f.6f, | 1b.2c.3d.4f.5a.6a, | |
| 1b.2c.3d.4f.5a.6b, | 1b.2c.3d.4f.5a.6c, | 1b.2c.3d.4f.5a.6d, | 1b.2c.3d.4f.5a.6e, | |
| 1b.2c.3d.4f.5a.6f, | 1b.2c.3d.4f.5b.6a, | 1b.2c.3d.4f.5b.6b, | 1b.2c.3d.4f.5b.6c, | |
| 1b.2c.3d.4f.5b.6d, | 1b.2c.3d.4f.5b.6e, | 1b.2c.3d.4f.5b.6f, | 1b.2c.3d.4f.5c.6a, | |
| 1b.2c.3d.4f.5c.6b, | 1b.2c.3d.4f.5c.6c, | 1b.2c.3d.4f.5c.6d, | 1b.2c.3d.4f.5c.6e, | 1b.2c.3d.4f.5c.6f, |
| 1b.2c.3d.4f.5d.6a, | 1b.2c.3d.4f.5d.6b, | 1b.2c.3d.4f.5d.6c, | 1b.2c.3d.4f.5d.6d, | |
| 1b.2c.3d.4f.5d.6e, | 1b.2c.3d.4f.5d.6f, | 1b.2c.3d.4f.5e.6a, | 1b.2c.3d.4f.5e.6b, | |
| 1b.2c.3d.4f.5e.6c, | 1b.2c.3d.4f.5e.6d, | 1b.2c.3d.4f.5e.6e, | 1b.2c.3d.4f.5e.6f, | 1b.2c.3d.4f.5f.6a, |
| 1b.2c.3d.4f.5f.6b, | 1b.2c.3d.4f.5f.6c, | 1b.2c.3d.4f.5f.6d, | 1b.2c.3d.4f.5f.6e, | 1b.2c.3d.4f.5f.6f, |
| 1b.2c.3e.4a.5a.6a, | 1b.2c.3e.4a.5a.6b, | 1b.2c.3e.4a.5a.6c, | 1b.2c.3e.4a.5a.6d, | |
| 1b.2c.3e.4a.5a.6e, | 1b.2c.3e.4a.5a.6f, | 1b.2c.3e.4a.5b.6a, | 1b.2c.3e.4a.5b.6b, | |
| 1b.2c.3e.4a.5b.6c, | 1b.2c.3e.4a.5b.6d, | 1b.2c.3e.4a.5b.6e, | 1b.2c.3e.4a.5b.6f, | |
| 1b.2c.3e.4a.5c.6a, | 1b.2c.3e.4a.5c.6b, | 1b.2c.3e.4a.5c.6c, | 1b.2c.3e.4a.5c.6d, | |
| 1b.2c.3e.4a.5c.6e, | 1b.2c.3e.4a.5c.6f, | 1b.2c.3e.4a.5d.6a, | 1b.2c.3e.4a.5d.6b, | |
| 1b.2c.3e.4a.5d.6c, | 1b.2c.3e.4a.5d.6d, | 1b.2c.3e.4a.5d.6e, | 1b.2c.3e.4a.5d.6f, | |
| 1b.2c.3e.4a.5e.6a, | 1b.2c.3e.4a.5e.6b, | 1b.2c.3e.4a.5e.6c, | 1b.2c.3e.4a.5e.6d, | |
| 1b.2c.3e.4a.5e.6e, | 1b.2c.3e.4a.5e.6f, | 1b.2c.3e.4a.5f.6a, | 1b.2c.3e.4a.5f.6b, | 1b.2c.3e.4a.5f.6c, |
| 1b.2c.3e.4a.5f.6d, | 1b.2c.3e.4a.5f.6e, | 1b.2c.3e.4a.5f.6f, | 1b.2c.3e.4b.5a.6a, | |
| 1b.2c.3e.4b.5a.6b, | 1b.2c.3e.4b.5a.6c, | 1b.2c.3e.4b.5a.6d, | 1b.2c.3e.4b.5a.6e, | |
| 1b.2c.3e.4b.5a.6f, | 1b.2c.3e.4b.5b.6a, | 1b.2c.3e.4b.5b.6b, | 1b.2c.3e.4b.5b.6c, | |
| 1b.2c.3e.4b.5b.6d, | 1b.2c.3e.4b.5b.6e, | 1b.2c.3e.4b.5b.6f, | 1b.2c.3e.4b.5c.6a, | |
| 1b.2c.3e.4b.5c.6b, | 1b.2c.3e.4b.5c.6c, | 1b.2c.3e.4b.5c.6d, | 1b.2c.3e.4b.5c.6e, | |
| 1b.2c.3e.4b.5c.6f, | 1b.2c.3e.4b.5d.6a, | 1b.2c.3e.4b.5d.6b, | 1b.2c.3e.4b.5d.6c, | |
| 1b.2c.3e.4b.5d.6d, | 1b.2c.3e.4b.5d.6e, | 1b.2c.3e.4b.5d.6f, | 1b.2c.3e.4b.5e.6a, | |
| 1b.2c.3e.4b.5e.6b, | 1b.2c.3e.4b.5e.6c, | 1b.2c.3e.4b.5e.6d, | 1b.2c.3e.4b.5e.6e, | |
| 1b.2c.3e.4b.5e.6f, | 1b.2c.3e.4b.5f.6a, | 1b.2c.3e.4b.5f.6b, | 1b.2c.3e.4b.5f.6c, | |
| 1b.2c.3e.4b.5f.6d, | 1b.2c.3e.4b.5f.6e, | 1b.2c.3e.4b.5f.6f, | 1b.2c.3e.4c.5a.6a, | |
| 1b.2c.3e.4c.5a.6b, | 1b.2c.3e.4c.5a.6c, | 1b.2c.3e.4c.5a.6d, | 1b.2c.3e.4c.5a.6e, | |
| 1b.2c.3e.4c.5a.6f, | 1b.2c.3e.4c.5b.6a, | 1b.2c.3e.4c.5b.6b, | 1b.2c.3e.4c.5b.6c, | |
| 1b.2c.3e.4c.5b.6d, | 1b.2c.3e.4c.5b.6e, | 1b.2c.3e.4c.5b.6f, | 1b.2c.3e.4c.5c.6a, | |
| 1b.2c.3e.4c.5c.6b, | 1b.2c.3e.4c.5c.6c, | 1b.2c.3e.4c.5c.6d, | 1b.2c.3e.4c.5c.6e, | 1b.2c.3e.4c.5c.6f, |
| 1b.2c.3e.4c.5d.6a, | 1b.2c.3e.4c.5d.6b, | 1b.2c.3e.4c.5d.6c, | 1b.2c.3e.4c.5d.6d, | |
| 1b.2c.3e.4c.5d.6e, | 1b.2c.3e.4c.5d.6f, | 1b.2c.3e.4c.5e.6a, | 1b.2c.3e.4c.5e.6b, | |
| 1b.2c.3e.4c.5e.6c, | 1b.2c.3e.4c.5e.6d, | 1b.2c.3e.4c.5e.6e, | 1b.2c.3e.4c.5e.6f, | 1b.2c.3e.4c.5f.6a, |
| 1b.2c.3e.4c.5f.6b, | 1b.2c.3e.4c.5f.6c, | 1b.2c.3e.4c.5f.6d, | 1b.2c.3e.4c.5f.6e, | 1b.2c.3e.4c.5f.6f, |
| 1b.2c.3e.4d.5a.6a, | 1b.2c.3e.4d.5a.6b, | 1b.2c.3e.4d.5a.6c, | 1b.2c.3e.4d.5a.6d, | |
| 1b.2c.3e.4d.5a.6e, | 1b.2c.3e.4d.5a.6f, | 1b.2c.3e.4d.5b.6a, | 1b.2c.3e.4d.5b.6b, | |
| 1b.2c.3e.4d.5b.6c, | 1b.2c.3e.4d.5b.6d, | 1b.2c.3e.4d.5b.6e, | 1b.2c.3e.4d.5b.6f, | |
| 1b.2c.3e.4d.5c.6a, | 1b.2c.3e.4d.5c.6b, | 1b.2c.3e.4d.5c.6c, | 1b.2c.3e.4d.5c.6d, | |
| 1b.2c.3e.4d.5c.6e, | 1b.2c.3e.4d.5c.6f, | 1b.2c.3e.4d.5d.6a, | 1b.2c.3e.4d.5d.6b, | |
| 1b.2c.3e.4d.5d.6c, | 1b.2c.3e.4d.5d.6d, | 1b.2c.3e.4d.5d.6e, | 1b.2c.3e.4d.5d.6f, | |
| 1b.2c.3e.4d.5e.6a, | 1b.2c.3e.4d.5e.6b, | 1b.2c.3e.4d.5e.6c, | 1b.2c.3e.4d.5e.6d, | |
| 1b.2c.3e.4d.5e.6e, | 1b.2c.3e.4d.5e.6f, | 1b.2c.3e.4d.5f.6a, | 1b.2c.3e.4d.5f.6b, | |
| 1b.2c.3e.4d.5f.6c, | 1b.2c.3e.4d.5f.6d, | 1b.2c.3e.4d.5f.6e, | 1b.2c.3e.4d.5f.6f, | |
| 1b.2c.3e.4e.5a.6a, | 1b.2c.3e.4e.5a.6b, | 1b.2c.3e.4e.5a.6c, | 1b.2c.3e.4e.5a.6d, | |
| 1b.2c.3e.4e.5a.6e, | 1b.2c.3e.4e.5a.6f, | 1b.2c.3e.4e.5b.6a, | 1b.2c.3e.4e.5b.6b, | |
| 1b.2c.3e.4e.5b.6c, | 1b.2c.3e.4e.5b.6d, | 1b.2c.3e.4e.5b.6e, | 1b.2c.3e.4e.5b.6f, | |
| 1b.2c.3e.4e.5c.6a, | 1b.2c.3e.4e.5c.6b, | 1b.2c.3e.4e.5c.6c, | 1b.2c.3e.4e.5c.6d, | |
| 1b.2c.3e.4e.5c.6e, | 1b.2c.3e.4e.5c.6f, | 1b.2c.3e.4e.5d.6a, | 1b.2c.3e.4e.5d.6b, | |
| 1b.2c.3e.4e.5d.6c, | 1b.2c.3e.4e.5d.6d, | 1b.2c.3e.4e.5d.6e, | 1b.2c.3e.4e.5d.6f, | |
| 1b.2c.3e.4e.5e.6a, | 1b.2c.3e.4e.5e.6b, | 1b.2c.3e.4e.5e.6c, | 1b.2c.3e.4e.5e.6d, | |
| 1b.2c.3e.4e.5e.6e, | 1b.2c.3e.4e.5e.6f, | 1b.2c.3e.4e.5f.6a, | 1b.2c.3e.4e.5f.6b, | 1b.2c.3e.4e.5f.6c, |
| 1b.2c.3e.4e.5f.6d, | 1b.2c.3e.4e.5f.6e, | 1b.2c.3e.4e.5f.6f, | 1b.2c.3e.4f.5a.6a, | 1b.2c.3e.4f.5a.6b, |
| 1b.2c.3e.4f.5a.6c, | 1b.2c.3e.4f.5a.6d, | 1b.2c.3e.4f.5a.6e, | 1b.2c.3e.4f.5a.6f, | 1b.2c.3e.4f.5b.6a, |

TABLE 7-continued

List of Compounds of Formula (II)

| | | | |
|---|---|---|---|
| 1b.2c.3e.4f.5b.6b, | 1b.2c.3e.4f.5b.6c, | 1b.2c.3e.4f.5b.6d, | 1b.2c.3e.4f.5b.6e, | 1b.2c.3e.4f.5b.6f, |
| 1b.2c.3e.4f.5c.6a, | 1b.2c.3e.4f.5c.6b, | 1b.2c.3e.4f.5c.6c, | 1b.2c.3e.4f.5c.6d, | 1b.2c.3e.4f.5c.6e, |
| 1b.2c.3e.4f.5c.6f, | 1b.2c.3e.4f.5d.6a, | 1b.2c.3e.4f.5d.6b, | 1b.2c.3e.4f.5d.6c, | |
| 1b.2c.3e.4f.5d.6d, | 1b.2c.3e.4f.5d.6e, | 1b.2c.3e.4f.5d.6f, | 1b.2c.3e.4f.5e.6a, | 1b.2c.3e.4f.5e.6b, |
| 1b.2c.3e.4f.5e.6c, | 1b.2c.3e.4f.5e.6d, | 1b.2c.3e.4f.5e.6e, | 1b.2c.3e.4f.5e.6f, | 1b.2c.3e.4f.5f.6a, |
| 1b.2c.3e.4f.5f.6b, | 1b.2c.3e.4f.5f.6c, | 1b.2c.3e.4f.5f.6d, | 1b.2c.3e.4f.5f.6e, | 1b.2c.3e.4f.5f.6f, |
| 1b.2c.3f.4a.5a.6a, | 1b.2c.3f.4a.5a.6b, | 1b.2c.3f.4a.5a.6c, | 1b.2c.3f.4a.5a.6d, | 1b.2c.3f.4a.5a.6e, |
| 1b.2c.3f.4a.5a.6f, | 1b.2c.3f.4a.5b.6a, | 1b.2c.3f.4a.5b.6b, | 1b.2c.3f.4a.5b.6c, | 1b.2c.3f.4a.5b.6d, |
| 1b.2c.3f.4a.5b.6e, | 1b.2c.3f.4a.5b.6f, | 1b.2c.3f.4a.5c.6a, | 1b.2c.3f.4a.5c.6b, | 1b.2c.3f.4a.5c.6c, |
| 1b.2c.3f.4a.5c.6d, | 1b.2c.3f.4a.5c.6e, | 1b.2c.3f.4a.5c.6f, | 1b.2c.3f.4a.5d.6a, | 1b.2c.3f.4a.5d.6b, |
| 1b.2c.3f.4a.5d.6c, | 1b.2c.3f.4a.5d.6d, | 1b.2c.3f.4a.5d.6e, | 1b.2c.3f.4a.5d.6f, | |
| 1b.2c.3f.4a.5e.6a, | 1b.2c.3f.4a.5e.6b, | 1b.2c.3f.4a.5e.6c, | 1b.2c.3f.4a.5e.6d, | 1b.2c.3f.4a.5e.6e, |
| 1b.2c.3f.4a.5e.6f, | 1b.2c.3f.4a.5f.6a, | 1b.2c.3f.4a.5f.6b, | 1b.2c.3f.4a.5f.6c, | 1b.2c.3f.4a.5f.6d, |
| 1b.2c.3f.4a.5f.6e, | 1b.2c.3f.4a.5f.6f, | 1b.2c.3f.4b.5a.6a, | 1b.2c.3f.4b.5a.6b, | 1b.2c.3f.4b.5a.6c, |
| 1b.2c.3f.4b.5a.6d, | 1b.2c.3f.4b.5a.6e, | 1b.2c.3f.4b.5a.6f, | 1b.2c.3f.4b.5b.6a, | |
| 1b.2c.3f.4b.5b.6b, | 1b.2c.3f.4b.5b.6c, | 1b.2c.3f.4b.5b.6d, | 1b.2c.3f.4b.5b.6e, | |
| 1b.2c.3f.4b.5b.6f, | 1b.2c.3f.4b.5c.6a, | 1b.2c.3f.4b.5c.6b, | 1b.2c.3f.4b.5c.6c, | 1b.2c.3f.4b.5c.6d, |
| 1b.2c.3f.4b.5c.6e, | 1b.2c.3f.4b.5c.6f, | 1b.2c.3f.4b.5d.6a, | 1b.2c.3f.4b.5d.6b, | |
| 1b.2c.3f.4b.5d.6c, | 1b.2c.3f.4b.5d.6d, | 1b.2c.3f.4b.5d.6e, | 1b.2c.3f.4b.5d.6f, | |
| 1b.2c.3f.4b.5e.6a, | 1b.2c.3f.4b.5e.6b, | 1b.2c.3f.4b.5e.6c, | 1b.2c.3f.4b.5e.6d, | |
| 1b.2c.3f.4b.5e.6e, | 1b.2c.3f.4b.5e.6f, | 1b.2c.3f.4b.5f.6a, | 1b.2c.3f.4b.5f.6b, | 1b.2c.3f.4b.5f.6c, |
| 1b.2c.3f.4b.5f.6d, | 1b.2c.3f.4b.5f.6e, | 1b.2c.3f.4b.5f.6f, | 1b.2c.3f.4c.5a.6a, | 1b.2c.3f.4c.5a.6b, |
| 1b.2c.3f.4c.5a.6c, | 1b.2c.3f.4c.5a.6d, | 1b.2c.3f.4c.5a.6e, | 1b.2c.3f.4c.5a.6f, | 1b.2c.3f.4c.5b.6a, |
| 1b.2c.3f.4c.5b.6b, | 1b.2c.3f.4c.5b.6c, | 1b.2c.3f.4c.5b.6d, | 1b.2c.3f.4c.5b.6e, | 1b.2c.3f.4c.5b.6f, |
| 1b.2c.3f.4c.5c.6a, | 1b.2c.3f.4c.5c.6b, | 1b.2c.3f.4c.5c.6c, | 1b.2c.3f.4c.5c.6d, | 1b.2c.3f.4c.5t.6e, |
| 1b.2c.3f.4c.5c.6f, | 1b.2c.3f.4c.5d.6a, | 1b.2c.3f.4c.5d.6b, | 1b.2c.3f.4c.5d.6c, | 1b.2c.3f.4c.5d.6d, |
| 1b.2c.3f.4c.5d.6e, | 1b.2c.3f.4c.5d.6f, | 1b.2c.3f.4c.5e.6a, | 1b.2c.3f.4c.5e.6b, | 1b.2c.3f.4c.5e.6c, |
| 1b.2c.3f.4c.5e.6d, | 1b.2c.3f.4c.5e.6e, | 1b.2c.3f.4c.5e.6f, | 1b.2c.3f.4c.5f.6a, | 1b.2c.3f.4c.5f.6b, |
| 1b.2c.3f.4c.5f.6c, | 1b.2c.3f.4c.5f.6d, | 1b.2c.3f.4c.5f.6e, | 1b.2c.3f.4c.5f.6f, | 1b.2c.3f.4d.5a.6a, |
| 1b.2c.3f.4d.5a.6b, | 1b.2c.3f.4d.5a.6c, | 1b.2c.3f.4d.5a.6d, | 1b.2c.3f.4d.5a.6e, | |
| 1b.2c.3f.4d.5a.6f, | 1b.2c.3f.4d.5b.6a, | 1b.2c.3f.4d.5b.6b, | 1b.2c.3f.4d.5b.6c, | |
| 1b.2c.3f.4d.5b.6d, | 1b.2c.3f.4d.5b.6e, | 1b.2c.3f.4d.5b.6f, | 1b.2c.3f.4d.5c.6a, | |
| 1b.2c.3f.4d.5c.6b, | 1b.2c.3f.4d.5c.6c, | 1b.2c.3f.4d.5c.6d, | 1b.2c.3f.4d.5c.6e, | 1b.2c.3f.4d.5c.6f, |
| 1b.2c.3f.4d.5d.6a, | 1b.2c.3f.4d.5d.6b, | 1b.2c.3f.4d.5d.6c, | 1b.2c.3f.4d.5d.6d, | |
| 1b.2c.3f.4d.5d.6e, | 1b.2c.3f.4d.5d.6f, | 1b.2c.3f.4d.5e.6a, | 1b.2c.3f.4d.5e.6b, | |
| 1b.2c.3f.4d.5e.6c, | 1b.2c.3f.4d.5e.6d, | 1b.2c.3f.4d.5e.6e, | 1b.2c.3f.4d.5e.6f, | 1b.2c.3f.4d.5f.6a, |
| 1b.2c.3f.4d.5f.6b, | 1b.2c.3f.4d.5f.6c, | 1b.2c.3f.4d.5f.6d, | 1b.2c.3f.4d.5f.6e, | 1b.2c.3f.4d.5f.6f, |
| 1b.2c.3f.4e.5a.6a, | 1b.2c.3f.4e.5a.6b, | 1b.2c.3f.4e.5a.6c, | 1b.2c.3f.4e.5a.6d, | 1b.2c.3f.4e.5a.6e, |
| 1b.2c.3f.4e.5a.6f, | 1b.2c.3f.4e.5b.6a, | 1b.2c.3f.4e.5b.6b, | 1b.2c.3f.4e.5b.6c, | 1b.2c.3f.4e.5b.6d, |
| 1b.2c.3f.4e.5b.6e, | 1b.2c.3f.4e.5b.6f, | 1b.2c.3f.4e.5c.6a, | 1b.2c.3f.4e.5c.6b, | 1b.2c.3f.4e.5c.6c, |
| 1b.2c.3f.4e.5c.6d, | 1b.2c.3f.4e.5c.6e, | 1b.2c.3f.4e.5c.6f, | 1b.2c.3f.4e.5d.6a, | 1b.2c.3f.4e.5d.6b, |
| 1b.2c.3f.4e.5d.6c, | 1b.2c.3f.4e.5d.6d, | 1b.2c.3f.4e.5d.6e, | 1b.2c.3f.4e.5d.6f, | 1b.2c.3f.4e.5e.6a, |
| 1b.2c.3f.4e.5e.6b, | 1b.2c.3f.4e.5e.6c, | 1b.2c.3f.4e.5e.6d, | 1b.2c.3f.4e.5e.6e, | 1b.2c.3f.4e.5e.6f, |
| 1b.2c.3f.4e.5f.6a, | 1b.2c.3f.4e.5f.6b, | 1b.2c.3f.4e.5f.6c, | 1b.2c.3f.4e.5f.6d, | 1b.2c.3f.4e.5f.6e, |
| 1b.2c.3f.4e.5f.6f, | 1b.2c.3f.4f.5a.6a, | 1b.2c.3f.4f.5a.6b, | 1b.2c.3f.4f.5a.6c, | 1b.2c.3f.4f.5a.6d, |
| 1b.2c.3f.4f.5a.6e, | 1b.2c.3f.4f.5a.6f, | 1b.2c.3f.4f.5b.6a, | 1b.2c.3f.4f.5b.6b, | 1b.2c.3f.4f.5b.6c, |
| 1b.2c.3f.4f.5b.6d, | 1b.2c.3f.4f.5b.6e, | 1b.2c.3f.4f.5b.6f, | 1b.2c.3f.4f.5c.6a, | 1b.2c.3f.4f.5c.6b, |
| 1b.2c.3f.4f.5c.6c, | 1b.2c.3f.4f.5c.6d, | 1b.2c.3f.4f.5c.6e, | 1b.2c.3f.4f.5c.6f, | 1b.2c.3f.4f.5d.6a, |
| 1b.2c.3f.4f.5d.6b, | 1b.2c.3f.4f.5d.6c, | 1b.2c.3f.4f.5d.6d, | 1b.2c.3f.4f.5d.6e, | 1b.2c.3f.4f.5d.6f, |
| 1b.2c.3f.4f.5e.6a, | 1b.2c.3f.4f.5e.6b, | 1b.2c.3f.4f.5e.6c, | 1b.2c.3f.4f.5e.6d, | 1b.2c.3f.4f.5e.6e, |
| 1b.2c.3f.4f.5e.6f, | 1b.2c.3f.4f.5f.6a, | 1b.2c.3f.4f.5f.6b, | 1b.2c.3f.4f.5f.6c, | 1b.2c.3f.4f.5f.6d, |
| 1b.2c.3f.4f.5f.6e, | 1b.2c.3f.4f.5f.6f, | 1b.2d.3a.4a.5a.6a, | 1b.2d.3a.4a.5a.6b, | 1b.2d.3a.4a.5a.6c, |
| 1b.2d.3a.4a.5a.6d, | 1b.2d.3a.4a.5a.6e, | 1b.2d.3a.4a.5a.6f, | 1b.2d.3a.4a.5b.6a, | |
| 1b.2d.3a.4a.5b.6b, | 1b.2d.3a.4a.5b.6c, | 1b.2d.3a.4a.5b.6d, | 1b.2d.3a.4a.5b.6e, | |
| 1b.2d.3a.4a.5b.6f, | 1b.2d.3a.4a.5c.6a, | 1b.2d.3a.4a.5c.6b, | 1b.2d.3a.4a.5c.6c, | |
| 1b.2d.3a.4a.5c.6d, | 1b.2d.3a.4a.5c.6e, | 1b.2d.3a.4a.5c.6f, | 1b.2d.3a.4a.5d.6a, | |
| 1b.2d.3a.4a.5d.6b, | 1b.2d.3a.4a.5d.6c, | 1b.2d.3a.4a.5d.6d, | 1b.2d.3a.4a.5d.6e, | |
| 1b.2d.3a.4a.5d.6f, | 1b.2d.3a.4a.5e.6a, | 1b.2d.3a.4a.5e.6b, | 1b.2d.3a.4a.5e.6c, | |
| 1b.2d.3a.4a.5e.6d, | 1b.2d.3a.4a.5e.6e, | 1b.2d.3a.4a.5e.6f, | 1b.2d.3a.4a.5f.6a, | |
| 1b.2d.3a.4a.5f.6b, | 1b.2d.3a.4a.5f.6c, | 1b.2d.3a.4a.5f.6d, | 1b.2d.3a.4a.5f.6e, | |
| 1b.2d.3a.4a.5f.6f, | 1b.2d.3a.4b.5a.6a, | 1b.2d.3a.4b.5a.6b, | 1b.2d.3a.4b.5a.6c, | |
| 1b.2d.3a.4b.5a.6d, | 1b.2d.3a.4b.5a.6e, | 1b.2d.3a.4b.5a.6f, | 1b.2d.3a.4b.5b.6a, | |
| 1b.2d.3a.4b.5b.6b, | 1b.2d.3a.4b.5b.6c, | 1b.2d.3a.4b.5b.6d, | 1b.2d.3a.4b.5b.6e, | |
| 1b.2d.3a.4b.5b.6f, | 1b.2d.3a.4b.5c.6a, | 1b.2d.3a.4b.5c.6b, | 1b.2d.3a.4b.5c.6c, | |
| 1b.2d.3a.4b.5c.6d, | 1b.2d.3a.4b.5c.6e, | 1b.2d.3a.4b.5c.6f, | 1b.2d.3a.4b.5d.6a, | |
| 1b.2d.3a.4b.5d.6b, | 1b.2d.3a.4b.5d.6c, | 1b.2d.3a.4b.5d.6d, | 1b.2d.3a.4b.5d.6e, | |
| 1b.2d.3a.4b.5d.6f, | 1b.2d.3a.4b.5e.6a, | 1b.2d.3a.4b.5e.6b, | 1b.2d.3a.4b.5e.6c, | |
| 1b.2d.3a.4b.5e.6d, | 1b.2d.3a.4b.5e.6e, | 1b.2d.3a.4b.5e.6f, | 1b.2d.3a.4b.5f.6a, | |
| 1b.2d.3a.4b.5f.6b, | 1b.2d.3a.4b.5f.6c, | 1b.2d.3a.4b.5f.6d, | 1b.2d.3a.4b.5f.6e, | |
| 1b.2d.3a.4b.5f.6f, | 1b.2d.3a.4c.5a.6a, | 1b.2d.3a.4c.5a.6b, | 1b.2d.3a.4c.5a.6c, | |
| 1b.2d.3a.4c.5a.6d, | 1b.2d.3a.4c.5a.6e, | 1b.2d.3a.4c.5a.6f, | 1b.2d.3a.4c.5b.6a, | |
| 1b.2d.3a.4c.5b.6b, | 1b.2d.3a.4c.5b.6c, | 1b.2d.3a.4c.5b.6d, | 1b.2d.3a.4c.5b.6e, | |
| 1b.2d.3a.4c.5b.6f, | 1b.2d.3a.4c.5c.6a, | 1b.2d.3a.4c.5c.6b, | 1b.2d.3a.4c.5c.6c, | |
| 1b.2d.3a.4c.5c.6d, | 1b.2d.3a.4c.5c.6e, | 1b.2d.3a.4c.5c.6f, | 1b.2d.3a.4c.5d.6a, | |
| 1b.2d.3a.4c.5d.6b, | 1b.2d.3a.4c.5d.6c, | 1b.2d.3a.4c.5d.6d, | 1b.2d.3a.4c.5d.6e, | |
| 1b.2d.3a.4c.5d.6f, | 1b.2d.3a.4c.5e.6a, | 1b.2d.3a.4c.5e.6b, | 1b.2d.3a.4c.5e.6c, | |
| 1b.2d.3a.4c.5e.6d, | 1b.2d.3a.4c.5e.6e, | 1b.2d.3a.4c.5e.6f, | 1b.2d.3a.4c.5f.6a, | |
| 1b.2d.3a.4c.5f.6b, | 1b.2d.3a.4c.5f.6c, | 1b.2d.3a.4c.5f.6d, | 1b.2d.3a.4c.5f.6e, | |

TABLE 7-continued

List of Compounds of Formula (II)

| | | | |
|---|---|---|---|
| 1b.2d.3a.4c.5f.6f, | 1b.2d.3a.4d.5a.6a, | 1b.2d.3a.4d.5a.6b, | 1b.2d.3a.4d.5a.6c, |
| 1b.2d.3a.4d.5a.6d, | 1b.2d.3a.4d.5a.6e, | 1b.2d.3a.4d.5a.6f, | 1b.2d.3a.4d.5b.6a, |
| 1b.2d.3a.4d.5b.6b, | 1b.2d.3a.4d.5b.6c, | 1b.2d.3a.4d.5b.6d, | 1b.2d.3a.4d.5b.6e, |
| 1b.2d.3a.4d.5b.6f, | 1b.2d.3a.4d.5c.6a, | 1b.2d.3a.4d.5c.6b, | 1b.2d.3a.4d.5c.6c, |
| 1b.2d.3a.4d.5c.6d, | 1b.2d.3a.4d.5c.6e, | 1b.2d.3a.4d.5c.6f, | 1b.2d.3a.4d.5d.6a, |
| 1b.2d.3a.4d.5d.6b, | 1b.2d.3a.4d.5d.6c, | 1b.2d.3a.4d.5d.6d, | 1b.2d.3a.4d.5d.6e, |
| 1b.2d.3a.4d.5d.6f, | 1b.2d.3a.4d.5e.6a, | 1b.2d.3a.4d.5e.6b, | 1b.2d.3a.4d.5e.6c, |
| 1b.2d.3a.4d.5e.6d, | 1b.2d.3a.4d.5e.6e, | 1b.2d.3a.4d.5e.6f, | 1b.2d.3a.4d.5f.6a, |
| 1b.2d.3a.4d.5f.6b, | 1b.2d.3a.4d.5f.6c, | 1b.2d.3a.4d.5f.6d, | 1b.2d.3a.4d.5f.6e, |
| 1b.2d.3a.4d.5f.6f, | 1b.2d.3a.4e.5a.6a, | 1b.2d.3a.4e.5a.6b, | 1b.2d.3a.4e.5a.6c, |
| 1b.2d.3a.4e.5a.6d, | 1b.2d.3a.4e.5a.6e, | 1b.2d.3a.4e.5a.6f, | 1b.2d.3a.4e.5b.6a, |
| 1b.2d.3a.4e.5b.6b, | 1b.2d.3a.4e.5b.6c, | 1b.2d.3a.4e.5b.6d, | 1b.2d.3a.4e.5b.6e, |
| 1b.2d.3a.4e.5b.6f, | 1b.2d.3a.4e.5c.6a, | 1b.2d.3a.4e.5c.6b, | 1b.2d.3a.4e.5c.6c, |
| 1b.2d.3a.4e.5c.6d, | 1b.2d.3a.4e.5c.6e, | 1b.2d.3a.4e.5c.6f, | 1b.2d.3a.4e.5d.6a, |
| 1b.2d.3a.4e.5d.6b, | 1b.2d.3a.4e.5d.6c, | 1b.2d.3a.4e.5d.6d, | 1b.2d.3a.4e.5d.6e, |
| 1b.2d.3a.4e.5d.6f, | 1b.2d.3a.4e.5e.6a, | 1b.2d.3a.4e.5e.6b, | 1b.2d.3a.4e.5e.6c, |
| 1b.2d.3a.4e.5e.6d, | 1b.2d.3a.4e.5e.6e, | 1b.2d.3a.4e.5e.6f, | 1b.2d.3a.4e.5f.6a, |
| 1b.2d.3a.4e.5f.6b, | 1b.2d.3a.4e.5f.6c, | 1b.2d.3a.4e.5f.6d, | 1b.2d.3a.4e.5f.6e, |
| 1b.2d.3a.4e.5f.6f, | 1b.2d.3a.4f.5a.6a, | 1b.2d.3a.4f.5a.6b, | 1b.2d.3a.4f.5a.6c, |
| 1b.2d.3a.4f.5a.6d, | 1b.2d.3a.4f.5a.6e, | 1b.2d.3a.4f.5a.6f, | 1b.2d.3a.4f.5b.6a, |
| 1b.2d.3a.4f.5b.6b, | 1b.2d.3a.4f.5b.6c, | 1b.2d.3a.4f.5b.6d, | 1b.2d.3a.4f.5b.6e, |
| 1b.2d.3a.4f.5b.6f, | 1b.2d.3a.4f.5c.6a, | 1b.2d.3a.4f.5c.6b, | 1b.2d.3a.4f.5c.6c, |
| 1b.2d.3a.4f.5c.6d, | 1b.2d.3a.4f.5c.6e, | 1b.2d.3a.4f.5c.6f, | 1b.2d.3a.4f.5d.6a, |
| 1b.2d.3a.4f.5d.6b, | 1b.2d.3a.4f.5d.6c, | 1b.2d.3a.4f.5d.6d, | 1b.2d.3a.4f.5d.6e, |
| 1b.2d.3a.4f.5d.6f, | 1b.2d.3a.4f.5e.6a, | 1b.2d.3a.4f.5e.6b, | 1b.2d.3a.4f.5e.6c, |
| 1b.2d.3a.4f.5e.6d, | 1b.2d.3a.4f.5e.6e, | 1b.2d.3a.4f.5e.6f, | 1b.2d.3a.4f.5f.6a, |
| 1b.2d.3a.4f.5f.6b, | 1b.2d.3a.4f.5f.6c, | 1b.2d.3a.4f.5f.6d, | 1b.2d.3a.4f.5f.6e, | 1b.2d.3a.4f.5f.6f, |
| 1b.2d.3b.4a.5a.6a, | 1b.2d.3b.4a.5a.6b, | 1b.2d.3b.4a.5a.6c, | 1b.2d.3b.4a.5a.6d, |
| 1b.2d.3b.4a.5a.6e, | 1b.2d.3b.4a.5a.6f, | 1b.2d.3b.4a.5b.6a, | 1b.2d.3b.4a.5b.6b, |
| 1b.2d.3b.4a.5b.6c, | 1b.2d.3b.4a.5b.6d, | 1b.2d.3b.4a.5b.6e, | 1b.2d.3b.4a.5b.6f, |
| 1b.2d.3b.4a.5c.6a, | 1b.2d.3b.4a.5c.6b, | 1b.2d.3b.4a.5c.6c, | 1b.2d.3b.4a.5c.6d, |
| 1b.2d.3b.4a.5c.6e, | 1b.2d.3b.4a.5c.6f, | 1b.2d.3b.4a.5d.6a, | 1b.2d.3b.4a.5d.6b, |
| 1b.2d.3b.4a.5d.6c, | 1b.2d.3b.4a.5d.6d, | 1b.2d.3b.4a.5d.6e, | 1b.2d.3b.4a.5d.6f, |
| 1b.2d.3b.4a.5e.6a, | 1b.2d.3b.4a.5e.6b, | 1b.2d.3b.4a.5e.6c, | 1b.2d.3b.4a.5e.6d, |
| 1b.2d.3b.4a.5e.6e, | 1b.2d.3b.4a.5e.6f, | 1b.2d.3b.4a.5f.6a, | 1b.2d.3b.4a.5f.6b, |
| 1b.2d.3b.4a.5f.6c, | 1b.2d.3b.4a.5f.6d, | 1b.2d.3b.4a.5f.6e, | 1b.2d.3b.4a.5f.6f, |
| 1b.2d.3b.4b.5a.6a, | 1b.2d.3b.4b.5a.6b, | 1b.2d.3b.4b.5a.6c, | 1b.2d.3b.4b.5a.6d, |
| 1b.2d.3b.4b.5a.6e, | 1b.2d.3b.4b.5a.6f, | 1b.2d.3b.4b.5b.6a, | 1b.2d.3b.4b.5b.6b, |
| 1b.2d.3b.4b.5b.6c, | 1b.2d.3b.4b.5b.6d, | 1b.2d.3b.4b.5b.6e, | 1b.2d.3b.4b.5b.6f, |
| 1b.2d.3b.4b.5c.6a, | 1b.2d.3b.4b.5c.6b, | 1b.2d.3b.4b.5c.6c, | 1b.2d.3b.4b.5c.6d, |
| 1b.2d.3b.4b.5c.6e, | 1b.2d.3b.4b.5c.6f, | 1b.2d.3b.4b.5d.6a, | 1b.2d.3b.4b.5d.6b, |
| 1b.2d.3b.4b.5d.6c, | 1b.2d.3b.4b.5d.6d, | 1b.2d.3b.4b.5d.6e, | 1b.2d.3b.4b.5d.6f, |
| 1b.2d.3b.4b.5e.6a, | 1b.2d.3b.4b.5e.6b, | 1b.2d.3b.4b.5e.6c, | 1b.2d.3b.4b.5e.6d, |
| 1b.2d.3b.4b.5e.6e, | 1b.2d.3b.4b.5e.6f, | 1b.2d.3b.4b.5f.6a, | 1b.2d.3b.4b.5f.6b, |
| 1b.2d.3b.4b.5f.6c, | 1b.2d.3b.4b.5f.6d, | 1b.2d.3b.4b.5f.6e, | 1b.2d.3b.4b.5f.6f, |
| 1b.2d.3b.4c.5a.6a, | 1b.2d.3b.4c.5a.6b, | 1b.2d.3b.4c.5a.6c, | 1b.2d.3b.4c.5a.6d, |
| 1b.2d.3b.4c.5a.6e, | 1b.2d.3b.4c.5a.6f, | 1b.2d.3b.4c.5b.6a, | 1b.2d.3b.4c.5b.6b, |
| 1b.2d.3b.4c.5b.6c, | 1b.2d.3b.4c.5b.6d, | 1b.2d.3b.4c.5b.6e, | 1b.2d.3b.4c.5b.6f, |
| 1b.2d.3b.4c.5c.6a, | 1b.2d.3b.4c.5c.6b, | 1b.2d.3b.4c.5c.6c, | 1b.2d.3b.4c.5c.6d, |
| 1b.2d.3b.4c.5c.6e, | 1b.2d.3b.4c.5c.6f, | 1b.2d.3b.4c.5d.6a, | 1b.2d.3b.4c.5d.6b, |
| 1b.2d.3b.4c.5d.6c, | 1b.2d.3b.4c.5d.6d, | 1b.2d.3b.4c.5d.6e, | 1b.2d.3b.4c.5d.6f, |
| 1b.2d.3b.4c.5e.6a, | 1b.2d.3b.4c.5e.6b, | 1b.2d.3b.4c.5e.6c, | 1b.2d.3b.4c.5e.6d, |
| 1b.2d.3b.4c.5e.6e, | 1b.2d.3b.4c.5e.6f, | 1b.2d.3b.4c.5f.6a, | 1b.2d.3b.4c.5f.6b, |
| 1b.2d.3b.4c.5f.6c, | 1b.2d.3b.4c.5f.6d, | 1b.2d.3b.4c.5f.6e, | 1b.2d.3b.4c.5f.6f, |
| 1b.2d.3b.4d.5a.6a, | 1b.2d.3b.4d.5a.6b, | 1b.2d.3b.4d.5a.6c, | 1b.2d.3b.4d.5a.6d, |
| 1b.2d.3b.4d.5a.6e, | 1b.2d.3b.4d.5a.6f, | 1b.2d.3b.4d.5b.6a, | 1b.2d.3b.4d.5b.6b, |
| 1b.2d.3b.4d.5b.6c, | 1b.2d.3b.4d.5b.6d, | 1b.2d.3b.4d.5b.6e, | 1b.2d.3b.4d.5b.6f, |
| 1b.2d.3b.4d.5c.6a, | 1b.2d.3b.4d.5c.6b, | 1b.2d.3b.4d.5c.6c, | 1b.2d.3b.4d.5c.6d, |
| 1b.2d.3b.4d.5c.6e, | 1b.2d.3b.4d.5c.6f, | 1b.2d.3b.4d.5d.6a, | 1b.2d.3b.4d.5d.6b, |
| 1b.2d.3b.4d.5d.6c, | 1b.2d.3b.4d.5d.6d, | 1b.2d.3b.4d.5d.6e, | 1b.2d.3b.4d.5d.6f, |
| 1b.2d.3b.4d.5e.6a, | 1b.2d.3b.4d.5e.6b, | 1b.2d.3b.4d.5e.6c, | 1b.2d.3b.4d.5e.6d, |
| 1b.2d.3b.4d.5e.6e, | 1b.2d.3b.4d.5e.6f, | 1b.2d.3b.4d.5f.6a, | 1b.2d.3b.4d.5f.6b, |
| 1b.2d.3b.4d.5f.6c, | 1b.2d.3b.4d.5f.6d, | 1b.2d.3b.4d.5f.6e, | 1b.2d.3b.4d.5f.6f, |
| 1b.2d.3b.4e.5a.6a, | 1b.2d.3b.4e.5a.6b, | 1b.2d.3b.4e.5a.6c, | 1b.2d.3b.4e.5a.6d, |
| 1b.2d.3b.4e.5a.6e, | 1b.2d.3b.4e.5a.6f, | 1b.2d.3b.4e.5b.6a, | 1b.2d.3b.4e.5b.6b, |
| 1b.2d.3b.4e.5b.6c, | 1b.2d.3b.4e.5b.6d, | 1b.2d.3b.4e.5b.6e, | 1b.2d.3b.4e.5b.6f, |
| 1b.2d.3b.4e.5c.6a, | 1b.2d.3b.4e.5c.6b, | 1b.2d.3b.4e.5c.6c, | 1b.2d.3b.4e.5c.6d, |
| 1b.2d.3b.4e.5c.6e, | 1b.2d.3b.4e.5c.6f, | 1b.2d.3b.4e.5d.6a, | 1b.2d.3b.4e.5d.6b, |
| 1b.2d.3b.4e.5d.6c, | 1b.2d.3b.4e.5d.6d, | 1b.2d.3b.4e.5d.6e, | 1b.2d.3b.4e.5d.6f, |
| 1b.2d.3b.4e.5e.6a, | 1b.2d.3b.4e.5e.6b, | 1b.2d.3b.4e.5e.6c, | 1b.2d.3b.4e.5e.6d, |
| 1b.2d.3b.4e.5e.6e, | 1b.2d.3b.4e.5e.6f, | 1b.2d.3b.4e.5f.6a, | 1b.2d.3b.4e.5f.6b, |
| 1b.2d.3b.4e.5f.6c, | 1b.2d.3b.4e.5f.6d, | 1b.2d.3b.4e.5f.6e, | 1b.2d.3b.4e.5f.6f, |
| 1b.2d.3b.4f.5a.6a, | 1b.2d.3b.4f.5a.6b, | 1b.2d.3b.4f.5a.6c, | 1b.2d.3b.4f.5a.6d, |
| 1b.2d.3b.4f.5a.6e, | 1b.2d.3b.4f.5a.6f, | 1b.2d.3b.4f.5b.6a, | 1b.2d.3b.4f.5b.6b, |
| 1b.2d.3b.4f.5b.6c, | 1b.2d.3b.4f.5b.6d, | 1b.2d.3b.4f.5b.6e, | 1b.2d.3b.4f.5b.6f, |
| 1b.2d.3b.4f.5c.6a, | 1b.2d.3b.4f.5c.6b, | 1b.2d.3b.4f.5c.6c, | 1b.2d.3b.4f.5c.6d, |
| 1b.2d.3b.4f.5c.6e, | 1b.2d.3b.4f.5c.6f, | 1b.2d.3b.4f.5d.6a, | 1b.2d.3b.4f.5d.6b, |
| 1b.2d.3b.4f.5d.6c, | 1b.2d.3b.4f.5d.6d, | 1b.2d.3b.4f.5d.6e, | 1b.2d.3b.4f.5d.6f, |

TABLE 7-continued

List of Compounds of Formula (II)

| | | | |
|---|---|---|---|
| 1b.2d.3b.4f.5e.6a, | 1b.2d.3b.4f.5e.6b, | 1b.2d.3b.4f.5e.6c, | 1b.2d.3b.4f.5e.6d, |
| 1b.2d.3b.4f.5e.6e, | 1b.2d.3b.4f.5e.6f, | 1b.2d.3b.4f.5f.6a, | 1b.2d.3b.4f.5f.6b, |
| 1b.2d.3b.4f.5f.6c, | 1b.2d.3b.4f.5f.6d, | 1b.2d.3b.4f.5f.6e, | 1b.2d.3b.4f.5f.6f, |
| 1b.2d.3c.4a.5a.6a, | 1b.2d.3c.4a.5a.6b, | 1b.2d.3c.4a.5a.6c, | 1b.2d.3c.4a.5a.6d, |
| 1b.2d.3c.4a.5a.6e, | 1b.2d.3c.4a.5a.6f, | 1b.2d.3c.4a.5b.6a, | 1b.2d.3c.4a.5b.6b, |
| 1b.2d.3c.4a.5b.6c, | 1b.2d.3c.4a.5b.6d, | 1b.2d.3c.4a.5b.6e, | 1b.2d.3c.4a.5b.6f, |
| 1b.2d.3c.4a.5c.6a, | 1b.2d.3c.4a.5c.6b, | 1b.2d.3c.4a.5c.6c, | 1b.2d.3c.4a.5c.6d, |
| 1b.2d.3c.4a.5c.6e, | 1b.2d.3c.4a.5c.6f, | 1b.2d.3c.4a.5d.6a, | 1b.2d.3c.4a.5d.6b, |
| 1b.2d.3c.4a.5d.6c, | 1b.2d.3c.4a.5d.6d, | 1b.2d.3c.4a.5d.6e, | 1b.2d.3c.4a.5d.6f, |
| 1b.2d.3c.4a.5e.6a, | 1b.2d.3c.4a.5e.6b, | 1b.2d.3c.4a.5e.6c, | 1b.2d.3c.4a.5e.6d, |
| 1b.2d.3c.4a.5e.6e, | 1b.2d.3c.4a.5e.6f, | 1b.2d.3c.4a.5f.6a, | 1b.2d.3c.4a.5f.6b, |
| 1b.2d.3c.4a.5f.6c, | 1b.2d.3c.4a.5f.6d, | 1b.2d.3c.4a.5f.6e, | 1b.2d.3c.4a.5f.6f, |
| 1b.2d.3c.4b.5a.6a, | 1b.2d.3c.4b.5a.6b, | 1b.2d.3c.4b.5a.6c, | 1b.2d.3c.4b.5a.6d, |
| 1b.2d.3c.4b.5a.6e, | 1b.2d.3c.4b.5a.6f, | 1b.2d.3c.4b.5b.6a, | 1b.2d.3c.4b.5b.6b, |
| 1b.2d.3c.4b.5b.6c, | 1b.2d.3c.4b.5b.6d, | 1b.2d.3c.4b.5b.6e, | 1b.2d.3c.4b.5b.6f, |
| 1b.2d.3c.4b.5c.6a, | 1b.2d.3c.4b.5c.6b, | 1b.2d.3c.4b.5c.6c, | 1b.2d.3c.4b.5c.6d, |
| 1b.2d.3c.4b.5c.6e, | 1b.2d.3c.4b.5c.6f, | 1b.2d.3c.4b.5d.6a, | 1b.2d.3c.4b.5d.6b, |
| 1b.2d.3c.4b.5d.6c, | 1b.2d.3c.4b.5d.6d, | 1b.2d.3c.4b.5d.6e, | 1b.2d.3c.4b.5d.6f, |
| 1b.2d.3c.4b.5e.6a, | 1b.2d.3c.4b.5e.6b, | 1b.2d.3c.4b.5e.6c, | 1b.2d.3c.4b.5e.6d, |
| 1b.2d.3c.4b.5e.6e, | 1b.2d.3c.4b.5e.6f, | 1b.2d.3c.4b.5f.6a, | 1b.2d.3c.4b.5f.6b, |
| 1b.2d.3c.4b.5f.6c, | 1b.2d.3c.4b.5f.6d, | 1b.2d.3c.4b.5f.6e, | 1b.2d.3c.4b.5f.6f, |
| 1b.2d.3c.4c.5a.6a, | 1b.2d.3c.4c.5a.6b, | 1b.2d.3c.4c.5a.6c, | 1b.2d.3c.4c.5a.6d, |
| 1b.2d.3c.4c.5a.6e, | 1b.2d.3c.4c.5a.6f, | 1b.2d.3c.4c.5b.6a, | 1b.2d.3c.4c.5b.6b, |
| 1b.2d.3c.4c.5b.6c, | 1b.2d.3c.4c.5b.6d, | 1b.2d.3c.4c.5b.6e, | 1b.2d.3c.4c.5b.6f, |
| 1b.2d.3c.4c.5c.6a, | 1b.2d.3c.4c.5c.6b, | 1b.2d.3c.4c.5c.6c, | 1b.2d.3c.4c.5c.6d, |
| 1b.2d.3c.4c.5c.6e, | 1b.2d.3c.4c.5c.6f, | 1b.2d.3c.4c.5d.6a, | 1b.2d.3c.4c.5d.6b, |
| 1b.2d.3c.4c.5d.6c, | 1b.2d.3c.4c.5d.6d, | 1b.2d.3c.4c.5d.6e, | 1b.2d.3c.4c.5d.6f, |
| 1b.2d.3c.4c.5e.6a, | 1b.2d.3c.4c.5e.6b, | 1b.2d.3c.4c.5e.6c, | 1b.2d.3c.4c.5e.6d, |
| 1b.2d.3c.4c.5e.6e, | 1b.2d.3c.4c.5e.6f, | 1b.2d.3c.4c.5f.6a, | 1b.2d.3c.4c.5f.6b, |
| 1b.2d.3c.4c.5f.6c, | 1b.2d.3c.4c.5f.6d, | 1b.2d.3c.4c.5f.6e, | 1b.2d.3c.4c.5f.6f, |
| 1b.2d.3c.4d.5a.6a, | 1b.2d.3c.4d.5a.6b, | 1b.2d.3c.4d.5a.6c, | 1b.2d.3c.4d.5a.6d, |
| 1b.2d.3c.4d.5a.6e, | 1b.2d.3c.4d.5a.6f, | 1b.2d.3c.4d.5b.6a, | 1b.2d.3c.4d.5b.6b, |
| 1b.2d.3c.4d.5b.6c, | 1b.2d.3c.4d.5b.6d, | 1b.2d.3c.4d.5b.6e, | 1b.2d.3c.4d.5b.6f, |
| 1b.2d.3c.4d.5c.6a, | 1b.2d.3c.4d.5c.6b, | 1b.2d.3c.4d.5c.6c, | 1b.2d.3c.4d.5c.6d, |
| 1b.2d.3c.4d.5c.6e, | 1b.2d.3c.4d.5c.6f, | 1b.2d.3c.4d.5d.6a, | 1b.2d.3c.4d.5d.6b, |
| 1b.2d.3c.4d.5d.6c, | 1b.2d.3c.4d.5d.6d, | 1b.2d.3c.4d.5d.6e, | 1b.2d.3c.4d.5d.6f, |
| 1b.2d.3c.4d.5e.6a, | 1b.2d.3c.4d.5e.6b, | 1b.2d.3c.4d.5e.6c, | 1b.2d.3c.4d.5e.6d, |
| 1b.2d.3c.4d.5e.6e, | 1b.2d.3c.4d.5e.6f, | 1b.2d.3c.4d.5f.6a, | 1b.2d.3c.4d.5f.6b, |
| 1b.2d.3c.4d.5f.6c, | 1b.2d.3c.4d.5f.6d, | 1b.2d.3c.4d.5f.6e, | 1b.2d.3c.4d.5f.6f, |
| 1b.2d.3c.4e.5a.6a, | 1b.2d.3c.4e.5a.6b, | 1b.2d.3c.4e.5a.6c, | 1b.2d.3c.4e.5a.6d, |
| 1b.2d.3c.4e.5a.6e, | 1b.2d.3c.4e.5a.6f, | 1b.2d.3c.4e.5b.6a, | 1b.2d.3c.4e.5b.6b, |
| 1b.2d.3c.4e.5b.6c, | 1b.2d.3c.4e.5b.6d, | 1b.2d.3c.4e.5b.6e, | 1b.2d.3c.4e.5b.6f, |
| 1b.2d.3c.4e.5c.6a, | 1b.2d.3c.4e.5c.6b, | 1b.2d.3c.4e.5c.6c, | 1b.2d.3c.4e.5c.6d, |
| 1b.2d.3c.4e.5c.6e, | 1b.2d.3c.4e.5c.6f, | 1b.2d.3c.4e.5d.6a, | 1b.2d.3c.4e.5d.6b, |
| 1b.2d.3c.4e.5d.6c, | 1b.2d.3c.4e.5d.6d, | 1b.2d.3c.4e.5d.6e, | 1b.2d.3c.4e.5d.6f, |
| 1b.2d.3c.4e.5e.6a, | 1b.2d.3c.4e.5e.6b, | 1b.2d.3c.4e.5e.6c, | 1b.2d.3c.4e.5e.6d, |
| 1b.2d.3c.4e.5e.6e, | 1b.2d.3c.4e.5e.6f, | 1b.2d.3c.4e.5f.6a, | 1b.2d.3c.4e.5f.6b, |
| 1b.2d.3c.4e.5f.6c, | 1b.2d.3c.4e.5f.6d, | 1b.2d.3c.4e.5f.6e, | 1b.2d.3c.4e.5f.6f, |
| 1b.2d.3c.4f.5a.6a, | 1b.2d.3c.4f.5a.6b, | 1b.2d.3c.4f.5a.6c, | 1b.2d.3c.4f.5a.6d, |
| 1b.2d.3c.4f.5a.6e, | 1b.2d.3c.4f.5a.6f, | 1b.2d.3c.4f.5b.6a, | 1b.2d.3c.4f.5b.6b, |
| 1b.2d.3c.4f.5b.6c, | 1b.2d.3c.4f.5b.6d, | 1b.2d.3c.4f.5b.6e, | 1b.2d.3c.4f.5b.6f, |
| 1b.2d.3c.4f.5c.6a, | 1b.2d.3c.4f.5c.6b, | 1b.2d.3c.4f.5c.6c, | 1b.2d.3c.4f.5c.6d, |
| 1b.2d.3c.4f.5c.6e, | 1b.2d.3c.4f.5c.6f, | 1b.2d.3c.4f.5d.6a, | 1b.2d.3c.4f.5d.6b, |
| 1b.2d.3c.4f.5d.6c, | 1b.2d.3c.4f.5d.6d, | 1b.2d.3c.4f.5d.6e, | 1b.2d.3c.4f.5d.6f, |
| 1b.2d.3c.4f.5e.6a, | 1b.2d.3c.4f.5e.6b, | 1b.2d.3c.4f.5e.6c, | 1b.2d.3c.4f.5e.6d, |
| 1b.2d.3c.4f.5e.6e, | 1b.2d.3c.4f.5e.6f, | 1b.2d.3c.4f.5f.6a, | 1b.2d.3c.4f.5f.6b, 1b.2d.3c.4f.5f.6c, |
| 1b.2d.3c.4f.5f.6d, | 1b.2d.3c.4f.5f.6e, | 1b.2d.3c.4f.5f.6f, | 1b.2d.3d.4a.5a.6a, |
| 1b.2d.3d.4a.5a.6b, | 1b.2d.3d.4a.5a.6c, | 1b.2d.3d.4a.5a.6d, | 1b.2d.3d.4a.5a.6e, |
| 1b.2d.3d.4a.5a.6f, | 1b.2d.3d.4a.5b.6a, | 1b.2d.3d.4a.5b.6b, | 1b.2d.3d.4a.5b.6c, |
| 1b.2d.3d.4a.5b.6d, | 1b.2d.3d.4a.5b.6e, | 1b.2d.3d.4a.5b.6f, | 1b.2d.3d.4a.5c.6a, |
| 1b.2d.3d.4a.5c.6b, | 1b.2d.3d.4a.5c.6c, | 1b.2d.3d.4a.5c.6d, | 1b.2d.3d.4a.5c.6e, |
| 1b.2d.3d.4a.5c.6f, | 1b.2d.3d.4a.5d.6a, | 1b.2d.3d.4a.5d.6b, | 1b.2d.3d.4a.5d.6c, |
| 1b.2d.3d.4a.5d.6d, | 1b.2d.3d.4a.5d.6e, | 1b.2d.3d.4a.5d.6f, | 1b.2d.3d.4a.5e.6a, |
| 1b.2d.3d.4a.5e.6b, | 1b.2d.3d.4a.5e.6c, | 1b.2d.3d.4a.5e.6d, | 1b.2d.3d.4a.5e.6e, |
| 1b.2d.3d.4a.5e.6f, | 1b.2d.3d.4a.5f.6a, | 1b.2d.3d.4a.5f.6b, | 1b.2d.3d.4a.5f.6c, |
| 1b.2d.3d.4a.5f.6d, | 1b.2d.3d.4a.5f.6e, | 1b.2d.3d.4a.5f.6f, | 1b.2d.3d.4b.5a.6a, |
| 1b.2d.3d.4b.5a.6b, | 1b.2d.3d.4b.5a.6c, | 1b.2d.3d.4b.5a.6d, | 1b.2d.3d.4b.5a.6e, |
| 1b.2d.3d.4b.5a.6f, | 1b.2d.3d.4b.5b.6a, | 1b.2d.3d.4b.5b.6b, | 1b.2d.3d.4b.5b.6c, |
| 1b.2d.3d.4b.5b.6d, | 1b.2d.3d.4b.5b.6e, | 1b.2d.3d.4b.5b.6f, | 1b.2d.3d.4b.5c.6a, |
| 1b.2d.3d.4b.5c.6b, | 1b.2d.3d.4b.5c.6c, | 1b.2d.3d.4b.5c.6d, | 1b.2d.3d.4b.5c.6e, |
| 1b.2d.3d.4b.5c.6f, | 1b.2d.3d.4b.5d.6a, | 1b.2d.3d.4b.5d.6b, | 1b.2d.3d.4b.5d.6c, |
| 1b.2d.3d.4b.5d.6d, | 1b.2d.3d.4b.5d.6e, | 1b.2d.3d.4b.5d.6f, | 1b.2d.3d.4b.5e.6a, |
| 1b.2d.3d.4b.5e.6b, | 1b.2d.3d.4b.5e.6c, | 1b.2d.3d.4b.5e.6d, | 1b.2d.3d.4b.5e.6e, |
| 1b.2d.3d.4b.5e.6f, | 1b.2d.3d.4b.5f.6a, | 1b.2d.3d.4b.5f.6b, | 1b.2d.3d.4b.5f.6c, |
| 1b.2d.3d.4b.5f.6d, | 1b.2d.3d.4b.5f.6e, | 1b.2d.3d.4b.5f.6f, | 1b.2d.3d.4c.5a.6a, |
| 1b.2d.3d.4c.5a.6b, | 1b.2d.3d.4c.5a.6c, | 1b.2d.3d.4c.5a.6d, | 1b.2d.3d.4c.5a.6e, |
| 1b.2d.3d.4c.5a.6f, | 1b.2d.3d.4c.5b.6a, | 1b.2d.3d.4c.5b.6b, | 1b.2d.3d.4c.5b.6c, |
| 1b.2d.3d.4c.5b.6d, | 1b.2d.3d.4c.5b.6e, | 1b.2d.3d.4c.5b.6f, | 1b.2d.3d.4c.5c.6a, |

TABLE 7-continued

List of Compounds of Formula (II)

| | | | |
|---|---|---|---|
| 1b.2d.3d.4c.5c.6b, | 1b.2d.3d.4c.5c.6c, | 1b.2d.3d.4c.5c.6d, | 1b.2d.3d.4c.5c.6e, |
| 1b.2d.3d.4c.5c.6f, | 1b.2d.3d.4c.5d.6a, | 1b.2d.3d.4c.5d.6b, | 1b.2d.3d.4c.5d.6c, |
| 1b.2d.3d.4c.5d.6d, | 1b.2d.3d.4c.5d.6e, | 1b.2d.3d.4c.5d.6f, | 1b.2d.3d.4c.5e.6a, |
| 1b.2d.3d.4c.5e.6b, | 1b.2d.3d.4c.5e.6c, | 1b.2d.3d.4c.5e.6d, | 1b.2d.3d.4c.5e.6e, |
| 1b.2d.3d.4c.5e.6f, | 1b.2d.3d.4c.5f.6a, | 1b.2d.3d.4c.5f.6b, | 1b.2d.3d.4c.5f.6c, |
| 1b.2d.3d.4c.5f.6d, | 1b.2d.3d.4c.5f.6e, | 1b.2d.3d.4c.5f.6f, | 1b.2d.3d.4d.5a.6a, |
| 1b.2d.3d.4d.5a.6b, | 1b.2d.3d.4d.5a.6c, | 1b.2d.3d.4d.5a.6d, | 1b.2d.3d.4d.5a.6e, |
| 1b.2d.3d.4d.5a.6f, | 1b.2d.3d.4d.5b.6a, | 1b.2d.3d.4d.5b.6b, | 1b.2d.3d.4d.5b.6c, |
| 1b.2d.3d.4d.5b.6d, | 1b.2d.3d.4d.5b.6e, | 1b.2d.3d.4d.5b.6f, | 1b.2d.3d.4d.5c.6a, |
| 1b.2d.3d.4d.5c.6b, | 1b.2d.3d.4d.5c.6c, | 1b.2d.3d.4d.5c.6d, | 1b.2d.3d.4d.5c.6e, |
| 1b.2d.3d.4d.5c.6f, | 1b.2d.3d.4d.5d.6a, | 1b.2d.3d.4d.5d.6b, | 1b.2d.3d.4d.5d.6c, |
| 1b.2d.3d.4d.5d.6d, | 1b.2d.3d.4d.5d.6e, | 1b.2d.3d.4d.5d.6f, | 1b.2d.3d.4d.5e.6a, |
| 1b.2d.3d.4d.5e.6b, | 1b.2d.3d.4d.5e.6c, | 1b.2d.3d.4d.5e.6d, | 1b.2d.3d.4d.5e.6e, |
| 1b.2d.3d.4d.5e.6f, | 1b.2d.3d.4d.5f.6a, | 1b.2d.3d.4d.5f.6b, | 1b.2d.3d.4d.5f.6c, |
| 1b.2d.3d.4d.5f.6d, | 1b.2d.3d.4d.5f.6e, | 1b.2d.3d.4d.5f.6f, | 1b.2d.3d.4e.5a.6a, |
| 1b.2d.3d.4e.5a.6b, | 1b.2d.3d.4e.5a.6c, | 1b.2d.3d.4e.5a.6d, | 1b.2d.3d.4e.5a.6e, |
| 1b.2d.3d.4e.5a.6f, | 1b.2d.3d.4e.5b.6a, | 1b.2d.3d.4e.5b.6b, | 1b.2d.3d.4e.5b.6c, |
| 1b.2d.3d.4e.5b.6d, | 1b.2d.3d.4e.5b.6e, | 1b.2d.3d.4e.5b.6f, | 1b.2d.3d.4e.5c.6a, |
| 1b.2d.3d.4e.5c.6b, | 1b.2d.3d.4e.5c.6c, | 1b.2d.3d.4e.5c.6d, | 1b.2d.3d.4e.5c.6e, |
| 1b.2d.3d.4e.5c.6f, | 1b.2d.3d.4e.5d.6a, | 1b.2d.3d.4e.5d.6b, | 1b.2d.3d.4e.5d.6c, |
| 1b.2d.3d.4e.5d.6d, | 1b.2d.3d.4e.5d.6e, | 1b.2d.3d.4e.5d.6f, | 1b.2d.3d.4e.5e.6a, |
| 1b.2d.3d.4e.5e.6b, | 1b.2d.3d.4e.5e.6c, | 1b.2d.3d.4e.5e.6d, | 1b.2d.3d.4e.5e.6e, |
| 1b.2d.3d.4e.5e.6f, | 1b.2d.3d.4e.5f.6a, | 1b.2d.3d.4e.5f.6b, | 1b.2d.3d.4e.5f.6c, |
| 1b.2d.3d.4e.5f.6d, | 1b.2d.3d.4e.5f.6e, | 1b.2d.3d.4e.5f.6f, | 1b.2d.3d.4f.5a.6a, |
| 1b.2d.3d.4f.5a.6b, | 1b.2d.3d.4f.5a.6c, | 1b.2d.3d.4f.5a.6d, | 1b.2d.3d.4f.5a.6e, |
| 1b.2d.3d.4f.5a.6f, | 1b.2d.3d.4f.5b.6a, | 1b.2d.3d.4f.5b.6b, | 1b.2d.3d.4f.5b.6c, |
| 1b.2d.3d.4f.5b.6d, | 1b.2d.3d.4f.5b.6e, | 1b.2d.3d.4f.5b.6f, | 1b.2d.3d.4f.5c.6a, |
| 1b.2d.3d.4f.5c.6b, | 1b.2d.3d.4f.5c.6c, | 1b.2d.3d.4f.5c.6d, | 1b.2d.3d.4f.5c.6e, |
| 1b.2d.3d.4f.5c.6f, | 1b.2d.3d.4f.5d.6a, | 1b.2d.3d.4f.5d.6b, | 1b.2d.3d.4f.5d.6c, |
| 1b.2d.3d.4f.5d.6d, | 1b.2d.3d.4f.5d.6e, | 1b.2d.3d.4f.5d.6f, | 1b.2d.3d.4f.5e.6a, |
| 1b.2d.3d.4f.5e.6b, | 1b.2d.3d.4f.5e.6c, | 1b.2d.3d.4f.5e.6d, | 1b.2d.3d.4f.5e.6e, |
| 1b.2d.3d.4f.5e.6f, | 1b.2d.3d.4f.5f.6a, | 1b.2d.3d.4f.5f.6b, | 1b.2d.3d.4f.5f.6c, |
| 1b.2d.3d.4f.5f.6d, | 1b.2d.3d.4f.5f.6e, | 1b.2d.3d.4f.5f.6f, | 1b.2d.3e.4a.5a.6a, |
| 1b.2d.3e.4a.5a.6b, | 1b.2d.3e.4a.5a.6c, | 1b.2d.3e.4a.5a.6d, | 1b.2d.3e.4a.5a.6e, |
| 1b.2d.3e.4a.5a.6f, | 1b.2d.3e.4a.5b.6a, | 1b.2d.3e.4a.5b.6b, | 1b.2d.3e.4a.5b.6c, |
| 1b.2d.3e.4a.5b.6d, | 1b.2d.3e.4a.5b.6e, | 1b.2d.3e.4a.5b.6f, | 1b.2d.3e.4a.5c.6a, |
| 1b.2d.3e.4a.5c.6b, | 1b.2d.3e.4a.5c.6c, | 1b.2d.3e.4a.5c.6d, | 1b.2d.3e.4a.5c.6e, |
| 1b.2d.3e.4a.5c.6f, | 1b.2d.3e.4a.5d.6a, | 1b.2d.3e.4a.5d.6b, | 1b.2d.3e.4a.5d.6c, |
| 1b.2d.3e.4a.5d.6d, | 1b.2d.3e.4a.5d.6e, | 1b.2d.3e.4a.5d.6f, | 1b.2d.3e.4a.5e.6a, |
| 1b.2d.3e.4a.5e.6b, | 1b.2d.3e.4a.5e.6c, | 1b.2d.3e.4a.5e.6d, | 1b.2d.3e.4a.5e.6e, |
| 1b.2d.3e.4a.5e.6f, | 1b.2d.3e.4a.5f.6a, | 1b.2d.3e.4a.5f.6b, | 1b.2d.3e.4a.5f.6c, |
| 1b.2d.3e.4a.5f.6d, | 1b.2d.3e.4a.5f.6e, | 1b.2d.3e.4a.5f.6f, | 1b.2d.3e.4b.5a.6a, |
| 1b.2d.3e.4b.5a.6b, | 1b.2d.3e.4b.5a.6c, | 1b.2d.3e.4b.5a.6d, | 1b.2d.3e.4b.5a.6e, |
| 1b.2d.3e.4b.5a.6f, | 1b.2d.3e.4b.5b.6a, | 1b.2d.3e.4b.5b.6b, | 1b.2d.3e.4b.5b.6c, |
| 1b.2d.3e.4b.5b.6d, | 1b.2d.3e.4b.5b.6e, | 1b.2d.3e.4b.5b.6f, | 1b.2d.3e.4b.5c.6a, |
| 1b.2d.3e.4b.5c.6b, | 1b.2d.3e.4b.5c.6c, | 1b.2d.3e.4b.5c.6d, | 1b.2d.3e.4b.5c.6e, |
| 1b.2d.3e.4b.5c.6f, | 1b.2d.3e.4b.5d.6a, | 1b.2d.3e.4b.5d.6b, | 1b.2d.3e.4b.5d.6c, |
| 1b.2d.3e.4b.5d.6d, | 1b.2d.3e.4b.5d.6e, | 1b.2d.3e.4b.5d.6f, | 1b.2d.3e.4b.5e.6a, |
| 1b.2d.3e.4b.5e.6b, | 1b.2d.3e.4b.5e.6c, | 1b.2d.3e.4b.5e.6d, | 1b.2d.3e.4b.5e.6e, |
| 1b.2d.3e.4b.5e.6f, | 1b.2d.3e.4b.5f.6a, | 1b.2d.3e.4b.5f.6b, | 1b.2d.3e.4b.5f.6c, |
| 1b.2d.3e.4b.5f.6d, | 1b.2d.3e.4b.5f.6e, | 1b.2d.3e.4b.5f.6f, | 1b.2d.3e.4c.5a.6a, |
| 1b.2d.3e.4c.5a.6b, | 1b.2d.3e.4c.5a.6c, | 1b.2d.3e.4c.5a.6d, | 1b.2d.3e.4c.5a.6e, |
| 1b.2d.3e.4c.5a.6f, | 1b.2d.3e.4c.5b.6a, | 1b.2d.3e.4c.5b.6b, | 1b.2d.3e.4c.5b.6c, |
| 1b.2d.3e.4c.5b.6d, | 1b.2d.3e.4c.5b.6e, | 1b.2d.3e.4c.5b.6f, | 1b.2d.3e.4c.5c.6a, |
| 1b.2d.3e.4c.5c.6b, | 1b.2d.3e.4c.5c.6c, | 1b.2d.3e.4c.5c.6d, | 1b.2d.3e.4c.5c.6e, |
| 1b.2d.3e.4c.5c.6f, | 1b.2d.3e.4c.5d.6a, | 1b.2d.3e.4c.5d.6b, | 1b.2d.3e.4c.5d.6c, |
| 1b.2d.3e.4c.5d.6d, | 1b.2d.3e.4c.5d.6e, | 1b.2d.3e.4c.5d.6f, | 1b.2d.3e.4c.5e.6a, |
| 1b.2d.3e.4c.5e.6b, | 1b.2d.3e.4c.5e.6c, | 1b.2d.3e.4c.5e.6d, | 1b.2d.3e.4c.5e.6e, |
| 1b.2d.3e.4c.5e.6f, | 1b.2d.3e.4c.5f.6a, | 1b.2d.3e.4c.5f.6b, | 1b.2d.3e.4c.5f.6c, |
| 1b.2d.3e.4c.5f.6d, | 1b.2d.3e.4c.5f.6e, | 1b.2d.3e.4c.5f.6f, | 1b.2d.3e.4d.5a.6a, |
| 1b.2d.3e.4d.5a.6b, | 1b.2d.3e.4d.5a.6c, | 1b.2d.3e.4d.5a.6d, | 1b.2d.3e.4d.5a.6e, |
| 1b.2d.3e.4d.5a.6f, | 1b.2d.3e.4d.5b.6a, | 1b.2d.3e.4d.5b.6b, | 1b.2d.3e.4d.5b.6c, |
| 1b.2d.3e.4d.5b.6d, | 1b.2d.3e.4d.5b.6e, | 1b.2d.3e.4d.5b.6f, | 1b.2d.3e.4d.5c.6a, |
| 1b.2d.3e.4d.5c.6b, | 1b.2d.3e.4d.5c.6c, | 1b.2d.3e.4d.5c.6d, | 1b.2d.3e.4d.5c.6e, |
| 1b.2d.3e.4d.5c.6f, | 1b.2d.3e.4d.5d.6a, | 1b.2d.3e.4d.5d.6b, | 1b.2d.3e.4d.5d.6c, |
| 1b.2d.3e.4d.5d.6d, | 1b.2d.3e.4d.5d.6e, | 1b.2d.3e.4d.5d.6f, | 1b.2d.3e.4d.5e.6a, |
| 1b.2d.3e.4d.5e.6b, | 1b.2d.3e.4d.5e.6c, | 1b.2d.3e.4d.5e.6d, | 1b.2d.3e.4d.5e.6e, |
| 1b.2d.3e.4d.5e.6f, | 1b.2d.3e.4d.5f.6a, | 1b.2d.3e.4d.5f.6b, | 1b.2d.3e.4d.5f.6c, |
| 1b.2d.3e.4d.5f.6d, | 1b.2d.3e.4d.5f.6e, | 1b.2d.3e.4d.5f.6f, | 1b.2d.3e.4e.5a.6a, |
| 1b.2d.3e.4e.5a.6b, | 1b.2d.3e.4e.5a.6c, | 1b.2d.3e.4e.5a.6d, | 1b.2d.3e.4e.5a.6e, |
| 1b.2d.3e.4e.5a.6f, | 1b.2d.3e.4e.5b.6a, | 1b.2d.3e.4e.5b.6b, | 1b.2d.3e.4e.5b.6c, |
| 1b.2d.3e.4e.5b.6d, | 1b.2d.3e.4e.5b.6e, | 1b.2d.3e.4e.5b.6f, | 1b.2d.3e.4e.5c.6a, |
| 1b.2d.3e.4e.5c.6b, | 1b.2d.3e.4e.5c.6c, | 1b.2d.3e.4e.5c.6d, | 1b.2d.3e.4e.5c.6e, |
| 1b.2d.3e.4e.5c.6f, | 1b.2d.3e.4e.5d.6a, | 1b.2d.3e.4e.5d.6b, | 1b.2d.3e.4e.5d.6c, |
| 1b.2d.3e.4e.5d.6d, | 1b.2d.3e.4e.5d.6e, | 1b.2d.3e.4e.5d.6f, | 1b.2d.3e.4e.5e.6a, |
| 1b.2d.3e.4e.5e.6b, | 1b.2d.3e.4e.5e.6c, | 1b.2d.3e.4e.5e.6d, | 1b.2d.3e.4e.5e.6e, |
| 1b.2d.3e.4e.5e.6f, | 1b.2d.3e.4e.5f.6a, | 1b.2d.3e.4e.5f.6b, | 1b.2d.3e.4e.5f.6c, |
| 1b.2d.3e.4e.5f.6d, | 1b.2d.3e.4e.5f.6e, | 1b.2d.3e.4e.5f.6f, | 1b.2d.3e.4f.5a.6a, |

TABLE 7-continued

List of Compounds of Formula (II)

| | | | |
|---|---|---|---|
| 1b.2d.3e.4f.5a.6b, | 1b.2d.3e.4f.5a.6c, | 1b.2d.3e.4f.5a.6d, | 1b.2d.3e.4f.5a.6e, |
| 1b.2d.3e.4f.5a.6f, | 1b.2d.3e.4f.5b.6a, | 1b.2d.3e.4f.5b.6b, | 1b.2d.3e.4f.5b.6c, |
| 1b.2d.3e.4f.5b.6d, | 1b.2d.3e.4f.5b.6e, | 1b.2d.3e.4f.5b.6f, | 1b.2d.3e.4f.5c.6a, |
| 1b.2d.36.4f.5c.6b, | 1b.2d.3e.4f.5c.6c, | 1b.2d.3e.4f.5c.6d, | 1b.2d.3e.4f.5c.6e, |
| 1b.2d.3e.4f.5c.6f, | 1b.2d.3e.4f.5d.6a, | 1b.2d.3e.4f.5d.6b, | 1b.2d.3e.4f.5d.6c, |
| 1b.2d.3e.4f.5d.6d, | 1b.2d.3e.4f.5d.6e, | 1b.2d.3e.4f.5d.6f, | 1b.2d.3e.4f.5e.6a, |
| 1b.2d.3e.4f.5e.6b, | 1b.2d.3e.4f.5e.6c, | 1b.2d.3e.4f.5e.6d, | 1b.2d.3e.4f.5e.6e, |
| 1b.2d.3e.4f.5e.6f, | 1b.2d.3e.4f.5f.6a, | 1b.2d.3e.4f.5f.6b, | 1b.2d.3e.4f.5f.6c, | 1b.2d.3e.4f.5f.6d, |
| 1b.2d.3e.4f.5f.6e, | 1b.2d.3e.4f.5f.6f, | 1b.2d.3f.4a.5a.6a, | 1b.2d.3f.4a.5a.6b, |
| 1b.2d.3f.4a.5a.6c, | 1b.2d.3f.4a.5a.6d, | 1b.2d.3f.4a.5a.6e, | 1b.2d.3f.4a.5a.6f, |
| 1b.2d.3f.4a.5b.6a, | 1b.2d.3f.4a.5b.6b, | 1b.2d.3f.4a.5b.6c, | 1b.2d.3f.4a.5b.6d, |
| 1b.2d.3f.4a.5b.6e, | 1b.2d.3f.4a.5b.6f, | 1b.2d.3f.4a.5c.6a, | 1b.2d.3f.4a.5c.6b, |
| 1b.2d.3f.4a.5c.6c, | 1b.2d.3f.4a.5c.6d, | 1b.2d.3f.4a.5c.6e, | 1b.2d.3f.4a.5c.6f, |
| 1b.2d.3f.4a.5d.6a, | 1b.2d.3f.4a.5d.6b, | 1b.2d.3f.4a.5d.6c, | 1b.2d.3f.4a.5d.6d, |
| 1b.2d.3f.4a.5d.6e, | 1b.2d.3f.4a.5d.6f, | 1b.2d.3f.4a.5e.6a, | 1b.2d.3f.4a.5e.6b, |
| 1b.2d.3f.4a.5e.6c, | 1b.2d.3f.4a.5e.6d, | 1b.2d.3f.4a.5e.6e, | 1b.2d.3f.4a.5e.6f, |
| 1b.2d.3f.4a.5f.6a, | 1b.2d.3f.4a.5f.6b, | 1b.2d.3f.4a.5f.6c, | 1b.2d.3f.4a.5f.6d, | 1b.2d.3f.4a.5f.6e, |
| 1b.2d.3f.4a.5f.6f, | 1b.2d.3f.4b.5a.6a, | 1b.2d.3f.4b.5a.6b, | 1b.2d.3f.4b.5a.6c, |
| 1b.2d.3f.4b.5a.6d, | 1b.2d.3f.4b.5a.6e, | 1b.2d.3f.4b.5a.6f, | 1b.2d.3f.4b.5b.6a, |
| 1b.2d.3f.4b.5b.6b, | 1b.2d.3f.4b.5b.6c, | 1b.2d.3f.4b.5b.6d, | 1b.2d.3f.4b.5b.6e, |
| 1b.2d.3f.4b.5b.6f, | 1b.2d.3f.4b.5c.6a, | 1b.2d.3f.4b.5c.6b, | 1b.2d.3f.4b.5c.6c, |
| 1b.2d.3f.4b.5c.6d, | 1b.2d.3f.4b.5c.6e, | 1b.2d.3f.4b.5c.6f, | 1b.2d.3f.4b.5d.6a, |
| 1b.2d.3f.4b.5d.6b, | 1b.2d.3f.4b.5d.6c, | 1b.2d.3f.4b.5d.6d, | 1b.2d.3f.4b.5d.6e, |
| 1b.2d.3f.4b.5d.6f, | 1b.2d.3f.4b.5e.6a, | 1b.2d.3f.4b.5e.6b, | 1b.2d.3f.4b.5e.6c, |
| 1b.2d.3f.4b.5e.6d, | 1b.2d.3f.4b.5e.6e, | 1b.2d.3f.4b.5e.6f, | 1b.2d.3f.4b.5f.6a, |
| 1b.2d.3f.4b.5f.6b, | 1b.2d.3f.4b.5f.6c, | 1b.2d.3f.4b.5f.6d, | 1b.2d.3f.4b.5f.6e, | 1b.2d.3f.4b.5f.6f, |
| 1b.2d.3f.4c.5a.6a, | 1b.2d.3f.4c.5a.6b, | 1b.2d.3f.4c.5a.6c, | 1b.2d.3f.4c.5a.6d, |
| 1b.2d.3f.4c.5a.6e, | 1b.2d.3f.4c.5a.6f, | 1b.2d.3f.4c.5b.6a, | 1b.2d.3f.4c.5b.6b, |
| 1b.2d.3f.4c.5b.6c, | 1b.2d.3f.4c.5b.6d, | 1b.2d.3f.4c.5b.6e, | 1b.2d.3f.4c.5b.6f, |
| 1b.2d.3f.4c.5c.6a, | 1b.2d.3f.4c.5c.6b, | 1b.2d.3f.4c.5c.6c, | 1b.2d.3f.4c.5c.6d, |
| 1b.2d.3f.4c.5c.6e, | 1b.2d.3f.4c.5c.6f, | 1b.2d.3f.4c.5d.6a, | 1b.2d.3f.4c.5d.6b, |
| 1b.2d.3f.4c.5d.6c, | 1b.2d.3f.4c.5d.6d, | 1b.2d.3f.4c.5d.6e, | 1b.2d.3f.4c.5d.6f, |
| 1b.2d.3f.4c.5e.6a, | 1b.2d.3f.4c.5e.6b, | 1b.2d.3f.4c.5e.6c, | 1b.2d.3f.4c.5e.6d, |
| 1b.2d.3f.4c.5e.6e, | 1b.2d.3f.4c.5e.6f, | 1b.2d.3f.4c.5f.6a, | 1b.2d.3f.4c.5f.6b, | 1b.2d.3f.4c.5f.6c, |
| 1b.2d.3f.4c.5f.6d, | 1b.2d.3f.4c.5f.6e, | 1b.2d.3f.4c.5f.6f, | 1b.2d.3f.4d.5a.6a, |
| 1b.2d.3f.4d.5a.6b, | 1b.2d.3f.4d.5a.6c, | 1b.2d.3f.4d.5a.6d, | 1b.2d.3f.4d.5a.6e, |
| 1b.2d.3f.4d.5a.6f, | 1b.2d.3f.4d.5b.6a, | 1b.2d.3f.4d.5b.6b, | 1b.2d.3f.4d.5b.6c, |
| 1b.2d.3f.4d.5b.6d, | 1b.2d.3f.4d.5b.6e, | 1b.2d.3f.4d.5b.6f, | 1b.2d.3f.4d.5c.6a, |
| 1b.2d.3f.4d.5c.6b, | 1b.2d.3f.4d.5c.6c, | 1b.2d.3f.4d.5c.6d, | 1b.2d.3f.4d.5c.6e, |
| 1b.2d.3f.4d.5c.6f, | 1b.2d.3f.4d.5d.6a, | 1b.2d.3f.4d.5d.6b, | 1b.2d.3f.4d.5d.6c, |
| 1b.2d.3f.4d.5d.6d, | 1b.2d.3f.4d.5d.6e, | 1b.2d.3f.4d.5d.6f, | 1b.2d.3f.4d.5e.6a, |
| 1b.2d.3f.4d.5e.6b, | 1b.2d.3f.4d.5e.6c, | 1b.2d.3f.4d.5e.6d, | 1b.2d.3f.4d.5e.6e, |
| 1b.2d.3f.4d.5e.6f, | 1b.2d.3f.4d.5f.6a, | 1b.2d.3f.4d.5f.6b, | 1b.2d.3f.4d.5f.6c, |
| 1b.2d.3f.4d.5f.6d, | 1b.2d.3f.4d.5f.6e, | 1b.2d.3f.4d.5f.6f, | 1b.2d.3f.4e.5a.6a, |
| 1b.2d.3f.4e.5a.6b, | 1b.2d.3f.4e.5a.6c, | 1b.2d.3f.4e.5a.6d, | 1b.2d.3f.4e.5a.6e, |
| 1b.2d.3f.4e.5a.6f, | 1b.2d.3f.4e.5b.6a, | 1b.2d.3f.4e.5b.6b, | 1b.2d.3f.4e.5b.6c, |
| 1b.2d.3f.4e.5b.6d, | 1b.2d.3f.4e.5b.6e, | 1b.2d.3f.4e.5b.6f, | 1b.2d.3f.4e.5c.6a, |
| 1b.2d.3f.4e.5c.6b, | 1b.2d.3f.4e.5c.6c, | 1b.2d.3f.4e.5c.6d, | 1b.2d.3f.4e.5c.6e, |
| 1b.2d.3f.4e.5c.6f, | 1b.2d.3f.4e.5d.6a, | 1b.2d.3f.4e.5d.6b, | 1b.2d.3f.4e.5d.6c, |
| 1b.2d.3f.4e.5d.6d, | 1b.2d.3f.4e.5d.6e, | 1b.2d.3f.4e.5d.6f, | 1b.2d.3f.4e.5e.6a, |
| 1b.2d.3f.4e.5e.6b, | 1b.2d.3f.4e.5e.6c, | 1b.2d.3f.4e.5e.6d, | 1b.2d.3f.4e.5e.6e, |
| 1b.2d.3f.4e.5e.6f, | 1b.2d.3f.4e.5f.6a, | 1b.2d.3f.4e.5f.6b, | 1b.2d.3f.4e.5f.6c, | 1b.2d.3f.4e.5f.6d, |
| 1b.2d.3f.4e.5f.6e, | 1b.2d.3f.4e.5f.6f, | 1b.2d.3f.4f.5a.6a, | 1b.2d.3f.4f.5a.6b, | 1b.2d.3f.4f.5a.6c, |
| 1b.2d.3f.4f.5a.6d, | 1b.2d.3f.4f.5a.6e, | 1b.2d.3f.4f.5a.6f, | 1b.2d.3f.4f.5b.6a, | 1b.2d.3f.4f.5b.6b, |
| 1b.2d.3f.4f.5b.6c, | 1b.2d.3f.4f.5b.6d, | 1b.2d.3f.4f.5b.6e, | 1b.2d.3f.4f.5b.6f, | 1b.2d.3f.4f.5c.6a, |
| 1b.2d.3f.4f.5c.6b, | 1b.2d.3f.4f.5c.6c, | 1b.2d.3f.4f.5c.6d, | 1b.2d.3f.4f.5c.6e, | 1b.2d.3f.4f.5c.6f, |
| 1b.2d.3f.4f.5d.6a, | 1b.2d.3f.4f.5d.6b, | 1b.2d.3f.4f.5d.6c, | 1b.2d.3f.4f.5d.6d, |
| 1b.2d.3f.4f.5d.6e, | 1b.2d.3f.4f.5d.6f, | 1b.2d.3f.4f.5e.6a, | 1b.2d.3f.4f.5e.6b, | 1b.2d.3f.4f.5e.6c, |
| 1b.2d.3f.4f.5e.6d, | 1b.2d.3f.4f.5e.6e, | 1b.2d.3f.4f.5e.6f, | 1b.2d.3f.4f.5f.6a, | 1b.2d.3f.4f.5f.6b, |
| 1b.2d.3f.4f.5f.6c, | 1b.2d.3f.4f.5f.6d, | 1b.2d.3f.4f.5f.6e, | 1b.2d.3f.4f.5f.6f, | 1b.2e.3a.4a.5a.6a, |
| 1b.2e.3a.4a.5a.6b, | 1b.2e.3a.4a.5a.6c, | 1b.2e.3a.4a.5a.6d, | 1b.2e.3a.4a.5a.6e, |
| 1b.2e.3a.4a.5a.6f, | 1b.2e.3a.4a.5b.6a, | 1b.2e.3a.4a.5b.6b, | 1b.2e.3a.4a.5b.6c, |
| 1b.2e.3a.4a.5b.6d, | 1b.2e.3a.4a.5b.6e, | 1b.2e.3a.4a.5b.6f, | 1b.2e.3a.4a.5c.6a, |
| 1b.2e.3a.4a.5c.6b, | 1b.2e.3a.4a.5c.6c, | 1b.2e.3a.4a.5c.6d, | 1b.2e.3a.4a.5c.6e, |
| 1b.2e.3a.4a.5c.6f, | 1b.2e.3a.4a.5d.6a, | 1b.2e.3a.4a.5d.6b, | 1b.2e.3a.4a.5d.6c, |
| 1b.2e.3a.4a.5d.6d, | 1b.2e.3a.4a.5d.6e, | 1b.2e.3a.4a.5d.6f, | 1b.2e.3a.4a.5e.6a, |
| 1b.2e.3a.4a.5e.6b, | 1b.2e.3a.4a.5e.6c, | 1b.2e.3a.4a.5e.6d, | 1b.2e.3a.4a.5e.6e, |
| 1b.2e.3a.4a.5e.6f, | 1b.2e.3a.4a.5f.6a, | 1b.2e.3a.4a.5f.6b, | 1b.2e.3a.4a.5f.6c, |
| 1b.2e.3a.4a.5f.6d, | 1b.2e.3a.4a.5f.6e, | 1b.2e.3a.4a.5f.6f, | 1b.2e.3a.4b.5a.6a, |
| 1b.2e.3a.4b.5a.6b, | 1b.2e.3a.4b.5a.6c, | 1b.2e.3a.4b.5a.6d, | 1b.2e.3a.4b.5a.6e, |
| 1b.2e.3a.4b.5a.6f, | 1b.2e.3a.4b.5b.6a, | 1b.2e.3a.4b.5b.6b, | 1b.2e.3a.4b.5b.6c, |
| 1b.2e.3a.4b.5b.6d, | 1b.2e.3a.4b.5b.6e, | 1b.2e.3a.4b.5b.6f, | 1b.2e.3a.4b.5c.6a, |
| 1b.2e.3a.4b.5c.6b, | 1b.2e.3a.4b.5c.6c, | 1b.2e.3a.4b.5c.6d, | 1b.2e.3a.4b.5c.6e, |
| 1b.2e.3a.4b.5c.6f, | 1b.2e.3a.4b.5d.6a, | 1b.2e.3a.4b.5d.6b, | 1b.2e.3a.4b.5d.6c, |
| 1b.2e.3a.4b.5d.6d, | 1b.2e.3a.4b.5d.6e, | 1b.2e.3a.4b.5d.6f, | 1b.2e.3a.4b.5e.6a, |
| 1b.2e.3a.4b.5e.6b, | 1b.2e.3a.4b.5e.6c, | 1b.2e.3a.4b.5e.6d, | 1b.2e.3a.4b.5e.6e, |
| 1b.2e.3a.4b.5e.6f, | 1b.2e.3a.4b.5f.6a, | 1b.2e.3a.4b.5f.6b, | 1b.2e.3a.4b.5f.6c, |
| 1b.2e.3a.4b.5f.6d, | 1b.2e.3a.4b.5f.6e, | 1b.2e.3a.4b.5f.6f, | 1b.2e.3a.4c.5a.6a, |

TABLE 7-continued

List of Compounds of Formula (II)

| | | | | |
|---|---|---|---|---|
| 1b.2e.3a.4c.5a.6b, | 1b.2e.3a.4c.5a.6c, | 1b.2e.3a.4c.5a.6d, | 1b.2e.3a.4c.5a.6e, | |
| 1b.2e.3a.4c.5a.6f, | 1b.2e.3a.4c.5b.6a, | 1b.2e.3a.4c.5b.6b, | 1b.2e.3a.4c.5b.6c, | |
| 1b.2e.3a.4c.5b.6d, | 1b.2e.3a.4c.5b.6e, | 1b.2e.3a.4c.5b.6f, | 1b.2e.3a.4c.5c.6a, | |
| 1b.2e.3a.4c.5c.6b, | 1b.2e.3a.4c.5c.6c, | 1b.2e.3a.4c.5c.6d, | 1b.2e.3a.4c.5c.6e, | |
| 1b.2e.3a.4c.5c.6f, | 1b.2e.3a.4c.5d.6a, | 1b.2e.3a.4c.5d.6b, | 1b.2e.3a.4c.5d.6c, | |
| 1b.2e.3a.4c.5d.6d, | 1b.2e.3a.4c.5d.6e, | 1b.2e.3a.4c.5d.6f, | 1b.2e.3a.4c.5e.6a, | |
| 1b.2e.3a.4c.5e.6b, | 1b.2e.3a.4c.5e.6c, | 1b.2e.3a.4c.5e.6d, | 1b.2e.3a.4c.5e.6e, | |
| 1b.2e.3a.4c.5e.6f, | 1b.2e.3a.4c.5f.6a, | 1b.2e.3a.4c.5f.6b, | 1b.2e.3a.4c.5f.6c, | 1b.2e.3a.4c.5f.6d, |
| 1b.2e.3a.4c.5f.6e, | 1b.2e.3a.4c.5f.6f, | 1b.2e.3a.4d.5a.6a, | 1b.2e.3a.4d.5a.6b, | |
| 1b.2e.3a.4d.5a.6c, | 1b.2e.3a.4d.5a.6d, | 1b.2e.3a.4d.5a.6e, | 1b.2e.3a.4d.5a.6f, | |
| 1b.2e.3a.4d.5b.6a, | 1b.2e.3a.4d.5b.6b, | 1b.2e.3a.4d.5b.6c, | 1b.2e.3a.4d.5b.6d, | |
| 1b.2e.3a.4d.5b.6e, | 1b.2e.3a.4d.5b.6f, | 1b.2e.3a.4d.5c.6a, | 1b.2e.3a.4d.5c.6b, | |
| 1b.2e.3a.4d.5c.6c, | 1b.2e.3a.4d.5c.6d, | 1b.2e.3a.4d.5c.6e, | 1b.2e.3a.4d.5c.6f, | |
| 1b.2e.3a.4d.5d.6a, | 1b.2e.3a.4d.5d.6b, | 1b.2e.3a.4d.5d.6c, | 1b.2e.3a.4d.5d.6d, | |
| 1b.2e.3a.4d.5d.6e, | 1b.2e.3a.4d.5d.6f, | 1b.2e.3a.4d.5e.6a, | 1b.2e.3a.4d.5e.6b, | |
| 1b.2e.3a.4d.5e.6c, | 1b.2e.3a.4d.5e.6d, | 1b.2e.3a.4d.5e.6e, | 1b.2e.3a.4d.5e.6f, | |
| 1b.2e.3a.4d.5f.6a, | 1b.2e.3a.4d.5f.6b, | 1b.2e.3a.4d.5f.6c, | 1b.2e.3a.4d.5f.6d, | |
| 1b.2e.3a.4d.5f.6e, | 1b.2e.3a.4d.5f.6f, | 1b.2e.3a.4e.5a.6a, | 1b.2e.3a.4e.5a.6b, | |
| 1b.2e.3a.4e.5a.6c, | 1b.2e.3a.4e.5a.6d, | 1b.2e.3a.4e.5a.6e, | 1b.2e.3a.4e.5a.6f, | |
| 1b.2e.3a.4e.5b.6a, | 1b.2e.3a.4e.5b.6b, | 1b.2e.3a.4e.5b.6c, | 1b.2e.3a.4e.5b.6d, | |
| 1b.2e.3a.4e.5b.6e, | 1b.2e.3a.4e.5b.6f, | 1b.2e.3a.4e.5c.6a, | 1b.2e.3a.4e.5c.6b, | |
| 1b.2e.3a.4e.5c.6c, | 1b.2e.3a.4e.5c.6d, | 1b.2e.3a.4e.5c.6e, | 1b.2e.3a.4e.5c.6f, | |
| 1b.2e.3a.4e.5d.6a, | 1b.2e.3a.4e.5d.6b, | 1b.2e.3a.4e.5d.6c, | 1b.2e.3a.4e.5d.6d, | |
| 1b.2e.3a.4e.5d.6e, | 1b.2e.3a.4e.5d.6f, | 1b.2e.3a.4e.5e.6a, | 1b.2e.3a.4e.5e.6b, | |
| 1b.2e.3a.4e.5e.6c, | 1b.2e.3a.4e.5e.6d, | 1b.2e.3a.4e.5e.6e, | 1b.2e.3a.4e.5e.6f, | |
| 1b.2e.3a.4e.5f.6a, | 1b.2e.3a.4e.5f.6b, | 1b.2e.3a.4e.5f.6c, | 1b.2e.3a.4e.5f.6d, | 1b.2e.3a.4e.5f.6e, |
| 1b.2e.3a.4e.5f.6f, | 1b.2e.3a.4f.5a.6a, | 1b.2e.3a.4f.5a.6b, | 1b.2e.3a.4f.5a.6c, | 1b.2e.3a.4f.5a.6d, |
| 1b.2e.3a.4f.5a.6e, | 1b.2e.3a.4f.5a.6f, | 1b.2e.3a.4f.5b.6a, | 1b.2e.3a.4f.5b.6b, | 1b.2e.3a.4f.5b.6c, |
| 1b.2e.3a.4f.5b.6d, | 1b.2e.3a.4f.5b.6e, | 1b.2e.3a.4f.5b.6f, | 1b.2e.3a.4f.5c.6a, | 1b.2e.3a.4f.5c.6b, |
| 1b.2e.3a.4f.5c.6c, | 1b.2e.3a.4f.5c.6d, | 1b.2e.3a.4f.5c.6e, | 1b.2e.3a.4f.5c.6f, | 1b.2e.3a.4f.5d.6a, |
| 1b.2e.3a.4f.5d.6b, | 1b.2e.3a.4f.5d.6c, | 1b.2e.3a.4f.5d.6d, | 1b.2e.3a.4f.5d.6e, | |
| 1b.2e.3a.4f.5d.6f, | 1b.2e.3a.4f.5e.6a, | 1b.2e.3a.4f.5e.6b, | 1b.2e.3a.4f.5e.6c, | 1b.2e.3a.4f.5e.6d, |
| 1b.2e.3a.4f.5e.6e, | 1b.2e.3a.4f.5e.6f, | 1b.2e.3a.4f.5f.6a, | 1b.2e.3a.4f.5f.6b, | 1b.2e.3a.4f.5f.6c, |
| 1b.2e.3a.4f.5f.6d, | 1b.2e.3a.4f.5f.6e, | 1b.2e.3a.4f.5f.6f, | 1b.2e.3b.4a.5a.6a, | 1b.2e.3b.4a.5a.6b, |
| 1b.2e.3b.4a.5a.6c, | 1b.2e.3b.4a.5a.6d, | 1b.2e.3b.4a.5a.6e, | 1b.2e.3b.4a.5a.6f, | |
| 1b.2e.3b.4a.5b.6a, | 1b.2e.3b.4a.5b.6b, | 1b.2e.3b.4a.5b.6c, | 1b.2e.3b.4a.5b.6d, | |
| 1b.2e.3b.4a.5b.6e, | 1b.2e.3b.4a.5b.6f, | 1b.2e.3b.4a.5c.6a, | 1b.2e.3b.4a.5c.6b, | |
| 1b.2e.3b.4a.5c.6c, | 1b.2e.3b.4a.5c.6d, | 1b.2e.3b.4a.5c.6e, | 1b.2e.3b.4a.5c.6f, | |
| 1b.2e.3b.4a.5d.6a, | 1b.2e.3b.4a.5d.6b, | 1b.2e.3b.4a.5d.6c, | 1b.2e.3b.4a.5d.6d, | |
| 1b.2e.3b.4a.5d.6e, | 1b.2e.3b.4a.5d.6f, | 1b.2e.3b.4a.5e.6a, | 1b.2e.3b.4a.5e.6b, | |
| 1b.2e.3b.4a.5e.6c, | 1b.2e.3b.4a.5e.6d, | 1b.2e.3b.4a.5e.6e, | 1b.2e.3b.4a.5e.6f, | |
| 1b.2e.3b.4a.5f.6a, | 1b.2e.3b.4a.5f.6b, | 1b.2e.3b.4a.5f.6c, | 1b.2e.3b.4a.5f.6d, | |
| 1b.2e.3b.4a.5f.6e, | 1b.2e.3b.4a.5f.6f, | 1b.2e.3b.4b.5a.6a, | 1b.2e.3b.4b.5a.6b, | |
| 1b.2e.3b.4b.5a.6c, | 1b.2e.3b.4b.5a.6d, | 1b.2e.3b.4b.5a.6e, | 1b.2e.3b.4b.5a.6f, | |
| 1b.2e.3b.4b.5b.6a, | 1b.2e.3b.4b.5b.6b, | 1b.2e.3b.4b.5b.6c, | 1b.2e.3b.4b.5b.6d, | |
| 1b.2e.3b.4b.5b.6e, | 1b.2e.3b.4b.5b.6f, | 1b.2e.3b.4b.5c.6a, | 1b.2e.3b.4b.5c.6b, | |
| 1b.2e.3b.4b.5c.6c, | 1b.2e.3b.4b.5c.6d, | 1b.2e.3b.4b.5c.6e, | 1b.2e.3b.4b.5c.6f, | |
| 1b.2e.3b.4b.5d.6a, | 1b.2e.3b.4b.5d.6b, | 1b.2e.3b.4b.5d.6c, | 1b.2e.3b.4b.5d.6d, | |
| 1b.2e.3b.4b.5d.6e, | 1b.2e.3b.4b.5d.6f, | 1b.2e.3b.4b.5e.6a, | 1b.2e.3b.4b.5e.6b, | |
| 1b.2e.3b.4b.5e.6c, | 1b.2e.3b.4b.5e.6d, | 1b.2e.3b.4b.5e.6e, | 1b.2e.3b.4b.5e.6f, | |
| 1b.2e.3b.4b.5f.6a, | 1b.2e.3b.4b.5f.6b, | 1b.2e.3b.4b.5f.6c, | 1b.2e.3b.4b.5f.6d, | |
| 1b.2e.3b.4b.5f.6e, | 1b.2e.3b.4b.5f.6f, | 1b.2e.3b.4c.5a.6a, | 1b.2e.3b.4c.5a.6b, | |
| 1b.2e.3b.4c.5a.6c, | 1b.2e.3b.4c.5a.6d, | 1b.2e.3b.4c.5a.6e, | 1b.2e.3b.4c.5a.6f, | |
| 1b.2e.3b.4c.5b.6a, | 1b.2e.3b.4c.5b.6b, | 1b.2e.3b.4c.5b.6c, | 1b.2e.3b.4c.5b.6d, | |
| 1b.2e.3b.4c.5b.6e, | 1b.2e.3b.4c.5b.6f, | 1b.2e.3b.4c.5c.6a, | 1b.2e.3b.4c.5c.6b, | |
| 1b.2e.3b.4c.5c.6c, | 1b.2e.3b.4c.5c.6d, | 1b.2e.3b.4c.5c.6e, | 1b.2e.3b.4c.5c.6f, | |
| 1b.2e.3b.4c.5d.6a, | 1b.2e.3b.4c.5d.6b, | 1b.2e.3b.4c.5d.6c, | 1b.2e.3b.4c.5d.6d, | |
| 1b.2e.3b.4c.5d.6e, | 1b.2e.3b.4c.5d.6f, | 1b.2e.3b.4c.5e.6a, | 1b.2e.3b.4c.5e.6b, | |
| 1b.2e.3b.4c.5e.6c, | 1b.2e.3b.4c.5e.6d, | 1b.2e.3b.4c.5e.6e, | 1b.2e.3b.4c.5e.6f, | |
| 1b.2e.3b.4c.5f.6a, | 1b.2e.3b.4c.5f.6b, | 1b.2e.3b.4c.5f.6c, | 1b.2e.3b.4c.5f.6d, | |
| 1b.2e.3b.4c.5f.6e, | 1b.2e.3b.4c.5f.6f, | 1b.2e.3b.4d.5a.6a, | 1b.2e.3b.4d.5a.6b, | |
| 1b.2e.3b.4d.5a.6c, | 1b.2e.3b.4d.5a.6d, | 1b.2e.3b.4d.5a.6e, | 1b.2e.3b.4d.5a.6f, | |
| 1b.2e.3b.4d.5b.6a, | 1b.2e.3b.4d.5b.6b, | 1b.2e.3b.4d.5b.6c, | 1b.2e.3b.4d.5b.6d, | |
| 1b.2e.3b.4d.5b.6e, | 1b.2e.3b.4d.5b.6f, | 1b.2e.3b.4d.5c.6a, | 1b.2e.3b.4d.5c.6b, | |
| 1b.2e.3b.4d.5c.6c, | 1b.2e.3b.4d.5c.6d, | 1b.2e.3b.4d.5c.6e, | 1b.2e.3b.4d.5c.6f, | |
| 1b.2e.3b.4d.5d.6a, | 1b.2e.3b.4d.5d.6b, | 1b.2e.3b.4d.5d.6c, | 1b.2e.3b.4d.5d.6d, | |
| 1b.2e.3b.4d.5d.6e, | 1b.2e.3b.4d.5d.6f, | 1b.2e.3b.4d.5e.6a, | 1b.2e.3b.4d.5e.6b, | |
| 1b.2e.3b.4d.5e.6c, | 1b.2e.3b.4d.5e.6d, | 1b.2e.3b.4d.5e.6e, | 1b.2e.3b.4d.5e.6f, | |
| 1b.2e.3b.4d.5f.6a, | 1b.2e.3b.4d.5f.6b, | 1b.2e.3b.4d.5f.6c, | 1b.2e.3b.4d.5f.6d, | |
| 1b.2e.3b.4d.5f.6e, | 1b.2e.3b.4d.5f.6f, | 1b.2e.3b.4e.5a.6a, | 1b.2e.3b.4e.5a.6b, | |
| 1b.2e.3b.4e.5a.6c, | 1b.2e.3b.4e.5a.6d, | 1b.2e.3b.4e.5a.6e, | 1b.2e.3b.4e.5a.6f, | |
| 1b.2e.3b.4e.5b.6a, | 1b.2e.3b.4e.5b.6b, | 1b.2e.3b.4e.5b.6c, | 1b.2e.3b.4e.5b.6d, | |
| 1b.2e.3b.4e.5b.6e, | 1b.2e.3b.4e.5b.6f, | 1b.2e.3b.4e.5c.6a, | 1b.2e.3b.4e.5c.6b, | |
| 1b.2e.3b.4e.5c.6c, | 1b.2e.3b.4e.5c.6d, | 1b.2e.3b.4e.5c.6e, | 1b.2e.3b.4e.5c.6f, | |
| 1b.2e.3b.4e.5d.6a, | 1b.2e.3b.4e.5d.6b, | 1b.2e.3b.4e.5d.6c, | 1b.2e.3b.4e.5d.6d, | |
| 1b.2e.3b.4e.5d.6e, | 1b.2e.3b.4e.5d.6f, | 1b.2e.3b.4e.5e.6a, | 1b.2e.3b.4e.5e.6b, | |
| 1b.2e.3b.4e.5e.6c, | 1b.2e.3b.4e.5e.6d, | 1b.2e.3b.4e.5e.6e, | 1b.2e.3b.4e.5e.6f, | |
| 1b.2e.3b.4e.5f.6a, | 1b.2e.3b.4e.5f.6b, | 1b.2e.3b.4e.5f.6c, | 1b.2e.3b.4e.5f.6d, | |

TABLE 7-continued

List of Compounds of Formula (II)

| | | | | |
|---|---|---|---|---|
| 1b.2e.3b.4e.5f.6e, | 1b.2e.3b.4e.5f.6f, | 1b.2e.3b.4f.5a.6a, | 1b.2e.3b.4f.5a.6b, | 1b.2e.3b.4f.5a.6c, |
| 1b.2e.3b.4f.5a.6d, | 1b.2e.3b.4f.5a.6e, | 1b.2e.3b.4f.5a.6f, | 1b.2e.3b.4f.5b.6a, | |
| 1b.2e.3b.4f.5b.6b, | 1b.2e.3b.4f.5b.6c, | 1b.2e.3b.4f.5b.6d, | 1b.2e.3b.4f.5b.6e, | |
| 1b.2e.3b.4f.5b.6f, | 1b.2e.3b.4f.5c.6a, | 1b.2e.3b.4f.5c.6b, | 1b.2e.3b.4f.5c.6c, | 1b.2e.3b.4f.5c.6d, |
| 1b.2e.3b.4f.5c.6e, | 1b.2e.3b.4f.5c.6f, | 1b.2e.3b.4f.5d.6a, | 1b.2e.3b.4f.5d.6b, | |
| 1b.2e.3b.4f.5d.6c, | 1b.2e.3b.4f.5d.6d, | 1b.2e.3b.4f.5d.6e, | 1b.2e.3b.4f.5d.6f, | |
| 1b.2e.3b.4f.5e.6a, | 1b.2e.3b.4f.5e.6b, | 1b.2e.3b.4f.5e.6c, | 1b.2e.3b.4f.5e.6d, | |
| 1b.2e.3b.4f.5e.6e, | 1b.2e.3b.4f.5e.6f, | 1b.2e.3b.4f.5f.6a, | 1b.2e.3b.4f.5f.6b, | 1b.2e.3b.4f.5f.6c, |
| 1b.2e.3b.4f.5f.6d, | 1b.2e.3b.4f.5f.6e, | 1b.2e.3b.4f.5f.6f, | 1b.2e.3c.4a.5a.6a, | 1b.2e.3c.4a.5a.6b, |
| 1b.2e.3c.4a.5a.6c, | 1b.2e.3c.4a.5a.6d, | 1b.2e.3c.4a.5a.6e, | 1b.2e.3c.4a.5a.6f, | |
| 1b.2e.3c.4a.5b.6a, | 1b.2e.3c.4a.5b.6b, | 1b.2e.3c.4a.5b.6c, | 1b.2e.3c.4a.5b.6d, | |
| 1b.2e.3c.4a.5b.6e, | 1b.2e.3c.4a.5b.6f, | 1b.2e.3c.4a.5c.6a, | 1b.2e.3c.4a.5c.6b, | |
| 1b.2e.3c.4a.5c.6c, | 1b.2e.3c.4a.5c.6d, | 1b.2e.3c.4a.5c.6e, | 1b.2e.3c.4a.5c.6f, | |
| 1b.2e.3c.4a.5d.6a, | 1b.2e.3c.4a.5d.6b, | 1b.2e.3c.4a.5d.6c, | 1b.2e.3c.4a.5d.6d, | |
| 1b.2e.3c.4a.5d.6e, | 1b.2e.3c.4a.5d.6f, | 1b.2e.3c.4a.5e.6a, | 1b.2e.3c.4a.5e.6b, | |
| 1b.2e.3c.4a.5e.6c, | 1b.2e.3c.4a.5e.6d, | 1b.2e.3c.4a.5e.6e, | 1b.2e.3c.4a.5e.6f, | |
| 1b.2e.3c.4a.5f.6a, | 1b.2e.3c.4a.5f.6b, | 1b.2e.3c.4a.5f.6c, | 1b.2e.3c.4a.5f.6d, | 1b.2e.3c.4a.5f.6e, |
| 1b.2e.3c.4a.5f.6f, | 1b.2e.3c.4b.5a.6a, | 1b.2e.3c.4b.5a.6b, | 1b.2e.3c.4b.5a.6c, | |
| 1b.2e.3c.4b.5a.6d, | 1b.2e.3c.4b.5a.6e, | 1b.2e.3c.4b.5a.6f, | 1b.2e.3c.4b.5b.6a, | |
| 1b.2e.3c.4b.5b.6b, | 1b.2e.3c.4b.5b.6c, | 1b.2e.3c.4b.5b.6d, | 1b.2e.3c.4b.5b.6e, | |
| 1b.2e.3c.4b.5b.6f, | 1b.2e.3c.4b.5c.6a, | 1b.2e.3c.4b.5c.6b, | 1b.2e.3c.4b.5c.6c, | |
| 1b.2e.3c.4b.5c.6d, | 1b.2e.3c.4b.5c.6e, | 1b.2e.3c.4b.5c.6f, | 1b.2e.3c.4b.5d.6a, | |
| 1b.2e.3c.4b.5d.6b, | 1b.2e.3c.4b.5d.6c, | 1b.2e.3c.4b.5d.6d, | 1b.2e.3c.4b.5d.6e, | |
| 1b.2e.3c.4b.5d.6f, | 1b.2e.3c.4b.5e.6a, | 1b.2e.3c.4b.5e.6b, | 1b.2e.3c.4b.5e.6c, | |
| 1b.2e.3c.4b.5e.6d, | 1b.2e.3c.4b.5e.6e, | 1b.2e.3c.4b.5e.6f, | 1b.2e.3c.4b.5f.6a, | |
| 1b.2e.3c.4b.5f.6b, | 1b.2e.3c.4b.5f.6c, | 1b.2e.3c.4b.5f.6d, | 1b.2e.3c.4b.5f.6e, | 1b.2e.3c.4b.5f.6f, |
| 1b.2e.3c.4c.5a.6a, | 1b.2e.3c.4c.5a.6b, | 1b.2e.3c.4c.5a.6c, | 1b.2e.3c.4c.5a.6d, | |
| 1b.2e.3c.4c.5a.6e, | 1b.2e.3c.4c.5a.6f, | 1b.2e.3c.4c.5b.6a, | 1b.2e.3c.4c.5b.6b, | |
| 1b.2e.3c.4c.5b.6c, | 1b.2e.3c.4c.5b.6d, | 1b.2e.3c.4c.5b.6e, | 1b.2e.3c.4c.5b.6f, | |
| 1b.2e.3c.4c.5c.6a, | 1b.2e.3c.4c.5c.6b, | 1b.2e.3c.4c.5c.6c, | 1b.2e.3c.4c.5c.6d, | |
| 1b.2e.3c.4c.5c.6e, | 1b.2e.3c.4c.5c.6f, | 1b.2e.3c.4c.5d.6a, | 1b.2e.3c.4c.5d.6b, | |
| 1b.2e.3c.4c.5d.6c, | 1b.2e.3c.4c.5d.6d, | 1b.2e.3c.4c.5d.6e, | 1b.2e.3c.4c.5d.6f, | |
| 1b.2e.3c.4c.5e.6a, | 1b.2e.3c.4c.5e.6b, | 1b.2e.3c.4c.5e.6c, | 1b.2e.3c.4c.5e.6d, | |
| 1b.2e.3c.4c.5e.6e, | 1b.2e.3c.4c.5e.6f, | 1b.2e.3c.4c.5f.6a, | 1b.2e.3c.4c.5f.6b, | 1b.2e.3c.4c.5f.6c, |
| 1b.2e.3c.4c.5f.6d, | 1b.2e.3c.4c.5f.6e, | 1b.2e.3c.4c.5f.6f, | 1b.2e.3c.4d.5a.6a, | |
| 1b.2e.3c.4d.5a.6b, | 1b.2e.3c.4d.5a.6c, | 1b.2e.3c.4d.5a.6d, | 1b.2e.3c.4d.5a.6e, | |
| 1b.2e.3c.4d.5a.6f, | 1b.2e.3c.4d.5b.6a, | 1b.2e.3c.4d.5b.6b, | 1b.2e.3c.4d.5b.6c, | |
| 1b.2e.3c.4d.5b.6d, | 1b.2e.3c.4d.5b.6e, | 1b.2e.3c.4d.5b.6f, | 1b.2e.3c.4d.5c.6a, | |
| 1b.2e.3c.4d.5c.6b, | 1b.2e.3c.4d.5c.6c, | 1b.2e.3c.4d.5c.6d, | 1b.2e.3c.4d.5c.6e, | |
| 1b.2e.3c.4d.5c.6f, | 1b.2e.3c.4d.5d.6a, | 1b.2e.3c.4d.5d.6b, | 1b.2e.3c.4d.5d.6c, | |
| 1b.2e.3c.4d.5d.6d, | 1b.2e.3c.4d.5d.6e, | 1b.2e.3c.4d.5d.6f, | 1b.2e.3c.4d.5e.6a, | |
| 1b.2e.3c.4d.5e.6b, | 1b.2e.3c.4d.5e.6c, | 1b.2e.3c.4d.5e.6d, | 1b.2e.3c.4d.5e.6e, | |
| 1b.2e.3c.4d.5e.6f, | 1b.2e.3c.4d.5f.6a, | 1b.2e.3c.4d.5f.6b, | 1b.2e.3c.4d.5f.6c, | |
| 1b.2e.3c.4d.5f.6d, | 1b.2e.3c.4d.5f.6e, | 1b.2e.3c.4d.5f.6f, | 1b.2e.3c.4e.5a.6a, | |
| 1b.2e.3c.4e.5a.6b, | 1b.2e.3c.4e.5a.6c, | 1b.2e.3c.4e.5a.6d, | 1b.2e.3c.4e.5a.6e, | |
| 1b.2e.3c.4e.5a.6f, | 1b.2e.3c.4e.5b.6a, | 1b.2e.3c.4e.5b.6b, | 1b.2e.3c.4e.5b.6c, | |
| 1b.2e.3c.4e.5b.6d, | 1b.2e.3c.4e.5b.6e, | 1b.2e.3c.4e.5b.6f, | 1b.2e.3c.4e.5c.6a, | |
| 1b.2e.3c.4e.5c.6b, | 1b.2e.3c.4e.5c.6c, | 1b.2e.3c.4e.5c.6d, | 1b.2e.3c.4e.5c.6e, | |
| 1b.2e.3c.4e.5c.6f, | 1b.2e.3c.4e.5d.6a, | 1b.2e.3c.4e.5d.6b, | 1b.2e.3c.4e.5d.6c, | |
| 1b.2e.3c.4e.5d.6d, | 1b.2e.3c.4e.5d.6e, | 1b.2e.3c.4e.5d.6f, | 1b.2e.3c.4e.5e.6a, | |
| 1b.2e.3c.4e.5e.6b, | 1b.2e.3c.4e.5e.6c, | 1b.2e.3c.4e.5e.6d, | 1b.2e.3c.4e.5e.6e, | |
| 1b.2e.3c.4e.5e.6f, | 1b.2e.3c.4e.5f.6a, | 1b.2e.3c.4e.5f.6b, | 1b.2e.3c.4e.5f.6c, | 1b.2e.3c.4e.5f.6d, |
| 1b.2e.3c.4e.5f.6e, | 1b.2e.3c.4e.5f.6f, | 1b.2e.3c.4f.5a.6a, | 1b.2e.3c.4f.5a.6b, | 1b.2e.3c.4f.5a.6c, |
| 1b.2e.3c.4f.5a.6d, | 1b.2e.3c.4f.5a.6e, | 1b.2e.3c.4f.5a.6f, | 1b.2e.3c.4f.5b.6a, | 1b.2e.3c.4f.5b.6b, |
| 1b.2e.3c.4f.5b.6c, | 1b.2e.3c.4f.5b.6d, | 1b.2e.3c.4f.5b.6e, | 1b.2e.3c.4f.5b.6f, | 1b.2e.3c.4f.5c.6a, |
| 1b.2e.3c.4f.5c.6b, | 1b.2e.3c.4f.5c.6c, | 1b.2e.3c.4f.5c.6d, | 1b.2e.3c.4f.5c.6e, | 1b.2e.3c.4f.5c.6f, |
| 1b.2e.3c.4f.5d.6a, | 1b.2e.3c.4f.5d.6b, | 1b.2e.3c.4f.5d.6c, | 1b.2e.3c.4f.5d.6d, | |
| 1b.2e.3c.4f.5d.6e, | 1b.2e.3c.4f.5d.6f, | 1b.2e.3c.4f.5e.6a, | 1b.2e.3c.4f.5e.6b, | 1b.2e.3c.4f.5e.6c, |
| 1b.2e.3c.4f.5e.6d, | 1b.2e.3c.4f.5e.6e, | 1b.2e.3c.4f.5e.6f, | 1b.2e.3c.4f.5f.6a, | 1b.2e.3c.4f.5f.6b, |
| 1b.2e.3c.4f.5f.6c, | 1b.2e.3c.4f.5f.6d, | 1b.2e.3c.4f.5f.6e, | 1b.2e.3c.4f.5f.6f, | 1b.2e.3d.4a.5a.6a, |
| 1b.2e.3d.4a.5a.6b, | 1b.2e.3d.4a.5a.6c, | 1b.2e.3d.4a.5a.6d, | 1b.2e.3d.4a.5a.6e, | |
| 1b.2e.3d.4a.5a.6f, | 1b.2e.3d.4a.5b.6a, | 1b.2e.3d.4a.5b.6b, | 1b.2e.3d.4a.5b.6c, | |
| 1b.2e.3d.4a.5b.6d, | 1b.2e.3d.4a.5b.6e, | 1b.2e.3d.4a.5b.6f, | 1b.2e.3d.4a.5c.6a, | |
| 1b.2e.3d.4a.5c.6b, | 1b.2e.3d.4a.5c.6c, | 1b.2e.3d.4a.5c.6d, | 1b.2e.3d.4a.5c.6e, | |
| 1b.2e.3d.4a.5c.6f, | 1b.2e.3d.4a.5d.6a, | 1b.2e.3d.4a.5d.6b, | 1b.2e.3d.4a.5d.6c, | |
| 1b.2e.3d.4a.5d.6d, | 1b.2e.3d.4a.5d.6e, | 1b.2e.3d.4a.5d.6f, | 1b.2e.3d.4a.5e.6a, | |
| 1b.2e.3d.4a.5e.6b, | 1b.2e.3d.4a.5e.6c, | 1b.2e.3d.4a.5e.6d, | 1b.2e.3d.4a.5e.6e, | |
| 1b.2e.3d.4a.5e.6f, | 1b.2e.3d.4a.5f.6a, | 1b.2e.3d.4a.5f.6b, | 1b.2e.3d.4a.5f.6c, | |
| 1b.2e.3d.4a.5f.6d, | 1b.2e.3d.4a.5f.6e, | 1b.2e.3d.4a.5f.6f, | 1b.2e.3d.4b.5a.6a, | |
| 1b.2e.3d.4b.5a.6b, | 1b.2e.3d.4b.5a.6c, | 1b.2e.3d.4b.5a.6d, | 1b.2e.3d.4b.5a.6e, | |
| 1b.2e.3d.4b.5a.6f, | 1b.2e.3d.4b.5b.6a, | 1b.2e.3d.4b.5b.6b, | 1b.2e.3d.4b.5b.6c, | |
| 1b.2e.3d.4b.5b.6d, | 1b.2e.3d.4b.5b.6e, | 1b.2e.3d.4b.5b.6f, | 1b.2e.3d.4b.5c.6a, | |
| 1b.2e.3d.4b.5c.6b, | 1b.2e.3d.4b.5c.6c, | 1b.2e.3d.4b.5c.6d, | 1b.2e.3d.4b.5c.6e, | |
| 1b.2e.3d.4b.5c.6f, | 1b.2e.3d.4b.5d.6a, | 1b.2e.3d.4b.5d.6b, | 1b.2e.3d.4b.5d.6c, | |
| 1b.2e.3d.4b.5d.6d, | 1b.2e.3d.4b.5d.6e, | 1b.2e.3d.4b.5d.6f, | 1b.2e.3d.4b.5e.6a, | |
| 1b.2e.3d.4b.5e.6b, | 1b.2e.3d.4b.5e.6c, | 1b.2e.3d.4b.5e.6d, | 1b.2e.3d.4b.5e.6e, | |
| 1b.2e.3d.4b.5e.6f, | 1b.2e.3d.4b.5f.6a, | 1b.2e.3d.4b.5f.6b, | 1b.2e.3d.4b.5f.6c, | |
| 1b.2e.3d.4b.5f.6d, | 1b.2e.3d.4b.5f.6e, | 1b.2e.3d.4b.5f.6f, | 1b.2e.3d.4c.5a.6a, | |

TABLE 7-continued

List of Compounds of Formula (II)

| | | | |
|---|---|---|---|
| 1b.2e.3d.4c.5a.6b, | 1b.2e.3d.4c.5a.6c, | 1b.2e.3d.4c.5a.6d, | 1b.2e.3d.4c.5a.6e, |
| 1b.2e.3d.4c.5a.6f, | 1b.2e.3d.4c.5b.6a, | 1b.2e.3d.4c.5b.6b, | 1b.2e.3d.4c.5b.6c, |
| 1b.2e.3d.4c.5b.6d, | 1b.2e.3d.4c.5b.6e, | 1b.2e.3d.4c.5b.6f, | 1b.2e.3d.4c.5c.6a, |
| 1b.2e.3d.4c.5c.6b, | 1b.2e.3d.4c.5c.6c, | 1b.2e.3d.4c.5c.6d, | 1b.2e.3d.4c.5c.6e, |
| 1b.2e.3d.4c.5c.6f, | 1b.2e.3d.4c.5d.6a, | 1b.2e.3d.4c.5d.6b, | 1b.2e.3d.4c.5d.6c, |
| 1b.2e.3d.4c.5d.6d, | 1b.2e.3d.4c.5d.6e, | 1b.2e.3d.4c.5d.6f, | 1b.2e.3d.4c.5e.6a, |
| 1b.2e.3d.4c.5e.6b, | 1b.2e.3d.4c.5e.6c, | 1b.2e.3d.4c.5e.6d, | 1b.2e.3d.4c.5e.6e, |
| 1b.2e.3d.4c.5e.6f, | 1b.2e.3d.4c.5f.6a, | 1b.2e.3d.4c.5f.6b, | 1b.2e.3d.4c.5f.6c, |
| 1b.2e.3d.4c.5f.6d, | 1b.2e.3d.4c.5f.6e, | 1b.2e.3d.4c.5f.6f, | 1b.2e.3d.4d.5a.6a, |
| 1b.2e.3d.4d.5a.6b, | 1b.2e.3d.4d.5a.6c, | 1b.2e.3d.4d.5a.6d, | 1b.2e.3d.4d.5a.6e, |
| 1b.2e.3d.4d.5a.6f, | 1b.2e.3d.4d.5b.6a, | 1b.2e.3d.4d.5b.6b, | 1b.2e.3d.4d.5b.6c, |
| 1b.2e.3d.4d.5b.6d, | 1b.2e.3d.4d.5b.6e, | 1b.2e.3d.4d.5b.6f, | 1b.2e.3d.4d.5c.6a, |
| 1b.2e.3d.4d.5c.6b, | 1b.2e.3d.4d.5c.6c, | 1b.2e.3d.4d.5c.6d, | 1b.2e.3d.4d.5c.6e, |
| 1b.2e.3d.4d.5c.6f, | 1b.2e.3d.4d.5d.6a, | 1b.2e.3d.4d.5d.6b, | 1b.2e.3d.4d.5d.6c, |
| 1b.2e.3d.4d.5d.6d, | 1b.2e.3d.4d.5d.6e, | 1b.2e.3d.4d.5d.6f, | 1b.2e.3d.4d.5e.6a, |
| 1b.2e.3d.4d.5e.6b, | 1b.2e.3d.4d.5e.6c, | 1b.2e.3d.4d.5e.6d, | 1b.2e.3d.4d.5e.6e, |
| 1b.2e.3d.4d.5e.6f, | 1b.2e.3d.4d.5f.6a, | 1b.2e.3d.4d.5f.6b, | 1b.2e.3d.4d.5f.6c, |
| 1b.2e.3d.4d.5f.6d, | 1b.2e.3d.4d.5f.6e, | 1b.2e.3d.4d.5f.6f, | 1b.2e.3d.4e.5a.6a, |
| 1b.2e.3d.4e.5a.6b, | 1b.2e.3d.4e.5a.6c, | 1b.2e.3d.4e.5a.6d, | 1b.2e.3d.4e.5a.6e, |
| 1b.2e.3d.4e.5a.6f, | 1b.2e.3d.4e.5b.6a, | 1b.2e.3d.4e.5b.6b, | 1b.2e.3d.4e.5b.6c, |
| 1b.2e.3d.4e.5b.6d, | 1b.2e.3d.4e.5b.6e, | 1b.2e.3d.4e.5b.6f, | 1b.2e.3d.4e.5c.6a, |
| 1b.2e.3d.4e.5c.6b, | 1b.2e.3d.4e.5c.6c, | 1b.2e.3d.4e.5c.6d, | 1b.2e.3d.4e.5c.6e, |
| 1b.2e.3d.4e.5c.6f, | 1b.2e.3d.4e.5d.6a, | 1b.2e.3d.4e.5d.6b, | 1b.2e.3d.4e.5d.6c, |
| 1b.2e.3d.4e.5d.6d, | 1b.2e.3d.4e.5d.6e, | 1b.2e.3d.4e.5d.6f, | 1b.2e.3d.4e.5e.6a, |
| 1b.2e.3d.4e.5e.6b, | 1b.2e.3d.4e.5e.6c, | 1b.2e.3d.4e.5e.6d, | 1b.2e.3d.4e.5e.6e, |
| 1b.2e.3d.4e.5e.6f, | 1b.2e.3d.4e.5f.6a, | 1b.2e.3d.4e.5f.6b, | 1b.2e.3d.4e.5f.6c, |
| 1b.2e.3d.4e.5f.6d, | 1b.2e.3d.4e.5f.6e, | 1b.2e.3d.4e.5f.6f, | 1b.2e.3d.4f.5a.6a, |
| 1b.2e.3d.4f.5a.6b, | 1b.2e.3d.4f.5a.6c, | 1b.2e.3d.4f.5a.6d, | 1b.2e.3d.4f.5a.6e, |
| 1b.2e.3d.4f.5a.6f, | 1b.2e.3d.4f.5b.6a, | 1b.2e.3d.4f.5b.6b, | 1b.2e.3d.4f.5b.6c, |
| 1b.2e.3d.4f.5b.6d, | 1b.2e.3d.4f.5b.6e, | 1b.2e.3d.4f.5b.6f, | 1b.2e.3d.4f.5c.6a, |
| 1b.2e.3d.4f.5c.6b, | 1b.2e.3d.4f.5c.6c, | 1b.2e.3d.4f.5c.6d, | 1b.2e.3d.4f.5c.6e, |
| 1b.2e.3d.4f.5c.6f, | 1b.2e.3d.4f.5d.6a, | 1b.2e.3d.4f.5d.6b, | 1b.2e.3d.4f.5d.6c, |
| 1b.2e.3d.4f.5d.6d, | 1b.2e.3d.4f.5d.6e, | 1b.2e.3d.4f.5d.6f, | 1b.2e.3d.4f.5e.6a, |
| 1b.2e.3d.4f.5e.6b, | 1b.2e.3d.4f.5e.6c, | 1b.2e.3d.4f.5e.6d, | 1b.2e.3d.4f.5e.6e, |
| 1b.2e.3d.4f.5e.6f, | 1b.2e.3d.4f.5f.6a, | 1b.2e.3d.4f.5f.6b, | 1b.2e.3d.4f.5f.6c, | 1b.2e.3d.4f.5f.6d, |
| 1b.2e.3d.4f.5f.6e, | 1b.2e.3d.4f.5f.6f, | 1b.2e.3e.4a.5a.6a, | 1b.2e.3e.4a.5a.6b, |
| 1b.2e.3e.4a.5a.6c, | 1b.2e.3e.4a.5a.6d, | 1b.2e.3e.4a.5a.6e, | 1b.2e.3e.4a.5a.6f, |
| 1b.2e.3e.4a.5b.6a, | 1b.2e.3e.4a.5b.6b, | 1b.2e.3e.4a.5b.6c, | 1b.2e.3e.4a.5b.6d, |
| 1b.2e.3e.4a.5b.6e, | 1b.2e.3e.4a.5b.6f, | 1b.2e.3e.4a.5c.6a, | 1b.2e.3e.4a.5c.6b, |
| 1b.2e.3e.4a.5c.6c, | 1b.2e.3e.4a.5c.6d, | 1b.2e.3e.4a.5c.6e, | 1b.2e.3e.4a.5c.6f, |
| 1b.2e.3e.4a.5d.6a, | 1b.2e.3e.4a.5d.6b, | 1b.2e.3e.4a.5d.6c, | 1b.2e.3e.4a.5d.6d, |
| 1b.2e.3e.4a.5d.6e, | 1b.2e.3e.4a.5d.6f, | 1b.2e.3e.4a.5e.6a, | 1b.2e.3e.4a.5e.6b, |
| 1b.2e.3e.4a.5e.6c, | 1b.2e.3e.4a.5e.6d, | 1b.2e.3e.4a.5e.6e, | 1b.2e.3e.4a.5e.6f, |
| 1b.2e.3e.4a.5f.6a, | 1b.2e.3e.4a.5f.6b, | 1b.2e.3e.4a.5f.6c, | 1b.2e.3e.4a.5f.6d, | 1b.2e.3e.4a.5f.6e, |
| 1b.2e.3e.4a.5f.6f, | 1b.2e.3e.4b.5a.6a, | 1b.2e.3e.4b.5a.6b, | 1b.2e.3e.4b.5a.6c, |
| 1b.2e.3e.4b.5a.6d, | 1b.2e.3e.4b.5a.6e, | 1b.2e.3e.4b.5a.6f, | 1b.2e.3e.4b.5b.6a, |
| 1b.2e.3e.4b.5b.6b, | 1b.2e.3e.4b.5b.6c, | 1b.2e.3e.4b.5b.6d, | 1b.2e.3e.4b.5b.6e, |
| 1b.2e.3e.4b.5b.6f, | 1b.2e.3e.4b.5c.6a, | 1b.2e.3e.4b.5c.6b, | 1b.2e.3e.4b.5c.6c, |
| 1b.2e.3e.4b.5c.6d, | 1b.2e.3e.4b.5c.6e, | 1b.2e.3e.4b.5c.6f, | 1b.2e.3e.4b.5d.6a, |
| 1b.2e.3e.4b.5d.6b, | 1b.2e.3e.4b.5d.6c, | 1b.2e.3e.4b.5d.6d, | 1b.2e.3e.4b.5d.6e, |
| 1b.2e.3e.4b.5d.6f, | 1b.2e.3e.4b.5e.6a, | 1b.2e.3e.4b.5e.6b, | 1b.2e.3e.4b.5e.6c, |
| 1b.2e.3e.4b.5e.6d, | 1b.2e.3e.4b.5e.6e, | 1b.2e.3e.4b.5e.6f, | 1b.2e.3e.4b.5f.6a, |
| 1b.2e.3e.4b.5f.6b, | 1b.2e.3e.4b.5f.6c, | 1b.2e.3e.4b.5f.6d, | 1b.2e.3e.4b.5f.6e, |
| 1b.2e.3e.4b.5f.6f, | 1b.2e.3e.4c.5a.6a, | 1b.2e.3e.4c.5a.6b, | 1b.2e.3e.4c.5a.6c, |
| 1b.2e.3e.4c.5a.6d, | 1b.2e.3e.4c.5a.6e, | 1b.2e.3e.4c.5a.6f, | 1b.2e.3e.4c.5b.6a, |
| 1b.2e.3e.4c.5b.6b, | 1b.2e.3e.4c.5b.6c, | 1b.2e.3e.4c.5b.6d, | 1b.2e.3e.4c.5b.6e, |
| 1b.2e.3e.4c.5b.6f, | 1b.2e.3e.4c.5c.6a, | 1b.2e.3e.4c.5c.6b, | 1b.2e.3e.4c.5c.6c, |
| 1b.2e.3e.4c.5c.6d, | 1b.2e.3e.4c.5c.6e, | 1b.2e.3e.4c.5c.6f, | 1b.2e.3e.4c.5d.6a, |
| 1b.2e.3e.4c.5d.6b, | 1b.2e.3e.4c.5d.6c, | 1b.2e.3e.4c.5d.6d, | 1b.2e.3e.4c.5d.6e, |
| 1b.2e.3e.4c.5d.6f, | 1b.2e.3e.4c.5e.6a, | 1b.2e.3e.4c.5e.6b, | 1b.2e.3e.4c.5e.6c, |
| 1b.2e.3e.4c.5e.6d, | 1b.2e.3e.4c.5e.6e, | 1b.2e.3e.4c.5e.6f, | 1b.2e.3e.4c.5f.6a, | 1b.2e.3e.4c.5f.6b, |
| 1b.2e.3e.4c.5f.6c, | 1b.2e.3e.4c.5f.6d, | 1b.2e.3e.4c.5f.6e, | 1b.2e.3e.4c.5f.6f, | 1b.2e.3e.4d.5a.6a, |
| 1b.2e.3e.4d.5a.6b, | 1b.2e.3e.4d.5a.6c, | 1b.2e.3e.4d.5a.6d, | 1b.2e.3e.4d.5a.6e, |
| 1b.2e.3e.4d.5a.6f, | 1b.2e.3e.4d.5b.6a, | 1b.2e.3e.4d.5b.6b, | 1b.2e.3e.4d.5b.6c, |
| 1b.2e.3e.4d.5b.6d, | 1b.2e.3e.4d.5b.6e, | 1b.2e.3e.4d.5b.6f, | 1b.2e.3e.4d.5c.6a, |
| 1b.2e.3e.4d.5c.6b, | 1b.2e.3e.4d.5c.6c, | 1b.2e.3e.4d.5c.6d, | 1b.2e.3e.4d.5c.6e, |
| 1b.2e.3e.4d.5c.6f, | 1b.2e.3e.4d.5d.6a, | 1b.2e.3e.4d.5d.6b, | 1b.2e.3e.4d.5d.6c, |
| 1b.2e.3e.4d.5d.6d, | 1b.2e.3e.4d.5d.6e, | 1b.2e.3e.4d.5d.6f, | 1b.2e.3e.4d.5e.6a, |
| 1b.2e.3e.4d.5e.6b, | 1b.2e.3e.4d.5e.6c, | 1b.2e.3e.4d.5e.6d, | 1b.2e.3e.4d.5e.6e, |
| 1b.2e.3e.4d.5e.6f, | 1b.2e.3e.4d.5f.6a, | 1b.2e.3e.4d.5f.6b, | 1b.2e.3e.4d.5f.6c, |
| 1b.2e.3e.4d.5f.6d, | 1b.2e.3e.4d.5f.6e, | 1b.2e.3e.4d.5f.6f, | 1b.2e.3e.4e.5a.6a, |
| 1b.2e.3e.4e.5a.6b, | 1b.2e.3e.4e.5a.6c, | 1b.2e.3e.4e.5a.6d, | 1b.2e.3e.4e.5a.6e, |
| 1b.2e.3e.4e.5a.6f, | 1b.2e.3e.4e.5b.6a, | 1b.2e.3e.4e.5b.6b, | 1b.2e.3e.4e.5b.6c, |
| 1b.2e.3e.4e.5b.6d, | 1b.2e.3e.4e.5b.6e, | 1b.2e.3e.4e.5b.6f, | 1b.2e.3e.4e.5c.6a, |
| 1b.2e.3e.4e.5c.6b, | 1b.2e.3e.4e.5c.6c, | 1b.2e.3e.4e.5c.6d, | 1b.2e.3e.4e.5c.6e, |
| 1b.2e.3e.4e.5c.6f, | 1b.2e.3e.4e.5d.6a, | 1b.2e.3e.4e.5d.6b, | 1b.2e.3e.4e.5d.6c, |
| 1b.2e.3e.4e.5d.6d, | 1b.2e.3e.4e.5d.6e, | 1b.2e.3e.4e.5d.6f, | 1b.2e.3e.4e.5e.6a, |
| 1b.2e.3e.4e.5e.6b, | 1b.2e.3e.4e.5e.6c, | 1b.2e.3e.4e.5e.6d, | 1b.2e.3e.4e.5e.6e, |

TABLE 7-continued

List of Compounds of Formula (II)

| | | | | |
|---|---|---|---|---|
| 1b.2e.3e.4e.5e.6f, | 1b.2e.3e.4e.5f.6a, | 1b.2e.3e.4e.5f.6b, | 1b.2e.3e.4e.5f.6c, | 1b.2e.3e.4e.5f.6d, |
| 1b.2e.3e.4e.5f.6e, | 1b.2e.3e.4e.5f.6f, | 1b.2e.3e.4f.5a.6a, | 1b.2e.3e.4f.5a.6b, | 1b.2e.3e.4f.5a.6c, |
| 1b.2e.3e.4f.5a.6d, | 1b.2e.3e.4f.5a.6e, | 1b.2e.3e.4f.5a.6f, | 1b.2e.3e.4f.5b.6a, | 1b.2e.3e.4f.5b.6b, |
| 1b.2e.3e.4f.5b.6c, | 1b.2e.3e.4f.5b.6d, | 1b.2e.3e.4f.5b.6e, | 1b.2e.3e.4f.5b.6f, | 1b.2e.3e.4f.5c.6a, |
| 1b.2e.3e.4f.5c.6b, | 1b.2e.3e.4f.5c.6c, | 1b.2e.3e.4f.5c.6d, | 1b.2e.3e.4f.5c.6e, | 1b.2e.3e.4f.5c.6f, |
| 1b.2e.3e.4f.5d.6a, | 1b.2e.3e.4f.5d.6b, | 1b.2e.3e.4f.5d.6c, | 1b.2e.3e.4f.5d.6d, | |
| 1b.2e.3e.4f.5d.6e, | 1b.2e.3e.4f.5d.6f, | 1b.2e.3e.4f.5e.6a, | 1b.2e.3e.4f.5e.6b, | 1b.2e.3e.4f.5e.6c, |
| 1b.2e.3e.4f.5e.6d, | 1b.2e.3e.4f.5e.6e, | 1b.2e.3e.4f.5e.6f, | 1b.2e.3e.4f.5f.6a, | 1b.2e.3e.4f.5f.6b, |
| 1b.2e.3e.4f.5f.6c, | 1b.2e.3e.4f.5f.6d, | 1b.2e.3e.4f.5f.6e, | 1b.2e.3e.4f.5f.6f, | 1b.2e.3f.4a.5a.6a, |
| 1b.2e.3f.4a.5a.6b, | 1b.2e.3f.4a.5a.6c, | 1b.2e.3f.4a.5a.6d, | 1b.2e.3f.4a.5a.6e, | 1b.2e.3f.4a.5a.6f, |
| 1b.2e.3f.4a.5b.6a, | 1b.2e.3f.4a.5b.6b, | 1b.2e.3f.4a.5b.6c, | 1b.2e.3f.4a.5b.6d, | |
| 1b.2e.3f.4a.5b.6e, | 1b.2e.3f.4a.5b.6f, | 1b.2e.3f.4a.5c.6a, | 1b.2e.3f.4a.5c.6b, | 1b.2e.3f.4a.5c.6c, |
| 1b.2e.3f.4a.5c.6d, | 1b.2e.3f.4a.5c.6e, | 1b.2e.3f.4a.5c.6f, | 1b.2e.3f.4a.5d.6a, | 1b.2e.3f.4a.5d.6b, |
| 1b.2e.3f.4a.5d.6c, | 1b.2e.3f.4a.5d.6d, | 1b.2e.3f.4a.5d.6e, | 1b.2e.3f.4a.5d.6f, | |
| 1b.2e.3f.4a.5e.6a, | 1b.2e.3f.4a.5e.6b, | 1b.2e.3f.4a.5e.6c, | 1b.2e.3f.4a.5e.6d, | 1b.2e.3f.4a.5e.6e, |
| 1b.2e.3f.4a.5e.6f, | 1b.2e.3f.4a.5f.6a, | 1b.2e.3f.4a.5f.6b, | 1b.2e.3f.4a.5f.6c, | 1b.2e.3f.4a.5f.6d, |
| 1b.2e.3f.4a.5f.6e, | 1b.2e.3f.4a.5f.6f, | 1b.2e.3f.4b.5a.6a, | 1b.2e.3f.4b.5a.6b, | 1b.2e.3f.4b.5a.6c, |
| 1b.2e.3f.4b.5a.6d, | 1b.2e.3f.4b.5a.6e, | 1b.2e.3f.4b.5a.6f, | 1b.2e.3f.4b.5b.6a, | |
| 1b.2e.3f.4b.5b.6b, | 1b.2e.3f.4b.5b.6c, | 1b.2e.3f.4b.5b.6d, | 1b.2e.3f.4b.5b.6e, | |
| 1b.2e.3f.4b.5b.6f, | 1b.2e.3f.4b.5c.6a, | 1b.2e.3f.4b.5c.6b, | 1b.2e.3f.4b.5c.6c, | 1b.2e.3f.4b.5c.6d, |
| 1b.2e.3f.4b.5c.6e, | 1b.2e.3f.4b.5c.6f, | 1b.2e.3f.4b.5d.6a, | 1b.2e.3f.4b.5d.6b, | |
| 1b.2e.3f.4b.5d.6c, | 1b.2e.3f.4b.5d.6d, | 1b.2e.3f.4b.5d.6e, | 1b.2e.3f.4b.5d.6f, | |
| 1b.2e.3f.4b.5e.6a, | 1b.2e.3f.4b.5e.6b, | 1b.2e.3f.4b.5e.6c, | 1b.2e.3f.4b.5e.6d, | |
| 1b.2e.3f.4b.5e.6e, | 1b.2e.3f.4b.5e.6f, | 1b.2e.3f.4b.5f.6a, | 1b.2e.3f.4b.5f.6b, | 1b.2e.3f.4b.5f.6c, |
| 1b.2e.3f.4b.5f.6d, | 1b.2e.3f.4b.5f.6e, | 1b.2e.3f.4b.5f.6f, | 1b.2e.3f.4c.5a.6a, | 1b.2e.3f.4c.5a.6b, |
| 1b.2e.3f.4c.5a.6c, | 1b.2e.3f.4c.5a.6d, | 1b.2e.3f.4c.5a.6e, | 1b.2e.3f.4c.5a.6f, | 1b.2e.3f.4c.5b.6a, |
| 1b.2e.3f.4c.5b.6b, | 1b.2e.3f.4c.5b.6c, | 1b.2e.3f.4c.5b.6d, | 1b.2e.3f.4c.5b.6e, | 1b.2e.3f.4c.5b.6f, |
| 1b.2e.3f.4c.5c.6a, | 1b.2e.3f.4c.5c.6b, | 1b.2e.3f.4c.5c.6c, | 1b.2e.3f.4c.5c.6d, | 1b.2e.3f.4c.5c.6e, |
| 1b.2e.3f.4c.5c.6f, | 1b.2e.3f.4c.5d.6a, | 1b.2e.3f.4c.5d.6b, | 1b.2e.3f.4c.5d.6c, | |
| 1b.2e.3f.4c.5d.6d, | 1b.2e.3f.4c.5d.6e, | 1b.2e.3f.4c.5d.6f, | 1b.2e.3f.4c.5e.6a, | 1b.2e.3f.4c.5e.6b, |
| 1b.2e.3f.4c.5e.6c, | 1b.2e.3f.4c.5e.6d, | 1b.2e.3f.4c.5e.6e, | 1b.2e.3f.4c.5e.6f, | 1b.2e.3f.4c.5f.6a, |
| 1b.2e.3f.4c.5f.6b, | 1b.2e.3f.4c.5f.6c, | 1b.2e.3f.4c.5f.6d, | 1b.2e.3f.4c.5f.6e, | 1b.2e.3f.4c.5f.6f, |
| 1b.2e.3f.4d.5a.6a, | 1b.2e.3f.4d.5a.6b, | 1b.2e.3f.4d.5a.6c, | 1b.2e.3f.4d.5a.6d, | |
| 1b.2e.3f.4d.5a.6e, | 1b.2e.3f.4d.5a.6f, | 1b.2e.3f.4d.5b.6a, | 1b.2e.3f.4d.5b.6b, | |
| 1b.2e.3f.4d.5b.6c, | 1b.2e.3f.4d.5b.6d, | 1b.2e.3f.4d.5b.6e, | 1b.2e.3f.4d.5b.6f, | |
| 1b.2e.3f.4d.5c.6a, | 1b.2e.3f.4d.5c.6b, | 1b.2e.3f.4d.5c.6c, | 1b.2e.3f.4d.5c.6d, | |
| 1b.2e.3f.4d.5c.6e, | 1b.2e.3f.4d.5c.6f, | 1b.2e.3f.4d.5d.6a, | 1b.2e.3f.4d.5d.6b, | |
| 1b.2e.3f.4d.5d.6c, | 1b.2e.3f.4d.5d.6d, | 1b.2e.3f.4d.5d.6e, | 1b.2e.3f.4d.5d.6f, | |
| 1b.2e.3f.4d.5e.6a, | 1b.2e.3f.4d.5e.6b, | 1b.2e.3f.4d.5e.6c, | 1b.2e.3f.4d.5e.6d, | |
| 1b.2e.3f.4d.5e.6e, | 1b.2e.3f.4d.5e.6f, | 1b.2e.3f.4d.5f.6a, | 1b.2e.3f.4d.5f.6b, | 1b.2e.3f.4d.5f.6c, |
| 1b.2e.3f.4d.5f.6d, | 1b.2e.3f.4d.5f.6e, | 1b.2e.3f.4d.5f.6f, | 1b.2e.3f.4e.5a.6a, | 1b.2e.3f.4e.5a.6b, |
| 1b.2e.3f.4e.5a.6c, | 1b.2e.3f.4e.5a.6d, | 1b.2e.3f.4e.5a.6e, | 1b.2e.3f.4e.5a.6f, | 1b.2e.3f.4e.5b.6a, |
| 1b.2e.3f.4e.5b.6b, | 1b.2e.3f.4e.5b.6c, | 1b.2e.3f.4e.5b.6d, | 1b.2e.3f.4e.5b.6e, | |
| 1b.2e.3f.4e.5b.6f, | 1b.2e.3f.4e.5c.6a, | 1b.2e.3f.4e.5c.6b, | 1b.2e.3f.4e.5c.6c, | 1b.2e.3f.4e.5c.6d, |
| 1b.2e.3f.4e.5c.6e, | 1b.2e.3f.4e.5c.6f, | 1b.2e.3f.4e.5d.6a, | 1b.2e.3f.4e.5d.6b, | 1b.2e.3f.4e.5d.6c, |
| 1b.2e.3f.4e.5d.6d, | 1b.2e.3f.4e.5d.6e, | 1b.2e.3f.4e.5d.6f, | 1b.2e.3f.4e.5e.6a, | |
| 1b.2e.3f.4e.5e.6b, | 1b.2e.3f.4e.5e.6c, | 1b.2e.3f.4e.5e.6d, | 1b.2e.3f.4e.5e.6e, | 1b.2e.3f.4e.5e.6f, |
| 1b.2e.3f.4e.5f.6a, | 1b.2e.3f.4e.5f.6b, | 1b.2e.3f.4e.5f.6c, | 1b.2e.3f.4e.5f.6d, | 1b.2e.3f.4e.5f.6e, |
| 1b.2e.3f.4e.5f.6f, | 1b.2e.3f.4f.5a.6a, | 1b.2e.3f.4f.5a.6b, | 1b.2e.3f.4f.5a.6c, | 1b.2e.3f.4f.5a.6d, |
| 1b.2e.3f.4f.5a.6e, | 1b.2e.3f.4f.5a.6f, | 1b.2e.3f.4f.5b.6a, | 1b.2e.3f.4f.5b.6b, | 1b.2e.3f.4f.5b.6c, |
| 1b.2e.3f.4f.5b.6d, | 1b.2e.3f.4f.5b.6e, | 1b.2e.3f.4f.5b.6f, | 1b.2e.3f.4f.5c.6a, | 1b.2e.3f.4f.5c.6b, |
| 1b.2e.3f.4f.5c.6c, | 1b.2e.3f.4f.5c.6d, | 1b.2e.3f.4f.5c.6e, | 1b.2e.3f.4f.5c.6f, | 1b.2e.3f.4f.5d.6a, |
| 1b.2e.3f.4f.5d.6b, | 1b.2e.3f.4f.5d.6c, | 1b.2e.3f.4f.5d.6d, | 1b.2e.3f.4f.5d.6e, | 1b.2e.3f.4f.5d.6f, |
| 1b.2e.3f.4f.5e.6a, | 1b.2e.3f.4f.5e.6b, | 1b.2e.3f.4f.5e.6c, | 1b.2e.3f.4f.5e.6d, | 1b.2e.3f.4f.5e.6e, |
| 1b.2e.3f.4f.5e.6f, | 1b.2e.3f.4f.5f.6a, | 1b.2e.3f.4f.5f.6b, | 1b.2e.3f.4f.5f.6c, | 1b.2e.3f.4f.5f.6d, |
| 1b.2e.3f.4f.5f.6e, | 1b.2e.3f.4f.5f.6f, | 1b.2f.3a.4a.5a.6a, | 1b.2f.3a.4a.5a.6b, | 1b.2f.3a.4a.5a.6c, |
| 1b.2f.3a.4a.5a.6d, | 1b.2f.3a.4a.5a.6e, | 1b.2f.3a.4a.5a.6f, | 1b.2f.3a.4a.5b.6a, | |
| 1b.2f.3a.4a.5b.6b, | 1b.2f.3a.4a.5b.6c, | 1b.2f.3a.4a.5b.6d, | 1b.2f.3a.4a.5b.6e, | |
| 1b.2f.3a.4a.5b.6f, | 1b.2f.3a.4a.5c.6a, | 1b.2f.3a.4a.5c.6b, | 1b.2f.3a.4a.5c.6c, | 1b.2f.3a.4a.5c.6d, |
| 1b.2f.3a.4a.5c.6e, | 1b.2f.3a.4a.5c.6f, | 1b.2f.3a.4a.5d.6a, | 1b.2f.3a.4a.5d.6b, | |
| 1b.2f.3a.4a.5d.6c, | 1b.2f.3a.4a.5d.6d, | 1b.2f.3a.4a.5d.6e, | 1b.2f.3a.4a.5d.6f, | |
| 1b.2f.3a.4a.5e.6a, | 1b.2f.3a.4a.5e.6b, | 1b.2f.3a.4a.5e.6c, | 1b.2f.3a.4a.5e.6d, | |
| 1b.2f.3a.4a.5e.6e, | 1b.2f.3a.4a.5e.6f, | 1b.2f.3a.4a.5f.6a, | 1b.2f.3a.4a.5f.6b, | 1b.2f.3a.4a.5f.6c, |
| 1b.2f.3a.4a.5f.6d, | 1b.2f.3a.4a.5f.6e, | 1b.2f.3a.4a.5f.6f, | 1b.2f.3a.4b.5a.6a, | 1b.2f.3a.4b.5a.6b, |
| 1b.2f.3a.4b.5a.6c, | 1b.2f.3a.4b.5a.6d, | 1b.2f.3a.4b.5a.6e, | 1b.2f.3a.4b.5a.6f, | |
| 1b.2f.3a.4b.5b.6a, | 1b.2f.3a.4b.5b.6b, | 1b.2f.3a.4b.5b.6c, | 1b.2f.3a.4b.5b.6d, | |
| 1b.2f.3a.4b.5b.6e, | 1b.2f.3a.4b.5b.6f, | 1b.2f.3a.4b.5c.6a, | 1b.2f.3a.4b.5c.6b, | |
| 1b.2f.3a.4b.5c.6c, | 1b.2f.3a.4b.5c.6d, | 1b.2f.3a.4b.5c.6e, | 1b.2f.3a.4b.5c.6f, | |
| 1b.2f.3a.4b.5d.6a, | 1b.2f.3a.4b.5d.6b, | 1b.2f.3a.4b.5d.6c, | 1b.2f.3a.4b.5d.6d, | |
| 1b.2f.3a.4b.5d.6e, | 1b.2f.3a.4b.5d.6f, | 1b.2f.3a.4b.5e.6a, | 1b.2f.3a.4b.5e.6b, | |
| 1b.2f.3a.4b.5e.6c, | 1b.2f.3a.4b.5e.6d, | 1b.2f.3a.4b.5e.6e, | 1b.2f.3a.4b.5e.6f, | 1b.2f.3a.4b.5f.6a, |
| 1b.2f.3a.4b.5f.6b, | 1b.2f.3a.4b.5f.6c, | 1b.2f.3a.4b.5f.6d, | 1b.2f.3a.4b.5f.6e, | 1b.2f.3a.4b.5f.6f, |
| 1b.2f.3a.4c.5a.6a, | 1b.2f.3a.4c.5a.6b, | 1b.2f.3a.4c.5a.6c, | 1b.2f.3a.4c.5a.6d, | 1b.2f.3a.4c.5a.6e, |
| 1b.2f.3a.4c.5a.6f, | 1b.2f.3a.4c.5b.6a, | 1b.2f.3a.4c.5b.6b, | 1b.2f.3a.4c.5b.6c, | 1b.2f.3a.4c.5b.6d, |
| 1b.2f.3a.4c.5b.6e, | 1b.2f.3a.4c.5b.6f, | 1b.2f.3a.4c.5c.6a, | 1b.2f.3a.4c.5c.6b, | 1b.2f.3a.4c.5c.6c, |
| 1b.2f.3a.4c.5c.6d, | 1b.2f.3a.4c.5c.6e, | 1b.2f.3a.4c.5c.6f, | 1b.2f.3a.4c.5d.6a, | 1b.2f.3a.4c.5d.6b, |
| 1b.2f.3a.4c.5d.6c, | 1b.2f.3a.4c.5d.6d, | 1b.2f.3a.4c.5d.6e, | 1b.2f.3a.4c.5d.6f, | |
| 1b.2f.3a.4c.5e.6a, | 1b.2f.3a.4c.5e.6b, | 1b.2f.3a.4c.5e.6c, | 1b.2f.3a.4c.5e.6d, | 1b.2f.3a.4c.5e.6e, |

TABLE 7-continued

List of Compounds of Formula (II)

| | | | | |
|---|---|---|---|---|
| 1b.2f.3a.4c.5e.6f, | 1b.2f.3a.4c.5f.6a, | 1b.2f.3a.4c.5f.6b, | 1b.2f.3a.4c.5f.6c, | 1b.2f.3a.4c.5f.6d, |
| 1b.2f.3a.4c.5f.6e, | 1b.2f.3a.4c.5f.6f, | 1b.2f.3a.4d.5a.6a, | 1b.2f.3a.4d.5a.6b, | 1b.2f.3a.4d.5a.6c, |
| 1b.2f.3a.4d.5a.6d, | 1b.2f.3a.4d.5a.6e, | 1b.2f.3a.4d.5a.6f, | 1b.2f.3a.4d.5b.6a, | |
| 1b.2f.3a.4d.5b.6b, | 1b.2f.3a.4d.5b.6c, | 1b.2f.3a.4d.5b.6d, | 1b.2f.3a.4d.5b.6e, | |
| 1b.2f.3a.4d.5b.6f, | 1b.2f.3a.4d.5c.6a, | 1b.2f.3a.4d.5c.6b, | 1b.2f.3a.4d.5c.6c, | |
| 1b.2f.3a.4d.5c.6d, | 1b.2f.3a.4d.5c.6e, | 1b.2f.3a.4d.5c.6f, | 1b.2f.3a.4d.5d.6a, | |
| 1b.2f.3a.4d.5d.6b, | 1b.2f.3a.4d.5d.6c, | 1b.2f.3a.4d.5d.6d, | 1b.2f.3a.4d.5d.6e, | |
| 1b.2f.3a.4d.5d.6f, | 1b.2f.3a.4d.5e.6a, | 1b.2f.3a.4d.5e.6b, | 1b.2f.3a.4d.5e.6c, | |
| 1b.2f.3a.4d.5e.6d, | 1b.2f.3a.4d.5e.6e, | 1b.2f.3a.4d.5e.6f, | 1b.2f.3a.4d.5f.6a, | |
| 1b.2f.3a.4d.5f.6b, | 1b.2f.3a.4d.5f.6c, | 1b.2f.3a.4d.5f.6d, | 1b.2f.3a.4d.5f.6e, | 1b.2f.3a.4d.5f.6f, |
| 1b.2f.3a.4e.5a.6a, | 1b.2f.3a.4e.5a.6b, | 1b.2f.3a.4e.5a.6c, | 1b.2f.3a.4e.5a.6d, | |
| 1b.2f.3a.4e.5a.6e, | 1b.2f.3a.4e.5a.6f, | 1b.2f.3a.4e.5b.6a, | 1b.2f.3a.4e.5b.6b, | 1b.2f.3a.4e.5b.6c, |
| 1b.2f.3a.4e.5b.6d, | 1b.2f.3a.4e.5b.6e, | 1b.2f.3a.4e.5b.6f, | 1b.2f.3a.4e.5c.6a, | 1b.2f.3a.4e.5c.6b, |
| 1b.2f.3a.4e.5c.6c, | 1b.2f.3a.4e.5c.6d, | 1b.2f.3a.4e.5c.6e, | 1b.2f.3a.4e.5c.6f, | 1b.2f.3a.4e.5d.6a, |
| 1b.2f.3a.4e.5d.6b, | 1b.2f.3a.4e.5d.6c, | 1b.2f.3a.4e.5d.6d, | 1b.2f.3a.4e.5d.6e, | |
| 1b.2f.3a.4e.5d.6f, | 1b.2f.3a.4e.5e.6a, | 1b.2f.3a.4e.5e.6b, | 1b.2f.3a.4e.5e.6c, | 1b.2f.3a.4e.5e.6d, |
| 1b.2f.3a.4e.5e.6e, | 1b.2f.3a.4e.5e.6f, | 1b.2f.3a.4e.5f.6a, | 1b.2f.3a.4e.5f.6b, | 1b.2f.3a.4e.5f.6c, |
| 1b.2f.3a.4e.5f.6d, | 1b.2f.3a.4e.5f.6e, | 1b.2f.3a.4e.5f.6f, | 1b.2f.3a.4f.5a.6a, | 1b.2f.3a.4f.5a.6b, |
| 1b.2f.3a.4f.5a.6c, | 1b.2f.3a.4f.5a.6d, | 1b.2f.3a.4f.5a.6e, | 1b.2f.3a.4f.5a.6f, | 1b.2f.3a.4f.5b.6a, |
| 1b.2f.3a.4f.5b.6b, | 1b.2f.3a.4f.5b.6c, | 1b.2f.3a.4f.5b.6d, | 1b.2f.3a.4f.5b.6e, | 1b.2f.3a.4f.5b.6f, |
| 1b.2f.3a.4f.5c.6a, | 1b.2f.3a.4f.5c.6b, | 1b.2f.3a.4f.5c.6c, | 1b.2f.3a.4f.5c.6d, | 1b.2f.3a.4f.5c.6e, |
| 1b.2f.3a.4f.5c.6f, | 1b.2f.3a.4f.5d.6a, | 1b.2f.3a.4f.5d.6b, | 1b.2f.3a.4f.5d.6c, | 1b.2f.3a.4f.5d.6d, |
| 1b.2f.3a.4f.5d.6e, | 1b.2f.3a.4f.5d.6f, | 1b.2f.3a.4f.5e.6a, | 1b.2f.3a.4f.5e.6b, | 1b.2f.3a.4f.5e.6c, |
| 1b.2f.3a.4f.5e.6d, | 1b.2f.3a.4f.5e.6e, | 1b.2f.3a.4f.5e.6f, | 1b.2f.3a.4f.5f.6a, | 1b.2f.3a.4f.5f.6b, |
| 1b.2f.3a.4f.5f.6c, | 1b.2f.3a.4f.5f.6d, | 1b.2f.3a.4f.5f.6e, | 1b.2f.3a.4f.5f.6f, | 1b.2f.3b.4a.5a.6a, |
| 1b.2f.3b.4a.5a.6b, | 1b.2f.3b.4a.5a.6c, | 1b.2f.3b.4a.5a.6d, | 1b.2f.3b.4a.5a.6e, | |
| 1b.2f.3b.4a.5a.6f, | 1b.2f.3b.4a.5b.6a, | 1b.2f.3b.4a.5b.6b, | 1b.2f.3b.4a.5b.6c, | |
| 1b.2f.3b.4a.5b.6d, | 1b.2f.3b.4a.5b.6e, | 1b.2f.3b.4a.5b.6f, | 1b.2f.3b.4a.5c.6a, | |
| 1b.2f.3b.4a.5c.6b, | 1b.2f.3b.4a.5c.6c, | 1b.2f.3b.4a.5c.6d, | 1b.2f.3b.4a.5c.6e, | 1b.2f.3b.4a.5c.6f, |
| 1b.2f.3b.4a.5d.6a, | 1b.2f.3b.4a.5d.6b, | 1b.2f.3b.4a.5d.6c, | 1b.2f.3b.4a.5d.6d, | |
| 1b.2f.3b.4a.5d.6e, | 1b.2f.3b.4a.5d.6f, | 1b.2f.3b.4a.5e.6a, | 1b.2f.3b.4a.5e.6b, | |
| 1b.2f.3b.4a.5e.6c, | 1b.2f.3b.4a.5e.6d, | 1b.2f.3b.4a.5e.6e, | 1b.2f.3b.4a.5e.6f, | 1b.2f.3b.4a.5f.6a, |
| 1b.2f.3b.4a.5f.6b, | 1b.2f.3b.4a.5f.6c, | 1b.2f.3b.4a.5f.6d, | 1b.2f.3b.4a.5f.6e, | 1b.2f.3b.4a.5f.6f, |
| 1b.2f.3b.4b.5a.6a, | 1b.2f.3b.4b.5a.6b, | 1b.2f.3b.4b.5a.6c, | 1b.2f.3b.4b.5a.6d, | |
| 1b.2f.3b.4b.5a.6e, | 1b.2f.3b.4b.5a.6f, | 1b.2f.3b.4b.5b.6a, | 1b.2f.3b.4b.5b.6b, | |
| 1b.2f.3b.4b.5b.6c, | 1b.2f.3b.4b.5b.6d, | 1b.2f.3b.4b.5b.6e, | 1b.2f.3b.4b.5b.6f, | |
| 1b.2f.3b.4b.5c.6a, | 1b.2f.3b.4b.5c.6b, | 1b.2f.3b.4b.5c.6c, | 1b.2f.3b.4b.5c.6d, | |
| 1b.2f.3b.4b.5c.6e, | 1b.2f.3b.4b.5c.6f, | 1b.2f.3b.4b.5d.6a, | 1b.2f.3b.4b.5d.6b, | |
| 1b.2f.3b.4b.5d.6c, | 1b.2f.3b.4b.5d.6d, | 1b.2f.3b.4b.5d.6e, | 1b.2f.3b.4b.5d.6f, | |
| 1b.2f.3b.4b.5e.6a, | 1b.2f.3b.4b.5e.6b, | 1b.2f.3b.4b.5e.6c, | 1b.2f.3b.4b.5e.6d, | |
| 1b.2f.3b.4b.5e.6e, | 1b.2f.3b.4b.5e.6f, | 1b.2f.3b.4b.5f.6a, | 1b.2f.3b.4b.5f.6b, | 1b.2f.3b.4b.5f.6c, |
| 1b.2f.3b.4b.5f.6d, | 1b.2f.3b.4b.5f.6e, | 1b.2f.3b.4b.5f.6f, | 1b.2f.3b.4c.5a.6a, | 1b.2f.3b.4c.5a.6b, |
| 1b.2f.3b.4c.5a.6c, | 1b.2f.3b.4c.5a.6d, | 1b.2f.3b.4c.5a.6e, | 1b.2f.3b.4c.5a.6f, | 1b.2f.3b.4c.5b.6a, |
| 1b.2f.3b.4c.5b.6b, | 1b.2f.3b.4c.5b.6c, | 1b.2f.3b.4c.5b.6d, | 1b.2f.3b.4c.5b.6e, | |
| 1b.2f.3b.4c.5b.6f, | 1b.2f.3b.4c.5c.6a, | 1b.2f.3b.4c.5c.6b, | 1b.2f.3b.4c.5c.6c, | 1b.2f.3b.4c.5c.6d, |
| 1b.2f.3b.4c.5c.6e, | 1b.2f.3b.4c.5c.6f, | 1b.2f.3b.4c.5d.6a, | 1b.2f.3b.4c.5d.6b, | |
| 1b.2f.3b.4c.5d.6c, | 1b.2f.3b.4c.5d.6d, | 1b.2f.3b.4c.5d.6e, | 1b.2f.3b.4c.5d.6f, | |
| 1b.2f.3b.4c.5e.6a, | 1b.2f.3b.4c.5e.6b, | 1b.2f.3b.4c.5e.6c, | 1b.2f.3b.4c.5e.6d, | |
| 1b.2f.3b.4c.5e.6e, | 1b.2f.3b.4c.5e.6f, | 1b.2f.3b.4c.5f.6a, | 1b.2f.3b.4c.5f.6b, | 1b.2f.3b.4c.5f.6c, |
| 1b.2f.3b.4c.5f.6d, | 1b.2f.3b.4c.5f.6e, | 1b.2f.3b.4c.5f.6f, | 1b.2f.3b.4d.5a.6a, | 1b.2f.3b.4d.5a.6b, |
| 1b.2f.3b.4d.5a.6c, | 1b.2f.3b.4d.5a.6d, | 1b.2f.3b.4d.5a.6e, | 1b.2f.3b.4d.5a.6f, | |
| 1b.2f.3b.4d.5b.6a, | 1b.2f.3b.4d.5b.6b, | 1b.2f.3b.4d.5b.6c, | 1b.2f.3b.4d.5b.6d, | |
| 1b.2f.3b.4d.5b.6e, | 1b.2f.3b.4d.5b.6f, | 1b.2f.3b.4d.5c.6a, | 1b.2f.3b.4d.5c.6b, | |
| 1b.2f.3b.4d.5c.6c, | 1b.2f.3b.4d.5c.6d, | 1b.2f.3b.4d.5c.6e, | 1b.2f.3b.4d.5c.6f, | |
| 1b.2f.3b.4d.5d.6a, | 1b.2f.3b.4d.5d.6b, | 1b.2f.3b.4d.5d.6c, | 1b.2f.3b.4d.5d.6d, | |
| 1b.2f.3b.4d.5d.6e, | 1b.2f.3b.4d.5d.6f, | 1b.2f.3b.4d.5e.6a, | 1b.2f.3b.4d.5e.6b, | |
| 1b.2f.3b.4d.5e.6c, | 1b.2f.3b.4d.5e.6d, | 1b.2f.3b.4d.5e.6e, | 1b.2f.3b.4d.5e.6f, | |
| 1b.2f.3b.4d.5f.6a, | 1b.2f.3b.4d.5f.6b, | 1b.2f.3b.4d.5f.6c, | 1b.2f.3b.4d.5f.6d, | |
| 1b.2f.3b.4d.5f.6e, | 1b.2f.3b.4d.5f.6f, | 1b.2f.3b.4e.5a.6a, | 1b.2f.3b.4e.5a.6b, | 1b.2f.3b.4e.5a.6c, |
| 1b.2f.3b.4e.5a.6d, | 1b.2f.3b.4e.5a.6e, | 1b.2f.3b.4e.5a.6f, | 1b.2f.3b.4e.5b.6a, | |
| 1b.2f.3b.4e.5b.6b, | 1b.2f.3b.4e.5b.6c, | 1b.2f.3b.4e.5b.6d, | 1b.2f.3b.4e.5b.6e, | |
| 1b.2f.3b.4e.5b.6f, | 1b.2f.3b.4e.5c.6a, | 1b.2f.3b.4e.5c.6b, | 1b.2f.3b.4e.5c.6c, | 1b.2f.3b.4e.5c.6d, |
| 1b.2f.3b.4e.5c.6e, | 1b.2f.3b.4e.5c.6f, | 1b.2f.3b.4e.5d.6a, | 1b.2f.3b.4e.5d.6b, | |
| 1b.2f.3b.4e.5d.6c, | 1b.2f.3b.4e.5d.6d, | 1b.2f.3b.4e.5d.6e, | 1b.2f.3b.4e.5d.6f, | |
| 1b.2f.3b.4e.5e.6a, | 1b.2f.3b.4e.5e.6b, | 1b.2f.3b.4e.5e.6c, | 1b.2f.3b.4e.5e.6d, | |
| 1b.2f.3b.4e.5e.6e, | 1b.2f.3b.4e.5e.6f, | 1b.2f.3b.4e.5f.6a, | 1b.2f.3b.4e.5f.6b, | 1b.2f.3b.4e.5f.6c, |
| 1b.2f.3b.4e.5f.6d, | 1b.2f.3b.4e.5f.6e, | 1b.2f.3b.4e.5f.6f, | 1b.2f.3b.4f.5a.6a, | 1b.2f.3b.4f.5a.6b, |
| 1b.2f.3b.4f.5a.6c, | 1b.2f.3b.4f.5a.6d, | 1b.2f.3b.4f.5a.6e, | 1b.2f.3b.4f.5a.6f, | 1b.2f.3b.4f.5b.6a, |
| 1b.2f.3b.4f.5b.6b, | 1b.2f.3b.4f.5b.6c, | 1b.2f.3b.4f.5b.6d, | 1b.2f.3b.4f.5b.6e, | 1b.2f.3b.4f.5b.6f, |
| 1b.2f.3b.4f.5c.6a, | 1b.2f.3b.4f.5c.6b, | 1b.2f.3b.4f.5c.6c, | 1b.2f.3b.4f.5c.6d, | 1b.2f.3b.4f.5c.6e, |
| 1b.2f.3b.4f.5c.6f, | 1b.2f.3b.4f.5d.6a, | 1b.2f.3b.4f.5d.6b, | 1b.2f.3b.4f.5d.6c, | 1b.2f.3b.4f.5d.6d, |
| 1b.2f.3b.4f.5d.6e, | 1b.2f.3b.4f.5d.6f, | 1b.2f.3b.4f.5e.6a, | 1b.2f.3b.4f.5e.6b, | 1b.2f.3b.4f.5e.6c, |
| 1b.2f.3b.4f.5e.6d, | 1b.2f.3b.4f.5e.6e, | 1b.2f.3b.4f.5e.6f, | 1b.2f.3b.4f.5f.6a, | 1b.2f.3b.4f.5f.6b, |
| 1b.2f.3b.4f.5f.6c, | 1b.2f.3b.4f.5f.6d, | 1b.2f.3b.4f.5f.6e, | 1b.2f.3b.4f.5f.6f, | 1b.2f.3c.4a.5a.6a, |
| 1b.2f.3c.4a.5a.6b, | 1b.2f.3c.4a.5a.6c, | 1b.2f.3c.4a.5a.6d, | 1b.2f.3c.4a.5a.6e, | 1b.2f.3c.4a.5a.6f, |
| 1b.2f.3c.4a.5b.6a, | 1b.2f.3c.4a.5b.6b, | 1b.2f.3c.4a.5b.6c, | 1b.2f.3c.4a.5b.6d, | |
| 1b.2f.3c.4a.5b.6e, | 1b.2f.3c.4a.5b.6f, | 1b.2f.3c.4a.5c.6a, | 1b.2f.3c.4a.5c.6b, | 1b.2f.3c.4a.5c.6c, |
| 1b.2f.3c.4a.5c.6d, | 1b.2f.3c.4a.5c.6e, | 1b.2f.3c.4a.5c.6f, | 1b.2f.3c.4a.5d.6a, | 1b.2f.3c.4a.5d.6b, |

TABLE 7-continued

List of Compounds of Formula (II)

| | | | |
|---|---|---|---|
| 1b.2f.3c.4a.5d.6c, | 1b.2f.3c.4a.5d.6d, | 1b.2f.3c.4a.5d.6e, | 1b.2f.3c.4a.5d.6f, |
| 1b.2f.3c.4a.5e.6a, | 1b.2f.3c.4a.5e.6b, | 1b.2f.3c.4a.5e.6c, | 1b.2f.3c.4a.5e.6d, | 1b.2f.3c.4a.5e.6e, |
| 1b.2f.3c.4a.5e.6f, | 1b.2f.3c.4a.5f.6a, | 1b.2f.3c.4a.5f.6b, | 1b.2f.3c.4a.5f.6c, | 1b.2f.3c.4a.5f.6d, |
| 1b.2f.3c.4a.5f.6e, | 1b.2f.3c.4a.5f.6f, | 1b.2f.3c.4b.5a.6a, | 1b.2f.3c.4b.5a.6b, | 1b.2f.3c.4b.5a.6c, |
| 1b.2f.3c.4b.5a.6d, | 1b.2f.3c.4b.5a.6e, | 1b.2f.3c.4b.5a.6f, | 1b.2f.3c.4b.5b.6a, |
| 1b.2f.3c.4b.5b.6b, | 1b.2f.3c.4b.5b.6c, | 1b.2f.3c.4b.5b.6d, | 1b.2f.3c.4b.5b.6e, |
| 1b.2f.3c.4b.5b.6f, | 1b.2f.3c.4b.5c.6a, | 1b.2f.3c.4b.5c.6b, | 1b.2f.3c.4b.5c.6c, | 1b.2f.3c.4b.5c.6d, |
| 1b.2f.3c.4b.5c.6e, | 1b.2f.3c.4b.5c.6f, | 1b.2f.3c.4b.5d.6a, | 1b.2f.3c.4b.5d.6b, |
| 1b.2f.3c.4b.5d.6c, | 1b.2f.3c.4b.5d.6d, | 1b.2f.3c.4b.5d.6e, | 1b.2f.3c.4b.5d.6f, |
| 1b.2f.3c.4b.5e.6a, | 1b.2f.3c.4b.5e.6b, | 1b.2f.3c.4b.5e.6c, | 1b.2f.3c.4b.5e.6d, |
| 1b.2f.3c.4b.5e.6e, | 1b.2f.3c.4b.5e.6f, | 1b.2f.3c.4b.5f.6a, | 1b.2f.3c.4b.5f.6b, | 1b.2f.3c.4b.5f.6c, |
| 1b.2f.3c.4b.5f.6d, | 1b.2f.3c.4b.5f.6e, | 1b.2f.3c.4b.5f.6f, | 1b.2f.3c.4c.5a.6a, | 1b.2f.3c.4c.5a.6b, |
| 1b.2f.3c.4c.5a.6c, | 1b.2f.3c.4c.5a.6d, | 1b.2f.3c.4c.5a.6e, | 1b.2f.3c.4c.5a.6f, | 1b.2f.3c.4c.5b.6a, |
| 1b.2f.3c.4c.5b.6b, | 1b.2f.3c.4c.5b.6c, | 1b.2f.3c.4c.5b.6d, | 1b.2f.3c.4c.5b.6e, | 1b.2f.3c.4c.5b.6f, |
| 1b.2f.3c.4c.5c.6a, | 1b.2f.3c.4c.5c.6b, | 1b.2f.3c.4c.5c.6c, | 1b.2f.3c.4c.5c.6d, | 1b.2f.3c.4c.5c.6e, |
| 1b.2f.3c.4c.5c.6f, | 1b.2f.3c.4c.5d.6a, | 1b.2f.3c.4c.5d.6b, | 1b.2f.3c.4c.5d.6c, | 1b.2f.3c.4c.5d.6d, |
| 1b.2f.3c.4c.5d.6e, | 1b.2f.3c.4c.5d.6f, | 1b.2f.3c.4c.5e.6a, | 1b.2f.3c.4c.5e.6b, | 1b.2f.3c.4c.5e.6c, |
| 1b.2f.3c.4c.5e.6d, | 1b.2f.3c.4c.5e.6e, | 1b.2f.3c.4c.5e.6f, | 1b.2f.3c.4c.5f.6a, | 1b.2f.3c.4c.5f.6b, |
| 1b.2f.3c.4c.5f.6c, | 1b.2f.3c.4c.5f.6d, | 1b.2f.3c.4c.5f.6e, | 1b.2f.3c.4c.5f.6f, | 1b.2f.3c.4d.5a.6a, |
| 1b.2f.3c.4d.5a.6b, | 1b.2f.3c.4d.5a.6c, | 1b.2f.3c.4d.5a.6d, | 1b.2f.3c.4d.5a.6e, |
| 1b.2f.3c.4d.5a.6f, | 1b.2f.3c.4d.5b.6a, | 1b.2f.3c.4d.5b.6b, | 1b.2f.3c.4d.5b.6c, |
| 1b.2f.3c.4d.5b.6d, | 1b.2f.3c.4d.5b.6e, | 1b.2f.3c.4d.5b.6f, | 1b.2f.3c.4d.5c.6a, |
| 1b.2f.3c.4d.5c.6b, | 1b.2f.3c.4d.5c.6c, | 1b.2f.3c.4d.5c.6d, | 1b.2f.3c.4d.5c.6e, | 1b.2f.3c.4d.5c.6f, |
| 1b.2f.3c.4d.5d.6a, | 1b.2f.3c.4d.5d.6b, | 1b.2f.3c.4d.5d.6c, | 1b.2f.3c.4d.5d.6d, |
| 1b.2f.3c.4d.5d.6e, | 1b.2f.3c.4d.5d.6f, | 1b.2f.3c.4d.5e.6a, | 1b.2f.3c.4d.5e.6b, |
| 1b.2f.3c.4d.5e.6c, | 1b.2f.3c.4d.5e.6d, | 1b.2f.3c.4d.5e.6e, | 1b.2f.3c.4d.5e.6f, | 1b.2f.3c.4d.5f.6a, |
| 1b.2f.3c.4d.5f.6b, | 1b.2f.3c.4d.5f.6c, | 1b.2f.3c.4d.5f.6d, | 1b.2f.3c.4d.5f.6e, | 1b.2f.3c.4d.5f.6f, |
| 1b.2f.3c.4e.5a.6a, | 1b.2f.3c.4e.5a.6b, | 1b.2f.3c.4e.5a.6c, | 1b.2f.3c.4e.5a.6d, | 1b.2f.3c.4e.5a.6e, |
| 1b.2f.3c.4e.5a.6f, | 1b.2f.3c.4e.5b.6a, | 1b.2f.3c.4e.5b.6b, | 1b.2f.3c.4e.5b.6c, | 1b.2f.3c.4e.5b.6d, |
| 1b.2f.3c.4e.5b.6e, | 1b.2f.3c.4e.5b.6f, | 1b.2f.3c.4e.5c.6a, | 1b.2f.3c.4e.5c.6b, | 1b.2f.3c.4e.5c.6c, |
| 1b.2f.3c.4e.5c.6d, | 1b.2f.3c.4e.5c.6e, | 1b.2f.3c.4e.5c.6f, | 1b.2f.3c.4e.5d.6a, | 1b.2f.3c.4e.5d.6b, |
| 1b.2f.3c.4e.5d.6c, | 1b.2f.3c.4e.5d.6d, | 1b.2f.3c.4e.5d.6e, | 1b.2f.3c.4e.5d.6f, | 1b.2f.3c.4e.5e.6a, |
| 1b.2f.3c.4e.5e.6b, | 1b.2f.3c.4e.5e.6c, | 1b.2f.3c.4e.5e.6d, | 1b.2f.3c.4e.5e.6e, | 1b.2f.3c.4e.5e.6f, |
| 1b.2f.3c.4e.5f.6a, | 1b.2f.3c.4e.5f.6b, | 1b.2f.3c.4e.5f.6c, | 1b.2f.3c.4e.5f.6d, | 1b.2f.3c.4e.5f.6e, |
| 1b.2f.3c.4e.5f.6f, | 1b.2f.3c.4f.5a.6a, | 1b.2f.3c.4f.5a.6b, | 1b.2f.3c.4f.5a.6c, | 1b.2f.3c.4f.5a.6d, |
| 1b.2f.3c.4f.5a.6e, | 1b.2f.3c.4f.5a.6f, | 1b.2f.3c.4f.5b.6a, | 1b.2f.3c.4f.5b.6b, | 1b.2f.3c.4f.5b.6c, |
| 1b.2f.3c.4f.5b.6d, | 1b.2f.3c.4f.5b.6e, | 1b.2f.3c.4f.5b.6f, | 1b.2f.3c.4f.5c.6a, | 1b.2f.3c.4f.5c.6b, |
| 1b.2f.3c.4f.5c.6c, | 1b.2f.3c.4f.5c.6d, | 1b.2f.3c.4f.5c.6e, | 1b.2f.3c.4f.5c.6f, | 1b.2f.3c.4f.5d.6a, |
| 1b.2f.3c.4f.5d.6b, | 1b.2f.3c.4f.5d.6c, | 1b.2f.3c.4f.5d.6d, | 1b.2f.3c.4f.5d.6e, | 1b.2f.3c.4f.5d.6f, |
| 1b.2f.3c.4f.5e.6a, | 1b.2f.3c.4f.5e.6b, | 1b.2f.3c.4f.5e.6c, | 1b.2f.3c.4f.5e.6d, | 1b.2f.3c.4f.5e.6e, |
| 1b.2f.3c.4f.5e.6f, | 1b.2f.3c.4f.5f.6a, | 1b.2f.3c.4f.5f.6b, | 1b.2f.3c.4f.5f.6c, | 1b.2f.3c.4f.5f.6d, |
| 1b.2f.3c.4f.5f.6e, | 1b.2f.3c.4f.5f.6f, | 1b.2f.3d.4a.5a.6a, | 1b.2f.3d.4a.5a.6b, | 1b.2f.3d.4a.5a.6c, |
| 1b.2f.3d.4a.5a.6d, | 1b.2f.3d.4a.5a.6e, | 1b.2f.3d.4a.5a.6f, | 1b.2f.3d.4a.5b.6a, |
| 1b.2f.3d.4a.5b.6b, | 1b.2f.3d.4a.5b.6c, | 1b.2f.3d.4a.5b.6d, | 1b.2f.3d.4a.5b.6e, |
| 1b.2f.3d.4a.5b.6f, | 1b.2f.3d.4a.5c.6a, | 1b.2f.3d.4a.5c.6b, | 1b.2f.3d.4a.5c.6c, |
| 1b.2f.3d.4a.5c.6d, | 1b.2f.3d.4a.5c.6e, | 1b.2f.3d.4a.5c.6f, | 1b.2f.3d.4a.5d.6a, |
| 1b.2f.3d.4a.5d.6b, | 1b.2f.3d.4a.5d.6c, | 1b.2f.3d.4a.5d.6d, | 1b.2f.3d.4a.5d.6e, |
| 1b.2f.3d.4a.5d.6f, | 1b.2f.3d.4a.5e.6a, | 1b.2f.3d.4a.5e.6b, | 1b.2f.3d.4a.5e.6c, |
| 1b.2f.3d.4a.5e.6d, | 1b.2f.3d.4a.5e.6e, | 1b.2f.3d.4a.5e.6f, | 1b.2f.3d.4a.5f.6a, |
| 1b.2f.3d.4a.5f.6b, | 1b.2f.3d.4a.5f.6c, | 1b.2f.3d.4a.5f.6d, | 1b.2f.3d.4a.5f.6e, | 1b.2f.3d.4a.5f.6f, |
| 1b.2f.3d.4b.5a.6a, | 1b.2f.3d.4b.5a.6b, | 1b.2f.3d.4b.5a.6c, | 1b.2f.3d.4b.5a.6d, |
| 1b.2f.3d.4b.5a.6e, | 1b.2f.3d.4b.5a.6f, | 1b.2f.3d.4b.5b.6a, | 1b.2f.3d.4b.5b.6b, |
| 1b.2f.3d.4b.5b.6c, | 1b.2f.3d.4b.5b.6d, | 1b.2f.3d.4b.5b.6e, | 1b.2f.3d.4b.5b.6f, |
| 1b.2f.3d.4b.5c.6a, | 1b.2f.3d.4b.5c.6b, | 1b.2f.3d.4b.5c.6c, | 1b.2f.3d.4b.5c.6d, |
| 1b.2f.3d.4b.5c.6e, | 1b.2f.3d.4b.5c.6f, | 1b.2f.3d.4b.5d.6a, | 1b.2f.3d.4b.5d.6b, |
| 1b.2f.3d.4b.5d.6c, | 1b.2f.3d.4b.5d.6d, | 1b.2f.3d.4b.5d.6e, | 1b.2f.3d.4b.5d.6f, |
| 1b.2f.3d.4b.5e.6a, | 1b.2f.3d.4b.5e.6b, | 1b.2f.3d.4b.5e.6c, | 1b.2f.3d.4b.5e.6d, |
| 1b.2f.3d.4b.5e.6e, | 1b.2f.3d.4b.5e.6f, | 1b.2f.3d.4b.5f.6a, | 1b.2f.3d.4b.5f.6b, |
| 1b.2f.3d.4b.5f.6c, | 1b.2f.3d.4b.5f.6d, | 1b.2f.3d.4b.5f.6e, | 1b.2f.3d.4b.5f.6f, | 1b.2f.3d.4c.5a.6a, |
| 1b.2f.3d.4c.5a.6b, | 1b.2f.3d.4c.5a.6c, | 1b.2f.3d.4c.5a.6d, | 1b.2f.3d.4c.5a.6e, |
| 1b.2f.3d.4c.5a.6f, | 1b.2f.3d.4c.5b.6a, | 1b.2f.3d.4c.5b.6b, | 1b.2f.3d.4c.5b.6c, |
| 1b.2f.3d.4c.5b.6d, | 1b.2f.3d.4c.5b.6e, | 1b.2f.3d.4c.5b.6f, | 1b.2f.3d.4c.5c.6a, |
| 1b.2f.3d.4c.5c.6b, | 1b.2f.3d.4c.5c.6c, | 1b.2f.3d.4c.5c.6d, | 1b.2f.3d.4c.5c.6e, | 1b.2f.3d.4c.5c.6f, |
| 1b.2f.3d.4c.5d.6a, | 1b.2f.3d.4c.5d.6b, | 1b.2f.3d.4c.5d.6c, | 1b.2f.3d.4c.5d.6d, |
| 1b.2f.3d.4c.5d.6e, | 1b.2f.3d.4c.5d.6f, | 1b.2f.3d.4c.5e.6a, | 1b.2f.3d.4c.5e.6b, |
| 1b.2f.3d.4c.5e.6c, | 1b.2f.3d.4c.5e.6d, | 1b.2f.3d.4c.5e.6e, | 1b.2f.3d.4c.5e.6f, | 1b.2f.3d.4c.5f.6a, |
| 1b.2f.3d.4c.5f.6b, | 1b.2f.3d.4c.5f.6c, | 1b.2f.3d.4c.5f.6d, | 1b.2f.3d.4c.5f.6e, | 1b.2f.3d.4c.5f.6f, |
| 1b.2f.3d.4d.5a.6a, | 1b.2f.3d.4d.5a.6b, | 1b.2f.3d.4d.5a.6c, | 1b.2f.3d.4d.5a.6d, |
| 1b.2f.3d.4d.5a.6e, | 1b.2f.3d.4d.5a.6f, | 1b.2f.3d.4d.5b.6a, | 1b.2f.3d.4d.5b.6b, |
| 1b.2f.3d.4d.5b.6c, | 1b.2f.3d.4d.5b.6d, | 1b.2f.3d.4d.5b.6e, | 1b.2f.3d.4d.5b.6f, |
| 1b.2f.3d.4d.5c.6a, | 1b.2f.3d.4d.5c.6b, | 1b.2f.3d.4d.5c.6c, | 1b.2f.3d.4d.5c.6d, |
| 1b.2f.3d.4d.5c.6e, | 1b.2f.3d.4d.5c.6f, | 1b.2f.3d.4d.5d.6a, | 1b.2f.3d.4d.5d.6b, |
| 1b.2f.3d.4d.5d.6c, | 1b.2f.3d.4d.5d.6d, | 1b.2f.3d.4d.5d.6e, | 1b.2f.3d.4d.5d.6f, |
| 1b.2f.3d.4d.5e.6a, | 1b.2f.3d.4d.5e.6b, | 1b.2f.3d.4d.5e.6c, | 1b.2f.3d.4d.5e.6d, |
| 1b.2f.3d.4d.5e.6e, | 1b.2f.3d.4d.5e.6f, | 1b.2f.3d.4d.5f.6a, | 1b.2f.3d.4d.5f.6b, |
| 1b.2f.3d.4d.5f.6c, | 1b.2f.3d.4d.5f.6d, | 1b.2f.3d.4d.5f.6e, | 1b.2f.3d.4d.5f.6f, |
| 1b.2f.3d.4e.5a.6a, | 1b.2f.3d.4e.5a.6b, | 1b.2f.3d.4e.5a.6c, | 1b.2f.3d.4e.5a.6d, |
| 1b.2f.3d.4e.5a.6e, | 1b.2f.3d.4e.5a.6f, | 1b.2f.3d.4e.5b.6a, | 1b.2f.3d.4e.5b.6b, |

TABLE 7-continued

List of Compounds of Formula (II)

| | | | |
|---|---|---|---|
| 1b.2f.3d.4e.5b.6c, | 1b.2f.3d.4e.5b.6d, | 1b.2f.3d.4e.5b.6e, | 1b.2f.3d.4e.5b.6f, |
| 1b.2f.3d.4e.5c.6a, | 1b.2f.3d.4e.5c.6b, | 1b.2f.3d.4e.5c.6c, | 1b.2f.3d.4e.5c.6d, |
| 1b.2f.3d.4e.5c.6e, | 1b.2f.3d.4e.5c.6f, | 1b.2f.3d.4e.5d.6a, | 1b.2f.3d.4e.5d.6b, |
| 1b.2f.3d.4e.5d.6c, | 1b.2f.3d.4e.5d.6d, | 1b.2f.3d.4e.5d.6e, | 1b.2f.3d.4e.5d.6f, |
| 1b.2f.3d.4e.5e.6a, | 1b.2f.3d.4e.5e.6b, | 1b.2f.3d.4e.5e.6c, | 1b.2f.3d.4e.5e.6d, |
| 1b.2f.3d.4e.5e.6e, | 1b.2f.3d.4e.5e.6f, | 1b.2f.3d.4e.5f.6a, | 1b.2f.3d.4e.5f.6b, | 1b.2f.3d.4e.5f.6c, |
| 1b.2f.3d.4e.5f.6d, | 1b.2f.3d.4e.5f.6e, | 1b.2f.3d.4e.5f.6f, | 1b.2f.3d.4f.5a.6a, | 1b.2f.3d.4f.5a.6b, |
| 1b.2f.3d.4f.5a.6c, | 1b.2f.3d.4f.5a.6d, | 1b.2f.3d.4f.5a.6e, | 1b.2f.3d.4f.5a.6f, | 1b.2f.3d.4f.5b.6a, |
| 1b.2f.3d.4f.5b.6b, | 1b.2f.3d.4f.5b.6c, | 1b.2f.3d.4f.5b.6d, | 1b.2f.3d.4f.5b.6e, | 1b.2f.3d.4f.5b.6f, |
| 1b.2f.3d.4f.5c.6a, | 1b.2f.3d.4f.5c.6b, | 1b.2f.3d.4f.5c.6c, | 1b.2f.3d.4f.5c.6d, | 1b.2f.3d.4f.5c.6e, |
| 1b.2f.3d.4f.5c.6f, | 1b.2f.3d.4f.5d.6a, | 1b.2f.3d.4f.5d.6b, | 1b.2f.3d.4f.5d.6c, |
| 1b.2f.3d.4f.5d.6d, | 1b.2f.3d.4f.5d.6e, | 1b.2f.3d.4f.5d.6f, | 1b.2f.3d.4f.5e.6a, |
| 1b.2f.3d.4f.5e.6b, | 1b.2f.3d.4f.5e.6c, | 1b.2f.3d.4f.5e.6d, | 1b.2f.3d.4f.5e.6e, | 1b.2f.3d.4f.5e.6f, |
| 1b.2f.3d.4f.5f.6a, | 1b.2f.3d.4f.5f.6b, | 1b.2f.3d.4f.5f.6c, | 1b.2f.3d.4f.5f.6d, | 1b.2f.3d.4f.5f.6e, |
| 1b.2f.3d.4f.5f.6f, | 1b.2f.3e.4a.5a.6a, | 1b.2f.3e.4a.5a.6b, | 1b.2f.3e.4a.5a.6c, | 1b.2f.3e.4a.5a.6d, |
| 1b.2f.3e.4a.5a.6e, | 1b.2f.3e.4a.5a.6f, | 1b.2f.3e.4a.5b.6a, | 1b.2f.3e.4a.5b.6b, | 1b.2f.3e.4a.5b.6c, |
| 1b.2f.3e.4a.5b.6d, | 1b.2f.3e.4a.5b.6e, | 1b.2f.3e.4a.5b.6f, | 1b.2f.3e.4a.5c.6a, | 1b.2f.3e.4a.5c.6b, |
| 1b.2f.3e.4a.5c.6c, | 1b.2f.3e.4a.5c.6d, | 1b.2f.3e.4a.5c.6e, | 1b.2f.3e.4a.5c.6f, | 1b.2f.3e.4a.5d.6a, |
| 1b.2f.3e.4a.5d.6b, | 1b.2f.3e.4a.5d.6c, | 1b.2f.3e.4a.5d.6d, | 1b.2f.3e.4a.5d.6e, |
| 1b.2f.3e.4a.5d.6f, | 1b.2f.3e.4a.5e.6a, | 1b.2f.3e.4a.5e.6b, | 1b.2f.3e.4a.5e.6c, | 1b.2f.3e.4a.5e.6d, |
| 1b.2f.3e.4a.5e.6e, | 1b.2f.3e.4a.5e.6f, | 1b.2f.3e.4a.5f.6a, | 1b.2f.3e.4a.5f.6b, | 1b.2f.3e.4a.5f.6c, |
| 1b.2f.3e.4a.5f.6d, | 1b.2f.3e.4a.5f.6e, | 1b.2f.3e.4a.5f.6f, | 1b.2f.3e.4b.5a.6a, | 1b.2f.3e.4b.5a.6b, |
| 1b.2f.3e.4b.5a.6c, | 1b.2f.3e.4b.5a.6d, | 1b.2f.3e.4b.5a.6e, | 1b.2f.3e.4b.5a.6f, |
| 1b.2f.3e.4b.5b.6a, | 1b.2f.3e.4b.5b.6b, | 1b.2f.3e.4b.5b.6c, | 1b.2f.3e.4b.5b.6d, |
| 1b.2f.3e.4b.5b.6e, | 1b.2f.3e.4b.5b.6f, | 1b.2f.3e.4b.5c.6a, | 1b.2f.3e.4b.5c.6b, | 1b.2f.3e.4b.5c.6c, |
| 1b.2f.3e.4b.5c.6d, | 1b.2f.3e.4b.5c.6e, | 1b.2f.3e.4b.5c.6f, | 1b.2f.3e.4b.5d.6a, |
| 1b.2f.3e.4b.5d.6b, | 1b.2f.3e.4b.5d.6c, | 1b.2f.3e.4b.5d.6d, | 1b.2f.3e.4b.5d.6e, |
| 1b.2f.3e.4b.5d.6f, | 1b.2f.3e.4b.5e.6a, | 1b.2f.3e.4b.5e.6b, | 1b.2f.3e.4b.5e.6c, |
| 1b.2f.3e.4b.5e.6d, | 1b.2f.3e.4b.5e.6e, | 1b.2f.3e.4b.5e.6f, | 1b.2f.3e.4b.5f.6a, | 1b.2f.3e.4b.5f.6b, |
| 1b.2f.3e.4b.5f.6c, | 1b.2f.3e.4b.5f.6d, | 1b.2f.3e.4b.5f.6e, | 1b.2f.3e.4b.5f.6f, | 1b.2f.3e.4c.5a.6a, |
| 1b.2f.3e.4c.5a.6b, | 1b.2f.3e.4c.5a.6c, | 1b.2f.3e.4c.5a.6d, | 1b.2f.3e.4c.5a.6e, | 1b.2f.3e.4c.5a.6f, |
| 1b.2f.3e.4c.5b.6a, | 1b.2f.3e.4c.5b.6b, | 1b.2f.3e.4c.5b.6c, | 1b.2f.3e.4c.5b.6d, |
| 1b.2f.3e.4c.5b.6e, | 1b.2f.3e.4c.5b.6f, | 1b.2f.3e.4c.5c.6a, | 1b.2f.3e.4c.5c.6b, | 1b.2f.3e.4c.5c.6c, |
| 1b.2f.3e.4c.5c.6d, | 1b.2f.3e.4c.5c.6e, | 1b.2f.3e.4c.5c.6f, | 1b.2f.3e.4c.5d.6a, | 1b.2f.3e.4c.5d.6b, |
| 1b.2f.3e.4c.5d.6c, | 1b.2f.3e.4c.5d.6d, | 1b.2f.3e.4c.5d.6e, | 1b.2f.3e.4c.5d.6f, | 1b.2f.3e.4c.5e.6a, |
| 1b.2f.3e.4c.5e.6b, | 1b.2f.3e.4c.5e.6c, | 1b.2f.3e.4c.5e.6d, | 1b.2f.3e.4c.5e.6e, | 1b.2f.3e.4c.5e.6f, |
| 1b.2f.3e.4c.5f.6a, | 1b.2f.3e.4c.5f.6b, | 1b.2f.3e.4c.5f.6c, | 1b.2f.3e.4c.5f.6d, | 1b.2f.3e.4c.5f.6e, |
| 1b.2f.3e.4c.5f.6f, | 1b.2f.3e.4d.5a.6a, | 1b.2f.3e.4d.5a.6b, | 1b.2f.3e.4d.5a.6c, |
| 1b.2f.3e.4d.5a.6d, | 1b.2f.3e.4d.5a.6e, | 1b.2f.3e.4d.5a.6f, | 1b.2f.3e.4d.5b.6a, |
| 1b.2f.3e.4d.5b.6b, | 1b.2f.3e.4d.5b.6c, | 1b.2f.3e.4d.5b.6d, | 1b.2f.3e.4d.5b.6e, |
| 1b.2f.3e.4d.5b.6f, | 1b.2f.3e.4d.5c.6a, | 1b.2f.3e.4d.5c.6b, | 1b.2f.3e.4d.5c.6c, |
| 11;.2f.3e.4d.5c.6d, | 1b.2f.3e.4d.5c.6e, | 1b.2f.3e.4d.5c.6f, | 1b.2f.3e.4d.5d.6a, |
| 1b.2f.3e.4d.5d.6b, | 1b.2f.3e.4d.5d.6c, | 1b.2f.3e.4d.5d.6d, | 1b.2f.3e.4d.5d.6e, |
| 1b.2f.3e.4d.5d.6f, | 1b.2f.3e.4d.5e.6a, | 1b.2f.3e.4d.5e.6b, | 1b.2f.3e.4d.5e.6c, |
| 1b.2f.3e.4d.5e.6d, | 1b.2f.3e.4d.5e.6e, | 1b.2f.3e.4d.5e.6f, | 1b.2f.3e.4d.5f.6a, |
| 1b.2f.3e.4d.5f.6b, | 1b.2f.3e.4d.5f.6c, | 1b.2f.3e.4d.5f.6d, | 1b.2f.3e.4d.5f.6e, | 1b.2f.3e.4d.5f.6f, |
| 1b.2f.3e.4e.5a.6a, | 1b.2f.3e.4e.5a.6b, | 1b.2f.3e.4e.5a.6c, | 1b.2f.3e.4e.5a.6d, | 1b.2f.3e.4e.5a.6e, |
| 1b.2f.3e.4e.5a.6f, | 1b.2f.3e.4e.5b.6a, | 1b.2f.3e.4e.5b.6b, | 1b.2f.3e.4e.5b.6c, |
| 1b.2f.3e.4e.5b.6d, | 1b.2f.3e.4e.5b.6e, | 1b.2f.3e.4e.5b.6f, | 1b.2f.3e.4e.5c.6a, | 1b.2f.3e.4e.5c.6b, |
| 1b.2f.3e.4e.5c.6c, | 1b.2f.3e.4e.5c.6d, | 1b.2f.3e.4e.5c.6e, | 1b.2f.3e.4e.5c.6f, | 1b.2f.3e.4e.5d.6a, |
| 1b.2f.3e.4e.5d.6b, | 1b.2f.3e.4e.5d.6c, | 1b.2f.3e.4e.5d.6d, | 1b.2f.3e.4e.5d.6e, |
| 1b.2f.3e.4e.5d.6f, | 1b.2f.3e.4e.5e.6a, | 1b.2f.3e.4e.5e.6b, | 1b.2f.3e.4e.5e.6c, | 1b.2f.3e.4e.5e.6d, |
| 1b.2f.3e.4e.5e.6e, | 1b.2f.3e.4e.5e.6f, | 1b.2f.3e.4e.5f.6a, | 1b.2f.3e.4e.5f.6b, | 1b.2f.3e.4e.5f.6c, |
| 1b.2f.3e.4e.5f.6d, | 1b.2f.3e.4e.5f.6e, | 1b.2f.3e.4e.5f.6f, | 1b.2f.3e.4f.5a.6a, | 1b.2f.3e.4f.5a.6b, |
| 1b.2f.3e.4f.5a.6c, | 1b.2f.3e.4f.5a.6d, | 1b.2f.3e.4f.5a.6e, | 1b.2f.3e.4f.5a.6f, | 1b.2f.3e.4f.5b.6a, |
| 1b.2f.3e.4f.5b.6b, | 1b.2f.3e.4f.5b.6c, | 1b.2f.3e.4f.5b.6d, | 1b.2f.3e.4f.5b.6e, | 1b.2f.3e.4f.5b.6f, |
| 1b.2f.3e.4f.5c.6a, | 1b.2f.3e.4f.5c.6b, | 1b.2f.3e.4f.5c.6c, | 1b.2f.3e.4f.5c.6d, | 1b.2f.3e.4f.5c.6e, |
| 1b.2f.3e.4f.5c.6f, | 1b.2f.3e.4f.5d.6a, | 1b.2f.3e.4f.5d.6b, | 1b.2f.3e.4f.5d.6c, | 1b.2f.3e.4f.5d.6d, |
| 1b.2f.3e.4f.5d.6e, | 1b.2f.3e.4f.5d.6f, | 1b.2f.3e.4f.5e.6a, | 1b.2f.3e.4f.5e.6b, | 1b.2f.3e.4f.5e.6c, |
| 1b.2f.3e.4f.5e.6d, | 1b.2f.3e.4f.5e.6e, | 1b.2f.3e.4f.5e.6f, | 1b.2f.3e.4f.5f.6a, | 1b.2f.3e.4f.5f.6b, |
| 1b.2f.3e.4f.5f.6c, | 1b.2f.3e.4f.5f.6d, | 1b.2f.3e.4f.5f.6e, | 1b.2f.3f.4a.5a.6a, |
| 1b.2f.3f.4a.5a.6b, | 1b.2f.3f.4a.5a.6c, | 1b.2f.3f.4a.5a.6d, | 1b.2f.3f.4a.5a.6e, | 1b.2f.3f.4a.5a.6f, |
| 1b.2f.3f.4a.5b.6a, | 1b.2f.3f.4a.5b.6b, | 1b.2f.3f.4a.5b.6c, | 1b.2f.3f.4a.5b.6d, | 1b.2f.3f.4a.5b.6e, |
| 1b.2f.3f.4a.5b.6f, | 1b.2f.3f.4a.5c.6a, | 1b.2f.3f.4a.5c.6b, | 1b.2f.3f.4a.5c.6c, | 1b.2f.3f.4a.5c.6d, |
| 1b.2f.3f.4a.5c.6e, | 1b.2f.3f.4a.5c.6f, | 1b.2f.3f.4a.5d.6a, | 1b.2f.3f.4a.5d.6b, | 1b.2f.3f.4a.5d.6c, |
| 1b.2f.3f.4a.5d.6d, | 1b.2f.3f.4a.5d.6e, | 1b.2f.3f.4a.5d.6f, | 1b.2f.3f.4a.5e.6a, | 1b.2f.3f.4a.5e.6b, |
| 1b.2f.3f.4a.5e.6c, | 1b.2f.3f.4a.5e.6d, | 1b.2f.3f.4a.5e.6e, | 1b.2f.3f.4a.5e.6f, | 1b.2f.3f.4a.5f.6a, |
| 1b.2f.3f.4a.5f.6b, | 1b.2f.3f.4a.5f.6c, | 1b.2f.3f.4a.5f.6d, | 1b.2f.3f.4a.5f.6e, | 1b.2f.3f.4a.5f.6f, |
| 1b.2f.3f.4b.5a.6a, | 1b.2f.3f.4b.5a.6b, | 1b.2f.3f.4b.5a.6c, | 1b.2f.3f.4b.5a.6d, | 1b.2f.3f.4b.5a.6e, |
| 1b.2f.3f.4b.5a.6f, | 1b.2f.3f.4b.5b.6a, | 1b.2f.3f.4b.5b.6b, | 1b.2f.3f.4b.5b.6c, | 1b.2f.3f.4b.5b.6d, |
| 1b.2f.3f.4b.5b.6e, | 1b.2f.3f.4b.5b.6f, | 1b.2f.3f.4b.5c.6a, | 1b.2f.3f.4b.5c.6b, | 1b.2f.3f.4b.5c.6c, |
| 1b.2f.3f.4b.5c.6d, | 1b.2f.3f.4b.5c.6e, | 1b.2f.3f.4b.5c.6f, | 1b.2f.3f.4b.5d.6a, | 1b.2f.3f.4b.5d.6b, |
| 1b.2f.3f.4b.5d.6c, | 1b.2f.3f.4b.5d.6d, | 1b.2f.3f.4b.5d.6e, | 1b.2f.3f.4b.5d.6f, | 1b.2f.3f.4b.5e.6a, |
| 1b.2f.3f.4b.5e.6b, | 1b.2f.3f.4b.5e.6c, | 1b.2f.3f.4b.5e.6d, | 1b.2f.3f.4b.5e.6e, | 1b.2f.3f.4b.5e.6f, |
| 1b.2f.3f.4b.5f.6a, | 1b.2f.3f.4b.5f.6b, | 1b.2f.3f.4b.5f.6c, | 1b.2f.3f.4b.5f.6d, | 1b.2f.3f.4b.5f.6e, |
| 1b.2f.3f.4b.5f.6f, | 1b.2f.3f.4c.5a.6a, | 1b.2f.3f.4c.5a.6b, | 1b.2f.3f.4c.5a.6c, | 1b.2f.3f.4c.5a.6d, |
| 1b.2f.3f.4c.5a.6e, | 1b.2f.3f.4c.5a.6f, | 1b.2f.3f.4c.5b.6a, | 1b.2f.3f.4c.5b.6b, | 1b.2f.3f.4c.5b.6c, |
| 1b.2f.3f.4c.5b.6d, | 1b.2f.3f.4c.5b.6e, | 1b.2f.3f.4c.5b.6f, | 1b.2f.3f.4c.5c.6a, | 1b.2f.3f.4c.5c.6b, |

TABLE 7-continued

List of Compounds of Formula (II)

| | | | | |
|---|---|---|---|---|
| 1b.2f.3f.4c.5c.6c, | 1b.2f.3f.4c.5c.6d, | 1b.2f.3f.4c.5c.6e, | 1b.2f.3f.4c.5c.6f, | 1b.2f.3f.4c.5d.6a, |
| 1b.2f.3f.4c.5d.6b, | 1b.2f.3f.4c.5d.6c, | 1b.2f.3f.4c.5d.6d, | 1b.2f.3f.4c.5d.6e, | 1b.2f.3f.4c.5d.6f, |
| 1b.2f.3f.4c.5e.6a, | 1b.2f.3f.4c.5e.6b, | 1b.2f.3f.4c.5e.6c, | 1b.2f.3f.4c.5e.6d, | 1b.2f.3f.4c.5e.6e, |
| 1b.2f.3f.4c.5e.6f, | 1b.2f.3f.4c.5f.6a, | 1b.2f.3f.4c.5f.6b, | 1b.2f.3f.4c.5f.6c, | 1b.2f.3f.4c.5f.6d, |
| 1b.2f.3f.4c.5f.6e, | 1b.2f.3f.4c.5f.6f, | 1b.2f.3f.4d.5a.6a, | 1b.2f.3f.4d.5a.6b, | 1b.2f.3f.4d.5a.6c, |
| 1b.2f.3f.4d.5a.6d, | 1b.2f.3f.4d.5a.6e, | 1b.2f.3f.4d.5a.6f, | 1b.2f.3f.4d.5b.6a, | 1b.2f.3f.4d.5b.6b, |
| 1b.2f.3f.4d.5b.6c, | 1b.2f.3f.4d.5b.6d, | 1b.2f.3f.4d.5b.6e, | 1b.2f.3f.4d.5b.6f, | 1b.2f.3f.4d.5c.6a, |
| 1b.2f.3f.4d.5c.6b, | 1b.2f.3f.4d.5c.6c, | 1b.2f.3f.4d.5c.6d, | 1b.2f.3f.4d.5c.6e, | 1b.2f.3f.4d.5c.6f, |
| 1b.2f.3f.4d.5d.6a, | 1b.2f.3f.4d.5d.6b, | 1b.2f.3f.4d.5d.6c, | 1b.2f.3f.4d.5d.6d, | |
| 1b.2f.3f.4d.5d.6e, | 1b.2f.3f.4d.5d.6f, | 1b.2f.3f.4d.5e.6a, | 1b.2f.3f.4d.5e.6b, | 1b.2f.3f.4d.5e.6c, |
| 1b.2f.3f.4d.5e.6d, | 1b.2f.3f.4d.5e.6e, | 1b.2f.3f.4d.5e.6f, | 1b.2f.3f.4d.5f.6a, | 1b.2f.3f.4d.5f.6b, |
| 1b.2f.3f.4d.5f.6c, | 1b.2f.3f.4d.5f.6d, | 1b.2f.3f.4d.5f.6e, | 1b.2f.3f.4d.5f.6f, | 1b.2f.3f.4e.5a.6a, |
| 1b.2f.3f.4e.5a.6b, | 1b.2f.3f.4e.5a.6c, | 1b.2f.3f.4e.5a.6d, | 1b.2f.3f.4e.5a.6e, | 1b.2f.3f.4e.5a.6f, |
| 1b.2f.3f.4e.5b.6a, | 1b.2f.3f.4e.5b.6b, | 1b.2f.3f.4e.5b.6c, | 1b.2f.3f.4e.5b.6d, | 1b.2f.3f.4e.5b.6e, |
| 1b.2f.3f.4e.5b.6f, | 1b.2f.3f.4e.5c.6a, | 1b.2f.3f.4e.5c.6b, | 1b.2f.3f.4e.5c.6c, | 1b.2f.3f.4e.5c.6d, |
| 1b.2f.3f.4e.5c.6e, | 1b.2f.3f.4e.5c.6f, | 1b.2f.3f.4e.5d.6a, | 1b.2f.3f.4e.5d.6b, | 1b.2f.3f.4e.5d.6c, |
| 1b.2f.3f.4e.5d.6d, | 1b.2f.3f.4e.5d.6e, | 1b.2f.3f.4e.5d.6f, | 1b.2f.3f.4e.5e.6a, | 1b.2f.3f.4e.5e.6b, |
| 1b.2f.3f.4e.5e.6c, | 1b.2f.3f.4e.5e.6d, | 1b.2f.3f.4e.5e.6e, | 1b.2f.3f.4e.5e.6f, | 1b.2f.3f.4e.5f.6a, |
| 1b.2f.3f.4e.5f.6b, | 1b.2f.3f.4e.5f.6c, | 1b.2f.3f.4e.5f.6d, | 1b.2f.3f.4e.5f.6e, | 1b.2f.3f.4e.5f.6f, |
| 1b.2f.3f.4f.5a.6a, | 1b.2f.3f.4f.5a.6b, | 1b.2f.3f.4f.5a.6c, | 1b.2f.3f.4f.5a.6d, | 1b.2f.3f.4f.5a.6e, |
| 1b.2f.3f.4f.5a.6f, | 1b.2f.3f.4f.5b.6a, | 1b.2f.3f.4f.5b.6b, | 1b.2f.3f.4f.5b.6c, | 1b.2f.3f.4f.5b.6d, |
| 1b.2f.3f.4f.5b.6e, | 1b.2f.3f.4f.5b.6f, | 1b.2f.3f.4f.5c.6a, | 1b.2f.3f.4f.5c.6b, | 1b.2f.3f.4f.5c.6c, |
| 1b.2f.3f.4f.5c.6d, | 1b.2f.3f.4f.5c.6e, | 1b.2f.3f.4f.5c.6f, | 1b.2f.3f.4f.5d.6a, | 1b.2f.3f.4f.5d.6b, |
| 1b.2f.3f.4f.5d.6c, | 1b.2f.3f.4f.5d.6d, | 1b.2f.3f.4f.5d.6e, | 1b.2f.3f.4f.5d.6f, | 1b.2f.3f.4f.5e.6a, |
| 1b.2f.3f.4f.5e.6b, | 1b.2f.3f.4f.5e.6c, | 1b.2f.3f.4f.5e.6d, | 1b.2f.3f.4f.5e.6e, | 1b.2f.3f.4f.5e.6f, |
| 1b.2f.3f.4f.5f.6a, | 1b.2f.3f.4f.5f.6b, | 1b.2f.3f.4f.5f.6c, | 1b.2f.3f.4f.5f.6d, | 1b.2f.3f.4f.5f.6e, |
| 1b.2f.3f.4f.5f.6f, | 1c.2a.3a.4a.5a.6a, | 1c.2a.3a.4a.5a.6b, | 1c.2a.3a.4a.5a.6c, | 1c.2a.3a.4a.5a.6d, |
| 1c.2a.3a.4a.5a.6e, | 1c.2a.3a.4a.5a.6f, | 1c.2a.3a.4a.5b.6a, | 1c.2a.3a.4a.5b.6b, | |
| 1c.2a.3a.4a.5b.6c, | 1c.2a.3a.4a.5b.6d, | 1c.2a.3a.4a.5b.6e, | 1c.2a.3a.4a.5b.6f, | |
| 1c.2a.3a.4a.5c.6a, | 1c.2a.3a.4a.5c.6b, | 1c.2a.3a.4a.5c.6c, | 1c.2a.3a.4a.5c.6d, | |
| 1c.2a.3a.4a.5c.6e, | 1c.2a.3a.4a.5c.6f, | 1c.2a.3a.4a.5d.6a, | 1c.2a.3a.4a.5d.6b, | |
| 1c.2a.3a.4a.5d.6c, | 1c.2a.3a.4a.5d.6d, | 1c.2a.3a.4a.5d.6e, | 1c.2a.3a.4a.5d.6f, | |
| 1c.2a.3a.4a.5e.6a, | 1c.2a.3a.4a.5e.6b, | 1c.2a.3a.4a.5e.6c, | 1c.2a.3a.4a.5e.6d, | |
| 1c.2a.3a.4a.5e.6e, | 1c.2a.3a.4a.5e.6f, | 1c.2a.3a.4a.5f.6a, | 1c.2a.3a.4a.5f.6b, | 1c.2a.3a.4a.5f.6c, |
| 1c.2a.3a.4a.5f.6d, | 1c.2a.3a.4a.5f.6e, | 1c.2a.3a.4a.5f.6f, | 1c.2a.3a.4b.5a.6a, | 1c.2a.3a.4b.5a.6b, |
| 1c.2a.3a.4b.5a.6c, | 1c.2a.3a.4b.5a.6d, | 1c.2a.3a.4b.5a.6e, | 1c.2a.3a.4b.5a.6f, | |
| 1c.2a.3a.4b.5b.6a, | 1c.2a.3a.4b.5b.6b, | 1c.2a.3a.4b.5b.6c, | 1c.2a.3a.4b.5b.6d, | |
| 1c.2a.3a.4b.5b.6e, | 1c.2a.3a.4b.5b.6f, | 1c.2a.3a.4b.5c.6a, | 1c.2a.3a.4b.5c.6b, | |
| 1c.2a.3a.4b.5c.6c, | 1c.2a.3a.4b.5c.6d, | 1c.2a.3a.4b.5c.6e, | 1c.2a.3a.4b.5c.6f, | |
| 1c.2a.3a.4b.5d.6a, | 1c.2a.3a.4b.5d.6b, | 1c.2a.3a.4b.5d.6c, | 1c.2a.3a.4b.5d.6d, | |
| 1c.2a.3a.4b.5d.6e, | 1c.2a.3a.4b.5d.6f, | 1c.2a.3a.4b.5e.6a, | 1c.2a.3a.4b.5e.6b, | |
| 1c.2a.3a.4b.5e.6c, | 1c.2a.3a.4b.5e.6d, | 1c.2a.3a.4b.5e.6e, | 1c.2a.3a.4b.5e.6f, | |
| 1c.2a.3a.4b.5f.6a, | 1c.2a.3a.4b.5f.6b, | 1c.2a.3a.4b.5f.6c, | 1c.2a.3a.4b.5f.6d, | 1c.2a.3a.4b.5f.6e, |
| 1c.2a.3a.4b.5f.6f, | 1c.2a.3a.4c.5a.6a, | 1c.2a.3a.4c.5a.6b, | 1c.2a.3a.4c.5a.6c, | 1c.2a.3a.4c.5a.6d, |
| 1c.2a.3a.4c.5a.6e, | 1c.2a.3a.4c.5a.6f, | 1c.2a.3a.4c.5b.6a, | 1c.2a.3a.4c.5b.6b, | |
| 1c.2a.3a.4c.5b.6c, | 1c.2a.3a.4c.5b.6d, | 1c.2a.3a.4c.5b.6e, | 1c.2a.3a.4c.5b.6f, | |
| 1c.2a.3a.4c.5c.6a, | 1c.2a.3a.4c.5c.6b, | 1c.2a.3a.4c.5c.6c, | 1c.2a.3a.4c.5c.6d, | 1c.2a.3a.4c.5c.6e, |
| 1c.2a.3a.4c.5c.6f, | 1c.2a.3a.4c.5d.6a, | 1c.2a.3a.4c.5d.6b, | 1c.2a.3a.4c.5d.6c, | |
| 1c.2a.3a.4c.5d.6d, | 1c.2a.3a.4c.5d.6e, | 1c.2a.3a.4c.5d.6f, | 1c.2a.3a.4c.5e.6a, | |
| 1c.2a.3a.4c.5e.6b, | 1c.2a.3a.4c.5e.6c, | 1c.2a.3a.4c.5e.6d, | 1c.2a.3a.4c.5e.6e, | 1c.2a.3a.4c.5e.6f, |
| 1c.2a.3a.4c.5f.6a, | 1c.2a.3a.4c.5f.6b, | 1c.2a.3a.4c.5f.6c, | 1c.2a.3a.4c.5f.6d, | 1c.2a.3a.4c.5f.6e, |
| 1c.2a.3a.4c.5f.6f, | 1c.2a.3a.4d.5a.6a, | 1c.2a.3a.4d.5a.6b, | 1c.2a.3a.4d.5a.6c, | |
| 1c.2a.3a.4d.5a.6d, | 1c.2a.3a.4d.5a.6e, | 1c.2a.3a.4d.5a.6f, | 1c.2a.3a.4d.5b.6a, | |
| 1c.2a.3a.4d.5b.6b, | 1c.2a.3a.4d.5b.6c, | 1c.2a.3a.4d.5b.6d, | 1c.2a.3a.4d.5b.6e, | |
| 1c.2a.3a.4d.5b.6f, | 1c.2a.3a.4d.5c.6a, | 1c.2a.3a.4d.5c.6b, | 1c.2a.3a.4d.5c.6c, | |
| 1c.2a.3a.4d.5c.6d, | 1c.2a.3a.4d.5c.6e, | 1c.2a.3a.4d.5c.6f, | 1c.2a.3a.4d.5d.6a, | |
| 1c.2a.3a.4d.5d.6b, | 1c.2a.3a.4d.5d.6c, | 1c.2a.3a.4d.5d.6d, | 1c.2a.3a.4d.5d.6e, | |
| 1c.2a.3a.4d.5d.6f, | 1c.2a.3a.4d.5e.6a, | 1c.2a.3a.4d.5e.6b, | 1c.2a.3a.4d.5e.6c, | |
| 1c.2a.3a.4d.5e.6d, | 1c.2a.3a.4d.5e.6e, | 1c.2a.3a.4d.5e.6f, | 1c.2a.3a.4d.5f.6a, | |
| 1c.2a.3a.4d.5f.6b, | 1c.2a.3a.4d.5f.6c, | 1c.2a.3a.4d.5f.6d, | 1c.2a.3a.4d.5f.6e, | 1c.2a.3a.4d.5f.6f, |
| 1c.2a.3a.4e.5a.6a, | 1c.2a.3a.4e.5a.6b, | 1c.2a.3a.4e.5a.6c, | 1c.2a.3a.4e.5a.6d, | |
| 1c.2a.3a.4e.5a.6e, | 1c.2a.3a.4e.5a.6f, | 1c.2a.3a.4e.5b.6a, | 1c.2a.3a.4e.5b.6b, | |
| 1c.2a.3a.4e.5b.6c, | 1c.2a.3a.4e.5b.6d, | 1c.2a.3a.4e.5b.6e, | 1c.2a.3a.4e.5b.6f, | |
| 1c.2a.3a.4e.5c.6a, | 1c.2a.3a.4e.5c.6b, | 1c.2a.3a.4e.5c.6c, | 1c.2a.3a.4e.5c.6d, | |
| 1c.2a.3a.4e.5c.6e, | 1c.2a.3a.4e.5c.6f, | 1c.2a.3a.4e.5d.6a, | 1c.2a.3a.4e.5d.6b, | |
| 1c.2a.3a.4e.5d.6c, | 1c.2a.3a.4e.5d.6d, | 1c.2a.3a.4e.5d.6e, | 1c.2a.3a.4e.5d.6f, | |
| 1c.2a.3a.4e.5e.6a, | 1c.2a.3a.4e.5e.6b, | 1c.2a.3a.4e.5e.6c, | 1c.2a.3a.4e.5e.6d, | |
| 1c.2a.3a.4e.5e.6e, | 1c.2a.3a.4e.5e.6f, | 1c.2a.3a.4e.5f.6a, | 1c.2a.3a.4e.5f.6b, | 1c.2a.3a.4e.5f.6c, |
| 1c.2a.3a.4e.5f.6d, | 1c.2a.3a.4e.5f.6e, | 1c.2a.3a.4e.5f.6f, | 1c.2a.3a.4f.5a.6a, | 1c.2a.3a.4f.5a.6b, |
| 1c.2a.3a.4f.5a.6c, | 1c.2a.3a.4f.5a.6d, | 1c.2a.3a.4f.5a.6e, | 1c.2a.3a.4f.5a.6f, | 1c.2a.3a.4f.5b.6a, |
| 1c.2a.3a.4f.5b.6b, | 1c.2a.3a.4f.5b.6c, | 1c.2a.3a.4f.5b.6d, | 1c.2a.3a.4f.5b.6e, | 1c.2a.3a.4f.5b.6f, |
| 1c.2a.3a.4f.5c.6a, | 1c.2a.3a.4f.5c.6b, | 1c.2a.3a.4f.5c.6c, | 1c.2a.3a.4f.5c.6d, | 1c.2a.3a.4f.5c.6e, |
| 1c.2a.3a.4f.5c.6f, | 1c.2a.3a.4f.5d.6a, | 1c.2a.3a.4f.5d.6b, | 1c.2a.3a.4f.5d.6c, | 1c.2a.3a.4f.5d.6d, |
| 1c.2a.3a.4f.5d.6e, | 1c.2a.3a.4f.5d.6f, | 1c.2a.3a.4f.5e.6a, | 1c.2a.3a.4f.5e.6b, | 1c.2a.3a.4f.5e.6c, |
| 1c.2a.3a.4f.5e.6d, | 1c.2a.3a.4f.5e.6e, | 1c.2a.3a.4f.5e.6f, | 1c.2a.3a.4f.5f.6a, | 1c.2a.3a.4f.5f.6b, |
| 1c.2a.3a.4f.5f.6c, | 1c.2a.3a.4f.5f.6d, | 1c.2a.3a.4f.5f.6e, | 1c.2a.3a.4f.5f.6f, | 1c.2a.3b.4a.5a.6a, |
| 1c.2a.3b.4a.5a.6b, | 1c.2a.3b.4a.5a.6c, | 1c.2a.3b.4a.5a.6d, | 1c.2a.3b.4a.5a.6e, | |
| 1c.2a.3b.4a.5a.6f, | 1c.2a.3b.4a.5b.6a, | 1c.2a.3b.4a.5b.6b, | 1c.2a.3b.4a.5b.6c, | |

TABLE 7-continued

List of Compounds of Formula (II)

| | | | |
|---|---|---|---|
| 1c.2a.3b.4a.5b.6d, | 1c.2a.3b.4a.5b.6e, | 1c.2a.3b.4a.5b.6f, | 1c.2a.3b.4a.5c.6a, |
| 1c.2a.3b.4a.5c.6b, | 1c.2a.3b.4a.5c.6c, | 1c.2a.3b.4a.5c.6d, | 1c.2a.3b.4a.5c.6e, |
| 1c.2a.3b.4a.5c.6f, | 1c.2a.3b.4a.5d.6a, | 1c.2a.3b.4a.5d.6b, | 1c.2a.3b.4a.5d.6c, |
| 1c.2a.3b.4a.5d.6d, | 1c.2a.3b.4a.5d.6e, | 1c.2a.3b.4a.5d.6f, | 1c.2a.3b.4a.5e.6a, |
| 1c.2a.3b.4a.5e.6b, | 1c.2a.3b.4a.5e.6c, | 1c.2a.3b.4a.5e.6d, | 1c.2a.3b.4a.5e.6e, |
| 1c.2a.3b.4a.5e.6f, | 1c.2a.3b.4a.5f.6a, | 1c.2a.3b.4a.5f.6b, | 1c.2a.3b.4a.5f.6c, | 1c.2a.3b.4a.5f.6d, |
| 1c.2a.3b.4a.5f.6e, | 1c.2a.3b.4a.5f.6f, | 1c.2a.3b.4b.5a.6a, | 1c.2a.3b.4b.5a.6b, |
| 1c.2a.3b.4b.5a.6c, | 1c.2a.3b.4b.5a.6d, | 1c.2a.3b.4b.5a.6e, | 1c.2a.3b.4b.5a.6f, |
| 1c.2a.3b.4b.5b.6a, | 1c.2a.3b.4b.5b.6b, | 1c.2a.3b.4b.5b.6c, | 1c.2a.3b.4b.5b.6d, |
| 1c.2a.3b.4b.5b.6e, | 1c.2a.3b.4b.5b.6f, | 1c.2a.3b.4b.5c.6a, | 1c.2a.3b.4b.5c.6b, |
| 1c.2a.3b.4b.5c.6c, | 1c.2a.3b.4b.5c.6d, | 1c.2a.3b.4b.5c.6e, | 1c.2a.3b.4b.5c.6f, |
| 1c.2a.3b.4b.5d.6a, | 1c.2a.3b.4b.5d.6b, | 1c.2a.3b.4b.5d.6c, | 1c.2a.3b.4b.5d.6d, |
| 1c.2a.3b.4b.5d.6e, | 1c.2a.3b.4b.5d.6f, | 1c.2a.3b.4b.5e.6a, | 1c.2a.3b.4b.5e.6b, |
| 1c.2a.3b.4b.5e.6c, | 1c.2a.3b.4b.5e.6d, | 1c.2a.3b.4b.5e.6e, | 1c.2a.3b.4b.5e.6f, |
| 1c.2a.3b.4b.5f.6a, | 1c.2a.3b.4b.5f.6b, | 1c.2a.3b.4b.5f.6c, | 1c.2a.3b.4b.5f.6d, |
| 1c.2a.3b.4b.5f.6e, | 1c.2a.3b.4b.5f.6f, | 1c.2a.3b.4c.5a.6a, | 1c.2a.3b.4c.5a.6b, |
| 1c.2a.3b.4c.5a.6c, | 1c.2a.3b.4c.5a.6d, | 1c.2a.3b.4c.5a.6e, | 1c.2a.3b.4c.5a.6f, |
| 1c.2a.3b.4c.5b.6a, | 1c.2a.3b.4c.5b.6b, | 1c.2a.3b.4c.5b.6c, | 1c.2a.3b.4c.5b.6d, |
| 1c.2a.3b.4c.5b.6e, | 1c.2a.3b.4c.5b.6f, | 1c.2a.3b.4c.5c.6a, | 1c.2a.3b.4c.5c.6b, |
| 1c.2a.3b.4c.5c.6c, | 1c.2a.3b.4c.5c.6d, | 1c.2a.3b.4c.5c.6e, | 1c.2a.3b.4c.5c.6f, |
| 1c.2a.3b.4c.5d.6a, | 1c.2a.3b.4c.5d.6b, | 1c.2a.3b.4c.5d.6c, | 1c.2a.3b.4c.5d.6d, |
| 1c.2a.3b.4c.5d.6e, | 1c.2a.3b.4c.5d.6f, | 1c.2a.3b.4c.5e.6a, | 1c.2a.3b.4c.5e.6b, |
| 1c.2a.3b.4c.5e.6c, | 1c.2a.3b.4c.5e.6d, | 1c.2a.3b.4c.5e.6e, | 1c.2a.3b.4c.5e.6f, | 1c.2a.3b.4c.5f.6a, |
| 1c.2a.3b.4c.5f.6b, | 1c.2a.3b.4c.5f.6c, | 1c.2a.3b.4c.5f.6d, | 1c.2a.3b.4c.5f.6e, | 1c.2a.3b.4c.5f.6f, |
| 1c.2a.3b.4d.5a.6a, | 1c.2a.3b.4d.5a.6b, | 1c.2a.3b.4d.5a.6c, | 1c.2a.3b.4d.5a.6d, |
| 1c.2a.3b.4d.5a.6e, | 1c.2a.3b.4d.5a.6f, | 1c.2a.3b.4d.5b.6a, | 1c.2a.3b.4d.5b.6b, |
| 1c.2a.3b.4d.5b.6c, | 1c.2a.3b.4d.5b.6d, | 1c.2a.3b.4d.5b.6e, | 1c.2a.3b.4d.5b.6f, |
| 1c.2a.3b.4d.5c.6a, | 1c.2a.3b.4d.5c.6b, | 1c.2a.3b.4d.5c.6c, | 1c.2a.3b.4d.5c.6d, |
| 1c.2a.3b.4d.5c.6e, | 1c.2a.3b.4d.5c.6f, | 1c.2a.3b.4d.5d.6a, | 1c.2a.3b.4d.5d.6b, |
| 1c.2a.3b.4d.5d.6c, | 1c.2a.3b.4d.5d.6d, | 1c.2a.3b.4d.5d.6e, | 1c.2a.3b.4d.5d.6f, |
| 1c.2a.3b.4d.5e.6a, | 1c.2a.3b.4d.5e.6b, | 1c.2a.3b.4d.5e.6c, | 1c.2a.3b.4d.5e.6d, |
| 1c.2a.3b.4d.5e.6e, | 1c.2a.3b.4d.5e.6f, | 1c.2a.3b.4d.5f.6a, | 1c.2a.3b.4d.5f.6b, |
| 1c.2a.3b.4d.5f.6c, | 1c.2a.3b.4d.5f.6d, | 1c.2a.3b.4d.5f.6e, | 1c.2a.3b.4d.5f.6f, |
| 1c.2a.3b.4e.5a.6a, | 1c.2a.3b.4e.5a.6b, | 1c.2a.3b.4e.5a.6c, | 1c.2a.3b.4e.5a.6d, |
| 1c.2a.3b.4e.5a.6e, | 1c.2a.3b.4e.5a.6f, | 1c.2a.3b.4e.5b.6a, | 1c.2a.3b.4e.5b.6b, |
| 1c.2a.3b.4e.5b.6c, | 1c.2a.3b.4e.5b.6d, | 1c.2a.3b.4e.5b.6e, | 1c.2a.3b.4e.5b.6f, |
| 1c.2a.3b.4e.5c.6a, | 1c.2a.3b.4e.5c.6b, | 1c.2a.3b.4e.5c.6c, | 1c.2a.3b.4e.5c.6d, |
| 1c.2a.3b.4e.5c.6e, | 1c.2a.3b.4e.5c.6f, | 1c.2a.3b.4e.5d.6a, | 1c.2a.3b.4e.5d.6b, |
| 1c.2a.3b.4e.5d.6c, | 1c.2a.3b.4e.5d.6d, | 1c.2a.3b.4e.5d.6e, | 1c.2a.3b.4e.5d.6f, |
| 1c.2a.3b.4e.5e.6a, | 1c.2a.3b.4e.5e.6b, | 1c.2a.3b.4e.5e.6c, | 1c.2a.3b.4e.5e.6d, |
| 1c.2a.3b.4e.5e.6e, | 1c.2a.3b.4e.5e.6f, | 1c.2a.3b.4e.5f.6a, | 1c.2a.3b.4e.5f.6b, | 1c.2a.3b.4e.5f.6c, |
| 1c.2a.3b.4e.5f.6d, | 1c.2a.3b.4e.5f.6e, | 1c.2a.3b.4e.5f.6f, | 1c.2a.3b.4f.5a.6a, | 1c.2a.3b.4f.5a.6b, |
| 1c.2a.3b.4f.5a.6c, | 1c.2a.3b.4f.5a.6d, | 1c.2a.3b.4f.5a.6e, | 1c.2a.3b.4f.5a.6f, | 1c.2a.3b.4f.5b.6a, |
| 1c.2a.3b.4f.5b.6b, | 1c.2a.3b.4f.5b.6c, | 1c.2a.3b.4f.5b.6d, | 1c.2a.3b.4f.5b.6e, | 1c.2a.3b.4f.5b.6f, |
| 1c.2a.3b.4f.5c.6a, | 1c.2a.3b.4f.5c.6b, | 1c.2a.3b.4f.5c.6c, | 1c.2a.3b.4f.5c.6d, | 1c.2a.3b.4f.5c.6e, |
| 1c.2a.3b.4f.5c.6f, | 1c.2a.3b.4f.5d.6a, | 1c.2a.3b.4f.5d.6b, | 1c.2a.3b.4f.5d.6c, |
| 1c.2a.3b.4f.5d.6d, | 1c.2a.3b.4f.5d.6e, | 1c.2a.3b.4f.5d.6f, | 1c.2a.3b.4f.5e.6a, |
| 1c.2a.3b.4f.5e.6b, | 1c.2a.3b.4f.5e.6c, | 1c.2a.3b.4f.5e.6d, | 1c.2a.3b.4f.5e.6e, | 1c.2a.3b.4f.5e.6f, |
| 1c.2a.3b.4f.5f.6a, | 1c.2a.3b.4f.5f.6b, | 1c.2a.3b.4f.5f.6c, | 1c.2a.3b.4f.5f.6d, | 1c.2a.3b.4f.5f.6e, |
| 1c.2a.3b.4f.5f.6f, | 1c.2a.3c.4a.5a.6a, | 1c.2a.3c.4a.5a.6b, | 1c.2a.3c.4a.5a.6c, | 1c.2a.3c.4a.5a.6d, |
| 1c.2a.3c.4a.5a.6e, | 1c.2a.3c.4a.5a.6f, | 1c.2a.3c.4a.5b.6a, | 1c.2a.3c.4a.5b.6b, |
| 1c.2a.3c.4a.5b.6c, | 1c.2a.3c.4a.5b.6d, | 1c.2a.3c.4a.5b.6e, | 1c.2a.3c.4a.5b.6f, |
| 1c.2a.3c.4a.5c.6a, | 1c.2a.3c.4a.5c.6b, | 1c.2a.3c.4a.5c.6c, | 1c.2a.3c.4a.5c.6d, | 1c.2a.3c.4a.5c.6e, |
| 1c.2a.3c.4a.5c.6f, | 1c.2a.3c.4a.5d.6a, | 1c.2a.3c.4a.5d.6b, | 1c.2a.3c.4a.5d.6c, |
| 1c.2a.3c.4a.5d.6d, | 1c.2a.3c.4a.5d.6e, | 1c.2a.3c.4a.5d.6f, | 1c.2a.3c.4a.5e.6a, |
| 1c.2a.3c.4a.5e.6b, | 1c.2a.3c.4a.5e.6c, | 1c.2a.3c.4a.5e.6d, | 1c.2a.3c.4a.5e.6e, | 1c.2a.3c.4a.5e.6f, |
| 1c.2a.3c.4a.5f.6a, | 1c.2a.3c.4a.5f.6b, | 1c.2a.3c.4a.5f.6c, | 1c.2a.3c.4a.5f.6d, | 1c.2a.3c.4a.5f.6e, |
| 1c.2a.3c.4a.5f.6f, | 1c.2a.3c.4b.5a.6a, | 1c.2a.3c.4b.5a.6b, | 1c.2a.3c.4b.5a.6c, |
| 1c.2a.3c.4b.5a.6d, | 1c.2a.3c.4b.5a.6e, | 1c.2a.3c.4b.5a.6f, | 1c.2a.3c.4b.5b.6a, |
| 1c.2a.3c.4b.5b.6b, | 1c.2a.3c.4b.5b.6c, | 1c.2a.3c.4b.5b.6d, | 1c.2a.3c.4b.5b.6e, |
| 1c.2a.3c.4b.5b.6f, | 1c.2a.3c.4b.5c.6a, | 1c.2a.3c.4b.5c.6b, | 1c.2a.3c.4b.5c.6c, |
| 1c.2a.3c.4b.5c.6d, | 1c.2a.3c.4b.5c.6e, | 1c.2a.3c.4b.5c.6f, | 1c.2a.3c.4b.5d.6a, |
| 1c.2a.3c.4b.5d.6b, | 1c.2a.3c.4b.5d.6c, | 1c.2a.3c.4b.5d.6d, | 1c.2a.3c.4b.5d.6e, |
| 1c.2a.3c.4b.5d.6f, | 1c.2a.3c.4b.5e.6a, | 1c.2a.3c.4b.5e.6b, | 1c.2a.3c.4b.5e.6c, |
| 1c.2a.3c.4b.5e.6d, | 1c.2a.3c.4b.5e.6e, | 1c.2a.3c.4b.5e.6f, | 1c.2a.3c.4b.5f.6a, | 1c.2a.3c.4b.5f.6b, |
| 1c.2a.3c.4b.5f.6c, | 1c.2a.3c.4b.5f.6d, | 1c.2a.3c.4b.5f.6e, | 1c.2a.3c.4b.5f.6f, | 1c.2a.3c.4c.5a.6a, |
| 1c.2a.3c.4c.5a.6b, | 1c.2a.3c.4c.5a.6c, | 1c.2a.3c.4c.5a.6d, | 1c.2a.3c.4c.5a.6e, | 1c.2a.3c.4c.5a.6f, |
| 1c.2a.3c.4c.5b.6a, | 1c.2a.3c.4c.5b.6b, | 1c.2a.3c.4c.5b.6c, | 1c.2a.3c.4c.5b.6d, |
| 1c.2a.3c.4c.5b.6e, | 1c.2a.3c.4c.5b.6f, | 1c.2a.3c.4c.5c.6a, | 1c.2a.3c.4c.5c.6b, | 1c.2a.3c.4c.5c.6c, |
| 1c.2a.3c.4c.5c.6d, | 1c.2a.3c.4c.5c.6e, | 1c.2a.3c.4c.5c.6f, | 1c.2a.3c.4c.5d.6a, | 1c.2a.3c.4c.5d.6b, |
| 1c.2a.3c.4c.5d.6c, | 1c.2a.3c.4c.5d.6d, | 1c.2a.3c.4c.5d.6e, | 1c.2a.3c.4c.5d.6f, |
| 1c.2a.3c.4c.5e.6a, | 1c.2a.3c.4c.5e.6b, | 1c.2a.3c.4c.5e.6c, | 1c.2a.3c.4c.5e.6d, | 1c.2a.3c.4c.5e.6e, |
| 1c.2a.3c.4c.5e.6f, | 1c.2a.3c.4c.5f.6a, | 1c.2a.3c.4c.5f.6b, | 1c.2a.3c.4c.5f.6c, | 1c.2a.3c.4c.5f.6d, |
| 1c.2a.3c.4c.5f.6e, | 1c.2a.3c.4c.5f.6f, | 1c.2a.3c.4d.5a.6a, | 1c.2a.3c.4d.5a.6b, | 1c.2a.3c.4d.5a.6c, |
| 1c.2a.3c.4d.5a.6d, | 1c.2a.3c.4d.5a.6e, | 1c.2a.3c.4d.5a.6f, | 1c.2a.3c.4d.5b.6a, |
| 1c.2a.3c.4d.5b.6b, | 1c.2a.3c.4d.5b.6c, | 1c.2a.3c.4d.5b.6d, | 1c.2a.3c.4d.5b.6e, |
| 1c.2a.3c.4d.5b.6f, | 1c.2a.3c.4d.5c.6a, | 1c.2a.3c.4d.5c.6b, | 1c.2a.3c.4d.5c.6c, |
| 1c.2a.3c.4d.5c.6d, | 1c.2a.3c.4d.5c.6e, | 1c.2a.3c.4d.5c.6f, | 1c.2a.3c.4d.5d.6a, |

TABLE 7-continued

List of Compounds of Formula (II)

| | | | | |
|---|---|---|---|---|
| 1c.2a.3c.4d.5d.6b, | 1c.2a.3c.4d.5d.6c, | 1c.2a.3c.4d.5d.6d, | 1c.2a.3c.4d.5d.6e, | |
| 1c.2a.3c.4d.5d.6f, | 1c.2a.3c.4d.5e.6a, | 1c.2a.3c.4d.5e.6b, | 1c.2a.3c.4d.5e.6c, | |
| 1c.2a.3c.4d.5e.6d, | 1c.2a.3c.4d.5e.6e, | 1c.2a.3c.4d.5e.6f, | 1c.2a.3c.4d.5f.6a, | |
| 1c.2a.3c.4d.5f.6b, | 1c.2a.3c.4d.5f.6c, | 1c.2a.3c.4d.5f.6d, | 1c.2a.3c.4d.5f.6e, | 1c.2a.3c.4d.5f.6f, |
| 1c.2a.3c.4e.5a.6a, | 1c.2a.3c.4e.5a.6b, | 1c.2a.3c.4e.5a.6c, | 1c.2a.3c.4e.5a.6d, | |
| 1c.2a.3c.4e.5a.6e, | 1c.2a.3c.4e.5a.6f, | 1c.2a.3c.4e.5b.6a, | 1c.2a.3c.4e.5b.6b, | 1c.2a.3c.4e.5b.6c, |
| 1c.2a.3c.4e.5b.6d, | 1c.2a.3c.4e.5b.6e, | 1c.2a.3c.4e.5b.6f, | 1c.2a.3c.4e.5c.6a, | 1c.2a.3c.4e.5c.6b, |
| 1c.2a.3c.4e.5c.6c, | 1c.2a.3c.4e.5c.6d, | 1c.2a.3c.4e.5c.6e, | 1c.2a.3c.4e.5c.6f, | 1c.2a.3c.4e.5d.6a, |
| 1c.2a.3c.4e.5d.6b, | 1c.2a.3c.4e.5d.6c, | 1c.2a.3c.4e.5d.6d, | 1c.2a.3c.4e.5d.6e, | |
| 1c.2a.3c.4e.5d.6f, | 1c.2a.3c.4e.5e.6a, | 1c.2a.3c.4e.5e.6b, | 1c.2a.3c.4e.5e.6c, | 1c.2a.3c.4e.5e.6d, |
| 1c.2a.3c.4e.5e.6e, | 1c.2a.3c.4e.5e.6f, | 1c.2a.3c.4e.5f.6a, | 1c.2a.3c.4e.5f.6b, | 1c.2a.3c.4e.5f.6c, |
| 1c.2a.3c.4e.5f.6d, | 1c.2a.3c.4e.5f.6e, | 1c.2a.3c.4e.5f.6f, | 1c.2a.3c.4f.5a.6a, | 1c.2a.3c.4f.5a.6b, |
| 1c.2a.3c.4f.5a.6c, | 1c.2a.3c.4f.5a.6d, | 1c.2a.3c.4f.5a.6e, | 1c.2a.3c.4f.5a.6f, | 1c.2a.3c.4f.5b.6a, |
| 1c.2a.3c.4f.5b.6b, | 1c.2a.3c.4f.5b.6c, | 1c.2a.3c.4f.5b.6d, | 1c.2a.3c.4f.5b.6e, | 1c.2a.3c.4f.5b.6f, |
| 1c.2a.3c.4f.5c.6a, | 1c.2a.3c.4f.5c.6b, | 1c.2a.3c.4f.5c.6c, | 1c.2a.3c.4f.5c.6d, | 1c.2a.3c.4f.5c.6e, |
| 1c.2a.3c.4f.5c.6f, | 1c.2a.3c.4f.5d.6a, | 1c.2a.3c.4f.5d.6b, | 1c.2a.3c.4f.5d.6c, | 1c.2a.3c.4f.5d.6d, |
| 1c.2a.3c.4f.5d.6e, | 1c.2a.3c.4f.5d.6f, | 1c.2a.3c.4f.5e.6a, | 1c.2a.3c.4f.5e.6b, | 1c.2a.3c.4f.5e.6c, |
| 1c.2a.3c.4f.5e.6d, | 1c.2a.3c.4f.5e.6e, | 1c.2a.3c.4f.5e.6f, | 1c.2a.3c.4f.5f.6a, | 1c.2a.3c.4f.5f.6b, |
| 1c.2a.3c.4f.5f.6c, | 1c.2a.3c.4f.5f.6d, | 1c.2a.3c.4f.5f.6e, | 1c.2a.3c.4f.5f.6f, | 1c.2a.3d.4a.5a.6a, |
| 1c.2a.3d.4a.5a.6b, | 1c.2a.3d.4a.5a.6c, | 1c.2a.3d.4a.5a.6d, | 1c.2a.3d.4a.5a.6e, | |
| 1c.2a.3d.4a.5a.6f, | 1c.2a.3d.4a.5b.6a, | 1c.2a.3d.4a.5b.6b, | 1c.2a.3d.4a.5b.6c, | |
| 1c.2a.3d.4a.5b.6d, | 1c.2a.3d.4a.5b.6e, | 1c.2a.3d.4a.5b.6f, | 1c.2a.3d.4a.5c.6a, | |
| 1c.2a.3d.4a.5c.6b, | 1c.2a.3d.4a.5c.6c, | 1c.2a.3d.4a.5c.6d, | 1c.2a.3d.4a.5c.6e, | |
| 1c.2a.3d.4a.5c.6f, | 1c.2a.3d.4a.5d.6a, | 1c.2a.3d.4a.5d.6b, | 1c.2a.3d.4a.5d.6c, | |
| 1c.2a.3d.4a.5d.6d, | 1c.2a.3d.4a.5d.6e, | 1c.2a.3d.4a.5d.6f, | 1c.2a.3d.4a.5e.6a, | |
| 1c.2a.3d.4a.5e.6b, | 1c.2a.3d.4a.5e.6c, | 1c.2a.3d.4a.5e.6d, | 1c.2a.3d.4a.5e.6e, | |
| 1c.2a.3d.4a.5e.6f, | 1c.2a.3d.4a.5f.6a, | 1c.2a.3d.4a.5f.6b, | 1c.2a.3d.4a.5f.6c, | |
| 1c.2a.3d.4a.5f.6d, | 1c.2a.3d.4a.5f.6e, | 1c.2a.3d.4a.5f.6f, | 1c.2a.3d.4b.5a.6a, | |
| 1c.2a.3d.4b.5a.6b, | 1c.2a.3d.4b.5a.6c, | 1c.2a.3d.4b.5a.6d, | 1c.2a.3d.4b.5a.6e, | |
| 1c.2a.3d.4b.5a.6f, | 1c.2a.3d.4b.5b.6a, | 1c.2a.3d.4b.5b.6b, | 1c.2a.3d.4b.5b.6c, | |
| 1c.2a.3d.4b.5b.6d, | 1c.2a.3d.4b.5b.6e, | 1c.2a.3d.4b.5b.6f, | 1c.2a.3d.4b.5c.6a, | |
| 1c.2a.3d.4b.5c.6b, | 1c.2a.3d.4b.5c.6c, | 1c.2a.3d.4b.5c.6d, | 1c.2a.3d.4b.5c.6e, | |
| 1c.2a.3d.4b.5c.6f, | 1c.2a.3d.4b.5d.6a, | 1c.2a.3d.4b.5d.6b, | 1c.2a.3d.4b.5d.6c, | |
| 1c.2a.3d.4b.5d.6d, | 1c.2a.3d.4b.5d.6e, | 1c.2a.3d.4b.5d.6f, | 1c.2a.3d.4b.5e.6a, | |
| 1c.2a.3d.4b.5e.6b, | 1c.2a.3d.4b.5e.6c, | 1c.2a.3d.4b.5e.6d, | 1c.2a.3d.4b.5e.6e, | |
| 1c.2a.3d.4b.5e.6f, | 1c.2a.3d.4b.5f.6a, | 1c.2a.3d.4b.5f.6b, | 1c.2a.3d.4b.5f.6c, | |
| 1c.2a.3d.4b.5f.6d, | 1c.2a.3d.4b.5f.6e, | 1c.2a.3d.4b.5f.6f, | 1c.2a.3d.4c.5a.6a, | |
| 1c.2a.3d.4c.5a.6b, | 1c.2a.3d.4c.5a.6c, | 1c.2a.3d.4c.5a.6d, | 1c.2a.3d.4c.5a.6e, | |
| 1c.2a.3d.4c.5a.6f, | 1c.2a.3d.4c.5b.6a, | 1c.2a.3d.4c.5b.6b, | 1c.2a.3d.4c.5b.6c, | |
| 1c.2a.3d.4c.5b.6d, | 1c.2a.3d.4c.5b.6e, | 1c.2a.3d.4c.5b.6f, | 1c.2a.3d.4c.5c.6a, | |
| 1c.2a.3d.4c.5c.6b, | 1c.2a.3d.4c.5c.6c, | 1c.2a.3d.4c.5c.6d, | 1c.2a.3d.4c.5c.6e, | |
| 1c.2a.3d.4c.5c.6f, | 1c.2a.3d.4c.5d.6a, | 1c.2a.3d.4c.5d.6b, | 1c.2a.3d.4c.5d.6c, | |
| 1c.2a.3d.4c.5d.6d, | 1c.2a.3d.4c.5d.6e, | 1c.2a.3d.4c.5d.6f, | 1c.2a.3d.4c.5e.6a, | |
| 1c.2a.3d.4c.5e.6b, | 1c.2a.3d.4c.5e.6c, | 1c.2a.3d.4c.5e.6d, | 1c.2a.3d.4c.5e.6e, | |
| 1c.2a.3d.4c.5e.6f, | 1c.2a.3d.4c.5f.6a, | 1c.2a.3d.4c.5f.6b, | 1c.2a.3d.4c.5f.6c, | 1c.2a.3d.4c.5f.6d, |
| 1c.2a.3d.4c.5f.6e, | 1c.2a.3d.4c.5f.6f, | 1c.2a.3d.4d.5a.6a, | 1c.2a.3d.4d.5a.6b, | |
| 1c.2a.3d.4d.5a.6c, | 1c.2a.3d.4d.5a.6d, | 1c.2a.3d.4d.5a.6e, | 1c.2a.3d.4d.5a.6f, | |
| 1c.2a.3d.4d.5b.6a, | 1c.2a.3d.4d.5b.6b, | 1c.2a.3d.4d.5b.6c, | 1c.2a.3d.4d.5b.6d, | |
| 1c.2a.3d.4d.5b.6e, | 1c.2a.3d.4d.5b.6f, | 1c.2a.3d.4d.5c.6a, | 1c.2a.3d.4d.5c.6b, | |
| 1c.2a.3d.4d.5c.6c, | 1c.2a.3d.4d.5c.6d, | 1c.2a.3d.4d.5c.6e, | 1c.2a.3d.4d.5c.6f, | |
| 1c.2a.3d.4d.5d.6a, | 1c.2a.3d.4d.5d.6b, | 1c.2a.3d.4d.5d.6c, | 1c.2a.3d.4d.5d.6d, | |
| 1c.2a.3d.4d.5d.6e, | 1c.2a.3d.4d.5d.6f, | 1c.2a.3d.4d.5e.6a, | 1c.2a.3d.4d.5e.6b, | |
| 1c.2a.3d.4d.5e.6c, | 1c.2a.3d.4d.5e.6d, | 1c.2a.3d.4d.5e.6e, | 1c.2a.3d.4d.5e.6f, | |
| 1c.2a.3d.4d.5f.6a, | 1c.2a.3d.4d.5f.6b, | 1c.2a.3d.4d.5f.6c, | 1c.2a.3d.4d.5f.6d, | |
| 1c.2a.3d.4d.5f.6e, | 1c.2a.3d.4d.5f.6f, | 1c.2a.3d.4e.5a.6a, | 1c.2a.3d.4e.5a.6b, | |
| 1c.2a.3d.4e.5a.6c, | 1c.2a.3d.4e.5a.6d, | 1c.2a.3d.4e.5a.6e, | 1c.2a.3d.4e.5a.6f, | |
| 1c.2a.3d.4e.5b.6a, | 1c.2a.3d.4e.5b.6b, | 1c.2a.3d.4e.5b.6c, | 1c.2a.3d.4e.5b.6d, | |
| 1c.2a.3d.4e.5b.6e, | 1c.2a.3d.4e.5b.6f, | 1c.2a.3d.4e.5c.6a, | 1c.2a.3d.4e.5c.6b, | |
| 1c.2a.3d.4e.5c.6c, | 1c.2a.3d.4e.5c.6d, | 1c.2a.3d.4e.5c.6e, | 1c.2a.3d.4e.5c.6f, | |
| 1c.2a.3d.4e.5d.6a, | 1c.2a.3d.4e.5d.6b, | 1c.2a.3d.4e.5d.6c, | 1c.2a.3d.4e.5d.6d, | |
| 1c.2a.3d.4e.5d.6e, | 1c.2a.3d.4e.5d.6f, | 1c.2a.3d.4e.5e.6a, | 1c.2a.3d.4e.5e.6b, | |
| 1c.2a.3d.4e.5e.6c, | 1c.2a.3d.4e.5e.6d, | 1c.2a.3d.4e.5e.6e, | 1c.2a.3d.4e.5e.6f, | |
| 1c.2a.3d.4e.5f.6a, | 1c.2a.3d.4e.5f.6b, | 1c.2a.3d.4e.5f.6c, | 1c.2a.3d.4e.5f.6d, | |
| 1c.2a.3d.4e.5f.6e, | 1c.2a.3d.4e.5f.6f, | 1c.2a.3d.4f.5a.6a, | 1c.2a.3d.4f.5a.6b, | 1c.2a.3d.4f.5a.6c, |
| 1c.2a.3d.4f.5a.6d, | 1c.2a.3d.4f.5a.6e, | 1c.2a.3d.4f.5a.6f, | 1c.2a.3d.4f.5b.6a, | |
| 1c.2a.3d.4f.5b.6b, | 1c.2a.3d.4f.5b.6c, | 1c.2a.3d.4f.5b.6d, | 1c.2a.3d.4f.5b.6e, | |
| 1c.2a.3d.4f.5b.6f, | 1c.2a.3d.4f.5c.6a, | 1c.2a.3d.4f.5c.6b, | 1c.2a.3d.4f.5c.6c, | 1c.2a.3d.4f.5c.6d, |
| 1c.2a.3d.4f.5c.6e, | 1c.2a.3d.4f.5c.6f, | 1c.2a.3d.4f.5d.6a, | 1c.2a.3d.4f.5d.6b, | |
| 1c.2a.3d.4f.5d.6c, | 1c.2a.3d.4f.5d.6d, | 1c.2a.3d.4f.5d.6e, | 1c.2a.3d.4f.5d.6f, | |
| 1c.2a.3d.4f.5e.6a, | 1c.2a.3d.4f.5e.6b, | 1c.2a.3d.4f.5e.6c, | 1c.2a.3d.4f.5e.6d, | |
| 1c.2a.3d.4f.5e.6e, | 1c.2a.3d.4f.5e.6f, | 1c.2a.3d.4f.5f.6a, | 1c.2a.3d.4f.5f.6b, | 1c.2a.3d.4f.5f.6c, |
| 1c.2a.3d.4f.5f.6d, | 1c.2a.3d.4f.5f.6e, | 1c.2a.3d.4f.5f.6f, | 1c.2a.3e.4a.5a.6a, | 1c.2a.3e.4a.5a.6b, |
| 1c.2a.3e.4a.5a.6c, | 1c.2a.3e.4a.5a.6d, | 1c.2a.3e.4a.5a.6e, | 1c.2a.3e.4a.5a.6f, | |
| 1c.2a.3e.4a.5b.6a, | 1c.2a.3e.4a.5b.6b, | 1c.2a.3e.4a.5b.6c, | 1c.2a.3e.4a.5b.6d, | |
| 1c.2a.3e.4a.5b.6e, | 1c.2a.3e.4a.5b.6f, | 1c.2a.3e.4a.5c.6a, | 1c.2a.3e.4a.5c.6b, | 1c.2a.3e.4a.5c.6c, |
| 1c.2a.3e.4a.5c.6d, | 1c.2a.3e.4a.5c.6e, | 1c.2a.3e.4a.5c.6f, | 1c.2a.3e.4a.5d.6a, | |
| 1c.2a.3e.4a.5d.6b, | 1c.2a.3e.4a.5d.6c, | 1c.2a.3e.4a.5d.6d, | 1c.2a.3e.4a.5d.6e, | |
| 1c.2a.3e.4a.5d.6f, | 1c.2a.3e.4a.5e.6a, | 1c.2a.3e.4a.5e.6b, | 1c.2a.3e.4a.5e.6c, | |

TABLE 7-continued

List of Compounds of Formula (II)

| | | | | |
|---|---|---|---|---|
| 1c.2a.3e.4a.5e.6d, | 1c.2a.3e.4a.5e.6e, | 1c.2a.3e.4a.5e.6f, | 1c.2a.3e.4a.5f.6a, | 1c.2a.3e.4a.5f.6b, |
| 1c.2a.3e.4a.5f.6c, | 1c.2a.3e.4a.5f.6d, | 1c.2a.3e.4a.5f.6e, | 1c.2a.3e.4a.5f.6f, | 1c.2a.3e.4b.5a.6a, |
| 1c.2a.3e.4b.5a.6b, | 1c.2a.3e.4b.5a.6c, | 1c.2a.3e.4b.5a.6d, | 1c.2a.3e.4b.5a.6e, | |
| 1c.2a.3e.4b.5a.6f, | 1c.2a.3e.4b.5b.6a, | 1c.2a.3e.4b.5b.6b, | 1c.2a.3e.4b.5b.6c, | |
| 1c.2a.3e.4b.5b.6d, | 1c.2a.3e.4b.5b.6e, | 1c.2a.3e.4b.5b.6f, | 1c.2a.3e.4b.5c.6a, | |
| 1c.2a.3e.4b.5c.6b, | 1c.2a.3e.4b.5c.6c, | 1c.2a.3e.4b.5c.6d, | 1c.2a.3e.4b.5c.6e, | |
| 1c.2a.3e.4b.5c.6f, | 1c.2a.3e.4b.5d.6a, | 1c.2a.3e.4b.5d.6b, | 1c.2a.3e.4b.5d.6c, | |
| 1c.2a.3e.4b.5d.6d, | 1c.2a.3e.4b.5d.6e, | 1c.2a.3e.4b.5d.6f, | 1c.2a.3e.4b.5e.6a, | |
| 1c.2a.3e.4b.5e.6b, | 1c.2a.3e.4b.5e.6c, | 1c.2a.3e.4b.5e.6d, | 1c.2a.3e.4b.5e.6e, | |
| 1c.2a.3e.4b.5e.6f, | 1c.2a.3e.4b.5f.6a, | 1c.2a.3e.4b.5f.6b, | 1c.2a.3e.4b.5f.6c, | 1c.2a.3e.4b.5f.6d, |
| 1c.2a.3e.4b.5f.6e, | 1c.2a.3e.4b.5f.6f, | 1c.2a.3e.4c.5a.6a, | 1c.2a.3e.4c.5a.6b, | 1c.2a.3e.4c.5a.6c, |
| 1c.2a.3e.4c.5a.6d, | 1c.2a.3e.4c.5a.6e, | 1c.2a.3e.4c.5a.6f, | 1c.2a.3e.4c.5b.6a, | |
| 1c.2a.3e.4c.5b.6b, | 1c.2a.3e.4c.5b.6c, | 1c.2a.3e.4c.5b.6d, | 1c.2a.3e.4c.5b.6e, | |
| 1c.2a.3e.4c.5b.6f, | 1c.2a.3e.4c.5c.6a, | 1c.2a.3e.4c.5c.6b, | 1c.2a.3e.4c.5c.6c, | 1c.2a.3e.4c.5c.6d, |
| 1c.2a.3e.4c.5c.6e, | 1c.2a.3e.4c.5c.6f, | 1c.2a.3e.4c.5d.6a, | 1c.2a.3e.4c.5d.6b, | 1c.2a.3e.4c.5d.6c, |
| 1c.2a.3e.4c.5d.6d, | 1c.2a.3e.4c.5d.6e, | 1c.2a.3e.4c.5d.6f, | 1c.2a.3e.4c.5e.6a, | |
| 1c.2a.3e.4c.5e.6b, | 1c.2a.3e.4c.5e.6c, | 1c.2a.3e.4c.5e.6d, | 1c.2a.3e.4c.5e.6e, | 1c.2a.3e.4c.5e.6f, |
| 1c.2a.3e.4c.5f.6a, | 1c.2a.3e.4c.5f.6b, | 1c.2a.3e.4c.5f.6c, | 1c.2a.3e.4c.5f.6d, | 1c.2a.3e.4c.5f.6e, |
| 1c.2a.3e.4c.5f.6f, | 1c.2a.3e.4d.5a.6a, | 1c.2a.3e.4d.5a.6b, | 1c.2a.3e.4d.5a.6c, | |
| 1c.2a.3e.4d.5a.6d, | 1c.2a.3e.4d.5a.6e, | 1c.2a.3e.4d.5a.6f, | 1c.2a.3e.4d.5b.6a, | |
| 1c.2a.3e.4d.5b.6b, | 1c.2a.3e.4d.5b.6c, | 1c.2a.3e.4d.5b.6d, | 1c.2a.3e.4d.5b.6e, | |
| 1c.2a.3e.4d.5b.6f, | 1c.2a.3e.4d.5c.6a, | 1c.2a.3e.4d.5c.6b, | 1c.2a.3e.4d.5c.6c, | |
| 1c.2a.3e.4d.5c.6d, | 1c.2a.3e.4d.5c.6e, | 1c.2a.3e.4d.5c.6f, | 1c.2a.3e.4d.5d.6a, | |
| 1c.2a.3e.4d.5d.6b, | 1c.2a.3e.4d.5d.6c, | 1c.2a.3e.4d.5d.6d, | 1c.2a.3e.4d.5d.6e, | |
| 1c.2a.3e.4d.5d.6f, | 1c.2a.3e.4d.5e.6a, | 1c.2a.3e.4d.5e.6b, | 1c.2a.3e.4d.5e.6c, | |
| 1c.2a.3e.4d.5e.6d, | 1c.2a.3e.4d.5e.6e, | 1c.2a.3e.4d.5e.6f, | 1c.2a.3e.4d.5f.6a, | |
| 1c.2a.3e.4d.5f.6b, | 1c.2a.3e.4d.5f.6c, | 1c.2a.3e.4d.5f.6d, | 1c.2a.3e.4d.5f.6e, | 1c.2a.3e.4d.5f.6f, |
| 1c.2a.3e.4e.5a.6a, | 1c.2a.3e.4e.5a.6b, | 1c.2a.3e.4e.5a.6c, | 1c.2a.3e.4e.5a.6d, | |
| 1c.2a.3e.4e.5a.6e, | 1c.2a.3e.4e.5a.6f, | 1c.2a.3e.4e.5b.6a, | 1c.2a.3e.4e.5b.6b, | |
| 1c.2a.3e.4e.5b.6c, | 1c.2a.3e.4e.5b.6d, | 1c.2a.3e.4e.5b.6e, | 1c.2a.3e.4e.5b.6f, | |
| 1c.2a.3e.4e.5c.6a, | 1c.2a.3e.4e.5c.6b, | 1c.2a.3e.4e.5c.6c, | 1c.2a.3e.4e.5c.6d, | 1c.2a.3e.4e.5c.6e, |
| 1c.2a.3e.4e.5c.6f, | 1c.2a.3e.4e.5d.6a, | 1c.2a.3e.4e.5d.6b, | 1c.2a.3e.4e.5d.6c, | |
| 1c.2a.3e.4e.5d.6d, | 1c.2a.3e.4e.5d.6e, | 1c.2a.3e.4e.5d.6f, | 1c.2a.3e.4e.5e.6a, | |
| 1c.2a.3e.4e.5e.6b, | 1c.2a.3e.4e.5e.6c, | 1c.2a.3e.4e.5e.6d, | 1c.2a.3e.4e.5e.6e, | 1c.2a.3e.4e.5e.6f, |
| 1c.2a.3e.4e.5f.6a, | 1c.2a.3e.4e.5f.6b, | 1c.2a.3e.4e.5f.6c, | 1c.2a.3e.4e.5f.6d, | 1c.2a.3e.4e.5f.6e, |
| 1c.2a.3e.4e.5f.6f, | 1c.2a.3e.4f.5a.6a, | 1c.2a.3e.4f.5a.6b, | 1c.2a.3e.4f.5a.6c, | 1c.2a.3e.4f.5a.6d, |
| 1c.2a.3e.4f.5a.6e, | 1c.2a.3e.4f.5a.6f, | 1c.2a.3e.4f.5b.6a, | 1c.2a.3e.4f.5b.6b, | 1c.2a.3e.4f.5b.6c, |
| 1c.2a.3e.4f.5b.6d, | 1c.2a.3e.4f.5b.6e, | 1c.2a.3e.4f.5b.6f, | 1c.2a.3e.4f.5c.6a, | 1c.2a.3e.4f.5c.6b, |
| 1c.2a.3e.4f.5c.6c, | 1c.2a.3e.4f.5c.6d, | 1c.2a.3e.4f.5c.6e, | 1c.2a.3e.4f.5c.6f, | 1c.2a.3e.4f.5d.6a, |
| 1c.2a.3e.4f.5d.6b, | 1c.2a.3e.4f.5d.6c, | 1c.2a.3e.4f.5d.6d, | 1c.2a.3e.4f.5d.6e, | 1c.2a.3e.4f.5d.6f, |
| 1c.2a.3e.4f.5e.6a, | 1c.2a.3e.4f.5e.6b, | 1c.2a.3e.4f.5e.6c, | 1c.2a.3e.4f.5e.6d, | 1c.2a.3e.4f.5e.6e, |
| 1c.2a.3e.4f.5e.6f, | 1c.2a.3e.4f.5f.6a, | 1c.2a.3e.4f.5f.6b, | 1c.2a.3e.4f.5f.6c, | 1c.2a.3e.4f.5f.6d, |
| 1c.2a.3e.4f.5f.6e, | 1c.2a.3e.4f.5f.6f, | 1c.2a.3f.4a.5a.6a, | 1c.2a.3f.4a.5a.6b, | 1c.2a.3f.4a.5a.6c, |
| 1c.2a.3f.4a.5a.6d, | 1c.2a.3f.4a.5a.6e, | 1c.2a.3f.4a.5a.6f, | 1c.2a.3f.4a.5b.6a, | 1c.2a.3f.4a.5b.6b, |
| 1c.2a.3f.4a.5b.6c, | 1c.2a.3f.4a.5b.6d, | 1c.2a.3f.4a.5b.6e, | 1c.2a.3f.4a.5b.6f, | 1c.2a.3f.4a.5c.6a, |
| 1c.2a.3f.4a.5c.6b, | 1c.2a.3f.4a.5c.6c, | 1c.2a.3f.4a.5c.6d, | 1c.2a.3f.4a.5c.6e, | 1c.2a.3f.4a.5c.6f, |
| 1c.2a.3f.4a.5d.6a, | 1c.2a.3f.4a.5d.6b, | 1c.2a.3f.4a.5d.6c, | 1c.2a.3f.4a.5d.6d, | |
| 1c.2a.3f.4a.5d.6e, | 1c.2a.3f.4a.5d.6f, | 1c.2a.3f.4a.5e.6a, | 1c.2a.3f.4a.5e.6b, | 1c.2a.3f.4a.5e.6c, |
| 1c.2a.3f.4a.5e.6d, | 1c.2a.3f.4a.5e.6e, | 1c.2a.3f.4a.5e.6f, | 1c.2a.3f.4a.5f.6a, | 1c.2a.3f.4a.5f.6b, |
| 1c.2a.3f.4a.5f.6c, | 1c.2a.3f.4a.5f.6d, | 1c.2a.3f.4a.5f.6e, | 1c.2a.3f.4a.5f.6f, | 1c.2a.3f.4b.5a.6a, |
| 1c.2a.3f.4b.5a.6b, | 1c.2a.3f.4b.5a.6c, | 1c.2a.3f.4b.5a.6d, | 1c.2a.3f.4b.5a.6e, | 1c.2a.3f.4b.5a.6f, |
| 1c.2a.3f.4b.5b.6a, | 1c.2a.3f.4b.5b.6b, | 1c.2a.3f.4b.5b.6c, | 1c.2a.3f.4b.5b.6d, | |
| 1c.2a.3f.4b.5b.6e, | 1c.2a.3f.4b.5b.6f, | 1c.2a.3f.4b.5c.6a, | 1c.2a.3f.4b.5c.6b, | 1c.2a.3f.4b.5c.6c, |
| 1c.2a.3f.4b.5c.6d, | 1c.2a.3f.4b.5c.6e, | 1c.2a.3f.4b.5c.6f, | 1c.2a.3f.4b.5d.6a, | 1c.2a.3f.4b.5d.6b, |
| 1c.2a.3f.4b.5d.6c, | 1c.2a.3f.4b.5d.6d, | 1c.2a.3f.4b.5d.6e, | 1c.2a.3f.4b.5d.6f, | |
| 1c.2a.3f.4b.5e.6a, | 1c.2a.3f.4b.5e.6b, | 1c.2a.3f.4b.5e.6c, | 1c.2a.3f.4b.5e.6d, | 1c.2a.3f.4b.5e.6e, |
| 1c.2a.3f.4b.5e.6f, | 1c.2a.3f.4b.5f.6a, | 1c.2a.3f.4b.5f.6b, | 1c.2a.3f.4b.5f.6c, | 1c.2a.3f.4b.5f.6d, |
| 1c.2a.3f.4b.5f.6e, | 1c.2a.3f.4b.5f.6f, | 1c.2a.3f.4c.5a.6a, | 1c.2a.3f.4c.5a.6b, | 1c.2a.3f.4c.5a.6c, |
| 1c.2a.3f.4c.5a.6d, | 1c.2a.3f.4c.5a.6e, | 1c.2a.3f.4c.5a.6f, | 1c.2a.3f.4c.5b.6a, | 1c.2a.3f.4c.5b.6b, |
| 1c.2a.3f.4c.5b.6c, | 1c.2a.3f.4c.5b.6d, | 1c.2a.3f.4c.5b.6e, | 1c.2a.3f.4c.5b.6f, | 1c.2a.3f.4c.5c.6a, |
| 1c.2a.3f.4c.5c.6b, | 1c.2a.3f.4c.5c.6c, | 1c.2a.3f.4c.5c.6d, | 1c.2a.3f.4c.5c.6e, | 1c.2a.3f.4c.5c.6f, |
| 1c.2a.3f.4c.5d.6a, | 1c.2a.3f.4c.5d.6b, | 1c.2a.3f.4c.5d.6c, | 1c.2a.3f.4c.5d.6d, | 1c.2a.3f.4c.5d.6e, |
| 1c.2a.3f.4c.5d.6f, | 1c.2a.3f.4c.5e.6a, | 1c.2a.3f.4c.5e.6b, | 1c.2a.3f.4c.5e.6c, | 1c.2a.3f.4c.5e.6d, |
| 1c.2a.3f.4c.5e.6e, | 1c.2a.3f.4c.5e.6f, | 1c.2a.3f.4c.5f.6a, | 1c.2a.3f.4c.5f.6b, | 1c.2a.3f.4c.5f.6c, |
| 1c.2a.3f.4c.5f.6d, | 1c.2a.3f.4c.5f.6e, | 1c.2a.3f.4c.5f.6f, | 1c.2a.3f.4d.5a.6a, | 1c.2a.3f.4d.5a.6b, |
| 1c.2a.3f.4d.5a.6c, | 1c.2a.3f.4d.5a.6d, | 1c.2a.3f.4d.5a.6e, | 1c.2a.3f.4d.5a.6f, | 1c.2a.3f.4d.5b.6a, |
| 1c.2a.3f.4d.5b.6b, | 1c.2a.3f.4d.5b.6c, | 1c.2a.3f.4d.5b.6d, | 1c.2a.3f.4d.5b.6e, | |
| 1c.2a.3f.4d.5b.6f, | 1c.2a.3f.4d.5c.6a, | 1c.2a.3f.4d.5c.6b, | 1c.2a.3f.4d.5c.6c, | 1c.2a.3f.4d.5c.6d, |
| 1c.2a.3f.4d.5c.6e, | 1c.2a.3f.4d.5c.6f, | 1c.2a.3f.4d.5d.6a, | 1c.2a.3f.4d.5d.6b, | |
| 1c.2a.3f.4d.5d.6c, | 1c.2a.3f.4d.5d.6d, | 1c.2a.3f.4d.5d.6e, | 1c.2a.3f.4d.5d.6f, | |
| 1c.2a.3f.4d.5e.6a, | 1c.2a.3f.4d.5e.6b, | 1c.2a.3f.4d.5e.6c, | 1c.2a.3l4.5e.6d, | |
| 1c.2a.3f.4d.5e.6e, | 1c.2a.3f.4d.5e.6f, | 1c.2a.3f.4d.5f.6a, | 1c.2a.3f.4d.5f.6b, | 1c.2a.3f.4d.5f.6c, |
| 1c.2a.3f.4d.5f.6d, | 1c.2a.3f.4d.5f.6e, | 1c.2a.3f.4d.5f.6f, | 1c.2a.3f.4e.5a.6a, | 1c.2a.3f.4e.5a.6b, |
| 1c.2a.3f.4e.5a.6c, | 1c.2a.3f.4e.5a.6d, | 1c.2a.3f.4e.5a.6e, | 1c.2a.3f.4e.5a.6f, | 1c.2a.3f.4e.5b.6a, |
| 1c.2a.3f.4e.5b.6b, | 1c.2a.3f.4e.5b.6c, | 1c.2a.3f.4e.5b.6d, | 1c.2a.3f.4e.5b.6e, | 1c.2a.3f.4e.5b.6f, |
| 1c.2a.3f.4e.5c.6a, | 1c.2a.3f.4e.5c.6b, | 1c.2a.3f.4e.5c.6c, | 1c.2a.3f.4e.5c.6d, | 1c.2a.3f.4e.5c.6e, |
| 1c.2a.3f.4e.5c.6f, | 1c.2a.3f.4e.5d.6a, | 1c.2a.3f.4e.5d.6b, | 1c.2a.3f.4e.5d.6c, | 1c.2a.3f.4e.5d.6d, |
| 1c.2a.3f.4e.5d.6e, | 1c.2a.3f.4e.5d.6f, | 1c.2a.3f.4e.5e.6a, | 1c.2a.3f.4e.5e.6b, | 1c.2a.3f.4e.5e.6c, |

TABLE 7-continued

List of Compounds of Formula (II)

| | | | | |
|---|---|---|---|---|
| 1c.2a.3f.4e.5e.6d, | 1c.2a.3f.4e.5e.6e, | 1c.2a.3f.4e.5e.6f, | 1c.2a.3f.4e.5f.6a, | 1c.2a.3f.4e.5f.6b, |
| 1c.2a.3f.4e.5f.6c, | 1c.2a.3f.4e.5f.6d, | 1c.2a.3f.4e.5f.6e, | 1c.2a.3f.4e.5f.6f, | 1c.2a.3f.4f.5a.6a, |
| 1c.2a.3f.4f.5a.6b, | 1c.2a.3f.4f.5a.6c, | 1c.2a.3f.4f.5a.6d, | 1c.2a.3f.4f.5a.6e, | 1,c.2a.3f.4f.5a.6f, |
| 1c.2a.3f.4f.5b.6a, | 1c.2a.3f.4f.5b.6b, | 1c.2a.3f.4f.5b.6c, | 1c.2a.3f.4f.5b.6d, | 1c.2a.3f.4f.5b.6e, |
| 1c.2a.3f.4f.5b.6f, | 1c.2a.3f.4f.5c.6a, | 1c.2a.3f.4f.5c.6b, | 1c.2a.3f.4f.5c.6c, | 1c.2a.3f.4f.5c.6d, |
| 1c.2a.3f.4f.5c.6e, | 1c.2a.3f.4f.5c.6f, | 1c.2a.3f.4f.5d.6a, | 1c.2a.3f.4f.5d.6b, | 1c.2a.3f.4f.5d.6c, |
| 1c.2a.3f.4f.5d.6d, | 1c.2a.3f.4f.5d.6e, | 1c.2a.3f.4f.5d.6f, | 1c.2a.3f.4f.5e.6a, | 1c.2a.3f.4f.5e.6b, |
| 1c.2a.3f.4f.5e.6c, | 1c.2a.3f.4f.5e.6d, | 1c.2a.3f.4f.5e.6e, | 1c.2a.3f.4f.5e.6f, | 1c.2a.3f.4f.5f.6a, |
| 1c.2a.3f.4f.5f.6b, | 1c.2a.3f.4f.5f.6c, | 1c.2a.3f.4f.5f.6d, | 1c.2a.3f.4f.5f.6e, | 1c.2a.3f.4f.5f.6f, |
| 1c.2b.3a.4a.5a.6a, | 1c.2b.3a.4a.5a.6b, | 1c.2b.3a.4a.5a.6c, | 1c.2b.3a.4a.5a.6d, | |
| 1c.2b.3a.4a.5a.6e, | 1c.2b.3a.4a.5a.6f, | 1c.2b.3a.4a.5b.6a, | 1c.2b.3a.4a.5b.6b, | |
| 1c.2b.3a.4a.5b.6c, | 1c.2b.3a.4a.5b.6d, | 1c.2b.3a.4a.5b.6e, | 1c.2b.3a.4a.5b.6f, | |
| 1c.2b.3a.4a.5c.6a, | 1c.2b.3a.4a.5c.6b, | 1c.2b.3a.4a.5c.6c, | 1c.2b.3a.4a.5c.6d, | |
| 1c.2b.3a.4a.5c.6e, | 1c.2b.3a.4a.5c.6f, | 1c.2b.3a.4a.5d.6a, | 1c.2b.3a.4a.5d.6b, | |
| 1c.2b.3a.4a.5d.6c, | 1c.2b.3a.4a.5d.6d, | 1c.2b.3a.4a.5d.6e, | 1c.2b.3a.4a.5d.6f, | |
| 1c.2b.3a.4a.5e.6a, | 1c.2b.3a.4a.5e.6b, | 1c.2b.3a.4a.5e.6c, | 1c.2b.3a.4a.5e.6d, | |
| 1c.2b.3a.4a.5e.6e, | 1c.2b.3a.4a.5e.6f, | 1c.2b.3a.4a.5f.6a, | 1c.2b.3a.4a.5f.6b, | 1c.2b.3a.4a.5f.6c, |
| 1c.2b.3a.4a.5f.6d, | 1c.2b.3a.4a.5f.6e, | 1c.2b.3a.4a.5f.6f, | 1c.2b.3a.4b.5a.6a, | |
| 1c.2b.3a.4b.5a.6b, | 1c.2b.3a.4b.5a.6c, | 1c.2b.3a.4b.5a.6d, | 1c.2b.3a.4b.5a.6e, | |
| 1c.2b.3a.4b.5a.6f, | 1c.2b.3a.4b.5b.6a, | 1c.2b.3a.4b.5b.6b, | 1c.2b.3a.4b.5b.6c, | |
| 1c.2b.3a.4b.5b.6d, | 1c.2b.3a.4b.5b.6e, | 1c.2b.3a.4b.5b.6f, | 1c.2b.3a.4b.5c.6a, | |
| 1c.2b.3a.4b.5c.6b, | 1c.2b.3a.4b.5c.6c, | 1c.2b.3a.4b.5c.6d, | 1c.2b.3a.4b.5c.6e, | |
| 1c.2b.3a.4b.5c.6f, | 1c.2b.3a.4b.5d.6a, | 1c.2b.3a.4b.5d.6b, | 1c.2b.3a.4b.5d.6c, | |
| 1c.2b.3a.4b.5d.6d, | 1c.2b.3a.4b.5d.6e, | 1c.2b.3a.4b.5d.6f, | 1c.2b.3a.4b.5e.6a, | |
| 1c.2b.3a.4b.5e.6b, | 1c.2b.3a.4b.5e.6c, | 1c.2b.3a.4b.5e.6d, | 1c.2b.3a.4b.5e.6e, | |
| 1c.2b.3a.4b.5e.6f, | 1c.2b.3a.4b.5f.6a, | 1c.2b.3a.4b.5f.6b, | 1c.2b.3a.4b.5f.6c, | |
| 1c.2b.3a.4b.5f.6d, | 1c.2b.3a.4b.5f.6e, | 1c.2b.3a.4b.5f.6f, | 1c.2b.3a.4c.5a.6a, | |
| 1c.2b.3a.4c.5a.6b, | 1c.2b.3a.4c.5a.6c, | 1c.2b.3a.4c.5a.6d, | 1c.2b.3a.4c.5a.6e, | |
| 1c.2b.3a.4c.5a.6f, | 1c.2b.3a.4c.5b.6a, | 1c.2b.3a.4c.5b.6b, | 1c.2b.3a.4c.5b.6c, | |
| 1c.2b.3a.4c.5b.6d, | 1c.2b.3a.4c.5b.6e, | 1c.2b.3a.4c.5b.6f, | 1c.2b.3a.4c.5c.6a, | |
| 1c.2b.3a.4c.5c.6b, | 1c.2b.3a.4c.5c.6c, | 1c.2b.3a.4c.5c.6d, | 1c.2b.3a.4c.5c.6e, | 1c.2b.3a.4c.5c.6f, |
| 1c.2b.3a.4c.5d.6a, | 1c.2b.3a.4c.5d.6b, | 1c.2b.3a.4c.5d.6c, | 1c.2b.3a.4c.5d.6d, | |
| 1c.2b.3a.4c.5d.6e, | 1c.2b.3a.4c.5d.6f, | 1c.2b.3a.4c.5e.6a, | 1c.2b.3a.4c.5e.6b, | |
| 1c.2b.3a.4c.5e.6c, | 1c.2b.3a.4c.5e.6d, | 1c.2b.3a.4c.5e.6e, | 1c.2b.3a.4c.5e.6f, | 1c.2b.3a.4c.5f.6a, |
| 1c.2b.3a.4c.5f.6b, | 1c.2b.3a.4c.5f.6c, | 1c.2b.3a.4c.5f.6d, | 1c.2b.3a.4c.5f.6e, | 1c.2b.3a.4c.5f.6f, |
| 1c.2b.3a.4d.5a.6a, | 1c.2b.3a.4d.5a.6b, | 1c.2b.3a.4d.5a.6c, | 1c.2b.3a.4d.5a.6d, | |
| 1c.2b.3a.4d.5a.6e, | 1c.2b.3a.4d.5a.6f, | 1c.2b.3a.4d.5b.6a, | 1c.2b.3a.4d.5b.6b, | |
| 1c.2b.3a.4d.5b.6c, | 1c.2b.3a.4d.5b.6d, | 1c.2b.3a.4d.5b.6e, | 1c.2b.3a.4d.5b.6f, | |
| 1c.2b.3a.4d.5c.6a, | 1c.2b.3a.4d.5c.6b, | 1c.2b.3a.4d.5c.6c, | 1c.2b.3a.4d.5c.6d, | |
| 1c.2b.3a.4d.5c.6e, | 1c.2b.3a.4d.5c.6f, | 1c.2b.3a.4d.5d.6a, | 1c.2b.3a.4d.5d.6b, | |
| 1c.2b.3a.4d.5d.6c, | 1c.2b.3a.4d.5d.6d, | 1c.2b.3a.4d.5d.6e, | 1c.2b.3a.4d.5d.6f, | |
| 1c.2b.3a.4d.5e.6a, | 1c.2b.3a.4d.5e.6b, | 1c.2b.3a.4d.5e.6c, | 1c.2b.3a.4d.5e.6d, | |
| 1c.2b.3a.4d.5e.6e, | 1c.2b.3a.4d.5e.6f, | 1c.2b.3a.4d.5f.6a, | 1c.2b.3a.4d.5f.6b, | |
| 1c.2b.3a.4d.5f.6c, | 1c.2b.3a.4d.5f.6d, | 1c.2b.3a.4d.5f.6e, | 1c.2b.3a.4d.5f.6f, | |
| 1c.2b.3a.4e.5a.6a, | 1c.2b.3a.4e.5a.6b, | 1c.2b.3a.4e.5a.6c, | 1c.2b.3a.4e.5a.6d, | |
| 1c.2b.3a.4e.5a.6e, | 1c.2b.3a.4e.5a.6f, | 1c.2b.3a.4e.5b.6a, | 1c.2b.3a.4e.5b.6b, | |
| 1c.2b.3a.4e.5b.6c, | 1c.2b.3a.4e.5b.6d, | 1c.2b.3a.4e.5b.6e, | 1c.2b.3a.4e.5b.6f, | |
| 1c.2b.3a.4e.5c.6a, | 1c.2b.3a.4e.5c.6b, | 1c.2b.3a.4e.5c.6c, | 1c.2b.3a.4e.5c.6d, | |
| 1c.2b.3a.4e.5c.6e, | 1c.2b.3a.4e.5c.6f, | 1c.2b.3a.4e.5d.6a, | 1c.2b.3a.4e.5d.6b, | |
| 1c.2b.3a.4e.5d.6c, | 1c.2b.3a.4e.5d.6d, | 1c.2b.3a.4e.5d.6e, | 1c.2b.3a.4e.5d.6f, | |
| 1c.2b.3a.4e.5e.6a, | 1c.2b.3a.4e.5e.6b, | 1c.2b.3a.4e.5e.6c, | 1c.2b.3a.4e.5e.6d, | |
| 1c.2b.3a.4e.5e.6e, | 1c.2b.3a.4e.5e.6f, | 1c.2b.3a.4e.5f.6a, | 1c.2b.3a.4e.5f.6b, | 1c.2b.3a.4e.5f.6c, |
| 1c.2b.3a.4e.5f.6d, | 1c.2b.3a.4e.5f.6e, | 1c.2b.3a.4e.5f.6f, | 1c.2b.3a.4f.5a.6a, | 1c.2b.3a.4f.5a.6b, |
| 1c.2b.3a.4f.5a.6c, | 1c.2b.3a.4f.5a.6d, | 1c.2b.3a.4f.5a.6e, | 1c.2b.3a.4f.5a.6f, | 1c.2b.3a.4f.5b.6a, |
| 1c.2b.3a.4f.5b.6b, | 1c.2b.3a.4f.5b.6c, | 1c.2b.3a.4f.5b.6d, | 1c.2b.3a.4f.5b.6e, | 1c.2b.3a.4f.5b.6f, |
| 1c.2b.3a.4f.5c.6a, | 1c.2b.3a.4f.5c.6b, | 1c.2b.3a.4f.5c.6c, | 1c.2b.3a.4f.5c.6d, | 1c.2b.3a.4f.5c.6e, |
| 1c.2b.3a.4f.5c.6f, | 1c.2b.3a.4f.5d.6a, | 1c.2b.3a.4f.5d.6b, | 1c.2b.3a.4f.5d.6c, | |
| 1c.2b.3a.4f.5d.6d, | 1c.2b.3a.4f.5d.6e, | 1c.2b.3a.4f.5d.6f, | 1c.2b.3a.4f.5e.6a, | |
| 1c.2b.3a.4f.5e.6b, | 1c.2b.3a.4f.5e.6c, | 1c.2b.3a.4f.5e.6d, | 1c.2b.3a.4f.5e.6e, | 1c.2b.3a.4f.5e.6f, |
| 1c.2b.3a.4f.5f.6a, | 1c.2b.3a.4f.5f.6b, | 1c.2b.3a.4f.5f.6c, | 1c.2b.3a.4f.5f.6d, | 1c.2b.3a.4f.5f.6e, |
| 1c.2b.3a.4f.5f.6f, | 1c.2b.3b.4a.5a.6a, | 1c.2b.3b.4a.5a.6b, | 1c.2b.3b.4a.5a.6c, | |
| 1c.2b.3b.4a.5a.6d, | 1c.2b.3b.4a.5a.6e, | 1c.2b.3b.4a.5a.6f, | 1c.2b.3b.4a.5b.6a, | |
| 1c.2b.3b.4a.5b.6b, | 1c.2b.3b.4a.5b.6c, | 1c.2b.3b.4a.5b.6d, | 1c.2b.3b.4a.5b.6e, | |
| 1c.2b.3b.4a.5b.6f, | 1c.2b.3b.4a.5c.6a, | 1c.2b.3b.4a.5c.6b, | 1c.2b.3b.4a.5c.6c, | |
| 1c.2b.3b.4a.5c.6d, | 1c.2b.3b.4a.5c.6e, | 1c.2b.3b.4a.5c.6f, | 1c.2b.3b.4a.5d.6a, | |
| 1c.2b.3b.4a.5d.6b, | 1c.2b.3b.4a.5d.6c, | 1c.2b.3b.4a.5d.6d, | 1c.2b.3b.4a.5d.6e, | |
| 1c.2b.3b.4a.5d.6f, | 1c.2b.3b.4a.5e.6a, | 1c.2b.3b.4a.5e.6b, | 1c.2b.3b.4a.5e.6c, | |
| 1c.2b.3b.4a.5e.6d, | 1c.2b.3b.4a.5e.6e, | 1c.2b.3b.4a.5e.6f, | 1c.2b.3b.4a.5f.6a, | |
| 1c.2b.3b.4a.5f.6b, | 1c.2b.3b.4a.5f.6c, | 1c.2b.3b.4a.5f.6d, | 1c.2b.3b.4a.5f.6e, | 1c.2b.3b.4a.5f.6f, |
| 1c.2b.3b.4b.5a.6a, | 1c.2b.3b.4b.5a.6b, | 1c.2b.3b.4b.5a.6c, | 1c.2b.3b.4b.5a.6d, | |
| 1c.2b.3b.4b.5a.6e, | 1c.2b.3b.4b.5a.6f, | 1c.2b.3b.4b.5b.6a, | 1c.2b.3b.4b.5b.6b, | |
| 1c.2b.3b.4b.5b.6c, | 1c.2b.3b.4b.5b.6d, | 1c.2b.3b.4b.5b.6e, | 1c.2b.3b.4b.5b.6f, | |
| 1c.2b.3b.4b.5c.6a, | 1c.2b.3b.4b.5c.6b, | 1c.2b.3b.4b.5c.6c, | 1c.2b.3b.4b.5c.6d, | |
| 1c.2b.3b.4b.5c.6e, | 1c.2b.3b.4b.5c.6f, | 1c.2b.3b.4b.5d.6a, | 1c.2b.3b.4b.5d.6b, | |
| 1c.2b.3b.4b.5d.6c, | 1c.2b.3b.4b.5d.6d, | 1c.2b.3b.4b.5d.6e, | 1c.2b.3b.4b.5d.6f, | |
| 1c.2b.3b.4b.5e.6a, | 1c.2b.3b.4b.5e.6b, | 1c.2b.3b.4b.5e.6c, | 1c.2b.3b.4b.5e.6d, | |
| 1c.2b.3b.4b.5e.6e, | 1c.2b.3b.4b.5e.6f, | 1c.2b.3b.4b.5f.6a, | 1c.2b.3b.4b.5f.6b, | |
| 1c.2b.3b.4b.5f.6c, | 1c.2b.3b.4b.5f.6d, | 1c.2b.3b.4b.5f.6e, | 1c.2b.3b.4b.5f.6f, | |

TABLE 7-continued

List of Compounds of Formula (II)

| | | | | |
|---|---|---|---|---|
| 1c.2b.3b.4c.5a.6a, | 1c.2b.3b.4c.5a.6b, | 1c.2b.3b.4c.5a.6c, | 1c.2b.3b.4c.5a.6d, | |
| 1c.2b.3b.4c.5a.6e, | 1c.2b.3b.4c.5a.6f, | 1c.2b.3b.4c.5b.6a, | 1c.2b.3b.4c.5b.6b, | |
| 1c.2b.3b.4c.5b.6c, | 1c.2b.3b.4c.5b.6d, | 1c.2b.3b.4c.5b.6e, | 1c.2b.3b.4c.5b.6f, | |
| 1c.2b.3b.4c.5c.6a, | 1c.2b.3b.4c.5c.6b, | 1c.2b.3b.4c.5c.6c, | 1c.2b.3b.4c.5c.6d, | |
| 1c.2b.3b.4c.5c.6e, | 1c.2b.3b.4c.5c.6f, | 1c.2b.3b.4c.5d.6a, | 1c.2b.3b.4c.5d.6b, | |
| 1c.2b.3b.4c.5d.6c, | 1c.2b.3b.4c.5d.6d, | 1c.2b.3b.4c.5d.6e, | 1c.2b.3b.4c.5d.6f, | |
| 1c.2b.3b.4c.5e.6a, | 1c.2b.3b.4c.5e.6b, | 1c.2b.3b.4c.5e.6c, | 1c.2b.3b.4c.5e.6d, | |
| 1c.2b.3b.4c.5e.6e, | 1c.2b.3b.4c.5e.6f, | 1c.2b.3b.4c.5f.6a, | 1c.2b.3b.4c.5f.6b, | 1c.2b.3b.4c.5f.6c, |
| 1c.2b.3b.4c.5f.6d, | 1c.2b.3b.4c.5f.6e, | 1c.2b.3b.4c.5f.6f, | 1c.2b.3b.4d.5a.6a, | |
| 1c.2b.3b.4d.5a.6b, | 1c.2b.3b.4d.5a.6c, | 1c.2b.3b.4d.5a.6d, | 1c.2b.3b.4d.5a.6e, | |
| 1c.2b.3b.4d.5a.6f, | 1c.2b.3b.4d.5b.6a, | 1c.2b.3b.4d.5b.6b, | 1c.2b.3b.4d.5b.6c, | |
| 1c.2b.3b.4d.5b.6d, | 1c.2b.3b.4d.5b.6e, | 1c.2b.3b.4d.5b.6f, | 1c.2b.3b.4d.5c.6a, | |
| 1c.2b.3b.4d.5c.6b, | 1c.2b.3b.4d.5c.6c, | 1c.2b.3b.4d.5c.6d, | 1c.2b.3b.4d.5c.6e, | |
| 1c.2b.3b.4d.5c.6f, | 1c.2b.3b.4d.5d.6a, | 1c.2b.3b.4d.5d.6b, | 1c.2b.3b.4d.5d.6c, | |
| 1c.2b.3b.4d.5d.6d, | 1c.2b.3b.4d.5d.6e, | 1c.2b.3b.4d.5d.6f, | 1c.2b.3b.4d.5e.6a, | |
| 1c.2b.3b.4d.5e.6b, | 1c.2b.3b.4d.5e.6c, | 1c.2b.3b.4d.5e.6d, | 1c.2b.3b.4d.5e.6e, | |
| 1c.2b.3b.4d.5e.6f, | 1c.2b.3b.4d.5f.6a, | 1c.2b.3b.4d.5f.6b, | 1c.2b.3b.4d.5f.6c, | |
| 1c.2b.3b.4d.5f.6d, | 1c.2b.3b.4d.5f.6e, | 1c.2b.3b.4d.5f.6f, | 1c.2b.3b.4e.5a.6a, | |
| 1c.2b.3b.4e.5a.6b, | 1c.2b.3b.4e.5a.6c, | 1c.2b.3b.4e.5a.6d, | 1c.2b.3b.4e.5a.6e, | |
| 1c.2b.3b.4e.5a.6f, | 1c.2b.3b.4e.5b.6a, | 1c.2b.3b.4e.5b.6b, | 1c.2b.3b.4e.5b.6c, | |
| 1c.2b.3b.4e.5b.6d, | 1c.2b.3b.4e.5b.6e, | 1c.2b.3b.4e.5b.6f, | 1c.2b.3b.4e.5c.6a, | |
| 1c.2b.3b.4e.5c.6b, | 1c.2b.3b.4e.5c.6c, | 1c.2b.3b.4e.5c.6d, | 1c.2b.3b.4e.5c.6e, | |
| 1c.2b.3b.4e.5c.6f, | 1c.2b.3b.4e.5d.6a, | 1c.2b.3b.4e.5d.6b, | 1c.2b.3b.4e.5d.6c, | |
| 1c.2b.3b.4e.5d.6d, | 1c.2b.3b.4e.5d.6e, | 1c.2b.3b.4e.5d.6f, | 1c.2b.3b.4e.5e.6a, | |
| 1c.2b.3b.4e.5e.6b, | 1c.2b.3b.4e.5e.6c, | 1c.2b.3b.4e.5e.6d, | 1c.2b.3b.4e.5e.6e, | |
| 1c.2b.3b.4e.5e.6f, | 1c.2b.3b.4e.5f.6a, | 1c.2b.3b.4e.5f.6b, | 1c.2b.3b.4e.5f.6c, | |
| 1c.2b.3b.4e.5f.6d, | 1c.2b.3b.4e.5f.6e, | 1c.2b.3b.4e.5f.6f, | 1c.2b.3b.4f.5a.6a, | 1c.2b.3b.4f.5a.6b, |
| 1c.2b.3b.4f.5a.6c, | 1c.2b.3b.4f.5a.6d, | 1c.2b.3b.4f.5a.6e, | 1c.2b.3b.4f.5a.6f, | 1c.2b.3b.4f.5b.6a, |
| 1c.2b.3b.4f.5b.6b, | 1c.2b.3b.4f.5b.6c, | 1c.2b.3b.4f.5b.6d, | 1c.2b.3b.4f.5b.6e, | |
| 1c.2b.3b.4f.5b.6f, | 1c.2b.3b.4f.5c.6a, | 1c.2b.3b.4f.5c.6b, | 1c.2b.3b.4f.5c.6c, | 1c.2b.3b.4f.5c.6d, |
| 1c.2b.3b.4f.5c.6e, | 1c.2b.3b.4f.5c.6f, | 1c.2b.3b.4f.5d.6a, | 1c.2b.3b.4f.5d.6b, | |
| 1c.2b.3b.4f.5d.6c, | 1c.2b.3b.4f.5d.6d, | 1c.2b.3b.4f.5d.6e, | 1c.2b.3b.4f.5d.6f, | |
| 1c.2b.3b.4f.5e.6a, | 1c.2b.3b.4f.5e.6b, | 1c.2b.3b.4f.5e.6c, | 1c.2b.3b.4f.5e.6d, | |
| 1c.2b.3b.4f.5e.6e, | 1c.2b.3b.4f.5e.6f, | 1c.2b.3b.4f.5f.6a, | 1c.2b.3b.4f.5f.6b, | 1c.2b.3b.4f.5f.6c, |
| 1c.2b.3b.4f.5f.6d, | 1c.2b.3b.4f.5f.6e, | 1c.2b.3b.4f.5f.6f, | 1c.2b.3c.4a.5a.6a, | 1c.2b.3c.4a.5a.6b, |
| 1c.2b.3c.4a.5a.6c, | 1c.2b.3c.4a.5a.6d, | 1c.2b.3c.4a.5a.6e, | 1c.2b.3c.4a.5a.6f, | |
| 1c.2b.3c.4a.5b.6a, | 1c.2b.3c.4a.5b.6b, | 1c.2b.3c.4a.5b.6c, | 1c.2b.3c.4a.5b.6d, | |
| 1c.2b.3c.4a.5b.6e, | 1c.2b.3c.4a.5b.6f, | 1c.2b.3c.4a.5c.6a, | 1c.2b.3c.4a.5c.6b, | |
| 1c.2b.3c.4a.5c.6c, | 1c.2b.3c.4a.5c.6d, | 1c.2b.3c.4a.5c.6e, | 1c.2b.3c.4a.5c.6f, | |
| 1c.2b.3c.4a.5d.6a, | 1c.2b.3c.4a.5d.6b, | 1c.2b.3c.4a.5d.6c, | 1c.2b.3c.4a.5d.6d, | |
| 1c.2b.3c.4a.5d.6e, | 1c.2b.3c.4a.5d.6f, | 1c.2b.3c.4a.5e.6a, | 1c.2b.3c.4a.5e.6b, | |
| 1c.2b.3c.4a.5e.6c, | 1c.2b.3c.4a.5e.6d, | 1c.2b.3c.4a.5e.6e, | 1c.2b.3c.4a.5e.6f, | 1c.2b.3c.4a.5f.6a, |
| 1c.2b.3c.4a.5f.6b, | 1c.2b.3c.4a.5f.6c, | 1c.2b.3c.4a.5f.6d, | 1c.2b.3c.4a.5f.6e, | 1c.2b.3c.4a.5f.6f, |
| 1c.2b.3c.4b.5a.6a, | 1c.2b.3c.4b.5a.6b, | 1c.2b.3c.4b.5a.6c, | 1c.2b.3c.4b.5a.6d, | |
| 1c.2b.3c.4b.5a.6e, | 1c.2b.3c.4b.5a.6f, | 1c.2b.3c.4b.5b.6a, | 1c.2b.3c.4b.5b.6b, | |
| 1c.2b.3c.4b.5b.6c, | 1c.2b.3c.4b.5b.6d, | 1c.2b.3c.4b.5b.6e, | 1c.2b.3c.4b.5b.6f, | |
| 1c.2b.3c.4b.5c.6a, | 1c.2b.3c.4b.5c.6b, | 1c.2b.3c.4b.5c.6c, | 1c.2b.3c.4b.5c.6d, | |
| 1c.2b.3c.4b.5c.6e, | 1c.2b.3c.4b.5c.6f, | 1c.2b.3c.4b.5d.6a, | 1c.2b.3c.4b.5d.6b, | |
| 1c.2b.3c.4b.5d.6c, | 1c.2b.3c.4b.5d.6d, | 1c.2b.3c.4b.5d.6e, | 1c.2b.3c.4b.5d.6f, | |
| 1c.2b.3c.4b.5e.6a, | 1c.2b.3c.4b.5e.6b, | 1c.2b.3c.4b.5e.6c, | 1c.2b.3c.4b.5e.6d, | |
| 1c.2b.3c.4b.5e.6e, | 1c.2b.3c.4b.5e.6f, | 1c.2b.3c.4b.5f.6a, | 1c.2b.3c.4b.5f.6b, | 1c.2b.3c.4b.5f.6c, |
| 1c.2b.3c.4b.5f.6d, | 1c.2b.3c.4b.5f.6e, | 1c.2b.3c.4b.5f.6f, | 1c.2b.3c.4c.5a.6a, | 1c.2b.3c.4c.5a.6b, |
| 1c.2b.3c.4c.5a.6c, | 1c.2b.3c.4c.5a.6d, | 1c.2b.3c.4c.5a.6e, | 1c.2b.3c.4c.5a.6f, | 1c.2b.3c.4c.5b.6a, |
| 1c.2b.3c.4c.5b.6b, | 1c.2b.3c.4c.5b.6c, | 1c.2b.3c.4c.5b.6d, | 1c.2b.3c.4c.5b.6e, | |
| 1c.2b.3c.4c.5b.6f, | 1c.2b.3c.4c.5c.6a, | 1c.2b.3c.4c.5c.6b, | 1c.2b.3c.4c.5c.6c, | 1c.2b.3c.4c.5c.6d, |
| 1c.2b.3c.4c.5c.6e, | 1c.2b.3c.4c.5c.6f, | 1c.2b.3c.4c.5d.6a, | 1c.2b.3c.4c.5d.6b, | |
| 1c.2b.3c.4c.5d.6c, | 1c.2b.3c.4c.5d.6d, | 1c.2b.3c.4c.5d.6e, | 1c.2b.3c.4c.5d.6f, | |
| 1c.2b.3c.4c.5e.6a, | 1c.2b.3c.4c.5e.6b, | 1c.2b.3c.4c.5e.6c, | 1c.2b.3c.4c.5e.6d, | |
| 1c.2b.3c.4c.5e.6e, | 1c.2b.3c.4c.5e.6f, | 1c.2b.3c.4c.5f.6a, | 1c.2b.3c.4c.5f.6b, | 1c.2b.3c.4c.5f.6c, |
| 1c.2b.3c.4c.5f.6d, | 1c.2b.3c.4c.5f.6e, | 1c.2b.3c.4c.5f.6f, | 1c.2b.3c.4d.5a.6a, | 1c.2b.3c.4d.5a.6b, |
| 1c.2b.3c.4d.5a.6c, | 1c.2b.3c.4d.5a.6d, | 1c.2b.3c.4d.5a.6e, | 1c.2b.3c.4d.5a.6f, | |
| 1c.2b.3c.4d.5b.6a, | 1c.2b.3c.4d.5b.6b, | 1c.2b.3c.4d.5b.6c, | 1c.2b.3c.4d.5b.6d, | |
| 1c.2b.3c.4d.5b.6e, | 1c.2b.3c.4d.5b.6f, | 1c.2b.3c.4d.5c.6a, | 1c.2b.3c.4d.5c.6b, | |
| 1c.2b.3c.4d.5c.6c, | 1c.2b.3c.4d.5c.6d, | 1c.2b.3c.4d.5c.6e, | 1c.2b.3c.4d.5c.6f, | |
| 1c.2b.3c.4d.5d.6a, | 1c.2b.3c.4d.5d.6b, | 1c.2b.3c.4d.5d.6c, | 1c.2b.3c.4d.5d.6d, | |
| 1c.2b.3c.4d.5d.6e, | 1c.2b.3c.4d.5d.6f, | 1c.2b.3c.4d.5e.6a, | 1c.2b.3c.4d.5e.6b, | |
| 1c.2b.3c.4d.5e.6c, | 1c.2b.3c.4d.5e.6d, | 1c.2b.3c.4d.5e.6e, | 1c.2b.3c.4d.5e.6f, | |
| 1c.2b.3c.4d.5f.6a, | 1c.2b.3c.4d.5f.6b, | 1c.2b.3c.4d.5f.6c, | 1c.2b.3c.4d.5f.6d, | |
| 1c.2b.3c.4d.5f.6e, | 1c.2b.3c.4d.5f.6f, | 1c.2b.3c.4e.5a.6a, | 1c.2b.3c.4e.5a.6b, | 1c.2b.3c.4e.5a.6c, |
| 1c.2b.3c.4e.5a.6d, | 1c.2b.3c.4e.5a.6e, | 1c.2b.3c.4e.5a.6f, | 1c.2b.3c.4e.5b.6a, | |
| 1c.2b.3c.4e.5b.6b, | 1c.2b.3c.4e.5b.6c, | 1c.2b.3c.4e.5b.6d, | 1c.2b.3c.4e.5b.6e, | |
| 1c.2b.3c.4e.5b.6f, | 1c.2b.3c.4e.5c.6a, | 1c.2b.3c.4e.5c.6b, | 1c.2b.3c.4e.5c.6c, | 1c.2b.3c.4e.5c.6d, |
| 1c.2b.3c.4e.5c.6e, | 1c.2b.3c.4e.5c.6f, | 1c.2b.3c.4e.5d.6a, | 1c.2b.3c.4e.5d.6b, | |
| 1c.2b.3c.4e.5d.6c, | 1c.2b.3c.4e.5d.6d, | 1c.2b.3c.4e.5d.6e, | 1c.2b.3c.4e.5d.6f, | |
| 1c.2b.3c.4e.5e.6a, | 1c.2b.3c.4e.5e.6b, | 1c.2b.3c.4e.5e.6c, | 1c.2b.3c.4e.5e.6d, | |
| 1c.2b.3c.4e.5e.6e, | 1c.2b.3c.4e.5e.6f, | 1c.2b.3c.4e.5f.6a, | 1c.2b.3c.4e.5f.6b, | 1c.2b.3c.4e.5f.6c, |
| 1c.2b.3c.4e.5f.6d, | 1c.2b.3c.4e.5f.6e, | 1c.2b.3c.4e.5f.6f, | 1c.2b.3c.4f.5a.6a, | 1c.2b.3c.4f.5a.6b, |
| 1c.2b.3c.4f.5a.6c, | 1c.2b.3c.4f.5a.6d, | 1c.2b.3c.4f.5a.6e, | 1c.2b.3c.4f.5a.6f, | 1c.2b.3c.4f.5b.6a, |

TABLE 7-continued

List of Compounds of Formula (II)

| | | | | |
|---|---|---|---|---|
| 1c.2b.3c.4f.5b.6b, | 1c.2b.3c.4f.5b.6c, | 1c.2b.3c.4f.5b.6d, | 1c.2b.3c.4f.5b.6e, | 1c.2b.3c.4f.5b.6f, |
| 1c.2b.3c.4f.5c.6a, | 1c.2b.3c.4f.5c.6b, | 1c.2b.3c.4f.5c.6c, | 1c.2b.3c.4f.5c.6d, | 1c.2b.3c.4f.5c.6e, |
| 1c.2b.3c.4f.5c.6f, | 1c.2b.3c.4f.5d.6a, | 1c.2b.3c.4f.5d.6b, | 1c.2b.3c.4f.5d.6c, | 1c.2b.3c.4f.5d.6d, |
| 1c.2b.3c.4f.5d.6e, | 1c.2b.3c.4f.5d.6f, | 1c.2b.3c.4f.5e.6a, | 1c.2b.3c.4f.5e.6b, | 1c.2b.3c.4f.5e.6c, |
| 1c.2b.3c.4f.5e.6d, | 1c.2b.3c.4f.5e.6e, | 1c.2b.3c.4f.5e.6f, | 1c.2b.3c.4f.5f.6a, | 1c.2b.3c.4f.5f.6b, |
| 1c.2b.3c.4f.5f.6c, | 1c.2b.3c.4f.5f.6d, | 1c.2b.3c.4f.5f.6e, | 1c.2b.3c.4f.5f.6f, | 1c.2b.3d.4a.5a.6a, |
| 1c.2b.3d.4a.5a.6b, | 1c.2b.3d.4a.5a.6c, | 1c.2b.3d.4a.5a.6d, | 1c.2b.3d.4a.5a.6e, | |
| 1c.2b.3d.4a.5a.6f, | 1c.2b.3d.4a.5b.6a, | 1c.2b.3d.4a.5b.6b, | 1c.2b.3d.4a.5b.6c, | |
| 1c.2b.3d.4a.5b.6d, | 1c.2b.3d.4a.5b.6e, | 1c.2b.3d.4a.5b.6f, | 1c.2b.3d.4a.5c.6a, | |
| 1c.2b.3d.4a.5c.6b, | 1c.2b.3d.4a.5c.6c, | 1c.2b.3d.4a.5c.6d, | 1c.2b.3d.4a.5c.6e, | |
| 1c.2b.3d.4a.5c.6f, | 1c.2b.3d.4a.5d.6a, | 1c.2b.3d.4a.5d.6b, | 1c.2b.3d.4a.5d.6c, | |
| 1c.2b.3d.4a.5d.6d, | 1c.2b.3d.4a.5d.6e, | 1c.2b.3d.4a.5d.6f, | 1c.2b.3d.4a.5e.6a, | |
| 1c.2b.3d.4a.5e.6b, | 1c.2b.3d.4a.5e.6c, | 1c.2b.3d.4a.5e.6d, | 1c.2b.3d.4a.5e.6e, | |
| 1c.2b.3d.4a.5e.6f, | 1c.2b.3d.4a.5f.6a, | 1c.2b.3d.4a.5f.6b, | 1c.2b.3d.4a.5f.6c, | |
| 1c.2b.3d.4a.5f.6d, | 1c.2b.3d.4a.5f.6e, | 1c.2b.3d.4a.5f.6f, | 1c.2b.3d.4b.5a.6a, | |
| 1c.2b.3d.4b.5a.6b, | 1c.2b.3d.4b.5a.6c, | 1c.2b.3d.4b.5a.6d, | 1c.2b.3d.4b.5a.6e, | |
| 1c.2b.3d.4b.5a.6f, | 1c.2b.3d.4b.5b.6a, | 1c.2b.3d.4b.5b.6b, | 1c.2b.3d.4b.5b.6c, | |
| 1c.2b.3d.4b.5b.6d, | 1c.2b.3d.4b.5b.6e, | 1c.2b.3d.4b.5b.6f, | 1c.2b.3d.4b.5c.6a, | |
| 1c.2b.3d.4b.5c.6b, | 1c.2b.3d.4b.5c.6c, | 1c.2b.3d.4b.5c.6d, | 1c.2b.3d.4b.5c.6e, | |
| 1c.2b.3d.4b.5c.6f, | 1c.2b.3d.4b.5d.6a, | 1c.2b.3d.4b.5d.6b, | 1c.2b.3d.4b.5d.6c, | |
| 1c.2b.3d.4b.5d.6d, | 1c.2b.3d.4b.5d.6e, | 1c.2b.3d.4b.5d.6f, | 1c.2b.3d.4b.5e.6a, | |
| 1c.2b.3d.4b.5e.6b, | 1c.2b.3d.4b.5e.6c, | 1c.2b.3d.4b.5e.6d, | 1c.2b.3d.4b.5e.6e, | |
| 1c.2b.3d.4b.5e.6f, | 1c.2b.3d.4b.5f.6a, | 1c.2b.3d.4b.5f.6b, | 1c.2b.3d.4b.5f.6c, | |
| 1c.2b.3d.4b.5f.6d, | 1c.2b.3d.4b.5f.6e, | 1c.2b.3d.4b.5f.6f, | 1c.2b.3d.4c.5a.6a, | |
| 1c.2b.3d.4c.5a.6b, | 1c.2b.3d.4c.5a.6c, | 1c.2b.3d.4c.5a.6d, | 1c.2b.3d.4c.5a.6e, | |
| 1c.2b.3d.4c.5a.6f, | 1c.2b.3d.4c.5b.6a, | 1c.2b.3d.4c.5b.6b, | 1c.2b.3d.4c.5b.6c, | |
| 1c.2b.3d.4c.5b.6d, | 1c.2b.3d.4c.5b.6e, | 1c.2b.3d.4c.5b.6f, | 1c.2b.3d.4c.5c.6a, | |
| 1c.2b.3d.4c.5c.6b, | 1c.2b.3d.4c.5c.6c, | 1c.2b.3d.4c.5c.6d, | 1c.2b.3d.4c.5c.6e, | |
| 1c.2b.3d.4c.5c.6f, | 1c.2b.3d.4c.5d.6a, | 1c.2b.3d.4c.5d.6b, | 1c.2b.3d.4c.5d.6c, | |
| 1c.2b.3d.4c.5d.6d, | 1c.2b.3d.4c.5d.6e, | 1c.2b.3d.4c.5d.6f, | 1c.2b.3d.4c.5e.6a, | |
| 1c.2b.3d.4c.5e.6b, | 1c.2b.3d.4c.5e.6c, | 1c.2b.3d.4c.5e.6d, | 1c.2b.3d.4c.5e.6e, | |
| 1c.2b.3d.4c.5e.6f, | 1c.2b.3d.4c.5f.6a, | 1c.2b.3d.4c.5f.6b, | 1c.2b.3d.4c.5f.6c, | |
| 1c.2b.3d.4c.5f.6d, | 1c.2b.3d.4c.5f.6e, | 1c.2b.3d.4c.5f.6f, | 1c.2b.3d.4d.5a.6a, | |
| 1c.2b.3d.4d.5a.6b, | 1c.2b.3d.4d.5a.6c, | 1c.2b.3d.4d.5a.6d, | 1c.2b.3d.4d.5a.6e, | |
| 1c.2b.3d.4d.5a.6f, | 1c.2b.3d.4d.5b.6a, | 1c.2b.3d.4d.5b.6b, | 1c.2b.3d.4d.5b.6c, | |
| 1c.2b.3d.4d.5b.6d, | 1c.2b.3d.4d.5b.6e, | 1c.2b.3d.4d.5b.6f, | 1c.2b.3d.4d.5c.6a, | |
| 1c.2b.3d.4d.5c.6b, | 1c.2b.3d.4d.5c.6c, | 1c.2b.3d.4d.5c.6d, | 1c.2b.3d.4d.5c.6e, | |
| 1c.2b.3d.4d.5c.6f, | 1c.2b.3d.4d.5d.6a, | 1c.2b.3d.4d.5d.6b, | 1c.2b.3d.4d.5d.6c, | |
| 1c.2b.3d.4d.5d.6d, | 1c.2b.3d.4d.5d.6e, | 1c.2b.3d.4d.5d.6f, | 1c.2b.3d.4d.5e.6a, | |
| 1c.2b.3d.4d.5e.6b, | 1c.2b.3d.4d.5e.6c, | 1c.2b.3d.4d.5e.6d, | 1c.2b.3d.4d.5e.6e, | |
| 1c.2b.3d.4d.5e.6f, | 1c.2b.3d.4d.5f.6a, | 1c.2b.3d.4d.5f.6b, | 1c.2b.3d.4d.5f.6c, | |
| 1c.2b.3d.4d.5f.6d, | 1c.2b.3d.4d.5f.6e, | 1c.2b.3d.4d.5f.6f, | 1c.2b.3d.4e.5a.6a, | |
| 1c.2b.3d.4e.5a.6b, | 1c.2b.3d.4e.5a.6c, | 1c.2b.3d.4e.5a.6d, | 1c.2b.3d.4e.5a.6e, | |
| 1c.2b.3d.4e.5a.6f, | 1c.2b.3d.4e.5b.6a, | 1c.2b.3d.4e.5b.6b, | 1c.2b.3d.4e.5b.6c, | |
| 1c.2b.3d.4e.5b.6d, | 1c.2b.3d.4e.5b.6e, | 1c.2b.3d.4e.5b.6f, | 1c.2b.3d.4e.5c.6a, | |
| 1c.2b.3d.4e.5c.6b, | 1c.2b.3d.4e.5c.6c, | 1c.2b.3d.4e.5c.6d, | 1c.2b.3d.4e.5c.6e, | |
| 1c.2b.3d.4e.5c.6f, | 1c.2b.3d.4e.5d.6a, | 1c.2b.3d.4e.5d.6b, | 1c.2b.3d.4e.5d.6c, | |
| 1c.2b.3d.4e.5d.6d, | 1c.2b.3d.4e.5d.6e, | 1c.2b.3d.4e.5d.6f, | 1c.2b.3d.4e.5e.6a, | |
| 1c.2b.3d.4e.5e.6b, | 1c.2b.3d.4e.5e.6c, | 1c.2b.3d.4e.5e.6d, | 1c.2b.3d.4e.5e.6e, | |
| 1c.2b.3d.4e.5e.6f, | 1c.2b.3d.4e.5f.6a, | 1c.2b.3d.4e.5f.6b, | 1c.2b.3d.4e.5f.6c, | |
| 1c.2b.3d.4e.5f.6d, | 1c.2b.3d.4e.5f.6e, | 1c.2b.3d.4e.5f.6f, | 1c.2b.3d.4f.5a.6a, | |
| 1c.2b.3d.4f.5a.6b, | 1c.2b.3d.4f.5a.6c, | 1c.2b.3d.4f.5a.6d, | 1c.2b.3d.4f.5a.6e, | |
| 1c.2b.3d.4f.5a.6f, | 1c.2b.3d.4f.5b.6a, | 1c.2b.3d.4f.5b.6b, | 1c.2b.3d.4f.5b.6c, | |
| 1c.2b.3d.4f.5b.6d, | 1c.2b.3d.4f.5b.6e, | 1c.2b.3d.4f.5b.6f, | 1c.2b.3d.4f.5c.6a, | |
| 1c.2b.3d.4f.5c.6b, | 1c.2b.3d.4f.5c.6c, | 1c.2b.3d.4f.5c.6d, | 1c.2b.3d.4f.5c.6e, | 1c.2b.3d.4f.5c.6f, |
| 1c.2b.3d.4f.5d.6a, | 1c.2b.3d.4f.5d.6b, | 1c.2b.3d.4f.5d.6c, | 1c.2b.3d.4f.5d.6d, | |
| 1c.2b.3d.4f.5d.6e, | 1c.2b.3d.4f.5d.6f, | 1c.2b.3d.4f.5e.6a, | 1c.2b.3d.4f.5e.6b, | |
| 1c.2b.3d.4f.5e.6c, | 1c.2b.3d.4f.5e.6d, | 1c.2b.3d.4f.5e.6e, | 1c.2b.3d.4f.5e.6f, | 1c.2b.3d.4f.5f.6a, |
| 1c.2b.3d.4f.5f.6b, | 1c.2b.3d.4f.5f.6c, | 1c.2b.3d.4f.5f.6d, | 1c.2b.3d.4f.5f.6e, | 1c.2b.3d.4f.5f.6f, |
| 1c.2b.3e.4a.5a.6a, | 1c.2b.3e.4a.5a.6b, | 1c.2b.3e.4a.5a.6c, | 1c.2b.3e.4a.5a.6d, | |
| 1c.2b.3e.4a.5a.6e, | 1c.2b.3e.4a.5a.6f, | 1c.2b.3e.4a.5b.6a, | 1c.2b.3e.4a.5b.6b, | |
| 1c.2b.3e.4a.5b.6c, | 1c.2b.3e.4a.5b.6d, | 1c.2b.3e.4a.5b.6e, | 1c.2b.3e.4a.5b.6f, | |
| 1c.2b.3e.4a.5c.6a, | 1c.2b.3e.4a.5c.6b, | 1c.2b.3e.4a.5c.6c, | 1c.2b.3e.4a.5c.6d, | |
| 1c.2b.3e.4a.5c.6e, | 1c.2b.3e.4a.5c.6f, | 1c.2b.3e.4a.5d.6a, | 1c.2b.3e.4a.5d.6b, | |
| 1c.2b.3e.4a.5d.6c, | 1c.2b.3e.4a.5d.6d, | 1c.2b.3e.4a.5d.6e, | 1c.2b.3e.4a.5d.6f, | |
| 1c.2b.3e.4a.5e.6a, | 1c.2b.3e.4a.5e.6b, | 1c.2b.3e.4a.5e.6c, | 1c.2b.3e.4a.5e.6d, | |
| 1c.2b.3e.4a.5e.6e, | 1c.2b.3e.4a.5e.6f, | 1c.2b.3e.4a.5f.6a, | 1c.2b.3e.4a.5f.6b, | 1c.2b.3e.4a.5f.6c, |
| 1c.2b.3e.4a.5f.6d, | 1c.2b.3e.4a.5f.6e, | 1c.2b.3e.4a.5f.6f, | 1c.2b.3e.4b.5a.6a, | |
| 1c.2b.3e.4b.5a.6b, | 1c.2b.3e.4b.5a.6c, | 1c.2b.3e.4b.5a.6d, | 1c.2b.3e.4b.5a.6e, | |
| 1c.2b.3e.4b.5a.6f, | 1c.2b.3e.4b.5b.6a, | 1c.2b.3e.4b.5b.6b, | 1c.2b.3e.4b.5b.6c, | |
| 1c.2b.3e.4b.5b.6d, | 1c.2b.3e.4b.5b.6e, | 1c.2b.3e.4b.5b.6f, | 1c.2b.3e.4b.5c.6a, | |
| 1c.2b.3e.4b.5c.6b, | 1c.2b.3e.4b.5c.6c, | 1c.2b.3e.4b.5c.6d, | 1c.2b.3e.4b.5c.6e, | |
| 1c.2b.3e.4b.5c.6f, | 1c.2b.3e.4b.5d.6a, | 1c.2b.3e.4b.5d.6b, | 1c.2b.3e.4b.5d.6c, | |
| 1c.2b.3e.4b.5d.6d, | 1c.2b.3e.4b.5d.6e, | 1c.2b.3e.4b.5d.6f, | 1c.2b.3e.4b.5e.6a, | |
| 1c.2b.3e.4b.5e.6b, | 1c.2b.3e.4b.5e.6c, | 1c.2b.3e.4b.5e.6d, | 1c.2b.3e.4b.5e.6e, | |
| 1c.2b.3e.4b.5e.6f, | 1c.2b.3e.4b.5f.6a, | 1c.2b.3e.4b.5f.6b, | 1c.2b.3e.4b.5f.6c, | |
| 1c.2b.3e.4b.5f.6d, | 1c.2b.3e.4b.5f.6e, | 1c.2b.3e.4b.5f.6f, | 1c.2b.3e.4c.5a.6a, | |
| 1c.2b.3e.4c.5a.6b, | 1c.2b.3e.4c.5a.6c, | 1c.2b.3e.4c.5a.6d, | 1c.2b.3e.4c.5a.6e, | |

TABLE 7-continued

List of Compounds of Formula (II)

| | | | | |
|---|---|---|---|---|
| 1c.2b.3e.4c.5a.6f, | 1c.2b.3e.4c.5b.6a, | 1c.2b.3e.4c.5b.6b, | 1c.2b.3e.4c.5b.6c, | |
| 1c.2b.3e.4c.5b.6d, | 1c.2b.3e.4c.5b.6e, | 1c.2b.3e.4c.5b.6f, | 1c.2b.3e.4c.5c.6a, | |
| 1c.2b.3e.4c.5c.6b, | 1c.2b.3e.4c.5c.6c, | 1c.2b.3e.4c.5c.6d, | 1c.2b.3e.4c.5c.6e, | 1c.2b.3e.4c.5c.6f, |
| 1c.2b.3e.4c.5d.6a, | 1c.2b.3e.4c.5d.6b, | 1c.2b.3e.4c.5d.6c, | 1c.2b.3e.4c.5d.6d, | |
| 1c.2b.3e.4c.5d.6e, | 1c.2b.3e.4c.5d.6f, | 1c.2b.3e.4c.5e.6a, | 1c.2b.3e.4c.5e.6b, | |
| 1c.2b.3e.4c.5e.6c, | 1c.2b.3e.4c.5e.6d, | 1c.2b.3e.4c.5e.6e, | 1c.2b.3e.4c.5e.6f, | 1c.2b.3e.4c.5f.6a, |
| 1c.2b.3e.4c.5f.6b, | 1c.2b.3e.4c.5f.6c, | 1c.2b.3e.4c.5f.6d, | 1c.2b.3e.4c.5f.6e, | 1c.2b.3e.4c.5f.6f, |
| 1c.2b.3e.4d.5a.6a, | 1c.2b.3e.4d.5a.6b, | 1c.2b.3e.4d.5a.6c, | 1c.2b.3e.4d.5a.6d, | |
| 1c.2b.3e.4d.5a.6e, | 1c.2b.3e.4d.5a.6f, | 1c.2b.3e.4d.5b.6a, | 1c.2b.3e.4d.5b.6b, | |
| 1c.2b.3e.4d.5b.6c, | 1c.2b.3e.4d.5b.6d, | 1c.2b.3e.4d.5b.6e, | 1c.2b.3e.4d.5b.6f, | |
| 1c.2b.3e.4d.5c.6a, | 1c.2b.3e.4d.5c.6b, | 1c.2b.3e.4d.5c.6c, | 1c.2b.3e.4d.5c.6d, | |
| 1c.2b.3e.4d.5c.6e, | 1c.2b.3e.4d.5c.6f, | 1c.2b.3e.4d.5d.6a, | 1c.2b.3e.4d.5d.6b, | |
| 1c.2b.3e.4d.5d.6c, | 1c.2b.3e.4d.5d.6d, | 1c.2b.3e.4d.5d.6e, | 1c.2b.3e.4d.5d.6f, | |
| 1c.2b.3e.4d.5e.6a, | 1c.2b.3e.4d.5e.6b, | 1c.2b.3e.4d.5e.6c, | 1c.2b.3e.4d.5e.6d, | |
| 1c.2b.3e.4d.5e.6e, | 1c.2b.3e.4d.5e.6f, | 1c.2b.3e.4d.5f.6a, | 1c.2b.3e.4d.5f.6b, | |
| 1c.2b.3e.4d.5f.6c, | 1c.2b.3e.4d.5f.6d, | 1c.2b.3e.4d.5f.6e, | 1c.2b.3e.4d.5f.6f, | |
| 1c.2b.3e.4e.5a.6a, | 1c.2b.3e.4e.5a.6b, | 1c.2b.3e.4e.5a.6c, | 1c.2b.3e.4e.5a.6d, | |
| 1c.2b.3e.4e.5a.6e, | 1c.2b.3e.4e.5a.6f, | 1c.2b.3e.4e.5b.6a, | 1c.2b.3e.4e.5b.6b, | |
| 1c.2b.3e.4e.5b.6c, | 1c.2b.3e.4e.5b.6d, | 1c.2b.3e.4e.5b.6e, | 1c.2b.3e.4e.5b.6f, | |
| 1c.2b.3e.4e.5c.6a, | 1c.2b.3e.4e.5c.6b, | 1c.2b.3e.4e.5c.6c, | 1c.2b.3e.4e.5c.6d, | |
| 1c.2b.3e.4e.5c.6e, | 1c.2b.3e.4e.5c.6f, | 1c.2b.3e.4e.5d.6a, | 1c.2b.3e.4e.5d.6b, | |
| 1c.2b.3e.4e.5d.6c, | 1c.2b.3e.4e.5d.6d, | 1c.2b.3e.4e.5d.6e, | 1c.2b.3e.4e.5d.6f, | |
| 1c.2b.3e.4e.5e.6a, | 1c.2b.3e.4e.5e.6b, | 1c.2b.3e.4e.5e.6c, | 1c.2b.3e.4e.5e.6d, | |
| 1c.2b.3e.4e.5e.6e, | 1c.2b.3e.4e.5e.6f, | 1c.2b.3e.4e.5f.6a, | 1c.2b.3e.4e.5f.6b, | 1c.2b.3e.4e.5f.6c, |
| 1c.2b.3e.4e.5f.6d, | 1c.2b.3e.4e.5f.6e, | 1c.2b.3e.4e.5f.6f, | 1c.2b.3e.4f.5a.6a, | 1c.2b.3e.4f.5a.6b, |
| 1c.2b.3e.4f.5a.6c, | 1c.2b.3e.4f.5a.6d, | 1c.2b.3e.4f.5a.6e, | 1c.2b.3e.4f.5a.6f, | 1c.2b.3e.4f.5b.6a, |
| 1c.2b.3e.4f.5b.6b, | 1c.2b.3e.4f.5b.6c, | 1c.2b.3e.4f.5b.6d, | 1c.2b.3e.4f.5b.6e, | 1c.2b.3e.4f.5b.6f, |
| 1c.2b.3e.4f.5c.6a, | 1c.2b.3e.4f.5c.6b, | 1c.2b.3e.4f.5c.6c, | 1c.2b.3e.4f.5c.6d, | 1c.2b.3e.4f.5c.6e, |
| 1c.2b.3e.4f.5c.6f, | 1c.2b.3e.4f.5d.6a, | 1c.2b.3e.4f.5d.6b, | 1c.2b.3e.4f.5d.6c, | |
| 1c.2b.3e.4f.5d.6d, | 1c.2b.3e.4f.5d.6e, | 1c.2b.3e.4f.5d.6f, | 1c.2b.3e.4f.5e.6a, | 1c.2b.3e.4f.5e.6b, |
| 1c.2b.3e.4f.5e.6c, | 1c.2b.3e.4f.5e.6d, | 1c.2b.3e.4f.5e.6e, | 1c.2b.3e.4f.5e.6f, | 1c.2b.3e.4f.5f.6a, |
| 1c.2b.3e.4f.5f.6b, | 1c.2b.3e.4f.5f.6c, | 1c.2b.3e.4f.5f.6d, | 1c.2b.3e.4f.5f.6e, | 1c.2b.3e.4f.5f.6f, |
| 1c.2b.3f.4a.5a.6a, | 1c.2b.3f.4a.5a.6b, | 1c.2b.3f.4a.5a.6c, | 1c.2b.3f.4a.5a.6d, | 1c.2b.3f.4a.5a.6e, |
| 1c.2b.3f.4a.5a.6f, | 1c.2b.3f.4a.5b.6a, | 1c.2b.3f.4a.5b.6b, | 1c.2b.3f.4a.5b.6c, | 1c.2b.3f.4a.5b.6d, |
| 1c.2b.3f.4a.5b.6e, | 1c.2b.3f.4a.5b.6f, | 1c.2b.3f.4a.5c.6a, | 1c.2b.3f.4a.5c.6b, | 1c.2b.3f.4a.5c.6c, |
| 1c.2b.3f.4a.5c.6d, | 1c.2b.3f.4a.5c.6e, | 1c.2b.3f.4a.5c.6f, | 1c.2b.3f.4a.5d.6a, | 1c.2b.3f.4a.5d.6b, |
| 1c.2b.3f.4a.5d.6c, | 1c.2b.3f.4a.5d.6d, | 1c.2b.3f.4a.5d.6e, | 1c.2b.3f.4a.5d.6f, | |
| 1c.2b.3f.4a.5e.6a, | 1c.2b.3f.4a.5e.6b, | 1c.2b.3f.4a.5e.6c, | 1c.2b.3f.4a.5e.6d, | 1c.2b.3f.4a.5e.6e, |
| 1c.2b.3f.4a.5e.6f, | 1c.2b.3f.4a.5f.6a, | 1c.2b.3f.4a.5f.6b, | 1c.2b.3f.4a.5f.6c, | 1c.2b.3f.4a.5f.6d, |
| 1c.2b.3f.4a.5f.6e, | 1c.2b.3f.4a.5f.6f, | 1c.2b.3f.4b.5a.6a, | 1c.2b.3f.4b.5a.6b, | 1c.2b.3f.4b.5a.6c, |
| 1c.2b.3f.4b.5a.6d, | 1c.2b.3f.4b.5a.6e, | 1c.2b.3f.4b.5a.6f, | 1c.2b.3f.4b.5b.6a, | |
| 1c.2b.3f.4b.5b.6b, | 1c.2b.3f.4b.5b.6c, | 1c.2b.3f.4b.5b.6d, | 1c.2b.3f.4b.5b.6e, | |
| 1c.2b.3f.4b.5b.6f, | 1c.2b.3f.4b.5c.6a, | 1c.2b.3f.4b.5c.6b, | 1c.2b.3f.4b.5c.6c, | 1c.2b.3f.4b.5c.6d, |
| 1c.2b.3f.4b.5c.6e, | 1c.2b.3f.4b.5c.6f, | 1c.2b.3f.4b.5d.6a, | 1c.2b.3f.4b.5d.6b, | |
| 1c.2b.3f.4b.5d.6c, | 1c.2b.3f.4b.5d.6d, | 1c.2b.3f.4b.5d.6e, | 1c.2b.3f.4b.5d.6f, | |
| 1c.2b.3f.4b.5e.6a, | 1c.2b.3f.4b.5e.6b, | 1c.2b.3f.4b.5e.6c, | 1c.2b.3f.4b.5e.6d, | |
| 1c.2b.3f.4b.5e.6e, | 1c.2b.3f.4b.5e.6f, | 1c.2b.3f.4b.5f.6a, | 1c.2b.3f.4b.5f.6b, | 1c.2b.3f.4b.5f.6c, |
| 1c.2b.3f.4b.5f.6d, | 1c.2b.3f.4b.5f.6e, | 1c.2b.3f.4b.5f.6f, | 1c.2b.3f.4c.5a.6a, | 1c.2b.3f.4c.5a.6b, |
| 1c.2b.3f.4c.5a.6c, | 1c.2b.3f.4c.5a.6d, | 1c.2b.3f.4c.5a.6e, | 1c.2b.3f.4c.5a.6f, | 1c.2b.3f.4c.5b.6a, |
| 1c.2b.3f.4c.5b.6b, | 1c.2b.3f.4c.5b.6c, | 1c.2b.3f.4c.5b.6d, | 1c.2b.3f.4c.5b.6e, | 1c.2b.3f.4c.5b.6f, |
| 1c.2b.3f.4c.5c.6a, | 1c.2b.3f.4c.5c.6b, | 1c.2b.3f.4c.5c.6c, | 1c.2b.3f.4c.5c.6d, | 1c.2b.3f.4c.5c.6e, |
| 1c.2b.3f.4c.5c.6f, | 1c.2b.3f.4c.5d.6a, | 1c.2b.3f.4c.5d.6b, | 1c.2b.3f.4c.5d.6c, | 1c.2b.3f.4c.5d.6d, |
| 1c.2b.3f.4c.5d.6e, | 1c.2b.3f.4c.5d.6f, | 1c.2b.3f.4c.5e.6a, | 1c.2b.3f.4c.5e.6b, | 1c.2b.3f.4c.5e.6c, |
| 1c.2b.3f.4c.5e.6d, | 1c.2b.3f.4c.5e.6e, | 1c.2b.3f.4c.5e.6f, | 1c.2b.3f.4c.5f.6a, | 1c.2b.3f.4c.5f.6b, |
| 1c.2b.3f.4c.5f.6c, | 1c.2b.3f.4c.5f.6d, | 1c.2b.3f.4c.5f.6e, | 1c.2b.3f.4c.5f.6f, | 1c.2b.3f.4d.5a.6a, |
| 1c.2b.3f.4d.5a.6b, | 1c.2b.3f.4d.5a.6c, | 1c.2b.3f.4d.5a.6d, | 1c.2b.3f.4d.5a.6e, | |
| 1c.2b.3f.4d.5a.6f, | 1c.2b.3f.4d.5b.6a, | 1c.2b.3f.4d.5b.6b, | 1c.2b.3f.4d.5b.6c, | |
| 1c.2b.3f.4d.5b.6d, | 1c.2b.3f.4d.5b.6e, | 1c.2b.3f.4d.5b.6f, | 1c.2b.3f.4d.5c.6a, | |
| 1c.2b.3f.4d.5c.6b, | 1c.2b.3f.4d.5c.6c, | 1c.2b.3f.4d.5c.6d, | 1c.2b.3f.4d.5c.6e, | 1c.2b.3f.4d.5c.6f, |
| 1c.2b.3f.4d.5d.6a, | 1c.2b.3f.4d.5d.6b, | 1c.2b.3f.4d.5d.6c, | 1c.2b.3f.4d.5d.6d, | |
| 1c.2b.3f.4d.5d.6e, | 1c.2b.3f.4d.5d.6f, | 1c.2b.3f.4d.5e.6a, | 1c.2b.3f.4d.5e.6b, | |
| 1c.2b.3f.4d.5e.6c, | 1c.2b.3f.4d.5e.6d, | 1c.2b.3f.4d.5e.6e, | 1c.2b.3f.4d.5e.6f, | 1c.2b.3f.4d.5f.6a, |
| 1c.2b.3f.4d.5f.6b, | 1c.2b.3f.4d.5f.6c, | 1c.2b.3f.4d.5f.6d, | 1c.2b.3f.4d.5f.6e, | 1c.2b.3f.4d.5f.6f, |
| 1c.2b.3f.4e.5a.6a, | 1c.2b.3f.4e.5a.6b, | 1c.2b.3f.4e.5a.6c, | 1c.2b.3f.4e.5a.6d, | 1c.2b.3f.4e.5a.6e, |
| 1c.2b.3f.4e.5a.6f, | 1c.2b.3f.4e.5b.6a, | 1c.2b.3f.4e.5b.6b, | 1c.2b.3f.4e.5b.6c, | 1c.2b.3f.4e.5b.6d, |
| 1c.2b.3f.4e.5b.6e, | 1c.2b.3f.4e.5b.6f, | 1c.2b.3f.4e.5c.6a, | 1c.2b.3f.4e.5c.6b, | 1c.2b.3f.4e.5c.6c, |
| 1c.2b.3f.4e.5c.6d, | 1c.2b.3f.4e.5c.6e, | 1c.2b.3f.4e.5c.6f, | 1c.2b.3f.4e.5d.6a, | 1c.2b.3f.4e.5d.6b, |
| 1c.2b.3f.4e.5d.6c, | 1c.2b.3f.4e.5d.6d, | 1c.2b.3f.4e.5d.6e, | 1c.2b.3f.4e.5d.6f, | 1c.2b.3f.4e.5e.6a, |
| 1c.2b.3f.4e.5e.6b, | 1c.2b.3f.4e.5e.6c, | 1c.2b.3f.4e.5e.6d, | 1c.2b.3f.4e.5e.6e, | 1c.2b.3f.4e.5e.6f, |
| 1c.2b.3f.4e.5f.6a, | 1c.2b.3f.4e.5f.6b, | 1c.2b.3f.4e.5f.6c, | 1c.2b.3f.4e.5f.6d, | 1c.2b.3f.4e.5f.6e, |
| 1c.2b.3f.4e.5f.6f, | 1c.2b.3f.4f.5a.6a, | 1c.2b.3f.4f.5a.6b, | 1c.2b.3f.4f.5a.6c, | 1c.2b.3f.4f.5a.6d, |
| 1c.2b.3f.4f.5a.6e, | 1c.2b.3f.4f.5a.6f, | 1c.2b.3f.4f.5b.6a, | 1c.2b.3f.4f.5b.6b, | 1c.2b.3f.4f.5b.6c, |
| 1c.2b.3f.4f.5b.6d, | 1c.2b.3f.4f.5b.6e, | 1c.2b.3f.4f.5b.6f, | 1c.2b.3f.4f.5c.6a, | 1c.2b.3f.4f.5c.6b, |
| 1c.2b.3f.4f.5c.6c, | 1c.2b.3f.4f.5c.6d, | 1c.2b.3f.4f.5c.6e, | 1c.2b.3f.4f.5c.6f, | 1c.2b.3f.4f.5d.6a, |
| 1c.2b.3f.4f.5d.6b, | 1c.2b.3f.4f.5d.6c, | 1c.2b.3f.4f.5d.6d, | 1c.2b.3f.4f.5d.6e, | 1c.2b.3f.4f.5d.6f, |
| 1c.2b.3f.4f.5e.6a, | 1c.2b.3f.4f.5e.6b, | 1c.2b.3f.4f.5e.6c, | 1c.2b.3f.4f.5e.6d, | 1c.2b.3f.4f.5e.6e, |
| 1c.2b.3f.4f.5e.6f, | 1c.2b.3f.4f.5f.6a, | 1c.2b.3f.4f.5f.6b, | 1c.2b.3f.4f.5f.6c, | 1c.2b.3f.4f.5f.6d, |
| 1c.2b.3f.4f.5f.6e, | 1c.2b.3f.4f.5f.6f, | 1c.2c.3a.4a.5a.6a, | 1c.2c.3a.4a.5a.6b, | 1c.2c.3a.4a.5a.6c, |

TABLE 7-continued

List of Compounds of Formula (II)

| | | | |
|---|---|---|---|
| 1c.2c.3a.4a.5a.6d, | 1c.2c.3a.4a.5a.6e, | 1c.2c.3a.4a.5a.6f, | 1c.2c.3a.4a.5b.6a, |
| 1c.2c.3a.4a.5b.6b, | 1c.2c.3a.4a.5b.6c, | 1c.2c.3a.4a.5b.6d, | 1c.2c.3a.4a.5b.6e, |
| 1c.2c.3a.4a.5b.6f, | 1c.2c.3a.4a.5c.6a, | 1c.2c.3a.4a.5c.6b, | 1c.2c.3a.4a.5c.6c, | 1c.2c.3a.4a.5c.6d, |
| 1c.2c.3a.4a.5c.6e, | 1c.2c.3a.4a.5c.6f, | 1c.2c.3a.4a.5d.6a, | 1c.2c.3a.4a.5d.6b, |
| 1c.2c.3a.4a.5d.6c, | 1c.2c.3a.4a.5d.6d, | 1c.2c.3a.4a.5d.6e, | 1c.2c.3a.4a.5d.6f, |
| 1c.2c.3a.4a.5e.6a, | 1c.2c.3a.4a.5e.6b, | 1c.2c.3a.4a.5e.6c, | 1c.2c.3a.4a.5e.6d, |
| 1c.2c.3a.4a.5e.6e, | 1c.2c.3a.4a.5e.6f, | 1c.2c.3a.4a.5f.6a, | 1c.2c.3a.4a.5f.6b, | 1c.2c.3a.4a.5f.6c, |
| 1c.2c.3a.4a.5f.6d, | 1c.2c.3a.4a.5f.6e, | 1c.2c.3a.4a.5f.6f, | 1c.2c.3a.4b.5a.6a, | 1c.2c.3a.4b.5a.6b, |
| 1c.2c.3a.4b.5a.6c, | 1c.2c.3a.4b.5a.6d, | 1c.2c.3a.4b.5a.6e, | 1c.2c.3a.4b.5a.6f, |
| 1c.2c.3a.4b.5b.6a, | 1c.2c.3a.4b.5b.6b, | 1c.2c.3a.4b.5b.6c, | 1c.2c.3a.4b.5b.6d, |
| 1c.2c.3a.4b.5b.6e, | 1c.2c.3a.4b.5b.6f, | 1c.2c.3a.4b.5c.6a, | 1c.2c.3a.4b.5c.6b, |
| 1c.2c.3a.4b.5c.6c, | 1c.2c.3a.4b.5c.6d, | 1c.2c.3a.4b.5c.6e, | 1c.2c.3a.4b.5c.6f, |
| 1c.2c.3a.4b.5d.6a, | 1c.2c.3a.4b.5d.6b, | 1c.2c.3a.4b.5d.6c, | 1c.2c.3a.4b.5d.6d, |
| 1c.2c.3a.4b.5d.6e, | 1c.2c.3a.4b.5d.6f, | 1c.2c.3a.4b.5e.6a, | 1c.2c.3a.4b.5e.6b, |
| 1c.2c.3a.4b.5e.6c, | 1c.2c.3a.4b.5e.6e, | 1c.2c.3a.4b.5e.6f, | 1c.2c.3a.4b.5f.6a, |
| 1c.2c.3a.4b.5f.6b, | 1c.2c.3a.4b.5f.6c, | 1c.2c.3a.4b.5f.6d, | 1c.2c.3a.4b.5f.6e, | 1c.2c.3a.4b.5f.6f, |
| 1c.2c.3a.4c.5a.6a, | 1c.2c.3a.4c.5a.6b, | 1c.2c.3a.4c.5a.6c, | 1c.2c.3a.4c.5a.6d, | 1c.2c.3a.4c.5a.6e, |
| 1c.2c.3a.4c.5a.6f, | 1c.2c.3a.4c.5b.6a, | 1c.2c.3a.4c.5b.6b, | 1c.2c.3a.4c.5b.6c, | 1c.2c.3a.4c.5b.6d, |
| 1c.2c.3a.4c.5b.6e, | 1c.2c.3a.4c.5b.6f, | 1c.2c.3a.4c.5c.6a, | 1c.2c.3a.4c.5c.6b, | 1c.2c.3a.4c.5c.6c, |
| 1c.2c.3a.4c.5c.6d, | 1c.2c.3a.4c.5c.6e, | 1c.2c.3a.4c.5c.6f, | 1c.2c.3a.4c.5d.6a, | 1c.2c.3a.4c.5d.6b, |
| 1c.2c.3a.4c.5d.6c, | 1c.2c.3a.4c.5d.6d, | 1c.2c.3a.4c.5d.6e, | 1c.2c.3a.4c.5d.6f, |
| 1c.2c.3a.4c.5e.6a, | 1c.2c.3a.4c.5e.6b, | 1c.2c.3a.4c.5e.6c, | 1c.2c.3a.4c.5e.6d, | 1c.2c.3a.4c.5e.6e, |
| 1c.2c.3a.4c.5e.6f, | 1c.2c.3a.4c.5f.6a, | 1c.2c.3a.4c.5f.6b, | 1c.2c.3a.4c.5f.6c, | 1c.2c.3a.4c.5f.6d, |
| 1c.2c.3a.4c.5f.6e, | 1c.2c.3a.4c.5f.6f, | 1c.2c.3a.4d.5a.6a, | 1c.2c.3a.4d.5a.6b, | 1c.2c.3a.4d.5a.6c, |
| 1c.2c.3a.4d.5a.6d, | 1c.2c.3a.4d.5a.6e, | 1c.2c.3a.4d.5a.6f, | 1c.2c.3a.4d.5b.6a, |
| 1c.2c.3a.4d.5b.6b, | 1c.2c.3a.4d.5b.6c, | 1c.2c.3a.4d.5b.6d, | 1c.2c.3a.4d.5b.6e, |
| 1c.2c.3a.4d.5b.6f, | 1c.2c.3a.4d.5c.6a, | 1c.2c.3a.4d.5c.6b, | 1c.2c.3a.4d.5c.6c, |
| 1c.2c.3a.4d.5c.6d, | 1c.2c.3a.4d.5c.6e, | 1c.2c.3a.4d.5c.6f, | 1c.2c.3a.4d.5d.6a, |
| 1c.2c.3a.4d.5d.6b, | 1c.2c.3a.4d.5d.6c, | 1c.2c.3a.4d.5d.6d, | 1c.2c.3a.4d.5d.6e, |
| 1c.2c.3a.4d.5d.6f, | 1c.2c.3a.4d.5e.6a, | 1c.2c.3a.4d.5e.6b, | 1c.2c.3a.4d.5e.6c, |
| 1c.2c.3a.4d.5e.6d, | 1c.2c.3a.4d.5e.6e, | 1c.2c.3a.4d.5e.6f, | 1c.2c.3a.4d.5f.6a, |
| 1c.2c.3a.4d.5f.6b, | 1c.2c.3a.4d.5f.6c, | 1c.2c.3a.4d.5f.6d, | 1c.2c.3a.4d.5f.6e, | 1c.2c.3a.4d.5f.6f, |
| 1c.2c.3a.4e.5a.6a, | 1c.2c.3a.4e.5a.6b, | 1c.2c.3a.4e.5a.6c, | 1c.2c.3a.4e.5a.6d, |
| 1c.2c.3a.4e.5a.6e, | 1c.2c.3a.4e.5a.6f, | 1c.2C.3a.4e.5b.6a, | 1c.2c.3a.4e.5b.6b, | 1c.2c.3a.4e.5b.6c, |
| 1c.2c.3a.4e.5b.6d, | 1c.2c.3a.4e.5b.6e, | 1c.2c.3a.4e.5b.6f, | 1c.2c.3a.4e.5c.6a, | 1c.2c.3a.4e.5c.6b, |
| 1c.2c.3a.4e.5c.6c, | 1c.2c.3a.4e.5c.6d, | 1c.2c.3a.4e.5c.6e, | 1c.2c.3a.4e.5c.6f, | 1c.2c.3a.4e.5d.6a, |
| 1c.2c.3a.4e.5d.6b, | 1c.2c.3a.4e.5d.6c, | 1c.2c.3a.4e.5d.6d, | 1c.2c.3a.4e.5d.6e, |
| 1c.2c.3a.4e.5d.6f, | 1c.2c.3a.4e.5e.6a, | 1c.2c.3a.4e.5e.6b, | 1c.2c.3a.4e.5e.6c, | 1c.2c.3a.4e.5e.6d, |
| 1c.2c.3a.4e.5e.6e, | 1c.2c.3a.4e.5e.6f, | 1c.2c.3a.4e.5f.6a, | 1c.2c.3a.4e.5f.6b, | 1c.2c.3a.4e.5f.6c, |
| 1c.2c.3a.4e.5f.6d, | 1c.2c.3a.4e.5f.6e, | 1c.2c.3a.4e.5f.6f, | 1c.2c.3a.4f.5a.6a, | 1c.2c.3a.4f.5a.6b, |
| 1c.2c.3a.4f.5a.6c, | 1c.2c.3a.4f.5a.6d, | 1c.2c.3a.4f.5a.6e, | 1c.2c.3a.4f.5a.6f, | 1c.2c.3a.4f.5b.6a, |
| 1c.2c.3a.4f.5b.6b, | 1c.2c.3a.4f.5b.6c, | 1c.2c.3a.4f.5b.6d, | 1c.2c.3a.4f.5b.6e, | 1c.2c.3a.4f.5b.6f, |
| 1c.2c.3a.4f.5c.6a, | 1c.2c.3a.4f.5c.6b, | 1c.2c.3a.4f.5c.6c, | 1c.2c.3a.4f.5c.6d, | 1c.2c.3a.4f.5c.6e, |
| 1c.2c.3a.4f.5c.6f, | 1c.2c.3a.4f.5d.6a, | 1c.2c.3a.4f.5d.6b, | 1c.2c.3a.4f.5d.6c, | 1c.2c.3a.4f.5d.6d, |
| 1c.2c.3a.4f.5d.6e, | 1c.2c.3a.4f.5d.6f, | 1c.2c.3a.4f.5e.6a, | 1c.2c.3a.4f.5e.6b, | 1c.2c.3a.4f.5e.6c, |
| 1c.2c.3a.4f.5e.6d, | 1c.2c.3a.4f.5e.6e, | 1c.2c.3a.4f.5e.6f, | 1c.2c.3a.4f.5f.6a, | 1c.2c.3a.4f.5f.6b, |
| 1c.2c.3a.4f.5f.6c, | 1c.2c.3a.4f.5f.6d, | 1c.2c.3a.4f.5f.6e, | 1c.2c.3a.4f.5f.6f, | 1c.2c.3b.4a.5a.6a, |
| 1c.2c.3b.4a.5a.6b, | 1c.2c.3b.4a.5a.6c, | 1c.2c.3b.4a.5a.6d, | 1c.2c.3b.4a.5a.6e, |
| 1c.2c.3b.4a.5a.6f, | 1c.2c.3b.4a.5b.6a, | 1c.2c.3b.4a.5b.6b, | 1c.2c.3b.4a.5b.6c, |
| 1c.2c.3b.4a.5b.6d, | 1c.2c.3b.4a.5b.6e, | 1c.2c.3b.4a.5b.6f, | 1c.2c.3b.4a.5c.6a, |
| 1c.2c.3b.4a.5c.6b, | 1c.2c.3b.4a.5c.6c, | 1c.2c.3b.4a.5c.6d, | 1c.2c.3b.4a.5c.6e, | 1c.2c.3b.4a.5c.6f, |
| 1c.2c.3b.4a.5d.6a, | 1c.2c.3b.4a.5d.6b, | 1c.2c.3b.4a.5d.6c, | 1c.2c.3b.4a.5d.6d, |
| 1c.2c.3b.4a.5d.6e, | 1c.2c.3b.4a.5d.6f, | 1c.2c.3b.4a.5e.6a, | 1c.2c.3b.4a.5e.6b, |
| 1c.2c.3b.4a.5e.6c, | 1c.2c.3b.4a.5e.6d, | 1c.2c.3b.4a.5e.6e, | 1c.2c.3b.4a.5e.6f, | 1c.2c.3b.4a.5f.6a, |
| 1c.2c.3b.4a.5f.6b, | 1c.2c.3b.4a.5f.6c, | 1c.2c.3b.4a.5f.6d, | 1c.2c.3b.4a.5f.6e, | 1c.2c.3b.4a.5f.6f, |
| 1c.2c.3b.4b.5a.6a, | 1c.2c.3b.4b.5a.6b, | 1c.2c.3b.4b.5a.6c, | 1c.2c.3b.4b.5a.6d, |
| 1c.2c.3b.4b.5a.6e, | 1c.2c.3b.4b.5a.6f, | 1c.2c.3b.4b.5b.6a, | 1c.2c.3b.4b.5b.6b, |
| 1c.2c.3b.4b.5b.6c, | 1c.2c.3b.4b.5b.6d, | 1c.2c.3b.4b.5b.6e, | 1c.2c.3b.4b.5b.6f, |
| 1c.2c.3b.4b.5c.6a, | 1c.2c.3b.4b.5c.6b, | 1c.2c.3b.4b.5c.6c, | 1c.2c.3b.4b.5c.6d, |
| 1c.2c.3b.4b.5c.6e, | 1c.2c.3b.4b.5c.6f, | 1c.2c.3b.4b.5d.6a, | 1c.2c.3b.4b.5d.6b, |
| 1c.2c.3b.4b.5d.6c, | 1c.2c.3b.4b.5d.6d, | 1c.2c.3b.4b.5d.6e, | 1c.2c.3b.4b.5d.6f, |
| 1c.2c.3b.4b.5e.6a, | 1c.2c.3b.4b.5e.6b, | 1c.2c.3b.4b.5e.6c, | 1c.2c.3b.4b.5e.6d, |
| 1c.2c.3b.4b.5e.6e, | 1c.2c.3b.4b.5e.6f, | 1c.2c.3b.4b.5f.6a, | 1c.2c.3b.4b.5f.6b, | 1c.2c.3b.4b.5f.6c, |
| 1c.2c.3b.4b.5f.6d, | 1c.2c.3b.4b.5f.6e, | 1c.2c.3b.4b.5f.6f, | 1c.2c.3b.4c.5a.6a, | 1c.2c.3b.4c.5a.6b, |
| 1c.2c.3b.4c.5a.6c, | 1c.2c.3b.4c.5a.6d, | 1c.2c.3b.4c.5a.6e, | 1c.2c.3b.4c.5a.6f, | 1c.2c.3b.4c.5b.6a, |
| 1c.2c.3b.4c.5b.6b, | 1c.2c.3b.4c.5b.6c, | 1c.2c.3b.4c.5b.6d, | 1c.2c.3b.4c.5b.6e, |
| 1c.2c.3b.4c.5b.6f, | 1c.2c.3b.4c.5c.6a, | 1c.2c.3b.4c.5c.6b, | 1c.2c.3b.4c.5c.6c, | 1c.2c.3b.4c.5c.6d, |
| 1c.2c.3b.4c.5c.6e, | 1c.2c.3b.4c.5c.6f, | 1c.2c.3b.4c.5d.6a, | 1c.2c.3b.4c.5d.6b, |
| 1c.2c.3b.4c.5d.6c, | 1c.2c.3b.4c.5d.6d, | 1c.2c.3b.4c.5d.6e, | 1c.2c.3b.4c.5d.6f, |
| 1c.2c.3b.4c.5e.6a, | 1c.2c.3b.4c.5e.6b, | 1c.2c.3b.4c.5e.6c, | 1c.2c.3b.4c.5e.6d, |
| 1c.2c.3b.4c.5e.6e, | 1c.2c.3b.4c.5e.6f, | 1c.2c.3b.4c.5f.6a, | 1c.2c.3b.4c.5f.6b, | 1c.2c.3b.4c.5f.6c, |
| 1c.2c.3b.4c.5f.6d, | 1c.2c.3b.4c.5f.6e, | 1c.2c.3b.4c.5f.6f, | 1c.2c.3b.4d.5a.6a, | 1c.2c.3b.4d.5a.6b, |
| 1c.2c.3b.4d.5a.6c, | 1c.2c.3b.4d.5a.6d, | 1c.2c.3b.4d.5a.6e, | 1c.2c.3b.4d.5a.6f, |
| 1c.2c.3b.4d.5b.6a, | 1c.2c.3b.4d.5b.6b, | 1c.2c.3b.4d.5b.6c, | 1c.2c.3b.4d.5b.6d, |
| 1c.2c.3b.4d.5b.6e, | 1c.2c.3b.4d.5b.6f, | 1c.2c.3b.4d.5c.6a, | 1c.2c.3b.4d.5c.6b, |
| 1c.2c.3b.4d.5c.6c, | 1c.2c.3b.4d.5c.6d, | 1c.2c.3b.4d.5c.6e, | 1c.2c.3b.4d.5c.6f, |
| 1c.2c.3b.4d.5d.6a, | 1c.2c.3b.4d.5d.6b, | 1c.2c.3b.4d.5d.6c, | 1c.2c.3b.4d.5d.6d, |
| 1c.2c.3b.4d.5d.6e, | 1c.2c.3b.4d.5d.6f, | 1c.2c.3b.4d.5e.6a, | 1c.2c.3b.4d.5e.6b, |

TABLE 7-continued

List of Compounds of Formula (II)

| | | | | |
|---|---|---|---|---|
| 1c.2c.3b.4d.5e.6c, | 1c.2c.3b.4d.5e.6d, | 1c.2c.3b.4d.5e.6e, | 1c.2c.3b.4d.5e.6f, | |
| 1c.2c.3b.4d.5f.6a, | 1c.2c.3b.4d.5f.6b, | 1c.2c.3b.4d.5f.6c, | 1c.2c.3b.4d.5f.6d, | |
| 1c.2c.3b.4d.5f.6e, | 1c.2c.3b.4d.5f.6f, | 1c.2c.3b.4e.5a.6a, | 1c.2c.3b.4e.5a.6b, | 1c.2c.3b.4e.5a.6c, |
| 1c.2c.3b.4e.5a.6d, | 1c.2c.3b.4e.5a.6e, | 1c.2c.3b.4e.5a.6f, | 1c.2c.3b.4e.5b.6a, | |
| 1c.2c.3b.4e.5b.6b, | 1c.2c.3b.4e.5b.6c, | 1c.2c.3b.4e.5b.6d, | 1c.2c.3b.4e.5b.6e, | |
| 1c.2c.3b.4e.5b.6f, | 1c.2c.3b.4e.5c.6a, | 1c.2c.3b.4e.5c.6b, | 1c.2c.3b.4e.5c.6c, | 1c.2c.3b.4e.5c.6d, |
| 1c.2c.3b.4e.5c.6e, | 1c.2c.3b.4e.5c.6f, | 1c.2c.3b.4e.5d.6a, | 1c.2c.3b.4e.5d.6b, | |
| 1c.2c.3b.4e.5d.6c, | 1c.2c.3b.4e.5d.6d, | 1c.2c.3b.4e.5d.6e, | 1c.2c.3b.4e.5d.6f, | |
| 1c.2c.3b.4e.5e.6a, | 1c.2c.3b.4e.5e.6b, | 1c.2c.3b.4e.5e.6c, | 1c.2c.3b.4e.5e.6d, | |
| 1c.2c.3b.4e.5e.6e, | 1c.2c.3b.4e.5e.6f, | 1c.2c.3b.4e.5f.6a, | 1c.2c.3b.4e.5f.6b, | 1c.2c.3b.4e.5f.6c, |
| 1c.2c.3b.4e.5f.6d, | 1c.2c.3b.4e.5f.6e, | 1c.2c.3b.4e.5f.6f, | 1c.2c.3b.4f.5a.6a, | 1c.2c.3b.4f.5a.6b, |
| 1c.2c.3b.4f.5a.6c, | 1c.2c.3b.4f.5a.6d, | 1c.2c.3b.4f.5a.6e, | 1c.2c.3b.4f.5a.6f, | 1c.2c.3b.4f.5b.6a, |
| 1c.2c.3b.4f.5b.6b, | 1c.2c.3b.4f.5b.6c, | 1c.2c.3b.4f.5b.6d, | 1c.2c.3b.4f.5b.6e, | 1c.2c.3b.4f.5b.6f, |
| 1c.2c.3b.4f.5c.6a, | 1c.2c.3b.4f.5c.6b, | 1c.2c.3b.4f.5c.6c, | 1c.2c.3b.4f.5c.6d, | 1c.2c.3b.4f.5c.6e, |
| 1c.2c.3b.4f.5c.6f, | 1c.2c.3b.4f.5d.6a, | 1c.2c.3b.4f.5d.6b, | 1c.2c.3b.4f.5d.6c, | 1c.2c.3b.4f.5d.6d, |
| 1c.2c.3b.4f.5d.6e, | 1c.2c.3b.4f.5d.6f, | 1c.2c.3b.4f.5e.6a, | 1c.2c.3b.4f.5e.6b, | 1c.2c.3b.4f.5e.6c, |
| 1c.2c.3b.4f.5e.6d, | 1c.2c.3b.4f.5e.6e, | 1c.2c.3b.4f.5e.6f, | 1c.2c.3b.4f.5f.6a, | 1c.2c.3b.4f.5f.6b, |
| 1c.2c.3b.4f.5f.6c, | 1c.2c.3b.4f.5f.6d, | 1c.2c.3b.4f.5f.6e, | 1c.2c.3b.4f.5f.6f, | 1c.2c.3c.4a.5a.6a, |
| 1c.2c.3c.4a.5a.6b, | 1c.2c.3c.4a.5a.6c, | 1c.2c.3c.4a.5a.6d, | 1c.2c.3c.4a.5a.6e, | 1c.2c.3c.4a.5a.6f, |
| 1c.2c.3c.4a.5b.6a, | 1c.2c.3c.4a.5b.6b, | 1c.2c.3c.4a.5b.6c, | 1c.2c.3c.4a.5b.6d, | |
| 1c.2c.3c.4a.5b.6e, | 1c.2c.3c.4a.5b.6f, | 1c.2c.3c.4a.5c.6a, | 1c.2c.3c.4a.5c.6b, | 1c.2c.3c.4a.5c.6c, |
| 1c.2c.3c.4a.5c.6d, | 1c.2c.3c.4a.5c.6e, | 1c.2c.3c.4a.5c.6f, | 1c.2c.3c.4a.5d.6a, | 1c.2c.3c.4a.5d.6b, |
| 1c.2c.3c.4a.5d.6c, | 1c.2c.3c.4a.5d.6d, | 1c.2c.3c.4a.5d.6e, | 1c.2c.3c.4a.5d.6f, | |
| 1c.2c.3c.4a.5e.6a, | 1c.2c.3c.4a.5e.6b, | 1c.2c.3c.4a.5e.6c, | 1c.2c.3c.4a.5e.6d, | 1c.2c.3c.4a.5e.6e, |
| 1c.2c.3c.4a.5e.6f, | 1c.2c.3c.4a.5f.6a, | 1c.2c.3c.4a.5f.6b, | 1c.2c.3c.4a.5f.6c, | 1c.2c.3c.4a.5f.6d, |
| 1c.2c.3c.4a.5f.6e, | 1c.2c.3c.4a.5f.6f, | 1c.2c.3c.4b.5a.6a, | 1c.2c.3c.4b.5a.6b, | 1c.2c.3c.4b.5a.6c, |
| 1c.2c.3c.4b.5a.6d, | 1c.2c.3c.4b.5a.6e, | 1c.2c.3c.4b.5a.6f, | 1c.2c.3c.4b.5b.6a, | |
| 1c.2c.3c.4b.5b.6b, | 1c.2c.3c.4b.5b.6c, | 1c.2c.3c.4b.5b.6d, | 1c.2c.3c.4b.5b.6e, | |
| 1c.2c.3c.4b.5b.6f, | 1c.2c.3c.4b.5c.6a, | 1c.2c.3c.4b.5c.6b, | 1c.2c.3c.4b.5c.6c, | 1c.2c.3c.4b.5c.6d, |
| 1c.2c.3c.4b.5c.6e, | 1c.2c.3c.4b.5c.6f, | 1c.2c.3c.4b.5d.6a, | 1c.2c.3c.4b.5d.6b, | |
| 1c.2c.3c.4b.5d.6c, | 1c.2c.3c.4b.5d.6d, | 1c.2c.3c.4b.5d.6e, | 1c.2c.3c.4b.5d.6f, | |
| 1c.2c.3c.4b.5e.6a, | 1c.2c.3c.4b.5e.6b, | 1c.2c.3c.4b.5e.6c, | 1c.2c.3c.4b.5e.6d, | |
| 1c.2c.3c.4b.5e.6e, | 1c.2c.3c.4b.5e.6f, | 1c.2c.3c.4b.5f.6a, | 1c.2c.3c.4b.5f.6b, | 1c.2c.3c.4b.5f.6c, |
| 1c.2c.3c.4b.5f.6d, | 1c.2c.3c.4b.5f.6e, | 1c.2c.3c.4b.5f.6f, | 1c.2c.3c.4c.5a.6a, | 1c.2c.3c.4c.5a.6b, |
| 1c.2c.3c.4c.5a.6c, | 1c.2c.3c.4c.5a.6d, | 1c.2c.3c.4c.5a.6e, | 1c.2c.3c.4c.5a.6f, | 1c.2c.3c.4c.5b.6a, |
| 1c.2c.3c.4c.5b.6b, | 1c.2c.3c.4c.5b.6c, | 1c.2c.3c.4c.5b.6d, | 1c.2c.3c.4c.5b.6e, | 1c.2c.3c.4c.5b.6f, |
| 1c.2c.3c.4c.5c.6a, | 1c.2c.3c.4c.5c.6b, | 1c.2c.3c.4c.5c.6c, | 1c.2c.3c.4c.5c.6d, | 1c.2c.3c.4c.5c.6e, |
| 1c.2c.3c.4c.5c.6f, | 1c.2c.3c.4c.5d.6a, | 1c.2c.3c.4c.5d.6b, | 1c.2c.3c.4c.5d.6c, | 1c.2c.3c.4c.5d.6d, |
| 1c.2c.3c.4c.5d.6e, | 1c.2c.3c.4c.5d.6f, | 1c.2c.3c.4c.5e.6a, | 1c.2c.3c.4c.5e.6b, | 1c.2c.3c.4c.5e.6c, |
| 1c.2c.3c.4c.5e.6d, | 1c.2c.3c.4c.5e.6e, | 1c.2c.3c.4c.5e.6f, | 1c.2c.3c.4c.5f.6a, | 1c.2c.3c.4c.5f.6b, |
| 1c.2c.3c.4c.5f.6c, | 1c.2c.3c.4c.5f.6d, | 1c.2c.3c.4c.5f.6e, | 1c.2c.3c.4c.5f.6f, | 1c.2c.3c.4d.5a.6a, |
| 1c.2c.3c.4d.5a.6b, | 1c.2c.3c.4d.5a.6c, | 1c.2c.3c.4d.5a.6d, | 1c.2c.3c.4d.5a.6e, | |
| 1c.2c.3c.4d.5a.6f, | 1c.2c.3c.4d.5b.6a, | 1c.2c.3c.4d.5b.6b, | 1c.2c.3c.4d.5b.6c, | |
| 1c.2c.3c.4d.5b.6d, | 1c.2c.3c.4d.5b.6e, | 1c.2c.3c.4d.5b.6f, | 1c.2c.3c.4d.5c.6a, | |
| 1c.2c.3c.4d.5c.6b, | 1c.2c.3c.4d.5c.6c, | 1c.2c.3c.4d.5c.6d, | 1c.2c.3c.4d.5c.6e, | 1c.2c.3c.4d.5c.6f, |
| 1c.2c.3c.4d.5d.6a, | 1c.2c.3c.4d.5d.6b, | 1c.2c.3c.4d.5d.6c, | 1c.2c.3c.4d.5d.6d, | |
| 1c.2c.3c.4d.5d.6e, | 1c.2c.3c.4d.5d.6f, | 1c.2c.3c.4d.5e.6a, | 1c.2c.3c.4d.5e.6b, | |
| 1c.2c.3c.4d.5e.6c, | 1c.2c.3c.4d.5e.6d, | 1c.2c.3c.4d.5e.6e, | 1c.2c.3c.4d.5e.6f, | 1c.2c.3c.4d.5f.6a, |
| 1c.2c.3c.4d.5f.6b, | 1c.2c.3c.4d.5f.6c, | 1c.2c.3c.4d.5f.6d, | 1c.2c.3c.4d.5f.6e, | 1c.2c.3c.4d.5f.6f, |
| 1c.2c.3c.4e.5a.6a, | 1c.2c.3c.4e.5a.6b, | 1c.2c.3c.4e.5a.6c, | 1c.2c.3c.4e.5a.6d, | 1c.2c.3c.4e.5a.6e, |
| 1c.2c.3c.4e.5a.6f, | 1c.2c.3c.4e.5b.6a, | 1c.2c.3c.4e.5b.6b, | 1c.2c.3c.4e.5b.6c, | 1c.2c.3c.4e.5b.6d, |
| 1c.2c.3c.4e.5b.6e, | 1c.2c.3c.4e.5b.6f, | 1c.2c.3c.4e.5c.6a, | 1c.2c.3c.4e.5c.6b, | 1c.2c.3c.4e.5c.6c, |
| 1c.2c.3c.4e.5c.6d, | 1c.2c.3c.4e.5c.6e, | 1c.2c.3c.4e.5c.6f, | 1c.2c.3c.4e.5d.6a, | 1c.2c.3c.4e.5d.6b, |
| 1c.2c.3c.4e.5d.6c, | 1c.2c.3c.4e.5d.6d, | 1c.2c.3c.4e.5d.6e, | 1c.2c.3c.4e.5d.6f, | 1c.2c.3c.4e.5e.6a, |
| 1c.2c.3c.4e.5e.6b, | 1c.2c.3c.4e.5e.6c, | 1c.2c.3c.4e.5e.6d, | 1c.2c.3c.4e.5e.6e, | 1c.2c.3c.4e.5e.6f, |
| 1c.2c.3c.4e.5f.6a, | 1c.2c.3c.4e.5f.6b, | 1c.2c.3c.4e.5f.6c, | 1c.2c.3c.4e.5f.6d, | 1c.2c.3c.4e.5f.6e, |
| 1c.2c.3c.4e.5f.6f, | 1c.2c.3c.4f.5a.6a, | 1c.2c.3c.4f.5a.6b, | 1c.2c.3c.4f.5a.6c, | 1c.2c.3c.4f.5a.6d, |
| 1c.2c.3c.4f.5a.6e, | 1c.2c.3c.4f.5a.6f, | 1c.2c.3c.4f.5b.6a, | 1c.2c.3c.4f.5b.6b, | 1c.2c.3c.4f.5b.6c, |
| 1c.2c.3c.4f.5b.6d, | 1c.2c.3c.4f.5b.6e, | 1c.2c.3c.4f.5b.6f, | 1c.2c.3c.4f.5c.6a, | 1c.2c.3c.4f.5c.6b, |
| 1c.2c.3c.4f.5c.6c, | 1c.2c.3c.4f.5c.6d, | 1c.2c.3c.4f.5c.6e, | 1c.2c.3c.4f.5c.6f, | 1c.2c.3c.4f.5d.6a, |
| 1c.2c.3c.4f.5d.6b, | 1c.2c.3c.4f.5d.6c, | 1c.2c.3c.4f.5d.6d, | 1c.2c.3c.4f.5d.6e, | 1c.2c.3c.4f.5d.6f, |
| 1c.2c.3c.4f.5e.6a, | 1c.2c.3c.4f.5e.6b, | 1c.2c.3c.4f.5e.6c, | 1c.2c.3c.4f.5e.6d, | 1c.2c.3c.4f.5e.6e, |
| 1c.2c.3c.4f.5e.6f, | 1c.2c.3c.4f.5f.6a, | 1c.2c.3c.4f.5f.6b, | 1c.2c.3c.4f.5f.6c, | 1c.2c.3c.4f.5f.6d, |
| 1c.2c.3c.4f.5f.6e, | 1c.2c.3c.4f.5f.6f, | 1c.2c.3d.4a.5a.6a, | 1c.2c.3d.4a.5a.6b, | 1c.2c.3d.4a.5a.6c, |
| 1c.2c.3d.4a.5a.6d, | 1c.2c.3d.4a.5a.6e, | 1c.2c.3d.4a.5a.6f, | 1c.2c.3d.4a.5b.6a, | |
| 1c.2c.3d.4a.5b.6b, | 1c.2c.3d.4a.5b.6c, | 1c.2c.3d.4a.5b.6d, | 1c.2c.3d.4a.5b.6e, | |
| 1c.2c.3d.4a.5b.6f, | 1c.2c.3d.4a.5c.6a, | 1c.2c.3d.4a.5c.6b, | 1c.2c.3d.4a.5c.6c, | |
| 1c.2c.3d.4a.5c.6d, | 1c.2c.3d.4a.5c.6e, | 1c.2c.3d.4a.5c.6f, | 1c.2c.3d.4a.5d.6a, | |
| 1c.2c.3d.4a.5d.6b, | 1c.2c.3d.4a.5d.6c, | 1c.2c.3d.4a.5d.6d, | 1c.2c.3d.4a.5d.6e, | |
| 1c.2c.3d.4a.5d.6f, | 1c.2c.3d.4a.5e.6a, | 1c.2c.3d.4a.5e.6b, | 1c.2c.3d.4a.5e.6c, | |
| 1c.2c.3d.4a.5e.6d, | 1c.2c.3d.4a.5e.6e, | 1c.2c.3d.4a.5e.6f, | 1c.2c.3d.4a.5f.6a, | |
| 1c.2c.3d.4a.5f.6b, | 1c.2c.3d.4a.5f.6c, | 1c.2c.3d.4a.5f.6d, | 1c.2c.3d.4a.5f.6e, | 1c.2c.3d.4a.5f.6f, |
| 1c.2c.3d.4b.5a.6a, | 1c.2c.3d.4b.5a.6b, | 1c.2c.3d.4b.5a.6c, | 1c.2c.3d.4b.5a.6d, | |
| 1c.2c.3d.4b.5a.6e, | 1c.2c.3d.4b.5a.6f, | 1c.2c.3d.4b.5b.6a, | 1c.2c.3d.4b.5b.6b, | |
| 1c.2c.3d.4b.5b.6c, | 1c.2c.3d.4b.5b.6d, | 1c.2c.3d.4b.5b.6e, | 1c.2c.3d.4b.5b.6f, | |
| 1c.2c.3d.4b.5c.6a, | 1c.2c.3d.4b.5c.6b, | 1c.2c.3d.4b.5c.6c, | 1c.2c.3d.4b.5c.6d, | |
| 1c.2c.3d.4b.5c.6e, | 1c.2c.3d.4b.5c.6f, | 1c.2c.3d.4b.5d.6a, | 1c.2c.3d.4b.5d.6b, | |
| 1c.2c.3d.4b.5d.6c, | 1c.2c.3d.4b.5d.6d, | 1c.2c.3d.4b.5d.6e, | 1c.2c.3d.4b.5d.6f, | |

TABLE 7-continued

List of Compounds of Formula (II)

| | | | | |
|---|---|---|---|---|
| 1c.2c.3d.4b.5e.6a, | 1c.2c.3d.4b.5e.6b, | 1c.2c.3d.4b.5e.6c, | 1c.2c.3d.4b.5e.6d, | |
| 1c.2c.3d.4b.5e.6e, | 1c.2c.3d.4b.5e.6f, | 1c.2c.3d.4b.5f.6a, | 1c.2c.3d.4b.5f.6b, | |
| 1c.2c.3d.4b.5f.6c, | 1c.2c.3d.4b.5f.6d, | 1c.2c.3d.4b.5f.6e, | 1c.2c.3d.4b.5f.6f, | 1c.2c.3d.4c.5a.6a, |
| 1c.2c.3d.4c.5a.6b, | 1c.2c.3d.4c.5a.6c, | 1c.2c.3d.4c.5a.6d, | 1c.2c.3d.4c.5a.6e, | |
| 1c.2c.3d.4c.5a.6f, | 1c.2c.3d.4c.5b.6a, | 1c.2c.3d.4c.5b.6b, | 1c.2c.3d.4c.5b.6c, | |
| 1c.2c.3d.4c.5b.6d, | 1c.2c.3d.4c.5b.6e, | 1c.2c.3d.4c.5b.6f, | 1c.2c.3d.4c.5c.6a, | |
| 1c.2c.3d.4c.5c.6b, | 1c.2c.3d.4c.5c.6c, | 1c.2c.3d.4c.5c.6d, | 1c.2c.3d.4c.5c.6e, | 1c.2c.3d.4c.5c.6f, |
| 1c.2c.3d.4c.5d.6a, | 1c.2c.3d.4c.5d.6b, | 1c.2c.3d.4c.5d.6c, | 1c.2c.3d.4c.5d.6d, | |
| 1c.2c.3d.4c.5d.6e, | 1c.2c.3d.4c.5d.6f, | 1c.2c.3d.4c.5e.6a, | 1c.2c.3d.4c.5e.6b, | |
| 1c.2c.3d.4c.5e.6c, | 1c.2c.3d.4c.5e.6d, | 1c.2c.3d.4c.5e.6e, | 1c.2c.3d.4c.5e.6f, | 1c.2c.3d.4c.5f.6a, |
| 1c.2c.3d.4c.5f.6b, | 1c.2c.3d.4c.5f.6c, | 1c.2c.3d.4c.5f.6d, | 1c.2c.3d.4c.5f.6e, | 1c.2c.3d.4c.5f.6f, |
| 1c.2c.3d.4d.5a.6a, | 1c.2c.3d.4d.5a.6b, | 1c.2c.3d.4d.5a.6c, | 1c.2c.3d.4d.5a.6d, | |
| 1c.2c.3d.4d.5a.6e, | 1c.2c.3d.4d.5a.6f, | 1c.2c.3d.4d.5b.6a, | 1c.2c.3d.4d.5b.6b, | |
| 1c.2c.3d.4d.5b.6c, | 1c.2c.3d.4d.5b.6d, | 1c.2c.3d.4d.5b.6e, | 1c.2c.3d.4d.5b.6f, | |
| 1c.2c.3d.4d.5c.6a, | 1c.2c.3d.4d.5c.6b, | 1c.2c.3d.4d.5c.6c, | 1c.2c.3d.4d.5c.6d, | |
| 1c.2c.3d.4d.5c.6e, | 1c.2c.3d.4d.5c.6f, | 1c.2c.3d.4d.5d.6a, | 1c.2c.3d.4d.5d.6b, | |
| 1c.2c.3d.4d.5d.6c, | 1c.2c.3d.4d.5d.6d, | 1c.2c.3d.4d.5d.6e, | 1c.2c.3d.4d.5d.6f, | |
| 1c.2c.3d.4d.5e.6a, | 1c.2c.3d.4d.5e.6b, | 1c.2c.3d.4d.5e.6c, | 1c.2c.3d.4d.5e.6d, | |
| 1c.2c.3d.4d.5e.6e, | 1c.2c.3d.4d.5e.6f, | 1c.2c.3d.4d.5f.6a, | 1c.2c.3d.4d.5f.6b, | |
| 1c.2c.3d.4d.5f.6c, | 1c.2c.3d.4d.5f.6d, | 1c.2c.3d.4d.5f.6e, | 1c.2c.3d.4d.5f.6f, | |
| 1c.2c.3d.4e.5a.6a, | 1c.2c.3d.4e.5a.6b, | 1c.2c.3d.4e.5a.6c, | 1c.2c.3d.4e.5a.6d, | |
| 1c.2c.3d.4e.5a.6e, | 1c.2c.3d.4e.5a.6f, | 1c.2c.c1.4e.5b.6a, | 1c.2c.3d.4e.5b.6b, | |
| 1c.2c.3d.4e.5b.6c, | 1c.2c.3d.4e.5b.6d, | 1c.2c.3d.4e.5b.6e, | 1c.2c.3d.4e.5b.6f, | |
| 1c.2c.3d.4e.5c.6a, | 1c.2c.3d.4e.5c.6b, | 1c.2c.3d.4e.5c.6c, | 1c.2c.3d.4e.5c.6d, | |
| 1c.2c.3d.4e.5c.6e, | 1c.2c.3d.4e.5c.6f, | 1c.2c.3d.4e.5d.6a, | 1c.2c.3d.4e.5d.6b, | |
| 1c.2c.3d.4e.5d.6c, | 1c.2c.3d.4e.5d.6d, | 1c.2c.3d.4e.5d.6e, | 1c.2c.3d.4e.5d.6f, | |
| 1c.2c.3d.4e.5e.6a, | 1c.2c.3d.4e.5e.6b, | 1c.2c.3d.4e.5e.6c, | 1c.2c.3d.4e.5e.6d, | |
| 1c.2c.3d.4e.5e.6e, | 1c.2c.3d.4e.5e.6f, | 1c.2c.3d.4e.5f.6a, | 1c.2c.3d.4e.5f.6b, | 1c.2c.3d.4e.5f.6c, |
| 1c.2c.3d.4e.5f.6d, | 1c.2c.3d.4e.5f.6e, | 1c.2c.3d.4e.5f.6f, | 1c.2c.3d.4f.5a.6a, | 1c.2c.3d.4f.5a.6b, |
| 1c.2c.3d.4f.5a.6c, | 1c.2c.3d.4f.5a.6d, | 1c.2c.3d.4f.5a.6e, | 1c.2c.3d.4f.5a.6f, | 1c.2c.3d.4f.5b.6a, |
| 1c.2c.3d.4f.5b.6b, | 1c.2c.3d.4f.5b.6c, | 1c.2c.3d.4f.5b.6d, | 1c.2c.3d.4f.5b.6e, | 1c.2c.3d.4f.5b.6f, |
| 1c.2c.3d.4f.5c.6a, | 1c.2c.3d.4f.5c.6b, | 1c.2c.3d.4f.5c.6c, | 1c.2c.3d.4f.5c.6d, | 1c.2c.3d.4f.5c.6e, |
| 1c.2c.3d.4f.5c.6f, | 1c.2c.3d.4f.5d.6a, | 1c.2c.3d.4f.5d.6b, | 1c.2c.3d.4f.5d.6c, | |
| 1c.2c.3d.4f.5d.6d, | 1c.2c.3d.4f.5d.6e, | 1c.2c.3d.4f.5d.6f, | 1c.2c.3d.4f.5e.6a, | |
| 1c.2c.3d.4f.5e.6b, | 1c.2c.3d.4f.5e.6c, | 1c.2c.3d.4f.5e.6d, | 1c.2c.3d.4f.5e.6e, | 1c.2c.3d.4f.5e.6f, |
| 1c.2c.3d.4f.5f.6a, | 1c.2c.3d.4f.5f.6b, | 1c.2c.3d.4f.5f.6c, | 1c.2c.3d.4f.5f.6d, | 1c.2c.3d.4f.5f.6e, |
| 1c.2c.3d.4f.5f.6f, | 1c.2c.3e.4a.5a.6a, | 1c.2c.3e.4a.5a.6b, | 1c.2c.3e.4a.5a.6c, | 1c.2c.3e.4a.5a.6d, |
| 1c.2c.3e.4a.5a.6e, | 1c.2c.3e.4a.5a.6f, | 1c.2c.3e.4a.5b.6a, | 1c.2c.3e.4a.5b.6b, | 1c.2c.3e.4a.5b.6c, |
| 1c.2c.3e.4a.5b.6d, | 1c.2c.3e.4a.5b.6e, | 1c.2c.3e.4a.5b.6f, | 1c.2c.3e.4a.5c.6a, | 1c.2c.3e.4a.5c.6b, |
| 1c.2c.3e.4a.5c.6c, | 1c.2c.3e.4a.5c.6d, | 1c.2c.3e.4a.5c.6e, | 1c.2c.3e.4a.5c.6f, | 1c.2c.3e.4a.5d.6a, |
| 1c.2c.3e.4a.5d.6b, | 1c.2c.3e.4a.5d.6c, | 1c.2c.3e.4a.5d.6d, | 1c.2c.3e.4a.5d.6e, | |
| 1c.2c.3e.4a.5d.6f, | 1c.2c.3e.4a.5e.6a, | 1c.2c.3e.4a.5e.6b, | 1c.2c.3e.4a.5e.6c, | 1c.2c.3e.4a.5e.6d, |
| 1c.2c.3e.4a.5e.6e, | 1c.2c.3e.4a.5e.6f, | 1c.2c.3e.4a.5f.6a, | 1c.2c.3e.4a.5f.6b, | 1c.2c.3e.4a.5f.6c, |
| 1c.2c.3e.4a.5f.6d, | 1c.2c.3e.4a.5f.6e, | 1c.2c.3e.4a.5f.6f, | 1c.2c.3e.4b.5a.6a, | 1c.2c.3e.4b.5a.6b, |
| 1c.2c.3e.4b.5a.6c, | 1c.2c.3e.4b.5a.6d, | 1c.2c.3e.4b.5a.6e, | 1c.2c.3e.4b.5a.6f, | |
| 1c.2c.3e.4b.5b.6a, | 1c.2c.3e.4b.5b.6b, | 1c.2c.3e.4b.5b.6c, | 1c.2c.3e.4b.5b.6d, | |
| 1c.2c.3e.4b.5b.6e, | 1c.2c.3e.4b.5b.6f, | 1c.2c.3e.4b.5c.6a, | 1c.2c.3e.4b.5c.6b, | 1c.2c.3e.4b.5c.6c, |
| 1c.2c.3e.4b.5c.6d, | 1c.2c.3e.4b.5c.6e, | 1c.2c.3e.4b.5c.6f, | 1c.2c.3e.4b.5d.6a, | |
| 1c.2c.3e.4b.5d.6b, | 1c.2c.3e.4b.5d.6c, | 1c.2c.3e.4b.5d.6d, | 1c.2c.3e.4b.5d.6e, | |
| 1c.2c.3e.4b.5d.6f, | 1c.2c.3e.4b.5e.6a, | 1c.2c.3e.4b.5e.6b, | 1c.2c.3e.4b.5e.6c, | |
| 1c.2c.3e.4b.5e.6d, | 1c.2c.3e.4b.5e.6e, | 1c.2c.3e.4b.5e.6f, | 1c.2c.3e.4b.5f.6a, | 1c.2c.3e.4b.5f.6b, |
| 1c.2c.3e.4b.5f.6c, | 1c.2c.3e.4b.5f.6d, | 1c.2c.3e.4b.5f.6e, | 1c.2c.3e.4b.5f.6f, | 1c.2c.3e.4c.5a.6a, |
| 1c.2c.3e.4c.5a.6b, | 1c.2c.3e.4c.5a.6c, | 1c.2c.3e.4c.5a.6d, | 1c.2c.3e.4c.5a.6e, | 1c.2c.3e.4c.5a.6f, |
| 1c.2c.3e.4c.5b.6a, | 1c.2c.3e.4c.5b.6b, | 1c.2c.3e.4c.5b.6c, | 1c.2c.3e.4c.5b.6d, | |
| 1c.2c.3e.4c.5b.6e, | 1c.2c.3e.4c.5b.6f, | 1c.2c.3e.4c.5c.6a, | 1c.2c.3e.4c.5c.6b, | 1c.2c.3e.4c.5c.6c, |
| 1c.2c.3e.4c.5c.6d, | 1c.2c.3e.4c.5c.6e, | 1c.2c.3e.4c.5c.6f, | 1c.2c.3e.4c.5d.6a, | 1c.2c.3e.4c.5d.6b, |
| 1c.2c.3e.4c.5d.6c, | 1c.2c.3e.4c.5d.6d, | 1c.2c.3e.4c.5d.6e, | 1c.2c.3e.4c.5d.6f, | 1c.2c.3e.4c.5e.6a, |
| 1c.2c.3e.4c.5e.6b, | 1c.2c.3e.4c.5e.6c, | 1c.2c.3e.4c.5e.6d, | 1c.2c.3e.4c.5e.6e, | 1c.2c.3e.4c.5e.6f, |
| 1c.2c.3e.4c.5f.6a, | 1c.2c.3e.4c.5f.6b, | 1c.2c.3e.4c.5f.6c, | 1c.2c.3e.4c.5f.6d, | 1c.2c.3e.4c.5f.6e, |
| 1c.2c.3e.4c.5f.6f, | 1c.2c.3e.4d.5a.6a, | 1c.2c.3e.4d.5a.6b, | 1c.2c.3e.4d.5a.6c, | |
| 1c.2c.3e.4d.5a.6d, | 1c.2c.3e.4d.5a.6e, | 1c.2c.3e.4d.5a.6f, | 1c.2c.3e.4d.5b.6a, | |
| 1c.2c.3e.4d.5b.6b, | 1c.2c.3e.4d.5b.6c, | 1c.2c.3e.4d.5b.6d, | 1c.2c.3e.4d.5b.6e, | |
| 1c.2c.3e.4d.5b.6f, | 1c.2c.3e.4d.5c.6a, | 1c.2c.3e.4d.5c.6b, | 1c.2c.3e.4d.5c.6c, | |
| 1c.2c.3e.4d.5c.6d, | 1c.2c.3e.4d.5c.6e, | 1c.2c.3e.4d.5c.6f, | 1c.2c.3e.4d.5d.6a, | |
| 1c.2c.3e.4d.5d.6b, | 1c.2c.3e.4d.5d.6c, | 1c.2c.3e.4d.5d.6d, | 1c.2c.3e.4d.5d.6e, | |
| 1c.2c.3e.4d.5d.6f, | 1c.2c.3e.4d.5e.6a, | 1c.2c.3e.4d.5e.6b, | 1c.2c.3e.4d.5e.6c, | |
| 1c.2c.3e.4d.5e.6d, | 1c.2c.3e.4d.5e.6e, | 1c.2c.3e.4d.5e.6f, | 1c.2c.3e.4d.5f.6a, | |
| 1c.2c.3e.4d.5f.6b, | 1c.2c.3e.4d.5f.6c, | 1c.2c.3e.4d.5f.6d, | 1c.2c.3e.4d.5f.6e, | 1c.2c.3e.4d.5f.6f, |
| 1c.2c.3e.4e.5a.6a, | 1c.2c.3e.4e.5a.6b, | 1c.2c.3e.4e.5a.6c, | 1c.2c.3e.4e.5a.6d, | 1c.2c.3e.4e.5a.6e, |
| 1c.2c.3e.4e.5a.6f, | 1c.2c.3e.4e.5b.6a, | 1c.2c.3e.4e.5b.6b, | 1c.2c.3e.4e.5b.6c, | |
| 1c.2c.3e.4e.5b.6d, | 1c.2c.3e.4e.5b.6e, | 1c.2c.3e.4e.5b.6f, | 1c.2c.3e.4e.5c.6a, | 1c.2c.3e.4e.5c.6b, |
| 1c.2c.3e.4e.5c.6c, | 1c.2c.3e.4e.5c.6d, | 1c.2c.3e.4e.5c.6e, | 1c.2c.3e.4e.5c.6f, | 1c.2c.3e.4e.5d.6a, |
| 1c.2c.3e.4e.5d.6b, | 1c.2c.3e.4e.5d.6c, | 1c.2c.3e.4e.5d.6d, | 1c.2c.3e.4e.5d.6e, | |
| 1c.2c.3e.4e.5d.6f, | 1c.2c.3e.4e.5e.6a, | 1c.2c.3e.4e.5e.6b, | 1c.2c.3e.4e.5e.6c, | 1c.2c.3e.4e.5e.6d, |
| 1c.2c.3e.4e.5e.6e, | 1c.2c.3e.4e.5e.6f, | 1c.2c.3e.4e.5f.6a, | 1c.2c.3e.4e.5f.6b, | 1c.2c.3e.4e.5f.6c, |
| 1c.2c.3e.4e.5f.6d, | 1c.2c.3e.4e.5f.6e, | 1c.2c.3e.4e.5f.6f, | 1c.2c.3e.4f.5a.6a, | 1c.2c.3e.4f.5a.6b, |
| 1c.2c.3e.4f.5a.6c, | 1c.2c.3e.4f.5a.6d, | 1c.2c.3e.4f.5a.6e, | 1c.2c.3e.4f.5a.6f, | 1c.2c.3e.4f.5b.6a, |
| 1c.2c.3e.4f.5b.6b, | 1c.2c.3e.4f.5b.6c, | 1c.2c.3e.4f.5b.6d, | 1c.2c.3e.4f.5b.6e, | 1c.2c.3e.4f.5b.6f, |

TABLE 7-continued

List of Compounds of Formula (II)

| | | | |
|---|---|---|---|
| 1c.2c.3e.4f.5c.6a, | 1c.2c.3e.4f.5c.6b, | 1c.2c.3e.4f.5c.6c, | 1c.2c.3e.4f.5c.6d, 1c.2c.3e.4f.5c.6e, |
| 1c.2c.3e.4f.5c.6f, | 1c.2c.3e.4f.5d.6a, | 1c.2c.3e.4f.5d.6b, | 1c.2c.3e.4f.5d.6c, 1c.2c.3e.4f.5d.6d, |
| 1c.2c.3e.4f.5d.6e, | 1c.2c.3e.4f.5d.6f, | 1c.2c.3e.4f.5e.6a, | 1c.2c.3e.4f.5e.6b, 1c.2c.3e.4f.5e.6c, |
| 1c.2c.3e.4f.5e.6d, | 1c.2c.3e.4f.5e.6e, | 1c.2c.3e.4f.5e.6f, | 1c.2c.3e.4f.5f.6a, 1c.2c.3e.4f.5f.6b, |
| 1c.2c.3e.4f.5f.6c, | 1c.2c.3e.4f.5f.6d, | 1c.2c.3e.4f.5f.6e, | 1c.2c.3e.4f.5f.6f, 1c.2c.3f.4a.5a.6a, |
| 1c.2c.3f.4a.5a.6b, | 1c.2c.3f.4a.5a.6c, | 1c.2c.3f.4a.5a.6d, | 1c.2c.3f.4a.5a.6e, 1c.2c.3f.4a.5a.6f, |
| 1c.2c.3f.4a.5b.6a, | 1c.2c.3f.4a.5b.6b, | 1c.2c.3f.4a.5b.6c, | 1c.2c.3f.4a.5b.6d, 1c.2c.3f.4a.5b.6e, |
| 1c.2c.3f.4a.5b.6f, | 1c.2c.3f.4a.5c.6a, | 1c.2c.3f.4a.5c.6b, | 1c.2c.3f.4a.5c.6c, 1c.2c.3f.4a.5c.6d, |
| 1c.2c.3f.4a.5c.6e, | 1c.2c.3f.4a.5c.6f, | 1c.2c.3f.4a.5d.6a, | 1c.2c.3f.4a.5d.6b, 1c.2c.3f.4a.5d.6c, |
| 1c.2c.3f.4a.5d.6d, | 1c.2c.3f.4a.5d.6e, | 1c.2c.3f.4a.5d.6f, | 1c.2c.3f.4a.5e.6a, 1c.2c.3f.4a.5e.6b, |
| 1c.2c.3f.4a.5e.6c, | 1c.2c.3f.4a.5e.6d, | 1c.2c.3f.4a.5e.6e, | 1c.2c.3f.4a.5e.6f, 1c.2c.3f.4a.5f.6a, |
| 1c.2c.3f.4a.5f.6b, | 1c.2c.3f.4a.5f.6c, | 1c.2c.3f.4a.5f.6d, | 1c.2c.3f.4a.5f.6e, 1c.2c.3f.4a.5f.6f, |
| 1c.2c.3f.4b.5a.6a, | 1c.2c.3f.4b.5a.6b, | 1c.2c.3f.4b.5a.6c, | 1c.2c.314b.5a.6d, 1c.2c.3f.4b.5a.6e, |
| 1c.2c.3f.4b.5a.6f, | 1c.2c.3f.4b.5b.6a, | 1c.2c.3f.4b.5b.6b, | 1c.2c.3f.4b.5b.6c, 1c.2c.3f.4b.5b.6d, |
| 1c.2c.3f.4b.5b.6e, | 1c.2c.3f.4b.5b.6f, | 1c.2c.3f.4b.5c.6a, | 1c.2c.3f.4b.5c.6b, 1c.2c.3f.4b.5c.6c, |
| 1c.2c.3f.4b.5c.6d, | 1c.2c.3f.4b.5c.6e, | 1c.2c.3f.4b.5c.6f, | 1c.2c.3f.4b.5d.6a, 1c.2c.3f.4b.5d.6b, |
| 1c.2c.3f.4b.5d.6c, | 1c.2c.3f.4b.5d.6d, | 1c.2c.3f.4b.5d.6e, | 1c.2c.3f.4b.5d.6f, 1c.2c.3f.4b.5e.6a, |
| 1c.2c.3f.4b.5e.6b, | 1c.2c.3f.4b.5e.6c, | 1c.2c.3f.4b.5e.6d, | 1c.2c.3f.4b.5e.6e, 1c.2c.3f.4b.5e.6f, |
| 1c.2c.3f.4b.5f.6a, | 1c.2c.3f.4b.5f.6b, | 1c.2c.3f.4b.5f.6c, | 1c.2c.3f.4b.5f.6d, 1c.2c.3f.4b.5f.6e, |
| 1c.2c.3f.4b.5f.6f, | 1c.2c.3f.4c.5a.6a, | 1c.2c.3f.4c.5a.6b, | 1c.2c.3f.4c.5a.6c, 1c.2c.3f.4c.5a.6d, |
| 1c.2c.3f.4c.5a.6e, | 1c.2c.3f.4c.5a.6f, | 1c.2c.3f.4c.5b.6a, | 1c.2c.3f.4c.5b.6b, 1c.2c.3f.4c.5b.6c, |
| 1c.2c.3f.4c.5b.6d, | 1c.2c.3f.4c.5b.6e, | 1c.2c.3f.4c.5b.6f, | 1c.2c.3f.4c.5c.6a, 1c.2c.3f.4c.5c.6b, |
| 1c.2c.3f.4c.5c.6c, | 1c.2c.3f.4c.5c.6d, | 1c.2c.3f.4c.5c.6e, | 1c.2c.3f.4c.5c.6f, 1c.2c.3f.4c.5d.6a, |
| 1c.2c.3f.4c.5d.6b, | 1c.2c.3f.4c.5d.6c, | 1c.2c.3f.4c.5d.6d, | 1c.2c.3f.4c.5d.6e, 1c.2c.3f.4c.5d.6f, |
| 1c.2c.3f.4c.5e.6a, | 1c.2c.3f.4c.5e.6b, | 1c.2c.3f.4c.5e.6c, | 1c.2c.3f.4c.5e.6d, 1c.2c.3f.4c.5e.6e, |
| 1c.2c.3f.4c.5e.6f, | 1c.2c.3f.4c.5f.6a, | 1c.2c.3f.4c.5f.6b, | 1c.2c.3f.4c.5f.6c, 1c.2c.3f.4c.5f.6d, |
| 1c.2c.3f.4c.5f.6e, | 1c.2c.3f.4c.5f.6f, | 1c.2c.3f.4d.5a.6a, | 1c.2c.3f.4d.5a.6b, 1c.2c.3f.4d.5a.6c, |
| 1c.2c.3f.4d.5a.6d, | 1c.2c.3f.4d.5a.6e, | 1c.2c.3f.4d.5a.6f, | 1c.2c.3f.4d.5b.6a, 1c.2c.3f.4d.5b.6b, |
| 1c.2c.3f.4d.5b.6c, | 1c.2c.3f.4d.5b.6d, | 1c.2c.3f.4d.5b.6e, | 1c.2c.3f.4d.5b.6f, 1c.2c.3f.4d.5c.6a, |
| 1c.2c.3f.4d.5c.6b, | 1c.2c.3f.4d.5c.6c, | 1c.2c.3f.4d.5c.6d, | 1c.2c.3f.4d.5c.6e, 1c.2c.3f.4d.5c.6f, |
| 1c.2c.3f.4d.5d.6a, | 1c.2c.3f.4d.5d.6b, | 1c.2c.3f.4d.5d.6c, | 1c.2c.3f.4d.5d.6d, |
| 1c.2c.3f.4d.5d.6e, | 1c.2c.3f.4d.5d.6f, | 1c.2c.3f.4d.5e.6a, | 1c.2c.3f.4d.5e.6b, 1c.2c.3f.4d.5e.6c, |
| 1c.2c.3f.4d.5e.6d, | 1c.2c.3f.4d.5e.6e, | 1c.2c.3f.4d.5e.6f, | 1c.2c.3f.4d.5f.6a, 1c.2c.3f.4d.5f.6b, |
| 1c.2c.3f.4d.5f.6c, | 1c.2c.3f.4d.5f.6d, | 1c.2c.3f.4d.5f.6e, | 1c.2c.3f.4d.5f.6f, 1c.2c.3f.4e.5a.6a, |
| 1c.2c.3f.4e.5a.6b, | 1c.2c.3f.4e.5a.6c, | 1c.2c.3f.4e.5a.6d, | 1c.2c.3f.4e.5a.6e, 1c.2c.3f.4e.5a.6f, |
| 1c.2c.3f.4e.5b.6a, | 1c.2c.3f.4e.5b.6b, | 1c.2c.3f.4e.5b.6c, | 1c.2c.3f.4e.5b.6d, 1c.2c.3f.4e.5b.6e, |
| 1c.2c.3f.4e.5b.6f, | 1c.2c.3f.4e.5c.6a, | 1c.2c.3f.4e.5c.6b, | 1c.2c.3f.4e.5c.6c, 1c.2c.3f.4e.5c.6d, |
| 1c.2c.3f.4e.5c.6e, | 1c.2c.3f.4e.5c.6f, | 1c.2c.3f.4e.5d.6a, | 1c.2c.3f.4e.5d.6b, 1c.2c.3f.4e.5d.6c, |
| 1c.2c.3f.4e.5d.6d, | 1c.2c.3f.4e.5d.6e, | 1c.2c.3f.4e.5d.6f, | 1c.2c.3f.4e.5e.6a, 1c.2c.3f.4e.5e.6b, |
| 1c.2c.3f.4e.5e.6c, | 1c.2c.3f.4e.5e.6d, | 1c.2c.3f.4e.5e.6e, | 1c.2c.3f.4e.5e.6f, 1c.2c.3f.4e.5f.6a, |
| 1c.2c.3f.4e.5f.6b, | 1c.2c.3f.4e.5f.6c, | 1c.2c.3f.4e.5f.6d, | 1c.2c.3f.4e.5f.6e, 1c.2c.3f.4e.5f.6f, |
| 1c.2c.3f.4f.5a.6a, | 1c.2c.3f.4f.5a.6b, | 1c.2c.3f.4f.5a.6c, | 1c.2c.3f.4f.5a.6d, 1c.2c.3f.4f.5a.6e, |
| 1c.2c.3f.4f.5a.6f, | 1c.2c.3f.4f.5b.6a, | 1c.2c.3f.4f.5b.6b, | 1c.2c.3f.4f.5b.6c, 1c.2c.3f.4f.5b.6d, |
| 1c.2c.3f.4f.5b.6e, | 1c.2c.3f.4f.5b.6f, | 1c.2c.3f.4f.5c.6a, | 1c.2c.3f.4f.5c.6b, 1c.2c.3f.4f.5c.6c, |
| 1c.2c.3f.4f.5c.6d, | 1c.2c.3f.4f.5c.6e, | 1c.2c.3f.4f.5c.6f, | 1c.2c.3f.4f.5d.6a, 1c.2c.3f.4f.5d.6b, |
| 1c.2c.3f.4f.5d.6c, | 1c.2c.3f.4f.5d.6d, | 1c.2c.3f.4f.5d.6e, | 1c.2c.3f.4f.5d.6f, 1c.2c.3f.4f.5e.6a, |
| 1c.2c.3f.4f.5e.6b, | 1c.2c.3f.4f.5e.6c, | 1c.2c.3f.4f.5e.6d, | 1c.2c.3f.4f.5e.6e, 1c.2c.3f.4f.5e.6f, |
| 1c.2c.3f.4f.5f.6a, | 1c.2c.3f.4f.5f.6b, | 1c.2c.3f.4f.5f.6c, | 1c.2c.3f.4f.5f.6d, 1c.2c.3f.4f.5f.6e, |
| 1c.2c.3f.4f.5f.6f, | 1c.2d.3a.4a.5a.6a, | 1c.2d.3a.4a.5a.6b, | 1c.2d.3a.4a.5a.6c, |
| 1c.2d.3a.4a.5a.6d, | 1c.2d.3a.4a.5a.6e, | 1c.2d.3a.4a.5a.6f, | 1c.2d.3a.4a.5b.6a, |
| 1c.2d.3a.4a.5b.6b, | 1c.2d.3a.4a.5b.6c, | 1c.2d.3a.4a.5b.6d, | 1c.2d.3a.4a.5b.6e, |
| 1c.2d.3a.4a.5b.6f, | 1c.2d.3a.4a.5c.6a, | 1c.2d.3a.4a.5c.6b, | 1c.2d.3a.4a.5c.6c, |
| 1c.2d.3a.4a.5c.6d, | 1c.2d.3a.4a.5c.6e, | 1c.2d.3a.4a.5c.6f, | 1c.2d.3a.4a.5d.6a, |
| 1c.2d.3a.4a.5d.6b, | 1c.2d.3a.4a.5d.6c, | 1c.2d.3a.4a.5d.6d, | 1c.2d.3a.4a.5d.6e, |
| 1c.2d.3a.4a.5d.6f, | 1c.2d.3a.4a.5e.6a, | 1c.2d.3a.4a.5e.6b, | 1c.2d.3a.4a.5e.6c, |
| 1c.2d.3a.4a.5e.6d, | 1c.2d.3a.4a.5e.6e, | 1c.2d.3a.4a.5e.6f, | 1c.2d.3a.4a.5f.6a, |
| 1c.2d.3a.4a.5f.6b, | 1c.2d.3a.4a.5f.6c, | 1c.2d.3a.4a.5f.6d, | 1c.2d.3a.4a.5f.6e, 1c.2d.3a.4a.5f.6f, |
| 1c.2d.3a.4b.5a.6a, | 1c.2d.3a.4b.5a.6b, | 1c.2d.3a.4b.5a.6c, | 1c.2d.3a.4b.5a.6d, |
| 1c.2d.3a.4b.5a.6e, | 1c.2d.3a.4b.5a.6f, | 1c.2d.3a.4b.5b.6a, | 1c.2d.3a.4b.5b.6b, |
| 1c.2d.3a.4b.5b.6c, | 1c.2d.3a.4b.5b.6d, | 1c.2d.3a.4b.5b.6e, | 1c.2d.3a.4b.5b.6f, |
| 1c.2d.3a.4b.5c.6a, | 1c.2d.3a.4b.5c.6b, | 1c.2d.3a.4b.5c.6c, | 1c.2d.3a.4b.5c.6d, |
| 1c.2d.3a.4b.5c.6e, | 1c.2d.3a.4b.5c.6f, | 1c.2d.3a.4b.5d.6a, | 1c.2d.3a.4b.5d.6b, |
| 1c.2d.3a.4b.5d.6c, | 1c.2d.3a.4b.5d.6d, | 1c.2d.3a.4b.5d.6e, | 1c.2d.3a.4b.5d.6f, |
| 1c.2d.3a.4b.5e.6a, | 1c.2d.3a.4b.5e.6b, | 1c.2d.3a.4b.5e.6c, | 1c.2d.3a.4b.5e.6d, |
| 1c.2d.3a.4b.5e.6e, | 1c.2d.3a.4b.5e.6f, | 1c.2d.3a.4b.5f.6a, | 1c.2d.3a.4b.5f.6b, |
| 1c.2d.3a.4b.5f.6c, | 1c.2d.3a.4b.5f.6d, | 1c.2d.3a.4b.5f.6e, | 1c.2d.3a.4b.5f.6f, |
| 1c.2d.3a.4c.5a.6a, | 1c.2d.3a.4c.5a.6b, | 1c.2d.3a.4c.5a.6c, | 1c.2d.3a.4c.5a.6d, |
| 1c.2d.3a.4c.5a.6e, | 1c.2d.3a.4c.5a.6f, | 1c.2d.3a.4c.5b.6a, | 1c.2d.3a.4c.5b.6b, |
| 1c.2d.3a.4c.5b.6c, | 1c.2d.3a.4c.5b.6d, | 1c.2d.3a.4c.5b.6e, | 1c.2d.3a.4c.5b.6f, |
| 1c.2d.3a.4c.5c.6a, | 1c.2d.3a.4c.5c.6b, | 1c.2d.3a.4c.5c.6c, | 1c.2d.3a.4c.5c.6d, |
| 1c.2d.3a.4c.5c.6e, | 1c.2d.3a.4c.5c.6f, | 1c.2d.3a.4c.5d.6a, | 1c.2d.3a.4c.5d.6b, |
| 1c.2d.3a.4c.5d.6c, | 1c.2d.3a.4c.5d.6d, | 1c.2d.3a.4c.5d.6e, | 1c.2d.3a.4c.5d.6f, |
| 1c.2d.3a.4c.5e.6a, | 1c.2d.3a.4c.5e.6b, | 1c.2d.3a.4c.5e.6c, | 1c.2d.3a.4c.5e.6d, |
| 1c.2d.3a.4c.5e.6e, | 1c.2d.3a.4c.5e.6f, | 1c.2d.3a.4c.5f.6a, | 1c.2d.3a.4c.5f.6b, 1c.2d.3a.4c.5f.6c, |
| 1c.2d.3a.4c.5f.6d, | 1c.2d.3a.4c.5f.6e, | 1c.2d.3a.4c.5f.6f, | 1c.2d.3a.4d.5a.6a, |
| 1c.2d.3a.4d.5a.6b, | 1c.2d.3a.4d.5a.6c, | 1c.2d.3a.4d.5a.6d, | 1c.2d.3a.4d.5a.6e, |
| 1c.2d.3a.4d.5a.6f, | 1c.2d.3a.4d.5b.6a, | 1c.2d.3a.4d.5b.6b, | 1c.2d.3a.4d.5b.6c, |
| 1c.2d.3a.4d.5b.6d, | 1c.2d.3a.4d.5b.6e, | 1c.2d.3a.4d.5b.6f, | 1c.2d.3a.4d.5c.6a, |

TABLE 7-continued

List of Compounds of Formula (II)

| | | | | |
|---|---|---|---|---|
| 1c.2d.3a.4d.5c.6b, | 1c.2d.3a.4d.5c.6c, | 1c.2d.3a.4d.5c.6d, | 1c.2d.3a.4d.5c.6e, | |
| 1c.2d.3a.4d.5c.6f, | 1c.2d.3a.4d.5d.6a, | 1c.2d.3a.4d.5d.6b, | 1c.2d.3a.4d.5d.6c, | |
| 1c.2d.3a.4d.5d.6d, | 1c.2d.3a.4d.5d.6e, | 1c.2d.3a.4d.5d.6f, | 1c.2d.3a.4d.5e.6a, | |
| 1c.2d.3a.4d.5e.6b, | 1c.2d.3a.4d.5e.6c, | 1c.2d.3a.4d.5e.6d, | 1c.2d.3a.4d.5e.6e, | |
| 1c.2d.3a.4d.5e.6f, | 1c.2d.3a.4d.5f.6a, | 1c.2d.3a.4d.5f.6b, | 1c.2d.3a.4d.5f.6c, | |
| 1c.2d.3a.4d.5f.6d, | 1c.2d.3a.4d.5f.6e, | 1c.2d.3a.4d.5f.6f, | 1c.2d.3a.4e.5a.6a, | |
| 1c.2d.3a.4e.5a.6b, | 1c.2d.3a.4e.5a.6c, | 1c.2d.3a.4e.5a.6d, | 1c.2d.3a.4e.5a.6e, | |
| 1c.2d.3a.4e.5a.6f, | 1c.2d.3a.4e.5b.6a, | 1c.2d.3a.4e.5b.6b, | 1c.2d.3a.4e.5b.6c, | |
| 1c.2d.3a.4e.5b.6d, | 1c.2d.3a.4e.5b.6e, | 1c.2d.3a.4e.5b.6f, | 1c.2d.3a.4e.5c.6a, | |
| 1c.2d.3a.4e.5c.6b, | 1c.2d.3a.4e.5c.6c, | 1c.2d.3a.4e.5c.6d, | 1c.2d.3a.4e.5c.6e, | |
| 1c.2d.3a.4e.5c.6f, | 1c.2d.3a.4e.5d.6a, | 1c.2d.3a.4e.5d.6b, | 1c.2d.3a.4e.5d.6c, | |
| 1c.2d.3a.4e.5d.6d, | 1c.2d.3a.4e.5d.6e, | 1c.2d.3a.4e.5d.6f, | 1c.2d.3a.4e.5e.6a, | |
| 1c.2d.3a.4e.5e.6b, | 1c.2d.3a.4e.5e.6c, | 1c.2d.3a.4e.5e.6d, | 1c.2d.3a.4e.5e.6e, | |
| 1c.2d.3a.4e.5e.6f, | 1c.2d.3a.4e.5f.6a, | 1c.2d.3a.4e.5f.6b, | 1c.2d.3a.4e.5f.6c, | |
| 1c.2d.3a.4e.5f.6d, | 1c.2d.3a.4e.5f.6e, | 1c.2d.3a.4e.5f.6f, | 1c.2d.3a.4f.5a.6a, | 1c.2d.3a.4f.5a.6b, |
| 1c.2d.3a.4f.5a.6c, | 1c.2d.3a.4f.5a.6d, | 1c.2d.3a.4f.5a.6e, | 1c.2d.3a.4f.5a.6f, | 1c.2d.3a.4f.5b.6a, |
| 1c.2d.3a.4f.5b.6b, | 1c.2d.3a.4f.5b.6c, | 1c.2d.3a.4f.5b.6d, | 1c.2d.3a.4f.5b.6e, | |
| 1c.2d.3a.4f.5b.6f, | 1c.2d.3a.4f.5c.6a, | 1c.2d.3a.4f.5c.6b, | 1c.2d.3a.4f.5c.6c, | 1c.2d.3a.4f.5c.6d, |
| 1c.2d.3a.4f.5c.6e, | 1c.2d.3a.4f.5c.6f, | 1c.2d.3a.4f.5d.6a, | 1c.2d.3a.4f.5d.6b, | |
| 1c.2d.3a.4f.5d.6c, | 1c.2d.3a.4f.5d.6d, | 1c.2d.3a.4f.5d.6e, | 1c.2d.3a.4f.5d.6f, | |
| 1c.2d.3a.4f.5e.6a, | 1c.2d.3a.4f.5e.6b, | 1c.2d.3a.4f.5e.6c, | 1c.2d.3a.4f.5e.6d, | |
| 1c.2d.3a.4f.5e.6e, | 1c.2d.3a.4f.5e.6f, | 1c.2d.3a.4f.5f.6a, | 1c.2d.3a.4f.5f.6b, | 1c.2d.3a.4f.5f.6c, |
| 1c.2d.3a.4f.5f.6d, | 1c.2d.3a.4f.5f.6e, | 1c.2d.3a.4f.5f.6f, | 1c.2d.3b.4a.5a.6a, | 1c.2d.3b.4a.5a.6b, |
| 1c.2d.3b.4a.5a.6c, | 1c.2d.3b.4a.5a.6d, | 1c.2d.3b.4a.5a.6e, | 1c.2d.3b.4a.5a.6f, | |
| 1c.2d.3b.4a.5b.6a, | 1c.2d.3b.4a.5b.6b, | 1c.2d.3b.4a.5b.6c, | 1c.2d.3b.4a.5b.6d, | |
| 1c.2d.3b.4a.5b.6e, | 1c.2d.3b.4a.5b.6f, | 1c.2d.3b.4a.5c.6a, | 1c.2d.3b.4a.5c.6b, | |
| 1c.2d.3b.4a.5c.6c, | 1c.2d.3b.4a.5c.6d, | 1c.2d.3b.4a.5c.6e, | 1c.2d.3b.4a.5c.6f, | |
| 1c.2d.3b.4a.5d.6a, | 1c.2d.3b.4a.5d.6b, | 1c.2d.3b.4a.5d.6c, | 1c.2d.3b.4a.5d.6d, | |
| 1c.2d.3b.4a.5d.6e, | 1c.2d.3b.4a.5d.6f, | 1c.2d.3b.4a.5e.6a, | 1c.2d.3b.4a.5e.6b, | |
| 1c.2d.3b.4a.5e.6c, | 1c.2d.3b.4a.5e.6d, | 1c.2d.3b.4a.5e.6e, | 1c.2d.3b.4a.5e.6f, | |
| 1c.2d.3b.4a.5f.6a, | 1c.2d.3b.4a.5f.6b, | 1c.2d.3b.4a.5f.6c, | 1c.2d.3b.4a.5f.6d, | |
| 1c.2d.3b.4a.5f.6e, | 1c.2d.3b.4a.5f.6f, | 1c.2d.3b.4b.5a.6a, | 1c.2d.3b.4b.5a.6b, | |
| 1c.2d.3b.4b.5a.6c, | 1c.2d.3b.4b.5a.6d, | 1c.2d.3b.4b.5a.6e, | 1c.2d.3b.4b.5a.6f, | |
| 1c.2d.3b.4b.5b.6a, | 1c.2d.3b.4b.5b.6b, | 1c.2d.3b.4b.5b.6c, | 1c.2d.3b.4b.5b.6d, | |
| 1c.2d.3b.4b.5b.6e, | 1c.2d.3b.4b.5b.6f, | 1c.2d.3b.4b.5c.6a, | 1c.2d.3b.4b.5c.6b, | |
| 1c.2d.3b.4b.5c.6c, | 1c.2d.3b.4b.5c.6d, | 1c.2d.3b.4b.5c.6e, | 1c.2d.3b.4b.5c.6f, | |
| 1c.2d.3b.4b.5d.6a, | 1c.2d.3b.4b.5d.6b, | 1c.2d.3b.4b.5d.6c, | 1c.2d.3b.4b.5d.6d, | |
| 1c.2d.3b.4b.5d.6e, | 1c.2d.3b.4b.5d.6f, | 1c.2d.3b.4b.5e.6a, | 1c.2d.3b.4b.5e.6b, | |
| 1c.2d.3b.4b.5e.6c, | 1c.2d.3b.4b.5e.6d, | 1c.2d.3b.4b.5e.6e, | 1c.2d.3b.4b.5e.6f, | |
| 1c.2d.3b.4b.5f.6a, | 1c.2d.3b.4b.5f.6b, | 1c.2d.3b.4b.5f.6c, | 1c.2d.3b.4b.5f.6d, | |
| 1c.2d.3b.4b.5f.6e, | 1c.2d.3b.4b.5f.6f, | 1c.2d.3b.4c.5a.6a, | 1c.2d.3b.4c.5a.6b, | |
| 1c.2d.3b.4c.5a.6c, | 1c.2d.3b.4c.5a.6d, | 1c.2d.3b.4c.5a.6e, | 1c.2d.3b.4c.5a.6f, | |
| 1c.2d.3b.4c.5b.6a, | 1c.2d.3b.4c.5b.6b, | 1c.2d.3b.4c.5b.6c, | 1c.2d.3b.4c.5b.6d, | |
| 1c.2d.3b.4c.5b.6e, | 1c.2d.3b.4c.5b.6f, | 1c.2d.3b.4c.5c.6a, | 1c.2d.3b.4c.5c.6b, | |
| 1c.2d.3b.4c.5c.6c, | 1c.2d.3b.4c.5c.6d, | 1c.2d.3b.4c.5c.6e, | 1c.2d.3b.4c.5c.6f, | |
| 1c.2d.3b.4c.5d.6a, | 1c.2d.3b.4c.5d.6b, | 1c.2d.3b.4c.5d.6c, | 1c.2d.3b.4c.5d.6d, | |
| 1c.2d.3b.4c.5d.6e, | 1c.2d.3b.4c.5d.6f, | 1c.2d.3b.4c.5e.6a, | 1c.2d.3b.4c.5e.6b, | |
| 1c.2d.3b.4c.5e.6c, | 1c.2d.3b.4c.5e.6d, | 1c.2d.3b.4c.5e.6e, | 1c.2d.3b.4c.5e.6f, | |
| 1c.2d.3b.4c.5f.6a, | 1c.2d.3b.4c.5f.6b, | 1c.2d.3b.4c.5f.6c, | 1c.2d.3b.4c.5f.6d, | |
| 1c.2d.3b.4c.5f.6e, | 1c.2d.3b.4c.5f.6f, | 1c.2d.3b.4d.5a.6a, | 1c.2d.3b.4d.5a.6b, | |
| 1c.2d.3b.4d.5a.6c, | 1c.2d.3b.4d.5a.6d, | 1c.2d.3b.4d.5a.6e, | 1c.2d.3b.4d.5a.6f, | |
| 1c.2d.3b.4d.5b.6a, | 1c.2d.3b.4d.5b.6b, | 1c.2d.3b.4d.5b.6c, | 1c.2d.3b.4d.5b.6d, | |
| 1c.2d.3b.4d.5b.6e, | 1c.2d.3b.4d.5b.6f, | 1c.2d.3b.4d.5c.6a, | 1c.2d.3b.4d.5c.6b, | |
| 1c.2d.3b.4d.5c.6c, | 1c.2d.3b.4d.5c.6d, | 1c.2d.3b.4d.5c.6e, | 1c.2d.3b.4d.5c.6f, | |
| 1c.2d.3b.4d.5d.6a, | 1c.2d.3b.4d.5d.6b, | 1c.2d.3b.4d.5d.6c, | 1c.2d.3b.4d.5d.6d, | |
| 1c.2d.3b.4d.5d.6e, | 1c.2d.3b.4d.5d.6f, | 1c.2d.3b.4d.5e.6a, | 1c.2d.3b.4d.5e.6b, | |
| 1c.2d.3b.4d.5e.6c, | 1c.2d.3b.4d.5e.6d, | 1c.2d.3b.4d.5e.6e, | 1c.2d.3b.4d.5e.6f, | |
| 1c.2d.3b.4d.5f.6a, | 1c.2d.3b.4d.5f.6b, | 1c.2d.3b.4d.5f.6c, | 1c.2d.3b.4d.5f.6d, | |
| 1c.2d.3b.4d.5f.6e, | 1c.2d.3b.4d.5f.6f, | 1c.2d.3b.4e.5a.6a, | 1c.2d.3b.4e.5a.6b, | |
| 1c.2d.3b.4e.5a.6c, | 1c.2d.3b.4e.5a.6d, | 1c.2d.3b.4e.5a.6e, | 1c.2d.3b.4e.5a.6f, | |
| 1c.2d.3b.4e.5b.6a, | 1c.2d.3b.4e.5b.6b, | 1c.2d.3b.4e.5b.6c, | 1c.2d.3b.4e.5b.6d, | |
| 1c.2d.3b.4e.5b.6e, | 1c.2d.3b.4e.5b.6f, | 1c.2d.3b.4e.5c.6a, | 1c.2d.3b.4e.5c.6b, | |
| 1c.2d.3b.4e.5c.6c, | 1c.2d.3b.4e.5c.6d, | 1c.2d.3b.4e.5c.6e, | 1c.2d.3b.4e.5c.6f, | |
| 1c.2d.3b.4e.5d.6a, | 1c.2d.3b.4e.5d.6b, | 1c.2d.3b.4e.5d.6c, | 1c.2d.3b.4e.5d.6d, | |
| 1c.2d.3b.4e.5d.6e, | 1c.2d.3b.4e.5d.6f, | 1c.2d.3b.4e.5e.6a, | 1c.2d.3b.4e.5e.6b, | |
| 1c.2d.3b.4e.5e.6c, | 1c.2d.3b.4e.5e.6d, | 1c.2d.3b.4e.5e.6e, | 1c.2d.3b.4e.5e.6f, | |
| 1c.2d.3b.4e.5f.6a, | 1c.2d.3b.4e.5f.6b, | 1c.2d.3b.4e.5f.6c, | 1c.2d.3b.4e.5f.6d, | |
| 1c.2d.3b.4e.5f.6e, | 1c.2d.3b.4e.5f.6f, | 1c.2d.3b.4f.5a.6a, | 1c.2d.3b.4f.5a.6b, | |
| 1c.2d.3b.4f.5a.6c, | 1c.2d.3b.4f.5a.6d, | 1c.2d.3b.4f.5a.6e, | 1c.2d.3b.4f.5a.6f, | |
| 1c.2d.3b.4f.5b.6a, | 1c.2d.3b.4f.5b.6b, | 1c.2d.3b.4f.5b.6c, | 1c.2d.3b.4f.5b.6d, | |
| 1c.2d.3b.4f.5b.6e, | 1c.2d.3b.4f.5b.6f, | 1c.2d.3b.4f.5c.6a, | 1c.2d.3b.4f.5c.6b, | |
| 1c.2d.3b.4f.5c.6c, | 1c.2d.3b.4f.5c.6d, | 1c.2d.3b.4f.5c.6e, | 1c.2d.3b.4f.5c.6f, | |
| 1c.2d.3b.4f.5d.6a, | 1c.2d.3b.4f.5d.6b, | 1c.2d.3b.4f.5d.6c, | 1c.2d.3b.4f.5d.6d, | |
| 1c.2d.3b.4f.5d.6e, | 1c.2d.3b.4f.5d.6f, | 1c.2d.3b.4f.5e.6a, | 1c.2d.3b.4f.5e.6b, | |
| 1c.2d.3b.4f.5e.6c, | 1c.2d.3b.4f.5e.6d, | 1c.2d.3b.4f.5e.6e, | 1c.2d.3b.4f.5e.6f, | 1c.2d.3b.4f.5f.6a, |
| 1c.2d.3b.4f.5f.6b, | 1c.2d.3b.4f.5f.6c, | 1c.2d.3b.4f.5f.6d, | 1c.2d.3b.4f.5f.6e, | 1c.2d.3b.4f.5f.6f, |
| 1c.2d.3c.4a.5a.6a, | 1c.2d.3c.4a.5a.6b, | 1c.2d.3c.4a.5a.6c, | 1c.2d.3c.4a.5a.6d, | |
| 1c.2d.3c.4a.5a.6e, | 1c.2d.3c.4a.5a.6f, | 1c.2d.3c.4a.5b.6a, | 1c.2d.3c.4a.5b.6b, | |

TABLE 7-continued

List of Compounds of Formula (II)

| | | | |
|---|---|---|---|
| 1c.2d.3c.4a.5b.6c, | 1c.2d.3c.4a.5b.6d, | 1c.2d.3c.4a.5b.6e, | 1c.2d.3c.4a.5b.6f, |
| 1c.2d.3c.4a.5c.6a, | 1c.2d.3c.4a.5c.6b, | 1c.2d.3c.4a.5c.6c, | 1c.2d.3c.4a.5c.6d, |
| 1c.2d.3c.4a.5c.6e, | 1c.2d.3c.4a.5c.6f, | 1c.2d.3c.4a.5d.6a, | 1c.2d.3c.4a.5d.6b, |
| 1c.2d.3c.4a.5d.6c, | 1c.2d.3c.4a.5d.6d, | 1c.2d.3c.4a.5d.6e, | 1c.2d.3c.4a.5d.6f, |
| 1c.2d.3c.4a.5e.6a, | 1c.2d.3c.4a.5e.6b, | 1c.2d.3c.4a.5e.6c, | 1c.2d.3c.4a.5e.6d, |
| 1c.2d.3c.4a.5e.6e, | 1c.2d.3c.4a.5e.6f, | 1c.2d.3c.4a.5f.6a, | 1c.2d.3c.4a.5f.6b, | 1c.2d.3c.4a.5f.6c, |
| 1c.2d.3c.4a.5f.6d, | 1c.2d.3c.4a.5f.6e, | 1c.2d.3c.4a.5f.6f, | 1c.2d.3c.4b.5a.6a, |
| 1c.2d.3c.4b.5a.6b, | 1c.2d.3c.4b.5a.6c, | 1c.2d.3c.4b.5a.6d, | 1c.2d.3c.4b.5a.6e, |
| 1c.2d.3c.4b.5a.6f, | 1c.2d.3c.4b.5b.6a, | 1c.2d.3c.4b.5b.6b, | 1c.2d.3c.4b.5b.6c, |
| 1c.2d.3c.4b.5b.6d, | 1c.2d.3c.4b.5b.6e, | 1c.2d.3c.4b.5b.6f, | 1c.2d.3c.4b.5c.6a, |
| 1c.2d.3c.4b.5c.6b, | 1c.2d.3c.4b.5c.6c, | 1c.2d.3c.4b.5c.6d, | 1c.2d.3c.4b.5c.6e, |
| 1c.2d.3c.4b.5c.6f, | 1c.2d.3c.4b.5d.6a, | 1c.2d.3c.4b.5d.6b, | 1c.2d.3c.4b.5d.6c, |
| 1c.2d.3c.4b.5d.6d, | 1c.2d.3c.4b.5d.6e, | 1c.2d.3c.4b.5d.6f, | 1c.2d.3c.4b.5e.6a, |
| 1c.2d.3c.4b.5e.6b, | 1c.2d.3c.4b.5e.6c, | 1c.2d.3c.4b.5e.6d, | 1c.2d.3c.4b.5e.6e, |
| 1c.2d.3c.4b.5e.6f, | 1c.2d.3c.4b.5f.6a, | 1c.2d.3c.4b.5f.6b, | 1c.2d.3c.4b.5f.6c, |
| 1c.2d.3c.4b.5f.6d, | 1c.2d.3c.4b.5f.6e, | 1c.2d.3c.4b.5f.6f, | 1c.2d.3c.4c.5a.6a, |
| 1c.2d.3c.4c.5a.6b, | 1c.2d.3c.4c.5a.6c, | 1c.2d.3c.4c.5a.6d, | 1c.2d.3c.4c.5a.6e, |
| 1c.2d.3c.4c.5a.6f, | 1c.2d.3c.4c.5b.6a, | 1c.2d.3c.4c.5b.6b, | 1c.2d.3c.4c.5b.6c, |
| 1c.2d.3c.4c.5b.6e, | 1c.2d.3c.4c.5b.6f, | 1c.2d.3c.4c.5c.6a, | |
| 1c.2d.3c.4c.5c.6b, | 1c.2d.3c.4c.5c.6c, | 1c.2d.3c.4c.5c.6d, | 1c.2d.3c.4c.5c.6e, | 1c.2d.3c.4c.5c.6f, |
| 1c.2d.3c.4c.5d.6a, | 1c.2d.3c.4c.5d.6b, | 1c.2d.3c.4c.5d.6c, | 1c.2d.3c.4c.5d.6d, |
| 1c.2d.3c.4c.5d.6e, | 1c.2d.3c.4c.5d.6f, | 1c.2d.3c.4c.5e.6a, | 1c.2d.3c.4c.5e.6b, |
| 1c.2d.3c.4c.5e.6c, | 1c.2d.3c.4c.5e.6d, | 1c.2d.3c.4c.5e.6e, | 1c.2d.3c.4c.5e.6f, | 1c.2d.3c.4c.5f.6a, |
| 1c.2d.3c.4c.5f.6b, | 1c.2d.3c.4c.5f.6c, | 1c.2d.3c.4c.5f.6d, | 1c.2d.3c.4c.5f.6e, | 1c.2d.3c.4c.5f.6f, |
| 1c.2d.3c.4d.5a.6a, | 1c.2d.3c.4d.5a.6b, | 1c.2d.3c.4d.5a.6c, | 1c.2d.3c.4d.5a.6d, |
| 1c.2d.3c.4d.5a.6e, | 1c.2d.3c.4d.5a.6f, | 1c.2d.3c.4d.5b.6a, | 1c.2d.3c.4d.5b.6b, |
| 1c.2d.3c.4d.5b.6c, | 1c.2d.3c.4d.5b.6d, | 1c.2d.3c.4d.5b.6e, | 1c.2d.3c.4d.5b.6f, |
| 1c.2d.3c.4d.5c.6a, | 1c.2d.3c.4d.5c.6b, | 1c.2d.3c.4d.5c.6c, | 1c.2d.3c.4d.5c.6d, |
| 1c.2d.3c.4d.5c.6e, | 1c.2d.3c.4d.5c.6f, | 1c.2d.3c.4d.5d.6a, | 1c.2d.3c.4d.5d.6b, |
| 1c.2d.3c.4d.5d.6c, | 1c.2d.3c.4d.5d.6d, | 1c.2d.3c.4d.5d.6e, | 1c.2d.3c.4d.5d.6f, |
| 1c.2d.3c.4d.5e.6a, | 1c.2d.3c.4d.5e.6b, | 1c.2d.3c.4d.5e.6c, | 1c.2d.3c.4d.5e.6d, |
| 1c.2d.3c.4d.5e.6e, | 1c.2d.3c.4d.5e.6f, | 1c.2d.3c.4d.5f.6a, | 1c.2d.3c.4d.5f.6b, |
| 1c.2d.3c.4d.5f.6c, | 1c.2d.3c.4d.5f.6d, | 1c.2d.3c.4d.5f.6e, | 1c.2d.3c.4d.5f.6f, |
| 1c.2d.3c.4e.5a.6a, | 1c.2d.3c.4e.5a.6b, | 1c.2d.3c.4e.5a.6c, | 1c.2d.3c.4e.5a.6d, |
| 1c.2d.3c.4e.5a.6e, | 1c.2d.3c.4e.5a.6f, | 1c.2d.3c.4e.5b.6a, | 1c.2d.3c.4e.5b.6b, |
| 1c.2d.3c.4e.5b.6c, | 1c.2d.3c.4e.5b.6d, | 1c.2d.3c.4e.5b.6e, | 1c.2d.3c.4e.5b.6f, |
| 1c.2d.3c.4e.5c.6a, | 1c.2d.3c.4e.5c.6b, | 1c.2d.3c.4e.5c.6c, | 1c.2d.3c.4e.5c.6d, |
| 1c.2d.3c.4e.5c.6e, | 1c.2d.3c.4e.5c.6f, | 1c.2d.3c.4e.5d.6a, | 1c.2d.3c.4e.5d.6b, |
| 1c.2d.3c.4e.5d.6c, | 1c.2d.3c.4e.5d.6d, | 1c.2d.3c.4e.5d.6e, | 1c.2d.3c.4e.5d.6f, |
| 1c.2d.3c.4e.5e.6a, | 1c.2d.3c.4e.5e.6b, | 1c.2d.3c.4e.5e.6c, | 1c.2d.3c.4e.5e.6d, |
| 1c.2d.3c.4e.5e.6e, | 1c.2d.3c.4e.5e.6f, | 1c.2d.3c.4e.5f.6a, | 1c.2d.3c.4e.5f.6b, | 1c.2d.3c.4e.5f.6c, |
| 1c.2d.3c.4e.5f.6d, | 1c.2d.3c.4e.5f.6e, | 1c.2d.3c.4e.5f.6f, | 1c.2d.3c.4f.5a.6a, | 1c.2d.3c.4f.5a.6b, |
| 1c.2d.3c.4f.5a.6c, | 1c.2d.3c.4f.5a.6d, | 1c.2d.3c.4f.5a.6e, | 1c.2d.3c.4f.5a.6f, | 1c.2d.3c.4f.5b.6a, |
| 1c.2d.3c.4f.5b.6b, | 1c.2d.3c.4f.5b.6c, | 1c.2d.3c.4f.5b.6d, | 1c.2d.3c.4f.5b.6e, | 1c.2d.3c.4f.5b.6f, |
| 1c.2d.3c.4f.5c.6a, | 1c.2d.3c.4f.5c.6b, | 1c.2d.3c.4f.5c.6c, | 1c.2d.3c.4f.5c.6d, | 1c.2d.3c.4f.5c.6e, |
| 1c.2d.3c.4f.5c.6f, | 1c.2d.3c.4f.5d.6a, | 1c.2d.3c.4f.5d.6b, | 1c.2d.3c.4f.5d.6c, |
| 1c.2d.3c.4f.5d.6d, | 1c.2d.3c.4f.5d.6e, | 1c.2d.3c.4f.5d.6f, | 1c.2d.3c.4f.5e.6a, |
| 1c.2d.3c.4f.5e.6b, | 1c.2d.3c.4f.5e.6c, | 1c.2d.3c.4f.5e.6d, | 1c.2d.3c.4f.5e.6e, | 1c.2d.3c.4f.5e.6f, |
| 1c.2d.3c.4f.5f.6a, | 1c.2d.3c.4f.5f.6b, | 1c.2d.3c.4f.5f.6c, | 1c.2d.3c.4f.5f.6d, | 1c.2d.3c.4f.5f.6e, |
| 1c.2d.3c.4f.5f.6f, | 1c.2d.3d.4a.5a.6a, | 1c.2d.3d.4a.5a.6b, | 1c.2d.3d.4a.5a.6c, |
| 1c.2d.3d.4a.5a.6d, | 1c.2d.3d.4a.5a.6e, | 1c.2d.3d.4a.5a.6f, | 1c.2d.3d.4a.5b.6a, |
| 1c.2d.3d.4a.5b.6b, | 1c.2d.3d.4a.5b.6c, | 1c.2d.3d.4a.5b.6d, | 1c.2d.3d.4a.5b.6e, |
| 1c.2d.3d.4a.5b.6f, | 1c.2d.3d.4a.5c.6a, | 1c.2d.3d.4a.5c.6b, | 1c.2d.3d.4a.5c.6c, |
| 1c.2d.3d.4a.5c.6d, | 1c.2d.3d.4a.5c.6e, | 1c.2d.3d.4a.5c.6f, | 1c.2d.3d.4a.5d.6a, |
| 1c.2d.3d.4a.5d.6b, | 1c.2d.3d.4a.5d.6c, | 1c.2d.3d.4a.5d.6d, | 1c.2d.3d.4a.5d.6e, |
| 1c.2d.3d.4a.5d.6f, | 1c.2d.3d.4a.5e.6a, | 1c.2d.3d.4a.5e.6b, | 1c.2d.3d.4a.5e.6c, |
| 1c.2d.3d.4a.5e.6d, | 1c.2d.3d.4a.5e.6e, | 1c.2d.3d.4a.5e.6f, | 1c.2d.3d.4a.5f.6a, |
| 1c.2d.3d.4a.5f.6b, | 1c.2d.3d.4a.5f.6c, | 1c.2d.3d.4a.5f.6d, | 1c.2d.3d.4a.5f.6e, |
| 1c.2d.3d.4a.5f.6f, | 1c.2d.3d.4b.5a.6a, | 1c.2d.3d.4b.5a.6b, | 1c.2d.3d.4b.5a.6c, |
| 1c.2d.3d.4b.5a.6d, | 1c.2d.3d.4b.5a.6e, | 1c.2d.3d.4b.5a.6f, | 1c.2d.3d.4b.5b.6a, |
| 1c.2d.3d.4b.5b.6b, | 1c.2d.3d.4b.5b.6c, | 1c.2d.3d.4b.5b.6d, | 1c.2d.3d.4b.5b.6e, |
| 1c.2d.3d.4b.5b.6f, | 1c.2d.3d.4b.5c.6a, | 1c.2d.3d.4b.5c.6b, | 1c.2d.3d.4b.5c.6c, |
| 1c.2d.3d.4b.5c.6d, | 1c.2d.3d.4b.5c.6e, | 1c.2d.3d.4b.5c.6f, | 1c.2d.3d.4b.5d.6a, |
| 1c.2d.3d.4b.5d.6b, | 1c.2d.3d.4b.5d.6c, | 1c.2d.3d.4b.5d.6d, | 1c.2d.3d.4b.5d.6e, |
| 1c.2d.3d.4b.5d.6f, | 1c.2d.3d.4b.5e.6a, | 1c.2d.3d.4b.5e.6b, | 1c.2d.3d.4b.5e.6c, |
| 1c.2d.3d.4b.5e.6d, | 1c.2d.3d.4b.5e.6e, | 1c.2d.3d.4b.5e.6f, | 1c.2d.3d.4b.5f.6a, |
| 1c.2d.3d.4b.5f.6b, | 1c.2d.3d.4b.5f.6c, | 1c.2d.3d.4b.5f.6d, | 1c.2d.3d.4b.5f.6e, |
| 1c.2d.3d.4b.5f.6f, | 1c.2d.3d.4c.5a.6a, | 1c.2d.3d.4c.5a.6b, | 1c.2d.3d.4c.5a.6c, |
| 1c.2d.3d.4c.5a.6d, | 1c.2d.3d.4c.5a.6e, | 1c.2d.3d.4c.5a.6f, | 1c.2d.3d.4c.5b.6a, |
| 1c.2d.3d.4c.5b.6b, | 1c.2d.3d.4c.5b.6c, | 1c.2d.3d.4c.5b.6d, | 1c.2d.3d.4c.5b.6e, |
| 1c.2d.3d.4c.5b.6f, | 1c.2d.3d.4c.5c.6a, | 1c.2d.3d.4c.5c.6b, | 1c.2d.3d.4c.5c.6c, |
| 1c.2d.3d.4c.5c.6d, | 1c.2d.3d.4c.5c.6e, | 1c.2d.3d.4c.5c.6f, | 1c.2d.3d.4c.5d.6a, |
| 1c.2d.3d.4c.5d.6b, | 1c.2d.3d.4c.5d.6c, | 1c.2d.3d.4c.5d.6d, | 1c.2d.3d.4c.5d.6e, |
| 1c.2d.3d.4c.5d.6f, | 1c.2d.3d.4c.5e.6a, | 1c.2d.3d.4c.5e.6b, | 1c.2d.3d.4c.5e.6c, |
| 1c.2d.3d.4c.5e.6d, | 1c.2d.3d.4c.5e.6e, | 1c.2d.3d.4c.5e.6f, | 1c.2d.3d.4c.5f.6a, |
| 1c.2d.3d.4c.5f.6b, | 1c.2d.3d.4c.5f.6c, | 1c.2d.3d.4c.5f.6d, | 1c.2d.3d.4c.5f.6e, |
| 1c.2d.3d.4c.5f.6f, | 1c.2d.3d.4d.5a.6a, | 1c.2d.3d.4d.5a.6b, | 1c.2d.3d.4d.5a.6c, |
| 1c.2d.3d.4d.5a.6d, | 1c.2d.3d.4d.5a.6e, | 1c.2d.3d.4d.5a.6f, | 1c.2d.3d.4d.5b.6a, |

TABLE 7-continued

List of Compounds of Formula (II)

| | | | | |
|---|---|---|---|---|
| 1c.2d.3d.4d.5b.6b, | 1c.2d.3d.4d.5b.6c, | 1c.2d.3d.4d.5b.6d, | 1c.2d.3d.4d.5b.6e, | |
| 1c.2d.3d.4d.5b.6f, | 1c.2d.3d.4d.5c.6a, | 1c.2d.3d.4d.5c.6b, | 1c.2d.3d.4d.5c.6c, | |
| 1c.2d.3d.4d.5c.6d, | 1c.2d.3d.4d.5c.6e, | 1c.2d.3d.4d.5c.6f, | 1c.2d.3d.4d.5d.6a, | |
| 1c.2d.3d.4d.5d.6b, | 1c.2d.3d.4d.5d.6c, | 1c.2d.3d.4d.5d.6d, | 1c.2d.3d.4d.5d.6e, | |
| 1c.2d.3d.4d.5d.6f, | 1c.2d.3d.4d.5e.6a, | 1c.2d.3d.4d.5e.6b, | 1c.2d.3d.4d.5e.6c, | |
| 1c.2d.3d.4d.5e.6d, | 1c.2d.3d.4d.5e.6e, | 1c.2d.3d.4d.5e.6f, | 1c.2d.3d.4d.5f.6a, | |
| 1c.2d.3d.4d.5f.6b, | 1c.2d.3d.4d.5f.6c, | 1c.2d.3d.4d.5f.6d, | 1c.2d.3d.4d.5f.6e, | |
| 1c.2d.3d.4d.5f.6f, | 1c.2d.3d.4e.5a.6a, | 1c.2d.3d.4e.5a.6b, | 1c.2d.3d.4e.5a.6c, | |
| 1c.2d.3d.4e.5a.6d, | 1c.2d.3d.4e.5a.6e, | 1c.2d.3d.4e.5a.6f, | 1c.2d.3d.4e.5b.6a, | |
| 1c.2d.3d.4e.5b.6b, | 1c.2d.3d.4e.5b.6c, | 1c.2d.3d.4e.5b.6d, | 1c.2d.3d.4e.5b.6e, | |
| 1c.2d.3d.4e.5b.6f, | 1c.2d.3d.4e.5c.6a, | 1c.2d.3d.4e.5c.6b, | 1c.2d.3d.4e.5c.6c, | |
| 1c.2d.3d.4e.5c.6d, | 1c.2d.3d.4e.5c.6e, | 1c.2d.3d.4e.5c.6f, | 1c.2d.3d.4e.5d.6a, | |
| 1c.2d.3d.4e.5d.6b, | 1c.2d.3d.4e.5d.6c, | 1c.2d.3d.4e.5d.6d, | 1c.2d.3d.4e.5d.6e, | |
| 1c.2d.3d.4e.5d.6f, | 1c.2d.3d.4e.5e.6a, | 1c.2d.3d.4e.5e.6b, | 1c.2d.3d.4e.5e.6c, | |
| 1c.2d.3d.4e.5e.6d, | 1c.2d.3d.4e.5e.6e, | 1c.2d.3d.4e.5e.6f, | 1c.2d.3d.4e.5f.6a, | |
| 1c.2d.3d.4e.5f.6b, | 1c.2d.3d.4e.5f.6c, | 1c.2d.3d.4e.5f.6d, | 1c.2d.3d.4e.5f.6e, | |
| 1c.2d.3d.4e.5f.6f, | 1c.2d.3d.4f.5a.6a, | 1c.2d.3d.4f.5a.6b, | 1c.2d.3d.4f.5a.6c, | |
| 1c.2d.3d.4f.5a.6d, | 1c.2d.3d.4f.5a.6e, | 1c.2d.3d.4f.5a.6f, | 1c.2d.3d.4f.5b.6a, | |
| 1c.2d.3d.4f.5b.6b, | 1c.2d.3d.4f.5b.6c, | 1c.2d.3d.4f.5b.6d, | 1c.2d.3d.4f.5b.6e, | |
| 1c.2d.3d.4f.5b.6f, | 1c.2d.3d.4f.5c.6a, | 1c.2d.3d.4f.5c.6b, | 1c.2d.3d.4f.5c.6c, | |
| 1c.2d.3d.4f.5c.6d, | 1c.2d.3d.4f.5c.6e, | 1c.2d.3d.4f.5c.6f, | 1c.2d.3d.4f.5d.6a, | |
| 1c.2d.3d.4f.5d.6b, | 1c.2d.3d.4f.5d.6c, | 1c.2d.3d.4f.5d.6d, | 1c.2d.3d.4f.5d.6e, | |
| 1c.2d.3d.4f.5d.6f, | 1c.2d.3d.4f.5e.6a, | 1c.2d.3d.4f.5e.6b, | 1c.2d.3d.4f.5e.6c, | |
| 1c.2d.3d.4f.5e.6d, | 1c.2d.3d.4f.5e.6e, | 1c.2d.3d.4f.5e.6f, | 1c.2d.3d.4f.5f.6a, | |
| 1c.2d.3d.4f.5f.6b, | 1c.2d.3d.4f.5f.6c, | 1c.2d.3d.4f.5f.6d, | 1c.2d.3d.4f.5f.6e, | 1c.2d.3d.4f.5f.6f, |
| 1c.2d.3e.4a.5a.6a, | 1c.2d.3e.4a.5a.6b, | 1c.2d.3e.4a.5a.6c, | 1c.2d.3e.4a.5a.6d, | |
| 1c.2d.3e.4a.5a.6e, | 1c.2d.3e.4a.5a.6f, | 1c.2d.3e.4a.5b.6a, | 1c.2d.3e.4a.5b.6b, | |
| 1c.2d.3e.4a.5b.6c, | 1c.2d.3e.4a.5b.6d, | 1c.2d.3e.4a.5b.6e, | 1c.2d.3e.4a.5b.6f, | |
| 1c.2d.3e.4a.5c.6a, | 1c.2d.3e.4a.5c.6b, | 1c.2d.3e.4a.5c.6c, | 1c.2d.3e.4a.5c.6d, | |
| 1c.2d.3e.4a.5c.6e, | 1c.2d.3e.4a.5c.6f, | 1c.2d.3e.4a.5d.6a, | 1c.2d.3e.4a.5d.6b, | |
| 1c.2d.3e.4a.5d.6c, | 1c.2d.3e.4a.5d.6d, | 1c.2d.3e.4a.5d.6e, | 1c.2d.3e.4a.5d.6f, | |
| 1c.2d.3e.4a.5e.6a, | 1c.2d.3e.4a.5e.6b, | 1c.2d.3e.4a.5e.6c, | 1c.2d.3e.4a.5e.6d, | |
| 1c.2d.3e.4a.5e.6e, | 1c.2d.3e.4a.5e.6f, | 1c.2d.3e.4a.5f.6a, | 1c.2d.3e.4a.5f.6b, | |
| 1c.2d.3e.4a.5f.6c, | 1c.2d.3e.4a.5f.6d, | 1c.2d.3e.4a.5f.6e, | 1c.2d.3e.4a.5f.6f, | |
| 1c.2d.3e.4b.5a.6a, | 1c.2d.3e.4b.5a.6b, | 1c.2d.3e.4b.5a.6c, | 1c.2d.3e.4b.5a.6d, | |
| 1c.2d.3e.4b.5a.6e, | 1c.2d.3e.4b.5a.6f, | 1c.2d.3e.4b.5b.6a, | 1c.2d.3e.4b.5b.6b, | |
| 1c.2d.3e.4b.5b.6c, | 1c.2d.3e.4b.5b.6d, | 1c.2d.3e.4b.5b.6e, | 1c.2d.3e.4b.5b.6f, | |
| 1c.2d.3e.4b.5c.6a, | 1c.2d.3e.4b.5c.6b, | 1c.2d.3e.4b.5c.6c, | 1c.2d.3e.4b.5c.6d, | |
| 1c.2d.3e.4b.5c.6e, | 1c.2d.3e.4b.5c.6f, | 1c.2d.3e.4b.5d.6a, | 1c.2d.3e.4b.5d.6b, | |
| 1c.2d.3e.4b.5d.6c, | 1c.2d.3e.4b.5d.6d, | 1c.2d.3e.4b.5d.6e, | 1c.2d.3e.4b.5d.6f, | |
| 1c.2d.3e.4b.5e.6a, | 1c.2d.3e.4b.5e.6b, | 1c.2d.3e.4b.5e.6c, | 1c.2d.3e.4b.5e.6d, | |
| 1c.2d.3e.4b.5e.6e, | 1c.2d.3e.4b.5e.6f, | 1c.2d.3e.4b.5f.6a, | 1c.2d.3e.4b.5f.6b, | |
| 1c.2d.3e.4b.5f.6c, | 1c.2d.3e.4b.5f.6d, | 1c.2d.3e.4b.5f.6e, | 1c.2d.3e.4b.5f.6f, | |
| 1c.2d.3e.4c.5a.6a, | 1c.2d.3e.4c.5a.6b, | 1c.2d.3e.4c.5a.6c, | 1c.2d.3e.4c.5a.6d, | |
| 1c.2d.3e.4c.5a.6e, | 1c.2d.3e.4c.5a.6f, | 1c.2d.3e.4c.5b.6a, | 1c.2d.3e.4c.5b.6b, | |
| 1c.2d.3e.4c.5b.6c, | 1c.2d.3e.4c.5b.6d, | 1c.2d.3e.4c.5b.6e, | 1c.2d.3e.4c.5b.6f, | |
| 1c.2d.3e.4c.5c.6a, | 1c.2d.3e.4c.5c.6b, | 1c.2d.3e.4c.5c.6c, | 1c.2d.3e.4c.5c.6d, | |
| 1c.2d.3e.4c.5c.6e, | 1c.2d.3e.4c.5c.6f, | 1c.2d.3e.4c.5d.6a, | 1c.2d.3e.4c.5d.6b, | |
| 1c.2d.3e.4c.5d.6c, | 1c.2d.3e.4c.5d.6d, | 1c.2d.3e.4c.5d.6e, | 1c.2d.3e.4c.5d.6f, | |
| 1c.2d.3e.4c.5e.6a, | 1c.2d.3e.4c.5e.6b, | 1c.2d.3e.4c.5e.6c, | 1c.2d.3e.4c.5e.6d, | |
| 1c.2d.3e.4c.5e.6e, | 1c.2d.3e.4c.5e.6f, | 1c.2d.3e.4c.5f.6a, | 1c.2d.3e.4c.5f.6b, | 1c.2d.3e.4c.5f.6c, |
| 1c.2d.3e.4c.5f.6d, | 1c.2d.3e.4c.5f.6e, | 1c.2d.3e.4c.5f.6f, | 1c.2d.3e.4d.5a.6a, | |
| 1c.2d.3e.4d.5a.6b, | 1c.2d.3e.4d.5a.6c, | 1c.2d.3e.4d.5a.6d, | 1c.2d.3e.4d.5a.6e, | |
| 1c.2d.3e.4d.5a.6f, | 1c.2d.3e.4d.5b.6a, | 1c.2d.3e.4d.5b.6b, | 1c.2d.3e.4d.5b.6c, | |
| 1c.2d.3e.4d.5b.6d, | 1c.2d.3e.4d.5b.6e, | 1c.2d.3e.4d.5b.6f, | 1c.2d.3e.4d.5c.6a, | |
| 1c.2d.3e.4d.5c.6b, | 1c.2d.3e.4d.5c.6c, | 1c.2d.3e.4d.5c.6d, | 1c.2d.3e.4d.5c.6e, | |
| 1c.2d.3e.4d.5c.6f, | 1c.2d.3e.4d.5d.6a, | 1c.2d.3e.4d.5d.6b, | 1c.2d.3e.4d.5d.6c, | |
| 1c.2d.3e.4d.5d.6d, | 1c.2d.3e.4d.5d.6e, | 1c.2d.3e.4d.5d.6f, | 1c.2d.3e.4d.5e.6a, | |
| 1c.2d.3e.4d.5e.6b, | 1c.2d.3e.4d.5e.6c, | 1c.2d.3e.4d.5e.6d, | 1c.2d.3e.4d.5e.6e, | |
| 1c.2d.3e.4d.5e.6f, | 1c.2d.3e.4d.5f.6a, | 1c.2d.3e.4d.5f.6b, | 1c.2d.3e.4d.5f.6c, | |
| 1c.2d.3e.4d.5f.6d, | 1c.2d.3e.4d.5f.6e, | 1c.2d.3e.4d.5f.6f, | 1c.2d.3e.4e.5a.6a, | |
| 1c.2d.3e.4e.5a.6b, | 1c.2d.3e.4e.5a.6c, | 1c.2d.3e.4e.5a.6d, | 1c.2d.3e.4e.5a.6e, | |
| 1c.2d.3e.4e.5a.6f, | 1c.2d.3e.4e.5b.6a, | 1c.2d.3e.4e.5b.6b, | 1c.2d.3e.4e.5b.6c, | |
| 1c.2d.3e.4e.5b.6d, | 1c.2d.3e.4e.5b.6e, | 1c.2d.3e.4e.5b.6f, | 1c.2d.3e.4e.5c.6a, | |
| 1c.2d.3e.4e.5c.6b, | 1c.2d.3e.4e.5c.6c, | 1c.2d.3e.4e.5c.6d, | 1c.2d.3e.4e.5c.6e, | |
| 1c.2d.3e.4e.5c.6f, | 1c.2d.3e.4e.5d.6a, | 1c.2d.3e.4e.5d.6b, | 1c.2d.3e.4e.5d.6c, | |
| 1c.2d.3e.4e.5d.6d, | 1c.2d.3e.4e.5d.6e, | 1c.2d.3e.4e.5d.6f, | 1c.2d.3e.4e.5e.6a, | |
| 1c.2d.3e.4e.5e.6b, | 1c.2d.3e.4e.5e.6c, | 1c.2d.3e.4e.5e.6d, | 1c.2d.3e.4e.5e.6e, | |
| 1c.2d.3e.4e.5f.6f, | 1c.2d.3e.4e.5f.6a, | 1c.2d.3e.4e.5f.6b, | 1c.2d.3e.4e.5f.6c, | 1c.2d.3e.4e.5f.6d, |
| 1c.2d.3e.4e.5f.6e, | 1c.2d.3e.4e.5f.6f, | 1c.2d.3e.4f.5a.6a, | 1c.2d.3e.4f.5a.6b, | 1c.2d.3e.4f.5a.6c, |
| 1c.2d.3e.4f.5a.6d, | 1c.2d.3e.4f.5a.6e, | 1c.2d.3e.4f.5a.6f, | 1c.2d.3e.4f.5b.6a, | |
| 1c.2d.3e.4f.5b.6b, | 1c.2d.3e.4f.5b.6c, | 1c.2d.3e.4f.5b.6d, | 1c.2d.3e.4f.5b.6e, | |
| 1c.2d.3e.4f.5b.6f, | 1c.2d.3e.4f.5c.6a, | 1c.2d.3e.4f.5c.6b, | 1c.2d.3e.4f.5c.6c, | 1c.2d.3e.4f.5c.6d, |
| 1c.2d.3e.4f.5c.6e, | 1c.2d.3e.4f.5c.6f, | 1c.2d.3e.4f.5d.6a, | 1c.2d.3e.4f.5d.6b, | 1c.2d.3e.4f.5d.6c, |
| 1c.2d.3e.4f.5d.6d, | 1c.2d.3e.4f.5d.6e, | 1c.2d.3e.4f.5d.6f, | 1c.2d.3e.4f.5e.6a, | |
| 1c.2d.3e.4f.5e.6b, | 1c.2d.3e.4f.5e.6c, | 1c.2d.3e.4f.5e.6d, | 1c.2d.3e.4f.5e.6e, | 1c.2d.3e.4f.5e.6f, |
| 1c.2d.3e.4f.5f.6a, | 1c.2d.3e.4f.5f.6b, | 1c.2d.3e.4f.5f.6c, | 1c.2d.3e.4f.5f.6d, | 1c.2d.3e.4f.5f.6e, |
| 1c.2d.3e.4f.5f.6f, | 1c.2d.3f.4a.5a.6a, | 1c.2d.3f.4a.5a.6b, | 1c.2d.3f.4a.5a.6c, | 1c.2d.3f.4a.5a.6d, |

TABLE 7-continued

List of Compounds of Formula (II)

| | | | |
|---|---|---|---|
| 1c.2d.3f.4a.5a.6e, | 1c.2d.3f.4a.5a.6f, | 1c.2d.3f.4a.5b.6a, | 1c.2d.3f.4a.5b.6b, |
| 1c.2d.3f.4a.5b.6c, | 1c.2d.3f.4a.5b.6d, | 1c.2d.3f.4a.5b.6e, | 1c.2d.3f.4a.5b.6f, |
| 1c.2d.3f.4a.5c.6a, | 1c.2d.3f.4a.5c.6b, | 1c.2d.3f.4a.5c.6c, | 1c.2d.3f.4a.5c.6d, | 1c.2d.3f.4a.5c.6e, |
| 1c.2d.3f.4a.5c.6f, | 1c.2d.3f.4a.5d.6a, | 1c.2d.3f.4a.5d.6b, | 1c.2d.3f.4a.5d.6c, |
| 1c.2d.3f.4a.5d.6d, | 1c.2d.3f.4a.5d.6e, | 1c.2d.3f.4a.5d.6f, | 1c.2d.3f.4a.5e.6a, |
| 1c.2d.3f.4a.5e.6b, | 1c.2d.3f.4a.5e.6c, | 1c.2d.3f.4a.5e.6d, | 1c.2d.3f.4a.5e.6e, | 1c.2d.3f.4a.5e.6f, |
| 1c.2d.3f.4a.5f.6a, | 1c.2d.3f.4a.5f.6b, | 1c.2d.3f.4a.5f.6c, | 1c.2d.3f.4a.5f.6d, | 1c.2d.3f.4a.5f.6e, |
| 1c.2d.3f.4a.5f.6f, | 1c.2d.3f.4b.5a.6a, | 1c.2d.3f.4b.5a.6b, | 1c.2d.3f.4b.5a.6c, |
| 1c.2d.3f.4b.5a.6d, | 1c.2d.3f.4b.5a.6e, | 1c.2d.3f.4b.5a.6f, | 1c.2d.3f.4b.5b.6a, |
| 1c.2d.3f.4b.5b.6b, | 1c.2d.3f.4b.5b.6c, | 1c.2d.3f.4b.5b.6d, | 1c.2d.3f.4b.5b.6e, |
| 1c.2d.3f.4b.5b.6f, | 1c.2d.3f.4b.5c.6a, | 1c.2d.3f.4b.5c.6b, | 1c.2d.3f.4b.5c.6c, |
| 1c.2d.3f.4b.5c.6d, | 1c.2d.3f.4b.5c.6e, | 1c.2d.3f.4b.5c.6f, | 1c.2d.3f.4b.5d.6a, |
| 1c.2d.3f.4b.5d.6b, | 1c.2d.3f.4b.5d.6c, | 1c.2d.3f.4b.5d.6d, | 1c.2d.3f.4b.5d.6e, |
| 1c.2d.3f.4b.5d.6f, | 1c.2d.3f.4b.5e.6a, | 1c.2d.3f.4b.5e.6b, | 1c.2d.3f.4b.5e.6c, |
| 1c.2d.3f.4b.5e.6d, | 1c.2d.3f.4b.5e.6e, | 1c.2d.3f.4b.5e.6f, | 1c.2d.3f.4b.5f.6a, | 1c.2d.3f.4b.5f.6b, |
| 1c.2d.3f.4b.5f.6c, | 1c.2d.3f.4b.5f.6d, | 1c.2d.3f.4b.5f.6e, | 1c.2d.3f.4b.5f.6f, | 1c.2d.3f.4c.5a.6a, |
| 1c.2d.3f.4c.5a.6b, | 1c.2d.3f.4c.5a.6c, | 1c.2d.3f.4c.5a.6d, | 1c.2d.3f.4c.5a.6e, | 1c.2d.3f.4c.5a.6f, |
| 1c.2d.3f.4c.5b.6a, | 1c.2d.3f.4c.5b.6b, | 1c.2d.3f.4c.5b.6c, | 1c.2d.3f.4c.5b.6d, |
| 1c.2d.3f.4c.5b.6e, | 1c.2d.3f.4c.5b.6f, | 1c.2d.3f.4c.5c.6a, | 1c.2d.3f.4c.5c.6b, | 1c.2d.3f.4c.5c.6c, |
| 1c.2d.3f.4c.5c.6d, | 1c.2d.3f.4c.5c.6e, | 1c.2d.3f.4c.5c.6f, | 1c.2d.3f.4c.5d.6a, | 1c.2d.3f.4c.5d.6b, |
| 1c.2d.3f.4c.5d.6c, | 1c.2d.3f.4c.5d.6d, | 1c.2d.3f.4c.5d.6e, | 1c.2d.3f.4c.5d.6f, |
| 1c.2d.3f.4c.5e.6a, | 1c.2d.3f.4c.5e.6b, | 1c.2d.3f.4c.5e.6c, | 1c.2d.3f.4c.5e.6d, | 1c.2d.3f.4c.5e.6e, |
| 1c.2d.3f.4c.5e.6f, | 1c.2d.3f.4c.5f.6a, | 1c.2d.3f.4c.5f.6b, | 1c.2d.3f.4c.5f.6c, | 1c.2d.3f.4c.5f.6d, |
| 1c.2d.3f.4c.5f.6e, | 1c.2d.3f.4c.5f.6f, | 1c.2d.3f.4d.5a.6a, | 1c.2d.3f.4d.5a.6b, | 1c.2d.3f.4d.5a.6c, |
| 1c.2d.3f.4d.5a.6d, | 1c.2d.3f.4d.5a.6e, | 1c.2d.3f.4d.5a.6f, | 1c.2d.3f.4d.5b.6a, |
| 1c.2d.3f.4d.5b.6b, | 1c.2d.3f.4d.5b.6c, | 1c.2d.3f.4d.5b.6d, | 1c.2d.3f.4d.5b.6e, |
| 1c.2d.3f.4d.5b.6f, | 1c.2d.3f.4d.5c.6a, | 1c.2d.3f.4d.5c.6b, | 1c.2d.3f.4d.5c.6c, |
| 1c.2d.3f.4d.5c.6d, | 1c.2d.3f.4d.5c.6e, | 1c.2d.3f.4d.5c.6f, | 1c.2d.3f.4d.5d.6a, |
| 1c.2d.3f.4d.5d.6b, | 1c.2d.3f.4d.5d.6c, | 1c.2d.3f.4d.5d.6d, | 1c.2d.3f.4d.5d.6e, |
| 1c.2d.3f.4d.5d.6f, | 1c.2d.3f.4d.5e.6a, | 1c.2d.3f.4d.5e.6b, | 1c.2d.3f.4d.5e.6c, |
| 1c.2d.3f.4d.5e.6d, | 1c.2d.3f.4d.5e.6e, | 1c.2d.3f.4d.5e.6f, | 1c.2d.3f.4d.5f.6a, |
| 1c.2d.3f.4d.5f.6b, | 1c.2d.3f.4d.5f.6c, | 1c.2d.3f.4d.5f.6d, | 1c.2d.3f.4d.5f.6e, | 1c.2d.3f.4d.5f.6f, |
| 1c.2d.3f.4e.5a.6a, | 1c.2d.3f.4e.5a.6b, | 1c.2d.3f.4e.5a.6c, | 1c.2d.3f.4e.5a.6d, |
| 1c.2d.3f.4e.5a.6e, | 1c.2d.3f.4e.5a.6f, | 1c.2d.3f.4e.5b.6a, | 1c.2d.3f.4e.5b.6b, | 1c.2d.3f.4e.5b.6c, |
| 1c.2d.3f.4e.5b.6d, | 1c.2d.3f.4e.5b.6e, | 1c.2d.3f.4e.5b.6f, | 1c.2d.3f.4e.5c.6a, | 1c.2d.3f.4e.5c.6b, |
| 1c.2d.3f.4e.5c.6c, | 1c.2d.3f.4e.5c.6d, | 1c.2d.3f.4e.5c.6e, | 1c.2d.3f.4e.5c.6f, | 1c.2d.3f.4e.5d.6a, |
| 1c.2d.3f.4e.5d.6b, | 1c.2d.3f.4e.5d.6c, | 1c.2d.3f.4e.5d.6d, | 1c.2d.3f.4e.5d.6e, |
| 1c.2d.3f.4e.5d.6f, | 1c.2d.3f.4e.5e.6a, | 1c.2d.3f.4e.5e.6b, | 1c.2d.3f.4e.5e.6c, | 1c.2d.3f.4e.5e.6d, |
| 1c.2d.3f.4e.5e.6e, | 1c.2d.3f.4e.5e.6f, | 1c.2d.3f.4e.5f.6a, | 1c.2d.3f.4e.5f.6b, | 1c.2d.3f.4e.5f.6c, |
| 1c.2d.3f.4e.5f.6d, | 1c.2d.3f.4e.5f.6e, | 1c.2d.3f.4e.5f.6f, | 1c.2d.3f.4f.5a.6a, | 1c.2d.3f.4f.5a.6b, |
| 1c.2d.3f.4f.5a.6c, | 1c.2d.3f.4f.5a.6d, | 1c.2d.3f.4f.5a.6e, | 1c.2d.3f.4f.5a.6f, | 1c.2d.3f.4f.5b.6a, |
| 1c.2d.3f.4f.5b.6b, | 1c.2d.3f.4f.5b.6c, | 1c.2d.3f.4f.5b.6d, | 1c.2d.3f.4f.5b.6e, | 1c.2d.3f.4f.5b.6f, |
| 1c.2d.3f.4f.5c.6a, | 1c.2d.3f.4f.5c.6b, | 1c.2d.3f.4f.5c.6c, | 1c.2d.3f.4f.5c.6d, | 1c.2d.3f.4f.5c.6e, |
| 1c.2d.3f.4f.5c.6f, | 1c.2d.3f.4f.5d.6a, | 1c.2d.3f.4f.5d.6b, | 1c.2d.3f.4f.5d.6c, | 1c.2d.3f.4f.5d.6d, |
| 1c.2d.3f.4f.5d.6e, | 1c.2d.3f.4f.5d.6f, | 1c.2d.3f.4f.5e.6a, | 1c.2d.3f.4f.5e.6b, | 1c.2d.3f.4f.5e.6c, |
| 1c.2d.3f.4f.5e.6d, | 1c.2d.3f.4f.5e.6e, | 1c.2d.3f.4f.5e.6f, | 1c.2d.3f.4f.5f.6a, | 1c.2d.3f.4f.5f.6b, |
| 1c.2d.3f.4f.5f.6c, | 1c.2d.3f.4f.5f.6d, | 1c.2d.3f.4f.5f.6e, | 1c.2d.3f.4f.5f.6f, | 1c.2e.3a.4a.5a.6a, |
| 1c.2e.3a.4a.5a.6b, | 1c.2e.3a.4a.5a.6c, | 1c.2e.3a.4a.5a.6d, | 1c.2e.3a.4a.5a.6e, |
| 1c.2e.3a.4a.5a.6f, | 1c.2e.3a.4a.5b.6a, | 1c.2e.3a.4a.5b.6b, | 1c.2e.3a.4a.5b.6c, |
| 1c.2e.3a.4a.5b.6d, | 1c.2e.3a.4a.5b.6e, | 1c.2e.3a.4a.5b.6f, | 1c.2e.3a.4a.5c.6a, |
| 1c.2e.3a.4a.5c.6b, | 1c.2e.3a.4a.5c.6c, | 1c.2e.3a.4a.5c.6d, | 1c.2e.3a.4a.5c.6e, | 1c.2e.3a.4a.5c.6f, |
| 1c.2e.3a.4a.5d.6a, | 1c.2e.3a.4a.5d.6b, | 1c.2e.3a.4a.5d.6c, | 1c.2e.3a.4a.5d.6d, |
| 1c.2e.3a.4a.5d.6e, | 1c.2e.3a.4a.5d.6f, | 1c.2e.3a.4a.5e.6a, | 1c.2e.3a.4a.5e.6b, |
| 1c.2e.3a.4a.5e.6c, | 1c.2e.3a.4a.5e.6d, | 1c.2e.3a.4a.5e.6e, | 1c.2e.3a.4a.5e.6f, | 1c.2e.3a.4a.5f.6a, |
| 1c.2e.3a.4a.5f.6b, | 1c.2e.3a.4a.5f.6c, | 1c.2e.3a.4a.5f.6d, | 1c.2e.3a.4a.5f.6e, | 1c.2e.3a.4a.5f.6f, |
| 1c.2e.3a.4b.5a.6a, | 1c.2e.3a.4b.5a.6b, | 1c.2e.3a.4b.5a.6c, | 1c.2e.3a.4b.5a.6d, |
| 1c.2e.3a.4b.5a.6e, | 1c.2e.3a.4b.5a.6f, | 1c.2e.3a.4b.5b.6a, | 1c.2e.3a.4b.5b.6b, |
| 1c.2e.3a.4b.5b.6c, | 1c.2e.3a.4b.5b.6d, | 1c.2e.3a.4b.5b.6e, | 1c.2e.3a.4b.5b.6f, |
| 1c.2e.3a.4b.5c.6a, | 1c.2e.3a.4b.5c.6b, | 1c.2e.3a.4b.5c.6c, | 1c.2e.3a.4b.5c.6d, |
| 1c.2e.3a.4b.5c.6e, | 1c.2e.3a.4b.5c.6f, | 1c.2e.3a.4b.5d.6a, | 1c.2e.3a.4b.5d.6b, |
| 1c.2e.3a.4b.5d.6c, | 1c.2e.3a.4b.5d.6d, | 1c.2e.3a.4b.5d.6e, | 1c.2e.3a.4b.5d.6f, |
| 1c.2e.3a.4b.5e.6a, | 1c.2e.3a.4b.5e.6b, | 1c.2e.3a.4b.5e.6c, | 1c.2e.3a.4b.5e.6d, |
| 1c.2e.3a.4b.5e.6e, | 1c.2e.3a.4b.5e.6f, | 1c.2e.3a.4b.5f.6a, | 1c.2e.3a.4b.5f.6b, | 1c.2e.3a.4b.5f.6c, |
| 1c.2e.3a.4b.5f.6d, | 1c.2e.3a.4b.5f.6e, | 1c.2e.3a.4b.5f.6f, | 1c.2e.3a.4c.5a.6a, | 1c.2e.3a.4c.5a.6b, |
| 1c.2e.3a.4c.5a.6c, | 1c.2e.3a.4c.5a.6d, | 1c.2e.3a.4c.5a.6e, | 1c.2e.3a.4c.5a.6f, | 1c.2e.3a.4c.5b.6a, |
| 1c.2e.3a.4c.5b.6b, | 1c.2e.3a.4c.5b.6c, | 1c.2e.3a.4c.5b.6d, | 1c.2e.3a.4c.5b.6e, |
| 1c.2e.3a.4c.5b.6f, | 1c.2e.3a.4c.5c.6a, | 1c.2e.3a.4c.5c.6b, | 1c.2e.3a.4c.5c.6c, | 1c.2e.3a.4c.5c.6d, |
| 1c.2e.3a.4c.5c.6e, | 1c.2e.3a.4c.5c.6f, | 1c.2e.3a.4c.5d.6a, | 1c.2e.3a.4c.5d.6b, | 1c.2e.3a.4c.5d.6c, |
| 1c.2e.3a.4c.5d.6d, | 1c.2e.3a.4c.5d.6e, | 1c.2e.3a.4c.5d.6f, | 1c.2e.3a.4c.5e.6a, |
| 1c.2e.3a.4c.5e.6b, | 1c.2e.3a.4c.5e.6c, | 1c.2e.3a.4c.5e.6d, | 1c.2e.3a.4c.5e.6e, | 1c.2e.3a.4c.5e.6f, |
| 1c.2e.3a.4c.5f.6a, | 1c.2e.3a.4c.5f.6b, | 1c.2e.3a.4c.5f.6c, | 1c.2e.3a.4c.5f.6d, | 1c.2e.3a.4c.5f.6e, |
| 1c.2e.3a.4c.5f.6f, | 1c.2e.3a.4d.5a.6a, | 1c.2e.3a.4d.5a.6b, | 1c.2e.3a.4d.5a.6c, |
| 1c.2e.3a.4d.5a.6d, | 1c.2e.3a.4d.5a.6e, | 1c.2e.3a.4d.5a.6f, | 1c.2e.3a.4d.5b.6a, |
| 1c.2e.3a.4d.5b.6b, | 1c.2e.3a.4d.5b.6c, | 1c.2e.3a.4d.5b.6d, | 1c.2e.3a.4d.5b.6e, |
| 1c.2e.3a.4d.5b.6f, | 1c.2e.3a.4d.5c.6a, | 1c.2e.3a.4d.5c.6b, | 1c.2e.3a.4d.5c.6c, |
| 1c.2e.3a.4d.5c.6d, | 1c.2e.3a.4d.5c.6e, | 1c.2e.3a.4d.5c.6f, | 1c.2e.3a.4d.5d.6a, |
| 1c.2e.3a.4d.5d.6b, | 1c.2e.3a.4d.5d.6c, | 1c.2e.3a.4d.5d.6d, | 1c.2e.3a.4d.5d.6e, |
| 1c.2e.3a.4d.5d.6f, | 1c.2e.3a.4d.5e.6a, | 1c.2e.3a.4d.5e.6b, | 1c.2e.3a.4d.5e.6c, |

TABLE 7-continued

List of Compounds of Formula (II)

| | | | | |
|---|---|---|---|---|
| 1c.2e.3a.4d.5e.6d, | 1c.2e.3a.4d.5e.6e, | 1c.2e.3a.4d.5e.6f, | 1c.2e.3a.4d.5f.6a, | |
| 1c.2e.3a.4d.5f.6b, | 1c.2e.3a.4d.5f.6c, | 1c.2e.3a.4d.5f.6d, | 1c.2e.3a.4d.5f.6e, | 1c.2e.3a.4d.5f.6f, |
| 1c.2e.3a.4e.5a.6a, | 1c.2e.3a.4e.5a.6b, | 1c.2e.3a.4e.5a.6c, | 1c.2e.3a.4e.5a.6d, | |
| 1c.2e.3a.4e.5a.6e, | 1c.2e.3a.4e.5a.6f, | 1c.2e.3a.4e.5b.6a, | 1c.2e.3a.4e.5b.6b, | |
| 1c.2e.3a.4e.5b.6c, | 1c.2e.3a.4e.5b.6d, | 1c.2e.3a.4e.5b.6e, | 1c.2e.3a.4e.5b.6f, | |
| 1c.2e.3a.4e.5c.6a, | 1c.2e.3a.4e.5c.6b, | 1c.2e.3a.4e.5c.6c, | 1c.2e.3a.4e.5c.6d, | 1c.2e.3a.4e.5c.6e, |
| 1c.2e.3a.4e.5c.6f, | 1c.2e.3a.4e.5d.6a, | 1c.2e.3a.4e.5d.6b, | 1c.2e.3a.4e.5d.6c, | |
| 1c.2e.3a.4e.5d.6d, | 1c.2e.3a.4e.5d.6e, | 1c.2e.3a.4e.5d.6f, | 1c.2e.3a.4e.5e.6a, | |
| 1c.2e.3a.4e.5e.6b, | 1c.2e.3a.4e.5e.6c, | 1c.2e.3a.4e.5e.6d, | 1c.2e.3a.4e.5e.6e, | 1c.2e.3a.4e.5e.6f, |
| 1c.2e.3a.4e.5f.6a, | 1c.2e.3a.4e.5f.6b, | 1c.2e.3a.4e.5f.6c, | 1c.2e.3a.4e.5f.6d, | 1c.2e.3a.4e.5f.6e, |
| 1c.2e.3a.4e.5f.6f, | 1c.2e.3a.4f.5a.6a, | 1c.2e.3a.4f.5a.6b, | 1c.2e.3a.4f.5a.6c, | 1c.2e.3a.4f.5a.6d, |
| 1c.2e.3a.4f.5a.6e, | 1c.2e.3a.4f.5a.6f, | 1c.2e.3a.4f.5b.6a, | 1c.2e.3a.4f.5b.6b, | 1c.2e.3a.4f.5b.6c, |
| 1c.2e.3a.4f.5b.6d, | 1c.2e.3a.4f.5b.6e, | 1c.2e.3a.4f.5b.6f, | 1c.2e.3a.4f.5c.6a, | 1c.2e.3a.4f.5c.6b, |
| 1c.2e.3a.4f.5c.6c, | 1c.2e.3a.4f.5c.6d, | 1c.2e.3a.4f.5c.6e, | 1c.2e.3a.4f.5c.6f, | 1c.2e.3a.4f.5d.6a, |
| 1c.2e.3a.4f.5d.6b, | 1c.2e.3a.4f.5d.6c, | 1c.2e.3a.4f.5d.6d, | 1c.2e.3a.4f.5d.6e, | 1c.2e.3a.4f.5d.6f, |
| 1c.2e.3a.4f.5e.6a, | 1c.2e.3a.4f.5e.6b, | 1c.2e.3a.4f.5e.6c, | 1c.2e.3a.4f.5e.6d, | 1c.2e.3a.4f.5e.6e, |
| 1c.2e.3a.4f.5e.6f, | 1c.2e.3a.4f.5f.6a, | 1c.2e.3a.4f.5f.6b, | 1c.2e.3a.4f.5f.6c, | 1c.2e.3a.4f.5f.6d, |
| 1c.2e.3a.4f.5f.6e, | 1c.2e.3a.4f.5f.6f, | 1c.2e.3b.4a.5a.6a, | 1c.2e.3b.4a.5a.6b, | 1c.2e.3b.4a.5a.6c, |
| 1c.2e.3b.4a.5a.6d, | 1c.2e.3b.4a.5a.6e, | 1c.2e.3b.4a.5a.6f, | 1c.2e.3b.4a.5b.6a, | |
| 1c.2e.3b.4a.5b.6b, | 1c.2e.3b.4a.5b.6c, | 1c.2e.3b.4a.5b.6d, | 1c.2e.3b.4a.5b.6e, | |
| 1c.2e.3b.4a.5b.6f, | 1c.2e.3b.4a.5c.6a, | 1c.2e.3b.4a.5c.6b, | 1c.2e.3b.4a.5c.6c, | |
| 1c.2e.3b.4a.5c.6d, | 1c.2e.3b.4a.5c.6e, | 1c.2e.3b.4a.5c.6f, | 1c.2e.3b.4a.5d.6a, | |
| 1c.2e.3b.4a.5d.6b, | 1c.2e.3b.4a.5d.6c, | 1c.2e.3b.4a.5d.6d, | 1c.2e.3b.4a.5d.6e, | |
| 1c.2e.3b.4a.5d.6f, | 1c.2e.3b.4a.5e.6a, | 1c.2e.3b.4a.5e.6b, | 1c.2e.3b.4a.5e.6c, | |
| 1c.2e.3b.4a.5e.6d, | 1c.2e.3b.4a.5e.6e, | 1c.2e.3b.4a.5e.6f, | 1c.2e.3b.4a.5f.6a, | |
| 1c.2e.3b.4a.5f.6b, | 1c.2e.3b.4a.5f.6c, | 1c.2e.3b.4a.5f.6d, | 1c.2e.3b.4a.5f.6e, | 1c.2e.3b.4a.5f.6f, |
| 1c.2e.3b.4b.5a.6a, | 1c.2e.3b.4b.5a.6b, | 1c.2e.3b.4b.5a.6c, | 1c.2e.3b.4b.5a.6d, | |
| 1c.2e.3b.4b.5a.6e, | 1c.2e.3b.4b.5a.6f, | 1c.2e.3b.4b.5b.6a, | 1c.2e.3b.4b.5b.6b, | |
| 1c.2e.3b.4b.5b.6c, | 1c.2e.3b.4b.5b.6d, | 1c.2e.3b.4b.5b.6e, | 1c.2e.3b.4b.5b.6f, | |
| 1c.2e.3b.4b.5c.6a, | 1c.2e.3b.4b.5c.6b, | 1c.2e.3b.4b.5c.6c, | 1c.2e.3b.4b.5c.6d, | |
| 1c.2e.3b.4b.5c.6e, | 1c.2e.3b.4b.5c.6f, | 1c.2e.3b.4b.5d.6a, | 1c.2e.3b.4b.5d.6b, | |
| 1c.2e.3b.4b.5d.6c, | 1c.2e.3b.4b.5d.6d, | 1c.2e.3b.4b.5d.6e, | 1c.2e.3b.4b.5d.6f, | |
| 1c.2e.3b.4b.5e.6a, | 1c.2e.3b.4b.5e.6b, | 1c.2e.3b.4b.5e.6c, | 1c.2e.3b.4b.5e.6d, | |
| 1c.2e.3b.4b.5e.6e, | 1c.2e.3b.4b.5e.6f, | 1c.2e.3b.4b.5f.6a, | 1c.2e.3b.4b.5f.6b, | |
| 1c.2e.3b.4b.5f.6c, | 1c.2e.3b.4b.5f.6d, | 1c.2e.3b.4b.5f.6e, | 1c.2e.3b.4b.5f.6f, | 1c.2e.3b.4c.5a.6a, |
| 1c.2e.3b.4c.5a.6b, | 1c.2e.3b.4c.5a.6c, | 1c.2e.3b.4c.5a.6d, | 1c.2e.3b.4c.5a.6e, | |
| 1c.2e.3b.4c.5a.6f, | 1c.2e.3b.4c.5b.6a, | 1c.2e.3b.4c.5b.6b, | 1c.2e.3b.4c.5b.6c, | |
| 1c.2e.3b.4c.5b.6d, | 1c.2e.3b.4c.5b.6e, | 1c.2e.3b.4c.5b.6f, | 1c.2e.3b.4c.5c.6a, | |
| 1c.2e.3b.4c.5c.6b, | 1c.2e.3b.4c.5c.6c, | 1c.2e.3b.4c.5c.6d, | 1c.2e.3b.4c.5c.6e, | 1c.2e.3b.4c.5c.6f, |
| 1c.2e.3b.4c.5d.6a, | 1c.2e.3b.4c.5d.6b, | 1c.2e.3b.4c.5d.6c, | 1c.2e.3b.4c.5d.6d, | |
| 1c.2e.3b.4c.5d.6e, | 1c.2e.3b.4c.5d.6f, | 1c.2e.3b.4c.5e.6a, | 1c.2e.3b.4c.5e.6b, | |
| 1c.2e.3b.4c.5e.6c, | 1c.2e.3b.4c.5e.6d, | 1c.2e.3b.4c.5e.6e, | 1c.2e.3b.4c.5e.6f, | 1c.2e.3b.4c.5f.6a, |
| 1c.2e.3b.4c.5f.6b, | 1c.2e.3b.4c.5f.6c, | 1c.2e.3b.4c.5f.6d, | 1c.2e.3b.4c.5f.6e, | 1c.2e.3b.4c.5f.6f, |
| 1c.2e.3b.4d.5a.6a, | 1c.2e.3b.4d.5a.6b, | 1c.2e.3b.4d.5a.6c, | 1c.2e.3b.4d.5a.6d, | |
| 1c.2e.3b.4d.5a.6e, | 1c.2e.3b.4d.5a.6f, | 1c.2e.3b.4d.5b.6a, | 1c.2e.3b.4d.5b.6b, | |
| 1c.2e.3b.4d.5b.6c, | 1c.2e.3b.4d.5b.6d, | 1c.2e.3b.4d.5b.6e, | 1c.2e.3b.4d.5b.6f, | |
| 1c.2e.3b.4d.5c.6a, | 1c.2e.3b.4d.5c.6b, | 1c.2e.3b.4d.5c.6c, | 1c.2e.3b.4d.5c.6d, | |
| 1c.2e.3b.4d.5c.6e, | 1c.2e.3b.4d.5c.6f, | 1c.2e.3b.4d.5d.6a, | 1c.2e.3b.4d.5d.6b, | |
| 1c.2e.3b.4d.5d.6c, | 1c.2e.3b.4d.5d.6d, | 1c.2e.3b.4d.5d.6e, | 1c.2e.3b.4d.5d.6f, | |
| 1c.2e.3b.4d.5e.6a, | 1c.2e.3b.4d.5e.6b, | 1c.2e.3b.4d.5e.6c, | 1c.2e.3b.4d.5e.6d, | |
| 1c.2e.3b.4d.5e.6e, | 1c.2e.3b.4d.5e.6f, | 1c.2e.3b.4d.5f.6a, | 1c.2e.3b.4d.5f.6b, | |
| 1c.2e.3b.4d.5f.6c, | 1c.2e.3b.4d.5f.6d, | 1c.2e.3b.4d.5f.6e, | 1c.2e.3b.4d.5f.6f, | |
| 1c.2e.3b.4e.5a.6a, | 1c.2e.3b.4e.5a.6b, | 1c.2e.3b.4e.5a.6c, | 1c.2e.3b.4e.5a.6d, | |
| 1c.2e.3b.4e.5a.6e, | 1c.2e.3b.4e.5a.6f, | 1c.2e.3b.4e.5b.6a, | 1c.2e.3b.4e.5b.6b, | |
| 1c.2e.3b.4e.5b.6c, | 1c.2e.3b.4e.5b.6d, | 1c.2e.3b.4e.5b.6e, | 1c.2e.3b.4e.5b.6f, | |
| 1c.2e.3b.4e.5c.6a, | 1c.2e.3b.4e.5c.6b, | 1c.2e.3b.4e.5c.6c, | 1c.2e.3b.4e.5c.6d, | |
| 1c.2e.3b.4e.5c.6e, | 1c.2e.3b.4e.5c.6f, | 1c.2e.3b.4e.5d.6a, | 1c.2e.3b.4e.5d.6b, | |
| 1c.2e.3b.4e.5d.6c, | 1c.2e.3b.4e.5d.6d, | 1c.2e.3b.4e.5d.6e, | 1c.2e.3b.4e.5d.6f, | |
| 1c.2e.3b.4e.5e.6a, | 1c.2e.3b.4e.5e.6b, | 1c.2e.3b.4e.5e.6c, | 1c.2e.3b.4e.5e.6d, | |
| 1c.2e.3b.4e.5e.6e, | 1c.2e.3b.4e.5e.6f, | 1c.2e.3b.4e.5f.6a, | 1c.2e.3b.4e.5f.6b, | 1c.2e.3b.4e.5f.6c, |
| 1c.2e.3b.4e.5f.6d, | 1c.2e.3b.4e.5f.6e, | 1c.2e.3b.4e.5f.6f, | 1c.2e.3b.4f.5a.6a, | 1c.2e.3b.4f.5a.6b, |
| 1c.2e.3b.4f.5a.6c, | 1c.2e.3b.4f.5a.6d, | 1c.2e.3b.4f.5a.6e, | 1c.2e.3b.4f.5a.6f, | 1c.2e.3b.4f.5b.6a, |
| 1c.2e.3b.4f.5b.6b, | 1c.2e.3b.4f.5b.6c, | 1c.2e.3b.4f.5b.6d, | 1c.2e.3b.4f.5b.6e, | 1c.2e.3b.4f.5b.6f, |
| 1c.2e.3b.4f.5c.6a, | 1c.2e.3b.4f.5c.6b, | 1c.2e.3b.4f.5c.6c, | 1c.2e.3b.4f.5c.6d, | 1c.2e.3b.4f.5c.6e, |
| 1c.2e.3b.4f.5c.6f, | 1c.2e.3b.4f.5d.6a, | 1c.2e.3b.4f.5d.6b, | 1c.2e.3b.4f.5d.6c, | |
| 1c.2e.3b.4f.5d.6d, | 1c.2e.3b.4f.5d.6e, | 1c.2e.3b.4f.5d.6f, | 1c.2e.3b.4f.5e.6a, | 1c.2e.3b.4f.5e.6b, |
| 1c.2e.3b.4f.5e.6c, | 1c.2e.3b.4f.5e.6d, | 1c.2e.3b.4f.5e.6e, | 1c.2e.3b.4f.5e.6f, | 1c.2e.3b.4f.5f.6a, |
| 1c.2e.3b.4f.5f.6b, | 1c.2e.3b.4f.5f.6c, | 1c.2e.3b.4f.5f.6d, | 1c.2e.3b.4f.5f.6e, | 1c.2e.3b.4f.5f.6f, |
| 1c.2e.3c.4a.5a.6a, | 1c.2e.3c.4a.5a.6b, | 1c.2e.3c.4a.5a.6c, | 1c.2e.3c.4a.5a.6d, | |
| 1c.2e.3c.4a.5a.6e, | 1c.2e.3c.4a.5a.6f, | 1c.2e.3c.4a.5b.6a, | 1c.2e.3c.4a.5b.6b, | 1c.2e.3c.4a.5b.6c, |
| 1c.2e.3c.4a.5b.6d, | 1c.2e.3c.4a.5b.6e, | 1c.2e.3c.4a.5b.6f, | 1c.2e.3c.4a.5c.6a, | 1c.2e.3c.4a.5c.6b, |
| 1c.2e.3c.4a.5c.6c, | 1c.2e.3c.4a.5c.6d, | 1c.2e.3c.4a.5c.6e, | 1c.2e.3c.4a.5c.6f, | 1c.2e.3c.4a.5d.6a, |
| 1c.2e.3c.4a.5d.6b, | 1c.2e.3c.4a.5d.6c, | 1c.2e.3c.4a.5d.6d, | 1c.2e.3c.4a.5d.6e, | |
| 1c.2e.3c.4a.5d.6f, | 1c.2e.3c.4a.5e.6a, | 1c.2e.3c.4a.5e.6b, | 1c.2e.3c.4a.5e.6c, | 1c.2e.3c.4a.5e.6d, |
| 1c.2e.3c.4a.5e.6e, | 1c.2e.3c.4a.5e.6f, | 1c.2e.3c.4a.5f.6a, | 1c.2e.3c.4a.5f.6b, | 1c.2e.3c.4a.5f.6c, |
| 1c.2e.3c.4a.5f.6d, | 1c.2e.3c.4a.5f.6e, | 1c.2e.3c.4a.5f.6f, | 1c.2e.3c.4b.5a.6a, | 1c.2e.3c.4b.5a.6b, |
| 1c.2e.3c.4b.5a.6c, | 1c.2e.3c.4b.5a.6d, | 1c.2e.3c.4b.5a.6e, | 1c.2e.3c.4b.5a.6f, | |
| 1c.2e.3c.4b.5b.6a, | 1c.2e.3c.4b.5b.6b, | 1c.2e.3c.4b.5b.6c, | 1c.2e.3c.4b.5b.6d, | |

TABLE 7-continued

List of Compounds of Formula (II)

| | | | |
|---|---|---|---|
| 1c.2e.3c.4b.5b.6e, | 1c.2e.3c.4b.5b.6f, | 1c.2e.3c.4b.5c.6a, | 1c.2e.3c.4b.5c.6b, 1c.2e.3c.4b.5c.6c, |
| 1c.2e.3c.4b.5c.6d, | 1c.2e.3c.4b.5c.6e, | 1c.2e.3c.4b.5c.6f, | 1c.2e.3c.4b.5d.6a, |
| 1c.2e.3c.4b.5d.6b, | 1c.2e.3c.4b.5d.6c, | 1c.2e.3c.4b.5d.6d, | 1c.2e.3c.4b.5d.6e, |
| 1c.2e.3c.4b.5d.6f, | 1c.2e.3c.4b.5e.6a, | 1c.2e.3c.4b.5e.6b, | 1c.2e.3c.4b.5e.6c, |
| 1c.2e.3c.4b.5e.6d, | 1c.2e.3c.4b.5e.6e, | 1c.2e.3c.4b.5e.6f, | 1c.2e.3c.4b.5f.6a, 1c.2e.3c.4b.5f.6b, |
| 1c.2e.3c.4b.5f.6c, | 1c.2e.3c.4b.5f.6d, | 1c.2e.3c.4b.5f.6e, | 1c.2e.3c.4b.5f.6f, 1c.2e.3c.4c.5a.6a, |
| 1c.2e.3c.4c.5a.6b, | 1c.2e.3c.4c.5a.6c, | 1c.2e.3c.4c.5a.6d, | 1c.2e.3c.4c.5a.6e, 1c.2e.3c.4c.5a.6f, |
| 1c.2e.3c.4c.5b.6a, | 1c.2e.3c.4c.5b.6b, | 1c.2e.3c.4c.5b.6c, | 1c.2e.3c.4c.5b.6d, |
| 1c.2e.3c.4c.5b.6e, | 1c.2e.3c.4c.5b.6f, | 1c.2e.3c.4c.5c.6a, | 1c.2e.3c.4c.5c.6b, 1c.2e.3c.4c.5c.6c, |
| 1c.2e.3c.4c.5c.6d, | 1c.2e.3c.4c.5c.6e, | 1c.2e.3c.4c.5c.6f, | 1c.2e.3c.4c.5d.6a, 1c.2e.3c.4c.5d.6b, |
| 1c.2e.3c.4c.5d.6c, | 1c.2e.3c.4c.5d.6d, | 1c.2e.3c.4c.5d.6e, | 1c.2e.3c.4c.5d.6f, 1c.2e.3c.4c.5e.6a, |
| 1c.2e.3c.4c.5e.6b, | 1c.2e.3c.4c.5e.6c, | 1c.2e.3c.4c.5e.6d, | 1c.2e.3c.4c.5e.6e, 1c.2e.3c.4c.5e.6f, |
| 1c.2e.3c.4c.5f.6a, | 1c.2e.3c.4c.5f.6b, | 1c.2e.3c.4c.5f.6c, | 1c.2e.3c.4c.5f.6d, 1c.2e.3c.4c.5f.6e, |
| 1c.2e.3c.4c.5f.6f, | 1c.2e.3c.4d.5a.6a, | 1c.2e.3c.4d.5a.6b, | 1c.2e.3c.4d.5a.6c, |
| 1c.2e.3c.4d.5a.6d, | 1c.2e.3c.4d.5a.6e, | 1c.2e.3c.4d.5a.6f, | 1c.2e.3c.4d.5b.6a, |
| 1c.2e.3c.4d.5b.6b, | 1c.2e.3c.4d.5b.6c, | 1c.2e.3c.4d.5b.6d, | 1c.2e.3c.4d.5b.6e, |
| 1c.2e.3c.4d.5b.6f, | 1c.2e.3c.4d.5c.6a, | 1c.2e.3c.4d.5c.6b, | 1c.2e.3c.4d.5c.6c, |
| 1c.2e.3c.4d.5c.6d, | 1c.2e.3c.4d.5c.6e, | 1c.2e.3c.4d.5c.6f, | 1c.2e.3c.4d.5d.6a, |
| 1c.2e.3c.4d.5d.6b, | 1c.2e.3c.4d.5d.6c, | 1c.2e.3c.4d.5d.6d, | 1c.2e.3c.4d.5d.6e, |
| 1c.2e.3c.4d.5d.6f, | 1c.2e.3c.4d.5e.6a, | 1c.2e.3c.4d.5e.6b, | 1c.2e.3c.4d.5e.6c, |
| 1c.2e.3c.4d.5e.6d, | 1c.2e.3c.4d.5e.6e, | 1c.2e.3c.4d.5e.6f, | 1c.2e.3c.4d.5f.6a, |
| 1c.2e.3c.4d.5f.6b, | 1c.2e.3c.4d.5f.6c, | 1c.2e.3c.4d.5f.6d, | 1c.2e.3c.4d.5f.6e, 1c.2e.3c.4d.5f.6f, |
| 1c.2e.3c.4e.5a.6a, | 1c.2e.3c.4e.5a.6b, | 1c.2e.3c.4e.5a.6c, | 1c.2e.3c.4e.5a.6d, 1c.2e.3c.4e.5a.6e, |
| 1c.2e.3c.4e.5a.6f, | 1c.2e.3c.4e.5b.6a, | 1c.2e.3c.4e.5b.6b, | 1c.2e.3c.4e.5b.6c, |
| 1c.2e.3c.4e.5b.6d, | 1c.2e.3c.4e.5b.6e, | 1c.2e.3c.4e.5b.6f, | 1c.2e.3c.4e.5c.6a, 1c.2e.3c.4e.5c.6b, |
| 1c.2e.3c.4e.5c.6c, | 1c.2e.3c.4e.5c.6d, | 1c.2e.3c.4e.5c.6e, | 1c.2e.3c.4e.5c.6f, 1c.2e.3c.4e.5d.6a, |
| 1c.2e.3c.4e.5d.6b, | 1c.2e.3c.4e.5d.6c, | 1c.2e.3c.4e.5d.6d, | 1c.2e.3c.4e.5d.6e, |
| 1c.2e.3c.4e.5d.6f, | 1c.2e.3c.4e.5e.6a, | 1c.2e.3c.4e.5e.6b, | 1c.2e.3c.4e.5e.6c, 1c.2e.3c.4e.5e.6d, |
| 1c.2e.3c.4e.5e.6e, | 1c.2e.3c.4e.5e.6f, | 1c.2e.3c.4e.5f.6a, | 1c.2e.3c.4e.5f.6b, 1c.2e.3c.4e.5f.6c, |
| 1c.2e.3c.4e.5f.6d, | 1c.2e.3c.4e.5f.6e, | 1c.2e.3c.4e.5f.6f, | 1c.2e.3c.4f.5a.6a, 1c.2e.3c.4f.5a.6b, |
| 1c.2e.3c.4f.5a.6c, | 1c.2e.3c.4f.5a.6d, | 1c.2e.3c.4f.5a.6e, | 1c.2e.3c.4f.5a.6f, 1c.2e.3c.4f.5b.6a, |
| 1c.2e.3c.4f.5b.6b, | 1c.2e.3c.4f.5b.6c, | 1c.2e.3c.4f.5b.6d, | 1c.2e.3c.4f.5b.6e, 1c.2e.3c.4f.5b.6f, |
| 1c.2e.3c.4f.5c.6a, | 1c.2e.3c.4f.5c.6b, | 1c.2e.3c.4f.5c.6c, | 1c.2e.3c.4f.5c.6d, 1c.2e.3c.4f.5c.6e, |
| 1c.2e.3c.4f.5c.6f, | 1c.2e.3c.4f.5d.6a, | 1c.2e.3c.4f.5d.6b, | 1c.2e.3c.4f.5d.6c, 1c.2e.3c.4f.5d.6d, |
| 1c.2e.3c.4f.5d.6e, | 1c.2e.3c.4f.5d.6f, | 1c.2e.3c.4f.5e.6a, | 1c.2e.3c.4f.5e.6b, 1c.2e.3c.4f.5e.6c, |
| 1c.2e.3c.4f.5e.6d, | 1c.2e.3c.4f.5e.6e, | 1c.2e.3c.4f.5e.6f, | 1c.2e.3c.4f.5f.6a, 1c.2e.3c.4f.5f.6b, |
| 1c.2e.3c.4f.5f.6c, | 1c.2e.3c.4f.5f.6d, | 1c.2e.3c.4f.5f.6e, | 1c.2e.3c.4f.5f.6f, 1c.2e.3d.4a.5a.6a, |
| 1c.2e.3d.4a.5a.6b, | 1c.2e.3d.4a.5a.6c, | 1c.2e.3d.4a.5a.6d, | 1c.2e.3d.4a.5a.6e, |
| 1c.2e.3d.4a.5a.6f, | 1c.2e.3d.4a.5b.6a, | 1c.2e.3d.4a.5b.6b, | 1c.2e.3d.4a.5b.6c, |
| 1c.2e.3d.4a.5b.6d, | 1c.2e.3d.4a.5b.6e, | 1c.2e.3d.4a.5b.6f, | 1c.2e.3d.4a.5c.6a, |
| 1c.2e.3d.4a.5c.6b, | 1c.2e.3d.4a.5c.6c, | 1c.2e.3d.4a.5c.6d, | 1c.2e.3d.4a.5c.6e, |
| 1c.2e.3d.4a.5c.6f, | 1c.2e.3d.4a.5d.6a, | 1c.2e.3d.4a.5d.6b, | 1c.2e.3d.4a.5d.6c, |
| 1c.2e.3d.4a.5d.6d, | 1c.2e.3d.4a.5d.6e, | 1c.2e.3d.4a.5d.6f, | 1c.2e.3d.4a.5e.6a, |
| 1c.2e.3d.4a.5e.6b, | 1c.2e.3d.4a.5e.6c, | 1c.2e.3d.4a.5e.6d, | 1c.2e.3d.4a.5e.6e, |
| 1c.2e.3d.4a.5e.6f, | 1c.2e.3d.4a.5f.6a, | 1c.2e.3d.4a.5f.6b, | 1c.2e.3d.4a.5f.6c, |
| 1c.2e.3d.4a.5f.6d, | 1c.2e.3d.4a.5f.6e, | 1c.2e.3d.4a.5f.6f, | 1c.2e.3d.4b.5a.6a, |
| 1c.2e.3d.4b.5a.6b, | 1c.2e.3d.4b.5a.6c, | 1c.2e.3d.4b.5a.6d, | 1c.2e.3d.4b.5a.6e, |
| 1c.2e.3d.4b.5a.6f, | 1c.2e.3d.4b.5b.6a, | 1c.2e.3d.4b.5b.6b, | 1c.2e.3d.4b.5b.6c, |
| 1c.2e.3d.4b.5b.6d, | 1c.2e.3d.4b.5b.6e, | 1c.2e.3d.4b.5b.6f, | 1c.2e.3d.4b.5c.6a, |
| 1c.2e.3d.4b.5c.6b, | 1c.2e.3d.4b.5c.6c, | 1c.2e.3d.4b.5c.6d, | 1c.2e.3d.4b.5c.6e, |
| 1c.2e.3d.4b.5c.6f, | 1c.2e.3d.4b.5d.6a, | 1c.2e.3d.4b.5d.6b, | 1c.2e.3d.4b.5d.6c, |
| 1c.2e.3d.4b.5d.6d, | 1c.2e.3d.4b.5d.6e, | 1c.2e.3d.4b.5d.6f, | 1c.2e.3d.4b.5e.6a, |
| 1c.2e.3d.4b.5e.6b, | 1c.2e.3d.4b.5e.6c, | 1c.2e.3d.4b.5e.6d, | 1c.2e.3d.4b.5e.6e, |
| 1c.2e.3d.4b.5e.6f, | 1c.2e.3d.4b.5f.6a, | 1c.2e.3d.4b.5f.6b, | 1c.2e.3d.4b.5f.6c, |
| 1c.2e.3d.4b.5f.6d, | 1c.2e.3d.4b.5f.6e, | 1c.2e.3d.4b.5f.6f, | 1c.2e.3d.4c.5a.6a, |
| 1c.2e.3d.4c.5a.6b, | 1c.2e.3d.4c.5a.6c, | 1c.2e.3d.4c.5a.6d, | 1c.2e.3d.4c.5a.6e, |
| 1c.2e.3d.4c.5a.6f, | 1c.2e.3d.4c.5b.6a, | 1c.2e.3d.4c.5b.6b, | 1c.2e.3d.4c.5b.6c, |
| 1c.2e.3d.4c.5b.6d, | 1c.2e.3d.4c.5b.6e, | 1c.2e.3d.4c.5b.6f, | 1c.2e.3d.4c.5c.6a, |
| 1c.2e.3d.4c.5c.6b, | 1c.2e.3d.4c.5c.6c, | 1c.2e.3d.4c.5c.6d, | 1c.2e.3d.4c.5c.6e, |
| 1c.2e.3d.4c.5c.6f, | 1c.2e.3d.4c.5d.6a, | 1c.2e.3d.4c.5d.6b, | 1c.2e.3d.4c.5d.6c, |
| 1c.2e.3d.4c.5d.6d, | 1c.2e.3d.4c.5d.6e, | 1c.2e.3d.4c.5d.6f, | 1c.2e.3d.4c.5e.6a, |
| 1c.2e.3d.4c.5e.6b, | 1c.2e.3d.4c.5e.6c, | 1c.2e.3d.4c.5e.6d, | 1c.2e.3d.4c.5e.6e, |
| 1c.2e.3d.4c.5e.6f, | 1c.2e.3d.4c.5f.6a, | 1c.2e.3d.4c.5f.6b, | 1c.2e.3d.4c.5f.6c, 1c.2e.3d.4c.5f.6d, |
| 1c.2e.3d.4c.5f.6e, | 1c.2e.3d.4c.5f.6f, | 1c.2e.3d.4d.5a.6a, | 1c.2e.3d.4d.5a.6b, |
| 1c.2e.3d.4d.5a.6c, | 1c.2e.3d.4d.5a.6d, | 1c.2e.3d.4d.5a.6e, | 1c.2e.3d.4d.5a.6f, |
| 1c.2e.3d.4d.5b.6a, | 1c.2e.3d.4d.5b.6b, | 1c.2e.3d.4d.5b.6c, | 1c.2e.3d.4d.5b.6d, |
| 1c.2e.3d.4d.5b.6e, | 1c.2e.3d.4d.5b.6f, | 1c.2e.3d.4d.5c.6a, | 1c.2e.3d.4d.5c.6b, |
| 1c.2e.3d.4d.5c.6c, | 1c.2e.3d.4d.5c.6d, | 1c.2e.3d.4d.5c.6e, | 1c.2e.3d.4d.5c.6f, |
| 1c.2e.3d.4d.5d.6a, | 1c.2e.3d.4d.5d.6b, | 1c.2e.3d.4d.5d.6c, | 1c.2e.3d.4d.5d.6d, |
| 1c.2e.3d.4d.5d.6e, | 1c.2e.3d.4d.5d.6f, | 1c.2e.3d.4d.5e.6a, | 1c.2e.3d.4d.5e.6b, |
| 1c.2e.3d.4d.5e.6c, | 1c.2e.3d.4d.5e.6d, | 1c.2e.3d.4d.5e.6e, | 1c.2e.3d.4d.5e.6f, |
| 1c.2e.3d.4d.5f.6a, | 1c.2e.3d.4d.5f.6b, | 1c.2e.3d.4d.5f.6c, | 1c.2e.3d.4d.5f.6d, |
| 1c.2e.3d.4d.5f.6e, | 1c.2e.3d.4d.5f.6f, | 1c.2e.3d.4e.5a.6a, | 1c.2e.3d.4e.5a.6b, |
| 1c.2e.3d.4e.5a.6c, | 1c.2e.3d.4e.5a.6d, | 1c.2e.3d.4e.5a.6e, | 1c.2e.3d.4e.5a.6f, |
| 1c.2e.3d.4e.5b.6a, | 1c.2e.3d.4e.5b.6b, | 1c.2e.3d.4e.5b.6c, | 1c.2e.3d.4e.5b.6d, |
| 1c.2e.3d.4e.5b.6e, | 1c.2e.3d.4e.5b.6f, | 1c.2e.3d.4e.5c.6a, | 1c.2e.3d.4e.5c.6b, |
| 1c.2e.3d.4e.5c.6c, | 1c.2e.3d.4e.5c.6d, | 1c.2e.3d.4e.5c.6e, | 1c.2e.3d.4e.5c.6f, |
| 1c.2e.3d.4e.5d.6a, | 1c.2e.3d.4e.5d.6b, | 1c.2e.3d.4e.5d.6c, | 1c.2e.3d.4e.5d.6d, |

TABLE 7-continued

List of Compounds of Formula (II)

| | | | | |
|---|---|---|---|---|
| 1c.2e.3d.4e.5d.6e, | 1c.2e.3d.4e.5d.6f, | 1c.2e.3d.4e.5e.6a, | 1c.2e.3d.4e.5e.6b, | |
| 1c.2e.3d.4e.5e.6c, | 1c.2e.3d.4e.5e.6d, | 1c.2e.3d.4e.5e.6e, | 1c.2e.3d.4e.5e.6f, | |
| 1c.2e.3d.4e.5f.6a, | 1c.2e.3d.4e.5f.6b, | 1c.2e.3d.4e.5f.6c, | 1c.2e.3d.4e.5f.6d, | 1c.2e.3d.4e.5f.6e, |
| 1c.2e.3d.4e.5f.6f, | 1c.2e.3d.4f.5a.6a, | 1c.2e.3d.4f.5a.6b, | 1c.2e.3d.4f.5a.6c, | 1c.2e.3d.4f.5a.6d, |
| 1c.2e.3d.4f.5a.6e, | 1c.2e.3d.4f.5a.6f, | 1c.2e.3d.4f.5b.6a, | 1c.2e.3d.4f.5b.6b, | 1c.2e.3d.4f.5b.6c, |
| 1c.2e.3d.4f.5b.6d, | 1c.2e.3d.4f.5b.6e, | 1c.2e.3d.4f.5b.6f, | 1c.2e.3d.4f.5c.6a, | 1c.2e.3d.4f.5c.6b, |
| 1c.2e.3d.4f.5c.6c, | 1c.2e.3d.4f.5c.6d, | 1c.2e.3d.4f.5c.6e, | 1c.2e.3d.4f.5c.6f, | 1c.2e.3d.4f.5d.6a, |
| 1c.2e.3d.4f.5d.6b, | 1c.2e.3d.4f.5d.6c, | 1c.2e.3d.4f.5d.6d, | 1c.2e.3d.4f.5d.6e, | |
| 1c.2e.3d.4f.5d.6f, | 1c.2e.3d.4f.5e.6a, | 1c.2e.3d.4f.5e.6b, | 1c.2e.3d.4f.5e.6c, | 1c.2e.3d.4f.5e.6d, |
| 1c.2e.3d.4f.5e.6e, | 1c.2e.3d.4f.5e.6f, | 1c.2e.3d.4f.5f.6a, | 1c.2e.3d.4f.5f.6b, | 1c.2e.3d.4f.5f.6c, |
| 1c.2e.3d.4f.5f.6d, | 1c.2e.3d.4f.5f.6e, | 1c.2e.3d.4f.5f.6f, | 1c.2e.3e.4a.5a.6a, | 1c.2e.3e.4a.5a.6b, |
| 1c.2e.3e.4a.5a.6c, | 1c.2e.3e.4a.5a.6d, | 1c.2e.3e.4a.5a.6e, | 1c.2e.3e.4a.5a.6f, | |
| 1c.2e.3e.4a.5b.6a, | 1c.2e.3e.4a.5b.6b, | 1c.2e.3e.4a.5b.6c, | 1c.2e.3e.4a.5b.6d, | |
| 1c.2e.3e.4a.5b.6e, | 1c.2e.3e.4a.5b.6f, | 1c.2e.3e.4a.5c.6a, | 1c.2e.3e.4a.5c.6b, | 1c.2e.3e.4a.5c.6c, |
| 1c.2e.3e.4a.5c.6d, | 1c.2e.3e.4a.5c.6e, | 1c.2e.3e.4a.5c.6f, | 1c.2e.3e.4a.5d.6a, | |
| 1c.2e.3e.4a.5d.6b, | 1c.2e.3e.4a.5d.6c, | 1c.2e.3e.4a.5d.6d, | 1c.2e.3e.4a.5d.6e, | |
| 1c.2e.3e.4a.5d.6f, | 1c.2e.3e.4a.5e.6a, | 1c.2e.3e.4a.5e.6b, | 1c.2e.3e.4a.5e.6c, | |
| 1c.2e.3e.4a.5e.6d, | 1c.2e.3e.4a.5e.6e, | 1c.2e.3e.4a.5e.6f, | 1c.2e.3e.4a.5f.6a, | 1c.2e.3e.4a.5f.6b, |
| 1c.2e.3e.4a.5f.6c, | 1c.2e.3e.4a.5f.6d, | 1c.2e.3e.4a.5f.6e, | 1c.2e.3e.4a.5f.6f, | 1c.2e.3e.4b.5a.6a, |
| 1c.2e.3e.4b.5a.6b, | 1c.2e.3e.4b.5a.6c, | 1c.2e.3e.4b.5a.6d, | 1c.2e.3e.4b.5a.6e, | |
| 1c.2e.3e.4b.5a.6f, | 1c.2e.3e.4b.5b.6a, | 1c.2e.3e.4b.5b.6b, | 1c.2e.3e.4b.5b.6c, | |
| 1c.2e.3e.4b.5b.6d, | 1c.2e.3e.4b.5b.6e, | 1c.2e.3e.4b.5b.6f, | 1c.2e.3e.4b.5c.6a, | |
| 1c.2e.3e.4b.5c.6b, | 1c.2e.3e.4b.5c.6c, | 1c.2e.3e.4b.5c.6d, | 1c.2e.3e.4b.5c.6e, | |
| 1c.2e.3e.4b.5c.6f, | 1c.2e.3e.4b.5d.6a, | 1c.2e.3e.4b.5d.6b, | 1c.2e.3e.4b.5d.6c, | |
| 1c.2e.3e.4b.5d.6d, | 1c.2e.3e.4b.5d.6e, | 1c.2e.3e.4b.5d.6f, | 1c.2e.3e.4b.5e.6a, | |
| 1c.2e.3e.4b.5e.6b, | 1c.2e.3e.4b.5e.6c, | 1c.2e.3e.4b.5e.6d, | 1c.2e.3e.4b.5e.6e, | |
| 1c.2e.3e.4b.5e.6f, | 1c.2e.3e.4b.5f.6a, | 1c.2e.3e.4b.5f.6b, | 1c.2e.3e.4b.5f.6c, | 1c.2e.3e.4b.5f.6d, |
| 1c.2e.3e.4b.5f.6e, | 1c.2e.3e.4b.5f.6f, | 1c.2e.3e.4c.5a.6a, | 1c.2e.3e.4c.5a.6b, | 1c.2e.3e.4c.5a.6c, |
| 1c.2e.3e.4c.5a.6d, | 1c.2e.3e.4c.5a.6e, | 1c.2e.3e.4c.5a.6f, | 1c.2e.3e.4c.5b.6a, | 1c.2e.3e.4c.5b.6b, |
| 1c.2e.3e.4c.5b.6c, | 1c.2e.3e.4c.5b.6d, | 1c.2e.3e.4c.5b.6e, | 1c.2e.3e.4c.5b.6f, | 1c.2e.3e.4c.5c.6a, |
| 1c.2e.3e.4c.5c.6b, | 1c.2e.3e.4c.5c.6c, | 1c.2e.3e.4c.5c.6d, | 1c.2e.3e.4c.5c.6e, | 1c.2e.3e.4c.5c.6f, |
| 1c.2e.3e.4c.5d.6a, | 1c.2e.3e.4c.5d.6b, | 1c.2e.3e.4c.5d.6c, | 1c.2e.3e.4c.5d.6d, | |
| 1c.2e.3e.4c.5d.6e, | 1c.2e.3e.4c.5d.6f, | 1c.2e.3e.4c.5e.6a, | 1c.2e.3e.4c.5e.6b, | 1c.2e.3e.4c.5e.6c, |
| 1c.2e.3e.4c.5e.6d, | 1c.2e.3e.4c.5e.6e, | 1c.2e.3e.4c.5e.6f, | 1c.2e.3e.4c.5f.6a, | 1c.2e.3e.4c.5f.6b, |
| 1c.2e.3e.4c.5f.6c, | 1c.2e.3e.4c.5f.6d, | 1c.2e.3e.4c.5f.6e, | 1c.2e.3e.4c.5f.6f, | 1c.2e.3e.4d.5a.6a, |
| 1c.2e.3e.4d.5a.6b, | 1c.2e.3e.4d.5a.6c, | 1c.2e.3e.4d.5a.6d, | 1c.2e.3e.4d.5a.6e, | |
| 1c.2e.3e.4d.5a.6f, | 1c.2e.3e.4d.5b.6a, | 1c.2e.3e.4d.5b.6b, | 1c.2e.3e.4d.5b.6c, | |
| 1c.2e.3e.4d.5b.6d, | 1c.2e.3e.4d.5b.6e, | 1c.2e.3e.4d.5b.6f, | 1c.2e.3e.4d.5c.6a, | |
| 1c.2e.3e.4d.5c.6b, | 1c.2e.3e.4d.5c.6c, | 1c.2e.3e.4d.5c.6d, | 1c.2e.3e.4d.5c.6e, | |
| 1c.2e.3e.4d.5c.6f, | 1c.2e.3e.4d.5d.6a, | 1c.2e.3e.4d.5d.6b, | 1c.2e.3e.4d.5d.6c, | |
| 1c.2e.3e.4d.5d.6d, | 1c.2e.3e.4d.5d.6e, | 1c.2e.3e.4d.5d.6f, | 1c.2e.3e.4d.5e.6a, | |
| 1c.2e.3e.4d.5e.6b, | 1c.2e.3e.4d.5e.6c, | 1c.2e.3e.4d.5e.6d, | 1c.2e.3e.4d.5e.6e, | |
| 1c.2e.3e.4d.5e.6f, | 1c.2e.3e.4d.5f.6a, | 1c.2e.3e.4d.5f.6b, | 1c.2e.3e.4d.5f.6c, | 1c.2e.3e.4d.5f.6d, |
| 1c.2e.3e.4d.5f.6e, | 1c.2e.3e.4d.5f.6f, | 1c.2e.3e.4e.5a.6a, | 1c.2e.3e.4e.5a.6b, | 1c.2e.3e.4e.5a.6c, |
| 1c.2e.3e.4e.5a.6d, | 1c.2e.3e.4e.5a.6e, | 1c.2e.3e.4e.5a.6f, | 1c.2e.3e.4e.5b.6a, | |
| 1c.2e.3e.4e.5b.6b, | 1c.2e.3e.4e.5b.6c, | 1c.2e.3e.4e.5b.6d, | 1c.2e.3e.4e.5b.6e, | |
| 1c.2e.3e.4e.5b.6f, | 1c.2e.3e.4e.5c.6a, | 1c.2e.3e.4e.5c.6b, | 1c.2e.3e.4e.5c.6c, | 1c.2e.3e.4e.5c.6d, |
| 1c.2e.3e.4e.5c.6e, | 1c.2e.3e.4e.5c.6f, | 1c.2e.3e.4e.5d.6a, | 1c.2e.3e.4e.5d.6b, | |
| 1c.2e.3e.4e.5d.6c, | 1c.2e.3e.4e.5d.6d, | 1c.2e.3e.4e.5d.6e, | 1c.2e.3e.4e.5d.6f, | |
| 1c.2e.3e.4e.5e.6a, | 1c.2e.3e.4e.5e.6b, | 1c.2e.3e.4e.5e.6c, | 1c.2e.3e.4e.5e.6d, | |
| 1c.2e.3e.4e.5e.6e, | 1c.2e.3e.4e.5e.6f, | 1c.2e.3e.4e.5f.6a, | 1c.2e.3e.4e.5f.6b, | 1c.2e.3e.4e.5f.6c, |
| 1c.2e.3e.4e.5f.6d, | 1c.2e.3e.4e.5f.6e, | 1c.2e.3e.4e.5f.6f, | 1c.2e.3e.4f.5a.6a, | 1c.2e.3e.4f.5a.6b, |
| 1c.2e.3e.4f.5a.6c, | 1c.2e.3e.4f.5a.6d, | 1c.2e.3e.4f.5a.6e, | 1c.2e.3e.4f.5a.6f, | 1c.2e.3e.4f.5b.6a, |
| 1c.2e.3e.4f.5b.6b, | 1c.2e.3e.4f.5b.6c, | 1c.2e.3e.4f.5b.6d, | 1c.2e.3e.4f.5b.6e, | 1c.2e.3e.4f.5b.6f, |
| 1c.2e.3e.4f.5c.6a, | 1c.2e.3e.4f.5c.6b, | 1c.2e.3e.4f.5c.6c, | 1c.2e.3e.4f.5c.6d, | 1c.2e.3e.4f.5c.6e, |
| 1c.2e.3e.4f.5c.6f, | 1c.2e.3e.4f.5d.6a, | 1c.2e.3e.4f.5d.6b, | 1c.2e.3e.4f.5d.6c, | 1c.2e.3e.4f.5d.6d, |
| 1c.2e.3e.4f.5d.6e, | 1c.2e.3e.4f.5d.6f, | 1c.2e.3e.4f.5e.6a, | 1c.2e.3e.4f.5e.6b, | 1c.2e.3e.4f.5e.6c, |
| 1c.2e.3e.4f.5e.6d, | 1c.2e.3e.4f.5e.6e, | 1c.2e.3e.4f.5e.6f, | 1c.2e.3e.4f.5f.6a, | 1c.2e.3e.4f.5f.6b, |
| 1c.2e.3e.4f.5f.6c, | 1c.2e.3e.4f.5f.6d, | 1c.2e.3e.4f.5f.6e, | 1c.2e.3e.4f.5f.6f, | 1c.2e.3f.4a.5a.6a, |
| 1c.2e.3f.4a.5a.6b, | 1c.2e.3f.4a.5a.6c, | 1c.2e.3f.4a.5a.6d, | 1c.2e.3f.4a.5a.6e, | 1c.2e.3f.4a.5a.6f, |
| 1c.2e.3f.4a.5b.6a, | 1c.2e.3f.4a.5b.6b, | 1c.2e.3f.4a.5b.6c, | 1c.2e.3f.4a.5b.6d, | 1c.2e.3f.4a.5b.6e, |
| 1c.2e.3f.4a.5b.6f, | 1c.2e.3f.4a.5c.6a, | 1c.2e.3f.4a.5c.6b, | 1c.2e.3f.4a.5c.6c, | 1c.2e.3f.4a.5c.6d, |
| 1c.2e.3f.4a.5c.6e, | 1c.2e.3f.4a.5c.6f, | 1c.2e.3f.4a.5d.6a, | 1c.2e.3f.4a.5d.6b, | 1c.2e.3f.4a.5d.6c, |
| 1c.2e.3f.4a.5d.6d, | 1c.2e.3f.4a.5d.6e, | 1c.2e.3f.4a.5d.6f, | 1c.2e.3f.4a.5e.6a, | 1c.2e.3f.4a.5e.6b, |
| 1c.2e.3f.4a.5e.6c, | 1c.2e.3f.4a.5e.6d, | 1c.2e.3f.4a.5e.6e, | 1c.2e.3f.4a.5e.6f, | 1c.2e.3f.4a.5f.6a, |
| 1c.2e.3f.4a.5f.6b, | 1c.2e.3f.4a.5f.6c, | 1c.2e.3f.4a.5f.6d, | 1c.2e.3f.4a.5f.6e, | 1c.2e.3f.4a.5f.6f, |
| 1c.2e.3f.4b.5a.6a, | 1c.2e.3f.4b.5a.6b, | 1c.2e.3f.4b.5a.6c, | 1c.2e.3f.4b.5a.6d, | 1c.2e.3f.4b.5a.6e, |
| 1c.2e.3f.4b.5a.6f, | 1c.2e.3f.4b.5b.6a, | 1c.2e.3f.4b.5b.6b, | 1c.2e.3f.4b.5b.6c, | 1c.2e.3f.4b.5b.6d, |
| 1c.2e.3f.4b.5b.6e, | 1c.2e.3f.4b.5b.6f, | 1c.2e.3f.4b.5c.6a, | 1c.2e.3f.4b.5c.6b, | 1c.2e.3f.4b.5c.6c, |
| 1c.2e.3f.4b.5c.6d, | 1c.2e.3f.4b.5c.6e, | 1c.2e.3f.4b.5c.6f, | 1c.2e.3f.4b.5d.6a, | 1c.2e.3f.4b.5d.6b, |
| 1c.2e.3f.4b.5d.6c, | 1c.2e.3f.4b.5d.6d, | 1c.2e.3f.4b.5d.6e, | 1c.2e.3f.4b.5d.6f, | 1c.2e.3f.4b.5e.6a, |
| 1c.2e.3f.4b.5e.6b, | 1c.2e.3f.4b.5e.6c, | 1c.2e.3f.4b.5e.6d, | 1c.2e.3f.4b.5e.6e, | 1c.2e.3f.4b.5e.6f, |
| 1c.2e.3f.4b.5f.6a, | 1c.2e.3f.4b.5f.6b, | 1c.2e.3f.4b.5f.6c, | 1c.2e.3f.4b.5f.6d, | 1c.2e.3f.4b.5f.6e, |
| 1c.2e.3f.4b.5f.6f, | 1c.2e.3f.4c.5a.6a, | 1c.2e.3f.4c.5a.6b, | 1c.2e.3f.4c.5a.6c, | 1c.2e.3f.4c.5a.6d, |
| 1c.2e.3f.4c.5a.6e, | 1c.2e.3f.4c.5a.6f, | 1c.2e.3f.4c.5b.6a, | 1c.2e.3f.4c.5b.6b, | 1c.2e.3f.4c.5b.6c, |
| 1c.2e.3f.4c.5b.6d, | 1c.2e.3f.4c.5b.6e, | 1c.2e.3f.4c.5b.6f, | 1c.2e.3f.4c.5c.6a, | 1c.2e.3f.4c.5c.6b, |
| 1c.2e.3f.4c.5c.6c, | 1c.2e.3f.4c.5c.6d, | 1c.2e.3f.4c.5c.6e, | 1c.2e.3f.4c.5c.6f, | 1c.2e.3f.4c.5d.6a, |
| 1c.2e.3f.4c.5d.6b, | 1c.2e.3f.4c.5d.6c, | 1c.2e.3f.4c.5d.6d, | 1c.2e.3f.4c.5d.6e, | 1c.2e.3f.4c.5d.6f, |

TABLE 7-continued

List of Compounds of Formula (II)

| | | | | |
|---|---|---|---|---|
| 1c.2e.3f.4c.5e.6a, | 1c.2e.3f.4c.5e.6b, | 1c.2e.3f.4c.5e.6c, | 1c.2e.3f.4c.5e.6d, | 1c.2e.3f.4c.5e.6e, |
| 1c.2e.3f.4c.5e.6f, | 1c.2e.3f.4c.5f.6a, | 1c.2e.3f.4c.5f.6b, | 1c.2e.3f.4c.5f.6c, | 1c.2e.3f.4c.5f.6d, |
| 1c.2e.3f.4c.5f.6e, | 1c.2e.3f.4c.5f.6f, | 1c.2e.3f.4d.5a.6a, | 1c.2e.3f.4d.5a.6b, | 1c.2e.3f.4d.5a.6c, |
| 1c.2e.3f.4d.5a.6d, | 1c.2e.3f.4d.5a.6e, | 1c.2e.3f.4d.5a.6f, | 1c.2e.3f.4d.5b.6a, | |
| 1c.2e.3f.4d.5b.6b, | 1c.2e.3f.4d.5b.6c, | 1c.2e.3f.4d.5b.6d, | 1c.2e.3f.4d.5b.6e, | |
| 1c.2e.3f.4d.5b.6f, | 1c.2e.3f.4d.5c.6a, | 1c.2e.3f.4d.5c.6b, | 1c.2e.3f.4d.5c.6c, | 1c.2e.3f.4d.5c.6d, |
| 1c.2e.3f.4d.5c.6e, | 1c.2e.3f.4d.5c.6f, | 1c.2e.3f.4d.5d.6a, | 1c.2e.3f.4d.5d.6b, | 1c.2e.3f.4d.5d.6c, |
| 1c.2e.3f.4d.5d.6d, | 1c.2e.3f.4d.5d.6e, | 1c.2e.3f.4d.5d.6f, | 1c.2e.3f.4d.5e.6a, | |
| 1c.2e.3f.4d.5e.6b, | 1c.2e.3f.4d.5e.6c, | 1c.2e.3f.4d.5e.6d, | 1c.2e.3f.4d.5e.6e, | 1c.2e.3f.4d.5e.6f, |
| 1c.2e.3f.4d.5f.6a, | 1c.2e.3f.4d.5f.6b, | 1c.2e.3f.4d.5f.6c, | 1c.2e.3f.4d.5f.6d, | 1c.2e.3f.4d.5f.6e, |
| 1c.2e.3f.4d.5f.6f, | 1c.2e.3f.4e.5a.6a, | 1c.2e.3f.4e.5a.6b, | 1c.2e.3f.4e.5a.6c, | 1c.2e.3f.4e.5a.6d, |
| 1c.2e.3f.4e.5a.6e, | 1c.2e.3f.4e.5a.6f, | 1c.2e.3f.4e.5b.6a, | 1c.2e.3f.4e.5b.6b, | 1c.2e.3f.4e.5b.6c, |
| 1c.2e.3f.4e.5b.6d, | 1c.2e.3f.4e.5b.6e, | 1c.2e.3f.4e.5b.6f, | 1c.2e.3f.4e.5c.6a, | 1c.2e.3f.4e.5c.6b, |
| 1c.2e.3f.4e.5c.6c, | 1c.2e.3f.4e.5c.6d, | 1c.2e.3f.4e.5c.6e, | 1c.2e.3f.4e.5c.6f, | 1c.2e.3f.4e.5d.6a, |
| 1c.2e.3f.4e.5d.6b, | 1c.2e.3f.4e.5d.6c, | 1c.2e.3f.4e.5d.6d, | 1c.2e.3f.4e.5d.6e, | 1c.2e.3f.4e.5d.6f, |
| 1c.2e.3f.4e.5e.6a, | 1c.2e.3f.4e.5e.6b, | 1c.2e.3f.4e.5e.6c, | 1c.2e.3f.4e.5e.6d, | 1c.2e.3f.4e.5e.6e, |
| 1c.2e.3f.4e.5e.6f, | 1c.2e.3f.4e.5f.6a, | 1c.2e.3f.4e.5f.6b, | 1c.2e.3f.4e.5f.6c, | 1c.2e.3f.4e.5f.6d, |
| 1c.2e.3f.4e.5f.6e, | 1c.2e.3f.4e.5f.6f, | 1c.2e.3f.4f.5a.6a, | 1c.2e.3f.4f.5a.6b, | 1c.2e.3f.4f.5a.6c, |
| 1c.2e.3f.4f.5a.6d, | 1c.2e.3f.4f.5a.6e, | 1c.2e.3f.4f.5a.6f, | 1c.2e.3f.4f.5b.6a, | 1c.2e.3f.4f.5b.6b, |
| 1c.2e.3f.4f.5b.6c, | 1c.2e.3f.4f.5b.6d, | 1c.2e.3f.4f.5b.6e, | 1c.2e.3f.4f.5b.6f, | 1c.2e.3f.4f.5c.6a, |
| 1c.2e.3f.4f.5c.6b, | 1c.2e.3f.4f.5c.6c, | 1c.2e.3f.4f.5c.6d, | 1c.2e.3f.4f.5c.6e, | 1c.2e.3f.4f.5c.6f, |
| 1c.2e.3f.4f.5d.6a, | 1c.2e.3f.4f.5d.6b, | 1c.2e.3f.4f.5d.6c, | 1c.2e.3f.4f.5d.6d, | 1c.2e.3f.4f.5d.6e, |
| 1c.2e.3f.4f.5d.6f, | 1c.2e.3f.4f.5e.6a, | 1c.2e.3f.4f.5e.6b, | 1c.2e.3f.4f.5e.6c, | 1c.2e.3f.4f.5e.6d, |
| 1c.2e.3f.4f.5e.6e, | 1c.2e.3f.4f.5e.6f, | 1c.2e.3f.4f.5f.6a, | 1c.2e.3f.4f.5f.6b, | 1c.2e.3f.4f.5f.6c, |
| 1c.2e.3f.4f.5f.6d, | 1c.2e.3f.4f.5f.6e, | 1c.2e.3f.4f.5f.6f, | 1c.2f.3a.4a.5a.6a, | 1c.2f.3a.4a.5a.6b, |
| 1c.2f.3a.4a.5a.6c, | 1c.2f.3a.4a.5a.6d, | 1c.2f.3a.4a.5a.6e, | 1c.2f.3a.4a.5a.6f, | 1c.2f.3a.4a.5b.6a, |
| 1c.2f.3a.4a.5b.6b, | 1c.2f.3a.4a.5b.6c, | 1c.2f.3a.4a.5b.6d, | 1c.2f.3a.4a.5b.6e, | 1c.2f.3a.4a.5b.6f, |
| 1c.2f.3a.4a.5c.6a, | 1c.2f.3a.4a.5c.6b, | 1c.2f.3a.4a.5c.6c, | 1c.2f.3a.4a.5c.6d, | 1c.2f.3a.4a.5c.6e, |
| 1c.2f.3a.4a.5c.6f, | 1c.2f.3a.4a.5d.6a, | 1c.2f.3a.4a.5d.6b, | 1c.2f.3a.4a.5d.6c, | 1c.2f.3a.4a.5d.6d, |
| 1c.2f.3a.4a.5d.6e, | 1c.2f.3a.4a.5d.6f, | 1c.2f.3a.4a.5e.6a, | 1c.2f.3a.4a.5e.6b, | 1c.2f.3a.4a.5e.6c, |
| 1c.2f.3a.4a.5e.6d, | 1c.2f.3a.4a.5e.6e, | 1c.2f.3a.4a.5e.6f, | 1c.2f.3a.4a.5f.6a, | 1c.2f.3a.4a.5f.6b, |
| 1c.2f.3a.4a.5f.6c, | 1c.2f.3a.4a.5f.6d, | 1c.2f.3a.4a.5f.6e, | 1c.2f.3a.4a.5f.6f, | 1c.2f.3a.4b.5a.6a, |
| 1c.2f.3a.4b.5a.6b, | 1c.2f.3a.4b.5a.6c, | 1c.2f.3a.4b.5a.6d, | 1c.2f.3a.4b.5a.6e, | 1c.2f.3a.4b.5a.6f, |
| 1c.2f.3a.4b.5b.6a, | 1c.2f.3a.4b.5b.6b, | 1c.2f.3a.4b.5b.6c, | 1c.2f.3a.4b.5b.6d, | |
| 1c.2f.3a.4b.5b.6e, | 1c.2f.3a.4b.5b.6f, | 1c.2f.3a.4b.5c.6a, | 1c.2f.3a.4b.5c.6b, | 1c.2f.3a.4b.5c.6c, |
| 1c.2f.3a.4b.5c.6d, | 1c.2f.3a.4b.5c.6e, | 1c.2f.3a.4b.5c.6f, | 1c.2f.3a.4b.5d.6a, | 1c.2f.3a.4b.5d.6b, |
| 1c.2f.3a.4b.5d.6c, | 1c.2f.3a.4b.5d.6d, | 1c.2f.3a.4b.5d.6e, | 1c.2f.3a.4b.5d.6f, | |
| 1c.2f.3a.4b.5e.6a, | 1c.2f.3a.4b.5e.6b, | 1c.2f.3a.4b.5e.6c, | 1c.2f.3a.4b.5e.6d, | 1c.2f.3a.4b.5e.6e, |
| 1c.2f.3a.4b.5e.6f, | 1c.2f.3a.4b.5f.6a, | 1c.2f.3a.4b.5f.6b, | 1c.2f.3a.4b.5f.6c, | 1c.2f.3a.4b.5f.6d, |
| 1c.2f.3a.4b.5f.6e, | 1c.2f.3a.4b.5f.6f, | 1c.2f.3a.4c.5a.6a, | 1c.2f.3a.4c.5a.6b, | 1c.2f.3a.4c.5a.6c, |
| 1c.2f.3a.4c.5a.6d, | 1c.2f.3a.4c.5a.6e, | 1c.2f.3a.4c.5a.6f, | 1c.2f.3a.4c.5b.6a, | 1c.2f.3a.4c.5b.6b, |
| 1c.2f.3a.4c.5b.6c, | 1c.2f.3a.4c.5b.6d, | 1c.2f.3a.4c.5b.6e, | 1c.2f.3a.4c.5b.6f, | 1c.213a.4c.5c.6a, |
| 1c.2f.3a.4c.5c.6b, | 1c.2f.3a.4c.5c.6c, | 1c.2f.3a.4c.5c.6d, | 1c.2f.3a.4c.5c.6e, | 1c.2f.3a.4c.5c.6f, |
| 1c.2f.3a.4c.5d.6a, | 1c.2f.3a.4c.5d.6b, | 1c.2f.3a.4c.5d.6c, | 1c.2f.3a.4c.5d.6d, | 1c.2f.3a.4c.5d.6e, |
| 1c.2f.3a.4c.5d.6f, | 1c.2f.3a.4c.5e.6a, | 1c.2f.3a.4c.5e.6b, | 1c.2f.3a.4c.5e.6c, | 1c.2f.3a.4c.5e.6d, |
| 1c.2f.3a.4c.5e.6e, | 1c.2f.3a.4c.5e.6f, | 1c.2f.3a.4c.5f.6a, | 1c.2f.3a.4c.5f.6b, | 1c.2f.3a.4c.5f.6c, |
| 1c.2f.3a.4c.5f.6d, | 1c.2f.3a.4c.5f.6e, | 1c.2f.3a.4c.5f.6f, | 1c.2f.3a.4d.5a.6a, | 1c.2f.3a.4d.5a.6b, |
| 1c.2f.3a.4d.5a.6c, | 1c.2f.3a.4d.5a.6d, | 1c.2f.3a.4d.5a.6e, | 1c.2f.3a.4d.5a.6f, | 1c.2f.3a.4d.5b.6a, |
| 1c.2f.3a.4d.5b.6b, | 1c.2f.3a.4d.5b.6c, | 1c.2f.3a.4d.5b.6d, | 1c.2f.3a.4d.5b.6e, | |
| 1c.2f.3a.4d.5b.6f, | 1c.2f.3a.4d.5c.6a, | 1c.2f.3a.4d.5c.6b, | 1c.2f.3a.4d.5c.6c, | 1c.2f.3a.4d.5c.6d, |
| 1c.2f.3a.4d.5c.6e, | 1c.2f.3a.4d.5c.6f, | 1c.2f.3a.4d.5d.6a, | 1c.2f.3a.4d.5d.6b, | |
| 1c.2f.3a.4d.5d.6c, | 1c.2f.3a.4d.5d.6d, | 1c.2f.3a.4d.5d.6e, | 1c.2f.3a.4d.5d.6f, | |
| 1c.2f.3a.4d.5e.6a, | 1c.2f.3a.4d.5e.6b, | 1c.2f.3a.4d.5e.6c, | 1c.2f.3a.4d.5e.6d, | |
| 1c.2f.3a.4d.5e.6e, | 1c.2f.3a.4d.5e.6f, | 1c.2f.3a.4d.5f.6a, | 1c.2f.3a.4d.5f.6b, | 1c.2f.3a.4d.5f.6c, |
| 1c.2f.3a.4d.5f.6d, | 1c.2f.3a.4d.5f.6e, | 1c.2f.3a.4d.5f.6f, | 1c.2f.3a.4e.5a.6a, | 1c.2f.3a.4e.5a.6b, |
| 1c.2f.3a.4e.5a.6c, | 1c.2f.3a.4e.5a.6d, | 1c.2f.3a.4e.5a.6e, | 1c.2f.3a.4e.5a.6f, | 1c.2f.3a.4e.5b.6a, |
| 1c.2f.3a.4e.5b.6b, | 1c.2f.3a.4e.5b.6c, | 1c.2f.3a.4e.5b.6d, | 1c.2f.3a.4e.5b.6e, | 1c.2f.3a.4e.5b.6f, |
| 1c.2f.3a.4e.5c.6a, | 1c.2f.3a.4e.5c.6b, | 1c.2f.3a.4e.5c.6c, | 1c.2f.3a.4e.5c.6d, | 1c.2f.3a.4e.5c.6e, |
| 1c.2f.3a.4e.5c.6f, | 1c.2f.3a.4e.5d.6a, | 1c.2f.3a.4e.5d.6b, | 1c.2f.3a.4e.5d.6c, | 1c.2f.3a.4e.5d.6d, |
| 1c.2f.3a.4e.5d.6e, | 1c.2f.3a.4e.5d.6f, | 1c.2f.3a.4e.5e.6a, | 1c.2f.3a.4e.5e.6b, | 1c.2f.3a.4e.5e.6c, |
| 1c.2f.3a.4e.5e.6d, | 1c.2f.3a.4e.5e.6e, | 1c.2f.3a.4e.5e.6f, | 1c.2f.3a.4e.5f.6a, | 1c.2f.3a.4e.5f.6b, |
| 1c.2f.3a.4e.5f.6c, | 1c.2f.3a.4e.5f.6d, | 1c.2f.3a.4e.5f.6e, | 1c.2f.3a.4e.5f.6f, | 1c.2f.3a.4f.5a.6a, |
| 1c.2f.3a.4f.5a.6b, | 1c.2f.3a.4f.5a.6c, | 1c.2f.3a.4f.5a.6d, | 1c.2f.3a.4f.5a.6e, | 1c.2f.3a.4f.5a.6f, |
| 1c.2f.3a.4f.5b.6a, | 1c.2f.3a.4f.5b.6b, | 1c.2f.3a.4f.5b.6c, | 1c.2f.3a.4f.5b.6d, | 1c.2f.3a.4f.5b.6e, |
| 1c.2f.3a.4f.5b.6f, | 1c.2f.3a.4f.5c.6a, | 1c.2f.3a.4f.5c.6b, | 1c.2f.3a.4f.5c.6c, | 1c.2f.3a.4f.5c.6d, |
| 1c.2f.3a.4f.5c.6e, | 1c.2f.3a.4f.5c.6f, | 1c.2f.3a.4f.5d.6a, | 1c.2f.3a.4f.5d.6b, | 1c.2f.3a.4f.5d.6c, |
| 1c.2f.3a.4f.5d.6d, | 1c.2f.3a.4f.5d.6e, | 1c.2f.3a.4f.5d.6f, | 1c.2f.3a.4f.5e.6a, | 1c.2f.3a.4f.5e.6b, |
| 1c.2f.3a.4f.5e.6c, | 1c.2f.3a.4f.5e.6d, | 1c.2f.3a.4f.5e.6e, | 1c.2f.3a.4f.5e.6f, | 1c.2f.3a.4f.5f.6a, |
| 1c.2f.3a.4f.5f.6b, | 1c.2f.3a.4f.5f.6c, | 1c.2f.3a.4f.5f.6d, | 1c.2f.3a.4f.5f.6e, | 1c.2f.3a.4f.5f.6f, |
| 1c.2f.3b.4a.5a.6a, | 1c.2f.3b.4a.5a.6b, | 1c.2f.3b.4a.5a.6c, | 1c.2f.3b.4a.5a.6d, | 1c.2f.3b.4a.5a.6e, |
| 1c.2f.3b.4a.5a.6f, | 1c.2f.3b.4a.5b.6a, | 1c.2f.3b.4a.5b.6b, | 1c.2f.3b.4a.5b.6c, | 1c.2f.3b.4a.5b.6d, |
| 1c.2f.3b.4a.5b.6e, | 1c.2f.3b.4a.5b.6f, | 1c.2f.3b.4a.5c.6a, | 1c.2f.3b.4a.5c.6b, | 1c.2f.3b.4a.5c.6c, |
| 1c.2f.3b.4a.5c.6d, | 1c.2f.3b.4a.5c.6e, | 1c.2f.3b.4a.5c.6f, | 1c.2f.3b.4a.5d.6a, | 1c.2f.3b.4a.5d.6b, |
| 1c.2f.3b.4a.5d.6c, | 1c.2f.3b.4a.5d.6d, | 1c.2f.3b.4a.5d.6e, | 1c.2f.3b.4a.5d.6f, | |
| 1c.2f.3b.4a.5e.6a, | 1c.2f.3b.4a.5e.6b, | 1c.2f.3b.4a.5e.6c, | 1c.2f.3b.4a.5e.6d, | 1c.2f.3b.4a.5e.6e, |
| 1c.2f.3b.4a.5e.6f, | 1c.2f.3b.4a.5f.6a, | 1c.2f.3b.4a.5f.6b, | 1c.2f.3b.4a.5f.6c, | 1c.2f.3b.4a.5f.6d, |
| 1c.2f.3b.4a.5f.6e, | 1c.2f.3b.4a.5f.6f, | 1c.2f.3b.4b.5a.6a, | 1c.2f.3b.4b.5a.6b, | 1c.2f.3b.4b.5a.6c, |
| 1c.2f.3b.4b.5a.6d, | 1c.2f.3b.4b.5a.6e, | 1c.2f.3b.4b.5a.6f, | 1c.2f.3b.4b.5b.6a, | |

TABLE 7-continued

List of Compounds of Formula (II)

| | | | |
|---|---|---|---|
| 1c.2f.3b.4b.5b.6b, | 1c.2f.3b.4b.5b.6c, | 1c.2f.3b.4b.5b.6d, | 1c.2f.3b.4b.5b.6e, |
| 1c.2f.3b.4b.5b.6f, | 1c.2f.3b.4b.5c.6a, | 1c.2f.3b.4b.5c.6b, | 1c.2f.3b.4b.5c.6c, | 1c.2f.3b.4b.5c.6d, |
| 1c.2f.3b.4b.5c.6e, | 1c.2f.3b.4b.5c.6f, | 1c.2f.3b.4b.5d.6a, | 1c.2f.3b.4b.5d.6b, |
| 1c.2f.3b.4b.5d.6c, | 1c.2f.3b.4b.5d.6d, | 1c.2f.3b.4b.5d.6e, | 1c.2f.3b.4b.5d.6f, |
| 1c.2f.3b.4b.5e.6a, | 1c.2f.3b.4b.5e.6b, | 1c.2f.3b.4b.5e.6c, | 1c.2f.3b.4b.5e.6d, |
| 1c.2f.3b.4b.5e.6e, | 1c.2f.3b.4b.5e.6f, | 1c.2f.3b.4b.5f.6a, | 1c.2f.3b.4b.5f.6b, | 1c.2f.3b.4b.5f.6c, |
| 1c.2f.3b.4b.5f.6d, | 1c.2f.3b.4b.5f.6e, | 1c.2f.3b.4b.5f.6f, | 1c.2f.3b.4c.5a.6a, | 1c.2f.3b.4c.5a.6b, |
| 1c.2f.3b.4c.5a.6c, | 1c.2f.3b.4c.5a.6d, | 1c.2f.3b.4c.5a.6e, | 1c.2f.3b.4c.5a.6f, | 1c.2f.3b.4c.5b.6a, |
| 1c.2f.3b.4c.5b.6b, | 1c.2f.3b.4c.5b.6c, | 1c.2f.3b.4c.5b.6d, | 1c.2f.3b.4c.5b.6e, | 1c.2f.3b.4c.5b.6f, |
| 1c.2f.3b.4c.5c.6a, | 1c.2f.3b.4c.5c.6b, | 1c.2f.3b.4c.5c.6c, | 1c.2f.3b.4c.5c.6d, | 1c.2f.3b.4c.5c.6e, |
| 1c.2f.3b.4c.5c.6f, | 1c.2f.3b.4c.5d.6a, | 1c.2f.3b.4c.5d.6b, | 1c.2f.3b.4c.5d.6c, | 1c.2f.3b.4c.5d.6d, |
| 1c.2f.3b.4c.5d.6e, | 1c.2f.3b.4c.5d.6f, | 1c.2f.3b.4c.5e.6a, | 1c.2f.3b.4c.5e.6b, | 1c.2f.3b.4c.5e.6c, |
| 1c.2f.3b.4c.5e.6d, | 1c.2f.3b.4c.5e.6e, | 1c.2f.3b.4c.5e.6f, | 1c.2f.3b.4c.5f.6a, | 1c.2f.3b.4c.5f.6b, |
| 1c.2f.3b.4c.5f.6c, | 1c.2f.3b.4c.5f.6d, | 1c.2f.3b.4c.5f.6e, | 1c.2f.3b.4c.5f.6f, | 1c.2f.3b.4d.5a.6a, |
| 1c.2f.3b.4d.5a.6b, | 1c.2f.3b.4d.5a.6c, | 1c.2f.3b.4d.5a.6d, | 1c.2f.3b.4d.5a.6e, |
| 1c.2f.3b.4d.5a.6f, | 1c.2f.3b.4d.5b.6a, | 1c.2f.3b.4d.5b.6b, | 1c.2f.3b.4d.5b.6c, |
| 1c.2f.3b.4d.5b.6d, | 1c.2f.3b.4d.5b.6e, | 1c.2f.3b.4d.5b.6f, | 1c.2f.3b.4d.5c.6a, |
| 1c.2f.3b.4d.5c.6b, | 1c.2f.3b.4d.5c.6c, | 1c.2f.3b.4d.5c.6d, | 1c.2f.3b.4d.5c.6e, | 1c.2f.3b.4d.5c.6f, |
| 1c.2f.3b.4d.5d.6a, | 1c.2f.3b.4d.5d.6b, | 1c.2f.3b.4d.5d.6c, | 1c.2f.3b.4d.5d.6d, |
| 1c.2f.3b.4d.5d.6e, | 1c.2f.3b.4d.5d.6f, | 1c.2f.3b.4d.5e.6a, | 1c.2f.3b.4d.5e.6b, |
| 1c.2f.3b.4d.5e.6c, | 1c.2f.3b.4d.5e.6d, | 1c.2f.3b.4d.5e.6e, | 1c.2f.3b.4d.5e.6f, | 1c.2f.3b.4d.5f.6a, |
| 1c.2f.3b.4d.5f.6b, | 1c.2f.3b.4d.5f.6c, | 1c.2f.3b.4d.5f.6d, | 1c.2f.3b.4d.5f.6e, | 1c.2f.3b.4d.5f.6f, |
| 1c.2f.3b.4e.5a.6a, | 1c.2f.3b.4e.5a.6b, | 1c.2f.3b.4e.5a.6c, | 1c.2f.3b.4e.5a.6d, | 1c.2f.3b.4e.5a.6e, |
| 1c.2f.3b.4e.5a.6f, | 1c.2f.3b.4e.5b.6a, | 1c.2f.3b.4e.5b.6b, | 1c.2f.3b.4e.5b.6c, | 1c.2f.3b.4e.5b.6d, |
| 1c.2f.3b.4e.5b.6e, | 1c.2f.3b.4e.5b.6f, | 1c.2f.3b.4e.5c.6a, | 1c.2f.3b.4e.5c.6b, | 1c.2f.3b.4e.5c.6c, |
| 1c.2f.3b.4e.5c.6d, | 1c.2f.3b.4e.5c.6e, | 1c.2f.3b.4e.5c.6f, | 1c.2f.3b.4e.5d.6a, | 1c.2f.3b.4e.5d.6b, |
| 1c.2f.3b.4e.5d.6c, | 1c.2f.3b.4e.5d.6d, | 1c.2f.3b.4e.5d.6e, | 1c.2f.3b.4e.5d.6f, | 1c.2f.3b.4e.5e.6a, |
| 1c.2f.3b.4e.5e.6b, | 1c.2f.3b.4e.5e.6c, | 1c.2f.3b.4e.5e.6d, | 1c.2f.3b.4e.5e.6e, | 1c.2f.3b.4e.5e.6f, |
| 1c.2f.3b.4e.5f.6a, | 1c.2f.3b.4e.5f.6b, | 1c.2f.3b.4e.5f.6c, | 1c.2f.3b.4e.5f.6d, | 1c.2f.3b.4e.5f.6e, |
| 1c.2f.3b.4e.5f.6f, | 1c.2f.3b.4f.5a.6a, | 1c.2f.3b.4f.5a.6b, | 1c.2f.3b.4f.5a.6c, | 1c.2f.3b.4f.5a.6d, |
| 1c.2f.3b.4f.5a.6e, | 1c.2f.3b.4f.5a.6f, | 1c.2f.3b.4f.5b.6a, | 1c.2f.3b.4f.5b.6b, | 1c.2f.3b.4f.5b.6c, |
| 1c.2f.3b.4f.5b.6d, | 1c.2f.3b.4f.5b.6e, | 1c.2f.3b.4f.5b.6f, | 1c.2f.3b.4f.5c.6a, | 1c.2f.3b.4f.5c.6b, |
| 1c.2f.3b.4f.5c.6c, | 1c.2f.3b.4f.5c.6d, | 1c.2f.3b.4f.5c.6e, | 1c.2f.3b.4f.5c.6f, | 1c.2f.3b.4f.5d.6a, |
| 1c.2f.3b.4f.5d.6b, | 1c.2f.3b.4f.5d.6c, | 1c.2f.3b.4f.5d.6d, | 1c.2f.3b.4f.5d.6e, | 1c.2f.3b.4f.5d.6f, |
| 1c.2f.3b.4f.5e.6a, | 1c.2f.3b.4f.5e.6b, | 1c.2f.3b.4f.5e.6c, | 1c.2f.3b.4f.5e.6d, | 1c.2f.3b.4f.5e.6e, |
| 1c.2f.3b.4f.5e.6f, | 1c.2f.3b.4f.5f.6a, | 1c.2f.3b.4f.5f.6b, | 1c.2f.3b.4f.5f.6c, | 1c.2f.3b.4f.5f.6d, |
| 1c.2f.3b.4f.5f.6e, | 1c.2f.3b.4f.5f.6f, | 1c.2f.3c.4a.5a.6a, | 1c.2f.3c.4a.5a.6b, | 1c.2f.3c.4a.5a.6c, |
| 1c.2f.3c.4a.5a.6d, | 1c.2f.3c.4a.5a.6e, | 1c.2f.3c.4a.5a.6f, | 1c.2f.3c.4a.5b.6a, | 1c.2f.3c.4a.5b.6b, |
| 1c.2f.3c.4a.5b.6c, | 1c.2f.3c.4a.5b.6d, | 1c.2f.3c.4a.5b.6e, | 1c.2f.3c.4a.5b.6f, | 1c.2f.3c.4a.5c.6a, |
| 1c.2f.3c.4a.5c.6b, | 1c.2f.3c.4a.5c.6c, | 1c.2f.3c.4a.5c.6d, | 1c.2f.3c.4a.5c.6e, | 1c.2f.3c.4a.5c.6f, |
| 1c.2f.3c.4a.5d.6a, | 1c.2f.3c.4a.5d.6b, | 1c.2f.3c.4a.5d.6c, | 1c.2f.3c.4a.5d.6d, | 1c.2f.3c.4a.5d.6e, |
| 1c.2f.3c.4a.5d.6f, | 1c.2f.3c.4a.5e.6a, | 1c.2f.3c.4a.5e.6b, | 1c.2f.3c.4a.5e.6c, | 1c.2f.3c.4a.5e.6d, |
| 1c.2f.3c.4a.5e.6e, | 1c.2f.3c.4a.5e.6f, | 1c.2f.3c.4a.5f.6a, | 1c.2f.3c.4a.5f.6b, | 1c.2f.3c.4a.5f.6c, |
| 1c.2f.3c.4a.5f.6d, | 1c.2f.3c.4a.5f.6e, | 1c.2f.3c.4a.5f.6f, | 1c.2f.3c.4b.5a.6a, | 1c.2f.3c.4b.5a.6b, |
| 1c.2f.3c.4b.5a.6c, | 1c.2f.3c.4b.5a.6d, | 1c.2f.3c.4b.5a.6e, | 1c.2f.3c.4b.5a.6f, | 1c.2f.3c.4b.5b.6a, |
| 1c.2f.3c.4b.5b.6b, | 1c.2f.3c.4b.5b.6c, | 1c.2f.3c.4b.5b.6d, | 1c.2f.3c.4b.5b.6e, | 1c.2f.3c.4b.5b.6f, |
| 1c.2f.3c.4b.5c.6a, | 1c.2f.3c.4b.5c.6b, | 1c.2f.3c.4b.5c.6c, | 1c.2f.3c.4b.5c.6d, | 1c.2f.3c.4b.5c.6e, |
| 1c.2f.3c.4b.5c.6f, | 1c.2f.3c.4b.5d.6a, | 1c.2f.3c.4b.5d.6b, | 1c.2f.3c.4b.5d.6c, | 1c.2f.3c.4b.5d.6d, |
| 1c.2f.3c.4b.5d.6e, | 1c.2f.3c.4b.5d.6f, | 1c.2f.3c.4b.5e.6a, | 1c.2f.3c.4b.5e.6b, | 1c.2f.3c.4b.5e.6c, |
| 1c.2f.3c.4b.5e.6d, | 1c.2f.3c.4b.5e.6e, | 1c.2f.3c.4b.5e.6f, | 1c.2f.3c.4b.5f.6a, | 1c.2f.3c.4b.5f.6b, |
| 1c.2f.3c.4b.5f.6c, | 1c.2f.3c.4b.5f.6d, | 1c.2f.3c.4b.5f.6e, | 1c.2f.3c.4b.5f.6f, | 1c.2f.3c.4c.5a.6a, |
| 1c.2f.3c.4c.5a.6b, | 1c.2f.3c.4c.5a.6c, | 1c.2f.3c.4c.5a.6d, | 1c.2f.3c.4c.5a.6e, | 1c.2f.3c.4c.5a.6f, |
| 1c.2f.3c.4c.5b.6a, | 1c.2f.3c.4c.5b.6b, | 1c.2f.3c.4c.5b.6c, | 1c.2f.3c.4c.5b.6d, | 1c.2f.3c.4c.5b.6e, |
| 1c.2f.3c.4c.5b.6f, | 1c.2f.3c.4c.5c.6a, | 1c.2f.3c.4c.5c.6b, | 1c.2f.3c.4c.5c.6c, | 1c.2f.3c.4c.5c.6d, |
| 1c.2f.3c.4c.5c.6e, | 1c.2f.3c.4c.5c.6f, | 1c.2f.3c.4c.5d.6a, | 1c.2f.3c.4c.5d.6b, | 1c.2f.3c.4c.5d.6c, |
| 1c.2f.3c.4c.5d.6d, | 1c.2f.3c.4c.5d.6e, | 1c.2f.3c.4c.5d.6f, | 1c.2f.3c.4c.5e.6a, | 1c.2f.3c.4c.5e.6b, |
| 1c.2f.3c.4c.5e.6c, | 1c.2f.3c.4c.5e.6d, | 1c.2f.3c.4c.5e.6e, | 1c.2f.3c.4c.5e.6f, | 1c.2f.3c.4c.5f.6a, |
| 1c.2f.3c.4c.5f.6b, | 1c.2f.3c.4c.5f.6c, | 1c.2f.3c.4c.5f.6d, | 1c.2f.3c.4c.5f.6e, | 1c.2f.3c.4c.5f.6f, |
| 1c.2f.3c.4d.5a.6a, | 1c.2f.3c.4d.5a.6b, | 1c.2f.3c.4d.5a.6c, | 1c.2f.3c.4d.5a.6d, | 1c.2f.3c.4d.5a.6e, |
| 1c.2f.3c.4d.5a.6f, | 1c.2f.3c.4d.5b.6a, | 1c.2f.3c.4d.5b.6b, | 1c.2f.3c.4d.5b.6c, | 1c.2f.3c.4d.5b.6d, |
| 1c.2f.3c.4d.5b.6e, | 1c.2f.3c.4d.5b.6f, | 1c.2f.3c.4d.5c.6a, | 1c.2f.3c.4d.5c.6b, | 1c.2f.3c.4d.5c.6c, |
| 1c.2f.3c.4d.5c.6d, | 1c.2f.3c.4d.5c.6e, | 1c.2f.3c.4d.5c.6f, | 1c.2f.3c.4d.5d.6a, | 1c.2f.3c.4d.5d.6b, |
| 1c.2f.3c.4d.5d.6c, | 1c.2f.3c.4d.5d.6d, | 1c.2f.3c.4d.5d.6e, | 1c.2f.3c.4d.5d.6f, |
| 1c.2f.3c.4d.5e.6a, | 1c.2f.3c.4d.5e.6b, | 1c.2f.3c.4d.5e.6c, | 1c.2f.3c.4d.5e.6d, | 1c.2f.3c.4d.5e.6e, |
| 1c.2f.3c.4d.5e.6f, | 1c.2f.3c.4d.5f.6a, | 1c.2f.3c.4d.5f.6b, | 1c.2f.3c.4d.5f.6c, | 1c.2f.3c.4d.5f.6d, |
| 1c.2f.3c.4d.5f.6e, | 1c.2f.3c.4d.5f.6f, | 1c.2f.3c.4e.5a.6a, | 1c.2f.3c.4e.5a.6b, | 1c.2f.3c.4e.5a.6c, |
| 1c.2f.3c.4e.5a.6d, | 1c.2f.3c.4e.5a.6e, | 1c.2f.3c.4e.5a.6f, | 1c.2f.3c.4e.5b.6a, | 1c.2f.3c.4e.5b.6b, |
| 1c.2f.3c.4e.5b.6c, | 1c.2f.3c.4e.5b.6d, | 1c.2f.3c.4e.5b.6e, | 1c.2f.3c.4e.5b.6f, | 1c.2f.3c.4e.5c.6a, |
| 1c.2f.3c.4e.5c.6b, | 1c.2f.3c.4e.5c.6c, | 1c.2f.3c.4e.5c.6d, | 1c.2f.3c.4e.5c.6e, | 1c.2f.3c.4e.5c.6f, |
| 1c.2f.3c.4e.5d.6a, | 1c.2f.3c.4e.5d.6b, | 1c.2f.3c.4e.5d.6c, | 1c.2f.3c.4e.5d.6d, | 1c.2f.3c.4e.5d.6e, |
| 1c.2f.3c.4e.5d.6f, | 1c.2f.3c.4e.5e.6a, | 1c.2f.3c.4e.5e.6b, | 1c.2f.3c.4e.5e.6c, | 1c.2f.3c.4e.5e.6d, |
| 1c.2f.3c.4e.5e.6e, | 1c.2f.3c.4e.5e.6f, | 1c.2f.3c.4e.5f.6a, | 1c.2f.3c.4e.5f.6b, | 1c.2f.3c.4e.5f.6c, |
| 1c.2f.3c.4e.5f.6d, | 1c.2f.3c.4e.5f.6e, | 1c.2f.3c.4e.5f.6f, | 1c.2f.3c.4f.5a.6a, | 1c.2f.3c.4f.5a.6b, |
| 1c.2f.3c.4f.5a.6c, | 1c.2f.3c.4f.5a.6d, | 1c.2f.3c.4f.5a.6e, | 1c.2f.3c.4f.5a.6f, | 1c.2f.3c.4f.5b.6a, |
| 1c.2f.3c.4f.5b.6b, | 1c.2f.3c.4f.5b.6c, | 1c.2f.3c.4f.5b.6d, | 1c.2f.3c.4f.5b.6e, | 1c.2f.3c.4f.5b.6f, |
| 1c.2f.3c.4f.5c.6a, | 1c.2f.3c.4f.5c.6b, | 1c.2f.3c.4f.5c.6c, | 1c.2f.3c.4f.5c.6d, | 1c.2f.3c.4f.5c.6e, |
| 1c.2f.3c.4f.5c.6f, | 1c.2f.3c.4f.5d.6a, | 1c.2f.3c.4f.5d.6b, | 1c.2f.3c.4f.5d.6c, | 1c.2f.3c.4f.5d.6d, |
| 1c.2f.3c.4f.5d.6e, | 1c.2f.3c.4f.5d.6f, | 1c.2f.3c.4f.5e.6a, | 1c.2f.3c.4f.5e.6b, | 1c.2f.3c.4f.5e.6c, |

TABLE 7-continued

List of Compounds of Formula (II)

| | | | | |
|---|---|---|---|---|
| 1c.2f.3c.4f.5e.6d, | 1c.2f.3c.4f.5e.6e, | 1c.2f.3c.4f.5e.6f, | 1c.2f.3c.4f.5f.6a, | 1c.2f.3c.4f.5f.6b, |
| 1c.2f.3c.4f.5f.6c, | 1c.2f.3c.4f.5f.6d, | 1c.2f.3c.4f.5f.6e, | 1c.2f.3c.4f.5f.6f, | 1c.2f.3d.4a.5a.6a, |
| 1c.2f.3d.4a.5a.6b, | 1c.2f.3d.4a.5a.6c, | 1c.2f.3d.4a.5a.6d, | 1c.2f.3d.4a.5a.6e, | 1c.2f.3d.4a.5a.6f, |
| 1c.2f.3d.4a.5b.6a, | 1c.2f.3d.4a.5b.6b, | 1c.2f.3d.4a.5b.6c, | 1c.2f.3d.4a.5b.6d, | |
| 1c.2f.3d.4a.5b.6e, | 1c.2f.3d.4a.5b.6f, | 1c.2f.3d.4a.5c.6a, | 1c.2f.3d.4a.5c.6b, | 1c.2f.3d.4a.5c.6c, |
| 1c.2f.3d.4a.5c.6d, | 1c.2f.3d.4a.5c.6e, | 1c.2f.3d.4a.5c.6f, | 1c.2f.3d.4a.5d.6a, | |
| 1c.2f.3d.4a.5d.6b, | 1c.2f.3d.4a.5d.6c, | 1c.2f.3d.4a.5d.6d, | 1c.2f.3d.4a.5d.6e, | |
| 1c.2f.3d.4a.5d.6f, | 1c.2f.3d.4a.5e.6a, | 1c.2f.3d.4a.5e.6b, | 1c.2f.3d.4a.5e.6c, | |
| 1c.2f.3d.4a.5e.6d, | 1c.2f.3d.4a.5e.6e, | 1c.2f.3d.4a.5e.6f, | 1c.2f.3d.4a.5f.6a, | 1c.2f.3d.4a.5f.6b, |
| 1c.2f.3d.4a.5f.6c, | 1c.2f.3d.4a.5f.6d, | 1c.2f.3d.4a.5f.6e, | 1c.2f.3d.4a.5f.6f, | 1c.2f.3d.4b.5a.6a, |
| 1c.2f.3d.4b.5a.6b, | 1c.2f.3d.4b.5a.6c, | 1c.2f.3d.4b.5a.6d, | 1c.2f.3d.4b.5a.6e, | |
| 1c.2f.3d.4b.5a.6f, | 1c.2f.3d.4b.5b.6a, | 1c.2f.3d.4b.5b.6b, | 1c.2f.3d.4b.5b.6c, | |
| 1c.2f.3d.4b.5b.6d, | 1c.2f.3d.4b.5b.6e, | 1c.2f.3d.4b.5b.6f, | 1c.2f.3d.4b.5c.6a, | |
| 1c.2f.3d.4b.5c.6b, | 1c.2f.3d.4b.5c.6c, | 1c.2f.3d.4b.5c.6d, | 1c.2f.3d.4b.5c.6e, | 1c.2f.3d.4b.5c.6f, |
| 1c.2f.3d.4b.5d.6a, | 1c.2f.3d.4b.5d.6b, | 1c.2f.3d.4b.5d.6c, | 1c.2f.3d.4b.5d.6d, | |
| 1c.2f.3d.4b.5d.6e, | 1c.2f.3d.4b.5d.6f, | 1c.2f.3d.4b.5e.6a, | 1c.2f.3d.4b.5e.6b, | |
| 1c.2f.3d.4b.5e.6c, | 1c.2f.3d.4b.5e.6d, | 1c.2f.3d.4b.5e.6e, | 1c.2f.3d.4b.5e.6f, | 1c.2f.3d.4b.5f.6a, |
| 1c.2f.3d.4b.5f.6b, | 1c.2f.3d.4b.5f.6c, | 1c.2f.3d.4b.5f.6d, | 1c.2f.3d.4b.5f.6e, | 1c.2f.3d.4b.5f.6f, |
| 1c.2f.3d.4c.5a.6a, | 1c.2f.3d.4c.5a.6b, | 1c.2f.3d.4c.5a.6c, | 1c.2f.3d.4c.5a.6d, | 1c.2f.3d.4c.5a.6e, |
| 1c.2f.3d.4c.5a.6f, | 1c.2f.3d.4c.5b.6a, | 1c.2f.3d.4c.5b.6b, | 1c.2f.3d.4c.5b.6c, | 1c.2f.3d.4c.5b.6d, |
| 1c.2f.3d.4c.5b.6e, | 1c.2f.3d.4c.5b.6f, | 1c.2f.3d.4c.5c.6a, | 1c.2f.3d.4c.5c.6b, | 1c.2f.3d.4c.5c.6c, |
| 1c.2f.3d.4c.5c.6d, | 1c.2f.3d.4c.5c.6e, | 1c.2f.3d.4c.5c.6f, | 1c.2f.3d.4c.5d.6a, | 1c.2f.3d.4c.5d.6b, |
| 1c.2f.3d.4c.5d.6c, | 1c.2f.3d.4c.5d.6d, | 1c.2f.3d.4c.5d.6e, | 1c.2f.3d.4c.5d.6f, | |
| 1c.2f.3d.4c.5e.6a, | 1c.2f.3d.4c.5e.6b, | 1c.2f.3d.4c.5e.6c, | 1c.2f.3d.4c.5e.6d, | 1c.2f.3d.4c.5e.6e, |
| 1c.2f.3d.4c.5e.6f, | 1c.2f.3d.4c.5f.6a, | 1c.2f.3d.4c.5f.6b, | 1c.2f.3d.4c.5f.6c, | 1c.2f.3d.4c.5f.6d, |
| 1c.2f.3d.4c.5f.6e, | 1c.2f.3d.4c.5f.6f, | 1c.2f.3d.4d.5a.6a, | 1c.2f.3d.4d.5a.6b, | 1c.2f.3d.4d.5a.6c, |
| 1c.2f.3d.4d.5a.6d, | 1c.2f.3d.4d.5a.6e, | 1c.2f.3d.4d.5a.6f, | 1c.2f.3d.4d.5b.6a, | |
| 1c.2f.3d.4d.5b.6b, | 1c.2f.3d.4d.5b.6c, | 1c.2f.3d.4d.5b.6d, | 1c.2f.3d.4d.5b.6e, | |
| 1c.2f.3d.4d.5b.6f, | 1c.2f.3d.4d.5c.6a, | 1c.2f.3d.4d.5c.6b, | 1c.2f.3d.4d.5c.6c, | |
| 1c.2f.3d.4d.5c.6d, | 1c.2f.3d.4d.5c.6e, | 1c.2f.3d.4d.5c.6f, | 1c.2f.3d.4d.5d.6a, | |
| 1c.2f.3d.4d.5d.6b, | 1c.2f.3d.4d.5d.6c, | 1c.2f.3d.4d.5d.6d, | 1c.2f.3d.4d.5d.6e, | |
| 1c.2f.3d.4d.5d.6f, | 1c.2f.3d.4d.5e.6a, | 1c.2f.3d.4d.5e.6b, | 1c.2f.3d.4d.5e.6c, | |
| 1c.2f.3d.4d.5e.6d, | 1c.2f.3d.4d.5e.6e, | 1c.2f.3d.4d.5e.6f, | 1c.2f.3d.4d.5f.6a, | |
| 1c.2f.3d.4d.5f.6b, | 1c.2f.3d.4d.5f.6c, | 1c.2f.3d.4d.5f.6d, | 1c.2f.3d.4d.5f.6e, | 1c.2f.3d.4d.5f.6f, |
| 1c.2f.3d.4e.5a.6a, | 1c.2f.3d.4e.5a.6b, | 1c.2f.3d.4e.5a.6c, | 1c.2f.3d.4e.5a.6d, | |
| 1c.2f.3d.4e.5a.6e, | 1c.2f.3d.4e.5a.6f, | 1c.2f.3d.4e.5b.6a, | 1c.2f.3d.4e.5b.6b, | 1c.2f.3d.4e.5b.6c, |
| 1c.2f.3d.4e.5b.6d, | 1c.2f.3d.4e.5b.6e, | 1c.2f.3d.4e.5b.6f, | 1c.2f.3d.4e.5c.6a, | 1c.2f.3d.4e.5c.6b, |
| 1c.2f.3d.4e.5c.6c, | 1c.2f.3d.4e.5c.6d, | 1c.2f.3d.4e.5c.6e, | 1c.2f.3d.4e.5c.6f, | 1c.2f.3d.4e.5d.6a, |
| 1c.2f.3d.4e.5d.6b, | 1c.2f.3d.4e.5d.6c, | 1c.2f.3d.4e.5d.6d, | 1c.2f.3d.4e.5d.6e, | |
| 1c.2f.3d.4e.5d.6f, | 1c.2f.3d.4e.5e.6a, | 1c.2f.3d.4e.5e.6b, | 1c.2f.3d.4e.5e.6c, | 1c.2f.3d.4e.5e.6d, |
| 1c.2f.3d.4e.5e.6e, | 1c.2f.3d.4e.5e.6f, | 1c.2f.3d.4e.5f.6a, | 1c.2f.3d.4e.5f.6b, | 1c.2f.3d.4e.5f.6c, |
| 1c.2f.3d.4e.5f.6d, | 1c.2f.3d.4e.5f.6e, | 1c.2f.3d.4e.5f.6f, | 1c.2f.3d.4f.5a.6a, | 1c.2f.3d.4f.5a.6b, |
| 1c.2f.3d.4f.5a.6c, | 1c.2f.3d.4f.5a.6d, | 1c.2f.3d.4f.5a.6e, | 1c.2f.3d.4f.5a.6f, | 1c.2f.3d.4f.5b.6a, |
| 1c.2f.3d.4f.5b.6b, | 1c.2f.3d.4f.5b.6c, | 1c.2f.3d.4f.5b.6d, | 1c.2f.3d.4f.5b.6e, | 1c.2f.3d.4f.5b.6f, |
| 1c.2f.3d.4f.5c.6a, | 1c.2f.3d.4f.5c.6b, | 1c.2f.3d.4f.5c.6c, | 1c.2f.3d.4f.5c.6d, | 1c.2f.3d.4f.5c.6e, |
| 1c.2f.3d.4f.5c.6f, | 1c.2f.3d.4f.5d.6a, | 1c.2f.3d.4f.5d.6b, | 1c.2f.3d.4f.5d.6c, | 1c.2f.3d.4f.5d.6d, |
| 1c.2f.3d.4f.5d.6e, | 1c.2f.3d.4f.5d.6f, | 1c.2f.3d.4f.5e.6a, | 1c.2f.3d.4f.5e.6b, | 1c.2f.3d.4f.5e.6c, |
| 1c.2f.3d.4f.5e.6d, | 1c.2f.3d.4f.5e.6e, | 1c.2f.3d.4f.5e.6f, | 1c.2f.3d.4f.5f.6a, | 1c.2f.3d.4f.5f.6b, |
| 1c.2f.3d.4f.5f.6c, | 1c.2f.3d.4f.5f.6d, | 1c.2f.3d.4f.5f.6e, | 1c.2f.3d.4f.5f.6f, | 1c.2f.3e.4a.5a.6a, |
| 1c.2f.3e.4a.5a.6b, | 1c.2f.3e.4a.5a.6c, | 1c.2f.3e.4a.5a.6d, | 1c.2f.3e.4a.5a.6e, | 1c.2f.3e.4a.5a.6f, |
| 1c.2f.3e.4a.5b.6a, | 1c.2f.3e.4a.5b.6b, | 1c.2f.3e.4a.5b.6c, | 1c.2f.3e.4a.5b.6d, | 1c.2f.3e.4a.5b.6e, |
| 1c.2f.3e.4a.5b.6f, | 1c.2f.3e.4a.5c.6a, | 1c.2f.3e.4a.5c.6b, | 1c.2f.3e.4a.5c.6c, | 1c.2f.3e.4a.5c.6d, |
| 1c.2f.3e.4a.5c.6e, | 1c.2f.3e.4a.5c.6f, | 1c.2f.3e.4a.5d.6a, | 1c.2f.3e.4a.5d.6b, | 1c.2f.3e.4a.5d.6c, |
| 1c.2f.3e.4a.5d.6d, | 1c.2f.3e.4a.5d.6e, | 1c.2f.3e.4a.5d.6f, | 1c.2f.3e.4a.5e.6a, | 1c.2f.3e.4a.5e.6b, |
| 1c.2f.3e.4a.5e.6c, | 1c.2f.3e.4a.5e.6d, | 1c.2f.3e.4a.5e.6e, | 1c.2f.3e.4a.5e.6f, | 1c.2f.3e.4a.5f.6a, |
| 1c.2f.3e.4a.5f.6b, | 1c.2f.3e.4a.5f.6c, | 1c.2f.3e.4a.5f.6d, | 1c.2f.3e.4a.5f.6e, | 1c.2f.3e.4a.5f.6f, |
| 1c.2f3e.4b.5a.6a, | 1c.2f.3e.4b.5a.6b, | 1c.2f.3e.4b.5a.6c, | 1c.2f.3e.4b.5a.6d, | 1c.2f.3e.4b.5a.6e, |
| 1c.2f.3e.4b.5a.6f, | 1c.2f.3e.4b.5b.6a, | 1c.2f.3e.4b.5b.6b, | 1c.2f.3e.4b.5b.6c, | 1c.2f.3e.4b.5b.6d, |
| 1c.2f.3e.4b.5b.6e, | 1c.2f.3e.4b.5b.6f, | 1c.2f.3e.4b.5c.6a, | 1c.2f.3e.4b.5c.6b, | 1c.2f.3e.4b.5c.6c, |
| 1c.2f.3e.4b.5c.6d, | 1c.2f.3e.4b.5c.6e, | 1c.2f.3e.4b.5c.6f, | 1c.2f.3e.4b.5d.6a, | 1c.2f.3e.4b.5d.6b, |
| 1c.2f.3e.4b.5d.6c, | 1c.2f.3e.4b.5d.6d, | 1c.2f.3e.4b.5d.6e, | 1c.2f.3e.4b.5d.6f, | 1c.2f.3e.4b.5e.6a, |
| 1c.2f.3e.4b.5e.6b, | 1c.2f.3e.4b.5e.6c, | 1c.2f.3e.4b.5e.6d, | 1c.2f.3e.4b.5e.6e, | 1c.2f.3e.4b.5e.6f, |
| 1c.2f.3e.4b.5f.6a, | 1c.2f.3e.4b.5f.6b, | 1c.2f.3e.4b.5f.6c, | 1c.2f.3e.4b.5f.6d, | 1c.2f.3e.4b.5f.6e, |
| 1c.2f.3e.4b.5f.6f, | 1c.2f.3e.4c.5a.6a, | 1c.2f.3e.4c.5a.6b, | 1c.2f.3e.4c.5a.6c, | 1c.2f.3e.4c.5a.6d, |
| 1c.2f.3e.4c.5a.6e, | 1c.2f.3e.4c.5a.6f, | 1c.2f.3e.4c.5b.6a, | 1c.2f.3e.4c.5b.6b, | 1c.2f.3e.4c.5b.6c, |
| 1c.2f.3e.4c.5b.6d, | 1c.2f.3e.4c.5b.6e, | 1c.2f.3e.4c.5b.6f, | 1c.2f.3e.4c.5c.6a, | 1c.2f.3e.4c.5c.6b, |
| 1c.2f.3e.4c.5c.6c, | 1c.2f.3e.4c.5c.6d, | 1c.2f.3e.4c.5c.6e, | 1c.2f.3e.4c.5c.6f, | 1c.2f.3e.4c.5d.6a, |
| 1c.2f.3e.4c.5d.6b, | 1c.2f.3e.4c.5d.6c, | 1c.2f.3e.4c.5d.6d, | 1c.2f.3e.4c.5d.6e, | 1c.2f.3e.4c.5d.6f, |
| 1c.2f.3e.4c.5e.6a, | 1c.2f.3e.4c.5e.6b, | 1c.2f.3e.4c.5e.6c, | 1c.2f.3e.4c.5e.6d, | 1c.2f.3e.4c.5e.6e, |
| 1c.2f.3e.4c.5e.6f, | 1c.2f.3e.4c.5f.6a, | 1c.2f.3e.4c.5f.6b, | 1c.2f.3e.4c.5f.6c, | 1c.2f.3e.4c.5f.6d, |
| 1c.2f.3e.4c.5f.6e, | 1c.2f.3e.4c.5f.6f, | 1c.2f.3e.4d.5a.6a, | 1c.2f.3e.4d.5a.6b, | 1c.2f.3e.4d.5a.6c, |
| 1c.2f.3e.4d.5a.6d, | 1c.2f.3e.4d.5a.6e, | 1c.2f.3e.4d.5a.6f, | 1c.2f.3e.4d.5b.6a, | |
| 1c.2f.3e.4d.5b.6b, | 1c.2f.3e.4d.5b.6c, | 1c.2f.3e.4d.5b.6d, | 1c.2f.3e.4d.5b.6e, | |
| 1c.2f.3e.4d.5b.6f, | 1c.2f.3e.4d.5c.6a, | 1c.2f.3e.4d.5c.6b, | 1c.2f.3e.4d.5c.6c, | 1c.2f.3e.4d.5c.6d, |
| 1c.2f.3e.4d.5c.6e, | 1c.2f.3e.4d.5c.6f, | 1c.2f.3e.4d.5d.6a, | 1c.2f.3e.4d.5d.6b, | 1c.2f.3e.4d.5d.6c, |
| 1c.2f.3e.4d.5d.6d, | 1c.2f.3e.4d.5d.6e, | 1c.2f.3e.4d.5d.6f, | 1c.2f.3e.4d.5e.6a, | |
| 1c.2f.3e.4d.5e.6b, | 1c.2f.3e.4d.5e.6c, | 1c.2f.3e.4d.5e.6d, | 1c.2f.3e.4d.5e.6e, | 1c.2f.3e.4d.5e.6f, |
| 1c.2f.3e.4d.5f.6a, | 1c.2f.3e.4d.5f.6b, | 1c.2f.3e.4d.5f.6c, | 1c.2f.3e.4d.5f.6d, | 1c.2f.3e.4d.5f.6e, |

TABLE 7-continued

List of Compounds of Formula (II)

| | | | |
|---|---|---|---|
| 1c.2f.3e.4d.5f.6f, | 1c.2f.3e.4e.5a.6a, | 1c.2f.3e.4e.5a.6b, | 1c.2f.3e.4e.5a.6c, | 1c.2f.3e.4e.5a.6d, |
| 1c.2f.3e.4e.5a.6e, | 1c.2f.3e.4e.5a.6f, | 1c.2f.3e.4e.5b.6a, | 1c.2f.3e.4e.5b.6b, | 1c.2f.3e.4e.5b.6c, |
| 1c.2f.3e.4e.5b.6d, | 1c.2f.3e.4e.5b.6e, | 1c.2f.3e.4e.5b.6f, | 1c.2f.3e.4e.5c.6a, | 1c.2f.3e.4e.5c.6b, |
| 1c.2f.3e.4e.5c.6c, | 1c.2f.3e.4e.5c.6d, | 1c.2f.3e.4e.5c.6e, | 1c.2f.3e.4e.5c.6f, | 1c.2f.3e.4e.5d.6a, |
| 1c.2f.3e.4e.5d.6b, | 1c.2f.3e.4e.5d.6c, | 1c.2f.3e.4e.5d.6d, | 1c.2f.3e.4e.5d.6e, | 1c.2f.3e.4e.5d.6f, |
| 1c.2f.3e.4e.5e.6a, | 1c.2f.3e.4e.5e.6b, | 1c.2f.3e.4e.5e.6c, | 1c.2f.3e.4e.5e.6d, | 1c.2f.3e.4e.5e.6e, |
| 1c.2f.3e.4e.5e.6f, | 1c.2f.3e.4e.5f.6a, | 1c.2f.3e.4e.5f.6b, | 1c.2f.3e.4e.5f.6c, | 1c.2f.3e.4e.5f.6d, |
| 1c.2f.3e.4e.5f.6e, | 1c.2f.3e.4e.5f.6f, | 1c.2f.3e.4f.5a.6a, | 1c.2f.3e.4f.5a.6b, | 1c.2f.3e.4f.5a.6c, |
| 1c.2f.3e.4f.5a.6d, | 1c.2f.3e.4f.5a.6e, | 1c.2f.3e.4f.5a.6f, | 1c.2f.3e.4f.5b.6a, | 1c.2f.3e.4f.5b.6b, |
| 1c.2f.3e.4f.5b.6c, | 1c.2f.3e.4f.5b.6d, | 1c.2f.3e.4f.5b.6e, | 1c.2f.3e.4f.5b.6f, | 1c.2f.3e.4f.5c.6a, |
| 1c.2f.3e.4f.5c.6b, | 1c.2f.3e.4f.5c.6c, | 1c.2f.3e.4f.5c.6d, | 1c.2f.3e.4f.5c.6e, | 1c.2f.3e.4f.5c.6f, |
| 1c.2f.3e.4f.5d.6a, | 1c.2f.3e.4f.5d.6b, | 1c.2f.3e.4f.5d.6c, | 1c.2f.3e.4f.5d.6d, | 1c.2f.3e.4f.5d.6e, |
| 1c.2f.3e.4f.5d.6f, | 1c.2f.3e.4f.5e.6a, | 1c.2f.3e.4f.5e.6b, | 1c.2f.3e.4f.5e.6c, | 1c.2f.3e.4f.5e.6d, |
| 1c.2f.3e.4f.5e.6e, | 1c.2f.3e.4f.5e.6f, | 1c.2f.3e.4f.5f.6a, | 1c.2f.3e.4f.5f.6b, | 1c.2f.3e.4f.5f.6c, |
| 1c.2f.3e.4f.5f.6d, | 1c.2f.3e.4f.5f.6e, | 1c.2f.3e.4f.5f.6f, | 1c.2f.3f.4a.5a.6a, | 1c.2f.3f.4a.5a.6b, |
| 1c.2f.3f.4a.5a.6c, | 1c.2f.3f.4a.5a.6d, | 1c.2f.3f.4a.5a.6e, | 1c.2f.3f.4a.5a.6f, | 1c.2f.3f.4a.5b.6a, |
| 1c.2f.3f.4a.5b.6b, | 1c.2f.3f.4a.5b.6c, | 1c.2f.3f.4a.5b.6d, | 1c.2f.3f.4a.5b.6e, | 1c.2f.3f.4a.5b.6f, |
| 1c.2f.3f.4a.5c.6a, | 1c.2f.3f.4a.5c.6b, | 1c.2f.3f.4a.5c.6c, | 1c.2f.3f.4a.5c.6d, | 1c.2f.3f.4a.5c.6e, |
| 1c.2f.3f.4a.5c.6f, | 1c.2f.3f.4a.5d.6a, | 1c.2f.3f.4a.5d.6b, | 1c.2f.3f.4a.5d.6c, | 1c.2f.3f.4a.5d.6d, |
| 1c.2f.3f.4a.5d.6e, | 1c.2f.3f.4a.5d.6f, | 1c.2f.3f.4a.5e.6a, | 1c.2f.3f.4a.5e.6b, | 1c.2f.3f.4a.5e.6c, |
| 1c.2f.3f.4a.5e.6d, | 1c.2f.3f.4a.5e.6e, | 1c.2f.3f.4a.5e.6f, | 1c.2f.3f.4a.5f.6a, | 1c.2f.3f.4a.5f.6b, |
| 1c.2f.3f.4a.5f.6c, | 1c.2f.3f.4a.5f.6d, | 1c.2f.3f.4a.5f.6e, | 1c.2f.3f.4a.5f.6f, | 1c.2f.3f.4b.5a.6a, |
| 1c.2f.3f.4b.5a.6b, | 1c.2f.3f.4b.5a.6c, | 1c.2f.3f.4b.5a.6d, | 1c.2f.3f.4b.5a.6e, | 1c.2f.3f.4b.5a.6f, |
| 1c.2f.3f.4b.5b.6a, | 1c.2f.3f.4b.5b.6b, | 1c.2f.3f.4b.5b.6c, | 1c.2f.3f.4b.5b.6d, | 1c.2f.3f.4b.5b.6e, |
| 1c.2f.3f.4b.5b.6f, | 1c.2f.3f.4b.5c.6a, | 1c.2f.3f.4b.5c.6b, | 1c.2f.3f.4b.5c.6c, | 1c.2f.3f.4b.5c.6d, |
| 1c.2f.3f.4b.5c.6e, | 1c.2f.3f.4b.5c.6f, | 1c.2f.3f.4b.5d.6a, | 1c.2f.3f.4b.5d.6b, | 1c.2f.3f.4b.5d.6c, |
| 1c.2f.3f.4b.5d.6d, | 1c.2f.3f.4b.5d.6e, | 1c.2f.3f.4b.5d.6f, | 1c.2f.3f.4b.5e.6a, | 1c.2f.3f.4b.5e.6b, |
| 1c.2f.3f.4b.5e.6c, | 1c.2f.3f.4b.5e.6d, | 1c.2f.3f.4b.5e.6e, | 1c.2f.3f.4b.5e.6f, | 1c.2f.3f.4b.5f.6a, |
| 1c.2f.3f.4b.5f.6b, | 1c.2f.3f.4b.5f.6c, | 1c.2f.3f.4b.5f.6d, | 1c.2f.3f.4b.5f.6e, | 1c.2f.3f.4b.5f.6f, |
| 1c.2f.3f.4c.5a.6a, | 1c.2f.3f.4c.5a.6b, | 1c.2f.3f.4c.5a.6c, | 1c.2f.3f.4c.5a.6d, | 1c.2f.3f.4c.5a.6e, |
| 1c.2f.3f.4c.5a.6f, | 1c.2f.3f.4c.5b.6a, | 1c.2f.3f.4c.5b.6b, | 1c.2f.3f.4c.5b.6c, | 1c.2f.3f.4c.5b.6d, |
| 1c.2f.3f.4c.5b.6e, | 1c.2f.3f.4c.5b.6f, | 1c.2f.3f.4c.5c.6a, | 1c.2f.3f.4c.5c.6b, | 1c.2f.3f.4c.5c.6c, |
| 1c.2f.3f.4c.5c.6d, | 1c.2f.3f.4c.5c.6e, | 1c.2f.3f.4c.5c.6f, | 1c.2f.3f.4c.5d.6a, | 1c.2f.3f.4c.5d.6b, |
| 1c.2f.3f.4c.5d.6c, | 1c.2f.3f.4c.5d.6d, | 1c.2f.3f.4c.5d.6e, | 1c.2f.3f.4c.5d.6f, | 1c.2f.3f.4c.5e.6a, |
| 1c.2f.3f.4c.5e.6b, | 1c.2f.3f.4c.5e.6c, | 1c.2f.3f.4c.5e.6d, | 1c.2f.3f.4c.5e.6e, | 1c.2f.3f.4c.5e.6f, |
| 1c.2f.3f.4c.5f.6a, | 1c.2f.3f.4c.5f.6b, | 1c.2f.3f.4c.5f.6c, | 1c.2f.3f.4c.5f.6d, | 1c.2f.3f.4c.5f.6e, |
| 1c.2f.3f.4c.5f.6f, | 1c.2f.3f.4d.5a.6a, | 1c.2f.3f.4d.5a.6b, | 1c.2f.3f.4d.5a.6c, | 1c.2f.3f.4d.5a.6d, |
| 1c.2f.3f.4d.5a.6e, | 1c.2f.3f.4d.5a.6f, | 1c.2f.3f.4d.5b.6a, | 1c.2f.3f.4d.5b.6b, | 1c.2f.3f.4d.5b.6c, |
| 1c.2f.3f.4d.5b.6d, | 1c.2f.3f.4d.5b.6e, | 1c.2f.3f.4d.5b.6f, | 1c.2f.3f.4d.5c.6a, | 1c.2f.3f.4d.5c.6b, |
| 1c.2f.3f.4d.5c.6c, | 1c.2f.3f.4d.5c.6d, | 1c.2f.3f.4d.5c.6e, | 1c.2f.3f.4d.5c.6f, | 1c.2f.3f.4d.5d.6a, |
| 1c.2f.3f.4d.5d.6b, | 1c.2f.3f.4d.5d.6c, | 1c.2f.3f.4d.5d.6d, | 1c.2f.3f.4d.5d.6e, | 1c.2f.3f.4d.5d.6f, |
| 1c.2f.3f.4d.5e.6a, | 1c.2f.3f.4d.5e.6b, | 1c.2f.3f.4d.5e.6c, | 1c.2f.3f.4d.5e.6d, | 1c.2f.3f.4d.5e.6e, |
| 1c.2f.3f.4d.5e.6f, | 1c.2f.3f.4d.5f.6a, | 1c.2f.3f.4d.5f.6b, | 1c.2f.3f.4d.5f.6c, | 1c.2f.3f.4d.5f.6d, |
| 1c.2f.3f.4d.5f.6e, | 1c.2f.3f.4d.5f.6f, | 1c.2f.3f.4e.5a.6a, | 1c.2f.3f.4e.5a.6b, | 1c.2f.3f.4e.5a.6c, |
| 1c.2f.3f.4e.5a.6d, | 1c.2f.3f.4e.5a.6e, | 1c.2f.3f.4e.5a.6f, | 1c.2f.3f.4e.5b.6a, | 1c.2f.3f.4e.5b.6b, |
| 1c.2f.3f.4e.5b.6c, | 1c.2f.3f.4e.5b.6d, | 1c.2f.3f.4e.5b.6e, | 1c.2f.3f.4e.5b.6f, | 1c.2f.3f.4e.5c.6a, |
| 1c.2f.3f.4e.5c.6b, | 1c.2f.3f.4e.5c.6c, | 1c.2f.3f.4e.5c.6d, | 1c.2f.3f.4e.5c.6e, | 1c.2f.3f.4e.5c.6f, |
| 1c.2f.3f.4e.5d.6a, | 1c.2f.3f.4e.5d.6b, | 1c.2f.3f.4e.5d.6c, | 1c.2f.3f.4e.5d.6d, | 1c.2f.3f.4e.5d.6e, |
| 1c.2f.3f.4e.5d.6f, | 1c.2f.3f.4e.5e.6a, | 1c.2f.3f.4e.5e.6b, | 1c.2f.3f.4e.5e.6c, | 1c.2f.3f.4e.5e.6d, |
| 1c.2f.3f.4e.5e.6e, | 1c.2f.3f.4e.5e.6f, | 1c.2f.3f.4e.5f.6a, | 1c.2f.3f.4e.5f.6b, | 1c.2f.3f.4e.5f.6c, |
| 1c.2f.3f.4e.5f.6d, | 1c.2f.3f.4e.5f.6e, | 1c.2f.3f.4e.5f.6f, | 1c.2f.3f.4f.5a.6a, | 1c.2f.3f.4f.5a.6b, |
| 1c.2f.3f.4f.5a.6c, | 1c.2f.3f.4f.5a.6d, | 1c.2f.3f.4f.5a.6e, | 1c.2f.3f.4f.5a.6f, | 1c.2f.3f.4f.5b.6a, |
| 1c.2f.3f.4f.5b.6b, | 1c.2f.3f.4f.5b.6c, | 1c.2f.3f.4f.5b.6d, | 1c.2f.3f.4f.5b.6e, | 1c.2f.3f.4f.5b.6f, |
| 1c.2f.3f.4f.5c.6a, | 1c.2f.3f.4f.5c.6b, | 1c.2f.3f.4f.5c.6c, | 1c.2f.3f.4f.5c.6d, | 1c.2f.3f.4f.5c.6e, |
| 1c.2f.3f.4f.5c.6f, | 1c.2f.3f.4f.5d.6a, | 1c.2f.3f.4f.5d.6b, | 1c.2f.3f.4f.5d.6c, | 1c.2f.3f.4f.5d.6d, |
| 1c.2f.3f.4f.5d.6e, | 1c.2f.3f.4f.5d.6f, | 1c.2f.3f.4f.5e.6a, | 1c.2f.3f.4f.5e.6b, | 1c.2f.3f.4f.5e.6c, |
| 1c.2f.3f.4f.5e.6d, | 1c.2f.3f.4f.5e.6e, | 1c.2f.3f.4f.5e.6f, | 1c.2f.3f.4f.5f.6a, | 1c.2f.3f.4f.5f.6b, |
| 1c.2f.3f.4f.5f.6c, | 1c.2f.3f.4f.5f.6d, | 1c.2f.3f.4f.5f.6e, | 1c.2f.3f.4f.5f.6f, | 1d.2a.3a.4a.5a.6a, |
| 1d.2a.3a.4a.5a.6b, | 1d.2a.3a.4a.5a.6c, | 1d.2a.3a.4a.5a.6d, | 1d.2a.3a.4a.5a.6e, | |
| 1d.2a.3a.4a.5a.6f, | 1d.2a.3a.4a.5b.6a, | 1d.2a.3a.4a.5b.6b, | 1d.2a.3a.4a.5b.6c, | |
| 1d.2a.3a.4a.5b.6d, | 1d.2a.3a.4a.5b.6e, | 1d.2a.3a.4a.5b.6f, | 1d.2a.3a.4a.5c.6a, | |
| 1d.2a.3a.4a.5c.6b, | 1d.2a.3a.4a.5c.6c, | 1d.2a.3a.4a.5c.6d, | 1d.2a.3a.4a.5c.6e, | |
| 1d.2a.3a.4a.5c.6f, | 1d.2a.3a.4a.5d.6a, | 1d.2a.3a.4a.5d.6b, | 1d.2a.3a.4a.5d.6c, | |
| 1d.2a.3a.4a.5d.6d, | 1d.2a.3a.4a.5d.6e, | 1d.2a.3a.4a.5d.6f, | 1d.2a.3a.4a.5e.6a, | |
| 1d.2a.3a.4a.5e.6b, | 1d.2a.3a.4a.5e.6c, | 1d.2a.3a.4a.5e.6d, | 1d.2a.3a.4a.5e.6e, | |
| 1d.2a.3a.4a.5e.6f, | 1d.2a.3a.4a.5f.6a, | 1d.2a.3a.4a.5f.6b, | 1d.2a.3a.4a.5f.6c, | |
| 1d.2a.3a.4a.5f.6d, | 1d.2a.3a.4a.5f.6e, | 1d.2a.3a.4a.5f.6f, | 1d.2a.3a.4b.5a.6a, | |
| 1d.2a.3a.4b.5a.6b, | 1d.2a.3a.4b.5a.6c, | 1d.2a.3a.4b.5a.6d, | 1d.2a.3a.4b.5a.6e, | |
| 1d.2a.3a.4b.5a.6f, | 1d.2a.3a.4b.5b.6a, | 1d.2a.3a.4b.5b.6b, | 1d.2a.3a.4b.5b.6c, | |
| 1d.2a.3a.4b.5b.6d, | 1d.2a.3a.4b.5b.6e, | 1d.2a.3a.4b.5b.6f, | 1d.2a.3a.4b.5c.6a, | |
| 1d.2a.3a.4b.5c.6b, | 1d.2a.3a.4b.5c.6c, | 1d.2a.3a.4b.5c.6d, | 1d.2a.3a.4b.5c.6e, | |
| 1d.2a.3a.4b.5c.6f, | 1d.2a.3a.4b.5d.6a, | 1d.2a.3a.4b.5d.6b, | 1d.2a.3a.4b.5d.6c, | |
| 1d.2a.3a.4b.5d.6d, | 1d.2a.3a.4b.5d.6e, | 1d.2a.3a.4b.5d.6f, | 1d.2a.3a.4b.5e.6a, | |
| 1d.2a.3a.4b.5e.6b, | 1d.2a.3a.4b.5e.6c, | 1d.2a.3a.4b.5e.6d, | 1d.2a.3a.4b.5e.6e, | |
| 1d.2a.3a.4b.5e.6f, | 1d.2a.3a.4b.5f.6a, | 1d.2a.3a.4b.5f.6b, | 1d.2a.3a.4b.5f.6c, | |
| 1d.2a.3a.4b.5f.6d, | 1d.2a.3a.4b.5f.6e, | 1d.2a.3a.4b.5f.6f, | 1d.2a.3a.4c.5a.6a, | |
| 1d.2a.3a.4c.5a.6b, | 1d.2a.3a.4c.5a.6c, | 1d.2a.3a.4c.5a.6d, | 1d.2a.3a.4c.5a.6e, | |
| 1d.2a.3a.4c.5a.6f, | 1d.2a.3a.4c.5b.6a, | 1d.2a.3a.4c.5b.6b, | 1d.2a.3a.4c.5b.6c, | |

TABLE 7-continued

List of Compounds of Formula (II)

| | | | | |
|---|---|---|---|---|
| 1d.2a.3a.4c.5b.6d, | 1d.2a.3a.4c.5b.6e, | 1d.2a.3a.4c.5b.6f, | 1d.2a.3a.4c.5c.6a, | |
| 1d.2a.3a.4c.5c.6b, | 1d.2a.3a.4c.5c.6c, | 1d.2a.3a.4c.5c.6d, | 1d.2a.3a.4c.5c.6e, | |
| 1d.2a.3a.4c.5c.6f, | 1d.2a.3a.4c.5d.6a, | 1d.2a.3a.4c.5d.6b, | 1d.2a.3a.4c.5d.6c, | |
| 1d.2a.3a.4c.5d.6d, | 1d.2a.3a.4c.5d.6e, | 1d.2a.3a.4c.5d.6f, | 1d.2a.3a.4c.5e.6a, | |
| 1d.2a.3a.4c.5e.6b, | 1d.2a.3a.4c.5e.6c, | 1d.2a.3a.4c.5e.6d, | 1d.2a.3a.4c.5e.6e, | |
| 1d.2a.3a.4c.5e.6f, | 1d.2a.3a.4c.5f.6a, | 1d.2a.3a.4c.5f.6b, | 1d.2a.3a.4c.5f.6c, | |
| 1d.2a.3a.4c.5f.6d, | 1d.2a.3a.4c.5f.6e, | 1d.2a.3a.4c.5f.6f, | 1d.2a.3a.4d.5a.6a, | |
| 1d.2a.3a.4d.5a.6b, | 1d.2a.3a.4d.5a.6c, | 1d.2a.3a.4d.5a.6d, | 1d.2a.3a.4d.5a.6e, | |
| 1d.2a.3a.4d.5a.6f, | 1d.2a.3a.4d.5b.6a, | 1d.2a.3a.4d.5b.6b, | 1d.2a.3a.4d.5b.6c, | |
| 1d.2a.3a.4d.5b.6d, | 1d.2a.3a.4d.5b.6e, | 1d.2a.3a.4d.5b.6f, | 1d.2a.3a.4d.5c.6a, | |
| 1d.2a.3a.4d.5c.6b, | 1d.2a.3a.4d.5c.6c, | 1d.2a.3a.4d.5c.6d, | 1d.2a.3a.4d.5c.6e, | |
| 1d.2a.3a.4d.5c.6f, | 1d.2a.3a.4d.5d.6a, | 1d.2a.3a.4d.5d.6b, | 1d.2a.3a.4d.5d.6c, | |
| 1d.2a.3a.4d.5d.6d, | 1d.2a.3a.4d.5d.6e, | 1d.2a.3a.4d.5d.6f, | 1d.2a.3a.4d.5e.6a, | |
| 1d.2a.3a.4d.5e.6b, | 1d.2a.3a.4d.5e.6c, | 1d.2a.3a.4d.5e.6d, | 1d.2a.3a.4d.5e.6e, | |
| 1d.2a.3a.4d.5e.6f, | 1d.2a.3a.4d.5f.6a, | 1d.2a.3a.4d.5f.6b, | 1d.2a.3a.4d.5f.6c, | |
| 1d.2a.3a.4d.5f.6d, | 1d.2a.3a.4d.5f.6e, | 1d.2a.3a.4d.5f.6f, | 1d.2a.3a.4e.5a.6a, | |
| 1d.2a.3a.4e.5a.6b, | 1d.2a.3a.4e.5a.6c, | 1d.2a.3a.4e.5a.6d, | 1d.2a.3a.4e.5a.6e, | |
| 1d.2a.3a.4e.5a.6f, | 1d.2a.3a.4e.5b.6a, | 1d.2a.3a.4e.5b.6b, | 1d.2a.3a.4e.5b.6c, | |
| 1d.2a.3a.4e.5b.6d, | 1d.2a.3a.4e.5b.6e, | 1d.2a.3a.4e.5b.6f, | 1d.2a.3a.4e.5c.6a, | |
| 1d.2a.3a.4e.5c.6b, | 1d.2a.3a.4e.5c.6c, | 1d.2a.3a.4e.5c.6d, | 1d.2a.3a.4e.5c.6e, | |
| 1d.2a.3a.4e.5c.6f, | 1d.2a.3a.4e.5d.6a, | 1d.2a.3a.4e.5d.6b, | 1d.2a.3a.4e.5d.6c, | |
| 1d.2a.3a.4e.5d.6d, | 1d.2a.3a.4e.5d.6e, | 1d.2a.3a.4e.5d.6f, | 1d.2a.3a.4e.5e.6a, | |
| 1d.2a.3a.4e.5e.6b, | 1d.2a.3a.4e.5e.6c, | 1d.2a.3a.4e.5e.6d, | 1d.2a.3a.4e.5e.6e, | |
| 1d.2a.3a.4e.5e.6f, | 1d.2a.3a.4e.5f.6a, | 1d.2a.3a.4e.5f.6b, | 1d.2a.3a.4e.5f.6c, | |
| 1d.2a.3a.4e.5f.6d, | 1d.2a.3a.4e.5f.6e, | 1d.2a.3a.4e.5f.6f, | 1d.2a.3a.4f.5a.6a, | |
| 1d.2a.3a.4f.5a.6b, | 1d.2a.3a.4f.5a.6c, | 1d.2a.3a.4f.5a.6d, | 1d.2a.3a.4f.5a.6e, | |
| 1d.2a.3a.4f.5a.6f, | 1d.2a.3a.4f.5b.6a, | 1d.2a.3a.4f.5b.6b, | 1d.2a.3a.4f.5b.6c, | |
| 1d.2a.3a.4f.5b.6d, | 1d.2a.3a.4f.5b.6e, | 1d.2a.3a.4f.5b.6f, | 1d.2a.3a.4f.5c.6a, | |
| 1d.2a.3a.4f.5c.6b, | 1d.2a.3a.4f.5c.6c, | 1d.2a.3a.4f.5c.6d, | 1d.2a.3a.4f.5c.6e, | 1d.2a.3a.4f.5c.6f, |
| 1d.2a.3a.4f.5d.6a, | 1d.2a.3a.4f.5d.6b, | 1d.2a.3a.4f.5d.6c, | 1d.2a.3a.4f.5d.6d, | |
| 1d.2a.3a.4f.5d.6e, | 1d.2a.3a.4f.5d.6f, | 1d.2a.3a.4f.5e.6a, | 1d.2a.3a.4f.5e.6b, | |
| 1d.2a.3a.4f.5e.6c, | 1d.2a.3a.4f.5e.6d, | 1d.2a.3a.4f.5e.6e, | 1d.2a.3a.4f.5e.6f, | 1d.2a.3a.4f.5f.6a, |
| 1d.2a.3a.4f.5f.6b, | 1d.2a.3a.4f.5f.6c, | 1d.2a.3a.4f.5f.6d, | 1d.2a.3a.4f.5f.6e, | 1d.2a.3a.4f.5f.6f, |
| 1d.2a.3b.4a.5a.6a, | 1d.2a.3b.4a.5a.6b, | 1d.2a.3b.4a.5a.6c, | 1d.2a.3b.4a.5a.6d, | |
| 1d.2a.3b.4a.5a.6e, | 1d.2a.3b.4a.5a.6f, | 1d.2a.3b.4a.5b.6a, | 1d.2a.3b.4a.5b.6b, | |
| 1d.2a.3b.4a.5b.6c, | 1d.2a.3b.4a.5b.6d, | 1d.2a.3b.4a.5b.6e, | 1d.2a.3b.4a.5b.6f, | |
| 1d.2a.3b.4a.5c.6a, | 1d.2a.3b.4a.5c.6b, | 1d.2a.3b.4a.5c.6c, | 1d.2a.3b.4a.5c.6d, | |
| 1d.2a.3b.4a.5c.6e, | 1d.2a.3b.4a.5c.6f, | 1d.2a.3b.4a.5d.6a, | 1d.2a.3b.4a.5d.6b, | |
| 1d.2a.3b.4a.5d.6c, | 1d.2a.3b.4a.5d.6d, | 1d.2a.3b.4a.5d.6e, | 1d.2a.3b.4a.5d.6f, | |
| 1d.2a.3b.4a.5e.6a, | 1d.2a.3b.4a.5e.6b, | 1d.2a.3b.4a.5e.6c, | 1d.2a.3b.4a.5e.6d, | |
| 1.d.2a.3b.4a.5e.6e, | 1d.2a.3b.4a.5e.6f, | 1d.2a.3b.4a.5f.6a, | 1d.2a.3b.4a.5f.6b, | |
| 1d.2a.3b.4a.5f.6c, | 1d.2a.3b.4a.5f.6d, | 1d.2a.3b.4a.5f.6e, | 1d.2a.3b.4a.5f.6f, | |
| 1d.2a.3b.4b.5a.6a, | 1d.2a.3b.4b.5a.6b, | 1d.2a.3b.4b.5a.6c, | 1d.2a.3b.4b.5a.6d, | |
| 1d.2a.3b.4b.5a.6e, | 1d.2a.3b.4b.5a.6f, | 1d.2a.3b.4b.5b.6a, | 1d.2a.3b.4b.5b.6b, | |
| 1d.2a.3b.4b.5b.6c, | 1d.2a.3b.4b.5b.6d, | 1d.2a.3b.4b.5b.6e, | 1d.2a.3b.4b.5b.6f, | |
| 1d.2a.3b.4b.5c.6a, | 1d.2a.3b.4b.5c.6b, | 1d.2a.3b.4b.5c.6c, | 1d.2a.3b.4b.5c.6d, | |
| 1d.2a.3b.4b.5c.6e, | 1d.2a.3b.4b.5c.6f, | 1d.2a.3b.4b.5d.6a, | 1d.2a.3b.4b.5d.6b, | |
| 1d.2a.3b.4b.5d.6c, | 1d.2a.3b.4b.5d.6d, | 1d.2a.3b.4b.5d.6e, | 1d.2a.3b.4b.5d.6f, | |
| 1d.2a.3b.4b.5e.6a, | 1d.2a.3b.4b.5e.6b, | 1d.2a.3b.4b.5e.6c, | 1d.2a.3b.4b.5e.6d, | |
| 1d.2a.3b.4b.5e.6e, | 1d.2a.3b.4b.5e.6f, | 1d.2a.3b.4b.5f.6a, | 1d.2a.3b.4b.5f.6b, | |
| 1d.2a.3b.4b.5f.6c, | 1d.2a.3b.4b.5f.6d, | 1d.2a.3b.4b.5f.6e, | 1d.2a.3b.4b.5f.6f, | |
| 1d.2a.3b.4c.5a.6a, | 1d.2a.3b.4c.5a.6b, | 1d.2a.3b.4c.5a.6c, | 1d.2a.3b.4c.5a.6d, | |
| 1d.2a.3b.4c.5a.6e, | 1d.2a.3b.4c.5a.6f, | 1d.2a.3b.4c.5b.6a, | 1d.2a.3b.4c.5b.6b, | |
| 1d.2a.3b.4c.5b.6c, | 1d.2a.3b.4c.5b.6d, | 1d.2a.3b.4c.5b.6e, | 1d.2a.3b.4c.5b.6f, | |
| 1d.2a.3b.4c.5c.6a, | 1d.2a.3b.4c.5c.6b, | 1d.2a.3b.4c.5c.6c, | 1d.2a.3b.4c.5c.6d, | |
| 1d.2a.3b.4c.5c.6e, | 1d.2a.3b.4c.5c.6f, | 1d.2a.3b.4c.5d.6a, | 1d.2a.3b.4c.5d.6b, | |
| 1d.2a.3b.4c.5d.6c, | 1d.2a.3b.4c.5d.6d, | 1d.2a.3b.4c.5d.6e, | 1d.2a.3b.4c.5d.6f, | |
| 1d.2a.3b.4c.5e.6a, | 1d.2a.3b.4c.5e.6b, | 1d.2a.3b.4c.5e.6c, | 1d.2a.3b.4c.5e.6d, | |
| 1d.2a.3b.4c.5e.6e, | 1d.2a.3b.4c.5e.6f, | 1d.2a.3b.4c.5f.6a, | 1d.2a.3b.4c.5f.6b, | |
| 1d.2a.3b.4c.5f.6c, | 1d.2a.3b.4c.5f.6d, | 1d.2a.3b.4c.5f.6e, | 1d.2a.3b.4c.5f.6f, | |
| 1d.2a.3b.4d.5a.6a, | 1d.2a.3b.4d.5a.6b, | 1d.2a.3b.4d.5a.6c, | 1d.2a.3b.4d.5a.6d, | |
| 1d.2a.3b.4d.5a.6e, | 1d.2a.3b.4d.5a.6f, | 1d.2a.3b.4d.5b.6a, | 1d.2a.3b.4d.5b.6b, | |
| 1d.2a.3b.4d.5b.6c, | 1d.2a.3b.4d.5b.6d, | 1d.2a.3b.4d.5b.6e, | 1d.2a.3b.4d.5b.6f, | |
| 1d.2a.3b.4d.5c.6a, | 1d.2a.3b.4d.5c.6b, | 1d.2a.3b.4d.5c.6c, | 1d.2a.3b.4d.5c.6d, | |
| 1d.2a.3b.4d.5c.6e, | 1d.2a.3b.4d.5c.6f, | 1d.2a.3b.4d.5d.6a, | 1d.2a.3b.4d.5d.6b, | |
| 1d.2a.3b.4d.5d.6c, | 1d.2a.3b.4d.5d.6d, | 1d.2a.3b.4d.5d.6e, | 1d.2a.3b.4d.5d.6f, | |
| 1d.2a.3b.4d.5e.6a, | 1d.2a.3b.4d.5e.6b, | 1d.2a.3b.4d.5e.6c, | 1d.2a.3b.4d.5e.6d, | |
| 1d.2a.3b.4d.5e.6e, | 1d.2a.3b.4d.5e.6f, | 1d.2a.3b.4d.5f.6a, | 1d.2a.3b.4d.5f.6b, | |
| 1d.2a.3b.4d.5f.6c, | 1d.2a.3b.4d.5f.6d, | 1d.2a.3b.4d.5f.6e, | 1d.2a.3b.4d.5f.6f, | |
| 1d.2a.3b.4e.5a.6a, | 1d.2a.3b.4e.5a.6b, | 1d.2a.3b.4e.5a.6c, | 1d.2a.3b.4e.5a.6d, | |
| 1d.2a.3b.4e.5a.6e, | 1d.2a.3b.4e.5a.6f, | 1d.2a.3b.4e.5b.6a, | 1d.2a.3b.4e.5b.6b, | |
| 1d.2a.3b.4e.5b.6c, | 1d.2a.3b.4e.5b.6d, | 1d.2a.3b.4e.5b.6e, | 1d.2a.3b.4e.5b.6f, | |
| 1d.2a.3b.4e.5c.6a, | 1d.2a.3b.4e.5c.6b, | 1d.2a.3b.4e.5c.6c, | 1d.2a.3b.4e.5c.6d, | |
| 1d.2a.3b.4e.5c.6e, | 1d.2a.3b.4e.5c.6f, | 1d.2a.3b.4e.5d.6a, | 1d.2a.3b.4e.5d.6b, | |
| 1d.2a.3b.4e.5d.6c, | 1d.2a.3b.4e.5d.6d, | 1d.2a.3b.4e.5d.6e, | 1d.2a.3b.4e.5d.6f, | |
| 1d.2a.3b.4e.5e.6a, | 1d.2a.3b.4e.5e.6b, | 1d.2a.3b.4e.5e.6c, | 1d.2a.3b.4e.5e.6d, | |
| 1d.2a.3b.4e.5e.6e, | 1d.2a.3b.4e.5e.6f, | 1d.2a.3b.4e.5f.6a, | 1d.2a.3b.4e.5f.6b, | |
| 1d.2a.3b.4e.5f.6c, | 1d.2a.3b.4e.5f.6d, | 1d.2a.3b.4e.5f.6e, | 1d.2a.3b.4e.5f.6f, | |

TABLE 7-continued

List of Compounds of Formula (II)

| | | | | |
|---|---|---|---|---|
| 1d.2a.3b.4f.5a.6a, | 1d.2a.3b.4f.5a.6b, | 1d.2a.3b.4f.5a.6c, | 1d.2a.3b.4f.5a.6d, | |
| 1d.2a.3b.4f.5a.6e, | 1d.2a.3b.4f.5a.6f, | 1d.2a.3b.4f.5b.6a, | 1d.2a.3b.4f.5b.6b, | |
| 1d.2a.3b.4f.5b.6c, | 1d.2a.3b.4f.5b.6d, | 1d.2a.3b.4f.5b.6e, | 1d.2a.3b.4f.5b.6f, | |
| 1d.2a.3b.4f.5c.6a, | 1d.2a.3b.4f.5c.6b, | 1d.2a.3b.4f.5c.6c, | 1d.2a.3b.4f.5c.6d, | |
| 1d.2a.3b.4f.5c.6e, | 1d.2a.3b.4f.5c.6f, | 1d.2a.3b.4f.5d.6a, | 1d.2a.3b.4f.5d.6b, | |
| 1d.2a.3b.4f.5d.6c, | 1d.2a.3b.4f.5d.6d, | 1d.2a.3b.4f.5d.6e, | 1d.2a.3b.4f.5d.6f, | |
| 1d.2a.3b.4f.5e.6a, | 1d.2a.3b.4f.5e.6b, | 1d.2a.3b.4f.5e.6c, | 1d.2a.3b.4f.5e.6d, | |
| 1d.2a.3b.4f.5e.6e, | 1d.2a.3b.4f.5e.6f, | 1d.2a.3b.4f.5f.6a, | 1d.2a.3b.4f.5f.6b, | 1d.2a.3b.4f.5f.6c, |
| 1d.2a.3b.4f.5f.6d, | 1d.2a.3b.4f.5f.6e, | 1d.2a.3b.4f.5f.6f, | 1d.2a.3c.4a.5a.6a, | |
| 1d.2a.3c.4a.5a.6b, | 1d.2a.3c.4a.5a.6c, | 1d.2a.3c.4a.5a.6d, | 1d.2a.3c.4a.5a.6e, | |
| 1d.2a.3c.4a.5a.6f, | 1d.2a.3c.4a.5b.6a, | 1d.2a.3c.4a.5b.6b, | 1d.2a.3c.4a.5b.6c, | |
| 1d.2a.3c.4a.5b.6d, | 1d.2a.3c.4a.5b.6e, | 1d.2a.3c.4a.5b.6f, | 1d.2a.3c.4a.5c.6a, | |
| 1d.2a.3c.4a.5c.6b, | 1d.2a.3c.4a.5c.6c, | 1d.2a.3c.4a.5c.6d, | 1d.2a.3c.4a.5c.6e, | |
| 1d.2a.3c.4a.5c.6f, | 1d.2a.3c.4a.5d.6a, | 1d.2a.3c.4a.5d.6b, | 1d.2a.3c.4a.5d.6c, | |
| 1d.2a.3c.4a.5d.6d, | 1d.2a.3c.4a.5d.6e, | 1d.2a.3c.4a.5d.6f, | 1d.2a.3c.4a.5e.6a, | |
| 1d.2a.3c.4a.5e.6b, | 1d.2a.3c.4a.5e.6c, | 1d.2a.3c.4a.5e.6d, | 1d.2a.3c.4a.5e.6e, | |
| 1d.2a.3c.4a.5e.6f, | 1d.2a.3c.4a.5f.6a, | 1d.2a.3c.4a.5f.6b, | 1d.2a.3c.4a.5f.6c, | |
| 1d.2a.3c.4a.5f.6d, | 1d.2a.3c.4a.5f.6e, | 1d.2a.3c.4a.5f.6f, | 1d.2a.3c.4b.5a.6a, | |
| 1d.2a.3c.4b.5a.6b, | 1d.2a.3c.4b.5a.6c, | 1d.2a.3c.4b.5a.6d, | 1d.2a.3c.4b.5a.6e, | |
| 1d.2a.3c.4b.5a.6f, | 1d.2a.3c.4b.5b.6a, | 1d.2a.3c.4b.5b.6b, | 1d.2a.3c.4b.5b.6c, | |
| 1d.2a.3c.4b.5b.6d, | 1d.2a.3c.4b.5b.6e, | 1d.2a.3c.4b.5b.6f, | 1d.2a.3c.4b.5c.6a, | |
| 1d.2a.3c.4b.5c.6b, | 1d.2a.3c.4b.5c.6c, | 1d.2a.3c.4b.5c.6d, | 1d.2a.3c.4b.5c.6e, | |
| 1d.2a.3c.4b.5c.6f, | 1d.2a.3c.4b.5d.6a, | 1d.2a.3c.4b.5d.6b, | 1d.2a.3c.4b.5d.6c, | |
| 1d.2a.3c.4b.5d.6d, | 1d.2a.3c.4b.5d.6e, | 1d.2a.3c.4b.5d.6f, | 1d.2a.3c.4b.5e.6a, | |
| 1d.2a.3c.4b.5e.6b, | 1d.2a.3c.4b.5e.6c, | 1d.2a.3c.4b.5e.6d, | 1d.2a.3c.4b.5e.6e, | |
| 1d.2a.3c.4b.5e.6f, | 1d.2a.3c.4b.5f.6a, | 1d.2a.3c.4b.5f.6b, | 1d.2a.3c.4b.5f.6c, | |
| 1d.2a.3c.4b.5f.6d, | 1d.2a.3c.4b.5f.6e, | 1d.2a.3c.4b.5f.6f, | 1d.2a.3c.4c.5a.6a, | |
| 1d.2a.3c.4c.5a.6b, | 1d.2a.3c.4c.5a.6c, | 1d.2a.3c.4c.5a.6d, | 1d.2a.3c.4c.5a.6e, | |
| 1d.2a.3c.4c.5a.6f, | 1d.2a.3c.4c.5b.6a, | 1d.2a.3c.4c.5b.6b, | 1d.2a.3c.4c.5b.6c, | |
| 1d.2a.3c.4c.5b.6d, | 1d.2a.3c.4c.5b.6e, | 1d.2a.3c.4c.5b.6f, | 1d.2a.3c.4c.5c.6a, | |
| 1d.2a.3c.4c.5c.6b, | 1d.2a.3c.4c.5c.6c, | 1d.2a.3c.4c.5c.6d, | 1d.2a.3c.4c.5c.6e, | |
| 1d.2a.3c.4c.5c.6f, | 1d.2a.3c.4c.5d.6a, | 1d.2a.3c.4c.5d.6b, | 1d.2a.3c.4c.5d.6c, | |
| 1d.2a.3c.4c.5d.6d, | 1d.2a.3c.4c.5d.6e, | 1d.2a.3c.4c.5d.6f, | 1d.2a.3c.4c.5e.6a, | |
| 1d.2a.3c.4c.5e.6b, | 1d.2a.3c.4c.5e.6c, | 1d.2a.3c.4c.5e.6d, | 1d.2a.3c.4c.5e.6e, | |
| 1d.2a.3c.4c.5e.6f, | 1d.2a.3c.4c.5f.6a, | 1d.2a.3c.4c.5f.6b, | 1d.2a.3c.4c.5f.6c, | 1d.2a.3c.4c.5f.6d, |
| 1d.2a.3c.4c.5f.6e, | 1d.2a.3c.4c.5f.6f, | 1d.2a.3c.4d.5a.6a, | 1d.2a.3c.4d.5a.6b, | |
| 1d.2a.3c.4d.5a.6c, | 1d.2a.3c.4d.5a.6d, | 1d.2a.3c.4d.5a.6e, | 1d.2a.3c.4d.5a.6f, | |
| 1d.2a.3c.4d.5b.6a, | 1d.2a.3c.4d.5b.6b, | 1d.2a.3c.4d.5b.6c, | 1d.2a.3c.4d.5b.6d, | |
| 1d.2a.3c.4d.5b.6e, | 1d.2a.3c.4d.5b.6f, | 1d.2a.3c.4d.5c.6a, | 1d.2a.3c.4d.5c.6b, | |
| 1d.2a.3c.4d.5c.6c, | 1d.2a.3c.4d.5c.6d, | 1d.2a.3c.4d.5c.6e, | 1d.2a.3c.4d.5c.6f, | |
| 1d.2a.3c.4d.5d.6a, | 1d.2a.3c.4d.5d.6b, | 1d.2a.3c.4d.5d.6c, | 1d.2a.3c.4d.5d.6d, | |
| 1d.2a.3c.4d.5d.6e, | 1d.2a.3c.4d.5d.6f, | 1d.2a.3c.4d.5e.6a, | 1d.2a.3c.4d.5e.6b, | |
| 1d.2a.3c.4d.5e.6c, | 1d.2a.3c.4d.5e.6d, | 1d.2a.3c.4d.5e.6e, | 1d.2a.3c.4d.5e.6f, | |
| 1d.2a.3c.4d.5f.6a, | 1d.2a.3c.4d.5f.6b, | 1d.2a.3c.4d.5f.6c, | 1d.2a.3c.4d.5f.6d, | |
| 1d.2a.3c.4d.5f.6e, | 1d.2a.3c.4d.5f.6f, | 1d.2a.3c.4e.5a.6a, | 1d.2a.3c.4e.5a.6b, | |
| 1d.2a.3c.4e.5a.6c, | 1d.2a.3c.4e.5a.6d, | 1d.2a.3c.4e.5a.6e, | 1d.2a.3c.4e.5a.6f, | |
| 1d.2a.3c.4e.5b.6a, | 1d.2a.3c.4e.5b.6b, | 1d.2a.3c.4e.5b.6c, | 1d.2a.3c.4e.5b.6d, | |
| 1d.2a.3c.4e.5b.6e, | 1d.2a.3c.4e.5b.6f, | 1d.2a.3c.4e.5c.6a, | 1d.2a.3c.4e.5c.6b, | |
| 1d.2a.3c.4e.5c.6c, | 1d.2a.3c.4e.5c.6d, | 1d.2a.3c.4e.5c.6e, | 1d.2a.3c.4e.5c.6f, | |
| 1d.2a.3c.4e.5d.6a, | 1d.2a.3c.4e.5d.6b, | 1d.2a.3c.4e.5d.6c, | 1d.2a.3c.4e.5d.6d, | |
| 1d.2a.3c.4e.5d.6e, | 1d.2a.3c.4e.5d.6f, | 1d.2a.3c.4e.5e.6a, | 1d.2a.3c.4e.5e.6b, | |
| 1d.2a.3c.4e.5e.6c, | 1d.2a.3c.4e.5e.6d, | 1d.2a.3c.4e.5e.6e, | 1d.2a.3c.4e.5e.6f, | |
| 1d.2a.3c.4e.5f.6a, | 1d.2a.3c.4e.5f.6b, | 1d.2a.3c.4e.5f.6c, | 1d.2a.3c.4e.5f.6d, | |
| 1d.2a.3c.4e.5f.6e, | 1d.2a.3c.4e.5f.6f, | 1d.2a.3c.4f.5a.6a, | 1d.2a.3c.4f.5a.6b, | 1d.2a.3c.4f.5a.6c, |
| 1d.2a.3c.4f.5a.6d, | 1d.2a.3c.4f.5a.6e, | 1d.2a.3c.4f.5a.6f, | 1d.2a.3c.4f.5b.6a, | |
| 1d.2a.3c.4f.5b.6b, | 1d.2a.3c.4f.5b.6c, | 1d.2a.3c.4f.5b.6d, | 1d.2a.3c.4f.5b.6e, | |
| 1d.2a.3c.4f.5b.6f, | 1d.2a.3c.4f.5c.6a, | 1d.2a.3c.4f.5c.6b, | 1d.2a.3c.4f.5c.6c, | 1d.2a.3c.4f.5c.6d, |
| 1d.2a.3c.4f.5c.6e, | 1d.2a.3c.4f.5c.6f, | 1d.2a.3c.4f.5d.6a, | 1d.2a.3c.4f.5d.6b, | |
| 1d.2a.3c.4f.5d.6c, | 1d.2a.3c.4f.5d.6d, | 1d.2a.3c.4f.5d.6e, | 1d.2a.3c.4f.5d.6f, | |
| 1d.2a.3c.4f.5e.6a, | 1d.2a.3c.4f.5e.6b, | 1d.2a.3c.4f.5e.6c, | 1d.2a.3c.4f.5e.6d, | |
| 1d.2a.3c.4f.5e.6e, | 1d.2a.3c.4f.5e.6f, | 1d.2a.3c.4f.5f.6a, | 1d.2a.3c.4f.5f.6b, | 1d.2a.3c.4f.5f.6c, |
| 1d.2a.3c.4f.5f.6d, | 1d.2a.3c.4f.5f.6e, | 1d.2a.3c.4f.5f.6f, | 1d.2a.3d.4a.5a.6a, | |
| 1d.2a.3d.4a.5a.6b, | 1d.2a.3d.4a.5a.6c, | 1d.2a.3d.4a.5a.6d, | 1d.2a.3d.4a.5a.6e, | |
| 1d.2a.3d.4a.5a.6f, | 1d.2a.3d.4a.5b.6a, | 1d.2a.3d.4a.5b.6b, | 1d.2a.3d.4a.5b.6c, | |
| 1d.2a.3d.4a.5b.6d, | 1d.2a.3d.4a.5b.6e, | 1d.2a.3d.4a.5b.6f, | 1d.2a.3d.4a.5c.6a, | |
| 1d.2a.3d.4a.5c.6b, | 1d.2a.3d.4a.5c.6c, | 1d.2a.3d.4a.5c.6d, | 1d.2a.3d.4a.5c.6e, | |
| 1d.2a.3d.4a.5c.6f, | 1d.2a.3d.4a.5d.6a, | 1d.2a.3d.4a.5d.6b, | 1d.2a.3d.4a.5d.6c, | |
| 1d.2a.3d.4a.5d.6d, | 1d.2a.3d.4a.5d.6e, | 1d.2a.3d.4a.5d.6f, | 1d.2a.3d.4a.5e.6a, | |
| 1d.2a.3d.4a.5e.6b, | 1d.2a.3d.4a.5e.6c, | 1d.2a.3d.4a.5e.6d, | 1d.2a.3d.4a.5e.6e, | |
| 1d.2a.3d.4a.5e.6f, | 1d.2a.3d.4a.5f.6a, | 1d.2a.3d.4a.5f.6b, | 1d.2a.3d.4a.5f.6c, | |
| 1d.2a.3d.4a.5f.6d, | 1d.2a.3d.4a.5f.6e, | 1d.2a.3d.4a.5f.6f, | 1d.2a.3d.4b.5a.6a, | |
| 1d.2a.3d.4b.5a.6b, | 1d.2a.3d.4b.5a.6c, | 1d.2a.3d.4b.5a.6d, | 1d.2a.3d.4b.5a.6e, | |
| 1d.2a.3d.4b.5a.6f, | 1d.2a.3d.4b.5b.6a, | 1d.2a.3d.4b.5b.6b, | 1d.2a.3d.4b.5b.6c, | |
| 1d.2a.3d.4b.5b.6d, | 1d.2a.3d.4b.5b.6e, | 1d.2a.3d.4b.5b.6f, | 1d.2a.3d.4b.5c.6a, | |
| 1d.2a.3d.4b.5c.6b, | 1d.2a.3d.4b.5c.6c, | 1d.2a.3d.4b.5c.6d, | 1d.2a.3d.4b.5c.6e, | |
| 1d.2a.3d.4b.5c.6f, | 1d.2a.3d.4b.5d.6a, | 1d.2a.3d.4b.5d.6b, | 1d.2a.3d.4b.5d.6c, | |
| 1d.2a.3d.4b.5d.6d, | 1d.2a.3d.4b.5d.6e, | 1d.2a.3d.4b.5d.6f, | 1d.2a.3d.4b.5e.6a, | |
| 1d.2a.3d.4b.5e.6b, | 1d.2a.3d.4b.5e.6c, | 1d.2a.3d.4b.5e.6d, | 1d.2a.3d.4b.5e.6e, | |

TABLE 7-continued

List of Compounds of Formula (II)

| | | | |
|---|---|---|---|
| 1d.2a.3d.4b.5e.6f, | 1d.2a.3d.4b.5f.6a, | 1d.2a.3d.4b.5f.6b, | 1d.2a.3d.4b.5f.6c, |
| 1d.2a.3d.4b.5f.6d, | 1d.2a.3d.4b.5f.6e, | 1d.2a.3d.4b.5f.6f, | 1d.2a.3d.4c.5a.6a, |
| 1d.2a.3d.4c.5a.6b, | 1d.2a.3d.4c.5a.6c, | 1d.2a.3d.4c.5a.6d, | 1d.2a.3d.4c.5a.6e, |
| 1d.2a.3d.4c.5a.6f, | 1d.2a.3d.4c.5b.6a, | 1d.2a.3d.4c.5b.6b, | 1d.2a.3d.4c.5b.6c, |
| 1d.2a.3d.4c.5b.6d, | 1d.2a.3d.4c.5b.6e, | 1d.2a.3d.4c.5b.6f, | 1d.2a.3d.4c.5c.6a, |
| 1d.2a.3d.4c.5c.6b, | 1d.2a.3d.4c.5c.6c, | 1d.2a.3d.4c.5c.6d, | 1d.2a.3d.4c.5c.6e, |
| 1d.2a.3d.4c.5c.6f, | 1d.2a.3d.4c.5d.6a, | 1d.2a.3d.4c.5d.6b, | 1d.2a.3d.4c.5d.6c, |
| 1d.2a.3d.4c.5d.6d, | 1d.2a.3d.4c.5d.6e, | 1d.2a.3d.4c.5d.6f, | 1d.2a.3d.4c.5e.6a, |
| 1d.2a.3d.4c.5e.6b, | 1d.2a.3d.4c.5e.6c, | 1d.2a.3d.4c.5e.6d, | 1d.2a.3d.4c.5e.6e, |
| 1d.2a.3d.4c.5e.6f, | 1d.2a.3d.4c.5f.6a, | 1d.2a.3d.4c.5f.6b, | 1d.2a.3d.4c.5f.6c, |
| 1d.2a.3d.4c.5f.6d, | 1d.2a.3d.4c.5f.6e, | 1d.2a.3d.4c.5f.6f, | 1d.2a.3d.4d.5a.6a, |
| 1d.2a.3d.4d.5a.6b, | 1d.2a.3d.4d.5a.6c, | 1d.2a.3d.4d.5a.6d, | 1d.2a.3d.4d.5a.6e, |
| 1d.2a.3d.4d.5a.6f, | 1d.2a.3d.4d.5b.6a, | 1d.2a.3d.4d.5b.6b, | 1d.2a.3d.4d.5b.6c, |
| 1d.2a.3d.4d.5b.6d, | 1d.2a.3d.4d.5b.6e, | 1d.2a.3d.4d.5b.6f, | 1d.2a.3d.4d.5c.6a, |
| 1d.2a.3d.4d.5c.6b, | 1d.2a.3d.4d.5c.6c, | 1d.2a.3d.4d.5c.6d, | 1d.2a.3d.4d.5c.6e, |
| 1d.2a.3d.4d.5c.6f, | 1d.2a.3d.4d.5d.6a, | 1d.2a.3d.4d.5d.6b, | 1d.2a.3d.4d.5d.6c, |
| 1d.2a.3d.4d.5d.6d, | 1d.2a.3d.4d.5d.6e, | 1d.2a.3d.4d.5d.6f, | 1d.2a.3d.4d.5e.6a, |
| 1d.2a.3d.4d.5e.6b, | 1d.2a.3d.4d.5e.6c, | 1d.2a.3d.4d.5e.6d, | 1d.2a.3d.4d.5e.6e, |
| 1d.2a.3d.4d.5e.6f, | 1d.2a.3d.4d.5f.6a, | 1d.2a.3d.4d.5f.6b, | 1d.2a.3d.4d.5f.6c, |
| 1d.2a.3d.4d.5f.6d, | 1d.2a.3d.4d.5f.6e, | 1d.2a.3d.4d.5f.6f, | 1d.2a.3d.4e.5a.6a, |
| 1d.2a.3d.4e.5a.6b, | 1d.2a.3d.4e.5a.6c, | 1d.2a.3d.4e.5a.6d, | 1d.2a.3d.4e.5a.6e, |
| 1d.2a.3d.4e.5a.6f, | 1d.2a.3d.4e.5b.6a, | 1d.2a.3d.4e.5b.6b, | 1d.2a.3d.4e.5b.6c, |
| 1d.2a.3d.4e.5b.6d, | 1d.2a.3d.4e.5b.6e, | 1d.2a.3d.4e.5b.6f, | 1d.2a.3d.4e.5c.6a, |
| 1d.2a.3d.4e.5c.6b, | 1d.2a.3d.4e.5c.6c, | 1d.2a.3d.4e.5c.6d, | 1d.2a.3d.4e.5c.6e, |
| 1d.2a.3d.4e.5c.6f, | 1d.2a.3d.4e.5d.6a, | 1d.2a.3d.4e.5d.6b, | 1d.2a.3d.4e.5d.6c, |
| 1d.2a.3d.4e.5d.6d, | 1d.2a.3d.4e.5d.6e, | 1d.2a.3d.4e.5d.6f, | 1d.2a.3d.4e.5e.6a, |
| 1d.2a.3d.4e.5e.6b, | 1d.2a.3d.4e.5e.6c, | 1d.2a.3d.4e.5e.6d, | 1d.2a.3d.4e.5e.6e, |
| 1d.2a.3d.4e.5e.6f, | 1d.2a.3d.4e.5f.6a, | 1d.2a.3d.4e.5f.6b, | 1d.2a.3d.4e.5f.6c, |
| 1d.2a.3d.4e.5f.6d, | 1d.2a.3d.4e.5f.6e, | 1d.2a.3d.4e.5f.6f, | 1d.2a.3d.4f.5a.6a, |
| 1d.2a.3d.4f.5a.6b, | 1d.2a.3d.4f.5a.6c, | 1d.2a.3d.4f.5a.6d, | 1d.2a.3d.4f.5a.6e, |
| 1d.2a.3d.4f.5a.6f, | 1d.2a.3d.4f.5b.6a, | 1d.2a.3d.4f.5b.6b, | 1d.2a.3d.4f.5b.6c, |
| 1d.2a.3d.4f.5b.6d, | 1d.2a.3d.4f.5b.6e, | 1d.2a.3d.4f.5b.6f, | 1d.2a.3d.4f.5c.6a, |
| 1d.2a.3d.4f.5c.6b, | 1d.2a.3d.4f.5c.6c, | 1d.2a.3d.4f.5c.6d, | 1d.2a.3d.4f.5c.6e, |
| 1d.2a.3d.4f.5c.6f, | 1d.2a.3d.4f.5d.6a, | 1d.2a.3d.4f.5d.6b, | 1d.2a.3d.4f.5d.6c, |
| 1d.2a.3d.4f.5d.6d, | 1d.2a.3d.4f.5d.6e, | 1d.2a.3d.4f.5d.6f, | 1d.2a.3d.4f.5e.6a, |
| 1d.2a.3d.4f.5e.6b, | 1d.2a.3d.4f.5e.6c, | 1d.2a.3d.4f.5e.6d, | 1d.2a.3d.4f.5e.6e, |
| 1d.2a.3d.4f.5e.6f, | 1d.2a.3d.4f.5f.6a, | 1d.2a.3d.4f.5f.6b, | 1d.2a.3d.4f.5f.6c, |
| 1d.2a.3d.4f.5f.6d, | 1d.2a.3d.4f.5f.6e, | 1d.2a.3d.4f.5f.6f, | 1d.2a.3e.4a.5a.6a, |
| 1d.2a.3e.4a.5a.6b, | 1d.2a.3e.4a.5a.6c, | 1d.2a.3e.4a.5a.6d, | 1d.2a.3e.4a.5a.6e, |
| 1d.2a.3e.4a.5a.6f, | 1d.2a.3e.4a.5b.6a, | 1d.2a.3e.4a.5b.6b, | 1d.2a.3e.4a.5b.6c, |
| 1d.2a.3e.4a.5b.6d, | 1d.2a.3e.4a.5b.6e, | 1d.2a.3e.4a.5b.6f, | 1d.2a.3e.4a.5c.6a, |
| 1d.2a.3e.4a.5c.6b, | 1d.2a.3e.4a.5c.6c, | 1d.2a.3e.4a.5c.6d, | 1d.2a.3e.4a.5c.6e, |
| 1d.2a.3e.4a.5c.6f, | 1d.2a.3e.4a.5d.6a, | 1d.2a.3e.4a.5d.6b, | 1d.2a.3e.4a.5d.6c, |
| 1d.2a.3e.4a.5d.6d, | 1d.2a.3e.4a.5d.6e, | 1d.2a.3e.4a.5d.6f, | 1d.2a.3e.4a.5e.6a, |
| 1d.2a.3e.4a.5e.6b, | 1d.2a.3e.4a.5e.6c, | 1d.2a.3e.4a.5e.6d, | 1d.2a.3e.4a.5e.6e, |
| 1d.2a.3e.4a.5e.6f, | 1d.2a.3e.4a.5f.6a, | 1d.2a.3e.4a.5f.6b, | 1d.2a.3e.4a.5f.6c, |
| 1d.2a.3e.4a.5f.6d, | 1d.2a.3e.4a.5f.6e, | 1d.2a.3e.4a.5f.6f, | 1d.2a.3e.4b.5a.6a, |
| 1d.2a.3e.4b.5a.6b, | 1d.2a.3e.4b.5a.6c, | 1d.2a.3e.4b.5a.6d, | 1d.2a.3e.4b.5a.6e, |
| 1d.2a.3e.4b.5a.6f, | 1d.2a.3e.4b.5b.6a, | 1d.2a.3e.4b.5b.6b, | 1d.2a.3e.4b.5b.6c, |
| 1d.2a.3e.4b.5b.6d, | 1d.2a.3e.4b.5b.6e, | 1d.2a.3e.4b.5b.6f, | 1d.2a.3e.4b.5c.6a, |
| 1d.2a.3e.4b.5c.6b, | 1d.2a.3e.4b.5c.6c, | 1d.2a.3e.4b.5c.6d, | 1d.2a.3e.4b.5c.6e, |
| 1d.2a.3e.4b.5c.6f, | 1d.2a.3e.4b.5d.6a, | 1d.2a.3e.4b.5d.6b, | 1d.2a.3e.4b.5d.6c, |
| 1d.2a.3e.4b.5d.6d, | 1d.2a.3e.4b.5d.6e, | 1d.2a.3e.4b.5d.6f, | 1d.2a.3e.4b.5e.6a, |
| 1d.2a.3e.4b.5e.6b, | 1d.2a.3e.4b.5e.6c, | 1d.2a.3e.4b.5e.6d, | 1d.2a.3e.4b.5e.6e, |
| 1d.2a.3e.4b.5e.6f, | 1d.2a.3e.4b.5f.6a, | 1d.2a.3e.4b.5f.6b, | 1d.2a.3e.4b.5f.6c, |
| 1d.2a.3e.4b.5f.6d, | 1d.2a.3e.4b.5f.6e, | 1d.2a.3e.4b.5f.6f, | 1d.2a.3e.4c.5a.6a, |
| 1d.2a.3e.4c.5a.6b, | 1d.2a.3e.4c.5a.6c, | 1d.2a.3e.4c.5a.6d, | 1d.2a.3e.4c.5a.6e, |
| 1d.2a.3e.4c.5a.6f, | 1d.2a.3e.4c.5b.6a, | 1d.2a.3e.4c.5b.6b, | 1d.2a.3e.4c.5b.6c, |
| 1d.2a.3e.4c.5b.6d, | 1d.2a.3e.4c.5b.6e, | 1d.2a.3e.4c.5b.6f, | 1d.2a.3e.4c.5c.6a, |
| 1d.2a.3e.4c.5c.6b, | 1d.2a.3e.4c.5c.6c, | 1d.2a.3e.4c.5c.6d, | 1d.2a.3e.4c.5c.6e, |
| 1d.2a.3e.4c.5c.6f, | 1d.2a.3e.4c.5d.6a, | 1d.2a.3e.4c.5d.6b, | 1d.2a.3e.4c.5d.6c, |
| 1d.2a.3e.4c.5d.6d, | 1d.2a.3e.4c.5d.6e, | 1d.2a.3e.4c.5d.6f, | 1d.2a.3e.4c.5e.6a, |
| 1d.2a.3e.4c.5e.6b, | 1d.2a.3e.4c.5e.6c, | 1d.2a.3e.4c.5e.6d, | 1d.2a.3e.4c.5e.6e, |
| 1d.2a.3e.4c.5e.6f, | 1d.2a.3e.4c.5f.6a, | 1d.2a.3e.4c.5f.6b, | 1d.2a.3e.4c.5f.6c, |
| 1d.2a.3e.4c.5f.6d, | 1d.2a.3e.4c.5f.6e, | 1d.2a.3e.4c.5f.6f, | 1d.2a.3e.4d.5a.6a, |
| 1d.2a.3e.4d.5a.6b, | 1d.2a.3e.4d.5a.6c, | 1d.2a.3e.4d.5a.6d, | 1d.2a.3e.4d.5a.6e, |
| 1d.2a.3e.4d.5a.6f, | 1d.2a.3e.4d.5b.6a, | 1d.2a.3e.4d.5b.6b, | 1d.2a.3e.4d.5b.6c, |
| 1d.2a.3e.4c1.5b.6d, | 1d.2a.3e.4d.5b.6e, | 1d.2a.3e.4d.5b.6f, | 1d.2a.3e.4d.5c.6a, |
| 1d.2a.3e.4d.5c.6b, | 1d.2a.3e.4d.5c.6c, | 1d.2a.3e.4d.5c.6d, | 1d.2a.3e.4d.5c.6e, |
| 1d.2a.3e.4d.5c.6f, | 1d.2a.3e.4d.5d.6a, | 1d.2a.3e.4d.5d.6b, | 1d.2a.3e.4d.5d.6c, |
| 1d.2a.3e.4d.5d.6d, | 1d.2a.3e.4d.5d.6e, | 1d.2a.3e.4d.5d.6f, | 1d.2a.3e.4d.5e.6a, |
| 1d.2a.3e.4d.5e.6b, | 1d.2a.3e.4d.5e.6c, | 1d.2a.3e.4d.5e.6d, | 1d.2a.3e.4d.5e.6e, |
| 1d.2a.3e.4d.5e.6f, | 1d.2a.3e.4d.5f.6a, | 1d.2a.3e.4d.5f.6b, | 1d.2a.3e.4d.5f.6c, |
| 1d.2a.3e.4d.5f.6d, | 1d.2a.3e.4d.5f.6e, | 1d.2a.3e.4d.5f.6f, | 1d.2a.3e.4e.5a.6a, |
| 1d.2a.3e.4e.5a.6b, | 1d.2a.3e.4e.5a.6c, | 1d.2a.3e.4e.5a.6d, | 1d.2a.3e.4e.5a.6e, |
| 1d.2a.3e.4e.5a.6f, | 1d.2a.3e.4e.5b.6a, | 1d.2a.3e.4e.5b.6b, | 1d.2a.3e.4e.5b.6c, |
| 1d.2a.3e.4e.5b.6d, | 1d.2a.3e.4e.5b.6e, | 1d.2a.3e.4e.5b.6f, | 1d.2a.3e.4e.5c.6a, |
| 1d.2a.3e.4e.5c.6b, | 1d.2a.3e.4e.5c.6c, | 1d.2a.3e.4e.5c.6d, | 1d.2a.3e.4e.5c.6e, |

TABLE 7-continued

List of Compounds of Formula (II)

| | | | | |
|---|---|---|---|---|
| 1d.2a.3e.4e.5c.6f, | 1d.2a.3e.4e.5d.6a, | 1d.2a.3e.4e.5d.6b, | 1d.2a.3e.4e.5d.6c, | |
| 1d.2a.3e.4e.5d.6d, | 1d.2a.3e.4e.5d.6e, | 1d.2a.3e.4e.5d.6f, | 1d.2a.3e.4e.5e.6a, | |
| 1d.2a.3e.4e.5e.6b, | 1d.2a.3e.4e.5e.6c, | 1d.2a.3e.4e.5e.6d, | 1d.2a.3e.4e.5e.6e, | |
| 1d.2a.3e.4e.5e.6f, | 1d.2a.3e.4e.5f.6a, | 1d.2a.3e.4e.5f.6b, | 1d.2a.3e.4e.5f.6c, | |
| 1d.2a.3e.4e.5f.6d, | 1d.2a.3e.4e.5f.6e, | 1d.2a.3e.4e.5f.6f, | 1d.2a.3e.4f.5a.6a, | |
| 1d.2a.3e.4f.5a.6b, | 1d.2a.3e.4f.5a.6c, | 1d.2a.3e.4f.5a.6d, | 1d.2a.3e.4f.5a.6e, | |
| 1d.2a.3e.4f.5a.6f, | 1d.2a.3e.4f.5b.6a, | 1d.2a.3e.4f.5b.6b, | 1d.2a.3e.4f.5b.6c, | |
| 1d.2a.3e.4f.5b.6d, | 1d.2a.3e.4f.5b.6e, | 1d.2a.3e.4f.5b.6f, | 1d.2a.3e.4f.5c.6a, | |
| 1d.2a.3e.4f.5c.6b, | 1d.2a.3e.4f.5c.6c, | 1d.2a.3e.4f.5c.6d, | 1d.2a.3e.4f.5c.6e, | 1d.2a.3e.4f.5c.6f, |
| 1d.2a.3e.4f.5d.6a, | 1d.2a.3e.4f.5d.6b, | 1d.2a.3e.4f.5d.6c, | 1d.2a.3e.4f.5d.6d, | |
| 1d.2a.3e.4f.5d.6e, | 1d.2a.3e.4f.5d.6f, | 1d.2a.3e.4f.5e.6a, | 1d.2a.3e.4f.5e.6b, | |
| 1d.2a.3e.4f.5e.6c, | 1d.2a.3e.4f.5e.6d, | 1d.2a.3e.4f.5e.6e, | 1d.2a.3e.4f.5e.6f, | 1d.2a.3e.4f.5f.6a, |
| 1d.2a.3e.4f.5f.6b, | 1d.2a.3e.4f.5f.6c, | 1d.2a.3e.4f.5f.6d, | 1d.2a.3e.4f.5f.6e, | 1d.2a.3e.4f.5f.6f, |
| 1d.2a.3f.4a.5a.6a, | 1d.2a.3f.4a.5a.6b, | 1d.2a.3f.4a.5a.6c, | 1d.2a.3f.4a.5a.6d, | |
| 1d.2a.3f.4a.5a.6e, | 1d.2a.3f.4a.5a.6f, | 1d.2a.3f.4a.5b.6a, | 1d.2a.3f.4a.5b.6b, | |
| 1d.2a.3f.4a.5b.6c, | 1d.2a.3f.4a.5b.6d, | 1d.2a.3f.4a.5b.6e, | 1d.2a.3f.4a.5b.6f, | |
| 1d.2a.3f.4a.5c.6a, | 1d.2a.3f.4a.5c.6b, | 1d.2a.3f.4a.5c.6c, | 1d.2a.3f.4a.5c.6d, | |
| 1d.2a.3f.4a.5c.6e, | 1d.2a.3f.4a.5c.6f, | 1d.2a.3f.4a.5d.6a, | 1d.2a.3f.4a.5d.6b, | |
| 1d.2a.3f.4a.5d.6c, | 1d.2a.3f.4a.5d.6d, | 1d.2a.3f.4a.5d.6e, | 1d.2a.3f.4a.5d.6f, | |
| 1d.2a.3f.4a.5e.6a, | 1d.2a.3f.4a.5e.6b, | 1d.2a.3f.4a.5e.6c, | 1d.2a.3f.4a.5e.6d, | |
| 1d.2a.3f.4a.5e.6e, | 1d.2a.3f.4a.5e.6f, | 1d.2a.3f.4a.5f.6a, | 1d.2a.3f.4a.5f.6b, | 1d.2a.3f.4a.5f.6c, |
| 1d.2a.3f.4a.5f.6d, | 1d.2a.3f.4a.5f.6e, | 1d.2a.3f.4a.5f.6f, | 1d.2a.3f.4b.5a.6a, | 1d.2a.3f.4b.5a.6b, |
| 1d.2a.3f.4b.5a.6c, | 1d.2a.3f.4b.5a.6d, | 1d.2a.3f.4b.5a.6e, | 1d.2a.3f.4b.5a.6f, | |
| 1d.2a.3f.4b.5b.6a, | 1d.2a.3f.4b.5b.6b, | 1d.2a.3f.4b.5b.6c, | 1d.2a.3f.4b.5b.6d, | |
| 1d.2a.3f.4b.5b.6e, | 1d.2a.3f.4b.5b.6f, | 1d.2a.3f.4b.5c.6a, | 1d.2a.3f.4b.5c.6b, | |
| 1d.2a.3f.4b.5c.6c, | 1d.2a.3f.4b.5c.6d, | 1d.2a.3f.4b.5c.6e, | 1d.2a.3f.4b.5c.6f, | |
| 1d.2a.3f.4b.5d.6a, | 1d.2a.3f.4b.5d.6b, | 1d.2a.3f.4b.5d.6c, | 1d.2a.3f.4b.5d.6d, | |
| 1d.2a.3f.4b.5d.6e, | 1d.2a.3f.4b.5d.6f, | 1d.2a.3f.4b.5e.6a, | 1d.2a.3f.4b.5e.6b, | |
| 1d.2a.3f.4b.5e.6c, | 1d.2a.3f.4b.5e.6d, | 1d.2a.3f.4b.5e.6e, | 1d.2a.3f.4b.5e.6f, | |
| 1d.2a.3f.4b.5f.6a, | 1d.2a.3f.4b.5f.6b, | 1d.2a.3f.4b.5f.6c, | 1d.2a.3f.4b.5f.6d, | 1d.2a.3f.4b.5f.6e, |
| 1d.2a.3f.4b.5f.6f, | 1d.2a.3f.4c.5a.6a, | 1d.2a.3f.4c.5a.6b, | 1d.2a.3f.4c.5a.6c, | 1d.2a.3f.4c.5a.6d, |
| 1d.2a.3f.4c.5a.6e, | 1d.2a.3f.4c.5a.6f, | 1d.2a.3f.4c.5b.6a, | 1d.2a.3f.4c.5b.6b, | |
| 1d.2a.3f.4c.5b.6c, | 1d.2a.3f.4c.5b.6d, | 1d.2a.3f.4c.5b.6e, | 1d.2a.3f.4c.5b.6f, | |
| 1d.2a.3f.4c.5c.6a, | 1d.2a.3f.4c.5c.6b, | 1d.2a.3f.4c.5c.6c, | 1d.2a.3f.4c.5c.6d, | 1d.2a.3f.4c.5c.6e, |
| 1d.2a.3f.4c.5c.6f, | 1d.2a.3f.4c.5d.6a, | 1d.2a.3f.4c.5d.6b, | 1d.2a.3f.4c.5d.6c, | |
| 1d.2a.3f.4c.5d.6d, | 1d.2a.3f.4c.5d.6e, | 1d.2a.3f.4c.5d.6f, | 1d.2a.3f.4c.5e.6a, | |
| 1d.2a.3f.4c.5e.6b, | 1d.2a.3f.4c.5e.6c, | 1d.2a.3f.4c.5e.6d, | 1d.2a.3f.4c.5e.6e, | 1d.2a.3f.4c.5e.6f, |
| 1d.2a.3f.4c.5f.6a, | 1d.2a.3f.4c.5f.6b, | 1d.2a.3f.4c.5f.6c, | 1d.2a.3f.4c.5f.6d, | 1d.2a.3f.4c.5f.6e, |
| 1d.2a.3f.4c.5f.6f, | 1d.2a.3f.4d.5a.6a, | 1d.2a.3f.4d.5a.6b, | 1d.2a.3f.4d.5a.6c, | |
| 1d.2a.3f.4d.5a.6d, | 1d.2a.3f.4d.5a.6e, | 1d.2a.3f.4d.5a.6f, | 1d.2a.3f.4d.5b.6a, | |
| 1d.2a.3f.4d.5b.6b, | 1d.2a.3f.4d.5b.6c, | 1d.2a.3f.4d.5b.6d, | 1d.2a.3f.4d.5b.6e, | |
| 1d.2a.3f.4d.5b.6f, | 1d.2a.3f.4d.5c.6a, | 1d.2a.3f.4d.5c.6b, | 1d.2a.3f.4d.5c.6c, | |
| 1d.2a.3f.4d.5c.6d, | 1d.2a.3f.4d.5c.6e, | 1d.2a.3f.4d.5c.6f, | 1d.2a.3f.4d.5d.6a, | |
| 1d.2a.3f.4d.5d.6b, | 1d.2a.3f.4d.5d.6c, | 1d.2a.3f.4d.5d.6d, | 1d.2a.3f.4d.5d.6e, | |
| 1d.2a.3f.4d.5d.6f, | 1d.2a.3f.4d.5e.6a, | 1d.2a.3f.4d.5e.6b, | 1d.2a.3f.4d.5e.6c, | |
| 1d.2a.3f.4d.5e.6d, | 1d.2a.3f.4d.5e.6e, | 1d.2a.3f.4d.5e.6f, | 1d.2a.3f.4d.5f.6a, | |
| 1d.2a.3f.4d.5f.6b, | 1d.2a.3f.4d.5f.6c, | 1d.2a.3f.4d.5f.6d, | 1d.2a.3f.4d.5f.6e, | 1d.2a.3f.4d.5f.6f, |
| 1d.2a.3f.4e.5a.6a, | 1d.2a.3f.4e.5a.6b, | 1d.2a.3f.4e.5a.6c, | 1d.2a.3f.4e.5a.6d, | |
| 1d.2a.3f.4e.5a.6e, | 1d.2a.3f.4e.5a.6f, | 1d.2a.3f.4e.5b.6a, | 1d.2a.3f.4e.5b.6b, | |
| 1d.2a.3f.4e.5b.6c, | 1d.2a.3f.4e.5b.6d, | 1d.2a.3f.4e.5b.6e, | 1d.2a.3f.4e.5b.6f, | |
| 1d.2a.3f.4e.5c.6a, | 1d.2a.3f.4e.5c.6b, | 1d.2a.3f.4e.5c.6c, | 1d.2a.3f.4e.5c.6d, | |
| 1d.2a.3f.4e.5c.6e, | 1d.2a.3f.4e.5c.6f, | 1d.2a.3f.4e.5d.6a, | 1d.2a.3f.4e.5d.6b, | |
| 1d.2a.3f.4e.5d.6c, | 1d.2a.3f.4e.5d.6d, | 1d.2a.3f.4e.5d.6e, | 1d.2a.3f.4e.5d.6f, | |
| 1d.2a.3f.4e.5e.6a, | 1d.2a.3f.4e.5e.6b, | 1d.2a.3f.4e.5e.6c, | 1d.2a.3f.4e.5e.6d, | |
| 1d.2a.3f.4e.5e.6e, | 1d.2a.3f.4e.5e.6f, | 1d.2a.3f.4e.5f.6a, | 1d.2a.3f.4e.5f.6b, | 1d.2a.3f.4e.5f.6c, |
| 1d.2a.3f.4e.5f.6d, | 1d.2a.3f.4e.5f.6e, | 1d.2a.3f.4e.5f.6f, | 1d.2a.3f.4f.5a.6a, | 1d.2a.3f.4f.5a.6b, |
| 1d.2a.3f.4f.5a.6c, | 1d.2a.3f.4f.5a.6d, | 1d.2a.3f.4f.5a.6e, | 1d.2a.3f.4f.5a.6f, | 1d.2a.3f.4f.5b.6a, |
| 1d.2a.3f.4f.5b.6b, | 1d.2a.3f.4f.5b.6c, | 1d.2a.3f.4f.5b.6d, | 1d.2a.3f.4f.5b.6e, | 1d.2a.3f.4f.5b.6f, |
| 1d.2a.3f.4f.5c.6a, | 1d.2a.3f.4f.5c.6b, | 1d.2a.3f.4f.5c.6c, | 1d.2a.3f.4f.5c.6d, | 1d.2a.3f.4f.5c.6e, |
| 1d.2a.3f.4f.5c.6f, | 1d.2a.3f.4f.5d.6a, | 1d.2a.3f.4f.5d.6b, | 1d.2a.3f.4f.5d.6c, | 1d.2a.3f.4f.5d.6d, |
| 1d.2a.3f.4f.5d.6e, | 1d.2a.3f.4f.5d.6f, | 1d.2a.3f.4f.5e.6b, | 1d.2a.3f.4f.5e.6c, | |
| 1d.2a.3f.4f.5e.6d, | 1d.2a.3f.4f.5e.6e, | 1d.2a.3f.4f.5e.6f, | 1d.2a.3f.4f.5f.6a, | 1d.2a.3f.4f.5f.6b, |
| 1d.2a.3f.4f.5f.6c, | 1d.2a.3f.4f.5f.6d, | 1d.2a.3f.4f.5f.6e, | 1d.2a.3f.4f.5f.6f, | 1d.2b.3a.4a.5a.6a, |
| 1d.2b.3a.4a.5a.6b, | 1d.2b.3a.4a.5a.6c, | 1d.2b.3a.4a.5a.6d, | 1d.2b.3a.4a.5a.6e, | |
| 1d.2b.3a.4a.5a.6f, | 1d.2b.3a.4a.5b.6a, | 1d.2b.3a.4a.5b.6b, | 1d.2b.3a.4a.5b.6c, | |
| 1d.2b.3a.4a.5b.6d, | 1d.2b.3a.4a.5b.6e, | 1d.2b.3a.4a.5b.6f, | 1d.2b.3a.4a.5c.6a, | |
| 1d.2b.3a.4a.5c.6b, | 1d.2b.3a.4a.5c.6c, | 1d.2b.3a.4a.5c.6d, | 1d.2b.3a.4a.5c.6e, | |
| 1d.2b.3a.4a.5c.6f, | 1d.2b.3a.4a.5d.6a, | 1d.2b.3a.4a.5d.6b, | 1d.2b.3a.4a.5d.6c, | |
| 1d.2b.3a.4a.5d.6d, | 1d.2b.3a.4a.5d.6e, | 1d.2b.3a.4a.5d.6f, | 1d.2b.3a.4a.5e.6a, | |
| 1d.2b.3a.4a.5e.6b, | 1d.2b.3a.4a.5e.6c, | 1d.2b.3a.4a.5e.6d, | 1d.2b.3a.4a.5e.6e, | |
| 1d.2b.3a.4a.5e.6f, | 1d.2b.3a.4a.5f.6a, | 1d.2b.3a.4a.5f.6b, | 1d.2b.3a.4a.5f.6c, | |
| 1d.2b.3a.4a.5f.6d, | 1d.2b.3a.4a.5f.6e, | 1d.2b.3a.4a.5f.6f, | 1d.2b.3a.4b.5a.6a, | |
| 1d.2b.3a.4b.5a.6b, | 1d.2b.3a.4b.5a.6c, | 1d.2b.3a.4b.5a.6d, | 1d.2b.3a.4b.5a.6e, | |
| 1d.2b.3a.4b.5a.6f, | 1d.2b.3a.4b.5b.6a, | 1d.2b.3a.4b.5b.6b, | 1d.2b.3a.4b.5b.6c, | |
| 1d.2b.3a.4b.5b.6d, | 1d.2b.3a.4b.5b.6e, | 1d.2b.3a.4b.5b.6f, | 1d.2b.3a.4b.5c.6a, | |
| 1d.2b.3a.4b.5c.6b, | 1d.2b.3a.4b.5c.6c, | 1d.2b.3a.4b.5c.6d, | 1d.2b.3a.4b.5c.6e, | |
| 1d.2b.3a.4b.5c.6f, | 1d.2b.3a.4b.5d.6a, | 1d.2b.3a.4b.5d.6b, | 1d.2b.3a.4b.5d.6c, | |
| 1d.2b.3a.4b.5d.6d, | 1d.2b.3a.4b.5d.6e, | 1d.2b.3a.4b.5d.6f, | 1d.2b.3a.4b.5e.6a, | |

TABLE 7-continued

List of Compounds of Formula (II)

| | | | | |
|---|---|---|---|---|
| 1d.2b.3a.4b.5e.6b, | 1d.2b.3a.4b.5e.6c, | 1d.2b.3a.4b.5e.6d, | 1d.2b.3a.4b.5e.6e, | |
| 1d.2b.3a.4b.5e.6f, | 1d.2b.3a.4b.5f.6a, | 1d.2b.3a.4b.5f.6b, | 1d.2b.3a.4b.5f.6c, | |
| 1d.2b.3a.4b.5f.6d, | 1d.2b.3a.4b.5f.6e, | 1d.2b.3a.4b.5f.6f, | 1d.2b.3a.4c.5a.6a, | |
| 1d.2b.3a.4c.5a.6b, | 1d.2b.3a.4c.5a.6c, | 1d.2b.3a.4c.5a.6d, | 1d.2b.3a.4c.5a.6e, | |
| 1d.2b.3a.4c.5a.6f, | 1d.2b.3a.4c.5b.6a, | 1d.2b.3a.4c.5b.6b, | 1d.2b.3a.4c.5b.6c, | |
| 1d.2b.3a.4c.5b.6d, | 1d.2b.3a.4c.5b.6e, | 1d.2b.3a.4c.5b.6f, | 1d.2b.3a.4c.5c.6a, | |
| 1d.2b.3a.4c.5c.6b, | 1d.2b.3a.4c.5c.6c, | 1d.2b.3a.4c.5c.6d, | 1d.2b.3a.4c.5c.6e, | |
| 1d.2b.3a.4c.5c.6f, | 1d.2b.3a.4c.5d.6a, | 1d.2b.3a.4c.5d.6b, | 1d.2b.3a.4c.5d.6c, | |
| 1d.2b.3a.4c.5d.6d, | 1d.2b.3a.4c.5d.6e, | 1d.2b.3a.4c.5d.6f, | 1d.2b.3a.4c.5e.6a, | |
| 1d.2b.3a.4c.5e.6b, | 1d.2b.3a.4c.5e.6c, | 1d.2b.3a.4c.5e.6d, | 1d.2b.3a.4c.5e.6e, | |
| 1d.2b.3a.4c.5e.6f, | 1d.2b.3a.4c.5f.6a, | 1d.2b.3a.4c.5f.6b, | 1d.2b.3a.4c.5f.6c, | |
| 1d.2b.3a.4c.5f.6d, | 1d.2b.3a.4c.5f.6e, | 1d.2b.3a.4c.5f.6f, | 1d.2b.3a.4d.5a.6a, | |
| 1d.2b.3a.4d.5a.6b, | 1d.2b.3a.4d.5a.6c, | 1d.2b.3a.4d.5a.6d, | 1d.2b.3a.4d.5a.6e, | |
| 1d.2b.3a.4d.5a.6f, | 1d.2b.3a.4d.5b.6a, | 1d.2b.3a.4d.5b.6b, | 1d.2b.3a.4d.5b.6c, | |
| 1d.2b.3a.4d.5b.6d, | 1d.2b.3a.4d.5b.6e, | 1d.2b.3a.4d.5b.6f, | 1d.2b.3a.4d.5c.6a, | |
| 1d.2b.3a.4d.5c.6b, | 1d.2b.3a.4d.5c.6c, | 1d.2b.3a.4d.5c.6d, | 1d.2b.3a.4d.5c.6e, | |
| 1d.2b.3a.4d.5c.6f, | 1d.2b.3a.4d.5d.6a, | 1d.2b.3a.4d.5d.6b, | 1d.2b.3a.4d.5d.6c, | |
| 1d.2b.3a.4d.5d.6d, | 1d.2b.3a.4d.5d.6e, | 1d.2b.3a.4d.5d.6f, | 1d.2b.3a.4d.5e.6a, | |
| 1d.2b.3a.4d.5e.6b, | 1d.2b.3a.4d.5e.6c, | 1d.2b.3a.4d.5e.6d, | 1d.2b.3a.4d.5e.6e, | |
| 1d.2b.3a.4d.5e.6f, | 1d.2b.3a.4d.5f.6a, | 1d.2b.3a.4d.5f.6b, | 1d.2b.3a.4d.5f.6c, | |
| 1d.2b.3a.4d.5f.6d, | 1d.2b.3a.4d.5f.6e, | 1d.2b.3a.4d.5f.6f, | 1d.2b.3a.4e.5a.6a, | |
| 1d.2b.3a.4e.5a.6b, | 1d.2b.3a.4e.5a.6c, | 1d.2b.3a.4e.5a.6d, | 1d.2b.3a.4e.5a.6e, | |
| 1d.2b.3a.4e.5a.6f, | 1d.2b.3a.4e.5b.6a, | 1d.2b.3a.4e.5b.6b, | 1d.2b.3a.4e.5b.6c, | |
| 1d.2b.3a.4e.5b.6d, | 1d.2b.3a.4e.5b.6e, | 1d.2b.3a.4e.5b.6f, | 1d.2b.3a.4e.5c.6a, | |
| 1d.2b.3a.4e.5c.6b, | 1d.2b.3a.4e.5c.6c, | 1d.2b.3a.4e.5c.6d, | 1d.2b.3a.4e.5c.6e, | |
| 1d.2b.3a.4e.5c.6f, | 1d.2b.3a.4e.5d.6a, | 1d.2b.3a.4e.5d.6b, | 1d.2b.3a.4e.5d.6c, | |
| 1d.2b.3a.4e.5d.6d, | 1d.2b.3a.4e.5d.6e, | 1d.2b.3a.4e.5d.6f, | 1d.2b.3a.4e.5e.6a, | |
| 1d.2b.3a.4e.5e.6b, | 1d.2b.3a.4e.5e.6c, | 1d.2b.3a.4e.5e.6d, | 1d.2b.3a.4e.5e.6e, | |
| 1d.2b.3a.4e.5e.6f, | 1d.2b.3a.4e.5f.6a, | 1d.2b.3a.4e.5f.6b, | 1d.2b.3a.4e.5f.6c, | |
| 1d.2b.3a.4e.5f.6d, | 1d.2b.3a.4e.5f.6e, | 1d.2b.3a.4e.5f.6f, | 1d.2b.3a.4f.5a.6a, | |
| 1d.2b.3a.4f.5a.6b, | 1d.2b.3a.4f.5a.6c, | 1d.2b.3a.4f.5a.6d, | 1d.2b.3a.4f.5a.6e, | |
| 1d.2b.3a.4f.5a.6f, | 1d.2b.3a.4f.5b.6a, | 1d.2b.3a.4f.5b.6b, | 1d.2b.3a.4f.5b.6c, | |
| 1d.2b.3a.4f.5b.6d, | 1d.2b.3a.4f.5b.6e, | 1d.2b.3a.4f.5b.6f, | 1d.2b.3a.4f.5c.6a, | |
| 1d.2b.3a.4f.5c.6b, | 1d.2b.3a.4f.5c.6c, | 1d.2b.3a.4f.5c.6d, | 1d.2b.3a.4f.5c.6e, | |
| 1d.2b.3a.4f.5c.6f, | 1d.2b.3a.4f.5d.6a, | 1d.2b.3a.4f.5d.6b, | 1d.2b.3a.4f.5d.6c, | |
| 1d.2b.3a.4f.5d.6d, | 1d.2b.3a.4f.5d.6e, | 1d.2b.3a.4f.5d.6f, | 1d.2b.3a.4f.5e.6a, | |
| 1d.2b.3a.4f.5e.6b, | 1d.2b.3a.4f.5e.6c, | 1d.2b.3a.4f.5e.6d, | 1d.2b.3a.4f.5e.6e, | |
| 1d.2b.3a.4f.5e.6f, | 1d.2b.3a.4f.5f.6a, | 1d.2b.3a.4f.5f.6b, | 1d.2b.3a.4f.5f.6c, | 1d.2b.3a.4f.5f.6d, |
| 1d.2b.3a.4f.5f.6e, | 1d.2b.3a.4f.5f.6f, | 1d.2b.3b.4a.5a.6a, | 1d.2b.3b.4a.5a.6b, | |
| 1d.2b.3b.4a.5a.6c, | 1d.2b.3b.4a.5a.6d, | 1d.2b.3b.4a.5a.6e, | 1d.2b.3b.4a.5a.6f, | |
| 1d.2b.3b.4a.5b.6a, | 1d.2b.3b.4a.5b.6b, | 1d.2b.3b.4a.5b.6c, | 1d.2b.3b.4a.5b.6d, | |
| 1d.2b.3b.4a.5b.6e, | 1d.2b.3b.4a.5b.6f, | 1d.2b.3b.4a.5c.6a, | 1d.2b.3b.4a.5c.6b, | |
| 1d.2b.3b.4a.5c.6c, | 1d.2b.3b.4a.5c.6d, | 1d.2b.3b.4a.5c.6e, | 1d.2b.3b.4a.5c.6f, | |
| 1d.2b.3b.4a.5d.6a, | 1d.2b.3b.4a.5d.6b, | 1d.2b.3b.4a.5d.6c, | 1d.2b.3b.4a.5d.6d, | |
| 1d.2b.3b.4a.5d.6e, | 1d.2b.3b.4a.5d.6f, | 1d.2b.3b.4a.5e.6a, | 1d.2b.3b.4a.5e.6b, | |
| 1d.2b.3b.4a.5e.6c, | 1d.2b.3b.4a.5e.6d, | 1d.2b.3b.4a.5e.6e, | 1d.2b.3b.4a.5e.6f, | |
| 1d.2b.3b.4a.5f.6a, | 1d.2b.3b.4a.5f.6b, | 1d.2b.3b.4a.5f.6c, | 1d.2b.3b.4a.5f.6d, | |
| 1d.2b.3b.4a.5f.6e, | 1d.2b.3b.4a.5f.6f, | 1d.2b.3b.4b.5a.6a, | 1d.2b.3b.4b.5a.6b, | |
| 1d.2b.3b.4b.5a.6c, | 1d.2b.3b.4b.5a.6d, | 1d.2b.3b.4b.5a.6e, | 1d.2b.3b.4b.5a.6f, | |
| 1d.2b.3b.4b.5b.6a, | 1d.2b.3b.4b.5b.6b, | 1d.2b.3b.4b.5b.6c, | 1d.2b.3b.4b.5b.6d, | |
| 1d.2b.3b.4b.5b.6e, | 1d.2b.3b.4b.5b.6f, | 1d.2b.3b.4b.5c.6a, | 1d.2b.3b.4b.5c.6b, | |
| 1d.2b.3b.4b.5c.6c, | 1d.2b.3b.4b.5c.6d, | 1d.2b.3b.4b.5c.6e, | 1d.2b.3b.4b.5c.6f, | |
| 1d.2b.3b.4b.5d.6a, | 1d.2b.3b.4b.5d.6b, | 1d.2b.3b.4b.5d.6c, | 1d.2b.3b.4b.5d.6d, | |
| 1d.2b.3b.4b.5d.6e, | 1d.2b.3b.4b.5d.6f, | 1d.2b.3b.4b.5e.6a, | 1d.2b.3b.4b.5e.6b, | |
| 1d.2b.3b.4b.5e.6c, | 1d.2b.3b.4b.5e.6d, | 1d.2b.3b.4b.5e.6e, | 1d.2b.3b.4b.5e.6f, | |
| 1d.2b.3b.4b.5f.6a, | 1d.2b.3b.4b.5f.6b, | 1d.2b.3b.4b.5f.6c, | 1d.2b.3b.4b.5f.6d, | |
| 1d.2b.3b.4b.5f.6e, | 1d.2b.3b.4b.5f.6f, | 1d.2b.3b.4c.5a.6a, | 1d.2b.3b.4c.5a.6b, | |
| 1d.2b.3b.4c.5a.6c, | 1d.2b.3b.4c.5a.6d, | 1d.2b.3b.4c.5a.6e, | 1d.2b.3b.4c.5a.6f, | |
| 1d.2b.3b.4c.5b.6a, | 1d.2b.3b.4c.5b.6b, | 1d.2b.3b.4c.5b.6c, | 1d.2b.3b.4c.5b.6d, | |
| 1d.2b.3b.4c.5b.6e, | 1d.2b.3b.4c.5b.6f, | 1d.2b.3b.4c.5c.6a, | 1d.2b.3b.4c.5c.6b, | |
| 1d.2b.3b.4c.5c.6c, | 1d.2b.3b.4c.5c.6d, | 1d.2b.3b.4c.5c.6e, | 1d.2b.3b.4c.5c.6f, | |
| 1d.2b.3b.4c.5d.6a, | 1d.2b.3b.4c.5d.6b, | 1d.2b.3b.4c.5d.6c, | 1d.2b.3b.4c.5d.6d, | |
| 1d.2b.3b.4c.5d.6e, | 1d.2b.3b.4c.5d.6f, | 1d.2b.3b.4c.5e.6a, | 1d.2b.3b.4c.5e.6b, | |
| 1d.2b.3b.4c.5e.6c, | 1d.2b.3b.4c.5e.6d, | 1d.2b.3b.4c.5e.6e, | 1d.2b.3b.4c.5e.6f, | |
| 1d.2b.3b.4c.5f.6a, | 1d.2b.3b.4c.5f.6b, | 1d.2b.3b.4c.5f.6c, | 1d.2b.3b.4c.5f.6d, | |
| 1d.2b.3b.4c.5f.6e, | 1d.2b.3b.4c.5f.6f, | 1d.2b.3b.4d.5a.6a, | 1d.2b.3b.4d.5a.6b, | |
| 1d.2b.3b.4d.5a.6c, | 1d.2b.3b.4d.5a.6d, | 1d.2b.3b.4d.5a.6e, | 1d.2b.3b.4d.5a.6f, | |
| 1d.2b.3b.4d.5b.6a, | 1d.2b.3b.4d.5b.6b, | 1d.2b.3b.4d.5b.6c, | 1d.2b.3b.4d.5b.6d, | |
| 1d.2b.3b.4d.5b.6e, | 1d.2b.3b.4d.5b.6f, | 1d.2b.3b.4d.5c.6a, | 1d.2b.3b.4d.5c.6b, | |
| 1d.2b.3b.4d.5c.6c, | 1d.2b.3b.4d.5c.6d, | 1d.2b.3b.4d.5c.6e, | 1d.2b.3b.4d.5c.6f, | |
| 1d.2b.3b.4d.5d.6a, | 1d.2b.3b.4d.5d.6b, | 1d.2b.3b.4d.5d.6c, | 1d.2b.3b.4d.5d.6d, | |
| 1d.2b.3b.4d.5d.6e, | 1d.2b.3b.4d.5d.6f, | 1d.2b.3b.4d.5e.6a, | 1d.2b.3b.4d.5e.6b, | |
| 1d.2b.3b.4d.5e.6c, | 1d.2b.3b.4d.5e.6d, | 1d.2b.3b.4d.5e.6e, | 1d.2b.3b.4d.5e.6f, | |
| 1d.2b.3b.4d.5f.6a, | 1d.2b.3b.4d.5f.6b, | 1d.2b.3b.4d.5f.6c, | 1d.2b.3b.4d.5f.6d, | |
| 1d.2b.3b.4d.5f.6e, | 1d.2b.3b.4d.5f.6f, | 1d.2b.3b.4e.5a.6a, | 1d.2b.3b.4e.5a.6b, | |
| 1d.2b.3b.4e.5a.6c, | 1d.2b.3b.4e.5a.6d, | 1d.2b.3b.4e.5a.6e, | 1d.2b.3b.4e.5a.6f, | |
| 1d.2b.3b.4e.5b.6a, | 1d.2b.3b.4e.5b.6b, | 1d.2b.3b.4e.5b.6c, | 1d.2b.3b.4e.5b.6d, | |
| 1d.2b.3b.4e.5b.6e, | 1d.2b.3b.4e.5b.6f, | 1d.2b.3b.4e.5c.6a, | 1d.2b.3b.4e.5c.6b, | |

TABLE 7-continued

List of Compounds of Formula (II)

| | | | | |
|---|---|---|---|---|
| 1d.2b.3b.4e.5c.6c, | 1d.2b.3b.4e.5c.6d, | 1d.2b.3b.4e.5c.6e, | 1d.2b.3b.4e.5c.6f, | |
| 1d.2b.3b.4e.5d.6a, | 1d.2b.3b.4e.5d.6b, | 1d.2b.3b.4e.5d.6c, | 1d.2b.3b.4e.5d.6d, | |
| 1d.2b.3b.4e.5d.6e, | 1d.2b.3b.4e.5d.6f, | 1d.2b.3b.4e.5e.6a, | 1d.2b.3b.4e.5e.6b, | |
| 1d.2b.3b.4e.5e.6c, | 1d.2b.3b.4e.5e.6d, | 1d.2b.3b.4e.5e.6e, | 1d.2b.3b.4e.5e.6f, | |
| 1d.2b.3b.4e.5f.6a, | 1d.2b.3b.4e.5f.6b, | 1d.2b.3b.4e.5f.6c, | 1d.2b.3b.4e.5f.6d, | |
| 1d.2b.3b.4e.5f.6e, | 1d.2b.3b.4e.5f.6f, | 1d.2b.3b.4f.5a.6a, | 1d.2b.3b.4f.5a.6b, | |
| 1d.2b.3b.4f.5a.6c, | 1d.2b.3b.4f.5a.6d, | 1d.2b.3b.4f.5a.6e, | 1d.2b.3b.4f.5a.6f, | |
| 1d.2b.3b.4f.5b.6a, | 1d.2b.3b.4f.5b.6b, | 1d.2b.3b.4f.5b.6c, | 1d.2b.3b.4f.5b.6d, | |
| 1d.2b.3b.4f.5b.6e, | 1d.2b.3b.4f.5b.6f, | 1d.2b.3b.4f.5c.6a, | 1d.2b.3b.4f.5c.6b, | |
| 1d.2b.3b.4f.5c.6c, | 1d.2b.3b.4f.5c.6d, | 1d.2b.3b.4f.5c.6e, | 1d.2b.3b.4f.5c.6f, | |
| 1d.2b.3b.4f.5d.6a, | 1d.2b.3b.4f.5d.6b, | 1d.2b.3b.4f.5d.6c, | 1d.2b.3b.4f.5d.6d, | |
| 1d.2b.3b.4f.5d.6e, | 1d.2b.3b.4f.5d.6f, | 1d.2b.3b.4f.5e.6a, | 1d.2b.3b.4f.5e.6b, | |
| 1d.2b.3b.4f.5e.6c, | 1d.2b.3b.4f.5e.6d, | 1d.2b.3b.4f.5e.6e, | 1d.2b.3b.4f.5e.6f, | |
| 1d.2b.3b.4f.5f.6a, | 1d.2b.3b.4f.5f.6b, | 1d.2b.3b.4f.5f.6c, | 1d.2b.3b.4f.5f.6d, | |
| 1d.2b.3b.4f.5f.6e, | 1d.2b.3b.4f.5f.6f, | 1d.2b.3c.4a.5a.6a, | 1d.2b.3c.4a.5a.6b, | |
| 1d.2b.3c.4a.5a.6c, | 1d.2b.3c.4a.5a.6d, | 1d.2b.3c.4a.5a.6e, | 1d.2b.3c.4a.5a.6f, | |
| 1d.2b.3c.4a.5b.6a, | 1d.2b.3c.4a.5b.6b, | 1d.2b.3c.4a.5b.6c, | 1d.2b.3c.4a.5b.6d, | |
| 1d.2b.3c.4a.5b.6e, | 1d.2b.3c.4a.5b.6f, | 1d.2b.3c.4a.5c.6a, | 1d.2b.3c.4a.5c.6b, | |
| 1d.2b.3c.4a.5c.6c, | 1d.2b.3c.4a.5c.6d, | 1d.2b.3c.4a.5c.6e, | 1d.2b.3c.4a.5c.6f, | |
| 1d.2b.3c.4a.5d.6a, | 1d.2b.3c.4a.5d.6b, | 1d.2b.3c.4a.5d.6c, | 1d.2b.3c.4a.5d.6d, | |
| 1d.2b.3c.4a.5d.6e, | 1d.2b.3c.4a.5d.6f, | 1d.2b.3c.4a.5e.6a, | 1d.2b.3c.4a.5e.6b, | |
| 1d.2b.3c.4a.5e.6c, | 1d.2b.3c.4a.5e.6d, | 1d.2b.3c.4a.5e.6e, | 1d.2b.3c.4a.5e.6f, | |
| 1d.2b.3c.4a.5f.6a, | 1d.2b.3c.4a.5f.6b, | 1d.2b.3c.4a.5f.6c, | 1d.2b.3c.4a.5f.6d, | |
| 1d.2b.3c.4a.5f.6e, | 1d.2b.3c.4a.5f.6f, | 1d.2b.3c.4b.5a.6a, | 1d.2b.3c.4b.5a.6b, | |
| 1d.2b.3c.4b.5a.6c, | 1d.2b.3c.4b.5a.6d, | 1d.2b.3c.4b.5a.6e, | 1d.2b.3c.4b.5a.6f, | |
| 1d.2b.3c.4b.5b.6a, | 1d.2b.3c.4b.5b.6b, | 1d.2b.3c.4b.5b.6c, | 1d.2b.3c.4b.5b.6d, | |
| 1d.2b.3c.4b.5b.6e, | 1d.2b.3c.4b.5b.6f, | 1d.2b.3c.4b.5c.6a, | 1d.2b.3c.4b.5c.6b, | |
| 1d.2b.3c.4b.5c.6c, | 1d.2b.3c.4b.5c.6d, | 1d.2b.3c.4b.5c.6e, | 1d.2b.3c.4b.5c.6f, | |
| 1d.2b.3c.4b.5d.6a, | 1d.2b.3c.4b.5d.6b, | 1d.2b.3c.4b.5d.6c, | 1d.2b.3c.4b.5d.6d, | |
| 1d.2b.3c.4b.5d.6e, | 1d.2b.3c.4b.5d.6f, | 1d.2b.3c.4b.5e.6a, | 1d.2b.3c.4b.5e.6b, | |
| 1d.2b.3c.4b.5e.6c, | 1d.2b.3c.4b.5e.6d, | 1d.2b.3c.4b.5e.6e, | 1d.2b.3c.4b.5e.6f, | |
| 1d.2b.3c.4b.5f.6a, | 1d.2b.3c.4b.5f.6b, | 1d.2b.3c.4b.5f.6c, | 1d.2b.3c.4b.5f.6d, | |
| 1d.2b.3c.4b.5f.6e, | 1d.2b.3c.4b.5f.6f, | 1d.2b.3c.4c.5a.6a, | 1d.2b.3c.4c.5a.6b, | |
| 1d.2b.3c.4c.5a.6c, | 1d.2b.3c.4c.5a.6d, | 1d.2b.3c.4c.5a.6e, | 1d.2b.3c.4c.5a.6f, | |
| 1d.2b.3c.4c.5b.6a, | 1d.2b.3c.4c.5b.6b, | 1d.2b.3c.4c.5b.6c, | 1d.2b.3c.4c.5b.6d, | |
| 1d.2b.3c.4c.5b.6e, | 1d.2b.3c.4c.5b.6f, | 1d.2b.3c.4c.5c.6a, | 1d.2b.3c.4c.5c.6b, | |
| 1d.2b.3c.4c.5c.6c, | 1d.2b.3c.4c.5c.6d, | 1d.2b.3c.4c.5c.6e, | 1d.2b.3c.4c.5c.6f, | |
| 1d.2b.3c.4c.5d.6a, | 1d.2b.3c.4c.5d.6b, | 1d.2b.3c.4c.5d.6c, | 1d.2b.3c.4c.5d.6d, | |
| 1d.2b.3c.4c.5d.6e, | 1d.2b.3c.4c.5d.6f, | 1d.2b.3c.4c.5e.6a, | 1d.2b.3c.4c.5e.6b, | |
| 1d.2b.3c.4c.5e.6c, | 1d.2b.3c.4c.5e.6d, | 1d.2b.3c.4c.5e.6e, | 1d.2b.3c.4c.5e.6f, | |
| 1d.2b.3c.4c.5f.6a, | 1d.2b.3c.4c.5f.6b, | 1d.2b.3c.4c.5f.6c, | 1d.2b.3c.4c.5f.6d, | |
| 1d.2b.3c.4c.5f.6e, | 1d.2b.3c.4c.5f.6f, | 1d.2b.3c.4d.5a.6a, | 1d.2b.3c.4d.5a.6b, | |
| 1d.2b.3c.4d.5a.6c, | 1d.2b.3c.4d.5a.6d, | 1d.2b.3c.4d.5a.6e, | 1d.2b.3c.4d.5a.6f, | |
| 1d.2b.3c.4d.5b.6a, | 1d.2b.3c.4d.5b.6b, | 1d.2b.3c.4d.5b.6c, | 1d.2b.3c.4d.5b.6d, | |
| 1d.2b.3c.4d.5b.6e, | 1d.2b.3c.4d.5b.6f, | 1d.2b.3c.4d.5c.6a, | 1d.2b.3c.4d.5c.6b, | |
| 1d.2b.3c.4d.5c.6c, | 1d.2b.3c.4d.5c.6d, | 1d.2b.3c.4d.5c.6e, | 1d.2b.3c.4d.5c.6f, | |
| 1d.2b.3c.4d.5d.6a, | 1d.2b.3c.4d.5d.6b, | 1d.2b.3c.4d.5d.6c, | 1d.2b.3c.4d.5d.6d, | |
| 1d.2b.3c.4d.5d.6e, | 1d.2b.3c.4d.5d.6f, | 1d.2b.3c.4d.5e.6a, | 1d.2b.3c.4d.5e.6b, | |
| 1d.2b.3c.4d.5e.6c, | 1d.2b.3c.4d.5e.6d, | 1d.2b.3c.4d.5e.6e, | 1d.2b.3c.4d.5e.6f, | |
| 1d.2b.3c.4d.5f.6a, | 1d.2b.3c.4d.5f.6b, | 1d.2b.3c.4d.5f.6c, | 1d.2b.3c.4d.5f.6d, | |
| 1d.2b.3c.4d.5f.6e, | 1d.2b.3c.4d.5f.6f, | 1d.2b.3c.4e.5a.6a, | 1d.2b.3c.4e.5a.6b, | |
| 1d.2b.3c.4e.5a.6c, | 1d.2b.3c.4e.5a.6d, | 1d.2b.3c.4e.5a.6e, | 1d.2b.3c.4e.5a.6f, | |
| 1d.2b.3c.4e.5b.6a, | 1d.2b.3c.4e.5b.6b, | 1d.2b.3c.4e.5b.6c, | 1d.2b.3c.4e.5b.6d, | |
| 1d.2b.3c.4e.5b.6e, | 1d.2b.3c.4e.5b.6f, | 1d.2b.3c.4e.5c.6a, | 1d.2b.3c.4e.5c.6b, | |
| 1d.2b.3c.4e.5c.6c, | 1d.2b.3c.4e.5c.6d, | 1d.2b.3c.4e.5c.6e, | 1d.2b.3c.4e.5c.6f, | |
| 1d.2b.3c.4e.5d.6a, | 1d.2b.3c.4e.5d.6b, | 1d.2b.3c.4e.5d.6c, | 1d.2b.3c.4e.5d.6d, | |
| 1d.2b.3c.4e.5d.6e, | 1d.2b.3c.4e.5d.6f, | 1d.2b.3c.4e.5e.6a, | 1d.2b.3c.4e.5e.6b, | |
| 1d.2b.3c.4e.5e.6c, | 1d.2b.3c.4e.5e.6d, | 1d.2b.3c.4e.5e.6e, | 1d.2b.3c.4e.5e.6f, | |
| 1d.2b.3c.4e.5f.6a, | 1d.2b.3c.4e.5f.6b, | 1d.2b.3c.4e.5f.6c, | 1d.2b.3c.4e.5f.6d, | |
| 1d.2b.3c.4e.5f.6e, | 1d.2b.3c.4e.5f.6f, | 1d.2b.3c.4f.5a.6a, | 1d.2b.3c.4f.5a.6b, | |
| 1d.2b.3c.4f.5a.6c, | 1d.2b.3c.4f.5a.6d, | 1d.2b.3c.4f.5a.6e, | 1d.2b.3c.4f.5a.6f, | |
| 1d.2b.3c.4f.5b.6a, | 1d.2b.3c.4f.5b.6b, | 1d.2b.3c.4f.5b.6c, | 1d.2b.3c.4f.5b.6d, | |
| 1d.2b.3c.4f.5b.6e, | 1d.2b.3c.4f.5b.6f, | 1d.2b.3c.4f.5c.6a, | 1d.2b.3c.4f.5c.6b, | |
| 1d.2b.3c.4f.5c.6c, | 1d.2b.3c.4f.5c.6d, | 1d.2b.3c.4f.5c.6e, | 1d.2b.3c.4f.5c.6f, | |
| 1d.2b.3c.4f.5d.6a, | 1d.2b.3c.4f.5d.6b, | 1d.2b.3c.4f.5d.6c, | 1d.2b.3c.4f.5d.6d, | |
| 1d.2b.3c.4f.5d.6e, | 1d.2b.3c.4f.5d.6f, | 1d.2b.3c.4f.5e.6a, | 1d.2b.3c.4f.5e.6b, | |
| 1d.2b.3c.4f.5e.6c, | 1d.2b.3c.4f.5e.6d, | 1d.2b.3c.4f.5e.6e, | 1d.2b.3c.4f.5e.6f, | 1d.2b.3c.4f.5f.6a, |
| 1d.2b.3c.4f.5f.6b, | 1d.2b.3c.4f.5f.6c, | 1d.2b.3c.4f.5f.6d, | 1d.2b.3c.4f.5f.6e, | 1d.2b.3c.4f.5f.6f, |
| 1d.2b.3d.4a.5a.6a, | 1d.2b.3d.4a.5a.6b, | 1d.2b.3d.4a.5a.6c, | 1d.2b.3d.4a.5a.6d, | |
| 1d.2b.3d.4a.5a.6e, | 1d.2b.3d.4a.5a.6f, | 1d.2b.3d.4a.5b.6a, | 1d.2b.3d.4a.5b.6b, | |
| 1d.2b.3d.4a.5b.6c, | 1d.2b.3d.4a.5b.6d, | 1d.2b.3d.4a.5b.6e, | 1d.2b.3d.4a.5b.6f, | |
| 1d.2b.3d.4a.5c.6a, | 1d.2b.3d.4a.5c.6b, | 1d.2b.3d.4a.5c.6c, | 1d.2b.3d.4a.5c.6d, | |
| 1d.2b.3d.4a.5c.6e, | 1d.2b.3d.4a.5c.6f, | 1d.2b.3d.4a.5d.6a, | 1d.2b.3d.4a.5d.6b, | |
| 1d.2b.3d.4a.5d.6c, | 1d.2b.3d.4a.5d.6d, | 1d.2b.3d.4a.5d.6e, | 1d.2b.3d.4a.5d.6f, | |
| 1d.2b.3d.4a.5e.6a, | 1d.2b.3d.4a.5e.6b, | 1d.2b.3d.4a.5e.6c, | 1d.2b.3d.4a.5e.6d, | |
| 1d.2b.3d.4a.5e.6e, | 1d.2b.3d.4a.5e.6f, | 1d.2b.3d.4a.5f.6a, | 1d.2b.3d.4a.5f.6b, | |
| 1d.2b.3d.4a.5f.6c, | 1d.2b.3d.4a.5f.6d, | 1d.2b.3d.4a.5f.6e, | 1d.2b.3d.4a.5f.6f, | |
| 1d.2b.3d.4b.5a.6a, | 1d.2b.3d.4b.5a.6b, | 1d.2b.3d.4b.5a.6c, | 1d.2b.3d.4b.5a.6d, | |

TABLE 7-continued

List of Compounds of Formula (II)

| | | | |
|---|---|---|---|
| 1d.2b.3d.4b.5a.6e, | 1d.2b.3d.4b.5a.6f, | 1d.2b.3d.4b.5b.6a, | 1d.2b.3d.4b.5b.6b, |
| 1d.2b.3d.4b.5b.6c, | 1d.2b.3d.4b.5b.6d, | 1d.2b.3d.4b.5b.6e, | 1d.2b.3d.4b.5b.6f, |
| 1d.2b.3d.4b.5c.6a, | 1d.2b.3d.4b.5c.6b, | 1d.2b.3d.4b.5c.6c, | 1d.2b.3d.4b.5c.6d, |
| 1d.2b.3d.4b.5c.6e, | 1d.2b.3d.4b.5c.6f, | 1d.2b.3d.4b.5d.6a, | 1d.2b.3d.4b.5d.6b, |
| 1d.2b.3d.4b.5d.6c, | 1d.2b.3d.4b.5d.6d, | 1d.2b.3d.4b.5d.6e, | 1d.2b.3d.4b.5d.6f, |
| 1d.2b.3d.4b.5e.6a, | 1d.2b.3d.4b.5e.6b, | 1d.2b.3d.4b.5e.6c, | 1d.2b.3d.4b.5e.6d, |
| 1d.2b.3d.4b.5e.6e, | 1d.2b.3d.4b.5e.6f, | 1d.2b.3d.4b.5f.6a, | 1d.2b.3d.4b.5f.6b, |
| 1d.2b.3d.4b.5f.6c, | 1d.2b.3d.4b.5f.6d, | 1d.2b.3d.4b.5f.6e, | 1d.2b.3d.4b.5f.6f, |
| 1d.2b.3d.4c.5a.6a, | 1d.2b.3d.4c.5a.6b, | 1d.2b.3d.4c.5a.6c, | 1d.2b.3d.4c.5a.6d, |
| 1d.2b.3d.4c.5a.6e, | 1d.2b.3d.4c.5a.6f, | 1d.2b.3d.4c.5b.6a, | 1d.2b.3d.4c.5b.6b, |
| 1d.2b.3d.4c.5b.6c, | 1d.2b.3d.4c.5b.6d, | 1d.2b.3d.4c.5b.6e, | 1d.2b.3d.4c.5b.6f, |
| 1d.2b.3d.4c.5c.6a, | 1d.2b.3d.4c.5c.6b, | 1d.2b.3d.4c.5c.6c, | 1d.2b.3d.4c.5c.6d, |
| 1d.2b.3d.4c.5c.6e, | 1d.2b.3d.4c.5c.6f, | 1d.2b.3d.4c.5d.6a, | 1d.2b.3d.4c.5d.6b, |
| 1d.2b.3d.4c.5d.6c, | 1d.2b.3d.4c.5d.6d, | 1d.2b.3d.4c.5d.6e, | 1d.2b.3d.4c.5d.6f, |
| 1d.2b.3d.4c.5e.6a, | 1d.2b.3d.4c.5e.6b, | 1d.2b.3d.4c.5e.6c, | 1d.2b.3d.4c.5e.6d, |
| 1d.2b.3d.4c.5e.6e, | 1d.2b.3d.4c.5e.6f, | 1d.2b.3d.4c.5f.6a, | 1d.2b.3d.4c.5f.6b, |
| 1d.2b.3d.4c.5f.6c, | 1d.2b.3d.4c.5f.6d, | 1d.2b.3d.4c.5f.6e, | 1d.2b.3d.4c.5f.6f, |
| 1d.2b.3d.4d.5a.6a, | 1d.2b.3d.4d.5a.6b, | 1d.2b.3d.4d.5a.6c, | 1d.2b.3d.4d.5a.6d, |
| 1d.2b.3d.4d.5a.6e, | 1d.2b.3d.4d.5a.6f, | 1d.2b.3d.4d.5b.6a, | 1d.2b.3d.4d.5b.6b, |
| 1d.2b.3d.4d.5b.6c, | 1d.2b.3d.4d.5b.6d, | 1d.2b.3d.4d.5b.6e, | 1d.2b.3d.4d.5b.6f, |
| 1d.2b.3d.4d.5c.6a, | 1d.2b.3d.4d.5c.6b, | 1d.2b.3d.4d.5c.6c, | 1d.2b.3d.4d.5c.6d, |
| 1d.2b.3d.4d.5c.6e, | 1d.2b.3d.4d.5c.6f, | 1d.2b.3d.4d.5d.6a, | 1d.2b.3d.4d.5d.6b, |
| 1d.2b.3d.4d.5d.6c, | 1d.2b.3d.4d.5d.6d, | 1d.2b.3d.4d.5d.6e, | 1d.2b.3d.4d.5d.6f, |
| 1d.2b.3d.4d.5e.6a, | 1d.2b.3d.4d.5e.6b, | 1d.2b.3d.4d.5e.6c, | 1d.2b.3d.4d.5e.6d, |
| 1d.2b.3d.4d.5e.6e, | 1d.2b.3d.4d.5e.6f, | 1d.2b.3d.4d.5f.6a, | 1d.2b.3d.4d.5f.6b, |
| 1d.2b.3d.4d.5f.6c, | 1d.2b.3d.4d.5f.6d, | 1d.2b.3d.4d.5f.6e, | 1d.2b.3d.4d.5f.6f, |
| 1d.2b.3d.4e.5a.6a, | 1d.2b.3d.4e.5a.6b, | 1d.2b.3d.4e.5a.6c, | 1d.2b.3d.4e.5a.6d, |
| 1d.2b.3d.4e.5a.6e, | 1d.2b.3d.4e.5a.6f, | 1d.2b.3d.4e.5b.6a, | 1d.2b.3d.4e.5b.6b, |
| 1d.2b.3d.4e.5b.6c, | 1d.2b.3d.4e.5b.6d, | 1d.2b.3d.4e.5b.6e, | 1d.2b.3d.4e.5b.6f, |
| 1d.2b.3d.4e.5c.6a, | 1d.2b.3d.4e.5c.6b, | 1d.2b.3d.4e.5c.6c, | 1d.2b.3d.4e.5c.6d, |
| 1d.2b.3d.4e.5c.6e, | 1d.2b.3d.4e.5c.6f, | 1d.2b.3d.4e.5d.6a, | 1d.2b.3d.4e.5d.6b, |
| 1d.2b.3d.4e.5d.6c, | 1d.2b.3d.4e.5d.6d, | 1d.2b.3d.4e.5d.6e, | 1d.2b.3d.4e.5d.6f, |
| 1d.2b.3d.4e.5e.6a, | 1d.2b.3d.4e.5e.6b, | 1d.2b.3d.4e.5e.6c, | 1d.2b.3d.4e.5e.6d, |
| 1d.2b.3d.4e.5e.6e, | 1d.2b.3d.4e.5e.6f, | 1d.2b.3d.4e.5f.6a, | 1d.2b.3d.4e.5f.6b, |
| 1d.2b.3d.4e.5f.6c, | 1d.2b.3d.4e.5f.6d, | 1d.2b.3d.4e.5f.6e, | 1d.2b.3d.4e.5f.6f, |
| 1d.2b.3d.4f.5a.6a, | 1d.2b.3d.4f.5a.6b, | 1d.2b.3d.4f.5a.6c, | 1d.2b.3d.4f.5a.6d, |
| 1d.2b.3d.4f.5a.6e, | 1d.2b.3d.4f.5a.6f, | 1d.2b.3d.4f.5b.6a, | 1d.2b.3d.4f.5b.6b, |
| 1d.2b.3d.4f.5b.6c, | 1d.2b.3d.4f.5b.6d, | 1d.2b.3d.4f.5b.6e, | 1d.2b.3d.4f.5b.6f, |
| 1d.2b.3d.4f.5c.6a, | 1d.2b.3d.4f.5c.6b, | 1d.2b.3d.4f.5c.6c, | 1d.2b.3d.4f.5c.6d, |
| 1d.2b.3d.4f.5c.6e, | 1d.2b.3d.4f.5c.6f, | 1d.2b.3d.4f.5d.6a, | 1d.2b.3d.4f.5d.6b, |
| 1d.2b.3d.4f.5d.6c, | 1d.2b.3d.4f.5d.6d, | 1d.2b.3d.4f.5d.6e, | 1d.2b.3d.4f.5d.6f, |
| 1d.2b.3d.4f.5e.6a, | 1d.2b.3d.4f.5e.6b, | 1d.2b.3d.4f.5e.6c, | 1d.2b.3d.4f.5e.6d, |
| 1d.2b.3d.4f.5e.6e, | 1d.2b.3d.4f.5e.6f, | 1d.2b.3d.4f.5f.6a, | 1d.2b.3d.4f.5f.6b, |
| 1d.2b.3d.4f.5f.6c, | 1d.2b.3d.4f.5f.6d, | 1d.2b.3d.4f.5f.6e, | 1d.2b.3d.4f.5f.6f, |
| 1d.2b.3e.4a.5a.6a, | 1d.2b.3e.4a.5a.6b, | 1d.2b.3e.4a.5a.6c, | 1d.2b.3e.4a.5a.6d, |
| 1d.2b.3e.4a.5a.6e, | 1d.2b.3e.4a.5a.6f, | 1d.2b.3e.4a.5b.6a, | 1d.2b.3e.4a.5b.6b, |
| 1d.2b.3e.4a.5b.6c, | 1d.2b.3e.4a.5b.6d, | 1d.2b.3e.4a.5b.6e, | 1d.2b.3e.4a.5b.6f, |
| 1d.2b.3e.4a.5c.6a, | 1d.2b.3e.4a.5c.6b, | 1d.2b.3e.4a.5c.6c, | 1d.2b.3e.4a.5c.6d, |
| 1d.2b.3e.4a.5c.6e, | 1d.2b.3e.4a.5c.6f, | 1d.2b.3e.4a.5d.6a, | 1d.2b.3e.4a.5d.6b, |
| 1d.2b.3e.4a.5d.6c, | 1d.2b.3e.4a.5d.6d, | 1d.2b.3e.4a.5d.6e, | 1d.2b.3e.4a.5d.6f, |
| 1d.2b.3e.4a.5e.6a, | 1d.2b.3e.4a.5e.6b, | 1d.2b.3e.4a.5e.6c, | 1d.2b.3e.4a.5e.6d, |
| 1d.2b.3e.4a.5e.6e, | 1d.2b.3e.4a.5e.6f, | 1d.2b.3e.4a.5f.6a, | 1d.2b.3e.4a.5f.6b, |
| 1d.2b.3e.4a.5f.6c, | 1d.2b.3e.4a.5f.6d, | 1d.2b.3e.4a.5f.6e, | 1d.2b.3e.4a.5f.6f, |
| 1d.2b.3e.4b.5a.6a, | 1d.2b.3e.4b.5a.6b, | 1d.2b.3e.4b.5a.6c, | 1d.2b.3e.4b.5a.6d, |
| 1d.2b.3e.4b.5a.6e, | 1d.2b.3e.4b.5a.6f, | 1d.2b.3e.4b.5b.6a, | 1d.2b.3e.4b.5b.6b, |
| 1d.2b.3e.4b.5b.6c, | 1d.2b.3e.4b.5b.6d, | 1d.2b.3e.4b.5b.6e, | 1d.2b.3e.4b.5b.6f, |
| 1d.2b.3e.4b.5c.6a, | 1d.2b.3e.4b.5c.6b, | 1d.2b.3e.4b.5c.6c, | 1d.2b.3e.4b.5c.6d, |
| 1d.2b.3e.4b.5c.6e, | 1d.2b.3e.4b.5c.6f, | 1d.2b.3e.4b.5d.6a, | 1d.2b.3e.4b.5d.6b, |
| 1d.2b.3e.4b.5d.6c, | 1d.2b.3e.4b.5d.6d, | 1d.2b.3e.4b.5d.6e, | 1d.2b.3e.4b.5d.6f, |
| 1d.2b.3e.4b.5e.6a, | 1d.2b.3e.4b.5e.6b, | 1d.2b.3e.4b.5e.6c, | 1d.2b.3e.4b.5e.6d, |
| 1d.2b.3e.4b.5e.6e, | 1d.2b.3e.4b.5e.6f, | 1d.2b.3e.4b.5f.6a, | 1d.2b.3e.4b.5f.6b, |
| 1d.2b.3e.4b.5f.6c, | 1d.2b.3e.4b.5f.6d, | 1d.2b.3e.4b.5f.6e, | 1d.2b.3e.4b.5f.6f, |
| 1d.2b.3e.4c.5a.6a, | 1d.2b.3e.4c.5a.6b, | 1d.2b.3e.4c.5a.6c, | 1d.2b.3e.4c.5a.6d, |
| 1d.2b.3e.4c.5a.6e, | 1d.2b.3e.4c.5a.6f, | 1d.2b.3e.4c.5b.6a, | 1d.2b.3e.4c.5b.6b, |
| 1d.2b.3e.4c.5b.6c, | 1d.2b.3e.4c.5b.6d, | 1d.2b.3e.4c.5b.6e, | 1d.2b.3e.4c.5b.6f, |
| 1d.2b.3e.4c.5c.6a, | 1d.2b.3e.4c.5c.6b, | 1d.2b.3e.4c.5c.6c, | 1d.2b.3e.4c.5c.6d, |
| 1d.2b.3e.4c.5c.6e, | 1d.2b.3e.4c.5c.6f, | 1d.2b.3e.4c.5d.6a, | 1d.2b.3e.4c.5d.6b, |
| 1d.2b.3e.4c.5d.6c, | 1d.2b.3e.4c.5d.6d, | 1d.2b.3e.4c.5d.6e, | 1d.2b.3e.4c.5d.6f, |
| 1d.2b.3e.4c.5e.6a, | 1d.2b.3e.4c.5e.6b, | 1d.2b.3e.4c.5e.6c, | 1d.2b.3e.4c.5e.6d, |
| 1d.2b.3e.4c.5e.6e, | 1d.2b.3e.4c.5e.6f, | 1d.2b.3e.4c.5f.6a, | 1d.2b.3e.4c.5f.6b, |
| 1d.2b.3e.4c.5f.6c, | 1d.2b.3e.4c.5f.6d, | 1d.2b.3e.4c.5f.6e, | 1d.2b.3e.4c.5f.6f, |
| 1d.2b.3e.4d.5a.6a, | 1d.2b.3e.4d.5a.6b, | 1d.2b.3e.4d.5a.6c, | 1d.2b.3e.4d.5a.6d, |
| 1d.2b.3e.4d.5a.6e, | 1d.2b.3e.4d.5a.6f, | 1d.2b.3e.4d.5b.6a, | 1d.2b.3e.4d.5b.6b, |
| 1d.2b.3e.4d.5b.6c, | 1d.2b.3e.4d.5b.6d, | 1d.2b.3e.4d.5b.6e, | 1d.2b.3e.4d.5b.6f, |
| 1d.2b.3e.4d.5c.6a, | 1d.2b.3e.4d.5c.6b, | 1d.2b.3e.4d.5c.6c, | 1d.2b.3e.4d.5c.6d, |
| 1d.2b.3e.4d.5c.6e, | 1d.2b.3e.4d.5c.6f, | 1d.2b.3e.4d.5d.6a, | 1d.2b.3e.4d.5d.6b, |
| 1d.2b.3e.4d.5d.6c, | 1d.2b.3e.4d.5d.6d, | 1d.2b.3e.4d.5d.6e, | 1d.2b.3e.4d.5d.6f, |
| 1d.2b.3e.4d.5e.6a, | 1d.2b.3e.4d.5e.6b, | 1d.2b.3e.4d.5e.6c, | 1d.2b.3e.4d.5e.6d, |

TABLE 7-continued

List of Compounds of Formula (II)

| | | | | |
|---|---|---|---|---|
| 1d.2b.3e.4d.5e.6e, | 1d.2b.3e.4d.5e.6f, | 1d.2b.3e.4d.5f.6a, | 1d.2b.3e.4d.5f.6b, | |
| 1d.2b.3e.4d.5f.6c, | 1d.2b.3e.4d.5f.6d, | 1d.2b.3e.4d.5f.6e, | 1d.2b.3e.4d.5f.6f, | |
| 1d.2b.3e.4e.5a.6a, | 1d.2b.3e.4e.5a.6b, | 1d.2b.3e.4e.5a.6c, | 1d.2b.3e.4e.5a.6d, | |
| 1d.2b.3e.4e.5a.6e, | 1d.2b.3e.4e.5a.6f, | 1d.2b.3e.4e.5b.6a, | 1d.2b.3e.4e.5b.6b, | |
| 1d.2b.3e.4e.5b.6c, | 1d.2b.3e.4e.5b.6d, | 1d.2b.3e.4e.5b.6e, | 1d.2b.3e.4e.5b.6f, | |
| 1d.2b.3e.4e.5c.6a, | 1d.2b.3e.4e.5c.6b, | 1d.2b.3e.4e.5c.6c, | 1d.2b.3e.4e.5c.6d, | |
| 1d.2b.3e.4e.5c.6e, | 1d.2b.3e.4e.5c.6f, | 1d.2b.3e.4e.5d.6a, | 1d.2b.3e.4e.5d.6b, | |
| 1d.2b.3e.4e.5d.6c, | 1d.2b.3e.4e.5d.6d, | 1d.2b.3e.4e.5d.6e, | 1d.2b.3e.4e.5d.6f, | |
| 1d.2b.3e.4e.5e.6a, | 1d.2b.3e.4e.5e.6b, | 1d.2b.3e.4e.5e.6c, | 1d.2b.3e.4e.5e.6d, | |
| 1d.2b.3e.4e.5e.6e, | 1d.2b.3e.4e.5e.6f, | 1d.2b.3e.4e.5f.6a, | 1d.2b.3e.4e.5f.6b, | |
| 1d.2b.3e.4e.5f.6c, | 1d.2b.3e.4e.5f.6d, | 1d.2b.3e.4e.5f.6e, | 1d.2b.3e.4e.5f.6f, | |
| 1d.2b.3e.4f.5a.6a, | 1d.2b.3e.4f.5a.6b, | 1d.2b.3e.4f.5a.6c, | 1d.2b.3e.4f.5a.6d, | |
| 1d.2b.3e.4f.5a.6e, | 1d.2b.3e.4f.5a.6f, | 1d.2b.3e.4f.5b.6a, | 1d.2b.3e.4f.5b.6b, | |
| 1d.2b.3e.4f.5b.6c, | 1d.2b.3e.4f.5b.6d, | 1d.2b.3e.4f.5b.6e, | 1d.2b.3e.4f.5b.6f, | |
| 1d.2b.3e.4f.5c.6a, | 1d.2b.3e.4f.5c.6b, | 1d.2b.3e.4f.5c.6c, | 1d.2b.3e.4f.5c.6d, | |
| 1d.2b.3e.4f.5c.6e, | 1d.2b.3e.4f.5c.6f, | 1d.2b.3e.4f.5d.6a, | 1d.2b.3e.4f.5d.6b, | |
| 1d.2b.3e.4f.5d.6c, | 1d.2b.3e.4f.5d.6d, | 1d.2b.3e.4f.5d.6e, | 1d.2b.3e.4f.5d.6f, | |
| 1d.2b.3e.4f.5e.6a, | 1d.2b.3e.4f.5e.6b, | 1d.2b.3e.4f.5e.6c, | 1d.2b.3e.4f.5e.6d, | |
| 1d.2b.3e.4f.5e.6e, | 1d.2b.3e.4f.5e.6f, | 1d.2b.3e.4f.5f.6a, | 1d.2b.3e.4f.5f.6b, | 1d.2b.3e.4f.5f.6c, |
| 1d.2b.3e.4f.5f.6d, | 1d.2b.3e.4f.5f.6e, | 1d.2b.3e.4f.5f.6f, | 1d.2b.3f.4a.5a.6a, | |
| 1d.2b.3f.4a.5a.6b, | 1d.2b.3f.4a.5a.6c, | 1d.2b.3f.4a.5a.6d, | 1d.2b.3f.4a.5a.6e, | |
| 1d.2b.3f.4a.5a.6f, | 1d.2b.3f.4a.5b.6a, | 1d.2b.3f.4a.5b.6b, | 1d.2b.3f.4a.5b.6c, | |
| 1d.2b.3f.4a.5b.6d, | 1d.2b.3f.4a.5b.6e, | 1d.2b.3f.4a.5b.6f, | 1d.2b.3f.4a.5c.6a, | |
| 1d.2b.3f.4a.5c.6b, | 1d.2b.3f.4a.5c.6c, | 1d.2b.3f.4a.5c.6d, | 1d.2b.3f.4a.5c.6e, | |
| 1d.2b.3f.4a.5c.6f, | 1d.2b.3f.4a.5d.6a, | 1d.2b.3f.4a.5d.6b, | 1d.2b.3f.4a.5d.6c, | |
| 1d.2b.3f.4a.5d.6d, | 1d.2b.3f.4a.5d.6e, | 1d.2b.3f.4a.5d.6f, | 1d.2b.3f.4a.5e.6a, | |
| 1d.2b.3f.4a.5e.6b, | 1d.2b.3f.4a.5e.6c, | 1d.2b.3f.4a.5e.6d, | 1d.2b.3f.4a.5e.6e, | |
| 1d.2b.3f.4a.5e.6f, | 1d.2b.3f.4a.5f.6a, | 1d.2b.3f.4a.5f.6b, | 1d.2b.3f.4a.5f.6c, | 1d.2b.3f.4a.5f.6d, |
| 1d.2b.3f.4a.5f.6e, | 1d.2b.3f.4a.5f.6f, | 1d.2b.3f.4b.5a.6a, | 1d.2b.3f.4b.5a.6b, | |
| 1d.2b.3f.4b.5a.6c, | 1d.2b.3f.4b.5a.6d, | 1d.2b.3f.4b.5a.6e, | 1d.2b.3f.4b.5a.6f, | |
| 1d.2b.3f.4b.5b.6a, | 1d.2b.3f.4b.5b.6b, | 1d.2b.3f.4b.5b.6c, | 1d.2b.3f.4b.5b.6d, | |
| 1d.2b.3f.4b.5b.6e, | 1d.2b.3f.4b.5b.6f, | 1d.2b.3f.4b.5c.6a, | 1d.2b.3f.4b.5c.6b, | |
| 1d.2b.3f.4b.5c.6c, | 1d.2b.3f.4b.5c.6d, | 1d.2b.3f.4b.5c.6e, | 1d.2b.3f.4b.5c.6f, | |
| 1d.2b.3f.4b.5d.6a, | 1d.2b.3f.4b.5d.6b, | 1d.2b.3f.4b.5d.6c, | 1d.2b.3f.4b.5d.6d, | |
| 1d.2b.3f.4b.5d.6e, | 1d.2b.3f.4b.5d.6f, | 1d.2b.3f.4b.5e.6a, | 1d.2b.3f.4b.5e.6b, | |
| 1d.2b.3f.4b.5e.6c, | 1d.2b.3f.4b.5e.6d, | 1d.2b.3f.4b.5e.6e, | 1d.2b.3f.4b.5e.6f, | |
| 1d.2b.3f.4b.5f.6a, | 1d.2b.3f.4b.5f.6b, | 1d.2b.3f.4b.5f.6c, | 1d.2b.3f.4b.5f.6d, | |
| 1d.2b.3f.4b.5f.6e, | 1d.2b.3f.4b.5f.6f, | 1d.2b.3f.4c.5a.6a, | 1d.2b.3f.4c.5a.6b, | |
| 1d.2b.3f.4c.5a.6c, | 1d.2b.3f.4c.5a.6d, | 1d.2b.3f.4c.5a.6e, | 1d.2b.3f.4c.5a.6f, | |
| 1d.2b.3f.4c.5b.6a, | 1d.2b.3f.4c.5b.6b, | 1d.2b.3f.4c.5b.6c, | 1d.2b.3f.4c.5b.6d, | |
| 1d.2b.3f.4c.5b.6e, | 1d.2b.3f.4c.5b.6f, | 1d.2b.3f.4c.5c.6a, | 1d.2b.3f.4c.5c.6b, | |
| 1d.2b.3f.4c.5c.6c, | 1d.2b.3f.4c.5c.6d, | 1d.2b.3f.4c.5c.6e, | 1d.2b.3f.4c.5c.6f, | |
| 1d.2b.3f.4c.5d.6a, | 1d.2b.3f.4c.5d.6b, | 1d.2b.3f.4c.5d.6c, | 1d.2b.3f.4c.5d.6d, | |
| 1d.2b.3f.4c.5d.6e, | 1d.2b.3f.4c.5d.6f, | 1d.2b.3f.4c.5e.6a, | 1d.2b.3f.4c.5e.6b, | |
| 1d.2b.3f.4c.5e.6c, | 1d.2b.3f.4c.5e.6d, | 1d.2b.3f.4c.5e.6e, | 1d.2b.3f.4c.5e.6f, | 1d.2b.3f.4c.5f.6a, |
| 1d.2b.3f.4c.5f.6b, | 1d.2b.3f.4c.5f.6c, | 1d.2b.3f.4c.5f.6d, | 1d.2b.3f.4c.5f.6e, | 1d.2b.3f.4c.5f.6f, |
| 1d.2b.3f.4d.5a.6a, | 1d.2b.3f.4d.5a.6b, | 1d.2b.3f.4d.5a.6c, | 1d.2b.3f.4d.5a.6d, | |
| 1d.2b.3f.4d.5a.6e, | 1d.2b.3f.4d.5a.6f, | 1d.2b.3f.4d.5b.6a, | 1d.2b.3f.4d.5b.6b, | |
| 1d.2b.3f.4d.5b.6c, | 1d.2b.3f.4d.5b.6d, | 1d.2b.3f.4d.5b.6e, | 1d.2b.3f.4d.5b.6f, | |
| 1d.2b.3f.4d.5c.6a, | 1d.2b.3f.4d.5c.6b, | 1d.2b.3f.4d.5c.6c, | 1d.2b.3f.4d.5c.6d, | |
| 1d.2b.3f.4d.5c.6e, | 1d.2b.3f.4d.5c.6f, | 1d.2b.3f.4d.5d.6a, | 1d.2b.3f.4d.5d.6b, | |
| 1d.2b.3f.4d.5d.6c, | 1d.2b.3f.4d.5d.6d, | 1d.2b.3f.4d.5d.6e, | 1d.2b.3f.4d.5d.6f, | |
| 1d.2b.3f.4d.5e.6a, | 1d.2b.3f.4d.5e.6b, | 1d.2b.3f.4d.5e.6c, | 1d.2b.3f.4d.5e.6d, | |
| 1d.2b.3f.4d.5e.6e, | 1d.2b.3f.4d.5e.6f, | 1d.2b.3f.4d.5f.6a, | 1d.2b.3f.4d.5f.6b, | |
| 1d.2b.3f.4d.5f.6c, | 1d.2b.3f.4d.5f.6d, | 1d.2b.3f.4d.5f.6e, | 1d.2b.3f.4d.5f.6f, | |
| 1d.2b.3f.4e.5a.6a, | 1d.2b.3f.4e.5a.6b, | 1d.2b.3f.4e.5a.6c, | 1d.2b.3f.4e.5a.6d, | |
| 1d.2b.3f.4e.5a.6e, | 1d.2b.3f.4e.5a.6f, | 1d.2b.3f.4e.5b.6a, | 1d.2b.3f.4e.5b.6b, | |
| 1d.2b.3f.4e.5b.6c, | 1d.2b.3f.4e.5b.6d, | 1d.2b.3f.4e.5b.6e, | 1d.2b.3f.4e.5b.6f, | |
| 1d.2b.3f.4e.5c.6a, | 1d.2b.3f.4e.5c.6b, | 1d.2b.3f.4e.5c.6c, | 1d.2b.3f.4e.5c.6d, | |
| 1d.2b.3f.4e.5c.6e, | 1d.2b.3f.4e.5c.6f, | 1d.2b.3f.4e.5d.6a, | 1d.2b.3f.4e.5d.6b, | |
| 1d.2b.3f.4e.5d.6c, | 1d.2b.3f.4e.5d.6d, | 1d.2b.3f.4e.5d.6e, | 1d.2b.3f.4e.5d.6f, | |
| 1d.2b.3f.4e.5e.6a, | 1d.2b.3f.4e.5e.6b, | 1d.2b.3f.4e.5e.6c, | 1d.2b.3f.4e.5e.6d, | |
| 1d.2b.3f.4e.5e.6e, | 1d.2b.3f.4e.5e.6f, | 1d.2b.3f.4e.5f.6a, | 1d.2b.3f.4e.5f.6b, | 1d.2b.3f.4e.5f.6c, |
| 1d.2b.3f.4e.5f.6d, | 1d.2b.3f.4e.5f.6e, | 1d.2b.3f.4e.5f.6f, | 1d.2b.3f.4f.5a.6a, | 1d.2b.3f.4f.5a.6b, |
| 1d.2b.3f.4f.5a.6c, | 1d.2b.3f.4f.5a.6d, | 1d.2b.3f.4f.5a.6e, | 1d.2b.3f.4f.5a.6f, | 1d.2b.3f.4f.5b.6a, |
| 1d.2b.3f.4f.5b.6b, | 1d.2b.3f.4f.5b.6c, | 1d.2b.3f.4f.5b.6d, | 1d.2b.3f.4f.5b.6e, | 1d.2b.3f.4f.5b.6f, |
| 1d.2b.3f.4f.5c.6a, | 1d.2b.3f.4f.5c.6b, | 1d.2b.3f.4f.5c.6c, | 1d.2b.3f.4f.5c.6d, | 1d.2b.3f.4f.5c.6e, |
| 1d.2b.3f.4f.5c.6f, | 1d.2b.3f.4f.5d.6a, | 1d.2b.3f.4f.5d.6b, | 1d.2b.3f.4f.5d.6c, | |
| 1d.2b.3f.4f.5d.6d, | 1d.2b.3f.4f.5d.6e, | 1d.2b.3f.4f.5d.6f, | 1d.2b.3f.4f.5e.6a, | |
| 1d.2b.3f.4f.5e.6b, | 1d.2b.3f.4f.5e.6c, | 1d.2b.3f.4f.5e.6d, | 1d.2b.3f.4f.5e.6e, | 1d.2b.3f.4f.5e.6f, |
| 1d.2b.3f.4f.5f.6a, | 1d.2b.3f.4f.5f.6b, | 1d.2b.3f.4f.5f.6c, | 1d.2b.3f.4f.5f.6d, | 1d.2b.3f.4f.5f.6e, |
| 1d.2b.3f.4f.5f.6f, | 1d.2c.3a.4a.5a.6a, | 1d.2c.3a.4a.5a.6b, | 1d.2c.3a.4a.5a.6c, | |
| 1d.2c.3a.4a.5a.6d, | 1d.2c.3a.4a.5a.6e, | 1d.2c.3a.4a.5a.6f, | 1d.2c.3a.4a.5b.6a, | |
| 1d.2c.3a.4a.5b.6b, | 1d.2c.3a.4a.5b.6c, | 1d.2c.3a.4a.5b.6d, | 1d.2c.3a.4a.5b.6e, | |
| 1d.2c.3a.4a.5b.6f, | 1d.2c.3a.4a.5c.6a, | 1d.2c.3a.4a.5c.6b, | 1d.2c.3a.4a.5c.6c, | |
| 1d.2c.3a.4a.5c.6d, | 1d.2c.3a.4a.5c.6e, | 1d.2c.3a.4a.5c.6f, | 1d.2c.3a.4a.5d.6a, | |
| 1d.2c.3a.4a.5d.6b, | 1d.2c.3a.4a.5d.6c, | 1d.2c.3a.4a.5d.6d, | 1d.2c.3a.4a.5d.6e, | |
| 1d.2c.3a.4a.5d.6f, | 1d.2c.3a.4a.5e.6a, | 1d.2c.3a.4a.5e.6b, | 1d.2c.3a.4a.5e.6c, | |

TABLE 7-continued

List of Compounds of Formula (II)

| | | | | |
|---|---|---|---|---|
| 1d.2c.3a.4a.5e.6d, | 1d.2c.3a.4a.5e.6e, | 1d.2c.3a.4a.5e.6f, | 1d.2c.3a.4a.5f.6a, | |
| 1d.2c.3a.4a.5f.6b, | 1d.2c.3a.4a.5f.6c, | 1d.2c.3a.4a.5f.6d, | 1d.2c.3a.4a.5f.6e, | 1d.2c.3a.4a.5f.6f, |
| 1d.2c.3a.4b.5a.6a, | 1d.2c.3a.4b.5a.6b, | 1d.2c.3a.4b.5a.6c, | 1d.2c.3a.4b.5a.6d, | |
| 1d.2c.3a.4b.5a.6e, | 1d.2c.3a.4b.5a.6f, | 1d.2c.3a.4b.5b.6a, | 1d.2c.3a.4b.5b.6b, | |
| 1d.2c.3a.4b.5b.6c, | 1d.2c.3a.4b.5b.6d, | 1d.2c.3a.4b.5b.6e, | 1d.2c.3a.4b.5b.6f, | |
| 1d.2c.3a.4b.5c.6a, | 1d.2c.3a.4b.5c.6b, | 1d.2c.3a.4b.5c.6c, | 1d.2c.3a.4b.5c.6d, | |
| 1d.2c.3a.4b.5c.6e, | 1d.2c.3a.4b.5c.6f, | 1d.2c.3a.4b.5d.6a, | 1d.2c.3a.4b.5d.6b, | |
| 1d.2c.3a.4b.5d.6c, | 1d.2c.3a.4b.5d.6d, | 1d.2c.3a.4b.5d.6e, | 1d.2c.3a.4b.5d.6f, | |
| 1d.2c.3a.4b.5e.6a, | 1d.2c.3a.4b.5e.6b, | 1d.2c.3a.4b.5e.6c, | 1d.2c.3a.4b.5e.6d, | |
| 1d.2c.3a.4b.5e.6e, | 1d.2c.3a.4b.5e.6f, | 1d.2c.3a.4b.5f.6a, | 1d.2c.3a.4b.5f.6b, | |
| 1d.2c.3a.4b.5f.6c, | 1d.2c.3a.4b.5f.6d, | 1d.2c.3a.4b.5f.6e, | 1d.2c.3a.4b.5f.6f, | |
| 1d.2c.3a.4c.5a.6a, | 1d.2c.3a.4c.5a.6b, | 1d.2c.3a.4c.5a.6c, | 1d.2c.3a.4c.5a.6d, | |
| 1d.2c.3a.4c.5a.6e, | 1d.2c.3a.4c.5a.6f, | 1d.2c.3a.4c.5b.6a, | 1d.2c.3a.4c.5b.6b, | |
| 1d.2c.3a.4c.5b.6c, | 1d.2c.3a.4c.5b.6d, | 1d.2c.3a.4c.5b.6e, | 1d.2c.3a.4c.5b.6f, | |
| 1d.2c.3a.4c.5c.6a, | 1d.2c.3a.4c.5c.6b, | 1d.2c.3a.4c.5c.6c, | 1d.2c.3a.4c.5c.6d, | |
| 1d.2c.3a.4c.5c.6e, | 1d.2c.3a.4c.5c.6f, | 1d.2c.3a.4c.5d.6a, | 1d.2c.3a.4c.5d.6b, | |
| 1d.2c.3a.4c.5d.6c, | 1d.2c.3a.4c.5d.6d, | 1d.2c.3a.4c.5d.6e, | 1d.2c.3a.4c.5d.6f, | |
| 1d.2c.3a.4c.5e.6a, | 1d.2c.3a.4c.5e.6b, | 1d.2c.3a.4c.5e.6c, | 1d.2c.3a.4c.5e.6d, | |
| 1d.2c.3a.4c.5e.6e, | 1d.2c.3a.4c.5e.6f, | 1d.2c.3a.4c.5f.6a, | 1d.2c.3a.4c.5f.6b, | 1d.2c.3a.4c.5f.6c, |
| 1d.2c.3a.4c.5f.6d, | 1d.2c.3a.4c.5f.6e, | 1d.2c.3a.4c.5f.6f, | 1d.2c.3a.4d.5a.6a, | |
| 1d.2c.3a.4d.5a.6b, | 1d.2c.3a.4d.5a.6c, | 1d.2c.3a.4d.5a.6d, | 1d.2c.3a.4d.5a.6e, | |
| 1d.2c.3a.4d.5a.6f, | 1d.2c.3a.4d.5b.6a, | 1d.2c.3a.4d.5b.6b, | 1d.2c.3a.4d.5b.6c, | |
| 1d.2c.3a.4d.5b.6d, | 1d.2c.3a.4d.5b.6e, | 1d.2c.3a.4d.5b.6f, | 1d.2c.3a.4d.5c.6a, | |
| 1d.2c.3a.4d.5c.6b, | 1d.2c.3a.4d.5c.6c, | 1d.2c.3a.4d.5c.6d, | 1d.2c.3a.4d.5c.6e, | |
| 1d.2c.3a.4d.5c.6f, | 1d.2c.3a.4d.5d.6a, | 1d.2c.3a.4d.5d.6b, | 1d.2c.3a.4d.5d.6c, | |
| 1d.2c.3a.4d.5d.6d, | 1d.2c.3a.4d.5d.6e, | 1d.2c.3a.4d.5d.6f, | 1d.2c.3a.4d.5e.6a, | |
| 1d.2c.3a.4d.5e.6b, | 1d.2c.3a.4d.5e.6c, | 1d.2c.3a.4d.5e.6d, | 1d.2c.3a.4d.5e.6e, | |
| 1d.2c.3a.4d.5e.6f, | 1d.2c.3a.4d.5f.6a, | 1d.2c.3a.4d.5f.6b, | 1d.2c.3a.4d.5f.6c, | |
| 1d.2c.3a.4d.5f.6d, | 1d.2c.3a.4d.5f.6e, | 1d.2c.3a.4d.5f.6f, | 1d.2c.3a.4e.5a.6a, | |
| 1d.2c.3a.4e.5a.6b, | 1d.2c.3a.4e.5a.6c, | 1d.2c.3a.4e.5a.6d, | 1d.2c.3a.4e.5a.6e, | |
| 1d.2c.3a.4e.5a.6f, | 1d.2c.3a.4e.5b.6a, | 1d.2c.3a.4e.5b.6b, | 1d.2c.3a.4e.5b.6c, | |
| 1d.2c.3a.4e.5b.6d, | 1d.2c.3a.4e.5b.6e, | 1d.2c.3a.4e.5b.6f, | 1d.2c.3a.4e.5c.6a, | |
| 1d.2c.3a.4e.5c.6b, | 1d.2c.3a.4e.5c.6c, | 1d.2c.3a.4e.5c.6d, | 1d.2c.3a.4e.5c.6e, | |
| 1d.2c.3a.4e.5c.6f, | 1d.2c.3a.4e.5d.6a, | 1d.2c.3a.4e.5d.6b, | 1d.2c.3a.4e.5d.6c, | |
| 1d.2c.3a.4e.5d.6d, | 1d.2c.3a.4e.5d.6e, | 1d.2c.3a.4e.5d.6f, | 1d.2c.3a.4e.5e.6a, | |
| 1d.2c.3a.4e.5e.6b, | 1d.2c.3a.4e.5e.6c, | 1d.2c.3a.4e.5e.6d, | 1d.2c.3a.4e.5e.6e, | |
| 1d.2c.3a.4e.5e.6f, | 1d.2c.3a.4e.5f.6a, | 1d.2c.3a.4e.5f.6b, | 1d.2c.3a.4e.5f.6c, | |
| 1d.2c.3a.4e.5f.6d, | 1d.2c.3a.4e.5f.6e, | 1d.2c.3a.4e.5f.6f, | 1d.2c.3a.4f.5a.6a, | 1d.2c.3a.4f.5a.6b, |
| 1d.2c.3a.4f.5a.6c, | 1d.2c.3a.4f.5a.6d, | 1d.2c.3a.4f.5a.6e, | 1d.2c.3a.4f.5a.6f, | 1d.2c.3a.4f.5b.6a, |
| 1d.2c.3a.4f.5b.6b, | 1d.2c.3a.4f.5b.6c, | 1d.2c.3a.4f.5b.6d, | 1d.2c.3a.4f.5b.6e, | |
| 1d.2c.3a.4f.5b.6f, | 1d.2c.3a.4f.5c.6a, | 1d.2c.3a.4f.5c.6b, | 1d.2c.3a.4f.5c.6c, | 1d.2c.3a.4f.5c.6d, |
| 1d.2c.3a.4f.5c.6e, | 1d.2c.3a.4f.5c.6f, | 1d.2c.3a.4f.5d.6a, | 1d.2c.3a.4f.5d.6b, | |
| 1d.2c.3a.4f.5d.6c, | 1d.2c.3a.4f.5d.6d, | 1d.2c.3a.4f.5d.6e, | 1d.2c.3a.4f.5d.6f, | |
| 1d.2c.3a.4f.5e.6a, | 1d.2c.3a.4f.5e.6b, | 1d.2c.3a.4f.5e.6c, | 1d.2c.3a.4f.5e.6d, | |
| 1d.2c.3a.4f.5e.6e, | 1d.2c.3a.4f.5e.6f, | 1d.2c.3a.4f.5f.6a, | 1d.2c.3a.4f.5f.6b, | 1d.2c.3a.4f.5f.6c, |
| 1d.2c.3a.4f.5f.6d, | 1d.2c.3a.4f.5f.6e, | 1d.2c.3a.4f.5f.6f, | 1d.2c.3b.4a.5a.6a, | 1d.2c.3b.4a.5a.6b, |
| 1d.2c.3b.4a.5a.6c, | 1d.2c.3b.4a.5a.6d, | 1d.2c.3b.4a.5a.6e, | 1d.2c.3b.4a.5a.6f, | |
| 1d.2c.3b.4a.5b.6a, | 1d.2c.3b.4a.5b.6b, | 1d.2c.3b.4a.5b.6c, | 1d.2c.3b.4a.5b.6d, | |
| 1d.2c.3b.4a.5b.6e, | 1d.2c.3b.4a.5b.6f, | 1d.2c.3b.4a.5c.6a, | 1d.2c.3b.4a.5c.6b, | |
| 1d.2c.3b.4a.5c.6c, | 1d.2c.3b.4a.5c.6d, | 1d.2c.3b.4a.5c.6e, | 1d.2c.3b.4a.5c.6f, | |
| 1d.2c.3b.4a.5d.6a, | 1d.2c.3b.4a.5d.6b, | 1d.2c.3b.4a.5d.6c, | 1d.2c.3b.4a.5d.6d, | |
| 1d.2c.3b.4a.5d.6e, | 1d.2c.3b.4a.5d.6f, | 1d.2c.3b.4a.5e.6a, | 1d.2c.3b.4a.5e.6b, | |
| 1d.2c.3b.4a.5e.6c, | 1d.2c.3b.4a.5e.6d, | 1d.2c.3b.4a.5e.6e, | 1d.2c.3b.4a.5e.6f, | |
| 1d.2c.3b.4a.5f.6a, | 1d.2c.3b.4a.5f.6b, | 1d.2c.3b.4a.5f.6c, | 1d.2c.3b.4a.5f.6d, | |
| 1d.2c.3b.4a.5f.6e, | 1d.2c.3b.4a.5f.6f, | 1d.2c.3b.4b.5a.6a, | 1d.2c.3b.4b.5a.6b, | |
| 1d.2c.3b.4b.5a.6c, | 1d.2c.3b.4b.5a.6d, | 1d.2c.3b.4b.5a.6e, | 1d.2c.3b.4b.5a.6f, | |
| 1d.2c.3b.4b.5b.6a, | 1d.2c.3b.4b.5b.6b, | 1d.2c.3b.4b.5b.6c, | 1d.2c.3b.4b.5b.6d, | |
| 1d.2c.3b.4b.5b.6e, | 1d.2c.3b.4b.5b.6f, | 1d.2c.3b.4b.5c.6a, | 1d.2c.3b.4b.5c.6b, | |
| 1d.2c.3b.4b.5c.6c, | 1d.2c.3b.4b.5c.6d, | 1d.2c.3b.4b.5c.6e, | 1d.2c.3b.4b.5c.6f, | |
| 1d.2c.3b.4b.5d.6a, | 1d.2c.3b.4b.5d.6b, | 1d.2c.3b.4b.5d.6c, | 1d.2c.3b.4b.5d.6d, | |
| 1d.2c.3b.4b.5d.6e, | 1d.2c.3b.4b.5d.6f, | 1d.2c.3b.4b.5e.6a, | 1d.2c.3b.4b.5e.6b, | |
| 1d.2c.3b.4b.5e.6c, | 1d.2c.3b.4b.5e.6d, | 1d.2c.3b.4b.5e.6e, | 1d.2c.3b.4b.5e.6f, | |
| 1d.2c.3b.4b.5f.6a, | 1d.2c.3b.4b.5f.6b, | 1d.2c.3b.4b.5f.6c, | 1d.2c.3b.4b.5f.6d, | |
| 1d.2c.3b.4b.5f.6e, | 1d.2c.3b.4b.5f.6f, | 1d.2c.3b.4c.5a.6a, | 1d.2c.3b.4c.5a.6b, | |
| 1d.2c.3b.4c.5a.6c, | 1d.2c.3b.4c.5a.6d, | 1d.2c.3b.4c.5a.6e, | 1d.2c.3b.4c.5a.6f, | |
| 1d.2c.3b.4c.5b.6a, | 1d.2c.3b.4c.5b.6b, | 1d.2c.3b.4c.5b.6c, | 1d.2c.3b.4c.5b.6d, | |
| 1d.2c.3b.4c.5b.6e, | 1d.2c.3b.4c.5b.6f, | 1d.2c.3b.4c.5c.6a, | 1d.2c.3b.4c.5c.6b, | |
| 1d.2c.3b.4c.5c.6c, | 1d.2c.3b.4c.5c.6d, | 1d.2c.3b.4c.5c.6e, | 1d.2c.3b.4c.5c.6f, | |
| 1d.2c.3b.4c.5d.6a, | 1d.2c.3b.4c.5d.6b, | 1d.2c.3b.4c.5d.6c, | 1d.2c.3b.4c.5d.6d, | |
| 1d.2c.3b.4c.5d.6e, | 1d.2c.3b.4c.5d.6f, | 1d.2c.3b.4c.5e.6a, | 1d.2c.3b.4c.5e.6b, | |
| 1d.2c.3b.4c.5e.6c, | 1d.2c.3b.4c.5e.6d, | 1d.2c.3b.4c.5e.6e, | 1d.2c.3b.4c.5e.6f, | |
| 1d.2c.3b.4c.5f.6a, | 1d.2c.3b.4c.5f.6b, | 1d.2c.3b.4c.5f.6c, | 1d.2c.3b.4c.5f.6d, | |
| 1d.2c.3b.4c.5f.6e, | 1d.2c.3b.4c.5f.6f, | 1d.2c.3b.4d.5a.6a, | 1d.2c.3b.4d.5a.6b, | |
| 1d.2c.3b.4d.5a.6c, | 1d.2c.3b.4d.5a.6d, | 1d.2c.3b.4d.5a.6e, | 1d.2c.3b.4d.5a.6f, | |
| 1d.2c.3b.4d.5b.6a, | 1d.2c.3b.4d.5b.6b, | 1d.2c.3b.4d.5b.6c, | 1d.2c.3b.4d.5b.6d, | |
| 1d.2c.3b.4d.5b.6e, | 1d.2c.3b.4d.5b.6f, | 1d.2c.3b.4d.5c.6a, | 1d.2c.3b.4d.5c.6b, | |
| 1d.2c.3b.4d.5c.6c, | 1d.2c.3b.4d.5c.6d, | 1d.2c.3b.4d.5c.6e, | 1d.2c.3b.4d.5c.6f, | |
| 1d.2c.3b.4d.5d.6a, | 1d.2c.3b.4d.5d.6b, | 1d.2c.3b.4d.5d.6c, | 1d.2c.3b.4d.5d.6d, | |

TABLE 7-continued

List of Compounds of Formula (II)

| | | | | |
|---|---|---|---|---|
| 1d.2c.3b.4d.5d.6e, | 1d.2c.3b.4d.5d.6f, | 1d.2c.3b.4d.5e.6a, | 1d.2c.3b.4d.5e.6b, | |
| 1d.2c.3b.4d.5e.6c, | 1d.2c.3b.4d.5e.6d, | 1d.2c.3b.4d.5e.6e, | 1d.2c.3b.4d.5e.6f, | |
| 1d.2c.3b.4d.5f.6a, | 1d.2c.3b.4d.5f.6b, | 1d.2c.3b.4d.5f.6c, | 1d.2c.3b.4d.5f.6d, | |
| 1d.2c.3b.4d.5f.6e, | 1d.2c.3b.4d.5f.6f, | 1d.2c.3b.4e.5a.6a, | 1d.2c.3b.4e.5a.6b, | |
| 1d.2c.3b.4e.5a.6c, | 1d.2c.3b.4e.5a.6d, | 1d.2c.3b.4e.5a.6e, | 1d.2c.3b.4e.5a.6f, | |
| 1d.2c.3b.4e.5b.6a, | 1d.2c.3b.4e.5b.6b, | 1d.2c.3b.4e.5b.6c, | 1d.2c.3b.4e.5b.6d, | |
| 1d.2c.3b.4e.5b.6e, | 1d.2c.3b.4e.5b.6f, | 1d.2c.3b.4e.5c.6a, | 1d.2c.3b.4e.5c.6b, | |
| 1d.2c.3b.4e.5c.6c, | 1d.2c.3b.4e.5c.6d, | 1d.2c.3b.4e.5c.6e, | 1d.2c.3b.4e.5c.6f, | |
| 1d.2c.3b.4e.5d.6a, | 1d.2c.3b.4e.5d.6b, | 1d.2c.3b.4e.5d.6c, | 1d.2c.3b.4e.5d.6d, | |
| 1d.2c.3b.4e.5d.6e, | 1d.2c.3b.4e.5d.6f, | 1d.2c.3b.4e.5e.6a, | 1d.2c.3b.4e.5e.6b, | |
| 1d.2c.3b.4e.5e.6c, | 1d.2c.3b.4e.5e.6d, | 1d.2c.3b.4e.5e.6e, | 1d.2c.3b.4e.5e.6f, | |
| 1d.2c.3b.4e.5f.6a, | 1d.2c.3b.4e.5f.6b, | 1d.2c.3b.4e.5f.6c, | 1d.2c.3b.4e.5f.6d, | |
| 1d.2c.3b.4e.5f.6e, | 1d.2c.3b.4e.5f.6f, | 1d.2c.3b.4f.5a.6a, | 1d.2c.3b.4f.5a.6b, | |
| 1d.2c.3b.4f.5a.6c, | 1d.2c.3b.4f.5a.6d, | 1d.2c.3b.4f.5a.6e, | 1d.2c.3b.4f.5a.6f, | |
| 1d.2c.3b.4f.5b.6a, | 1d.2c.3b.4f.5b.6b, | 1d.2c.3b.4f.5b.6c, | 1d.2c.3b.4f.5b.6d, | |
| 1d.2c.3b.4f.5b.6e, | 1d.2c.3b.4f.5b.6f, | 1d.2c.3b.4f.5c.6a, | 1d.2c.3b.4f.5c.6b, | |
| 1d.2c.3b.4f.5c.6c, | 1d.2c.3b.4f.5c.6d, | 1d.2c.3b.4f.5c.6e, | 1d.2c.3b.4f.5c.6f, | |
| 1d.2c.3b.4f.5d.6a, | 1d.2c.3b.4f.5d.6b, | 1d.2c.3b.4f.5d.6c, | 1d.2c.3b.4f.5d.6d, | |
| 1d.2c.3b.4f.5d.6e, | 1d.2c.3b.4f.5d.6f, | 1d.2c.3b.4f.5e.6a, | 1d.2c.3b.4f.5e.6b, | |
| 1d.2c.3b.4f.5e.6c, | 1d.2c.3b.4f.5e.6d, | 1d.2c.3b.4f.5e.6e, | 1d.2c.3b.4f.5e.6f, | 1d.2c.3b.4f.5f.6a, |
| 1d.2c.3b.4f.5f.6b, | 1d.2c.3b.4f.5f.6c, | 1d.2c.3b.4f.5f.6d, | 1d.2c.3b.4f.5f.6e, | 1d.2c.3b.4f.5f.6f, |
| 1d.2c.3c.4a.5a.6a, | 1d.2c.3c.4a.5a.6b, | 1d.2c.3c.4a.5a.6c, | 1d.2c.3c.4a.5a.6d, | |
| 1d.2c.3c.4a.5a.6e, | 1d.2c.3c.4a.5a.6f, | 1d.2c.3c.4a.5b.6a, | 1d.2c.3c.4a.5b.6b, | |
| 1d.2c.3c.4a.5b.6c, | 1d.2c.3c.4a.5b.6d, | 1d.2c.3c.4a.5b.6e, | 1d.2c.3c.4a.5b.6f, | |
| 1d.2c.3c.4a.5c.6a, | 1d.2c.3c.4a.5c.6b, | 1d.2c.3c.4a.5c.6c, | 1d.2c.3c.4a.5c.6d, | |
| 1d.2c.3c.4a.5c.6e, | 1d.2c.3c.4a.5c.6f, | 1d.2c.3c.4a.5d.6a, | 1d.2c.3c.4a.5d.6b, | |
| 1d.2c.3c.4a.5d.6c, | 1d.2c.3c.4a.5d.6d, | 1d.2c.3c.4a.5d.6e, | 1d.2c.3c.4a.5d.6f, | |
| 1d.2c.3c.4a.5e.6a, | 1d.2c.3c.4a.5e.6b, | 1d.2c.3c.4a.5e.6c, | 1d.2c.3c.4a.5e.6d, | |
| 1d.2c.3c.4a.5e.6e, | 1d.2c.3c.4a.5e.6f, | 1d.2c.3c.4a.5f.6a, | 1d.2c.3c.4a.5f.6b, | 1d.2c.3c.4a.5f.6c, |
| 1d.2c.3c.4a.5f.6d, | 1d.2c.3c.4a.5f.6e, | 1d.2c.3c.4a.5f.6f, | 1d.2c.3c.4b.5a.6a, | |
| 1d.2c.3c.4b.5a.6b, | 1d.2c.3c.4b.5a.6c, | 1d.2c.3c.4b.5a.6d, | 1d.2c.3c.4b.5a.6e, | |
| 1d.2c.3c.4b.5a.6f, | 1d.2c.3c.4b.5b.6a, | 1d.2c.3c.4b.5b.6b, | 1d.2c.3c.4b.5b.6c, | |
| 1d.2c.3c.4b.5b.6d, | 1d.2c.3c.4b.5b.6e, | 1d.2c.3c.4b.5b.6f, | 1d.2c.3c.4b.5c.6a, | |
| 1d.2c.3c.4b.5c.6b, | 1d.2c.3c.4b.5c.6c, | 1d.2c.3c.4b.5c.6d, | 1d.2c.3c.4b.5c.6e, | |
| 1d.2c.3c.4b.5c.6f, | 1d.2c.3c.4b.5d.6a, | 1d.2c.3c.4b.5d.6b, | 1d.2c.3c.4b.5d.6c, | |
| 1d.2c.3c.4b.5d.6d, | 1d.2c.3c.4b.5d.6e, | 1d.2c.3c.4b.5d.6f, | 1d.2c.3c.4b.5e.6a, | |
| 1d.2c.3c.4b.5e.6b, | 1d.2c.3c.4b.5e.6c, | 1d.2c.3c.4b.5e.6d, | 1d.2c.3c.4b.5e.6e, | |
| 1d.2c.3c.4b.5e.6f, | 1d.2c.3c.4b.5f.6a, | 1d.2c.3c.4b.5f.6b, | 1d.2c.3c.4b.5f.6c, | |
| 1d.2c.3c.4b.5f.6d, | 1d.2c.3c.4b.5f.6e, | 1d.2c.3c.4b.5f.6f, | 1d.2c.3c.4c.5a.6a, | |
| 1d.2c.3c.4c.5a.6b, | 1d.2c.3c.4c.5a.6c, | 1d.2c.3c.4c.5a.6d, | 1d.2c.3c.4c.5a.6e, | |
| 1d.2c.3c.4c.5a.6f, | 1d.2c.3c.4c.5b.6a, | 1d.2c.3c.4c.5b.6b, | 1d.2c.3c.4c.5b.6c, | |
| 1d.2c.3c.4c.5b.6d, | 1d.2c.3c.4c.5b.6e, | 1d.2c.3c.4c.5b.6f, | 1d.2c.3c.4c.5c.6a, | |
| 1d.2c.3c.4c.5c.6b, | 1d.2c.3c.4c.5c.6c, | 1d.2c.3c.4c.5c.6d, | 1d.2c.3c.4c.5c.6e, | 1d.2c.3c.4c.5c.6f, |
| 1d.2c.3c.4c.5d.6a, | 1d.2c.3c.4c.5d.6b, | 1d.2c.3c.4c.5d.6c, | 1d.2c.3c.4c.5d.6d, | |
| 1d.2c.3c.4c.5d.6e, | 1d.2c.3c.4c.5d.6f, | 1d.2c.3c.4c.5e.6a, | 1d.2c.3c.4c.5e.6b, | |
| 1d.2c.3c.4c.5e.6c, | 1d.2c.3c.4c.5e.6d, | 1d.2c.3c.4c.5e.6e, | 1d.2c.3c.4c.5e.6f, | 1d.2c.3c.4c.5f.6a, |
| 1d.2c.3c.4c.5f.6b, | 1d.2c.3c.4c.5f.6c, | 1d.2c.3c.4c.5f.6d, | 1d.2c.3c.4c.5f.6e, | 1d.2c.3c.4c.5f.6f, |
| 1d.2c.3c.4d.5a.6a, | 1d.2c.3c.4d.5a.6b, | 1d.2c.3c.4d.5a.6c, | 1d.2c.3c.4d.5a.6d, | |
| 1d.2c.3c.4d.5a.6e, | 1d.2c.3c.4d.5a.6f, | 1d.2c.3c.4d.5b.6a, | 1d.2c.3c.4d.5b.6b, | |
| 1d.2c.3c.4d.5b.6c, | 1d.2c.3c.4d.5b.6d, | 1d.2c.3c.4d.5b.6e, | 1d.2c.3c.4d.5b.6f, | |
| 1d.2c.3c.4d.5c.6a, | 1d.2c.3c.4d.5c.6b, | 1d.2c.3c.4d.5c.6c, | 1d.2c.3c.4d.5c.6d, | |
| 1d.2c.3c.4d.5c.6e, | 1d.2c.3c.4d.5c.6f, | 1d.2c.3c.4d.5d.6a, | 1d.2c.3c.4d.5d.6b, | |
| 1d.2c.3c.4d.5d.6c, | 1d.2c.3c.4d.5d.6d, | 1d.2c.3c.4d.5d.6e, | 1d.2c.3c.4d.5d.6f, | |
| 1d.2c.3c.4d.5e.6a, | 1d.2c.3c.4d.5e.6b, | 1d.2c.3c.4d.5e.6c, | 1d.2c.3c.4d.5e.6d, | |
| 1d.2c.3c.4d.5e.6e, | 1d.2c.3c.4d.5e.6f, | 1d.2c.3c.4d.5f.6a, | 1d.2c.3c.4d.5f.6b, | |
| 1d.2c.3c.4d.5f.6c, | 1d.2c.3c.4d.5f.6d, | 1d.2c.3c.4d.5f.6e, | 1d.2c.3c.4d.5f.6f, | |
| 1d.2c.3c.4e.5a.6a, | 1d.2c.3c.4e.5a.6b, | 1d.2c.3c.4e.5a.6c, | 1d.2c.3c.4e.5a.6d, | |
| 1d.2c.3c.4e.5a.6e, | 1d.2c.3c.4e.5a.6f, | 1d.2c.3c.4e.5b.6a, | 1d.2c.3c.4e.5b.6b, | |
| 1d.2c.3c.4e.5b.6c, | 1d.2c.3c.4e.5b.6d, | 1d.2c.3c.4e.5b.6e, | 1d.2c.3c.4e.5b.6f, | |
| 1d.2c.3c.4e.5c.6a, | 1d.2c.3c.4e.5c.6b, | 1d.2c.3c.4e.5c.6c, | 1d.2c.3c.4e.5c.6d, | |
| 1d.2c.3c.4e.5c.6e, | 1d.2c.3c.4e.5c.6f, | 1d.2c.3c.4e.5d.6a, | 1d.2c.3c.4e.5d.6b, | |
| 1d.2c.3c.4e.5d.6c, | 1d.2c.3c.4e.5d.6d, | 1d.2c.3c.4e.5d.6e, | 1d.2c.3c.4e.5d.6f, | |
| 1d.2c.3c.4e.5e.6a, | 1d.2c.3c.4e.5e.6b, | 1d.2c.3c.4e.5e.6c, | 1d.2c.3c.4e.5e.6d, | |
| 1d.2c.3c.4e.5e.6e, | 1d.2c.3c.4e.5e.6f, | 1d.2c.3c.4e.5f.6a, | 1d.2c.3c.4e.5f.6b, | 1d.2c.3c.4e.5f.6c, |
| 1d.2c.3c.4e.5f.6d, | 1d.2c.3c.4e.5f.6e, | 1d.2c.3c.4e.5f.6f, | 1d.2c.3c.4f.5a.6a, | 1d.2c.3c.4f.5a.6b, |
| 1d.2c.3c.4f.5a.6c, | 1d.2c.3c.4f.5a.6d, | 1d.2c.3c.4f.5a.6e, | 1d.2c.3c.4f.5a.6f, | 1d.2c.3c.4f.5b.6a, |
| 1d.2c.3c.4f.5b.6b, | 1d.2c.3c.4f.5b.6c, | 1d.2c.3c.4f.5b.6d, | 1d.2c.3c.4f.5b.6e, | 1d.2c.3c.4f.5b.6f, |
| 1d.2c.3c.4f.5c.6a, | 1d.2c.3c.4f.5c.6b, | 1d.2c.3c.4f.5c.6c, | 1d.2c.3c.4f.5c.6d, | 1d.2c.3c.4f.5c.6e, |
| 1d.2c.3c.4f.5c.6f, | 1d.2c.3c.4f.5d.6a, | 1d.2c.3c.4f.5d.6b, | 1d.2c.3c.4f.5d.6c, | |
| 1d.2c.3c.4f.5d.6d, | 1d.2c.3c.4f.5d.6e, | 1d.2c.3c.4f.5d.6f, | 1d.2c.3c.4f.5e.6a, | |
| 1d.2c.3c.4f.5e.6b, | 1d.2c.3c.4f.5e.6c, | 1d.2c.3c.4f.5e.6d, | 1d.2c.3c.4f.5e.6e, | 1d.2c.3c.4f.5e.6f, |
| 1d.2c.3c.4f.5f.6a, | 1d.2c.3c.4f.5f.6b, | 1d.2c.3c.4f.5f.6c, | 1d.2c.3c.4f.5f.6d, | 1d.2c.3c.4f.5f.6e, |
| 1d.2c.3c.4f.5f.6f, | 1d.2c.3d.4a.5a.6a, | 1d.2c.3d.4a.5a.6b, | 1d.2c.3d.4a.5a.6c, | |
| 1d.2c.3d.4a.5a.6d, | 1d.2c.3d.4a.5a.6e, | 1d.2c.3d.4a.5a.6f, | 1d.2c.3d.4a.5b.6a, | |
| 1d.2c.3d.4a.5b.6b, | 1d.2c.3d.4a.5b.6c, | 1d.2c.3d.4a.5b.6d, | 1d.2c.3d.4a.5b.6e, | |
| 1d.2c.3d.4a.5b.6f, | 1d.2c.3d.4a.5c.6a, | 1d.2c.3d.4a.5c.6b, | 1d.2c.3d.4a.5c.6c, | |
| 1d.2c.3d.4a.5c.6d, | 1d.2c.3d.4a.5c.6e, | 1d.2c.3d.4a.5c.6f, | 1d.2c.3d.4a.5d.6a, | |
| 1d.2c.3d.4a.5d.6b, | 1d.2c.3d.4a.5d.6c, | 1d.2c.3d.4a.5d.6d, | 1d.2c.3d.4a.5d.6e, | |

TABLE 7-continued

List of Compounds of Formula (II)

| | | | |
|---|---|---|---|
| 1d.2c.3d.4a.5d.6f, | 1d.2c.3d.4a.5e.6a, | 1d.2c.3d.4a.5e.6b, | 1d.2c.3d.4a.5e.6c, |
| 1d.2c.3d.4a.5e.6d, | 1d.2c.3d.4a.5e.6e, | 1d.2c.3d.4a.5e.6f, | 1d.2c.3d.4a.5f.6a, |
| 1d.2c.3d.4a.5f.6b, | 1d.2c.3d.4a.5f.6c, | 1d.2c.3d.4a.5f.6d, | 1d.2c.3d.4a.5f.6e, |
| 1d.2c.3d.4a.5f.6f, | 1d.2c.3d.4b.5a.6a, | 1d.2c.3d.4b.5a.6b, | 1d.2c.3d.4b.5a.6c, |
| 1d.2c.3d.4b.5a.6d, | 1d.2c.3d.4b.5a.6e, | 1d.2c.3d.4b.5a.6f, | 1d.2c.3d.4b.5b.6a, |
| 1d.2c.3d.4b.5b.6b, | 1d.2c.3d.4b.5b.6c, | 1d.2c.3d.4b.5b.6d, | 1d.2c.3d.4b.5b.6e, |
| 1d.2c.3d.4b.5b.6f, | 1d.2c.3d.4b.5c.6a, | 1d.2c.3d.4b.5c.6b, | 1d.2c.3d.4b.5c.6c, |
| 1d.2c.3d.4b.5c.6d, | 1d.2c.3d.4b.5c.6e, | 1d.2c.3d.4b.5c.6f, | 1d.2c.3d.4b.5d.6a, |
| 1d.2c.3d.4b.5d.6b, | 1d.2c.3d.4b.5d.6c, | 1d.2c.3d.4b.5d.6d, | 1d.2c.3d.4b.5d.6e, |
| 1d.2c.3d.4b.5d.6f, | 1d.2c.3d.4b.5e.6a, | 1d.2c.3d.4b.5e.6b, | 1d.2c.3d.4b.5e.6c, |
| 1d.2c.3d.4b.5e.6d, | 1d.2c.3d.4b.5e.6e, | 1d.2c.3d.4b.5e.6f, | 1d.2c.3d.4b.5f.6a, |
| 1d.2c.3d.4b.5f.6b, | 1d.2c.3d.4b.5f.6c, | 1d.2c.3d.4b.5f.6d, | 1d.2c.3d.4b.5f.6e, |
| 1d.2c.3d.4b.5f.6f, | 1d.2c.3d.4c.5a.6a, | 1d.2c.3d.4c.5a.6b, | 1d.2c.3d.4c.5a.6c, |
| 1d.2c.3d.4c.5a.6d, | 1d.2c.3d.4c.5a.6e, | 1d.2c.3d.4c.5a.6f, | 1d.2c.3d.4c.5b.6a, |
| 1d.2c.3d.4c.5b.6b, | 1d.2c.3d.4c.5b.6c, | 1d.2c.3d.4c.5b.6d, | 1d.2c.3d.4c.5b.6e, |
| 1d.2c.3d.4c.5b.6f, | 1d.2c.3d.4c.5c.6a, | 1d.2c.3d.4c.5c.6b, | 1d.2c.3d.4c.5c.6c, |
| 1d.2c.3d.4c.5c.6d, | 1d.2c.3d.4c.5c.6e, | 1d.2c.3d.4c.5c.6f, | 1d.2c.3d.4c.5d.6a, |
| 1d.2c.3d.4c.5d.6b, | 1d.2c.3d.4c.5d.6c, | 1d.2c.3d.4c.5d.6d, | 1d.2c.3d.4c.5d.6e, |
| 1d.2c.3d.4c.5d.6f, | 1d.2c.3d.4c.5e.6a, | 1d.2c.3d.4c.5e.6b, | 1d.2c.3d.4c.5e.6c, |
| 1d.2c.3d.4c.5e.6d, | 1d.2c.3d.4c.5e.6e, | 1d.2c.3d.4c.5e.6f, | 1d.2c.3d.4c.5f.6a, |
| 1d.2c.3d.4c.5f.6b, | 1d.2c.3d.4c.5f.6c, | 1d.2c.3d.4c.5f.6d, | 1d.2c.3d.4c.5f.6e, |
| 1d.2c.3d.4c.5f.6f, | 1d.2c.3d.4d.5a.6a, | 1d.2c.3d.4d.5a.6b, | 1d.2c.3d.4d.5a.6c, |
| 1d.2c.3d.4d.5a.6d, | 1d.2c.3d.4d.5a.6e, | 1d.2c.3d.4d.5a.6f, | 1d.2c.3d.4d.5b.6a, |
| 1d.2c.3d.4d.5b.6b, | 1d.2c.3d.4d.5b.6c, | 1d.2c.3d.4d.5b.6d, | 1d.2c.3d.4d.5b.6e, |
| 1d.2c.3d.4d.5b.6f, | 1d.2c.3d.4d.5c.6a, | 1d.2c.3d.4d.5c.6b, | 1d.2c.3d.4d.5c.6c, |
| 1d.2c.3d.4d.5c.6d, | 1d.2c.3d.4d.5c.6e, | 1d.2c.3d.4d.5c.6f, | 1d.2c.3d.4d.5d.6a, |
| 1d.2c.3d.4d.5d.6b, | 1d.2c.3d.4d.5d.6c, | 1d.2c.3d.4d.5d.6d, | 1d.2c.3d.4d.5d.6e, |
| 1d.2c.3d.4d.5d.6f, | 1d.2c.3d.4d.5e.6a, | 1d.2c.3d.4d.5e.6b, | 1d.2c.3d.4d.5e.6c, |
| 1d.2c.3d.4d.5e.6d, | 1d.2c.3d.4d.5e.6e, | 1d.2c.3d.4d.5e.6f, | 1d.2c.3d.4d.5f.6a, |
| 1d.2c.3d.4d.5f.6b, | 1d.2c.3d.4d.5f.6c, | 1d.2c.3d.4d.5f.6d, | 1d.2c.3d.4d.5f.6e, |
| 1d.2c.3d.4d.5f.6f, | 1d.2c.3d.4e.5a.6a, | 1d.2c.3d.4e.5a.6b, | 1d.2c.3d.4e.5a.6c, |
| 1d.2c.3d.4e.5a.6d, | 1d.2c.3d.4e.5a.6e, | 1d.2c.3d.4e.5a.6f, | 1d.2c.3d.4e.5b.6a, |
| 1d.2c.3d.4e.5b.6b, | 1d.2c.3d.4e.5b.6c, | 1d.2c.3d.4e.5b.6d, | 1d.2c.3d.4e.5b.6e, |
| 1d.2c.3d.4e.5b.6f, | 1d.2c.3d.4e.5c.6a, | 1d.2c.3d.4e.5c.6b, | 1d.2c.3d.4e.5c.6c, |
| 1d.2c.3d.4e.5c.6d, | 1d.2c.3d.4e.5c.6e, | 1d.2c.3d.4e.5c.6f, | 1d.2c.3d.4e.5d.6a, |
| 1d.2c.3d.4e.5d.6b, | 1d.2c.3d.4e.5d.6c, | 1d.2c.3d.4e.5d.6d, | 1d.2c.3d.4e.5d.6e, |
| 1d.2c.3d.4e.5d.6f, | 1d.2c.3d.4e.5e.6a, | 1d.2c.3d.4e.5e.6b, | 1d.2c.3d.4e.5e.6c, |
| 1d.2c.3d.4e.5e.6d, | 1d.2c.3d.4e.5e.6e, | 1d.2c.3d.4e.5e.6f, | 1d.2c.3d.4e.5f.6a, |
| 1d.2c.3d.4e.5f.6b, | 1d.2c.3d.4e.5f.6c, | 1d.2c.3d.4e.5f.6d, | 1d.2c.3d.4e.5f.6e, |
| 1d.2c.3d.4e.5f.6f, | 1d.2c.3d.4f.5a.6a, | 1d.2c.3d.4f.5a.6b, | 1d.2c.3d.4f.5a.6c, |
| 1d.2c.3d.4f.5a.6d, | 1d.2c.3d.4f.5a.6e, | 1d.2c.3d.4f.5a.6f, | 1d.2c.3d.4f.5b.6a, |
| 1d.2c.3d.4f.5b.6b, | 1d.2c.3d.4f.5b.6c, | 1d.2c.3d.4f.5b.6d, | 1d.2c.3d.4f.5b.6e, |
| 1d.2c.3d.4f.5b.6f, | 1d.2c.3d.4f.5c.6a, | 1d.2c.3d.4f.5c.6b, | 1d.2c.3d.4f.5c.6c, |
| 1d.2c.3d.4f.5c.6d, | 1d.2c.3d.4f.5c.6e, | 1d.2c.3d.4f.5c.6f, | 1d.2c.3d.4f.5d.6a, |
| 1d.2c.3d.4f.5d.6b, | 1d.2c.3d.4f.5d.6c, | 1d.2c.3d.4f.5d.6d, | 1d.2c.3d.4f.5d.6e, |
| 1d.2c.3d.4f.5d.6f, | 1d.2c.3d.4f.5e.6a, | 1d.2c.3d.4f.5e.6b, | 1d.2c.3d.4f.5e.6c, |
| 1d.2c.3d.4f.5e.6d, | 1d.2c.3d.4f.5e.6e, | 1d.2c.3d.4f.5e.6f, | 1d.2c.3d.4f.5f.6a, |
| 1d.2c.3d.4f.5f.6b, | 1d.2c.3d.4f.5f.6c, | 1d.2c.3d.4f.5f.6d, | 1d.2c.3d.4f.5f.6e, 1d.2c.3d.4f.5f.6f, |
| 1d.2c.3e.4a.5a.6a, | 1d.2c.3e.4a.5a.6b, | 1d.2c.3e.4a.5a.6c, | 1d.2c.3e.4a.5a.6d, |
| 1d.2c.3e.4a.5a.6e, | 1d.2c.3e.4a.5a.6f, | 1d.2c.3e.4a.5b.6a, | 1d.2c.3e.4a.5b.6b, |
| 1d.2c.3e.4a.5b.6c, | 1d.2c.3e.4a.5b.6d, | 1d.2c.3e.4a.5b.6e, | 1d.2c.3e.4a.5b.6f, |
| 1d.2c.3e.4a.5c.6a, | 1d.2c.3e.4a.5c.6b, | 1d.2c.3e.4a.5c.6c, | 1d.2c.3e.4a.5c.6d, |
| 1d.2c.3e.4a.5c.6e, | 1d.2c.3e.4a.5c.6f, | 1d.2c.3e.4a.5d.6a, | 1d.2c.3e.4a.5d.6b, |
| 1d.2c.3e.4a.5d.6c, | 1d.2c.3e.4a.5d.6d, | 1d.2c.3e.4a.5d.6e, | 1d.2c.3e.4a.5d.6f, |
| 1d.2c.3e.4a.5e.6a, | 1d.2c.3e.4a.5e.6b, | 1d.2c.3e.4a.5e.6c, | 1d.2c.3e.4a.5e.6d, |
| 1d.2c.3e.4a.5e.6e, | 1d.2c.3e.4a.5e.6f, | 1d.2c.3e.4a.5f.6a, | 1d.2c.3e.4a.5f.6b, |
| 1d.2c.3e.4a.5f.6c, | 1d.2c.3e.4a.5f.6d, | 1d.2c.3e.4a.5f.6e, | 1d.2c.3e.4a.5f.6f, |
| 1d.2c.3e.4b.5a.6a, | 1d.2c.3e.4b.5a.6b, | 1d.2c.3e.4b.5a.6c, | 1d.2c.3e.4b.5a.6d, |
| 1d.2c.3e.4b.5a.6e, | 1d.2c.3e.4b.5a.6f, | 1d.2c.3e.4b.5b.6a, | 1d.2c.3e.4b.5b.6b, |
| 1d.2c.3e.4b.5b.6c, | 1d.2c.3e.4b.5b.6d, | 1d.2c.3e.4b.5b.6e, | 1d.2c.3e.4b.5b.6f, |
| 1d.2c.3e.4b.5c.6a, | 1d.2c.3e.4b.5c.6b, | 1d.2c.3e.4b.5c.6c, | 1d.2c.3e.4b.5c.6d, |
| 1d.2c.3e.4b.5c.6e, | 1d.2c.3e.4b.5c.6f, | 1d.2c.3e.4b.5d.6a, | 1d.2c.3e.4b.5d.6b, |
| 1d.2c.3e.4b.5d.6c, | 1d.2c.3e.4b.5d.6d, | 1d.2c.3e.4b.5d.6e, | 1d.2c.3e.4b.5d.6f, |
| 1d.2c.3e.4b.5e.6a, | 1d.2c.3e.4b.5e.6b, | 1d.2c.3e.4b.5e.6c, | 1d.2c.3e.4b.5e.6d, |
| 1d.2c.3e.4b.5e.6e, | 1d.2c.3e.4b.5e.6f, | 1d.2c.3e.4b.5f.6a, | 1d.2c.3e.4b.5f.6b, |
| 1d.2c.3e.4b.5f.6c, | 1d.2c.3e.4b.5f.6d, | 1d.2c.3e.4b.5f.6e, | 1d.2c.3e.4b.5f.6f, |
| 1d.2c.3e.4c.5a.6a, | 1d.2c.3e.4c.5a.6b, | 1d.2c.3e.4c.5a.6c, | 1d.2c.3e.4c.5a.6d, |
| 1d.2c.3e.4c.5a.6e, | 1d.2c.3e.4c.5a.6f, | 1d.2c.3e.4c.5b.6a, | 1d.2c.3e.4c.5b.6b, |
| 1d.2c.3e.4c.5b.6c, | 1d.2c.3e.4c.5b.6d, | 1d.2c.3e.4c.5b.6e, | 1d.2c.3e.4c.5b.6f, |
| 1d.2c.3e.4c.5c.6a, | 1d.2c.3e.4c.5c.6b, | 1d.2c.3e.4c.5c.6c, | 1d.2c.3e.4c.5c.6d, |
| 1d.2c.3e.4c.5c.6e, | 1d.2c.3e.4c.5c.6f, | 1d.2c.3e.4c.5d.6a, | 1d.2c.3e.4c.5d.6b, |
| 1d.2c.3e.4c.5d.6c, | 1d.2c.3e.4c.5d.6d, | 1d.2c.3e.4c.5d.6e, | 1d.2c.3e.4c.5d.6f, |
| 1d.2c.3e.4c.5e.6a, | 1d.2c.3e.4c.5e.6b, | 1d.2c.3e.4c.5e.6c, | 1d.2c.3e.4c.5e.6d, |
| 1d.2c.3e.4c.5e.6e, | 1d.2c.3e.4c.5e.6f, | 1d.2c.3e.4c.5f.6a, | 1d.2c.3e.4c.5f.6b, 1d.2c.3e.4c.5f.6c, |
| 1d.2c.3e.4c.5f.6d, | 1d.2c.3e.4c.5f.6e, | 1d.2c.3e.4c.5f.6f, | 1d.2c.3e.4d.5a.6a, |
| 1d.2c.3e.4d.5a.6b, | 1d.2c.3e.4d.5a.6c, | 1d.2c.3e.4d.5a.6d, | 1d.2c.3e.4d.5a.6e, |
| 1d.2c.3e.4d.5a.6f, | 1d.2c.3e.4d.5b.6a, | 1d.2c.3e.4d.5b.6b, | 1d.2c.3e.4d.5b.6c, |
| 1d.2c.3e.4d.5b.6d, | 1d.2c.3e.4d.5b.6e, | 1d.2c.3e.4d.5b.6f, | 1d.2c.3e.4d.5c.6a, |

TABLE 7-continued

List of Compounds of Formula (II)

| | | | |
|---|---|---|---|
| 1d.2c.3e.4d.5c.6b, | 1d.2c.3e.4d.5c.6c, | 1d.2c.3e.4d.5c.6d, | 1d.2c.3e.4d.5c.6e, |
| 1d.2c.3e.4d.5c.6f, | 1d.2c.3e.4d.5d.6a, | 1d.2c.3e.4d.5d.6b, | 1d.2c.3e.4d.5d.6c, |
| 1d.2c.3e.4d.5d.6d, | 1d.2c.3e.4d.5d.6e, | 1d.2c.3e.4d.5d.6f, | 1d.2c.3e.4d.5e.6a, |
| 1d.2c.3e.4d.5e.6b, | 1d.2c.3e.4d.5e.6c, | 1d.2c.3e.4d.5e.6d, | 1d.2c.3e.4d.5e.6e, |
| 1d.2c.3e.4d.5e.6f, | 1d.2c.3e.4d.5f.6a, | 1d.2c.3e.4d.5f.6b, | 1d.2c.3e.4d.5f.6c, |
| 1d.2c.3e.4d.5f.6d, | 1d.2c.3e.4d.5f.6e, | 1d.2c.3e.4d.5f.6f, | 1d.2c.3e.4e.5a.6a, |
| 1d.2c.3e.4e.5a.6b, | 1d.2c.3e.4e.5a.6c, | 1d.2c.3e.4e.5a.6d, | 1d.2c.3e.4e.5a.6e, |
| 1d.2c.3e.4e.5a.6f, | 1d.2c.3e.4e.5b.6a, | 1d.2c.3e.4e.5b.6b, | 1d.2c.3e.4e.5b.6c, |
| 1d.2c.3e.4e.5b.6d, | 1d.2c.3e.4e.5b.6e, | 1d.2c.3e.4e.5b.6f, | 1d.2c.3e.4e.5c.6a, |
| 1d.2c.3e.4e.5c.6b, | 1d.2c.3e.4e.5c.6c, | 1d.2c.3e.4e.5c.6d, | 1d.2c.3e.4e.5c.6e, |
| 1d.2c.3e.4e.5c.6f, | 1d.2c.3e.4e.5d.6a, | 1d.2c.3e.4e.5d.6b, | 1d.2c.3e.4e.5d.6c, |
| 1d.2c.3e.4e.5d.6d, | 1d.2c.3e.4e.5d.6e, | 1d.2c.3e.4e.5d.6f, | 1d.2c.3e.4e.5e.6a, |
| 1d.2c.3e.4e.5e.6b, | 1d.2c.3e.4e.5e.6c, | 1d.2c.3e.4e.5e.6d, | 1d.2c.3e.4e.5e.6e, |
| 1d.2c.3e.4e.5e.6f, | 1d.2c.3e.4e.5f.6a, | 1d.2c.3e.4e.5f.6b, | 1d.2c.3e.4e.5f.6c, | 1d.2c.3e.4e.5f.6d, |
| 1d.2c.3e.4e.5f.6e, | 1d.2c.3e.4e.5f.6f, | 1d.2c.3e.4f.5a.6a, | 1d.2c.3e.4f.5a.6b, | 1d.2c.3e.4f.5a.6c, |
| 1d.2c.3e.4f.5a.6d, | 1d.2c.3e.4f.5a.6e, | 1d.2c.3e.4f.5a.6f, | 1d.2c.3e.4f.5b.6a, |
| 1d.2c.3e.4f.5b.6b, | 1d.2c.3e.4f.5b.6c, | 1d.2c.3e.4f.5b.6d, | 1d.2c.3e.4f.5b.6e, |
| 1d.2c.3e.4f.5b.6f, | 1d.2c.3e.4f.5c.6a, | 1d.2c.3e.4f.5c.6b, | 1d.2c.3e.4f.5c.6c, | 1d.2c.3e.4f.5c.6d, |
| 1d.2c.3e.4f.5c.6e, | 1d.2c.3e.4f.5c.6f, | 1d.2c.3e.4f.5d.6a, | 1d.2c.3e.4f.5d.6b, | 1d.2c.3e.4f.5d.6c, |
| 1d.2c.3e.4f.5d.6d, | 1d.2c.3e.4f.5d.6e, | 1d.2c.3e.4f.5d.6f, | 1d.2c.3e.4f.5e.6a, |
| 1d.2c.3e.4f.5e.6b, | 1d.2c.3e.4f.5e.6c, | 1d.2c.3e.4f.5e.6d, | 1d.2c.3e.4f.5e.6e, | 1d.2c.3e.4f.5e.6f, |
| 1d.2c.3e.4f.5f.6a, | 1d.2c.3e.4f.5f.6b, | 1d.2c.3e.4f.5f.6c, | 1d.2c.3e.4f.5f.6d, | 1d.2c.3e.4f.5f.6e, |
| 1d.2c.3e.4f.5f.6f, | 1d.2c.3f.4a.5a.6a, | 1d.2c.3f.4a.5a.6b, | 1d.2c.3f.4a.5a.6c, | 1d.2c.3f.4a.5a.6d, |
| 1d.2c.3f.4a.5a.6e, | 1d.2c.3f.4a.5a.6f, | 1d.2c.3f.4a.5b.6a, | 1d.2c.3f.4a.5b.6b, |
| 1d.2c.3f.4a.5b.6c, | 1d.2c.3f.4a.5b.6d, | 1d.2c.3f.4a.5b.6e, | 1d.2c.3f.4a.5b.6f, |
| 1d.2c.3f.4a.5c.6a, | 1d.2c.3f.4a.5c.6b, | 1d.2c.3f.4a.5c.6c, | 1d.2c.3f.4a.5c.6d, | 1d.2c.3f.4a.5c.6e, |
| 1d.2c.3f.4a.5c.6f, | 1d.2c.3f.4a.5d.6a, | 1d.2c.3f.4a.5d.6b, | 1d.2c.3f.4a.5d.6c, |
| 1d.2c.3f.4a.5d.6d, | 1d.2c.3f.4a.5d.6e, | 1d.2c.3f.4a.5d.6f, | 1d.2c.3f.4a.5e.6a, |
| 1d.2c.3f.4a.5e.6b, | 1d.2c.3f.4a.5e.6c, | 1d.2c.3f.4a.5e.6d, | 1d.2c.3f.4a.5e.6e, | 1d.2c.3f.4a.5e.6f, |
| 1d.2c.3f.4a.5f.6a, | 1d.2c.3f.4a.5f.6b, | 1d.2c.3f.4a.5f.6c, | 1d.2c.3f.4a.5f.6d, | 1d.2c.3f.4a.5f.6e, |
| 1d.2c.3f.4a.5f.6f, | 1d.2c.3f.4b.5a.6a, | 1d.2c.3f.4b.5a.6b, | 1d.2c.3f.4b.5a.6c, |
| 1d.2c.3f.4b.5a.6d, | 1d.2c.3f.4b.5a.6e, | 1d.2c.3f.4b.5a.6f, | 1d.2c.3f.4b.5b.6a, |
| 1d.2c.3f.4b.5b.6b, | 1d.2c.3f.4b.5b.6c, | 1d.2c.3f.4b.5b.6d, | 1d.2c.3f.4b.5b.6e, |
| 1d.2c.3f.4b.5b.6f, | 1d.2c.3f.4b.5c.6a, | 1d.2c.3f.4b.5c.6b, | 1d.2c.3f.4b.5c.6c, |
| 1d.2c.3f.4b.5c.6d, | 1d.2c.3f.4b.5c.6e, | 1d.2c.3f.4b.5c.6f, | 1d.2c.3f.4b.5d.6a, |
| 1d.2c.3f.4b.5d.6b, | 1d.2c.3f.4b.5d.6c, | 1d.2c.3f.4b.5d.6d, | 1d.2c.3f.4b.5d.6e, |
| 1d.2c.3f.4b.5d.6f, | 1d.2c.3f.4b.5e.6a, | 1d.2c.3f.4b.5e.6b, | 1d.2c.3f.4b.5e.6c, |
| 1d.2c.3f.4b.5e.6d, | 1d.2c.3f.4b.5e.6e, | 1d.2c.3f.4b.5e.6f, | 1d.2c.3f.4b.5f.6a, | 1d.2c.3f.4b.5f.6b, |
| 1d.2c.3f.4b.5f.6c, | 1d.2c.3f.4b.5f.6d, | 1d.2c.3f.4b.5f.6e, | 1d.2c.3f.4b.5f.6f, | 1d.2c.3f.4c.5a.6a, |
| 1d.2c.3f.4c.5a.6b, | 1d.2c.3f.4c.5a.6c, | 1d.2c.3f.4c.5a.6d, | 1d.2c.3f.4c.5a.6e, | 1d.2c.3f.4c.5a.6f, |
| 1d.2c.3f.4c.5b.6a, | 1d.2c.3f.4c.5b.6b, | 1d.2c.3f.4c.5b.6c, | 1d.2c.3f.4c.5b.6d, |
| 1d.2c.3f.4c.5b.6e, | 1d.2c.3f.4c.5b.6f, | 1d.2c.3f.4c.5c.6a, | 1d.2c.3f.4c.5c.6b, | 1d.2c.3f.4c.5c.6c, |
| 1d.2c.3f.4c.5c.6d, | 1d.2c.3f.4c.5c.6e, | 1d.2c.3f.4c.5c.6f, | 1d.2c.3f.4c.5d.6a, | 1d.2c.3f.4c.5d.6b, |
| 1d.2c.3f.4c.5d.6c, | 1d.2c.3f.4c.5d.6d, | 1d.2c.3f.4c.5d.6e, | 1d.2c.3f.4c.5d.6f, |
| 1d.2c.3f.4c.5e.6a, | 1d.2c.3f.4c.5e.6b, | 1d.2c.3f.4c.5e.6c, | 1d.2c.3f.4c.5e.6d, | 1d.2c.3f.4c.5e.6e, |
| 1d.2c.3f.4c.5e.6f, | 1d.2c.3f.4c.5f.6a, | 1d.2c.3f.4c.5f.6b, | 1d.2c.3f.4c.5f.6c, | 1d.2c.3f.4c.5f.6d, |
| 1d.2c.3f.4c.5f.6e, | 1d.2c.3f.4c.5f.6f, | 1d.2c.3f.4d.5a.6a, | 1d.2c.3f.4d.5a.6b, | 1d.2c.3f.4d.5a.6c, |
| 1d.2c.3f.4d.5a.6d, | 1d.2c.3f.4d.5a.6e, | 1d.2c.3f.4d.5a.6f, | 1d.2c.3f.4d.5b.6a, |
| 1d.2c.3f.4d.5b.6b, | 1d.2c.3f.4d.5b.6c, | 1d.2c.3f.4d.5b.6d, | 1d.2c.3f.4d.5b.6e, |
| 1d.2c.3f.4d.5b.6f, | 1d.2c.3f.4d.5c.6a, | 1d.2c.3f.4d.5c.6b, | 1d.2c.3f.4d.5c.6c, |
| 1d.2c.3f.4d.5c.6d, | 1d.2c.3f.4d.5c.6e, | 1d.2c.3f.4d.5c.6f, | 1d.2c.3f.4d.5d.6a, |
| 1d.2c.3f.4d.5d.6b, | 1d.2c.3f.4d.5d.6c, | 1d.2c.3f.4d.5d.6d, | 1d.2c.3f.4d.5d.6e, |
| 1d.2c.3f.4d.5d.6f, | 1d.2c.3f.4d.5e.6a, | 1d.2c.3f.4d.5e.6b, | 1d.2c.3f.4d.5e.6c, |
| 1d.2c.3f.4d.5e.6d, | 1d.2c.3f.4d.5e.6e, | 1d.2c.3f.4d.5e.6f, | 1d.2c.3f.4d.5f.6a, |
| 1d.2c.3f.4d.5f.6b, | 1d.2c.3f.4d.5f.6c, | 1d.2c.3f.4d.5f.6d, | 1d.2c.3f.4d.5f.6e, | 1d.2c.3f.4d.5f.6f, |
| 1d.2c.3f.4e.5a.6a, | 1d.2c.3f.4e.5a.6b, | 1d.2c.3f.4e.5a.6c, | 1d.2c.3f.4e.5a.6d, |
| 1d.2c.3f.4e.5a.6e, | 1d.2c.3f.4e.5a.6f, | 1d.2c.3f.4e.5b.6a, | 1d.2c.3f.4e.5b.6b, | 1d.2c.3f.4e.5b.6c, |
| 1d.2c.3f.4e.5b.6d, | 1d.2c.3f.4e.5b.6e, | 1d.2c.3f.4e.5b.6f, | 1d.2c.3f.4e.5c.6a, | 1d.2c.3f.4e.5c.6b, |
| 1d.2c.3f.4e.5c.6c, | 1d.2c.3f.4e.5c.6d, | 1d.2c.3f.4e.5c.6e, | 1d.2c.3f.4e.5c.6f, | 1d.2c.3f.4e.5d.6a, |
| 1d.2c.3f.4e.5d.6b, | 1d.2c.3f.4e.5d.6c, | 1d.2c.3f.4e.5d.6d, | 1d.2c.3f.4e.5d.6e, |
| 1d.2c.3f.4e.5d.6f, | 1d.2c.3f.4e.5e.6a, | 1d.2c.3f.4e.5e.6b, | 1d.2c.3f.4e.5e.6c, | 1d.2c.3f.4e.5e.6d, |
| 1d.2c.3f.4e.5e.6e, | 1d.2c.3f.4e.5e.6f, | 1d.2c.3f.4e.5f.6a, | 1d.2c.3f.4e.5f.6b, | 1d.2c.3f.4e.5f.6c, |
| 1d.2c.3f.4e.5f.6d, | 1d.2c.3f.4e.5f.6e, | 1d.2c.3f.4e.5f.6f, | 1d.2c.3f.4f.5a.6a, | 1d.2c.3f.4f.5a.6b, |
| 1d.2c.3f.4f.5a.6c, | 1d.2c.3f.4f.5a.6d, | 1d.2c.3f.4f.5a.6e, | 1d.2c.3f.4f.5a.6f, | 1d.2c.3f.4f.5b.6a, |
| 1d.2c.3f.4f.5b.6b, | 1d.2c.3f.4f.5b.6c, | 1d.2c.3f.4f.5b.6d, | 1d.2c.3f.4f.5b.6e, | 1d.2c.3f.4f.5b.6f, |
| 1d.2c.3f.4f.5c.6a, | 1d.2c.3f.4f.5c.6b, | 1d.2c.3f.4f.5c.6c, | 1d.2c.3f.4f.5c.6d, | 1d.2c.3f.4f.5c.6e, |
| 1d.2c.3f.4f.5c.6f, | 1d.2c.3f.4f.5d.6a, | 1d.2c.3f.4f.5d.6b, | 1d.2c.3f.4f.5d.6c, | 1d.2c.3f.4f.5d.6d, |
| 1d.2c.3f.4f.5d.6e, | 1d.2c.3f.4f.5d.6f, | 1d.2c.3f.4f.5e.6a, | 1d.2c.3f.4f.5e.6b, | 1d.2c.3f.4f.5e.6c, |
| 1d.2c.3f.4f.5e.6d, | 1d.2c.3f.4f.5e.6e, | 1d.2c.3f.4f.5e.6f, | 1d.2c.3f.4f.5f.6a, | 1d.2c.3f.4f.5f.6b, |
| 1d.2c.3f.4f.5f.6c, | 1d.2c.3f.4f.5f.6d, | 1d.2c.3f.4f.5f.6e, | 1d.2c.3f.4f.5f.6f, | 1d.2d.3a.4a.5a.6a, |
| 1d.2d.3a.4a.5a.6b, | 1d.2d.3a.4a.5a.6c, | 1d.2d.3a.4a.5a.6d, | 1d.2d.3a.4a.5a.6e, |
| 1d.2d.3a.4a.5a.6f, | 1d.2d.3a.4a.5b.6a, | 1d.2d.3a.4a.5b.6b, | 1d.2d.3a.4a.5b.6c, |
| 1d.2d.3a.4a.5b.6d, | 1d.2d.3a.4a.5b.6e, | 1d.2d.3a.4a.5b.6f, | 1d.2d.3a.4a.5c.6a, |
| 1d.2d.3a.4a.5c.6b, | 1d.2d.3a.4a.5c.6c, | 1d.2d.3a.4a.5c.6d, | 1d.2d.3a.4a.5c.6e, |
| 1d.2d.3a.4a.5c.6f, | 1d.2d.3a.4a.5d.6a, | 1d.2d.3a.4a.5d.6b, | 1d.2d.3a.4a.5d.6c, |
| 1d.2d.3a.4a.5d.6d, | 1d.2d.3a.4a.5d.6e, | 1d.2d.3a.4a.5d.6f, | 1d.2d.3a.4a.5e.6a, |
| 1d.2d.3a.4a.5e.6b, | 1d.2d.3a.4a.5e.6c, | 1d.2d.3a.4a.5e.6d, | 1d.2d.3a.4a.5e.6e, |
| 1d.2d.3a.4a.5e.6f, | 1d.2d.3a.4a.5f.6a, | 1d.2d.3a.4a.5f.6b, | 1d.2d.3a.4a.5f.6c, |

TABLE 7-continued

List of Compounds of Formula (II)

| | | | |
|---|---|---|---|
| 1d.2d.3a.4a.5f.6d, | 1d.2d.3a.4a.5f.6e, | 1d.2d.3a.4a.5f.6f, | 1d.2d.3a.4b.5a.6a, |
| 1d.2d.3a.4b.5a.6b, | 1d.2d.3a.4b.5a.6c, | 1d.2d.3a.4b.5a.6d, | 1d.2d.3a.4b.5a.6e, |
| 1d.2d.3a.4b.5a.6f, | 1d.2d.3a.4b.5b.6a, | 1d.2d.3a.4b.5b.6b, | 1d.2d.3a.4b.5b.6c, |
| 1d.2d.3a.4b.5b.6d, | 1d.2d.3a.4b.5b.6e, | 1d.2d.3a.4b.5b.6f, | 1d.2d.3a.4b.5c.6a, |
| 1d.2d.3a.4b.5c.6b, | 1d.2d.3a.4b.5c.6c, | 1d.2d.3a.4b.5c.6d, | 1d.2d.3a.4b.5c.6e, |
| 1d.2d.3a.4b.5c.6f, | 1d.2d.3a.4b.5d.6a, | 1d.2d.3a.4b.5d.6b, | 1d.2d.3a.4b.5d.6c, |
| 1d.2d.3a.4b.5d.6d, | 1d.2d.3a.4b.5d.6e, | 1d.2d.3a.4b.5d.6f, | 1d.2d.3a.4b.5e.6a, |
| 1d.2d.3a.4b.5e.6b, | 1d.2d.3a.4b.5e.6c, | 1d.2d.3a.4b.5e.6d, | 1d.2d.3a.4b.5e.6e, |
| 1d.2d.3a.4b.5e.6f, | 1d.2d.3a.4b.5f.6a, | 1d.2d.3a.4b.5f.6b, | 1d.2d.3a.4b.5f.6c, |
| 1d.2d.3a.4b.5f.6d, | 1d.2d.3a.4b.5f.6e, | 1d.2d.3a.4b.5f.6f, | 1d.2d.3a.4c.5a.6a, |
| 1d.2d.3a.4c.5a.6b, | 1d.2d.3a.4c.5a.6c, | 1d.2d.3a.4c.5a.6d, | 1d.2d.3a.4c.5a.6e, |
| 1d.2d.3a.4c.5a.6f, | 1d.2d.3a.4c.5b.6a, | 1d.2d.3a.4c.5b.6b, | 1d.2d.3a.4c.5b.6c, |
| 1d.2d.3a.4c.5b.6d, | 1d.2d.3a.4c.5b.6e, | 1d.2d.3a.4c.5b.6f, | 1d.2d.3a.4c.5c.6a, |
| 1d.2d.3a.4c.5c.6b, | 1d.2d.3a.4c.5c.6c, | 1d.2d.3a.4c.5c.6d, | 1d.2d.3a.4c.5c.6e, |
| 1d.2d.3a.4c.5c.6f, | 1d.2d.3a.4c.5d.6a, | 1d.2d.3a.4c.5d.6b, | 1d.2d.3a.4c.5d.6c, |
| 1d.2d.3a.4c.5d.6d, | 1d.2d.3a.4c.5d.6e, | 1d.2d.3a.4c.5d.6f, | 1d.2d.3a.4c.5e.6a, |
| 1d.2d.3a.4c.5e.6b, | 1d.2d.3a.4c.5e.6c, | 1d.2d.3a.4c.5e.6d, | 1d.2d.3a.4c.5e.6e, |
| 1d.2d.3a.4c.5e.6f, | 1d.2d.3a.4c.5f.6a, | 1d.2d.3a.4c.5f.6b, | 1d.2d.3a.4c.5f.6c, |
| 1d.2d.3a.4c.5f.6d, | 1d.2d.3a.4c.5f.6e, | 1d.2d.3a.4c.5f.6f, | 1d.2d.3a.4d.5a.6a, |
| 1d.2d.3a.4d.5a.6b, | 1d.2d.3a.4d.5a.6c, | 1d.2d.3a.4d.5a.6d, | 1d.2d.3a.4d.5a.6e, |
| 1d.2d.3a.4d.5a.6f, | 1d.2d.3a.4d.5b.6a, | 1d.2d.3a.4d.5b.6b, | 1d.2d.3a.4d.5b.6c, |
| 1d.2d.3a.4d.5b.6d, | 1d.2d.3a.4d.5b.6e, | 1d.2d.3a.4d.5b.6f, | 1d.2d.3a.4d.5c.6a, |
| 1d.2d.3a.4d.5c.6b, | 1d.2d.3a.4d.5c.6c, | 1d.2d.3a.4d.5c.6d, | 1d.2d.3a.4d.5c.6e, |
| 1d.2d.3a.4d.5c.6f, | 1d.2d.3a.4d.5d.6a, | 1d.2d.3a.4d.5d.6b, | 1d.2d.3a.4d.5d.6c, |
| 1d.2d.3a.4d.5d.6d, | 1d.2d.3a.4d.5d.6e, | 1d.2d.3a.4d.5d.6f, | 1d.2d.3a.4d.5e.6a, |
| 1d.2d.3a.4d.5e.6b, | 1d.2d.3a.4d.5e.6c, | 1d.2d.3a.4d.5e.6d, | 1d.2d.3a.4d.5e.6e, |
| 1d.2d.3a.4d.5e.6f, | 1d.2d.3a.4d.5f.6a, | 1d.2d.3a.4d.5f.6b, | 1d.2d.3a.4d.5f.6c, |
| 1d.2d.3a.4d.5f.6d, | 1d.2d.3a.4d.5f.6e, | 1d.2d.3a.4d.5f.6f, | 1d.2d.3a.4e.5a.6a, |
| 1d.2d.3a.4e.5a.6b, | 1d.2d.3a.4e.5a.6c, | 1d.2d.3a.4e.5a.6d, | 1d.2d.3a.4e.5a.6e, |
| 1d.2d.3a.4e.5a.6f, | 1d.2d.3a.4e.5b.6a, | 1d.2d.3a.4e.5b.6b, | 1d.2d.3a.4e.5b.6c, |
| 1d.2d.3a.4e.5b.6d, | 1d.2d.3a.4e.5b.6e, | 1d.2d.3a.4e.5b.6f, | 1d.2d.3a.4e.5c.6a, |
| 1d.2d.3a.4e.5c.6b, | 1d.2d.3a.4e.5c.6c, | 1d.2d.3a.4e.5c.6d, | 1d.2d.3a.4e.5c.6e, |
| 1d.2d.3a.4e.5c.6f, | 1d.2d.3a.4e.5d.6a, | 1d.2d.3a.4e.5d.6b, | 1d.2d.3a.4e.5d.6c, |
| 1d.2d.3a.4e.5d.6d, | 1d.2d.3a.4e.5d.6e, | 1d.2d.3a.4e.5d.6f, | 1d.2d.3a.4e.5e.6a, |
| 1d.2d.3a.4e.5e.6b, | 1d.2d.3a.4e.5e.6c, | 1d.2d.3a.4e.5e.6d, | 1d.2d.3a.4e.5e.6e, |
| 1d.2d.3a.4e.5e.6f, | 1d.2d.3a.4e.5f.6a, | 1d.2d.3a.4e.5f.6b, | 1d.2d.3a.4e.5f.6c, |
| 1d.2d.3a.4e.5f.6d, | 1d.2d.3a.4e.5f.6e, | 1d.2d.3a.4e.5f.6f, | 1d.2d.3a.4f.5a.6a, |
| 1d.2d.3a.4f.5a.6b, | 1d.2d.3a.4f.5a.6c, | 1d.2d.3a.4f.5a.6d, | 1d.2d.3a.4f.5a.6e, |
| 1d.2d.3a.4f.5a.6f, | 1d.2d.3a.4f.5b.6a, | 1d.2d.3a.4f.5b.6b, | 1d.2d.3a.4f.5b.6c, |
| 1d.2d.3a.4f.5b.6d, | 1d.2d.3a.4f.5b.6e, | 1d.2d.3a.4f.5b.6f, | 1d.2d.3a.4f.5c.6a, |
| 1d.2d.3a.4f.5c.6b, | 1d.2d.3a.4f.5c.6c, | 1d.2d.3a.4f.5c.6d, | 1d.2d.3a.4f.5c.6e, |
| 1d.2d.3a.4f.5c.6f, | 1d.2d.3a.4f.5d.6a, | 1d.2d.3a.4f.5d.6b, | 1d.2d.3a.4f.5d.6c, |
| 1d.2d.3a.4f.5d.6d, | 1d.2d.3a.4f.5d.6e, | 1d.2d.3a.4f.5d.6f, | 1d.2d.3a.4f.5e.6a, |
| 1d.2d.3a.4f.5e.6b, | 1d.2d.3a.4f.5e.6c, | 1d.2d.3a.4f.5e.6d, | 1d.2d.3a.4f.5e.6e, |
| 1d.2d.3a.4f.5e.6f, | 1d.2d.3a.4f.5f.6a, | 1d.2d.3a.4f.5f.6b, | 1d.2d.3a.4f.5f.6c, |
| 1d.2d.3a.4f.5f.6d, | 1d.2d.3a.4f.5f.6e, | 1d.2d.3a.4f.5f.6f, | 1d.2d.3b.4a.5a.6a, |
| 1d.2d.3b.4a.5a.6b, | 1d.2d.3b.4a.5a.6c, | 1d.2d.3b.4a.5a.6d, | 1d.2d.3b.4a.5a.6e, |
| 1d.2d.3b.4a.5a.6f, | 1d.2d.3b.4a.5b.6a, | 1d.2d.3b.4a.5b.6b, | 1d.2d.3b.4a.5b.6c, |
| 1d.2d.3b.4a.5b.6d, | 1d.2d.3b.4a.5b.6e, | 1d.2d.3b.4a.5b.6f, | 1d.2d.3b.4a.5c.6a, |
| 1d.2d.3b.4a.5c.6b, | 1d.2d.3b.4a.5c.6c, | 1d.2d.3b.4a.5c.6d, | 1d.2d.3b.4a.5c.6e, |
| 1d.2d.3b.4a.5c.6f, | 1d.2d.3b.4a.5d.6a, | 1d.2d.3b.4a.5d.6b, | 1d.2d.3b.4a.5d.6c, |
| 1d.2d.3b.4a.5d.6d, | 1d.2d.3b.4a.5d.6e, | 1d.2d.3b.4a.5d.6f, | 1d.2d.3b.4a.5e.6a, |
| 1d.2d.3b.4a.5e.6b, | 1d.2d.3b.4a.5e.6c, | 1d.2d.3b.4a.5e.6d, | 1d.2d.3b.4a.5e.6e, |
| 1d.2d.3b.4a.5e.6f, | 1d.2d.3b.4a.5f.6a, | 1d.2d.3b.4a.5f.6b, | 1d.2d.3b.4a.5f.6c, |
| 1d.2d.3b.4a.5f.6d, | 1d.2d.3b.4a.5f.6e, | 1d.2d.3b.4a.5f.6f, | 1d.2d.3b.4b.5a.6a, |
| 1d.2d.3b.4b.5a.6b, | 1d.2d.3b.4b.5a.6c, | 1d.2d.3b.4b.5a.6d, | 1d.2d.3b.4b.5a.6e, |
| 1d.2d.3b.4b.5a.6f, | 1d.2d.3b.4b.5b.6a, | 1d.2d.3b.4b.5b.6b, | 1d.2d.3b.4b.5b.6c, |
| 1d.2d.3b.4b.5b.6d, | 1d.2d.3b.4b.5b.6e, | 1d.2d.3b.4b.5b.6f, | 1d.2d.3b.4b.5c.6a, |
| 1d.2d.3b.4b.5c.6b, | 1d.2d.3b.4b.5c.6c, | 1d.2d.3b.4b.5c.6d, | 1d.2d.3b.4b.5c.6e, |
| 1d.2d.3b.4b.5c.6f, | 1d.2d.3b.4b.5d.6a, | 1d.2d.3b.4b.5d.6b, | 1d.2d.3b.4b.5d.6c, |
| 1d.2d.3b.4b.5d.6d, | 1d.2d.3b.4b.5d.6e, | 1d.2d.3b.4b.5d.6f, | 1d.2d.3b.4b.5e.6a, |
| 1d.2d.3b.4b.5e.6b, | 1d.2d.3b.4b.5e.6c, | 1d.2d.3b.4b.5e.6d, | 1d.2d.3b.4b.5e.6e, |
| 1d.2d.3b.4b.5e.6f, | 1d.2d.3b.4b.5f.6a, | 1d.2d.3b.4b.5f.6b, | 1d.2d.3b.4b.5f.6c, |
| 1d.2d.3b.4b.5f.6d, | 1d.2d.3b.4b.5f.6e, | 1d.2d.3b.4b.5f.6f, | 1d.2d.3b.4c.5a.6a, |
| 1d.2d.3b.4c.5a.6b, | 1d.2d.3b.4c.5a.6c, | 1d.2d.3b.4c.5a.6d, | 1d.2d.3b.4c.5a.6e, |
| 1d.2d.3b.4c.5a.6f, | 1d.2d.3b.4c.5b.6a, | 1d.2d.3b.4c.5b.6b, | 1d.2d.3b.4c.5b.6c, |
| 1d.2d.3b.4c.5b.6d, | 1d.2d.3b.4c.5b.6e, | 1d.2d.3b.4c.5b.6f, | 1d.2d.3b.4c.5c.6a, |
| 1d.2d.3b.4c.5c.6b, | 1d.2d.3b.4c.5c.6c, | 1d.2d.3b.4c.5c.6d, | 1d.2d.3b.4c.5c.6e, |
| 1d.2d.3b.4c.5c.6f, | 1d.2d.3b.4c.5d.6a, | 1d.2d.3b.4c.5d.6b, | 1d.2d.3b.4c.5d.6c, |
| 1d.2d.3b.4c.5d.6d, | 1d.2d.3b.4c.5d.6e, | 1d.2d.3b.4c.5d.6f, | 1d.2d.3b.4c.5e.6a, |
| 1d.2d.3b.4c.5e.6b, | 1d.2d.3b.4c.5e.6c, | 1d.2d.3b.4c.5e.6d, | 1d.2d.3b.4c.5e.6e, |
| 1d.2d.3b.4c.5e.6f, | 1d.2d.3b.4c.5f.6a, | 1d.2d.3b.4c.5f.6b, | 1d.2d.3b.4c.5f.6c, |
| 1d.2d.3b.4c.5f.6d, | 1d.2d.3b.4c.5f.6e, | 1d.2d.3b.4c.5f.6f, | 1d.2d.3b.4d.5a.6a, |
| 1d.2d.3b.4d.5a.6b, | 1d.2d.3b.4d.5a.6c, | 1d.2d.3b.4d.5a.6d, | 1d.2d.3b.4d.5a.6e, |
| 1d.2d.3b.4d.5a.6f, | 1d.2d.3b.4d.5b.6a, | 1d.2d.3b.4d.5b.6b, | 1d.2d.3b.4d.5b.6c, |
| 1d.2d.3b.4d.5b.6d, | 1d.2d.3b.4d.5b.6e, | 1d.2d.3b.4d.5b.6f, | 1d.2d.3b.4d.5c.6a, |
| 1d.2d.3b.4d.5c.6b, | 1d.2d.3b.4d.5c.6c, | 1d.2d.3b.4d.5c.6d, | 1d.2d.3b.4d.5c.6e, |
| 1d.2d.3b.4d.5c.6f, | 1d.2d.3b.4d.5d.6a, | 1d.2d.3b.4d.5d.6b, | 1d.2d.3b.4d.5d.6c, |

TABLE 7-continued

List of Compounds of Formula (II)

| | | | | |
|---|---|---|---|---|
| 1d.2d.3b.4d.5d.6d, | 1d.2d.3b.4d.5d.6e, | 1d.2d.3b.4d.5d.6f, | 1d.2d.3b.4d.5e.6a, | |
| 1d.2d.3b.4d.5e.6b, | 1d.2d.3b.4d.5e.6c, | 1d.2d.3b.4d.5e.6d, | 1d.2d.3b.4d.5e.6e, | |
| 1d.2d.3b.4d.5e.6f, | 1d.2d.3b.4d.5f.6a, | 1d.2d.3b.4d.5f.6b, | 1d.2d.3b.4d.5f.6c, | |
| 1d.2d.3b.4d.5f.6d, | 1d.2d.3b.4d.5f.6e, | 1d.2d.3b.4d.5f.6f, | 1d.2d.3b.4e.5a.6a, | |
| 1d.2d.3b.4e.5a.6b, | 1d.2d.3b.4e.5a.6c, | 1d.2d.3b.4e.5a.6d, | 1d.2d.3b.4e.5a.6e, | |
| 1d.2d.3b.4e.5a.6f, | 1d.2d.3b.4e.5b.6a, | 1d.2d.3b.4e.5b.6b, | 1d.2d.3b.4e.5b.6c, | |
| 1d.2d.3b.4e.5b.6d, | 1d.2d.3b.4e.5b.6e, | 1d.2d.3b.4e.5b.6f, | 1d.2d.3b.4e.5c.6a, | |
| 1d.2d.3b.4e.5c.6b, | 1d.2d.3b.4e.5c.6c, | 1d.2d.3b.4e.5c.6d, | 1d.2d.3b.4e.5c.6e, | |
| 1d.2d.3b.4e.5c.6f, | 1d.2d.3b.4e.5d.6a, | 1d.2d.3b.4e.5d.6b, | 1d.2d.3b.4e.5d.6c, | |
| 1d.2d.3b.4e.5d.6d, | 1d.2d.3b.4e.5d.6e, | 1d.2d.3b.4e.5d.6f, | 1d.2d.3b.4e.5e.6a, | |
| 1d.2d.3b.4e.5e.6b, | 1d.2d.3b.4e.5e.6c, | 1d.2d.3b.4e.5e.6d, | 1d.2d.3b.4e.5e.6e, | |
| 1d.2d.3b.4e.5e.6f, | 1d.2d.3b.4e.5f.6a, | 1d.2d.3b.4e.5f.6b, | 1d.2d.3b.4e.5f.6c, | |
| 1d.2d.3b.4e.5f.6d, | 1d.2d.3b.4e.5f.6e, | 1d.2d.3b.4e.5f.6f, | 1d.2d.3b.4f.5a.6a, | |
| 1d.2d.3b.4f.5a.6b, | 1d.2d.3b.4f.5a.6c, | 1d.2d.3b.4f.5a.6d, | 1d.2d.3b.4f.5a.6e, | |
| 1d.2d.3b.4f.5a.6f, | 1d.2d.3b.4f.5b.6a, | 1d.2d.3b.4f.5b.6b, | 1d.2d.3b.4f.5b.6c, | |
| 1d.2d.3b.4f.5b.6d, | 1d.2d.3b.4f.5b.6e, | 1d.2d.3b.4f.5b.6f, | 1d.2d.3b.4f.5c.6a, | |
| 1d.2d.3b.4f.5c.6b, | 1d.2d.3b.4f.5c.6c, | 1d.2d.3b.4f.5c.6d, | 1d.2d.3b.4f.5c.6e, | |
| 1d.2d.3b.4f.5c.6f, | 1d.2d.3b.4f.5d.6a, | 1d.2d.3b.4f.5d.6b, | 1d.2d.3b.4f.5d.6c, | |
| 1d.2d.3b.4f.5d.6d, | 1d.2d.3b.4f.5d.6e, | 1d.2d.3b.4f.5d.6f, | 1d.2d.3b.4f.5e.6a, | |
| 1d.2d.3b.4f.5e.6b, | 1d.2d.3b.4f.5e.6c, | 1d.2d.3b.4f.5e.6d, | 1d.2d.3b.4f.5e.6e, | |
| 1d.2d.3b.4f.5e.6f, | 1d.2d.3b.4f.5f.6a, | 1d.2d.3b.4f.5f.6b, | 1d.2d.3b.4f.5f.6c, | |
| 1d.2d.3b.4f.5f.6d, | 1d.2d.3b.4f.5f.6e, | 1d.2d.3b.4f.5f.6f, | 1d.2d.3c.4a.5a.6a, | |
| 1d.2d.3c.4a.5a.6b, | 1d.2d.3c.4a.5a.6c, | 1d.2d.3c.4a.5a.6d, | 1d.2d.3c.4a.5a.6e, | |
| 1d.2d.3c.4a.5a.6f, | 1d.2d.3c.4a.5b.6a, | 1d.2d.3c.4a.5b.6b, | 1d.2d.3c.4a.5b.6c, | |
| 1d.2d.3c.4a.5b.6d, | 1d.2d.3c.4a.5b.6e, | 1d.2d.3c.4a.5b.6f, | 1d.2d.3c.4a.5c.6a, | |
| 1d.2d.3c.4a.5c.6b, | 1d.2d.3c.4a.5c.6c, | 1d.2d.3c.4a.5c.6d, | 1d.2d.3c.4a.5c.6e, | |
| 1d.2d.3c.4a.5c.6f, | 1d.2d.3c.4a.5d.6a, | 1d.2d.3c.4a.5d.6b, | 1d.2d.3c.4a.5d.6c, | |
| 1d.2d.3c.4a.5d.6d, | 1d.2d.3c.4a.5d.6e, | 1d.2d.3c.4a.5d.6f, | 1d.2d.3c.4a.5e.6a, | |
| 1d.2d.3c.4a.5e.6b, | 1d.2d.3c.4a.5e.6c, | 1d.2d.3c.4a.5e.6d, | 1d.2d.3c.4a.5e.6e, | |
| 1d.2d.3c.4a.5e.6f, | 1d.2d.3c.4a.5f.6a, | 1d.2d.3c.4a.5f.6b, | 1d.2d.3c.4a.5f.6c, | |
| 1d.2d.3c.4a.5f.6d, | 1d.2d.3c.4a.5f.6e, | 1d.2d.3c.4a.5f.6f, | 1d.2d.3c.4b.5a.6a, | |
| 1d.2d.3c.4b.5a.6b, | 1d.2d.3c.4b.5a.6c, | 1d.2d.3c.4b.5a.6d, | 1d.2d.3c.4b.5a.6e, | |
| 1d.2d.3c.4b.5a.6f, | 1d.2d.3c.4b.5b.6a, | 1d.2d.3c.4b.5b.6b, | 1d.2d.3c.4b.5b.6c, | |
| 1d.2d.3c.4b.5b.6d, | 1d.2d.3c.4b.5b.6e, | 1d.2d.3c.4b.5b.6f, | 1d.2d.3c.4b.5c.6a, | |
| 1d.2d.3c.4b.5c.6b, | 1d.2d.3c.4b.5c.6c, | 1d.2d.3c.4b.5c.6d, | 1d.2d.3c.4b.5c.6e, | |
| 1d.2d.3c.4b.5c.6f, | 1d.2d.3c.4b.5d.6a, | 1d.2d.3c.4b.5d.6b, | 1d.2d.3c.4b.5d.6c, | |
| 1d.2d.3c.4b.5d.6d, | 1d.2d.3c.4b.5d.6e, | 1d.2d.3c.4b.5d.6f, | 1d.2d.3c.4b.5e.6a, | |
| 1d.2d.3c.4b.5e.6b, | 1d.2d.3c.4b.5e.6c, | 1d.2d.3c.4b.5e.6d, | 1d.2d.3c.4b.5e.6e, | |
| 1d.2d.3c.4b.5e.6f, | 1d.2d.3c.4b.5f.6a, | 1d.2d.3c.4b.5f.6b, | 1d.2d.3c.4b.5f.6c, | |
| 1d.2d.3c.4b.5f.6d, | 1d.2d.3c.4b.5f.6e, | 1d.2d.3c.4b.5f.6f, | 1d.2d.3c.4c.5a.6a, | |
| 1d.2d.3c.4c.5a.6b, | 1d.2d.3c.4c.5a.6c, | 1d.2d.3c.4c.5a.6d, | 1d.2d.3c.4c.5a.6e, | |
| 1d.2d.3c.4c.5a.6f, | 1d.2d.3c.4c.5b.6a, | 1d.2d.3c.4c.5b.6b, | 1d.2d.3c.4c.5b.6c, | |
| 1d.2d.3c.4c.5b.6d, | 1d.2d.3c.4c.5b.6e, | 1d.2d.3c.4c.5b.6f, | 1d.2d.3c.4c.5c.6a, | |
| 1d.2d.3c.4c.5c.6b, | 1d.2d.3c.4c.5c.6c, | 1d.2d.3c.4c.5c.6d, | 1d.2d.3c.4c.5c.6e, | |
| 1d.2d.3c.4c.5c.6f, | 1d.2d.3c.4c.5d.6a, | 1d.2d.3c.4c.5d.6b, | 1d.2d.3c.4c.5d.6c, | |
| 1d.2d.3c.4c.5d.6d, | 1d.2d.3c.4c.5d.6e, | 1d.2d.3c.4c.5d.6f, | 1d.2d.3c.4c.5e.6a, | |
| 1d.2d.3c.4c.5e.6b, | 1d.2d.3c.4c.5e.6c, | 1d.2d.3c.4c.5e.6d, | 1d.2d.3c.4c.5e.6e, | |
| 1d.2d.3c.4c.5e.6f, | 1d.2d.3c.4c.5f.6a, | 1d.2d.3c.4c.5f.6b, | 1d.2d.3c.4c.5f.6c, | |
| 1d.2d.3c.4c.5f.6d, | 1d.2d.3c.4c.5f.6e, | 1d.2d.3c.4c.5f.6f, | 1d.2d.3c.4d.5a.6a, | |
| 1d.2d.3c.4d.5a.6b, | 1d.2d.3c.4d.5a.6c, | 1d.2d.3c.4d.5a.6d, | 1d.2d.3c.4d.5a.6e, | |
| 1d.2d.3c.4d.5a.6f, | 1d.2d.3c.4d.5b.6a, | 1d.2d.3c.4d.5b.6b, | 1d.2d.3c.4d.5b.6c, | |
| 1d.2d.3c.4d.5b.6d, | 1d.2d.3c.4d.5b.6e, | 1d.2d.3c.4d.5b.6f, | 1d.2d.3c.4d.5c.6a, | |
| 1d.2d.3c.4d.5c.6b, | 1d.2d.3c.4d.5c.6c, | 1d.2d.3c.4d.5c.6d, | 1d.2d.3c.4d.5c.6e, | |
| 1d.2d.3c.4d.5c.6f, | 1d.2d.3c.4d.5d.6a, | 1d.2d.3c.4d.5d.6b, | 1d.2d.3c.4d.5d.6c, | |
| 1d.2d.3c.4d.5d.6d, | 1d.2d.3c.4d.5d.6e, | 1d.2d.3c.4d.5d.6f, | 1d.2d.3c.4d.5e.6a, | |
| 1d.2d.3c.4d.5e.6b, | 1d.2d.3c.4d.5e.6c, | 1d.2d.3c.4d.5e.6d, | 1d.2d.3c.4d.5e.6e, | |
| 1d.2d.3c.4d.5e.6f, | 1d.2d.3c.4d.5f.6a, | 1d.2d.3c.4d.5f.6b, | 1d.2d.3c.4d.5f.6c, | |
| 1d.2d.3c.4d.5f.6d, | 1d.2d.3c.4d.5f.6e, | 1d.2d.3c.4d.5f.6f, | 1d.2d.3c.4e.5a.6a, | |
| 1d.2d.3c.4e.5a.6b, | 1d.2d.3c.4e.5a.6c, | 1d.2d.3c.4e.5a.6d, | 1d.2d.3c.4e.5a.6e, | |
| 1d.2d.3c.4e.5a.6f, | 1d.2d.3c.4e.5b.6a, | 1d.2d.3c.4e.5b.6b, | 1d.2d.3c.4e.5b.6c, | |
| 1d.2d.3c.4e.5b.6d, | 1d.2d.3c.4e.5b.6e, | 1d.2d.3c.4e.5b.6f, | 1d.2d.3c.4e.5c.6a, | |
| 1d.2d.3c.4e.5c.6b, | 1d.2d.3c.4e.5c.6c, | 1d.2d.3c.4e.5c.6d, | 1d.2d.3c.4e.5c.6e, | |
| 1d.2d.3c.4e.5c.6f, | 1d.2d.3c.4e.5d.6a, | 1d.2d.3c.4e.5d.6b, | 1d.2d.3c.4e.5d.6c, | |
| 1d.2d.3c.4e.5d.6d, | 1d.2d.3c.4e.5d.6e, | 1d.2d.3c.4e.5d.6f, | 1d.2d.3c.4e.5e.6a, | |
| 1d.2d.3c.4e.5e.6b, | 1d.2d.3c.4e.5e.6c, | 1d.2d.3c.4e.5e.6d, | 1d.2d.3c.4e.5e.6e, | |
| 1d.2d.3c.4e.5e.6f, | 1d.2d.3c.4e.5f.6a, | 1d.2d.3c.4e.5f.6b, | 1d.2d.3c.4e.5f.6c, | |
| 1d.2d.3c.4e.5f.6d, | 1d.2d.3c.4e.5f.6e, | 1d.2d.3c.4e.5f.6f, | 1d.2d.3c.4f.5a.6a, | |
| 1d.2d.3c.4f.5a.6b, | 1d.2d.3c.4f.5a.6c, | 1d.2d.3c.4f.5a.6d, | 1d.2d.3c.4f.5a.6e, | |
| 1d.2d.3c.4f.5a.6f, | 1d.2d.3c.4f.5b.6a, | 1d.2d.3c.4f.5b.6b, | 1d.2d.3c.4f.5b.6c, | |
| 1d.2d.3c.4f.5b.6d, | 1d.2d.3c.4f.5b.6e, | 1d.2d.3c.4f.5b.6f, | 1d.2d.3c.4f.5c.6a, | |
| 1d.2d.3c.4f.5c.6b, | 1d.2d.3c.4f.5c.6c, | 1d.2d.3c.4f.5c.6d, | 1d.2d.3c.4f.5c.6e, | |
| 1d.2d.3c.4f.5c.6f, | 1d.2d.3c.4f.5d.6a, | 1d.2d.3c.4f.5d.6b, | 1d.2d.3c.4f.5d.6c, | |
| 1d.2d.3c.4f.5d.6d, | 1d.2d.3c.4f.5d.6e, | 1d.2d.3c.4f.5d.6f, | 1d.2d.3c.4f.5e.6a, | |
| 1d.2d.3c.4f.5e.6b, | 1d.2d.3c.4f.5e.6c, | 1d.2d.3c.4f.5e.6d, | 1d.2d.3c.4f.5e.6e, | |
| 1d.2d.3c.4f.5e.6f, | 1d.2d.3c.4f.5f.6a, | 1d.2d.3c.4f.5f.6b, | 1d.2d.3c.4f.5f.6c, | 1d.2d.3c.4f.5f.6d, |
| 1d.2d.3c.4f.5f.6e, | 1d.2d.3c.4f.5f.6f, | 1d.2d.3d.4a.5a.6a, | 1d.2d.3d.4a.5a.6b, | |
| 1d.2d.3d.4a.5a.6c, | 1d.2d.3d.4a.5a.6d, | 1d.2d.3d.4a.5a.6e, | 1d.2d.3d.4a.5a.6f, | |
| 1d.2d.3d.4a.5b.6a, | 1d.2d.3d.4a.5b.6b, | 1d.2d.3d.4a.5b.6c, | 1d.2d.3d.4a.5b.6d, | |

TABLE 7-continued

List of Compounds of Formula (II)

| | | | |
|---|---|---|---|
| 1d.2d.3d.4a.5b.6e, | 1d.2d.3d.4a.5b.6f, | 1d.2d.3d.4a.5c.6a, | 1d.2d.3d.4a.5c.6b, |
| 1d.2d.3d.4a.5c.6c, | 1d.2d.3d.4a.5c.6d, | 1d.2d.3d.4a.5c.6e, | 1d.2d.3d.4a.5c.6f, |
| 1d.2d.3d.4a.5d.6a, | 1d.2d.3d.4a.5d.6b, | 1d.2d.3d.4a.5d.6c, | 1d.2d.3d.4a.5d.6d, |
| 1d.2d.3d.4a.5d.6e, | 1d.2d.3d.4a.5d.6f, | 1d.2d.3d.4a.5e.6a, | 1d.2d.3d.4a.5e.6b, |
| 1d.2d.3d.4a.5e.6c, | 1d.2d.3d.4a.5e.6d, | 1d.2d.3d.4a.5e.6e, | 1d.2d.3d.4a.5e.6f, |
| 1d.2d.3d.4a.5f.6a, | 1d.2d.3d.4a.5f.6b, | 1d.2d.3d.4a.5f.6c, | 1d.2d.3d.4a.5f.6d, |
| 1d.2d.3d.4a.5f.6e, | 1d.2d.3d.4a.5f.6f, | 1d.2d.3d.4b.5a.6a, | 1d.2d.3d.4b.5a.6b, |
| 1d.2d.3d.4b.5a.6c, | 1d.2d.3d.4b.5a.6d, | 1d.2d.3d.4b.5a.6e, | 1d.2d.3d.4b.5a.6f, |
| 1d.2d.3d.4b.5b.6a, | 1d.2d.3d.4b.5b.6b, | 1d.2d.3d.4b.5b.6c, | 1d.2d.3d.4b.5b.6d, |
| 1d.2d.3d.4b.5b.6e, | 1d.2d.3d.4b.5b.6f, | 1d.2d.3d.4b.5c.6a, | 1d.2d.3d.4b.5c.6b, |
| 1d.2d.3d.4b.5c.6c, | 1d.2d.3d.4b.5c.6d, | 1d.2d.3d.4b.5c.6e, | 1d.2d.3d.4b.5c.6f, |
| 1d.2d.3d.4b.5d.6a, | 1d.2d.3d.4b.5d.6b, | 1d.2d.3d.4b.5d.6c, | 1d.2d.3d.4b.5d.6d, |
| 1d.2d.3d.4b.5d.6e, | 1d.2d.3d.4b.5d.6f, | 1d.2d.3d.4b.5e.6a, | 1d.2d.3d.4b.5e.6b, |
| 1d.2d.3d.4b.5e.6c, | 1d.2d.3d.4b.5e.6d, | 1d.2d.3d.4b.5e.6e, | 1d.2d.3d.4b.5e.6f, |
| 1d.2d.3d.4b.5f.6a, | 1d.2d.3d.4b.5f.6b, | 1d.2d.3d.4b.5f.6c, | 1d.2d.3d.4b.5f.6d, |
| 1d.2d.3d.4b.5f.6e, | 1d.2d.3d.4b.5f.6f, | 1d.2d.3d.4c.5a.6a, | 1d.2d.3d.4c.5a.6b, |
| 1d.2d.3d.4c.5a.6c, | 1d.2d.3d.4c.5a.6d, | 1d.2d.3d.4c.5a.6e, | 1d.2d.3d.4c.5a.6f, |
| 1d.2d.3d.4c.5b.6a, | 1d.2d.3d.4c.5b.6b, | 1d.2d.3d.4c.5b.6c, | 1d.2d.3d.4c.5b.6d, |
| 1d.2d.3d.4c.5b.6e, | 1d.2d.3d.4c.5b.6f, | 1d.2d.3d.4c.5c.6a, | 1d.2d.3d.4c.5c.6b, |
| 1d.2d.3d.4c.5c.6c, | 1d.2d.3d.4c.5c.6d, | 1d.2d.3d.4c.5c.6e, | 1d.2d.3d.4c.5c.6f, |
| 1d.2d.3d.4c.5d.6a, | 1d.2d.3d.4c.5d.6b, | 1d.2d.3d.4c.5d.6c, | 1d.2d.3d.4c.5d.6d, |
| 1d.2d.3d.4c.5d.6e, | 1d.2d.3d.4c.5d.6f, | 1d.2d.3d.4c.5e.6a, | 1d.2d.3d.4c.5e.6b, |
| 1d.2d.3d.4c.5e.6c, | 1d.2d.3d.4c.5e.6d, | 1d.2d.3d.4c.5e.6e, | 1d.2d.3d.4c.5e.6f, |
| 1d.2d.3d.4c.5f.6a, | 1d.2d.3d.4c.5f.6b, | 1d.2d.3d.4c.5f.6c, | 1d.2d.3d.4c.5f.6d, |
| 1d.2d.3d.4c.5f.6e, | 1d.2d.3d.4c.5f.6f, | 1d.2d.3d.4d.5a.6a, | 1d.2d.3d.4d.5a.6b, |
| 1d.2d.3d.4d.5a.6c, | 1d.2d.3d.4d.5a.6d, | 1d.2d.3d.4d.5a.6e, | 1d.2d.3d.4d.5a.6f, |
| 1d.2d.3d.4d.5b.6a, | 1d.2d.3d.4d.5b.6b, | 1d.2d.3d.4d.5b.6c, | 1d.2d.3d.4d.5b.6d, |
| 1d.2d.3d.4d.5b.6e, | 1d.2d.3d.4d.5b.6f, | 1d.2d.3d.4d.5c.6a, | 1d.2d.3d.4d.5c.6b, |
| 1d.2d.3d.4d.5c.6c, | 1d.2d.3d.4d.5c.6d, | 1d.2d.3d.4d.5c.6e, | 1d.2d.3d.4d.5c.6f, |
| 1d.2d.3d.4d.5d.6a, | 1d.2d.3d.4d.5d.6b, | 1d.2d.3d.4d.5d.6c, | 1d.2d.3d.4d.5d.6d, |
| 1d.2d.3d.4d.5d.6e, | 1d.2d.3d.4d.5d.6f, | 1d.2d.3d.4d.5e.6a, | 1d.2d.3d.4d.5e.6b, |
| 1d.2d.3d.4d.5e.6c, | 1d.2d.3d.4d.5e.6d, | 1d.2d.3d.4d.5e.6e, | 1d.2d.3d.4d.5e.6f, |
| 1d.2d.3d.4d.5f.6a, | 1d.2d.3d.4d.5f.6b, | 1d.2d.3d.4d.5f.6c, | 1d.2d.3d.4d.5f.6d, |
| 1d.2d.3d.4d.5f.6e, | 1d.2d.3d.4d.5f.6f, | 1d.2d.3d.4e.5a.6a, | 1d.2d.3d.4e.5a.6b, |
| 1d.2d.3d.4e.5a.6c, | 1d.2d.3d.4e.5a.6d, | 1d.2d.3d.4e.5a.6e, | 1d.2d.3d.4e.5a.6f, |
| 1d.2d.3d.4e.5b.6a, | 1d.2d.3d.4e.5b.6b, | 1d.2d.3d.4e.5b.6c, | 1d.2d.3d.4e.5b.6d, |
| 1d.2d.3d.4e.5b.6e, | 1d.2d.3d.4e.5b.6f, | 1d.2d.3d.4e.5c.6a, | 1d.2d.3d.4e.5c.6b, |
| 1d.2d.3d.4e.5c.6c, | 1d.2d.3d.4e.5c.6d, | 1d.2d.3d.4e.5c.6e, | 1d.2d.3d.4e.5c.6f, |
| 1d.2d.3d.4e.5d.6a, | 1d.2d.3d.4e.5d.6b, | 1d.2d.3d.4e.5d.6c, | 1d.2d.3d.4e.5d.6d, |
| 1d.2d.3d.4e.5d.6e, | 1d.2d.3d.4e.5d.6f, | 1d.2d.3d.4e.5e.6a, | 1d.2d.3d.4e.5e.6b, |
| 1d.2d.3d.4e.5e.6c, | 1d.2d.3d.4e.5e.6d, | 1d.2d.3d.4e.5e.6e, | 1d.2d.3d.4e.5e.6f, |
| 1d.2d.3d.4e.5f.6a, | 1d.2d.3d.4e.5f.6b, | 1d.2d.3d.4e.5f.6c, | 1d.2d.3d.4e.5f.6d, |
| 1d.2d.3d.4e.5f.6e, | 1d.2d.3d.4e.5f.6f, | 1d.2d.3d.4f.5a.6a, | 1d.2d.3d.4f.5a.6b, |
| 1d.2d.3d.4f.5a.6c, | 1d.2d.3d.4f.5a.6d, | 1d.2d.3d.4f.5a.6e, | 1d.2d.3d.4f.5a.6f, |
| 1d.2d.3d.4f.5b.6a, | 1d.2d.3d.4f.5b.6b, | 1d.2d.3d.4f.5b.6c, | 1d.2d.3d.4f.5b.6d, |
| 1d.2d.3d.4f.5b.6e, | 1d.2d.3d.4f.5b.6f, | 1d.2d.3d.4f.5c.6a, | 1d.2d.3d.4f.5c.6b, |
| 1d.2d.3d.4f.5c.6c, | 1d.2d.3d.4f.5c.6d, | 1d.2d.3d.4f.5c.6e, | 1d.2d.3d.4f.5c.6f, |
| 1d.2d.3d.4f.5d.6a, | 1d.2d.3d.4f.5d.6b, | 1d.2d.3d.4f.5d.6c, | 1d.2d.3d.4f.5d.6d, |
| 1d.2d.3d.4f.5d.6e, | 1d.2d.3d.4f.5d.6f, | 1d.2d.3d.4f.5e.6a, | 1d.2d.3d.4f.5e.6b, |
| 1d.2d.3d.4f.5e.6c, | 1d.2d.3d.4f.5e.6d, | 1d.2d.3d.4f.5e.6e, | 1d.2d.3d.4f.5e.6f, |
| 1d.2d.3d.4f.5f.6a, | 1d.2d.3d.4f.5f.6b, | 1d.2d.3d.4f.5f.6c, | 1d.2d.3d.4f.5f.6d, |
| 1d.2d.3d.4f.5f.6e, | 1d.2d.3d.4f.5f.6f, | 1d.2d.3e.4a.5a.6a, | 1d.2d.3e.4a.5a.6b, |
| 1d.2d.3e.4a.5a.6c, | 1d.2d.3e.4a.5a.6d, | 1d.2d.3e.4a.5a.6e, | 1d.2d.3e.4a.5a.6f, |
| 1d.2d.3e.4a.5b.6a, | 1d.2d.3e.4a.5b.6b, | 1d.2d.3e.4a.5b.6c, | 1d.2d.3e.4a.5b.6d, |
| 1d.2d.3e.4a.5b.6e, | 1d.2d.3e.4a.5b.6f, | 1d.2d.3e.4a.5c.6a, | 1d.2d.3e.4a.5c.6b, |
| 1d.2d.3e.4a.5c.6c, | 1d.2d.3e.4a.5c.6d, | 1d.2d.3e.4a.5c.6e, | 1d.2d.3e.4a.5c.6f, |
| 1d.2d.3e.4a.5d.6a, | 1d.2d.3e.4a.5d.6b, | 1d.2d.3e.4a.5d.6c, | 1d.2d.3e.4a.5d.6d, |
| 1d.2d.3e.4a.5d.6e, | 1d.2d.3e.4a.5d.6f, | 1d.2d.3e.4a.5e.6a, | 1d.2d.3e.4a.5e.6b, |
| 1d.2d.3e.4a.5e.6c, | 1d.2d.3e.4a.5e.6d, | 1d.2d.3e.4a.5e.6e, | 1d.2d.3e.4a.5e.6f, |
| 1d.2d.3e.4a.5f.6a, | 1d.2d.3e.4a.5f.6b, | 1d.2d.3e.4a.5f.6c, | 1d.2d.3e.4a.5f.6d, |
| 1d.2d.3e.4a.5f.6e, | 1d.2d.3e.4a.5f.6f, | 1d.2d.3e.4b.5a.6a, | 1d.2d.3e.4b.5a.6b, |
| 1d.2d.3e.4b.5a.6c, | 1d.2d.3e.4b.5a.6d, | 1d.2d.3e.4b.5a.6e, | 1d.2d.3e.4b.5a.6f, |
| 1d.2d.3e.4b.5b.6a, | 1d.2d.3e.4b.5b.6b, | 1d.2d.3e.4b.5b.6c, | 1d.2d.3e.4b.5b.6d, |
| 1d.2d.3e.4b.5b.6e, | 1d.2d.3e.4b.5b.6f, | 1d.2d.3e.4b.5c.6a, | 1d.2d.3e.4b.5c.6b, |
| 1d.2d.3e.4b.5c.6c, | 1d.2d.3e.4b.5c.6d, | 1d.2d.3e.4b.5c.6e, | 1d.2d.3e.4b.5c.6f, |
| 1d.2d.3e.4b.5d.6a, | 1d.2d.3e.4b.5d.6b, | 1d.2d.3e.4b.5d.6c, | 1d.2d.3e.4b.5d.6d, |
| 1d.2d.3e.4b.5d.6e, | 1d.2d.3e.4b.5d.6f, | 1d.2d.3e.4b.5e.6a, | 1d.2d.3e.4b.5e.6b, |
| 1d.2d.3e.4b.5e.6c, | 1d.2d.3e.4b.5e.6d, | 1d.2d.3e.4b.5e.6e, | 1d.2d.3e.4b.5e.6f, |
| 1d.2d.3e.4b.5f.6a, | 1d.2d.3e.4b.5f.6b, | 1d.2d.3e.4b.5f.6c, | 1d.2d.3e.4b.5f.6d, |
| 1d.2d.3e.4b.5f.6e, | 1d.2d.3e.4b.5f.6f, | 1d.2d.3e.4c.5a.6a, | 1d.2d.3e.4c.5a.6b, |
| 1d.2d.3e.4c.5a.6c, | 1d.2d.3e.4c.5a.6d, | 1d.2d.3e.4c.5a.6e, | 1d.2d.3e.4c.5a.6f, |
| 1d.2d.3e.4c.5b.6a, | 1d.2d.3e.4c.5b.6b, | 1d.2d.3e.4c.5b.6c, | 1d.2d.3e.4c.5b.6d, |
| 1d.2d.3e.4c.5b.6e, | 1d.2d.3e.4c.5b.6f, | 1d.2d.3e.4c.5c.6a, | 1d.2d.3e.4c.5c.6b, |
| 1d.2d.3e.4c.5c.6c, | 1d.2d.3e.4c.5c.6d, | 1d.2d.3e.4c.5c.6e, | 1d.2d.3e.4c.5c.6f, |
| 1d.2d.3e.4c.5d.6a, | 1d.2d.3e.4c.5d.6b, | 1d.2d.3e.4c.5d.6c, | 1d.2d.3e.4c.5d.6d, |
| 1d.2d.3e.4c.5d.6e, | 1d.2d.3e.4c.5d.6f, | 1d.2d.3e.4c.5e.6a, | 1d.2d.3e.4c.5e.6b, |
| 1d.2d.3e.4c.5e.6c, | 1d.2d.3e.4c.5e.6d, | 1d.2d.3e.4c.5e.6e, | 1d.2d.3e.4c.5e.6f, |
| 1d.2d.3e.4c.5f.6a, | 1d.2d.3e.4c.5f.6b, | 1d.2d.3e.4c.5f.6c, | 1d.2d.3e.4c.5f.6d, |

TABLE 7-continued

List of Compounds of Formula (II)

| | | | | |
|---|---|---|---|---|
| 1d.2d.3e.4c.5f.6e, | 1d.2d.3e.4c.5f.6f, | 1d.2d.3e.4d.5a.6a, | 1d.2d.3e.4d.5a.6b, | |
| 1d.2d.3e.4d.5a.6c, | 1d.2d.3e.4d.5a.6d, | 1d.2d.3e.4d.5a.6e, | 1d.2d.3e.4d.5a.6f, | |
| 1d.2d.3e.4d.5b.6a, | 1d.2d.3e.4d.5b.6b, | 1d.2d.3e.4d.5b.6c, | 1d.2d.3e.4d.5b.6d, | |
| 1d.2d.3e.4d.5b.6e, | 1d.2d.3e.4d.5b.6f, | 1d.2d.3e.4d.5c.6a, | 1d.2d.3e.4d.5c.6b, | |
| 1d.2d.3e.4d.5c.6c, | 1d.2d.3e.4d.5c.6d, | 1d.2d.3e.4d.5c.6e, | 1d.2d.3e.4d.5c.6f, | |
| 1d.2d.3e.4d.5d.6a, | 1d.2d.3e.4d.5d.6b, | 1d.2d.3e.4d.5d.6c, | 1d.2d.3e.4d.5d.6d, | |
| 1d.2d.3e.4d.5d.6e, | 1d.2d.3e.4d.5d.6f, | 1d.2d.3e.4d.5e.6a, | 1d.2d.3e.4d.5e.6b, | |
| 1d.2d.3e.4d.5e.6c, | 1d.2d.3e.4d.5e.6d, | 1d.2d.3e.4d.5e.6e, | 1d.2d.3e.4d.5e.6f, | |
| 1d.2d.3e.4d.5f.6a, | 1d.2d.3e.4d.5f.6b, | 1d.2d.3e.4d.5f.6c, | 1d.2d.3e.4d.5f.6d, | |
| 1d.2d.3e.4d.5f.6e, | 1d.2d.3e.4d.5f.6f, | 1d.2d.3e.4e.5a.6a, | 1d.2d.3e.4e.5a.6b, | |
| 1d.2d.3e.4e.5a.6c, | 1d.2d.3e.4e.5a.6d, | 1d.2d.3e.4e.5a.6e, | 1d.2d.3e.4e.5a.6f, | |
| 1d.2d.3e.4e.5b.6a, | 1d.2d.3e.4e.5b.6b, | 1d.2d.3e.4e.5b.6c, | 1d.2d.3e.4e.5b.6d, | |
| 1d.2d.3e.4e.5b.6e, | 1d.2d.3e.4e.5b.6f, | 1d.2d.3e.4e.5c.6a, | 1d.2d.3e.4e.5c.6b, | |
| 1d.2d.3e.4e.5c.6c, | 1d.2d.3e.4e.5c.6d, | 1d.2d.3e.4e.5c.6e, | 1d.2d.3e.4e.5c.6f, | |
| 1d.2d.3e.4e.5d.6a, | 1d.2d.3e.4e.5d.6b, | 1d.2d.3e.4e.5d.6c, | 1d.2d.3e.4e.5d.6d, | |
| 1d.2d.3e.4e.5d.6e, | 1d.2d.3e.4e.5d.6f, | 1d.2d.3e.4e.5e.6a, | 1d.2d.3e.4e.5e.6b, | |
| 1d.2d.3e.4e.5e.6c, | 1d.2d.3e.4e.5e.6d, | 1d.2d.3e.4e.5e.6e, | 1d.2d.3e.4e.5e.6f, | |
| 1d.2d.3e.4e.5f.6a, | 1d.2d.3e.4e.5f.6b, | 1d.2d.3e.4e.5f.6c, | 1d.2d.3e.4e.5f.6d, | |
| 1d.2d.3e.4e.5f.6e, | 1d.2d.3e.4e.5f.6f, | 1d.2d.3e.4f.5a.6a, | 1d.2d.3e.4f.5a.6b, | |
| 1d.2d.3e.4f.5a.6c, | 1d.2d.3e.4f.5a.6d, | 1d.2d.3e.4f.5a.6e, | 1d.2d.3e.4f.5a.6f, | |
| 1d.2d.3e.4f.5b.6a, | 1d.2d.3e.4f.5b.6b, | 1d.2d.3e.4f.5b.6c, | 1d.2d.3e.4f.5b.6d, | |
| 1d.2d.3e.4f.5b.6e, | 1d.2d.3e.4f.5b.6f, | 1d.2d.3e.4f.5c.6a, | 1d.2d.3e.4f.5c.6b, | |
| 1d.2d.3e.4f.5c.6c, | 1d.2d.3e.4f.5c.6d, | 1d.2d.3e.4f.5c.6e, | 1d.2d.3e.4f.5c.6f, | |
| 1d.2d.3e.4f.5d.6a, | 1d.2d.3e.4f.5d.6b, | 1d.2d.3e.4f.5d.6c, | 1d.2d.3e.4f.5d.6d, | |
| 1d.2d.3e.4f.5d.6e, | 1d.2d.3e.4f.5d.6f, | 1d.2d.3e.4f.5e.6a, | 1d.2d.3e.4f.5e.6b, | |
| 1d.2d.3e.4f.5e.6c, | 1d.2d.3e.4f.5e.6d, | 1d.2d.3e.4f.5e.6e, | 1d.2d.3e.4f.5e.6f, | |
| 1d.2d.3e.4f.5f.6a, | 1d.2d.3e.4f.5f.6b, | 1d.2d.3e.4f.5f.6c, | 1d.2d.3e.4f.5f.6d, | |
| 1d.2d.3e.4f.5f.6e, | 1d.2d.3e.4f.5f.6f, | 1d.2d.3f.4a.5a.6a, | 1d.2d.3f.4a.5a.6b, | |
| 1d.2d.3f.4a.5a.6c, | 1d.2d.3f.4a.5a.6d, | 1d.2d.3f.4a.5a.6e, | 1d.2d.3f.4a.5a.6f, | |
| 1d.2d.3f.4a.5b.6a, | 1d.2d.3f.4a.5b.6b, | 1d.2d.3f.4a.5b.6c, | 1d.2d.3f.4a.5b.6d, | |
| 1d.2d.3f.4a.5b.6e, | 1d.2d.3f.4a.5b.6f, | 1d.2d.3f.4a.5c.6a, | 1d.2d.3f.4a.5c.6b, | |
| 1d.2d.3f.4a.5c.6c, | 1d.2d.3f.4a.5c.6d, | 1d.2d.3f.4a.5c.6e, | 1d.2d.3f.4a.5c.6f, | |
| 1d.2d.3f.4a.5d.6a, | 1d.2d.3f.4a.5d.6b, | 1d.2d.3f.4a.5d.6c, | 1d.2d.3f.4a.5d.6d, | |
| 1d.2d.3f.4a.5d.6e, | 1d.2d.3f.4a.5d.6f, | 1d.2d.3f.4a.5e.6a, | 1d.2d.3f.4a.5e.6b, | |
| 1d.2d.3f.4a.5e.6c, | 1d.2d.3f.4a.5e.6d, | 1d.2d.3f.4a.5e.6e, | 1d.2d.3f.4a.5e.6f, | |
| 1d.2d.3f.4a.5f.6a, | 1d.2d.3f.4a.5f.6b, | 1d.2d.3f.4a.5f.6c, | 1d.2d.3f.4a.5f.6d, | |
| 1d.2d.3f.4a.5f.6e, | 1d.2d.3f.4a.5f.6f, | 1d.2d.3f.4b.5a.6a, | 1d.2d.3f.4b.5a.6b, | |
| 1d.2d.3f.4b.5a.6c, | 1d.2d.3f.4b.5a.6d, | 1d.2d.3f.4b.5a.6e, | 1d.2d.3f.4b.5a.6f, | |
| 1d.2d.3f.4b.5b.6a, | 1d.2d.3f.4b.5b.6b, | 1d.2d.3f.4b.5b.6c, | 1d.2d.3f.4b.5b.6d, | |
| 1d.2d.3f.4b.5b.6e, | 1d.2d.3f.4b.5b.6f, | 1d.2d.3f.4b.5c.6a, | 1d.2d.3f.4b.5c.6b, | |
| 1d.2d.3f.4b.5c.6c, | 1d.2d.3f.4b.5c.6d, | 1d.2d.3f.4b.5c.6e, | 1d.2d.3f.4b.5c.6f, | |
| 1d.2d.3f.4b.5d.6a, | 1d.2d.3f.4b.5d.6b, | 1d.2d.3f.4b.5d.6c, | 1d.2d.3f.4b.5d.6d, | |
| 1d.2d.3f.4b.5d.6e, | 1d.2d.3f.4b.5d.6f, | 1d.2d.3f.4b.5e.6a, | 1d.2d.3f.4b.5e.6b, | |
| 1d.2d.3f.4b.5e.6c, | 1d.2d.3f.4b.5e.6d, | 1d.2d.3f.4b.5e.6e, | 1d.2d.3f.4b.5e.6f, | |
| 1d.2d.3f.4b.5f.6a, | 1d.2d.3f.4b.5f.6b, | 1d.2d.3f.4b.5f.6c, | 1d.2d.3f.4b.5f.6d, | |
| 1d.2d.3f.4b.5f.6e, | 1d.2d.3f.4b.5f.6f, | 1d.2d.3f.4c.5a.6a, | 1d.2d.3f.4c.5a.6b, | |
| 1d.2d.3f.4c.5a.6c, | 1d.2d.3f.4c.5a.6d, | 1d.2d.3f.4c.5a.6e, | 1d.2d.3f.4c.5a.6f, | |
| 1d.2d.3f.4c.5b.6a, | 1d.2d.3f.4c.5b.6b, | 1d.2d.3f.4c.5b.6c, | 1d.2d.3f.4c.5b.6d, | |
| 1d.2d.3f.4c.5b.6e, | 1d.2d.3f.4c.5b.6f, | 1d.2d.3f.4c.5c.6a, | 1d.2d.3f.4c.5c.6b, | |
| 1d.2d.3f.4c.5c.6c, | 1d.2d.3f.4c.5c.6d, | 1d.2d.3f.4c.5c.6e, | 1d.2d.3f.4c.5c.6f, | |
| 1d.2d.3f.4c.5d.6a, | 1d.2d.3f.4c.5d.6b, | 1d.2d.3f.4c.5d.6c, | 1d.2d.3f.4c.5d.6d, | |
| 1d.2d.3f.4c.5d.6e, | 1d.2d.3f.4c.5d.6f, | 1d.2d.3f.4c.5e.6a, | 1d.2d.3f.4c.5e.6b, | |
| 1d.2d.3f.4c.5e.6c, | 1d.2d.3f.4c.5e.6d, | 1d.2d.3f.4c.5e.6e, | 1d.2d.3f.4c.5e.6f, | |
| 1d.2d.3f.4c.5f.6a, | 1d.2d.3f.4c.5f.6b, | 1d.2d.3f.4c.5f.6c, | 1d.2d.3f.4c.5f.6d, | 1d.2d.3f.4c.5f.6e, |
| 1d.2d.3f.4c.5f.6f, | 1d.2d.3f.4d.5a.6a, | 1d.2d.3f.4d.5a.6b, | 1d.2d.3f.4d.5a.6c, | |
| 1d.2d.3f.4d.5a.6d, | 1d.2d.3f.4d.5a.6e, | 1d.2d.3f.4d.5a.6f, | 1d.2d.3f.4d.5b.6a, | |
| 1d.2d.3f.4d.5b.6b, | 1d.2d.3f.4d.5b.6c, | 1d.2d.3f.4d.5b.6d, | 1d.2d.3f.4d.5b.6e, | |
| 1d.2d.3f.4d.5b.6f, | 1d.2d.3f.4d.5c.6a, | 1d.2d.3f.4d.5c.6b, | 1d.2d.3f.4d.5c.6c, | |
| 1d.2d.3f.4d.5c.6d, | 1d.2d.3f.4d.5c.6e, | 1d.2d.3f.4d.5c.6f, | 1d.2d.3f.4d.5d.6a, | |
| 1d.2d.3f.4d.5d.6b, | 1d.2d.3f.4d.5d.6c, | 1d.2d.3f.4d.5d.6d, | 1d.2d.3f.4d.5d.6e, | |
| 1d.2d.3f.4d.5d.6f, | 1d.2d.3f.4d.5e.6a, | 1d.2d.3f.4d.5e.6b, | 1d.2d.3f.4d.5e.6c, | |
| 1d.2d.3f.4d.5e.6d, | 1d.2d.3f.4d.5e.6e, | 1d.2d.3f.4d.5e.6f, | 1d.2d.3f.4d.5f.6a, | |
| 1d.2d.3f.4d.5f.6b, | 1d.2d.3f.4d.5f.6c, | 1d.2d.3f.4d.5f.6d, | 1d.2d.3f.4d.5f.6e, | |
| 1d.2d.3f.4d.5f.6f, | 1d.2d.3f.4e.5a.6a, | 1d.2d.3f.4e.5a.6b, | 1d.2d.3f.4e.5a.6c, | |
| 1d.2d.3f.4e.5a.6d, | 1d.2d.3f.4e.5a.6e, | 1d.2d.3f.4e.5a.6f, | 1d.2d.3f.4e.5b.6a, | |
| 1d.2d.3f.4e.5b.6b, | 1d.2d.3f.4e.5b.6c, | 1d.2d.3f.4e.5b.6d, | 1d.2d.3f.4e.5b.6e, | |
| 1d.2d.3f.4e.5b.6f, | 1d.2d.3f.4e.5c.6a, | 1d.2d.3f.4e.5c.6b, | 1d.2d.3f.4e.5c.6c, | |
| 1d.2d.3f.4e.5c.6d, | 1d.2d.3f.4e.5c.6e, | 1d.2d.3f.4e.5c.6f, | 1d.2d.3f.4e.5d.6a, | |
| 1d.2d.3f.4e.5d.6b, | 1d.2d.3f.4e.5d.6c, | 1d.2d.3f.4e.5d.6d, | 1d.2d.3f.4e.5d.6e, | |
| 1d.2d.3f.4e.5d.6f, | 1d.2d.3f.4e.5e.6a, | 1d.2d.3f.4e.5e.6b, | 1d.2d.3f.4e.5e.6c, | |
| 1d.2d.3f.4e.5e.6d, | 1d.2d.3f.4e.5e.6e, | 1d.2d.3f.4e.5e.6f, | 1d.2d.3f.4e.5f.6a, | |
| 1d.2d.3f.4e.5f.6b, | 1d.2d.3f.4e.5f.6c, | 1d.2d.3f.4e.5f.6d, | 1d.2d.3f.4e.5f.6e, | 1d.2d.3f.4e.5f.6f, |
| 1d.2d.3f.4f.5a.6a, | 1d.2d.3f.4f.5a.6b, | 1d.2d.3f.4f.5a.6c, | 1d.2d.3f.4f.5a.6d, | |
| 1d.2d.3f.4f.5a.6e, | 1d.2d.3f.4f.5a.6f, | 1d.2d.3f.4f.5b.6a, | 1d.2d.3f.4f.5b.6b, | |
| 1d.2d.3f.4f.5b.6c, | 1d.2d.3f.4f.5b.6d, | 1d.2d.3f.4f.5b.6e, | 1d.2d.3f.4f.5b.6f, | |
| 1d.2d.3f.4f.5c.6a, | 1d.2d.3f.4f.5c.6b, | 1d.2d.3f.4f.5c.6c, | 1d.2d.3f.4f.5c.6d, | 1d.2d.3f.4f.5c.6e, |
| 1d.2d.3f.4f.5c.6f, | 1d.2d.3f.4f.5d.6a, | 1d.2d.3f.4f.5d.6b, | 1d.2d.3f.4f.5d.6c, | |
| 1d.2d.3f.4f.5d.6d, | 1d.2d.3f.4f.5d.6e, | 1d.2d.3f.4f.5d.6f, | 1d.2d.3f.4f.5e.6a, | |

TABLE 7-continued

List of Compounds of Formula (II)

| | | | | |
|---|---|---|---|---|
| 1d.2d.3f.4f.5e.6b, | 1d.2d.3f.4f.5e.6c, | 1d.2d.3f.4f.5e.6d, | 1d.2d.3f.4f.5e.6e, | 1d.2d.3f.4f.5e.6f, |
| 1d.2d.3f.4f.5f.6a, | 1d.2d.3f.4f.5f.6b, | 1d.2d.3f.4f.5f.6c, | 1d.2d.3f.4f.5f.6d, | 1d.2d.3f.4f.5f.6e, |
| 1d.2d.3f.4f.5f.6f, | 1d.2e.3a.4a.5a.6a, | 1d.2e.3a.4a.5a.6b, | 1d.2e.3a.4a.5a.6c, | |
| 1d.2e.3a.4a.5a.6d, | 1d.2e.3a.4a.5a.6e, | 1d.2e.3a.4a.5a.6f, | 1d.2e.3a.4a.5b.6a, | |
| 1d.2e.3a.4a.5b.6b, | 1d.2e.3a.4a.5b.6c, | 1d.2e.3a.4a.5b.6d, | 1d.2e.3a.4a.5b.6e, | |
| 1d.2e.3a.4a.5b.6f, | 1d.2e.3a.4a.5c.6a, | 1d.2e.3a.4a.5c.6b, | 1d.2e.3a.4a.5c.6c, | |
| 1d.2e.3a.4a.5c.6d, | 1d.2e.3a.4a.5c.6e, | 1d.2e.3a.4a.5c.6f, | 1d.2e.3a.4a.5d.6a, | |
| 1d.2e.3a.4a.5d.6b, | 1d.2e.3a.4a.5d.6c, | 1d.2e.3a.4a.5d.6d, | 1d.2e.3a.4a.5d.6e, | |
| 1d.2e.3a.4a.5d.6f, | 1d.2e.3a.4a.5e.6a, | 1d.2e.3a.4a.5e.6b, | 1d.2e.3a.4a.5e.6c, | |
| 1d.2e.3a.4a.5e.6d, | 1d.2e.3a.4a.5e.6e, | 1d.2e.3a.4a.5e.6f, | 1d.2e.3a.4a.5f.6a, | |
| 1d.2e.3a.4a.5f.6b, | 1d.2e.3a.4a.5f.6c, | 1d.2e.3a.4a.5f.6d, | 1d.2e.3a.4a.5f.6e, | |
| 1d.2e.3a.4a.5f.6f, | 1d.2e.3a.4b.5a.6a, | 1d.2e.3a.4b.5a.6b, | 1d.2e.3a.4b.5a.6c, | |
| 1d.2e.3a.4b.5a.6d, | 1d.2e.3a.4b.5a.6e, | 1d.2e.3a.4b.5a.6f, | 1d.2e.3a.4b.5b.6a, | |
| 1d.2e.3a.4b.5b.6b, | 1d.2e.3a.4b.5b.6c, | 1d.2e.3a.4b.5b.6d, | 1d.2e.3a.4b.5b.6e, | |
| 1d.2e.3a.4b.5b.6f, | 1d.2e.3a.4b.5c.6a, | 1d.2e.3a.4b.5c.6b, | 1d.2e.3a.4b.5c.6c, | |
| 1d.2e.3a.4b.5c.6d, | 1d.2e.3a.4b.5c.6e, | 1d.2e.3a.4b.5c.6f, | 1d.2e.3a.4b.5d.6a, | |
| 1d.2e.3a.4b.5d.6b, | 1d.2e.3a.4b.5d.6c, | 1d.2e.3a.4b.5d.6d, | 1d.2e.3a.4b.5d.6e, | |
| 1d.2e.3a.4b.5d.6f, | 1d.2e.3a.4b.5e.6a, | 1d.2e.3a.4b.5e.6b, | 1d.2e.3a.4b.5e.6c, | |
| 1d.2e.3a.4b.5e.6d, | 1d.2e.3a.4b.5e.6e, | 1d.2e.3a.4b.5e.6f, | 1d.2e.3a.4b.5f.6a, | |
| 1d.2e.3a.4b.5f.6b, | 1d.2e.3a.4b.5f.6c, | 1d.2e.3a.4b.5f.6d, | 1d.2e.3a.4b.5f.6e, | |
| 1d.2e.3a.4b.5f.6f, | 1d.2e.3a.4c.5a.6a, | 1d.2e.3a.4c.5a.6b, | 1d.2e.3a.4c.5a.6c, | |
| 1d.2e.3a.4c.5a.6d, | 1d.2e.3a.4c.5a.6e, | 1d.2e.3a.4c.5a.6f, | 1d.2e.3a.4c.5b.6a, | |
| 1d.2e.3a.4c.5b.6b, | 1d.2e.3a.4c.5b.6c, | 1d.2e.3a.4c.5b.6d, | 1d.2e.3a.4c.5b.6e, | |
| 1d.2e.3a.4c.5b.6f, | 1d.2e.3a.4c.5c.6a, | 1d.2e.3a.4c.5c.6b, | 1d.2e.3a.4c.5c.6c, | |
| 1d.2e.3a.4c.5c.6d, | 1d.2e.3a.4c.5c.6e, | 1d.2e.3a.4c.5c.6f, | 1d.2e.3a.4c.5d.6a, | |
| 1d.2e.3a.4c.5d.6b, | 1d.2e.3a.4c.5d.6c, | 1d.2e.3a.4c.5d.6d, | 1d.2e.3a.4c.5d.6e, | |
| 1d.2e.3a.4c.5d.6f, | 1d.2e.3a.4c.5e.6a, | 1d.2e.3a.4c.5e.6b, | 1d.2e.3a.4c.5e.6c, | |
| 1d.2e.3a.4c.5e.6d, | 1d.2e.3a.4c.5e.6e, | 1d.2e.3a.4c.5e.6f, | 1d.2e.3a.4c.5f.6a, | |
| 1d.2e.3a.4c.5f.6b, | 1d.2e.3a.4c.5f.6c, | 1d.2e.3a.4c.5f.6d, | 1d.2e.3a.4c.5f.6e, | 1d.2e.3a.4c.5f.6f, |
| 1d.2e.3a.4d.5a.6a, | 1d.2e.3a.4d.5a.6b, | 1d.2e.3a.4d.5a.6c, | 1d.2e.3a.4d.5a.6d, | |
| 1d.2e.3a.4d.5a.6e, | 1d.2e.3a.4d.5a.6f, | 1d.2e.3a.4d.5b.6a, | 1d.2e.3a.4d.5b.6b, | |
| 1d.2e.3a.4d.5b.6c, | 1d.2e.3a.4d.5b.6d, | 1d.2e.3a.4d.5b.6e, | 1d.2e.3a.4d.5b.6f, | |
| 1d.2e.3a.4d.5c.6a, | 1d.2e.3a.4d.5c.6b, | 1d.2e.3a.4d.5c.6c, | 1d.2e.3a.4d.5c.6d, | |
| 1d.2e.3a.4d.5c.6e, | 1d.2e.3a.4d.5c.6f, | 1d.2e.3a.4d.5d.6a, | 1d.2e.3a.4d.5d.6b, | |
| 1d.2e.3a.4d.5d.6c, | 1d.2e.3a.4d.5d.6d, | 1d.2e.3a.4d.5d.6e, | 1d.2e.3a.4d.5d.6f, | |
| 1d.2e.3a.4d.5e.6a, | 1d.2e.3a.4d.5e.6b, | 1d.2e.3a.4d.5e.6c, | 1d.2e.3a.4d.5e.6d, | |
| 1d.2e.3a.4d.5e.6e, | 1d.2e.3a.4d.5e.6f, | 1d.2e.3a.4d.5f.6a, | 1d.2e.3a.4d.5f.6b, | |
| 1d.2e.3a.4d.5f.6c, | 1d.2e.3a.4d.5f.6d, | 1d.2e.3a.4d.5f.6e, | 1d.2e.3a.4d.5f.6f, | |
| 1d.2e.3a.4e.5a.6a, | 1d.2e.3a.4e.5a.6b, | 1d.2e.3a.4e.5a.6c, | 1d.2e.3a.4e.5a.6d, | |
| 1d.2e.3a.4e.5a.6e, | 1d.2e.3a.4e.5a.6f, | 1d.2e.3a.4e.5b.6a, | 1d.2e.3a.4e.5b.6b, | |
| 1d.2e.3a.4e.5b.6c, | 1d.2e.3a.4e.5b.6d, | 1d.2e.3a.4e.5b.6e, | 1d.2e.3a.4e.5b.6f, | |
| 1d.2e.3a.4e.5c.6a, | 1d.2e.3a.4e.5c.6b, | 1d.2e.3a.4e.5c.6c, | 1d.2e.3a.4e.5c.6d, | |
| 1d.2e.3a.4e.5c.6e, | 1d.2e.3a.4e.5c.6f, | 1d.2e.3a.4e.5d.6a, | 1d.2e.3a.4e.5d.6b, | |
| 1d.2e.3a.4e.5d.6c, | 1d.2e.3a.4e.5d.6d, | 1d.2e.3a.4e.5d.6e, | 1d.2e.3a.4e.5d.6f, | |
| 1d.2e.3a.4e.5e.6a, | 1d.2e.3a.4e.5e.6b, | 1d.2e.3a.4e.5e.6c, | 1d.2e.3a.4e.5e.6d, | |
| 1d.2e.3a.4e.5e.6e, | 1d.2e.3a.4e.5e.6f, | 1d.2e.3a.4e.5f.6a, | 1d.2e.3a.4e.5f.6b, | |
| 1d.2e.3a.4e.5f.6c, | 1d.2e.3a.4e.5f.6d, | 1d.2e.3a.4e.5f.6e, | 1d.2e.3a.4e.5f.6f, | |
| 1d.2e.3a.4f.5a.6a, | 1d.2e.3a.4f.5a.6b, | 1d.2e.3a.4f.5a.6c, | 1d.2e.3a.4f.5a.6d, | |
| 1d.2e.3a.4f.5a.6e, | 1d.2e.3a.4f.5a.6f, | 1d.2e.3a.4f.5b.6a, | 1d.2e.3a.4f.5b.6b, | |
| 1d.2e.3a.4f.5b.6c, | 1d.2e.3a.4f.5b.6d, | 1d.2e.3a.4f.5b.6e, | 1d.2e.3a.4f.5b.6f, | |
| 1d.2e.3a.4f.5c.6a, | 1d.2e.3a.4f.5c.6b, | 1d.2e.3a.4f.5c.6c, | 1d.2e.3a.4f.5c.6d, | |
| 1d.2e.3a.4f.5c.6e, | 1d.2e.3a.4f.5c.6f, | 1d.2e.3a.4f.5d.6a, | 1d.2e.3a.4f.5d.6b, | |
| 1d.2e.3a.4f.5d.6c, | 1d.2e.3a.4f.5d.6d, | 1d.2e.3a.4f.5d.6e, | 1d.2e.3a.4f.5d.6f, | |
| 1d.2e.3a.4f.5e.6a, | 1d.2e.3a.4f.5e.6b, | 1d.2e.3a.4f.5e.6c, | 1d.2e.3a.4f.5e.6d, | |
| 1d.2e.3a.4f.5e.6e, | 1d.2e.3a.4f.5e.6f, | 1d.2e.3a.4f.5f.6a, | 1d.2e.3a.4f.5f.6b, | 1d.2e.3a.4f.5f.6c, |
| 1d.2e.3a.4f.5f.6d, | 1d.2e.3a.4f.5f.6e, | 1d.2e.3a.4f.5f.6f, | 1d.2e.3b.4a.5a.6a, | |
| 1d.2e.3b.4a.5a.6b, | 1d.2e.3b.4a.5a.6c, | 1d.2e.3b.4a.5a.6d, | 1d.2e.3b.4a.5a.6e, | |
| 1d.2e.3b.4a.5a.6f, | 1d.2e.3b.4a.5b.6a, | 1d.2e.3b.4a.5b.6b, | 1d.2e.3b.4a.5b.6c, | |
| 1d.2e.3b.4a.5b.6d, | 1d.2e.3b.4a.5b.6e, | 1d.2e.3b.4a.5b.6f, | 1d.2e.3b.4a.5c.6a, | |
| 1d.2e.3b.4a.5c.6b, | 1d.2e.3b.4a.5c.6c, | 1d.2e.3b.4a.5c.6d, | 1d.2e.3b.4a.5c.6e, | |
| 1d.2e.3b.4a.5c.6f, | 1d.2e.3b.4a.5d.6a, | 1d.2e.3b.4a.5d.6b, | 1d.2e.3b.4a.5d.6c, | |
| 1d.2e.3b.4a.5d.6d, | 1d.2e.3b.4a.5d.6e, | 1d.2e.3b.4a.5d.6f, | 1d.2e.3b.4a.5e.6a, | |
| 1d.2e.3b.4a.5e.6b, | 1d.2e.3b.4a.5e.6c, | 1d.2e.3b.4a.5e.6d, | 1d.2e.3b.4a.5e.6e, | |
| 1d.2e.3b.4a.5e.6f, | 1d.2e.3b.4a.5f.6a, | 1d.2e.3b.4a.5f.6b, | 1d.2e.3b.4a.5f.6c, | |
| 1d.2e.3b.4a.5f.6d, | 1d.2e.3b.4a.5f.6e, | 1d.2e.3b.4a.5f.6f, | 1d.2e.3b.4b.5a.6a, | |
| 1d.2e.3b.4b.5a.6b, | 1d.2e.3b.4b.5a.6c, | 1d.2e.3b.4b.5a.6d, | 1d.2e.3b.4b.5a.6e, | |
| 1d.2e.3b.4b.5a.6f, | 1d.2e.3b.4b.5b.6a, | 1d.2e.3b.4b.5b.6b, | 1d.2e.3b.4b.5b.6c, | |
| 1d.2e.3b.4b.5b.6d, | 1d.2e.3b.4b.5b.6e, | 1d.2e.3b.4b.5b.6f, | 1d.2e.3b.4b.5c.6a, | |
| 1d.2e.3b.4b.5c.6b, | 1d.2e.3b.4b.5c.6c, | 1d.2e.3b.4b.5c.6d, | 1d.2e.3b.4b.5c.6e, | |
| 1d.2e.3b.4b.5c.6f, | 1d.2e.3b.4b.5d.6a, | 1d.2e.3b.4b.5d.6b, | 1d.2e.3b.4b.5d.6c, | |
| 1d.2e.3b.4b.5d.6d, | 1d.2e.3b.4b.5d.6e, | 1d.2e.3b.4b.5d.6f, | 1d.2e.3b.4b.5e.6a, | |
| 1d.2e.3b.4b.5e.6b, | 1d.2e.3b.4b.5e.6c, | 1d.2e.3b.4b.5e.6d, | 1d.2e.3b.4b.5e.6e, | |
| 1d.2e.3b.4b.5e.6f, | 1d.2e.3b.4b.5f.6a, | 1d.2e.3b.4b.5f.6b, | 1d.2e.3b.4b.5f.6c, | |
| 1d.2e.3b.4b.5f.6d, | 1d.2e.3b.4b.5f.6e, | 1d.2e.3b.4b.5f.6f, | 1d.2e.3b.4c.5a.6a, | |
| 1d.2e.3b.4c.5a.6b, | 1d.2e.3b.4c.5a.6c, | 1d.2e.3b.4c.5a.6d, | 1d.2e.3b.4c.5a.6e, | |
| 1d.2e.3b.4c.5a.6f, | 1d.2e.3b.4c.5b.6a, | 1d.2e.3b.4c.5b.6b, | 1d.2e.3b.4c.5b.6c, | |
| 1d.2e.3b.4c.5b.6d, | 1d.2e.3b.4c.5b.6e, | 1d.2e.3b.4c.5b.6f, | 1d.2e.3b.4c.5c.6a, | |
| 1d.2e.3b.4c.5c.6b, | 1d.2e.3b.4c.5c.6c, | 1d.2e.3b.4c.5c.6d, | 1d.2e.3b.4c.5c.6e, | |

TABLE 7-continued

List of Compounds of Formula (II)

| | | | | |
|---|---|---|---|---|
| 1d.2e.3b.4c.5c.6f, | 1d.2e.3b.4c.5d.6a, | 1d.2e.3b.4c.5d.6b, | 1d.2e.3b.4c.5d.6c, | |
| 1d.2e.3b.4c.5d.6d, | 1d.2e.3b.4c.5d.6e, | 1d.2e.3b.4c.5d.6f, | 1d.2e.3b.4c.5e.6a, | |
| 1d.2e.3b.4c.5e.6b, | 1d.2e.3b.4c.5e.6c, | 1d.2e.3b.4c.5e.6d, | 1d.2e.3b.4c.5e.6e, | |
| 1d.2e.3b.4c.5e.6f, | 1d.2e.3b.4c.5f.6a, | 1d.2e.3b.4c.5f.6b, | 1d.2e.3b.4c.5f.6c, | |
| 1d.2e.3b.4c.5f.6d, | 1d.2e.3b.4c.5f.6e, | 1d.2e.3b.4c.5f.6f, | 1d.2e.3b.4d.5a.6a, | |
| 1d.2e.3b.4d.5a.6b, | 1d.2e.3b.4d.5a.6c, | 1d.2e.3b.4d.5a.6d, | 1d.2e.3b.4d.5a.6e, | |
| 1d.2e.3b.4d.5a.6f, | 1d.2e.3b.4d.5b.6a, | 1d.2e.3b.4d.5b.6b, | 1d.2e.3b.4d.5b.6c, | |
| 1d.2e.3b.4d.5b.6d, | 1d.2e.3b.4d.5b.6e, | 1d.2e.3b.4d.5b.6f, | 1d.2e.3b.4d.5c.6a, | |
| 1d.2e.3b.4d.5c.6b, | 1d.2e.3b.4d.5c.6c, | 1d.2e.3b.4d.5c.6d, | 1d.2e.3b.4d.5c.6e, | |
| 1d.2e.3b.4d.5c.6f, | 1d.2e.3b.4d.5d.6a, | 1d.2e.3b.4d.5d.6b, | 1d.2e.3b.4d.5d.6c, | |
| 1d.2e.3b.4d.5d.6d, | 1d.2e.3b.4d.5d.6e, | 1d.2e.3b.4d.5d.6f, | 1d.2e.3b.4d.5e.6a, | |
| 1d.2e.3b.4d.5e.6b, | 1d.2e.3b.4d.5e.6c, | 1d.2e.3b.4d.5e.6d, | 1d.2e.3b.4d.5e.6e, | |
| 1d.2e.3b.4d.5e.6f, | 1d.2e.3b.4d.5f.6a, | 1d.2e.3b.4d.5f.6b, | 1d.2e.3b.4d.5f.6c, | |
| 1d.2e.3b.4d.5f.6d, | 1d.2e.3b.4d.5f.6e, | 1d.2e.3b.4d.5f.6f, | 1d.2e.3b.4e.5a.6a, | |
| 1d.2e.3b.4e.5a.6b, | 1d.2e.3b.4e.5a.6c, | 1d.2e.3b.4e.5a.6d, | 1d.2e.3b.4e.5a.6e, | |
| 1d.2e.3b.4e.5a.6f, | 1d.2e.3b.4e.5b.6a, | 1d.2e.3b.4e.5b.6b, | 1d.2e.3b.4e.5b.6c, | |
| 1d.2e.3b.4e.5b.6d, | 1d.2e.3b.4e.5b.6e, | 1d.2e.3b.4e.5b.6f, | 1d.2e.3b.4e.5c.6a, | |
| 1d.2e.3b.4e.5c.6b, | 1d.2e.3b.4e.5c.6c, | 1d.2e.3b.4e.5c.6d, | 1d.2e.3b.4e.5c.6e, | |
| 1d.2e.3b.4e.5c.6f, | 1d.2e.3b.4e.5d.6a, | 1d.2e.3b.4e.5d.6b, | 1d.2e.3b.4e.5d.6c, | |
| 1d.2e.3b.4e.5d.6d, | 1d.2e.3b.4e.5d.6e, | 1d.2e.3b.4e.5d.6f, | 1d.2e.3b.4e.5e.6a, | |
| 1d.2e.3b.4e.5e.6b, | 1d.2e.3b.4e.5e.6c, | 1d.2e.3b.4e.5e.6d, | 1d.2e.3b.4e.5e.6e, | |
| 1d.2e.3b.4e.5e.6f, | 1d.2e.3b.4e.5f.6a, | 1d.2e.3b.4e.5f.6b, | 1d.2e.3b.4e.5f.6c, | |
| 1d.2e.3b.4e.5f.6d, | 1d.2e.3b.4e.5f.6e, | 1d.2e.3b.4e.5f.6f, | 1d.2e.3b.4f.5a.6a, | |
| 1d.2e.3b.4f.5a.6b, | 1d.2e.3b.4f.5a.6c, | 1d.2e.3b.4f.5a.6d, | 1d.2e.3b.4f.5a.6e, | |
| 1d.2e.3b.4f.5a.6f, | 1d.2e.3b.4f.5b.6a, | 1d.2e.3b.4f.5b.6b, | 1d.2e.3b.4f.5b.6c, | |
| 1d.2e.3b.4f.5b.6d, | 1d.2e.3b.4f.5b.6e, | 1d.2e.3b.4f.5b.6f, | 1d.2e.3b.4f.5c.6a, | |
| 1d.2e.3b.4f.5c.6b, | 1d.2e.3b.4f.5c.6c, | 1d.2e.3b.4f.5c.6d, | 1d.2e.3b.4f.5c.6e, | |
| 1d.2e.3b.4f.5c.6f, | 1d.2e.3b.4f.5d.6a, | 1d.2e.3b.4f.5d.6b, | 1d.2e.3b.4f.5d.6c, | |
| 1d.2e.3b.4f.5d.6d, | 1d.2e.3b.4f.5d.6e, | 1d.2e.3b.4f.5d.6f, | 1d.2e.3b.4f.5e.6a, | |
| 1d.2e.3b.4f.5e.6b, | 1d.2e.3b.4f.5e.6c, | 1d.2e.3b.4f.5e.6d, | 1d.2e.3b.4f.5e.6e, | |
| 1d.2e.3b.4f.5e.6f, | 1d.2e.3b.4f.5f.6a, | 1d.2e.3b.4f.5f.6b, | 1d.2e.3b.4f.5f.6c, | 1d.2e.3b.4f.5f.6d, |
| 1d.2e.3b.4f.5f.6e, | 1d.2e.3b.4f.5f.6f, | 1d.2e.3c.4a.5a.6a, | 1d.2e.3c.4a.5a.6b, | |
| 1d.2e.3c.4a.5a.6c, | 1d.2e.3c.4a.5a.6d, | 1d.2e.3c.4a.5a.6e, | 1d.2e.3c.4a.5a.6f, | |
| 1d.2e.3c.4a.5b.6a, | 1d.2e.3c.4a.5b.6b, | 1d.2e.3c.4a.5b.6c, | 1d.2e.3c.4a.5b.6d, | |
| 1d.2e.3c.4a.5b.6e, | 1d.2e.3c.4a.5b.6f, | 1d.2e.3c.4a.5c.6a, | 1d.2e.3c.4a.5c.6b, | |
| 1d.2e.3c.4a.5c.6c, | 1d.2e.3c.4a.5c.6d, | 1d.2e.3c.4a.5c.6e, | 1d.2e.3c.4a.5c.6f, | |
| 1d.2e.3c.4a.5d.6a, | 1d.2e.3c.4a.5d.6b, | 1d.2e.3c.4a.5d.6c, | 1d.2e.3c.4a.5d.6d, | |
| 1d.2e.3c.4a.5d.6e, | 1d.2e.3c.4a.5d.6f, | 1d.2e.3c.4a.5e.6a, | 1d.2e.3c.4a.5e.6b, | |
| 1d.2e.3c.4a.5e.6c, | 1d.2e.3c.4a.5e.6d, | 1d.2e.3c.4a.5e.6e, | 1d.2e.3c.4a.5e.6f, | |
| 1d.2e.3c.4a.5f.6a, | 1d.2e.3c.4a.5f.6b, | 1d.2e.3c.4a.5f.6c, | 1d.2e.3c.4a.5f.6d, | |
| 1d.2e.3c.4a.5f.6e, | 1d.2e.3c.4a.5f.6f, | 1d.2e.3c.4b.5a.6a, | 1d.2e.3c.4b.5a.6b, | |
| 1d.2e.3c.4b.5a.6c, | 1d.2e.3c.4b.5a.6d, | 1d.2e.3c.4b.5a.6e, | 1d.2e.3c.4b.5a.6f, | |
| 1d.2e.3c.4b.5b.6a, | 1d.2e.3c.4b.5b.6b, | 1d.2e.3c.4b.5b.6c, | 1d.2e.3c.4b.5b.6d, | |
| 1d.2e.3c.4b.5b.6e, | 1d.2e.3c.4b.5b.6f, | 1d.2e.3c.4b.5c.6a, | 1d.2e.3c.4b.5c.6b, | , |
| 1d.2e.3c.4b.5c.6c, | 1d.2e.3c.4b.5c.6d, | 1d.2e.3c.4b.5c.6e, | 1d.2e.3c.4b.5c.6f, | |
| 1d.2e.3c.4b.5d.6a, | 1d.2e.3c.4b.5d.6b, | 1d.2e.3c.4b.5d.6c, | 1d.2e.3c.4b.5d.6d, | |
| 1d.2e.3c.4b.5d.6e, | 1d.2e.3c.4b.5d.6f, | 1d.2e.3c.4b.5e.6a, | 1d.2e.3c.4b.5e.6b, | |
| 1d.2e.3c.4b.5e.6c, | 1d.2e.3c.4b.5e.6d, | 1d.2e.3c.4b.5e.6e, | 1d.2e.3c.4b.5e.6f, | |
| 1d.2e.3c.4b.5f.6a, | 1d.2e.3c.4b.5f.6b, | 1d.2e.3c.4b.5f.6c, | 1d.2e.3c.4b.5f.6d, | |
| 1d.2e.3c.4b.5f.6e, | 1d.2e.3c.4b.5f.6f, | 1d.2e.3c.4c.5a.6a, | 1d.2e.3c.4c.5a.6b, | |
| 1d.2e.3c.4c.5a.6c, | 1d.2e.3c.4c.5a.6d, | 1d.2e.3c.4c.5a.6e, | 1d.2e.3c.4c.5a.6f, | |
| 1d.2e.3c.4c.5b.6a, | 1d.2e.3c.4c.5b.6b, | 1d.2e.3c.4c.5b.6c, | 1d.2e.3c.4c.5b.6d, | |
| 1d.2e.3c.4c.5b.6e, | 1d.2e.3c.4c.5b.6f, | 1d.2e.3c.4c.5c.6a, | 1d.2e.3c.4c.5c.6b, | |
| 1d.2e.3c.4c.5c.6c, | 1d.2e.3c.4c.5c.6d, | 1d.2e.3c.4c.5c.6e, | 1d.2e.3c.4c.5c.6f, | |
| 1d.2e.3c.4c.5d.6a, | 1d.2e.3c.4c.5d.6b, | 1d.2e.3c.4c.5d.6c, | 1d.2e.3c.4c.5d.6d, | |
| 1d.2e.3c.4c.5d.6e, | 1d.2e.3c.4c.5d.6f, | 1d.2e.3c.4c.5e.6a, | 1d.2e.3c.4c.5e.6b, | |
| 1d.2e.3c.4c.5e.6c, | 1d.2e.3c.4c.5e.6d, | 1d.2e.3c.4c.5e.6e, | 1d.2e.3c.4c.5e.6f, | |
| 1d.2e.3c.4c.5f.6a, | 1d.2e.3c.4c.5f.6b, | 1d.2e.3c.4c.5f.6c, | 1d.2e.3c.4c.5f.6d, | 1d.2e.3c.4c.5f.6e, |
| 1d.2e.3c.4c.5f.6f, | 1d.2e.3c.4d.5a.6a, | 1d.2e.3c.4d.5a.6b, | 1d.2e.3c.4d.5a.6c, | |
| 1d.2e.3c.4d.5a.6d, | 1d.2e.3c.4d.5a.6e, | 1d.2e.3c.4d.5a.6f, | 1d.2e.3c.4d.5b.6a, | |
| 1d.2e.3c.4d.5b.6b, | 1d.2e.3c.4d.5b.6c, | 1d.2e.3c.4d.5b.6d, | 1d.2e.3c.4d.5b.6e, | |
| 1d.2e.3c.4d.5b.6f, | 1d.2e.3c.4d.5c.6a, | 1d.2e.3c.4d.5c.6b, | 1d.2e.3c.4d.5c.6c, | |
| 1d.2e.3c.4d.5c.6d, | 1d.2e.3c.4d.5c.6e, | 1d.2e.3c.4d.5c.6f, | 1d.2e.3c.4d.5d.6a, | |
| 1d.2e.3c.4d.5d.6b, | 1d.2e.3c.4d.5d.6c, | 1d.2e.3c.4d.5d.6d, | 1d.2e.3c.4d.5d.6e, | |
| 1d.2e.3c.4d.5d.6f, | 1d.2e.3c.4d.5e.6a, | 1d.2e.3c.4d.5e.6b, | 1d.2e.3c.4d.5e.6c, | |
| 1d.2e.3c.4d.5e.6d, | 1d.2e.3c.4d.5e.6e, | 1d.2e.3c.4d.5e.6f, | 1d.2e.3c.4d.5f.6a, | |
| 1d.2e.3c.4d.5f.6b, | 1d.2e.3c.4d.5f.6c, | 1d.2e.3c.4d.5f.6d, | 1d.2e.3c.4d.5f.6e, | |
| 1d.2e.3c.4d.5f.6f, | 1d.2e.3c.4e.5a.6a, | 1d.2e.3c.4e.5a.6b, | 1d.2e.3c.4e.5a.6c, | |
| 1d.2e.3c.4e.5a.6d, | 1d.2e.3c.4e.5a.6e, | 1d.2e.3c.4e.5a.6f, | 1d.2e.3c.4e.5b.6a, | |
| 1d.2e.3c.4e.5b.6b, | 1d.2e.3c.4e.5b.6c, | 1d.2e.3c.4e.5b.6d, | 1d.2e.3c.4e.5b.6e, | |
| 1d.2e.3c.4e.5b.6f, | 1d.2e.3c.4e.5c.6a, | 1d.2e.3c.4e.5c.6b, | 1d.2e.3c.4e.5c.6c, | |
| 1d.2e.3c.4e.5c.6d, | 1d.2e.3c.4e.5c.6e, | 1d.2e.3c.4e.5c.6f, | 1d.2e.3c.4e.5d.6a, | |
| 1d.2e.3c.4e.5d.6b, | 1d.2e.3c.4e.5d.6c, | 1d.2e.3c.4e.5d.6d, | 1d.2e.3c.4e.5d.6e, | |
| 1d.2e.3c.4e.5d.6f, | 1d.2e.3c.4e.5e.6a, | 1d.2e.3c.4e.5e.6b, | 1d.2e.3c.4e.5e.6c, | |
| 1d.2e.3c.4e.5e.6d, | 1d.2e.3c.4e.5e.6e, | 1d.2e.3c.4e.5e.6f, | 1d.2e.3c.4e.5f.6a, | |
| 1d.2e.3c.4e.5f.6b, | 1d.2e.3c.4e.5f.6c, | 1d.2e.3c.4e.5f.6d, | 1d.2e.3c.4e.5f.6e, | 1d.2e.3c.4e.5f.6f, |
| 1d.2e.3c.4f.5a.6a, | 1d.2e.3c.4f.5a.6b, | 1d.2e.3c.4f.5a.6c, | 1d.2e.3c.4f.5a.6d, | |
| 1d.2e.3c.4f.5a.6e, | 1d.2e.3c.4f.5a.6f, | 1d.2e.3c.4f.5b.6a, | 1d.2e.3c.4f.5b.6b, | 1d.2e.3c.4f.5b.6c, |

TABLE 7-continued

List of Compounds of Formula (II)

| | | | | |
|---|---|---|---|---|
| 1d.2e.3c.4f.5b.6d, | 1d.2e.3c.4f.5b.6e, | 1d.2e.3c.4f.5b.6f, | 1d.2e.3c.4f.5c.6a, | 1d.2e.3c.4f.5c.6b, |
| 1d.2e.3c.4f.5c.6c, | 1d.2e.3c.4f.5c.6d, | 1d.2e.3c.4f.5c.6e, | 1d.2e.3c.4f.5c.6f, | 1d.2e.3c.4f.5d.6a, |
| 1d.2e.3c.4f.5d.6b, | 1d.2e.3c.4f.5d.6c, | 1d.2e.3c.4f.5d.6d, | 1d.2e.3c.4f.5d.6e, | |
| 1d.2e.3c.4f.5d.6f, | 1d.2e.3c.4f.5e.6a, | 1d.2e.3c.4f.5e.6b, | 1d.2e.3c.4f.5e.6c, | 1d.2e.3c.4f.5e.6d, |
| 1d.2e.3c.4f.5e.6e, | 1d.2e.3c.4f.5e.6f, | 1d.2e.3c.4f.5f.6a, | 1d.2e.3c.4f.5f.6b, | 1d.2e.3c.4f.5f.6c, |
| 1d.2e.3c.4f.5f.6d, | 1d.2e.3c.4f.5f.6e, | 1d.2e.3c.4f.5f.6f, | 1d.2e.3d.4a.5a.6a, | |
| 1d.2e.3d.4a.5a.6b, | 1d.2e.3d.4a.5a.6c, | 1d.2e.3d.4a.5a.6d, | 1d.2e.3d.4a.5a.6e, | |
| 1d.2e.3d.4a.5a.6f, | 1d.2e.3d.4a.5b.6a, | 1d.2e.3d.4a.5b.6b, | 1d.2e.3d.4a.5b.6c, | |
| 1d.2e.3d.4a.5b.6d, | 1d.2e.3d.4a.5b.6e, | 1d.2e.3d.4a.5b.6f, | 1d.2e.3d.4a.5c.6a, | |
| 1d.2e.3d.4a.5c.6b, | 1d.2e.3d.4a.5c.6c, | 1d.2e.3d.4a.5c.6d, | 1d.2e.3d.4a.5c.6e, | |
| 1d.2e.3d.4a.5c.6f, | 1d.2e.3d.4a.5d.6a, | 1d.2e.3d.4a.5d.6b, | 1d.2e.3d.4a.5d.6c, | |
| 1d.2e.3d.4a.5d.6d, | 1d.2e.3d.4a.5d.6e, | 1d.2e.3d.4a.5d.6f, | 1d.2e.3d.4a.5e.6a, | |
| 1d.2e.3d.4a.5e.6b, | 1d.2e.3d.4a.5e.6c, | 1d.2e.3d.4a.5e.6d, | 1d.2e.3d.4a.5e.6e, | |
| 1d.2e.3d.4a.5e.6f, | 1d.2e.3d.4a.5f.6a, | 1d.2e.3d.4a.5f.6b, | 1d.2e.3d.4a.5f.6c, | |
| 1d.2e.3d.4a.5f.6d, | 1d.2e.3d.4a.5f.6e, | 1d.2e.3d.4a.5f.6f, | 1d.2e.3d.4b.5a.6a, | |
| 1d.2e.3d.4b.5a.6b, | 1d.2e.3d.4b.5a.6c, | 1d.2e.3d.4b.5a.6d, | 1d.2e.3d.4b.5a.6e, | |
| 1d.2e.3d.4b.5a.6f, | 1d.2e.3d.4b.5b.6a, | 1d.2e.3d.4b.5b.6b, | 1d.2e.3d.4b.5b.6c, | |
| 1d.2e.3d.4b.5b.6d, | 1d.2e.3d.4b.5b.6e, | 1d.2e.3d.4b.5b.6f, | 1d.2e.3d.4b.5c.6a, | |
| 1d.2e.3d.4b.5c.6b, | 1d.2e.3d.4b.5c.6c, | 1d.2e.3d.4b.5c.6d, | 1d.2e.3d.4b.5c.6e, | |
| 1d.2e.3d.4b.5c.6f, | 1d.2e.3d.4b.5d.6a, | 1d.2e.3d.4b.5d.6b, | 1d.2e.3d.4b.5d.6c, | |
| 1d.2e.3d.4b.5d.6d, | 1d.2e.3d.4b.5d.6e, | 1d.2e.3d.4b.5d.6f, | 1d.2e.3d.4b.5e.6a, | |
| 1d.2e.3d.4b.5e.6b, | 1d.2e.3d.4b.5e.6c, | 1d.2e.3d.4b.5e.6d, | 1d.2e.3d.4b.5e.6e, | |
| 1d.2e.3d.4b.5e.6f, | 1d.2e.3d.4b.5f.6a, | 1d.2e.3d.4b.5f.6b, | 1d.2e.3d.4b.5f.6c, | |
| 1d.2e.3d.4b.5f.6d, | 1d.2e.3d.4b.5f.6e, | 1d.2e.3d.4b.5f.6f, | 1d.2e.3d.4c.5a.6a, | |
| 1d.2e.3d.4c.5a.6b, | 1d.2e.3d.4c.5a.6c, | 1d.2e.3d.4c.5a.6d, | 1d.2e.3d.4c.5a.6e, | |
| 1d.2e.3d.4c.5a.6f, | 1d.2e.3d.4c.5b.6a, | 1d.2e.3d.4c.5b.6b, | 1d.2e.3d.4c.5b.6c, | |
| 1d.2e.3d.4c.5b.6d, | 1d.2e.3d.4c.5b.6e, | 1d.2e.3d.4c.5b.6f, | 1d.2e.3d.4c.5c.6a, | |
| 1d.2e.3d.4c.5c.6b, | 1d.2e.3d.4c.5c.6c, | 1d.2e.3d.4c.5c.6d, | 1d.2e.3d.4c.5c.6e, | |
| 1d.2e.3d.4c.5c.6f, | 1d.2e.3d.4c.5d.6a, | 1d.2e.3d.4c.5d.6b, | 1d.2e.3d.4c.5d.6c, | |
| 1d.2e.3d.4c.5d.6d, | 1d.2e.3d.4c.5d.6e, | 1d.2e.3d.4c.5d.6f, | 1d.2e.3d.4c.5e.6a, | |
| 1d.2e.3d.4c.5e.6b, | 1d.2e.3d.4c.5e.6c, | 1d.2e.3d.4c.5e.6d, | 1d.2e.3d.4c.5e.6e, | |
| 1d.2e.3d.4c.5e.6f, | 1d.2e.3d.4c.5f.6a, | 1d.2e.3d.4c.5f.6b, | 1d.2e.3d.4c.5f.6c, | |
| 1d.2e.3d.4c.5f.6d, | 1d.2e.3d.4c.5f.6e, | 1d.2e.3d.4c.5f.6f, | 1d.2e.3d.4d.5a.6a, | |
| 1d.2e.3d.4d.5a.6b, | 1d.2e.3d.4d.5a.6c, | 1d.2e.3d.4d.5a.6d, | 1d.2e.3d.4d.5a.6e, | |
| 1d.2e.3d.4d.5a.6f, | 1d.2e.3d.4d.5b.6a, | 1d.2e.3d.4d.5b.6b, | 1d.2e.3d.4d.5b.6c, | |
| 1d.2e.3d.4d.5b.6d, | 1d.2e.3d.4d.5b.6e, | 1d.2e.3d.4d.5b.6f, | 1d.2e.3d.4d.5c.6a, | |
| 1d.2e.3d.4d.5c.6b, | 1d.2e.3d.4d.5c.6c, | 1d.2e.3d.4d.5c.6d, | 1d.2e.3d.4d.5c.6e, | |
| 1d.2e.3d.4d.5c.6f, | 1d.2e.3d.4d.5d.6a, | 1d.2e.3d.4d.5d.6b, | 1d.2e.3d.4d.5d.6c, | |
| 1d.2e.3d.4d.5d.6d, | 1d.2e.3d.4d.5d.6e, | 1d.2e.3d.4d.5d.6f, | 1d.2e.3d.4d.5e.6a, | |
| 1d.2e.3d.4d.5e.6b, | 1d.2e.3d.4d.5e.6c, | 1d.2e.3d.4d.5e.6d, | 1d.2e.3d.4d.5e.6e, | |
| 1d.2e.3d.4d.5e.6f, | 1d.2e.3d.4d.5f.6a, | 1d.2e.3d.4d.5f.6b, | 1d.2e.3d.4d.5f.6c, | |
| 1d.2e.3d.4d.5f.6d, | 1d.2e.3d.4d.5f.6e, | 1d.2e.3d.4d.5f.6f, | 1d.2e.3d.4e.5a.6a, | |
| 1d.2e.3d.4e.5a.6b, | 1d.2e.3d.4e.5a.6c, | 1d.2e.3d.4e.5a.6d, | 1d.2e.3d.4e.5a.6e, | |
| 1d.2e.3d.4e.5a.6f, | 1d.2e.3d.4e.5b.6a, | 1d.2e.3d.4e.5b.6b, | 1d.2e.3d.4e.5b.6c, | |
| 1d.2e.3d.4e.5b.6d, | 1d.2e.3d.4e.5b.6e, | 1d.2e.3d.4e.5b.6f, | 1d.2e.3d.4e.5c.6a, | |
| 1d.2e.3d.4e.5c.6b, | 1d.2e.3d.4e.5c.6c, | 1d.2e.3d.4e.5c.6d, | 1d.2e.3d.4e.5c.6e, | |
| 1d.2e.3d.4e.5c.6f, | 1d.2e.3d.4e.5d.6a, | 1d.2e.3d.4e.5d.6b, | 1d.2e.3d.4e.5d.6c, | |
| 1d.2e.3d.4e.5d.6d, | 1d.2e.3d.4e.5d.6e, | 1d.2e.3d.4e.5d.6f, | 1d.2e.3d.4e.5e.6a, | |
| 1d.2e.3d.4e.5e.6b, | 1d.2e.3d.4e.5e.6c, | 1d.2e.3d.4e.5e.6d, | 1d.2e.3d.4e.5e.6e, | |
| 1d.2e.3d.4e.5e.6f, | 1d.2e.3d.4e.5f.6a, | 1d.2e.3d.4e.5f.6b, | 1d.2e.3d.4e.5f.6c, | |
| 1d.2e.3d.4e.5f.6d, | 1d.2e.3d.4e.5f.6e, | 1d.2e.3d.4e.5f.6f, | 1d.2e.3d.4f.5a.6a, | |
| 1d.2e.3d.4f.5a.6b, | 1d.2e.3d.4f.5a.6c, | 1d.2e.3d.4f.5a.6d, | 1d.2e.3d.4f.5a.6e, | |
| 1d.2e.3d.4f.5a.6f, | 1d.2e.3d.4f.5b.6a, | 1d.2e.3d.4f.5b.6b, | 1d.2e.3d.4f.5b.6c, | |
| 1d.2e.3d.4f.5b.6d, | 1d.2e.3d.4f.5b.6e, | 1d.2e.3d.4f.5b.6f, | 1d.2e.3d.4f.5c.6a, | |
| 1d.2e.3d.4f.5c.6b, | 1d.2e.3d.4f.5c.6c, | 1d.2e.3d.4f.5c.6d, | 1d.2e.3d.4f.5c.6e, | |
| 1d.2e.3d.4f.5c.6f, | 1d.2e.3d.4f.5d.6a, | 1d.2e.3d.4f.5d.6b, | 1d.2e.3d.4f.5d.6c, | |
| 1d.2e.3d.4f.5d.6d, | 1d.2e.3d.4f.5d.6e, | 1d.2e.3d.4f.5d.6f, | 1d.2e.3d.4f.5e.6a, | |
| 1d.2e.3d.4f.5e.6b, | 1d.2e.3d.4f.5e.6c, | 1d.2e.3d.4f.5e.6d, | 1d.2e.3d.4f.5e.6e, | |
| 1d.2e.3d.4f.5e.6f, | 1d.2e.3d.4f.5f.6a, | 1d.2e.3d.4f.5f.6b, | 1d.2e.3d.4f.5f.6c, | |
| 1d.2e.3d.4f.5f.6d, | 1d.2e.3d.4f.5f.6e, | 1d.2e.3d.4f.5f.6f, | 1d.2e.3e.4a.5a.6a, | |
| 1d.2e.3e.4a.5a.6b, | 1d.2e.3e.4a.5a.6c, | 1d.2e.3e.4a.5a.6d, | 1d.2e.3e.4a.5a.6e, | |
| 1d.2e.3e.4a.5a.6f, | 1d.2e.3e.4a.5b.6a, | 1d.2e.3e.4a.5b.6b, | 1d.2e.3e.4a.5b.6c, | |
| 1d.2e.3e.4a.5b.6d, | 1d.2e.3e.4a.5b.6e, | 1d.2e.3e.4a.5b.6f, | 1d.2e.3e.4a.5c.6a, | |
| 1d.2e.3e.4a.5c.6b, | 1d.2e.3e.4a.5c.6c, | 1d.2e.3e.4a.5c.6d, | 1d.2e.3e.4a.5c.6e, | |
| 1d.2e.3e.4a.5c.6f, | 1d.2e.3e.4a.5d.6a, | 1d.2e.3e.4a.5d.6b, | 1d.2e.3e.4a.5d.6c, | |
| 1d.2e.3e.4a.5d.6d, | 1d.2e.3e.4a.5d.6e, | 1d.2e.3e.4a.5d.6f, | 1d.2e.3e.4a.5e.6a, | |
| 1d.2e.3e.4a.5e.6b, | 1d.2e.3e.4a.5e.6c, | 1d.2e.3e.4a.5e.6d, | 1d.2e.3e.4a.5e.6e, | |
| 1d.2e.3e.4a.5e.6f, | 1d.2e.3e.4a.5f.6a, | 1d.2e.3e.4a.5f.6b, | 1d.2e.3e.4a.5f.6c, | |
| 1d.2e.3e.4a.5f.6d, | 1d.2e.3e.4a.5f.6e, | 1d.2e.3e.4a.5f.6f, | 1d.2e.3e.4b.5a.6a, | |
| 1d.2e.3e.4b.5a.6b, | 1d.2e.3e.4b.5a.6c, | 1d.2e.3e.4b.5a.6d, | 1d.2e.3e.4b.5a.6e, | |
| 1d.2e.3e.4b.5a.6f, | 1d.2e.3e.4b.5b.6a, | 1d.2e.3e.4b.5b.6b, | 1d.2e.3e.4b.5b.6c, | |
| 1d.2e.3e.4b.5b.6d, | 1d.2e.3e.4b.5b.6e, | 1d.2e.3e.4b.5b.6f, | 1d.2e.3e.4b.5c.6a, | |
| 1d.2e.3e.4b.5c.6b, | 1d.2e.3e.4b.5c.6c, | 1d.2e.3e.4b.5c.6d, | 1d.2e.3e.4b.5c.6e, | |
| 1d.2e.3e.4b.5c.6f, | 1d.2e.3e.4b.5d.6a, | 1d.2e.3e.4b.5d.6b, | 1d.2e.3e.4b.5d.6c, | |
| 1d.2e.3e.4b.5d.6d, | 1d.2e.3e.4b.5d.6e, | 1d.2e.3e.4b.5d.6f, | 1d.2e.3e.4b.5e.6a, | |
| 1d.2e.3e.4b.5e.6b, | 1d.2e.3e.4b.5e.6c, | 1d.2e.3e.4b.5e.6d, | 1d.2e.3e.4b.5e.6e, | |
| 1d.2e.3e.4b.5e.6f, | 1d.2e.3e.4b.5f.6a, | 1d.2e.3e.4b.5f.6b, | 1d.2e.3e.4b.5f.6c, | |
| 1d.2e.3e.4b.5f.6d, | 1d.2e.3e.4b.5f.6e, | 1d.2e.3e.4b.5f.6f, | 1d.2e.3e.4c.5a.6a, | |

TABLE 7-continued

List of Compounds of Formula (II)

| | | | | |
|---|---|---|---|---|
| 1d.2e.3e.4c.5a.6b, | 1d.2e.3e.4c.5a.6c, | 1d.2e.3e.4c.5a.6d, | 1d.2e.3e.4c.5a.6e, | |
| 1d.2e.3e.4c.5a.6f, | 1d.2e.3e.4c.5b.6a, | 1d.2e.3e.4c.5b.6b, | 1d.2e.3e.4c.5b.6c, | |
| 1d.2e.3e.4c.5b.6d, | 1d.2e.3e.4c.5b.6e, | 1d.2e.3e.4c.5b.6f, | 1d.2e.3e.4c.5c.6a, | |
| 1d.2e.3e.4c.5c.6b, | 1d.2e.3e.4c.5c.6c, | 1d.2e.3e.4c.5c.6d, | 1d.2e.3e.4c.5c.6e, | |
| 1d.2e.3e.4c.5c.6f, | 1d.2e.3e.4c.5d.6a, | 1d.2e.3e.4c.5d.6b, | 1d.2e.3e.4c.5d.6c, | |
| 1d.2e.3e.4c.5d.6d, | 1d.2e.3e.4c.5d.6e, | 1d.2e.3e.4c.5d.6f, | 1d.2e.3e.4c.5e.6a, | |
| 1d.2e.3e.4c.5e.6b, | 1d.2e.3e.4c.5e.6c, | 1d.2e.3e.4c.5e.6d, | 1d.2e.3e.4c.5e.6e, | |
| 1d.2e.3e.4c.5e.6f, | 1d.2e.3e.4c.5f.6a, | 1d.2e.3e.4c.5f.6b, | 1d.2e.3e.4c.5f.6c, | 1d.2e.3e.4c.5f.6d, |
| 1d.2e.3e.4c.5f.6e, | 1d.2e.3e.4c.5f.6f, | 1d.2e.3e.4d.5a.6a, | 1d.2e.3e.4d.5a.6b, | |
| 1d.2e.3e.4d.5a.6c, | 1d.2e.3e.4d.5a.6d, | 1d.2e.3e.4d.5a.6e, | 1d.2e.3e.4d.5a.6f, | |
| 1d.2e.3e.4d.5b.6a, | 1d.2e.3e.4d.5b.6b, | 1d.2e.3e.4d.5b.6c, | 1d.2e.3e.4d.5b.6d, | |
| 1d.2e.3e.4d.5b.6e, | 1d.2e.3e.4d.5b.6f, | 1d.2e.3e.4d.5c.6a, | 1d.2e.3e.4d.5c.6b, | |
| 1d.2e.3e.4d.5c.6c, | 1d.2e.3e.4d.5c.6d, | 1d.2e.3e.4d.5c.6e, | 1d.2e.3e.4d.5c.6f, | |
| 1d.2e.3e.4d.5d.6a, | 1d.2e.3e.4d.5d.6b, | 1d.2e.3e.4d.5d.6c, | 1d.2e.3e.4d.5d.6d, | |
| 1d.2e.3e.4d.5d.6e, | 1d.2e.3e.4d.5d.6f, | 1d.2e.3e.4d.5e.6a, | 1d.2e.3e.4d.5e.6b, | |
| 1d.2e.3e.4d.5e.6c, | 1d.2e.3e.4d.5e.6d, | 1d.2e.3e.4d.5e.6e, | 1d.2e.3e.4d.5e.6f, | |
| 1d.2e.3e.4d.5f.6a, | 1d.2e.3e.4d.5f.6b, | 1d.2e.3e.4d.5f.6c, | 1d.2e.3e.4d.5f.6d, | |
| 1d.2e.3e.4d.5f.6e, | 1d.2e.3e.4d.5f.6f, | 1d.2e.3e.4e.5a.6a, | 1d.2e.3e.4e.5a.6b, | |
| 1d.2e.3e.4e.5a.6c, | 1d.2e.3e.4e.5a.6d, | 1d.2e.3e.4e.5a.6e, | 1d.2e.3e.4e.5a.6f, | |
| 1d.2e.3e.4e.5b.6a, | 1d.2e.3e.4e.5b.6b, | 1d.2e.3e.4e.5b.6c, | 1d.2e.3e.4e.5b.6d, | |
| 1d.2e.3e.4e.5b.6e, | 1d.2e.3e.4e.5b.6f, | 1d.2e.3e.4e.5c.6a, | 1d.2e.3e.4e.5c.6b, | |
| 1d.2e.3e.4e.5c.6c, | 1d.2e.3e.4e.5c.6d, | 1d.2e.3e.4e.5c.6e, | 1d.2e.3e.4e.5c.6f, | |
| 1d.2e.3e.4e.5d.6a, | 1d.2e.3e.4e.5d.6b, | 1d.2e.3e.4e.5d.6c, | 1d.2e.3e.4e.5d.6d, | |
| 1d.2e.3e.4e.5d.6e, | 1d.2e.3e.4e.5d.6f, | 1d.2e.3e.4e.5e.6a, | 1d.2e.3e.4e.5e.6b, | |
| 1d.2e.3e.4e.5e.6c, | 1d.2e.3e.4e.5e.6d, | 1d.2e.3e.4e.5e.6e, | 1d.2e.3e.4e.5e.6f, | |
| 1d.2e.3e.4e.5f.6a, | 1d.2e.3e.4e.5f.6b, | 1d.2e.3e.4e.5f.6c, | 1d.2e.3e.4e.5f.6d, | |
| 1d.2e.3e.4e.5f.6e, | 1d.2e.3e.4e.5f.6f, | 1d.2e.3e.4f.5a.6a, | 1d.2e.3e.4f.5a.6b, | 1d.2e.3e.4f.5a.6c, |
| 1d.2e.3e.4f.5a.6d, | 1d.2e.3e.4f.5a.6e, | 1d.2e.3e.4f.5a.6f, | 1d.2e.3e.4f.5b.6a, | |
| 1d.2e.3e.4f.5b.6b, | 1d.2e.3e.4f.5b.6c, | 1d.2e.3e.4f.5b.6d, | 1d.2e.3e.4f.5b.6e, | |
| 1d.2e.3e.4f.5b.6f, | 1d.2e.3e.4f.5c.6a, | 1d.2e.3e.4f.5c.6b, | 1d.2e.3e.4f.5c.6c, | 1d.2e.3e.4f.5c.6d, |
| 1d.2e.3e.4f.5c.6e, | 1d.2e.3e.4f.5c.6f, | 1d.2e.3e.4f.5d.6a, | 1d.2e.3e.4f.5d.6b, | |
| 1d.2e.3e.4f.5d.6c, | 1d.2e.3e.4f.5d.6d, | 1d.2e.3e.4f.5d.6e, | 1d.2e.3e.4f.5d.6f, | |
| 1d.2e.3e.4f.5e.6a, | 1d.2e.3e.4f.5e.6b, | 1d.2e.3e.4f.5e.6c, | 1d.2e.3e.4f.5e.6d, | |
| 1d.2e.3e.4f.5e.6e, | 1d.2e.3e.4f.5e.6f, | 1d.2e.3e.4f.5f.6a, | 1d.2e.3e.4f.5f.6b, | 1d.2e.3e.4f.5f.6c, |
| 1d.2e.3e.4f.5f.6d, | 1d.2e.3e.4f.5f.6e, | 1d.2e.3e.4f.5f.6f, | 1d.2e.3f.4a.5a.6a, | 1d.2e.3f.4a.5a.6b, |
| 1d.2e.3f.4a.5a.6c, | 1d.2e.3f.4a.5a.6d, | 1d.2e.3f.4a.5a.6e, | 1d.2e.3f.4a.5a.6f, | |
| 1d.2e.3f.4a.5b.6a, | 1d.2e.3f.4a.5b.6b, | 1d.2e.3f.4a.5b.6c, | 1d.2e.3f.4a.5b.6d, | |
| 1d.2e.3f.4a.5b.6e, | 1d.2e.3f.4a.5b.6f, | 1d.2e.3f.4a.5c.6a, | 1d.2e.3f.4a.5c.6b, | 1d.2e.3f.4a.5c.6c, |
| 1d.2e.3f.4a.5c.6d, | 1d.2e.3f.4a.5c.6e, | 1d.2e.3f.4a.5c.6f, | 1d.2e.3f.4a.5d.6a, | |
| 1d.2e.3f.4a.5d.6b, | 1d.2e.3f.4a.5d.6c, | 1d.2e.3f.4a.5d.6d, | 1d.2e.3f.4a.5d.6e, | |
| 1d.2e.3f.4a.5d.6f, | 1d.2e.3f.4a.5e.6a, | 1d.2e.3f.4a.5e.6b, | 1d.2e.3f.4a.5e.6c, | |
| 1d.2e.3f.4a.5e.6d, | 1d.2e.3f.4a.5e.6e, | 1d.2e.3f.4a.5e.6f, | 1d.2e.3f.4a.5f.6a, | 1d.2e.3f.4a.5f.6b, |
| 1d.2e.3f.4a.5f.6c, | 1d.2e.3f.4a.5f.6d, | 1d.2e.3f.4a.5f.6e, | 1d.2e.3f.4a.5f.6f, | 1d.2e.3f.4b.5a.6a, |
| 1d.2e.3f.4b.5a.6b, | 1d.2e.3f.4b.5a.6c, | 1d.2e.3f.4b.5a.6d, | 1d.2e.3f.4b.5a.6e, | |
| 1d.2e.3f.4b.5a.6f, | 1d.2e.3f.4b.5b.6a, | 1d.2e.3f.4b.5b.6b, | 1d.2e.3f.4b.5b.6c, | |
| 1d.2e.3f.4b.5b.6d, | 1d.2e.3f.4b.5b.6e, | 1d.2e.3f.4b.5b.6f, | 1d.2e.3f.4b.5c.6a, | |
| 1d.2e.3f.4b.5c.6b, | 1d.2e.3f.4b.5c.6c, | 1d.2e.3f.4b.5c.6d, | 1d.2e.3f.4b.5c.6e, | |
| 1d.2e.3f.4b.5c.6f, | 1d.2e.3f.4b.5d.6a, | 1d.2e.3f.4b.5d.6b, | 1d.2e.3f.4b.5d.6c, | |
| 1d.2e.3f.4b.5d.6d, | 1d.2e.3f.4b.5d.6e, | 1d.2e.3f.4b.5d.6f, | 1d.2e.3f.4b.5e.6a, | |
| 1d.2e.3f.4b.5e.6b, | 1d.2e.3f.4b.5e.6c, | 1d.2e.3f.4b.5e.6d, | 1d.2e.3f.4b.5e.6e, | |
| 1d.2e.3f.4b.5e.6f, | 1d.2e.3f.4b.5f.6a, | 1d.2e.3f.4b.5f.6b, | 1d.2e.3f.4b.5f.6c, | 1d.2e.3f.4b.5f.6d, |
| 1d.2e.3f.4b.5f.6e, | 1d.2e.3f.4b.5f.6f, | 1d.2e.3f.4c.5a.6a, | 1d.2e.3f.4c.5a.6b, | 1d.2e.3f.4c.5a.6c, |
| 1d.2e.3f.4c.5a.6d, | 1d.2e.3f.4c.5a.6e, | 1d.2e.3f.4c.5a.6f, | 1d.2e.3f.4c.5b.6a, | |
| 1d.2e.3f.4c.5b.6b, | 1d.2e.3f.4c.5b.6c, | 1d.2e.3f.4c.5b.6d, | 1d.2e.3f.4c.5b.6e, | |
| 1d.2e.3f.4c.5b.6f, | 1d.2e.3f.4c.5c.6a, | 1d.2e.3f.4c.5c.6b, | 1d.2e.3f.4c.5c.6c, | 1d.2e.3f.4c.5c.6d, |
| 1d.2e.3f.4c.5c.6e, | 1d.2e.3f.4c.5c.6f, | 1d.2e.3f.4c.5d.6a, | 1d.2e.3f.4c.5d.6b, | 1d.2e.3f.4c.5d.6c, |
| 1d.2e.3f.4c.5d.6d, | 1d.2e.3f.4c.5d.6e, | 1d.2e.3f.4c.5d.6f, | 1d.2e.3f.4c.5e.6a, | |
| 1d.2e.3f.4c.5e.6b, | 1d.2e.3f.4c.5e.6c, | 1d.2e.3f.4c.5e.6d, | 1d.2e.3f.4c.5e.6e, | 1d.2e.3f.4c.5e.6f, |
| 1d.2e.3f.4c.5f.6a, | 1d.2e.3f.4c.5f.6b, | 1d.2e.3f.4c.5f.6c, | 1d.2e.3f.4c.5f.6d, | 1d.2e.3f.4c.5f.6e, |
| 1d.2e.3f.4c.5f.6f, | 1d.2e.3f.4d.5a.6a, | 1d.2e.3f.4d.5a.6b, | 1d.2e.3f.4d.5a.6c, | |
| 1d.2e.3f.4d.5a.6d, | 1d.2e.3f.4d.5a.6e, | 1d.2e.3f.4d.5a.6f, | 1d.2e.3f.4d.5b.6a, | |
| 1d.2e.3f.4d.5b.6b, | 1d.2e.3f.4d.5b.6c, | 1d.2e.3f.4d.5b.6d, | 1d.2e.3f.4d.5b.6e, | |
| 1d.2e.3f.4d.5b.6f, | 1d.2e.3f.4d.5c.6a, | 1d.2e.3f.4d.5c.6b, | 1d.2e.3f.4d.5c.6c, | |
| 1d.2e.3f.4d.5c.6d, | 1d.2e.3f.4d.5c.6e, | 1d.2e.3f.4d.5c.6f, | 1d.2e.3f.4d.5d.6a, | |
| 1d.2e.3f.4d.5d.6b, | 1d.2e.3f.4d.5d.6c, | 1d.2e.3f.4d.5d.6d, | 1d.2e.3f.4d.5d.6e, | |
| 1d.2e.3f.4d.5d.6f, | 1d.2e.3f.4d.5e.6a, | 1d.2e.3f.4d.5e.6b, | 1d.2e.3f.4d.5e.6c, | |
| 1d.2e.3f.4d.5e.6d, | 1d.2e.3f.4d.5e.6e, | 1d.2e.3f.4d.5e.6f, | 1d.2e.3f.4d.5f.6a, | |
| 1d.2e.3f.4d.5f.6b, | 1d.2e.3f.4d.5f.6c, | 1d.2e.3f.4d.5f.6d, | 1d.2e.3f.4d.5f.6e, | 1d.2e.3f.4d.5f.6f, |
| 1d.2e.3f.4e.5a.6a, | 1d.2e.3f.4e.5a.6b, | 1d.2e.3f.4e.5a.6c, | 1d.2e.3f.4e.5a.6d, | |
| 1d.2e.3f.4e.5a.6e, | 1d.2e.3f.4e.5a.6f, | 1d.2e.3f.4e.5b.6a, | 1d.2e.3f.4e.5b.6b, | |
| 1d.2e.3f.4e.5b.6c, | 1d.2e.3f.4e.5b.6d, | 1d.2e.3f.4e.5b.6e, | 1d.2e.3f.4e.5b.6f, | |
| 1d.2e.3f.4e.5c.6a, | 1d.2e.3f.4e.5c.6b, | 1d.2e.3f.4e.5c.6c, | 1d.2e.3f.4e.5c.6d, | 1d.2e.3f.4e.5c.6e, |
| 1d.2e.3f.4e.5c.6f, | 1d.2e.3f.4e.5d.6a, | 1d.2e.3f.4e.5d.6b, | 1d.2e.3f.4e.5d.6c, | |
| 1d.2e.3f.4e.5d.6d, | 1d.2e.3f.4e.5d.6e, | 1d.2e.3f.4e.5d.6f, | 1d.2e.3f.4e.5e.6a, | |
| 1d.2e.3f.4e.5e.6b, | 1d.2e.3f.4e.5e.6c, | 1d.2e.3f.4e.5e.6d, | 1d.2e.3f.4e.5e.6e, | 1d.2e.3f.4e.5e.6f, |
| 1d.2e.3f.4e.5f.6a, | 1d.2e.3f.4e.5f.6b, | 1d.2e.3f.4e.5f.6c, | 1d.2e.3f.4e.5f.6d, | 1d.2e.3f.4e.5f.6e, |
| 1d.2e.3f.4e.5f.6f, | 1d.2e.3f.4f.5a.6a, | 1d.2e.3f.4f.5a.6b, | 1d.2e.3f.4f.5a.6c, | 1d.2e.3f.4f.5a.6d, |
| 1d.2e.3f.4f.5a.6e, | 1d.2e.3f.4f.5a.6f, | 1d.2e.3f.4f.5b.6a, | 1d.2e.3f.4f.5b.6b, | 1d.2e.3f.4f.5b.6c, |

TABLE 7-continued

List of Compounds of Formula (II)

| | | | | |
|---|---|---|---|---|
| 1d.2e.3f.4f.5b.6d, | 1d.2e.3f.4f.5b.6e, | 1d.2e.3f.4f.5b.6f, | 1d.2e.3f.4f.5c.6a, | 1d.2e.3f.4f.5c.6b, |
| 1d.2e.3f.4f.5c.6c, | 1d.2e.3f.4f.5c.6d, | 1d.2e.3f.4f.5c.6e, | 1d.2e.3f.4f.5c.6f, | 1d.2e.3f.4f.5d.6a, |
| 1d.2e.3f.4f.5d.6b, | 1d.2e.3f.4f.5d.6c, | 1d.2e.3f.4f.5d.6d, | 1d.2e.3f.4f.5d.6e, | 1d.2e.3f.4f.5d.6f, |
| 1d.2e.3f.4f.5e.6a, | 1d.2e.3f.4f.5e.6b, | 1d.2e.3f.4f.5e.6c, | 1d.2e.3f.4f.5e.6d, | 1d.2e.3f.4f.5e.6e, |
| 1d.2e.3f.4f.5e.6f, | 1d.2e.3f.4f.5f.6a, | 1d.2e.3f.4f.5f.6b, | 1d.2e.3f.4f.5f.6c, | 1d.2e.3f.4f.5f.6d, |
| 1d.2e.3f.4f.5f.6e, | 1d.2e.3f.4f.5f.6f, | 1d.2f.3a.4a.5a.6a, | 1d.2f.3a.4a.5a.6b, | 1d.2f.3a.4a.5a.6c, |
| 1d.2f.3a.4a.5a.6d, | 1d.2f.3a.4a.5a.6e, | 1d.2f.3a.4a.5a.6f, | 1d.2f.3a.4a.5b.6a, | |
| 1d.2f.3a.4a.5b.6b, | 1d.2f.3a.4a.5b.6c, | 1d.2f.3a.4a.5b.6d, | 1d.2f.3a.4a.5b.6e, | |
| 1d.2f.3a.4a.5b.6f, | 1d.2f.3a.4a.5c.6a, | 1d.2f.3a.4a.5c.6b, | 1d.2f.3a.4a.5c.6c, | |
| 1d.2f.3a.4a.5c.6d, | 1d.2f.3a.4a.5c.6e, | 1d.2f.3a.4a.5c.6f, | 1d.2f.3a.4a.5d.6a, | |
| 1d.2f.3a.4a.5d.6b, | 1d.2f.3a.4a.5d.6c, | 1d.2f.3a.4a.5d.6d, | 1d.2f.3a.4a.5d.6e, | |
| 1d.2f.3a.4a.5d.6f, | 1d.2f.3a.4a.5e.6a, | 1d.2f.3a.4a.5e.6b, | 1d.2f.3a.4a.5e.6c, | |
| 1d.2f.3a.4a.5e.6d, | 1d.2f.3a.4a.5e.6e, | 1d.2f.3a.4a.5e.6f, | 1d.2f.3a.4a.5f.6a, | 1d.2f.3a.4a.5f.6b, |
| 1d.2f.3a.4a.5f.6c, | 1d.2f.3a.4a.5f.6d, | 1d.2f.3a.4a.5f.6e, | 1d.2f.3a.4a.5f.6f, | 1d.2f.3a.4b.5a.6a, |
| 1d.2f.3a.4b.5a.6b, | 1d.2f.3a.4b.5a.6c, | 1d.2f.3a.4b.5a.6d, | 1d.2f.3a.4b.5a.6e, | |
| 1d.2f.3a.4b.5a.6f, | 1d.2f.3a.4b.5b.6a, | 1d.2f.3a.4b.5b.6b, | 1d.2f.3a.4b.5b.6c, | |
| 1d.2f.3a.4b.5b.6d, | 1d.2f.3a.4b.5b.6e, | 1d.2f.3a.4b.5b.6f, | 1d.2f.3a.4b.5c.6a, | |
| 1d.2f.3a.4b.5c.6b, | 1d.2f.3a.4b.5c.6c, | 1d.2f.3a.4b.5c.6d, | 1d.2f.3a.4b.5c.6e, | |
| 1d.2f.3a.4b.5c.6f, | 1d.2f.3a.4b.5d.6a, | 1d.2f.3a.4b.5d.6b, | 1d.2f.3a.4b.5d.6c, | |
| 1d.2f.3a.4b.5d.6d, | 1d.2f.3a.4b.5d.6e, | 1d.2f.3a.4b.5d.6f, | 1d.2f.3a.4b.5e.6a, | |
| 1d.2f.3a.4b.5e.6b, | 1d.2f.3a.4b.5e.6c, | 1d.2f.3a.4b.5e.6d, | 1d.2f.3a.4b.5e.6e, | |
| 1d.2f.3a.4b.5e.6f, | 1d.2f.3a.4b.5f.6a, | 1d.2f.3a.4b.5f.6b, | 1d.2f.3a.4b.5f.6c, | 1d.2f.3a.4b.5f.6d, |
| 1d.2f.3a.4b.5f.6e, | 1d.2f.3a.4b.5f.6f, | 1d.2f.3a.4c.5a.6a, | 1d.2f.3a.4c.5a.6b, | 1d.2f.3a.4c.5a.6c, |
| 1d.2f.3a.4c.5a.6d, | 1d.2f.3a.4c.5a.6e, | 1d.2f.3a.4c.5a.6f, | 1d.2f.3a.4c.5b.6a, | |
| 1d.2f.3a.4c.5b.6b, | 1d.2f.3a.4c.5b.6c, | 1d.2f.3a.4c.5b.6d, | 1d.2f.3a.4c.5b.6e, | |
| 1d.2f.3a.4c.5b.6f, | 1d.2f.3a.4c.5c.6a, | 1d.2f.3a.4c.5c.6b, | 1d.2f.3a.4c.5c.6c, | 1d.2f.3a.4c.5c.6d, |
| 1d.2f.3a.4c.5c.6e, | 1d.2f.3a.4c.5c.6f, | 1d.2f.3a.4c.5d.6a, | 1d.2f.3a.4c.5d.6b, | |
| 1d.2f.3a.4c.5d.6c, | 1d.2f.3a.4c.5d.6d, | 1d.2f.3a.4c.5d.6e, | 1d.2f.3a.4c.5d.6f, | |
| 1d.2f.3a.4c.5e.6a, | 1d.2f.3a.4c.5e.6b, | 1d.2f.3a.4c.5e.6c, | 1d.2f.3a.4c.5e.6d, | |
| 1d.2f.3a.4c.5e.6e, | 1d.2f.3a.4c.5e.6f, | 1d.2f.3a.4c.5f.6a, | 1d.2f.3a.4c.5f.6b, | 1d.2f.3a.4c.5f.6c, |
| 1d.2f.3a.4c.5f.6d, | 1d.2f.3a.4c.5f.6e, | 1d.2f.3a.4c.5f.6f, | 1d.2f.3a.4d.5a.6a, | 1d.2f.3a.4d.5a.6b, |
| 1d.2f.3a.4d.5a.6c, | 1d.2f.3a.4d.5a.6d, | 1d.2f.3a.4d.5a.6e, | 1d.2f.3a.4d.5a.6f, | |
| 1d.2f.3a.4d.5b.6a, | 1d.2f.3a.4d.5b.6b, | 1d.2f.3a.4d.5b.6c, | 1d.2f.3a.4d.5b.6d, | |
| 1d.2f.3a.4d.5b.6e, | 1d.2f.3a.4d.5b.6f, | 1d.2f.3a.4d.5c.6a, | 1d.2f.3a.4d.5c.6b, | |
| 1d.2f.3a.4d.5c.6c, | 1d.2f.3a.4d.5c.6d, | 1d.2f.3a.4d.5c.6e, | 1d.2f.3a.4d.5c.6f, | |
| 1d.2f.3a.4d.5d.6a, | 1d.2f.3a.4d.5d.6b, | 1d.2f.3a.4d.5d.6c, | 1d.2f.3a.4d.5d.6d, | |
| 1d.2f.3a.4d.5d.6e, | 1d.2f.3a.4d.5d.6f, | 1d.2f.3a.4d.5e.6a, | 1d.2f.3a.4d.5e.6b, | |
| 1d.2f.3a.4d.5e.6c, | 1d.2f.3a.4d.5e.6d, | 1d.2f.3a.4d.5e.6e, | 1d.2f.3a.4d.5e.6f, | |
| 1d.2f.3a.4d.5f.6a, | 1d.2f.3a.4d.5f.6b, | 1d.2f.3a.4d.5f.6c, | 1d.2f.3a.4d.5f.6d, | |
| 1d.2f.3a.4d.5f.6e, | 1d.2f.3a.4d.5f.6f, | 1d.2f.3a.4e.5a.6a, | 1d.2f.3a.4e.5a.6b, | 1d.2f.3a.4e.5a.6c, |
| 1d.2f.3a.4e.5a.6d, | 1d.2f.3a.4e.5a.6e, | 1d.2f.3a.4e.5a.6f, | 1d.2f.3a.4e.5b.6a, | |
| 1d.2f.3a.4e.5b.6b, | 1d.2f.3a.4e.5b.6c, | 1d.2f.3a.4e.5b.6d, | 1d.2f.3a.4e.5b.6e, | |
| 1d.2f.3a.4e.5b.6f, | 1d.2f.3a.4e.5c.6a, | 1d.2f.3a.4e.5c.6b, | 1d.2f.3a.4e.5c.6c, | |
| 1d.2f.3a.4e.5c.6d, | 1d.2f.3a.4e.5c.6e, | 1d.2f.3a.4e.5c.6f, | 1d.2f.3a.4e.5d.6a, | |
| 1d.2f.3a.4e.5d.6b, | 1d.2f.3a.4e.5d.6c, | 1d.2f.3a.4e.5d.6d, | 1d.2f.3a.4e.5d.6e, | |
| 1d.2f.3a.4e.5d.6f, | 1d.2f.3a.4e.5e.6a, | 1d.2f.3a.4e.5e.6b, | 1d.2f.3a.4e.5e.6c, | |
| 1d.2f.3a.4e.5e.6d, | 1d.2f.3a.4e.5e.6e, | 1d.2f.3a.4e.5e.6f, | 1d.2f.3a.4e.5f.6a, | 1d.2f.3a.4e.5f.6b, |
| 1d.2f.3a.4e.5f.6c, | 1d.2f.3a.4e.5f.6d, | 1d.2f.3a.4e.5f.6e, | 1d.2f.3a.4e.5f.6f, | 1d.2f.3a.4f.5a.6a, |
| 1d.2f.3a.4f.5a.6b, | 1d.2f.3a.4f.5a.6c, | 1d.2f.3a.4f.5a.6d, | 1d.2f.3a.4f.5a.6e, | 1d.2f.3a.4f.5a.6f, |
| 1d.2f.3a.4f.5b.6a, | 1d.2f.3a.4f.5b.6b, | 1d.2f.3a.4f.5b.6c, | 1d.2f.3a.4f.5b.6d, | 1d.2f.3a.4f.5b.6e, |
| 1d.2f.3a.4f.5b.6f, | 1d.2f.3a.4f.5c.6a, | 1d.2f.3a.4f.5c.6b, | 1d.2f.3a.4f.5c.6c, | 1d.2f.3a.4f.5c.6d, |
| 1d.2f.3a.4f.5c.6e, | 1d.2f.3a.4f.5c.6f, | 1d.2f.3a.4f.5d.6a, | 1d.2f.3a.4f.5d.6b, | 1d.2f.3a.4f.5d.6c, |
| 1d.2f.3a.4f.5d.6d, | 1d.2f.3a.4f.5d.6e, | 1d.2f.3a.4f.5d.6f, | 1d.2f.3a.4f.5e.6a, | 1d.2f.3a.4f.5e.6b, |
| 1d.2f.3a.4f.5e.6c, | 1d.2f.3a.4f.5e.6d, | 1d.2f.3a.4f.5e.6e, | 1d.2f.3a.4f.5e.6f, | 1d.2f.3a.4f.5f.6a, |
| 1d.2f.3a.4f.5f.6b, | 1d.2f.3a.4f.5f.6c, | 1d.2f.3a.4f.5f.6d, | 1d.2f.3a.4f.5f.6e, | 1d.2f.3a.4f.5f.6f |
| 1d.2f.3b.4a.5a.6a, | 1d.2f.3b.4a.5a.6b, | 1d.2f.3b.4a.5a.6c, | 1d.2f.3b.4a.5a.6d, | |
| 1d.2f.3b.4a.5a.6e, | 1d.2f.3b.4a.5a.6f, | 1d.2f.3b.4a.5b.6a, | 1d.2f.3b.4a.5b.6b, | |
| 1d.2f.3b.4a.5b.6c, | 1d.2f.3b.4a.5b.6d, | 1d.2f.3b.4a.5b.6e, | 1d.2f.3b.4a.5b.6f, | |
| 1d.2f.3b.4a.5c.6a, | 1d.2f.3b.4a.5c.6b, | 1d.2f.3b.4a.5c.6c, | 1d.2f.3b.4a.5c.6d, | |
| 1d.2f.3b.4a.5c.6e, | 1d.2f.3b.4a.5c.6f, | 1d.2f.3b.4a.5d.6a, | 1d.2f.3b.4a.5d.6b, | |
| 1d.2f.3b.4a.5d.6c, | 1d.2f.3b.4a.5d.6d, | 1d.2f.3b.4a.5d.6e, | 1d.2f.3b.4a.5d.6f, | |
| 1d.2f.3b.4a.5e.6a, | 1d.2f.3b.4a.5e.6b, | 1d.2f.3b.4a.5e.6c, | 1d.2f.3b.4a.5e.6d, | |
| 1d.2f.3b.4a.5e.6e, | 1d.2f.3b.4a.5e.6f, | 1d.2f.3b.4a.5f.6a, | 1d.2f.3b.4a.5f.6b, | 1d.2f.3b.4a.5f.6c, |
| 1d.2f.3b.4a.5f.6d, | 1d.2f.3b.4a.5f.6e, | 1d.2f.3b.4a.5f.6f, | 1d.2f.3b.4b.5a.6a, | |
| 1d.2f.3b.4b.5a.6b, | 1d.2f.3b.4b.5a.6c, | 1d.2f.3b.4b.5a.6d, | 1d.2f.3b.4b.5a.6e, | |
| 1d.2f.3b.4b.5a.6f, | 1d.2f.3b.4b.5b.6a, | 1d.2f.3b.4b.5b.6b, | 1d.2f.3b.4b.5b.6c, | |
| 1d.2f.3b.4b.5b.6d, | 1d.2f.3b.4b.5b.6e, | 1d.2f.3b.4b.5b.6f, | 1d.2f.3b.4b.5c.6a, | |
| 1d.2f.3b.4b.5c.6b, | 1d.2f.3b.4b.5c.6c, | 1d.2f.3b.4b.5c.6d, | 1d.2f.3b.4b.5c.6e, | |
| 1d.2f.3b.4b.5c.6f, | 1d.2f.3b.4b.5d.6a, | 1d.2f.3b.4b.5d.6b, | 1d.2f.3b.4b.5d.6c, | |
| 1d.2f.3b.4b.5d.6d, | 1d.2f.3b.4b.5d.6e, | 1d.2f.3b.4b.5d.6f, | 1d.2f.3b.4b.5e.6a, | |
| 1d.2f.3b.4b.5e.6b, | 1d.2f.3b.4b.5e.6c, | 1d.2f.3b.4b.5e.6d, | 1d.2f.3b.4b.5e.6e, | |
| 1d.2f.3b.4b.5e.6f, | 1d.2f.3b.4b.5f.6a, | 1d.2f.3b.4b.5f.6b, | 1d.2f.3b.4b.5f.6c, | |
| 1d.2f.3b.4b.5f.6d, | 1d.2f.3b.4b.5f.6e, | 1d.2f.3b.4b.5f.6f, | 1d.2f.3b.4c.5a.6a, | |
| 1d.2f.3b.4c.5a.6b, | 1d.2f.3b.4c.5a.6c, | 1d.2f.3b.4c.5a.6d, | 1d.2f.3b.4c.5a.6e, | |
| 1d.2f.3b.4c.5a.6f, | 1d.2f.3b.4c.5b.6a, | 1d.2f.3b.4c.5b.6b, | 1d.2f.3b.4c.5b.6c, | |
| 1d.2f.3b.4c.5b.6d, | 1d.2f.3b.4c.5b.6e, | 1d.2f.3b.4c.5b.6f, | 1d.2f.3b.4c.5c.6a, | |
| 1d.2f.3b.4c.5c.6b, | 1d.2f.3b.4c.5c.6c, | 1d.2f.3b.4c.5c.6d, | 1d.2f.3b.4c.5c.6e, | 1d.2f.3b.4c.5c.6f, |
| 1d.2f.3b.4c.5d.6a, | 1d.2f.3b.4c.5d.6b, | 1d.2f.3b.4c.5d.6c, | 1d.2f.3b.4c.5d.6d, | |

TABLE 7-continued

List of Compounds of Formula (II)

| | | | |
|---|---|---|---|
| 1d.2f.3b.4c.5d.6e, | 1d.2f.3b.4c.5d.6f, | 1d.2f.3b.4c.5e.6a, | 1d.2f.3b.4c.5e.6b, |
| 1d.2f.3b.4c.5e.6c, | 1d.2f.3b.4c.5e.6d, | 1d.2f.3b.4c.5e.6e, | 1d.2f.3b.4c.5e.6f, | 1d.2f.3b.4c.5f.6a, |
| 1d.2f.3b.4c.5f.6b, | 1d.2f.3b.4c.5f.6c, | 1d.2f.3b.4c.5f.6d, | 1d.2f.3b.4c.5f.6e, | 1d.2f.3b.4c.5f.6f, |
| 1d.2f.3b.4d.5a.6a, | 1d.2f.3b.4d.5a.6b, | 1d.2f.3b.4d.5a.6c, | 1d.2f.3b.4d.5a.6d, |
| 1d.2f.3b.4d.5a.6e, | 1d.2f.3b.4d.5a.6f, | 1d.2f.3b.4d.5b.6a, | 1d.2f.3b.4d.5b.6b, |
| 1d.2f.3b.4d.5b.6c, | 1d.2f.3b.4d.5b.6d, | 1d.2f.3b.4d.5b.6e, | 1d.2f.3b.4d.5b.6f, |
| 1d.2f.3b.4d.5c.6a, | 1d.2f.3b.4d.5c.6b, | 1d.2f.3b.4d.5c.6c, | 1d.2f.3b.4d.5c.6d, |
| 1d.2f.3b.4d.5c.6e, | 1d.2f.3b.4d.5c.6f, | 1d.2f.3b.4d.5d.6a, | 1d.2f.3b.4d.5d.6b, |
| 1d.2f.3b.4d.5d.6c, | 1d.2f.3b.4d.5d.6d, | 1d.2f.3b.4d.5d.6e, | 1d.2f.3b.4d.5d.6f, |
| 1d.2f.3b.4d.5e.6a, | 1d.2f.3b.4d.5e.6b, | 1d.2f.3b.4d.5e.6c, | 1d.2f.3b.4d.5e.6d, |
| 1d.2f.3b.4d.5e.6e, | 1d.2f.3b.4d.5e.6f, | 1d.2f.3b.4d.5f.6a, | 1d.2f.3b.4d.5f.6b, |
| 1d.2f.3b.4d.5f.6c, | 1d.2f.3b.4d.5f.6d, | 1d.2f.3b.4d.5f.6e, | 1d.2f.3b.4d.5f.6f, |
| 1d.2f.3b.4e.5a.6a, | 1d.2f.3b.4e.5a.6b, | 1d.2f.3b.4e.5a.6c, | 1d.2f.3b.4e.5a.6d, |
| 1d.2f.3b.4e.5a.6e, | 1d.2f.3b.4e.5a.6f, | 1d.2f.3b.4e.5b.6a, | 1d.2f.3b.4e.5b.6b, |
| 1d.2f.3b.4e.5b.6c, | 1d.2f.3b.4e.5b.6d, | 1d.2f.3b.4e.5b.6e, | 1d.2f.3b.4e.5b.6f, |
| 1d.2f.3b.4e.5c.6a, | 1d.2f.3b.4e.5c.6b, | 1d.2f.3b.4e.5c.6c, | 1d.2f.3b.4e.5c.6d, |
| 1d.2f.3b.4e.5c.6e, | 1d.2f.3b.4e.5c.6f, | 1d.2f.3b.4e.5d.6a, | 1d.2f.3b.4e.5d.6b, |
| 1d.2f.3b.4e.5d.6c, | 1d.2f.3b.4e.5d.6d, | 1d.2f.3b.4e.5d.6e, | 1d.2f.3b.4e.5d.6f, |
| 1d.2f.3b.4e.5e.6a, | 1d.2f.3b.4e.5e.6b, | 1d.2f.3b.4e.5e.6c, | 1d.2f.3b.4e.5e.6d, |
| 1d.2f.3b.4e.5e.6e, | 1d.2f.3b.4e.5e.6f, | 1d.2f.3b.4e.5f.6a, | 1d.2f.3b.4e.5f.6b, | 1d.2f.3b.4e.5f.6c, |
| 1d.2f.3b.4e.5f.6d, | 1d.2f.3b.4e.5f.6e, | 1d.2f.3b.4e.5f.6f, | 1d.2f.3b.4f.5a.6a, | 1d.2f.3b.4f.5a.6b, |
| 1d.2f.3b.4f.5a.6c, | 1d.2f.3b.4f.5a.6d, | 1d.2f.3b.4f.5a.6e, | 1d.2f.3b.4f.5a.6f, | 1d.2f.3b.4f.5b.6a, |
| 1d.2f.3b.4f.5b.6b, | 1d.2f.3b.4f.5b.6c, | 1d.2f.3b.4f.5b.6d, | 1d.2f.3b.4f.5b.6e, | 1d.2f.3b.4f.5b.6f, |
| 1d.2f.3b.4f.5c.6a, | 1d.2f.3b.4f.5c.6b, | 1d.2f.3b.4f.5c.6c, | 1d.2f.3b.4f.5c.6d, | 1d.2f.3b.4f.5c.6e, |
| 1d.2f.3b.4f.5c.6f, | 1d.2f.3b.4f.5d.6a, | 1d.2f.3b.4f.5d.6b, | 1d.2f.3b.4f.5d.6c, |
| 1d.2f.3b.4f.5d.6d, | 1d.2f.3b.4f.5d.6e, | 1d.2f.3b.4f.5d.6f, | 1d.2f.3b.4f.5e.6a, |
| 1d.2f.3b.4f.5e.6b, | 1d.2f.3b.4f.5e.6c, | 1d.2f.3b.4f.5e.6d, | 1d.2f.3b.4f.5e.6e, | 1d.2f.3b.4f.5e.6f, |
| 1d.2f.3b.4f.5f.6a, | 1d.2f.3b.4f.5f.6b, | 1d.2f.3b.4f.5f.6c, | 1d.2f.3b.4f.5f.6d, | 1d.2f.3b.4f.5f.6e, |
| 1d.2f.3b.4f.5f.6f, | 1d.2f.3c.4a.5a.6a, | 1d.2f.3c.4a.5a.6b, | 1d.2f.3c.4a.5a.6c, | 1d.2f.3c.4a.5a.6d, |
| 1d.2f.3c.4a.5a.6e, | 1d.2f.3c.4a.5a.6f, | 1d.2f.3c.4a.5b.6a, | 1d.2f.3c.4a.5b.6b, |
| 1d.2f.3c.4a.5b.6c, | 1d.2f.3c.4a.5b.6d, | 1d.2f.3c.4a.5b.6e, | 1d.2f.3c.4a.5b.6f, |
| 1d.2f.3c.4a.5c.6a, | 1d.2f.3c.4a.5c.6b, | 1d.2f.3c.4a.5c.6c, | 1d.2f.3c.4a.5c.6d, | 1d.2f.3c.4a.5c.6e, |
| 1d.2f.3c.4a.5c.6f, | 1d.2f.3c.4a.5d.6a, | 1d.2f.3c.4a.5d.6b, | 1d.2f.3c.4a.5d.6c, |
| 1d.2f.3c.4a.5d.6d, | 1d.2f.3c.4a.5d.6e, | 1d.2f.3c.4a.5d.6f, | 1d.2f.3c.4a.5e.6a, |
| 1d.2f.3c.4a.5e.6b, | 1d.2f.3c.4a.5e.6c, | 1d.2f.3c.4a.5e.6d, | 1d.2f.3c.4a.5e.6e, | 1d.2f.3c.4a.5e.6f, |
| 1d.2f.3c.4a.5f.6a, | 1d.2f.3c.4a.5f.6b, | 1d.2f.3c.4a.5f.6c, | 1d.2f.3c.4a.5f.6d, | 1d.2f.3c.4a.5f.6e, |
| 1d.2f.3c.4a.5f.6f, | 1d.2f.3c.4b.5a.6a, | 1d.2f.3c.4b.5a.6b, | 1d.2f.3c.4b.5a.6c, |
| 1d.2f.3c.4b.5a.6d, | 1d.2f.3c.4b.5a.6e, | 1d.2f.3c.4b.5a.6f, | 1d.2f.3c.4b.5b.6a, |
| 1d.2f.3c.4b.5b.6b, | 1d.2f.3c.4b.5b.6c, | 1d.2f.3c.4b.5b.6d, | 1d.2f.3c.4b.5b.6e, |
| 1d.2f.3c.4b.5b.6f, | 1d.2f.3c.4b.5c.6a, | 1d.2f.3c.4b.5c.6b, | 1d.2f.3c.4b.5c.6c, |
| 1d.2f.3c.4b.5c.6d, | 1d.2f.3c.4b.5c.6e, | 1d.2f.3c.4b.5c.6f, | 1d.2f.3c.4b.5d.6a, |
| 1d.2f.3c.4b.5d.6b, | 1d.2f.3c.4b.5d.6c, | 1d.2f.3c.4b.5d.6d, | 1d.2f.3c.4b.5d.6e, |
| 1d.2f.3c.4b.5d.6f, | 1d.2f.3c.4b.5e.6a, | 1d.2f.3c.4b.5e.6b, | 1d.2f.3c.4b.5e.6c, |
| 1d.2f.3c.4b.5e.6d, | 1d.2f.3c.4b.5e.6e, | 1d.2f.3c.4b.5e.6f, | 1d.2f.3c.4b.5f.6a, | 1d.2f.3c.4b.5f.6b, |
| 1d.2f.3c.4b.5f.6c, | 1d.2f.3c.4b.5f.6d, | 1d.2f.3c.4b.5L6e, | 1d.2f.3c.4b.5f.6f, | 1d.2f.3c.4c.5a.6a, |
| 1d.2f.3c.4c.5a.6b, | 1d.2f.3c.4c.5a.6c, | 1d.2f.3c.4c.5a.6d, | 1d.2f.3c.4c.5a.6e, | 1d.2f.3c.4c.5a.6f, |
| 1d.2f.3c.4c.5b.6a, | 1d.2f.3c.4c.5b.6b, | 1d.2f.3c.4c.5b.6c, | 1d.2f.3c.4c.5b.6d, |
| 1d.2f.3c.4c.5b.6e, | 1d.2f.3c.4c.5b.6f, | 1d.2f.3c.4c.5c.6a, | 1d.2f.3c.4c.5c.6b, | 1d.2f.3c.4c.5c.6c, |
| 1d.2f.3c.4c.5c.6d, | 1d.2f.3c.4c.5c.6e, | 1d.2f.3c.4c.5c.6f, | 1d.2f.3c.4c.5d.6a, | 1d.2f.3c.4c.5d.6b, |
| 1d.2f.3c.4c.5d.6c, | 1d.2f.3c.4c.5d.6d, | 1d.2f.3c.4c.5d.6e, | 1d.2f.3c.4c.5d.6f, |
| 1d.2f.3c.4c.5e.6a, | 1d.2f.3c.4c.5e.6b, | 1d.2f.3c.4c.5e.6c, | 1d.2f.3c.4c.5e.6d, | 1d.2f.3c.4c.5e.6e, |
| 1d.2f.3c.4c.5e.6f, | 1d.2f.3c.4c.5f.6a, | 1d.2f.3c.4c.5f.6b, | 1d.2f.3c.4c.5f.6c, | 1d.2f.3c.4c.5f.6d, |
| 1d.2f.3c.4c.5f.6e, | 1d.2f.3c.4c.5f.6f, | 1d.2f.3c.4d.5a.6a, | 1d.2f.3c.4d.5a.6b, | 1d.2f.3c.4d.5a.6c, |
| 1d.2f.3c.4d.5a.6d, | 1d.2f.3c.4d.5a.6e, | 1d.2f.3c.4d.5a.6f, | 1d.2f.3c.4d.5b.6a, |
| 1d.2f.3c.4d.5b.6b, | 1d.2f.3c.4d.5b.6c, | 1d.2f.3c.4d.5b.6d, | 1d.2f.3c.4d.5b.6e, |
| 1d.2f.3c.4d.5b.6f, | 1d.2f.3c.4d.5c.6a, | 1d.2f.3c.4d.5c.6b, | 1d.2f.3c.4d.5c.6c, |
| 1d.2f.3c.4d.5c.6d, | 1d.2f.3c.4d.5c.6e, | 1d.2f.3c.4d.5c.6f, | 1d.2f.3c.4d.5d.6a, |
| 1d.2f.3c.4d.5d.6b, | 1d.2f.3c.4d.5d.6c, | 1d.2f.3c.4d.5d.6d, | 1d.2f.3c.4d.5d.6e, |
| 1d.2f.3c.4d.5d.6f, | 1d.2f.3c.4d.5e.6a, | 1d.2f.3c.4d.5e.6b, | 1d.2f.3c.4d.5e.6c, |
| 1d.2f.3c.4d.5e.6d, | 1d.2f.3c.4d.5e.6e, | 1d.2f.3c.4d.5e.6f, | 1d.2f.3c.4d.5f.6a, |
| 1d.2f.3c.4d.5f.6b, | 1d.2f.3c.4d.5f.6c, | 1d.2f.3c.4d.5f.6d, | 1d.2f.3c.4d.5f.6e, | 1d.2f.3c.4d.5f.6f, |
| 1d.2f.3c.4e.5a.6a, | 1d.2f.3c.4e.5a.6b, | 1d.2f.3c.4e.5a.6c, | 1d.2f.3c.4e.5a.6d, |
| 1d.2f.3c.4e.5a.6e, | 1d.2f.3c.4e.5a.6f, | 1d.2f.3c.4e.5b.6a, | 1d.2f.3c.4e.5b.6b, | 1d.2f.3c.4e.5b.6c, |
| 1d.2f.3c.4e.5b.6d, | 1d.2f.3c.4e.5b.6e, | 1d.2f.3c.4e.5b.6f, | 1d.2f.3c.4e.5c.6a, | 1d.2f.3c.4e.5c.6b, |
| 1d.2f.3c.4e.5c.6c, | 1d.2f.3c.4e.5c.6d, | 1d.2f.3c.4e.5c.6e, | 1d.2f.3c.4e.5c.6f, | 1d.2f.3c.4e.5d.6a, |
| 1d.2f.3c.4e.5d.6b, | 1d.2f.3c.4e.5d.6c, | 1d.2f.3c.4e.5d.6d, | 1d.2f.3c.4e.5d.6e, |
| 1d.2f.3c.4e.5d.6f, | 1d.2f.3c.4e.5e.6a, | 1d.2f.3c.4e.5e.6b, | 1d.2f.3c.4e.5e.6c, | 1d.2f.3c.4e.5e.6d, |
| 1d.2f.3c.4e.5e.6e, | 1d.2f.3c.4e.5e.6f, | 1d.2f.3c.4e.5f.6a, | 1d.2f.3c.4e.5f.6b, | 1d.2f.3c.4e.5f.6c, |
| 1d.2f.3c.4e.5f.6d, | 1d.2f.3c.4e.5f.6e, | 1d.2f.3c.4e.5f.6f, | 1d.2f.3c.4f.5a.6a, | 1d.2f.3c.4f.5a.6b, |
| 1d.2f.3c.4f.5a.6c, | 1d.2f.3c.4f.5a.6d, | 1d.2f.3c.4f.5a.6e, | 1d.2f.3c.4f.5a.6f, | 1d.2f.3c.4f.5b.6a, |
| 1d.2f.3c.4f.5b.6b, | 1d.2f.3c.4f.5b.6c, | 1d.2f.3c.4f.5b.6d, | 1d.2f.3c.4f.5b.6e, | 1d.2f.3c.4f.5b.6f, |
| 1d.2f.3c.4f.5c.6a, | 1d.2f.3c.4f.5c.6b, | 1d.2f.3c.4f.5c.6c, | 1d.2f.3c.4f.5c.6d, | 1d.2f.3c.4f.5c.6e, |
| 1d.2f.3c.4f.5c.6f, | 1d.2f.3c.4f.5d.6a, | 1d.2f.3c.4f.5d.6b, | 1d.2f.3c.4f.5d.6c, | 1d.2f.3c.4f.5d.6d, |
| 1d.2f.3c.4f.5d.6e, | 1d.2f.3c.4f.5d.6f, | 1d.2f.3c.4f.5e.6a, | 1d.2f.3c.4f.5e.6b, | 1d.2f.3c.4f.5e.6c, |
| 1d.2f.3c.4f.5e.6d, | 1d.2f.3c.4f.5e.6e, | 1d.2f.3c.4f.5e.6f, | 1d.2f.3c.4f.5f.6a, | 1d.2f.3c.4f.5f.6b, |
| 1d.2f.3c.4f.5f.6c, | 1d.2f.3c.4f.5f.6d, | 1d.2f.3c.4f.5f.6e, | 1d.2f.3c.4f.5f.6f, | 1d.2f.3d.4a.5a.6a, |
| 1d.2f.3d.4a.5a.6b, | 1d.2f.3d.4a.5a.6c, | 1d.2f.3d.4a.5a.6d, | 1d.2f.3d.4a.5a.6e, |
| 1d.2f.3d.4a.5a.6f, | 1d.2f.3d.4a.5b.6a, | 1d.2f.3d.4a.5b.6b, | 1d.2f.3d.4a.5b.6c, |

TABLE 7-continued

List of Compounds of Formula (II)

| | | | |
|---|---|---|---|
| 1d.2f.3d.4a.5b.6d, | 1d.2f.3d.4a.5b.6e, | 1d.2f.3d.4a.5b.6f, | 1d.2f.3d.4a.5c.6a, |
| 1d.2f.3d.4a.5c.6b, | 1d.2f.3d.4a.5c.6c, | 1d.2f.3d.4a.5c.6d, | 1d.2f.3d.4a.5c.6e, |
| 1d.2f.3d.4a.5c.6f, | 1d.2f.3d.4a.5d.6a, | 1d.2f.3d.4a.5d.6b, | 1d.2f.3d.4a.5d.6c, |
| 1d.2f.3d.4a.5d.6d, | 1d.2f.3d.4a.5d.6e, | 1d.2f.3d.4a.5d.6f, | 1d.2f.3d.4a.5e.6a, |
| 1d.2f.3d.4a.5e.6b, | 1d.2f.3d.4a.5e.6c, | 1d.2f.3d.4a.5e.6d, | 1d.2f.3d.4a.5e.6e, |
| 1d.2f.3d.4a.5e.6f, | 1d.2f.3d.4a.5f.6a, | 1d.2f.3d.4a.5f.6b, | 1d.2f.3d.4a.5f.6c, |
| 1d.2f.3d.4a.5f.6d, | 1d.2f.3d.4a.5f.6e, | 1d.2f.3d.4a.5f.6f, | 1d.2f.3d.4b.5a.6a, |
| 1d.2f.3d.4b.5a.6b, | 1d.2f.3d.4b.5a.6c, | 1d.2f.3d.4b.5a.6d, | 1d.2f.3d.4b.5a.6e, |
| 1d.2f.3d.4b.5a.6f, | 1d.2f.3d.4b.5b.6a, | 1d.2f.3d.4b.5b.6b, | 1d.2f.3d.4b.5b.6c, |
| 1d.2f.3d.4b.5b.6d, | 1d.2f.3d.4b.5b.6e, | 1d.2f.3d.4b.5b.6f, | 1d.2f.3d.4b.5c.6a, |
| 1d.2f.3d.4b.5c.6b, | 1d.2f.3d.4b.5c.6c, | 1d.2f.3d.4b.5c.6d, | 1d.2f.3d.4b.5c.6e, |
| 1d.2f.3d.4b.5c.6f, | 1d.2f.3d.4b.5d.6a, | 1d.2f.3d.4b.5d.6b, | 1d.2f.3d.4b.5d.6c, |
| 1d.2f.3d.4b.5d.6d, | 1d.2f.3d.4b.5d.6e, | 1d.2f.3d.4b.5d.6f, | 1d.2f.3d.4b.5e.6a, |
| 1d.2f.3d.4b.5e.6b, | 1d.2f.3d.4b.5e.6c, | 1d.2f.3d.4b.5e.6d, | 1d.2f.3d.4b.5e.6e, |
| 1d.2f.3d.4b.5e.6f, | 1d.2f.3d.4b.5f.6a, | 1d.2f.3d.4b.5f.6b, | 1d.2f.3d.4b.5f.6c, |
| 1d.2f.3d.4b.5f.6d, | 1d.2f.3d.4b.5f.6e, | 1d.2f.3d.4b.5f.6f, | 1d.2f.3d.4c.5a.6a, |
| 1d.2f.3d.4c.5a.6b, | 1d.2f.3d.4c.5a.6c, | 1d.2f.3d.4c.5a.6d, | 1d.2f.3d.4c.5a.6e, |
| 1d.2f.3d.4c.5a.6f, | 1d.2f.3d.4c.5b.6a, | 1d.2f.3d.4c.5b.6b, | 1d.2f.3d.4c.5b.6c, |
| 1d.2f.3d.4c.5b.6d, | 1d.2f.3d.4c.5b.6e, | 1d.2f.3d.4c.5b.6f, | 1d.2f.3d.4c.5c.6a, |
| 1d.2f.3d.4c.5c.6b, | 1d.2f.3d.4c.5c.6c, | 1d.2f.3d.4c.5c.6d, | 1d.2f.3d.4c.5c.6e, |
| 1d.2f.3d.4c.5c.6f, | 1d.2f.3d.4c.5d.6a, | 1d.2f.3d.4c.5d.6b, | 1d.2f.3d.4c.5d.6c, |
| 1d.2f.3d.4c.5d.6d, | 1d.2f.3d.4c.5d.6e, | 1d.2f.3d.4c.5d.6f, | 1d.2f.3d.4c.5e.6a, |
| 1d.2f.3d.4c.5e.6b, | 1d.2f.3d.4c.5e.6c, | 1d.2f.3d.4c.5e.6d, | 1d.2f.3d.4c.5e.6e, |
| 1d.2f.3d.4c.5e.6f, | 1d.2f.3d.4c.5f.6a, | 1d.2f.3d.4c.5f.6b, | 1d.2f.3d.4c.5f.6c, | 1d.2f.3d.4c.516d, |
| 1d.2f.3d.4c.5f.6e, | 1d.2f.3d.4c.5f.6f, | 1d.2f.3d.4d.5a.6a, | 1d.2f.3d.4d.5a.6b, |
| 1d.2f.3d.4d.5a.6c, | 1d.2f.3d.4d.5a.6d, | 1d.2f.3d.4d.5a.6e, | 1d.2f.3d.4d.5a.6f, |
| 1d.2f.3d.4d.5b.6a, | 1d.2f.3d.4d.5b.6b, | 1d.2f.3d.4d.5b.6c, | 1d.2f.3d.4d.5b.6d, |
| 1d.2f.3d.4d.5b.6e, | 1d.2f.3d.4d.5b.6f, | 1d.2f.3d.4d.5c.6a, | 1d.2f.3d.4d.5c.6b, |
| 1d.2f.3d.4d.5c.6c, | 1d.2f.3d.4d.5c.6d, | 1d.2f.3d.4d.5c.6e, | 1d.2f.3d.4d.5c.6f, |
| 1d.2f.3d.4d.5d.6a, | 1d.2f.3d.4d.5d.6b, | 1d.2f.3d.4d.5d.6c, | 1d.2f.3d.4d.5d.6d, |
| 1d.2f.3d.4d.5d.6e, | 1d.2f.3d.4d.5d.6f, | 1d.2f.3d.4d.5e.6a, | 1d.2f.3d.4d.5e.6b, |
| 1d.2f.3d.4d.5e.6c, | 1d.2f.3d.4d.5e.6d, | 1d.2f.3d.4d.5e.6e, | 1d.2f.3d.4d.5e.6f, |
| 1d.2f.3d.4d.5f.6a, | 1d.2f.3d.4d.5f.6b, | 1d.2f.3d.4d.5f.6c, | 1d.2f.3d.4d.5f.6d, |
| 1d.2f.3d.4d.5f.6e, | 1d.2f.3d.4d.5f.6f, | 1d.2f.3d.4e.5a.6a, | 1d.2f.3d.4e.5a.6b, |
| 1d.2f.3d.4e.5a.6c, | 1d.2f.3d.4e.5a.6d, | 1d.2f.3d.4e.5a.6e, | 1d.2f.3d.4e.5a.6f, |
| 1d.2f.3d.4e.5b.6a, | 1d.2f.3d.4e.5b.6b, | 1d.2f.3d.4e.5b.6c, | 1d.2f.3d.4e.5b.6d, |
| 1d.2f.3d.4e.5b.6e, | 1d.2f.3d.4e.5b.6f, | 1d.2f.3d.4e.5c.6a, | 1d.2f.3d.4e.5c.6b, |
| 1d.2f.3d.4e.5c.6c, | 1d.2f.3d.4e.5c.6d, | 1d.2f.3d.4e.5c.6e, | 1d.2f.3d.4e.5c.6f, |
| 1d.2f.3d.4e.5d.6a, | 1d.2f.3d.4e.5d.6b, | 1d.2f.3d.4e.5d.6c, | 1d.2f.3d.4e.5d.6d, |
| 1d.2f.3d.4e.5d.6e, | 1d.2f.3d.4e.5d.6f, | 1d.2f.3d.4e.5e.6a, | 1d.2f.3d.4e.5e.6b, |
| 1d.2f.3d.4e.5e.6c, | 1d.2f.3d.4e.5e.6d, | 1d.2f.3d.4e.5e.6e, | 1d.2f.3d.4e.5e.6f, |
| 1d.2f.3d.4e.5f.6a, | 1d.2f.3d.4e.5f.6b, | 1d.2f.3d.4e.5f.6c, | 1d.2f.3d.4e.5f.6d, |
| 1d.2f.3d.4e.5f.6e, | 1d.2f.3d.4e.5f.6f, | 1d.2f.3d.4f.5a.6a, | 1d.2f.3d.4f.5a.6b, | 1d.2f.3d.4f.5a.6c, |
| 1d.2f.3d.4f.5a.6d, | 1d.2f.3d.4f.5a.6e, | 1d.2f.3d.4f.5a.6f, | 1d.2f.3d.4f.5b.6a, |
| 1d.2f.3d.4f.5b.6b, | 1d.2f.3d.4f.5b.6c, | 1d.2f.3d.4f.5b.6d, | 1d.2f.3d.4f.5b.6e, |
| 1d.2f.3d.4f.5b.6f, | 1d.2f.3d.4f.5c.6a, | 1d.2f.3d.4f.5c.6b, | 1d.2f.3d.4f.5c.6c, | 1d.2f.3d.4f.5c.6d, |
| 1d.2f.3d.4f.5c.6e, | 1d.2f.3d.4f.5c.6f, | 1d.2f.3d.4f.5d.6a, | 1d.2f.3d.4f.5d.6b, |
| 1d.2f.3d.4f.5d.6c, | 1d.2f.3d.4f.5d.6d, | 1d.2f.3d.4f.5d.6e, | 1d.2f.3d.4f.5d.6f, |
| 1d.2f.3d.4f.5e.6a, | 1d.2f.3d.4f.5e.6b, | 1d.2f.3d.4f.5e.6c, | 1d.2f.3d.4f.5e.6d, |
| 1d.2f.3d.4f.5e.6e, | 1d.2f.3d.4f.5e.6f, | 1d.2f.3d.4f.5f.6a, | 1d.2f.3d.4f.5f.6b, | 1d.2f.3d.4f.5f.6c, |
| 1d.2f.3d.4f.5f.6d, | 1d.2f.3d.4f.5f.6e, | 1d.2f.3d.4f.5f.6f, | 1d.2f.3e.4a.5a.6a, | 1d.2f.3e.4a.5a.6b, |
| 1d.2f.3e.4a.5a.6c, | 1d.2f.3e.4a.5a.6d, | 1d.2f.3e.4a.5a.6e, | 1d.2f.3e.4a.5a.6f, |
| 1d.2f.3e.4a.5b.6a, | 1d.2f.3e.4a.5b.6b, | 1d.2f.3e.4a.5b.6c, | 1d.2f.3e.4a.5b.6d, |
| 1d.2f.3e.4a.5b.6e, | 1d.2f.3e.4a.5b.6f, | 1d.2f.3e.4a.5c.6a, | 1d.2f.3e.4a.5c.6b, | 1d.2f.3e.4a.5c.6c, |
| 1d.2f.3e.4a.5c.6d, | 1d.2f.3e.4a.5c.6e, | 1d.2f.3e.4a.5c.6f, | 1d.2f.3e.4a.5d.6a, |
| 1d.2f.3e.4a.5d.6b, | 1d.2f.3e.4a.5d.6c, | 1d.2f.3e.4a.5d.6d, | 1d.2f.3e.4a.5d.6e, |
| 1d.2f.3e.4a.5d.6f, | 1d.2f.3e.4a.5e.6a, | 1d.2f.3e.4a.5e.6b, | 1d.2f.3e.4a.5e.6c, |
| 1d.2f.3e.4a.5e.6d, | 1d.2f.3e.4a.5e.6e, | 1d.2f.3e.4a.5e.6f, | 1d.2f.3e.4a.5f.6a, | 1d.2f.3e.4a.5f.6b, |
| 1d.2f.3e.4a.5f.6c, | 1d.2f.3e.4a.5f.6d, | 1d.2f.3e.4a.5f.6e, | 1d.2f.3e.4a.5f.6f, | 1d.2f.3e.4b.5a.6a, |
| 1d.2f.3e.4b.5a.6b, | 1d.2f.3e.4b.5a.6c, | 1d.2f.3e.4b.5a.6d, | 1d.2f.3e.4b.5a.6e, |
| 1d.2f.3e.4b.5a.6f, | 1d.2f.3e.4b.5b.6a, | 1d.2f.3e.4b.5b.6b, | 1d.2f.3e.4b.5b.6c, |
| 1d.2f.3e.4b.5b.6d, | 1d.2f.3e.4b.5b.6e, | 1d.2f.3e.4b.5b.6f, | 1d.2f.3e.4b.5c.6a, |
| 1d.2f.3e.4b.5c.6b, | 1d.2f.3e.4b.5c.6c, | 1d.2f.3e.4b.5c.6d, | 1d.2f.3e.4b.5c.6e, |
| 1d.2f.3e.4b.5c.6f, | 1d.2f.3e.4b.5d.6a, | 1d.2f.3e.4b.5d.6b, | 1d.2f.3e.4b.5d.6c, |
| 1d.2f.3e.4b.5d.6d, | 1d.2f.3e.4b.5d.6e, | 1d.2f.3e.4b.5d.6f, | 1d.2f.3e.4b.5e.6a, |
| 1d.2f.3e.4b.5e.6b, | 1d.2f.3e.4b.5e.6c, | 1d.2f.3e.4b.5e.6d, | 1d.2f.3e.4b.5e.6e, |
| 1d.2f.3e.4b.5e.6f, | 1d.2f.3e.4b.5f.6a, | 1d.2f.3e.4b.5f.6b, | 1d.2f.3e.4b.5f.6c, | 1d.2f.3e.4b.5f.6d, |
| 1d.2f.3e.4b.5f.6e, | 1d.2f.3e.4b.5f.6f, | 1d.2f.3e.4c.5a.6a, | 1d.2f.3e.4c.5a.6b, | 1d.2f.3e.4c.5a.6c, |
| 1d.2f.3e.4c.5a.6d, | 1d.2f.3e.4c.5a.6e, | 1d.2f.3e.4c.5a.6f, | 1d.2f.3e.4c.5b.6a, |
| 1d.2f.3e.4c.5b.6b, | 1d.2f.3e.4c.5b.6c, | 1d.2f.3e.4c.5b.6d, | 1d.2f.3e.4c.5b.6e, |
| 1d.2f.3e.4c.5b.6f, | 1d.2f.3e.4c.5c.6a, | 1d.2f.3e.4c.5c.6b, | 1d.2f.3e.4c.5c.6c, | 1d.2f.3e.4c.5c.6d, |
| 1d.2f.3e.4c.5c.6e, | 1d.2f.3e.4c.5c.6f, | 1d.2f.3e.4c.5d.6a, | 1d.2f.3e.4c.5d.6b, | 1d.2f.3e.4c.5d.6c, |
| 1d.2f.3e.4c.5d.6d, | 1d.2f.3e.4c.5d.6e, | 1d.2f.3e.4c.5d.6f, | 1d.2f.3e.4c.5e.6a, |
| 1d.2f.3e.4c.5e.6b, | 1d.2f.3e.4c.5e.6c, | 1d.2f.3e.4c.5e.6d, | 1d.2f.3e.4c.5e.6e, | 1d.2f.3e.4c.5e.6f, |
| 1d.2f.3e.4c.5f.6a, | 1d.2f.3e.4c.5f.6b, | 1d.2f.3e.4c.5f.6c, | 1d.2f.3e.4c.5f.6d, | 1d.2f.3e.4c.5f.6e, |
| 1d.2f.3e.4c.5f.6f, | 1d.2f.3e.4d.5a.6a, | 1d.2f.3e.4d.5a.6b, | 1d.2f.3e.4d.5a.6c, |
| 1d.2f.3e.4d.5a.6d, | 1d.2f.3e.4d.5a.6e, | 1d.2f.3e.4d.5a.6f, | 1d.2f.3e.4d.5b.6a, |
| 1d.2f.3e.4d.5b.6b, | 1d.2f.3e.4d.5b.6c, | 1d.2f.3e.4d.5b.6d, | 1d.2f.3e.4d.5b.6e, |

TABLE 7-continued

List of Compounds of Formula (II)

| | | | | |
|---|---|---|---|---|
| 1d.2f.3e.4d.5b.6f, | 1d.2f.3e.4d.5c.6a, | 1d.2f.3e.4d.5c.6b, | 1d.2f.3e.4d.5c.6c, | |
| 1d.2f.3e.4d.5c.6d, | 1d.2f.3e.4d.5c.6e, | 1d.2f.3e.4d.5c.6f, | 1d.2f.3e.4d.5d.6a, | |
| 1d.2f.3e.4d.5d.6b, | 1d.2f.3e.4d.5d.6c, | 1d.2f.3e.4d.5d.6d, | 1d.2f.3e.4d.5d.6e, | |
| 1d.2f.3e.4d.5d.6f, | 1d.2f.3e.4d.5e.6a, | 1d.2f.3e.4d.5e.6b, | 1d.2f.3e.4d.5e.6c, | |
| 1d.2f.3e.4d.5e.6d, | 1d.2f.3e.4d.5e.6e, | 1d.2f.3e.4d.5e.6f, | 1d.2f.3e.4d.5f.6a, | |
| 1d.2f.3e.4d.5f.6b, | 1d.2f.3e.4d.5f.6c, | 1d.2f.3e.4d.5f.6d, | 1d.2f.3e.4d.5f.6e, | 1d.2f.3e.4d.5f.6f, |
| 1d.2f.3e.4e.5a.6a, | 1d.2f.3e.4e.5a.6b, | 1d.2f.3e.4e.5a.6c, | 1d.2f.3e.4e.5a.6d, | |
| 1d.2f.3e.4e.5a.6e, | 1d.2f.3e.4e.5a.6f, | 1d.2f.3e.4e.5b.6a, | 1d.2f.3e.4e.5b.6b, | |
| 1d.2f.3e.4e.5b.6c, | 1d.2f.3e.4e.5b.6d, | 1d.2f.3e.4e.5b.6e, | 1d.2f.3e.4e.5b.6f, | |
| 1d.2f.3e.4e.5c.6a, | 1d.2f.3e.4e.5c.6b, | 1d.2f.3e.4e.5c.6c, | 1d.2f.3e.4e.5c.6d, | 1d.2f.3e.4e.5c.6e, |
| 1d.2f.3e.4e.5c.6f, | 1d.2f.3e.4e.5d.6a, | 1d.2f.3e.4e.5d.6b, | 1d.2f.3e.4e.5d.6c, | |
| 1d.2f.3e.4e.5d.6d, | 1d.2f.3e.4e.5d.6e, | 1d.2f.3e.4e.5d.6f, | 1d.2f.3e.4e.5e.6a, | |
| 1d.2f.3e.4e.5e.6b, | 1d.2f.3e.4e.5e.6c, | 1d.2f.3e.4e.5e.6d, | 1d.2f.3e.4e.5e.6e, | 1d.2f.3e.4e.5e.6f, |
| 1d.2f.3e.4e.5f.6a, | 1d.2f.3e.4e.5f.6b, | 1d.2f.3e.4e.5f.6c, | 1d.2f.3e.4e.5f.6d, | 1d.2f.3e.4e.5f.6e, |
| 1d.2f.3e.4e.5f.6f, | 1d.2f.3e.4f.5a.6a, | 1d.2f.3e.4f.5a.6b, | 1d.2f.3e.4f.5a.6c, | 1d.2f.3e.4f.5a.6d, |
| 1d.2f.3e.4f.5a.6e, | 1d.2f.3e.4f.5a.6f, | 1d.2f.3e.4f.5b.6a, | 1d.2f.3e.4f.5b.6b, | 1d.2f.3e.4f.5b.6c, |
| 1d.2f.3e.4f.5b.6d, | 1d.2f.3e.4f.5b.6e, | 1d.2f.3e.4f.5b.6f, | 1d.2f.3e.4f.5c.6a, | 1d.2f.3e.4f.5c.6b, |
| 1d.2f.3e.4f.5c.6c, | 1d.2f.3e.4f.5c.6d, | 1d.2f.3e.4f.5c.6e, | 1d.2f.3e.4f.5c.6f, | 1d.2f.3e.4f.5d.6a, |
| 1d.2f.3e.4f.5d.6b, | 1d.2f.3e.4f.5d.6c, | 1d.2f.3e.4f.5d.6d, | 1d.2f.3e.4f.5d.6e, | 1d.2f.3e.4f.5d.6f, |
| 1d.2f.3e.4f.5e.6a, | 1d.2f.3e.4f.5e.6b, | 1d.2f.3e.4f.5e.6c, | 1d.2f.3e.4f.5e.6d, | 1d.2f.3e.4f.5e.6e, |
| 1d.2f.3e.4f.5e.6f, | 1d.2f.3e.4f.5f.6a, | 1d.2f.3e.4f.5f.6b, | 1d.2f.3e.4f.5f.6c, | 1d.2f.3e.4f.5f.6d, |
| 1d.2f.3e.4f.5f.6e, | 1d.2f.3e.4f.5f.6f, | 1d.2f.3f.4a.5a.6a, | 1d.2f.3f.4a.5a.6b, | 1d.2f.3f.4a.5a.6c, |
| 1d.2f.3f.4a.5a.6d, | 1d.2f.3f.4a.5a.6e, | 1d.2f.3f.4a.5a.6f, | 1d.2f.3f.4a.5b.6a, | 1d.2f.3f.4a.5b.6b, |
| 1d.2f.3f.4a.5b.6c, | 1d.2f.3f.4a.5b.6d, | 1d.2f.3f.4a.5b.6e, | 1d.2f.3f.4a.5b.6f, | 1d.2f.3f.4a.5c.6a, |
| 1d.2f.3f.4a.5c.6b, | 1d.2f.3f.4a.5c.6c, | 1d.2f.3f.4a.5c.6d, | 1d.2f.3f.4a.5c.6e, | 1d.2f.3f.4a.5c.6f, |
| 1d.2f.3f.4a.5d.6a, | 1d.2f.3f.4a.5d.6b, | 1d.2f.3f.4a.5d.6c, | 1d.2f.3f.4a.5d.6d, | |
| 1d.2f.3f.4a.5d.6e, | 1d.2f.3f.4a.5d.6f, | 1d.2f.3f.4a.5e.6a, | 1d.2f.3f.4a.5e.6b, | 1d.2f.3f.4a.5e.6c, |
| 1d.2f.3f.4a.5e.6d, | 1d.2f.3f.4a.5e.6e, | 1d.2f.3f.4a.5e.6f, | 1d.2f.3f.4a.5f.6a, | 1d.2f.3f.4a.5f.6b, |
| 1d.2f.314a.5f.6c, | 1d.2f.3f.4a.5f.6d, | 1d.2f.3f.4a.5f.6e, | 1d.2f.3f.4a.5f.6f, | 1d.2f.3f.4b.5a.6a, |
| 1d.2f.3f.4b.5a.6b, | 1d.2f.3f.4b.5a.6c, | 1d.2f.3f.4b.5a.6d, | 1d.2f.3f.4b.5a.6e, | 1d.2f.3f.4b.5a.6f, |
| 1d.2f.3f.4b.5b.6a, | 1d.2f.3f.4b.5b.6b, | 1d.2f.3f.4b.5b.6c, | 1d.2f.3f.4b.5b.6d, | |
| 1d.2f.3f.4b.5b.6e, | 1d.2f.3f.4b.5b.6f, | 1d.2f.3f.4b.5c.6a, | 1d.2f.3f.4b.5c.6b, | 1d.2f.3f.4b.5c.6c, |
| 1d.2f.3f.4b.5c.6d, | 1d.2f.3f.4b.5c.6e, | 1d.2f.3f.4b.5c.6f, | 1d.2f.3f.4b.5d.6a, | 1d.2f.3f.4b.5d.6b, |
| 1d.2f.3f.4b.5d.6c, | 1d.2f.3f.4b.5d.6d, | 1d.2f.3f.4b.5d.6e, | 1d.2f.3f.4b.5d.6f, | |
| 1d.2f.3f.4b.5e.6a, | 1d.2f.3f.4b.5e.6b, | 1d.2f.3f.4b.5e.6c, | 1d.2f.3f.4b.5e.6d, | 1d.2f.3f.4b.5e.6e, |
| 1d.2f.3f.4b.5e.6f, | 1d.2f.3f.4b.5f.6a, | 1d.2f.3f.4b.5f.6b, | 1d.2f.3f.4b.5f.6c, | 1d.2f.3f.4b.5f.6d, |
| 1d.2f.3f.4b.5f.6e, | 1d.2f.3f.4b.5f.6f, | 1d.2f.3f.4c.5a.6a, | 1d.2f.3f.4c.5a.6b, | 1d.2f.3f.4c.5a.6c, |
| 1d.2f.3f.4c.5a.6d, | 1d.2f.3f.4c.5a.6e, | 1d.2f.3f.4c.5a.6f, | 1d.2f.3f.4c.5b.6a, | 1d.2f.3f.4c.5b.6b, |
| 1d.2f.3f.4c.5b.6c, | 1d.2f.3f.4c.5b.6d, | 1d.2f.3f.4c.5b.6e, | 1d.2f.3f.4c.5b.6f, | 1d.2f.3f.4c.5c.6a, |
| 1d.2f.3f.4c.5c.6b, | 1d.2f.3f.4c.5c.6c, | 1d.2f.3f.4c.5c.6d, | 1d.2f.3f.4c.5c.6e, | 1d.2f.3f.4c.5c.6f, |
| 1d.2f.3f.4c.5d.6a, | 1d.2f.3f.4c.5d.6b, | 1d.2f.3f.4c.5d.6c, | 1d.2f.3f.4c.5d.6d, | 1d.2f.3f.4c.5d.6e, |
| 1d.2f.3f.4c.5d.6f, | 1d.2f.3f.4c.5e.6a, | 1d.2f.3f.4c.5e.6b, | 1d.2f.3f.4c.5e.6c, | 1d.2f.3f.4c.5e.6d, |
| 1d.2f.3f.4c.5e.6e, | 1d.2f.3f.4c.5e.6f, | 1d.2f.3f.4c.5f.6a, | 1d.2f.3f.4c.5f.6b, | 1d.2f.3f.4c.5f.6c, |
| 1d.2f.3f.4c.5f.6e, | 1d.2f.3f.4c.5f.6f, | 1d.2f.3f.4d.5a.6a, | 1d.2f.3f.4d.5a.6b, | |
| 1d.2f.3f.4d.5a.6c, | 1d.2f.3f.4d.5a.6d, | 1d.2f.3f.4d.5a.6e, | 1d.2f.3f.4d.5a.6f, | 1d.2f.3f.4d.5b.6a, |
| 1d.2f.3f.4d.5b.6b, | 1d.2f.3f.4d.5b.6c, | 1d.2f.3f.4d.5b.6d, | 1d.2f.3f.4d.5b.6e, | |
| 1d.2f.3f.4d.5b.6f, | 1d.2f.3f.4d.5c.6a, | 1d.2f.3f.4d.5c.6b, | 1d.2f.3f.4d.5c.6c, | 1d.2f.3f.4d.5c.6d, |
| 1d.2f.3f.4d.5c.6e, | 1d.2f.3f.4d.5c.6f, | 1d.2f.3f.4d.5d.6a, | 1d.2f.3f.4d.5d.6b, | |
| 1d.2f.3f.4d.5d.6c, | 1d.2f.3f.4d.5d.6d, | 1d.2f.3f.4d.5d.6e, | 1d.2f.3f.4d.5d.6f, | |
| 1d.2f.3f.4d.5e.6a, | 1d.2f.3f.4d.5e.6b, | 1d.2f.3f.4d.5e.6c, | 1d.2f.3f.4d.5e.6d, | |
| 1d.2f.3f.4d.5e.6e, | 1d.2f.3f.4d.5e.6f, | 1d.2f.3f.4d.5f.6a, | 1d.2f.3f.4d.5f.6b, | 1d.2f.3f.4d.5f.6c, |
| 1d.2f.3f.4d.5f.6d, | 1d.2f.3f.4d.5f.6e, | 1d.2f.3f.4d.5f.6f, | 1d.2f.3f.4e.5a.6a, | 1d.2f.3f.4e.5a.6b, |
| 1d.2f.3f.4e.5a.6c, | 1d.2f.3f.4e.5a.6d, | 1d.2f.3f.4e.5a.6e, | 1d.2f.3f.4e.5a.6f, | 1d.2f.3f.4e.5b.6a, |
| 1d.2f.3f.4e.5b.6b, | 1d.2f.3f.4e.5b.6c, | 1d.2f.3f.4e.5b.6d, | 1d.2f.3f.4e.5b.6e, | 1d.2f.3f.4e.5b.6f, |
| 1d.2f.3f.4e.5c.6a, | 1d.2f.3f.4e.5c.6b, | 1d.2f.3f.4e.5c.6c, | 1d.2f.3f.4e.5c.6d, | 1d.2f.3f.4e.5c.6e, |
| 1d.2f.3f.4e.5c.6f, | 1d.2f.3f.4e.5d.6a, | 1d.2f.3f.4e.5d.6b, | 1d.2f.3f.4e.5d.6c, | 1d.2f.3f.4e.5d.6d, |
| 1d.2f.3f.4e.5d.6e, | 1d.2f.3f.4e.5d.6f, | 1d.2f.3f.4e.5e.6a, | 1d.2f.3f.4e.5e.6b, | 1d.2f.3f.4e.5e.6c, |
| 1d.2f.3f.4e.5e.6d, | 1d.2f.3f.4e.5e.6e, | 1d.2f.3f.4e.5e.6f, | 1d.2f.3f.4e.5f.6a, | 1d.2f.3f.4e.5f.6b, |
| 1d.2f.3f.4e.5f.6c, | 1d.2f.3f.4e.5f.6d, | 1d.2f.3f.4e.5f.6e, | 1d.2f.3f.4e.5f.6f, | 1d.2f.3f.4f.5a.6a, |
| 1d.2f.3f.4f.5a.6b, | 1d.2f.3f.4f.5a.6c, | 1d.2f.3f.4f.5a.6d, | 1d.2f.3f.4f.5a.6e, | 1d.2f.3f.4f.5a.6f, |
| 1d.2f.3f.4f.5b.6a, | 1d.2f.3f.4f.5b.6b, | 1d.2f.3f.4f.5b.6c, | 1d.2f.3f.4f.5b.6d, | 1d.2f.3f.4f.5b.6e, |
| 1d.2f.3f.4f.5b.6f, | 1d.2f.3f.4f.5c.6a, | 1d.2f.3f.4f.5c.6b, | 1d.2f.3f.4f.5c.6c, | 1d.2f.3f.4f.5c.6d, |
| 1d.2f.3f.4f.5c.6e, | 1d.2f.3f.4f.5c.6f, | 1d.2f.3f.4f.5d.6a, | 1d.2f.3f.4f.5d.6b, | 1d.2f.3f.4f.5d.6c, |
| 1d.2f.3f.4f.5d.6d, | 1d.2f.3f.4f.5d.6e, | 1d.2f.3f.4f.5d.6f, | 1d.2f.3f.4f.5e.6a, | 1d.2f.3f.4f.5e.6b, |
| 1d.2f.3f.4f.5e.6c, | 1d.2f.3f.4f.5e.6d, | 1d.2f.3f.4f.5e.6e, | 1d.2f.3f.4f.5f.6a, | |
| 1d.2f.3f.4f.5f.6b, | 1d.2f.3f.4f.5f.6c, | 1d.2f.3f.4f.5f.6d, | 1d.2f.3f.4f.5f.6e, | 1d.2f.3f.4f.5f.6f, |
| 1e.2a.3a.4a.5a.6a, | 1e.2a.3a.4a.5a.6b, | 1e.2a.3a.4a.5a.6c, | 1e.2a.3a.4a.5a.6d, | |
| 1e.2a.3a.4a.5a.6e, | 1e.2a.3a.4a.5a.6f, | 1e.2a.3a.4a.5b.6a, | 1e.2a.3a.4a.5b.6b, | |
| 1e.2a.3a.4a.5b.6c, | 1e.2a.3a.4a.5b.6d, | 1e.2a.3a.4a.5b.6e, | 1e.2a.3a.4a.5b.6f, | |
| 1e.2a.3a.4a.5c.6a, | 1e.2a.3a.4a.5c.6b, | 1e.2a.3a.4a.5c.6c, | 1e.2a.3a.4a.5c.6d, | |
| 1e.2a.3a.4a.5c.6e, | 1e.2a.3a.4a.5c.6f, | 1e.2a.3a.4a.5d.6a, | 1e.2a.3a.4a.5d.6b, | |
| 1e.2a.3a.4a.5d.6c, | 1e.2a.3a.4a.5d.6d, | 1e.2a.3a.4a.5d.6e, | 1e.2a.3a.4a.5d.6f, | |
| 1e.2a.3a.4a.5e.6a, | 1e.2a.3a.4a.5e.6b, | 1e.2a.3a.4a.5e.6c, | 1e.2a.3a.4a.5e.6d, | |
| 1e.2a.3a.4a.5e.6e, | 1e.2a.3a.4a.5e.6f, | 1e.2a.3a.4a.5f.6a, | 1e.2a.3a.4a.5f.6b, | 1e.2a.3a.4a.5f.6c, |
| 1e.2a.3a.4a.5f.6d, | 1e.2a.3a.4a.5f.6e, | 1e.2a.3a.4a.5f.6f, | 1e.2a.3a.4b.5a.6a, | |
| 1e.2a.3a.4b.5a.6b, | 1e.2a.3a.4b.5a.6c, | 1e.2a.3a.4b.5a.6d, | 1e.2a.3a.4b.5a.6e, | |
| 1e.2a.3a.4b.5a.6f, | 1e.2a.3a.4b.5b.6a, | 1e.2a.3a.4b.5b.6b, | 1e.2a.3a.4b.5b.6c, | |
| 1e.2a.3a.4b.5b.6d, | 1e.2a.3a.4b.5b.6e, | 1e.2a.3a.4b.5b.6f, | 1e.2a.3a.4b.5c.6a, | |

TABLE 7-continued

List of Compounds of Formula (II)

| | | | | |
|---|---|---|---|---|
| 1e.2a.3a.4b.5c.6b, | 1e.2a.3a.4b.5c.6c, | 1e.2a.3a.4b.5c.6d, | 1e.2a.3a.4b.5c.6e, | |
| 1e.2a.3a.4b.5c.6f, | 1e.2a.3a.4b.5d.6a, | 1e.2a.3a.4b.5d.6b, | 1e.2a.3a.4b.5d.6c, | |
| 1e.2a.3a.4b.5d.6d, | 1e.2a.3a.4b.5d.6e, | 1e.2a.3a.4b.5d.6f, | 1e.2a.3a.4b.5e.6a, | |
| 1e.2a.3a.4b.5e.6b, | 1e.2a.3a.4b.5e.6c, | 1e.2a.3a.4b.5e.6d, | 1e.2a.3a.4b.5e.6e, | |
| 1e.2a.3a.4b.5e.6f, | 1e.2a.3a.4b.5f.6a, | 1e.2a.3a.4b.5f.6b, | 1e.2a.3a.4b.5f.6c, | |
| 1e.2a.3a.4b.5f.6d, | 1e.2a.3a.4b.5f.6e, | 1e.2a.3a.4b.5f.6f, | 1e.2a.3a.4c.5a.6a, | |
| 1e.2a.3a.4c.5a.6b, | 1e.2a.3a.4c.5a.6c, | 1e.2a.3a.4c.5a.6d, | 1e.2a.3a.4c.5a.6e, | |
| 1e.2a.3a.4c.5a.6f, | 1e.2a.3a.4c.5b.6a, | 1e.2a.3a.4c.5b.6b, | 1e.2a.3a.4c.5b.6c, | |
| 1e.2a.3a.4c.5b.6d, | 1e.2a.3a.4c.5b.6e, | 1e.2a.3a.4c.5b.6f, | 1e.2a.3a.4c.5c.6a, | |
| 1e.2a.3a.4c.5c.6b, | 1e.2a.3a.4c.5c.6c, | 1e.2a.3a.4c.5c.6d, | 1e.2a.3a.4c.5c.6e, | 1e.2a.3a.4c.5c.6f, |
| 1e.2a.3a.4c.5d.6a, | 1e.2a.3a.4c.5d.6b, | 1e.2a.3a.4c.5d.6c, | 1e.2a.3a.4c.5d.6d, | |
| 1e.2a.3a.4c.5d.6e, | 1e.2a.3a.4c.5d.6f, | 1e.2a.3a.4c.5e.6a, | 1e.2a.3a.4c.5e.6b, | |
| 1e.2a.3a.4c.5e.6c, | 1e.2a.3a.4c.5e.6d, | 1e.2a.3a.4c.5e.6e, | 1e.2a.3a.4c.5e.6f, | 1e.2a.3a.4c.5f.6a, |
| 1e.2a.3a.4c.5f.6b, | 1e.2a.3a.4c.5f.6c, | 1e.2a.3a.4c.5f.6d, | 1e.2a.3a.4c.5f.6e, | 1e.2a.3a.4c.5f.6f, |
| 1e.2a.3a.4d.5a.6a, | 1e.2a.3a.4d.5a.6b, | 1e.2a.3a.4d.5a.6c, | 1e.2a.3a.4d.5a.6d, | |
| 1e.2a.3a.4d.5a.6e, | 1e.2a.3a.4d.5a.6f, | 1e.2a.3a.4d.5b.6a, | 1e.2a.3a.4d.5b.6b, | |
| 1e.2a.3a.4d.5b.6c, | 1e.2a.3a.4d.5b.6d, | 1e.2a.3a.4d.5b.6e, | 1e.2a.3a.4d.5b.6f, | |
| 1e.2a.3a.4d.5c.6a, | 1e.2a.3a.4d.5c.6b, | 1e.2a.3a.4d.5c.6c, | 1e.2a.3a.4d.5c.6d, | |
| 1e.2a.3a.4d.5c.6e, | 1e.2a.3a.4d.5c.6f, | 1e.2a.3a.4d.5d.6a, | 1e.2a.3a.4d.5d.6b, | |
| 1e.2a.3a.4d.5d.6c, | 1e.2a.3a.4d.5d.6d, | 1e.2a.3a.4d.5d.6e, | 1e.2a.3a.4d.5d.6f, | |
| 1e.2a.3a.4d.5e.6a, | 1e.2a.3a.4d.5e.6b, | 1e.2a.3a.4d.5e.6c, | 1e.2a.3a.4d.5e.6d, | |
| 1e.2a.3a.4d.5e.6e, | 1e.2a.3a.4d.5e.6f, | 1e.2a.3a.4d.5f.6a, | 1e.2a.3a.4d.5f.6b, | |
| 1e.2a.3a.4d.5f.6c, | 1e.2a.3a.4d.5f.6d, | 1e.2a.3a.4d.5f.6e, | 1e.2a.3a.4d.5f.6f, | |
| 1e.2a.3a.4e.5a.6a, | 1e.2a.3a.4e.5a.6b, | 1e.2a.3a.4e.5a.6c, | 1e.2a.3a.4e.5a.6d, | |
| 1e.2a.3a.4e.5a.6e, | 1e.2a.3a.4e.5a.6f, | 1e.2a.3a.4e.5b.6a, | 1e.2a.3a.4e.5b.6b, | |
| 1e.2a.3a.4e.5b.6c, | 1e.2a.3a.4e.5b.6d, | 1e.2a.3a.4e.5b.6e, | 1e.2a.3a.4e.5b.6f, | |
| 1e.2a.3a.4e.5c.6a, | 1e.2a.3a.4e.5c.6b, | 1e.2a.3a.4e.5c.6c, | 1e.2a.3a.4e.5c.6d, | |
| 1e.2a.3a.4e.5c.6e, | 1e.2a.3a.4e.5c.6f, | 1e.2a.3a.4e.5d.6a, | 1e.2a.3a.4e.5d.6b, | |
| 1e.2a.3a.4e.5d.6c, | 1e.2a.3a.4e.5d.6d, | 1e.2a.3a.4e.5d.6e, | 1e.2a.3a.4e.5d.6f, | |
| 1e.2a.3a.4e.5e.6a, | 1e.2a.3a.4e.5e.6b, | 1e.2a.3a.4e.5e.6c, | 1e.2a.3a.4e.5e.6d, | |
| 1e.2a.3a.4e.5e.6e, | 1e.2a.3a.4e.5e.6f, | 1e.2a.3a.4e.5f.6a, | 1e.2a.3a.4e.5f.6b, | 1e.2a.3a.4e.5f.6c, |
| 1e.2a.3a.4e.5f.6d, | 1e.2a.3a.4e.5f.6e, | 1e.2a.3a.4e.5f.6f, | 1e.2a.3a.4f.5a.6a, | 1e.2a.3a.4f.5a.6b, |
| 1e.2a.3a.4f.5a.6c, | 1e.2a.3a.4f.5a.6d, | 1e.2a.3a.4f.5a.6e, | 1e.2a.3a.4f.5a.6f, | 1e.2a.3a.4f.5b.6a, |
| 1e.2a.3a.4f.5b.6b, | 1e.2a.3a.4f.5b.6c, | 1e.2a.3a.4f.5b.6d, | 1e.2a.3a.4f.5b.6e, | 1e.2a.3a.4f.5b.6f, |
| 1e.2a.3a.4f.5c.6a, | 1e.2a.3a.4f.5c.6b, | 1e.2a.3a.4f.5c.6c, | 1e.2a.3a.4f.5c.6d, | 1e.2a.3a.4f.5c.6e, |
| 1e.2a.3a.4f.5c.6f, | 1e.2a.3a.4f.5d.6a, | 1e.2a.3a.4f.5d.6b, | 1e.2a.3a.4f.5d.6c, | |
| 1e.2a.3a.4f.5d.6d, | 1e.2a.3a.4f.5d.6e, | 1e.2a.3a.4f.5d.6f, | 1e.2a.3a.4f.5e.6a, | 1e.2a.3a.4f.5e.6b, |
| 1e.2a.3a.4f.5e.6c, | 1e.2a.3a.4f.5e.6d, | 1e.2a.3a.4f.5e.6e, | 1e.2a.3a.4f.5e.6f, | 1e.2a.3a.4f.5f.6a, |
| 1e.2a.3a.4f.5f.6b, | 1e.2a.3a.4f.5f.6c, | 1e.2a.3a.4f.5f.6d, | 1e.2a.3a.4f.5f.6e, | 1e.2a.3a.4f.5f.6f, |
| 1e.2a.3b.4a.5a.6a, | 1e.2a.3b.4a.5a.6b, | 1e.2a.3b.4a.5a.6c, | 1e.2a.3b.4a.5a.6d, | |
| 1e.2a.3b.4a.5a.6e, | 1e.2a.3b.4a.5a.6f, | 1e.2a.3b.4a.5b.6a, | 1e.2a.3b.4a.5b.6b, | |
| 1e.2a.3b.4a.5b.6c, | 1e.2a.3b.4a.5b.6d, | 1e.2a.3b.4a.5b.6e, | 1e.2a.3b.4a.5b.6f, | |
| 1e.2a.3b.4a.5c.6a, | 1e.2a.3b.4a.5c.6b, | 1e.2a.3b.4a.5c.6c, | 1e.2a.3b.4a.5c.6d, | |
| 1e.2a.3b.4a.5c.6e, | 1e.2a.3b.4a.5c.6f, | 1e.2a.3b.4a.5d.6a, | 1e.2a.3b.4a.5d.6b, | |
| 1e.2a.3b.4a.5d.6c, | 1e.2a.3b.4a.5d.6d, | 1e.2a.3b.4a.5d.6e, | 1e.2a.3b.4a.5d.6f, | |
| 1e.2a.3b.4a.5e.6a, | 1e.2a.3b.4a.5e.6b, | 1e.2a.3b.4a.5e.6c, | 1e.2a.3b.4a.5e.6d, | |
| 1e.2a.3b.4a.5e.6e, | 1e.2a.3b.4a.5e.6f, | 1e.2a.3b.4a.5f.6a, | 1e.2a.3b.4a.5f.6b, | |
| 1e.2a.3b.4a.5f.6c, | 1e.2a.3b.4a.5f.6d, | 1e.2a.3b.4a.5f.6e, | 1e.2a.3b.4a.5f.6f, | |
| 1e.2a.3b.4b.5a.6a, | 1e.2a.3b.4b.5a.6b, | 1e.2a.3b.4b.5a.6c, | 1e.2a.3b.4b.5a.6d, | |
| 1e.2a.3b.4b.5a.6e, | 1e.2a.3b.4b.5a.6f, | 1e.2a.3b.4b.5b.6a, | 1e.2a.3b.4b.5b.6b, | |
| 1e.2a.3b.4b.5b.6c, | 1e.2a.3b.4b.5b.6d, | 1e.2a.3b.4b.5b.6e, | 1e.2a.3b.4b.5b.6f, | |
| 1e.2a.3b.4b.5c.6a, | 1e.2a.3b.4b.5c.6b, | 1e.2a.3b.4b.5c.6c, | 1e.2a.3b.4b.5c.6d, | |
| 1e.2a.3b.4b.5c.6e, | 1e.2a.3b.4b.5c.6f, | 1e.2a.3b.4b.5d.6a, | 1e.2a.3b.4b.5d.6b, | |
| 1e.2a.3b.4b.5d.6c, | 1e.2a.3b.4b.5d.6d, | 1e.2a.3b.4b.5d.6e, | 1e.2a.3b.4b.5d.6f, | |
| 1e.2a.3b.4b.5e.6a, | 1e.2a.3b.4b.5e.6b, | 1e.2a.3b.4b.5e.6c, | 1e.2a.3b.4b.5e.6d, | |
| 1e.2a.3b.4b.5e.6e, | 1e.2a.3b.4b.5e.6f, | 1e.2a.3b.4b.5f.6a, | 1e.2a.3b.4b.5f.6b, | |
| 1e.2a.3b.4b.5f.6c, | 1e.2a.3b.4b.5f.6d, | 1e.2a.3b.4b.5f.6e, | 1e.2a.3b.4b.5f.6f, | |
| 1e.2a.3b.4c.5a.6a, | 1e.2a.3b.4c.5a.6b, | 1e.2a.3b.4c.5a.6c, | 1e.2a.3b.4c.5a.6d, | |
| 1e.2a.3b.4c.5a.6e, | 1e.2a.3b.4c.5a.6f, | 1e.2a.3b.4c.5b.6a, | 1e.2a.3b.4c.5b.6b, | |
| 1e.2a.3b.4c.5b.6c, | 1e.2a.3b.4c.5b.6d, | 1e.2a.3b.4c.5b.6e, | 1e.2a.3b.4c.5b.6f, | |
| 1e.2a.3b.4c.5c.6a, | 1e.2a.3b.4c.5c.6b, | 1e.2a.3b.4c.5c.6c, | 1e.2a.3b.4c.5c.6d, | |
| 1e.2a.3b.4c.5c.6e, | 1e.2a.3b.4c.5c.6f, | 1e.2a.3b.4c.5d.6a, | 1e.2a.3b.4c.5d.6b, | |
| 1e.2a.3b.4c.5d.6c, | 1e.2a.3b.4c.5d.6d, | 1e.2a.3b.4c.5d.6e, | 1e.2a.3b.4c.5d.6f, | |
| 1e.2a.3b.4c.5e.6a, | 1e.2a.3b.4c.5e.6b, | 1e.2a.3b.4c.5e.6c, | 1e.2a.3b.4c.5e.6d, | |
| 1e.2a.3b.4c.5e.6e, | 1e.2a.3b.4c.5e.6f, | 1e.2a.3b.4c.5f.6a, | 1e.2a.3b.4c.5f.6b, | 1e.2a.3b.4c.5f.6c, |
| 1e.2a.3b.4c.5f.6d, | 1e.2a.3b.4c.5f.6e, | 1e.2a.3b.4c.5f.6f, | 1e.2a.3b.4d.5a.6a, | |
| 1e.2a.3b.4d.5a.6b, | 1e.2a.3b.4d.5a.6c, | 1e.2a.3b.4d.5a.6d, | 1e.2a.3b.4d.5a.6e, | |
| 1e.2a.3b.4d.5a.6f, | 1e.2a.3b.4d.5b.6a, | 1e.2a.3b.4d.5b.6b, | 1e.2a.3b.4d.5b.6c, | |
| 1e.2a.3b.4d.5b.6d, | 1e.2a.3b.4d.5b.6e, | 1e.2a.3b.4d.5b.6f, | 1e.2a.3b.4d.5c.6a, | |
| 1e.2a.3b.4d.5c.6b, | 1e.2a.3b.4d.5c.6c, | 1e.2a.3b.4d.5c.6d, | 1e.2a.3b.4d.5c.6e, | |
| 1e.2a.3b.4d.5c.6f, | 1e.2a.3b.4d.5d.6a, | 1e.2a.3b.4d.5d.6b, | 1e.2a.3b.4d.5d.6c, | |
| 1e.2a.3b.4d.5d.6d, | 1e.2a.3b.4d.5d.6e, | 1e.2a.3b.4d.5d.6f, | 1e.2a.3b.4d.5e.6a, | |
| 1e.2a.3b.4d.5e.6b, | 1e.2a.3b.4d.5e.6c, | 1e.2a.3b.4d.5e.6d, | 1e.2a.3b.4d.5e.6e, | |
| 1e.2a.3b.4d.5e.6f, | 1e.2a.3b.4d.5f.6a, | 1e.2a.3b.4d.5f.6b, | 1e.2a.3b.4d.5f.6c, | |
| 1e.2a.3b.4d.5f.6d, | 1e.2a.3b.4d.5f.6e, | 1e.2a.3b.4d.5f.6f, | 1e.2a.3b.4e.5a.6a, | |
| 1e.2a.3b.4e.5a.6b, | 1e.2a.3b.4e.5a.6c, | 1e.2a.3b.4e.5a.6d, | 1e.2a.3b.4e.5a.6e, | |
| 1e.2a.3b.4e.5a.6f, | 1e.2a.3b.4e.5b.6a, | 1e.2a.3b.4e.5b.6b, | 1e.2a.3b.4e.5b.6c, | |
| 1e.2a.3b.4e.5b.6d, | 1e.2a.3b.4e.5b.6e, | 1e.2a.3b.4e.5b.6f, | 1e.2a.3b.4e.5c.6a, | |

TABLE 7-continued

List of Compounds of Formula (II)

| | | | |
|---|---|---|---|
| 1e.2a.3b.4e.5c.6b, | 1e.2a.3b.4e.5c.6c, | 1e.2a.3b.4e.5c.6d, | 1e.2a.3b.4e.5c.6e, |
| 1e.2a.3b.4e.5c.6f, | 1e.2a.3b.4e.5d.6a, | 1e.2a.3b.4e.5d.6b, | 1e.2a.3b.4e.5d.6c, |
| 1e.2a.3b.4e.5d.6d, | 1e.2a.3b.4e.5d.6e, | 1e.2a.3b.4e.5d.6f, | 1e.2a.3b.4e.5e.6a, |
| 1e.2a.3b.4e.5e.6b, | 1e.2a.3b.4e.5e.6c, | 1e.2a.3b.4e.5e.6d, | 1e.2a.3b.4e.5e.6e, |
| 1e.2a.3b.4e.5e.6f, | 1e.2a.3b.4e.5f.6a, | 1e.2a.3b.4e.5f.6b, | 1e.2a.3b.4e.5f.6c, | 1e.2a.3b.4e.5f.6d, |
| 1e.2a.3b.4e.5f.6e, | 1e.2a.3b.4e.5f.6f, | 1e.2a.3b.4f.5a.6a, | 1e.2a.3b.4f.5a.6b, | 1e.2a.3b.4f.5a.6c, |
| 1e.2a.3b.4f.5a.6d, | 1e.2a.3b.4f.5a.6e, | 1e.2a.3b.4f.5a.6f, | 1e.2a.3b.4f.5b.6a, |
| 1e.2a.3b.4f.5b.6b, | 1e.2a.3b.4f.5b.6c, | 1e.2a.3b.4f.5b.6d, | 1e.2a.3b.4f.5b.6e, |
| 1e.2a.3b.4f.5b.6f, | 1e.2a.3b.4f.5c.6a, | 1e.2a.3b.4f.5c.6b, | 1e.2a.3b.4f.5c.6c, | 1e.2a.3b.4f.5c.6d, |
| 1e.2a.3b.4f.5c.6e, | 1e.2a.3b.415c.6f, | 1e.2a.3b.4f.5d.6a, | 1e.2a.3b.4f.5d.6b, | 1e.2a.3b.4f.5d.6c, |
| 1e.2a.3b.4f.5d.6d, | 1e.2a.3b.4f.5d.6e, | 1e.2a.3b.4f.5d.6f, | 1e.2a.3b.4f.5e.6a, |
| 1e.2a.3b.4f.5e.6b, | 1e.2a.3b.4f.5e.6c, | 1e.2a.3b.4f.5e.6d, | 1e.2a.3b.4f.5e.6e, | 1e.2a.3b.4f.5e.6f, |
| 1e.2a.3b.4f.5f.6a, | 1e.2a.3b.4f.5f.6b, | 1e.2a.3b.4f.5f.6c, | 1e.2a.3b.4f.5f.6d, | 1e.2a.3b.4f.5f.6e, |
| 1e.2a.3b.4f.5f.6f, | 1e.2a.3c.4a.5a.6a, | 1e.2a.3c.4a.5a.6b, | 1e.2a.3c.4a.5a.6c, | 1e.2a.3c.4a.5a.6d, |
| 1e.2a.3c.4a.5a.6e, | 1e.2a.3c.4a.5a.6f, | 1e.2a.3c.4a.5b.6a, | 1e.2a.3c.4a.5b.6b, |
| 1e.2a.3c.4a.5b.6c, | 1e.2a.3c.4a.5b.6d, | 1e.2a.3c.4a.5b.6e, | 1e.2a.3c.4a.5b.6f, |
| 1e.2a.3c.4a.5c.6a, | 1e.2a.3c.4a.5c.6b, | 1e.2a.3c.4a.5c.6c, | 1e.2a.3c.4a.5c.6d, |
| 1e.2a.3c.4a.5c.6e, | 1e.2a.3c.4a.5c.6f, | 1e.2a.3c.4a.5d.6a, | 1e.2a.3c.4a.5d.6b, |
| 1e.2a.3c.4a.5d.6c, | 1e.2a.3c.4a.5d.6d, | 1e.2a.3c.4a.5d.6e, | 1e.2a.3c.4a.5d.6f, |
| 1e.2a.3c.4a.5e.6a, | 1e.2a.3c.4a.5e.6b, | 1e.2a.3c.4a.5e.6c, | 1e.2a.3c.4a.5e.6d, |
| 1e.2a.3c.4a.5e.6e, | 1e.2a.3c.4a.5e.6f, | 1e.2a.3c.4a.5f.6a, | 1e.2a.3c.4a.5f.6b, | 1e.2a.3c.4a.5f.6c, |
| 1e.2a.3c.4a.5f.6d, | 1e.2a.3c.4a.5f.6e, | 1e.2a.3c.4a.5f.6f, | 1e.2a.3c.4b.5a.6a, | 1e.2a.3c.4b.5a.6b, |
| 1e.2a.3c.4b.5a.6c, | 1e.2a.3c.4b.5a.6d, | 1e.2a.3c.4b.5a.6e, | 1e.2a.3c.4b.5a.6f, |
| 1e.2a.3c.4b.5b.6a, | 1e.2a.3c.4b.5b.6b, | 1e.2a.3c.4b.5b.6c, | 1e.2a.3c.4b.5b.6d, |
| 1e.2a.3c.4b.5b.6e, | 1e.2a.3c.4b.5b.6f, | 1e.2a.3c.4b.5c.6a, | 1e.2a.3c.4b.5c.6b, |
| 1e.2a.3c.4b.5c.6c, | 1e.2a.3c.4b.5c.6d, | 1e.2a.3c.4b.5c.6e, | 1e.2a.3c.4b.5c.6f, |
| 1e.2a.3c.4b.5d.6a, | 1e.2a.3c.4b.5d.6b, | 1e.2a.3c.4b.5d.6c, | 1e.2a.3c.4b.5d.6d, |
| 1e.2a.3c.4b.5d.6e, | 1e.2a.3c.4b.5d.6f, | 1e.2a.3c.4b.5e.6a, | 1e.2a.3c.4b.5e.6b, |
| 1e.2a.3c.4b.5e.6c, | 1e.2a.3c.4b.5e.6d, | 1e.2a.3c.4b.5e.6e, | 1e.2a.3c.4b.5e.6f, |
| 1e.2a.3c.4b.5f.6a, | 1e.2a.3c.4b.5f.6b, | 1e.2a.3c.4b.5f.6c, | 1e.2a.3c.4b.5f.6d, | 1e.2a.3c.4b.5f.6e, |
| 1e.2a.3c.4b.5f.6f, | 1e.2a.3c.4c.5a.6a, | 1e.2a.3c.4c.5a.6b, | 1e.2a.3c.4c.5a.6c, | 1e.2a.3c.4c.5a.6d, |
| 1e.2a.3c.4c.5a.6e, | 1e.2a.3c.4c.5a.6f, | 1e.2a.3c.4c.5b.6a, | 1e.2a.3c.4c.5b.6b, | 1e.2a.3c.4c.5b.6c, |
| 1e.2a.3c.4c.5b.6d, | 1e.2a.3c.4c.5b.6e, | 1e.2a.3c.4c.5b.6f, | 1e.2a.3c.4c.5c.6a, | 1e.2a.3c.4c.5c.6b, |
| 1e.2a.3c.4c.5c.6c, | 1e.2a.3c.4c.5c.6d, | 1e.2a.3c.4c.5c.6e, | 1e.2a.3c.4c.5c.6f, | 1e.2a.3c.4c.5d.6a, |
| 1e.2a.3c.4c.5d.6b, | 1e.2a.3c.4c.5d.6c, | 1e.2a.3c.4c.5d.6d, | 1e.2a.3c.4c.5d.6e, |
| 1e.2a.3c.4c.5d.6f, | 1e.2a.3c.4c.5e.6a, | 1e.2a.3c.4c.5e.6b, | 1e.2a.3c.4c.5e.6c, | 1e.2a.3c.4c.5e.6d, |
| 1e.2a.3c.4c.5e.6e, | 1e.2a.3c.4c.5e.6f, | 1e.2a.3c.4c.5f.6a, | 1e.2a.3c.4c.5f.6b, | 1e.2a.3c.4c.5f.6c, |
| 1e.2a.3c.4c.5f.6d, | 1e.2a.3c.4c.5f.6e, | 1e.2a.3c.4c.5f.6f, | 1e.2a.3c.4d.5a.6a, | 1e.2a.3c.4d.5a.6b, |
| 1e.2a.3c.4d.5a.6c, | 1e.2a.3c.4d.5a.6d, | 1e.2a.3c.4d.5a.6e, | 1e.2a.3c.4d.5a.6f, |
| 1e.2a.3c.4d.5b.6a, | 1e.2a.3c.4d.5b.6b, | 1e.2a.3c.4d.5b.6c, | 1e.2a.3c.4d.5b.6d, |
| 1e.2a.3c.4d.5b.6e, | 1e.2a.3c.4d.5b.6f, | 1e.2a.3c.4d.5c.6a, | 1e.2a.3c.4d.5c.6b, |
| 1e.2a.3c.4d.5c.6c, | 1e.2a.3c.4d.5c.6d, | 1e.2a.3c.4d.5c.6e, | 1e.2a.3c.4d.5c.6f, |
| 1e.2a.3c.4d.5d.6a, | 1e.2a.3c.4d.5d.6b, | 1e.2a.3c.4d.5d.6c, | 1e.2a.3c.4d.5d.6d, |
| 1e.2a.3c.4d.5d.6e, | 1e.2a.3c.4d.5d.6f, | 1e.2a.3c.4d.5e.6a, | 1e.2a.3c.4d.5e.6b, |
| 1e.2a.3c.4d.5e.6c, | 1e.2a.3c.4d.5e.6d, | 1e.2a.3c.4d.5e.6e, | 1e.2a.3c.4d.5e.6f, |
| 1e.2a.3c.4d.5f.6a, | 1e.2a.3c.4d.5f.6b, | 1e.2a.3c.4d.5f.6c, | 1e.2a.3c.4d.5f.6d, |
| 1e.2a.3c.4d.5f.6e, | 1e.2a.3c.4d.5f.6f, | 1e.2a.3c.4e.5a.6a, | 1e.2a.3c.4e.5a.6b, | 1e.2a.3c.4e.5a.6c, |
| 1e.2a.3c.4e.5a.6d, | 1e.2a.3c.4e.5a.6e, | 1e.2a.3c.4e.5a.6f, | 1e.2a.3c.4e.5b.6a, |
| 1e.2a.3c.4e.5b.6b, | 1e.2a.3c.4e.5b.6c, | 1e.2a.3c.4e.5b.6d, | 1e.2a.3c.4e.5b.6e, |
| 1e.2a.3c.4e.5b.6f, | 1e.2a.3c.4e.5c.6a, | 1e.2a.3c.4e.5c.6b, | 1e.2a.3c.4e.5c.6c, | 1e.2a.3c.4e.5c.6d, |
| 1e.2a.3c.4e.5c.6e, | 1e.2a.3c.4e.5c.6f, | 1e.2a.3c.4e.5d.6a, | 1e.2a.3c.4e.5d.6b, |
| 1e.2a.3c.4e.5d.6c, | 1e.2a.3c.4e.5d.6d, | 1e.2a.3c.4e.5d.6e, | 1e.2a.3c.4e.5d.6f, |
| 1e.2a.3c.4e.5e.6a, | 1e.2a.3c.4e.5e.6b, | 1e.2a.3c.4e.5e.6c, | 1e.2a.3c.4e.5e.6d, |
| 1e.2a.3c.4e.5e.6e, | 1e.2a.3c.4e.5e.6f, | 1e.2a.3c.4e.5f.6a, | 1e.2a.3c.4e.5f.6b, | 1e.2a.3c.4e.5f.6c, |
| 1e.2a.3c.4e.5f.6d, | 1e.2a.3c.4e.5f.6e, | 1e.2a.3c.4e.5f.6f, | 1e.2a.3c.4f.5a.6a, | 1e.2a.3c.4f.5a.6b, |
| 1e.2a.3c.4f.5a.6c, | 1e.2a.3c.4f.5a.6d, | 1e.2a.3c.4f.5a.6e, | 1e.2a.3c.4f.5a.6f, | 1e.2a.3c.4f.5b.6a, |
| 1e.2a.3c.4f.5b.6b, | 1e.2a.3c.4f.5b.6c, | 1e.2a.3c.4f.5b.6d, | 1e.2a.3c.4f.5b.6e, | 1e.2a.3c.4f.5b.6f, |
| 1e.2a.3c.4f.5c.6a, | 1e.2a.3c.4f.5c.6b, | 1e.2a.3c.4f.5c.6c, | 1e.2a.3c.4f.5c.6d, | 1e.2a.3c.4f.5c.6e, |
| 1e.2a.3c.4f.5c.6f, | 1e.2a.3c.4f.5d.6a, | 1e.2a.3c.4f.5d.6b, | 1e.2a.3c.4f.5d.6c, | 1e.2a.3c.4f.5d.6d, |
| 1e.2a.3c.4f.5d.6e, | 1e.2a.3c.4f.5d.6f, | 1e.2a.3c.4f.5e.6a, | 1e.2a.3c.4f.5e.6b, | 1e.2a.3c.4f.5e.6c, |
| 1e.2a.3c.4f.5e.6d, | 1e.2a.3c.4f.5e.6e, | 1e.2a.3c.4f.5f.6a, | 1e.2a.3c.4f.5f.6b, |
| 1e.2a.3c.4f.5f.6c, | 1e.2a.3c.4f.5f.6d, | 1e.2a.3c.4f.5f.6e, | 1e.2a.3c.4f.5f.6f, | 1e.2a.3d.4a.5a.6a, |
| 1e.2a.3d.4a.5a.6b, | 1e.2a.3d.4a.5a.6c, | 1e.2a.3d.4a.5a.6d, | 1e.2a.3d.4a.5a.6e, |
| 1e.2a.3d.4a.5a.6f, | 1e.2a.3d.4a.5b.6a, | 1e.2a.3d.4a.5b.6b, | 1e.2a.3d.4a.5b.6c, |
| 1e.2a.3d.4a.5b.6d, | 1e.2a.3d.4a.5b.6e, | 1e.2a.3d.4a.5b.6f, | 1e.2a.3d.4a.5c.6a, |
| 1e.2a.3d.4a.5c.6b, | 1e.2a.3d.4a.5c.6c, | 1e.2a.3d.4a.5c.6d, | 1e.2a.3d.4a.5c.6e, |
| 1e.2a.3d.4a.5c.6f, | 1e.2a.3d.4a.5d.6a, | 1e.2a.3d.4a.5d.6b, | 1e.2a.3d.4a.5d.6c, |
| 1e.2a.3d.4a.5d.6d, | 1e.2a.3d.4a.5d.6e, | 1e.2a.3d.4a.5d.6f, | 1e.2a.3d.4a.5e.6a, |
| 1e.2a.3d.4a.5e.6b, | 1e.2a.3d.4a.5e.6c, | 1e.2a.3d.4a.5e.6d, | 1e.2a.3d.4a.5e.6e, |
| 1e.2a.3d.4a.5e.6f, | 1e.2a.3d.4a.5f.6a, | 1e.2a.3d.4a.5f.6b, | 1e.2a.3d.4a.5f.6c, |
| 1e.2a.3d.4a.5f.6d, | 1e.2a.3d.4a.5f.6e, | 1e.2a.3d.4a.5f.6f, | 1e.2a.3d.4b.5a.6a, |
| 1e.2a.3d.4b.5a.6b, | 1e.2a.3d.4b.5a.6c, | 1e.2a.3d.4b.5a.6d, | 1e.2a.3d.4b.5a.6e, |
| 1e.2a.3d.4b.5a.6f, | 1e.2a.3d.4b.5b.6a, | 1e.2a.3d.4b.5b.6b, | 1e.2a.3d.4b.5b.6c, |
| 1e.2a.3d.4b.5b.6d, | 1e.2a.3d.4b.5b.6e, | 1e.2a.3d.4b.5b.6f, | 1e.2a.3d.4b.5c.6a, |
| 1e.2a.3d.4b.5c.6b, | 1e.2a.3d.4b.5c.6c, | 1e.2a.3d.4b.5c.6d, | 1e.2a.3d.4b.5c.6e, |
| 1e.2a.3d.4b.5c.6f, | 1e.2a.3d.4b.5d.6a, | 1e.2a.3d.4b.5d.6b, | 1e.2a.3d.4b.5d.6c, |
| 1e.2a.3d.4b.5d.6d, | 1e.2a.3d.4b.5d.6e, | 1e.2a.3d.4b.5d.6f, | 1e.2a.3d.4b.5e.6a, |
| 1e.2a.3d.4b.5e.6b, | 1e.2a.3d.4b.5e.6c, | 1e.2a.3d.4b.5e.6d, | 1e.2a.3d.4b.5e.6e, |

TABLE 7-continued

List of Compounds of Formula (II)

| | | | | |
|---|---|---|---|---|
| 1e.2a.3d.4b.5e.6f, | 1e.2a.3d.4b.5f.6a, | 1e.2a.3d.4b.5f.6b, | 1e.2a.3d.4b.5f.6c, | |
| 1e.2a.3d.4b.5f.6d, | 1e.2a.3d.4b.5f.6e, | 1e.2a.3d.4b.5f.6f, | 1e.2a.3d.4c.5a.6a, | |
| 1e.2a.3d.4c.5a.6b, | 1e.2a.3d.4c.5a.6c, | 1e.2a.3d.4c.5a.6d, | 1e.2a.3d.4c.5a.6e, | |
| 1e.2a.3d.4c.5a.6f, | 1e.2a.3d.4c.5b.6a, | 1e.2a.3d.4c.5b.6b, | 1e.2a.3d.4c.5b.6c, | |
| 1e.2a.3d.4c.5b.6d, | 1e.2a.3d.4c.5b.6e, | 1e.2a.3d.4c.5b.6f, | 1e.2a.3d.4c.5c.6a, | |
| 1e.2a.3d.4c.5c.6b, | 1e.2a.3d.4c.5c.6c, | 1e.2a.3d.4c.5c.6d, | 1e.2a.3d.4c.5c.6e, | |
| 1e.2a.3d.4c.5c.6f, | 1e.2a.3d.4c.5d.6a, | 1e.2a.3d.4c.5d.6b, | 1e.2a.3d.4c.5d.6c, | |
| 1e.2a.3d.4c.5d.6d, | 1e.2a.3d.4c.5d.6e, | 1e.2a.3d.4c.5d.6f, | 1e.2a.3d.4c.5e.6a, | |
| 1e.2a.3d.4c.5e.6b, | 1e.2a.3d.4c.5e.6c, | 1e.2a.3d.4c.5e.6d, | 1e.2a.3d.4c.5e.6e, | |
| 1e.2a.3d.4c.5e.6f, | 1e.2a.3d.4c.5f.6a, | 1e.2a.3d.4c.5f.6b, | 1e.2a.3d.4c.5f.6c, | |
| 1e.2a.3d.4c.5f.6d, | 1e.2a.3d.4c.5f.6e, | 1e.2a.3d.4c.5f.6f, | 1e.2a.3d.4d.5a.6a, | |
| 1e.2a.3d.4d.5a.6b, | 1e.2a.3d.4d.5a.6c, | 1e.2a.3d.4d.5a.6d, | 1e.2a.3d.4d.5a.6e, | |
| 1e.2a.3d.4d.5a.6f, | 1e.2a.3d.4d.5b.6a, | 1e.2a.3d.4d.5b.6b, | 1e.2a.3d.4d.5b.6c, | |
| 1e.2a.3d.4d.5b.6d, | 1e.2a.3d.4d.5b.6e, | 1e.2a.3d.4d.5b.6f, | 1e.2a.3d.4d.5c.6a, | |
| 1e.2a.3d.4d.5c.6b, | 1e.2a.3d.4d.5c.6c, | 1e.2a.3d.4d.5c.6d, | 1e.2a.3d.4d.5c.6e, | |
| 1e.2a.3d.4d.5c.6f, | 1e.2a.3d.4d.5d.6a, | 1e.2a.3d.4d.5d.6b, | 1e.2a.3d.4d.5d.6c, | |
| 1e.2a.3d.4d.5d.6d, | 1e.2a.3d.4d.5d.6e, | 1e.2a.3d.4d.5d.6f, | 1e.2a.3d.4d.5e.6a, | |
| 1e.2a.3d.4d.5e.6b, | 1e.2a.3d.4d.5e.6c, | 1e.2a.3d.4d.5e.6d, | 1e.2a.3d.4d.5e.6e, | |
| 1e.2a.3d.4d.5e.6f, | 1e.2a.3d.4d.5f.6a, | 1e.2a.3d.4d.5f.6b, | 1e.2a.3d.4d.5f.6c, | |
| 1e.2a.3d.4d.5f.6d, | 1e.2a.3d.4d.5f.6e, | 1e.2a.3d.4d.5f.6f, | 1e.2a.3d.4e.5a.6a, | |
| 1e.2a.3d.4e.5a.6b, | 1e.2a.3d.4e.5a.6c, | 1e.2a.3d.4e.5a.6d, | 1e.2a.3d.4e.5a.6e, | |
| 1e.2a.3d.4e.5a.6f, | 1e.2a.3d.4e.5b.6a, | 1e.2a.3d.4e.5b.6b, | 1e.2a.3d.4e.5b.6c, | |
| 1e.2a.3d.4e.5b.6d, | 1e.2a.3d.4e.5b.6e, | 1e.2a.3d.4e.5b.6f, | 1e.2a.3d.4e.5c.6a, | |
| 1e.2a.3d.4e.5c.6b, | 1e.2a.3d.4e.5c.6c, | 1e.2a.3d.4e.5c.6d, | 1e.2a.3d.4e.5c.6e, | |
| 1e.2a.3d.4e.5c.6f, | 1e.2a.3d.4e.5d.6a, | 1e.2a.3d.4e.5d.6b, | 1e.2a.3d.4e.5d.6c, | |
| 1e.2a.3d.4e.5d.6d, | 1e.2a.3d.4e.5d.6e, | 1e.2a.3d.4e.5d.6f, | 1e.2a.3d.4e.5e.6a, | |
| 1e.2a.3d.4e.5e.6b, | 1e.2a.3d.4e.5e.6c, | 1e.2a.3d.4e.5e.6d, | 1e.2a.3d.4e.5e.6e, | |
| 1e.2a.3d.4e.5e.6f, | 1e.2a.3d.4e.5f.6a, | 1e.2a.3d.4e.5f.6b, | 1e.2a.3d.4e.5f.6c, | |
| 1e.2a.3d.4e.5f.6d, | 1e.2a.3d.4e.5f.6e, | 1e.2a.3d.4e.5f.6f, | 1e.2a.3d.4f.5a.6a, | |
| 1e.2a.3d.4f.5a.6b, | 1e.2a.3d.4f.5a.6c, | 1e.2a.3d.4f.5a.6d, | 1e.2a.3d.4f.5a.6e, | |
| 1e.2a.3d.4f.5a.6f, | 1e.2a.3d.4f.5b.6a, | 1e.2a.3d.4f.5b.6b, | 1e.2a.3d.4f.5b.6c, | |
| 1e.2a.3d.4f.5b.6d, | 1e.2a.3d.4f.5b.6e, | 1e.2a.3d.4f.5b.6f, | 1e.2a.3d.4f.5c.6a, | |
| 1e.2a.3d.4f.5c.6b, | 1e.2a.3d.4f.5c.6c, | 1e.2a.3d.4f.5c.6d, | 1e.2a.3d.4f.5c.6e, | 1e.2a.3d.4f.5c.6f, |
| 1e.2a.3d.4f.5d.6a, | 1e.2a.3d.4f.5d.6b, | 1e.2a.3d.4f.5d.6c, | 1e.2a.3d.4f.5d.6d, | |
| 1e.2a.3d.4f.5d.6e, | 1e.2a.3d.4f.5d.6f, | 1e.2a.3d.4f.5e.6a, | 1e.2a.3d.4f.5e.6b, | |
| 1e.2a.3d.4f.5e.6c, | 1e.2a.3d.4f.5e.6d, | 1e.2a.3d.4f.5e.6e, | 1e.2a.3d.4f.5e.6f, | 1e.2a.3d.4f.5f.6a, |
| 1e.2a.3d.4f.5f.6b, | 1e.2a.3d.4f.5f.6c, | 1e.2a.3d.4f.5f.6d, | 1e.2a.3d.4f.5f.6e, | 1e.2a.3d.4f.5f.6f, |
| 1e.2a.3e.4a.5a.6a, | 1e.2a.3e.4a.5a.6b, | 1e.2a.3e.4a.5a.6c, | 1e.2a.3e.4a.5a.6d, | |
| 1e.2a.3e.4a.5a.6e, | 1e.2a.3e.4a.5a.6f, | 1e.2a.3e.4a.5b.6a, | 1e.2a.3e.4a.5b.6b, | |
| 1e.2a.3e.4a.5b.6c, | 1e.2a.3e.4a.5b.6d, | 1e.2a.3e.4a.5b.6e, | 1e.2a.3e.4a.5b.6f, | |
| 1e.2a.3e.4a.5c.6a, | 1e.2a.3e.4a.5c.6b, | 1e.2a.3e.4a.5c.6c, | 1e.2a.3e.4a.5c.6d, | |
| 1e.2a.3e.4a.5c.6e, | 1e.2a.3e.4a.5c.6f, | 1e.2a.3e.4a.5d.6a, | 1e.2a.3e.4a.5d.6b, | |
| 1e.2a.3e.4a.5d.6c, | 1e.2a.3e.4a.5d.6d, | 1e.2a.3e.4a.5d.6e, | 1e.2a.3e.4a.5d.6f, | |
| 1e.2a.3e.4a.5e.6a, | 1e.2a.3e.4a.5e.6b, | 1e.2a.3e.4a.5e.6c, | 1e.2a.3e.4a.5e.6d, | |
| 1e.2a.3e.4a.5e.6e, | 1e.2a.3e.4a.5e.6f, | 1e.2a.3e.4a.5f.6a, | 1e.2a.3e.4a.5f.6b, | 1e.2a.3e.4a.5f.6c, |
| 1e.2a.3e.4a.5f.6d, | 1e.2a.3e.4a.5f.6e, | 1e.2a.3e.4a.5f.6f, | 1e.2a.3e.4b.5a.6a, | |
| 1e.2a.3e.4b.5a.6b, | 1e.2a.3e.4b.5a.6c, | 1e.2a.3e.4b.5a.6d, | 1e.2a.3e.4b.5a.6e, | |
| 1e.2a.3e.4b.5a.6f, | 1e.2a.3e.4b.5b.6a, | 1e.2a.3e.4b.5b.6b, | 1e.2a.3e.4b.5b.6c, | |
| 1e.2a.3e.4b.5b.6d, | 1e.2a.3e.4b.5b.6e, | 1e.2a.3e.4b.5b.6f, | 1e.2a.3e.4b.5c.6a, | |
| 1e.2a.3e.4b.5c.6b, | 1e.2a.3e.4b.5c.6c, | 1e.2a.3e.4b.5c.6d, | 1e.2a.3e.4b.5c.6e, | |
| 1e.2a.3e.4b.5c.6f, | 1e.2a.3e.4b.5d.6a, | 1e.2a.3e.4b.5d.6b, | 1e.2a.3e.4b.5d.6c, | |
| 1e.2a.3e.4b.5d.6d, | 1e.2a.3e.4b.5d.6e, | 1e.2a.3e.4b.5d.6f, | 1e.2a.3e.4b.5e.6a, | |
| 1e.2a.3e.4b.5e.6b, | 1e.2a.3e.4b.5e.6c, | 1e.2a.3e.4b.5e.6d, | 1e.2a.3e.4b.5e.6e, | |
| 1e.2a.3e.4b.5e.6f, | 1e.2a.3e.4b.5f.6a, | 1e.2a.3e.4b.5f.6b, | 1e.2a.3e.4b.5f.6c, | 1e.2a.3e.4b.5f.6d, |
| 1e.2a.3e.4b.5f.6e, | 1e.2a.3e.4b.5f.6f, | 1e.2a.3e.4c.5a.6a, | 1e.2a.3e.4c.5a.6b, | 1e.2a.3e.4c.5a.6c, |
| 1e.2a.3e.4c.5a.6d, | 1e.2a.3e.4c.5a.6e, | 1e.2a.3e.4c.5a.6f, | 1e.2a.3e.4c.5b.6a, | |
| 1e.2a.3e.4c.5b.6b, | 1e.2a.3e.4c.5b.6c, | 1e.2a.3e.4c.5b.6d, | 1e.2a.3e.4c.5b.6e, | |
| 1e.2a.3e.4c.5b.6f, | 1e.2a.3e.4c.5c.6a, | 1e.2a.3e.4c.5c.6b, | 1e.2a.3e.4c.5c.6c, | 1e.2a.3e.4c.5c.6d, |
| 1e.2a.3e.4c.5c.6e, | 1e.2a.3e.4c.5c.6f, | 1e.2a.3e.4c.5d.6a, | 1e.2a.3e.4c.5d.6b, | |
| 1e.2a.3e.4c.5d.6c, | 1e.2a.3e.4c.5d.6d, | 1e.2a.3e.4c.5d.6e, | 1e.2a.3e.4c.5d.6f, | |
| 1e.2a.3e.4c.5e.6a, | 1e.2a.3e.4c.5e.6b, | 1e.2a.3e.4c.5e.6c, | 1e.2a.3e.4c.5e.6d, | |
| 1e.2a.3e.4c.5e.6e, | 1e.2a.3e.4c.5e.6f, | 1e.2a.3e.4c.5f.6a, | 1e.2a.3e.4c.5f.6b, | 1e.2a.3e.4c.5f.6c, |
| 1e.2a.3e.4c.5f.6d, | 1e.2a.3e.4c.5f.6e, | 1e.2a.3e.4c.5f.6f, | 1e.2a.3e.4d.5a.6a, | 1e.2a.3e.4d.5a.6b, |
| 1e.2a.3e.4d.5a.6c, | 1e.2a.3e.4d.5a.6d, | 1e.2a.3e.4d.5a.6e, | 1e.2a.3e.4d.5a.6f, | |
| 1e.2a.3e.4d.5b.6a, | 1e.2a.3e.4d.5b.6b, | 1e.2a.3e.4d.5b.6c, | 1e.2a.3e.4d.5b.6d, | |
| 1e.2a.3e.4d.5b.6e, | 1e.2a.3e.4d.5b.6f, | 1e.2a.3e.4d.5c.6a, | 1e.2a.3e.4d.5c.6b, | |
| 1e.2a.3e.4d.5c.6c, | 1e.2a.3e.4d.5c.6d, | 1e.2a.3e.4d.5c.6e, | 1e.2a.3e.4d.5c.6f, | |
| 1e.2a.3e.4d.5d.6a, | 1e.2a.3e.4d.5d.6b, | 1e.2a.3e.4d.5d.6c, | 1e.2a.3e.4d.5d.6d, | |
| 1e.2a.3e.4d.5d.6e, | 1e.2a.3e.4d.5d.6f, | 1e.2a.3e.4d.5e.6a, | 1e.2a.3e.4d.5e.6b, | |
| 1e.2a.3e.4d.5e.6c, | 1e.2a.3e.4d.5e.6d, | 1e.2a.3e.4d.5e.6e, | 1e.2a.3e.4d.5e.6f, | |
| 1e.2a.3e.4d.5f.6a, | 1e.2a.3e.4d.5f.6b, | 1e.2a.3e.4d.5f.6c, | 1e.2a.3e.4d.5f.6d, | |
| 1e.2a.3e.4d.5f.6e, | 1e.2a.3e.4d.5f.6f, | 1e.2a.3e.4e.5a.6a, | 1e.2a.3e.4e.5a.6b, | |
| 1e.2a.3e.4e.5a.6c, | 1e.2a.3e.4e.5a.6d, | 1e.2a.3e.4e.5a.6e, | 1e.2a.3e.4e.5a.6f, | |
| 1e.2a.3e.4e.5b.6a, | 1e.2a.3e.4e.5b.6b, | 1e.2a.3e.4e.5b.6c, | 1e.2a.3e.4e.5b.6d, | |
| 1e.2a.3e.4e.5b.6e, | 1e.2a.3e.4e.5b.6f, | 1e.2a.3e.4e.5c.6a, | 1e.2a.3e.4e.5c.6b, | |
| 1e.2a.3e.4e.5c.6c, | 1e.2a.3e.4e.5c.6d, | 1e.2a.3e.4e.5c.6e, | 1e.2a.3e.4e.5c.6f, | |
| 1e.2a.3e.4e.5d.6a, | 1e.2a.3e.4e.5d.6b, | 1e.2a.3e.4e.5d.6c, | 1e.2a.3e.4e.5d.6d, | |
| 1e.2a.3e.4e.5d.6e, | 1e.2a.3e.4e.5d.6f, | 1e.2a.3e.4e.5e.6a, | 1e.2a.3e.4e.5e.6b, | |

TABLE 7-continued

List of Compounds of Formula (II)

| | | | | |
|---|---|---|---|---|
| 1e.2a.3e.4e.5e.6c, | 1e.2a.3e.4e.5e.6d, | 1e.2a.3e.4e.5e.6e, | 1e.2a.3e.4e.5e.6f, | 1e.2a.3e.4e.5f.6a, |
| 1e.2a.3e.4e.5f.6b, | 1e.2a.3e.4e.5f.6c, | 1e.2a.3e.4e.5f.6d, | 1e.2a.3e.4e.5f.6e, | 1e.2a.3e.4e.5f.6f, |
| 1e.2a.3e.4f.5a.6a, | 1e.2a.3e.4f.5a.6b, | 1e.2a.3e.4f.5a.6c, | 1e.2a.3e.4f.5a.6d, | 1e.2a.3e.4f.5a.6e, |
| 1e.2a.3e.4f.5a.6f, | 1e.2a.3e.4f.5b.6a, | 1e.2a.3e.4f.5b.6b, | 1e.2a.3e.4f.5b.6c, | 1e.2a.3e.4f.5b.6d, |
| 1e.2a.3e.4f.5b.6e, | 1e.2a.3e.4f.5b.6f, | 1e.2a.3e.4f.5c.6a, | 1e.2a.3e.4f.5c.6b, | 1e.2a.3e.4f.5c.6c, |
| 1e.2a.3e.4f.5c.6d, | 1e.2a.3e.4f.5c.6e, | 1e.2a.3e.4f.5c.6f, | 1e.2a.3e.4f.5d.6a, | 1e.2a.3e.4f.5d.6b, |
| 1e.2a.3e.4f.5d.6c, | 1e.2a.3e.4f.5d.6d, | 1e.2a.3e.4f.5d.6e, | 1e.2a.3e.4f.5d.6f, | 1e.2a.3e.4f.5e.6a, |
| 1e.2a.3e.4f.5e.6b, | 1e.2a.3e.4f.5e.6c, | 1e.2a.3e.4f.5e.6d, | 1e.2a.3e.4f.5e.6e, | 1e.2a.3e.4f.5e.6f, |
| 1e.2a.3e.4f.5f.6a, | 1e.2a.3e.4f.5f.6b, | 1e.2a.3e.4f.5f.6c, | 1e.2a.3e.4f.5f.6d, | 1e.2a.3e.4f.5f.6e, |
| 1e.2a.3e.4f.5f.6f, | 1e.2a.3f.4a.5a.6a, | 1e.2a.3f.4a.5a.6b, | 1e.2a.3f.4a.5a.6c, | 1e.2a.3f.4a.5a.6d, |
| 1e.2a.3f.4a.5a.6e, | 1e.2a.3f.4a.5a.6f, | 1e.2a.3f.4a.5b.6a, | 1e.2a.3f.4a.5b.6b, | 1e.2a.3f.4a.5b.6c, |
| 1e.2a.3f.4a.5b.6d, | 1e.2a.3f.4a.5b.6e, | 1e.2a.3f.4a.5b.6f, | 1e.2a.3f.4a.5c.6a, | 1e.2a.3f.4a.5c.6b, |
| 1e.2a.3f.4a.5c.6c, | 1e.2a.3f.4a.5c.6d, | 1e.2a.3f.4a.5c.6e, | 1e.2a.3f.4a.5c.6f, | 1e.2a.3f.4a.5d.6a, |
| 1e.2a.3f.4a.5d.6b, | 1e.2a.3f.4a.5d.6c, | 1e.2a.3f.4a.5d.6d, | 1e.2a.3f.4a.5d.6e, | |
| 1e.2a.3f.4a.5d.6f, | 1e.2a.3f.4a.5e.6a, | 1e.2a.3f.4a.5e.6b, | 1e.2a.3f.4a.5e.6c, | 1e.2a.3f.4a.5e.6d, |
| 1e.2a.3f.4a.5e.6e, | 1e.2a.3f.4a.5e.6f, | 1e.2a.3f.4a.5f.6a, | 1e.2a.3f.4a.5f.6b, | 1e.2a.3f.4a.5f.6c, |
| 1e.2a.3f.4a.5f.6d, | 1e.2a.3f.4a.5f.6e, | 1e.2a.3f.4a.5f.6f, | 1e.2a.3f.4b.5a.6a, | 1e.2a.3f.4b.5a.6b, |
| 1e.2a.3f.4b.5a.6c, | 1e.2a.3f.4b.5a.6d, | 1e.2a.3f.4b.5a.6e, | 1e.2a.3f.4b.5a.6f, | 1e.2a.3f.4b.5b.6a, |
| 1e.2a.3f.4b.5b.6b, | 1e.2a.3f.4b.5b.6c, | 1e.2a.3f.4b.5b.6d, | 1e.2a.3f.4b.5b.6e, | |
| 1e.2a.3f.4b.5b.6f, | 1e.2a.3f.4b.5c.6a, | 1e.2a.3f.4b.5c.6b, | 1e.2a.3f.4b.5c.6c, | 1e.2a.3f.4b.5c.6d, |
| 1e.2a.3f.4b.5c.6e, | 1e.2a.3f.4b.5c.6f, | 1e.2a.3f.4b.5d.6a, | 1e.2a.3f.4b.5d.6b, | 1e.2a.3f.4b.5d.6c, |
| 1e.2a.3f.4b.5d.6d, | 1e.2a.3f.4b.5d.6e, | 1e.2a.3f.4b.5d.6f, | 1e.2a.3f.4b.5e.6a, | |
| 1e.2a.3f.4b.5e.6b, | 1e.2a.3f.4b.5e.6c, | 1e.2a.3f.4b.5e.6d, | 1e.2a.3f.4b.5e.6e, | 1e.2a.3f.4b.5e.6f, |
| 1e.2a.3f.4b.5f.6a, | 1e.2a.3f.4b.5f.6b, | 1e.2a.3f.4b.5f.6c, | 1e.2a.3f.4b.5f.6d, | 1e.2a.3f.4b.5f.6e, |
| 1e.2a.3f.4b.5f.6f, | 1e.2a.3f.4c.5a.6a, | 1e.2a.3f.4c.5a.6b, | 1e.2a.3f.4c.5a.6c, | 1e.2a.3f.4c.5a.6d, |
| 1e.2a.3f.4c.5a.6e, | 1e.2a.3f.4c.5a.6f, | 1e.2a.3f.4c.5b.6a, | 1e.2a.3f.4c.5b.6b, | 1e.2a.3f.4c.5b.6c, |
| 1e.2a.3f.4c.5b.6d, | 1e.2a.3f.4c.5b.6e, | 1e.2a.3f.4c.5b.6f, | 1e.2a.3f.4c.5c.6a, | 1e.2a.3f.4c.5c.6b, |
| 1e.2a.3f.4c.5c.6c, | 1e.2a.3f.4c.5c.6d, | 1e.2a.3f.4c.5c.6e, | 1e.2a.3f.4c.5c.6f, | 1e.2a.3f.4c.5d.6a, |
| 1e.2a.3f.4c.5d.6b, | 1e.2a.3f.4c.5d.6c, | 1e.2a.3f.4c.5d.6d, | 1e.2a.3f.4c.5d.6e, | 1e.2a.3f.4c.5d.6f, |
| 1e.2a.3f.4c.5e.6a, | 1e.2a.3f.4c.5e.6b, | 1e.2a.3f.4c.5e.6c, | 1e.2a.3f.4c.5e.6d, | 1e.2a.3f.4c.5e.6e, |
| 1e.2a.3f.4c.5e.6f, | 1e.2a.3f.4c.5f.6a, | 1e.2a.3f.4c.5f.6b, | 1e.2a.3f.4c.5f.6c, | 1e.2a.3f.4c.5f.6d, |
| 1e.2a.3f.4c.5f.6e, | 1e.2a.3f.4c.5f.6f, | 1e.2a.3f.4d.5a.6a, | 1e.2a.3f.4d.5a.6b, | 1e.2a.3f.4d.5a.6c, |
| 1e.2a.3f.4d.5a.6d, | 1e.2a.3f.4d.5a.6e, | 1e.2a.3f.4d.5a.6f, | 1e.2a.3f.4d.5b.6a, | |
| 1e.2a.3f.4d.5b.6b, | 1e.2a.3f.4d.5b.6c, | 1e.2a.3f.4d.5b.6d, | 1e.2a.3f.4d.5b.6e, | |
| 1e.2a.3f.4d.5b.6f, | 1e.2a.3f.4d.5c.6a, | 1e.2a.3f.4d.5c.6b, | 1e.2a.3f.4d.5c.6c, | |
| 1e.2a.3f.4d.5c.6d, | 1e.2a.3f.4d.5c.6e, | 1e.2a.3f.4d.5c.6f, | 1e.2a.3f.4d.5d.6a, | |
| 1e.2a.3f.4d.5d.6b, | 1e.2a.3f.4d.5d.6c, | 1e.2a.3f.4d.5d.6d, | 1e.2a.3f.4d.5d.6e, | |
| 1e.2a.3f.4d.5d.6f, | 1e.2a.3f.4d.5e.6a, | 1e.2a.3f.4d.5e.6b, | 1e.2a.3f.4d.5e.6c, | |
| 1e.2a.3f.4d.5e.6d, | 1e.2a.3f.4d.5e.6e, | 1e.2a.3f.4d.5e.6f, | 1e.2a.3f.4d.5f.6a, | 1e.2a.3f.4d.5f.6b, |
| 1e.2a.3f.4d.5f.6c, | 1e.2a.3f.4d.5f.6d, | 1e.2a.3f.4d.5f.6e, | 1e.2a.3f.4d.5f.6f, | 1e.2a.3f.4e.5a.6a, |
| 1e.2a.3f.4e.5a.6b, | 1e.2a.3f.4e.5a.6c, | 1e.2a.3f.4e.5a.6d, | 1e.2a.3f.4e.5a.6e, | 1e.2a.3f.4e.5a.6f, |
| 1e.2a.3f.4e.5b.6a, | 1e.2a.3f.4e.5b.6b, | 1e.2a.3f.4e.5b.6c, | 1e.2a.3f.4e.5b.6d, | 1e.2a.3f.4e.5b.6e, |
| 1e.2a.3f.4e.5b.6f, | 1e.2a.3f.4e.5c.6a, | 1e.2a.3f.4e.5c.6b, | 1e.2a.3f.4e.5c.6c, | 1e.2a.3f.4e.5c.6d, |
| 1e.2a.3f.4e.5c.6e, | 1e.2a.3f.4e.5c.6f, | 1e.2a.3f.4e.5d.6a, | 1e.2a.3f.4e.5d.6b, | 1e.2a.3f.4e.5d.6c, |
| 1e.2a.3f.4e.5d.6d, | 1e.2a.3f.4e.5d.6e, | 1e.2a.3f.4e.5d.6f, | 1e.2a.3f.4e.5e.6a, | 1e.2a.3f.4e.5e.6b, |
| 1e.2a.3f.4e.5e.6c, | 1e.2a.3f.4e.5e.6d, | 1e.2a.3f.4e.5e.6e, | 1e.2a.3f.4e.5e.6f, | 1e.2a.3f.4e.5f.6a, |
| 1e.2a.3f.4e.5f.6b, | 1e.2a.3f.4e.5f.6c, | 1e.2a.3f.4e.5f.6d, | 1e.2a.3f.4e.5f.6e, | 1e.2a.3f.4e.5f.6f, |
| 1e.2a.3f.4f.5a.6a, | 1e.2a.3f.4f.5a.6b, | 1e.2a.3f.4f.5a.6c, | 1e.2a.3f.4f.5a.6d, | 1e.2a.3f.4f.5a.6e, |
| 1e.2a.3f.4f.5a.6f, | 1e.2a.3f.4f.5b.6a, | 1e.2a.3f.4f.5b.6b, | 1e.2a.3f.4f.5b.6c, | 1e.2a.3f.4f.5b.6d, |
| 1e.2a.3f.4f.5b.6e, | 1e.2a.3f.4f.5b.6f, | 1e.2a.3f.4f.5c.6a, | 1e.2a.3f.4f.5c.6b, | 1e.2a.3f.4f.5c.6c, |
| 1e.2a.3f.4f.5c.6d, | 1e.2a.3f.4f.5c.6e, | 1e.2a.3f.4f.5c.6f, | 1e.2a.3f.4f.5d.6a, | 1e.2a.3f.4f.5d.6b, |
| 1e.2a.3f.4f.5d.6c, | 1e.2a.3f.4f.5d.6d, | 1e.2a.3f.4f.5d.6e, | 1e.2a.3f.4f.5d.6f, | 1e.2a.3f.4f.5e.6a, |
| 1e.2a.3f.4f.5e.6b, | 1e.2a.3f.4f.5e.6c, | 1e.2a.3f.4f.5e.6d, | 1e.2a.3f.4f.5e.6e, | 1e.2a.3f.4f.5e.6f, |
| 1e.2a.3f.4f.5f.6a, | 1e.2a.3f.4f.5f.6b, | 1e.2a.3f.4f.5f.6c, | 1e.2a.3f.4f.5f.6d, | 1e.2a.3f.4f.5f.6e, |
| 1e.2a.3f.4f.5f.6f, | 1e.2b.3a.4a.5a.6a, | 1e.2b.3a.4a.5a.6b, | 1e.2b.3a.4a.5a.6c, | |
| 1e.2b.3a.4a.5a.6d, | 1e.2b.3a.4a.5a.6e, | 1e.2b.3a.4a.5a.6f, | 1e.2b.3a.4a.5b.6a, | |
| 1e.2b.3a.4a.5b.6b, | 1e.2b.3a.4a.5b.6c, | 1e.2b.3a.4a.5b.6d, | 1e.2b.3a.4a.5b.6e, | |
| 1e.2b.3a.4a.5b.6f, | 1e.2b.3a.4a.5c.6a, | 1e.2b.3a.4a.5c.6b, | 1e.2b.3a.4a.5c.6c, | |
| 1e.2b.3a.4a.5c.6d, | 1e.2b.3a.4a.5c.6e, | 1e.2b.3a.4a.5c.6f, | 1e.2b.3a.4a.5d.6a, | |
| 1e.2b.3a.4a.5d.6b, | 1e.2b.3a.4a.5d.6c, | 1e.2b.3a.4a.5d.6d, | 1e.2b.3a.4a.5d.6e, | |
| 1e.2b.3a.4a.5d.6f, | 1e.2b.3a.4a.5e.6a, | 1e.2b.3a.4a.5e.6b, | 1e.2b.3a.4a.5e.6c, | |
| 1e.2b.3a.4a.5e.6d, | 1e.2b.3a.4a.5e.6e, | 1e.2b.3a.4a.5e.6f, | 1e.2b.3a.4a.5f.6a, | |
| 1e.2b.3a.4a.5f.6b, | 1e.2b.3a.4a.5f.6c, | 1e.2b.3a.4a.5f.6d, | 1e.2b.3a.4a.5f.6e, | 1e.2b.3a.4a.5f.6f, |
| 1e.2b.3a.4b.5a.6a, | 1e.2b.3a.4b.5a.6b, | 1e.2b.3a.4b.5a.6c, | 1e.2b.3a.4b.5a.6d, | |
| 1e.2b.3a.4b.5a.6e, | 1e.2b.3a.4b.5a.6f, | 1e.2b.3a.4b.5b.6a, | 1e.2b.3a.4b.5b.6b, | |
| 1e.2b.3a.4b.5b.6c, | 1e.2b.3a.4b.5b.6d, | 1e.2b.3a.4b.5b.6e, | 1e.2b.3a.4b.5b.6f, | |
| 1e.2b.3a.4b.5c.6a, | 1e.2b.3a.4b.5c.6b, | 1e.2b.3a.4b.5c.6c, | 1e.2b.3a.4b.5c.6d, | |
| 1e.2b.3a.4b.5c.6e, | 1e.2b.3a.4b.5c.6f, | 1e.2b.3a.4b.5d.6a, | 1e.2b.3a.4b.5d.6b, | |
| 1e.2b.3a.4b.5d.6c, | 1e.2b.3a.4b.5d.6d, | 1e.2b.3a.4b.5d.6e, | 1e.2b.3a.4b.5d.6f, | |
| 1e.2b.3a.4b.5e.6a, | 1e.2b.3a.4b.5e.6b, | 1e.2b.3a.4b.5e.6c, | 1e.2b.3a.4b.5e.6d, | |
| 1e.2b.3a.4b.5e.6e, | 1e.2b.3a.4b.5e.6f, | 1e.2b.3a.4b.5f.6a, | 1e.2b.3a.4b.5f.6b, | |
| 1e.2b.3a.4b.5f.6c, | 1e.2b.3a.4b.5f.6d, | 1e.2b.3a.4b.5f.6e, | 1e.2b.3a.4b.5f.6f, | |
| 1e.2b.3a.4c.5a.6a, | 1e.2b.3a.4c.5a.6b, | 1e.2b.3a.4c.5a.6c, | 1e.2b.3a.4c.5a.6d, | |
| 1e.2b.3a.4c.5a.6e, | 1e.2b.3a.4c.5a.6f, | 1e.2b.3a.4c.5b.6a, | 1e.2b.3a.4c.5b.6b, | |
| 1e.2b.3a.4c.5b.6c, | 1e.2b.3a.4c.5b.6d, | 1e.2b.3a.4c.5b.6e, | 1e.2b.3a.4c.5b.6f, | |
| 1e.2b.3a.4c.5c.6a, | 1e.2b.3a.4c.5c.6b, | 1e.2b.3a.4c.5c.6c, | 1e.2b.3a.4c.5c.6d, | |
| 1e.2b.3a.4c.5c.6e, | 1e.2b.3a.4c.5c.6f, | 1e.2b.3a.4c.5d.6a, | 1e.2b.3a.4c.5d.6b, | |
| 1e.2b.3a.4c.5d.6c, | 1e.2b.3a.4c.5d.6d, | 1e.2b.3a.4c.5d.6e, | 1e.2b.3a.4c.5d.6f, | |

TABLE 7-continued

List of Compounds of Formula (II)

| | | | | |
|---|---|---|---|---|
| 1e.2b.3a.4c.5e.6a, | 1e.2b.3a.4c.5e.6b, | 1e.2b.3a.4c.5e.6c, | 1e.2b.3a.4c.5e.6d, | |
| 1e.2b.3a.4c.5e.6e, | 1e.2b.3a.4c.5e.6f, | 1e.2b.3a.4c.5f.6a, | 1e.2b.3a.4c.5f.6b, | 1e.2b.3a.4c.5f.6c, |
| 1e.2b.3a.4c.5f.6d, | 1e.2b.3a.4c.5f.6e, | 1e.2b.3a.4c.5f.6f, | 1e.2b.3a.4d.5a.6a, | |
| 1e.2b.3a.4d.5a.6b, | 1e.2b.3a.4d.5a.6c, | 1e.2b.3a.4d.5a.6d, | 1e.2b.3a.4d.5a.6e, | |
| 1e.2b.3a.4d.5a.6f, | 1e.2b.3a.4d.5b.6a, | 1e.2b.3a.4d.5b.6b, | 1e.2b.3a.4d.5b.6c, | |
| 1e.2b.3a.4d.5b.6d, | 1e.2b.3a.4d.5b.6e, | 1e.2b.3a.4d.5b.6f, | 1e.2b.3a.4d.5c.6a, | |
| 1e.2b.3a.4d.5c.6b, | 1e.2b.3a.4d.5c.6c, | 1e.2b.3a.4d.5c.6d, | 1e.2b.3a.4d.5c.6e, | |
| 1e.2b.3a.4d.5c.6f, | 1e.2b.3a.4d.5d.6a, | 1e.2b.3a.4d.5d.6b, | 1e.2b.3a.4d.5d.6c, | |
| 1e.2b.3a.4d.5d.6d, | 1e.2b.3a.4d.5d.6e, | 1e.2b.3a.4d.5d.6f, | 1e.2b.3a.4d.5e.6a, | |
| 1e.2b.3a.4d.5e.6b, | 1e.2b.3a.4d.5e.6c, | 1e.2b.3a.4d.5e.6d, | 1e.2b.3a.4d.5e.6e, | |
| 1e.2b.3a.4d.5e.6f, | 1e.2b.3a.4d.5f.6a, | 1e.2b.3a.4d.5f.6b, | 1e.2b.3a.4d.5f.6c, | |
| 1e.2b.3a.4d.5f.6d, | 1e.2b.3a.4d.5f.6e, | 1e.2b.3a.4d.5f.6f, | 1e.2b.3a.4e.5a.6a, | |
| 1e.2b.3a.4e.5a.6b, | 1e.2b.3a.4e.5a.6c, | 1e.2b.3a.4e.5a.6d, | 1e.2b.3a.4e.5a.6e, | |
| 1e.2b.3a.4e.5a.6f, | 1e.2b.3a.4e.5b.6a, | 1e.2b.3a.4e.5b.6b, | 1e.2b.3a.4e.5b.6c, | |
| 1e.2b.3a.4e.5b.6d, | 1e.2b.3a.4e.5b.6e, | 1e.2b.3a.4e.5b.6f, | 1e.2b.3a.4e.5c.6a, | |
| 1e.2b.3a.4e.5c.6b, | 1e.2b.3a.4e.5c.6c, | 1e.2b.3a.4e.5c.6d, | 1e.2b.3a.4e.5c.6e, | |
| 1e.2b.3a.4e.5c.6f, | 1e.2b.3a.4e.5d.6a, | 1e.2b.3a.4e.5d.6b, | 1e.2b.3a.4e.5d.6c, | |
| 1e.2b.3a.4e.5d.6d, | 1e.2b.3a.4e.5d.6e, | 1e.2b.3a.4e.5d.6f, | 1e.2b.3a.4e.5e.6a, | |
| 1e.2b.3a.4e.5e.6c, | 1e.2b.3a.4e.5e.6b, | | 1e.2b.3a.4e.5e.6e, | |
| 1e.2b.3a.4e.5e.6f, | 1e.2b.3a.4e.5f.6a, | 1e.2b.3a.4e.5f.6b, | 1e.2b.3a.4e.5f.6c, | 1e.2b.3a.4e.5f.6d, |
| 1e.2b.3a.4e.5f.6e, | 1e.2b.3a.4e.5f.6f, | 1e.2b.3a.4f.5a.6a, | 1e.2b.3a.4f.5a.6b, | 1e.2b.3a.4f.5a.6c, |
| 1e.2b.3a.4f.5a.6d, | 1e.2b.3a.4f.5a.6e, | 1e.2b.3a.4f.5a.6f, | 1e.2b.3a.4f.5b.6a, | |
| 1e.2b.3a.4f.5b.6b, | 1e.2b.3a.4f.5b.6c, | 1e.2b.3a.4f.5b.6d, | 1e.2b.3a.4f.5b.6e, | |
| 1e.2b.3a.4f.5b.6f, | 1e.2b.3a.4f.5c.6a, | 1e.2b.3a.4f.5c.6b, | 1e.2b.3a.4f.5c.6c, | 1e.2b.3a.4f.5c.6d, |
| 1e.2b.3a.4f.5c.6e, | 1e.2b.3a.4f.5c.6f, | 1e.2b.3a.4f.5d.6a, | 1e.2b.3a.4f.5d.6b, | 1e.2b.3a.4f.5d.6c, |
| 1e.2b.3a.4f.5d.6d, | 1e.2b.3a.4f.5d.6e, | 1e.2b.3a.4f.5d.6f, | 1e.2b.3a.4f.5e.6a, | |
| 1e.2b.3a.4f.5e.6b, | 1e.2b.3a.4f.5e.6c, | 1e.2b.3a.4f.5e.6d, | 1e.2b.3a.4f.5e.6e, | 1e.2b.3a.4f.5e.6f, |
| 1e.2b.3a.4f.5f.6a, | 1e.2b.3a.4f.5f.6b, | 1e.2b.3a.4f.5f.6c, | 1e.2b.3a.4f.5f.6d, | 1e.2b.3a.4f.5f.6e, |
| 1e.2b.3a.4f.5f.6f, | 1e.2b.3b.4a.5a.6a, | 1e.2b.3b.4a.5a.6b, | 1e.2b.3b.4a.5a.6c, | |
| 1e.2b.3b.4a.5a.6d, | 1e.2b.3b.4a.5a.6e, | 1e.2b.3b.4a.5a.6f, | 1e.2b.3b.4a.5b.6a, | |
| 1e.2b.3b.4a.5b.6b, | 1e.2b.3b.4a.5b.6c, | 1e.2b.3b.4a.5b.6d, | 1e.2b.3b.4a.5b.6e, | |
| 1e.2b.3b.4a.5b.6f, | 1e.2b.3b.4a.5c.6a, | 1e.2b.3b.4a.5c.6b, | 1e.2b.3b.4a.5c.6c, | |
| 1e.2b.3b.4a.5c.6d, | 1e.2b.3b.4a.5c.6e, | 1e.2b.3b.4a.5c.6f, | 1e.2b.3b.4a.5d.6a, | |
| 1e.2b.3b.4a.5d.6b, | 1e.2b.3b.4a.5d.6c, | 1e.2b.3b.4a.5d.6d, | 1e.2b.3b.4a.5d.6e, | |
| 1e.2b.3b.4a.5d.6f, | 1e.2b.3b.4a.5e.6a, | 1e.2b.3b.4a.5e.6b, | 1e.2b.3b.4a.5e.6c, | |
| 1e.2b.3b.4a.5e.6d, | 1e.2b.3b.4a.5e.6e, | 1e.2b.3b.4a.5e.6f, | 1e.2b.3b.4a.5f.6a, | |
| 1e.2b.3b.4a.5f.6b, | 1e.2b.3b.4a.5f.6c, | 1e.2b.3b.4a.5f.6d, | 1e.2b.3b.4a.5f.6e, | |
| 1e.2b.3b.4a.5f.6f, | 1e.2b.3b.4b.5a.6a, | 1e.2b.3b.4b.5a.6b, | 1e.2b.3b.4b.5a.6c, | |
| 1e.2b.3b.4b.5a.6d, | 1e.2b.3b.4b.5a.6e, | 1e.2b.3b.4b.5a.6f, | 1e.2b.3b.4b.5b.6a, | |
| 1e.2b.3b.4b.5b.6b, | 1e.2b.3b.4b.5b.6c, | 1e.2b.3b.4b.5b.6d, | 1e.2b.3b.4b.5b.6e, | |
| 1e.2b.3b.4b.5b.6f, | 1e.2b.3b.4b.5c.6a, | 1e.2b.3b.4b.5c.6b, | 1e.2b.3b.4b.5c.6c, | |
| 1e.2b.3b.4b.5c.6d, | 1e.2b.3b.4b.5c.6e, | 1e.2b.3b.4b.5c.6f, | 1e.2b.3b.4b.5d.6a, | |
| 1e.2b.3b.4b.5d.6b, | 1e.2b.3b.4b.5d.6c, | 1e.2b.3b.4b.5d.6d, | 1e.2b.3b.4b.5d.6e, | |
| 1e.2b.3b.4b.5d.6f, | 1e.2b.3b.4b.5e.6a, | 1e.2b.3b.4b.5e.6b, | 1e.2b.3b.4b.5e.6c, | |
| 1e.2b.3b.4b.5e.6d, | 1e.2b.3b.4b.5e.6e, | 1e.2b.3b.4b.5e.6f, | 1e.2b.3b.4b.5f.6a, | |
| 1e.2b.3b.4b.5f.6b, | 1e.2b.3b.4b.5f.6c, | 1e.2b.3b.4b.5f.6d, | 1e.2b.3b.4b.5f.6e, | |
| 1e.2b.3b.4b.5f.6f, | 1e.2b.3b.4c.5a.6a, | 1e.2b.3b.4c.5a.6b, | 1e.2b.3b.4c.5a.6c, | |
| 1e.2b.3b.4c.5a.6d, | 1e.2b.3b.4c.5a.6e, | 1e.2b.3b.4c.5a.6f, | 1e.2b.3b.4c.5b.6a, | |
| 1e.2b.3b.4c.5b.6b, | 1e.2b.3b.4c.5b.6c, | 1e.2b.3b.4c.5b.6d, | 1e.2b.3b.4c.5b.6e, | |
| 1e.2b.3b.4c.5b.6f, | 1e.2b.3b.4c.5c.6a, | 1e.2b.3b.4c.5c.6b, | 1e.2b.3b.4c.5c.6c, | |
| 1e.2b.3b.4c.5c.6d, | 1e.2b.3b.4c.5c.6e, | 1e.2b.3b.4c.5c.6f, | 1e.2b.3b.4c.5d.6a, | |
| 1e.2b.3b.4c.5d.6b, | 1e.2b.3b.4c.5d.6c, | 1e.2b.3b.4c.5d.6d, | 1e.2b.3b.4c.5d.6e, | |
| 1e.2b.3b.4c.5d.6f, | 1e.2b.3b.4c.5e.6a, | 1e.2b.3b.4c.5e.6b, | 1e.2b.3b.4c.5e.6c, | |
| 1e.2b.3b.4c.5e.6d, | 1e.2b.3b.4c.5e.6e, | 1e.2b.3b.4c.5e.6f, | 1e.2b.3b.4c.5f.6a, | |
| 1e.2b.3b.4c.5f.6b, | 1e.2b.3b.4c.5f.6c, | 1e.2b.3b.4c.5f.6d, | 1e.2b.3b.4c.5f.6e, | 1e.2b.3b.4c.5f.6f, |
| 1e.2b.3b.4d.5a.6a, | 1e.2b.3b.4d.5a.6b, | 1e.2b.3b.4d.5a.6c, | 1e.2b.3b.4d.5a.6d, | |
| 1e.2b.3b.4d.5a.6e, | 1e.2b.3b.4d.5a.6f, | 1e.2b.3b.4d.5b.6a, | 1e.2b.3b.4d.5b.6b, | |
| 1e.2b.3b.4d.5b.6c, | 1e.2b.3b.4d.5b.6d, | 1e.2b.3b.4d.5b.6e, | 1e.2b.3b.4d.5b.6f, | |
| 1e.2b.3b.4d.5c.6a, | 1e.2b.3b.4d.5c.6b, | 1e.2b.3b.4d.5c.6c, | 1e.2b.3b.4d.5c.6d, | |
| 1e.2b.3b.4d.5c.6e, | 1e.2b.3b.4d.5c.6f, | 1e.2b.3b.4d.5d.6a, | 1e.2b.3b.4d.5d.6b, | |
| 1e.2b.3b.4d.5d.6c, | 1e.2b.3b.4d.5d.6d, | 1e.2b.3b.4d.5d.6e, | 1e.2b.3b.4d.5d.6f, | |
| 1e.2b.3b.4d.5e.6a, | 1e.2b.3b.4d.5e.6b, | 1e.2b.3b.4d.5e.6c, | 1e.2b.3b.4d.5e.6d, | |
| 1e.2b.3b.4d.5e.6e, | 1e.2b.3b.4d.5e.6f, | 1e.2b.3b.4d.5f.6a, | 1e.2b.3b.4d.5f.6b, | |
| 1e.2b.3b.4d.5f.6c, | 1e.2b.3b.4d.5f.6d, | 1e.2b.3b.4d.5f.6e, | 1e.2b.3b.4d.5f.6f, | |
| 1e.2b.3b.4e.5a.6a, | 1e.2b.3b.4e.5a.6b, | 1e.2b.3b.4e.5a.6c, | 1e.2b.3b.4e.5a.6d, | |
| 1e.2b.3b.4e.5a.6e, | 1e.2b.3b.4e.5a.6f, | 1e.2b.3b.4e.5b.6a, | 1e.2b.3b.4e.5b.6b, | |
| 1e.2b.3b.4e.5b.6c, | 1e.2b.3b.4e.5b.6d, | 1e.2b.3b.4e.5b.6e, | 1e.2b.3b.4e.5b.6f, | |
| 1e.2b.3b.4e.5c.6a, | 1e.2b.3b.4e.5c.6b, | 1e.2b.3b.4e.5c.6c, | 1e.2b.3b.4e.5c.6d, | |
| 1e.2b.3b.4e.5c.6e, | 1e.2b.3b.4e.5c.6f, | 1e.2b.3b.4e.5d.6a, | 1e.2b.3b.4e.5d.6b, | |
| 1e.2b.3b.4e.5d.6c, | 1e.2b.3b.4e.5d.6d, | 1e.2b.3b.4e.5d.6e, | 1e.2b.3b.4e.5d.6f, | |
| 1e.2b.3b.4e.5e.6a, | 1e.2b.3b.4e.5e.6b, | 1e.2b.3b.4e.5e.6c, | 1e.2b.3b.4e.5e.6d, | |
| 1e.2b.3b.4e.5e.6e, | 1e.2b.3b.4e.5e.6f, | 1e.2b.3b.4e.5f.6a, | 1e.2b.3b.4e.5f.6b, | |
| 1e.2b.3b.4e.5f.6c, | 1e.2b.3b.4e.5f.6d, | 1e.2b.3b.4e.5f.6e, | 1e.2b.3b.4e.5f.6f, | |
| 1e.2b.3b.4f.5a.6a, | 1e.2b.3b.4f.5a.6b, | 1e.2b.3b.4f.5a.6c, | 1e.2b.3b.4f.5a.6d, | |
| 1e.2b.3b.4f.5a.6e, | 1e.2b.3b.4f.5a.6f, | 1e.2b.3b.4f.5b.6a, | 1e.2b.3b.4f.5b.6b, | |
| 1e.2b.3b.4f.5b.6c, | 1e.2b.3b.4f.5b.6d, | 1e.2b.3b.4f.5b.6e, | 1e.2b.3b.4f.5b.6f, | |
| 1e.2b.3b.4f.5c.6a, | 1e.2b.3b.4f.5c.6b, | 1e.2b.3b.4f.5c.6c, | 1e.2b.3b.4f.5c.6d, | |
| 1e.2b.3b.4f.5c.6e, | 1e.2b.3b.4f.5c.6f, | 1e.2b.3b.4f.5d.6a, | 1e.2b.3b.4f.5d.6b, | |

TABLE 7-continued

List of Compounds of Formula (II)

| | | | | |
|---|---|---|---|---|
| 1e.2b.3b.4f.5d.6c, | 1e.2b.3b.4f.5d.6d, | 1e.2b.3b.4f.5d.6e, | 1e.2b.3b.4f.5d.6f, | |
| 1e.2b.3b.4f.5e.6a, | 1e.2b.3b.4f.5e.6b, | 1e.2b.3b.4f.5e.6c, | 1e.2b.3b.4f.5e.6d, | |
| 1e.2b.3b.4f.5e.6e, | 1e.2b.3b.4f.5e.6f, | 1e.2b.3b.4f.5f.6a, | 1e.2b.3b.4f.5f.6b, | 1e.2b.3b.4f.5f.6c, |
| 1e.2b.3b.4f.5f.6d, | 1e.2b.3b.4f.5f.6e, | 1e.2b.3b.4f.5f.6f, | 1e.2b.3c.4a.5a.6a, | 1e.2b.3c.4a.5a.6b, |
| 1e.2b.3c.4a.5a.6c, | 1e.2b.3c.4a.5a.6d, | 1e.2b.3c.4a.5a.6e, | 1e.2b.3c.4a.5a.6f, | |
| 1e.2b.3c.4a.5b.6a, | 1e.2b.3c.4a.5b.6b, | 1e.2b.3c.4a.5b.6c, | 1e.2b.3c.4a.5b.6d, | |
| 1e.2b.3c.4a.5b.6e, | 1e.2b.3c.4a.5b.6f, | 1e.2b.3c.4a.5c.6a, | 1e.2b.3c.4a.5c.6b, | |
| 1e.2b.3c.4a.5c.6c, | 1e.2b.3c.4a.5c.6d, | 1e.2b.3c.4a.5c.6e, | 1e.2b.3c.4a.5c.6f, | |
| 1e.2b.3c.4a.5d.6a, | 1e.2b.3c.4a.5d.6b, | 1e.2b.3c.4a.5d.6c, | 1e.2b.3c.4a.5d.6d, | |
| 1e.2b.3c.4a.5d.6e, | 1e.2b.3c.4a.5d.6f, | 1e.2b.3c.4a.5e.6a, | 1e.2b.3c.4a.5e.6b, | |
| 1e.2b.3c.4a.5e.6c, | 1e.2b.3c.4a.5e.6d, | 1e.2b.3c.4a.5e.6e, | 1e.2b.3c.4a.5e.6f, | |
| 1e.2b.3c.4a.5f.6a, | 1e.2b.3c.4a.5f.6b, | 1e.2b.3c.4a.5f.6c, | 1e.2b.3c.4a.5f.6d, | 1e.2b.3c.4a.5f.6e, |
| 1e.2b.3c.4a.5f.6f, | 1e.2b.3c.4b.5a.6a, | 1e.2b.3c.4b.5a.6b, | 1e.2b.3c.4b.5a.6c, | |
| 1e.2b.3c.4b.5a.6d, | 1e.2b.3c.4b.5a.6e, | 1e.2b.3c.4b.5a.6f, | 1e.2b.3c.4b.5b.6a, | |
| 1e.2b.3c.4b.5b.6b, | 1e.2b.3c.4b.5b.6c, | 1e.2b.3c.4b.5b.6d, | 1e.2b.3c.4b.5b.6e, | |
| 1e.2b.3c.4b.5b.6f, | 1e.2b.3c.4b.5c.6a, | 1e.2b.3c.4b.5c.6b, | 1e.2b.3c.4b.5c.6c, | |
| 1e.2b.3c.4b.5c.6d, | 1e.2b.3c.4b.5c.6e, | 1e.2b.3c.4b.5c.6f, | 1e.2b.3c.4b.5d.6a, | |
| 1e.2b.3c.4b.5d.6b, | 1e.2b.3c.4b.5d.6c, | 1e.2b.3c.4b.5d.6d, | 1e.2b.3c.4b.5d.6e, | |
| 1e.2b.3c.4b.5d.6f, | 1e.2b.3c.4b.5e.6a, | 1e.2b.3c.4b.5e.6b, | 1e.2b.3c.4b.5e.6c, | |
| 1e.2b.3c.4b.5e.6d, | 1e.2b.3c.4b.5e.6e, | 1e.2b.3c.4b.5e.6f, | 1e.2b.3c.4b.5f.6a, | |
| 1e.2b.3c.4b.5f.6b, | 1e.2b.3c.4b.5f.6c, | 1e.2b.3c.4b.5f.6d, | 1e.2b.3c.4b.5f.6e, | 1e.2b.3c.4b.5f.6f, |
| 1e.2b.3c.4c.5a.6a, | 1e.2b.3c.4c.5a.6b, | 1e.2b.3c.4c.5a.6c, | 1e.2b.3c.4c.5a.6d, | |
| 1e.2b.3c.4c.5a.6e, | 1e.2b.3c.4c.5a.6f, | 1e.2b.3c.4c.5b.6a, | 1e.2b.3c.4c.5b.6b, | |
| 1e.2b.3c.4c.5b.6c, | 1e.2b.3c.4c.5b.6d, | 1e.2b.3c.4c.5b.6e, | 1e.2b.3c.4c.5b.6f, | |
| 1e.2b.3c.4c.5c.6a, | 1e.2b.3c.4c.5c.6b, | 1e.2b.3c.4c.5c.6c, | 1e.2b.3c.4c.5c.6d, | |
| 1e.2b.3c.4c.5c.6e, | 1e.2b.3c.4c.5c.6f, | 1e.2b.3c.4c.5d.6a, | 1e.2b.3c.4c.5d.6b, | |
| 1e.2b.3c.4c.5d.6c, | 1e.2b.3c.4c.5d.6d, | 1e.2b.3c.4c.5d.6e, | 1e.2b.3c.4c.5d.6f, | |
| 1e.2b.3c.4c.5e.6a, | 1e.2b.3c.4c.5e.6b, | 1e.2b.3c.4c.5e.6c, | 1e.2b.3c.4c.5e.6d, | |
| 1e.2b.3c.4c.5e.6e, | 1e.2b.3c.4c.5e.6f, | 1e.2b.3c.4c.5f.6a, | 1e.2b.3c.4c.5f.6b, | 1e.2b.3c.4c.5f.6c, |
| 1e.2b.3c.4c.5f.6d, | 1e.2b.3c.4c.5f.6e, | 1e.2b.3c.4c.5f.6f, | 1e.2b.3c.4d.5a.6a, | |
| 1e.2b.3c.4d.5a.6b, | 1e.2b.3c.4d.5a.6c, | 1e.2b.3c.4d.5a.6d, | 1e.2b.3c.4d.5a.6e, | |
| 1e.2b.3c.4d.5a.6f, | 1e.2b.3c.4d.5b.6a, | 1e.2b.3c.4d.5b.6b, | 1e.2b.3c.4d.5b.6c, | |
| 1e.2b.3c.4d.5b.6d, | 1e.2b.3c.4d.5b.6e, | 1e.2b.3c.4d.5b.6f, | 1e.2b.3c.4d.5c.6a, | |
| 1e.2b.3c.4d.5c.6b, | 1e.2b.3c.4d.5c.6c, | 1e.2b.3c.4d.5c.6d, | 1e.2b.3c.4d.5c.6e, | |
| 1e.2b.3c.4d.5c.6f, | 1e.2b.3c.4d.5d.6a, | 1e.2b.3c.4d.5d.6b, | 1e.2b.3c.4d.5d.6c, | |
| 1e.2b.3c.4d.5d.6d, | 1e.2b.3c.4d.5d.6e, | 1e.2b.3c.4d.5d.6f, | 1e.2b.3c.4d.5e.6a, | |
| 1e.2b.3c.4d.5e.6b, | 1e.2b.3c.4d.5e.6c, | 1e.2b.3c.4d.5e.6d, | 1e.2b.3c.4d.5e.6e, | |
| 1e.2b.3c.4d.5e.6f, | 1e.2b.3c.4d.5f.6a, | 1e.2b.3c.4d.5f.6b, | 1e.2b.3c.4d.5f.6c, | |
| 1e.2b.3c.4d.5f.6d, | 1e.2b.3c.4d.5f.6e, | 1e.2b.3c.4d.5f.6f, | 1e.2b.3c.4e.5a.6a, | |
| 1e.2b.3c.4e.5a.6b, | 1e.2b.3c.4e.5a.6c, | 1e.2b.3c.4e.5a.6d, | 1e.2b.3c.4e.5a.6e, | |
| 1e.2b.3c.4e.5a.6f, | 1e.2b.3c.4e.5b.6a, | 1e.2b.3c.4e.5b.6b, | 1e.2b.3c.4e.5b.6c, | |
| 1e.2b.3c.4e.5b.6d, | 1e.2b.3c.4e.5b.6e, | 1e.2b.3c.4e.5b.6f, | 1e.2b.3c.4e.5c.6a, | |
| 1e.2b.3c.4e.5c.6b, | 1e.2b.3c.4e.5c.6c, | 1e.2b.3c.4e.5c.6d, | 1e.2b.3c.4e.5c.6e, | |
| 1e.2b.3c.4e.5c.6f, | 1e.2b.3c.4e.5d.6a, | 1e.2b.3c.4e.5d.6b, | 1e.2b.3c.4e.5d.6c, | |
| 1e.2b.3c.4e.5d.6d, | 1e.2b.3c.4e.5d.6e, | 1e.2b.3c.4e.5d.6f, | 1e.2b.3c.4e.5e.6a, | |
| 1e.2b.3c.4e.5e.6b, | 1e.2b.3c.4e.5e.6c, | 1e.2b.3c.4e.5e.6d, | 1e.2b.3c.4e.5e.6e, | |
| 1e.2b.3c.4e.5e.6f, | 1e.2b.3c.4e.5f.6a, | 1e.2b.3c.4e.5f.6b, | 1e.2b.3c.4e.5f.6c, | 1e.2b.3c.4e.5f.6d, |
| 1e.2b.3c.4e.5f.6e, | 1e.2b.3c.4e.5f.6f, | 1e.2b.3c.4f.5a.6a, | 1e.2b.3c.4f.5a.6b, | 1e.2b.3c.4f.5a.6c, |
| 1e.2b.3c.4f.5a.6d, | 1e.2b.3c.4f.5a.6e, | 1e.2b.3c.4f.5a.6f, | 1e.2b.3c.4f.5b.6a, | 1e.2b.3c.4f.5b.6b, |
| 1e.2b.3c.4f.5b.6c, | 1e.2b.3c.4f.5b.6d, | 1e.2b.3c.4f.5b.6e, | 1e.2b.3c.4f.5b.6f, | 1e.2b.3c.4f.5c.6a, |
| 1e.2b.3c.4f.5c.6b, | 1e.2b.3c.4f.5c.6c, | 1e.2b.3c.4f.5c.6d, | 1e.2b.3c.4f.5c.6e, | 1e.2b.3c.4f.5c.6f, |
| 1e.2b.3c.4f.5d.6a, | 1e.2b.3c.4f.5d.6b, | 1e.2b.3c.4f.5d.6c, | 1e.2b.3c.4f.5d.6d, | |
| 1e.2b.3c.4f.5d.6e, | 1e.2b.3c.4f.5d.6f, | 1e.2b.3c.4f.5e.6a, | 1e.2b.3c.4f.5e.6b, | 1e.2b.3c.4f.5e.6c, |
| 1e.2b.3c.4f.5e.6d, | 1e.2b.3c.4f.5e.6e, | 1e.2b.3c.4f.5e.6f, | 1e.2b.3c.4f.5f.6a, | 1e.2b.3c.4f.5f.6b, |
| 1e.2b.3c.4f.5f.6c, | 1e.2b.3c.4f.5f.6d, | 1e.2b.3c.4f.5f.6e, | 1e.2b.3c.4f.5f.6f, | 1e.2b.3d.4a.5a.6a, |
| 1e.2b.3d.4a.5a.6b, | 1e.2b.3d.4a.5a.6c, | 1e.2b.3d.4a.5a.6d, | 1e.2b.3d.4a.5a.6e, | |
| 1e.2b.3d.4a.5a.6f, | 1e.2b.3d.4a.5b.6a, | 1e.2b.3d.4a.5b.6b, | 1e.2b.3d.4a.5b.6c, | |
| 1e.2b.3d.4a.5b.6d, | 1e.2b.3d.4a.5b.6e, | 1e.2b.3d.4a.5b.6f, | 1e.2b.3d.4a.5c.6a, | |
| 1e.2b.3d.4a.5c.6b, | 1e.2b.3d.4a.5c.6c, | 1e.2b.3d.4a.5c.6d, | 1e.2b.3d.4a.5c.6e, | |
| 1e.2b.3d.4a.5c.6f, | 1e.2b.3d.4a.5d.6a, | 1e.2b.3d.4a.5d.6b, | 1e.2b.3d.4a.5d.6c, | |
| 1e.2b.3d.4a.5d.6d, | 1e.2b.3d.4a.5d.6e, | 1e.2b.3d.4a.5d.6f, | 1e.2b.3d.4a.5e.6a, | |
| 1e.2b.3d.4a.5e.6b, | 1e.2b.3d.4a.5e.6c, | 1e.2b.3d.4a.5e.6d, | 1e.2b.3d.4a.5e.6e, | |
| 1e.2b.3d.4a.5e.6f, | 1e.2b.3d.4a.5f.6a, | 1e.2b.3d.4a.5f.6b, | 1e.2b.3d.4a.5f.6c, | |
| 1e.2b.3d.4a.5f.6d, | 1e.2b.3d.4a.5f.6e, | 1e.2b.3d.4a.5f.6f, | 1e.2b.3d.4b.5a.6a, | |
| 1e.2b.3d.4b.5a.6b, | 1e.2b.3d.4b.5a.6c, | 1e.2b.3d.4b.5a.6d, | 1e.2b.3d.4b.5a.6e, | |
| 1e.2b.3d.4b.5a.6f, | 1e.2b.3d.4b.5b.6a, | 1e.2b.3d.4b.5b.6b, | 1e.2b.3d.4b.5b.6c, | |
| 1e.2b.3d.4b.5b.6d, | 1e.2b.3d.4b.5b.6e, | 1e.2b.3d.4b.5b.6f, | 1e.2b.3d.4b.5c.6a, | |
| 1e.2b.3d.4b.5c.6b, | 1e.2b.3d.4b.5c.6c, | 1e.2b.3d.4b.5c.6d, | 1e.2b.3d.4b.5c.6e, | |
| 1e.2b.3d.4b.5c.6f, | 1e.2b.3d.4b.5d.6a, | 1e.2b.3d.4b.5d.6b, | 1e.2b.3d.4b.5d.6c, | |
| 1e.2b.3d.4b.5d.6d, | 1e.2b.3d.4b.5d.6e, | 1e.2b.3d.4b.5d.6f, | 1e.2b.3d.4b.5e.6a, | |
| 1e.2b.3d.4b.5e.6b, | 1e.2b.3d.4b.5e.6c, | 1e.2b.3d.4b.5e.6d, | 1e.2b.3d.4b.5e.6e, | |
| 1e.2b.3d.4b.5e.6f, | 1e.2b.3d.4b.5f.6a, | 1e.2b.3d.4b.5f.6b, | 1e.2b.3d.4b.5f.6c, | |
| 1e.2b.3d.4b.5f.6d, | 1e.2b.3d.4b.5f.6e, | 1e.2b.3d.4b.5f.6f, | 1e.2b.3d.4c.5a.6a, | |
| 1e.2b.3d.4c.5a.6b, | 1e.2b.3d.4c.5a.6c, | 1e.2b.3d.4c.5a.6d, | 1e.2b.3d.4c.5a.6e, | |
| 1e.2b.3d.4c.5a.6f, | 1e.2b.3d.4c.5b.6a, | 1e.2b.3d.4c.5b.6b, | 1e.2b.3d.4c.5b.6c, | |
| 1e.2b.3d.4c.5b.6d, | 1e.2b.3d.4c.5b.6e, | 1e.2b.3d.4c.5b.6f, | 1e.2b.3d.4c.5c.6a, | |
| 1e.2b.3d.4c.5c.6b, | 1e.2b.3d.4c.5c.6c, | 1e.2b.3d.4c.5c.6d, | 1e.2b.3d.4c.5c.6e, | |
| 1e.2b.3d.4c.5c.6f, | 1e.2b.3d.4c.5d.6a, | 1e.2b.3d.4c.5d.6b, | 1e.2b.3d.4c.5d.6c, | |

TABLE 7-continued

List of Compounds of Formula (II)

| | | | | |
|---|---|---|---|---|
| 1e.2b.3d.4c.5d.6d, | 1e.2b.3d.4c.5d.6e, | 1e.2b.3d.4c.5d.6f, | 1e.2b.3d.4c.5e.6a, | |
| 1e.2b.3d.4c.5e.6b, | 1e.2b.3d.4c.5e.6c, | 1e.2b.3d.4c.5e.6d, | 1e.2b.3d.4c.5e.6e, | |
| 1e.2b.3d.4c.5e.6f, | 1e.2b.3d.4c.5f.6a, | 1e.2b.3d.4c.5f.6b, | 1e.2b.3d.4c.5f.6c, | |
| 1e.2b.3d.4c.5f.6d, | 1e.2b.3d.4c.5f.6e, | 1e.2b.3d.4c.5f.6f, | 1e.2b.3d.4d.5a.6a, | |
| 1e.2b.3d.4d.5a.6b, | 1e.2b.3d.4d.5a.6c, | 1e.2b.3d.4d.5a.6d, | 1e.2b.3d.4d.5a.6e, | |
| 1e.2b.3d.4d.5a.6f, | 1e.2b.3d.4d.5b.6a, | 1e.2b.3d.4d.5b.6b, | 1e.2b.3d.4d.5b.6c, | |
| 1e.2b.3d.4d.5b.6d, | 1e.2b.3d.4d.5b.6e, | 1e.2b.3d.4d.5b.6f, | 1e.2b.3d.4d.5c.6a, | |
| 1e.2b.3d.4d.5c.6b, | 1e.2b.3d.4d.5c.6c, | 1e.2b.3d.4d.5c.6d, | 1e.2b.3d.4d.5c.6e, | |
| 1e.2b.3d.4d.5c.6f, | 1e.2b.3d.4d.5d.6a, | 1e.2b.3d.4d.5d.6b, | 1e.2b.3d.4d.5d.6c, | |
| 1e.2b.3d.4d.5d.6d, | 1e.2b.3d.4d.5d.6e, | 1e.2b.3d.4d.5d.6f, | 1e.2b.3d.4d.5e.6a, | |
| 1e.2b.3d.4d.5e.6b, | 1e.2b.3d.4d.5e.6c, | 1e.2b.3d.4d.5e.6d, | 1e.2b.3d.4d.5e.6e, | |
| 1e.2b.3d.4d.5e.6f, | 1e.2b.3d.4d.5f.6a, | 1e.2b.3d.4d.5f.6b, | 1e.2b.3d.4d.5f.6c, | |
| 1e.2b.3d.4d.5f.6d, | 1e.2b.3d.4d.5f.6e, | 1e.2b.3d.4d.5f.6f, | 1e.2b.3d.4e.5a.6a, | |
| 1e.2b.3d.4e.5a.6b, | 1e.2b.3d.4e.5a.6c, | 1e.2b.3d.4e.5a.6d, | 1e.2b.3d.4e.5a.6e, | |
| 1e.2b.3d.4e.5a.6f, | 1e.2b.3d.4e.5b.6a, | 1e.2b.3d.4e.5b.6b, | 1e.2b.3d.4e.5b.6c, | |
| 1e.2b.3d.4e.5b.6d, | 1e.2b.3d.4e.5b.6e, | 1e.2b.3d.4e.5b.6f, | 1e.2b.3d.4e.5c.6a, | |
| 1e.2b.3d.4e.5c.6b, | 1e.2b.3d.4e.5c.6c, | 1e.2b.3d.4e.5c.6d, | 1e.2b.3d.4e.5c.6e, | |
| 1e.2b.3d.4e.5c.6f, | 1e.2b.3d.4e.5d.6a, | 1e.2b.3d.4e.5d.6b, | 1e.2b.3d.4e.5d.6c, | |
| 1e.2b.3d.4e.5d.6d, | 1e.2b.3d.4e.5d.6e, | 1e.2b.3d.4e.5d.6f, | 1e.2b.3d.4e.5e.6a, | |
| 1e.2b.3d.4e.5e.6b, | 1e.2b.3d.4e.5e.6c, | 1e.2b.3d.4e.5e.6d, | 1e.2b.3d.4e.5e.6e, | |
| 1e.2b.3d.4e.5e.6f, | 1e.2b.3d.4e.5f.6a, | 1e.2b.3d.4e.5f.6b, | 1e.2b.3d.4e.5f.6c, | |
| 1e.2b.3d.4e.5f.6d, | 1e.2b.3d.4e.5f.6e, | 1e.2b.3d.4e.5f.6f, | 1e.2b.3d.4f.5a.6a, | |
| 1e.2b.3d.4f.5a.6b, | 1e.2b.3d.4f.5a.6c, | 1e.2b.3d.4f.5a.6d, | 1e.2b.3d.4f.5a.6e, | |
| 1e.2b.3d.4f.5a.6f, | 1e.2b.3d.4f.5b.6a, | 1e.2b.3d.4f.5b.6b, | 1e.2b.3d.4f.5b.6c, | |
| 1e.2b.3d.4f.5b.6d, | 1e.2b.3d.4f.5b.6e, | 1e.2b.3d.4f.5b.6f, | 1e.2b.3d.4f.5c.6a, | |
| 1e.2b.3d.4f.5c.6b, | 1e.2b.3d.4f.5c.6c, | 1e.2b.3d.4f.5c.6d, | 1e.2b.3d.4f.5c.6e, | |
| 1e.2b.3d.4f.5c.6f, | 1e.2b.3d.4f.5d.6a, | 1e.2b.3d.4f.5d.6b, | 1e.2b.3d.4f.5d.6c, | |
| 1e.2b.3d.4f.5d.6d, | 1e.2b.3d.4f.5d.6e, | 1e.2b.3d.4f.5d.6f, | 1e.2b.3d.4f.5e.6a, | |
| 1e.2b.3d.4f.5e.6b, | 1e.2b.3d.4f.5e.6c, | 1e.2b.3d.4f.5e.6d, | 1e.2b.3d.4f.5e.6e, | |
| 1e.2b.3d.4f.5e.6f, | 1e.2b.3d.4f.5f.6a, | 1e.2b.3d.4f.5f.6b, | 1e.2b.3d.4f.5f.6c, | 1e.2b.3d.4f.5f.6d, |
| 1e.2b.3d.4f.5f.6e, | 1e.2b.3d.4f.5f.6f, | 1e.2b.3e.4a.5a.6a, | 1e.2b.3e.4a.5a.6b, | |
| 1e.2b.3e.4a.5a.6c, | 1e.2b.3e.4a.5a.6d, | 1e.2b.3e.4a.5a.6e, | 1e.2b.3e.4a.5a.6f, | |
| 1e.2b.3e.4a.5b.6a, | 1e.2b.3e.4a.5b.6b, | 1e.2b.3e.4a.5b.6c, | 1e.2b.3e.4a.5b.6d, | |
| 1e.2b.3e.4a.5b.6e, | 1e.2b.3e.4a.5b.6f, | 1e.2b.3e.4a.5c.6a, | 1e.2b.3e.4a.5c.6b, | |
| 1e.2b.3e.4a.5c.6c, | 1e.2b.3e.4a.5c.6d, | 1e.2b.3e.4a.5c.6e, | 1e.2b.3e.4a.5c.6f, | |
| 1e.2b.3e.4a.5d.6a, | 1e.2b.3e.4a.5d.6b, | 1e.2b.3e.4a.5d.6c, | 1e.2b.3e.4a.5d.6d, | |
| 1e.2b.3e.4a.5d.6e, | 1e.2b.3e.4a.5d.6f, | 1e.2b.3e.4a.5e.6a, | 1e.2b.3e.4a.5e.6b, | |
| 1e.2b.3e.4a.5e.6c, | 1e.2b.3e.4a.5e.6d, | 1e.2b.3e.4a.5e.6e, | 1e.2b.3e.4a.5e.6f, | |
| 1e.2b.3e.4a.5f.6a, | 1e.2b.3e.4a.5f.6b, | 1e.2b.3e.4a.5f.6c, | 1e.2b.3e.4a.5f.6d, | 1e.2b.3e.4a.5f.6e, |
| 1e.2b.3e.4a.5f.6f, | 1e.2b.3e.4b.5a.6a, | 1e.2b.3e.4b.5a.6b, | 1e.2b.3e.4b.5a.6c, | |
| 1e.2b.3e.4b.5a.6d, | 1e.2b.3e.4b.5a.6e, | 1e.2b.3e.4b.5a.6f, | 1e.2b.3e.4b.5b.6a, | |
| 1e.2b.3e.4b.5b.6b, | 1e.2b.3e.4b.5b.6c, | 1e.2b.3e.4b.5b.6d, | 1e.2b.3e.4b.5b.6e, | |
| 1e.2b.3e.4b.5b.6f, | 1e.2b.3e.4b.5c.6a, | 1e.2b.3e.4b.5c.6b, | 1e.2b.3e.4b.5c.6c, | |
| 1e.2b.3e.4b.5c.6d, | 1e.2b.3e.4b.5c.6e, | 1e.2b.3e.4b.5c.6f, | 1e.2b.3e.4b.5d.6a, | |
| 1e.2b.3e.4b.5d.6b, | 1e.2b.3e.4b.5d.6c, | 1e.2b.3e.4b.5d.6d, | 1e.2b.3e.4b.5d.6e, | |
| 1e.2b.3e.4b.5d.6f, | 1e.2b.3e.4b.5e.6a, | 1e.2b.3e.4b.5e.6b, | 1e.2b.3e.4b.5e.6c, | |
| 1e.2b.3e.4b.5e.6d, | 1e.2b.3e.4b.5e.6e, | 1e.2b.3e.4b.5e.6f, | 1e.2b.3e.4b.5f.6a, | |
| 1e.2b.3e.4b.5f.6b, | 1e.2b.3e.4b.5f.6c, | 1e.2b.3e.4b.5f.6d, | 1e.2b.3e.4b.5f.6e, | |
| 1e.2b.3e.4b.5f.6f, | 1e.2b.3e.4c.5a.6a, | 1e.2b.3e.4c.5a.6b, | 1e.2b.3e.4c.5a.6c, | |
| 1e.2b.3e.4c.5a.6d, | 1e.2b.3e.4c.5a.6e, | 1e.2b.3e.4c.5a.6f, | 1e.2b.3e.4c.5b.6a, | |
| 1e.2b.3e.4c.5b.6b, | 1e.2b.3e.4c.5b.6c, | 1e.2b.3e.4c.5b.6d, | 1e.2b.3e.4c.5b.6e, | |
| 1e.2b.3e.4c.5b.6f, | 1e.2b.3e.4c.5c.6a, | 1e.2b.3e.4c.5c.6b, | 1e.2b.3e.4c.5c.6c, | |
| 1e.2b.3e.4c.5c.6d, | 1e.2b.3e.4c.5c.6e, | 1e.2b.3e.4c.5c.6f, | 1e.2b.3e.4c.5d.6a, | |
| 1e.2b.3e.4c.5d.6b, | 1e.2b.3e.4c.5d.6c, | 1e.2b.3e.4c.5d.6d, | 1e.2b.3e.4c.5d.6e, | |
| 1e.2b.3e.4c.5d.6f, | 1e.2b.3e.4c.5e.6a, | 1e.2b.3e.4c.5e.6b, | 1e.2b.3e.4c.5e.6c, | |
| 1e.2b.3e.4c.5e.6d, | 1e.2b.3e.4c.5e.6e, | 1e.2b.3e.4c.5e.6f, | 1e.2b.3e.4c.5f.6a, | 1e.2b.3e.4c.5f.6b, |
| 1e.2b.3e.4c.5f.6c, | 1e.2b.3e.4c.5f.6d, | 1e.2b.3e.4c.5f.6e, | 1e.2b.3e.4c.5f.6f, | 1e.2b.3e.4d.5a.6a, |
| 1e.2b.3e.4d.5a.6b, | 1e.2b.3e.4d.5a.6c, | 1e.2b.3e.4d.5a.6d, | 1e.2b.3e.4d.5a.6e, | |
| 1e.2b.3e.4d.5a.6f, | 1e.2b.3e.4d.5b.6a, | 1e.2b.3e.4d.5b.6b, | 1e.2b.3e.4d.5b.6c, | |
| 1e.2b.3e.4d.5b.6d, | 1e.2b.3e.4d.5b.6e, | 1e.2b.3e.4d.5b.6f, | 1e.2b.3e.4d.5c.6a, | |
| 1e.2b.3e.4d.5c.6b, | 1e.2b.3e.4d.5c.6c, | 1e.2b.3e.4d.5c.6d, | 1e.2b.3e.4d.5c.6e, | |
| 1e.2b.3e.4d.5c.6f, | 1e.2b.3e.4d.5d.6a, | 1e.2b.3e.4d.5d.6b, | 1e.2b.3e.4d.5d.6c, | |
| 1e.2b.3e.4d.5d.6d, | 1e.2b.3e.4d.5d.6e, | 1e.2b.3e.4d.5d.6f, | 1e.2b.3e.4d.5e.6a, | |
| 1e.2b.3e.4d.5e.6b, | 1e.2b.3e.4d.5e.6c, | 1e.2b.3e.4d.5e.6d, | 1e.2b.3e.4d.5e.6e, | |
| 1e.2b.3e.4d.5e.6f, | 1e.2b.3e.4d.5f.6a, | 1e.2b.3e.4d.5f.6b, | 1e.2b.3e.4d.5f.6c, | |
| 1e.2b.3e.4d.5f.6d, | 1e.2b.3e.4d.5f.6e, | 1e.2b.3e.4d.5f.6f, | 1e.2b.3e.4e.5a.6a, | |
| 1e.2b.3e.4e.5a.6b, | 1e.2b.3e.4e.5a.6c, | 1e.2b.3e.4e.5a.6d, | 1e.2b.3e.4e.5a.6e, | |
| 1e.2b.3e.4e.5a.6f, | 1e.2b.3e.4e.5b.6a, | 1e.2b.3e.4e.5b.6b, | 1e.2b.3e.4e.5b.6c, | |
| 1e.2b.3e.4e.5b.6d, | 1e.2b.3e.4e.5b.6e, | 1e.2b.3e.4e.5b.6f, | 1e.2b.3e.4e.5c.6a, | |
| 1e.2b.3e.4e.5c.6b, | 1e.2b.3e.4e.5c.6c, | 1e.2b.3e.4e.5c.6d, | 1e.2b.3e.4e.5c.6e, | |
| 1e.2b.3e.4e.5c.6f, | 1e.2b.3e.4e.5d.6a, | 1e.2b.3e.4e.5d.6b, | 1e.2b.3e.4e.5d.6c, | |
| 1e.2b.3e.4e.5d.6d, | 1e.2b.3e.4e.5d.6e, | 1e.2b.3e.4e.5d.6f, | 1e.2b.3e.4e.5e.6a, | |
| 1e.2b.3e.4e.5e.6b, | 1e.2b.3e.4e.5e.6c, | 1e.2b.3e.4e.5e.6d, | 1e.2b.3e.4e.5e.6e, | |
| 1e.2b.3e.4e.5e.6f, | 1e.2b.3e.4e.5f.6a, | 1e.2b.3e.4e.5f.6b, | 1e.2b.3e.4e.5f.6c, | 1e.2b.3e.4e.5f.6d, |
| 1e.2b.3e.4e.5f.6e, | 1e.2b.3e.4e.5f.6f, | 1e.2b.3e.4f.5a.6a, | 1e.2b.3e.4f.5a.6b, | 1e.2b.3e.4f.5a.6c, |
| 1e.2b.3e.4f.5a.6d, | 1e.2b.3e.4f.5a.6e, | 1e.2b.3e.4f.5a.6f, | 1e.2b.3e.4f.5b.6a, | 1e.2b.3e.4f.5b.6b, |
| 1e.2b.3e.4f.5b.6c, | 1e.2b.3e.4f.5b.6d, | 1e.2b.3e.4f.5b.6e, | 1e.2b.3e.4f.5b.6f, | 1e.2b.3e.4f.5c.6a, |
| 1e.2b.3e.4f.5c.6b, | 1e.2b.3e.4f.5c.6c, | 1e.2b.3e.4f.5c.6d, | 1e.2b.3e.4f.5c.6e, | 1e.2b.3e.4f.5c.6f, |

TABLE 7-continued

List of Compounds of Formula (II)

| | | | |
|---|---|---|---|
| 1e.2b.3e.4f.5d.6a, | 1e.2b.3e.4f.5d.6b, | 1e.2b.3e.4f.5d.6c, | 1e.2b.3e.4f.5d.6d, |
| 1e.2b.3e.4f.5d.6e, | 1e.2b.3e.4f.5d.6f, | 1e.2b.3e.4f.5e.6a, | 1e.2b.3e.4f.5e.6b, | 1e.2b.3e.4f.5e.6c, |
| 1e.2b.3e.4f.5e.6d, | 1e.2b.3e.4f.5e.6e, | 1e.2b.3e.4f.5e.6f, | 1e.2b.3e.4f.5f.6a, | 1e.2b.3e.4f.5f.6b, |
| 1e.2b.3e.4f.5f.6c, | 1e.2b.3e.4f.5f.6d, | 1e.2b.3e.4f.5f.6e, | 1e.2b.3e.4f.5f.6f, | 1e.2b.3f.4a.5a.6a, |
| 1e.2b.3f.4a.5a.6b, | 1e.2b.3f.4a.5a.6c, | 1e.2b.3f.4a.5a.6d, | 1e.2b.3f.4a.5a.6e, | 1e.2b.3f.4a.5a.6f, |
| 1e.2b.3f.4a.5b.6a, | 1e.2b.3f.4a.5b.6b, | 1e.2b.3f.4a.5b.6c, | 1e.2b.3f.4a.5b.6d, |
| 1e.2b.3f.4a.5b.6e, | 1e.2b.3f.4a.5b.6f, | 1e.2b.3f.4a.5c.6a, | 1e.2b.3f.4a.5c.6b, | 1e.2b.3f.4a.5c.6c, |
| 1e.2b.3f.4a.5c.6d, | 1e.2b.3f.4a.5c.6e, | 1e.2b.3f.4a.5c.6f, | 1e.2b.3f.4a.5d.6a, | 1e.2b.3f.4a.5d.6b, |
| 1e.2b.3f.4a.5d.6c, | 1e.2b.3f.4a.5d.6d, | 1e.2b.3f.4a.5d.6e, | 1e.2b.3f.4a.5d.6f, |
| 1e.2b.3f.4a.5e.6a, | 1e.2b.3f.4a.5e.6b, | 1e.2b.3f.4a.5e.6c, | 1e.2b.3f.4a.5e.6d, | 1e.2b.3f.4a.5e.6e, |
| 1e.2b.3f.4a.5e.6f, | 1e.2b.3f.4a.5f.6a, | 1e.2b.3f.4a.5f.6b, | 1e.2b.3f.4a.5f.6c, | 1e.2b.3f.4a.5f.6d, |
| 1e.2b.3f.4a.5f.6e, | 1e.2b.3f.4a.5f.6f, | 1e.2b.3f.4b.5a.6a, | 1e.2b.3f.4b.5a.6b, | 1e.2b.3f.4b.5a.6c, |
| 1e.2b.3f.4b.5a.6d, | 1e.2b.3f.4b.5a.6e, | 1e.2b.3f.4b.5a.6f, | 1e.2b.3f.4b.5b.6a, |
| 1e.2b.3f.4b.5b.6b, | 1e.2b.3f.4b.5b.6c, | 1e.2b.3f.4b.5b.6d, | 1e.2b.3f.4b.5b.6e, |
| 1e.2b.3f.4b.5b.6f, | 1e.2b.3f.4b.5c.6a, | 1e.2b.3f.4b.5c.6b, | 1e.2b.3f.4b.5c.6c, | 1e.2b.3f.4b.5c.6d, |
| 1e.2b.3f.4b.5c.6e, | 1e.2b.3f.4b.5c.6f, | 1e.2b.3f.4b.5d.6a, | 1e.2b.3f.4b.5d.6b, |
| 1e.2b.3f.4b.5d.6c, | 1e.2b.3f.4b.5d.6d, | 1e.2b.3f.4b.5d.6e, | 1e.2b.3f.4b.5d.6f, |
| 1e.2b.3f.4b.5e.6a, | 1e.2b.3f.4b.5e.6b, | 1e.2b.3f.4b.5e.6c, | 1e.2b.3f.4b.5e.6d, |
| 1e.2b.3f.4b.5e.6e, | 1e.2b.3f.4b.5e.6f, | 1e.2b.3f.4b.5f.6a, | 1e.2b.3f.4b.5f.6b, | 1e.2b.3f.4b.5f.6c, |
| 1e.2b.3f.4b.5f.6d, | 1e.2b.3f.4b.5f.6e, | 1e.2b.3f.4b.5f.6f, | 1e.2b.3f.4c.5a.6a, | 1e.2b.3f.4c.5a.6b, |
| 1e.2b.3f.4c.5a.6c, | 1e.2b.3f.4c.5a.6d, | 1e.2b.3f.4c.5a.6e, | 1e.2b.3f.4c.5a.6f, | 1e.2b.3f.4c.5b.6a, |
| 1e.2b.3f.4c.5b.6b, | 1e.2b.3f.4c.5b.6c, | 1e.2b.3f.4c.5b.6d, | 1e.2b.3f.4c.5b.6e, | 1e.2b.3f.4c.5b.6f, |
| 1e.2b.3f.4c.5c.6a, | 1e.2b.3f.4c.5c.6b, | 1e.2b.3f.4c.5c.6c, | 1e.2b.3f.4c.5c.6d, | 1e.2b.3f.4c.5c.6e, |
| 1e.2b.3f.4c.5c.6f, | 1e.2b.3f.4c.5d.6a, | 1e.2b.3f.4c.5d.6b, | 1e.2b.3f.4c.5d.6c, |
| 1e.2b.3f.4c.5d.6d, | 1e.2b.3f.4c.5d.6e, | 1e.2b.3f.4c.5d.6f, | 1e.2b.3f.4c.5e.6a, | 1e.2b.3f.4c.5e.6b, |
| 1e.2b.3f.4c.5e.6c, | 1e.2b.3f.4c.5e.6d, | 1e.2b.3f.4c.5e.6e, | 1e.2b.3f.4c.5e.6f, | 1e.2b.3f.4c.5f.6a, |
| 1e.2b.3f.4c.5f.6b, | 1e.2b.3f.4c.5f.6c, | 1e.2b.3f.4c.5f.6d, | 1e.2b.3f.4c.5f.6e, | 1e.2b.3f.4c.5f.6f, |
| 1e.2b.3f.4d.5a.6a, | 1e.2b.3f.4d.5a.6b, | 1e.2b.3f.4d.5a.6c, | 1e.2b.3f.4d.5a.6d, |
| 1e.2b.3f.4d.5a.6e, | 1e.2b.3f.4d.5a.6f, | 1e.2b.3f.4d.5b.6a, | 1e.2b.3f.4d.5b.6b, |
| 1e.2b.3f.4d.5b.6c, | 1e.2b.3f.4d.5b.6d, | 1e.2b.3f.4d.5b.6e, | 1e.2b.3f.4d.5b.6f, |
| 1e.2b.3f.4d.5c.6a, | 1e.2b.3f.4d.5c.6b, | 1e.2b.3f.4d.5c.6c, | 1e.2b.3f.4d.5c.6d, |
| 1e.2b.3f.4d.5c.6e, | 1e.2b.3f.4d.5c.6f, | 1e.2b.3f.4d.5d.6a, | 1e.2b.3f.4d.5d.6b, |
| 1e.2b.3f.4d.5d.6c, | 1e.2b.3f.4d.5d.6d, | 1e.2b.3f.4d.5d.6e, | 1e.2b.3f.4d.5d.6f, |
| 1e.2b.3f.4d.5e.6a, | 1e.2b.3f.4d.5e.6b, | 1e.2b.3f.4d.5e.6c, | 1e.2b.3f.4d.5e.6d, |
| 1e.2b.3f.4d.5e.6e, | 1e.2b.3f.4d.5e.6f, | 1e.2b.3f.4d.5f.6a, | 1e.2b.3f.4d.5f.6b, | 1e.2b.3f.4d.5f.6c, |
| 1e.2b.3f.4d.5f.6d, | 1e.2b.3f.4d.5f.6e, | 1e.2b.3f.4d.5f.6f, | 1e.2b.3f.4e.5a.6a, | 1e.2b.3f.4e.5a.6b, |
| 1e.2b.3f.4e.5a.6c, | 1e.2b.3f.4e.5a.6d, | 1e.2b.3f.4e.5a.6e, | 1e.2b.3f.4e.5a.6f, | 1e.2b.3f.4e.5b.6a, |
| 1e.2b.3f.4e.5b.6b, | 1e.2b.3f.4e.5b.6c, | 1e.2b.3f.4e.5b.6d, | 1e.2b.3f.4e.5b.6e, |
| 1e.2b.3f.4e.5b.6f, | 1e.2b.3f.4e.5c.6a, | 1e.2b.3f.4e.5c.6b, | 1e.2b.3f.4e.5c.6c, | 1e.2b.3f.4e.5c.6d, |
| 1e.2b.3f.4e.5c.6e, | 1e.2b.3f.4e.5c.6f, | 1e.2b.3f.4e.5d.6a, | 1e.2b.3f.4e.5d.6b, | 1e.2b.3f.4e.5d.6c, |
| 1e.2b.3f.4e.5d.6d, | 1e.2b.3f.4e.5d.6e, | 1e.2b.3f.4e.5d.6f, | 1e.2b.3f.4e.5e.6a, |
| 1e.2b.3f.4e.5e.6b, | 1e.2b.3f.4e.5e.6c, | 1e.2b.3f.4e.5e.6d, | 1e.2b.3f.4e.5e.6e, | 1e.2b.3f.4e.5e.6f, |
| 1e.2b.3f.4e.5f.6a, | 1e.2b.3f.4e.5f.6b, | 1e.2b.3f.4e.5f.6c, | 1e.2b.3f.4e.5f.6d, | 1e.2b.3f.4e.5f.6e, |
| 1e.2b.3f.4e.5f.6f, | 1e.2b.3f.4f.5a.6a, | 1e.2b.3f.4f.5a.6b, | 1e.2b.3f.4f.5a.6c, | 1e.2b.3f.4f.5a.6d, |
| 1e.2b.3f.4f.5a.6e, | 1e.2b.3f.4f.5a.6f, | 1e.2b.3f.4f.5b.6a, | 1e.2b.3f.4f.5b.6b, | 1e.2b.3f.4f.5b.6c, |
| 1e.2b.3f.4f.5b.6d, | 1e.2b.3f.4f.5b.6e, | 1e.2b.3f.4f.5b.6f, | 1e.2b.3f.4f.5c.6a, | 1e.2b.3f.4f.5c.6b, |
| 1e.2b.3f.4f.5c.6c, | 1e.2b.3f.4f.5c.6d, | 1e.2b.3f.4f.5c.6e, | 1e.2b.3f.4f.5c.6f, | 1e.2b.3f.4f.5d.6a, |
| 1e.2b.3f.4f.5d.6b, | 1e.2b.3f.4f.5d.6c, | 1e.2b.3f.4f.5d.6d, | 1e.2b.3f.4f.5d.6e, | 1e.2b.3f.4f.5d.6f, |
| 1e.2b.3f.4f.5e.6a, | 1e.2b.3f.4f.5e.6b, | 1e.2b.3f.4f.5e.6c, | 1e.2b.3f.4f.5e.6d, | 1e.2b.3f.4f.5e.6e, |
| 1e.2b.3f.4f.5e.6f, | 1e.2b.3f.4f.5f.6a, | 1e.2b.3f.4f.5f.6b, | 1e.2b.3f.4f.5f.6c, | 1e.2b.3f.4f.5f.6d, |
| 1e.2b.3f.4f.5f.6e, | 1e.2b.3f.4f.5f.6f, | 1e.2c.3a.4a.5a.6a, | 1e.2c.3a.4a.5a.6b, | 1e.2c.3a.4a.5a.6c, |
| 1e.2c.3a.4a.5a.6d, | 1e.2c.3a.4a.5a.6e, | 1e.2c.3a.4a.5a.6f, | 1e.2c.3a.4a.5b.6a, |
| 1e.2c.3a.4a.5b.6b, | 1e.2c.3a.4a.5b.6c, | 1e.2c.3a.4a.5b.6d, | 1e.2c.3a.4a.5b.6e, |
| 1e.2c.3a.4a.5b.6f, | 1e.2c.3a.4a.5c.6a, | 1e.2c.3a.4a.5c.6b, | 1e.2c.3a.4a.5c.6c, |
| 1e.2c.3a.4a.5c.6d, | 1e.2c.3a.4a.5c.6e, | 1e.2c.3a.4a.5c.6f, | 1e.2c.3a.4a.5d.6a, |
| 1e.2c.3a.4a.5d.6b, | 1e.2c.3a.4a.5d.6c, | 1e.2c.3a.4a.5d.6d, | 1e.2c.3a.4a.5d.6e, |
| 1e.2c.3a.4a.5d.6f, | 1e.2c.3a.4a.5e.6a, | 1e.2c.3a.4a.5e.6b, | 1e.2c.3a.4a.5e.6c, |
| 1e.2c.3a.4a.5e.6d, | 1e.2c.3a.4a.5e.6e, | 1e.2c.3a.4a.5e.6f, | 1e.2c.3a.4a.5f.6a, | 1e.2c.3a.4a.5f.6b, |
| 1e.2c.3a.4a.5f.6c, | 1e.2c.3a.4a.5f.6d, | 1e.2c.3a.4a.5f.6e, | 1e.2c.3a.4a.5f.6f, | 1e.2c.3a.4b.5a.6a, |
| 1e.2c.3a.4b.5a.6b, | 1e.2c.3a.4b.5a.6c, | 1e.2c.3a.4b.5a.6d, | 1e.2c.3a.4b.5a.6e, |
| 1e.2c.3a.4b.5a.6f, | 1e.2c.3a.4b.5b.6a, | 1e.2c.3a.4b.5b.6b, | 1e.2c.3a.4b.5b.6c, |
| 1e.2c.3a.4b.5b.6d, | 1e.2c.3a.4b.5b.6e, | 1e.2c.3a.4b.5b.6f, | 1e.2c.3a.4b.5c.6a, |
| 1e.2c.3a.4b.5c.6b, | 1e.2c.3a.4b.5c.6c, | 1e.2c.3a.4b.5c.6d, | 1e.2c.3a.4b.5c.6e, |
| 1e.2c.3a.4b.5c.6f, | 1e.2c.3a.4b.5d.6a, | 1e.2c.3a.4b.5d.6b, | 1e.2c.3a.4b.5d.6c, |
| 1e.2c.3a.4b.5d.6d, | 1e.2c.3a.4b.5d.6e, | 1e.2c.3a.4b.5d.6f, | 1e.2c.3a.4b.5e.6a, |
| 1e.2c.3a.4b.5e.6b, | 1e.2c.3a.4b.5e.6c, | 1e.2c.3a.4b.5e.6d, | 1e.2c.3a.4b.5e.6e, |
| 1e.2c.3a.4b.5e.6f, | 1e.2c.3a.4b.5f.6a, | 1e.2c.3a.4b.5f.6b, | 1e.2c.3a.4b.5f.6c, | 1e.2c.3a.4b.5f.6d, |
| 1e.2c.3a.4b.5f.6e, | 1e.2c.3a.4b.5f.6f, | 1e.2c.3a.4c.5a.6a, | 1e.2c.3a.4c.5a.6b, | 1e.2c.3a.4c.5a.6c, |
| 1e.2c.3a.4c.5a.6d, | 1e.2c.3a.4c.5a.6e, | 1e.2c.3a.4c.5a.6f, | 1e.2c.3a.4c.5b.6a, |
| 1e.2c.3a.4c.5b.6b, | 1e.2c.3a.4c.5b.6c, | 1e.2c.3a.4c.5b.6d, | 1e.2c.3a.4c.5b.6e, |
| 1e.2c.3a.4c.5b.6f, | 1e.2c.3a.4c.5c.6a, | 1e.2c.3a.4c.5c.6b, | 1e.2c.3a.4c.5c.6c, | 1e.2c.3a.4c.5c.6d, |
| 1e.2c.3a.4c.5c.6e, | 1e.2c.3a.4c.5c.6f, | 1e.2c.3a.4c.5d.6a, | 1e.2c.3a.4c.5d.6b, | 1e.2c.3a.4c.5d.6c, |
| 1e.2c.3a.4c.5d.6d, | 1e.2c.3a.4c.5d.6e, | 1e.2c.3a.4c.5d.6f, | 1e.2c.3a.4c.5e.6a, |
| 1e.2c.3a.4c.5e.6b, | 1e.2c.3a.4c.5e.6c, | 1e.2c.3a.4c.5e.6d, | 1e.2c.3a.4c.5e.6e, | 1e.2c.3a.4c.5e.6f, |
| 1e.2c.3a.4c.5f.6a, | 1e.2c.3a.4c.5f.6b, | 1e.2c.3a.4c.5f.6c, | 1e.2c.3a.4c.5f.6d, | 1e.2c.3a.4c.5f.6e, |
| 1e.2c.3a.4c.5f.6f, | 1e.2c.3a.4d.5a.6a, | 1e.2c.3a.4d.5a.6b, | 1e.2c.3a.4d.5a.6c, |
| 1e.2c.3a.4d.5a.6d, | 1e.2c.3a.4d.5a.6e, | 1e.2c.3a.4d.5a.6f, | 1e.2c.3a.4d.5b.6a, |
| 1e.2c.3a.4d.5b.6b, | 1e.2c.3a.4d.5b.6c, | 1e.2c.3a.4d.5b.6d, | 1e.2c.3a.4d.5b.6e, |

TABLE 7-continued

List of Compounds of Formula (II)

| | | | | |
|---|---|---|---|---|
| 1e.2c.3a.4d.5b.6f, | 1e.2c.3a.4d.5c.6a, | 1e.2c.3a.4d.5c.6b, | 1e.2c.3a.4d.5c.6c, | |
| 1e.2c.3a.4d.5c.6d, | 1e.2c.3a.4d.5c.6e, | 1e.2c.3a.4d.5c.6f, | 1e.2c.3a.4d.5d.6a, | |
| 1e.2c.3a.4d.5d.6b, | 1e.2c.3a.4d.5d.6c, | 1e.2c.3a.4d.5d.6d, | 1e.2c.3a.4d.5d.6e, | |
| 1e.2c.3a.4d.5d.6f, | 1e.2c.3a.4d.5e.6a, | 1e.2c.3a.4d.5e.6b, | 1e.2c.3a.4d.5e.6c, | |
| 1e.2c.3a.4d.5e.6d, | 1e.2c.3a.4d.5e.6e, | 1e.2c.3a.4d.5e.6f, | 1e.2c.3a.4d.5f.6a, | |
| 1e.2c.3a.4d.5f.6b, | 1e.2c.3a.4d.5f.6c, | 1e.2c.3a.4d.5f.6d, | 1e.2c.3a.4d.5f.6e, | 1e.2c.3a.4d.5f.6f, |
| 1e.2c.3a.4e.5a.6a, | 1e.2c.3a.4e.5a.6b, | 1e.2c.3a.4e.5a.6c, | 1e.2c.3a.4e.5a.6d, | |
| 1e.2c.3a.4e.5a.6e, | 1e.2c.3a.4e.5a.6f, | 1e.2c.3a.4e.5b.6a, | 1e.2c.3a.4e.5b.6b, | |
| 1e.2c.3a.4e.5b.6c, | 1e.2c.3a.4e.5b.6d, | 1e.2c.3a.4e.5b.6e, | 1e.2c.3a.4e.5b.6f, | |
| 1e.2c.3a.4e.5c.6a, | 1e.2c.3a.4e.5c.6b, | 1e.2c.3a.4e.5c.6c, | 1e.2c.3a.4e.5c.6d, | 1e.2c.3a.4e.5c.6e, |
| 1e.2c.3a.4e.5c.6f, | 1e.2c.3a.4e.5d.6a, | 1e.2c.3a.4e.5d.6b, | 1e.2c.3a.4e.5d.6c, | |
| 1e.2c.3a.4e.5d.6d, | 1e.2c.3a.4e.5d.6e, | 1e.2c.3a.4e.5d.6f, | 1e.2c.3a.4e.5e.6a, | |
| 1e.2c.3a.4e.5e.6b, | 1e.2c.3a.4e.5e.6c, | 1e.2c.3a.4e.5e.6d, | 1e.2c.3a.4e.5e.6e, | 1e.2c.3a.4e.5e.6f, |
| 1e.2c.3a.4e.5f.6a, | 1e.2c.3a.4e.5f.6b, | 1e.2c.3a.4e.5f.6c, | 1e.2c.3a.4e.5f.6d, | 1e.2c.3a.4e.5f.6e, |
| 1e.2c.3a.4e.5f.6f, | 1e.2c.3a.4f.5a.6a, | 1e.2c.3a.4f.5a.6b, | 1e.2c.3a.4f.5a.6c, | 1e.2c.3a.4f.5a.6d, |
| 1e.2c.3a.4f.5a.6e, | 1e.2c.3a.4f.5a.6f, | 1e.2c.3a.4f.5b.6a, | 1e.2c.3a.4f.5b.6b, | 1e.2c.3a.4f.5b.6c, |
| 1e.2c.3a.4f.5b.6d, | 1e.2c.3a.4f.5b.6e, | 1e.2c.3a.4f.5b.6f, | 1e.2c.3a.4f.5c.6a, | 1e.2c.3a.4f.5c.6b, |
| 1e.2c.3a.4f.5c.6c, | 1e.2c.3a.4f.5c.6d, | 1e.2c.3a.4f.5c.6e, | 1e.2c.3a.4f.5c.6f, | 1e.2c.3a.4f.5d.6a, |
| 1e.2c.3a.4f.5d.6b, | 1e.2c.3a.4f.5d.6c, | 1e.2c.3a.4f.5d.6d, | 1e.2c.3a.4f.5d.6e, | 1e.2c.3a.4f.5d.6f, |
| 1e.2c.3a.4f.5e.6a, | 1e.2c.3a.4f.5e.6b, | 1e.2c.3a.4f.5e.6c, | 1e.2c.3a.4f.5e.6d, | 1e.2c.3a.4f.5e.6e, |
| 1e.2c.3a.4f.5e.6f, | 1e.2c.3a.4f.5f.6a, | 1e.2c.3a.4f.5f.6b, | 1e.2c.3a.4f.5f.6c, | 1e.2c.3a.4f.5f.6d, |
| 1e.2c.3a.4f.5f.6e, | 1e.2c.3a.4f.5f.6f, | 1e.2c.3b.4a.5a.6a, | 1e.2c.3b.4a.5a.6b, | 1e.2c.3b.4a.5a.6c, |
| 1e.2c.3b.4a.5a.6d, | 1e.2c.3b.4a.5a.6e, | 1e.2c.3b.4a.5a.6f, | 1e.2c.3b.4a.5b.6a, | |
| 1e.2c.3b.4a.5b.6b, | 1e.2c.3b.4a.5b.6c, | 1e.2c.3b.4a.5b.6d, | 1e.2c.3b.4a.5b.6e, | |
| 1e.2c.3b.4a.5b.6f, | 1e.2c.3b.4a.5c.6a, | 1e.2c.3b.4a.5c.6b, | 1e.2c.3b.4a.5c.6c, | |
| 1e.2c.3b.4a.5c.6d, | 1e.2c.3b.4a.5c.6e, | 1e.2c.3b.4a.5c.6f, | 1e.2c.3b.4a.5d.6a, | |
| 1e.2c.3b.4a.5d.6b, | 1e.2c.3b.4a.5d.6c, | 1e.2c.3b.4a.5d.6d, | 1e.2c.3b.4a.5d.6e, | |
| 1e.2c.3b.4a.5d.6f, | 1e.2c.3b.4a.5e.6a, | 1e.2c.3b.4a.5e.6b, | 1e.2c.3b.4a.5e.6c, | |
| 1e.2c.3b.4a.5e.6d, | 1e.2c.3b.4a.5e.6e, | 1e.2c.3b.4a.5e.6f, | 1e.2c.3b.4a.5f.6a, | |
| 1e.2c.3b.4a.5f.6b, | 1e.2c.3b.4a.5f.6c, | 1e.2c.3b.4a.5f.6d, | 1e.2c.3b.4a.5f.6e, | 1e.2c.3b.4a.5f.6f, |
| 1e.2c.3b.4b.5a.6a, | 1e.2c.3b.4b.5a.6b, | 1e.2c.3b.4b.5a.6c, | 1e.2c.3b.4b.5a.6d, | |
| 1e.2c.3b.4b.5a.6e, | 1e.2c.3b.4b.5a.6f, | 1e.2c.3b.4b.5b.6a, | 1e.2c.3b.4b.5b.6b, | |
| 1e.2c.3b.4b.5b.6c, | 1e.2c.3b.4b.5b.6d, | 1e.2c.3b.4b.5b.6e, | 1e.2c.3b.4b.5b.6f, | |
| 1e.2c.3b.4b.5c.6a, | 1e.2c.3b.4b.5c.6b, | 1e.2c.3b.4b.5c.6c, | 1e.2c.3b.4b.5c.6d, | |
| 1e.2c.3b.4b.5c.6e, | 1e.2c.3b.4b.5c.6f, | 1e.2c.3b.4b.5d.6a, | 1e.2c.3b.4b.5d.6b, | |
| 1e.2c.3b.4b.5d.6c, | 1e.2c.3b.4b.5d.6d, | 1e.2c.3b.4b.5d.6e, | 1e.2c.3b.4b.5d.6f, | |
| 1e.2c.3b.4b.5e.6a, | 1e.2c.3b.4b.5e.6b, | 1e.2c.3b.4b.5e.6c, | 1e.2c.3b.4b.5e.6d, | |
| 1e.2c.3b.4b.5e.6e, | 1e.2c.3b.4b.5e.6f, | 1e.2c.3b.4b.5f.6a, | 1e.2c.3b.4b.5f.6b, | |
| 1e.2c.3b.4b.5f.6c, | 1e.2c.3b.4b.5f.6d, | 1e.2c.3b.4b.5f.6e, | 1e.2c.3b.4b.5f.6f, | 1e.2c.3b.4c.5a.6a, |
| 1e.2c.3b.4c.5a.6b, | 1e.2c.3b.4c.5a.6c, | 1e.2c.3b.4c.5a.6d, | 1e.2c.3b.4c.5a.6e, | |
| 1e.2c.3b.4c.5a.6f, | 1e.2c.3b.4c.5b.6a, | 1e.2c.3b.4c.5b.6b, | 1e.2c.3b.4c.5b.6c, | |
| 1e.2c.3b.4c.5b.6d, | 1e.2c.3b.4c.5b.6e, | 1e.2c.3b.4c.5b.6f, | 1e.2c.3b.4c.5c.6a, | |
| 1e.2c.3b.4c.5c.6b, | 1e.2c.3b.4c.5c.6c, | 1e.2c.3b.4c.5c.6d, | 1e.2c.3b.4c.5c.6e, | 1e.2c.3b.4c.5c.6f, |
| 1e.2c.3b.4c.5d.6a, | 1e.2c.3b.4c.5d.6b, | 1e.2c.3b.4c.5d.6c, | 1e.2c.3b.4c.5d.6d, | |
| 1e.2c.3b.4c.5d.6e, | 1e.2c.3b.4c.5d.6f, | 1e.2c.3b.4c.5e.6a, | 1e.2c.3b.4c.5e.6b, | |
| 1e.2c.3b.4c.5e.6c, | 1e.2c.3b.4c.5e.6d, | 1e.2c.3b.4c.5e.6e, | 1e.2c.3b.4c.5e.6f, | 1e.2c.3b.4c.5f.6a, |
| 1e.2c.3b.4c.5f.6b, | 1e.2c.3b.4c.5f.6c, | 1e.2c.3b.4c.5f.6d, | 1e.2c.3b.4c.5f.6e, | 1e.2c.3b.4c.5f.6f, |
| 1e.2c.3b.4d.5a.6a, | 1e.2c.3b.4d.5a.6b, | 1e.2c.3b.4d.5a.6c, | 1e.2c.3b.4d.5a.6d, | |
| 1e.2c.3b.4d.5a.6e, | 1e.2c.3b.4d.5a.6f, | 1e.2c.3b.4d.5b.6a, | 1e.2c.3b.4d.5b.6b, | |
| 1e.2c.3b.4d.5b.6c, | 1e.2c.3b.4d.5b.6d, | 1e.2c.3b.4d.5b.6e, | 1e.2c.3b.4d.5b.6f, | |
| 1e.2c.3b.4d.5c.6a, | 1e.2c.3b.4d.5c.6b, | 1e.2c.3b.4d.5c.6c, | 1e.2c.3b.4d.5c.6d, | |
| 1e.2c.3b.4d.5c.6e, | 1e.2c.3b.4d.5c.6f, | 1e.2c.3b.4d.5d.6a, | 1e.2c.3b.4d.5d.6b, | |
| 1e.2c.3b.4d.5d.6c, | 1e.2c.3b.4d.5d.6d, | 1e.2c.3b.4d.5d.6e, | 1e.2c.3b.4d.5d.6f, | |
| 1e.2c.3b.4d.5e.6a, | 1e.2c.3b.4d.5e.6b, | 1e.2c.3b.4d.5e.6c, | 1e.2c.3b.4d.5e.6d, | |
| 1e.2c.3b.4d.5e.6e, | 1e.2c.3b.4d.5e.6f, | 1e.2c.3b.4d.5f.6a, | 1e.2c.3b.4d.5f.6b, | |
| 1e.2c.3b.4d.5f.6c, | 1e.2c.3b.4d.5f.6d, | 1e.2c.3b.4d.5f.6e, | 1e.2c.3b.4d.5f.6f, | |
| 1e.2c.3b.4e.5a.6a, | 1e.2c.3b.4e.5a.6b, | 1e.2c.3b.4e.5a.6c, | 1e.2c.3b.4e.5a.6d, | |
| 1e.2c.3b.4e.5a.6e, | 1e.2c.3b.4e.5a.6f, | 1e.2c.3b.4e.5b.6a, | 1e.2c.3b.4e.5b.6b, | |
| 1e.2c.3b.4e.5b.6c, | 1e.2c.3b.4e.5b.6d, | 1e.2c.3b.4e.5b.6e, | 1e.2c.3b.4e.5b.6f, | |
| 1e.2c.3b.4e.5c.6a, | 1e.2c.3b.4e.5c.6b, | 1e.2c.3b.4e.5c.6c, | 1e.2c.3b.4e.5c.6d, | |
| 1e.2c.3b.4e.5c.6e, | 1e.2c.3b.4e.5c.6f, | 1e.2c.3b.4e.5d.6a, | 1e.2c.3b.4e.5d.6b, | |
| 1e.2c.3b.4e.5d.6c, | 1e.2c.3b.4e.5d.6d, | 1e.2c.3b.4e.5d.6e, | 1e.2c.3b.4e.5d.6f, | |
| 1e.2c.3b.4e.5e.6a, | 1e.2c.3b.4e.5e.6b, | 1e.2c.3b.4e.5e.6c, | 1e.2c.3b.4e.5e.6d, | |
| 1e.2c.3b.4e.5e.6e, | 1e.2c.3b.4e.5e.6f, | 1e.2c.3b.4e.5f.6a, | 1e.2c.3b.4e.5f.6b, | 1e.2c.3b.4e.5f.6c, |
| 1e.2c.3b.4e.5f.6d, | 1e.2c.3b.4e.5f.6e, | 1e.2c.3b.4e.5f.6f, | 1e.2c.3b.4f.5a.6a, | 1e.2c.3b.4f.5a.6b, |
| 1e.2c.3b.4f.5a.6c, | 1e.2c.3b.4f.5a.6d, | 1e.2c.3b.4f.5a.6e, | 1e.2c.3b.4f.5a.6f, | 1e.2c.3b.4f.5b.6a, |
| 1e.2c.3b.4f.5b.6b, | 1e.2c.3b.4f.5b.6c, | 1e.2c.3b.4f.5b.6d, | 1e.2c.3b.4f.5b.6e, | 1e.2c.3b.4f.5b.6f, |
| 1e.2c.3b.4f.5c.6a, | 1e.2c.3b.4f.5c.6b, | 1e.2c.3b.4f.5c.6c, | 1e.2c.3b.4f.5c.6d, | 1e.2c.3b.4f.5c.6e, |
| 1e.2c.3b.4f.5c.6f, | 1e.2c.3b.4f.5d.6a, | 1e.2c.3b.4f.5d.6b, | 1e.2c.3b.4f.5d.6c, | |
| 1e.2c.3b.4f.5d.6d, | 1e.2c.3b.4f.5d.6e, | 1e.2c.3b.4f.5d.6f, | 1e.2c.3b.4f.5e.6a, | 1e.2c.3b.4f.5e.6b, |
| 1e.2c.3b.4f.5e.6c, | 1e.2c.3b.4f.5e.6d, | 1e.2c.3b.4f.5e.6e, | 1e.2c.3b.4f.5e.6f, | 1e.2c.3b.4f.5f.6a, |
| 1e.2c.3b.4f.5f.6b, | 1e.2c.3b.4f.5f.6c, | 1e.2c.3b.4f.5f.6d, | 1e.2c.3b.4f.5f.6e, | 1e.2c.3b.4f.5f.6f, |
| 1e.2c.3c.4a.5a.6a, | 1e.2c.3c.4a.5a.6b, | 1e.2c.3c.4a.5a.6c, | 1e.2c.3c.4a.5a.6d, | |
| 1e.2c.3c.4a.5a.6e, | 1e.2c.3c.4a.5a.6f, | 1e.2c.3c.4a.5b.6a, | 1e.2c.3c.4a.5b.6b, | 1e.2c.3c.4a.5b.6c, |
| 1e.2c.3c.4a.5b.6d, | 1e.2c.3c.4a.5b.6e, | 1e.2c.3c.4a.5b.6f, | 1e.2c.3c.4a.5c.6a, | 1e.2c.3c.4a.5c.6b, |
| 1e.2c.3c.4a.5c.6c, | 1e.2c.3c.4a.5c.6d, | 1e.2c.3c.4a.5c.6e, | 1e.2c.3c.4a.5c.6f, | 1e.2c.3c.4a.5d.6a, |
| 1e.2c.3c.4a.5d.6b, | 1e.2c.3c.4a.5d.6c, | 1e.2c.3c.4a.5d.6d, | 1e.2c.3c.4a.5d.6e, | |
| 1e.2c.3c.4a.5d.6f, | 1e.2c.3c.4a.5e.6a, | 1e.2c.3c.4a.5e.6b, | 1e.2c.3c.4a.5e.6c, | 1e.2c.3c.4a.5e.6d, |

TABLE 7-continued

List of Compounds of Formula (II)

| | | | |
|---|---|---|---|
| 1e.2c.3c.4a.5e.6e, | 1e.2c.3c.4a.5e.6f, | 1e.2c.3c.4a.5f.6a, | 1e.2c.3c.4a.5f.6b, | 1e.2c.3c.4a.5f.6c, |
| 1e.2c.3c.4a.5f.6d, | 1e.2c.3c.4a.5f.6e, | 1e.2c.3c.4a.5f.6f, | 1e.2c.3c.4b.5a.6a, | 1e.2c.3c.4b.5a.6b, |
| 1e.2c.3c.4b.5a.6c, | 1e.2c.3c.4b.5a.6d, | 1e.2c.3c.4b.5a.6e, | 1e.2c.3c.4b.5a.6f, |
| 1e.2c.3c.4b.5b.6a, | 1e.2c.3c.4b.5b.6b, | 1e.2c.3c.4b.5b.6c, | 1e.2c.3c.4b.5b.6d, |
| 1e.2c.3c.4b.5b.6e, | 1e.2c.3c.4b.5b.6f, | 1e.2c.3c.4b.5c.6a, | 1e.2c.3c.4b.5c.6b, | 1e.2c.3c.4b.5c.6c, |
| 1e.2c.3c.4b.5c.6d, | 1e.2c.3c.4b.5c.6e, | 1e.2c.3c.4b.5c.6f, | 1e.2c.3c.4b.5d.6a, |
| 1e.2c.3c.4b.5d.6b, | 1e.2c.3c.4b.5d.6c, | 1e.2c.3c.4b.5d.6d, | 1e.2c.3c.4b.5d.6e, |
| 1e.2c.3c.4b.5d.6f, | 1e.2c.3c.4b.5e.6a, | 1e.2c.3c.4b.5e.6b, | 1e.2c.3c.4b.5e.6c, |
| 1e.2c.3c.4b.5e.6d, | 1e.2c.3c.4b.5e.6e, | 1e.2c.3c.4b.5e.6f, | 1e.2c.3c.4b.5f.6a, | 1e.2c.3c.4b.5f.6b, |
| 1e.2c.3c.4b.5f.6c, | 1e.2c.3c.4b.5f.6d, | 1e.2c.3c.4b.5f.6e, | 1e.2c.3c.4b.5f.6f, | 1e.2c.3c.4c.5a.6a, |
| 1e.2c.3c.4c.5a.6b, | 1e.2c.3c.4c.5a.6c, | 1e.2c.3c.4c.5a.6d, | 1e.2c.3c.4c.5a.6e, | 1e.2c.3c.4c.5a.6f, |
| 1e.2c.3c.4c.5b.6a, | 1e.2c.3c.4c.5b.6b, | 1e.2c.3c.4c.5b.6c, | 1e.2c.3c.4c.5b.6d, |
| 1e.2c.3c.4c.5b.6e, | 1e.2c.3c.4c.5b.6f, | 1e.2c.3c.4c.5c.6a, | 1e.2c.3c.4c.5c.6b, | 1e.2c.3c.4c.5c.6c, |
| 1e.2c.3c.4c.5c.6d, | 1e.2c.3c.4c.5c.6e, | 1e.2c.3c.4c.5c.6f, | 1e.2c.3c.4c.5d.6a, | 1e.2c.3c.4c.5d.6b, |
| 1e.2c.3c.4c.5d.6c, | 1e.2c.3c.4c.5d.6d, | 1e.2c.3c.4c.5d.6e, | 1e.2c.3c.4c.5d.6f, | 1e.2c.3c.4c.5e.6a, |
| 1e.2c.3c.4c.5e.6b, | 1e.2c.3c.4c.5e.6c, | 1e.2c.3c.4c.5e.6d, | 1e.2c.3c.4c.5e.6e, | 1e.2c.3c.4c.5e.6f, |
| 1e.2c.3c.4c.5f.6a, | 1e.2c.3c.4c.5f.6b, | 1e.2c.3c.4c.5f.6c, | 1e.2c.3c.4c.5f.6d, | 1e.2c.3c.4c.5f.6e, |
| 1e.2c.3c.4c.5f.6f, | 1e.2c.3c.4d.5a.6a, | 1e.2c.3c.4d.5a.6b, | 1e.2c.3c.4d.5a.6c, |
| 1e.2c.3c.4d.5a.6d, | 1e.2c.3c.4d.5a.6e, | 1e.2c.3c.4d.5a.6f, | 1e.2c.3c.4d.5b.6a, |
| 1e.2c.3c.4d.5b.6b, | 1e.2c.3c.4d.5b.6c, | 1e.2c.3c.4d.5b.6d, | 1e.2c.3c.4d.5b.6e, |
| 1e.2c.3c.4d.5b.6f, | 1e.2c.3c.4d.5c.6a, | 1e.2c.3c.4d.5c.6b, | 1e.2c.3c.4d.5c.6c, |
| 1e.2c.3c.4d.5c.6d, | 1e.2c.3c.4d.5c.6e, | 1e.2c.3c.4d.5c.6f, | 1e.2c.3c.4d.5d.6a, |
| 1e.2c.3c.4d.5d.6b, | 1e.2c.3c.4d.5d.6c, | 1e.2c.3c.4d.5d.6d, | 1e.2c.3c.4d.5d.6e, |
| 1e.2c.3c.4d.5d.6f, | 1e.2c.3c.4d.5e.6a, | 1e.2c.3c.4d.5e.6b, | 1e.2c.3c.4d.5e.6c, |
| 1e.2c.3c.4d.5e.6d, | 1e.2c.3c.4d.5e.6e, | 1e.2c.3c.4d.5e.6f, | 1e.2c.3c.4d.5f.6a, |
| 1e.2c.3c.4d.5f.6b, | 1e.2c.3c.4d.5f.6c, | 1e.2c.3c.4d.5f.6d, | 1e.2c.3c.4d.5f.6e, | 1e.2c.3c.4d.5f.6f, |
| 1e.2c.3c.4e.5a.6a, | 1e.2c.3c.4e.5a.6b, | 1e.2c.3c.4e.5a.6c, | 1e.2c.3c.4e.5a.6d, | 1e.2c.3c.4e.5a.6e, |
| 1e.2c.3c.4e.5a.6f, | 1e.2c.3c.4e.5b.6a, | 1e.2c.3c.4e.5b.6b, | 1e.2c.3c.4e.5b.6c, |
| 1e.2c.3c.4e.5b.6d, | 1e.2c.3c.4e.5b.6e, | 1e.2c.3c.4e.5b.6f, | 1e.2c.3c.4e.5c.6a, | 1e.2c.3c.4e.5c.6b, |
| 1e.2c.3c.4e.5c.6c, | 1e.2c.3c.4e.5c.6d, | 1e.2c.3c.4e.5c.6e, | 1e.2c.3c.4e.5c.6f, | 1e.2c.3c.4e.5d.6a, |
| 1e.2c.3c.4e.5d.6b, | 1e.2c.3c.4e.5d.6c, | 1e.2c.3c.4e.5d.6d, | 1e.2c.3c.4e.5d.6e, |
| 1e.2c.3c.4e.5d.6f, | 1e.2c.3c.4e.5e.6a, | 1e.2c.3c.4e.5e.6b, | 1e.2c.3c.4e.5e.6c, | 1e.2c.3c.4e.5e.6d, |
| 1e.2c.3c.4e.5e.6e, | 1e.2c.3c.4e.5e.6f, | 1e.2c.3c.4e.5f.6a, | 1e.2c.3c.4e.5f.6b, | 1e.2c.3c.4e.5f.6c, |
| 1e.2c.3c.4e.5f.6d, | 1e.2c.3c.4e.5f.6e, | 1e.2c.3c.4e.5f.6f, | 1e.2c.3c.4f.5a.6a, | 1e.2c.3c.4f.5a.6b, |
| 1e.2c.3c.4f.5a.6c, | 1e.2c.3c.4f.5a.6d, | 1e.2c.3c.4f.5a.6e, | 1e.2c.3c.4f.5a.6f, | 1e.2c.3c.4f.5b.6a, |
| 1e.2c.3c.4f.5b.6b, | 1e.2c.3c.4f.5b.6c, | 1e.2c.3c.4f.5b.6d, | 1e.2c.3c.4f.5b.6e, | 1e.2c.3c.4f.5b.6f, |
| 1e.2c.3c.4f.5c.6a, | 1e.2c.3c.4f.5c.6b, | 1e.2c.3c.4f.5c.6c, | 1e.2c.3c.4f.5c.6d, | 1e.2c.3c.4f.5c.6e, |
| 1e.2c.3c.4f.5c.6f, | 1e.2c.3c.4f.5d.6a, | 1e.2c.3c.4f.5d.6b, | 1e.2c.3c.4f.5d.6c, | 1e.2c.3c.4f.5d.6d, |
| 1e.2c.3c.4f.5d.6e, | 1e.2c.3c.4f.5d.6f, | 1e.2c.3c.4f.5e.6a, | 1e.2c.3c.4f.5e.6b, | 1e.2c.3c.4f.5e.6c, |
| 1e.2c.3c.4f.5e.6d, | 1e.2c.3c.4f.5e.6e, | 1e.2c.3c.4f.5e.6f, | 1e.2c.3c.4f.5f.6a, | 1e.2c.3c.4f.5f.6b, |
| 1e.2c.3c.4f.5f.6c, | 1e.2c.3c.4f.5f.6d, | 1e.2c.3c.4f.5f.6e, | 1e.2c.3c.4f.5f.6f, | 1e.2c.3d.4a.5a.6a, |
| 1e.2c.3d.4a.5a.6b, | 1e.2c.3d.4a.5a.6c, | 1e.2c.3d.4a.5a.6d, | 1e.2c.3d.4a.5a.6e, |
| 1e.2c.3d.4a.5a.6f, | 1e.2c.3d.4a.5b.6a, | 1e.2c.3d.4a.5b.6b, | 1e.2c.3d.4a.5b.6c, |
| 1e.2c.3d.4a.5b.6d, | 1e.2c.3d.4a.5b.6e, | 1e.2c.3d.4a.5b.6f, | 1e.2c.3d.4a.5c.6a, |
| 1e.2c.3d.4a.5c.6b, | 1e.2c.3d.4a.5c.6c, | 1e.2c.3d.4a.5c.6d, | 1e.2c.3d.4a.5c.6e, |
| 1e.2c.3d.4a.5c.6f, | 1e.2c.3d.4a.5d.6a, | 1e.2c.3d.4a.5d.6b, | 1e.2c.3d.4a.5d.6c, |
| 1e.2c.3d.4a.5d.6d, | 1e.2c.3d.4a.5d.6e, | 1e.2c.3d.4a.5d.6f, | 1e.2c.3d.4a.5e.6a, |
| 1e.2c.3d.4a.5e.6b, | 1e.2c.3d.4a.5e.6c, | 1e.2c.3d.4a.5e.6d, | 1e.2c.3d.4a.5e.6e, |
| 1e.2c.3d.4a.5e.6f, | 1e.2c.3d.4a.5f.6a, | 1e.2c.3d.4a.5f.6b, | 1e.2c.3d.4a.5f.6c, |
| 1e.2c.3d.4a.5f.6d, | 1e.2c.3d.4a.5f.6e, | 1e.2c.3d.4a.5f.6f, | 1e.2c.3d.4b.5a.6a, |
| 1e.2c.3d.4b.5a.6b, | 1e.2c.3d.4b.5a.6c, | 1e.2c.3d.4b.5a.6d, | 1e.2c.3d.4b.5a.6e, |
| 1e.2c.3d.4b.5a.6f, | 1e.2c.3d.4b.5b.6a, | 1e.2c.3d.4b.5b.6b, | 1e.2c.3d.4b.5b.6c, |
| 1e.2c.3d.4b.5b.6d, | 1e.2c.3d.4b.5b.6e, | 1e.2c.3d.4b.5b.6f, | 1e.2c.3d.4b.5c.6a, |
| 1e.2c.3d.4b.5c.6b, | 1e.2c.3d.4b.5c.6c, | 1e.2c.3d.4b.5c.6d, | 1e.2c.3d.4b.5c.6e, |
| 1e.2c.3d.4b.5c.6f, | 1e.2c.3d.4b.5d.6a, | 1e.2c.3d.4b.5d.6b, | 1e.2c.3d.4b.5d.6c, |
| 1e.2c.3d.4b.5d.6d, | 1e.2c.3d.4b.5d.6e, | 1e.2c.3d.4b.5d.6f, | 1e.2c.3d.4b.5e.6a, |
| 1e.2c.3d.4b.5e.6b, | 1e.2c.3d.4b.5e.6c, | 1e.2c.3d.4b.5e.6d, | 1e.2c.3d.4b.5e.6e, |
| 1e.2c.3d.4b.5e.6f, | 1e.2c.3d.4b.5f.6a, | 1e.2c.3d.4b.5f.6b, | 1e.2c.3d.4b.5f.6c, |
| 1e.2c.3d.4b.5f.6d, | 1e.2c.3d.4b.5f.6e, | 1e.2c.3d.4b.5f.6f, | 1e.2c.3d.4c.5a.6a, |
| 1e.2c.3d.4c.5a.6b, | 1e.2c.3d.4c.5a.6c, | 1e.2c.3d.4c.5a.6d, | 1e.2c.3d.4c.5a.6e, |
| 1e.2c.3d.4c.5a.6f, | 1e.2c.3d.4c.5b.6a, | 1e.2c.3d.4c.5b.6b, | 1e.2c.3d.4c.5b.6c, |
| 1e.2c.3d.4c.5b.6d, | 1e.2c.3d.4c.5b.6e, | 1e.2c.3d.4c.5b.6f, | 1e.2c.3d.4c.5c.6a, |
| 1e.2c.3d.4c.5c.6b, | 1e.2c.3d.4c.5c.6c, | 1e.2c.3d.4c.5c.6d, | 1e.2c.3d.4c.5c.6e, |
| 1e.2c.3d.4c.5c.6f, | 1e.2c.3d.4c.5d.6a, | 1e.2c.3d.4c.5d.6b, | 1e.2c.3d.4c.5d.6c, |
| 1e.2c.3d.4c.5d.6d, | 1e.2c.3d.4c.5d.6e, | 1e.2c.3d.4c.5d.6f, | 1e.2c.3d.4c.5e.6a, |
| 1e.2c.3d.4c.5e.6b, | 1e.2c.3d.4c.5e.6c, | 1e.2c.3d.4c.5e.6d, | 1e.2c.3d.4c.5e.6e, |
| 1e.2c.3d.4c.5e.6f, | 1e.2c.3d.4c.5f.6a, | 1e.2c.3d.4c.5f.6b, | 1e.2c.3d.4c.5f.6c, | 1e.2c.3d.4c.5f.6d, |
| 1e.2c.3d.4c.5f.6e, | 1e.2c.3d.4c.5f.6f, | 1e.2c.3d.4d.5a.6a, | 1e.2c.3d.4d.5a.6b, |
| 1e.2c.3d.4d.5a.6c, | 1e.2c.3d.4d.5a.6d, | 1e.2c.3d.4d.5a.6e, | 1e.2c.3d.4d.5a.6f, |
| 1e.2c.3d.4d.5b.6a, | 1e.2c.3d.4d.5b.6b, | 1e.2c.3d.4d.5b.6c, | 1e.2c.3d.4d.5b.6d, |
| 1e.2c.3d.4d.5b.6e, | 1e.2c.3d.4d.5b.6f, | 1e.2c.3d.4d.5c.6a, | 1e.2c.3d.4d.5c.6b, |
| 1e.2c.3d.4d.5c.6c, | 1e.2c.3d.4d.5c.6d, | 1e.2c.3d.4d.5c.6e, | 1e.2c.3d.4d.5c.6f, |
| 1e.2c.3d.4d.5d.6a, | 1e.2c.3d.4d.5d.6b, | 1e.2c.3d.4d.5d.6c, | 1e.2c.3d.4d.5d.6d, |
| 1e.2c.3d.4d.5d.6e, | 1e.2c.3d.4d.5d.6f, | 1e.2c.3d.4d.5e.6a, | 1e.2c.3d.4d.5e.6b, |
| 1e.2c.3d.4d.5e.6c, | 1e.2c.3d.4d.5e.6d, | 1e.2c.3d.4d.5e.6e, | 1e.2c.3d.4d.5e.6f, |
| 1e.2c.3d.4d.5f.6a, | 1e.2c.3d.4d.5f.6b, | 1e.2c.3d.4d.5f.6c, | 1e.2c.3d.4d.5f.6d, |
| 1e.2c.3d.4d.5f.6e, | 1e.2c.3d.4d.5f.6f, | 1e.2c.3d.4e.5a.6a, | 1e.2c.3d.4e.5a.6b, |
| 1e.2c.3d.4e.5a.6c, | 1e.2c.3d.4e.5a.6d, | 1e.2c.3d.4e.5a.6e, | 1e.2c.3d.4e.5a.6f, |

TABLE 7-continued

List of Compounds of Formula (II)

| | | | | |
|---|---|---|---|---|
| 1e.2c.3d.4e.5b.6a, | 1e.2c.3d.4e.5b.6b, | 1e.2c.3d.4e.5b.6c, | 1e.2c.3d.4e.5b.6d, | |
| 1e.2c.3d.4e.5b.6e, | 1e.2c.3d.4e.5b.6f, | 1e.2c.3d.4e.5c.6a, | 1e.2c.3d.4e.5c.6b, | |
| 1e.2c.3d.4e.5c.6c, | 1e.2c.3d.4e.5c.6d, | 1e.2c.3d.4e.5c.6e, | 1e.2c.3d.4e.5c.6f, | |
| 1e.2c.3d.4e.5d.6a, | 1e.2c.3d.4e.5d.6b, | 1e.2c.3d.4e.5d.6c, | 1e.2c.3d.4e.5d.6d, | |
| 1e.2c.3d.4e.5d.6e, | 1e.2c.3d.4e.5d.6f, | 1e.2c.3d.4e.5e.6a, | 1e.2c.3d.4e.5e.6b, | |
| 1e.2c.3d.4e.5e.6c, | 1e.2c.3d.4e.5e.6d, | 1e.2c.3d.4e.5e.6e, | 1e.2c.3d.4e.5e.6f, | |
| 1e.2c.3d.4e.5f.6a, | 1e.2c.3d.4e.5f.6b, | 1e.2c.3d.4e.5f.6c, | 1e.2c.3d.4e.5f.6d, | 1e.2c.3d.4e.5f.6e, |
| 1e.2c.3d.4e.5f.6f, | 1e.2c.3d.4f.5a.6a, | 1e.2c.3d.4f.5a.6b, | 1e.2c.3d.4f.5a.6c, | 1e.2c.3d.4f.5a.6d, |
| 1e.2c.3d.4f.5a.6e, | 1e.2c.3d.4f.5a.6f, | 1e.2c.3d.4f.5b.6a, | 1e.2c.3d.4f.5b.6b, | 1e.2c.3d.4f.5b.6c, |
| 1e.2c.3d.4f.5b.6d, | 1e.2c.3d.4f.5b.6e, | 1e.2c.3d.4f.5b.6f, | 1e.2c.3d.4f.5c.6a, | 1e.2c.3d.4f.5c.6b, |
| 1e.2c.3d.4f.5c.6c, | 1e.2c.3d.4f.5c.6d, | 1e.2c.3d.4f.5c.6e, | 1e.2c.3d.4f.5c.6f, | 1e.2c.3d.4f.5d.6a, |
| 1e.2c.3d.4f.5d.6b, | 1e.2c.3d.4f.5d.6c, | 1e.2c.3d.4f.5d.6d, | 1e.2c.3d.4f.5d.6e, | |
| 1e.2c.3d.4f.5d.6f, | 1e.2c.3d.4f.5e.6a, | 1e.2c.3d.4f.5e.6b, | 1e.2c.3d.4f.5e.6c, | 1e.2c.3d.4f.5e.6d, |
| 1e.2c.3d.4f.5e.6e, | 1e.2c.3d.4f.5e.6f, | 1e.2c.3d.4f.5f.6a, | 1e.2c.3d.4f.5f.6b, | 1e.2c.3d.4f.5f.6c, |
| 1e.2c.3d.4f.5f.6d, | 1e.2c.3d.4f.5f.6e, | 1e.2c.3d.4f.5f.6f, | 1e.2c.3e.4a.5a.6a, | 1e.2c.3e.4a.5a.6b, |
| 1e.2c.3e.4a.5a.6c, | 1e.2c.3e.4a.5a.6d, | 1e.2c.3e.4a.5a.6e, | 1e.2c.3e.4a.5a.6f, | |
| 1e.2c.3e.4a.5b.6a, | 1e.2c.3e.4a.5b.6b, | 1e.2c.3e.4a.5b.6c, | 1e.2c.3e.4a.5b.6d, | |
| 1e.2c.3e.4a.5b.6e, | 1e.2c.3e.4a.5b.6f, | 1e.2c.3e.4a.5c.6a, | 1e.2c.3e.4a.5c.6b, | 1e.2c.3e.4a.5c.6c, |
| 1e.2c.3e.4a.5c.6d, | 1e.2c.3e.4a.5c.6e, | 1e.2c.3e.4a.5c.6f, | 1e.2c.3e.4a.5d.6a, | |
| 1e.2c.3e.4a.5d.6b, | 1e.2c.3e.4a.5d.6c, | 1e.2c.3e.4a.5d.6d, | 1e.2c.3e.4a.5d.6e, | |
| 1e.2c.3e.4a.5d.6f, | 1e.2c.3e.4a.5e.6a, | 1e.2c.3e.4a.5e.6b, | 1e.2c.3e.4a.5e.6c, | |
| 1e.2c.3e.4a.5e.6d, | 1e.2c.3e.4a.5e.6e, | 1e.2c.3e.4a.5e.6f, | 1e.2c.3e.4a.5f.6a, | 1e.2c.3e.4a.5f.6b, |
| 1e.2c.3e.4a.5f.6c, | 1e.2c.3e.4a.5f.6d, | 1e.2c.3e.4a.5f.6e, | 1e.2c.3e.4a.5f.6f, | 1e.2c.3e.4b.5a.6a, |
| 1e.2c.3e.4b.5a.6b, | 1e.2c.3e.4b.5a.6c, | 1e.2c.3e.4b.5a.6d, | 1e.2c.3e.4b.5a.6e, | |
| 1e.2c.3e.4b.5a.6f, | 1e.2c.3e.4b.5b.6a, | 1e.2c.3e.4b.5b.6b, | 1e.2c.3e.4b.5b.6c, | |
| 1e.2c.3e.4b.5b.6d, | 1e.2c.3e.4b.5b.6e, | 1e.2c.3e.4b.5b.6f, | 1e.2c.3e.4b.5c.6a, | |
| 1e.2c.3e.4b.5c.6b, | 1e.2c.3e.4b.5c.6c, | 1e.2c.3e.4b.5c.6d, | 1e.2c.3e.4b.5c.6e, | |
| 1e.2c.3e.4b.5c.6f, | 1e.2c.3e.4b.5d.6a, | 1e.2c.3e.4b.5d.6b, | 1e.2c.3e.4b.5d.6c, | |
| 1e.2c.3e.4b.5d.6d, | 1e.2c.3e.4b.5d.6e, | 1e.2c.3e.4b.5d.6f, | 1e.2c.3e.4b.5e.6a, | |
| 1e.2c.3e.4b.5e.6b, | 1e.2c.3e.4b.5e.6c, | 1e.2c.3e.4b.5e.6d, | 1e.2c.3e.4b.5e.6e, | |
| 1e.2c.3e.4b.5e.6f, | 1e.2c.3e.4b.5f.6a, | 1e.2c.3e.4b.5f.6b, | 1e.2c.3e.4b.5f.6c, | 1e.2c.3e.4b.5f.6d, |
| 1e.2c.3e.4b.5f.6e, | 1e.2c.3e.4b.5f.6f, | 1e.2c.3e.4c.5a.6a, | 1e.2c.3e.4c.5a.6b, | 1e.2c.3e.4c.5a.6c, |
| 1e.2c.3e.4c.5a.6d, | 1e.2c.3e.4c.5a.6e, | 1e.2c.3e.4c.5a.6f, | 1e.2c.3e.4c.5b.6a, | 1e.2c.3e.4c.5b.6b, |
| 1e.2c.3e.4c.5b.6c, | 1e.2c.3e.4c.5b.6d, | 1e.2c.3e.4c.5b.6e, | 1e.2c.3e.4c.5b.6f, | 1e.2c.3e.4c.5c.6a, |
| 1e.2c.3e.4c.5c.6b, | 1e.2c.3e.4c.5c.6c, | 1e.2c.3e.4c.5c.6d, | 1e.2c.3e.4c.5c.6e, | 1e.2c.3e.4c.5c.6f, |
| 1e.2c.3e.4c.5d.6a, | 1e.2c.3e.4c.5d.6b, | 1e.2c.3e.4c.5d.6c, | 1e.2c.3e.4c.5d.6d, | |
| 1e.2c.3e.4c.5d.6e, | 1e.2c.3e.4c.5d.6f, | 1e.2c.3e.4c.5e.6a, | 1e.2c.3e.4c.5e.6b, | 1e.2c.3e.4c.5e.6c, |
| 1e.2c.3e.4c.5e.6d, | 1e.2c.3e.4c.5e.6e, | 1e.2c.3e.4c.5e.6f, | 1e.2c.3e.4c.5f.6a, | 1e.2c.3e.4c.5f.6b, |
| 1e.2c.3e.4c.5f.6c, | 1e.2c.3e.4c.5f.6d, | 1e.2c.3e.4c.5f.6e, | 1e.2c.3e.4c.5f.6f, | 1e.2c.3e.4d.5a.6a, |
| 1e.2c.3e.4d.5a.6b, | 1e.2c.3e.4d.5a.6c, | 1e.2c.3e.4d.5a.6d, | 1e.2c.3e.4d.5a.6e, | |
| 1e.2c.3e.4d.5a.6f, | 1e.2c.3e.4d.5b.6a, | 1e.2c.3e.4d.5b.6b, | 1e.2c.3e.4d.5b.6c, | |
| 1e.2c.3e.4d.5b.6d, | 1e.2c.3e.4d.5b.6e, | 1e.2c.3e.4d.5b.6f, | 1e.2c.3e.4d.5c.6a, | |
| 1e.2c.3e.4d.5c.6b, | 1e.2c.3e.4d.5c.6c, | 1e.2c.3e.4d.5c.6d, | 1e.2c.3e.4d.5c.6e, | |
| 1e.2c.3e.4d.5c.6f, | 1e.2c.3e.4d.5d.6a, | 1e.2c.3e.4d.5d.6b, | 1e.2c.3e.4d.5d.6c, | |
| 1e.2c.3e.4d.5d.6d, | 1e.2c.3e.4d.5d.6e, | 1e.2c.3e.4d.5d.6f, | 1e.2c.3e.4d.5e.6a, | |
| 1e.2c.3e.4d.5e.6b, | 1e.2c.3e.4d.5e.6c, | 1e.2c.3e.4d.5e.6d, | 1e.2c.3e.4d.5e.6e, | |
| 1e.2c.3e.4d.5e.6f, | 1e.2c.3e.4d.5f.6a, | 1e.2c.3e.4d.5f.6b, | 1e.2c.3e.4d.5f.6c, | 1e.2c.3e.4d.5f.6d, |
| 1e.2c.3e.4d.5f.6e, | 1e.2c.3e.4d.5f.6f, | 1e.2c.3e.4e.5a.6a, | 1e.2c.3e.4e.5a.6b, | 1e.2c.3e.4e.5a.6c, |
| 1e.2c.3e.4e.5a.6d, | 1e.2c.3e.4e.5a.6e, | 1e.2c.3e.4e.5a.6f, | 1e.2c.3e.4e.5b.6a, | |
| 1e.2c.3e.4e.5b.6b, | 1e.2c.3e.4e.5b.6c, | 1e.2c.3e.4e.5b.6d, | 1e.2c.3e.4e.5b.6e, | |
| 1e.2c.3e.4e.5b.6f, | 1e.2c.3e.4e.5c.6a, | 1e.2c.3e.4e.5c.6b, | 1e.2c.3e.4e.5c.6c, | 1e.2c.3e.4e.5c.6d, |
| 1e.2c.3e.4e.5c.6e, | 1e.2c.3e.4e.5c.6f, | 1e.2c.3e.4e.5d.6a, | 1e.2c.3e.4e.5d.6b, | |
| 1e.2c.3e.4e.5d.6c, | 1e.2c.3e.4e.5d.6d, | 1e.2c.3e.4e.5d.6e, | 1e.2c.3e.4e.5d.6f, | |
| 1e.2c.3e.4e.5e.6a, | 1e.2c.3e.4e.5e.6b, | 1e.2c.3e.4e.5e.6c, | 1e.2c.3e.4e.5e.6d, | |
| 1e.2c.3e.4e.5e.6e, | 1e.2c.3e.4e.5e.6f, | 1e.2c.3e.4e.5f.6a, | 1e.2c.3e.4e.5f.6b, | 1e.2c.3e.4e.5f.6c, |
| 1e.2c.3e.4e.5f.6d, | 1e.2c.3e.4e.5f.6e, | 1e.2c.3e.4e.5f.6f, | 1e.2c.3e.4f.5a.6a, | 1e.2c.3e.4f.5a.6b, |
| 1e.2c.3e.4f.5a.6c, | 1e.2c.3e.4f.5a.6d, | 1e.2c.3e.4f.5a.6e, | 1e.2c.3e.4f.5a.6f, | 1e.2c.3e.4f.5b.6a, |
| 1e.2c.3e.4f.5b.6b, | 1e.2c.3e.4f.5b.6c, | 1e.2c.3e.4f.5b.6d, | 1e.2c.3e.4f.5b.6e, | 1e.2c.3e.4f.5b.6f, |
| 1e.2c.3e.4f.5c.6a, | 1e.2c.3e.4f.5c.6b, | 1e.2c.3e.4f.5c.6c, | 1e.2c.3e.4f.5c.6d, | 1e.2c.3e.4f.5c.6e, |
| 1e.2c.3e.4f.5c.6f, | 1e.2c.3e.4f.5d.6a, | 1e.2c.3e.4f.5d.6b, | 1e.2c.3e.4f.5d.6c, | 1e.2c.3e.4f.5d.6d, |
| 1e.2c.3e.4f.5d.6e, | 1e.2c.3e.4f.5d.6f, | 1e.2c.3e.4f.5e.6a, | 1e.2c.3e.4f.5e.6b, | 1e.2c.3e.4f.5e.6c, |
| 1e.2c.3e.4f.5e.6d, | 1e.2c.3e.4f.5e.6e, | 1e.2c.3e.4f.5e.6f, | 1e.2c.3e.4f.5f.6a, | 1e.2c.3e.4f.5f.6b, |
| 1e.2c.3e.4f.5f.6c, | 1e.2c.3e.4f.5f.6d, | 1e.2c.3e.4f.5f.6e, | 1e.2c.3e.4f.5f.6f, | 1e.2c.3f.4a.5a.6a, |
| 1e.2c.3f.4a.5a.6b, | 1e.2c.3f.4a.5a.6c, | 1e.2c.3f.4a.5a.6d, | 1e.2c.3f.4a.5a.6e, | 1e.2c.3f.4a.5a.6f, |
| 1e.2c.3f.4a.5b.6a, | 1e.2c.3f.4a.5b.6b, | 1e.2c.3f.4a.5b.6c, | 1e.2c.3f.4a.5b.6d, | 1e.2c.3f.4a.5b.6e, |
| 1e.2c.3f.4a.5b.6f, | 1e.2c.3f.4a.5c.6a, | 1e.2c.3f.4a.5c.6b, | 1e.2c.3f.4a.5c.6c, | 1e.2c.3f.4a.5c.6d, |
| 1e.2c.3f.4a.5c.6e, | 1e.2c.3f.4a.5c.6f, | 1e.2c.3f.4a.5d.6a, | 1e.2c.3f.4a.5d.6b, | 1e.2c.3f.4a.5d.6c, |
| 1e.2c.3f.4a.5d.6d, | 1e.2c.3f.4a.5d.6e, | 1e.2c.3f.4a.5d.6f, | 1e.2c.3f.4a.5e.6a, | 1e.2c.3f.4a.5e.6b, |
| 1e.2c.3f.4a.5e.6c, | 1e.2c.3f.4a.5e.6d, | 1e.2c.3f.4a.5e.6e, | 1e.2c.3f.4a.5e.6f, | 1e.2c.3f.4a.5f.6a, |
| 1e.2c.3f.4a.5f.6b, | 1e.2c.3f.4a.5f.6c, | 1e.2c.3f.4a.5f.6d, | 1e.2c.3f.4a.5f.6e, | 1e.2c.3f.4a.5f.6f, |
| 1e.2c.3f.4b.5a.6a, | 1e.2c.3f.4b.5a.6b, | 1e.2c.3f.4b.5a.6c, | 1e.2c.3f.4b.5a.6d, | 1e.2c.3f.4b.5a.6e, |
| 1e.2c.3f.4b.5a.6f, | 1e.2c.3f.4b.5b.6a, | 1e.2c.3f.4b.5b.6b, | 1e.2c.3f.4b.5b.6c, | 1e.2c.3f.4b.5b.6d, |
| 1e.2c.3f.4b.5b.6e, | 1e.2c.3f.4b.5b.6f, | 1e.2c.3f.4b.5c.6a, | 1e.2c.3f.4b.5c.6b, | 1e.2c.3f.4b.5c.6c, |
| 1e.2c.3f.4b.5c.6d, | 1e.2c.3f.4b.5c.6e, | 1e.2c.3f.4b.5c.6f, | 1e.2c.3f.4b.5d.6a, | 1e.2c.3f.4b.5d.6b, |
| 1e.2c.3f.4b.5d.6c, | 1e.2c.3f.4b.5d.6d, | 1e.2c.3f.4b.5d.6e, | 1e.2c.3f.4b.5d.6f, | 1e.2c.3f.4b.5e.6a, |
| 1e.2c.3f.4b.5e.6b, | 1e.2c.3f.4b.5e.6c, | 1e.2c.3f.4b.5e.6d, | 1e.2c.3f.4b.5e.6e, | 1e.2c.3f.4b.5e.6f, |
| 1e.2c.3f.4b.5f.6a, | 1e.2c.3f.4b.5f.6b, | 1e.2c.3f.4b.5f.6c, | 1e.2c.3f.4b.5f.6d, | 1e.2c.3f.4b.5f.6e, |
| 1e.2c.3f.4b.5f.6f, | 1e.2c.3f.4c.5a.6a, | 1e.2c.3f.4c.5a.6b, | 1e.2c.3f.4c.5a.6c, | 1e.2c.3f.4c.5a.6d, |

TABLE 7-continued

List of Compounds of Formula (II)

| | | | | |
|---|---|---|---|---|
| 1e.2c.3f.4c.5a.6e, | 1e.2c.3f.4c.5a.6f, | 1e.2c.3f.4c.5b.6a, | 1e.2c.3f.4c.5b.6b, | 1e.2c.3f.4c.5b.6c, |
| 1e.2c.3f.4c.5b.6d, | 1e.2c.3f.4c.5b.6e, | 1e.2c.3f.4c.5b.6f, | 1e.2c.3f.4c.5c.6a, | 1e.2c.3f.4c.5c.6b, |
| 1e.2c.3f.4c.5c.6c, | 1e.2c.3f.4c.5c.6d, | 1e.2c.3f.4c.5c.6e, | 1e.2c.3f.4c.5c.6f, | 1e.2c.3f.4c.5d.6a, |
| 1e.2c.3f.4c.5d.6b, | 1e.2c.3f.4c.5d.6c, | 1e.2c.3f.4c.5d.6d, | 1e.2c.3f.4c.5d.6e, | 1e.2c.3f.4c.5d.6f, |
| 1e.2c.3f.4c.5e.6a, | 1e.2c.3f.4c.5e.6b, | 1e.2c.3f.4c.5e.6c, | 1e.2c.3f.4c.5e.6d, | 1e.2c.3f.4c.5e.6e, |
| 1e.2c.3f.4c.5e.6f, | 1e.2c.3f.4c.5f.6a, | 1e.2c.3f.4c.5f.6b, | 1e.2c.3f.4c.5f.6c, | 1e.2c.3f.4c.5f.6d, |
| 1e.2c.3f.4c.5f.6e, | 1e.2c.3f.4c.5f.6f, | 1e.2c.3f.4d.5a.6a, | 1e.2c.3f.4d.5a.6b, | 1e.2c.3f.4d.5a.6c, |
| 1e.2c.3f.4d.5a.6d, | 1e.2c.3f.4d.5a.6e, | 1e.2c.3f.4d.5a.6f, | 1e.2c.3f.4d.5b.6a, | |
| 1e.2c.3f.4d.5b.6b, | 1e.2c.3f.4d.5b.6c, | 1e.2c.3f.4d.5b.6d, | 1e.2c.3f.4d.5b.6e, | |
| 1e.2c.3f.4d.5b.6f, | 1e.2c.3f.4d.5c.6a, | 1e.2c.3f.4d.5c.6b, | 1e.2c.3f.4d.5c.6c, | 1e.2c.3f.4d.5c.6d, |
| 1e.2c.3f.4d.5c.6e, | 1e.2c.3f.4d.5c.6f, | 1e.2c.3f.4d.5d.6a, | 1e.2c.3f.4d.5d.6b, | 1e.2c.3f.4d.5d.6c, |
| 1e.2c.3f.4d.5d.6d, | 1e.2c.3f.4d.5d.6e, | 1e.2c.3f.4d.5d.6f, | 1e.2c.3f.4d.5e.6a, | |
| 1e.2c.3f.4d.5e.6b, | 1e.2c.3f.4d.5e.6c, | 1e.2c.3f.4d.5e.6d, | 1e.2c.3f.4d.5e.6e, | 1e.2c.3f.4d.5e.6f, |
| 1e.2c.3f.4d.5f.6a, | 1e.2c.3f.4d.5f.6b, | 1e.2c.3f.4d.5f.6c, | 1e.2c.3f.4d.5f.6d, | 1e.2c.3f.4d.5f.6e, |
| 1e.2c.3f.4d.5f.6f, | 1e.2c.3f.4e.5a.6a, | 1e.2c.3f.4e.5a.6b, | 1e.2c.3f.4e.5a.6c, | 1e.2c.3f.4e.5a.6d, |
| 1e.2c.3f.4e.5a.6e, | 1e.2c.3f.4e.5a.6f, | 1e.2c.3f.4e.5b.6a, | 1e.2c.3f.4e.5b.6b, | 1e.2c.3f.4e.5b.6c, |
| 1e.2c.3f.4e.5b.6d, | 1e.2c.3f.4e.5b.6e, | 1e.2c.3f.4e.5b.6f, | 1e.2c.3f.4e.5c.6a, | 1e.2c.3f.4e.5c.6b, |
| 1e.2c.3f.4e.5c.6c, | 1e.2c.3f.4e.5c.6d, | 1e.2c.3f.4e.5c.6e, | 1e.2c.3f.4e.5c.6f, | 1e.2c.3f.4e.5d.6a, |
| 1e.2c.3f.4e.5d.6b, | 1e.2c.3f.4e.5d.6c, | 1e.2c.3f.4e.5d.6d, | 1e.2c.3f.4e.5d.6e, | 1e.2c.3f.4e.5d.6f, |
| 1e.2c.3f.4e.5e.6a, | 1e.2c.3f.4e.5e.6b, | 1e.2c.3f.4e.5e.6c, | 1e.2c.3f.4e.5e.6d, | 1e.2c.3f.4e.5e.6e, |
| 1e.2c.3f.4e.5e.6f, | 1e.2c.3f.4e.5f.6a, | 1e.2c.3f.4e.5f.6b, | 1e.2c.3f.4e.5f.6c, | 1e.2c.3f.4e.5f.6d, |
| 1e.2c.3f.4e.5f.6e, | 1e.2c.3f.4e.5f.6f, | 1e.2c.3f.4f.5a.6a, | 1e.2c.3f.4f.5a.6b, | 1e.2c.3f.4f.5a.6c, |
| 1e.2c.3f.4f.5a.6d, | 1e.2c.3f.4f.5a.6e, | 1e.2c.3f.4f.5a.6f, | 1e.2c.3f.4f.5b.6a, | 1e.2c.3f.4f.5b.6b, |
| 1e.2c.3f.4f.5b.6c, | 1e.2c.3f.4f.5b.6d, | 1e.2c.3f.4f.5b.6e, | 1e.2c.3f.4f.5b.6f, | 1e.2c.3f.4f.5c.6a, |
| 1e.2c.3f.4f.5c.6b, | 1e.2c.3f.4f.5c.6c, | 1e.2c.3f.4f.5c.6d, | 1e.2c.3f.4f.5c.6e, | 1e.2c.3f.4f.5c.6f, |
| 1e.2c.3f.4f.5d.6a, | 1e.2c.3f.4f.5d.6b, | 1e.2c.3f.4f.5d.6c, | 1e.2c.3f.4f.5d.6d, | 1e.2c.3f.4f.5d.6e, |
| 1e.2c.3f.4f.5d.6f, | 1e.2c.3f.4f.5e.6a, | 1e.2c.3f.4f.5e.6b, | 1e.2c.3f.4f.5e.6c, | 1e.2c.3f.4f.5e.6d, |
| 1e.2c.3f.4f.5e.6e, | 1e.2c.3f.4f.5e.6f, | 1e.2c.3f.4f.5f.6a, | 1e.2c.3f.4f.5f.6b, | 1e.2c.3f.4f.5f.6c, |
| 1e.2c.3f.4f.5f.6d, | 1e.2c.3f.4f.5f.6e, | 1e.2c.3f.4f.5f.6f, | 1e.2d.3a.4a.5a.6a, | 1e.2d.3a.4a.5a.6b, |
| 1e.2d.3a.4a.5a.6c, | 1e.2d.3a.4a.5a.6d, | 1e.2d.3a.4a.5a.6e, | 1e.2d.3a.4a.5a.6f, | |
| 1e.2d.3a.4a.5b.6a, | 1e.2d.3a.4a.5b.6b, | 1e.2d.3a.4a.5b.6c, | 1e.2d.3a.4a.5b.6d, | |
| 1e.2d.3a.4a.5b.6e, | 1e.2d.3a.4a.5b.6f, | 1e.2d.3a.4a.5c.6a, | 1e.2d.3a.4a.5c.6b, | |
| 1e.2d.3a.4a.5c.6c, | 1e.2d.3a.4a.5c.6d, | 1e.2d.3a.4a.5c.6e, | 1e.2d.3a.4a.5c.6f, | |
| 1e.2d.3a.4a.5d.6a, | 1e.2d.3a.4a.5d.6b, | 1e.2d.3a.4a.5d.6c, | 1e.2d.3a.4a.5d.6d, | |
| 1e.2d.3a.4a.5d.6e, | 1e.2d.3a.4a.5d.6f, | 1e.2d.3a.4a.5e.6a, | 1e.2d.3a.4a.5e.6b, | |
| 1e.2d.3a.4a.5e.6c, | 1e.2d.3a.4a.5e.6d, | 1e.2d.3a.4a.5e.6e, | 1e.2d.3a.4a.5e.6f, | |
| 1e.2d.3a.4a.5f.6a, | 1e.2d.3a.4a.5f.6b, | 1e.2d.3a.4a.5f.6c, | 1e.2d.3a.4a.5f.6d, | |
| 1e.2d.3a.4a.5f.6e, | 1e.2d.3a.4a.5f.6f, | 1e.2d.3a.4b.5a.6a, | 1e.2d.3a.4b.5a.6b, | |
| 1e.2d.3a.4b.5a.6c, | 1e.2d.3a.4b.5a.6d, | 1e.2d.3a.4b.5a.6e, | 1e.2d.3a.4b.5a.6f, | |
| 1e.2d.3a.4b.5b.6a, | 1e.2d.3a.4b.5b.6b, | 1e.2d.3a.4b.5b.6c, | 1e.2d.3a.4b.5b.6d, | |
| 1e.2d.3a.4b.5b.6e, | 1e.2d.3a.4b.5b.6f, | 1e.2d.3a.4b.5c.6a, | 1e.2d.3a.4b.5c.6b, | |
| 1e.2d.3a.4b.5c.6c, | 1e.2d.3a.4b.5c.6d, | 1e.2d.3a.4b.5c.6e, | 1e.2d.3a.4b.5c.6f, | |
| 1e.2d.3a.4b.5d.6a, | 1e.2d.3a.4b.5d.6b, | 1e.2d.3a.4b.5d.6c, | 1e.2d.3a.4b.5d.6d, | |
| 1e.2d.3a.4b.5d.6e, | 1e.2d.3a.4b.5d.6f, | 1e.2d.3a.4b.5e.6a, | 1e.2d.3a.4b.5e.6b, | |
| 1e.2d.3a.4b.5e.6c, | 1e.2d.3a.4b.5e.6d, | 1e.2d.3a.4b.5e.6e, | 1e.2d.3a.4b.5e.6f, | |
| 1e.2d.3a.4b.5f.6a, | 1e.2d.3a.4b.5f.6b, | 1e.2d.3a.4b.5f.6c, | 1e.2d.3a.4b.5f.6d, | |
| 1e.2d.3a.4b.5f.6e, | 1e.2d.3a.4b.5f.6f, | 1e.2d.3a.4c.5a.6a, | 1e.2d.3a.4c.5a.6b, | |
| 1e.2d.3a.4c.5a.6c, | 1e.2d.3a.4c.5a.6d, | 1e.2d.3a.4c.5a.6e, | 1e.2d.3a.4c.5a.6f, | |
| 1e.2d.3a.4c.5b.6a, | 1e.2d.3a.4c.5b.6b, | 1e.2d.3a.4c.5b.6c, | 1e.2d.3a.4c.5b.6d, | |
| 1e.2d.3a.4c.5b.6e, | 1e.2d.3a.4c.5b.6f, | 1e.2d.3a.4c.5c.6a, | 1e.2d.3a.4c.5c.6b, | |
| 1e.2d.3a.4c.5c.6c, | 1e.2d.3a.4c.5c.6d, | 1e.2d.3a.4c.5c.6e, | 1e.2d.3a.4c.5c.6f, | |
| 1e.2d.3a.4c.5d.6a, | 1e.2d.3a.4c.5d.6b, | 1e.2d.3a.4c.5d.6c, | 1e.2d.3a.4c.5d.6d, | |
| 1e.2d.3a.4c.5d.6e, | 1e.2d.3a.4c.5d.6f, | 1e.2d.3a.4c.5e.6a, | 1e.2d.3a.4c.5e.6b, | |
| 1e.2d.3a.4c.5e.6c, | 1e.2d.3a.4c.5e.6d, | 1e.2d.3a.4c.5e.6e, | 1e.2d.3a.4c.5e.6f, | |
| 1e.2d.3a.4c.5f.6a, | 1e.2d.3a.4c.5f.6b, | 1e.2d.3a.4c.5f.6c, | 1e.2d.3a.4c.5f.6d, | |
| 1e.2d.3a.4c.5f.6e, | 1e.2d.3a.4c.5f.6f, | 1e.2d.3a.4d.5a.6a, | 1e.2d.3a.4d.5a.6b, | |
| 1e.2d.3a.4d.5a.6c, | 1e.2d.3a.4d.5a.6d, | 1e.2d.3a.4d.5a.6e, | 1e.2d.3a.4d.5a.6f, | |
| 1e.2d.3a.4d.5b.6a, | 1e.2d.3a.4d.5b.6b, | 1e.2d.3a.4d.5b.6c, | 1e.2d.3a.4d.5b.6d, | |
| 1e.2d.3a.4d.5b.6e, | 1e.2d.3a.4d.5b.6f, | 1e.2d.3a.4d.5c.6a, | 1e.2d.3a.4d.5c.6b, | |
| 1e.2d.3a.4d.5c.6c, | 1e.2d.3a.4d.5c.6d, | 1e.2d.3a.4d.5c.6e, | 1e.2d.3a.4d.5c.6f, | |
| 1e.2d.3a.4d.5d.6a, | 1e.2d.3a.4d.5d.6b, | 1e.2d.3a.4d.5d.6c, | 1e.2d.3a.4d.5d.6d, | |
| 1e.2d.3a.4d.5d.6e, | 1e.2d.3a.4d.5d.6f, | 1e.2d.3a.4d.5e.6a, | 1e.2d.3a.4d.5e.6b, | |
| 1e.2d.3a.4d.5e.6c, | 1e.2d.3a.4d.5e.6d, | 1e.2d.3a.4d.5e.6e, | 1e.2d.3a.4d.5e.6f, | |
| 1e.2d.3a.4d.5f.6a, | 1e.2d.3a.4d.5f.6b, | 1e.2d.3a.4d.5f.6c, | 1e.2d.3a.4d.5f.6d, | |
| 1e.2d.3a.4d.5f.6e, | 1e.2d.3a.4d.5f.6f, | 1e.2d.3a.4e.5a.6a, | 1e.2d.3a.4e.5a.6b, | |
| 1e.2d.3a.4e.5a.6c, | 1e.2d.3a.4e.5a.6d, | 1e.2d.3a.4e.5a.6e, | 1e.2d.3a.4e.5a.6f, | |
| 1e.2d.3a.4e.5b.6a, | 1e.2d.3a.4e.5b.6b, | 1e.2d.3a.4e.5b.6c, | 1e.2d.3a.4e.5b.6d, | |
| 1e.2d.3a.4e.5b.6e, | 1e.2d.3a.4e.5b.6f, | 1e.2d.3a.4e.5c.6a, | 1e.2d.3a.4e.5c.6b, | |
| 1e.2d.3a.4e.5c.6c, | 1e.2d.3a.4e.5c.6d, | 1e.2d.3a.4e.5c.6e, | 1e.2d.3a.4e.5c.6f, | |
| 1e.2d.3a.4e.5d.6a, | 1e.2d.3a.4e.5d.6b, | 1e.2d.3a.4e.5d.6c, | 1e.2d.3a.4e.5d.6d, | |
| 1e.2d.3a.4e.5d.6e, | 1e.2d.3a.4e.5d.6f, | 1e.2d.3a.4e.5e.6a, | 1e.2d.3a.4e.5e.6b, | |
| 1e.2d.3a.4e.5e.6c, | 1e.2d.3a.4e.5e.6d, | 1e.2d.3a.4e.5e.6e, | 1e.2d.3a.4e.5e.6f, | |
| 1e.2d.3a.4e.5f.6a, | 1e.2d.3a.4e.5f.6b, | 1e.2d.3a.4e.5f.6c, | 1e.2d.3a.4e.5f.6d, | |
| 1e.2d.3a.4e.5f.6e, | 1e.2d.3a.4e.5f.6f, | 1e.2d.3a.4f.5a.6a, | 1e.2d.3a.4f.5a.6b, | |
| 1e.2d.3a.4f.5a.6c, | 1e.2d.3a.4f.5a.6d, | 1e.2d.3a.4f.5a.6e, | 1e.2d.3a.4f.5a.6f, | |
| 1e.2d.3a.4f.5b.6a, | 1e.2d.3a.4f.5b.6b, | 1e.2d.3a.4f.5b.6c, | 1e.2d.3a.4f.5b.6d, | |
| 1e.2d.3a.4f.5b.6e, | 1e.2d.3a.4f.5b.6f, | 1e.2d.3a.4f.5c.6a, | 1e.2d.3a.4f.5c.6b, | 1e.2d.3a.4f.5c.6c, |
| 1e.2d.3a.4f.5c.6d, | 1e.2d.3a.4f.5c.6e, | 1e.2d.3a.4f.5c.6f, | 1e.2d.3a.4f.5d.6a, | |

TABLE 7-continued

List of Compounds of Formula (II)

| | | | | |
|---|---|---|---|---|
| 1e.2d.3a.4f.5d.6b, | 1e.2d.3a.4f.5d.6c, | 1e.2d.3a.4f.5d.6d, | 1e.2d.3a.4f.5d.6e, | |
| 1e.2d.3a.4f.5d.6f, | 1e.2d.3a.4f.5e.6a, | 1e.2d.3a.4f.5e.6b, | 1e.2d.3a.4f.5e.6c, | |
| 1e.2d.3a.4f.5e.6d, | 1e.2d.3a.4f.5e.6e, | 1e.2d.3a.4f.5e.6f, | 1e.2d.3a.4f.5f.6a, | 1e.2d.3a.4f.5f.6b, |
| 1e.2d.3a.4f.5f.6c, | 1e.2d.3a.4f.5f.6d, | 1e.2d.3a.4f.5f.6e, | 1e.2d.3a.4f.5f.6f, | 1e.2d.3b.4a.5a.6a, |
| 1e.2d.3b.4a.5a.6b, | 1e.2d.3b.4a.5a.6c, | 1e.2d.3b.4a.5a.6d, | 1e.2d.3b.4a.5a.6e, | |
| 1e.2d.3b.4a.5a.6f, | 1e.2d.3b.4a.5b.6a, | 1e.2d.3b.4a.5b.6b, | 1e.2d.3b.4a.5b.6c, | |
| 1e.2d.3b.4a.5b.6d, | 1e.2d.3b.4a.5b.6e, | 1e.2d.3b.4a.5b.6f, | 1e.2d.3b.4a.5c.6a, | |
| 1e.2d.3b.4a.5c.6b, | 1e.2d.3b.4a.5c.6c, | 1e.2d.3b.4a.5c.6d, | 1e.2d.3b.4a.5c.6e, | |
| 1e.2d.3b.4a.5c.6f, | 1e.2d.3b.4a.5d.6a, | 1e.2d.3b.4a.5d.6b, | 1e.2d.3b.4a.5d.6c, | |
| 1e.2d.3b.4a.5d.6d, | 1e.2d.3b.4a.5d.6e, | 1e.2d.3b.4a.5d.6f, | 1e.2d.3b.4a.5e.6a, | |
| 1e.2d.3b.4a.5e.6b, | 1e.2d.3b.4a.5e.6c, | 1e.2d.3b.4a.5e.6d, | 1e.2d.3b.4a.5e.6e, | |
| 1e.2d.3b.4a.5e.6f, | 1e.2d.3b.4a.5f.6a, | 1e.2d.3b.4a.5f.6b, | 1e.2d.3b.4a.5f.6c, | |
| 1e.2d.3b.4a.5f.6d, | 1e.2d.3b.4a.5f.6e, | 1e.2d.3b.4a.5f.6f, | 1e.2d.3b.4b.5a.6a, | |
| 1e.2d.3b.4b.5a.6b, | 1e.2d.3b.4b.5a.6c, | 1e.2d.3b.4b.5a.6d, | 1e.2d.3b.4b.5a.6e, | |
| 1e.2d.3b.4b.5a.6f, | 1e.2d.3b.4b.5b.6a, | 1e.2d.3b.4b.5b.6b, | 1e.2d.3b.4b.5b.6c, | |
| 1e.2d.3b.4b.5b.6d, | 1e.2d.3b.4b.5b.6e, | 1e.2d.3b.4b.5b.6f, | 1e.2d.3b.4b.5c.6a, | |
| 1e.2d.3b.4b.5c.6b, | 1e.2d.3b.4b.5c.6c, | 1e.2d.3b.4b.5c.6d, | 1e.2d.3b.4b.5c.6e, | |
| 1e.2d.3b.4b.5c.6f, | 1e.2d.3b.4b.5d.6a, | 1e.2d.3b.4b.5d.6b, | 1e.2d.3b.4b.5d.6c, | |
| 1e.2d.3b.4b.5d.6d, | 1e.2d.3b.4b.5d.6e, | 1e.2d.3b.4b.5d.6f, | 1e.2d.3b.4b.5e.6a, | |
| 1e.2d.3b.4b.5e.6b, | 1e.2d.3b.4b.5e.6c, | 1e.2d.3b.4b.5e.6d, | 1e.2d.3b.4b.5e.6e, | |
| 1e.2d.3b.4b.5e.6f, | 1e.2d.3b.4b.5f.6a, | 1e.2d.3b.4b.5f.6b, | 1e.2d.3b.4b.5f.6c, | |
| 1e.2d.3b.4b.5f.6d, | 1e.2d.3b.4b.5f.6e, | 1e.2d.3b.4b.5f.6f, | 1e.2d.3b.4c.5a.6a, | |
| 1e.2d.3b.4c.5a.6b, | 1e.2d.3b.4c.5a.6c, | 1e.2d.3b.4c.5a.6d, | 1e.2d.3b.4c.5a.6e, | |
| 1e.2d.3b.4c.5a.6f, | 1e.2d.3b.4c.5b.6a, | 1e.2d.3b.4c.5b.6b, | 1e.2d.3b.4c.5b.6c, | |
| 1e.2d.3b.4c.5b.6d, | 1e.2d.3b.4c.5b.6e, | 1e.2d.3b.4c.5b.6f, | 1e.2d.3b.4c.5c.6a, | |
| 1e.2d.3b.4c.5c.6b, | 1e.2d.3b.4c.5c.6c, | 1e.2d.3b.4c.5c.6d, | 1e.2d.3b.4c.5c.6e, | |
| 1e.2d.3b.4c.5c.6f, | 1e.2d.3b.4c.5d.6a, | 1e.2d.3b.4c.5d.6b, | 1e.2d.3b.4c.5d.6c, | |
| 1e.2d.3b.4c.5d.6d, | 1e.2d.3b.4c.5d.6e, | 1e.2d.3b.4c.5d.6f, | 1e.2d.3b.4c.5e.6a, | |
| 1e.2d.3b.4c.5e.6b, | 1e.2d.3b.4c.5e.6c, | 1e.2d.3b.4c.5e.6d, | 1e.2d.3b.4c.5e.6e, | |
| 1e.2d.3b.4c.5e.6f, | 1e.2d.3b.4c.5f.6a, | 1e.2d.3b.4c.5f.6b, | 1e.2d.3b.4c.5f.6c, | |
| 1e.2d.3b.4c.5f.6d, | 1e.2d.3b.4c.5f.6e, | 1e.2d.3b.4c.5f.6f, | 1e.2d.3b.4d.5a.6a, | |
| 1e.2d.3b.4d.5a.6b, | 1e.2d.3b.4d.5a.6c, | 1e.2d.3b.4d.5a.6d, | 1e.2d.3b.4d.5a.6e, | |
| 1e.2d.3b.4d.5a.6f, | 1e.2d.3b.4d.5b.6a, | 1e.2d.3b.4d.5b.6b, | 1e.2d.3b.4d.5b.6c, | |
| 1e.2d.3b.4d.5b.6d, | 1e.2d.3b.4d.5b.6e, | 1e.2d.3b.4d.5b.6f, | 1e.2d.3b.4d.5c.6a, | |
| 1e.2d.3b.4d.5c.6b, | 1e.2d.3b.4d.5c.6c, | 1e.2d.3b.4d.5c.6d, | 1e.2d.3b.4d.5c.6e, | |
| 1e.2d.3b.4d.5c.6f, | 1e.2d.3b.4d.5d.6a, | 1e.2d.3b.4d.5d.6b, | 1e.2d.3b.4d.5d.6c, | |
| 1e.2d.3b.4d.5d.6d, | 1e.2d.3b.4d.5d.6e, | 1e.2d.3b.4d.5d.6f, | 1e.2d.3b.4d.5e.6a, | |
| 1e.2d.3b.4d.5e.6b, | 1e.2d.3b.4d.5e.6c, | 1e.2d.3b.4d.5e.6d, | 1e.2d.3b.4d.5e.6e, | |
| 1e.2d.3b.4d.5e.6f, | 1e.2d.3b.4d.5f.6a, | 1e.2d.3b.4d.5f.6b, | 1e.2d.3b.4d.5f.6c, | |
| 1e.2d.3b.4d.5f.6d, | 1e.2d.3b.4d.5f.6e, | 1e.2d.3b.4d.5f.6f, | 1e.2d.3b.4e.5a.6a, | |
| 1e.2d.3b.4e.5a.6b, | 1e.2d.3b.4e.5a.6c, | 1e.2d.3b.4e.5a.6d, | 1e.2d.3b.4e.5a.6e, | |
| 1e.2d.3b.4e.5a.6f, | 1e.2d.3b.4e.5b.6a, | 1e.2d.3b.4e.5b.6b, | 1e.2d.3b.4e.5b.6c, | |
| 1e.2d.3b.4e.5b.6d, | 1e.2d.3b.4e.5b.6e, | 1e.2d.3b.4e.5b.6f, | 1e.2d.3b.4e.5c.6a, | |
| 1e.2d.3b.4e.5c.6b, | 1e.2d.3b.4e.5c.6c, | 1e.2d.3b.4e.5c.6d, | 1e.2d.3b.4e.5c.6e, | |
| 1e.2d.3b.4e.5c.6f, | 1e.2d.3b.4e.5d.6a, | 1e.2d.3b.4e.5d.6b, | 1e.2d.3b.4e.5d.6c, | |
| 1e.2d.3b.4e.5d.6d, | 1e.2d.3b.4e.5d.6e, | 1e.2d.3b.4e.5d.6f, | 1e.2d.3b.4e.5e.6a, | |
| 1e.2d.3b.4e.5e.6b, | 1e.2d.3b.4e.5e.6c, | 1e.2d.3b.4e.5e.6d, | 1e.2d.3b.4e.5e.6e, | |
| 1e.2d.3b.4e.5e.6f, | 1e.2d.3b.4e.5f.6a, | 1e.2d.3b.4e.5f.6b, | 1e.2d.3b.4e.5f.6c, | |
| 1e.2d.3b.4e.5f.6d, | 1e.2d.3b.4e.5f.6e, | 1e.2d.3b.4e.5f.6f, | 1e.2d.3b.4f.5a.6a, | |
| 1e.2d.3b.4f.5a.6b, | 1e.2d.3b.4f.5a.6c, | 1e.2d.3b.4f.5a.6d, | 1e.2d.3b.4f.5a.6e, | |
| 1e.2d.3b.4f.5a.6f, | 1e.2d.3b.4f.5b.6a, | 1e.2d.3b.4f.5b.6b, | 1e.2d.3b.4f.5b.6c, | |
| 1e.2d.3b.4f.5b.6d, | 1e.2d.3b.4f.5b.6e, | 1e.2d.3b.4f.5b.6f, | 1e.2d.3b.4f.5c.6a, | |
| 1e.2d.3b.4f.5c.6b, | 1e.2d.3b.4f.5c.6c, | 1e.2d.3b.4f.5c.6d, | 1e.2d.3b.4f.5c.6e, | |
| 1e.2d.3b.4f.5c.6f, | 1e.2d.3b.4f.5d.6a, | 1e.2d.3b.4f.5d.6b, | 1e.2d.3b.4f.5d.6c, | |
| 1e.2d.3b.4f.5d.6d, | 1e.2d.3b.4f.5d.6e, | 1e.2d.3b.4f.5d.6f, | 1e.2d.3b.4f.5e.6a, | |
| 1e.2d.3b.4f.5e.6b, | 1e.2d.3b.4f.5e.6c, | 1e.2d.3b.4f.5e.6d, | 1e.2d.3b.4f.5e.6e, | |
| 1e.2d.3b.4f.5e.6f, | 1e.2d.3b.4f.5f.6a, | 1e.2d.3b.4f.5f.6b, | 1e.2d.3b.4f.5f.6c, | 1e.2d.3b.4f.5f.6d, |
| 1e.2d.3b.4f.5f.6e, | 1e.2d.3b.4f.5f.6f, | 1e.2d.3c.4a.5a.6a, | 1e.2d.3c.4a.5a.6b, | |
| 1e.2d.3c.4a.5a.6c, | 1e.2d.3c.4a.5a.6d, | 1e.2d.3c.4a.5a.6e, | 1e.2d.3c.4a.5a.6f, | |
| 1e.2d.3c.4a.5b.6a, | 1e.2d.3c.4a.5b.6b, | 1e.2d.3c.4a.5b.6c, | 1e.2d.3c.4a.5b.6d, | |
| 1e.2d.3c.4a.5b.6e, | 1e.2d.3c.4a.5b.6f, | 1e.2d.3c.4a.5c.6a, | 1e.2d.3c.4a.5c.6b, | |
| 1e.2d.3c.4a.5c.6c, | 1e.2d.3c.4a.5c.6d, | 1e.2d.3c.4a.5c.6e, | 1e.2d.3c.4a.5c.6f, | |
| 1e.2d.3c.4a.5d.6a, | 1e.2d.3c.4a.5d.6b, | 1e.2d.3c.4a.5d.6c, | 1e.2d.3c.4a.5d.6d, | |
| 1e.2d.3c.4a.5d.6e, | 1e.2d.3c.4a.5d.6f, | 1e.2d.3c.4a.5e.6a, | 1e.2d.3c.4a.5e.6b, | |
| 1e.2d.3c.4a.5e.6c, | 1e.2d.3c.4a.5e.6d, | 1e.2d.3c.4a.5e.6e, | 1e.2d.3c.4a.5e.6f, | |
| 1e.2d.3c.4a.5f.6a, | 1e.2d.3c.4a.5f.6b, | 1e.2d.3c.4a.5f.6c, | 1e.2d.3c.4a.5f.6d, | |
| 1e.2d.3c.4a.5f.6e, | 1e.2d.3c.4a.5f.6f, | 1e.2d.3c.4b.5a.6a, | 1e.2d.3c.4b.5a.6b, | |
| 1e.2d.3c.4b.5a.6c, | 1e.2d.3c.4b.5a.6d, | 1e.2d.3c.4b.5a.6e, | 1e.2d.3c.4b.5a.6f, | |
| 1e.2d.3c.4b.5b.6a, | 1e.2d.3c.4b.5b.6b, | 1e.2d.3c.4b.5b.6c, | 1e.2d.3c.4b.5b.6d, | |
| 1e.2d.3c.4b.5b.6e, | 1e.2d.3c.4b.5b.6f, | 1e.2d.3c.4b.5c.6a, | 1e.2d.3c.4b.5c.6b, | |
| 1e.2d.3c.4b.5c.6c, | 1e.2d.3c.4b.5c.6d, | 1e.2d.3c.4b.5c.6e, | 1e.2d.3c.4b.5c.6f, | |
| 1e.2d.3c.4b.5d.6a, | 1e.2d.3c.4b.5d.6b, | 1e.2d.3c.4b.5d.6c, | 1e.2d.3c.4b.5d.6d, | |
| 1e.2d.3c.4b.5d.6e, | 1e.2d.3c.4b.5d.6f, | 1e.2d.3c.4b.5e.6a, | 1e.2d.3c.4b.5e.6b, | |
| 1e.2d.3c.4b.5e.6c, | 1e.2d.3c.4b.5e.6d, | 1e.2d.3c.4b.5e.6e, | 1e.2d.3c.4b.5e.6f, | |
| 1e.2d.3c.4b.5f.6a, | 1e.2d.3c.4b.5f.6b, | 1e.2d.3c.4b.5f.6c, | 1e.2d.3c.4b.5f.6d, | |
| 1e.2d.3c.4b.5f.6e, | 1e.2d.3c.4b.5f.6f, | 1e.2d.3c.4c.5a.6a, | 1e.2d.3c.4c.5a.6b, | |
| 1e.2d.3c.4c.5a.6c, | 1e.2d.3c.4c.5a.6d, | 1e.2d.3c.4c.5a.6e, | 1e.2d.3c.4c.5a.6f, | |
| 1e.2d.3c.4c.5b.6a, | 1e.2d.3c.4c.5b.6b, | 1e.2d.3c.4c.5b.6c, | 1e.2d.3c.4c.5b.6d, | |

TABLE 7-continued

List of Compounds of Formula (II)

| | | | | |
|---|---|---|---|---|
| 1e.2d.3c.4c.5b.6e, | 1e.2d.3c.4c.5b.6f, | 1e.2d.3c.4c.5c.6a, | 1e.2d.3c.4c.5c.6b, | |
| 1e.2d.3c.4c.5c.6c, | 1e.2d.3c.4c.5c.6d, | 1e.2d.3c.4c.5c.6e, | 1e.2d.3c.4c.5c.6f, | |
| 1e.2d.3c.4c.5d.6a, | 1e.2d.3c.4c.5d.6b, | 1e.2d.3c.4c.5d.6c, | 1e.2d.3c.4c.5d.6d, | |
| 1e.2d.3c.4c.5d.6e, | 1e.2d.3c.4c.5d.6f, | 1e.2d.3c.4c.5e.6a, | 1e.2d.3c.4c.5e.6b, | |
| 1e.2d.3c.4c.5e.6c, | 1e.2d.3c.4c.5e.6d, | 1e.2d.3c.4c.5e.6e, | 1e.2d.3c.4c.5e.6f, | |
| 1e.2d.3c.4c.5f.6a, | 1e.2d.3c.4c.5f.6b, | 1e.2d.3c.4c.5f.6c, | 1e.2d.3c.4c.5f.6d, | 1e.2d.3c.4c.5f.6e, |
| 1e.2d.3c.4c.5f.6f, | 1e.2d.3c.4d.5a.6a, | 1e.2d.3c.4d.5a.6b, | 1e.2d.3c.4d.5a.6c, | |
| 1e.2d.3c.4d.5a.6d, | 1e.2d.3c.4d.5a.6e, | 1e.2d.3c.4d.5a.6f, | 1e.2d.3c.4d.5b.6a, | |
| 1e.2d.3c.4d.5b.6b, | 1e.2d.3c.4d.5b.6c, | 1e.2d.3c.4d.5b.6d, | 1e.2d.3c.4d.5b.6e, | |
| 1e.2d.3c.4d.5b.6f, | 1e.2d.3c.4d.5c.6a, | 1e.2d.3c.4d.5c.6b, | 1e.2d.3c.4d.5c.6c, | |
| 1e.2d.3c.4d.5c.6d, | 1e.2d.3c.4d.5c.6e, | 1e.2d.3c.4d.5c.6f, | 1e.2d.3c.4d.5d.6a, | |
| 1e.2d.3c.4d.5d.6b, | 1e.2d.3c.4d.5d.6c, | 1e.2d.3c.4d.5d.6d, | 1e.2d.3c.4d.5d.6e, | |
| 1e.2d.3c.4d.5d.6f, | 1e.2d.3c.4d.5e.6a, | 1e.2d.3c.4d.5e.6b, | 1e.2d.3c.4d.5e.6c, | |
| 1e.2d.3c.4d.5e.6d, | 1e.2d.3c.4d.5e.6e, | 1e.2d.3c.4d.5e.6f, | 1e.2d.3c.4d.5f.6a, | |
| 1e.2d.3c.4d.5f.6b, | 1e.2d.3c.4d.5f.6c, | 1e.2d.3c.4d.5f.6d, | 1e.2d.3c.4d.5f.6e, | |
| 1e.2d.3c.4d.5f.6f, | 1e.2d.3c.4e.5a.6a, | 1e.2d.3c.4e.5a.6b, | 1e.2d.3c.4e.5a.6c, | |
| 1e.2d.3c.4e.5a.6d, | 1e.2d.3c.4e.5a.6e, | 1e.2d.3c.4e.5a.6f, | 1e.2d.3c.4e.5b.6a, | |
| 1e.2d.3c.4e.5b.6b, | 1e.2d.3c.4e.5b.6c, | 1e.2d.3c.4e.5b.6d, | 1e.2d.3c.4e.5b.6e, | |
| 1e.2d.3c.4e.5b.6f, | 1e.2d.3c.4e.5c.6a, | 1e.2d.3c.4e.5c.6b, | 1e.2d.3c.4e.5c.6c, | |
| 1e.2d.3c.4e.5c.6d, | 1e.2d.3c.4e.5c.6e, | 1e.2d.3c.4e.5c.6f, | 1e.2d.3c.4e.5d.6a, | |
| 1e.2d.3c.4e.5d.6b, | 1e.2d.3c.4e.5d.6c, | 1e.2d.3c.4e.5d.6d, | 1e.2d.3c.4e.5d.6e, | |
| 1e.2d.3c.4e.5d.6f, | 1e.2d.3c.4e.5e.6a, | 1e.2d.3c.4e.5e.6b, | 1e.2d.3c.4e.5e.6c, | |
| 1e.2d.3c.4e.5e.6d, | 1e.2d.3c.4e.5e.6e, | 1e.2d.3c.4e.5e.6f, | 1e.2d.3c.4e.5f.6a, | |
| 1e.2d.3c.4e.5f.6b, | 1e.2d.3c.4e.5f.6c, | 1e.2d.3c.4e.5f.6d, | 1e.2d.3c.4e.5f.6e, | 1e.2d.3c.4e.5f.6f, |
| 1e.2d.3c.4f.5a.6a, | 1e.2d.3c.4f.5a.6b, | 1e.2d.3c.4f.5a.6c, | 1e.2d.3c.4f.5a.6d, | |
| 1e.2d.3c.4f.5a.6e, | 1e.2d.3c.4f.5a.6f, | 1e.2d.3c.4f.5b.6a, | 1e.2d.3c.4f.5b.6b, | 1e.2d.3c.4f.5b.6c, |
| 1e.2d.3c.4f.5b.6d, | 1e.2d.3c.4f.5b.6e, | 1e.2d.3c.4f.5b.6f, | 1e.2d.3c.4f.5c.6a, | 1e.2d.3c.4f.5c.6b, |
| 1e.2d.3c.4f.5c.6c, | 1e.2d.3c.4f.5c.6d, | 1e.2d.3c.4f.5c.6e, | 1e.2d.3c.4f.5c.6f, | 1e.2d.3c.4f.5d.6a, |
| 1e.2d.3c.4f.5d.6b, | 1e.2d.3c.4f.5d.6c, | 1e.2d.3c.4f.5d.6d, | 1e.2d.3c.4f.5d.6e, | |
| 1e.2d.3c.4f.5d.6f, | 1e.2d.3c.4f.5e.6a, | 1e.2d.3c.4f.5e.6b, | 1e.2d.3c.4f.5e.6c, | 1e.2d.3c.4f.5e.6d, |
| 1e.2d.3c.4f.5e.6e, | 1e.2d.3c.4f.5e.6f, | 1e.2d.3c.4f.5f.6a, | 1e.2d.3c.4f.5f.6b, | 1e.2d.3c.4f.5f.6c, |
| 1e.2d.3c.4f.5f.6d, | 1e.2d.3c.4f.5f.6e, | 1e.2d.3c.4f.5f.6f, | 1e.2d.3d.4a.5a.6a, | |
| 1e.2d.3d.4a.5a.6b, | 1e.2d.3d.4a.5a.6c, | 1e.2d.3d.4a.5a.6d, | 1e.2d.3d.4a.5a.6e, | |
| 1e.2d.3d.4a.5a.6f, | 1e.2d.3d.4a.5b.6a, | 1e.2d.3d.4a.5b.6b, | 1e.2d.3d.4a.5b.6c, | |
| 1e.2d.3d.4a.5b.6d, | 1e.2d.3d.4a.5b.6e, | 1e.2d.3d.4a.5b.6f, | 1e.2d.3d.4a.5c.6a, | |
| 1e.2d.3d.4a.5c.6b, | 1e.2d.3d.4a.5c.6c, | 1e.2d.3d.4a.5c.6d, | 1e.2d.3d.4a.5c.6e, | |
| 1e.2d.3d.4a.5c.6f, | 1e.2d.3d.4a.5d.6a, | 1e.2d.3d.4a.5d.6b, | 1e.2d.3d.4a.5d.6c, | |
| 1e.2d.3d.4a.5d.6d, | 1e.2d.3d.4a.5d.6e, | 1e.2d.3d.4a.5d.6f, | 1e.2d.3d.4a.5e.6a, | |
| 1e.2d.3d.4a.5e.6b, | 1e.2d.3d.4a.5e.6c, | 1e.2d.3d.4a.5e.6d, | 1e.2d.3d.4a.5e.6e, | |
| 1e.2d.3d.4a.5e.6f, | 1e.2d.3d.4a.5f.6a, | 1e.2d.3d.4a.5f.6b, | 1e.2d.3d.4a.5f.6c, | |
| 1e.2d.3d.4a.5f.6d, | 1e.2d.3d.4a.5f.6e, | 1e.2d.3d.4a.5f.6f, | 1e.2d.3d.4b.5a.6a, | |
| 1e.2d.3d.4b.5a.6b, | 1e.2d.3d.4b.5a.6c, | 1e.2d.3d.4b.5a.6d, | 1e.2d.3d.4b.5a.6e, | |
| 1e.2d.3d.4b.5a.6f, | 1e.2d.3d.4b.5b.6a, | 1e.2d.3d.4b.5b.6b, | 1e.2d.3d.4b.5b.6c, | |
| 1e.2d.3d.4b.5b.6d, | 1e.2d.3d.4b.5b.6e, | 1e.2d.3d.4b.5b.6f, | 1e.2d.3d.4b.5c.6a, | |
| 1e.2d.3d.4b.5c.6b, | 1e.2d.3d.4b.5c.6c, | 1e.2d.3d.4b.5c.6d, | 1e.2d.3d.4b.5c.6e, | |
| 1e.2d.3d.4b.5c.6f, | 1e.2d.3d.4b.5d.6a, | 1e.2d.3d.4b.5d.6b, | 1e.2d.3d.4b.5d.6c, | |
| 1e.2d.3d.4b.5d.6d, | 1e.2d.3d.4b.5d.6e, | 1e.2d.3d.4b.5d.6f, | 1e.2d.3d.4b.5e.6a, | |
| 1e.2d.3d.4b.5e.6b, | 1e.2d.3d.4b.5e.6c, | 1e.2d.3d.4b.5e.6d, | 1e.2d.3d.4b.5e.6e, | |
| 1e.2d.3d.4b.5e.6f, | 1e.2d.3d.4b.5f.6a, | 1e.2d.3d.4b.5f.6b, | 1e.2d.3d.4b.5f.6c, | |
| 1e.2d.3d.4b.5f.6d, | 1e.2d.3d.4b.5f.6e, | 1e.2d.3d.4b.5f.6f, | 1e.2d.3d.4c.5a.6a, | |
| 1e.2d.3d.4c.5a.6b, | 1e.2d.3d.4c.5a.6c, | 1e.2d.3d.4c.5a.6d, | 1e.2d.3d.4c.5a.6e, | |
| 1e.2d.3d.4c.5a.6f, | 1e.2d.3d.4c.5b.6a, | 1e.2d.3d.4c.5b.6b, | 1e.2d.3d.4c.5b.6c, | |
| 1e.2d.3d.4c.5b.6d, | 1e.2d.3d.4c.5b.6e, | 1e.2d.3d.4c.5b.6f, | 1e.2d.3d.4c.5c.6a, | |
| 1e.2d.3d.4c.5c.6b, | 1e.2d.3d.4c.5c.6c, | 1e.2d.3d.4c.5c.6d, | 1e.2d.3d.4c.5c.6e, | |
| 1e.2d.3d.4c.5c.6f, | 1e.2d.3d.4c.5d.6a, | 1e.2d.3d.4c.5d.6b, | 1e.2d.3d.4c.5d.6c, | |
| 1e.2d.3d.4c.5d.6d, | 1e.2d.3d.4c.5d.6e, | 1e.2d.3d.4c.5d.6f, | 1e.2d.3d.4c.5e.6a, | |
| 1e.2d.3d.4c.5e.6b, | 1e.2d.3d.4c.5e.6c, | 1e.2d.3d.4c.5e.6d, | 1e.2d.3d.4c.5e.6e, | |
| 1e.2d.3d.4c.5e.6f, | 1e.2d.3d.4c.5f.6a, | 1e.2d.3d.4c.5f.6b, | 1e.2d.3d.4c.5f.6c, | |
| 1e.2d.3d.4c.5f.6d, | 1e.2d.3d.4c.5f.6e, | 1e.2d.3d.4c.5f.6f, | 1e.2d.3d.4d.5a.6a, | |
| 1e.2d.3d.4d.5a.6b, | 1e.2d.3d.4d.5a.6c, | 1e.2d.3d.4d.5a.6d, | 1e.2d.3d.4d.5a.6e, | |
| 1e.2d.3d.4d.5a.6f, | 1e.2d.3d.4d.5b.6a, | 1e.2d.3d.4d.5b.6b, | 1e.2d.3d.4d.5b.6c, | |
| 1e.2d.3d.4d.5b.6d, | 1e.2d.3d.4d.5b.6e, | 1e.2d.3d.4d.5b.6f, | 1e.2d.3d.4d.5c.6a, | |
| 1e.2d.3d.4d.5c.6b, | 1e.2d.3d.4d.5c.6c, | 1e.2d.3d.4d.5c.6d, | 1e.2d.3d.4d.5c.6e, | |
| 1e.2d.3d.4d.5c.6f, | 1e.2d.3d.4d.5d.6a, | 1e.2d.3d.4d.5d.6b, | 1e.2d.3d.4d.5d.6c, | |
| 1e.2d.3d.4d.5d.6d, | 1e.2d.3d.4d.5d.6e, | 1e.2d.3d.4d.5d.6f, | 1e.2d.3d.4d.5e.6a, | |
| 1e.2d.3d.4d.5e.6b, | 1e.2d.3d.4d.5e.6c, | 1e.2d.3d.4d.5e.6d, | 1e.2d.3d.4d.5e.6e, | |
| 1e.2d.3d.4d.5e.6f, | 1e.2d.3d.4d.5f.6a, | 1e.2d.3d.4d.5f.6b, | 1e.2d.3d.4d.5f.6c, | |
| 1e.2d.3d.4d.5f.6d, | 1e.2d.3d.4d.5f.6e, | 1e.2d.3d.4d.5f.6f, | 1e.2d.3d.4e.5a.6a, | |
| 1e.2d.3d.4e.5a.6b, | 1e.2d.3d.4e.5a.6c, | 1e.2d.3d.4e.5a.6d, | 1e.2d.3d.4e.5a.6e, | |
| 1e.2d.3d.4e.5a.6f, | 1e.2d.3d.4e.5b.6a, | 1e.2d.3d.4e.5b.6b, | 1e.2d.3d.4e.5b.6c, | |
| 1e.2d.3d.4e.5b.6d, | 1e.2d.3d.4e.5b.6e, | 1e.2d.3d.4e.5b.6f, | 1e.2d.3d.4e.5c.6a, | |
| 1e.2d.3d.4e.5c.6b, | 1e.2d.3d.4e.5c.6c, | 1e.2d.3d.4e.5c.6d, | 1e.2d.3d.4e.5c.6e, | |
| 1e.2d.3d.4e.5c.6f, | 1e.2d.3d.4e.5d.6a, | 1e.2d.3d.4e.5d.6b, | 1e.2d.3d.4e.5d.6c, | |
| 1e.2d.3d.4e.5d.6d, | 1e.2d.3d.4e.5d.6e, | 1e.2d.3d.4e.5d.6f, | 1e.2d.3d.4e.5e.6a, | |
| 1e.2d.3d.4e.5e.6b, | 1e.2d.3d.4e.5e.6c, | 1e.2d.3d.4e.5e.6d, | 1e.2d.3d.4e.5e.6e, | |
| 1e.2d.3d.4e.5e.6f, | 1e.2d.3d.4e.5f.6a, | 1e.2d.3d.4e.5f.6b, | 1e.2d.3d.4e.5f.6c, | |
| 1e.2d.3d.4e.5f.6d, | 1e.2d.3d.4e.5f.6e, | 1e.2d.3d.4e.5f.6f, | 1e.2d.3d.4f.5a.6a, | |
| 1e.2d.3d.4f.5a.6b, | 1e.2d.3d.4f.5a.6c, | 1e.2d.3d.4f.5a.6d, | 1e.2d.3d.4f.5a.6e, | |

TABLE 7-continued

List of Compounds of Formula (II)

| | | | | |
|---|---|---|---|---|
| 1e.2d.3d.4f.5a.6f, | 1e.2d.3d.4f.5b.6a, | 1e.2d.3d.4f.5b.6b, | 1e.2d.3d.4f.5b.6c, | |
| 1e.2d.3d.4f.5b.6d, | 1e.2d.3d.4f.5b.6e, | 1e.2d.3d.4f.5b.6f, | 1e.2d.3d.4f.5c.6a, | |
| 1e.2d.3d.4f.5c.6b, | 1e.2d.3d.4f.5c.6c, | 1e.2d.3d.4f.5c.6d, | 1e.2d.3d.4f.5c.6e, | |
| 1e.2d.3d.4f.5c.6f, | 1e.2d.3d.4f.5d.6a, | 1e.2d.3d.4f.5d.6b, | 1e.2d.3d.4f.5d.6c, | |
| 1e.2d.3d.4f.5d.6d, | 1e.2d.3d.4f.5d.6e, | 1e.2d.3d.4f.5d.6f, | 1e.2d.3d.4f.5e.6a, | |
| 1e.2d.3d.4f.5e.6b, | 1e.2d.3d.4f.5e.6c, | 1e.2d.3d.4f.5e.6d, | 1e.2d.3d.4f.5e.6e, | |
| 1e.2d.3d.4f.5e.6f, | 1e.2d.3d.4f.5f.6a, | 1e.2d.3d.4f.5f.6b, | 1e.2d.3d.4f.5f.6c, | |
| 1e.2d.3d.4f.5f.6d, | 1e.2d.3d.4f.5f.6e, | 1e.2d.3d.4f.5f.6f, | 1e.2d.3e.4a.5a.6a, | |
| 1e.2d.3e.4a.5a.6b, | 1e.2d.3e.4a.5a.6c, | 1e.2d.3e.4a.5a.6d, | 1e.2d.3e.4a.5a.6e, | |
| 1e.2d.3e.4a.5a.6f, | 1e.2d.3e.4a.5b.6a, | 1e.2d.3e.4a.5b.6b, | 1e.2d.3e.4a.5b.6c, | |
| 1e.2d.3e.4a.5b.6d, | 1e.2d.3e.4a.5b.6e, | 1e.2d.3e.4a.5b.6f, | 1e.2d.3e.4a.5c.6a, | |
| 1e.2d.3e.4a.5c.6b, | 1e.2d.3e.4a.5c.6c, | 1e.2d.3e.4a.5c.6d, | 1e.2d.3e.4a.5c.6e, | |
| 1e.2d.3e.4a.5c.6f, | 1e.2d.3e.4a.5d.6a, | 1e.2d.3e.4a.5d.6b, | 1e.2d.3e.4a.5d.6c, | |
| 1e.2d.3e.4a.5d.6d, | 1e.2d.3e.4a.5d.6e, | 1e.2d.3e.4a.5d.6f, | 1e.2d.3e.4a.5e.6a, | |
| 1e.2d.3e.4a.5e.6b, | 1e.2d.3e.4a.5e.6c, | 1e.2d.3e.4a.5e.6d, | 1e.2d.3e.4a.5e.6e, | |
| 1e.2d.3e.4a.5e.6f, | 1e.2d.3e.4a.5f.6a, | 1e.2d.3e.4a.5f.6b, | 1e.2d.3e.4a.5f.6c, | |
| 1e.2d.3e.4a.5f.6d, | 1e.2d.3e.4a.5f.6e, | 1e.2d.3e.4a.5f.6f, | 1e.2d.3e.4b.5a.6a, | |
| 1e.2d.3e.4b.5a.6b, | 1e.2d.3e.4b.5a.6c, | 1e.2d.3e.4b.5a.6d, | 1e.2d.3e.4b.5a.6e, | |
| 1e.2d.3e.4b.5a.6f, | 1e.2d.3e.4b.5b.6a, | 1e.2d.3e.4b.5b.6b, | 1e.2d.3e.4b.5b.6c, | |
| 1e.2d.3e.4b.5b.6d, | 1e.2d.3e.4b.5b.6e, | 1e.2d.3e.4b.5b.6f, | 1e.2d.3e.4b.5c.6a, | |
| 1e.2d.3e.4b.5c.6b, | 1e.2d.3e.4b.5c.6c, | 1e.2d.3e.4b.5c.6d, | 1e.2d.3e.4b.5c.6e, | |
| 1e.2d.3e.4b.5c.6f, | 1e.2d.3e.4b.5d.6a, | 1e.2d.3e.4b.5d.6b, | 1e.2d.3e.4b.5d.6c, | |
| 1e.2d.3e.4b.5d.6d, | 1e.2d.3e.4b.5d.6e, | 1e.2d.3e.4b.5d.6f, | 1e.2d.3e.4b.5e.6a, | |
| 1e.2d.3e.4b.5e.6b, | 1e.2d.3e.4b.5e.6c, | 1e.2d.3e.4b.5e.6d, | 1e.2d.3e.4b.5e.6e, | |
| 1e.2d.3e.4b.5e.6f, | 1e.2d.3e.4b.5f.6a, | 1e.2d.3e.4b.5f.6b, | 1e.2d.3e.4b.5f.6c, | |
| 1e.2d.3e.4b.5f.6d, | 1e.2d.3e.4b.5f.6e, | 1e.2d.3e.4b.5f.6f, | 1e.2d.3e.4c.5a.6a, | |
| 1e.2d.3e.4c.5a.6b, | 1e.2d.3e.4c.5a.6c, | 1e.2d.3e.4c.5a.6d, | 1e.2d.3e.4c.5a.6e, | |
| 1e.2d.3e.4c.5a.6f, | 1e.2d.3e.4c.5b.6a, | 1e.2d.3e.4c.5b.6b, | 1e.2d.3e.4c.5b.6c, | |
| 1e.2d.3e.4c.5b.6d, | 1e.2d.3e.4c.5b.6e, | 1e.2d.3e.4c.5b.6f, | 1e.2d.3e.4c.5c.6a, | |
| 1e.2d.3e.4c.5c.6b, | 1e.2d.3e.4c.5c.6c, | 1e.2d.3e.4c.5c.6d, | 1e.2d.3e.4c.5c.6e, | |
| 1e.2d.3e.4c.5c.6f, | 1e.2d.3e.4c.5d.6a, | 1e.2d.3e.4c.5d.6b, | 1e.2d.3e.4c.5d.6c, | |
| 1e.2d.3e.4c.5d.6d, | 1e.2d.3e.4c.5d.6e, | 1e.2d.3e.4c.5d.6f, | 1e.2d.3e.4c.5e.6a, | |
| 1e.2d.3e.4c.5e.6b, | 1e.2d.3e.4c.5e.6c, | 1e.2d.3e.4c.5e.6d, | 1e.2d.3e.4c.5e.6e, | |
| 1e.2d.3e.4c.5e.6f, | 1e.2d.3e.4c.5f.6a, | 1e.2d.3e.4c.5f.6b, | 1e.2d.3e.4c.5f.6c, | 1e.2d.3e.4c.5f.6d, |
| 1e.2d.3e.4c.5f.6e, | 1e.2d.3e.4c.5f.6f, | 1e.2d.3e.4d.5a.6a, | 1e.2d.3e.4d.5a.6b, | |
| 1e.2d.3e.4d.5a.6c, | 1e.2d.3e.4d.5a.6d, | 1e.2d.3e.4d.5a.6e, | 1e.2d.3e.4d.5a.6f, | |
| 1e.2d.3e.4d.5b.6a, | 1e.2d.3e.4d.5b.6b, | 1e.2d.3e.4d.5b.6c, | 1e.2d.3e.4d.5b.6d, | |
| 1e.2d.3e.4d.5b.6e, | 1e.2d.3e.4d.5b.6f, | 1e.2d.3e.4d.5c.6a, | 1e.2d.3e.4d.5c.6b, | |
| 1e.2d.3e.4d.5c.6c, | 1e.2d.3e.4d.5c.6d, | 1e.2d.3e.4d.5c.6e, | 1e.2d.3e.4d.5c.6f, | |
| 1e.2d.3e.4d.5d.6a, | 1e.2d.3e.4d.5d.6b, | 1e.2d.3e.4d.5d.6c, | 1e.2d.3e.4d.5d.6d, | |
| 1e.2d.3e.4d.5d.6e, | 1e.2d.3e.4d.5d.6f, | 1e.2d.3e.4d.5e.6a, | 1e.2d.3e.4d.5e.6b, | |
| 1e.2d.3e.4d.5e.6c, | 1e.2d.3e.4d.5e.6d, | 1e.2d.3e.4d.5e.6e, | 1e.2d.3e.4d.5e.6f, | |
| 1e.2d.3e.4d.5f.6a, | 1e.2d.3e.4d.5f.6b, | 1e.2d.3e.4d.5f.6c, | 1e.2d.3e.4d.5f.6d, | |
| 1e.2d.3e.4d.5f.6e, | 1e.2d.3e.4d.5f.6f, | 1e.2d.3e.4e.5a.6a, | 1e.2d.3e.4e.5a.6b, | |
| 1e.2d.3e.4e.5a.6c, | 1e.2d.3e.4e.5a.6d, | 1e.2d.3e.4e.5a.6e, | 1e.2d.3e.4e.5a.6f, | |
| 1e.2d.3e.4e.5b.6a, | 1e.2d.3e.4e.5b.6b, | 1e.2d.3e.4e.5b.6c, | 1e.2d.3e.4e.5b.6d, | |
| 1e.2d.3e.4e.5b.6e, | 1e.2d.3e.4e.5b.6f, | 1e.2d.3e.4e.5c.6a, | 1e.2d.3e.4e.5c.6b, | |
| 1e.2d.3e.4e.5c.6c, | 1e.2d.3e.4e.5c.6d, | 1e.2d.3e.4e.5c.6e, | 1e.2d.3e.4e.5c.6f, | |
| 1e.2d.3e.4e.5d.6a, | 1e.2d.3e.4e.5d.6b, | 1e.2d.3e.4e.5d.6c, | 1e.2d.3e.4e.5d.6d, | |
| 1e.2d.3e.4e.5d.6e, | 1e.2d.3e.4e.5d.6f, | 1e.2d.3e.4e.5e.6a, | 1e.2d.3e.4e.5e.6b, | |
| 1e.2d.3e.4e.5e.6c, | 1e.2d.3e.4e.5e.6d, | 1e.2d.3e.4e.5e.6e, | 1e.2d.3e.4e.5e.6f, | |
| 1e.2d.3e.4e.5f.6a, | 1e.2d.3e.4e.5f.6b, | 1e.2d.3e.4e.5f.6c, | 1e.2d.3e.4e.5f.6d, | |
| 1e.2d.3e.4e.5f.6e, | 1e.2d.3e.4e.5f.6f, | 1e.2d.3e.4f.5a.6a, | 1e.2d.3e.4f.5a.6b, | 1e.2d.3e.4f.5a.6c, |
| 1e.2d.3e.4f.5a.6d, | 1e.2d.3e.4f.5a.6e, | 1e.2d.3e.4f.5a.6f, | 1e.2d.3e.4f.5b.6a, | |
| 1e.2d.3e.4f.5b.6b, | 1e.2d.3e.4f.5b.6c, | 1e.2d.3e.4f.5b.6d, | 1e.2d.3e.4f.5b.6e, | |
| 1e.2d.3e.4f.5b.6f, | 1e.2d.3e.4f.5c.6a, | 1e.2d.3e.4f.5c.6b, | 1e.2d.3e.4f.5c.6c, | 1e.2d.3e.4f.5c.6d, |
| 1e.2d.3e.4f.5c.6e, | 1e.2d.3e.4f.5c.6f, | 1e.2d.3e.4f.5d.6a, | 1e.2d.3e.4f.5d.6b, | |
| 1e.2d.3e.4f.5d.6c, | 1e.2d.3e.4f.5d.6d, | 1e.2d.3e.4f.5d.6e, | 1e.2d.3e.4f.5d.6f, | |
| 1e.2d.3e.4f.5e.6a, | 1e.2d.3e.4f.5e.6b, | 1e.2d.3e.4f.5e.6c, | 1e.2d.3e.4f.5e.6d, | |
| 1e.2d.3e.4f.5e.6e, | 1e.2d.3e.4f.5e.6f, | 1e.2d.3e.4f.5f.6a, | 1e.2d.3e.4f.5f.6b, | 1e.2d.3e.4f.5f.6c, |
| 1e.2d.3e.4f.5f.6d, | 1e.2d.3e.4f.5f.6e, | 1e.2d.3e.4f.5f.6f, | 1e.2d.3f.4a.5a.6a, | 1e.2d.3f.4a.5a.6b, |
| 1e.2d.3f.4a.5a.6c, | 1e.2d.3f.4a.5a.6d, | 1e.2d.3f.4a.5a.6e, | 1e.2d.3f.4a.5a.6f, | |
| 1e.2d.3f.4a.5b.6a, | 1e.2d.3f.4a.5b.6b, | 1e.2d.3f.4a.5b.6c, | 1e.2d.3f.4a.5b.6d, | |
| 1e.2d.3f.4a.5b.6e, | 1e.2d.3f.4a.5b.6f, | 1e.2d.3f.4a.5c.6a, | 1e.2d.3f.4a.5c.6b, | 1e.2d.3f.4a.5c.6c, |
| 1e.2d.3f.4a.5c.6d, | 1e.2d.3f.4a.5c.6e, | 1e.2d.3f.4a.5c.6f, | 1e.2d.3f.4a.5d.6a, | |
| 1e.2d.3f.4a.5d.6b, | 1e.2d.3f.4a.5d.6c, | 1e.2d.3f.4a.5d.6d, | 1e.2d.3f.4a.5d.6e, | |
| 1e.2d.3f.4a.5d.6f, | 1e.2d.3f.4a.5e.6a, | 1e.2d.3f.4a.5e.6b, | 1e.2d.3f.4a.5e.6c, | |
| 1e.2d.3f.4a.5e.6d, | 1e.2d.3f.4a.5e.6e, | 1e.2d.3f.4a.5e.6f, | 1e.2d.3f.4a.5f.6a, | 1e.2d.3f.4a.5f.6b, |
| 1e.2d.3f.4a.5f.6c, | 1e.2d.3f.4a.5f.6d, | 1e.2d.3f.4a.5f.6e, | 1e.2d.3f.4a.5f.6f, | 1e.2d.3f.4b.5a.6a, |
| 1e.2d.3f.4b.5a.6b, | 1e.2d.3f.4b.5a.6c, | 1e.2d.3f.4b.5a.6d, | 1e.2d.3f.4b.5a.6e, | |
| 1e.2d.3f.4b.5a.6f, | 1e.2d.3f.4b.5b.6a, | 1e.2d.3f.4b.5b.6b, | 1e.2d.3f.4b.5b.6c, | |
| 1e.2d.3f.4b.5b.6d, | 1e.2d.3f.4b.5b.6e, | 1e.2d.3f.4b.5b.6f, | 1e.2d.3f.4b.5c.6a, | |
| 1e.2d.3f.4b.5c.6b, | 1e.2d.3f.4b.5c.6c, | 1e.2d.3f.4b.5c.6d, | 1e.2d.3f.4b.5c.6e, | |
| 1e.2d.3f.4b.5c.6f, | 1e.2d.3f.4b.5d.6a, | 1e.2d.3f.4b.5d.6b, | 1e.2d.3f.4b.5d.6c, | |
| 1e.2d.3f.4b.5d.6d, | 1e.2d.3f.4b.5d.6e, | 1e.2d.3f.4b.5d.6f, | 1e.2d.3f.4b.5e.6a, | |
| 1e.2d.3f.4b.5e.6b, | 1e.2d.3f.4b.5e.6c, | 1e.2d.3f.4b.5e.6d, | 1e.2d.3f.4b.5e.6e, | |
| 1e.2d.3f.4b.5e.6f, | 1e.2d.3f.4b.5f.6a, | 1e.2d.3f.4b.5f.6b, | 1e.2d.3f.4b.5f.6c, | 1e.2d.3f.4b.5f.6d, |
| 1e.2d.3f.4b.5f.6e, | 1e.2d.3f.4b.5f.6f, | 1e.2d.3f.4c.5a.6a, | 1e.2d.3f.4c.5a.6b, | 1e.2d.3f.4c.5a.6c, |

TABLE 7-continued

List of Compounds of Formula (II)

| | | | | |
|---|---|---|---|---|
| 1e.2d.3f.4c.5a.6d, | 1e.2d.3f.4c.5a.6e, | 1e.2d.3f.4c.5a.6f, | 1e.2d.3f.4c.5b.6a, | |
| 1e.2d.3f.4c.5b.6b, | 1e.2d.3f.4c.5b.6c, | 1e.2d.3f.4c.5b.6d, | 1e.2d.3f.4c.5b.6e, | |
| 1e.2d.3f.4c.5b.6f, | 1e.2d.3f.4c.5c.6a, | 1e.2d.3f.4c.5c.6b, | 1e.2d.3f.4c.5c.6c, | 1e.2d.3f.4c.5c.6d, |
| 1e.2d.3f.4c.5c.6e, | 1e.2d.3f.4c.5c.6f, | 1e.2d.3f.4c.5d.6a, | 1e.2d.3f.4c.5d.6b, | 1e.2d.3f.4c.5d.6c, |
| 1e.2d.3f.4c.5d.6d, | 1e.2d.3f.4c.5d.6e, | 1e.2d.3f.4c.5d.6f, | 1e.2d.3f.4c.5e.6a, | |
| 1e.2d.3f.4c.5e.6b, | 1e.2d.3f.4c.5e.6c, | 1e.2d.3f.4c.5e.6d, | 1e.2d.3f.4c.5e.6e, | 1e.2d.3f.4c.5e.6f, |
| 1e.2d.3f.4c.5f.6a, | 1e.2d.3f.4c.5f.6b, | 1e.2d.3f.4c.5f.6c, | 1e.2d.3f.4c.5f.6d, | 1e.2d.3f.4c.5f.6e, |
| 1e.2d.3f.4c.5f.6f, | 1e.2d.3f.4d.5a.6a, | 1e.2d.3f.4d.5a.6b, | 1e.2d.3f.4d.5a.6c, | |
| 1e.2d.3f.4d.5a.6d, | 1e.2d.3f.4d.5a.6e, | 1e.2d.3f.4d.5a.6f, | 1e.2d.3f.4d.5b.6a, | |
| 1e.2d.3f.4d.5b.6b, | 1e.2d.3f.4d.5b.6c, | 1e.2d.3f.4d.5b.6d, | 1e.2d.3f.4d.5b.6e, | |
| 1e.2d.3f.4d.5b.6f, | 1e.2d.3f.4d.5c.6a, | 1e.2d.3f.4d.5c.6b, | 1e.2d.3f.4d.5c.6c, | |
| 1e.2d.3f.4d.5c.6d, | 1e.2d.3f.4d.5c.6e, | 1e.2d.3f.4d.5c.6f, | 1e.2d.3f.4d.5d.6a, | |
| 1e.2d.3f.4d.5d.6b, | 1e.2d.3f.4d.5d.6c, | 1e.2d.3f.4d.5d.6d, | 1e.2d.3f.4d.5d.6e, | |
| 1e.2d.3f.4d.5d.6f, | 1e.2d.3f.4d.5e.6a, | 1e.2d.3f.4d.5e.6b, | 1e.2d.3f.4d.5e.6c, | |
| 1e.2d.3f.4d.5e.6d, | 1e.2d.3f.4d.5e.6e, | 1e.2d.3f.4d.5e.6f, | 1e.2d.3f.4d.5f.6a, | |
| 1e.2d.3f.4d.5f.6b, | 1e.2d.3f.4d.5f.6c, | 1e.2d.3f.4d.5f.6d, | 1e.2d.3f.4d.5f.6e, | 1e.2d.3f.4d.5f.6f, |
| 1e.2d.3f.4e.5a.6a, | 1e.2d.3f.4e.5a.6b, | 1e.2d.3f.4e.5a.6c, | 1e.2d.3f.4e.5a.6d, | |
| 1e.2d.3f.4e.5a.6e, | 1e.2d.3f.4e.5a.6f, | 1e.2d.3f.4e.5b.6a, | 1e.2d.3f.4e.5b.6b, | |
| 1e.2d.3f.4e.5b.6c, | 1e.2d.3f.4e.5b.6d, | 1e.2d.3f.4e.5b.6e, | 1e.2d.3f.4e.5b.6f, | |
| 1e.2d.3f.4e.5c.6a, | 1e.2d.3f.4e.5c.6b, | 1e.2d.3f.4e.5c.6c, | 1e.2d.3f.4e.5c.6d, | 1e.2d.3f.4e.5c.6e, |
| 1e.2d.3f.4e.5c.6f, | 1e.2d.3f.4e.5d.6a, | 1e.2d.3f.4e.5d.6b, | 1e.2d.3f.4e.5d.6c, | |
| 1e.2d.3f.4e.5d.6d, | 1e.2d.3f.4e.5d.6e, | 1e.2d.3f.4e.5d.6f, | 1e.2d.3f.4e.5e.6a, | |
| 1e.2d.3f.4e.5e.6b, | 1e.2d.3f.4e.5e.6c, | 1e.2d.3f.4e.5e.6d, | 1e.2d.3f.4e.5e.6e, | 1e.2d.3f.4e.5e.6f, |
| 1e.2d.3f.4e.5f.6a, | 1e.2d.3f.4e.5f.6b, | 1e.2d.3f.4e.5f.6c, | 1e.2d.3f.4e.5f.6d, | 1e.2d.3f.4e.5f.6e, |
| 1e.2d.3f.4e.5f.6f, | 1e.2d.3f.4f.5a.6a, | 1e.2d.3f.4f.5a.6b, | 1e.2d.3f.4f.5a.6c, | 1e.2d.3f.4f.5a.6d, |
| 1e.2d.3f.4f.5a.6e, | 1e.2d.3f.4f.5a.6f, | 1e.2d.3f.4f.5b.6a, | 1e.2d.3f.4f.5b.6b, | 1e.2d.3f.4f.5b.6c, |
| 1e.2d.3f.4f.5b.6d, | 1e.2d.3f.4f.5b.6e, | 1e.2d.3f.4f.5b.6f, | 1e.2d.3f.4f.5c.6a, | 1e.2d.3f.4f.5c.6b, |
| 1e.2d.3f.4f.5c.6c, | 1e.2d.3f.4f.5c.6d, | 1e.2d.3f.4f.5c.6e, | 1e.2d.3f.4f.5c.6f, | 1e.2d.3f.4f.5d.6a, |
| 1e.2d.3f.4f.5d.6b, | 1e.2d.3f.4f.5d.6c, | 1e.2d.3f.4f.5d.6d, | 1e.2d.3f.4f.5d.6e, | 1e.2d.3f.4f.5d.6f, |
| 1e.2d.3f.4f.5e.6a, | 1e.2d.3f.4f.5e.6b, | 1e.2d.3f.4f.5e.6c, | 1e.2d.3f.4f.5e.6d, | 1e.2d.3f.4f.5e.6e, |
| 1e.2d.3f.4f.5e.6f, | 1e.2d.3f.4f.5f.6a, | 1e.2d.3f.4f.5f.6b, | 1e.2d.3f.4f.5f.6c, | 1e.2d.3f.4f.5f.6d, |
| 1e.2d.3f.4f.5f.6e, | 1e.2d.3f.4f.5f.6f, | 1e.2e.3a.4a.5a.6a, | 1e.2e.3a.4a.5a.6b, | 1e.2e.3a.4a.5a.6c, |
| 1e.2e.3a.4a.5a.6d, | 1e.2e.3a.4a.5a.6e, | 1e.2e.3a.4a.5a.6f, | 1e.2e.3a.4a.5b.6a, | |
| 1e.2e.3a.4a.5b.6b, | 1e.2e.3a.4a.5b.6c, | 1e.2e.3a.4a.5b.6d, | 1e.2e.3a.4a.5b.6e, | |
| 1e.2e.3a.4a.5b.6f, | 1e.2e.3a.4a.5c.6a, | 1e.2e.3a.4a.5c.6b, | 1e.2e.3a.4a.5c.6c, | |
| 1e.2e.3a.4a.5c.6d, | 1e.2e.3a.4a.5c.6e, | 1e.2e.3a.4a.5c.6f, | 1e.2e.3a.4a.5d.6a, | |
| 1e.2e.3a.4a.5d.6b, | 1e.2e.3a.4a.5d.6c, | 1e.2e.3a.4a.5d.6d, | 1e.2e.3a.4a.5d.6e, | |
| 1e.2e.3a.4a.5d.6f, | 1e.2e.3a.4a.5e.6a, | 1e.2e.3a.4a.5e.6b, | 1e.2e.3a.4a.5e.6c, | |
| 1e.2e.3a.4a.5e.6d, | 1e.2e.3a.4a.5e.6e, | 1e.2e.3a.4a.5e.6f, | 1e.2e.3a.4a.5f.6a, | 1e.2e.3a.4a.5f.6b, |
| 1e.2e.3a.4a.5f.6c, | 1e.2e.3a.4a.5f.6d, | 1e.2e.3a.4a.5f.6e, | 1e.2e.3a.4a.5f.6f, | 1e.2e.3a.4b.5a.6a, |
| 1e.2e.3a.4b.5a.6b, | 1e.2e.3a.4b.5a.6c, | 1e.2e.3a.4b.5a.6d, | 1e.2e.3a.4b.5a.6e, | |
| 1e.2e.3a.4b.5a.6f, | 1e.2e.3a.4b.5b.6a, | 1e.2e.3a.4b.5b.6b, | 1e.2e.3a.4b.5b.6c, | |
| 1e.2e.3a.4b.5b.6d, | 1e.2e.3a.4b.5b.6e, | 1e.2e.3a.4b.5b.6f, | 1e.2e.3a.4b.5c.6a, | |
| 1e.2e.3a.4b.5c.6b, | 1e.2e.3a.4b.5c.6c, | 1e.2e.3a.4b.5c.6d, | 1e.2e.3a.4b.5c.6e, | |
| 1e.2e.3a.4b.5c.6f, | 1e.2e.3a.4b.5d.6a, | 1e.2e.3a.4b.5d.6b, | 1e.2e.3a.4b.5d.6c, | |
| 1e.2e.3a.4b.5d.6d, | 1e.2e.3a.4b.5d.6e, | 1e.2e.3a.4b.5d.6f, | 1e.2e.3a.4b.5e.6a, | |
| 1e.2e.3a.4b.5e.6b, | 1e.2e.3a.4b.5e.6c, | 1e.2e.3a.4b.5e.6d, | 1e.2e.3a.4b.5e.6e, | |
| 1e.2e.3a.4b.5e.6f, | 1e.2e.3a.4b.5f.6a, | 1e.2e.3a.4b.5f.6b, | 1e.2e.3a.4b.5f.6c, | 1e.2e.3a.4b.5f.6d, |
| 1e.2e.3a.4b.5f.6e, | 1e.2e.3a.4b.5f.6f, | 1e.2e.3a.4c.5a.6a, | 1e.2e.3a.4c.5a.6b, | 1e.2e.3a.4c.5a.6c, |
| 1e.2e.3a.4c.5a.6d, | 1e.2e.3a.4c.5a.6e, | 1e.2e.3a.4c.5a.6f, | 1e.2e.3a.4c.5b.6a, | |
| 1e.2e.3a.4c.5b.6b, | 1e.2e.3a.4c.5b.6c, | 1e.2e.3a.4c.5b.6d, | 1e.2e.3a.4c.5b.6e, | |
| 1e.2e.3a.4c.5b.6f, | 1e.2e.3a.4c.5c.6a, | 1e.2e.3a.4c.5c.6b, | 1e.2e.3a.4c.5c.6c, | 1e.2e.3a.4c.5c.6d, |
| 1e.2e.3a.4c.5c.6e, | 1e.2e.3a.4c.5c.6f, | 1e.2e.3a.4c.5d.6a, | 1e.2e.3a.4c.5d.6b, | |
| 1e.2e.3a.4c.5d.6c, | 1e.2e.3a.4c.5d.6d, | 1e.2e.3a.4c.5d.6e, | 1e.2e.3a.4c.5d.6f, | |
| 1e.2e.3a.4c.5e.6a, | 1e.2e.3a.4c.5e.6b, | 1e.2e.3a.4c.5e.6c, | 1e.2e.3a.4c.5e.6d, | |
| 1e.2e.3a.4c.5e.6e, | 1e.2e.3a.4c.5e.6f, | 1e.2e.3a.4c.5f.6a, | 1e.2e.3a.4c.5f.6b, | 1e.2e.3a.4c.5f.6c, |
| 1e.2e.3a.4c.5f.6d, | 1e.2e.3a.4c.5f.6e, | 1e.2e.3a.4c.5f.6f, | 1e.2e.3a.4d.5a.6a, | 1e.2e.3a.4d.5a.6b, |
| 1e.2e.3a.4d.5a.6c, | 1e.2e.3a.4d.5a.6d, | 1e.2e.3a.4d.5a.6e, | 1e.2e.3a.4d.5a.6f, | |
| 1e.2e.3a.4d.5b.6a, | 1e.2e.3a.4d.5b.6b, | 1e.2e.3a.4d.5b.6c, | 1e.2e.3a.4d.5b.6d, | |
| 1e.2e.3a.4d.5b.6e, | 1e.2e.3a.4d.5b.6f, | 1e.2e.3a.4d.5c.6a, | 1e.2e.3a.4d.5c.6b, | |
| 1e.2e.3a.4d.5c.6c, | 1e.2e.3a.4d.5c.6d, | 1e.2e.3a.4d.5c.6e, | 1e.2e.3a.4d.5c.6f, | |
| 1e.2e.3a.4d.5d.6a, | 1e.2e.3a.4d.5d.6b, | 1e.2e.3a.4d.5d.6c, | 1e.2e.3a.4d.5d.6d, | |
| 1e.2e.3a.4d.5d.6e, | 1e.2e.3a.4d.5d.6f, | 1e.2e.3a.4d.5e.6a, | 1e.2e.3a.4d.5e.6b, | |
| 1e.2e.3a.4d.5e.6c, | 1e.2e.3a.4d.5e.6d, | 1e.2e.3a.4d.5e.6e, | 1e.2e.3a.4d.5e.6f, | |
| 1e.2e.3a.4d.5f.6a, | 1e.2e.3a.4d.5f.6b, | 1e.2e.3a.4d.5f.6c, | 1e.2e.3a.4d.5f.6d, | |
| 1e.2e.3a.4d.5f.6e, | 1e.2e.3a.4d.5f.6f, | 1e.2e.3a.4e.5a.6a, | 1e.2e.3a.4e.5a.6b, | |
| 1e.2e.3a.4e.5a.6c, | 1e.2e.3a.4e.5a.6d, | 1e.2e.3a.4e.5a.6e, | 1e.2e.3a.4e.5a.6f, | |
| 1e.2e.3a.4e.5b.6a, | 1e.2e.3a.4e.5b.6b, | 1e.2e.3a.4e.5b.6c, | 1e.2e.3a.4e.5b.6d, | |
| 1e.2e.3a.4e.5b.6e, | 1e.2e.3a.4e.5b.6f, | 1e.2e.3a.4e.5c.6a, | 1e.2e.3a.4e.5c.6b, | |
| 1e.2e.3a.4e.5c.6c, | 1e.2e.3a.4e.5c.6d, | 1e.2e.3a.4e.5c.6e, | 1e.2e.3a.4e.5c.6f, | |
| 1e.2e.3a.4e.5d.6a, | 1e.2e.3a.4e.5d.6b, | 1e.2e.3a.4e.5d.6c, | 1e.2e.3a.4e.5d.6d, | |
| 1e.2e.3a.4e.5d.6e, | 1e.2e.3a.4e.5d.6f, | 1e.2e.3a.4e.5e.6a, | 1e.2e.3a.4e.5e.6b, | |
| 1e.2e.3a.4e.5e.6c, | 1e.2e.3a.4e.5e.6d, | 1e.2e.3a.4e.5e.6e, | 1e.2e.3a.4e.5e.6f, | 1e.2e.3a.4e.5f.6a, |
| 1e.2e.3a.4e.5f.6b, | 1e.2e.3a.4e.5f.6c, | 1e.2e.3a.4e.5f.6d, | 1e.2e.3a.4e.5f.6e, | 1e.2e.3a.4e.5f.6f, |
| 1e.2e.3a.4f.5a.6a, | 1e.2e.3a.4f.5a.6b, | 1e.2e.3a.4f.5a.6c, | 1e.2e.3a.4f.5a.6d, | 1e.2e.3a.4f.5a.6e, |
| 1e.2e.3a.4f.5a.6f, | 1e.2e.3a.4f.5b.6a, | 1e.2e.3a.4f.5b.6b, | 1e.2e.3a.4f.5b.6c, | 1e.2e.3a.4f.5b.6d, |
| 1e.2e.3a.4f.5b.6e, | 1e.2e.3a.4f.5b.6f, | 1e.2e.3a.4f.5c.6a, | 1e.2e.3a.4f.5c.6b, | 1e.2e.3a.4f.5c.6c, |
| 1e.2e.3a.4f.5c.6d, | 1e.2e.3a.4f.5c.6e, | 1e.2e.3a.4f.5c.6f, | 1e.2e.3a.4f.5d.6a, | 1e.2e.3a.4f.5d.6b, |

TABLE 7-continued

List of Compounds of Formula (II)

| | | | | |
|---|---|---|---|---|
| 1e.2e.3a.4f.5d.6c, | 1e.2e.3a.4f.5d.6d, | 1e.2e.3a.4f.5d.6e, | 1e.2e.3a.4f.5d.6f, | 1e.2e.3a.4f.5e.6a, |
| 1e.2e.3a.4f.5e.6b, | 1e.2e.3a.4f.5e.6c, | 1e.2e.3a.4f.5e.6d, | 1e.2e.3a.4f.5e.6e, | 1e.2e.3a.4f.5e.6f, |
| 1e.2e.3a.4f.5f.6a, | 1e.2e.3a.4f.5f.6b, | 1e.2e.3a.4f.5f.6c, | 1e.2e.3a.4f.5f.6d, | 1e.2e.3a.4f.5f.6e, |
| 1e.2e.3a.4f.5f.6f, | 1e.2e.3b.4a.5a.6a, | 1e.2e.3b.4a.5a.6b, | 1e.2e.3b.4a.5a.6c, | |
| 1e.2e.3b.4a.5a.6d, | 1e.2e.3b.4a.5a.6e, | 1e.2e.3b.4a.5a.6f, | 1e.2e.3b.4a.5b.6a, | |
| 1e.2e.3b.4a.5b.6b, | 1e.2e.3b.4a.5b.6c, | 1e.2e.3b.4a.5b.6d, | 1e.2e.3b.4a.5b.6e, | |
| 1e.2e.3b.4a.5b.6f, | 1e.2e.3b.4a.5c.6a, | 1e.2e.3b.4a.5c.6b, | 1e.2e.3b.4a.5c.6c, | |
| 1e.2e.3b.4a.5c.6d, | 1e.2e.3b.4a.5c.6e, | 1e.2e.3b.4a.5c.6f, | 1e.2e.3b.4a.5d.6a, | |
| 1e.2e.3b.4a.5d.6b, | 1e.2e.3b.4a.5d.6c, | 1e.2e.3b.4a.5d.6d, | 1e.2e.3b.4a.5d.6e, | |
| 1e.2e.3b.4a.5d.6f, | 1e.2e.3b.4a.5e.6a, | 1e.2e.3b.4a.5e.6b, | 1e.2e.3b.4a.5e.6c, | |
| 1e.2e.3b.4a.5e.6d, | 1e.2e.3b.4a.5e.6e, | 1e.2e.3b.4a.5e.6f, | 1e.2e.3b.4a.5f.6a, | |
| 1e.2e.3b.4a.5f.6b, | 1e.2e.3b.4a.5f.6c, | 1e.2e.3b.4a.5f.6d, | 1e.2e.3b.4a.5f.6e, | 1e.2e.3b.4a.5f.6f, |
| 1e.2e.3b.4b.5a.6a, | 1e.2e.3b.4b.5a.6b, | 1e.2e.3b.4b.5a.6c, | 1e.2e.3b.4b.5a.6d, | |
| 1e.2e.3b.4b.5a.6e, | 1e.2e.3b.4b.5a.6f, | 1e.2e.3b.4b.5b.6a, | 1e.2e.3b.4b.5b.6b, | |
| 1e.2e.3b.4b.5b.6c, | 1e.2e.3b.4b.5b.6d, | 1e.2e.3b.4b.5b.6e, | 1e.2e.3b.4b.5b.6f, | |
| 1e.2e.3b.4b.5c.6a, | 1e.2e.3b.4b.5c.6b, | 1e.2e.3b.4b.5c.6c, | 1e.2e.3b.4b.5c.6d, | |
| 1e.2e.3b.4b.5c.6e, | 1e.2e.3b.4b.5c.6f, | 1e.2e.3b.4b.5d.6a, | 1e.2e.3b.4b.5d.6b, | |
| 1e.2e.3b.4b.5d.6c, | 1e.2e.3b.4b.5d.6d, | 1e.2e.3b.4b.5d.6e, | 1e.2e.3b.4b.5d.6f, | |
| 1e.2e.3b.4b.5e.6a, | 1e.2e.3b.4b.5e.6b, | 1e.2e.3b.4b.5e.6c, | 1e.2e.3b.4b.5e.6d, | |
| 1e.2e.3b.4b.5e.6e, | 1e.2e.3b.4b.5e.6f, | 1e.2e.3b.4b.5f.6a, | 1e.2e.3b.4b.5f.6b, | |
| 1e.2e.3b.4b.5f.6c, | 1e.2e.3b.4b.5f.6d, | 1e.2e.3b.4b.5f.6e, | 1e.2e.3b.4b.5f.6f, | |
| 1e.2e.3b.4c.5a.6a, | 1e.2e.3b.4c.5a.6b, | 1e.2e.3b.4c.5a.6c, | 1e.2e.3b.4c.5a.6d, | |
| 1e.2e.3b.4c.5a.6e, | 1e.2e.3b.4c.5a.6f, | 1e.2e.3b.4c.5b.6a, | 1e.2e.3b.4c.5b.6b, | |
| 1e.2e.3b.4c.5b.6c, | 1e.2e.3b.4c.5b.6d, | 1e.2e.3b.4c.5b.6e, | 1e.2e.3b.4c.5b.6f, | |
| 1e.2e.3b.4c.5c.6a, | 1e.2e.3b.4c.5c.6b, | 1e.2e.3b.4c.5c.6c, | 1e.2e.3b.4c.5c.6d, | |
| 1e.2e.3b.4c.5c.6e, | 1e.2e.3b.4c.5c.6f, | 1e.2e.3b.4c.5d.6a, | 1e.2e.3b.4c.5d.6b, | |
| 1e.2e.3b.4c.5d.6c, | 1e.2e.3b.4c.5d.6d, | 1e.2e.3b.4c.5d.6e, | 1e.2e.3b.4c.5d.6f, | |
| 1e.2e.3b.4c.5e.6a, | 1e.2e.3b.4c.5e.6b, | 1e.2e.3b.4c.5e.6c, | 1e.2e.3b.4c.5e.6d, | |
| 1e.2e.3b.4c.5e.6e, | 1e.2e.3b.4c.5e.6f, | 1e.2e.3b.4c.5f.6a, | 1e.2e.3b.4c.5f.6b, | 1e.2e.3b.4c.5f.6c, |
| 1e.2e.3b.4c.5f.6d, | 1e.2e.3b.4c.5f.6e, | 1e.2e.3b.4c.5f.6f, | 1e.2e.3b.4d.5a.6a, | |
| 1e.2e.3b.4d.5a.6b, | 1e.2e.3b.4d.5a.6c, | 1e.2e.3b.4d.5a.6d, | 1e.2e.3b.4d.5a.6e, | |
| 1e.2e.3b.4d.5a.6f, | 1e.2e.3b.4d.5b.6a, | 1e.2e.3b.4d.5b.6b, | 1e.2e.3b.4d.5b.6c, | |
| 1e.2e.3b.4d.5b.6d, | 1e.2e.3b.4d.5b.6e, | 1e.2e.3b.4d.5b.6f, | 1e.2e.3b.4d.5c.6a, | |
| 1e.2e.3b.4d.5c.6b, | 1e.2e.3b.4d.5c.6c, | 1e.2e.3b.4d.5c.6d, | 1e.2e.3b.4d.5c.6e, | |
| 1e.2e.3b.4d.5c.6f, | 1e.2e.3b.4d.5d.6a, | 1e.2e.3b.4d.5d.6b, | 1e.2e.3b.4d.5d.6c, | |
| 1e.2e.3b.4d.5d.6d, | 1e.2e.3b.4d.5d.6e, | 1e.2e.3b.4d.5d.6f, | 1e.2e.3b.4d.5e.6a, | |
| 1e.2e.3b.4d.5e.6b, | 1e.2e.3b.4d.5e.6c, | 1e.2e.3b.4d.5e.6d, | 1e.2e.3b.4d.5e.6e, | |
| 1e.2e.3b.4d.5e.6f, | 1e.2e.3b.4d.5f.6a, | 1e.2e.3b.4d.5f.6b, | 1e.2e.3b.4d.5f.6c, | |
| 1e.2e.3b.4d.5f.6d, | 1e.2e.3b.4d.5f.6e, | 1e.2e.3b.4d.5f.6f, | 1e.2e.3b.4e.5a.6a, | |
| 1e.2e.3b.4e.5a.6b, | 1e.2e.3b.4e.5a.6c, | 1e.2e.3b.4e.5a.6d, | 1e.2e.3b.4e.5a.6e, | |
| 1e.2e.3b.4e.5a.6f, | 1e.2e.3b.4e.5b.6a, | 1e.2e.3b.4e.5b.6b, | 1e.2e.3b.4e.5b.6c, | |
| 1e.2e.3b.4e.5b.6d, | 1e.2e.3b.4e.5b.6e, | 1e.2e.3b.4e.5b.6f, | 1e.2e.3b.4e.5c.6a, | |
| 1e.2e.3b.4e.5c.6b, | 1e.2e.3b.4e.5c.6c, | 1e.2e.3b.4e.5c.6d, | 1e.2e.3b.4e.5c.6e, | |
| 1e.2e.3b.4e.5c.6f, | 1e.2e.3b.4e.5d.6a, | 1e.2e.3b.4e.5d.6b, | 1e.2e.3b.4e.5d.6c, | |
| 1e.2e.3b.4e.5d.6d, | 1e.2e.3b.4e.5d.6e, | 1e.2e.3b.4e.5d.6f, | 1e.2e.3b.4e.5e.6a, | |
| 1e.2e.3b.4e.5e.6b, | 1e.2e.3b.4e.5e.6c, | 1e.2e.3b.4e.5e.6d, | 1e.2e.3b.4e.5e.6e, | |
| 1e.2e.3b.4e.5e.6f, | 1e.2e.3b.4e.5f.6a, | 1e.2e.3b.4e.5f.6b, | 1e.2e.3b.4e.5f.6c, | 1e.2e.3b.4e.5f.6d, |
| 1e.2e.3b.4e.5f.6e, | 1e.2e.3b.4e.5f.6f, | 1e.2e.3b.4f.5a.6a, | 1e.2e.3b.4f.5a.6b, | 1e.2e.3b.4f.5a.6c, |
| 1e.2e.3b.4f.5a.6d, | 1e.2e.3b.4f.5a.6e, | 1e.2e.3b.4f.5a.6f, | 1e.2e.3b.4f.5b.6a, | 1e.2e.3b.4f.5b.6b, |
| 1e.2e.3b.4f.5b.6c, | 1e.2e.3b.4f.5b.6d, | 1e.2e.3b.4f.5b.6e, | 1e.2e.3b.4f.5b.6f, | 1e.2e.3b.4f.5c.6a, |
| 1e.2e.3b.4f.5c.6b, | 1e.2e.3b.4f.5c.6c, | 1e.2e.3b.4f.5c.6d, | 1e.2e.3b.4f.5c.6e, | 1e.2e.3b.4f.5c.6f, |
| 1e.2e.3b.4f.5d.6a, | 1e.2e.3b.4f.5d.6b, | 1e.2e.3b.4f.5d.6c, | 1e.2e.3b.4f.5d.6d, | |
| 1e.2e.3b.4f.5d.6e, | 1e.2e.3b.4f.5d.6f, | 1e.2e.3b.4f.5e.6a, | 1e.2e.3b.4f.5e.6b, | 1e.2e.3b.4f.5e.6c, |
| 1e.2e.3b.4f.5e.6d, | 1e.2e.3b.4f.5e.6e, | 1e.2e.3b.4f.5e.6f, | 1e.2e.3b.4f.5f.6a, | 1e.2e.3b.4f.5f.6b, |
| 1e.2e.3b.4f.5f.6c, | 1e.2e.3b.4f.5f.6d, | 1e.2e.3b.4f.5f.6e, | 1e.2e.3b.4f.5f.6f, | 1e.2e.3c.4a.5a.6a, |
| 1e.2e.3c.4a.5a.6b, | 1e.2e.3c.4a.5a.6c, | 1e.2e.3c.4a.5a.6d, | 1e.2e.3c.4a.5a.6e, | |
| 1e.2e.3c.4a.5a.6f, | 1e.2e.3c.4a.5b.6a, | 1e.2e.3c.4a.5b.6b, | 1e.2e.3c.4a.5b.6c, | |
| 1e.2e.3c.4a.5b.6d, | 1e.2e.3c.4a.5b.6e, | 1e.2e.3c.4a.5b.6f, | 1e.2e.3c.4a.5c.6a, | |
| 1e.2e.3c.4a.5c.6b, | 1e.2e.3c.4a.5c.6c, | 1e.2e.3c.4a.5c.6d, | 1e.2e.3c.4a.5c.6e, | 1e.2e.3c.4a.5c.6f, |
| 1e.2e.3c.4a.5d.6a, | 1e.2e.3c.4a.5d.6b, | 1e.2e.3c.4a.5d.6c, | 1e.2e.3c.4a.5d.6d, | |
| 1e.2e.3c.4a.5d.6e, | 1e.2e.3c.4a.5d.6f, | 1e.2e.3c.4a.5e.6a, | 1e.2e.3c.4a.5e.6b, | |
| 1e.2e.3c.4a.5e.6c, | 1e.2e.3c.4a.5e.6d, | 1e.2e.3c.4a.5e.6e, | 1e.2e.3c.4a.5e.6f, | 1e.2e.3c.4a.5f.6a, |
| 1e.2e.3c.4a.5f.6b, | 1e.2e.3c.4a.5f.6c, | 1e.2e.3c.4a.5f.6d, | 1e.2e.3c.4a.5f.6e, | 1e.2e.3c.4a.5f.6f, |
| 1e.2e.3c.4b.5a.6a, | 1e.2e.3c.4b.5a.6b, | 1e.2e.3c.4b.5a.6c, | 1e.2e.3c.4b.5a.6d, | |
| 1e.2e.3c.4b.5a.6e, | 1e.2e.3c.4b.5a.6f, | 1e.2e.3c.4b.5b.6a, | 1e.2e.3c.4b.5b.6b, | |
| 1e.2e.3c.4b.5b.6c, | 1e.2e.3c.4b.5b.6d, | 1e.2e.3c.4b.5b.6e, | 1e.2e.3c.4b.5b.6f, | |
| 1e.2e.3c.4b.5c.6a, | 1e.2e.3c.4b.5c.6b, | 1e.2e.3c.4b.5c.6c, | 1e.2e.3c.4b.5c.6d, | |
| 1e.2e.3c.4b.5c.6e, | 1e.2e.3c.4b.5c.6f, | 1e.2e.3c.4b.5d.6a, | 1e.2e.3c.4b.5d.6b, | |
| 1e.2e.3c.4b.5d.6c, | 1e.2e.3c.4b.5d.6d, | 1e.2e.3c.4b.5d.6e, | 1e.2e.3c.4b.5d.6f, | |
| 1e.2e.3c.4b.5e.6a, | 1e.2e.3c.4b.5e.6b, | 1e.2e.3c.4b.5e.6c, | 1e.2e.3c.4b.5e.6d, | |
| 1e.2e.3c.4b.5e.6e, | 1e.2e.3c.4b.5e.6f, | 1e.2e.3c.4b.5f.6a, | 1e.2e.3c.4b.5f.6b, | 1e.2e.3c.4b.5f.6c, |
| 1e.2e.3c.4b.5f.6d, | 1e.2e.3c.4b.5f.6e, | 1e.2e.3c.4b.5f.6f, | 1e.2e.3c.4c.5a.6a, | 1e.2e.3c.4c.5a.6b, |
| 1e.2e.3c.4c.5a.6c, | 1e.2e.3c.4c.5a.6d, | 1e.2e.3c.4c.5a.6e, | 1e.2e.3c.4c.5a.6f, | 1e.2e.3c.4c.5b.6a, |
| 1e.2e.3c.4c.5b.6b, | 1e.2e.3c.4c.5b.6c, | 1e.2e.3c.4c.5b.6d, | 1e.2e.3c.4c.5b.6e, | |
| 1e.2e.3c.4c.5b.6f, | 1e.2e.3c.4c.5c.6a, | 1e.2e.3c.4c.5c.6b, | 1e.2e.3c.4c.5c.6c, | 1e.2e.3c.4c.5c.6d, |
| 1e.2e.3c.4c.5c.6e, | 1e.2e.3c.4c.5c.6f, | 1e.2e.3c.4c.5d.6a, | 1e.2e.3c.4c.5d.6b, | 1e.2e.3c.4c.5d.6c, |
| 1e.2e.3c.4c.5d.6d, | 1e.2e.3c.4c.5d.6e, | 1e.2e.3c.4c.5d.6f, | 1e.2e.3c.4c.5e.6a, | |
| 1e.2e.3c.4c.5e.6b, | 1e.2e.3c.4c.5e.6c, | 1e.2e.3c.4c.5e.6d, | 1e.2e.3c.4c.5e.6e, | 1e.2e.3c.4c.5e.6f, |

TABLE 7-continued

List of Compounds of Formula (II)

| | | | | |
|---|---|---|---|---|
| 1e.2e.3c.4c.5f.6a, | 1e.2e.3c.4c.5f.6b, | 1e.2e.3c.4c.5f.6c, | 1e.2e.3c.4c.5f.6d, | 1e.2e.3c.4c.5f.6e, |
| 1e.2e.3c.4c.5f.6f, | 1e.2e.3c.4d.5a.6a, | 1e.2e.3c.4d.5a.6b, | 1e.2e.3c.4d.5a.6c, | |
| 1e.2e.3c.4d.5a.6d, | 1e.2e.3c.4d.5a.6e, | 1e.2e.3c.4d.5a.6f, | 1e.2e.3c.4d.5b.6a, | |
| 1e.2e.3c.4d.5b.6b, | 1e.2e.3c.4d.5b.6c, | 1e.2e.3c.4d.5b.6d, | 1e.2e.3c.4d.5b.6e, | |
| 1e.2e.3c.4d.5b.6f, | 1e.2e.3c.4d.5c.6a, | 1e.2e.3c.4d.5c.6b, | 1e.2e.3c.4d.5c.6c, | |
| 1e.2e.3c.4d.5c.6d, | 1e.2e.3c.4d.5c.6e, | 1e.2e.3c.4d.5c.6f, | 1e.2e.3c.4d.5d.6a, | |
| 1e.2e.3c.4d.5d.6b, | 1e.2e.3c.4d.5d.6c, | 1e.2e.3c.4d.5d.6d, | 1e.2e.3c.4d.5d.6e, | |
| 1e.2e.3c.4d.5d.6f, | 1e.2e.3c.4d.5e.6a, | 1e.2e.3c.4d.5e.6b, | 1e.2e.3c.4d.5e.6c, | |
| 1e.2e.3c.4d.5e.6d, | 1e.2e.3c.4d.5e.6e, | 1e.2e.3c.4d.5e.6f, | 1e.2e.3c.4d.5f.6a, | |
| 1e.2e.3c.4d.5f.6b, | 1e.2e.3c.4d.5f.6c, | 1e.2e.3c.4d.5f.6d, | 1e.2e.3c.4d.5f.6e, | 1e.2e.3c.4d.5f.6f, |
| 1e.2e.3c.4e.5a.6a, | 1e.2e.3c.4e.5a.6b, | 1e.2e.3c.4e.5a.6c, | 1e.2e.3c.4e.5a.6d, | |
| 1e.2e.3c.4e.5a.6e, | 1e.2e.3c.4e.5a.6f, | 1e.2e.3c.4e.5b.6a, | 1e.2e.3c.4e.5b.6b, | |
| 1e.2e.3c.4e.5b.6c, | 1e.2e.3c.4e.5b.6d, | 1e.2e.3c.4e.5b.6e, | 1e.2e.3c.4e.5b.6f, | |
| 1e.2e.3c.4e.5c.6a, | 1e.2e.3c.4e.5c.6b, | 1e.2e.3c.4e.5c.6c, | 1e.2e.3c.4e.5c.6d, | 1e.2e.3c.4e.5c.6e, |
| 1e.2e.3c.4e.5c.6f, | 1e.2e.3c.4e.5d.6a, | 1e.2e.3c.4e.5d.6b, | 1e.2e.3c.4e.5d.6c, | |
| 1e.2e.3c.4e.5d.6d, | 1e.2e.3c.4e.5d.6e, | 1e.2e.3c.4e.5d.6f, | 1e.2e.3c.4e.5e.6a, | |
| 1e.2e.3c.4e.5e.6b, | 1e.2e.3c.4e.5e.6c, | 1e.2e.3c.4e.5e.6d, | 1e.2e.3c.4e.5e.6e, | 1e.2e.3c.4e.5e.6f, |
| 1e.2e.3c.4e.5f.6a, | 1e.2e.3c.4e.5f.6b, | 1e.2e.3c.4e.5f.6c, | 1e.2e.3c.4e.5f.6d, | 1e.2e.3c.4e.5f.6e, |
| 1e.2e.3c.4e.5f.6f, | 1e.2e.3c.4f.5a.6a, | 1e.2e.3c.4f.5a.6b, | 1e.2e.3c.4f.5a.6c, | 1e.2e.3c.4f.5a.6d, |
| 1e.2e.3c.4f.5a.6e, | 1e.2e.3c.4f.5a.6f, | 1e.2e.3c.4f.5b.6a, | 1e.2e.3c.4f.5b.6b, | 1e.2e.3c.4f.5b.6c, |
| 1e.2e.3c.4f.5b.6d, | 1e.2e.3c.4f.5b.6e, | 1e.2e.3c.4f.5b.6f, | 1e.2e.3c.4f.5c.6a, | 1e.2e.3c.4f.5c.6b, |
| 1e.2e.3c.4f.5c.6c, | 1e.2e.3c.4f.5c.6d, | 1e.2e.3c.4f.5c.6e, | 1e.2e.3c.4f.5c.6f, | 1e.2e.3c.4f.5d.6a, |
| 1e.2e.3c.4f.5d.6b, | 1e.2e.3c.4f.5d.6c, | 1e.2e.3c.4f.5d.6d, | 1e.2e.3c.4f.5d.6e, | 1e.2e.3c.4f.5d.6f, |
| 1e.2e.3c.4f.5e.6a, | 1e.2e.3c.4f.5e.6b, | 1e.2e.3c.4f.5e.6c, | 1e.2e.3c.4f.5e.6d, | 1e.2e.3c.4f.5e.6e, |
| 1e.2e.3c.4f.5e.6f, | 1e.2e.3c.4f.5f.6a, | 1e.2e.3c.4f.5f.6b, | 1e.2e.3c.4f.5f.6c, | 1e.2e.3c.4f.5f.6d, |
| 1e.2e.3c.4f.5f.6e, | 1e.2e.3c.4f.5f.6f, | 1e.2e.3d.4a.5a.6a, | 1e.2e.3d.4a.5a.6b, | 1e.2e.3d.4a.5a.6c, |
| 1e.2e.3d.4a.5a.6d, | 1e.2e.3d.4a.5a.6e, | 1e.2e.3d.4a.5a.6f, | 1e.2e.3d.4a.5b.6a, | |
| 1e.2e.3d.4a.5b.6b, | 1e.2e.3d.4a.5b.6c, | 1e.2e.3d.4a.5b.6d, | 1e.2e.3d.4a.5b.6e, | |
| 1e.2e.3d.4a.5b.6f, | 1e.2e.3d.4a.5c.6a, | 1e.2e.3d.4a.5c.6b, | 1e.2e.3d.4a.5c.6c, | |
| 1e.2e.3d.4a.5c.6d, | 1e.2e.3d.4a.5c.6e, | 1e.2e.3d.4a.5c.6f, | 1e.2e.3d.4a.5d.6a, | |
| 1e.2e.3d.4a.5d.6b, | 1e.2e.3d.4a.5d.6c, | 1e.2e.3d.4a.5d.6d, | 1e.2e.3d.4a.5d.6e, | |
| 1e.2e.3d.4a.5d.6f, | 1e.2e.3d.4a.5e.6a, | 1e.2e.3d.4a.5e.6b, | 1e.2e.3d.4a.5e.6c, | |
| 1e.2e.3d.4a.5e.6d, | 1e.2e.3d.4a.5e.6e, | 1e.2e.3d.4a.5e.6f, | 1e.2e.3d.4a.5f.6a, | |
| 1e.2e.3d.4a.5f.6b, | 1e.2e.3d.4a.5f.6c, | 1e.2e.3d.4a.5f.6d, | 1e.2e.3d.4a.5f.6e, | |
| 1e.2e.3d.4a.5f.6f, | 1e.2e.3d.4b.5a.6a, | 1e.2e.3d.4b.5a.6b, | 1e.2e.3d.4b.5a.6c, | |
| 1e.2e.3d.4b.5a.6d, | 1e.2e.3d.4b.5a.6e, | 1e.2e.3d.4b.5a.6f, | 1e.2e.3d.4b.5b.6a, | |
| 1e.2e.3d.4b.5b.6b, | 1e.2e.3d.4b.5b.6c, | 1e.2e.3d.4b.5b.6d, | 1e.2e.3d.4b.5b.6e, | |
| 1e.2e.3d.4b.5b.6f, | 1e.2e.3d.4b.5c.6a, | 1e.2e.3d.4b.5c.6b, | 1e.2e.3d.4b.5c.6c, | |
| 1e.2e.3d.4b.5c.6d, | 1e.2e.3d.4b.5c.6e, | 1e.2e.3d.4b.5c.6f, | 1e.2e.3d.4b.5d.6a, | |
| 1e.2e.3d.4b.5d.6b, | 1e.2e.3d.4b.5d.6c, | 1e.2e.3d.4b.5d.6d, | 1e.2e.3d.4b.5d.6e, | |
| 1e.2e.3d.4b.5d.6f, | 1e.2e.3d.4b.5e.6a, | 1e.2e.3d.4b.5e.6b, | 1e.2e.3d.4b.5e.6c, | |
| 1e.2e.3d.4b.5e.6d, | 1e.2e.3d.4b.5e.6e, | 1e.2e.3d.4b.5e.6f, | 1e.2e.3d.4b.5f.6a, | |
| 1e.2e.3d.4b.5f.6b, | 1e.2e.3d.4b.5f.6c, | 1e.2e.3d.4b.5f.6d, | 1e.2e.3d.4b.5f.6e, | |
| 1e.2e.3d.4b.5f.6f, | 1e.2e.3d.4c.5a.6a, | 1e.2e.3d.4c.5a.6b, | 1e.2e.3d.4c.5a.6c, | |
| 1e.2e.3d.4c.5a.6d, | 1e.2e.3d.4c.5a.6e, | 1e.2e.3d.4c.5a.6f, | 1e.2e.3d.4c.5b.6a, | |
| 1e.2e.3d.4c.5b.6b, | 1e.2e.3d.4c.5b.6c, | 1e.2e.3d.4c.5b.6d, | 1e.2e.3d.4c.5b.6e, | |
| 1e.2e.3d.4c.5b.6f, | 1e.2e.3d.4c.5c.6a, | 1e.2e.3d.4c.5c.6b, | 1e.2e.3d.4c.5c.6c, | |
| 1e.2e.3d.4c.5c.6d, | 1e.2e.3d.4c.5c.6e, | 1e.2e.3d.4c.5c.6f, | 1e.2e.3d.4c.5d.6a, | |
| 1e.2e.3d.4c.5d.6b, | 1e.2e.3d.4c.5d.6c, | 1e.2e.3d.4c.5d.6d, | 1e.2e.3d.4c.5d.6e, | |
| 1e.2e.3d.4c.5d.6f, | 1e.2e.3d.4c.5e.6a, | 1e.2e.3d.4c.5e.6b, | 1e.2e.3d.4c.5e.6c, | |
| 1e.2e.3d.4c.5e.6d, | 1e.2e.3d.4c.5e.6e, | 1e.2e.3d.4c.5e.6f, | 1e.2e.3d.4c.5f.6a, | |
| 1e.2e.3d.4c.5f.6b, | 1e.2e.3d.4c.5f.6c, | 1e.2e.3d.4c.5f.6d, | 1e.2e.3d.4c.5f.6e, | 1e.2e.3d.4c.5f.6f, |
| 1e.2e.3d.4d.5a.6a, | 1e.2e.3d.4d.5a.6b, | 1e.2e.3d.4d.5a.6c, | 1e.2e.3d.4d.5a.6d, | |
| 1e.2e.3d.4d.5a.6e, | 1e.2e.3d.4d.5a.6f, | 1e.2e.3d.4d.5b.6a, | 1e.2e.3d.4d.5b.6b, | |
| 1e.2e.3d.4d.5b.6c, | 1e.2e.3d.4d.5b.6d, | 1e.2e.3d.4d.5b.6e, | 1e.2e.3d.4d.5b.6f, | |
| 1e.2e.3d.4d.5c.6a, | 1e.2e.3d.4d.5c.6b, | 1e.2e.3d.4d.5c.6c, | 1e.2e.3d.4d.5c.6d, | |
| 1e.2e.3d.4d.5c.6e, | 1e.2e.3d.4d.5c.6f, | 1e.2e.3d.4d.5d.6a, | 1e.2e.3d.4d.5d.6b, | |
| 1e.2e.3d.4d.5d.6c, | 1e.2e.3d.4d.5d.6d, | 1e.2e.3d.4d.5d.6e, | 1e.2e.3d.4d.5d.6f, | |
| 1e.2e.3d.4d.5e.6a, | 1e.2e.3d.4d.5e.6b, | 1e.2e.3d.4d.5e.6c, | 1e.2e.3d.4d.5e.6d, | |
| 1e.2e.3d.4d.5e.6e, | 1e.2e.3d.4d.5e.6f, | 1e.2e.3d.4d.5f.6a, | 1e.2e.3d.4d.5f.6b, | |
| 1e.2e.3d.4d.5f.6c, | 1e.2e.3d.4d.5f.6d, | 1e.2e.3d.4d.5f.6e, | 1e.2e.3d.4d.5f.6f, | |
| 1e.2e.3d.4e.5a.6a, | 1e.2e.3d.4e.5a.6b, | 1e.2e.3d.4e.5a.6c, | 1e.2e.3d.4e.5a.6d, | |
| 1e.2e.3d.4e.5a.6e, | 1e.2e.3d.4e.5a.6f, | 1e.2e.3d.4e.5b.6a, | 1e.2e.3d.4e.5b.6b, | |
| 1e.2e.3d.4e.5b.6c, | 1e.2e.3d.4e.5b.6d, | 1e.2e.3d.4e.5b.6e, | 1e.2e.3d.4e.5b.6f, | |
| 1e.2e.3d.4e.5c.6a, | 1e.2e.3d.4e.5c.6b, | 1e.2e.3d.4e.5c.6c, | 1e.2e.3d.4e.5c.6d, | |
| 1e.2e.3d.4e.5c.6e, | 1e.2e.3d.4e.5c.6f, | 1e.2e.3d.4e.5d.6a, | 1e.2e.3d.4e.5d.6b, | |
| 1e.2e.3d.4e.5d.6c, | 1e.2e.3d.4e.5d.6d, | 1e.2e.3d.4e.5d.6e, | 1e.2e.3d.4e.5d.6f, | |
| 1e.2e.3d.4e.5e.6a, | 1e.2e.3d.4e.5e.6b, | 1e.2e.3d.4e.5e.6c, | 1e.2e.3d.4e.5e.6d, | |
| 1e.2e.3d.4e.5e.6e, | 1e.2e.3d.4e.5e.6f, | 1e.2e.3d.4e.5f.6a, | 1e.2e.3d.4e.5f.6b, | |
| 1e.2e.3d.4e.5f.6c, | 1e.2e.3d.4e.5f.6d, | 1e.2e.3d.4e.5f.6e, | 1e.2e.3d.4e.5f.6f, | 1e.2e.3d.4f.5a.6a, |
| 1e.2e.3d.4f.5a.6b, | 1e.2e.3d.4f.5a.6c, | 1e.2e.3d.4f.5a.6d, | 1e.2e.3d.4f.5a.6e, | |
| 1e.2e.3d.4f.5a.6f, | 1e.2e.3d.4f.5b.6a, | 1e.2e.3d.4f.5b.6b, | 1e.2e.3d.4f.5b.6c, | |
| 1e.2e.3d.4f.5b.6d, | 1e.2e.3d.4f.5b.6e, | 1e.2e.3d.4f.5b.6f, | 1e.2e.3d.4f.5c.6a, | |
| 1e.2e.3d.4f.5c.6b, | 1e.2e.3d.4f.5c.6c, | 1e.2e.3d.4f.5c.6d, | 1e.2e.3d.4f.5c.6e, | 1e.2e.3d.4f.5c.6f, |
| 1e.2e.3d.4f.5d.6a, | 1e.2e.3d.4f.5d.6b, | 1e.2e.3d.4f.5d.6c, | 1e.2e.3d.4f.5d.6d, | |
| 1e.2e.3d.4f.5d.6e, | 1e.2e.3d.4f.5d.6f, | 1e.2e.3d.4f.5e.6a, | 1e.2e.3d.4f.5e.6b, | |
| 1e.2e.3d.4f.5e.6c, | 1e.2e.3d.4f.5e.6d, | 1e.2e.3d.4f.5e.6e, | 1e.2e.3d.4f.5e.6f, | 1e.2e.3d.4f.5f.6a, |
| 1e.2e.3d.4f.5f.6b, | 1e.2e.3d.4f.5f.6c, | 1e.2e.3d.4f.5f.6d, | 1e.2e.3d.4f.5f.6e, | 1e.2e.3d.4f.5f.6f, |

TABLE 7-continued

List of Compounds of Formula (II)

| | | | | |
|---|---|---|---|---|
| 1e.2e.3e.4a.5a.6a, | 1e.2e.3e.4a.5a.6b, | 1e.2e.3e.4a.5a.6c, | 1e.2e.3e.4a.5a.6d, | |
| 1e.2e.3e.4a.5a.6e, | 1e.2e.3e.4a.5a.6f, | 1e.2e.3e.4a.5b.6a, | 1e.2e.3e.4a.5b.6b, | |
| 1e.2e.3e.4a.5b.6c, | 1e.2e.3e.4a.5b.6d, | 1e.2e.3e.4a.5b.6e, | 1e.2e.3e.4a.5b.6f, | |
| 1e.2e.3e.4a.5c.6a, | 1e.2e.3e.4a.5c.6b, | 1e.2e.3e.4a.5c.6c, | 1e.2e.3e.4a.5c.6d, | |
| 1e.2e.3e.4a.5c.6e, | 1e.2e.3e.4a.5c.6f, | 1e.2e.3e.4a.5d.6a, | 1e.2e.3e.4a.5d.6b, | |
| 1e.2e.3e.4a.5d.6c, | 1e.2e.3e.4a.5d.6d, | 1e.2e.3e.4a.5d.6e, | 1e.2e.3e.4a.5d.6f, | |
| 1e.2e.3e.4a.5e.6a, | 1e.2e.3e.4a.5e.6b, | 1e.2e.3e.4a.5e.6c, | 1e.2e.3e.4a.5e.6d, | |
| 1e.2e.3e.4a.5e.6e, | 1e.2e.3e.4a.5e.6f, | 1e.2e.3e.4a.5f.6a, | 1e.2e.3e.4a.5f.6b, | 1e.2e.3e.4a.5f.6c, |
| 1e.2e.3e.4a.5f.6d, | 1e.2e.3e.4a.5f.6e, | 1e.2e.3e.4a.5f.6f, | 1e.2e.3e.4b.5a.6a, | 1e.2e.3e.4b.5a.6b, |
| 1e.2e.3e.4b.5a.6c, | 1e.2e.3e.4b.5a.6d, | 1e.2e.3e.4b.5a.6e, | 1e.2e.3e.4b.5a.6f, | |
| 1e.2e.3e.4b.5b.6a, | 1e.2e.3e.4b.5b.6b, | 1e.2e.3e.4b.5b.6c, | 1e.2e.3e.4b.5b.6d, | |
| 1e.2e.3e.4b.5b.6e, | 1e.2e.3e.4b.5b.6f, | 1e.2e.3e.4b.5c.6a, | 1e.2e.3e.4b.5c.6b, | |
| 1e.2e.3e.4b.5c.6c, | 1e.2e.3e.4b.5c.6d, | 1e.2e.3e.4b.5c.6e, | 1e.2e.3e.4b.5c.6f, | |
| 1e.2e.3e.4b.5d.6a, | 1e.2e.3e.4b.5d.6b, | 1e.2e.3e.4b.5d.6c, | 1e.2e.3e.4b.5d.6d, | |
| 1e.2e.3e.4b.5d.6e, | 1e.2e.3e.4b.5d.6f, | 1e.2e.3e.4b.5e.6a, | 1e.2e.3e.4b.5e.6b, | |
| 1e.2e.3e.4b.5e.6c, | 1e.2e.3e.4b.5e.6d, | 1e.2e.3e.4b.5e.6e, | 1e.2e.3e.4b.5e.6f, | |
| 1e.2e.3e.4b.5f.6a, | 1e.2e.3e.4b.5f.6b, | 1e.2e.3e.4b.5f.6c, | 1e.2e.3e.4b.5f.6d, | 1e.2e.3e.4b.5f.6e, |
| 1e.2e.3e.4b.5f.6f, | 1e.2e.3e.4c.5a.6a, | 1e.2e.3e.4c.5a.6b, | 1e.2e.3e.4c.5a.6c, | 1e.2e.3e.4c.5a.6d, |
| 1e.2e.3e.4c.5a.6e, | 1e.2e.3e.4c.5a.6f, | 1e.2e.3e.4c.5b.6a, | 1e.2e.3e.4c.5b.6b, | |
| 1e.2e.3e.4c.5b.6c, | 1e.2e.3e.4c.5b.6d, | 1e.2e.3e.4c.5b.6e, | 1e.2e.3e.4c.5b.6f, | |
| 1e.2e.3e.4c.5c.6a, | 1e.2e.3e.4c.5c.6b, | 1e.2e.3e.4c.5c.6c, | 1e.2e.3e.4c.5c.6d, | 1e.2e.3e.4c.5c.6e, |
| 1e.2e.3e.4c.5c.6f, | 1e.2e.3e.4c.5d.6a, | 1e.2e.3e.4c.5d.6b, | 1e.2e.3e.4c.5d.6c, | |
| 1e.2e.3e.4c.5d.6d, | 1e.2e.3e.4c.5d.6e, | 1e.2e.3e.4c.5d.6f, | 1e.2e.3e.4c.5e.6a, | |
| 1e.2e.3e.4c.5e.6b, | 1e.2e.3e.4c.5e.6c, | 1e.2e.3e.4c.5e.6d, | 1e.2e.3e.4c.5e.6e, | 1e.2e.3e.4c.5e.6f, |
| 1e.2e.3e.4c.5f.6a, | 1e.2e.3e.4c.5f.6b, | 1e.2e.3e.4c.5f.6c, | 1e.2e.3e.4c.5f.6d, | 1e.2e.3e.4c.5f.6e, |
| 1e.2e.3e.4c.5f.6f, | 1e.2e.3e.4d.5a.6a, | 1e.2e.3e.4d.5a.6b, | 1e.2e.3e.4d.5a.6c, | |
| 1e.2e.3e.4d.5a.6d, | 1e.2e.3e.4d.5a.6e, | 1e.2e.3e.4d.5a.6f, | 1e.2e.3e.4d.5b.6a, | |
| 1e.2e.3e.4d.5b.6b, | 1e.2e.3e.4d.5b.6c, | 1e.2e.3e.4d.5b.6d, | 1e.2e.3e.4d.5b.6e, | |
| 1e.2e.3e.4d.5b.6f, | 1e.2e.3e.4d.5c.6a, | 1e.2e.3e.4d.5c.6b, | 1e.2e.3e.4d.5c.6c, | |
| 1e.2e.3e.4d.5c.6d, | 1e.2e.3e.4d.5c.6e, | 1e.2e.3e.4d.5c.6f, | 1e.2e.3e.4d.5d.6a, | |
| 1e.2e.3e.4d.5d.6b, | 1e.2e.3e.4d.5d.6c, | 1e.2e.3e.4d.5d.6d, | 1e.2e.3e.4d.5d.6e, | |
| 1e.2e.3e.4d.5d.6f, | 1e.2e.3e.4d.5e.6a, | 1e.2e.3e.4d.5e.6b, | 1e.2e.3e.4d.5e.6c, | |
| 1e.2e.3e.4d.5e.6d, | 1e.2e.3e.4d.5e.6e, | 1e.2e.3e.4d.5e.6f, | 1e.2e.3e.4d.5f.6a, | |
| 1e.2e.3e.4d.5f.6b, | 1e.2e.3e.4d.5f.6c, | 1e.2e.3e.4d.5f.6d, | 1e.2e.3e.4d.5f.6e, | 1e.2e.3e.4d.5f.6f, |
| 1e.2e.3e.4e.5a.6a, | 1e.2e.3e.4e.5a.6b, | 1e.2e.3e.4e.5a.6c, | 1e.2e.3e.4e.5a.6d, | |
| 1e.2e.3e.4e.5a.6e, | 1e.2e.3e.4e.5a.6f, | 1e.2e.3e.4e.5b.6a, | 1e.2e.3e.4e.5b.6b, | |
| 1e.2e.3e.4e.5b.6c, | 1e.2e.3e.4e.5b.6d, | 1e.2e.3e.4e.5b.6e, | 1e.2e.3e.4e.5b.6f, | |
| 1e.2e.3e.4e.5c.6a, | 1e.2e.3e.4e.5c.6b, | 1e.2e.3e.4e.5c.6c, | 1e.2e.3e.4e.5c.6d, | |
| 1e.2e.3e.4e.5c.6e, | 1e.2e.3e.4e.5c.6f, | 1e.2e.3e.4e.5d.6a, | 1e.2e.3e.4e.5d.6b, | |
| 1e.2e.3e.4e.5d.6c, | 1e.2e.3e.4e.5d.6d, | 1e.2e.3e.4e.5d.6e, | 1e.2e.3e.4e.5d.6f, | |
| 1e.2e.3e.4e.5e.6a, | 1e.2e.3e.4e.5e.6b, | 1e.2e.3e.4e.5e.6c, | 1e.2e.3e.4e.5e.6d, | |
| 1e.2e.3e.4e.5e.6e, | 1e.2e.3e.4e.5e.6f, | 1e.2e.3e.4e.5f.6a, | 1e.2e.3e.4e.5f.6b, | 1e.2e.3e.4e.5f.6c, |
| 1e.2e.3e.4e.5f.6d, | 1e.2e.3e.4e.5f.6e, | 1e.2e.3e.4e.5f.6f, | 1e.2e.3e.4f.5a.6a, | 1e.2e.3e.4f.5a.6b, |
| 1e.2e.3e.4f.5a.6c, | 1e.2e.3e.4f.5a.6d, | 1e.2e.3e.4f.5a.6e, | 1e.2e.3e.4f.5a.6f, | 1e.2e.3e.4f.5b.6a, |
| 1e.2e.3e.4f.5b.6b, | 1e.2e.3e.4f.5b.6c, | 1e.2e.3e.4f.5b.6d, | 1e.2e.3e.4f.5b.6e, | 1e.2e.3e.4f.5b.6f, |
| 1e.2e.3e.4f.5c.6a, | 1e.2e.3e.4f.5c.6b, | 1e.2e.3e.4f.5c.6c, | 1e.2e.3e.4f.5c.6d, | 1e.2e.3e.4f.5c.6e, |
| 1e.2e.3e.4f.5c.6f, | 1e.2e.3e.4f.5d.6a, | 1e.2e.3e.4f.5d.6b, | 1e.2e.3e.4f.5d.6c, | 1e.2e.3e.4f.5d.6d, |
| 1e.2e.3e.4f.5d.6e, | 1e.2e.3e.4f.5d.6f, | 1e.2e.3e.4f.5e.6a, | 1e.2e.3e.4f.5e.6b, | 1e.2e.3e.4f.5e.6c, |
| 1e.2e.3e.4f.5e.6d, | 1e.2e.3e.4f.5e.6e, | 1e.2e.3e.4f.5e.6f, | 1e.2e.3e.4f.5f.6a, | 1e.2e.3e.4f.5f.6b, |
| 1e.2e.3e.4f.5f.6c, | 1e.2e.3e.4f.5f.6d, | 1e.2e.3e.4f.5f.6e, | 1e.2e.3e.4f.5f.6f, | 1e.2e.3f.4a.5a.6a, |
| 1e.2e.3f.4a.5a.6b, | 1e.2e.3f.4a.5a.6c, | 1e.2e.3f.4a.5a.6d, | 1e.2e.3f.4a.5a.6e, | 1e.2e.3f.4a.5a.6f, |
| 1e.2e.3f.4a.5b.6a, | 1e.2e.3f.4a.5b.6b, | 1e.2e.3f.4a.5b.6c, | 1e.2e.3f.4a.5b.6d, | 1e.2e.3f.4a.5b.6e, |
| 1e.2e.3f.4a.5b.6f, | 1e.2e.3f.4a.5c.6a, | 1e.2e.3f.4a.5c.6b, | 1e.2e.3f.4a.5c.6c, | 1e.2e.3f.4a.5c.6d, |
| 1e.2e.3f.4a.5c.6e, | 1e.2e.3f.4a.5c.6f, | 1e.2e.3f.4a.5d.6a, | 1e.2e.3f.4a.5d.6b, | 1e.2e.3f.4a.5d.6c, |
| 1e.2e.3f.4a.5d.6d, | 1e.2e.3f.4a.5d.6e, | 1e.2e.3f.4a.5d.6f, | 1e.2e.3f.4a.5e.6a, | 1e.2e.3f.4a.5e.6b, |
| 1e.2e.3f.4a.5e.6c, | 1e.2e.3f.4a.5e.6d, | 1e.2e.3f.4a.5e.6e, | 1e.2e.3f.4a.5e.6f, | 1e.2e.3f.4a.5f.6a, |
| 1e.2e.3f.4a.5f.6b, | 1e.2e.3f.4a.5f.6c, | 1e.2e.3f.4a.5f.6d, | 1e.2e.3f.4a.5f.6e, | 1e.2e.3f.4a.5f.6f, |
| 1e.2e.3f.4b.5a.6a, | 1e.2e.3f.4b.5a.6b, | 1e.2e.3f.4b.5a.6c, | 1e.2e.3f.4b.5a.6d, | 1e.2e.3f.4b.5a.6e, |
| 1e.2e.3f.4b.5a.6f, | 1e.2e.3f.4b.5b.6a, | 1e.2e.3f.4b.5b.6b, | 1e.2e.3f.4b.5b.6c, | |
| 1e.2e.3f.4b.5b.6d, | 1e.2e.3f.4b.5b.6e, | 1e.2e.3f.4b.5b.6f, | 1e.2e.3f.4b.5c.6a, | 1e.2e.3f.4b.5c.6b, |
| 1e.2e.3f.4b.5c.6c, | 1e.2e.3f.4b.5c.6d, | 1e.2e.3f.4b.5c.6e, | 1e.2e.3f.4b.5c.6f, | 1e.2e.3f.4b.5d.6a, |
| 1e.2e.3f.4b.5d.6b, | 1e.2e.3f.4b.5d.6c, | 1e.2e.3f.4b.5d.6d, | 1e.2e.3f.4b.5d.6e, | |
| 1e.2e.3f.4b.5d.6f, | 1e.2e.3f.4b.5e.6a, | 1e.2e.3f.4b.5e.6b, | 1e.2e.3f.4b.5e.6c, | 1e.2e.3f.4b.5e.6d, |
| 1e.2e.3f.4b.5e.6e, | 1e.2e.3f.4b.5e.6f, | 1e.2e.3f.4b.5f.6a, | 1e.2e.3f.4b.5f.6b, | 1e.2e.3f.4b.5f.6c, |
| 1e.2e.3f.4b.5f.6d, | 1e.2e.3f.4b.5f.6e, | 1e.2e.3f.4b.5f.6f, | 1e.2e.3f.4c.5a.6a, | 1e.2e.3f.4c.5a.6b, |
| 1e.2e.3f.4c.5a.6c, | 1e.2e.3f.4c.5a.6d, | 1e.2e.3f.4c.5a.6e, | 1e.2e.3f.4c.5a.6f, | 1e.2e.3f.4c.5b.6a, |
| 1e.2e.3f.4c.5b.6b, | 1e.2e.3f.4c.5b.6c, | 1e.2e.3f.4c.5b.6d, | 1e.2e.3f.4c.5b.6e, | 1e.2e.3f.4c.5b.6f, |
| 1e.2e.3f.4c.5c.6a, | 1e.2e.3f.4c.5c.6b, | 1e.2e.3f.4c.5c.6c, | 1e.2e.3f.4c.5c.6d, | 1e.2e.3f.4c.5c.6e, |
| 1e.2e.3f.4c.5c.6f, | 1e.2e.3f.4c.5d.6a, | 1e.2e.3f.4c.5d.6b, | 1e.2e.3f.4c.5d.6c, | 1e.2e.3f.4c.5d.6d, |
| 1e.2e.3f.4c.5d.6e, | 1e.2e.3f.4c.5d.6f, | 1e.2e.3f.4c.5e.6a, | 1e.2e.3f.4c.5e.6b, | 1e.2e.3f.4c.5e.6c, |
| 1e.2e.3f.4c.5e.6d, | 1e.2e.3f.4c.5e.6e, | 1e.2e.3f.4c.5e.6f, | 1e.2e.3f.4c.5f.6a, | 1e.2e.3f.4c.5f.6b, |
| 1e.2e.3f.4c.5f.6c, | 1e.2e.3f.4c.5f.6d, | 1e.2e.3f.4c.5f.6e, | 1e.2e.3f.4c.5f.6f, | 1e.2e.3f.4d.5a.6a, |
| 1e.2e.3f.4d.5a.6b, | 1e.2e.3f.4d.5a.6c, | 1e.2e.3f.4d.5a.6d, | 1e.2e.3f.4d.5a.6e, | |
| 1e.2e.3f.4d.5a.6f, | 1e.2e.3f.4d.5b.6a, | 1e.2e.3f.4d.5b.6b, | 1e.2e.3f.4d.5b.6c, | |
| 1e.2e.3f.4d.5b.6d, | 1e.2e.3f.4d.5b.6e, | 1e.2e.3f.4d.5b.6f, | 1e.2e.3f.4d.5c.6a, | |
| 1e.2e.3f.4d.5c.6b, | 1e.2e.3f.4d.5c.6c, | 1e.2e.3f.4d.5c.6d, | 1e.2e.3f.4d.5c.6e, | 1e.2e.3f.4d.5c.6f, |
| 1e.2e.3f.4d.5d.6a, | 1e.2e.3f.4d.5d.6b, | 1e.2e.3f.4d.5d.6c, | 1e.2e.3f.4d.5d.6d, | |
| 1e.2e.3f.4d.5d.6e, | 1e.2e.3f.4d.5d.6f, | 1e.2e.3f.4d.5e.6a, | 1e.2e.3f.4d.5e.6b, | |

TABLE 7-continued

List of Compounds of Formula (II)

| | | | | |
|---|---|---|---|---|
| 1e.2e.3f.4d.5e.6c, | 1e.2e.3f.4d.5e.6d, | 1e.2e.3f.4d.5e.6e, | 1e.2e.3f.4d.5e.6f, | 1e.2e.3f.4d.5f.6a, |
| 1e.2e.3f.4d.5f.6b, | 1e.2e.3f.4d.5f.6c, | 1e.2e.3f.4d.5f.6d, | 1e.2e.3f.4d.5f.6e, | 1e.2e.3f.4d.5f.6f, |
| 1e.2e.3f.4e.5a.6a, | 1e.2e.3f.4e.5a.6b, | 1e.2e.3f.4e.5a.6c, | 1e.2e.3f.4e.5a.6d, | 1e.2e.3f.4e.5a.6e, |
| 1e.2e.3f.4e.5a.6f, | 1e.2e.3f.4e.5b.6a, | 1e.2e.3f.4e.5b.6b, | 1e.2e.3f.4e.5b.6c, | 1e.2e.3f.4e.5b.6d, |
| 1e.2e.3f.4e.5b.6e, | 1e.2e.3f.4e.5b.6f, | 1e.2e.3f.4e.5c.6a, | 1e.2e.3f.4e.5c.6b, | 1e.2e.3f.4e.5c.6c, |
| 1e.2e.3f.4e.5c.6d, | 1e.2e.3f.4e.5c.6e, | 1e.2e.3f.4e.5c.6f, | 1e.2e.3f.4e.5d.6a, | 1e.2e.3f.4e.5d.6b, |
| 1e.2e.3f.4e.5d.6c, | 1e.2e.3f.4e.5d.6d, | 1e.2e.3f.4e.5d.6e, | 1e.2e.3f.4e.5d.6f, | 1e.2e.3f.4e.5e.6a, |
| 1e.2e.3f.4e.5e.6b, | 1e.2e.3f.4e.5e.6c, | 1e.2e.3f.4e.5e.6d, | 1e.2e.3f.4e.5e.6e, | 1e.2e.3f.4e.5e.6f, |
| 1e.2e.3f.4e.5f.6a, | 1e.2e.3f.4e.5f.6b, | 1e.2e.3f.4e.5f.6c, | 1e.2e.3f.4e.5f.6d, | 1e.2e.3f.4e.5f.6e, |
| 1e.2e.3f.4e.5f.6f, | 1e.2e.3f.4f.5a.6a, | 1e.2e.3f.4f.5a.6b, | 1e.2e.3f.4f.5a.6c, | 1e.2e.3f.4f.5a.6d, |
| 1e.2e.3f.4f.5a.6e, | 1e.2e.3f.4f.5a.6f, | 1e.2e.3f.4f.5b.6a, | 1e.2e.3f.4f.5b.6b, | 1e.2e.3f.4f.5b.6c, |
| 1e.2e.3f.4f.5b.6d, | 1e.2e.3f.4f.5b.6e, | 1e.2e.3f.4f.5b.6f, | 1e.2e.3f.4f.5c.6a, | 1e.2e.3f.4f.5c.6b, |
| 1e.2e.3f.4f.5c.6c, | 1e.2e.3f.4f.5c.6d, | 1e.2e.3f.4f.5c.6e, | 1e.2e.3f.4f.5c.6f, | 1e.2e.3f.4f.5d.6a, |
| 1e.2e.3f.4f.5d.6b, | 1e.2e.3f.4f.5d.6c, | 1e.2e.3f.4f.5d.6d, | 1e.2e.3f.4f.5d.6e, | 1e.2e.3f.4f.5d.6f, |
| 1e.2e.3f.4f.5e.6a, | 1e.2e.3f.4f.5e.6b, | 1e.2e.3f.4f.5e.6c, | 1e.2e.3f.4f.5e.6d, | 1e.2e.3f.4f.5e.6e, |
| 1e.2e.3f.4f.5e.6f, | 1e.2e.3f.4f.5f.6a, | 1e.2e.3f.4f.5f.6b, | 1e.2e.3f.4f.5f.6c, | 1e.2e.3f.4f.5f.6d, |
| 1e.2e.3f.4f.5f.6e, | 1e.2e.3f.4f.5f.6f, | 1e.2f.3a.4a.5a.6a, | 1e.2f.3a.4a.5a.6b, | 1e.2f.3a.4a.5a.6c, |
| 1e.2f.3a.4a.5a.6d, | 1e.2f.3a.4a.5a.6e, | 1e.2f.3a.4a.5a.6f, | 1e.2f.3a.4a.5b.6a, | 1e.2f.3a.4a.5b.6b, |
| 1e.2f.3a.4a.5b.6c, | 1e.2f.3a.4a.5b.6d, | 1e.2f.3a.4a.5b.6e, | 1e.2f.3a.4a.5b.6f, | 1e.2f.3a.4a.5c.6a, |
| 1e.2f.3a.4a.5c.6b, | 1e.2f.3a.4a.5c.6c, | 1e.2f.3a.4a.5c.6d, | 1e.2f.3a.4a.5c.6e, | 1e.2f.3a.4a.5c.6f, |
| 1e.2f.3a.4a.5d.6a, | 1e.2f.3a.4a.5d.6b, | 1e.2f.3a.4a.5d.6c, | 1e.2f.3a.4a.5d.6d, | |
| 1e.2f.3a.4a.5d.6e, | 1e.2f.3a.4a.5d.6f, | 1e.2f.3a.4a.5e.6a, | 1e.2f.3a.4a.5e.6b, | 1e.2f.3a.4a.5e.6c, |
| 1e.2f.3a.4a.5e.6d, | 1e.2f.3a.4a.5e.6e, | 1e.2f.3a.4a.5e.6f, | 1e.2f.3a.4a.5f.6a, | 1e.2f.3a.4a.5f.6b, |
| 1e.2f.3a.4a.5f.6c, | 1e.2f.3a.4a.5f.6d, | 1e.2f.3a.4a.5f.6e, | 1e.2f.3a.4a.5f.6f, | 1e.2f.3a.4b.5a.6a, |
| 1e.2f.3a.4b.5a.6b, | 1e.2f.3a.4b.5a.6c, | 1e.2f.3a.4b.5a.6d, | 1e.2f.3a.4b.5a.6e, | 1e.2f.3a.4b.5a.6f, |
| 1e.2f.3a.4b.5b.6a, | 1e.2f.3a.4b.5b.6b, | 1e.2f.3a.4b.5b.6c, | 1e.2f.3a.4b.5b.6d, | |
| 1e.2f.3a.4b.5b.6e, | 1e.2f.3a.4b.5b.6f, | 1e.2f.3a.4b.5c.6a, | 1e.2f.3a.4b.5c.6b, | 1e.2f.3a.4b.5c.6c, |
| 1e.2f.3a.4b.5c.6d, | 1e.2f.3a.4b.5c.6e, | 1e.2f.3a.4b.5c.6f, | 1e.2f.3a.4b.5d.6a, | 1e.2f.3a.4b.5d.6b, |
| 1e.2f.3a.4b.5d.6c, | 1e.2f.3a.4b.5d.6d, | 1e.2f.3a.4b.5d.6e, | 1e.2f.3a.4b.5d.6f, | |
| 1e.2f.3a.4b.5e.6a, | 1e.2f.3a.4b.5e.6b, | 1e.2f.3a.4b.5e.6c, | 1e.2f.3a.4b.5e.6d, | 1e.2f.3a.4b.5e.6e, |
| 1e.2f.3a.4b.5f.6f, | 1e.2f.3a.4b.5f.6a, | 1e.2f.3a.4b.5f.6b, | 1e.2f.3a.4b.5f.6c, | 1e.2f.3a.4b.5f.6d, |
| 1e.2f.3a.4b.5f.6e, | 1e.2f.3a.4b.5f.6f, | 1e.2f.3a.4c.5a.6a, | 1e.2f.3a.4c.5a.6b, | 1e.2f.3a.4c.5a.6c, |
| 1e.2f.3a.4c.5a.6d, | 1e.2f.3a.4c.5a.6e, | 1e.2f.3a.4c.5a.6f, | 1e.2f.3a.4c.5b.6a, | 1e.2f.3a.4c.5b.6b, |
| 1e.2f.3a.4c.5b.6c, | 1e.2f.3a.4c.5b.6d, | 1e.2f.3a.4c.5b.6e, | 1e.2f.3a.4c.5b.6f, | 1e.2f.3a.4c.5c.6a, |
| 1e.2f.3a.4c.5c.6b, | 1e.2f.3a.4c.5c.6c, | 1e.2f.3a.4c.5c.6d, | 1e.2f.3a.4c.5c.6e, | 1e.2f.3a.4c.5c.6f, |
| 1e.2f.3a.4c.5d.6a, | 1e.2f.3a.4c.5d.6b, | 1e.2f.3a.4c.5d.6c, | 1e.2f.3a.4c.5d.6d, | |
| 1e.2f.3a.4c.5d.6e, | 1e.2f.3a.4c.5d.6f, | 1e.2f.3a.4c.5e.6a, | 1e.2f.3a.4c.5e.6b, | 1e.2f.3a.4c.5e.6c, |
| 1e.2f.3a.4c.5e.6d, | 1e.2f.3a.4c.5e.6e, | 1e.2f.3a.4c.5e.6f, | 1e.2f.3a.4c.5f.6a, | 1e.2f.3a.4c.5f.6b, |
| 1e.2f.3a.4c.5f.6c, | 1e.2f.3a.4c.5f.6d, | 1e.2f.3a.4c.5f.6e, | 1e.2f.3a.4c.5f.6f, | 1e.2f.3a.4d.5a.6a, |
| 1e.2f.3a.4d.5a.6b, | 1e.2f.3a.4d.5a.6c, | 1e.2f.3a.4d.5a.6d, | 1e.2f.3a.4d.5a.6e, | |
| 1e.2f.3a.4d.5a.6f, | 1e.2f.3a.4d.5b.6a, | 1e.2f.3a.4d.5b.6b, | 1e.2f.3a.4d.5b.6c, | |
| 1e.2f.3a.4d.5b.6d, | 1e.2f.3a.4d.5b.6e, | 1e.2f.3a.4d.5b.6f, | 1e.2f.3a.4d.5c.6a, | |
| 1e.2f.3a.4d.5c.6b, | 1e.2f.3a.4d.5c.6c, | 1e.2f.3a.4d.5c.6d, | 1e.2f.3a.4d.5c.6e, | 1e.2f.3a.4d.5c.6f, |
| 1e.2f.3a.4d.5d.6a, | 1e.2f.3a.4d.5d.6b, | 1e.2f.3a.4d.5d.6c, | 1e.2f.3a.4d.5d.6d, | |
| 1e.2f.3a.4d.5d.6e, | 1e.2f.3a.4d.5d.6f, | 1e.2f.3a.4d.5e.6a, | 1e.2f.3a.4d.5e.6b, | |
| 1e.2f.3a.4d.5e.6c, | 1e.2f.3a.4d.5e.6d, | 1e.2f.3a.4d.5e.6e, | 1e.2f.3a.4d.5e.6f, | 1e.2f.3a.4d.5f.6a, |
| 1e.2f.3a.4d.5f.6b, | 1e.2f.3a.4d.5f.6c, | 1e.2f.3a.4d.5f.6d, | 1e.2f.3a.4d.5f.6e, | 1e.2f.3a.4d.5f.6f, |
| 1e.2f.3a.4e.5a.6a, | 1e.2f.3a.4e.5a.6b, | 1e.2f.3a.4e.5a.6c, | 1e.2f.3a.4e.5a.6d, | 1e.2f.3a.4e.5a.6e, |
| 1e.2f.3a.4e.5a.6f, | 1e.2f.3a.4e.5b.6a, | 1e.2f.3a.4e.5b.6b, | 1e.2f.3a.4e.5b.6c, | 1e.2f.3a.4e.5b.6d, |
| 1e.2f.3a.4e.5b.6e, | 1e.2f.3a.4e.5b.6f, | 1e.2f.3a.4e.5c.6a, | 1e.2f.3a.4e.5c.6b, | 1e.2f.3a.4e.5c.6c, |
| 1e.2f.3a.4e.5c.6d, | 1e.2f.3a.4e.5c.6e, | 1e.2f.3a.4e.5c.6f, | 1e.2f.3a.4e.5d.6a, | 1e.2f.3a.4e.5d.6b, |
| 1e.2f.3a.4e.5d.6c, | 1e.2f.3a.4e.5d.6d, | 1e.2f.3a.4e.5d.6e, | 1e.2f.3a.4e.5d.6f, | 1e.2f.3a.4e.5e.6a, |
| 1e.2f.3a.4e.5e.6b, | 1e.2f.3a.4e.5e.6c, | 1e.2f.3a.4e.5e.6d, | 1e.2f.3a.4e.5e.6e, | 1e.2f.3a.4e.5e.6f, |
| 1e.2f.3a.4e.5f.6a, | 1e.2f.3a.4e.5f.6b, | 1e.2f.3a.4e.5f.6c, | 1e.2f.3a.4e.5f.6d, | 1e.2f.3a.4e.5f.6e, |
| 1e.2f.3a.4e.5f.6f, | 1e.2f.3a.4f.5a.6a, | 1e.2f.3a.4f.5a.6b, | 1e.2f.3a.4f.5a.6c, | 1e.2f.3a.4f.5a.6d, |
| 1e.2f.3a.4f.5a.6e, | 1e.2f.3a.4f.5a.6f, | 1e.2f.3a.4f.5b.6a, | 1e.2f.3a.4f.5b.6b, | 1e.2f.3a.4f.5b.6c, |
| 1e.2f.3a.4f.5b.6d, | 1e.2f.3a.4f.5b.6e, | 1e.2f.3a.4f.5b.6f, | 1e.2f.3a.4f.5c.6a, | 1e.2f.3a.4f.5c.6b, |
| 1e.2f.3a.4f.5c.6c, | 1e.2f.3a.4f.5c.6d, | 1e.2f.3a.4f.5c.6e, | 1e.2f.3a.4f.5c.6f, | 1e.2f.3a.4f.5d.6a, |
| 1e.2f.3a.4f.5d.6b, | 1e.2f.3a.4f.5d.6c, | 1e.2f.3a.4f.5d.6d, | 1e.2f.3a.4f.5d.6e, | 1e.2f.3a.4f.5d.6f, |
| 1e.2f.3a.4f.5e.6a, | 1e.2f.3a.4f.5e.6b, | 1e.2f.3a.4f.5e.6c, | 1e.2f.3a.4f.5e.6d, | 1e.2f.3a.4f.5e.6e, |
| 1e.2f.3a.4f.5e.6f, | 1e.2f.3a.4f.5f.6a, | 1e.2f.3a.4f.5f.6b, | 1e.2f.3a.4f.5f.6c, | 1e.2f.3a.4f.5f.6d, |
| 1e.2f.3a.4f.5f.6e, | 1e.2f.3a.4f.5f.6f, | 1e.2f.3b.4a.5a.6a, | 1e.2f.3b.4a.5a.6b, | 1e.2f.3b.4a.5a.6c, |
| 1e.2f.3b.4a.5a.6d, | 1e.2f.3b.4a.5a.6e, | 1e.2f.3b.4a.5a.6f, | 1e.2f.3b.4a.5b.6a, | |
| 1e.2f.3b.4a.5b.6b, | 1e.2f.3b.4a.5b.6c, | 1e.2f.3b.4a.5b.6d, | 1e.2f.3b.4a.5b.6e, | |
| 1e.2f.3b.4a.5b.6f, | 1e.2f.3b.4a.5c.6a, | 1e.2f.3b.4a.5c.6b, | 1e.2f.3b.4a.5c.6c, | 1e.2f.3b.4a.5c.6d, |
| 1e.2f.3b.4a.5c.6e, | 1e.2f.3b.4a.5c.6f, | 1e.2f.3b.4a.5d.6a, | 1e.2f.3b.4a.5d.6b, | 1e.2f.3b.4a.5d.6c, |
| 1e.2f.3b.4a.5d.6d, | 1e.2f.3b.4a.5d.6e, | 1e.2f.3b.4a.5d.6f, | 1e.2f.3b.4a.5e.6a, | |
| 1e.2f.3b.4a.5e.6b, | 1e.2f.3b.4a.5e.6c, | 1e.2f.3b.4a.5e.6d, | 1e.2f.3b.4a.5e.6e, | 1e.2f.3b.4a.5e.6f, |
| 1e.2f.3b.4a.5f.6a, | 1e.2f.3b.4a.5f.6b, | 1e.2f.3b.4a.5f.6c, | 1e.2f.3b.4a.5f.6d, | 1e.2f.3b.4a.5f.6e, |
| 1e.2f.3b.4a.5f.6f, | 1e.2f.3b.4b.5a.6a, | 1e.2f.3b.4b.5a.6b, | 1e.2f.3b.4b.5a.6c, | 1e.2f.3b.4b.5a.6d, |
| 1e.2f.3b.4b.5a.6e, | 1e.2f.3b.4b.5a.6f, | 1e.2f.3b.4b.5b.6a, | 1e.2f.3b.4b.5b.6b, | |
| 1e.2f.3b.4b.5b.6c, | 1e.2f.3b.4b.5b.6d, | 1e.2f.3b.4b.5b.6e, | 1e.2f.3b.4b.5b.6f, | |
| 1e.2f.3b.4b.5c.6a, | 1e.2f.3b.4b.5c.6b, | 1e.2f.3b.4b.5c.6c, | 1e.2f.3b.4b.5c.6d, | |
| 1e.2f.3b.4b.5c.6e, | 1e.2f.3b.4b.5c.6f, | 1e.2f.3b.4b.5d.6a, | 1e.2f.3b.4b.5d.6b, | |
| 1e.2f.3b.4b.5d.6c, | 1e.2f.3b.4b.5d.6d, | 1e.2f.3b.4b.5d.6e, | 1e.2f.3b.4b.5d.6f, | |
| 1e.2f.3b.4b.5e.6a, | 1e.2f.3b.4b.5e.6b, | 1e.2f.3b.4b.5e.6c, | 1e.2f.3b.4b.5e.6d, | |
| 1e.2f.3b.4b.5e.6e, | 1e.2f.3b.4b.5e.6f, | 1e.2f.3b.4b.5f.6a, | 1e.2f.3b.4b.5f.6b, | 1e.2f.3b.4b.5f.6c, |
| 1e.2f.3b.4b.5f.6d, | 1e.2f.3b.4b.5f.6e, | 1e.2f.3b.4b.5f.6f, | 1e.2f.3b.4c.5a.6a, | 1e.2f.3b.4c.5a.6b, |

TABLE 7-continued

List of Compounds of Formula (II)

| | | | | |
|---|---|---|---|---|
| 1e.2f.3b.4c.5a.6c, | 1e.2f.3b.4c.5a.6d, | 1e.2f.3b.4c.5a.6e, | 1e.2f.3b.4c.5a.6f, | 1e.2f.3b.4c.5b.6a, |
| 1e.2f.3b.4c.5b.6b, | 1e.2f.3b.4c.5b.6c, | 1e.2f.3b.4c.5b.6d, | 1e.2f.3b.4c.5b.6e, | 1e.2f.3b.4c.5b.6f, |
| 1e.2f.3b.4c.5c.6a, | 1e.2f.3b.4c.5c.6b, | 1e.2f.3b.4c.5c.6c, | 1e.2f.3b.4c.5c.6d, | 1e.2f.3b.4c.5c.6e, |
| 1e.2f.3b.4c.5c.6f, | 1e.2f.3b.4c.5d.6a, | 1e.2f.3b.4c.5d.6b, | 1e.2f.3b.4c.5d.6c, | |
| 1e.2f.3b.4c.5d.6d, | 1e.2f.3b.4c.5d.6e, | 1e.2f.3b.4c.5d.6f, | 1e.2f.3b.4c.5e.6a, | 1e.2f.3b.4c.5e.6b, |
| 1e.2f.3b.4c.5e.6c, | 1e.2f.3b.4c.5e.6d, | 1e.2f.3b.4c.5e.6e, | 1e.2f.3b.4c.5e.6f, | 1e.2f.3b.4c.5f.6a, |
| 1e.2f.3b.4c.5f.6b, | 1e.2f.3b.4c.5f.6c, | 1e.2f.3b.4c.5f.6d, | 1e.2f.3b.4c.5f.6e, | 1e.2f.3b.4c.5f.6f, |
| 1e.2f.3b.4d.5a.6a, | 1e.2f.3b.4d.5a.6b, | 1e.2f.3b.4d.5a.6c, | 1e.2f.3b.4d.5a.6d, | |
| 1e.2f.3b.4d.5a.6e, | 1e.2f.3b.4d.5a.6f, | 1e.2f.3b.4d.5b.6a, | 1e.2f.3b.4d.5b.6b, | |
| 1e.2f.3b.4d.5b.6c, | 1e.2f.3b.4d.5b.6d, | 1e.2f.3b.4d.5b.6e, | 1e.2f.3b.4d.5b.6f, | |
| 1e.2f.3b.4d.5c.6a, | 1e.2f.3b.4d.5c.6b, | 1e.2f.3b.4d.5c.6c, | 1e.2f.3b.4d.5c.6d, | |
| 1e.2f.3b.4d.5c.6e, | 1e.2f.3b.4d.5c.6f, | 1e.2f.3b.4d.5d.6a, | 1e.2f.3b.4d.5d.6b, | |
| 1e.2f.3b.4d.5d.6c, | 1e.2f.3b.4d.5d.6d, | 1e.2f.3b.4d.5d.6e, | 1e.2f.3b.4d.5d.6f, | |
| 1e.2f.3b.4d.5e.6a, | 1e.2f.3b.4d.5e.6b, | 1e.2f.3b.4d.5e.6c, | 1e.2f.3b.4d.5e.6d, | |
| 1e.2f.3b.4d.5e.6e, | 1e.2f.3b.4d.5e.6f, | 1e.2f.3b.4d.5f.6a, | 1e.2f.3b.4d.5f.6b, | 1e.2f.3b.4d.5f.6c, |
| 1e.2f.3b.4d.5f.6d, | 1e.2f.3b.4d.5f.6e, | 1e.2f.3b.4d.5f.6f, | 1e.2f.3b.4e.5a.6a, | 1e.2f.3b.4e.5a.6b, |
| 1e.2f.3b.4e.5a.6c, | 1e.2f.3b.4e.5a.6d, | 1e.2f.3b.4e.5a.6e, | 1e.2f.3b.4e.5a.6f, | 1e.2f.3b.4e.5b.6a, |
| 1e.2f.3b.4e.5b.6b, | 1e.2f.3b.4e.5b.6c, | 1e.2f.3b.4e.5b.6d, | 1e.2f.3b.4e.5b.6e, | |
| 1e.2f.3b.4e.5b.6f, | 1e.2f.3b.4e.5c.6a, | 1e.2f.3b.4e.5c.6b, | 1e.2f.3b.4e.5c.6c, | 1e.2f.3b.4e.5c.6d, |
| 1e.2f.3b.4e.5c.6e, | 1e.2f.3b.4e.5c.6f, | 1e.2f.3b.4e.5d.6a, | 1e.2f.3b.4e.5d.6b, | 1e.2f.3b.4e.5d.6c, |
| 1e.2f.3b.4e.5d.6d, | 1e.2f.3b.4e.5d.6e, | 1e.2f.3b.4e.5d.6f, | 1e.2f.3b.4e.5e.6a, | |
| 1e.2f.3b.4e.5e.6b, | 1e.2f.3b.4e.5e.6c, | 1e.2f.3b.4e.5e.6d, | 1e.2f.3b.4e.5e.6e, | 1e.2f.3b.4e.5e.6f, |
| 1e.2f.3b.4e.5f.6a, | 1e.2f.3b.4e.5f.6b, | 1e.2f.3b.4e.5f.6c, | 1e.2f.3b.4e.5f.6d, | 1e.2f.3b.4e.5f.6e, |
| 1e.2f.3b.4e.5f.6f, | 1e.2f.3b.4f.5a.6a, | 1e.2f.3b.4f.5a.6b, | 1e.2f.3b.4f.5a.6c, | 1e.2f.3b.4f.5a.6d, |
| 1e.2f.3b.4f.5a.6e, | 1e.2f.3b.4f.5a.6f, | 1e.2f.3b.4f.5b.6a, | 1e.2f.3b.4f.5b.6b, | 1e.2f.3b.4f.5b.6c, |
| 1e.2f.3b.4f.5b.6d, | 1e.2f.3b.4f.5b.6e, | 1e.2f.3b.4f.5b.6f, | 1e.2f.3b.4f.5c.6a, | 1e.2f.3b.4f.5c.6b, |
| 1e.2f.3b.4f.5c.6c, | 1e.2f.3b.4f.5c.6d, | 1e.2f.3b.4f.5c.6e, | 1e.2f.3b.4f.5c.6f, | 1e.2f.3b.4f.5d.6a, |
| 1e.2f.3b.4f.5d.6b, | 1e.2f.3b.4f.5d.6c, | 1e.2f.3b.4f.5d.6d, | 1e.2f.3b.4f.5d.6e, | 1e.2f.3b.4f.5d.6f, |
| 1e.2f.3b.4f.5e.6a, | 1e.2f.3b.4f.5e.6b, | 1e.2f.3b.4f.5e.6c, | 1e.2f.3b.4f.5e.6d, | 1e.2f.3b.4f.5e.6e, |
| 1e.2f.3b.4f.5e.6f, | 1e.2f.3b.4f.5f.6a, | 1e.2f.3b.4f.5f.6b, | 1e.2f.3b.4f.5f.6c, | 1e.2f.3b.4f.5f.6d, |
| 1e.2f.3b.4f.5f.6e, | 1e.2f.3b.4f.5f.6f, | 1e.2f.3c.4a.5a.6a, | 1e.2f.3c.4a.5a.6b, | 1e.2f.3c.4a.5a.6c, |
| 1e.2f.3c.4a.5a.6d, | 1e.2f.3c.4a.5a.6e, | 1e.2f.3c.4a.5a.6f, | 1e.2f.3c.4a.5b.6a, | 1e.2f.3c.4a.5b.6b, |
| 1e.2f.3c.4a.5b.6c, | 1e.2f.3c.4a.5b.6d, | 1e.2f.3c.4a.5b.6e, | 1e.2f.3c.4a.5b.6f, | 1e.2f.3c.4a.5c.6a, |
| 1e.2f.3c.4a.5c.6b, | 1e.2f.3c.4a.5c.6c, | 1e.2f.3c.4a.5c.6d, | 1e.2f.3c.4a.5c.6e, | 1e.2f.3c.4a.5c.6f, |
| 1e.2f.3c.4a.5d.6a, | 1e.2f.3c.4a.5d.6b, | 1e.2f.3c.4a.5d.6c, | 1e.2f.3c.4a.5d.6d, | |
| 1e.2f.3c.4a.5d.6e, | 1e.2f.3c.4a.5d.6f, | 1e.2f.3c.4a.5e.6a, | 1e.2f.3c.4a.5e.6b, | 1e.2f.3c.4a.5e.6c, |
| 1e.2f.3c.4a.5e.6d, | 1e.2f.3c.4a.5e.6e, | 1e.2f.3c.4a.5e.6f, | 1e.2f.3c.4a.5f.6a, | 1e.2f.3c.4a.5f.6b, |
| 1e.2f.3c.4a.5f.6c, | 1e.2f.3c.4a.5f.6d, | 1e.2f.3c.4a.5f.6e, | 1e.2f.3c.4a.5f.6f, | 1e.2f.3c.4b.5a.6a, |
| 1e.2f.3c.4b.5a.6b, | 1e.2f.3c.4b.5a.6c, | 1e.2f.3c.4b.5a.6d, | 1e.2f.3c.4b.5a.6e, | 1e.2f.3c.4b.5a.6f, |
| 1e.2f.3c.4b.5b.6a, | 1e.2f.3c.4b.5b.6b, | 1e.2f.3c.4b.5b.6c, | 1e.2f.3c.4b.5b.6d, | |
| 1e.2f.3c.4b.5b.6e, | 1e.2f.3c.4b.5b.6f, | 1e.2f.3c.4b.5c.6a, | 1e.2f.3c.4b.5c.6b, | 1e.2f.3c.4b.5c.6c, |
| 1e.2f.3c.4b.5c.6d, | 1e.2f.3c.4b.5c.6e, | 1e.2f.3c.4b.5c.6f, | 1e.2f.3c.4b.5d.6a, | 1e.2f.3c.4b.5d.6b, |
| 1e.2f.3c.4b.5d.6c, | 1e.2f.3c.4b.5d.6d, | 1e.2f.3c.4b.5d.6e, | 1e.2f.3c.4b.5d.6f, | 1e.2f.3c.4b.5e.6a, |
| 1e.2f.3c.4b.5e.6b, | 1e.2f.3c.4b.5e.6c, | 1e.2f.3c.4b.5e.6d, | 1e.2f.3c.4b.5e.6e, | 1e.2f.3c.4b.5e.6f, |
| 1e.2f.3c.4b.5f.6a, | 1e.2f.3c.4b.5f.6b, | 1e.2f.3c.4b.5f.6c, | 1e.2f.3c.4b.5f.6d, | 1e.2f.3c.4b.5f.6e, |
| 1e.2f.3c.4b.5f.6f, | 1e.2f.3c.4c.5a.6a, | 1e.2f.3c.4c.5a.6b, | 1e.2f.3c.4c.5a.6c, | 1e.2f.3c.4c.5a.6d, |
| 1e.2f.3c.4c.5a.6e, | 1e.2f.3c.4c.5a.6f, | 1e.2f.3c.4c.5b.6a, | 1e.2f.3c.4c.5b.6b, | 1e.2f.3c.4c.5b.6c, |
| 1e.2f.3c.4c.5b.6d, | 1e.2f.3c.4c.5b.6e, | 1e.2f.3c.4c.5b.6f, | 1e.2f.3c.4c.5c.6a, | 1e.2f.3c.4c.5c.6b, |
| 1e.2f.3c.4c.5c.6c, | 1e.2f.3c.4c.5c.6d, | 1e.2f.3c.4c.5c.6e, | 1e.2f.3c.4c.5c.6f, | 1e.2f.3c.4c.5d.6a, |
| 1e.2f.3c.4c.5d.6b, | 1e.2f.3c.4c.5d.6c, | 1e.2f.3c.4c.5d.6d, | 1e.2f.3c.4c.5d.6e, | 1e.2f.3c.4c.5d.6f, |
| 1e.2f.3c.4c.5e.6a, | 1e.2f.3c.4c.5e.6b, | 1e.2f.3c.4c.5e.6c, | 1e.2f.3c.4c.5e.6d, | 1e.2f.3c.4c.5e.6e, |
| 1e.2f.3c.4c.5e.6f, | 1e.2f.3c.4c.5f.6a, | 1e.2f.3c.4c.5f.6b, | 1e.2f.3c.4c.5f.6c, | 1e.2f.3c.4c.5f.6d, |
| 1e.2f.3c.4c.5f.6e, | 1e.2f.3c.4c.5f.6f, | 1e.2f.3c.4d.5a.6a, | 1e.2f.3c.4d.5a.6b, | 1e.2f.3c.4d.5a.6c, |
| 1e.2f.3c.4d.5a.6d, | 1e.2f.3c.4d.5a.6e, | 1e.2f.3c.4d.5a.6f, | 1e.2f.3c.4d.5b.6a, | |
| 1e.2f.3c.4d.5b.6b, | 1e.2f.3c.4d.5b.6c, | 1e.2f.3c.4d.5b.6d, | 1e.2f.3c.4d.5b.6e, | |
| 1e.2f.3c.4d.5b.6f, | 1e.2f.3c.4d.5c.6a, | 1e.2f.3c.4d.5c.6b, | 1e.2f.3c.4d.5c.6c, | 1e.2f.3c.4d.5c.6d, |
| 1e.2f.3c.4d.5c.6e, | 1e.2f.3c.4d.5c.6f, | 1e.2f.3c.4d.5d.6a, | 1e.2f.3c.4d.5d.6b, | 1e.2f.3c.4d.5d.6c, |
| 1e.2f.3c.4d.5d.6d, | 1e.2f.3c.4d.5d.6e, | 1e.2f.3c.4d.5d.6f, | 1e.2f.3c.4d.5e.6a, | |
| 1e.2f.3c.4d.5e.6b, | 1e.2f.3c.4d.5e.6c, | 1e.2f.3c.4d.5e.6d, | 1e.2f.3c.4d.5e.6e, | 1e.2f.3c.4d.5e.6f, |
| 1e.2f.3c.4d.5f.6a, | 1e.2f.3c.4d.5f.6b, | 1e.2f.3c.4d.5f.6c, | 1e.2f.3c.4d.5f.6d, | 1e.2f.3c.4d.5f.6e, |
| 1e.2f.3c.4d.5f.6f, | 1e.2f.3c.4e.5a.6a, | 1e.2f.3c.4e.5a.6b, | 1e.2f.3c.4e.5a.6c, | 1e.2f.3c.4e.5a.6d, |
| 1e.2f.3c.4e.5a.6e, | 1e.2f.3c.4e.5a.6f, | 1e.2f.3c.4e.5b.6a, | 1e.2f.3c.4e.5b.6b, | 1e.2f.3c.4e.5b.6c, |
| 1e.2f.3c.4e.5b.6d, | 1e.2f.3c.4e.5b.6e, | 1e.2f.3c.4e.5b.6f, | 1e.2f.3c.4e.5c.6a, | 1e.2f.3c.4e.5c.6b, |
| 1e.2f.3c.4e.5c.6c, | 1e.2f.3c.4e.5c.6d, | 1e.2f.3c.4e.5c.6e, | 1e.2f.3c.4e.5c.6f, | 1e.2f.3c.4e.5d.6a, |
| 1e.2f.3c.4e.5d.6b, | 1e.2f.3c.4e.5d.6c, | 1e.2f.3c.4e.5d.6d, | 1e.2f.3c.4e.5d.6e, | 1e.2f.3c.4e.5d.6f, |
| 1e.2f.3c.4e.5e.6a, | 1e.2f.3c.4e.5e.6b, | 1e.2f.3c.4e.5e.6c, | 1e.2f.3c.4e.5e.6d, | 1e.2f.3c.4e.5e.6e, |
| 1e.2f.3c.4e.5e.6f, | 1e.2f.3c.4e.5f.6a, | 1e.2f.3c.4e.5f.6b, | 1e.2f.3c.4e.5f.6c, | 1e.2f.3c.4e.5f.6d, |
| 1e.2f.3c.4e.5f.6e, | 1e.2f.3c.4e.5f.6f, | 1e.2f.3c.4f.5a.6a, | 1e.2f.3c.4f.5a.6b, | 1e.2f.3c.4f.5a.6c, |
| 1e.2f.3c.4f.5a.6d, | 1e.2f.3c.4f.5a.6e, | 1e.2f.3c.4f.5a.6f, | 1e.2f.3c.4f.5b.6a, | 1e.2f.3c.4f.5b.6b, |
| 1e.2f.3c.4f.5b.6c, | 1e.2f.3c.4f.5b.6d, | 1e.2f.3c.4f.5b.6e, | 1e.2f.3c.4f.5b.6f, | 1e.2f.3c.4f.5c.6a, |
| 1e.2f.3c.4f.5c.6b, | 1e.2f.3c.4f.5c.6c, | 1e.2f.3c.4f.5c.6d, | 1e.2f.3c.4f.5c.6e, | 1e.2f.3c.4f.5c.6f, |
| 1e.2f.3c.4f.5d.6a, | 1e.2f.3c.4f.5d.6b, | 1e.2f.3c.4f.5d.6c, | 1e.2f.3c.4f.5d.6d, | 1e.2f.3c.4f.5d.6e, |
| 1e.2f.3c.4f.5d.6f, | 1e.2f.3c.4f.5e.6a, | 1e.2f.3c.4f.5e.6b, | 1e.2f.3c.4f.5e.6c, | 1e.2f.3c.4f.5e.6d, |
| 1e.2f.3c.4f.5e.6e, | 1e.2f.3c.4f.5e.6f, | 1e.2f.3c.4f.5f.6a, | 1e.2f.3c.4f.5f.6b, | 1e.2f.3c.4f.5f.6c, |
| 1e.2f.3c.4f.5f.6d, | 1e.2f.3c.4f.5f.6e, | 1e.2f.3c.4f.5f.6f, | 1e.2f.3d.4a.5a.6a, | 1e.2f.3d.4a.5a.6b, |
| 1e.2f.3d.4a.5a.6c, | 1e.2f.3d.4a.5a.6d, | 1e.2f.3d.4a.5a.6e, | 1e.2f.3d.4a.5a.6f, | |
| 1e.2f.3d.4a.5b.6a, | 1e.2f.3d.4a.5b.6b, | 1e.2f.3d.4a.5b.6c, | 1e.2f.3d.4a.5b.6d, | |
| 1e.2f.3d.4a.5b.6e, | 1e.2f.3d.4a.5b.6f, | 1e.2f.3d.4a.5c.6a, | 1e.2f.3d.4a.5c.6b, | 1e.2f.3d.4a.5c.6c, |

TABLE 7-continued

List of Compounds of Formula (II)

| | | | | |
|---|---|---|---|---|
| 1e.2f.3d.4a.5c.6d, | 1e.2f.3d.4a.5c.6e, | 1e.2f.3d.4a.5c.6f, | 1e.2f.3d.4a.5d.6a, | |
| 1e.2f.3d.4a.5d.6b, | 1e.2f.3d.4a.5d.6c, | 1e.2f.3d.4a.5d.6d, | 1e.2f.3d.4a.5d.6e, | |
| 1e.2f.3d.4a.5d.6f, | 1e.2f.3d.4a.5e.6a, | 1e.2f.3d.4a.5e.6b, | 1e.2f.3d.4a.5e.6c, | |
| 1e.2f.3d.4a.5e.6d, | 1e.2f.3d.4a.5e.6e, | 1e.2f.3d.4a.5e.6f, | 1e.2f.3d.4a.5f.6a, | 1e.2f.3d.4a.5f.6b, |
| 1e.2f.3d.4a.5f.6c, | 1e.2f.3d.4a.5f.6d, | 1e.2f.3d.4a.5f.6e, | 1e.2f.3d.4a.5f.6f, | 1e.2f.3d.4b.5a.6a, |
| 1e.2f.3d.4b.5a.6b, | 1e.2f.3d.4b.5a.6c, | 1e.2f.3d.4b.5a.6d, | 1e.2f.3d.4b.5a.6e, | |
| 1e.2f.3d.4b.5a.6f, | 1e.2f.3d.4b.5b.6a, | 1e.2f.3d.4b.5b.6b, | 1e.2f.3d.4b.5b.6c, | |
| 1e.2f.3d.4b.5b.6d, | 1e.2f.3d.4b.5b.6e, | 1e.2f.3d.4b.5b.6f, | 1e.2f.3d.4b.5c.6a, | |
| 1e.2f.3d.4b.5c.6b, | 1e.2f.3d.4b.5c.6c, | 1e.2f.3d.4b.5c.6d, | 1e.2f.3d.4b.5c.6e, | |
| 1e.2f.3d.4b.5c.6f, | 1e.2f.3d.4b.5d.6a, | 1e.2f.3d.4b.5d.6b, | 1e.2f.3d.4b.5d.6c, | |
| 1e.2f.3d.4b.5d.6d, | 1e.2f.3d.4b.5d.6e, | 1e.2f.3d.4b.5d.6f, | 1e.2f.3d.4b.5e.6a, | |
| 1e.2f.3d.4b.5e.6b, | 1e.2f.3d.4b.5e.6c, | 1e.2f.3d.4b.5e.6d, | 1e.2f.3d.4b.5e.6e, | |
| 1e.2f.3d.4b.5e.6f, | 1e.2f.3d.4b.5f.6a, | 1e.2f.3d.4b.5f.6b, | 1e.2f.3d.4b.5f.6c, | 1e.2f.3d.4b.5f.6d, |
| 1e.2f.3d.4b.5f.6e, | 1e.2f.3d.4b.5f.6f, | 1e.2f.3d.4c.5a.6a, | 1e.2f.3d.4c.5a.6b, | 1e.2f.3d.4c.5a.6c, |
| 1e.2f.3d.4c.5a.6d, | 1e.2f.3d.4c.5a.6e, | 1e.2f.3d.4c.5a.6f, | 1e.2f.3d.4c.5b.6a, | |
| 1e.2f.3d.4c.5b.6b, | 1e.2f.3d.4c.5b.6c, | 1e.2f.3d.4c.5b.6d, | 1e.2f.3d.4c.5b.6e, | |
| 1e.2f.3d.4c.5b.6f, | 1e.2f.3d.4c.5c.6a, | 1e.2f.3d.4c.5c.6b, | 1e.2f.3d.4c.5c.6c, | 1e.2f.3d.4c.5c.6d, |
| 1e.2f.3d.4c.5c.6e, | 1e.2f.3d.4c.5c.6f, | 1e.2f.3d.4c.5d.6a, | 1e.2f.3d.4c.5d.6b, | 1e.2f.3d.4c.5d.6c, |
| 1e.2f.3d.4c.5d.6d, | 1e.2f.3d.4c.5d.6e, | 1e.2f.3d.4c.5d.6f, | 1e.2f.3d.4c.5e.6a, | |
| 1e.2f.3d.4c.5e.6b, | 1e.2f.3d.4c.5e.6c, | 1e.2f.3d.4c.5e.6d, | 1e.2f.3d.4c.5e.6e, | 1e.2f.3d.4c.5e.6f, |
| 1e.2f.3d.4c.5f.6a, | 1e.2f.3d.4c.5f.6b, | 1e.2f.3d.4c.5f.6c, | 1e.2f.3d.4c.5f.6d, | 1e.2f.3d.4c.5f.6e, |
| 1e.2f.3d.4c.5f.6f, | 1e.2f.3d.4d.5a.6a, | 1e.2f.3d.4d.5a.6b, | 1e.2f.3d.4d.5a.6c, | |
| 1e.2f.3d.4d.5a.6d, | 1e.2f.3d.4d.5a.6e, | 1e.2f.3d.4d.5a.6f, | 1e.2f.3d.4d.5b.6a, | |
| 1e.2f.3d.4d.5b.6b, | 1e.2f.3d.4d.5b.6c, | 1e.2f.3d.4d.5b.6d, | 1e.2f.3d.4d.5b.6e, | |
| 1e.2f.3d.4d.5b.6f, | 1e.2f.3d.4d.5c.6a, | 1e.2f.3d.4d.5c.6b, | 1e.2f.3d.4d.5c.6c, | |
| 1e.2f.3d.4d.5c.6d, | 1e.2f.3d.4d.5c.6e, | 1e.2f.3d.4d.5c.6f, | 1e.2f.3d.4d.5d.6a, | |
| 1e.2f.3d.4d.5d.6b, | 1e.2f.3d.4d.5d.6c, | 1e.2f.3d.4d.5d.6d, | 1e.2f.3d.4d.5d.6e, | |
| 1e.2f.3d.4d.5d.6f, | 1e.2f.3d.4d.5e.6a, | 1e.2f.3d.4d.5e.6b, | 1e.2f.3d.4d.5e.6c, | |
| 1e.2f.3d.4d.5e.6d, | 1e.2f.3d.4d.5e.6e, | 1e.2f.3d.4d.5e.6f, | 1e.2f.3d.4d.5f.6a, | |
| 1e.2f.3d.4d.5f.6b, | 1e.2f.3d.4d.5f.6c, | 1e.2f.3d.4d.5f.6d, | 1e.2f.3d.4d.5f.6e, | 1e.2f.3d.4d.5f.6f, |
| 1e.2f.3d.4e.5a.6a, | 1e.2f.3d.4e.5a.6b, | 1e.2f.3d.4e.5a.6c, | 1e.2f.3d.4e.5a.6d, | |
| 1e.2f.3d.4e.5a.6e, | 1e.2f.3d.4e.5a.6f, | 1e.2f.3d.4e.5b.6a, | 1e.2f.3d.4e.5b.6b, | |
| 1e.2f.3d.4e.5b.6c, | 1e.2f.3d.4e.5b.6d, | 1e.2f.3d.4e.5b.6e, | 1e.2f.3d.4e.5b.6f, | |
| 1e.2f.3d.4e.5c.6a, | 1e.2f.3d.4e.5c.6b, | 1e.2f.3d.4e.5c.6c, | 1e.2f.3d.4e.5c.6d, | 1e.2f.3d.4e.5c.6e, |
| 1e.2f.3d.4e.5c.6f, | 1e.2f.3d.4e.5d.6a, | 1e.2f.3d.4e.5d.6b, | 1e.2f.3d.4e.5d.6c, | |
| 1e.2f.3d.4e.5d.6d, | 1e.2f.3d.4e.5d.6e, | 1e.2f.3d.4e.5d.6f, | 1e.2f.3d.4e.5e.6a, | |
| 1e.2f.3d.4e.5e.6b, | 1e.2f.3d.4e.5e.6c, | 1e.2f.3d.4e.5e.6d, | 1e.2f.3d.4e.5e.6e, | 1e.2f.3d.4e.5e.6f, |
| 1e.2f.3d.4e.5f.6a, | 1e.2f.3d.4e.5f.6b, | 1e.2f.3d.4e.5f.6c, | 1e.2f.3d.4e.5f.6d, | 1e.2f.3d.4e.5f.6e, |
| 1e.2f.3d.4e.5f.6f, | 1e.2f.3d.4f.5a.6a, | 1e.2f.3d.4f.5a.6b, | 1e.2f.3d.4f.5a.6c, | 1e.2f.3d.4f.5a.6d, |
| 1e.2f.3d.4f.5a.6e, | 1e.2f.3d.4f.5a.6f, | 1e.2f.3d.4f.5b.6a, | 1e.2f.3d.4f.5b.6b, | 1e.2f.3d.4f.5b.6c, |
| 1e.2f.3d.4f.5b.6d, | 1e.2f.3d.4f.5b.6e, | 1e.2f.3d.4f.5b.6f, | 1e.2f.3d.4f.5c.6a, | 1e.2f.3d.4f.5c.6b, |
| 1e.2f.3d.4f.5c.6c, | 1e.2f.3d.4f.5c.6d, | 1e.2f.3d.4f.5c.6e, | 1e.2f.3d.4f.5c.6f, | 1e.2f.3d.4f.5d.6a, |
| 1e.2f.3d.4f.5d.6b, | 1e.2f.3d.4f.5d.6c, | 1e.2f.3d.4f.5d.6d, | 1e.2f.3d.4f.5d.6e, | 1e.2f.3d.4f.5d.6f, |
| 1e.2f.3d.4f.5e.6a, | 1e.2f.3d.4f.5e.6b, | 1e.2f.3d.4f.5e.6c, | 1e.2f.3d.4f.5e.6d, | 1e.2f.3d.4f.5e.6e, |
| 1e.2f.3d.4f.5e.6f, | 1e.2f.3d.4f.5f.6a, | 1e.2f.3d.4f.5f.6b, | 1e.2f.3d.4f.5f.6c, | 1e.2f.3d.4f.5f.6d, |
| 1e.2f.3d.4f.5f.6e, | 1e.2f.3d.4f.5f.6f, | 1e.2f.3e.4a.5a.6a, | 1e.2f.3e.4a.5a.6b, | 1e.2f.3e.4a.5a.6c, |
| 1e.2f.3e.4a.5a.6d, | 1e.2f.3e.4a.5a.6e, | 1e.2f.3e.4a.5a.6f, | 1e.2f.3e.4a.5b.6a, | 1e.2f.3e.4a.5b.6b, |
| 1e.2f.3e.4a.5b.6c, | 1e.2f.3e.4a.5b.6d, | 1e.2f.3e.4a.5b.6e, | 1e.2f.3e.4a.5b.6f, | 1e.2f.3e.4a.5c.6a, |
| 1e.2f.3e.4a.5c.6b, | 1e.2f.3e.4a.5c.6c, | 1e.2f.3e.4a.5c.6d, | 1e.2f.3e.4a.5c.6e, | 1e.2f.3e.4a.5c.6f, |
| 1e.2f.3e.4a.5d.6a, | 1e.2f.3e.4a.5d.6b, | 1e.2f.3e.4a.5d.6c, | 1e.2f.3e.4a.5d.6d, | |
| 1e.2f.3e.4a.5d.6e, | 1e.2f.3e.4a.5d.6f, | 1e.2f.3e.4a.5e.6a, | 1e.2f.3e.4a.5e.6b, | 1e.2f.3e.4a.5e.6c, |
| 1e.2f.3e.4a.5e.6d, | 1e.2f.3e.4a.5e.6e, | 1e.2f.3e.4a.5e.6f, | 1e.2f.3e.4a.5f.6a, | 1e.2f.3e.4a.5f.6b, |
| 1e.2f.3e.4a.5f.6c, | 1e.2f.3e.4a.5f.6d, | 1e.2f.3e.4a.5f.6e, | 1e.2f.3e.4a.5f.6f, | 1e.2f.3e.4b.5a.6a, |
| 1e.2f.3e.4b.5a.6b, | 1e.2f.3e.4b.5a.6c, | 1e.2f.3e.4b.5a.6d, | 1e.2f.3e.4b.5a.6e, | 1e.2f.3e.4b.5a.6f, |
| 1e.2f.3e.4b.5b.6a, | 1e.2f.3e.4b.5b.6b, | 1e.2f.3e.4b.5b.6c, | 1e.2f.3e.4b.5b.6d, | |
| 1e.2f.3e.4b.5b.6e, | 1e.2f.3e.4b.5b.6f, | 1e.2f.3e.4b.5c.6a, | 1e.2f.3e.4b.5c.6b, | 1e.2f.3e.4b.5c.6c, |
| 1e.2f.3e.4b.5c.6d, | 1e.2f.3e.4b.5c.6e, | 1e.2f.3e.4b.5c.6f, | 1e.2f.3e.4b.5d.6a, | 1e.2f.3e.4b.5d.6b, |
| 1e.2f.3e.4b.5d.6c, | 1e.2f.3e.4b.5d.6d, | 1e.2f.3e.4b.5d.6e, | 1e.2f.3e.4b.5d.6f, | |
| 1e.2f.3e.4b.5e.6a, | 1e.2f.3e.4b.5e.6b, | 1e.2f.3e.4b.5e.6c, | 1e.2f.3e.4b.5e.6d, | 1e.2f.3e.4b.5e.6e, |
| 1e.2f.3e.4b.5e.6f, | 1e.2f.3e.4b.5f.6a, | 1e.2f.3e.4b.5f.6b, | 1e.2f.3e.4b.5f.6c, | 1e.2f.3e.4b.5f.6d, |
| 1e.2f.3e.4b.5f.6e, | 1e.2f.3e.4b.5f.6f, | 1e.2f.3e.4c.5a.6a, | 1e.2f.3e.4c.5a.6b, | 1e.2f.3e.4c.5a.6c, |
| 1e.2f.3e.4c.5a.6d, | 1e.2f.3e.4c.5a.6e, | 1e.2f.3e.4c.5a.6f, | 1e.2f.3e.4c.5b.6a, | 1e.2f.3e.4c.5b.6b, |
| 1e.2f.3e.4c.5b.6c, | 1e.2f.3e.4c.5b.6d, | 1e.2f.3e.4c.5b.6e, | 1e.2f.3e.4c.5b.6f, | 1e.2f.3e.4c.5c.6a, |
| 1e.2f.3e.4c.5c.6b, | 1e.2f.3e.4c.5c.6c, | 1e.2f.3e.4c.5c.6d, | 1e.2f.3e.4c.5c.6e, | 1e.2f.3e.4c.5c.6f, |
| 1e.2f.3e.4c.5d.6a, | 1e.2f.3e.4c.5d.6b, | 1e.2f.3e.4c.5d.6c, | 1e.2f.3e.4c.5d.6d, | 1e.2f.3e.4c.5d.6e, |
| 1e.2f.3e.4c.5d.6f, | 1e.2f.3e.4c.5e.6a, | 1e.2f.3e.4c.5e.6b, | 1e.2f.3e.4c.5e.6c, | 1e.2f.3e.4c.5e.6d, |
| 1e.2f.3e.4c.5e.6e, | 1e.2f.3e.4c.5e.6f, | 1e.2f.3e.4c.5f.6a, | 1e.2f.3e.4c.5f.6b, | 1e.2f.3e.4c.5f.6c, |
| 1e.2f.3e.4c.5f.6d, | 1e.2f.3e.4c.5f.6e, | 1e.2f.3e.4c.5f.6f, | 1e.2f.3e.4d.5a.6a, | 1e.2f.3e.4d.5a.6b, |
| 1e.2f.3e.4d.5a.6c, | 1e.2f.3e.4d.5a.6d, | 1e.2f.3e.4d.5a.6e, | 1e.2f.3e.4d.5a.6f, | |
| 1e.2f.3e.4d.5b.6a, | 1e.2f.3e.4d.5b.6b, | 1e.2f.3e.4d.5b.6c, | 1e.2f.3e.4d.5b.6d, | |
| 1e.2f.3e.4d.5b.6e, | 1e.2f.3e.4d.5b.6f, | 1e.2f.3e.4d.5c.6a, | 1e.2f.3e.4d.5c.6b, | 1e.2f.3e.4d.5c.6c, |
| 1e.2f.3e.4d.5c.6d, | 1e.2f.3e.4d.5c.6e, | 1e.2f.3e.4d.5c.6f, | 1e.2f.3e.4d.5d.6a, | |
| 1e.2f.3e.4d.5d.6b, | 1e.2f.3e.4d.5d.6c, | 1e.2f.3e.4d.5d.6d, | 1e.2f.3e.4d.5d.6e, | |
| 1e.2f.3e.4d.5d.6f, | 1e.2f.3e.4d.5e.6a, | 1e.2f.3e.4d.5e.6b, | 1e.2f.3e.4d.5e.6c, | |
| 1e.2f.3e.4d.5e.6d, | 1e.2f.3e.4d.5e.6e, | 1e.2f.3e.4d.5e.6f, | 1e.2f.3e.4d.5f.6a, | 1e.2f.3e.4d.5f.6b, |
| 1e.2f.3e.4d.5f.6c, | 1e.2f.3e.4d.5f.6d, | 1e.2f.3e.4d.5f.6e, | 1e.2f.3e.4d.5f.6f, | 1e.2f.3e.4e.5a.6a, |
| 1e.2f.3e.4e.5a.6b, | 1e.2f.3e.4e.5a.6c, | 1e.2f.3e.4e.5a.6d, | 1e.2f.3e.4e.5a.6e, | 1e.2f.3e.4e.5a.6f, |
| 1e.2f.3e.4e.5b.6a, | 1e.2f.3e.4e.5b.6b, | 1e.2f.3e.4e.5b.6c, | 1e.2f.3e.4e.5b.6d, | 1e.2f.3e.4e.5b.6e, |

TABLE 7-continued

List of Compounds of Formula (II)

| | | | | |
|---|---|---|---|---|
| 1e.2f.3e.4e.5b.6f, | 1e.2f.3e.4e.5c.6a, | 1e.2f.3e.4e.5c.6b, | 1e.2f.3e.4e.5c.6c, | 1e.2f.3e.4e.5c.6d, |
| 1e.2f.3e.4e.5c.6e, | 1e.2f.3e.4e.5c.6f, | 1e.2f.3e.4e.5d.6a, | 1e.2f.3e.4e.5d.6b, | 1e.2f.3e.4e.5d.6c, |
| 1e.2f.3e.4e.5d.6d, | 1e.2f.3e.4e.5d.6e, | 1e.2f.3e.4e.5d.6f, | 1e.2f.3e.4e.5e.6a, | 1e.2f.3e.4e.5e.6b, |
| 1e.2f.3e.4e.5e.6c, | 1e.2f.3e.4e.5e.6d, | 1e.2f.3e.4e.5e.6e, | 1e.2f.3e.4e.5e.6f, | 1e.2f.3e.4e.5f.6a, |
| 1e.2f.3e.4e.5f.6b, | 1e.2f.3e.4e.5f.6c, | 1e.2f.3e.4e.5f.6d, | 1e.2f.3e.4e.5f.6e, | 1e.2f.3e.4e.5f.6f, |
| 1e.2f.3e.4f.5a.6a, | 1e.2f.3e.4f.5a.6b, | 1e.2f.3e.4f.5a.6c, | 1e.2f.3e.4f.5a.6d, | 1e.2f.3e.4f.5a.6e, |
| 1e.2f.3e.4f.5a.6f, | 1e.2f.3e.4f.5b.6a, | 1e.2f.3e.4f.5b.6b, | 1e.2f.3e.4f.5b.6c, | 1e.2f.3e.4f.5b.6d, |
| 1e.2f.3e.4f.5b.6e, | 1e.2f.3e.4f.5b.6f, | 1e.2f.3e.4f.5c.6a, | 1e.2f.3e.4f.5c.6b, | 1e.2f.3e.4f.5c.6c, |
| 1e.2f.3e.4f.5c.6d, | 1e.2f.3e.4f.5c.6e, | 1e.2f.3e.4f.5c.6f, | 1e.2f.3e.4f.5d.6a, | 1e.2f.3e.4f.5d.6b, |
| 1e.2f.3e.4f.5d.6c, | 1e.2f.3e.4f.5d.6d, | 1e.2f.3e.4f.5d.6e, | 1e.2f.3e.4f.5d.6f, | 1e.2f.3e.4f.5e.6a, |
| 1e.2f.3e.4f.5e.6b, | 1e.2f.3e.4f.5e.6c, | 1e.2f.3e.4f.5e.6d, | 1e.2f.3e.4f.5e.6e, | 1e.2f.3e.4f.5e.6f, |
| 1e.2f.3e.4f.5f.6a, | 1e.2f.3e.4f.5f.6b, | 1e.2f.3e.4f.5f.6c, | 1e.2f.3e.4f.5f.6d, | 1e.2f.3e.4f.5f.6e, |
| 1e.2f.3e.4f.5f.6f, | 1e.2f.3f.4a.5a.6a, | 1e.2f.3f.4a.5a.6b, | 1e.2f.3f.4a.5a.6c, | 1e.2f.3f.4a.5a.6d, |
| 1e.2f.3f.4a.5a.6e, | 1e.2f.3f.4a.5a.6f, | 1e.2f.3f.4a.5b.6a, | 1e.2f.3f.4a.5b.6b, | 1e.2f.3f.4a.5b.6c, |
| 1e.2f.3f.4a.5b.6d, | 1e.2f.3f.4a.5b.6e, | 1e.2f.3f.4a.5b.6f, | 1e.2f.3f.4a.5c.6a, | 1e.2f.3f.4a.5c.6b, |
| 1e.2f.3f.4a.5c.6c, | 1e.2f.3f.4a.5c.6d, | 1e.2f.3f.4a.5c.6e, | 1e.2f.3f.4a.5c.6f, | 1e.2f.3f.4a.5d.6a, |
| 1e.2f.3f.4a.5d.6b, | 1e.2f.3f.4a.5d.6c, | 1e.2f.3f.4a.5d.6d, | 1e.2f.3f.4a.5d.6e, | 1e.2f.3f.4a.5d.6f, |
| 1e.2f.3f.4a.5e.6a, | 1e.2f.3f.4a.5e.6b, | 1e.2f.3f.4a.5e.6c, | 1e.2f.3f.4a.5e.6d, | 1e.2f.3f.4a.5e.6e, |
| 1e.2f.3f.4a.5e.6f, | 1e.2f.3f.4a.5f.6a, | 1e.2f.3f.4a.5f.6b, | 1e.2f.3f.4a.5f.6c, | 1e.2f.3f.4a.5f.6d, |
| 1e.2f.3f.4a.5f.6e, | 1e.2f.3f.4a.5f.6f, | 1e.2f.3f.4b.5a.6a, | 1e.2f.3f.4b.5a.6b, | 1e.2f.3f.4b.5a.6c, |
| 1e.2f.3f.4b.5a.6d, | 1e.2f.3f.4b.5a.6e, | 1e.2f.3f.4b.5a.6f, | 1e.2f.3f.4b.5b.6a, | 1e.2f.3f.4b.5b.6b, |
| 1e.2f.3f.4b.5b.6c, | 1e.2f.3f.4b.5b.6d, | 1e.2f.3f.4b.5b.6e, | 1e.2f.3f.4b.5b.6f, | 1e.2f.3f.4b.5c.6a, |
| 1e.2f.3f.4b.5c.6b, | 1e.2f.3f.4b.5c.6c, | 1e.2f.3f.4b.5c.6d, | 1e.2f.3f.4b.5c.6e, | 1e.2f.3f.4b.5c.6f, |
| 1e.2f.3f.4b.5d.6a, | 1e.2f.3f.4b.5d.6b, | 1e.2f.3f.4b.5d.6c, | 1e.2f.3f.4b.5d.6d, | 1e.2f.3f.4b.5d.6e, |
| 1e.2f.3f.4b.5d.6f, | 1e.2f.3f.4b.5e.6a, | 1e.2f.3f.4b.5e.6b, | 1e.2f.3f.4b.5e.6c, | 1e.2f.3f.4b.5e.6d, |
| 1e.2f.3f.4b.5e.6e, | 1e.2f.3f.4b.5e.6f, | 1e.2f.3f.4b.5f.6a, | 1e.2f.3f.4b.5f.6b, | 1e.2f.3f.4b.5f.6c, |
| 1e.2f.3f.4b.5f.6d, | 1e.2f.3f.4b.5f.6e, | 1e.2f.3f.4b.5f.6f, | 1e.2f.3f.4c.5a.6a, | 1e.2f.3f.4c.5a.6b, |
| 1e.2f.3f.4c.5a.6c, | 1e.2f.3f.4c.5a.6d, | 1e.2f.3f.4c.5a.6e, | 1e.2f.3f.4c.5a.6f, | 1e.2f.3f.4c.5b.6a, |
| 1e.2f.3f.4c.5b.6b, | 1e.2f.3f.4c.5b.6c, | 1e.2f.3f.4c.5b.6d, | 1e.2f.3f.4c.5b.6e, | 1e.2f.3f.4c.5b.6f, |
| 1e.2f.3f.4c.5c.6a, | 1e.2f.3f.4c.5c.6b, | 1e.2f.3f.4c.5c.6c, | 1e.2f.3f.4c.5c.6d, | 1e.2f.3f.4c.5c.6e, |
| 1e.2f.3f.4c.5c.6f, | 1e.2f.3f.4c.5d.6a, | 1e.2f.3f.4c.5d.6b, | 1e.2f.3f.4c.5d.6c, | 1e.2f.3f.4c.5d.6d, |
| 1e.2f.3f.4c.5d.6e, | 1e.2f.3f.4c.5d.6f, | 1e.2f.3f.4c.5e.6a, | 1e.2f.3f.4c.5e.6b, | 1e.2f.3f.4c.5e.6c, |
| 1e.2f.3f.4c.5e.6d, | 1e.2f.3f.4c.5e.6e, | 1e.2f.3f.4c.5e.6f, | 1e.2f.3f.4c.5f.6a, | 1e.2f.3f.4c.5f.6b, |
| 1e.2f.3f.4c.5f.6c, | 1e.2f.3f.4c.5f.6d, | 1e.2f.3f.4c.5f.6e, | 1e.2f.3f.4c.5f.6f, | 1e.2f.3f.4d.5a.6a, |
| 1e.2f.3f.4d.5a.6b, | 1e.2f.3f.4d.5a.6c, | 1e.2f.3f.4d.5a.6d, | 1e.2f.3f.4d.5a.6e, | 1e.2f.3f.4d.5a.6f, |
| 1e.2f.3f.4d.5b.6a, | 1e.2f.3f.4d.5b.6b, | 1e.2f.3f.4d.5b.6c, | 1e.2f.3f.4d.5b.6d, | 1e.2f.3f.4d.5b.6e, |
| 1e.2f.3f.4d.5b.6f, | 1e.2f.3f.4d.5c.6a, | 1e.2f.3f.4d.5c.6b, | 1e.2f.3f.4d.5c.6c, | 1e.2f.3f.4d.5c.6d, |
| 1e.2f.3f.4d.5c.6e, | 1e.2f.3f.4d.5c.6f, | 1e.2f.3f.4d.5d.6a, | 1e.2f.3f.4d.5d.6b, | 1e.2f.3f.4d.5d.6c, |
| 1e.2f.3f.4d.5d.6d, | 1e.2f.3f.4d.5d.6e, | 1e.2f.3f.4d.5d.6f, | 1e.2f.3f.4d.5e.6a, | 1e.2f.3f.4d.5e.6b, |
| 1e.2f.3f.4d.5e.6c, | 1e.2f.3f.4d.5e.6d, | 1e.2f.3f.4d.5e.6e, | 1e.2f.3f.4d.5e.6f, | 1e.2f.3f.4d.5f.6a, |
| 1e.2f.3f.4d.5f.6b, | 1e.2f.3f.4d.5f.6c, | 1e.2f.3f.4d.5f.6d, | 1e.2f.3f.4d.5f.6e, | 1e.2f.3f.4d.5f.6f, |
| 1e.2f.3f.4e.5a.6a, | 1e.2f.3f.4e.5a.6b, | 1e.2f.3f.4e.5a.6c, | 1e.2f.3f.4e.5a.6d, | 1e.2f.3f.4e.5a.6e, |
| 1e.2f.3f.4e.5a.6f, | 1e.2f.3f.4e.5b.6a, | 1e.2f.3f.4e.5b.6b, | 1e.2f.3f.4e.5b.6c, | 1e.2f.3f.4e.5b.6d, |
| 1e.2f.3f.4e.5b.6e, | 1e.2f.3f.4e.5b.6f, | 1e.2f.3f.4e.5c.6a, | 1e.2f.3f.4e.5c.6b, | 1e.2f.3f.4e.5c.6c, |
| 1e.2f.3f.4e.5c.6d, | 1e.2f.3f.4e.5c.6e, | 1e.2f.3f.4e.5c.6f, | 1e.2f.3f.4e.5d.6a, | 1e.2f.3f.4e.5d.6b, |
| 1e.2f.3f.4e.5d.6c, | 1e.2f.3f.4e.5d.6d, | 1e.2f.3f.4e.5d.6e, | 1e.2f.3f.4e.5d.6f, | 1e.2f.3f.4e.5e.6a, |
| 1e.2f.3f.4e.5e.6b, | 1e.2f.3f.4e.5e.6c, | 1e.2f.3f.4e.5e.6d, | 1e.2f.3f.4e.5e.6e, | 1e.2f.3f.4e.5e.6f, |
| 1e.2f.3f.4e.5f.6a, | 1e.2f.3f.4e.5f.6b, | 1e.2f.3f.4e.5f.6c, | 1e.2f.3f.4e.5f.6d, | 1e.2f.3f.4e.5f.6e, |
| 1e.2f.3f.4e.5f.6f, | 1e.2f.3f.4f.5a.6a, | 1e.2f.3f.4f.5a.6b, | 1e.2f.3f.4f.5a.6c, | 1e.2f.3f.4f.5a.6d, |
| 1e.2f.3f.4f.5a.6e, | 1e.2f.3f.4f.5a.6f, | 1e.2f.3f.4f.5b.6a, | 1e.2f.3f.4f.5b.6b, | 1e.2f.3f.4f.5b.6c, |
| 1e.2f.3f.4f.5b.6d, | 1e.2f.3f.4f.5b.6e, | 1e.2f.3f.4f.5b.6f, | 1e.2f.3f.4f.5c.6a, | 1e.2f.3f.4f.5c.6b, |
| 1e.2f.3f.4f.5c.6c, | 1e.2f.3f.4f.5c.6d, | 1e.2f.3f.4f.5c.6e, | 1e.2f.3f.4f.5c.6f, | 1e.2f.3f.4f.5d.6a, |
| 1e.2f.3f.4f.5d.6b, | 1e.2f.3f.4f.5d.6c, | 1e.2f.3f.4f.5d.6d, | 1e.2f.3f.4f.5d.6e, | 1e.2f.3f.4f.5d.6f, |
| 1e.2f.3f.4f.5e.6a, | 1e.2f.3f.4f.5e.6b, | 1e.2f.3f.4f.5e.6c, | 1e.2f.3f.4f.5e.6d, | 1e.2f.3f.4f.5e.6e, |
| 1e.2f.3f.4f.5e.6f, | 1e.2f.3f.4f.5f.6a, | 1e.2f.3f.4f.5f.6b, | 1e.2f.3f.4f.5f.6c, | 1e.2f.3f.4f.5f.6d, |
| 1e.2f.3f.4f.5f.6e, | 1e.2f.3f.4f.5f.6f, | 1f.2a.3a.4a.5a.6a, | 1f.2a.3a.4a.5a.6b, | 1f.2a.3a.4a.5a.6c, |
| 1f.2a.3a.4a.5a.6d, | 1f.2a.3a.4a.5a.6e, | 1f.2a.3a.4a.5a.6f, | 1f.2a.3a.4a.5b.6a, | 1f.2a.3a.4a.5b.6b, |
| 1f.2a.3a.4a.5b.6c, | 1f.2a.3a.4a.5b.6d, | 1f.2a.3a.4a.5b.6e, | 1f.2a.3a.4a.5b.6f, | 1f.2a.3a.4a.5c.6a, |
| 1f.2a.3a.4a.5c.6b, | 1f.2a.3a.4a.5c.6c, | 1f.2a.3a.4a.5c.6d, | 1f.2a.3a.4a.5c.6e, | 1f.2a.3a.4a.5c.6f, |
| 1f.2a.3a.4a.5d.6a, | 1f.2a.3a.4a.5d.6b, | 1f.2a.3a.4a.5d.6c, | 1f.2a.3a.4a.5d.6d, | |
| 1f.2a.3a.4a.5d.6e, | 1f.2a.3a.4a.5d.6f, | 1f.2a.3a.4a.5e.6b, | 1f.2a.3a.4a.5e.6b, | 1f.2a.3a.4a.5e.6c, |
| 1f.2a.3a.4a.5e.6d, | 1f.2a.3a.4a.5e.6e, | 1f.2a.3a.4a.5e.6f, | 1f.2a.3a.4a.5f.6a, | 1f.2a.3a.4a.5f.6b, |
| 1f.2a.3a.4a.5f.6c, | 1f.2a.3a.4a.5f.6d, | 1f.2a.3a.4a.5f.6e, | 1f.2a.3a.4a.5f.6f, | 1f.2a.3a.4b.5a.6a, |
| 1f.2a.3a.4b.5a.6b, | 1f.2a.3a.4b.5a.6c, | 1f.2a.3a.4b.5a.6d, | 1f.2a.3a.4b.5a.6e, | 1f.2a.3a.4b.5a.6f, |
| 1f.2a.3a.4b.5b.6a, | 1f.2a.3a.4b.5b.6b, | 1f.2a.3a.4b.5b.6c, | 1f.2a.3a.4b.5b.6d, | |
| 1f.2a.3a.4b.5b.6e, | 1f.2a.3a.4b.5b.6f, | 1f.2a.3a.4b.5c.6a, | 1f.2a.3a.4b.5c.6b, | 1f.2a.3a.4b.5c.6c, |
| 1f.2a.3a.4b.5c.6d, | 1f.2a.3a.4b.5c.6e, | 1f.2a.3a.4b.5c.6f, | 1f.2a.3a.4b.5d.6a, | |
| 1f.2a.3a.4b.5d.6b, | 1f.2a.3a.4b.5d.6c, | 1f.2a.3a.4b.5d.6d, | 1f.2a.3a.4b.5d.6e, | |
| 1f.2a.3a.4b.5d.6f, | 1f.2a.3a.4b.5e.6a, | 1f.2a.3a.4b.5e.6b, | 1f.2a.3a.4b.5e.6c, | |
| 1f.2a.3a.4b.5e.6d, | 1f.2a.3a.4b.5e.6e, | 1f.2a.3a.4b.5e.6f, | 1f.2a.3a.4b.5f.6a, | 1f.2a.3a.4b.5f.6b, |
| 1f.2a.3a.4b.5f.6c, | 1f.2a.3a.4b.5f.6d, | 1f.2a.3a.4b.5f.6e, | 1f.2a.3a.4b.5f.6f, | 1f.2a.3a.4c.5a.6a, |
| 1f.2a.3a.4c.5a.6b, | 1f.2a.3a.4c.5a.6c, | 1f.2a.3a.4c.5a.6d, | 1f.2a.3a.4c.5a.6e, | 1f.2a.3a.4c.5a.6f, |
| 1f.2a.3a.4c.5b.6a, | 1f.2a.3a.4c.5b.6b, | 1f.2a.3a.4c.5b.6c, | 1f.2a.3a.4c.5b.6d, | 1f.2a.3a.4c.5b.6e, |
| 1f.2a.3a.4c.5b.6f, | 1f.2a.3a.4c.5c.6a, | 1f.2a.3a.4c.5c.6b, | 1f.2a.3a.4c.5c.6c, | 1f.2a.3a.4c.5c.6d, |
| 1f.2a.3a.4c.5c.6e, | 1f.2a.3a.4c.5c.6f, | 1f.2a.3a.4c.5d.6a, | 1f.2a.3a.4c.5d.6b, | 1f.2a.3a.4c.5d.6c, |
| 1f.2a.3a.4c.5d.6d, | 1f.2a.3a.4c.5d.6e, | 1f.2a.3a.4c.5d.6f, | 1f.2a.3a.4c.5e.6a, | 1f.2a.3a.4c.5e.6b, |
| 1f.2a.3a.4c.5e.6c, | 1f.2a.3a.4c.5e.6d, | 1f.2a.3a.4c.5e.6e, | 1f.2a.3a.4c.5e.6f, | 1f.2a.3a.4c.5f.6a, |
| 1f.2a.3a.4c.5f.6b, | 1f.2a.3a.4c.5f.6c, | 1f.2a.3a.4c.5f.6d, | 1f.2a.3a.4c.5f.6e, | 1f.2a.3a.4c.5f.6f, |

TABLE 7-continued

List of Compounds of Formula (II)

| | | | |
|---|---|---|---|
| 1f.2a.3a.4d.5a.6a, | 1f.2a.3a.4d.5a.6b, | 1f.2a.3a.4d.5a.6c, | 1f.2a.3a.4d.5a.6d, |
| 1f.2a.3a.4d.5a.6e, | 1f.2a.3a.4d.5a.6f, | 1f.2a.3a.4d.5b.6a, | 1f.2a.3a.4d.5b.6b, |
| 1f.2a.3a.4d.5b.6c, | 1f.2a.3a.4d.5b.6d, | 1f.2a.3a.4d.5b.6e, | 1f.2a.3a.4d.5b.6f, |
| 1f.2a.3a.4d.5c.6a, | 1f.2a.3a.4d.5c.6b, | 1f.2a.3a.4d.5c.6c, | 1f.2a.3a.4d.5c.6d, |
| 1f.2a.3a.4d.5c.6e, | 1f.2a.3a.4d.5c.6f, | 1f.2a.3a.4d.5d.6a, | 1f.2a.3a.4d.5d.6b, |
| 1f.2a.3a.4d.5d.6c, | 1f.2a.3a.4d.5d.6d, | 1f.2a.3a.4d.5d.6e, | 1f.2a.3a.4d.5d.6f, |
| 1f.2a.3a.4d.5e.6a, | 1f.2a.3a.4d.5e.6b, | 1f.2a.3a.4d.5e.6c, | 1f.2a.3a.4d.5e.6d, |
| 1f.2a.3a.4d.5e.6e, | 1f.2a.3a.4d.5e.6f, | 1f.2a.3a.4d.5f.6a, | 1f.2a.3a.4d.5f.6b, | 1f.2a.3a.4d.5f.6c, |
| 1f.2a.3a.4d.5f.6d, | 1f.2a.3a.4d.5f.6e, | 1f.2a.3a.4d.5f.6f, | 1f.2a.3a.4e.5a.6a, | 1f.2a.3a.4e.5a.6b, |
| 1f.2a.3a.4e.5a.6c, | 1f.2a.3a.4e.5a.6d, | 1f.2a.3a.4e.5a.6e, | 1f.2a.3a.4e.5a.6f, | 1f.2a.3a.4e.5b.6a, |
| 1f.2a.3a.4e.5b.6b, | 1f.2a.3a.4e.5b.6c, | 1f.2a.3a.4e.5b.6d, | 1f.2a.3a.4e.5b.6e, | 1f.2a.3a.4e.5b.6f, |
| 1f.2a.3a.4e.5c.6a, | 1f.2a.3a.4e.5c.6b, | 1f.2a.3a.4e.5c.6c, | 1f.2a.3a.4e.5c.6d, | 1f.2a.3a.4e.5c.6e, |
| 1f.2a.3a.4e.5c.6f, | 1f.2a.3a.4e.5d.6a, | 1f.2a.3a.4e.5d.6b, | 1f.2a.3a.4e.5d.6c, | |
| 1f.2a.3a.4e.5d.6d, | 1f.2a.3a.4e.5d.6e, | 1f.2a.3a.4e.5d.6f, | 1f.2a.3a.4e.5e.6a, | 1f.2a.3a.4e.5e.6b, |
| 1f.2a.3a.4e.5e.6c, | 1f.2a.3a.4e.5e.6d, | 1f.2a.3a.4e.5e.6e, | 1f.2a.3a.4e.5e.6f, | 1f.2a.3a.4e.5f.6a, |
| 1f.2a.3a.4e.5f.6b, | 1f.2a.3a.4e.5f.6c, | 1f.2a.3a.4e.5f.6d, | 1f.2a.3a.4e.5f.6e, | 1f.2a.3a.4e.5f.6f, |
| 1f.2a.3a.4f.5a.6a, | 1f.2a.3a.4f.5a.6b, | 1f.2a.3a.4f.5a.6c, | 1f.2a.3a.4f.5a.6d, | 1f.2a.3a.4f.5a.6e, |
| 1f.2a.3a.4f.5a.6f, | 1f.2a.3a.4f.5b.6a, | 1f.2a.3a.4f.5b.6b, | 1f.2a.3a.4f.5b.6c, | 1f.2a.3a.4f.5b.6d, |
| 1f.2a.3a.4f.5b.6e, | 1f.2a.3a.4f.5b.6f, | 1f.2a.3a.4f.5c.6a, | 1f.2a.3a.4f.5c.6b, | 1f.2a.3a.4f.5c.6c, |
| 1f.2a.3a.4f.5c.6d, | 1f.2a.3a.4f.5c.6e, | 1f.2a.3a.4f.5c.6f, | 1f.2a.3a.4f.5d.6a, | 1f.2a.3a.4f.5d.6b, |
| 1f.2a.3a.4f.5d.6c, | 1f.2a.3a.4f.5d.6d, | 1f.2a.3a.4f.5d.6e, | 1f.2a.3a.4f.5d.6f, | 1f.2a.3a.4f.5e.6a, |
| 1f.2a.3a.4f.5e.6b, | 1f.2a.3a.4f.5e.6c, | 1f.2a.3a.4f.5e.6d, | 1f.2a.3a.4f.5e.6e, | 1f.2a.3a.4f.5e.6f, |
| 1f.2a.3a.4f.5f.6a, | 1f.2a.3a.4f.5f.6b, | 1f.2a.3a.4f.5f.6c, | 1f.2a.3a.4f.5f.6d, | 1f.2a.3a.4f.5f.6e, |
| 1f.2a.3a.4f.5f.6f, | 1f.2a.3b.4a.5a.6a, | 1f.2a.3b.4a.5a.6b, | 1f.2a.3b.4a.5a.6c, | 1f.2a.3b.4a.5a.6d, |
| 1f.2a.3b.4a.5a.6e, | 1f.2a.3b.4a.5a.6f, | 1f.2a.3b.4a.5b.6a, | 1f.2a.3b.4a.5b.6b, | |
| 1f.2a.3b.4a.5b.6c, | 1f.2a.3b.4a.5b.6d, | 1f.2a.3b.4a.5b.6e, | 1f.2a.3b.4a.5b.6f, | |
| 1f.2a.3b.4a.5c.6a, | 1f.2a.3b.4a.5c.6b, | 1f.2a.3b.4a.5c.6c, | 1f.2a.3b.4a.5c.6d, | 1f.2a.3b.4a.5c.6e, |
| 1f.2a.3b.4a.5c.6f, | 1f.2a.3b.4a.5d.6a, | 1f.2a.3b.4a.5d.6b, | 1f.2a.3b.4a.5d.6c, | |
| 1f.2a.3b.4a.5d.6d, | 1f.2a.3b.4a.5d.6e, | 1f.2a.3b.4a.5d.6f, | 1f.2a.3b.4a.5e.6a, | |
| 1f.2a.3b.4a.5e.6b, | 1f.2a.3b.4a.5e.6c, | 1f.2a.3b.4a.5e.6d, | 1f.2a.3b.4a.5e.6e, | 1f.2a.3b.4a.5e.6f, |
| 1f.2a.3b.4a.5f.6a, | 1f.2a.3b.4a.5f.6b, | 1f.2a.3b.4a.5f.6c, | 1f.2a.3b.4a.5f.6d, | 1f.2a.3b.4a.5f.6e, |
| 1f.2a.3b.4a.5f.6f, | 1f.2a.3b.4b.5a.6a, | 1f.2a.3b.4b.5a.6b, | 1f.2a.3b.4b.5a.6c, | |
| 1f.2a.3b.4b.5a.6d, | 1f.2a.3b.4b.5a.6e, | 1f.2a.3b.4b.5a.6f, | 1f.2a.3b.4b.5b.6a, | |
| 1f.2a.3b.4b.5b.6b, | 1f.2a.3b.4b.5b.6c, | 1f.2a.3b.4b.5b.6d, | 1f.2a.3b.4b.5b.6e, | |
| 1f.2a.3b.4b.5b.6f, | 1f.2a.3b.4b.5c.6a, | 1f.2a.3b.4b.5c.6b, | 1f.2a.3b.4b.5c.6c, | |
| 1f.2a.3b.4b.5c.6d, | 1f.2a.3b.4b.5c.6e, | 1f.2a.3b.4b.5c.6f, | 1f.2a.3b.4b.5d.6a, | |
| 1f.2a.3b.4b.5d.6b, | 1f.2a.3b.4b.5d.6c, | 1f.2a.3b.4b.5d.6d, | 1f.2a.3b.4b.5d.6e, | |
| 1f.2a.3b.4b.5d.6f, | 1f.2a.3b.4b.5e.6a, | 1f.2a.3b.4b.5e.6b, | 1f.2a.3b.4b.5e.6c, | |
| 1f.2a.3b.4b.5e.6d, | 1f.2a.3b.4b.5e.6e, | 1f.2a.3b.4b.5e.6f, | 1f.2a.3b.4b.5f.6a, | 1f.2a.3b.4b.5f.6b, |
| 1f.2a.3b.4b.5f.6c, | 1f.2a.3b.4b.5f.6d, | 1f.2a.3b.4b.5f.6e, | 1f.2a.3b.4b.5f.6f, | 1f.2a.3b.4c.5a.6a, |
| 1f.2a.3b.4c.5a.6b, | 1f.2a.3b.4c.5a.6c, | 1f.2a.3b.4c.5a.6d, | 1f.2a.3b.4c.5a.6e, | 1f.2a.3b.4c.5a.6f, |
| 1f.2a.3b.4c.5b.6a, | 1f.2a.3b.4c.5b.6b, | 1f.2a.3b.4c.5b.6c, | 1f.2a.3b.4c.5b.6d, | |
| 1f.2a.3b.4c.5b.6e, | 1f.2a.3b.4c.5b.6f, | 1f.2a.3b.4c.5c.6a, | 1f.2a.3b.4c.5c.6b, | 1f.2a.3b.4c.5c.6c, |
| 1f.2a.3b.4c.5c.6d, | 1f.2a.3b.4c.5c.6e, | 1f.2a.3b.4c.5c.6f, | 1f.2a.3b.4c.5d.6a, | 1f.2a.3b.4c.5d.6b, |
| 1f.2a.3b.4c.5d.6c, | 1f.2a.3b.4c.5d.6d, | 1f.2a.3b.4c.5d.6e, | 1f.2a.3b.4c.5d.6f, | |
| 1f.2a.3b.4c.5e.6a, | 1f.2a.3b.4c.5e.6b, | 1f.2a.3b.4c.5e.6c, | 1f.2a.3b.4c.5e.6d, | 1f.2a.3b.4c.5e.6e, |
| 1f.2a.3b.4c.5e.6f, | 1f.2a.3b.4c.5f.6a, | 1f.2a.3b.4c.5f.6b, | 1f.2a.3b.4c.5f.6c, | 1f.2a.3b.4c.5f.6d, |
| 1f.2a.3b.4c.5f.6e, | 1f.2a.3b.4c.5f.6f, | 1f.2a.3b.4d.5a.6a, | 1f.2a.3b.4d.5a.6b, | 1f.2a.3b.4d.5a.6c, |
| 1f.2a.3b.4d.5a.6d, | 1f.2a.3b.4d.5a.6e, | 1f.2a.3b.4d.5a.6f, | 1f.2a.3b.4d.5b.6a, | |
| 1f.2a.3b.4d.5b.6b, | 1f.2a.3b.4d.5b.6c, | 1f.2a.3b.4d.5b.6d, | 1f.2a.3b.4d.5b.6e, | |
| 1f.2a.3b.4d.5b.6f, | 1f.2a.3b.4d.5c.6a, | 1f.2a.3b.4d.5c.6b, | 1f.2a.3b.4d.5c.6c, | |
| 1f.2a.3b.4d.5c.6d, | 1f.2a.3b.4d.5c.6e, | 1f.2a.3b.4d.5c.6f, | 1f.2a.3b.4d.5d.6a, | |
| 1f.2a.3b.4d.5d.6b, | 1f.2a.3b.4d.5d.6c, | 1f.2a.3b.4d.5d.6d, | 1f.2a.3b.4d.5d.6e, | |
| 1f.2a.3b.4d.5d.6f, | 1f.2a.3b.4d.5e.6a, | 1f.2a.3b.4d.5e.6b, | 1f.2a.3b.4d.5e.6c, | |
| 1f.2a.3b.4d.5e.6d, | 1f.2a.3b.4d.5e.6e, | 1f.2a.3b.4d.5e.6f, | 1f.2a.3b.4d.5f.6a, | |
| 1f.2a.3b.4d.5f.6b, | 1f.2a.3b.4d.5f.6c, | 1f.2a.3b.4d.5f.6d, | 1f.2a.3b.4d.5f.6e, | 1f.2a.3b.4d.5f.6f, |
| 1f.2a.3b.4e.5a.6a, | 1f.2a.3b.4e.5a.6b, | 1f.2a.3b.4e.5a.6c, | 1f.2a.3b.4e.5a.6d, | |
| 1f.2a.3b.4e.5a.6e, | 1f.2a.3b.4e.5a.6f, | 1f.2a.3b.4e.5b.6a, | 1f.2a.3b.4e.5b.6b, | 1f.2a.3b.4e.5b.6c, |
| 1f.2a.3b.4e.5b.6d, | 1f.2a.3b.4e.5b.6e, | 1f.2a.3b.4e.5b.6f, | 1f.2a.3b.4e.5c.6a, | 1f.2a.3b.4e.5c.6b, |
| 1f.2a.3b.4e.5c.6c, | 1f.2a.3b.4e.5c.6d, | 1f.2a.3b.4e.5c.6e, | 1f.2a.3b.4e.5c.6f, | 1f.2a.3b.4e.5d.6a, |
| 1f.2a.3b.4e.5d.6b, | 1f.2a.3b.4e.5d.6c, | 1f.2a.3b.4e.5d.6d, | 1f.2a.3b.4e.5d.6e, | |
| 1f.2a.3b.4e.5d.6f, | 1f.2a.3b.4e.5e.6a, | 1f.2a.3b.4e.5e.6b, | 1f.2a.3b.4e.5e.6c, | 1f.2a.3b.4e.5e.6d, |
| 1f.2a.3b.4e.5e.6e, | 1f.2a.3b.4e.5e.6f, | 1f.2a.3b.4e.5f.6a, | 1f.2a.3b.4e.5f.6b, | 1f.2a.3b.4e.5f.6c, |
| 1f.2a.3b.4e.5f.6d, | 1f.2a.3b.4e.5f.6e, | 1f.2a.3b.4e.5f.6f, | 1f.2a.3b.4f.5a.6a, | 1f.2a.3b.4f.5a.6b, |
| 1f.2a.3b.4f.5a.6c, | 1f.2a.3b.4f.5a.6d, | 1f.2a.3b.4f.5a.6e, | 1f.2a.3b.4f.5a.6f, | 1f.2a.3b.4f.5b.6a, |
| 1f.2a.3b.4f.5b.6b, | 1f.2a.3b.4f.5b.6c, | 1f.2a.3b.4f.5b.6d, | 1f.2a.3b.4f.5b.6e, | 1f.2a.3b.4f.5b.6f, |
| 1f.2a.3b.4f.5c.6a, | 1f.2a.3b.4f.5c.6b, | 1f.2a.3b.4f.5c.6c, | 1f.2a.3b.4f.5c.6d, | 1f.2a.3b.4f.5c.6e, |
| 1f.2a.3b.4f.5c.6f, | 1f.2a.3b.4f.5d.6a, | 1f.2a.3b.4f.5d.6b, | 1f.2a.3b.4f.5d.6c, | 1f.2a.3b.4f.5d.6d, |
| 1f.2a.3b.4f.5d.6e, | 1f.2a.3b.4f.5d.6f, | 1f.2a.3b.4f.5e.6a, | 1f.2a.3b.4f.5e.6b, | 1f.2a.3b.4f.5e.6c, |
| 1f.2a.3b.4f.5e.6d, | 1f.2a.3b.4f.5e.6e, | 1f.2a.3b.4f.5e.6f, | 1f.2a.3b.4f.5f.6a, | 1f.2a.3b.4f.5f.6b, |
| 1f.2a.3b.4f.5f.6c, | 1f.2a.3b.4f.5f.6d, | 1f.2a.3b.4f.5f.6e, | 1f.2a.3b.4f.5f.6f, | 1f.2a.3c.4a.5a.6a, |
| 1f.2a.3c.4a.5a.6b, | 1f.2a.3c.4a.5a.6c, | 1f.2a.3c.4a.5a.6d, | 1f.2a.3c.4a.5a.6e, | 1f.2a.3c.4a.5a.6f, |
| 1f.2a.3c.4a.5b.6a, | 1f.2a.3c.4a.5b.6b, | 1f.2a.3c.4a.5b.6c, | 1f.2a.3c.4a.5b.6d, | 1f.2a.3c.4a.5b.6e, |
| 1f.2a.3c.4a.5b.6f, | 1f.2a.3c.4a.5c.6a, | 1f.2a.3c.4a.5c.6b, | 1f.2a.3c.4a.5c.6c, | 1f.2a.3c.4a.5c.6d, |
| 1f.2a.3c.4a.5c.6e, | 1f.2a.3c.4a.5c.6f, | 1f.2a.3c.4a.5d.6a, | 1f.2a.3c.4a.5d.6b, | 1f.2a.3c.4a.5d.6c, |
| 1f.2a.3c.4a.5d.6d, | 1f.2a.3c.4a.5d.6e, | 1f.2a.3c.4a.5d.6f, | 1f.2a.3c.4a.5e.6a, | 1f.2a.3c.4a.5e.6b, |
| 1f.2a.3c.4a.5e.6c, | 1f.2a.3c.4a.5e.6d, | 1f.2a.3c.4a.5e.6e, | 1f.2a.3c.4a.5e.6f, | 1f.2a.3c.4a.5f.6a, |
| 1f.2a.3c.4a.5f.6b, | 1f.2a.3c.4a.5f.6c, | 1f.2a.3c.4a.5f.6d, | 1f.2a.3c.4a.5f.6e, | 1f.2a.3c.4a.5f.6f, |

TABLE 7-continued

List of Compounds of Formula (II)

| | | | | |
|---|---|---|---|---|
| 1f.2a.3c.4b.5a.6a, | 1f.2a.3c.4b.5a.6b, | 1f.2a.3c.4b.5a.6c, | 1f.2a.3c.4b.5a.6d, | 1f.2a.3c.4b.5a.6e, |
| 1f.2a.3c.4b.5a.6f, | 1f.2a.3c.4b.5b.6a, | 1f.2a.3c.4b.5b.6b, | 1f.2a.3c.4b.5b.6c, | 1f.2a.3c.4b.5b.6d, |
| 1f.2a.3c.4b.5b.6e, | 1f.2a.3c.4b.5b.6f, | 1f.2a.3c.4b.5c.6a, | 1f.2a.3c.4b.5c.6b, | 1f.2a.3c.4b.5c.6c, |
| 1f.2a.3c.4b.5c.6d, | 1f.2a.3c.4b.5c.6e, | 1f.2a.3c.4b.5c.6f, | 1f.2a.3c.4b.5d.6a, | 1f.2a.3c.4b.5d.6b, |
| 1f.2a.3c.4b.5d.6c, | 1f.2a.3c.4b.5d.6d, | 1f.2a.3c.4b.5d.6e, | 1f.2a.3c.4b.5d.6f, | |
| 1f.2a.3c.4b.5e.6a, | 1f.2a.3c.4b.5e.6b, | 1f.2a.3c.4b.5e.6c, | 1f.2a.3c.4b.5e.6d, | 1f.2a.3c.4b.5e.6e, |
| 1f.2a.3c.4b.5e.6f, | 1f.2a.3c.4b.5f.6a, | 1f.2a.3c.4b.5f.6b, | 1f.2a.3c.4b.5f.6c, | 1f.2a.3c.4b.5f.6d, |
| 1f.2a.3c.4b.5f.6e, | 1f.2a.3c.4b.5f.6f, | 1f.2a.3c.4c.5a.6a, | 1f.2a.3c.4c.5a.6b, | 1f.2a.3c.4c.5a.6c, |
| 1f.2a.3c.4c.5a.6d, | 1f.2a.3c.4c.5a.6e, | 1f.2a.3c.4c.5a.6f, | 1f.2a.3c.4c.5b.6a, | 1f.2a.3c.4c.5b.6b, |
| 1f.2a.3c.4c.5b.6c, | 1f.2a.3c.4c.5b.6d, | 1f.2a.3c.4c.5b.6e, | 1f.2a.3c.4c.5b.6f, | 1f.2a.3c.4c.5c.6a, |
| 1f.2a.3c.4c.5c.6b, | 1f.2a.3c.4c.5c.6c, | 1f.2a.3c.4c.5c.6d, | 1f.2a.3c.4c.5c.6e, | 1f.2a.3c.4c.5c.6f, |
| 1f.2a.3c.4c.5d.6a, | 1f.2a.3c.4c.5d.6b, | 1f.2a.3c.4c.5d.6c, | 1f.2a.3c.4c.5d.6d, | 1f.2a.3c.4c.5d.6e, |
| 1f.2a.3c.4c.5d.6f, | 1f.2a.3c.4c.5e.6a, | 1f.2a.3c.4c.5e.6b, | 1f.2a.3c.4c.5e.6c, | 1f.2a.3c.4c.5e.6d, |
| 1f.2a.3c.4c.5e.6e, | 1f.2a.3c.4c.5e.6f, | 1f.2a.3c.4c.5f.6a, | 1f.2a.3c.4c.5f.6b, | 1f.2a.3c.4c.5f.6c, |
| 1f.2a.3c.4c.5f.6d, | 1f.2a.3c.4c.5f.6e, | 1f.2a.3c.4c.5f.6f, | 1f.2a.3c.4d.5a.6a, | 1f.2a.3c.4d.5a.6b, |
| 1f.2a.3c.4d.5a.6c, | 1f.2a.3c.4d.5a.6d, | 1f.2a.3c.4d.5a.6e, | 1f.2a.3c.4d.5a.6f, | 1f.2a.3c.4d.5b.6a, |
| 1f.2a.3c.4d.5b.6b, | 1f.2a.3c.4d.5b.6c, | 1f.2a.3c.4d.5b.6d, | 1f.2a.3c.4d.5b.6e, | |
| 1f.2a.3c.4d.5b.6f, | 1f.2a.3c.4d.5c.6a, | 1f.2a.3c.4d.5c.6b, | 1f.2a.3c.4d.5c.6c, | 1f.2a.3c.4d.5c.6d, |
| 1f.2a.3c.4d.5c.6e, | 1f.2a.3c.4d.5c.6f, | 1f.2a.3c.4d.5d.6a, | 1f.2a.3c.4d.5d.6b, | |
| 1f.2a.3c.4d.5d.6c, | 1f.2a.3c.4d.5d.6d, | 1f.2a.3c.4d.5d.6e, | 1f.2a.3c.4d.5d.6f, | |
| 1f.2a.3c.4d.5e.6a, | 1f.2a.3c.4d.5e.6b, | 1f.2a.3c.4d.5e.6c, | 1f.2a.3c.4d.5e.6d, | |
| 1f.2a.3c.4d.5e.6e, | 1f.2a.3c.4d.5e.6f, | 1f.2a.3c.4d.5f.6a, | 1f.2a.3c.4d.5f.6b, | 1f.2a.3c.4d.5f.6c, |
| 112.3c.4d.5f.6d, | 1f.2a.3c.4d.5f.6e, | 1f.2a.3c.4d.5f.6f, | 1f.2a.3c.4e.5a.6a, | 1f.2a.3c.4e.5a.6b, |
| 1f.2a.3c.4e.5a.6c, | 1f.2a.3c.4e.5a.6d, | 1f.2a.3c.4e.5a.6e, | 1f.2a.3c.4e.5a.6f, | 1f.2a.3c.4e.5b.6a, |
| 1f.2a.3c.4e.5b.6b, | 1f.2a.3c.4e.5b.6c, | 1f.2a.3c.4e.5b.6d, | 1f.2a.3c.4e.5b.6e, | 1f.2a.3c.4e.5b.6f, |
| 1f.2a.3c.4e.5c.6a, | 1f.2a.3c.4e.5c.6b, | 1f.2a.3c.4e.5c.6c, | 1f.2a.3c.4e.5c.6d, | 1f.2a.3c.4e.5c.6e, |
| 1f.2a.3c.4e.5c.6f, | 1f.2a.3c.4e.5d.6a, | 1f.2a.3c.4e.5d.6b, | 1f.2a.3c.4e.5d.6c, | 1f.2a.3c.4e.5d.6d, |
| 1f.2a.3c.4e.5d.6e, | 1f.2a.3c.4e.5d.6f, | 1f.2a.3c.4e.5e.6a, | 1f.2a.3c.4e.5e.6b, | 1f.2a.3c.4e.5e.6c, |
| 1f.2a.3c.4e.5e.6d, | 1f.2a.3c.4e.5e.6e, | 1f.2a.3c.4e.5e.6f, | 1f.2a.3c.4e.5f.6a, | 1f.2a.3c.4e.5f.6b, |
| 1f.2a.3c.4e.5f.6c, | 1f.2a.3c.4e.5f.6d, | 1f.2a.3c.4e.5f.6e, | 1f.2a.3c.4e.5f.6f, | 1f.2a.3c.4f.5a.6a, |
| 1f.2a.3c.4f.5a.6b, | 1f.2a.3c.4f.5a.6c, | 1f.2a.3c.4f.5a.6d, | 1f.2a.3c.4f.5a.6e, | 1f.2a.3c.4f.5a.6f, |
| 1f.2a.3c.4f.5b.6a, | 1f.2a.3c.4f.5b.6b, | 1f.2a.3c.4f.5b.6c, | 1f.2a.3c.4f.5b.6d, | 1f.2a.3c.4f.5b.6e, |
| 1f.2a.3c.4f.5b.6f, | 1f.2a.3c.4f.5c.6a, | 1f.2a.3c.4f.5c.6b, | 1f.2a.3c.4f.5c.6c, | 1f.2a.3c.4f.5c.6d, |
| 1f.2a.3c.4f.5c.6e, | 1f.2a.3c.4f.5c.6f, | 1f.2a.3c.4f.5d.6a, | 1f.2a.3c.4f.5d.6b, | 1f.2a.3c.4f.5d.6c, |
| 1f.2a.3c.4f.5d.6d, | 1f.2a.3c.4f.5d.6e, | 1f.2a.3c.4f.5d.6f, | 1f.2a.3c.4f.5e.6a, | 1f.2a.3c.4f.5e.6b, |
| 1f.2a.3c.4f.5e.6c, | 1f.2a.3c.4f.5e.6d, | 1f.2a.3c.4f.5e.6e, | 1f.2a.3c.4f.5f.6a, | |
| 1f.2a.3c.4f.5f.6b, | 1f.2a.3c.4f.5f.6c, | 1f.2a.3c.4f.5f.6d, | 1f.2a.3c.4f.5f.6e, | 1f.2a.3c.4f.5f.6f, |
| 1f.2a.3d.4a.5a.6a, | 1f.2a.3d.4a.5a.6b, | 1f.2a.3d.4a.5a.6c, | 1f.2a.3d.4a.5a.6d, | |
| 1f.2a.3d.4a.5a.6e, | 1f.2a.3d.4a.5a.6f, | 1f.2a.3d.4a.5b.6a, | 1f.2a.3d.4a.5b.6b, | |
| 1f.2a.3d.4a.5b.6c, | 1f.2a.3d.4a.5b.6d, | 1f.2a.3d.4a.5b.6e, | 1f.2a.3d.4a.5b.6f, | |
| 1f.2a.3d.4a.5c.6a, | 1f.2a.3d.4a.5c.6b, | 1f.2a.3d.4a.5c.6c, | 1f.2a.3d.4a.5c.6d, | |
| 1f.2a.3d.4a.5c.6e, | 1f.2a.3d.4a.5c.6f, | 1f.2a.3d.4a.5d.6a, | 1f.2a.3d.4a.5d.6b, | |
| 1f.2a.3d.4a.5d.6c, | 1f.2a.3d.4a.5d.6d, | 1f.2a.3d.4a.5d.6e, | 1f.2a.3d.4a.5d.6f, | |
| 1f.2a.3d.4a.5e.6a, | 1f.2a.3d.4a.5e.6b, | 1f.2a.3d.4a.5e.6c, | 1f.2a.3d.4a.5e.6d, | |
| 1f.2a.3d.4a.5e.6e, | 1f.2a.3d.4a.5e.6f, | 1f.2a.3d.4a.5f.6a, | 1f.2a.3d.4a.5f.6b, | 1f.2a.3d.4a.5f.6c, |
| 1f.2a.3d.4a.5f.6d, | 1f.2a.3d.4a.5f.6e, | 1f.2a.3d.4a.5f.6f, | 1f.2a.3d.4b.5a.6a, | 1f.2a.3d.4b.5a.6b, |
| 1f.2a.3d.4b.5a.6c, | 1f.2a.3d.4b.5a.6d, | 1f.2a.3d.4b.5a.6e, | 1f.2a.3d.4b.5a.6f, | |
| 1f.2a.3d.4b.5b.6a, | 1f.2a.3d.4b.5b.6b, | 1f.2a.3d.4b.5b.6c, | 1f.2a.3d.4b.5b.6d, | |
| 1f.2a.3d.4b.5b.6e, | 1f.2a.3d.4b.5b.6f, | 1f.2a.3d.4b.5c.6a, | 1f.2a.3d.4b.5c.6b, | |
| 1f.2a.3d.4b.5c.6c, | 1f.2a.3d.4b.5c.6d, | 1f.2a.3d.4b.5c.6e, | 1f.2a.3d.4b.5c.6f, | |
| 1f.2a.3d.4b.5d.6a, | 1f.2a.3d.4b.5d.6b, | 1f.2a.3d.4b.5d.6c, | 1f.2a.3d.4b.5d.6d, | |
| 1f.2a.3d.4b.5d.6e, | 1f.2a.3d.4b.5d.6f, | 1f.2a.3d.4b.5e.6a, | 1f.2a.3d.4b.5e.6b, | |
| 1f.2a.3d.4b.5e.6c, | 1f.2a.3d.4b.5e.6d, | 1f.2a.3d.4b.5e.6e, | 1f.2a.3d.4b.5e.6f, | |
| 1f.2a.3d.4b.5f.6a, | 1f.2a.3d.4b.5f.6b, | 1f.2a.3d.4b.5f.6c, | 1f.2a.3d.4b.5f.6d, | 1f.2a.3d.4b.5f.6e, |
| 1f.2a.3d.4b.5f.6f, | 1f.2a.3d.4c.5a.6a, | 1f.2a.3d.4c.5a.6b, | 1f.2a.3d.4c.5a.6c, | 1f.2a.3d.4c.5a.6d, |
| 1f.2a.3d.4c.5a.6e, | 1f.2a.3d.4c.5a.6f, | 1f.2a.3d.4c.5b.6a, | 1f.2a.3d.4c.5b.6b, | |
| 1f.2a.3d.4c.5b.6c, | 1f.2a.3d.4c.5b.6d, | 1f.2a.3d.4c.5b.6e, | 1f.2a.3d.4c.5b.6f, | |
| 1f.2a.3d.4c.5c.6a, | 1f.2a.3d.4c.5c.6b, | 1f.2a.3d.4c.5c.6c, | 1f.2a.3d.4c.5c.6d, | 1f.2a.3d.4c.5c.6e, |
| 1f.2a.3d.4c.5c.6f, | 1f.2a.3d.4c.5d.6a, | 1f.2a.3d.4c.5d.6b, | 1f.2a.3d.4c.5d.6c, | |
| 1f.2a.3d.4c.5d.6d, | 1f.2a.3d.4c.5d.6e, | 1f.2a.3d.4c.5d.6f, | 1f.2a.3d.4c.5e.6a, | |
| 1f.2a.3d.4c.5e.6b, | 1f.2a.3d.4c.5e.6c, | 1f.2a.3d.4c.5e.6d, | 1f.2a.3d.4c.5e.6e, | 1f.2a.3d.4c.5e.6f, |
| 1f.2a.3d.4c.5f.6a, | 1f.2a.3d.4c.5f.6b, | 1f.2a.3d.4c.5f.6c, | 1f.2a.3d.4c.5f.6d, | 1f.2a.3d.4c.5f.6e, |
| 1f.2a.3d.4c.5f.6f, | 1f.2a.3d.4d.5a.6a, | 1f.2a.3d.4d.5a.6b, | 1f.2a.3d.4d.5a.6c, | |
| 1f.2a.3d.4d.5a.6d, | 1f.2a.3d.4d.5a.6e, | 1f.2a.3d.4d.5a.6f, | 1f.2a.3d.4d.5b.6a, | |
| 1f.2a.3d.4d.5b.6b, | 1f.2a.3d.4d.5b.6c, | 1f.2a.3d.4d.5b.6d, | 1f.2a.3d.4d.5b.6e, | |
| 1f.2a.3d.4d.5b.6f, | 1f.2a.3d.4d.5c.6a, | 1f.2a.3d.4d.5c.6b, | 1f.2a.3d.4d.5c.6c, | |
| 1f.2a.3d.4d.5c.6d, | 1f.2a.3d.4d.5c.6e, | 1f.2a.3d.4d.5c.6f, | 1f.2a.3d.4d.5d.6a, | |
| 1f.2a.3d.4d.5d.6b, | 1f.2a.3d.4d.5d.6c, | 1f.2a.3d.4d.5d.6d, | 1f.2a.3d.4d.5d.6e, | |
| 1f.2a.3d.4d.5d.6f, | 1f.2a.3d.4d.5e.6a, | 1f.2a.3d.4d.5e.6b, | 1f.2a.3d.4d.5e.6c, | |
| 1f.2a.3d.4d.5e.6d, | 1f.2a.3d.4d.5e.6e, | 1f.2a.3d.4d.5e.6f, | 1f.2a.3d.4d.5f.6a, | |
| 1f.2a.3d.4d.5f.6b, | 1f.2a.3d.4d.5f.6c, | 1f.2a.3d.4d.5f.6d, | 1f.2a.3d.4d.5f.6e, | 1f.2a.3d.4d.5f.6f, |
| 1f.2a.3d.4e.5a.6a, | 1f.2a.3d.4e.5a.6b, | 1f.2a.3d.4e.5a.6c, | 1f.2a.3d.4e.5a.6d, | |
| 1f.2a.3d.4e.5a.6e, | 1f.2a.3d.4e.5a.6f, | 1f.2a.3d.4e.5b.6a, | 1f.2a.3d.4e.5b.6b, | |
| 1f.2a.3d.4e.5b.6c, | 1f.2a.3d.4e.5b.6d, | 1f.2a.3d.4e.5b.6e, | 1f.2a.3d.4e.5b.6f, | |
| 1f.2a.3d.4e.5c.6a, | 1f.2a.3d.4e.5c.6b, | 1f.2a.3d.4e.5c.6c, | 1f.2a.3d.4e.5c.6d, | |
| 1f.2a.3d.4e.5c.6e, | 1f.2a.3d.4e.5c.6f, | 1f.2a.3d.4e.5d.6a, | 1f.2a.3d.4e.5d.6b, | |
| 1f.2a.3d.4e.5d.6c, | 1f.2a.3d.4e.5d.6d, | 1f.2a.3d.4e.5d.6e, | 1f.2a.3d.4e.5d.6f, | |
| 1f.2a.3d.4e.5e.6a, | 1f.2a.3d.4e.5e.6b, | 1f.2a.3d.4e.5e.6c, | 1f.2a.3d.4e.5e.6d, | |

TABLE 7-continued

List of Compounds of Formula (II)

| | | | | |
|---|---|---|---|---|
| 1f.2a.3d.4e.5e.6e, | 1f.2a.3d.4e.5e.6f, | 1f.2a.3d.4e.5f.6a, | 1f.2a.3d.4e.5f.6b, | 1f.2a.3d.4e.5f.6c, |
| 1f.2a.3d.4e.5f.6d, | 1f.2a.3d.4e.5f.6e, | 1f.2a.3d.4e.5f.6f, | 1f.2a.3d.4f.5a.6a, | 1f.2a.3d.4f.5a.6b, |
| 1f.2a.3d.4f.5a.6c, | 1f.2a.3d.4f.5a.6d, | 1f.2a.3d.4f.5a.6e, | 1f.2a.3d.4f.5a.6f, | 1f.2a.3d.4f.5b.6a, |
| 1f.2a.3d.4f.5b.6b, | 1f.2a.3d.4f.5b.6c, | 1f.2a.3d.4f.5b.6d, | 1f.2a.3d.4f.5b.6e, | 1f.2a.3d.4f.5b.6f, |
| 1f.2a.3d.4f.5c.6a, | 1f.2a.3d.4f.5c.6b, | 1f.2a.3d.4f.5c.6c, | 1f.2a.3d.4f.5c.6d, | 1f.2a.3d.4f.5c.6e, |
| 1f.2a.3d.4f.5c.6f, | 1f.2a.3d.4f.5d.6a, | 1f.2a.3d.4f.5d.6b, | 1f.2a.3d.4f.5d.6c, | 1f.2a.3d.4f.5d.6d, |
| 1f.2a.3d.4f.5d.6e, | 1f.2a.3d.4f.5d.6f, | 1f.2a.3d.4f.5e.6a, | 1f.2a.3d.4f.5e.6b, | 1f.2a.3d.4f.5e.6c, |
| 1f.2a.3d.4f.5e.6d, | 1f.2a.3d.4f.5e.6e, | 1f.2a.3d.4f.5e.6f, | 1f.2a.3d.4f.5f.6a, | 1f.2a.3d.4f.5f.6b, |
| 1f.2a.3d.4f.5f.6c, | 1f.2a.3d.4f.5f.6d, | 1f.2a.3d.4f.5f.6e, | 1f.2a.3d.4f.5f.6f, | 1f.2a.3e.4a.5a.6a, |
| 1f.2a.3e.4a.5a.6b, | 1f.2a.3e.4a.5a.6c, | 1f.2a.3e.4a.5a.6d, | 1f.2a.3e.4a.5a.6e, | 1f.2a.3e.4a.5a.6f, |
| 1f.2a.3e.4a.5b.6a, | 1f.2a.3e.4a.5b.6b, | 1f.2a.3e.4a.5b.6c, | 1f.2a.3e.4a.5b.6d, | |
| 1f.2a.3e.4a.5b.6e, | 1f.2a.3e.4a.5b.6f, | 1f.2a.3e.4a.5c.6a, | 1f.2a.3e.4a.5c.6b, | 1f.2a.3e.4a.5c.6c, |
| 1f.2a.3e.4a.5c.6d, | 1f.2a.3e.4a.5c.6e, | 1f.2a.3e.4a.5c.6f, | 1f.2a.3e.4a.5d.6a, | 1f.2a.3e.4a.5d.6b, |
| 1f.2a.3e.4a.5d.6c, | 1f.2a.3e.4a.5d.6d, | 1f.2a.3e.4a.5d.6e, | 1f.2a.3e.4a.5d.6f, | 1f.2a.3e.4a.5e.6a, |
| 1f.2a.3e.4a.5e.6b, | 1f.2a.3e.4a.5e.6c, | 1f.2a.3e.4a.5e.6d, | 1f.2a.3e.4a.5e.6e, | 1f.2a.3e.4a.5e.6f, |
| 1f.2a.3e.4a.5f.6a, | 1f.2a.3e.4a.5f.6b, | 1f.2a.3e.4a.5f.6c, | 1f.2a.3e.4a.5f.6d, | 1f.2a.3e.4a.5f.6e, |
| 1f.2a.3e.4a.5f.6f, | 1f.2a.3e.4b.5a.6a, | 1f.2a.3e.4b.5a.6b, | 1f.2a.3e.4b.5a.6c, | 1f.2a.3e.4b.5a.6d, |
| 1f.2a.3e.4b.5a.6e, | 1f.2a.3e.4b.5a.6f, | 1f.2a.3e.4b.5b.6a, | 1f.2a.3e.4b.5b.6b, | 1f.2a.3e.4b.5b.6c, |
| 1f.2a.3e.4b.5b.6d, | 1f.2a.3e.4b.5b.6e, | 1f.2a.3e.4b.5b.6f, | 1f.2a.3e.4b.5c.6a, | 1f.2a.3e.4b.5c.6b, |
| 1f.2a.3e.4b.5c.6c, | 1f.2a.3e.4b.5c.6d, | 1f.2a.3e.4b.5c.6e, | 1f.2a.3e.4b.5c.6f, | 1f.2a.3e.4b.5d.6a, |
| 1f.2a.3e.4b.5d.6b, | 1f.2a.3e.4b.5d.6c, | 1f.2a.3e.4b.5d.6d, | 1f.2a.3e.4b.5d.6e, | |
| 1f.2a.3e.4b.5d.6f, | 1f.2a.3e.4b.5e.6a, | 1f.2a.3e.4b.5e.6b, | 1f.2a.3e.4b.5e.6c, | 1f.2a.3e.4b.5e.6d, |
| 1f.2a.3e.4b.5e.6e, | 1f.2a.3e.4b.5e.6f, | 1f.2a.3e.4b.5f.6a, | 1f.2a.3e.4b.5f.6b, | 1f.2a.3e.4b.5f.6c, |
| 1f.2a.3e.4b.5f.6d, | 1f.2a.3e.4b.5f.6e, | 1f.2a.3e.4b.5f.6f, | 1f.2a.3e.4c.5a.6a, | 1f.2a.3e.4c.5a.6b, |
| 1f.2a.3e.4c.5a.6c, | 1f.2a.3e.4c.5a.6d, | 1f.2a.3e.4c.5a.6e, | 1f.2a.3e.4c.5a.6f, | 1f.2a.3e.4c.5b.6a, |
| 1f.2a.3e.4c.5b.6b, | 1f.2a.3e.4c.5b.6c, | 1f.2a.3e.4c.5b.6d, | 1f.2a.3e.4c.5b.6e, | 1f.2a.3e.4c.5b.6f, |
| 1f.2a.3e.4c.5c.6a, | 1f.2a.3e.4c.5c.6b, | 1f.2a.3e.4c.5c.6c, | 1f.2a.3e.4c.5c.6d, | 1f.2a.3e.4c.5c.6e, |
| 112a.3e.4c.5c.6f, | 1f.2a.3e.4c.5d.6a, | 1f.2a.3e.4c.5d.6b, | 1f.2a.3e.4c.5d.6c, | 1f.2a.3e.4c.5d.6d, |
| 1f.2a.3e.4c.5d.6e, | 1f.2a.3e.4c.5d.6f, | 1f.2a.3e.4c.5e.6a, | 1f.2a.3e.4c.5e.6b, | 1f.2a.3e.4c.5e.6c, |
| 1f.2a.3e.4c.5e.6d, | 1f.2a.3e.4c.5e.6e, | 1f.2a.3e.4c.5e.6f, | 1f.2a.3e.4c.5f.6a, | 1f.2a.3e.4c.5f.6b, |
| 112a.3e.4c.5f.6c, | 1f.2a.3e.4c.5f.6d, | 1f.2a.3e.4c.5f.6e, | 1f.2a.3e.4c.5f.6f, | 1f.2a.3e.4d.5a.6a, |
| 1f.2a.3e.4d.5a.6b, | 1f.2a.3e.4d.5a.6c, | 1f.2a.3e.4d.5a.6d, | 1f.2a.3e.4d.5a.6e, | |
| 1f.2a.3e.4d.5a.6f, | 1f.2a.3e.4d.5b.6a, | 1f.2a.3e.4d.5b.6b, | 1f.2a.3e.4d.5b.6c, | |
| 1f.2a.3e.4d.5b.6d, | 1f.2a.3e.4d.5b.6e, | 1f.2a.3e.4d.5b.6f, | 1f.2a.3e.4d.5c.6a, | |
| 1f.2a.3e.4d.5c.6b, | 1f.2a.3e.4d.5c.6c, | 1f.2a.3e.4d.5c.6d, | 1f.2a.3e.4d.5c.6e, | 1f.2a.3e.4d.5c.6f, |
| 1f.2a.3e.4d.5d.6a, | 1f.2a.3e.4d.5d.6b, | 1f.2a.3e.4d.5d.6c, | 1f.2a.3e.4d.5d.6d, | |
| 1f.2a.3e.4d.5d.6e, | 1f.2a.3e.4d.5d.6f, | 1f.2a.3e.4d.5e.6a, | 1f.2a.3e.4d.5e.6b, | |
| 1f.2a.3e.4d.5e.6c, | 1f.2a.3e.4d.5e.6d, | 1f.2a.3e.4d.5e.6e, | 1f2a.3e.4d.5e.6f, | 1f.2a.3e.4d.5f.6a, |
| 1f.2a.3e.4d.5f.6b, | 1f.2a.3e.4d.5f.6c, | 1f.2a.3e.4d.5f.6d, | 1f.2a.3e.4d.5f.6e, | 1f.2a.3e.4d.5f.6f, |
| 1f.2a.3e.4e.5a.6a, | 1f.2a.3e.4e.5a.6b, | 1f.2a.3e.4e.5a.6c, | 1f.2a.3e.4e.5a.6d, | 1f.2a.3e.4e.5a.6e, |
| 1f.2a.3e.4e.5a.6f, | 1f.2a.3e.4e.5b.6a, | 1f.2a.3e.4e.5b.6b, | 1f.2a.3e.4e.5b.6c, | 1f.2a.3e.4e.5b.6d, |
| 1f.2a.3e.4e.5b.6e, | 1f.2a.3e.4e.5b.6f, | 1f.2a.3e.4e.5c.6a, | 1f.2a.3e.4e.5c.6b, | 1f.2a.3e.4e.5c.6c, |
| 1f.2a.3e.4e.5c.6d, | 1f.2a.3e.4e.5c.6e, | 1f.2a.3e.4e.5c.6f, | 1f.2a.3e.4e.5d.6a, | 1f.2a.3e.4e.5d.6b, |
| 1f.2a.3e.4e.5d.6c, | 1f.2a.3e.4e.5d.6d, | 1f.2a.3e.4e.5d.6e, | 1f.2a.3e.4e.5d.6f, | 1f.2a.3e.4e.5e.6a, |
| 1f.2a.3e.4e.5e.6b, | 1f.2a.3e.4e.5e.6c, | 1f.2a.3e.4e.5e.6d, | 1f.2a.3e.4e.5e.6e, | 1f.2a.3e.4e.5e.6f, |
| 1f.2a.3e.4e.5f.6a, | 1f.2a.3e.4e.5f.6b, | 1f.2a.3e.4e.5f.6c, | 1f.2a.3e.4e.5f.6d, | 1f.2a.3e.4e.5f.6e, |
| 1f.2a.3e.4e.5f.6f, | 1f.2a.3e.4f.5a.6a, | 1f.2a.3e.4f.5a.6b, | 1f.2a.3e.4f.5a.6c, | 1f.2a.3e.4f.5a.6d, |
| 1f.2a.3e.4f.5a.6e, | 1f.2a.3e.4f.5a.6f, | 1f.2a.3e.4f.5b.6a, | 1f.2a.3e.4f.5b.6b, | 1f.2a.3e.4f.5b.6c, |
| 1f.2a.3e.4f.5b.6d, | 1f.2a.3e.4f.5b.6e, | 1f.2a.3e.4f.5b.6f, | 1f.2a.3e.4f.5c.6a, | 1f.2a.3e.4f.5c.6b, |
| 1f.2a.3e.4f.5c.6c, | 1f.2a.3e.4f.5c.6d, | 1f.2a.3e.4f.5c.6e, | 1f.2a.3e.4f.5c.6f, | 1f.2a.3e.4f.5d.6a, |
| 1f.2a.3e.4f.5d.6b, | 1f.2a.3e.4f.5d.6c, | 1f.2a.3e.4f.5d.6d, | 1f.2a.3e.4f.5d.6e, | 1f.2a.3e.4f.5d.6f, |
| 1f.2a.3e.4f.5e.6a, | 1f.2a.3e.4f.5e.6b, | 1f.2a.3e.4f.5e.6c, | 1f.2a.3e.4f.5e.6d, | 1f.2a.3e.4f.5e.6e, |
| 1f.2a.3e.4f.5e.6f, | 1f.2a.3e.4f.5f.6a, | 1f.2a.3e.4f.5f.6b, | 1f.2a.3e.4f.5f.6c, | 1f.2a.3e.4f.5f.6d, |
| 1f.2a.3e.4f.5f.6e, | 1f.2a.3e.4f.5f.6f, | 1f.2a.3f.4a.5a.6a, | 1f.2a.3f.4a.5a.6b, | 1f.2a.3f.4a.5a.6c, |
| 1f.2a.3f.4a.5a.6d, | 1f.2a.3f.4a.5a.6e, | 1f.2a.3f.4a.5a.6f, | 1f.2a.3f.4a.5b.6a, | 1f.2a.3f.4a.5b.6b, |
| 1f.2a.3f.4a.5b.6c, | 1f.2a.3f.4a.5b.6d, | 1f.2a.3f.4a.5b.6e, | 1f.2a.3f.4a.5b.6f, | 1f.2a.3f.4a.5c.6a, |
| 1f.2a.3f.4a.5c.6b, | 1f.2a.3f.4a.5c.6c, | 1f.2a.3f.4a.5c.6d, | 1f.2a.3f.4a.5c.6e, | 1f.2a.3f.4a.5c.6f, |
| 1f.2a.3f.4a.5d.6a, | 1f.2a.3f.4a.5d.6b, | 1f.2a.3f.4a.5d.6c, | 1f.2a.3f.4a.5d.6d, | 1f.2a.3f.4a.5d.6e, |
| 1f.2a.3f.4a.5d.6f, | 1f.2a.3f.4a.5e.6a, | 1f.2a.3f.4a.5e.6b, | 1f.2a.3f.4a.5e.6c, | 1f.2a.3f.4a.5e.6d, |
| 1f.2a.3f.4a.5e.6e, | 1f.2a.3f.4a.5e.6f, | 1f.2a.3f.4a.5f.6a, | 1f.2a.3f.4a.5f.6b, | 1f.2a.3f.4a.5f.6c, |
| 1f.2a.3f.4a.5f.6d, | 1f.2a.3f.4a.5f.6e, | 1f.2a.3f.4a.5f.6f, | 1f.2a.3f.4b.5a.6a, | 1f.2a.3f.4b.5a.6b, |
| 1f.2a.3f.4b.5a.6c, | 1f.2a.3f.4b.5a.6d, | 1f.2a.3f.4b.5a.6e, | 1f.2a.3f.4b.5a.6f, | 1f.2a.3f.4b.5b.6a, |
| 1f.2a.3f.4b.5b.6b, | 1f.2a.3f.4b.5b.6c, | 1f.2a.3f.4b.5b.6d, | 1f.2a.3f.4b.5b.6e, | 1f.2a.3f.4b.5b.6f, |
| 1f.2a.3f.4b.5c.6a, | 1f.2a.3f.4b.5c.6b, | 1f.2a.3f.4b.5c.6c, | 1f.2a.3f.4b.5c.6d, | 1f.2a.3f.4b.5c.6e, |
| 1f.2a.3f.4b.5c.6f, | 1f.2a.3f.4b.5d.6a, | 1f.2a.3f.4b.5d.6b, | 1f.2a.3f.4b.5d.6c, | 1f.2a.3f.4b.5d.6d, |
| 1f.2a.3f.4b.5d.6e, | 1f.2a.3f.4b.5d.6f, | 1f.2a.3f.4b.5e.6a, | 1f.2a.3f.4b.5e.6b, | 1f.2a.3f.4b.5e.6c, |
| 1f.2a.3f.4b.5e.6d, | 1f.2a.3f.4b.5e.6e, | 1f.2a.3f.4b.5e.6f, | 1f.2a.3f.4b.5f.6a, | 1f.2a.3f.4b.5f.6b, |
| 1f.2a.3f.4b.5f.6c, | 1f.2a.3f.4b.5f.6d, | 1f.2a.3f.4b.5f.6e, | 1f.2a.3f.4b.5f.6f, | 1f.2a.3f.4c.5a.6a, |
| 1f.2a.3f.4c.5a.6b, | 1f.2a.3f.4c.5a.6c, | 1f.2a.3f.4c.5a.6d, | 1f.2a.3f.4c.5a.6e, | 1f.2a.3f.4c.5a.6f, |
| 1f.2a.3f.4c.5b.6a, | 1f.2a.3f.4c.5b.6b, | 1f.2a.3f.4c.5b.6c, | 1f.2a.3f.4c.5b.6d, | 1f.2a.3f.4c.5b.6e, |
| 1f.2a.3f.4c.5b.6f, | 1f.2a.3f.4c.5c.6a, | 1f.2a.3f.4c.5c.6b, | 1f.2a.3f.4c.5c.6c, | 1f.2a.3f.4c.5c.6d, |
| 1f.2a.3f.4c.5c.6e, | 1f.2a.3f.4c.5c.6f, | 1f.2a.3f.4c.5d.6a, | 1f.2a.3f.4c.5d.6b, | 1f.2a.3f.4c.5d.6c, |
| 1f.2a.3f.4c.5d.6d, | 1f.2a.3f.4c.5d.6e, | 1f.2a.3f.4c.5d.6f, | 1f.2a.3f.4c.5e.6a, | 1f.2a.3f.4c.5e.6b, |
| 1f.2a.3f.4c.5e.6c, | 1f.2a.3f.4c.5e.6d, | 1f.2a.3f.4c.5e.6e, | 1f.2a.3f.4c.5e.6f, | 1f.2a.3f.4c.5f.6a, |
| 1f.2a.3f.4c.5f.6b, | 1f.2a.3f.4c.5f.6c, | 1f.2a.3f.4c.5f.6d, | 1f.2a.3f.4c.5f.6e, | 1f.2a.3f.4c.5f.6f, |
| 1f.2a.3f.4d.5a.6a, | 1f.2a.3f.4d.5a.6b, | 1f.2a.3f.4d.5a.6c, | 1f.2a.3f.4d.5a.6d, | 1f.2a.3f.4d.5a.6e, |
| 1f.2a.3f.4d.5a.6f, | 1f.2a.3f.4d.5b.6a, | 1f.2a.3f.4d.5b.6b, | 1f.2a.3f.4d.5b.6c, | 1f.2a.3f.4d.5b.6d, |
| 1f.2a.3f.4d.5b.6e, | 1f.2a.3f.4d.5b.6f, | 1f.2a.3f.4d.5c.6a, | 1f.2a.3f.4d.5c.6b, | 1f.2a.3f.4d.5c.6c, |

TABLE 7-continued

List of Compounds of Formula (II)

| | | | | |
|---|---|---|---|---|
| 1f.2a.3f.4d.5c.6d, | 1f.2a.3f.4d.5c.6e, | 1f.2a.3f.4d.5c.6f, | 1f.2a.3f.4d.5d.6a, | 1f.2a.3f.4d.5d.6b, |
| 1f.2a.3f.4d.5d.6c, | 1f.2a.3f.4d.5d.6d, | 1f.2a.3f.4d.5d.6e, | 1f.2a.3f.4d.5d.6f, | 1f.2a.3f.4d.5e.6a, |
| 1f.2a.3f.4d.5e.6b, | 1f.2a.3f.4d.5e.6c, | 1f.2a.3f.4d.5e.6d, | 1f.2a.3f.4d.5e.6e, | 1f.2a.3f.4d.5e.6f, |
| 1f.2a.3f.4d.5f.6a, | 1f.2a.3f.4d.5f.6b, | 1f.2a.3f.4d.5f.6c, | 1f.2a.3f.4d.5f.6d, | 1f.2a.3f.4d.5f.6e, |
| 1f.2a.3f.4d.5f.6f, | 1f.2a.3f.4e.5a.6a, | 1f.2a.3f.4e.5a.6b, | 1f.2a.3f.4e.5a.6c, | 1f.2a.3f.4e.5a.6d, |
| 1f.2a.3f.4e.5a.6e, | 1f.2a.3f.4e.5a.6f, | 1f.2a.3f.4e.5b.6a, | 1f.2a.3f.4e.5b.6b, | 1f.2a.3f.4e.5b.6c, |
| 1f.2a.3f.4e.5b.6d, | 1f.2a.3f.4e.5b.6e, | 1f.2a.3f.4e.5b.6f, | 1f.2a.3f.4e.5c.6a, | 1f.2a.3f.4e.5c.6b, |
| 1f.2a.3f.4e.5c.6c, | 1f.2a.3f.4e.5c.6d, | 1f.2a.3f.4e.5c.6e, | 1f.2a.3f.4e.5c.6f, | 1f.2a.3f.4e.5d.6a, |
| 1f.2a.3f.4e.5d.6b, | 1f.2a.3f.4e.5d.6c, | 1f.2a.3f.4e.5d.6d, | 1f.2a.3f.4e.5d.6e, | 1f.2a.3f.4e.5d.6f, |
| 1f.2a.3f.4e.5e.6a, | 1f.2a.3f.4e.5e.6b, | 1f.2a.3f.4e.5e.6c, | 1f.2a.3f.4e.5e.6d, | 1f.2a.3f.4e.5e.6e, |
| 1f.2a.3f.4e.5e.6f, | 1f.2a.3f.4e.5f.6a, | 1f.2a.3f.4e.5f.6b, | 1f.2a.3f.4e.5f.6c, | 1f.2a.3f.4e.5f.6d, |
| 1f.2a.3f.4e.5f.6e, | 1f.2a.3f.4e.5f.6f, | 1f.2a.3f.4f.5a.6a, | 1f.2a.3f.4f.5a.6b, | 1f.2a.3f.4f.5a.6c, |
| 1f.2a.3f.4f.5a.6d, | 1f.2a.3f.4f.5a.6e, | 1f.2a.3f.4f.5a.6f, | 1f.2a.3f.4f.5b.6a, | 1f.2a.3f.4f.5b.6b, |
| 1f.2a.3f.4f.5b.6c, | 1f.2a.3f.4f.5b.6d, | 1f.2a.3f.4f.5b.6e, | 1f.2a.3f.4f.5b.6f, | 1f.2a.3f.4f.5c.6a, |
| 1f.2a.3f.4f.5c.6b, | 1f.2a.3f.4f.5c.6c, | 1f.2a.3f.4f.5c.6d, | 1f.2a.3f.4f.5c.6e, | 1f.2a.3f.4f.5c.6f, |
| 1f.2a.3f.4f.5d.6a, | 1f.2a.3f.4f.5d.6b, | 1f.2a.3f.4f.5d.6c, | 1f.2a.3f.4f.5d.6d, | 1f.2a.3f.4f.5d.6e, |
| 1f.2a.3f.4f.5d.6f, | 1f.2a.3f.4f.5e.6a, | 1f.2a.3f.4f.5e.6b, | 1f.2a.3f.4f.5e.6c, | 1f.2a.3f.4f.5e.6d, |
| 1f.2a.3f.4f.5e.6e, | 1f.2a.3f.4f.5e.6f, | 1f.2a.3f.4f.5f.6a, | 1f.2a.3f.4f.5f.6b, | 1f.2a.3f.4f.5f.6c, |
| 1f.2a.3f.4f.5f.6d, | 1f.2a.3f.4f.5f.6e, | 1f.2a.3f.4f.5f.6f, | 1f.2b.3a.4a.5a.6a, | 1f.2b.3a.4a.5a.6b, |
| 1f.2b.3a.4a.5a.6c, | 1f.2b.3a.4a.5a.6d, | 1f.2b.3a.4a.5a.6e, | 1f.2b.3a.4a.5a.6f, | 1f.2b.3a.4a.5b.6a, |
| 1f.2b.3a.4a.5b.6b, | 1f.2b.3a.4a.5b.6c, | 1f.2b.3a.4a.5b.6d, | 1f.2b.3a.4a.5b.6e, | |
| 1f.2b.3a.4a.5b.6f, | 1f.2b.3a.4a.5c.6a, | 1f.2b.3a.4a.5c.6b, | 1f.2b.3a.4a.5c.6c, | 1f.2b.3a.4a.5c.6d, |
| 1f.2b.3a.4a.5c.6e, | 1f.2b.3a.4a.5c.6f, | 1f.2b.3a.4a.5d.6a, | 1f.2b.3a.4a.5d.6b, | |
| 1f.2b.3a.4a.5d.6c, | 1f.2b.3a.4a.5d.6d, | 1f.2b.3a.4a.5d.6e, | 1f.2b.3a.4a.5d.6f, | |
| 1f.2b.3a.4a.5e.6a, | 1f.2b.3a.4a.5e.6b, | 1f.2b.3a.4a.5e.6c, | 1f.2b.3a.4a.5e.6d, | |
| 1f.2b.3a.4a.5e.6e, | 1f.2b.3a.4a.5e.6f, | 1f.2b.3a.4a.5f.6a, | 1f.2b.3a.4a.5f.6b, | 1f.2b.3a.4a.5f.6c, |
| 1f.2b.3a.4a.5f.6d, | 1f.2b.3a.4a.5f.6e, | 1f.2b.3a.4a.5f.6f, | 1f.2b.3a.4b.5a.6a, | 1f.2b.3a.4b.5a.6b, |
| 1f.2b.3a.4b.5a.6c, | 1f.2b.3a.4b.5a.6d, | 1f.2b.3a.4b.5a.6e, | 1f.2b.3a.4b.5a.6f, | |
| 1f.2b.3a.4b.5b.6a, | 1f.2b.3a.4b.5b.6b, | 1f.2b.3a.4b.5b.6c, | 1f.2b.3a.4b.5b.6d, | |
| 1f.2b.3a.4b.5b.6e, | 1f.2b.3a.4b.5b.6f, | 1f.2b.3a.4b.5c.6a, | 1f.2b.3a.4b.5c.6b, | |
| 1f.2b.3a.4b.5c.6c, | 1f.2b.3a.4b.5c.6d, | 1f.2b.3a.4b.5c.6e, | 1f.2b.3a.4b.5c.6f, | |
| 1f.2b.3a.4b.5d.6a, | 1f.2b.3a.4b.5d.6b, | 1f.2b.3a.4b.5d.6c, | 1f.2b.3a.4b.5d.6d, | |
| 1f.2b.3a.4b.5d.6e, | 1f.2b.3a.4b.5d.6f, | 1f.2b.3a.4b.5e.6a, | 1f.2b.3a.4b.5e.6b, | |
| 1f.2b.3a.4b.5e.6c, | 1f.2b.3a.4b.5e.6d, | 1f.2b.3a.4b.5e.6e, | 1f.2b.3a.4b.5e.6f, | 1f.2b.3a.4b.5f.6a, |
| 1f.2b.3a.4b.5f.6b, | 1f.2b.3a.4b.5f.6c, | 1f.2b.3a.4b.5f.6d, | 1f.2b.3a.4b.5f.6e, | 1f.2b.3a.4b.5f.6f, |
| 1f.2b.3a.4c.5a.6a, | 1f.2b.3a.4c.5a.6b, | 1f.2b.3a.4c.5a.6c, | 1f.2b.3a.4c.5a.6d, | 1f.2b.3a.4c.5a.6e, |
| 1f.2b.3a.4c.5a.6f, | 1f.2b.3a.4c.5b.6a, | 1f.2b.3a.4c.5b.6b, | 1f.2b.3a.4c.5b.6c, | 1f.2b.3a.4c.5b.6d, |
| 1f.2b.3a.4c.5b.6e, | 1f.2b.3a.4c.5b.6f, | 1f.2b.3a.4c.5c.6a, | 1f.2b.3a.4c.5c.6b, | 1f.2b.3a.4c.5c.6c, |
| 1f.2b.3a.4c.5c.6d, | 1f.2b.3a.4c.5c.6e, | 1f.2b.3a.4c.5c.6f, | 1f.2b.3a.4c.5d.6a, | 1f.2b.3a.4c.5d.6b, |
| 1f.2b.3a.4c.5d.6c, | 1f.2b.3a.4c.5d.6d, | 1f.2b.3a.4c.5d.6e, | 1f.2b.3a.4c.5d.6f, | |
| 1f.2b.3a.4c.5e.6a, | 1f.2b.3a.4c.5e.6b, | 1f.2b.3a.4c.5e.6c, | 1f.2b.3a.4c.5e.6d, | 1f.2b.3a.4c.5e.6e, |
| 1f.2b.3a.4c.5e.6f, | 1f.2b.3a.4c.5f.6a, | 1f.2b.3a.4c.5f.6b, | 1f.2b.3a.4c.5f.6c, | 1f.2b.3a.4c.5f.6d, |
| 1f.2b.3a.4c.5f.6e, | 1f.2b.3a.4c.5f.6f, | 1f.2b.3a.4d.5a.6a, | 1f.2b.3a.4d.5a.6b, | 1f.2b.3a.4d.5a.6c, |
| 1f.2b.3a.4d.5a.6d, | 1f.2b.3a.4d.5a.6e, | 1f.2b.3a.4d.5a.6f, | 1f.2b.3a.4d.5b.6a, | |
| 1f.2b.3a.4d.5b.6b, | 1f.2b.3a.4d.5b.6c, | 1f.2b.3a.4d.5b.6d, | 1f.2b.3a.4d.5b.6e, | |
| 1f.2b.3a.4d.5b.6f, | 1f.2b.3a.4d.5c.6a, | 1f.2b.3a.4d.5c.6b, | 1f.2b.3a.4d.5c.6c, | |
| 1f.2b.3a.4d.5c.6d, | 1f.2b.3a.4d.5c.6e, | 1f.2b.3a.4d.5c.6f, | 1f.2b.3a.4d.5d.6a, | |
| 1f.2b.3a.4d.5d.6b, | 1f.2b.3a.4d.5d.6c, | 1f.2b.3a.4d.5d.6d, | 1f.2b.3a.4d.5d.6e, | |
| 1f.2b.3a.4d.5d.6f, | 1f.2b.3a.4d.5e.6a, | 1f.2b.3a.4d.5e.6b, | 1f.2b.3a.4d.5e.6c, | |
| 1f.2b.3a.4d.5e.6d, | 1f.2b.3a.4d.5e.6e, | 1f.2b.3a.4d.5e.6f, | 1f.2b.3a.4d.5f.6a, | |
| 1f.2b.3a.4d.5f.6b, | 1f.2b.3a.4d.5f.6c, | 1f.2b.3a.4d.5f.6d, | 1f.2b.3a.4d.5f.6e, | 1f.2b.3a.4d.5f.6f, |
| 1f.2b.3a.4e.5a.6a, | 1f.2b.3a.4e.5a.6b, | 1f.2b.3a.4e.5a.6c, | 1f.2b.3a.4e.5a.6d, | |
| 1f.2b.3a.4e.5a.6e, | 1f.2b.3a.4e.5a.6f, | 1f.2b.3a.4e.5b.6a, | 1f.2b.3a.4e.5b.6b, | 1f.2b.3a.4e.5b.6c, |
| 1f.2b.3a.4e.5b.6d, | 1f.2b.3a.4e.5b.6e, | 1f.2b.3a.4e.5b.6f, | 1f.2b.3a.4e.5c.6a, | 1f.2b.3a.4e.5c.6b, |
| 1f.2b.3a.4e.5c.6c, | 1f.2b.3a.4e.5c.6d, | 1f.2b.3a.4e.5c.6e, | 1f.2b.3a.4e.5c.6f, | 1f.2b.3a.4e.5d.6a, |
| 1f.2b.3a.4e.5d.6b, | 1f.2b.3a.4e.5d.6c, | 1f.2b.3a.4e.5d.6d, | 1f.2b.3a.4e.5d.6e, | |
| 1f.2b.3a.4e.5d.6f, | 1f.2b.3a.4e.5e.6a, | 1f.2b.3a.4e.5e.6b, | 1f.2b.3a.4e.5e.6c, | 1f.2b.3a.4e.5e.6d, |
| 1f.2b.3a.4e.5e.6e, | 1f.2b.3a.4e.5e.6f, | 1f.2b.3a.4e.5f.6a, | 1f.2b.3a.4e.5f.6b, | 1f.2b.3a.4e.5f.6c, |
| 1f.2b.3a.4e.5f.6d, | 1f.2b.3a.4e.5f.6e, | 1f.2b.3a.4e.5f.6f, | 1f.2b.3a.4f.5a.6a, | 1f.2b.3a.4f.5a.6b, |
| 1f.2b.3a.4f.5a.6c, | 1f.2b.3a.4f.5a.6d, | 1f.2b.3a.4f.5a.6e, | 1f.2b.3a.4f.5a.6f, | 1f.2b.3a.4f.5b.6a, |
| 1f.2b.3a.4f.5b.6b, | 1f.2b.3a.4f.5b.6c, | 1f.2b.3a.4f.5b.6d, | 1f.2b.3a.4f.5b.6e, | 1f.2b.3a.4f.5b.6f, |
| 1f.2b.3a.4f.5c.6a, | 1f.2b.3a.4f.5c.6b, | 1f.2b.3a.4f.5c.6c, | 1f.2b.3a.4f.5c.6d, | 1f.2b.3a.4f.5c.6e, |
| 1f.2b.3a.4f.5c.6f, | 1f.2b.3a.4f.5d.6a, | 1f.2b.3a.4f.5d.6b, | 1f.2b.3a.4f.5d.6c, | 1f.2b.3a.4f.5d.6d, |
| 1f.2b.3a.4f.5d.6e, | 1f.2b.3a.4f.5d.6f, | 1f.2b.3a.4f.5e.6a, | 1f.2b.3a.4f.5e.6b, | 1f.2b.3a.4f.5e.6c, |
| 1f.2b.3a.4f.5e.6d, | 1f.2b.3a.4f.5e.6e, | 1f.2b.3a.4f.5e.6f, | 1f.2b.3a.4f.5f.6a, | 1f.2b.3a.4f.5f.6b, |
| 1f.2b.3a.4f.5f.6c, | 1f.2b.3a.4f.5f.6d, | 1f.2b.3a.4f.5f.6e, | 1f.2b.3a.4f.5f.6f, | 1f.2b.3b.4a.5a.6a, |
| 1f.2b.3b.4a.5a.6b, | 1f.2b.3b.4a.5a.6c, | 1f.2b.3b.4a.5a.6d, | 1f.2b.3b.4a.5a.6e, | |
| 1f.2b.3b.4a.5a.6f, | 1f.2b.3b.4a.5b.6a, | 1f.2b.3b.4a.5b.6b, | 1f.2b.3b.4a.5b.6c, | |
| 1f.2b.3b.4a.5b.6d, | 1f.2b.3b.4a.5b.6e, | 1f.2b.3b.4a.5b.6f, | 1f.2b.3b.4a.5c.6a, | |
| 1f.2b.3b.4a.5c.6b, | 1f.2b.3b.4a.5c.6c, | 1f.2b.3b.4a.5c.6d, | 1f.2b.3b.4a.5c.6e, | 1f.2b.3b.4a.5c.6f, |
| 1f.2b.3b.4a.5d.6a, | 1f.2b.3b.4a.5d.6b, | 1f.2b.3b.4a.5d.6c, | 1f.2b.3b.4a.5d.6d, | |
| 1f.2b.3b.4a.5d.6e, | 1f.2b.3b.4a.5d.6f, | 1f.2b.3b.4a.5e.6a, | 1f.2b.3b.4a.5e.6b, | |
| 1f.2b.3b.4a.5e.6c, | 1f.2b.3b.4a.5e.6d, | 1f.2b.3b.4a.5e.6e, | 1f.2b.3b.4a.5e.6f, | 1f.2b.3b.4a.5f.6a, |
| 1f.2b.3b.4a.5f.6b, | 1f.2b.3b.4a.5f.6c, | 1f.2b.3b.4a.5f.6d, | 1f.2b.3b.4a.5f.6e, | 1f.2b.3b.4a.5f.6f, |
| 1f.2b.3b.4b.5a.6a, | 1f.2b.3b.4b.5a.6b, | 1f.2b.3b.4b.5a.6c, | 1f.2b.3b.4b.5a.6d, | |
| 1f.2b.3b.4b.5a.6e, | 1f.2b.3b.4b.5a.6f, | 1f.2b.3b.4b.5b.6a, | 1f.2b.3b.4b.5b.6b, | |
| 1f.2b.3b.4b.5b.6c, | 1f.2b.3b.4b.5b.6d, | 1f.2b.3b.4b.5b.6e, | 1f.2b.3b.4b.5b.6f, | |
| 1f.2b.3b.4b.5c.6a, | 1f.2b.3b.4b.5c.6b, | 1f.2b.3b.4b.5c.6c, | 1f.2b.3b.4b.5c.6d, | |

TABLE 7-continued

List of Compounds of Formula (II)

| | | | | |
|---|---|---|---|---|
| 1f.2b.3b.4b.5c.6e, | 1f.2b.3b.4b.5c.6f, | 1f.2b.3b.4b.5d.6a, | 1f.2b.3b.4b.5d.6b, | |
| 1f.2b.3b.4b.5d.6c, | 1f.2b.3b.4b.5d.6d, | 1f.2b.3b.4b.5d.6e, | 1f.2b.3b.4b.5d.6f, | |
| 1f.2b.3b.4b.5e.6a, | 1f.2b.3b.4b.5e.6b, | 1f.2b.3b.4b.5e.6c, | 1f.2b.3b.4b.5e.6d, | |
| 1f.2b.3b.4b.5e.6e, | 1f.2b.3b.4b.5e.6f, | 1f.2b.3b.4b.5f.6a, | 1f.2b.3b.4b.5f.6b, | 1f.2b.3b.4b.5f.6c, |
| 1f.2b.3b.4b.5f.6d, | 1f.2b.3b.4b.5f.6e, | 1f.2b.3b.4b.5f.6f, | 1f.2b.3b.4c.5a.6a, | 1f.2b.3b.4c.5a.6b, |
| 1f.2b.3b.4c.5a.6c, | 1f.2b.3b.4c.5a.6d, | 1f.2b.3b.4c.5a.6e, | 1f.2b.3b.4c.5a.6f, | 1f.2b.3b.4c.5b.6a, |
| 1f.2b.3b.4c.5b.6b, | 1f.2b.3b.4c.5b.6c, | 1f.2b.3b.4c.5b.6d, | 1f.2b.3b.4c.5b.6e, | |
| 1f.2b.3b.4c.5b.6f, | 1f.2b.3b.4c.5c.6a, | 1f.2b.3b.4c.5c.6b, | 1f.2b.3b.4c.5c.6c, | 1f.2b.3b.4c.5c.6d, |
| 1f.2b.3b.4c.5c.6e, | 1f.2b.3b.4c.5c.6f, | 1f.2b.3b.4c.5d.6a, | 1f.2b.3b.4c.5d.6b, | |
| 1f.2b.3b.4c.5d.6c, | 1f.2b.3b.4c.5d.6d, | 1f.2b.3b.4c.5d.6e, | 1f.2b.3b.4c.5d.6f, | |
| 1f.2b.3b.4c.5e.6a, | 1f.2b.3b.4c.5e.6b, | 1f.2b.3b.4c.5e.6c, | 1f.2b.3b.4c.5e.6d, | |
| 1f.2b.3b.4c.5e.6e, | 1f.2b.3b.4c.5e.6f, | 1f.2b.3b.4c.5f.6a, | 1f.2b.3b.4c.5f.6b, | 1f.2b.3b.4c.5f.6c, |
| 1f.2b.3b.4c.5f.6d, | 1f.2b.3b.4c.5f.6e, | 1f.2b.3b.4c.5f.6f, | 1f.2b.3b.4d.5a.6a, | 1f.2b.3b.4d.5a.6b, |
| 1f.2b.3b.4d.5a.6c, | 1f.2b.3b.4d.5a.6d, | 1f.2b.3b.4d.5a.6e, | 1f.2b.3b.4d.5a.6f, | |
| 1f.2b.3b.4d.5b.6a, | 1f.2b.3b.4d.5b.6b, | 1f.2b.3b.4d.5b.6c, | 1f.2b.3b.4d.5b.6d, | |
| 1f.2b.3b.4d.5b.6e, | 1f.2b.3b.4d.5b.6f, | 1f.2b.3b.4d.5c.6a, | 1f.2b.3b.4d.5c.6b, | |
| 1f.2b.3b.4d.5c.6c, | 1f.2b.3b.4d.5c.6d, | 1f.2b.3b.4d.5c.6e, | 1f.2b.3b.4d.5c.6f, | |
| 1f.2b.3b.4d.5d.6a, | 1f.2b.3b.4d.5d.6b, | 1f.2b.3b.4d.5d.6c, | 1f.2b.3b.4d.5d.6d, | |
| 1f.2b.3b.4d.5d.6e, | 1f.2b.3b.4d.5d.6f, | 1f.2b.3b.4d.5e.6a, | 1f.2b.3b.4d.5e.6b, | |
| 1f.2b.3b.4d.5e.6c, | 1f.2b.3b.4d.5e.6d, | 1f.2b.3b.4d.5e.6e, | 1f.2b.3b.4d.5e.6f, | |
| 1f.2b.3b.4d.5f.6a, | 1f.2b.3b.4d.5f.6b, | 1f.2b.3b.4d.5f.6c, | 1f.2b.3b.4d.5f.6d, | |
| 1f.2b.3b.4d.5f.6e, | 1f.2b.3b.4d.5f.6f, | 1f.2b.3b.4e.5a.6a, | 1f.2b.3b.4e.5a.6b, | 1f.2b.3b.4e.5a.6c, |
| 1f.2b.3b.4e.5a.6d, | 1f.2b.3b.4e.5a.6e, | 1f.2b.3b.4e.5a.6f, | 1f.2b.3b.4e.5b.6a, | |
| 1f.2b.3b.4e.5b.6b, | 1f.2b.3b.4e.5b.6c, | 1f.2b.3b.4e.5b.6d, | 1f.2b.3b.4e.5b.6e, | |
| 1f.2b.3b.4e.5b.6f, | 1f.2b.3b.4e.5c.6a, | 1f.2b.3b.4e.5c.6b, | 1f.2b.3b.4e.5c.6c, | 1f.2b.3b.4e.5c.6d, |
| 1f.2b.3b.4e.5c.6e, | 1f.2b.3b.4e.5c.6f, | 1f.2b.3b.4e.5d.6a, | 1f.2b.3b.4e.5d.6b, | |
| 1f.2b.3b.4e.5d.6c, | 1f.2b.3b.4e.5d.6d, | 1f.2b.3b.4e.5d.6e, | 1f.2b.3b.4e.5d.6f, | |
| 1f.2b.3b.4e.5e.6a, | 1f.2b.3b.4e.5e.6b, | 1f.2b.3b.4e.5e.6c, | 1f.2b.3b.4e.5e.6d, | |
| 1f.2b.3b.4e.5e.6e, | 1f.2b.3b.4e.5e.6f, | 1f.2b.3b.4e.5f.6a, | 1f.2b.3b.4e.5f.6b, | 1f.2b.3b.4e.5f.6c, |
| 1f.2b.3b.4e.5f.6d, | 1f.2b.3b.4e.5f.6e, | 1f.2b.3b.4e.5f.6f, | 1f.2b.3b.4f.5a.6a, | 1f.2b.3b.4f.5a.6b, |
| 1f.2b.3b.4f.5a.6c, | 1f.2b.3b.4f.5a.6d, | 1f.2b.3b.4f.5a.6e, | 1f.2b.3b.4f.5a.6f, | 1f.2b.3b.4f.5b.6a, |
| 1f.2b.3b.4f.5b.6b, | 1f.2b.3b.4f.5b.6c, | 1f.2b.3b.4f.5b.6d, | 1f.2b.3b.4f.5b.6e, | 1f.2b.3b.4f.5b.6f, |
| 1f.2b.3b.4f.5c.6a, | 1f.2b.3b.4f.5c.6b, | 1f.2b.3b.4f.5c.6c, | 1f.2b.3b.4f.5c.6d, | 1f.2b.3b.4f.5c.6e, |
| 1f.2b.3b.4f.5c.6f, | 1f.2b.3b.4f.5d.6a, | 1f.2b.3b.4f.5d.6b, | 1f.2b.3b.4f.5d.6c, | 1f.2b.3b.4f.5d.6d, |
| 1f.2b.3b.4f.5d.6e, | 1f.2b.3b.4f.5d.6f, | 1f.2b.3b.4f.5e.6a, | 1f.2b.3b.4f.5e.6b, | 1f.2b.3b.4f.5e.6c, |
| 1f.2b.3b.4f.5e.6d, | 1f.2b.3b.4f.5e.6e, | 1f.2b.3b.4f.5e.6f, | 1f.2b.3b.4f.5f.6a, | 1f.2b.3b.4f.5f.6b, |
| 1f.2b.3b.4f.5f.6c, | 1f.2b.3b.4f.5f.6d, | 1f.2b.3b.4f.5f.6e, | 1f.2b.3b.4f.5f.6f, | 1f.2b.3c.4a.5a.6a, |
| 1f.2b.3c.4a.5a.6b, | 1f.2b.3c.4a.5a.6c, | 1f.2b.3c.4a.5a.6d, | 1f.2b.3c.4a.5a.6e, | 1f.2b.3c.4a.5a.6f, |
| 1f.2b.3c.4a.5b.6a, | 1f.2b.3c.4a.5b.6b, | 1f.2b.3c.4a.5b.6c, | 1f.2b.3c.4a.5b.6d, | |
| 1f.2b.3c.4a.5b.6e, | 1f.2b.3c.4a.5b.6f, | 1f.2b.3c.4a.5c.6a, | 1f.2b.3c.4a.5c.6b, | 1f.2b.3c.4a.5c.6c, |
| 1f.2b.3c.4a.5c.6d, | 1f.2b.3c.4a.5c.6e, | 1f.2b.3c.4a.5c.6f, | 1f.2b.3c.4a.5d.6a, | 1f.2b.3c.4a.5d.6b, |
| 1f.2b.3c.4a.5d.6c, | 1f.2b.3c.4a.5d.6d, | 1f.2b.3c.4a.5d.6e, | 1f.2b.3c.4a.5d.6f, | |
| 1f.2b.3c.4a.5e.6a, | 1f.2b.3c.4a.5e.6b, | 1f.2b.3c.4a.5e.6c, | 1f.2b.3c.4a.5e.6d, | 1f.2b.3c.4a.5e.6e, |
| 1f.2b.3c.4a.5e.6f, | 1f.2b.3c.4a.5f.6a, | 1f.2b.3c.4a.5f.6b, | 1f.2b.3c.4a.5f.6c, | 1f.2b.3c.4a.5f.6d, |
| 1f.2b.3c.4a.5f.6e, | 1f.2b.3c.4a.5f.6f, | 1f.2b.3c.4b.5a.6a, | 1f.2b.3c.4b.5a.6b, | 1f.2b.3c.4b.5a.6c, |
| 1f.2b.3c.4b.5a.6d, | 1f.2b.3c.4b.5a.6e, | 1f.2b.3c.4b.5a.6f, | 1f.2b.3c.4b.5b.6a, | |
| 1f.2b.3c.4b.5b.6b, | 1f.2b.3c.4b.5b.6c, | 1f.2b.3c.4b.5b.6d, | 1f.2b.3c.4b.5b.6e, | |
| 1f.2b.3c.4b.5b.6f, | 1f.2b.3c.4b.5c.6a, | 1f.2b.3c.4b.5c.6b, | 1f.2b.3c.4b.5c.6c, | 1f.2b.3c.4b.5c.6d, |
| 1f.2b.3c.4b.5c.6e, | 1f.2b.3c.4b.5c.6f, | 1f.2b.3c.4b.5d.6a, | 1f.2b.3c.4b.5d.6b, | |
| 1f.2b.3c.4b.5d.6c, | 1f.2b.3c.4b.5d.6d, | 1f.2b.3c.4b.5d.6e, | 1f.2b.3c.4b.5d.6f, | |
| 1f.2b.3c.4b.5e.6a, | 1f.2b.3c.4b.5e.6b, | 1f.2b.3c.4b.5e.6c, | 1f.2b.3c.4b.5e.6d, | |
| 1f.2b.3c.4b.5e.6e, | 1f.2b.3c.4b.5e.6f, | 1f.2b.3c.4b.5f.6a, | 1f.2b.3c.4b.5f.6b, | 1f.2b.3c.4b.5f.6c, |
| 1f.2b.3c.4b.5f.6d, | 1f.2b.3c.4b.5f.6e, | 1f.2b.3c.4b.5f.6f, | 1f.2b.3c.4c.5a.6a, | 1f.2b.3c.4c.5a.6b, |
| 1f.2b.3c.4c.5a.6c, | 1f.2b.3c.4c.5a.6d, | 1f.2b.3c.4c.5a.6e, | 1f.2b.3c.4c.5a.6f, | 1f.2b.3c.4c.5b.6a, |
| 1f.2b.3c.4c.5b.6b, | 1f.2b.3c.4c.5b.6c, | 1f.2b.3c.4c.5b.6d, | 1f.2b.3c.4c.5b.6e, | 1f.2b.3c.4c.5b.6f, |
| 1f.2b.3c.4c.5c.6a, | 1f.2b.3c.4c.5c.6b, | 1f.2b.3c.4c.5c.6c, | 1f.2b.3c.4c.5c.6d, | 1f.2b.3c.4c.5c.6e, |
| 1f.2b.3c.4c.5c.6f, | 1f.2b.3c.4c.5d.6a, | 1f.2b.3c.4c.5d.6b, | 1f.2b.3c.4c.5d.6c, | 1f.2b.3c.4c.5d.6d, |
| 1f.2b.3c.4c.5d.6e, | 1f.2b.3c.4c.5d.6f, | 1f.2b.3c.4c.5e.6a, | 1f.2b.3c.4c.5e.6b, | 1f.2b.3c.4c.5e.6c, |
| 1f.2b.3c.4c.5e.6d, | 1f.2b.3c.4c.5e.6e, | 1f.2b.3c.4c.5e.6f, | 1f.2b.3c.4c.5f.6a, | 1f.2b.3c.4c.5f.6b, |
| 1f.2b.3c.4c.5f.6c, | 1f.2b.3c.4c.5f.6d, | 1f.2b.3c.4c.5f.6e, | 1f.2b.3c.4c.5f.6f, | 1f.2b.3c.4d.5a.6a, |
| 1f.2b.3c.4d.5a.6b, | 1f.2b.3c.4d.5a.6c, | 1f.2b.3c.4d.5a.6d, | 1f.2b.3c.4d.5a.6e, | |
| 1f.2b.3c.4d.5a.6f, | 1f.2b.3c.4d.5b.6a, | 1f.2b.3c.4d.5b.6b, | 1f.2b.3c.4d.5b.6c, | |
| 1f.2b.3c.4d.5b.6d, | 1f.2b.3c.4d.5b.6e, | 1f.2b.3c.4d.5b.6f, | 1f.2b.3c.4d.5c.6a, | |
| 1f.2b.3c.4d.5c.6b, | 1f.2b.3c.4d.5c.6c, | 1f.2b.3c.4d.5c.6d, | 1f.2b.3c.4d.5c.6e, | 1f.2b.3c.4d.5c.6f, |
| 1f.2b.3c.4d.5d.6a, | 1f.2b.3c.4d.5d.6b, | 1f.2b.3c.4d.5d.6c, | 1f.2b.3c.4d.5d.6d, | |
| 1f.2b.3c.4d.5d.6e, | 1f.2b.3c.4d.5d.6f, | 1f.2b.3c.4d.5e.6a, | 1f.2b.3c.4d.5e.6b, | |
| 1f.2b.3c.4d.5e.6c, | 1f.2b.3c.4d.5e.6d, | 1f.2b.3c.4d.5e.6e, | 1f.2b.3c.4d.5e.6f, | 1f.2b.3c.4d.5f.6a, |
| 1f.2b.3c.4d.5f.6b, | 1f.2b.3c.4d.5f.6c, | 1f.2b.3c.4d.5f.6d, | 1f.2b.3c.4d.5f.6e, | 1f.2b.3c.4d.5f.6f, |
| 1f.2b.3c.4e.5a.6a, | 1f.2b.3c.4e.5a.6b, | 1f.2b.3c.4e.5a.6c, | 1f.2b.3c.4e.5a.6d, | 1f.2b.3c.4e.5a.6e, |
| 1f.2b.3c.4e.5a.6f, | 1f.2b.3c.4e.5b.6a, | 1f.2b.3c.4e.5b.6b, | 1f.2b.3c.4e.5b.6c, | 1f.2b.3c.4e.5b.6d, |
| 1f.2b.3c.4e.5b.6e, | 1f.2b.3c.4e.5b.6f, | 1f.2b.3c.4e.5c.6a, | 1f.2b.3c.4e.5c.6b, | 1f.2b.3c.4e.5c.6c, |
| 1f.2b.3c.4e.5c.6d, | 1f.2b.3c.4e.5c.6e, | 1f.2b.3c.4e.5c.6f, | 1f.2b.3c.4e.5d.6a, | 1f.2b.3c.4e.5d.6b, |
| 1f.2b.3c.4e.5d.6c, | 1f.2b.3c.4e.5d.6d, | 1f.2b.3c.4e.5d.6e, | 1f.2b.3c.4e.5d.6f, | 1f.2b.3c.4e.5e.6a, |
| 1f.2b.3c.4e.5e.6b, | 1f.2b.3c.4e.5e.6c, | 1f.2b.3c.4e.5e.6d, | 1f.2b.3c.4e.5e.6e, | 1f.2b.3c.4e.5e.6f, |
| 1f.2b.3c.4e.5f.6a, | 1f.2b.3c.4e.5f.6b, | 1f.2b.3c.4e.5f.6c, | 1f.2b.3c.4e.5f.6d, | 1f.2b.3c.4e.5f.6e, |
| 1f.2b.3c.4e.5f.6f, | 1f.2b.3c.4f.5a.6a, | 1f.2b.3c.4f.5a.6b, | 1f.2b.3c.4f.5a.6c, | 1f.2b.3c.4f.5a.6d, |
| 1f.2b.3c.4f.5a.6e, | 1f.2b.3c.4f.5a.6f, | 1f.2b.3c.4f.5b.6a, | 1f.2b.3c.4f.5b.6b, | 1f.2b.3c.4f.5b.6c, |
| 1f.2b.3c.4f.5b.6d, | 1f.2b.3c.4f.5b.6e, | 1f.2b.3c.4f.5b.6f, | 1f.2b.3c.4f.5c.6a, | 1f.2b.3c.4f.5c.6b, |

TABLE 7-continued

List of Compounds of Formula (II)

| | | | | |
|---|---|---|---|---|
| 1f.2b.3c.4f.5c.6c, | 1f.2b.3c.4f.5c.6d, | 1f.2b.3c.4f.5c.6e, | 1f.2b.3c.4f.5c.6f, | 1f.2b.3c.4f.5d.6a, |
| 1f.2b.3c.4f.5d.6b, | 1f.2b.3c.4f.5d.6c, | 1f.2b.3c.4f.5d.6d, | 1f.2b.3c.4f.5d.6e, | 1f.2b.3c.4f.5d.6f, |
| 1f.2b.3c.4f.5e.6a, | 1f.2b.3c.4f.5e.6b, | 1f.2b.3c.4f.5e.6c, | 1f.2b.3c.4f.5e.6d, | 1f.2b.3c.4f.5e.6e, |
| 1f.2b.3c.4f.5e.6f, | 1f.2b.3c.4f.5f.6a, | 1f.2b.3c.4f.5f.6b, | 1f.2b.3c.4f.5f.6c, | 1f.2b.3c.4f.5f.6d, |
| 1f.2b.3c.4f.5f.6e, | 1f.2b.3c.4f.5f.6f, | 1f.2b.3d.4a.5a.6a, | 1f.2b.3d.4a.5a.6b, | 1f.2b.3d.4a.5a.6c, |
| 1f.2b.3d.4a.5a.6d, | 1f.2b.3d.4a.5a.6e, | 1f.2b.3d.4a.5a.6f, | 1f.2b.3d.4a.5b.6a, | |
| 1f.2b.3d.4a.5b.6b, | 1f.2b.3d.4a.5b.6c, | 1f.2b.3d.4a.5b.6d, | 1f.2b.3d.4a.5b.6e, | |
| 1f.2b.3d.4a.5b.6f, | 1f.2b.3d.4a.5c.6a, | 1f.2b.3d.4a.5c.6b, | 1f.2b.3d.4a.5c.6c, | |
| 1f.2b.3d.4a.5c.6d, | 1f.2b.3d.4a.5c.6e, | 1f.2b.3d.4a.5c.6f, | 1f.2b.3d.4a.5d.6a, | |
| 1f.2b.3d.4a.5d.6b, | 1f.2b.3d.4a.5d.6c, | 1f.2b.3d.4a.5d.6d, | 1f.2b.3d.4a.5d.6e, | |
| 1f.2b.3d.4a.5d.6f, | 1f.2b.3d.4a.5e.6a, | 1f.2b.3d.4a.5e.6b, | 1f.2b.3d.4a.5e.6c, | |
| 1f.2b.3d.4a.5e.6d, | 1f.2b.3d.4a.5e.6e, | 1f.2b.3d.4a.5e.6f, | 1f.2b.3d.4a.5f.6a, | |
| 1f.2b.3d.4a.5f.6b, | 1f.2b.3d.4a.5f.6c, | 1f.2b.3d.4a.5f.6d, | 1f.2b.3d.4a.5f.6e, | 1f.2b.3d.4a.5f.6f, |
| 1f.2b.3d.4b.5a.6a, | 1f.2b.3d.4b.5a.6b, | 1f.2b.3d.4b.5a.6c, | 1f.2b.3d.4b.5a.6d, | |
| 1f.2b.3d.4b.5a.6e, | 1f.2b.3d.4b.5a.6f, | 1f.2b.3d.4b.5b.6a, | 1f.2b.3d.4b.5b.6b, | |
| 1f.2b.3d.4b.5b.6c, | 1f.2b.3d.4b.5b.6d, | 1f.2b.3d.4b.5b.6e, | 1f.2b.3d.4b.5b.6f, | |
| 1f.2b.3d.4b.5c.6a, | 1f.2b.3d.4b.5c.6b, | 1f.2b.3d.4b.5c.6c, | 1f.2b.3d.4b.5c.6d, | |
| 1f.213.3d.4b.5c.6e, | 1f.2b.3d.4b.5c.6f, | 1f.2b.3d.4b.5d.6a, | 1f.2b.3d.4b.5d.6b, | |
| 1f.2b.3d.4b.5d.6c, | 1f.2b.3d.4b.5d.6d, | 1f.2b.3d.4b.5d.6e, | 1f.2b.3d.4b.5d.6f, | |
| 1f.2b.3d.4b.5e.6a, | 1f.2b.3d.4b.5e.6b, | 1f.2b.3d.4b.5e.6c, | 1f.2b.3d.4b.5e.6d, | |
| 1f.2b.3d.4b.5e.6e, | 1f.2b.3d.4b.5e.6f, | 1f.2b.3d.4b.5f.6a, | 1f.2b.3d.4b.5f.6b, | |
| 1f.2b.3d.4b.5f.6c, | 1f.2b.3d.4b.5f.6d, | 1f.2b.3d.4b.5f.6e, | 1f.2b.3d.4b.5f.6f, | 1f.2b.3d.4c.5a.6a, |
| 1f.2b.3d.4c.5a.6b, | 1f.2b.3d.4c.5a.6c, | 1f.2b.3d.4c.5a.6d, | 1f.2b.3d.4c.5a.6e, | |
| 1f.2b.3d.4c.5a.6f, | 1f.2b.3d.4c.5b.6a, | 1f.2b.3d.4c.5b.6b, | 1f.2b.3d.4c.5b.6c, | |
| 1f.2b.3d.4c.5b.6d, | 1f.2b.3d.4c.5b.6e, | 1f.2b.3d.4c.5b.6f, | 1f.2b.3d.4c.5c.6a, | |
| 1f.2b.3d.4c.5c.6b, | 1f.2b.3d.4c.5c.6c, | 1f.2b.3d.4c.5c.6d, | 1f.2b.3d.4c.5c.6e, | 1f.2b.3d.4c.5c.6f, |
| 1f.2b.3d.4c.5d.6a, | 1f.2b.3d.4c.5d.6b, | 1f.2b.3d.4c.5d.6c, | 1f.2b.3d.4c.5d.6d, | |
| 1f.2b.3d.4c.5d.6e, | 1f.2b.3d.4c.5d.6f, | 1f.2b.3d.4c.5e.6a, | 1f.2b.3d.4c.5e.6b, | |
| 1f.2b.3d.4c.5e.6c, | 1f.2b.3d.4c.5e.6d, | 1f.2b.3d.4c.5e.6e, | 1f.2b.3d.4c.5e.6f, | 1f.2b.3d.4c.5f.6a, |
| 1f.2b.3d.4c.5f.6b, | 1f.2b.3d.4c.5f.6c, | 1f.2b.3d.4c.5f.6d, | 1f.2b.3d.4c.5f.6e, | 1f.2b.3d.4c.5f.6f, |
| 1f.2b.3d.4d.5a.6a, | 1f.2b.3d.4d.5a.6b, | 1f.2b.3d.4d.5a.6c, | 1f.2b.3d.4d.5a.6d, | |
| 1f.2b.3d.4d.5a.6e, | 1f.2b.3d.4d.5a.6f, | 1f.2b.3d.4d.5b.6a, | 1f.2b.3d.4d.5b.6b, | |
| 1f.2b.3d.4d.5b.6c, | 1f.2b.3d.4d.5b.6d, | 1f.2b.3d.4d.5b.6e, | 1f.2b.3d.4d.5b.6f, | |
| 1f.2b.3d.4d.5c.6a, | 1f.2b.3d.4d.5c.6b, | 1f.2b.3d.4d.5c.6c, | 1f.2b.3d.4d.5c.6d, | |
| 1f.2b.3d.4d.5c.6e, | 1f.2b.3d.4d.5c.6f, | 1f.2b.3d.4d.5d.6a, | 1f.2b.3d.4d.5d.6b, | |
| 1f.2b.3d.4d.5d.6c, | 1f.2b.3d.4d.5d.6d, | 1f.2b.3d.4d.5d.6e, | 1f.2b.3d.4d.5d.6f, | |
| 1f.2b.3d.4d.5e.6a, | 1f.2b.3d.4d.5e.6b, | 1f.2b.3d.4d.5e.6c, | 1f.2b.3d.4d.5e.6d, | |
| 1f.2b.3d.4d.5e.6e, | 1f.2b.3d.4d.5e.6f, | 1f.2b.3d.4d.5f.6a, | 1f.2b.3d.4d.5f.6b, | |
| 1f.2b.3d.4d.5f.6c, | 1f.2b.3d.4d.5f.6d, | 1f.2b.3d.4d.5f.6e, | 1f.2b.3d.4d.5f.6f, | |
| 1f.2b.3d.4e.5a.6a, | 1f.2b.3d.4e.5a.6b, | 1f.2b.3d.4e.5a.6c, | 1f.2b.3d.4e.5a.6d, | |
| 1f.2b.3d.4e.5a.6e, | 1f.2b.3d.4e.5a.6f, | 1f.2b.3d.4e.5b.6a, | 1f.2b.3d.4e.5b.6b, | |
| 1f.2b.3d.4e.5b.6c, | 1f.2b.3d.4e.5b.6d, | 1f.2b.3d.4e.5b.6e, | 1f.2b.3d.4e.5b.6f, | |
| 1f.2b.3d.4e.5c.6a, | 1f.2b.3d.4e.5c.6b, | 1f.2b.3d.4e.5c.6c, | 1f.2b.3d.4e.5c.6d, | |
| 1f.2b.3d.4e.5c.6e, | 1f.2b.3d.4e.5c.6f, | 1f.2b.3d.4e.5d.6a, | 1f.2b.3d.4e.5d.6b, | |
| 1f.2b.3d.4e.5d.6c, | 1f.2b.3d.4e.5d.6d, | 1f.2b.3d.4e.5d.6e, | 1f.2b.3d.4e.5d.6f, | |
| 1f.2b.3d.4e.5e.6a, | 1f.2b.3d.4e.5e.6b, | 1f.2b.3d.4e.5e.6c, | 1f.2b.3d.4e.5e.6d, | |
| 1f.2b.3d.4e.5e.6e, | 1f.2b.3d.4e.5e.6f, | 1f.2b.3d.4e.5f.6a, | 1f.2b.3d.4e.5f.6b, | 1f.2b.3d.4e.5f.6c, |
| 1f.2b.3d.4e.5f.6d, | 1f.2b.3d.4e.5f.6e, | 1f.2b.3d.4e.5f.6f, | 1f.2b.3d.4f.5a.6a, | 1f.2b.3d.4f.5a.6b, |
| 1f.2b.3d.4f.5a.6c, | 1f.2b.3d.4f.5a.6d, | 1f.2b.3d.4f.5a.6e, | 1f.2b.3d.4f.5a.6f, | 1f.2b.3d.4f.5b.6a, |
| 1f.2b.3d.4f.5b.6b, | 1f.2b.3d.4f.5b.6c, | 1f.2b.3d.4f.5b.6d, | 1f.2b.3d.4f.5b.6e, | 1f.2b.3d.4f.5b.6f, |
| 1f.2b.3d.4f.5c.6a, | 1f.2b.3d.4f.5c.6b, | 1f.2b.3d.4f.5c.6c, | 1f.2b.3d.4f.5c.6d, | 1f.2b.3d.4f.5c.6e, |
| 1f.2b.3d.4f.5c.6f, | 1f.2b.3d.4f.5d.6a, | 1f.2b.3d.4f.5d.6b, | 1f.2b.3d.4f.5d.6c, | |
| 1f.2b.3d.4f.5d.6d, | 1f.2b.3d.4f.5d.6e, | 1f.2b.3d.4f.5d.6f, | 1f.2b.3d.4f.5e.6a, | |
| 1f.2b.3d.4f.5e.6b, | 1f.2b.3d.4f.5e.6c, | 1f.2b.3d.4f.5e.6d, | 1f.2b.3d.4f.5e.6e, | 1f.2b.3d.4f.5e.6f, |
| 1f.2b.3d.4f.5f.6a, | 1f.2b.3d.4f.5f.6b, | 1f.2b.3d.4f.5f.6c, | 1f.2b.3d.4f.5f.6d, | 1f.2b.3d.4f.5f.6e, |
| 1f.2b.3d.4f.5f.6f, | 1f.2b.3e.4a.5a.6a, | 1f.2b.3e.4a.5a.6b, | 1f.2b.3e.4a.5a.6c, | 1f.2b.3e.4a.5a.6d, |
| 1f.2b.3e.4a.5a.6e, | 1f.2b.3e.4a.5a.6f, | 1f.2b.3e.4a.5b.6a, | 1f.2b.3e.4a.5b.6b, | 1f.2b.3e.4a.5b.6c, |
| 1f.2b.3e.4a.5b.6d, | 1f.2b.3e.4a.5b.6e, | 1f.2b.3e.4a.5b.6f, | 1f.2b.3e.4a.5c.6a, | 1f.2b.3e.4a.5c.6b, |
| 1f.2b.3e.4a.5c.6c, | 1f.2b.3e.4a.5c.6d, | 1f.2b.3e.4a.5c.6e, | 1f.2b.3e.4a.5c.6f, | 1f.2b.3e.4a.5d.6a, |
| 1f.2b.3e.4a.5d.6b, | 1f.2b.3e.4a.5d.6c, | 1f.2b.3e.4a.5d.6d, | 1f.2b.3e.4a.5d.6e, | |
| 1f.2b.3e.4a.5d.6f, | 1f.2b.3e.4a.5e.6a, | 1f.2b.3e.4a.5e.6b, | 1f.2b.3e.4a.5e.6c, | 1f.2b.3e.4a.5e.6d, |
| 1f.2b.3e.4a.5e.6e, | 1f.2b.3e.4a.5e.6f, | 1f.2b.3e.4a.5f.6a, | 1f.2b.3e.4a.5f.6b, | 1f.2b.3e.4a.5f.6c, |
| 1f.2b.3e.4a.5f.6d, | 1f.2b.3e.4a.5f.6e, | 1f.2b.3e.4a.5f.6f, | 1f.2b.3e.4b.5a.6a, | 1f.2b.3e.4b.5a.6b, |
| 1f.2b.3e.4b.5a.6c, | 1f.2b.3e.4b.5a.6d, | 1f.2b.3e.4b.5a.6e, | 1f.2b.3e.4b.5a.6f, | |
| 1f.2b.3e.4b.5b.6a, | 1f.2b.3e.4b.5b.6b, | 1f.2b.3e.4b.5b.6c, | 1f.2b.3e.4b.5b.6d, | |
| 1f.2b.3e.4b.5b.6e, | 1f.2b.3e.4b.5b.6f, | 1f.2b.3e.4b.5c.6a, | 1f.2b.3e.4b.5c.6b, | 1f.2b.3e.4b.5c.6c, |
| 1f.2b.3e.4b.5c.6d, | 1f.2b.3e.4b.5c.6e, | 1f.2b.3e.4b.5c.6f, | 1f.2b.3e.4b.5d.6a, | |
| 1f.2b.3e.4b.5d.6b, | 1f.2b.3e.4b.5d.6c, | 1f.2b.3e.4b.5d.6d, | 1f.2b.3e.4b.5d.6e, | |
| 1f.2b.3e.4b.5d.6f, | 1f.2b.3e.4b.5e.6a, | 1f.2b.3e.4b.5e.6b, | 1f.2b.3e.4b.5e.6c, | |
| 1f.2b.3e.4b.5e.6d, | 1f.2b.3e.4b.5e.6e, | 1f.2b.3e.4b.5e.6f, | 1f.2b.3e.4b.5f.6a, | 1f.2b.3e.4b.5f.6b, |
| 1f.2b.3e.4b.5f.6c, | 1f.2b.3e.4b.5f.6d, | 1f.2b.3e.4b.5f.6e, | 1f.2b.3e.4b.5f.6f, | 1f.2b.3e.4c.5a.6a, |
| 1f.2b.3e.4c.5a.6b, | 1f.2b.3e.4c.5a.6c, | 1f.2b.3e.4c.5a.6d, | 1f.2b.3e.4c.5a.6e, | 1f.2b.3e.4c.5a.6f, |
| 1f.2b.3e.4c.5b.6a, | 1f.2b.3e.4c.5b.6b, | 1f.2b.3e.4c.5b.6c, | 1f.2b.3e.4c.5b.6d, | |
| 1f.2b.3e.4c.5b.6e, | 1f.2b.3e.4c.5b.6f, | 1f.2b.3e.4c.5c.6a, | 1f.2b.3e.4c.5c.6b, | 1f.2b.3e.4c.5c.6c, |
| 1f.2b.3e.4c.5c.6d, | 1f.2b.3e.4c.5c.6e, | 1f.2b.3e.4c.5c.6f, | 1f.2b.3e.4c.5d.6a, | 1f.2b.3e.4c.5d.6b, |
| 1f.2b.3e.4c.5d.6c, | 1f.2b.3e.4c.5d.6d, | 1f.2b.3e.4c.5d.6e, | 1f.2b.3e.4c.5d.6f, | 1f.2b.3e.4c.5e.6a, |
| 1f.2b.3e.4c.5e.6b, | 1f.2b.3e.4c.5e.6c, | 1f.2b.3e.4c.5e.6d, | 1f.2b.3e.4c.5e.6e, | 1f.2b.3e.4c.5e.6f, |
| 1f.2b.3e.4c.5f.6a, | 1f.2b.3e.4c.5f.6b, | 1f.2b.3e.4c.5f.6c, | 1f.2b.3e.4c.5f.6d, | 1f.2b.3e.4c.5f.6e, |

TABLE 7-continued

List of Compounds of Formula (II)

| | | | | |
|---|---|---|---|---|
| 1f.2b.3e.4c.5f.6f, | 1f.2b.3e.4d.5a.6a, | 1f.2b.3e.4d.5a.6b, | 1f.2b.3e.4d.5a.6c, | |
| 1f.2b.3e.4d.5a.6d, | 1f.2b.3e.4d.5a.6e, | 1f.2b.3e.4d.5a.6f, | 1f.2b.3e.4d.5b.6a, | |
| 1f.2b.3e.4d.5b.6b, | 1f.2b.3e.4d.5b.6c, | 1f.2b.3e.4d.5b.6d, | 1f.2b.3e.4d.5b.6e, | |
| 1f.2b.3e.4d.5b.6f, | 1f.2b.3e.4d.5c.6a, | 1f.2b.3e.4d.5c.6b, | 1f.2b.3e.4d.5c.6c, | |
| 1f.2b.3e.4d.5c.6d, | 1f.2b.3e.4d.5c.6e, | 1f.2b.3e.4d.5c.6f, | 1f.2b.3e.4d.5d.6a, | |
| 1f.2b.3e.4d.5d.6b, | 1f.2b.3e.4d.5d.6c, | 1f.2b.3e.4d.5d.6d, | 1f.2b.3e.4d.5d.6e, | |
| 1f.2b.3e.4d.5d.6f, | 1f.2b.3e.4d.5e.6a, | 1f.2b.3e.4d.5e.6b, | 1f.2b.3e.4d.5e.6c, | |
| 1f.2b.3e.4d.5e.6d, | 1f.2b.3e.4d.5e.6e, | 1f.2b.3e.4d.5e.6f, | 1f.2b.3e.4d.5f.6a, | |
| 1f.2b.3e.4d.5f.6b, | 1f.2b.3e.4d.5f.6c, | 1f.2b.3e.4d.5f.6d, | 1f.2b.3e.4d.5f.6e, | 1f.2b.3e.4d.5f.6f, |
| 1f.2b.3e.4e.5a.6a, | 1f.2b.3e.4e.5a.6b, | 1f.2b.3e.4e.5a.6c, | 1f.2b.3e.4e.5a.6d, | 1f.2b.3e.4e.5a.6e, |
| 1f.2b.3e.4e.5a.6f, | 1f.2b.3e.4e.5b.6a, | 1f.2b.3e.4e.5b.6b, | 1f.2b.3e.4e.5b.6c, | |
| 1f.2b.3e.4e.5b.6d, | 1f.2b.3e.4e.5b.6e, | 1f.2b.3e.4e.5b.6f, | 1f.2b.3e.4e.5c.6a, | 1f.2b.3e.4e.5c.6b, |
| 1f.2b.3e.4e.5c.6c, | 1f.2b.3e.4e.5c.6d, | 1f.2b.3e.4e.5c.6e, | 1f.2b.3e.4e.5c.6f, | 1f.2b.3e.4e.5d.6a, |
| 1f.2b.3e.4e.5d.6b, | 1f.2b.3e.4e.5d.6c, | 1f.2b.3e.4e.5d.6d, | 1f.2b.3e.4e.5d.6e, | |
| 1f.2b.3e.4e.5d.6f, | 1f.2b.3e.4e.5e.6a, | 1f.2b.3e.4e.5e.6b, | 1f.2b.3e.4e.5e.6c, | 1f.2b.3e.4e.5e.6d, |
| 1f.2b.3e.4e.5e.6e, | 1f.2b.3e.4e.5e.6f, | 1f.2b.3e.4e.5f.6a, | 1f.2b.3e.4e.5f.6b, | 1f.2b.3e.4e.5f.6c, |
| 1f.2b.3e.4e.5f.6d, | 1f.2b.3e.4e.5f.6e, | 1f.2b.3e.4e.5f.6f, | 1f.2b.3e.4f.5a.6a, | 1f.2b.3e.4f.5a.6b, |
| 1f.2b.3e.4f.5a.6c, | 1f.2b.3e.4f.5a.6d, | 1f.2b.3e.4f.5a.6e, | 1f.2b.3e.4f.5a.6f, | 1f.2b.3e.4f.5b.6a, |
| 1f.2b.3e.4f.5b.6b, | 1f.2b.3e.4f.5b.6c, | 1f.2b.3e.4f.5b.6d, | 1f.2b.3e.4f.5b.6e, | 1f.2b.3e.4f.5b.6f, |
| 1f.2b.3e.4f.5c.6a, | 1f.2b.3e.4f.5c.6b, | 1f.2b.3e.4f.5c.6c, | 1f.2b.3e.4f.5c.6d, | 1f.2b.3e.4f.5c.6e, |
| 1f.2b.3e.4f.5c.6f, | 1f.2b.3e.4f.5d.6a, | 1f.2b.3e.4f.5d.6b, | 1f.2b.3e.4f.5d.6c, | 1f.2b.3e.4f.5d.6d, |
| 1f.2b.3e.4f.5d.6e, | 1f.2b.3e.4f.5d.6f, | 1f.2b.3e.4f.5e.6a, | 1f.2b.3e.4f.5e.6b, | 1f.2b.3e.4f.5e.6c, |
| 1f.2b.3e.4f.5e.6d, | 1f.2b.3e.4f.5e.6e, | 1f.2b.3e.4f.5e.6f, | 1f.2b.3e.4f.5f.6a, | 1f.2b.3e.4f.5f.6b, |
| 1f.2b.3e.4f.5f.6c, | 1f.2b.3e.4f.5f.6d, | 1f.2b.3e.4f.5f.6e, | 1f.2b.3e.4f.5f.6f, | 1f.2b.3f.4a.5a.6a, |
| 1f.2b.3f.4a.5a.6b, | 1f.2b.3f.4a.5a.6c, | 1f.2b.3f.4a.5a.6d, | 1f.2b.3f.4a.5a.6e, | 1f.2b.3f.4a.5a.6f, |
| 1f.2b.3f.4a.5b.6a, | 1f.2b.3f.4a.5b.6b, | 1f.2b.3f.4a.5b.6c, | 1f.2b.3f.4a.5b.6d, | 1f.2b.3f.4a.5b.6e, |
| 1f.2b.3f.4a.5b.6f, | 1f.2b.3f.4a.5c.6a, | 1f.2b.3f.4a.5c.6b, | 1f.2b.3f.4a.5c.6c, | 1f.2b.3f.4a.5c.6d, |
| 1f.2b.3f.4a.5c.6e, | 1f.2b.3f.4a.5c.6f, | 1f.2b.3f.4a.5d.6a, | 1f.2b.3f.4a.5d.6b, | 1f.2b.3f.4a.5d.6c, |
| 1f.2b.3f.4a.5d.6d, | 1f.2b.3f.4a.5d.6e, | 1f.2b.3f.4a.5d.6f, | 1f.2b.3f.4a.5e.6a, | 1f.2b.3f.4a.5e.6b, |
| 1f.2b.3f.4a.5e.6c, | 1f.2b.3f.4a.5e.6d, | 1f.2b.3f.4a.5e.6e, | 1f.2b.3f.4a.5e.6f, | 1f.2b.3f.4a.5f.6a, |
| 1f.2b.3f.4a.5f.6b, | 1f.2b.3f.4a.5f.6c, | 1f.2b.3f.4a.5f.6d, | 1f.2b.3f.4a.5f.6e, | 1f.2b.3f.4a.5f.6f, |
| 1f.2b.3f.4b.5a.6a, | 1f.2b.3f.4b.5a.6b, | 1f.2b.3f.4b.5a.6c, | 1f.2b.3f.4b.5a.6d, | 1f.2b.3f.4b.5a.6e, |
| 1f.2b.3f.4b.5a.6f, | 1f.2b.3f.4b.5b.6a, | 1f.2b.3f.4b.5b.6b, | 1f.2b.3f.4b.5b.6c, | 1f.2b.3f.4b.5b.6d, |
| 1f.2b.3f.4b.5b.6e, | 1f.2b.3f.4b.5b.6f, | 1f.2b.3f.4b.5c.6a, | 1f.2b.3f.4b.5c.6b, | 1f.2b.3f.4b.5c.6c, |
| 1f.2b.3f.4b.5c.6d, | 1f.2b.3f.4b.5c.6e, | 1f.2b.3f.4b.5c.6f, | 1f.2b.3f.4b.5d.6a, | 1f.2b.3f.4b.5d.6b, |
| 1f.2b.3f.4b.5d.6c, | 1f.2b.3f.4b.5d.6d, | 1f.2b.3f.4b.5d.6e, | 1f.2b.3f.4b.5d.6f, | 1f.2b.3f.4b.5e.6a, |
| 1f.2b.3f.4b.5e.6b, | 1f.2b.3f.4b.5e.6c, | 1f.2b.3f.4b.5e.6d, | 1f.2b.3f.4b.5e.6e, | 1f.2b.3f.4b.5e.6f, |
| 1f.2b.3f.4b.5f.6a, | 1f.2b.3f.4b.5f.6b, | 1f.2b.3f.4b.5f.6c, | 1f.2b.3f.4b.5f.6d, | 1f.2b.3f.4b.5f.6e, |
| 1f.2b.3f.4b.5f.6f, | 1f.2b.3f.4c.5a.6a, | 1f.2b.3f.4c.5a.6b, | 1f.2b.3f.4c.5a.6c, | 1f.2b.3f.4c.5a.6d, |
| 1f.2b.3f.4c.5a.6e, | 1f.2b.3f.4c.5a.6f, | 1f.2b.3f.4c.5b.6a, | 1f.2b.3f.4c.5b.6b, | 1f.2b.3f.4c.5b.6c, |
| 1f.2b.3f.4c.5b.6d, | 1f.2b.3f.4c.5b.6e, | 1f.2b.3f.4c.5b.6f, | 1f.2b.3f.4c.5c.6a, | 1f.2b.3f.4c.5c.6b, |
| 1f.2b.3f.4c.5c.6c, | 1f.2b.3f.4c.5c.6d, | 1f.2b.3f.4c.5c.6e, | 1f.2b.3f.4c.5c.6f, | 1f.2b.3f.4c.5d.6a, |
| 1f.2b.3f.4c.5d.6b, | 1f.2b.3f.4c.5d.6c, | 1f.2b.3f.4c.5d.6d, | 1f.2b.3f.4c.5d.6e, | 1f.2b.3f.4c.5d.6f, |
| 1f.2b.3f.4c.5e.6a, | 1f.2b.3f.4c.5e.6b, | 1f.2b.3f.4c.5e.6c, | 1f.2b.3f.4c.5e.6d, | 1f.2b.3f.4c.5e.6e, |
| 1f.2b.3f.4c.5e.6f, | 1f.2b.3f.4c.5f.6a, | 1f.2b.3f.4c.5f.6b, | 1f.2b.3f.4c.5f.6c, | 1f.2b.3f.4c.5f.6d, |
| 1f.2b.3f.4c.5f.6e, | 1f.2b.3f.4c.5f.6f, | 1f.2b.3f.4d.5a.6a, | 1f.2b.3f.4d.5a.6b, | 1f.2b.3f.4d.5a.6c, |
| 1f.2b.3f.4d.5a.6d, | 1f.2b.3f.4d.5a.6e, | 1f.2b.3f.4d.5a.6f, | 1f.2b.3f.4d.5b.6a, | 1f.2b.3f.4d.5b.6b, |
| 1f.2b.3f.4d.5b.6c, | 1f.2b.3f.4d.5b.6d, | 1f.2b.3f.4d.5b.6e, | 1f.2b.3f.4d.5b.6f, | 1f.2b.3f.4d.5c.6a, |
| 1f.2b.3f.4d.5c.6b, | 1f.2b.3f.4d.5c.6c, | 1f.2b.3f.4d.5c.6d, | 1f.2b.3f.4d.5c.6e, | 1f.2b.3f.4d.5c.6f, |
| 1f.2b.3f.4d.5d.6a, | 1f.2b.3f.4d.5d.6b, | 1f.2b.3f.4d.5d.6c, | 1f.2b.3f.4d.5d.6d, | |
| 1f.2b.3f.4d.5d.6e, | 1f.2b.3f.4d.5d.6f, | 1f.2b.3f.4d.5e.6a, | 1f.2b.3f.4d.5e.6b, | 1f.2b.3f.4d.5e.6c, |
| 1f.2b.3f.4d.5e.6d, | 1f.2b.3f.4d.5e.6e, | 1f.2b.3f.4d.5e.6f, | 1f.2b.3f.4d.5f.6a, | 1f.2b.3f.4d.5f.6b, |
| 1f.2b.3f.4d.5f.6c, | 1f.2b.3f.4d.5f.6d, | 1f.2b.3f.4d.5f.6e, | 1f.2b.3f.4d.5f.6f, | 1f.2b.3f.4e.5a.6a, |
| 1f.2b.3f.4e.5a.6b, | 1f.2b.3f.4e.5a.6c, | 1f.2b.3f.4e.5a.6d, | 1f.2b.3f.4e.5a.6e, | 1f.2b.3f.4e.5a.6f, |
| 1f.2b.3f.4e.5b.6a, | 1f.2b.3f.4e.5b.6b, | 1f.2b.3f.4e.5b.6c, | 1f.2b.3f.4e.5b.6d, | 1f.2b.3f.4e.5b.6e, |
| 1f.2b.3f.4e.5b.6f, | 1f.2b.3f.4e.5c.6a, | 1f.2b.3f.4e.5c.6b, | 1f.2b.3f.4e.5c.6c, | 1f.2b.3f.4e.5c.6d, |
| 1f.2b.3f.4e.5c.6e, | 1f.2b.3f.4e.5c.6f, | 1f.2b.3f.4e.5d.6a, | 1f.2b.3f.4e.5d.6b, | 1f.2b.3f.4e.5d.6c, |
| 1f.2b.3f.4e.5d.6d, | 1f.2b.3f.4e.5d.6e, | 1f.2b.3f.4e.5d.6f, | 1f.2b.3f.4e.5e.6a, | 1f.2b.3f.4e.5e.6b, |
| 1f.2b.3f.4e.5e.6c, | 1f.2b.3f.4e.5e.6d, | 1f.2b.3f.4e.5e.6e, | 1f.2b.3f.4e.5e.6f, | 1f.2b.3f.4e.5f.6a, |
| 1f.2b.3f.4e.5f.6b, | 1f.2b.3f.4e.5f.6c, | 1f.2b.3f.4e.5f.6d, | 1f.2b.3f.4e.5f.6e, | 1f.2b.3f.4e.5f.6f, |
| 1f.2b.3f.4f.5a.6a, | 1f.2b.3f.4f.5a.6b, | 1f.2b.3f.4f.5a.6c, | 1f.2b.3f.4f.5a.6d, | 1f.2b.3f.4f.5a.6e, |
| 1f.2b.3f.4f.5a.6f, | 1f.2b.3f.4f.5b.6a, | 1f.2b.3f.4f.5b.6b, | 1f.2b.3f.4f.5b.6c, | 1f.2b.3f.4f.5b.6d, |
| 1f.2b.3f.4f.5b.6e, | 1f.2b.3f.4f.5b.6f, | 1f.2b.3f.4f.5c.6a, | 1f.2b.3f.4f.5c.6b, | 1f.2b.3f.4f.5c.6c, |
| 1f.2b.3f.4f.5c.6d, | 1f.2b.3f.4f.5c.6e, | 1f.2b.3f.4f.5c.6f, | 1f.2b.3f.4f.5d.6a, | 1f.2b.3f.4f.5d.6b, |
| 1f.2b.3f.4f.5d.6c, | 1f.2b.3f.4f.5d.6d, | 1f.2b.3f.4f.5d.6e, | 1f.2b.3f.4f.5d.6f, | 1f.2b.3f.4f.5e.6a, |
| 1f.2b.3f.4f.5e.6b, | 1f.2b.3f.4f.5e.6c, | 1f.2b.3f.4f.5e.6d, | 1f.2b.3f.4f.5e.6e, | 1f.2b.3f.4f.5e.6f, |
| 1f.2b.3f.4f.5f.6a, | 1f.2b.3f.4f.5f.6b, | 1f.2b.3f.4f.5f.6c, | 1f.2b.3f.4f.5f.6d, | 1f.2b.3f.4f.5f.6e, |
| 1f.2b.3f.4f.5f.6f, | 1f.2c.3a.4a.5a.6a, | 1f.2c.3a.4a.5a.6b, | 1f.2c.3a.4a.5a.6c, | 1f.2c.3a.4a.5a.6d, |
| 1f.2c.3a.4a.5a.6e, | 1f.2c.3a.4a.5a.6f, | 1f.2c.3a.4a.5b.6a, | 1f.2c.3a.4a.5b.6b, | 1f.2c.3a.4a.5b.6c, |
| 1f.2c.3a.4a.5b.6d, | 1f.2c.3a.4a.5b.6e, | 1f.2c.3a.4a.5b.6f, | 1f.2c.3a.4a.5c.6a, | 1f.2c.3a.4a.5c.6b, |
| 1f.2c.3a.4a.5c.6c, | 1f.2c.3a.4a.5c.6d, | 1f.2c.3a.4a.5c.6e, | 1f.2c.3a.4a.5c.6f, | 1f.2c.3a.4a.5d.6a, |
| 1f.2c.3a.4a.5d.6b, | 1f.2c.3a.4a.5d.6c, | 1f.2c.3a.4a.5d.6d, | 1f.2c.3a.4a.5d.6e, | 1f.2c.3a.4a.5d.6f, |
| 1f.2c.3a.4a.5e.6a, | 1f.2c.3a.4a.5e.6b, | 1f.2c.3a.4a.5e.6c, | 1f.2c.3a.4a.5e.6d, | 1f.2c.3a.4a.5e.6e, |
| 1f.2c.3a.4a.5e.6f, | 1f.2c.3a.4a.5f.6a, | 1f.2c.3a.4a.5f.6b, | 1f.2c.3a.4a.5f.6c, | 1f.2c.3a.4a.5f.6d, |
| 1f.2c.3a.4a.5f.6e, | 1f.2c.3a.4a.5f.6f, | 1f.2c.3a.4b.5a.6a, | 1f.2c.3a.4b.5a.6b, | 1f.2c.3a.4b.5a.6c, |
| 1f.2c.3a.4b.5a.6d, | 1f.2c.3a.4b.5a.6e, | 1f.2c.3a.4b.5a.6f, | 1f.2c.3a.4b.5b.6a, | 1f.2c.3a.4b.5b.6b, |
| 1f.2c.3a.4b.5b.6c, | 1f.2c.3a.4b.5b.6d, | 1f.2c.3a.4b.5b.6e, | 1f.2c.3a.4b.5b.6f, | 1f.2c.3a.4b.5c.6a, |
| 1f.2c.3a.4b.5c.6b, | 1f.2c.3a.4b.5c.6c, | 1f.2c.3a.4b.5c.6d, | 1f.2c.3a.4b.5c.6e, | 1f.2c.3a.4b.5c.6f, |

TABLE 7-continued

List of Compounds of Formula (II)

| | | | |
|---|---|---|---|
| 1f.2c.3a.4b.5d.6a, | 1f.2c.3a.4b.5d.6b, | 1f.2c.3a.4b.5d.6c, | 1f.2c.3a.4b.5d.6d, |
| 1f.2c.3a.4b.5d.6e, | 1f.2c.3a.4b.5d.6f, | 1f.2c.3a.4b.5e.6a, | 1f.2c.3a.4b.5e.6b, | 1f.2c.3a.4b.5e.6c, |
| 1f.2c.3a.4b.5e.6d, | 1f.2c.3a.4b.5e.6e, | 1f.2c.3a.4b.5e.6f, | 1f.2c.3a.4b.5f.6a, | 1f.2c.3a.4b.5f.6b, |
| 1f.2c.3a.4b.5f.6c, | 1f.2c.3a.4b.5f.6d, | 1f.2c.3a.4b.5f.6e, | 1f.2c.3a.4b.5f.6f, | 1f.2c.3a.4c.5a.6a, |
| 1f.2c.3a.4c.5a.6b, | 1f.2c.3a.4c.5a.6c, | 1f.2c.3a.4c.5a.6d, | 1f.2c.3a.4c.5a.6e, | 1f.2c.3a.4c.5a.6f, |
| 1f.2c.3a.4c.5b.6a, | 1f.2c.3a.4c.5b.6b, | 1f.2c.3a.4c.5b.6c, | 1f.2c.3a.4c.5b.6d, | 1f.2c.3a.4c.5b.6e, |
| 1f.2c.3a.4c.5b.6f, | 1f.2c.3a.4c.5c.6a, | 1f.2c.3a.4c.5c.6b, | 1f.2c.3a.4c.5c.6c, | 1f.2c.3a.4c.5c.6d, |
| 1f.2c.3a.4c.5c.6e, | 1f.2c.3a.4c.5c.6f, | 1f.2c.3a.4c.5d.6a, | 1f.2c.3a.4c.5d.6b, | 1f.2c.3a.4c.5d.6c, |
| 1f.2c.3a.4c.5d.6d, | 1f.2c.3a.4c.5d.6e, | 1f.2c.3a.4c.5d.6f, | 1f.2c.3a.4c.5e.6a, | 1f.2c.3a.4c.5e.6b, |
| 1f.2c.3a.4c.5e.6c, | 1f.2c.3a.4c.5e.6d, | 1f.2c.3a.4c.5e.6e, | 1f.2c.3a.4c.5e.6f, | 1f.2c.3a.4c.5f.6a, |
| 1f.2c.3a.4c.5f.6b, | 1f.2c.3a.4c.5f.6c, | 1f.2c.3a.4c.5f.6d, | 1f.2c.3a.4c.5f.6e, | 1f.2c.3a.4c.5f.6f, |
| 1f.2c.3a.4d.5a.6a, | 1f.2c.3a.4d.5a.6b, | 1f.2c.3a.4d.5a.6c, | 1f.2c.3a.4d.5a.6d, | |
| 1f.2c.3a.4d.5a.6e, | 1f.2c.3a.4d.5a.6f, | 1f.2c.3a.4d.5b.6a, | 1f.2c.3a.4d.5b.6b, | |
| 1f.2c.3a.4d.5b.6c, | 1f.2c.3a.4d.5b.6d, | 1f.2c.3a.4d.5b.6e, | 1f.2c.3a.4d.5b.6f, | |
| 1f.2c.3a.4d.5c.6a, | 1f.2c.3a.4d.5c.6b, | 1f.2c.3a.4d.5c.6c, | 1f.2c.3a.4d.5c.6d, | 1f.2c.3a.4d.5c.6e, |
| 1f.2c.3a.4d.5c.6f, | 1f.2c.3a.4d.5d.6a, | 1f.2c.3a.4d.5d.6b, | 1f.2c.3a.4d.5d.6c, | |
| 1f.2c.3a.4d.5d.6d, | 1f.2c.3a.4d.5d.6e, | 1f.2c.3a.4d.5d.6f, | 1f.2c.3a.4d.5e.6a, | |
| 1f.2c.3a.4d.5e.6b, | 1f.2c.3a.4d.5e.6c, | 1f.2c.3a.4d.5e.6d, | 1f.2c.3a.4d.5e.6e, | 1f.2c.3a.4d.5e.6f, |
| 1f.2c.3a.4d.5f.6a, | 1f.2c.3a.4d.5f.6b, | 1f.2c.3a.4d.5f.6c, | 1f.2c.3a.4d.5f.6d, | 1f.2c.3a.4d.5f.6e, |
| 1f.2c.3a.4d.5f.6f, | 1f.2c.3a.4e.5a.6a, | 1f.2c.3a.4e.5a.6b, | 1f.2c.3a.4e.5a.6c, | 1f.2c.3a.4e.5a.6d, |
| 1f.2c.3a.4e.5a.6e, | 1f.2c.3a.4e.5a.6f, | 1f.2c.3a.4e.5b.6a, | 1f.2c.3a.4e.5b.6b, | 1f.2c.3a.4e.5b.6c, |
| 1f.2c.3a.4e.5b.6d, | 1f.2c.3a.4e.5b.6e, | 1f.2c.3a.4e.5b.6f, | 1f.2c.3a.4e.5c.6a, | 1f.2c.3a.4e.5c.6b, |
| 1f.2c.3a.4e.5c.6c, | 1f.2c.3a.4e.5c.6d, | 1f.2c.3a.4e.5c.6e, | 1f.2c.3a.4e.5c.6f, | 1f.2c.3a.4e.5d.6a, |
| 1f.2c.3a.4e.5d.6b, | 1f.2c.3a.4e.5d.6c, | 1f.2c.3a.4e.5d.6d, | 1f.2c.3a.4e.5d.6e, | 1f.2c.3a.4e.5d.6f, |
| 1f.2c.3a.4e.5e.6a, | 1f.2c.3a.4e.5e.6b, | 1f.2c.3a.4e.5e.6c, | 1f.2c.3a.4e.5e.6d, | 1f.2c.3a.4e.5e.6e, |
| 1f.2c.3a.4e.5e.6f, | 1f.2c.3a.4e.5f.6a, | 1f.2c.3a.4e.5f.6b, | 1f.2c.3a.4e.5f.6c, | 1f.2c.3a.4e.5f.6d, |
| 1f.2c.3a.4e.5f.6e, | 1f.2c.3a.4e.5f.6f, | 1f.2c.3a.4f.5a.6a, | 1f.2c.3a.4f.5a.6b, | 1f.2c.3a.4f.5a.6c, |
| 1f.2c.3a.4f.5a.6d, | 1f.2c.3a.4f.5a.6e, | 1f.2c.3a.4f.5a.6f, | 1f.2c.3a.4f.5b.6a, | 1f.2c.3a.4f.5b.6b, |
| 1f.2c.3a.4f.5b.6c, | 1f.2c.3a.4f.5b.6d, | 1f.2c.3a.4f.5b.6e, | 1f.2c.3a.4f.5b.6f, | 1f.2c.3a.4f.5c.6a, |
| 1f.2c.3a.4f.5c.6b, | 1f.2c.3a.4f.5c.6c, | 1f.2c.3a.4f.5c.6d, | 1f.2c.3a.4f.5c.6e, | 1f.2c.3a.4f.5c.6f, |
| 1f.2c.3a.4f.5d.6a, | 1f.2c.3a.4f.5d.6b, | 1f.2c.3a.4f.5d.6c, | 1f.2c.3a.4f.5d.6d, | 1f.2c.3a.4f.5d.6e, |
| 1f.2c.3a.4f.5d.6f, | 1f.2c.3a.4f.5e.6a, | 1f.2c.3a.4f.5e.6b, | 1f.2c.3a.4f.5e.6c, | 1f.2c.3a.4f.5e.6d, |
| 1f.2c.3a.4f.5e.6e, | 1f.2c.3a.4f.5e.6f, | 1f.2c.3a.4f.5f.6a, | 1f.2c.3a.4f.5f.6b, | 1f.2c.3a.4f.5f.6c, |
| 1f.2c.3a.4f.5f.6d, | 1f.2c.3a.4f.5f.6e, | 1f.2c.3a.4f.5f.6f, | 1f.2c.3b.4a.5a.6a, | 1f.2c.3b.4a.5a.6b, |
| 1f.2c.3b.4a.5a.6c, | 1f.2c.3b.4a.5a.6d, | 1f.2c.3b.4a.5a.6e, | 1f.2c.3b.4a.5a.6f, | 1f.2c.3b.4a.5b.6a, |
| 1f.2c.3b.4a.5b.6b, | 1f.2c.3b.4a.5b.6c, | 1f.2c.3b.4a.5b.6d, | 1f.2c.3b.4a.5b.6e, | 1f.2c.3b.4a.5b.6f, |
| 1f.2c.3b.4a.5c.6a, | 1f.2c.3b.4a.5c.6b, | 1f.2c.3b.4a.5c.6c, | 1f.2c.3b.4a.5c.6d, | 1f.2c.3b.4a.5c.6e, |
| 1f.2c.3b.4a.5c.6f, | 1f.2c.3b.4a.5d.6a, | 1f.2c.3b.4a.5d.6b, | 1f.2c.3b.4a.5d.6c, | |
| 1f.2c.3b.4a.5d.6d, | 1f.2c.3b.4a.5d.6e, | 1f.2c.3b.4a.5d.6f, | 1f.2c.3b.4a.5e.6a, | |
| 1f.2c.3b.4a.5e.6b, | 1f.2c.3b.4a.5e.6c, | 1f.2c.3b.4a.5e.6d, | 1f.2c.3b.4a.5e.6e, | 1f.2c.3b.4a.5e.6f, |
| 1f.2c.3b.4a.5f.6a, | 1f.2c.3b.4a.5f.6b, | 1f.2c.3b.4a.5f.6c, | 1f.2c.3b.4a.5f.6d, | 1f.2c.3b.4a.5f.6e, |
| 1f.2c.3b.4a.5f.6f, | 1f.2c.3b.4b.5a.6a, | 1f.2c.3b.4b.5a.6b, | 1f.2c.3b.4b.5a.6c, | 1f.2c.3b.4b.5a.6d, |
| 1f.2c.3b.4b.5a.6e, | 1f.2c.3b.4b.5a.6f, | 1f.2c.3b.4b.5b.6a, | 1f.2c.3b.4b.5b.6b, | |
| 1f.2c.3b.4b.5b.6c, | 1f.2c.3b.4b.5b.6d, | 1f.2c.3b.4b.5b.6e, | 1f.2c.3b.4b.5b.6f, | |
| 1f.2c.3b.4b.5c.6a, | 1f.2c.3b.4b.5c.6b, | 1f.2c.3b.4b.5c.6c, | 1f.2c.3b.4b.5c.6d, | 1f.2c.3b.4b.5c.6e, |
| 1f.2c.3b.4b.5c.6f, | 1f.2c.3b.4b.5d.6a, | 1f.2c.3b.4b.5d.6b, | 1f.2c.3b.4b.5d.6c, | |
| 1f.2c.3b.4b.5d.6d, | 1f.2c.3b.4b.5d.6e, | 1f.2c.3b.4b.5d.6f, | 1f.2c.3b.4b.5e.6a, | |
| 1f.2c.3b.4b.5e.6b, | 1f.2c.3b.4b.5e.6c, | 1f.2c.3b.4b.5e.6d, | 1f.2c.3b.4b.5e.6e, | 1f.2c.3b.4b.5e.6f, |
| 1f.2c.3b.4b.5f.6a, | 1f.2c.3b.4b.5f.6b, | 1f.2c.3b.4b.5f.6c, | 1f.2c.3b.4b.5f.6d, | 1f.2c.3b.4b.5f.6e, |
| 1f.2c.3b.4b.5f.6f, | 1f.2c.3b.4c.5a.6a, | 1f.2c.3b.4c.5a.6b, | 1f.2c.3b.4c.5a.6c, | 1f.2c.3b.4c.5a.6d, |
| 1f.2c.3b.4c.5a.6e, | 1f.2c.3b.4c.5a.6f, | 1f.2c.3b.4c.5b.6a, | 1f.2c.3b.4c.5b.6b, | 1f.2c.3b.4c.5b.6c, |
| 1f.2c.3b.4c.5b.6d, | 1f.2c.3b.4c.5b.6e, | 1f.2c.3b.4c.5b.6f, | 1f.2c.3b.4c.5c.6a, | 1f.2c.3b.4c.5c.6b, |
| 1f.2c.3b.4c.5c.6c, | 1f.2c.3b.4c.5c.6d, | 1f.2c.3b.4c.5c.6e, | 1f.2c.3b.4c.5c.6f, | 1f.2c.3b.4c.5d.6a, |
| 1f.2c.3b.4c.5d.6b, | 1f.2c.3b.4c.5d.6c, | 1f.2c.3b.4c.5d.6d, | 1f.2c.3b.4c.5d.6e, | 1f.2c.3b.4c.5d.6f, |
| 1f.2c.3b.4c.5e.6a, | 1f.2c.3b.4c.5e.6b, | 1f.2c.3b.4c.5e.6c, | 1f.2c.3b.4c.5e.6d, | 1f.2c.3b.4c.5e.6e, |
| 1f.2c.3b.4c.5e.6f, | 1f.2c.3b.4c.5f.6a, | 1f.2c.3b.4c.5f.6b, | 1f.2c.3b.4c.5f.6c, | 1f.2c.3b.4c.5f.6d, |
| 1f.2c.3b.4c.5f.6e, | 1f.2c.3b.4c.5f.6f, | 1f.2c.3b.4d.5a.6a, | 1f.2c.3b.4d.5a.6b, | 1f.2c.3b.4d.5a.6c, |
| 1f.2c.3b.4d.5a.6d, | 1f.2c.3b.4d.5a.6e, | 1f.2c.3b.4d.5a.6f, | 1f.2c.3b.4d.5b.6a, | |
| 1f.2c.3b.4d.5b.6b, | 1f.2c.3b.4d.5b.6c, | 1f.2c.3b.4d.5b.6d, | 1f.2c.3b.4d.5b.6e, | |
| 1f.2c.3b.4d.5b.6f, | 1f.2c.3b.4d.5c.6a, | 1f.2c.3b.4d.5c.6b, | 1f.2c.3b.4d.5c.6c, | |
| 1f.2c.3b.4d.5c.6d, | 1f.2c.3b.4d.5c.6e, | 1f.2c.3b.4d.5c.6f, | 1f.2c.3b.4d.5d.6a, | |
| 1f.2c.3b.4d.5d.6b, | 1f.2c.3b.4d.5d.6c, | 1f.2c.3b.4d.5d.6d, | 1f.2c.3b.4d.5d.6e, | |
| 1f.2c.3b.4d.5d.6f, | 1f.2c.3b.4d.5e.6a, | 1f.2c.3b.4d.5e.6b, | 1f.2c.3b.4d.5e.6c, | |
| 1f.2c.3b.4d.5e.6d, | 1f.2c.3b.4d.5e.6e, | 1f.2c.3b.4d.5e.6f, | 1f.2c.3b.4d.5f.6a, | 1f.2c.3b.4d.5f.6b, |
| 1f.2c.3b.4d.5f.6c, | 1f.2c.3b.4d.5f.6d, | 1f.2c.3b.4d.5f.6e, | 1f.2c.3b.4d.5f.6f, | 1f.2c.3b.4e.5a.6a, |
| 1f.2c.3b.4e.5a.6b, | 1f.2c.3b.4e.5a.6c, | 1f.2c.3b.4e.5a.6d, | 1f.2c.3b.4e.5a.6e, | 1f.2c.3b.4e.5a.6f, |
| 1f.2c.3b.4e.5b.6a, | 1f.2c.3b.4e.5b.6b, | 1f.2c.3b.4e.5b.6c, | 1f.2c.3b.4e.5b.6d, | |
| 1f.2c.3b.4e.5b.6e, | 1f.2c.3b.4e.5b.6f, | 1f.2c.3b.4e.5c.6a, | 1f.2c.3b.4e.5c.6b, | 1f.2c.3b.4e.5c.6c, |
| 1f.2c.3b.4e.5c.6d, | 1f.2c.3b.4e.5c.6e, | 1f.2c.3b.4e.5c.6f, | 1f.2c.3b.4e.5d.6a, | 1f.2c.3b.4e.5d.6b, |
| 1f.2c.3b.4e.5d.6c, | 1f.2c.3b.4e.5d.6d, | 1f.2c.3b.4e.5d.6e, | 1f.2c.3b.4e.5d.6f, | 1f.2c.3b.4e.5e.6a, |
| 1f.2c.3b.4e.5e.6b, | 1f.2c.3b.4e.5e.6c, | 1f.2c.3b.4e.5e.6d, | 1f.2c.3b.4e.5e.6e, | 1f.2c.3b.4e.5e.6f, |
| 1f.2c.3b.4e.5f.6a, | 1f.2c.3b.4e.5f.6b, | 1f.2c.3b.4e.5f.6c, | 1f.2c.3b.4e.5f.6d, | 1f.2c.3b.4e.5f.6e, |
| 1f.2c.3b.4e.5f.6f, | 1f.2c.3b.4f.5a.6a, | 1f.2c.3b.4f.5a.6b, | 1f.2c.3b.4f.5a.6c, | 1f.2c.3b.4f.5a.6d, |
| 1f.2c.3b.4f.5a.6e, | 1f.2c.3b.4f.5a.6f, | 1f.2c.3b.4f.5b.6a, | 1f.2c.3b.4f.5b.6b, | 1f.2c.3b.4f.5b.6c, |
| 1f.2c.3b.4f.5b.6d, | 1f.2c.3b.4f.5b.6e, | 1f.2c.3b.4f.5b.6f, | 1f.2c.3b.4f.5c.6a, | 1f.2c.3b.4f.5c.6b, |
| 1f.2c.3b.4f.5c.6c, | 1f.2c.3b.4f.5c.6d, | 1f.2c.3b.4f.5c.6e, | 1f.2c.3b.4f.5c.6f, | 1f.2c.3b.4f.5d.6a, |
| 1f.2c.3b.4f.5d.6b, | 1f.2c.3b.4f.5d.6c, | 1f.2c.3b.4f.5d.6d, | 1f.2c.3b.4f.5d.6e, | 1f.2c.3b.4f.5d.6f, |
| 1f.2c.3b.4f.5e.6a, | 1f.2c.3b.4f.5e.6b, | 1f.2c.3b.4f.5e.6c, | 1f.2c.3b.4f.5e.6d, | 1f.2c.3b.4f.5e.6e, |

TABLE 7-continued

List of Compounds of Formula (II)

| | | | | |
|---|---|---|---|---|
| 1f.2c.3b.4f.5e.6f, | 1f.2c.3b.4f.5f.6a, | 1f.2c.3b.4f.5f.6b, | 1f.2c.3b.4f.5f.6c, | 1f.2c.3b.4f.5f.6d, |
| 1f.2c.3b.4f.5f.6e, | 1f.2c.3b.4f.5f.6f, | 1f.2c.3c.4a.5a.6a, | 1f.2c.3c.4a.5a.6b, | 1f.2c.3c.4a.5a.6c, |
| 1f.2c.3c.4a.5a.6d, | 1f.2c.3c.4a.5a.6e, | 1f.2c.3c.4a.5a.6f, | 1f.2c.3c.4a.5b.6a, | 1f.2c.3c.4a.5b.6b, |
| 1f.2c.3c.4a.5b.6c, | 1f.2c.3c.4a.5b.6d, | 1f.2c.3c.4a.5b.6e, | 1f.2c.3c.4a.5b.6f, | 1f.2c.3c.4a.5c.6a, |
| 1f.2c.3c.4a.5c.6b, | 1f.2c.3c.4a.5c.6c, | 1f.2c.3c.4a.5c.6d, | 1f.2c.3c.4a.5c.6e, | 1f.2c.3c.4a.5c.6f, |
| 1f.2c.3c.4a.5d.6a, | 1f.2c.3c.4a.5d.6b, | 1f.2c.3c.4a.5d.6c, | 1f.2c.3c.4a.5d.6d, | 1f.2c.3c.4a.5d.6e, |
| 1f.2c.3c.4a.5d.6f, | 1f.2c.3c.4a.5e.6a, | 1f.2c.3c.4a.5e.6b, | 1f.2c.3c.4a.5e.6c, | 1f.2c.3c.4a.5e.6d, |
| 1f.2c.3c.4a.5e.6e, | 1f.2c.3c.4a.5e.6f, | 1f.2c.3c.4a.5f.6a, | 1f.2c.3c.4a.5f.6b, | 1f.2c.3c.4a.5f.6c, |
| 1f.2c.3c.4a.5f.6d, | 1f.2c.3c.4a.5f.6e, | 1f.2c.3c.4a.5f.6f, | 1f.2c.3c.4b.5a.6a, | 1f.2c.3c.4b.5a.6b, |
| 1f.2c.3c.4b.5a.6c, | 1f.2c.3c.4b.5a.6d, | 1f.2c.3c.4b.5a.6e, | 1f.2c.3c.4b.5a.6f, | 1f.2c.3c.4b.5b.6a, |
| 1f.2c.3c.4b.5b.6b, | 1f.2c.3c.4b.5b.6c, | 1f.2c.3c.4b.5b.6d, | 1f.2c.3c.4b.5b.6e, | 1f.2c.3c.4b.5b.6f, |
| 1f.2c.3c.4b.5c.6a, | 1f.2c.3c.4b.5c.6b, | 1f.2c.3c.4b.5c.6c, | 1f.2c.3c.4b.5c.6d, | 1f.2c.3c.4b.5c.6e, |
| 1f.2c.3c.4b.5c.6f, | 1f.2c.3c.4b.5d.6a, | 1f.2c.3c.4b.5d.6b, | 1f.2c.3c.4b.5d.6c, | 1f.2c.3c.4b.5d.6d, |
| 1f.2c.3c.4b.5d.6e, | 1f.2c.3c.4b.5d.6f, | 1f.2c.3c.4b.5e.6a, | 1f.2c.3c.4b.5e.6b, | 1f.2c.3c.4b.5e.6c, |
| 1f.2c.3c.4b.5e.6d, | 1f.2c.3c.4b.5e.6e, | 1f.2c.3c.4b.5e.6f, | 1f.2c.3c.4b.5f.6a, | 1f.2c.3c.4b.5f.6b, |
| 1f.2c.3c.4b.5f.6c, | 1f.2c.3c.4b.5f.6d, | 1f.2c.3c.4b.5f.6e, | 1f.2c.3c.4b.5f.6f, | 1f.2c.3c.4c.5a.6a, |
| 1f.2c.3c.4c.5a.6b, | 1f.2c.3c.4c.5a.6c, | 1f.2c.3c.4c.5a.6d, | 1f.2c.3c.4c.5a.6e, | 1f.2c.3c.4c.5a.6f, |
| 1f.2c.3c.4c.5b.6a, | 1f.2c.3c.4c.5b.6b, | 1f.2c.3c.4c.5b.6c, | 1f.2c.3c.4c.5b.6d, | 1f.2c.3c.4c.5b.6e, |
| 1f.2c.3c.4c.5b.6f, | 1f.2c.3c.4c.5c.6a, | 1f.2c.3c.4c.5c.6b, | 1f.2c.3c.4c.5c.6c, | 1f.2c.3c.4c.5c.6d, |
| 1f.2c.3c.4c.5c.6e, | 1f.2c.3c.4c.5c.6f, | 1f.2c.3c.4c.5d.6a, | 1f.2c.3c.4c.5d.6b, | 1f.2c.3c.4c.5d.6c, |
| 1f.2c.3c.4c.5d.6d, | 1f.2c.3c.4c.5d.6e, | 1f.2c.3c.4c.5d.6f, | 1f.2c.3c.4c.5e.6a, | 1f.2c.3c.4c.5e.6b, |
| 1f.2c.3c.4c.5e.6c, | 1f.2c.3c.4c.5e.6d, | 1f.2c.3c.4c.5e.6e, | 1f.2c.3c.4c.5e.6f, | 1f.2c.3c.4c.5f.6a, |
| 1f.2c.3c.4c.5f.6b, | 1f.2c.3c.4c.5f.6c, | 1f.2c.3c.4c.5f.6d, | 1f.2c.3c.4c.5f.6e, | 1f.2c.3c.4c.5f.6f, |
| 1f.2c.3c.4d.5a.6a, | 1f.2c.3c.4d.5a.6b, | 1f.2c.3c.4d.5a.6c, | 1f.2c.3c.4d.5a.6d, | 1f.2c.3c.4d.5a.6e, |
| 1f.2c.3c.4d.5a.6f, | 1f.2c.3c.4d.5b.6a, | 1f.2c.3c.4d.5b.6b, | 1f.2c.3c.4d.5b.6c, | 1f.2c.3c.4d.5b.6d, |
| 1f.2c.3c.4d.5b.6e, | 1f.2c.3c.4d.5b.6f, | 1f.2c.3c.4d.5c.6a, | 1f.2c.3c.4d.5c.6b, | 1f.2c.3c.4d.5c.6c, |
| 1f.2c.3c.4d.5c.6d, | 1f.2c.3c.4d.5c.6e, | 1f.2c.3c.4d.5c.6f, | 1f.2c.3c.4d.5d.6a, | 1f.2c.3c.4d.5d.6b, |
| 1f.2c.3c.4d.5d.6c, | 1f.2c.3c.4d.5d.6d, | 1f.2c.3c.4d.5d.6e, | 1f.2c.3c.4d.5d.6f, | |
| 1f.2c.3c.4d.5e.6a, | 1f.2c.3c.4d.5e.6b, | 1f.2c.3c.4d.5e.6c, | 1f.2c.3c.4d.5e.6d, | 1f.2c.3c.4d.5e.6e, |
| 1f.2c.3c.4d.5e.6f, | 1f.2c.3c.4d.5f.6a, | 1f.2c.3c.4d.5f.6b, | 1f.2c.3c.4d.5f.6c, | 1f.2c.3c.4d.5f.6d, |
| 1f.2c.3c.4d.5f.6e, | 1f.2c.3c.4d.5f.6f, | 1f.2c.3c.4e.5a.6a, | 1f.2c.3c.4e.5a.6b, | 1f.2c.3c.4e.5a.6c, |
| 1f.2c.3c.4e.5a.6d, | 1f.2c.3c.4e.5a.6e, | 1f.2c.3c.4e.5a.6f, | 1f.2c.3c.4e.5b.6a, | 1f.2c.3c.4e.5b.6b, |
| 1f.2c.3c.4e.5b.6c, | 1f.2c.3c.4e.5b.6d, | 1f.2c.3c.4e.5b.6e, | 1f.2c.3c.4e.5b.6f, | 1f.2c.3c.4e.5c.6a, |
| 1f.2c.3c.4e.5c.6b, | 1f.2c.3c.4e.5c.6c, | 1f.2c.3c.4e.5c.6d, | 1f.2c.3c.4e.5c.6e, | 1f.2c.3c.4e.5c.6f, |
| 1f.2c.3c.4e.5d.6a, | 1f.2c.3c.4e.5d.6b, | 1f.2c.3c.4e.5d.6c, | 1f.2c.3c.4e.5d.6d, | 1f.2c.3c.4e.5d.6e, |
| 1f.2c.3c.4e.5d.6f, | 1f.2c.3c.4e.5e.6a, | 1f.2c.3c.4e.5e.6b, | 1f.2c.3c.4e.5e.6c, | 1f.2c.3c.4e.5e.6d, |
| 1f.2c.3c.4e.5e.6e, | 1f.2c.3c.4e.5e.6f, | 1f.2c.3c.4e.5f.6a, | 1f.2c.3c.4e.5f.6b, | 1f.2c.3c.4e.5f.6c, |
| 1f.2c.3c.4e.5f.6d, | 1f.2c.3c.4e.5f.6e, | 1f.2c.3c.4e.5f.6f, | 1f.2c.3c.4f.5a.6a, | 1f.2c.3c.4f.5a.6b, |
| 1f.2c.3c.4f.5a.6c, | 1f.2c.3c.4f.5a.6d, | 1f.2c.3c.4f.5a.6e, | 1f.2c.3c.4f.5a.6f, | 1f.2c.3c.4f.5b.6a, |
| 1f.2c.3c.4f.5b.6b, | 1f.2c.3c.4f.5b.6c, | 1f.2c.3c.4f.5b.6d, | 1f.2c.3c.4f.5b.6e, | 1f.2c.3c.4f.5b.6f, |
| 1f.2c.3c.4f.5c.6a, | 1f.2c.3c.4f.5c.6b, | 1f.2c.3c.4f.5c.6c, | 1f.2c.3c.4f.5c.6d, | 1f.2c.3c.4f.5c.6e, |
| 1f.2c.3c.4f.5c.6f, | 1f.2c.3c.4f.5d.6a, | 1f.2c.3c.4f.5d.6b, | 1f.2c.3c.4f.5d.6c, | 1f.2c.3c.4f.5d.6d, |
| 1f.2c.3c.4f.5d.6e, | 1f.2c.3c.4f.5d.6f, | 1f.2c.3c.4f.5e.6a, | 1f.2c.3c.4f.5e.6b, | 1f.2c.3c.4f.5e.6c, |
| 1f.2c.3c.4f.5e.6d, | 1f.2c.3c.4f.5e.6e, | 1f.2c.3c.4f.5e.6f, | 1f.2c.3c.4f.5f.6a, | 1f.2c.3c.4f.5f.6b, |
| 1f.2c.3c.4f.5f.6c, | 1f.2c.3c.4f.5f.6d, | 1f.2c.3c.4f.5f.6e, | 1f.2c.3c.4f.5f.6f, | 1f.2c.3d.4a.5a.6a, |
| 1f.2c.3d.4a.5a.6b, | 1f.2c.3d.4a.5a.6c, | 1f.2c.3d.4a.5a.6d, | 1f.2c.3d.4a.5a.6e, | 1f.2c.3d.4a.5a.6f, |
| 1f.2c.3d.4a.5b.6a, | 1f.2c.3d.4a.5b.6b, | 1f.2c.3d.4a.5b.6c, | 1f.2c.3d.4a.5b.6d, | |
| 1f.2c.3d.4a.5b.6e, | 1f.2c.3d.4a.5b.6f, | 1f.2c.3d.4a.5c.6a, | 1f.2c.3d.4a.5c.6b, | 1f.2c.3d.4a.5c.6c, |
| 1f.2c.3d.4a.5c.6d, | 1f.2c.3d.4a.5c.6e, | 1f.2c.3d.4a.5c.6f, | 1f.2c.3d.4a.5d.6a, | |
| 1f.2c.3d.4a.5d.6b, | 1f.2c.3d.4a.5d.6c, | 1f.2c.3d.4a.5d.6d, | 1f.2c.3d.4a.5d.6e, | |
| 1f.2c.3d.4a.5d.6f, | 1f.2c.3d.4a.5e.6a, | 1f.2c.3d.4a.5e.6b, | 1f.2c.3d.4a.5e.6c, | |
| 1f.2c.3d.4a.5e.6d, | 1f.2c.3d.4a.5e.6e, | 1f.2c.3d.4a.5e.6f, | 1f.2c.3d.4a.5f.6a, | 1f.2c.3d.4a.5f.6b, |
| 1f.2c.3d.4a.5f.6c, | 1f.2c.3d.4a.5f.6d, | 1f.2c.3d.4a.5f.6e, | 1f.2c.3d.4a.5f.6f, | 1f.2c.3d.4b.5a.6a, |
| 1f.2c.3d.4b.5a.6b, | 1f.2c.3d.4b.5a.6c, | 1f.2c.3d.4b.5a.6d, | 1f.2c.3d.4b.5a.6e, | |
| 1f.2c.3d.4b.5a.6f, | 1f.2c.3d.4b.5b.6a, | 1f.2c.3d.4b.5b.6b, | 1f.2c.3d.4b.5b.6c, | |
| 1f.2c.3d.4b.5b.6d, | 1f.2c.3d.4b.5b.6e, | 1f.2c.3d.4b.5b.6f, | 1f.2c.3d.4b.5c.6a, | |
| 1f.2c.3d.4b.5c.6b, | 1f.2c.3d.4b.5c.6c, | 1f.2c.3d.4b.5c.6d, | 1f.2c.3d.4b.5c.6e, | 1f.2c.3d.4b.5c.6f, |
| 1f.2c.3d.4b.5d.6a, | 1f.2c.3d.4b.5d.6b, | 1f.2c.3d.4b.5d.6c, | 1f.2c.3d.4b.5d.6d, | |
| 1f.2c.3d.4b.5d.6e, | 1f.2c.3d.4b.5d.6f, | 1f.2c.3d.4b.5e.6a, | 1f.2c.3d.4b.5e.6b, | |
| 1f.2c.3d.4b.5e.6c, | 1f.2c.3d.4b.5e.6d, | 1f.2c.3d.4b.5e.6e, | 1f.2c.3d.4b.5e.6f, | 1f.2c.3d.4b.5f.6a, |
| 1f.2c.3d.4b.5f.6b, | 1f.2c.3d.4b.5f.6c, | 1f.2c.3d.4b.5f.6d, | 1f.2c.3d.4b.5f.6e, | 1f.2c.3d.4b.5f.6f, |
| 1f.2c.3d.4c.5a.6a, | 1f.2c.3d.4c.5a.6b, | 1f.2c.3d.4c.5a.6c, | 1f.2c.3d.4c.5a.6d, | 1f.2c.3d.4c.5a.6e, |
| 1f.2c.3d.4c.5a.6f, | 1f.2c.3d.4c.5b.6a, | 1f.2c.3d.4c.5b.6b, | 1f.2c.3d.4c.5b.6c, | 1f.2c.3d.4c.5b.6d, |
| 1f.2c.3d.4c.5b.6e, | 1f.2c.3d.4c.5b.6f, | 1f.2c.3d.4c.5c.6a, | 1f.2c.3d.4c.5c.6b, | 1f.2c.3d.4c.5c.6c, |
| 1f.2c.3d.4c.5c.6d, | 1f.2c.3d.4c.5c.6e, | 1f.2c.3d.4c.5c.6f, | 1f.2c.3d.4c.5d.6a, | 1f.2c.3d.4c.5d.6b, |
| 1f.2c.3d.4c.5d.6c, | 1f.2c.3d.4c.5d.6d, | 1f.2c.3d.4c.5d.6e, | 1f.2c.3d.4c.5d.6f, | |
| 1f.2c.3d.4c.5e.6a, | 1f.2c.3d.4c.5e.6b, | 1f.2c.3d.4c.5e.6c, | 1f.2c.3d.4c.5e.6d, | 1f.2c.3d.4c.5e.6e, |
| 1f.2c.3d.4c.5e.6f, | 1f.2c.3d.4c.5f.6a, | 1f.2c.3d.4c.5f.6b, | 1f.2c.3d.4c.5f.6c, | 1f.2c.3d.4c.5f.6d, |
| 1f.2c.3d.4c.5f.6e, | 1f.2c.3d.4c.5f.6f, | 1f.2c.3d.4d.5a.6a, | 1f.2c.3d.4d.5a.6b, | 1f.2c.3d.4d.5a.6c, |
| 1f.2c.3d.4d.5a.6d, | 1f.2c.3d.4d.5a.6e, | 1f.2c.3d.4d.5a.6f, | 1f.2c.3d.4d.5b.6a, | |
| 1f.2c.3d.4d.5b.6b, | 1f.2c.3d.4d.5b.6c, | 1f.2c.3d.4d.5b.6d, | 1f.2c.3d.4d.5b.6e, | |
| 1f.2c.3d.4d.5b.6f, | 1f.2c.3d.4d.5c.6a, | 1f.2c.3d.4d.5c.6b, | 1f.2c.3d.4d.5c.6c, | |
| 1f.2c.3d.4d.5c.6d, | 1f.2c.3d.4d.5c.6e, | 1f.2c.3d.4d.5c.6f, | 1f.2c.3d.4d.5d.6a, | |
| 1f.2c.3d.4d.5d.6b, | 1f.2c.3d.4d.5d.6c, | 1f.2c.3d.4d.5d.6d, | 1f.2c.3d.4d.5d.6e, | |
| 1f.2c.3d.4d.5d.6f, | 1f.2c.3d.4d.5e.6a, | 1f.2c.3d.4d.5e.6b, | 1f.2c.3d.4d.5e.6c, | |
| 1f.2c.3d.4d.5e.6d, | 1f.2c.3d.4d.5e.6e, | 1f.2c.3d.4d.5e.6f, | 1f.2c.3d.4d.5f.6a, | |
| 1f.2c.3d.4d.5f.6b, | 1f.2c.3d.4d.5f.6c, | 1f.2c.3d.4d.5f.6d, | 1f.2c.3d.4d.5f.6e, | 1f.2c.3d.4d.5f.6f, |
| 1f.2c.3d.4e.5a.6a, | 1f.2c.3d.4e.5a.6b, | 1f.2c.3d.4e.5a.6c, | 1f.2c.3d.4e.5a.6d, | |

TABLE 7-continued

List of Compounds of Formula (II)

| | | | |
|---|---|---|---|
| 1f.2c.3d.4e.5a.6e, | 1f.2c.3d.4e.5a.6f, | 1f.2c.3d.4e.5b.6a, | 1f.2c.3d.4e.5b.6b, | 1f.2c.3d.4e.5b.6c, |
| 1f.2c.3d.4e.5b.6d, | 1f.2c.3d.4e.5b.6e, | 1f.2c.3d.4e.5b.6f, | 1f.2c.3d.4e.5c.6a, | 1f.2c.3d.4e.5c.6b, |
| 1f.2c.3d.4e.5c.6c, | 1f.2c.3d.4e.5c.6d, | 1f.2c.3d.4e.5c.6e, | 1f.2c.3d.4e.5c.6f, | 1f.2c.3d.4e.5d.6a, |
| 1f.2c.3d.4e.5d.6b, | 1f.2c.3d.4e.5d.6c, | 1f.2c.3d.4e.5d.6d, | 1f.2c.3d.4e.5d.6e, | |
| 1f.2c.3d.4e.5d.6f, | 1f.2c.3d.4e.5e.6a, | 1f.2c.3d.4e.5e.6b, | 1f.2c.3d.4e.5e.6c, | 1f.2c.3d.4e.5e.6d, |
| 1f.2c.3d.4e.5e.6e, | 1f.2c.3d.4e.5e.6f, | 1f.2c.3d.4e.5f.6a, | 1f.2c.3d.4e.5f.6b, | 1f.2c.3d.4e.5f.6c, |
| 1f.2c.3d.4e.5f.6d, | 1f.2c.3d.4e.5f.6e, | 1f.2c.3d.4e.5f.6f, | 1f.2c.3d.4f.5a.6a, | 1f.2c.3d.4f.5a.6b, |
| 1f.2c.3d.4f.5a.6c, | 1f.2c.3d.4f.5a.6d, | 1f.2c.3d.4f.5a.6e, | 1f.2c.3d.4f.5a.6f, | 1f.2c.3d.4f.5b.6a, |
| 1f.2c.3d.4f.5b.6b, | 1f.2c.3d.4f.5b.6c, | 1f.2c.3d.4f.5b.6d, | 1f.2c.3d.4f.5b.6e, | 1f.2c.3d.4f.5b.6f, |
| 1f.2c.3d.4f.5c.6a, | 1f.2c.3d.4f.5c.6b, | 1f.2c.3d.4f.5c.6c, | 1f.2c.3d.4f.5c.6d, | 1f.2c.3d.4f.5c.6e, |
| 1f.2c.3d.4f.5c.6f, | 1f.2c.3d.4f.5d.6a, | 1f.2c.3d.4f.5d.6b, | 1f.2c.3d.4f.5d.6c, | 1f.2c.3d.4f.5d.6d, |
| 1f.2c.3d.4f.5d.6e, | 1f.2c.3d.4f.5d.6f, | 1f.2c.3d.4f.5e.6a, | 1f.2c.3d.4f.5e.6b, | 1f.2c.3d.4f.5e.6c, |
| 1f.2c.3d.4f.5e.6d, | 1f.2c.3d.4f.5e.6e, | 1f.2c.3d.4f.5e.6f, | 1f.2c.3d.4f.5f.6a, | 1f.2c.3d.4f.5f.6b, |
| 1f.2c.3d.4f.5f.6c, | 1f.2c.3d.4f.5f.6d, | 1f.2c.3d.4f.5f.6e, | 1f.2c.3d.4f.5f.6f, | 1f.2c.3e.4a.5a.6a, |
| 1f.2c.3e.4a.5a.6b, | 1f.2c.3e.4a.5a.6c, | 1f.2c.3e.4a.5a.6d, | 1f.2c.3e.4a.5a.6e, | 1f.2c.3e.4a.5a.6f, |
| 1f.2c.3e.4a.5b.6a, | 1f.2c.3e.4a.5b.6b, | 1f.2c.3e.4a.5b.6c, | 1f.2c.3e.4a.5b.6d, | 1f.2c.3e.4a.5b.6e, |
| 1f.2c.3e.4a.5b.6f, | 1f.2c.3e.4a.5c.6a, | 1f.2c.3e.4a.5c.6b, | 1f.2c.3e.4a.5c.6c, | 1f.2c.3e.4a.5c.6d, |
| 1f.2c.3e.4a.5c.6e, | 1f.2c.3e.4a.5c.6f, | 1f.2c.3e.4a.5d.6a, | 1f.2c.3e.4a.5d.6b, | 1f.2c.3e.4a.5d.6c, |
| 1f.2c.3e.4a.5d.6d, | 1f.2c.3e.4a.5d.6e, | 1f.2c.3e.4a.5d.6f, | 1f.2c.3e.4a.5e.6a, | 1f.2c.3e.4a.5e.6b, |
| 1f.2c.3e.4a.5e.6c, | 1f.2c.3e.4a.5e.6d, | 1f.2c.3e.4a.5e.6e, | 1f.2c.3e.4a.5e.6f, | 1f.2c.3e.4a.5f.6a, |
| 1f.2c.3e.4a.5f.6b, | 1f.2c.3e.4a.5f.6c, | 1f.2c.3e.4a.5f.6d, | 1f.2c.3e.4a.5f.6e, | 1f.2c.3e.4a.5f.6f, |
| 1f.2c.3e.4b.5a.6a, | 1f.2c.3e.4b.5a.6b, | 1f.2c.3e.4b.5a.6c, | 1f.2c.3e.4b.5a.6d, | 1f.2c.3e.4b.5a.6e, |
| 1f.2c.3e.4b.5a.6f, | 1f.2c.3e.4b.5b.6a, | 1f.2c.3e.4b.5b.6b, | 1f.2c.3e.4b.5b.6c, | 1f.2c.3e.4b.5b.6d, |
| 1f.2c.3e.4b.5b.6e, | 1f.2c.3e.4b.5b.6f, | 1f.2c.3e.4b.5c.6a, | 1f.2c.3e.4b.5c.6b, | 1f.2c.3e.4b.5c.6c, |
| 1f.2c.3e.4b.5c.6d, | 1f.2c.3e.4b.5c.6e, | 1f.2c.3e.4b.5c.6f, | 1f.2c.3e.4b.5d.6a, | 1f.2c.3e.4b.5d.6b, |
| 1f.2c.3e.4b.5d.6c, | 1f.2c.3e.4b.5d.6d, | 1f.2c.3e.4b.5d.6e, | 1f.2c.3e.4b.5d.6f, | 1f.2c.3e.4b.5e.6a, |
| 1f.2c.3e.4b.5e.6b, | 1f.2c.3e.4b.5e.6c, | 1f.2c.3e.4b.5e.6d, | 1f.2c.3e.4b.5e.6e, | 1f.2c.3e.4b.5e.6f, |
| 1f.2c.3e.4b.5f.6a, | 1f.2c.3e.4b.5f.6b, | 1f.2c.3e.4b.5f.6c, | 1f.2c.3e.4b.5f.6d, | 1f.2c.3e.4b.5f.6e, |
| 1f.2c.3e.4b.5f.6f, | 1f.2c.3e.4c.5a.6a, | 1f.2c.3e.4c.5a.6b, | 1f.2c.3e.4c.5a.6c, | 1f.2c.3e.4c.5a.6d, |
| 1f.2c.3e.4c.5a.6e, | 1f.2c.3e.4c.5a.6f, | 1f.2c.3e.4c.5b.6a, | 1f.2c.3e.4c.5b.6b, | 1f.2c.3e.4c.5b.6c, |
| 1f.2c.3e.4c.5b.6d, | 1f.2c.3e.4c.5b.6e, | 1f.2c.3e.4c.5b.6f, | 1f.2c.3e.4c.5c.6a, | 1f.2c.3e.4c.5c.6b, |
| 1f.2c.3e.4c.5c.6c, | 1f.2c.3e.4c.5c.6d, | 1f.2c.3e.4c.5c.6e, | 1f.2c.3e.4c.5c.6f, | 1f.2c.3e.4c.5d.6a, |
| 1f.2c.3e.4c.5d.6b, | 1f.2c.3e.4c.5d.6c, | 1f.2c.3e.4c.5d.6d, | 1f.2c.3e.4c.5d.6e, | 1f.2c.3e.4c.5d.6f, |
| 1f.2c.3e.4c.5e.6a, | 1f.2c.3e.4c.5e.6b, | 1f.2c.3e.4c.5e.6c, | 1f.2c.3e.4c.5e.6d, | 1f.2c.3e.4c.5e.6e, |
| 1f.2c.3e.4c.5e.6f, | 1f.2c.3e.4c.5f.6a, | 1f.2c.3e.4c.5f.6b, | 1f.2c.3e.4c.5f.6c, | 1f.2c.3e.4c.5f.6d, |
| 1f.2c.3e.4c.5f.6e, | 1f.2c.3e.4c.5f.6f, | 1f.2c.3e.4d.5a.6a, | 1f.2c.3e.4d.5a.6b, | 1f.2c.3e.4d.5a.6c, |
| 1f.2c.3e.4d.5a.6d, | 1f.2c.3e.4d.5a.6e, | 1f.2c.3e.4d.5a.6f, | 1f.2c.3e.4d.5b.6a, | |
| 1f.2c.3e.4d.5b.6b, | 1f.2c.3e.4d.5b.6c, | 1f.2c.3e.4d.5b.6d, | 1f.2c.3e.4d.5b.6e, | |
| 1f.2c.3e.4d.5b.6f, | 1f.2c.3e.4d.5c.6a, | 1f.2c.3e.4d.5c.6b, | 1f.2c.3e.4d.5c.6c, | 1f.2c.3e.4d.5c.6d, |
| 1f.2c.3e.4d.5c.6e, | 1f.2c.3e.4d.5c.6f, | 1f.2c.3e.4d.5d.6a, | 1f.2c.3e.4d.5d.6b, | 1f.2c.3e.4d.5d.6c, |
| 1f.2c.3e.4d.5d.6d, | 1f.2c.3e.4d.5d.6e, | 1f.2c.3e.4d.5d.6f, | 1f.2c.3e.4d.5e.6a, | |
| 1f.2c.3e.4d.5e.6b, | 1f.2c.3e.4d.5e.6c, | 1f.2c.3e.4d.5e.6d, | 1f.2c.3e.4d.5e.6e, | 1f.2c.3e.4d.5e.6f, |
| 1f.2c.3e.4d.5f.6a, | 1f.2c.3e.4d.5f.6b, | 1f.2c.3e.4d.5f.6c, | 1f.2c.3e.4d.5f.6d, | 1f.2c.3e.4d.5f.6e, |
| 1f.2c.3e.4d.5f.6f, | 1f.2c.3e.4e.5a.6a, | 1f.2c.3e.4e.5a.6b, | 1f.2c.3e.4e.5a.6c, | 1f.2c.3e.4e.5a.6d, |
| 1f.2c.3e.4e.5a.6e, | 1f.2c.3e.4e.5a.6f, | 1f.2c.3e.4e.5b.6a, | 1f.2c.3e.4e.5b.6b, | 1f.2c.3e.4e.5b.6c, |
| 1f.2c.3e.4e.5b.6d, | 1f.2c.3e.4e.5b.6e, | 1f.2c.3e.4e.5b.6f, | 1f.2c.3e.4e.5c.6a, | 1f.2c.3e.4e.5c.6b, |
| 1f.2c.3e.4e.5c.6c, | 1f.2c.3e.4e.5c.6d, | 1f.2c.3e.4e.5c.6e, | 1f.2c.3e.4e.5c.6f, | 1f.2c.3e.4e.5d.6a, |
| 1f.2c.3e.4e.5d.6b, | 1f.2c.3e.4e.5d.6c, | 1f.2c.3e.4e.5d.6d, | 1f.2c.3e.4e.5d.6e, | 1f.2c.3e.4e.5d.6f, |
| 1f.2c.3e.4e.5e.6a, | 1f.2c.3e.4e.5e.6b, | 1f.2c.3e.4e.5e.6c, | 1f.2c.3e.4e.5e.6d, | 1f.2c.3e.4e.5e.6e, |
| 1f.2c.3e.4e.5e.6f, | 1f.2c.3e.4e.5f.6a, | 1f.2c.3e.4e.5f.6b, | 1f.2c.3e.4e.5f.6c, | 1f.2c.3e.4e.5f.6d, |
| 1f.2c.3e.4e.5f.6e, | 1f.2c.3e.4e.5f.6f, | 1f.2c.3e.4f.5a.6a, | 1f.2c.3e.4f.5a.6b, | 1f.2c.3e.4f.5a.6c, |
| 1f.2c.3e.4f.5a.6d, | 1f.2c.3e.4f.5a.6e, | 1f.2c.3e.4f.5a.6f, | 1f.2c.3e.4f.5b.6a, | 1f.2c.3e.4f.5b.6b, |
| 1f.2c.3e.4f.5b.6c, | 1f.2c.3e.4f.5b.6d, | 1f.2c.3e.4f.5b.6e, | 1f.2c.3e.4f.5b.6f, | 1f.2c.3e.4f.5c.6a, |
| 1f.2c.3e.4f.5c.6b, | 1f.2c.3e.4f.5c.6c, | 1f.2c.3e.4f.5c.6d, | 1f.2c.3e.4f.5c.6e, | 1f.2c.3e.4f.5c.6f, |
| 1f.2c.3e.4f.5d.6a, | 1f.2c.3e.4f.5d.6b, | 1f.2c.3e.4f.5d.6c, | 1f.2c.3e.4f.5d.6d, | 1f.2c.3e.4f.5d.6e, |
| 1f.2c.3e.4f.5d.6f, | 1f.2c.3e.4f.5e.6a, | 1f.2c.3e.4f.5e.6b, | 1f.2c.3e.4f.5e.6c, | 1f.2c.3e.4f.5e.6d, |
| 1f.2c.3e.4f.5e.6e, | 1f.2c.3e.4f.5e.6f, | 1f.2c.3e.4f.5f.6a, | 1f.2c.3e.4f.5f.6b, | 1f.2c.3e.4f.5f.6c, |
| 1f.2c.3e.4f.5f.6d, | 1f.2c.3e.4f.5f.6e, | 1f.2c.3e.4f.5f.6f, | 1f.2c.3f.4a.5a.6a, | 1f.2c.3f.4a.5a.6b, |
| 1f.2c.3f.4a.5a.6c, | 1f.2c.3f.4a.5a.6d, | 1f.2c.3f.4a.5a.6e, | 1f.2c.3f.4a.5a.6f, | 1f.2c.3f.4a.5b.6a, |
| 1f.2c.3f.4a.5b.6b, | 1f.2c.3f.4a.5b.6c, | 1f.2c.3f.4a.5b.6d, | 1f.2c.3f.4a.5b.6e, | 1f.2c.3f.4a.5b.6f, |
| 1f.2c.3f.4a.5c.6a, | 1f.2c.3f.4a.5c.6b, | 1f.2c.3f.4a.5c.6c, | 1f.2c.3f.4a.5c.6d, | 1f.2c.3f.4a.5c.6e, |
| 1f.2c.3f.4a.5c.6f, | 1f.2c.3f.4a.5d.6a, | 1f.2c.3f.4a.5d.6b, | 1f.2c.3f.4a.5d.6c, | 1f.2c.3f.4a.5d.6d, |
| 1f.2c.3f.4a.5d.6e, | 1f.2c.3f.4a.5d.6f, | 1f.2c.3f.4a.5e.6a, | 1f.2c.3f.4a.5e.6b, | 1f.2c.3f.4a.5e.6c, |
| 1f.2c.3f.4a.5e.6d, | 1f.2c.3f.4a.5e.6e, | 1f.2c.3f.4a.5e.6f, | 1f.2c.3f.4a.5f.6a, | 1f.2c.3f.4a.5f.6b, |
| 1f.2c.3f.4a.5f.6c, | 1f.2c.3f.4a.5f.6d, | 1f.2c.3f.4a.5f.6e, | 1f.2c.3f.4a.5f.6f, | 1f.2c.3f.4b.5a.6a, |
| 1f.2c.3f.4b.5a.6b, | 1f.2c.3f.4b.5a.6c, | 1f.2c.3f.4b.5a.6d, | 1f.2c.3f.4b.5a.6e, | 1f.2c.3f.4b.5a.6f, |
| 1f.2c.3f.4b.5b.6a, | 1f.2c.3f.4b.5b.6b, | 1f.2c.3f.4b.5b.6c, | 1f.2c.3f.4b.5b.6d, | 1f.2c.3f.4b.5b.6e, |
| 1f.2c.3f.4b.5b.6f, | 1f.2c.3f.4b.5c.6a, | 1f.2c.3f.4b.5c.6b, | 1f.2c.3f.4b.5c.6c, | 1f.2c.3f.4b.5c.6d, |
| 1f.2c.3f.4b.5c.6e, | 1f.2c.3f.4b.5c.6f, | 1f.2c.3f.4b.5d.6a, | 1f.2c.3f.4b.5d.6b, | 1f.2c.3f.4b.5d.6c, |
| 1f.2c.3f.4b.5d.6d, | 1f.2c.3f.4b.5d.6e, | 1f.2c.3f.4b.5d.6f, | 1f.2c.3f.4b.5e.6a, | 1f.2c.3f.4b.5e.6b, |
| 1f.2c.3f.4b.5e.6c, | 1f.2c.3f.4b.5e.6d, | 1f.2c.3f.4b.5e.6e, | 1f.2c.3f.4b.5e.6f, | 1f.2c.3f.4b.5f.6a, |
| 1f.2c.3f.4b.5f.6b, | 1f.2c.3f.4b.5f.6c, | 1f.2c.3f.4b.5f.6d, | 1f.2c.3f.4b.5f.6e, | 1f.2c.3f.4b.5f.6f, |
| 1f.2c.3f.4c.5a.6a, | 1f.2c.3f.4c.5a.6b, | 1f.2c.3f.4c.5a.6c, | 1f.2c.3f.4c.5a.6d, | 1f.2c.3f.4c.5a.6e, |
| 1f.2c.3f.4c.5a.6f, | 1f.2c.3f.4c.5b.6a, | 1f.2c.3f.4c.5b.6b, | 1f.2c.3f.4c.5b.6c, | 1f.2c.3f.4c.5b.6d, |
| 1f.2c.3f.4c.5b.6e, | 1f.2c.3f.4c.5b.6f, | 1f.2c.3f.4c.5c.6a, | 1f.2c.3f.4c.5c.6b, | 1f.2c.3f.4c.5c.6c, |
| 1f.2c.3f.4c.5c.6d, | 1f.2c.3f.4c.5c.6e, | 1f.2c.3f.4c.5c.6f, | 1f.2c.3f.4c.5d.6a, | 1f.2c.3f.4c.5d.6b, |
| 1f.2c.3f.4c.5d.6c, | 1f.2c.3f.4c.5d.6d, | 1f.2c.3f.4c.5d.6e, | 1f.2c.3f.4c.5d.6f, | 1f.2c.3f.4c.5e.6a, |
| 1f.2c.3f.4c.5e.6b, | 1f.2c.3f.4c.5e.6c, | 1f.2c.3f.4c.5e.6d, | 1f.2c.3f.4c.5e.6e, | 1f.2c.3f.4c.5e.6f, |

TABLE 7-continued

List of Compounds of Formula (II)

| | | | | |
|---|---|---|---|---|
| 1f.2c.3f.4c.5f.6a, | 1f.2c.3f.4c.5f.6b, | 1f.2c.3f.4c.5f.6c, | 1f.2c.3f.4c.5f.6d, | 1f.2c.3f.4c.5f.6e, |
| 1f.2c.3f.4c.5f.6f, | 1f.2c.3f.4d.5a.6a, | 1f.2c.3f.4d.5a.6b, | 1f.2c.3f.4d.5a.6c, | 1f.2c.3f.4d.5a.6d, |
| 1f.2c.3f.4d.5a.6e, | 1f.2c.3f.4d.5a.6f, | 1f.2c.3f.4d.5b.6a, | 1f.2c.3f.4d.5b.6b, | 1f.2c.3f.4d.5b.6c, |
| 1f.2c.3f.4d.5b.6d, | 1f.2c.3f.4d.5b.6e, | 1f.2c.3f.4d.5b.6f, | 1f.2c.3f.4d.5c.6a, | 1f.2c.3f.4d.5c.6b, |
| 1f.2c.3f.4d.5c.6c, | 1f.2c.3f.4d.5c.6d, | 1f.2c.3f.4d.5c.6e, | 1f.2c.3f.4d.5c.6f, | 1f.2c.3f.4d.5d.6a, |
| 1f.2c.3f.4d.5d.6b, | 1f.2c.3f.4d.5d.6c, | 1f.2c.3f.4d.5d.6d, | 1f.2c.3f.4d.5d.6e, | 1f.2c.3f.4d.5d.6f, |
| 1f.2c.3f.4d.5e.6a, | 1f.2c.3f.4d.5e.6b, | 1f.2c.3f.4d.5e.6c, | 1f.2c.3f.4d.5e.6d, | 1f.2c.3f.4d.5e.6e, |
| 1f.2c.3f.4d.5e.6f, | 1f.2c.3f.4d.5f.6a, | 1f.2c.3f.4d.5f.6b, | 1f.2c.3f.4d.5f.6c, | 1f.2c.3f.4d.5f.6d, |
| 1f.2c.3f.4d.5f.6e, | 1f.2c.3f.4d.5f.6f, | 1f.2c.3f.4e.5a.6a, | 1f.2c.3f.4e.5a.6b, | 1f.2c.3f.4e.5a.6c, |
| 1f.2c.3f.4e.5a.6d, | 1f.2c.3f.4e.5a.6e, | 1f.2c.3f.4e.5a.6f, | 1f.2c.3f.4e.5b.6a, | 1f.2c.3f.4e.5b.6b, |
| 1f.2c.3f.4e.5b.6c, | 1f.2c.3f.4e.5b.6d, | 1f.2c.3f.4e.5b.6e, | 1f.2c.3f.4e.5b.6f, | 1f.2c.3f.4e.5c.6a, |
| 1f.2c.3f.4e.5c.6b, | 1f.2c.3f.4e.5c.6c, | 1f.2c.3f.4e.5c.6d, | 1f.2c.3f.4e.5c.6e, | 1f.2c.3f.4e.5c.6f, |
| 1f.2c.3f.4e.5d.6a, | 1f.2c.3f.4e.5d.6b, | 1f.2c.3f.4e.5d.6c, | 1f.2c.3f.4e.5d.6d, | 1f.2c.3f.4e.5d.6e, |
| 1f.2c.3f.4e.5d.6f, | 1f.2c.3f.4e.5e.6a, | 1f.2c.3f.4e.5e.6b, | 1f.2c.3f.4e.5e.6c, | 1f.2c.3f.4e.5e.6d, |
| 1f.2c.3f.4e.5e.6e, | 1f.2c.3f.4e.5e.6f, | 1f.2c.3f.4e.5f.6a, | 1f.2c.3f.4e.5f.6b, | 1f.2c.3f.4e.5f.6c, |
| 1f.2c.3f.4e.5f.6d, | 1f.2c.3f.4e.5f.6e, | 1f.2c.3f.4e.5f.6f, | 1f.2c.3f.4f.5a.6a, | 1f.2c.3f.4f.5a.6b, |
| 1f.2c.3f.4f.5a.6c, | 1f.2c.3f.4f.5a.6d, | 1f.2c.3f.4f.5a.6e, | 1f.2c.3f.4f.5a.6f, | 1f.2c.3f.4f.5b.6a, |
| 1f.2c.3f.4f.5b.6b, | 1f.2c.3f.4f.5b.6c, | 1f.2c.3f.4f.5b.6d, | 1f.2c.3f.4f.5b.6e, | 1f.2c.3f.4f.5b.6f, |
| 1f.2c.3f.4f.5c.6a, | 1f.2c.3f.4f.5c.6b, | 1f.2c.3f.4f.5c.6c, | 1f.2c.3f.4f.5c.6d, | 1f.2c.3f.4f.5c.6e, |
| 1f.2c.3f.4f.5c.6f, | 1f.2c.3f.4f.5d.6a, | 1f.2c.3f.4f.5d.6b, | 1f.2c.3f.4f.5d.6c, | 1f.2c.3f.4f.5d.6d, |
| 1f.2c.3f.4f.5d.6e, | 1f.2c.3f.4f.5d.6f, | 1f.2c.3f.4f.5e.6a, | 1f.2c.3f.4f.5e.6b, | 1f.2c.3f.4f.5e.6c, |
| 1f.2c.3f.4f.5e.6d, | 1f.2c.3f.4f.5e.6e, | 1f.2c.3f.4f.5e.6f, | 1f.2c.3f.4f.5f.6a, | 1f.2c.3f.4f.5f.6b, |
| 1f.2c.3f.4f.5f.6c, | 1f.2c.3f.4f.5f.6d, | 1f.2c.3f.4f.5f.6e, | 1f.2c.3f.4f.5f.6f, | 1f.2d.3a.4a.5a.6a, |
| 1f.2d.3a.4a.5a.6b, | 1f.2d.3a.4a.5a.6c, | 1f.2d.3a.4a.5a.6d, | 1f.2d.3a.4a.5a.6e, | |
| 1f.2d.3a.4a.5a.6f, | 1f.2d.3a.4a.5b.6a, | 1f.2d.3a.4a.5b.6b, | 1f.2d.3a.4a.5b.6c, | |
| 1f.2d.3a.4a.5b.6d, | 1f.2d.3a.4a.5b.6e, | 1f.2d.3a.4a.5b.6f, | 1f.2d.3a.4a.5c.6a, | |
| 1f.2d.3a.4a.5c.6b, | 1f.2d.3a.4a.5c.6c, | 1f.2d.3a.4a.5c.6d, | 1f.2d.3a.4a.5c.6e, | 1f.2d.3a.4a.5c.6f, |
| 1f.2d.3a.4a.5d.6a, | 1f.2d.3a.4a.5d.6b, | 1f.2d.3a.4a.5d.6c, | 1f.2d.3a.4a.5d.6d, | |
| 1f.2d.3a.4a.5d.6e, | 1f.2d.3a.4a.5d.6f, | 1f.2d.3a.4a.5e.6a, | 1f.2d.3a.4a.5e.6b, | |
| 1f.2d.3a.4a.5e.6c, | 1f.2d.3a.4a.5e.6d, | 1f.2d.3a.4a.5e.6e, | 1f.2d.3a.4a.5e.6f, | 1f.2d.3a.4a.5f.6a, |
| 1f.2d.3a.4a.5f.6b, | 1f.2d.3a.4a.5f.6c, | 1f.2d.3a.4a.5f.6d, | 1f.2d.3a.4a.5f.6e, | 1f.2d.3a.4a.5f.6f, |
| 1f.2d.3a.4b.5a.6a, | 1f.2d.3a.4b.5a.6b, | 1f.2d.3a.4b.5a.6c, | 1f.2d.3a.4b.5a.6d, | |
| 1f.2d.3a.4b.5a.6e, | 1f.2d.3a.4b.5a.6f, | 1f.2d.3a.4b.5b.6a, | 1f.2d.3a.4b.5b.6b, | |
| 1f.2d.3a.4b.5b.6c, | 1f.2d.3a.4b.5b.6d, | 1f.2d.3a.4b.5b.6e, | 1f.2d.3a.4b.5b.6f, | |
| 1f.2d.3a.4b.5c.6a, | 1f.2d.3a.4b.5c.6b, | 1f.2d.3a.4b.5c.6c, | 1f.2d.3a.4b.5c.6d, | |
| 1f.2d.3a.4b.5c.6e, | 1f.2d.3a.4b.5c.6f, | 1f.2d.3a.4b.5d.6a, | 1f.2d.3a.4b.5d.6b, | |
| 1f.2d.3a.4b.5d.6c, | 1f.2d.3a.4b.5d.6d, | 1f.2d.3a.4b.5d.6e, | 1f.2d.3a.4b.5d.6f, | |
| 1f.2d.3a.4b.5e.6a, | 1f.2d.3a.4b.5e.6b, | 1f.2d.3a.4b.5e.6c, | 1f.2d.3a.4b.5e.6d, | |
| 1f.2d.3a.4b.5e.6e, | 1f.2d.3a.4b.5e.6f, | 1f.2d.3a.4b.5f.6a, | 1f.2d.3a.4b.5f.6b, | 1f.2d.3a.4b.5f.6c, |
| 1f.2d.3a.4b.5f.6d, | 1f.2d.3a.4b.5f.6e, | 1f.2d.3a.4b.5f.6f, | 1f.2d.3a.4c.5a.6a, | 1f.2d.3a.4c.5a.6b, |
| 1f.2d.3a.4c.5a.6c, | 1f.2d.3a.4c.5a.6d, | 1f.2d.3a.4c.5a.6e, | 1f.2d.3a.4c.5a.6f, | 1f.2d.3a.4c.5b.6a, |
| 1f.2d.3a.4c.5b.6b, | 1f.2d.3a.4c.5b.6c, | 1f.2d.3a.4c.5b.6d, | 1f.2d.3a.4c.5b.6e, | |
| 1f.2d.3a.4c.5b.6f, | 1f.2d.3a.4c.5c.6a, | 1f.2d.3a.4c.5c.6b, | 1f.2d.3a.4c.5c.6c, | 1f.2d.3a.4c.5c.6d, |
| 1f.2d.3a.4c.5c.6e, | 1f.2d.3a.4c.5c.6f, | 1f.2d.3a.4c.5d.6a, | 1f.2d.3a.4c.5d.6b, | |
| 1f.2d.3a.4c.5d.6c, | 1f.2d.3a.4c.5d.6d, | 1f.2d.3a.4c.5d.6e, | 1f.2d.3a.4c.5d.6f, | |
| 1f.2d.3a.4c.5e.6a, | 1f.2d.3a.4c.5e.6b, | 1f.2d.3a.4c.5e.6c, | 1f.2d.3a.4c.5e.6d, | |
| 1f.2d.3a.4c.5e.6e, | 1f.2d.3a.4c.5e.6f, | 1f.2d.3a.4c.5f.6a, | 1f.2d.3a.4c.5f.6b, | 1f.2d.3a.4c.5f.6c, |
| 1f.2d.3a.4c.5f.6d, | 1f.2d.3a.4c.5f.6e, | 1f.2d.3a.4c.5f.6f, | 1f.2d.3a.4d.5a.6a, | 1f.2d.3a.4d.5a.6b, |
| 1f.2d.3a.4d.5a.6c, | 1f.2d.3a.4d.5a.6d, | 1f.2d.3a.4d.5a.6e, | 1f.2d.3a.4d.5a.6f, | |
| 1f.2d.3a.4d.5b.6a, | 1f.2d.3a.4d.5b.6b, | 1f.2d.3a.4d.5b.6c, | 1f.2d.3a.4d.5b.6d, | |
| 1f.2d.3a.4d.5b.6e, | 1f.2d.3a.4d.5b.6f, | 1f.2d.3a.4d.5c.6a, | 1f.2d.3a.4d.5c.6b, | |
| 1f.2d.3a.4d.5c.6c, | 1f.2d.3a.4d.5c.6d, | 1f.2d.3a.4d.5c.6e, | 1f.2d.3a.4d.5c.6f, | |
| 1f.2d.3a.4d.5d.6a, | 1f.2d.3a.4d.5d.6b, | 1f.2d.3a.4d.5d.6c, | 1f.2d.3a.4d.5d.6d; | |
| 1f.2d.3a.4d.5d.6e, | 1f.2d.3a.4d.5d.6f, | 1f.2d.3a.4d.5e.6a, | 1f.2d.3a.4d.5e.6b, | |
| 1f.2d.3a.4d.5e.6c, | 1f.2d.3a.4d.5e.6d, | 1f.2d.3a.4d.5e.6e, | 1f.2d.3a.4d.5e.6f, | |
| 1f.2d.3a.4d.5f.6a, | 1f.2d.3a.4d.5f.6b, | 1f.2d.3a.4d.5f.6c, | 1f.2d.3a.4d.5f.6d, | |
| 1f.2d.3a.4d.5f.6e, | 1f.2d.3a.4d.5f.6f, | 1f.2d.3a.4e.5a.6a, | 1f.2d.3a.4e.5a.6b, | 1f.2d.3a.4e.5a.6c, |
| 1f.2d.3a.4e.5a.6d, | 1f.2d.3a.4e.5a.6e, | 1f.2d.3a.4e.5a.6f, | 1f.2d.3a.4e.5b.6a, | |
| 1f.2d.3a.4e.5b.6b, | 1f.2d.3a.4e.5b.6c, | 1f.2d.3a.4e.5b.6d, | 1f.2d.3a.4e.5b.6e, | |
| 1f.2d.3a.4e.5b.6f, | 1f.2d.3a.4e.5c.6a, | 1f.2d.3a.4e.5c.6b, | 1f.2d.3a.4e.5c.6c, | |
| 1f.2d.3a.4e.5c.6d, | 1f.2d.3a.4e.5c.6e, | 1f.2d.3a.4e.5c.6f, | 1f.2d.3a.4e.5d.6a, | |
| 1f.2d.3a.4e.5d.6b, | 1f.2d.3a.4e.5d.6c, | 1f.2d.3a.4e.5d.6d, | 1f.2d.3a.4e.5d.6e, | |
| 1f.2d.3a.4e.5d.6f, | 1f.2d.3a.4e.5e.6a, | 1f.2d.3a.4e.5e.6b, | 1f.2d.3a.4e.5e.6c, | |
| 1f.2d.3a.4e.5e.6d, | 1f.2d.3a.4e.5e.6e, | 1f.2d.3a.4e.5e.6f, | 1f.2d.3a.4e.5f.6a, | 1f.2d.3a.4e.5f.6b, |
| 1f.2d.3a.4e.5f.6c, | 1f.2d.3a.4e.5f.6d, | 1f.2d.3a.4e.5f.6e, | 1f.2d.3a.4e.5f.6f, | 1f.2d.3a.4f.5a.6a, |
| 1f.2d.3a.4f.5a.6b, | 1f.2d.3a.4f.5a.6c, | 1f.2d.3a.4f.5a.6d, | 1f.2d.3a.4f.5a.6e, | 1f.2d.3a.4f.5a.6f, |
| 1f.2d.3a.4f.5b.6a, | 1f.2d.3a.4f.5b.6b, | 1f.2d.3a.4f.5b.6c, | 1f.2d.3a.4f.5b.6d, | 1f.2d.3a.4f.5b.6e, |
| 1f.2d.3a.4f.5b.6f, | 1f.2d.3a.4f.5c.6a, | 1f.2d.3a.4f.5c.6b, | 1f.2d.3a.4f.5c.6c, | 1f.2d.3a.4f.5c.6d, |
| 1f.2d.3a.4f.5c.6e, | 1f.2d.3a.4f.5c.6f, | 1f.2d.3a.4f.5d.6a, | 1f.2d.3a.4f.5d.6b, | 1f.2d.3a.4f.5d.6c, |
| 1f.2d.3a.4f.5d.6d, | 1f.2d.3a.4f.5d.6e, | 1f.2d.3a.4f.5d.6f, | 1f.2d.3a.4f.5e.6a, | 1f.2d.3a.4f.5e.6b, |
| 1f.2d.3a.4f.5e.6c, | 1f.2d.3a.4f.5e.6d, | 1f.2d.3a.4f.5e.6e, | 1f.2d.3a.4f.5e.6f, | 1f.2d.3a.4f.5f.6a, |
| 1f.2d.3a.4f.5f.6b, | 1f.2d.3a.4f.5f.6c, | 1f.2d.3a.4f.5f.6d, | 1f.2d.3a.4f.5f.6e, | 1f.2d.3a.4f.5f.6f |
| 1f.2d.3b.4a.5a.6a, | 1f.2d.3b.4a.5a.6b, | 1f.2d.3b.4a.5a.6c, | 1f.2d.3b.4a.5a.6d, | |
| 1f.2d.3b.4a.5a.6e, | 1f.2d.3b.4a.5a.6f, | 1f.2d.3b.4a.5b.6a, | 1f.2d.3b.4a.5b.6b, | |
| 1f.2d.3b.4a.5b.6c, | 1f.2d.3b.4a.5b.6d, | 1f.2d.3b.4a.5b.6e, | 1f.2d.3b.4a.5b.6f, | |
| 1f.2d.3b.4a.5c.6a, | 1f.2d.3b.4a.5c.6b, | 1f.2d.3b.4a.5c.6c, | 1f.2d.3b.4a.5c.6d, | |
| 1f.2d.3b.4a.5c.6e, | 1f.2d.3b.4a.5c.6f, | 1f.2d.3b.4a.5d.6a, | 1f.2d.3b.4a.5d.6b, | |
| 1f.2d.3b.4a.5d.6c, | 1f.2d.3b.4a.5d.6d, | 1f.2d.3b.4a.5d.6e, | 1f.2d.3b.4a.5d.6f, | |

TABLE 7-continued

List of Compounds of Formula (II)

| | | | | |
|---|---|---|---|---|
| 1f.2d.3b.4a.5e.6a, | 1f.2d.3b.4a.5e.6b, | 1f.2d.3b.4a.5e.6c, | 1f.2d.3b.4a.5e.6d, | |
| 1f.2d.3b.4a.5e.6e, | 1f.2d.3b.4a.5e.6f, | 1f.2d.3b.4a.5f.6a, | 1f.2d.3b.4a.5f.6b, | 1f.2d.3b.4a.5f.6c, |
| 1f.2d.3b.4a.5f.6d, | 1f.2d.3b.4a.5f.6e, | 1f.2d.3b.4a.5f.6f, | 1f.2d.3b.4b.5a.6a, | |
| 1f.2d.3b.4b.5a.6b, | 1f.2d.3b.4b.5a.6c, | 1f.2d.3b.4b.5a.6d, | 1f.2d.3b.4b.5a.6e, | |
| 1f.2d.3b.4b.5a.6f, | 1f.2d.3b.4b.5b.6a, | 1f.2d.3b.4b.5b.6b, | 1f.2d.3b.4b.5b.6c, | |
| 1f.2d.3b.4b.5b.6d, | 1f.2d.3b.4b.5b.6e, | 1f.2d.3b.4b.5b.6f, | 1f.2d.3b.4b.5c.6a, | |
| 1f.2d.3b.4b.5c.6b, | 1f.2d.3b.4b.5c.6c, | 1f.2d.3b.4b.5c.6d, | 1f.2d.3b.4b.5c.6e, | |
| 1f.2d.3b.4b.5c.6f, | 1f.2d.3b.4b.5d.6a, | 1f.2d.3b.4b.5d.6b, | 1f.2d.3b.4b.5d.6c, | |
| 1f.2d.3b.4b.5d.6d, | 1f.2d.3b.4b.5d.6e, | 1f.2d.3b.4b.5d.6f, | 1f.2d.3b.4b.5e.6a, | |
| 1f.2d.3b.4b.5e.6b, | 1f.2d.3b.4b.5e.6c, | 1f.2d.3b.4b.5e.6d, | 1f.2d.3b.4b.5e.6e, | |
| 1f.2d.3b.4b.5e.6f, | 1f.2d.3b.4b.5f.6a, | 1f.2d.3b.4b.5f.6b, | 1f.2d.3b.4b.5f.6c, | |
| 1f.2d.3b.4b.5f.6d, | 1f.2d.3b.4b.5f.6e, | 1f.2d.3b.4b.5f.6f, | 1f.2d.3b.4c.5a.6a, | |
| 1f.2d.3b.4c.5a.6b, | 1f.2d.3b.4c.5a.6c, | 1f.2d.3b.4c.5a.6d, | 1f.2d.3b.4c.5a.6e, | |
| 1f.2d.3b.4c.5a.6f, | 1f.2d.3b.4c.5b.6a, | 1f.2d.3b.4c.5b.6b, | 1f.2d.3b.4c.5b.6c, | |
| 1f.2d.3b.4c.5b.6d, | 1f.2d.3b.4c.5b.6e, | 1f.2d.3b.4c.5b.6f, | 1f.2d.3b.4c.5c.6a, | |
| 1f.2d.3b.4c.5c.6b, | 1f.2d.3b.4c.5c.6c, | 1f.2d.3b.4c.5c.6d, | 1f.2d.3b.4c.5c.6e, | 1f.2d.3b.4c.5c.6f, |
| 1f.2d.3b.4c.5d.6a, | 1f.2d.3b.4c.5d.6b, | 1f.2d.3b.4c.5d.6c, | 1f.2d.3b.4c.5d.6d, | |
| 1f.2d.3b.4c.5d.6e, | 1f.2d.3b.4c.5d.6f, | 1f.2d.3b.4c.5e.6a, | 1f.2d.3b.4c.5e.6b, | |
| 1f.2d.3b.4c.5e.6c, | 1f.2d.3b.4c.5e.6d, | 1f.2d.3b.4c.5e.6e, | 1f.2d.3b.4c.5e.6f, | 1f.2d.3b.4c.5f.6a, |
| 1f.2d.3b.4c.5f.6b, | 1f.2d.3b.4c.5f.6c, | 1f.2d.3b.4c.5f.6d, | 1f.2d.3b.4c.5f.6e, | 1f.2d.3b.4c.5f.6f, |
| 1f.2d.3b.4d.5a.6a, | 1f.2d.3b.4d.5a.6b, | 1f.2d.3b.4d.5a.6c, | 1f.2d.3b.4d.5a.6d, | |
| 1f.2d.3b.4d.5a.6e, | 1f.2d.3b.4d.5a.6f, | 1f.2d.3b.4d.5b.6a, | 1f.2d.3b.4d.5b.6b, | |
| 1f.2d.3b.4d.5b.6c, | 1f.2d.3b.4d.5b.6d, | 1f.2d.3b.4d.5b.6e, | 1f.2d.3b.4d.5b.6f, | |
| 1f.2d.3b.4d.5c.6a, | 1f.2d.3b.4d.5c.6b, | 1f.2d.3b.4d.5c.6c, | 1f.2d.3b.4d.5c.6d, | |
| 1f.2d.3b.4d.5c.6e, | 1f.2d.3b.4d.5c.6f, | 1f.2d.3b.4d.5d.6a, | 1f.2d.3b.4d.5d.6b, | |
| 1f.2d.3b.4d.5d.6c, | 1f.2d.3b.4d.5d.6d, | 1f.2d.3b.4d.5d.6e, | 1f.2d.3b.4d.5d.6f, | |
| 1f.2d.3b.4d.5e.6a, | 1f.2d.3b.4d.5e.6b, | 1f.2d.3b.4d.5e.6c, | 1f.2d.3b.4d.5e.6d, | |
| 1f.2d.3b.4d.5e.6e, | 1f.2d.3b.4d.5e.6f, | 1f.2d.3b.4d.5f.6a, | 1f.2d.3b.4d.5f.6b, | |
| 1f.2d.3b.4d.5f.6c, | 1f.2d.3b.4d.5f.6d, | 1f.2d.3b.4d.5f.6e, | 1f.2d.3b.4d.5f.6f, | |
| 1f.2d.3b.4e.5a.6a, | 1f.2d.3b.4e.5a.6b, | 1f.2d.3b.4e.5a.6c, | 1f.2d.3b.4e.5a.6d, | |
| 1f.2d.3b.4e.5a.6e, | 1f.2d.3b.4e.5a.6f, | 1f.2d.3b.4e.5b.6a, | 1f.2d.3b.4e.5b.6b, | |
| 1f.2d.3b.4e.5b.6c, | 1f.2d.3b.4e.5b.6d, | 1f.2d.3b.4e.5b.6e, | 1f.2d.3b.4e.5b.6f, | |
| 1f.2d.3b.4e.5c.6a, | 1f.2d.3b.4e.5c.6b, | 1f.2d.3b.4e.5c.6c, | 1f.2d.3b.4e.5c.6d, | |
| 1f.2d.3b.4e.5c.6e, | 1f.2d.3b.4e.5c.6f, | 1f.2d.3b.4e.5d.6a, | 1f.2d.3b.4e.5d.6b, | |
| 1f.2d.3b.4e.5d.6c, | 1f.2d.3b.4e.5d.6d, | 1f.2d.3b.4e.5d.6e, | 1f.2d.3b.4e.5d.6f, | |
| 1f.2d.3b.4e.5e.6a, | 1f.2d.3b.4e.5e.6b, | 1f.2d.3b.4e.5e.6c, | 1f.2d.3b.4e.5e.6d, | |
| 1f.2d.3b.4e.5e.6e, | 1f.2d.3b.4e.5e.6f, | 1f.2d.3b.4e.5f.6a, | 1f.2d.3b.4e.5f.6b, | 1f.2d.3b.4e.5f.6c, |
| 1f.2d.3b.4e.5f.6d, | 1f.2d.3b.4e.5f.6e, | 1f.2d.3b.4e.5f.6f, | 1f.2d.3b.4f.5a.6a, | 1f.2d.3b.4f.5a.6b, |
| 1f.2d.3b.4f.5a.6c, | 1f.2d.3b.4f.5a.6d, | 1f.2d.3b.4f.5a.6e, | 1f.2d.3b.4f.5a.6f, | 1f.2d.3b.4f.5b.6a, |
| 1f.2d.3b.4f.5b.6b, | 1f.2d.3b.4f.5b.6c, | 1f.2d.3b.4f.5b.6d, | 1f.2d.3b.4f.5b.6e, | 1f.2d.3b.4f.5b.6f, |
| 1f.2d.3b.4f.5c.6a, | 1f.2d.3b.4f.5c.6b, | 1f.2d.3b.4f.5c.6c, | 1f.2d.3b.4f.5c.6d, | 1f.2d.3b.4f.5c.6e, |
| 1f.2d.3b.4f.5c.6f, | 1f.2d.3b.4f.5d.6a, | 1f.2d.3b.4f.5d.6b, | 1f.2d.3b.4f.5d.6c, | |
| 1f.2d.3b.4f.5d.6d, | 1f.2d.3b.4f.5d.6e, | 1f.2d.3b.4f.5d.6f, | 1f.2d.3b.4f.5e.6a, | |
| 1f.2d.3b.4f.5e.6b, | 1f.2d.3b.4f.5e.6c, | 1f.2d.3b.4f.5e.6d, | 1f.2d.3b.4f.5e.6e, | 1f.2d.3b.4f.5e.6f, |
| 1f.2d.3b.4f.5f.6a, | 1f.2d.3b.4f.5f.6b, | 1f.2d.3b.4f.5f.6c, | 1f.2d.3b.4f.5f.6d, | 1f.2d.3b.4f.5f.6e, |
| 1f.2d.3b.4f.5f.6f, | 1f.2d.3c.4a.5a.6a, | 1f.2d.3c.4a.5a.6b, | 1f.2d.3c.4a.5a.6c, | 1f.2d.3c.4a.5a.6d, |
| 1f.2d.3c.4a.5a.6e, | 1f.2d.3c.4a.5a.6f, | 1f.2d.3c.4a.5b.6a, | 1f.2d.3c.4a.5b.6b, | |
| 1f.2d.3c.4a.5b.6c, | 1f.2d.3c.4a.5b.6d, | 1f.2d.3c.4a.5b.6e, | 1f.2d.3c.4a.5b.6f, | |
| 1f.2d.3c.4a.5c.6a, | 1f.2d.3c.4a.5c.6b, | 1f.2d.3c.4a.5c.6c, | 1f.2d.3c.4a.5c.6d, | 1f.2d.3c.4a.5c.6e, |
| 1f.2d.3c.4a.5c.6f, | 1f.2d.3c.4a.5d.6a, | 1f.2d.3c.4a.5d.6b, | 1f.2d.3c.4a.5d.6c, | |
| 1f.2d.3c.4a.5d.6d, | 1f.2d.3c.4a.5d.6e, | 1f.2d.3c.4a.5d.6f, | 1f.2d.3c.4a.5e.6a, | |
| 1f.2d.3c.4a.5e.6b, | 1f.2d.3c.4a.5e.6c, | 1f.2d.3c.4a.5e.6d, | 1f.2d.3c.4a.5e.6e, | 1f.2d.3c.4a.5e.6f, |
| 1f.2d.3c.4a.5f.6a, | 1f.2d.3c.4a.5f.6b, | 1f.2d.3c.4a.5f.6c, | 1f.2d.3c.4a.5f.6d, | 1f.2d.3c.4a.5f.6e, |
| 1f.2d.3c.4a.5f.6f, | 1f.2d.3c.4b.5a.6a, | 1f.2d.3c.4b.5a.6b, | 1f.2d.3c.4b.5a.6c, | |
| 1f.2d.3c.4b.5a.6d, | 1f.2d.3c.4b.5a.6e, | 1f.2d.3c.4b.5a.6f, | 1f.2d.3c.4b.5b.6a, | |
| 1f.2d.3c.4b.5b.6b, | 1f.2d.3c.4b.5b.6c, | 1f.2d.3c.4b.5b.6d, | 1f.2d.3c.4b.5b.6e, | |
| 1f.2d.3c.4b.5b.6f, | 1f.2d.3c.4b.5c.6a, | 1f.2d.3c.4b.5c.6b, | 1f.2d.3c.4b.5c.6c, | |
| 1f.2d.3c.4b.5c.6d, | 1f.2d.3c.4b.5c.6e, | 1f.2d.3c.4b.5c.6f, | 1f.2d.3c.4b.5d.6a, | |
| 1f.2d.3c.4b.5d.6b, | 1f.2d.3c.4b.5d.6c, | 1f.2d.3c.4b.5d.6d, | 1f.2d.3c.4b.5d.6e, | |
| 1f.2d.3c.4b.5d.6f, | 1f.2d.3c.4b.5e.6a, | 1f.2d.3c.4b.5e.6b, | 1f.2d.3c.4b.5e.6c, | |
| 1f.2d.3c.4b.5e.6d, | 1f.2d.3c.4b.5e.6e, | 1f.2d.3c.4b.5e.6f, | 1f.2d.3c.4b.5f.6a, | 1f.2d.3c.4b.5f.6b, |
| 1f.2d.3c.4b.5f.6c, | 1f.2d.3c.4b.5f.6d, | 1f.2d.3c.4b.5f.6e, | 1f.2d.3c.4b.5f.6f, | 1f.2d.3c.4c.5a.6a, |
| 1f.2d.3c.4c.5a.6b, | 1f.2d.3c.4c.5a.6c, | 1f.2d.3c.4c.5a.6d, | 1f.2d.3c.4c.5a.6e, | 1f.2d.3c.4c.5a.6f, |
| 1f.2d.3c.4c.5b.6a, | 1f.2d.3c.4c.5b.6b, | 1f.2d.3c.4c.5b.6c, | 1f.2d.3c.4c.5b.6d, | |
| 1f.2d.3c.4c.5b.6e, | 1f.2d.3c.4c.5b.6f, | 1f.2d.3c.4c.5c.6a, | 1f.2d.3c.4c.5c.6b, | 1f.2d.3c.4c.5c.6c, |
| 1f.2d.3c.4c.5c.6d, | 1f.2d.3c.4c.5c.6e, | 1f.2d.3c.4c.5c.6f, | 1f.2d.3c.4c.5d.6a, | 1f.2d.3c.4c.5d.6b, |
| 1f.2d.3c.4c.5d.6c, | 1f.2d.3c.4c.5d.6d, | 1f.2d.3c.4c.5d.6e, | 1f.2d.3c.4c.5d.6f, | |
| 1f.2d.3c.4c.5e.6a, | 1f.2d.3c.4c.5e.6b, | 1f.2d.3c.4c.5e.6c, | 1f.2d.3c.4c.5e.6d, | 1f.2d.3c.4c.5e.6e, |
| 1f.2d.3c.4c.5e.6f, | 1f.2d.3c.4c.5f.6a, | 1f.2d.3c.4c.5f.6b, | 1f.2d.3c.4c.5f.6c, | 1f.2d.3c.4c.5f.6d, |
| 1f.2d.3c.4c.5f.6e, | 1f.2d.3c.4c.5f.6f, | 1f.2d.3c.4d.5a.6a, | 1f.2d.3c.4d.5a.6b, | 1f.2d.3c.4d.5a.6c, |
| 1f.2d.3c.4d.5a.6d, | 1f.2d.3c.4d.5a.6e, | 1f.2d.3c.4d.5a.6f, | 1f.2d.3c.4d.5b.6a, | |
| 1f.2d.3c.4d.5b.6b, | 1f.2d.3c.4d.5b.6c, | 1f.2d.3c.4d.5b.6d, | 1f.2d.3c.4d.5b.6e, | |
| 1f.2d.3c.4d.5b.6f, | 1f.2d.3c.4d.5c.6a, | 1f.2d.3c.4d.5c.6b, | 1f.2d.3c.4d.5c.6c, | |
| 1f.2d.3c.4d.5c.6d, | 1f.2d.3c.4d.5c.6e, | 1f.2d.3c.4d.5c.6f, | 1f.2d.3c.4d.5d.6a, | |
| 1f.2d.3c.4d.5d.6b, | 1f.2d.3c.4d.5d.6c, | 1f.2d.3c.4d.5d.6d, | 1f.2d.3c.4d.5d.6e, | |
| 1f.2d.3c.4d.5d.6f, | 1f.2d.3c.4d.5e.6a, | 1f.2d.3c.4d.5e.6b, | 1f.2d.3c.4d.5e.6c, | |
| 1f.2d.3c.4d.5e.6d, | 1f.2d.3c.4d.5e.6e, | 1f.2d.3c.4d.5e.6f, | 1f.2d.3c.4d.5f.6a, | |
| 1f.2d.3c.4d.5f.6b, | 1f.2d.3c.4d.5f.6c, | 1f.2d.3c.4d.5f.6d, | 1f.2d.3c.4d.5f.6e, | 1f.2d.3c.4d.5f.6f, |

TABLE 7-continued

List of Compounds of Formula (II)

| | | | | |
|---|---|---|---|---|
| 1f.2d.3c.4e.5a.6a, | 1f.2d.3c.4e.5a.6b, | 1f.2d.3c.4e.5a.6c, | 1f.2d.3c.4e.5a.6d, | |
| 1f.2d.3c.4e.5a.6e, | 1f.2d.3c.4e.5a.6f, | 1f.2d.3c.4e.5b.6a, | 1f.2d.3c.4e.5b.6b, | 1f.2d.3c.4e.5b.6c, |
| 1f.2d.3c.4e.5b.6d, | 1f.2d.3c.4e.5b.6e, | 1f.2d.3c.4e.5b.6f, | 1f.2d.3c.4e.5c.6a, | 1f.2d.3c.4e.5c.6b, |
| 1f.2d.3c.4e.5c.6c, | 1f.2d.3c.4e.5c.6d, | 1f.2d.3c.4e.5c.6e, | 1f.2d.3c.4e.5c.6f, | 1f.2d.3c.4e.5d.6a, |
| 1f.2d.3c.4e.5d.6b, | 1f.2d.3c.4e.5d.6c, | 1f.2d.3c.4e.5d.6d, | 1f.2d.3c.4e.5d.6e, | |
| 1f.2d.3c.4e.5d.6f, | 1f.2d.3c.4e.5e.6a, | 1f.2d.3c.4e.5e.6b, | 1f.2d.3c.4e.5e.6c, | 1f.2d.3c.4e.5e.6d, |
| 1f.2d.3c.4e.5e.6e, | 1f.2d.3c.4e.5e.6f, | 1f.2d.3c.4e.5f.6a, | 1f.2d.3c.4e.5f.6b, | 1f.2d.3c.4e.5f.6c, |
| 1f.2d.3c.4e.5f.6d, | 1f.2d.3c.4e.5f.6e, | 1f.2d.3c.4e.5f.6f, | 1f.2d.3c.4f.5a.6a, | 1f.2d.3c.4f.5a.6b, |
| 1f.2d.3c.4f.5a.6c, | 1f.2d.3c.4f.5a.6d, | 1f.2d.3c.4f.5a.6e, | 1f.2d.3c.4f.5a.6f, | 1f.2d.3c.4f.5b.6a, |
| 1f.2d.3c.4f.5b.6b, | 1f.2d.3c.4f.5b.6c, | 1f.2d.3c.4f.5b.6d, | 1f.2d.3c.4f.5b.6e, | 1f.2d.3c.4f.5b.6f, |
| 1f.2d.3c.4f.5c.6a, | 1f.2d.3c.4f.5c.6b, | 1f.2d.3c.4f.5c.6c, | 1f.2d.3c.4f.5c.6d, | 1f.2d.3c.4f.5c.6e, |
| 1f.2d.3c.4f.5c.6f, | 1f.2d.3c.4f.5d.6a, | 1f.2d.3c.4f.5d.6b, | 1f.2d.3c.4f.5d.6c, | 1f.2d.3c.4f.5d.6d, |
| 1f.2d.3c.4f.5d.6e, | 1f.2d.3c.4f.5d.6f, | 1f.2d.3c.4f.5e.6a, | 1f.2d.3c.4f.5e.6b, | 1f.2d.3c.4f.5e.6c, |
| 1f.2d.3c.4f.5e.6d, | 1f.2d.3c.4f.5e.6e, | 1f.2d.3c.4f.5e.6f, | 1f.2d.3c.4f.5f.6a, | 1f.2d.3c.4f.5f.6b, |
| 1f.2d.3c.4f.5f.6c, | 1f.2d.3c.4f.5f.6d, | 1f.2d.3c.4f.5f.6e, | 1f.2d.3c.4f.5f.6f, | 1f.2d.3d.4a.5a.6a, |
| 1f.2d.3d.4a.5a.6b, | 1f.2d.3d.4a.5a.6c, | 1f.2d.3d.4a.5a.6d, | 1f.2d.3d.4a.5a.6e, | |
| 1f.2d.3d.4a.5a.6f, | 1f.2d.3d.4a.5b.6a, | 1f.2d.3d.4a.5b.6b, | 1f.2d.3d.4a.5b.6c, | |
| 1f.2d.3d.4a.5b.6d, | 1f.2d.3d.4a.5b.6e, | 1f.2d.3d.4a.5b.6f, | 1f.2d.3d.4a.5c.6a, | |
| 1f.2d.3d.4a.5c.6b, | 1f.2d.3d.4a.5c.6c, | 1f.2d.3d.4a.5c.6d, | 1f.2d.3d.4a.5c.6e, | |
| 1f.2d.3d.4a.5c.6f, | 1f.2d.3d.4a.5d.6a, | 1f.2d.3d.4a.5d.6b, | 1f.2d.3d.4a.5d.6c, | |
| 1f.2d.3d.4a.5d.6d, | 1f.2d.3d.4a.5d.6e, | 1f.2d.3d.4a.5d.6f, | 1f.2d.3d.4a.5e.6a, | |
| 1f.2d.3d.4a.5e.6b, | 1f.2d.3d.4a.5e.6c, | 1f.2d.3d.4a.5e.6d, | 1f.2d.3d.4a.5e.6e, | |
| 1f.2d.3d.4a.5e.6f, | 1f.2d.3d.4a.5f.6a, | 1f.2d.3d.4a.5f.6b, | 1f.2d.3d.4a.5f.6c, | |
| 1f.2d.3d.4a.5f.6d, | 1f.2d.3d.4a.5f.6e, | 1f.2d.3d.4a.5f.6f, | 1f.2d.3d.4b.5a.6a, | |
| 1f.2d.3d.4b.5a.6b, | 1f.2d.3d.4b.5a.6c, | 1f.2d.3d.4b.5a.6d, | 1f.2d.3d.4b.5a.6e, | |
| 1f.2d.3d.4b.5a.6f, | 1f.2d.3d.4b.5b.6a, | 1f.2d.3d.4b.5b.6b, | 1f.2d.3d.4b.5b.6c, | |
| 1f.2d.3d.4b.5b.6d, | 1f.2d.3d.4b.5b.6e, | 1f.2d.3d.4b.5b.6f, | 1f.2d.3d.4b.5c.6a, | |
| 1f.2d.3d.4b.5c.6b, | 1f.2d.3d.4b.5c.6c, | 1f.2d.3d.4b.5c.6d, | 1f.2d.3d.4b.5c.6e, | |
| 1f.2d.3d.4b.5c.6f, | 1f.2d.3d.4b.5d.6a, | 1f.2d.3d.4b.5d.6b, | 1f.2d.3d.4b.5d.6c, | |
| 1f.2d.3d.4b.5d.6d, | 1f.2d.3d.4b.5d.6e, | 1f.2d.3d.4b.5d.6f, | 1f.2d.3d.4b.5e.6a, | |
| 1f.2d.3d.4b.5e.6b, | 1f.2d.3d.4b.5e.6c, | 1f.2d.3d.4b.5e.6d, | 1f.2d.3d.4b.5e.6e, | |
| 1f.2d.3d.4b.5e.6f, | 1f.2d.3d.4b.5f.6a, | 1f.2d.3d.4b.5f.6b, | 1f.2d.3d.4b.5f.6c, | |
| 1f.2d.3d.4b.5f.6d, | 1f.2d.3d.4b.5f.6e, | 1f.2d.3d.4b.5f.6f, | 1f.2d.3d.4c.5a.6a, | |
| 1f.2d.3d.4c.5a.6b, | 1f.2d.3d.4c.5a.6c, | 1f.2d.3d.4c.5a.6d, | 1f.2d.3d.4c.5a.6e, | |
| 1f.2d.3d.4c.5a.6f, | 1f.2d.3d.4c.5b.6a, | 1f.2d.3d.4c.5b.6b, | 1f.2d.3d.4c.5b.6c, | |
| 1f.2d.3d.4c.5b.6d, | 1f.2d.3d.4c.5b.6e, | 1f.2d.3d.4c.5b.6f, | 1f.2d.3d.4c.5c.6a, | |
| 1f.2d.3d.4c.5c.6b, | 1f.2d.3d.4c.5c.6c, | 1f.2d.3d.4c.5c.6d, | 1f.2d.3d.4c.5c.6e, | |
| 1f.2d.3d.4c.5c.6f, | 1f.2d.3d.4c.5d.6a, | 1f.2d.3d.4c.5d.6b, | 1f.2d.3d.4c.5d.6c, | |
| 1f.2d.3d.4c.5d.6d, | 1f.2d.3d.4c.5d.6e, | 1f.2d.3d.4c.5d.6f, | 1f.2d.3d.4c.5e.6a, | |
| 1f.2d.3d.4c.5e.6b, | 1f.2d.3d.4c.5e.6c, | 1f.2d.3d.4c.5e.6d, | 1f.2d.3d.4c.5e.6e, | |
| 1f.2d.3d.4c.5e.6f, | 1f.2d.3d.4c.5f.6a, | 1f.2d.3d.4c.5f.6b, | 1f.2d.3d.4c.5f.6c, | 1f.2d.3d.4c.5f.6d, |
| 1f.2d.3d.4c.5f.6e, | 1f.2d.3d.4c.5f.6f, | 1f.2d.3d.4d.5a.6a, | 1f.2d.3d.4d.5a.6b, | |
| 1f.2d.3d.4d.5a.6c, | 1f.2d.3d.4d.5a.6d, | 1f.2d.3d.4d.5a.6e, | 1f.2d.3d.4d.5a.6f, | |
| 1f.2d.3d.4d.5b.6a, | 1f.2d.3d.4d.5b.6b, | 1f.2d.3d.4d.5b.6c, | 1f.2d.3d.4d.5b.6d, | |
| 1f.2d.3d.4d.5b.6e, | 1f.2d.3d.4d.5b.6f, | 1f.2d.3d.4d.5c.6a, | 1f.2d.3d.4d.5c.6b, | |
| 1f.2d.3d.4d.5c.6c, | 1f.2d.3d.4d.5c.6d, | 1f.2d.3d.4d.5c.6e, | 1f.2d.3d.4d.5c.6f, | |
| 1f.2d.3d.4d.5d.6a, | 1f.2d.3d.4d.5d.6b, | 1f.2d.3d.4d.5d.6c, | 1f.2d.3d.4d.5d.6d, | |
| 1f.2d.3d.4d.5d.6e, | 1f.2d.3d.4d.5d.6f, | 1f.2d.3d.4d.5e.6a, | 1f.2d.3d.4d.5e.6b, | |
| 1f.2d.3d.4d.5e.6c, | 1f.2d.3d.4d.5e.6d, | 1f.2d.3d.4d.5e.6e, | 1f.2d.3d.4d.5e.6f, | |
| 1f.2d.3d.4d.5f.6a, | 1f.2d.3d.4d.5f.6b, | 1f.2d.3d.4d.5f.6c, | 1f.2d.3d.4d.5f.6d, | |
| 1f.2d.3d.4d.5f.6e, | 1f.2d.3d.4d.5f.6f, | 1f.2d.3d.4e.5a.6a, | 1f.2d.3d.4e.5a.6b, | |
| 1f.2d.3d.4e.5a.6c, | 1f.2d.3d.4e.5a.6d, | 1f.2d.3d.4e.5a.6e, | 1f.2d.3d.4e.5a.6f, | |
| 1f.2d.3d.4e.5b.6a, | 1f.2d.3d.4e.5b.6b, | 1f.2d.3d.4e.5b.6c, | 1f.2d.3d.4e.5b.6d, | |
| 1f.2d.3d.4e.5b.6e, | 1f.2d.3d.4e.5b.6f, | 1f.2d.3d.4e.5c.6a, | 1f.2d.3d.4e.5c.6b, | |
| 1f.2d.3d.4e.5c.6c, | 1f.2d.3d.4e.5c.6d, | 1f.2d.3d.4e.5c.6e, | 1f.2d.3d.4e.5c.6f, | |
| 1f.2d.3d.4e.5d.6a, | 1f.2d.3d.4e.5d.6b, | 1f.2d.3d.4e.5d.6c, | 1f.2d.3d.4e.5d.6d, | |
| 1f.2d.3d.4e.5d.6e, | 1f.2d.3d.4e.5d.6f, | 1f.2d.3d.4e.5e.6a, | 1f.2d.3d.4e.5e.6b, | |
| 1f.2d.3d.4e.5e.6c, | 1f.2d.3d.4e.5e.6d, | 1f.2d.3d.4e.5e.6e, | 1f.2d.3d.4e.5e.6f, | |
| 1f.2d.3d.4e.5f.6a, | 1f.2d.3d.4e.5f.6b, | 1f.2d.3d.4e.5f.6c, | 1f.2d.3d.4e.5f.6d, | |
| 1f.2d.3d.4e.5f.6e, | 1f.2d.3d.4e.5f.6f, | 1f.2d.3d.4f.5a.6a, | 1f.2d.3d.4f.5a.6b, | 1f.2d.3d.4f.5a.6c, |
| 1f.2d.3d.4f.5a.6d, | 1f.2d.3d.4f.5a.6e, | 1f.2d.3d.4f.5a.6f, | 1f.2d.3d.4f.5b.6a, | |
| 1f.2d.3d.4f.5b.6b, | 1f.2d.3d.4f.5b.6c, | 1f.2d.3d.4f.5b.6d, | 1f.2d.3d.4f.5b.6e, | |
| 1f.2d.3d.4f.5b.6f, | 1f.2d.3d.4f.5c.6a, | 1f.2d.3d.4f.5c.6b, | 1f.2d.3d.4f.5c.6c, | 1f.2d.3d.4f.5c.6d, |
| 1f.2d.3d.4f.5c.6e, | 1f.2d.3d.4f.5c.6f, | 1f.2d.3d.4f.5d.6a, | 1f.2d.3d.4f.5d.6b, | |
| 1f.2d.3d.4f.5d.6c, | 1f.2d.3d.4f.5d.6d, | 1f.2d.3d.4f.5d.6e, | 1f.2d.3d.4f.5d.6f, | |
| 1f.2d.3d.4f.5e.6a, | 1f.2d.3d.4f.5e.6b, | 1f.2d.3d.4f.5e.6c, | 1f.2d.3d.4f.5e.6d, | |
| 1f.2d.3d.4f.5e.6e, | 1f.2d.3d.4f.5e.6f, | 1f.2d.3d.4f.5f.6a, | 1f.2d.3d.4f.5f.6b, | 1f.2d.3d.4f.5f.6c, |
| 1f.2d.3d.4f.5f.6d, | 1f.2d.3d.4f.5f.6e, | 1f.2d.3d.4f.5f.6f, | 1f.2d.3e.4a.5a.6a, | 1f.2d.3e.4a.5a.6b, |
| 1f.2d.3e.4a.5a.6c, | 1f.2d.3e.4a.5a.6d, | 1f.2d.3e.4a.5a.6e, | 1f.2d.3e.4a.5a.6f, | |
| 1f.2d.3e.4a.5b.6a, | 1f.2d.3e.4a.5b.6b, | 1f.2d.3e.4a.5b.6c, | 1f.2d.3e.4a.5b.6d, | |
| 1f.2d.3e.4a.5b.6e, | 1f.2d.3e.4a.5b.6f, | 1f.2d.3e.4a.5c.6a, | 1f.2d.3e.4a.5c.6b, | 1f.2d.3e.4a.5c.6c, |
| 1f.2d.3e.4a.5c.6d, | 1f.2d.3e.4a.5c.6e, | 1f.2d.3e.4a.5c.6f, | 1f.2d.3e.4a.5d.6a, | |
| 1f.2d.3e.4a.5d.6b, | 1f.2d.3e.4a.5d.6c, | 1f.2d.3e.4a.5d.6d, | 1f.2d.3e.4a.5d.6e, | |
| 1f.2d.3e.4a.5d.6f, | 1f.2d.3e.4a.5e.6a, | 1f.2d.3e.4a.5e.6b, | 1f.2d.3e.4a.5e.6c, | |
| 1f.2d.3e.4a.5e.6d, | 1f.2d.3e.4a.5e.6e, | 1f.2d.3e.4a.5e.6f, | 1f.2d.3e.4a.5f.6a, | 1f.2d.3e.4a.5f.6b, |
| 1f.2d.3e.4a.5f.6c, | 1f.2d.3e.4a.5f.6d, | 1f.2d.3e.4a.5f.6e, | 1f.2d.3e.4a.5f.6f, | 1f.2d.3e.4b.5a.6a, |
| 1f.2d.3e.4b.5a.6b, | 1f.2d.3e.4b.5a.6c, | 1f.2d.3e.4b.5a.6d, | 1f.2d.3e.4b.5a.6e, | |
| 1f.2d.3e.4b.5a.6f, | 1f.2d.3e.4b.5b.6a, | 1f.2d.3e.4b.5b.6b, | 1f.2d.3e.4b.5b.6c, | |

TABLE 7-continued

List of Compounds of Formula (II)

| | | | | |
|---|---|---|---|---|
| 1f.2d.3e.4b.5b.6d, | 1f.2d.3e.4b.5b.6e, | 1f.2d.3e.4b.5b.6f, | 1f.2d.3e.4b.5c.6a, | |
| 1f.2d.3e.4b.5c.6b, | 1f.2d.3e.4b.5c.6c, | 1f.2d.3e.4b.5c.6d, | 1f.2d.3e.4b.5c.6e, | |
| 1f.2d.3e.4b.5c.6f, | 1f.2d.3e.4b.5d.6a, | 1f.2d.3e.4b.5d.6b, | 1f.2d.3e.4b.5d.6c, | |
| 1f.2d.3e.4b.5d.6d, | 1f.2d.3e.4b.5d.6e, | 1f.2d.3e.4b.5d.6f, | 1f.2d.3e.4b.5e.6a, | |
| 1f.2d.3e.4b.5e.6b, | 1f.2d.3e.4b.5e.6c, | 1f.2d.3e.4b.5e.6d, | 1f.2d.3e.4b.5e.6e, | |
| 1f.2d.3e.4b.5e.6f, | 1f.2d.3e.4b.5f.6a, | 1f.2d.3e.4b.5f.6b, | 1f.2d.3e.4b.5f.6c, | 1f.2d.3e.4b.5f.6d, |
| 1f.2d.3e.4b.5f.6e, | 1f.2d.3e.4b.5f.6f, | 1f.2d.3e.4c.5a.6a, | 1f.2d.3e.4c.5a.6b, | 1f.2d.3e.4c.5a.6c, |
| 1f.2d.3e.4c.5a.6d, | 1f.2d.3e.4c.5a.6e, | 1f.2d.3e.4c.5a.6f, | 1f.2d.3e.4c.5b.6a, | |
| 1f.2d.3e.4c.5b.6b, | 1f.2d.3e.4c.5b.6c, | 1f.2d.3e.4c.5b.6d, | 1f.2d.3e.4c.5b.6e, | |
| 1f.2d.3e.4c.5b.6f, | 1f.2d.3e.4c.5c.6a, | 1f.2d.3e.4c.5c.6b, | 1f.2d.3e.4c.5c.6c, | 1f.2d.3e.4c.5c.6d, |
| 1f.2d.3e.4c.5c.6e, | 1f.2d.3e.4c.5c.6f, | 1f.2d.3e.4c.5d.6a, | 1f.2d.3e.4c.5d.6b, | 1f.2d.3e.4c.5d.6c, |
| 1f.2d.3e.4c.5d.6d, | 1f.2d.3e.4c.5d.6e, | 1f.2d.3e.4c.5d.6f, | 1f.2d.3e.4c.5e.6a, | |
| 1f.2d.3e.4c.5e.6b, | 1f.2d.3e.4c.5e.6c, | 1f.2d.3e.4c.5e.6d, | 1f.2d.3e.4c.5e.6e, | 1f.2d.3e.4c.5e.6f, |
| 1f.2d.3e.4c.5f.6a, | 1f.2d.3e.4c.5f.6b, | 1f.2d.3e.4c.5f.6c, | 1f.2d.3e.4c.5f.6d, | 1f.2d.3e.4c.5f.6e, |
| 1f.2d.3e.4c.5f.6f, | 1f.2d.3e.4d.5a.6a, | 1f.2d.3e.4d.5a.6b, | 1f.2d.3e.4d.5a.6c, | |
| 1f.2d.3e.4d.5a.6d, | 1f.2d.3e.4d.5a.6e, | 1f.2d.3e.4d.5a.6f, | 1f.2d.3e.4d.5b.6a, | |
| 1f.2d.3e.4d.5b.6b, | 1f.2d.3e.4d.5b.6c, | 1f.2d.3e.4d.5b.6d, | 1f.2d.3e.4d.5b.6e, | |
| 1f.2d.3e.4d.5b.6f, | 1f.2d.3e.4d.5c.6a, | 1f.2d.3e.4d.5c.6b, | 1f.2d.3e.4d.5c.6c, | |
| 1f.2d.3e.4d.5c.6d, | 1f.2d.3e.4d.5c.6e, | 1f.2d.3e.4d.5c.6f, | 1f.2d.3e.4d.5d.6a, | |
| 1f.2d.3e.4d.5d.6b, | 1f.2d.3e.4d.5d.6c, | 1f.2d.3e.4d.5d.6d, | 1f.2d.3e.4d.5d.6e, | |
| 1f.2d.3e.4d.5d.6f, | 1f.2d.3e.4d.5e.6a, | 1f.2d.3e.4d.5e.6b, | 1f.2d.3e.4d.5e.6c, | |
| 1f.2d.3e.4d.5e.6d, | 1f.2d.3e.4d.5e.6e, | 1f.2d.3e.4d.5e.6f, | 1f.2d.3e.4d.5f.6a, | |
| 1f.2d.3e.4d.5f.6b, | 1f.2d.3e.4d.5f.6c, | 1f.2d.3e.4d.5f.6d, | 1f.2d.3e.4d.5f.6e, | 1f.2d.3e.4d.5f.6f, |
| 1f.2d.3e.4e.5a.6a, | 1f.2d.3e.4e.5a.6b, | 1f.2d.3e.4e.5a.6c, | 1f.2d.3e.4e.5a.6d, | |
| 1f.2d.3e.4e.5a.6e, | 1f.2d.3e.4e.5a.6f, | 1f.2d.3e.4e.5b.6a, | 1f.2d.3e.4e.5b.6b, | |
| 1f.2d.3e.4e.5b.6c, | 1f.2d.3e.4e.5b.6d, | 1f.2d.3e.4e.5b.6e, | 1f.2d.3e.4e.5b.6f, | |
| 1f.2d.3e.4e.5c.6a, | 1f.2d.3e.4e.5c.6b, | 1f.2d.3e.4e.5c.6c, | 1f.2d.3e.4e.5c.6d, | 1f.2d.3e.4e.5c.6e, |
| 1f.2d.3e.4e.5c.6f, | 1f.2d.3e.4e.5d.6a, | 1f.2d.3e.4e.5d.6b, | 1f.2d.3e.4e.5d.6c, | |
| 1f.2d.3e.4e.5d.6d, | 1f.2d.3e.4e.5d.6e, | 1f.2d.3e.4e.5d.6f, | 1f.2d.3e.4e.5e.6a, | |
| 1f.2d.3e.4e.5e.6b, | 1f.2d.3e.4e.5e.6c, | 1f.2d.3e.4e.5e.6d, | 1f.2d.3e.4e.5e.6e, | 1f.2d.3e.4e.5e.6f, |
| 1f.2d.3e.4e.5f.6a, | 1f.2d.3e.4e.5f.6b, | 1f.2d.3e.4e.5f.6c, | 1f.2d.3e.4e.5f.6d, | 1f.2d.3e.4e.5f.6e, |
| 1f.2d.3e.4e.5f.6f, | 1f.2d.3e.4f.5a.6a, | 1f.2d.3e.4f.5a.6b, | 1f.2d.3e.4f.5a.6c, | 1f.2d.3e.4f.5a.6d, |
| 1f.2d.3e.4f.5a.6e, | 1f.2d.3e.4f.5a.6f, | 1f.2d.3e.4f.5b.6a, | 1f.2d.3e.4f.5b.6b, | 1f.2d.3e.4f.5b.6c, |
| 1f.2d.3e.4f.5b.6d, | 1f.2d.3e.4f.5b.6e, | 1f.2d.3e.4f.5b.6f, | 1f.2d.3e.4f.5c.6a, | 1f.2d.3e.4f.5c.6b, |
| 1f.2d.3e.4f.5c.6c, | 1f.2d.3e.4f.5c.6d, | 1f.2d.3e.4f.5c.6e, | 1f.2d.3e.4f.5c.6f, | 1f.2d.3e.4f.5d.6a, |
| 1f.2d.3e.4f.5d.6b, | 1f.2d.3e.4f.5d.6c, | 1f.2d.3e.4f.5d.6d, | 1f.2d.3e.4f.5d.6e, | 1f.2d.3e.4f.5d.6f, |
| 1f.2d.3e.4f.5e.6a, | 1f.2d.3e.4f.5e.6b, | 1f.2d.3e.4f.5e.6c, | 1f.2d.3e.4f.5e.6d, | 1f.2d.3e.4f.5e.6e, |
| 1f.2d.3e.4f.5e.6f, | 1f.2d.3e.4f.5f.6a, | 1f.2d.3e.4f.5f.6b, | 1f.2d.3e.4f.5f.6c, | 1f.2d.3e.4f.5f.6d, |
| 1f.2d.3e.4f.5f.6e, | 1f.2d.3e.4f.5f.6f, | 1f.2d.3f.4a.5a.6a, | 1f.2d.3f.4a.5a.6b, | 1f.2d.3f.4a.5a.6c, |
| 1f.2d.3f.4a.5a.6d, | 1f.2d.3f.4a.5a.6e, | 1f.2d.3f.4a.5a.6f, | 1f.2d.3f.4a.5b.6a, | 1f.2d.3f.4a.5b.6b, |
| 1f.2d.3f.4a.5b.6c, | 1f.2d.3f.4a.5b.6d, | 1f.2d.3f.4a.5b.6e, | 1f.2d.3f.4a.5b.6f, | 1f.2d.3f.4a.5c.6a, |
| 1f.2d.3f.4a.5c.6b, | 1f.2d.3f.4a.5c.6c, | 1f.2d.3f.4a.5c.6d, | 1f.2d.3f.4a.5c.6e, | 1f.2d.3f.4a.5c.6f, |
| 1f.2d.3f.4a.5d.6a, | 1f.2d.3f.4a.5d.6b, | 1f.2d.3f.4a.5d.6c, | 1f.2d.3f.4a.5d.6d, | |
| 1f.2d.3f.4a.5d.6e, | 1f.2d.3f.4a.5d.6f, | 1f.2d.3f.4a.5e.6a, | 1f.2d.3f.4a.5e.6b, | 1f.2d.3f.4a.5e.6c, |
| 1f.2d.3f.4a.5e.6d, | 1f.2d.3f.4a.5e.6e, | 1f.2d.3f.4a.5e.6f, | 1f.2d.3f.4a.5f.6a, | 1f.2d.3f.4a.5f.6b, |
| 1f.2d.3f.4a.516c, | 1f.2d.3f.4a.5f.6d, | 1f.2d.3f.4a.5f.6e, | 1f.2d.3f.4a.5f.6f, | 1f.2d.3f.4b.5a.6a, |
| 1f.2d.3f.4b.5a.6b, | 1f.2d.3f.4b.5a.6c, | 1f.2d.3f.4b.5a.6d, | 1f.2d.3f.4b.5a.6e, | 1f.2d.3f.4b.5a.6f, |
| 1f.2d.3f.4b.5b.6a, | 1f.2d.3f.4b.5b.6b, | 1f.2d.3f.4b.5b.6c, | 1f.2d.3f.4b.5b.6d, | |
| 1f.2d.3f.4b.5b.6e, | 1f.2d.3f.4b.5b.6f, | 1f.2d.3f.4b.5c.6a, | 1f.2d.3f.4b.5c.6b, | 1f.2d.3f.4b.5c.6c, |
| 1f.2d.3f.4b.5c.6d, | 1f.2d.3f.4b.5c.6e, | 1f.2d.3f.4b.5c.6f, | 1f.2d.3f.4b.5d.6a, | 1f.2d.3f.4b.5d.6b, |
| 1f.2d.3f.4b.5d.6c, | 1f.2d.3f.4b.5d.6d, | 1f.2d.3f.4b.5d.6e, | 1f.2d.3f.4b.5d.6f, | |
| 1f.2d.3f.4b.5e.6a, | 1f.2d.3f.4b.5e.6b, | 1f.2d.3f.4b.5e.6c, | 1f.2d.3f.4b.5e.6d, | 1f.2d.3f.4b.5e.6e, |
| 1f.2d.3f.4b.5e.6f, | 1f.2d.3f.4b.5f.6a, | 1f.2d.3f.4b.5f.6b, | 1f.2d.3f.4b.5f.6c, | 1f.2d.3f.4b.5f.6d, |
| 1f.2d.3f.4b.5f.6e, | 1f.2d.3f.4b.5f.6f, | 1f.2d.3f.4c.5a.6a, | 1f.2d.3f.4c.5a.6b, | 1f.2d.3f.4c.5a.6c, |
| 1f.2d.3f.4c.5a.6d, | 1f.2d.3f.4c.5a.6e, | 1f.2d.3f.4c.5a.6f, | 1f.2d.3f.4c.5b.6a, | 1f.2d.3f.4c.5b.6b, |
| 1f.2d.3f.4c.5b.6c, | 1f.2d.3f.4c.5b.6d, | 1f.2d.3f.4c.5b.6e, | 1f.2d.3f.4c.5b.6f, | 1f.2d.3f.4c.5c.6a, |
| 1f.2d.3f.4c.5c.6b, | 1f.2d.3f.4c.5c.6c, | 1f.2d.3f.4c.5c.6d, | 1f.2d.3f.4c.5c.6e, | 1f.2d.3f.4c.5c.6f, |
| 1f.2d.3f.4c.5d.6a, | 1f.2d.3f.4c.5d.6b, | 1f.2d.3f.4c.5d.6c, | 1f.2d.3f.4c.5d.6d, | 1f.2d.3f.4c.5d.6e, |
| 1f.2d.3f.4c.5d.6f, | 1f.2d.3f.4c.5e.6a, | 1f.2d.3f.4c.5e.6b, | 1f.2d.3f.4c.5e.6c, | 1f.2d.3f.4c.5e.6d, |
| 1f.2d.3f.4c.5e.6e, | 1f.2d.3f.4c.5e.6f, | 1f.2d.3f.4c.5f.6a, | 1f.2d.3f.4c.5f.6b, | 1f.2d.3f.4c.5f.6c, |
| 1f.2d.3f.4c.5f.6d, | 1f.2d.3f.4c.5f.6e, | 1f.2d.3f.4c.5f.6f, | 1f.2d.3f.4d.5a.6a, | 1f.2d.3f.4d.5a.6b, |
| 1f.2d.3f.4d.5a.6c, | 1f.2d.3f.4d.5a.6d, | 1f.2d.3f.4d.5a.6e, | 1f.2d.3f.4d.5a.6f, | 1f.2d.3f.4d.5b.6a, |
| 1f.2d.3f.4d.5b.6b, | 1f.2d.3f.4d.5b.6c, | 1f.2d.3f.4d.5b.6d, | 1f.2d.3f.4d.5b.6e, | |
| 1f.2d.3f.4d.5b.6f, | 1f.2d.3f.4d.5c.6a, | 1f.2d.3f.4d.5c.6b, | 1f.2d.3f.4d.5c.6c, | 1f.2d.3f.4d.5c.6d, |
| 1f.2d.3f.4d.5c.6e, | 1f.2d.3f.4d.5c.6f, | 1f.2d.3f.4d.5d.6a, | 1f.2d.3f.4d.5d.6b, | |
| 1f.2d.3f.4d.5d.6c, | 1f.2d.3f.4d.5d.6d, | 1f.2d.3f.4d.5d.6e, | 1f.2d.3f.4d.5d.6f, | |
| 1f.2d.3f.4d.5e.6a, | 1f.2d.3f.4d.5e.6b, | 1f.2d.3f.4d.5e.6c, | 1f.2d.3f.4d.5e.6d, | |
| 1f.2d.3f.4d.5e.6e, | 1f.2d.3f.4d.5e.6f, | 1f.2d.3f.4d.5f.6a, | 1f.2d.3f.4d.5f.6b, | 1f.2d.3f.4d.5f.6c, |
| 1f.2d.3f.4d.5f.6d, | 1f.2d.3f.4d.5f.6e, | 1f.2d.3f.4d.5f.6f, | 1f.2d.3f.4e.5a.6a, | 1f.2d.3f.4e.5a.6b, |
| 1f.2d.3f.4e.5a.6c, | 1f.2d.3f.4e.5a.6d, | 1f.2d.3f.4e.5a.6e, | 1f.2d.3f.4e.5a.6f, | 1f.2d.3f.4e.5b.6a, |
| 1f.2d.3f.4e.5b.6b, | 1f.2d.3f.4e.5b.6c, | 1f.2d.3f.4e.5b.6d, | 1f.2d.3f.4e.5b.6e, | 1f.2d.3f.4e.5b.6f, |
| 1f.2d.3f.4e.5c.6a, | 1f.2d.3f.4e.5c.6b, | 1f.2d.3f.4e.5c.6c, | 1f.2d.3f.4e.5c.6d, | 1f.2d.3f.4e.5c.6e, |
| 1f.2d.3f.4e.5c.6f, | 1f.2d.3f.4e.5d.6a, | 1f.2d.3f.4e.5d.6b, | 1f.2d.3f.4e.5d.6c, | 1f.2d.3f.4e.5d.6d, |
| 1f.2d.3f.4e.5d.6e, | 1f.2d.3f.4e.5d.6f, | 1f.2d.3f.4e.5e.6a, | 1f.2d.3f.4e.5e.6b, | 1f.2d.3f.4e.5e.6c, |
| 1f.2d.3f.4e.5e.6d, | 1f.2d.3f.4e.5e.6e, | 1f.2d.3f.4e.5e.6f, | 1f.2d.3f.4e.5f.6a, | 1f.2d.3f.4e.5f.6b, |
| 1f.2d.3f.4e.5f.6c, | 1f.2d.3f.4e.5f.6d, | 1f.2d.3f.4e.5f.6e, | 1f.2d.3f.4e.5f.6f, | 1f.2d.3f.4f.5a.6a, |
| 1f.2d.3f.4f.5a.6b, | 1f.2d.3f.4f.5a.6c, | 1f.2d.3f.4f.5a.6d, | 1f.2d.3f.4f.5a.6e, | 1f.2d.3f.4f.5a.6f, |
| 1f.2d.3f.4f.5b.6a, | 1f.2d.3f.4f.5b.6b, | 1f.2d.3f.4f.5b.6c, | 1f.2d.3f.4f.5b.6d, | 1f.2d.3f.4f.5b.6e, |

TABLE 7-continued

List of Compounds of Formula (II)

| | | | | |
|---|---|---|---|---|
| 1f.2d.3f.4f.5b.6f, | 1f.2d.3f.4f.5c.6a, | 1f.2d.3f.4f.5c.6b, | 1f.2d.3f.4f.5c.6c, | 1f.2d.3f.4f.5c.6d, |
| 1f.2d.3f.4f.5c.6e, | 1f.2d.3f.4f.5c.6f, | 1f.2d.3f.4f.5d.6a, | 1f.2d.3f.4f.5d.6b, | 1f.2d.3f.4f.5d.6c, |
| 1f.2d.3f.4f.5d.6d, | 1f.2d.3f.4f.5d.6e, | 1f.2d.3f.4f.5d.6f, | 1f.2d.3f.4f.5e.6a, | 1f.2d.3f.4f.5e.6b, |
| 1f.2d.3f.4f.5e.6c, | 1f.2d.3f.4f.5e.6d, | 1f.2d.3f.4f.5e.6e, | 1f.2d.3f.4f.5e.6f, | 1f.2d.3f.4f.5f.6a, |
| 1f.2d.3f.4f.5f.6b, | 1f.2d.3f.4f.5f.6c, | 1f.2d.3f.4f.5f.6d, | 1f.2d.3f.4f.5f.6e, | 1f.2d.3f.4f.5f.6f, |
| 1f.2e.3a.4a.5a.6a, | 1f.2e.3a.4a.5a.6b, | 1f.2e.3a.4a.5a.6c, | 1f.2e.3a.4a.5a.6d, | 1f.2e.3a.4a.5a.6e, |
| 1f.2e.3a.4a.5a.6f, | 1f.2e.3a.4a.5b.6a, | 1f.2e.3a.4a.5b.6b, | 1f.2e.3a.4a.5b.6c, | 1f.2e.3a.4a.5b.6d, |
| 1f.2e.3a.4a.5b.6e, | 1f.2e.3a.4a.5b.6f, | 1f.2e.3a.4a.5c.6a, | 1f.2e.3a.4a.5c.6b, | 1f.2e.3a.4a.5c.6c, |
| 1f.2e.3a.4a.5c.6d, | 1f.2e.3a.4a.5c.6e, | 1f.2e.3a.4a.5c.6f, | 1f.2e.3a.4a.5d.6a, | 1f.2e.3a.4a.5d.6b, |
| 1f.2e.3a.4a.5d.6c, | 1f.2e.3a.4a.5d.6d, | 1f.2e.3a.4a.5d.6e, | 1f.2e.3a.4a.5d.6f, | 1f.2e.3a.4a.5e.6a, |
| 1f.2e.3a.4a.5e.6b, | 1f.2e.3a.4a.5e.6c, | 1f.2e.3a.4a.5e.6d, | 1f.2e.3a.4a.5e.6e, | 1f.2e.3a.4a.5e.6f, |
| 1f.2e.3a.4a.5f.6a, | 1f.2e.3a.4a.5f.6b, | 1f.2e.3a.4a.5f.6c, | 1f.2e.3a.4a.5f.6d, | 1f.2e.3a.4a.5f.6e, |
| 1f.2e.3a.4a.5f.6f, | 1f.2e.3a.4b.5a.6a, | 1f.2e.3a.4b.5a.6b, | 1f.2e.3a.4b.5a.6c, | 1f.2e.3a.4b.5a.6d, |
| 1f.2e.3a.4b.5a.6e, | 1f.2e.3a.4b.5a.6f, | 1f.2e.3a.4b.5b.6a, | 1f.2e.3a.4b.5b.6b, | 1f.2e.3a.4b.5b.6c, |
| 1f.2e.3a.4b.5b.6d, | 1f.2e.3a.4b.5b.6e, | 1f.2e.3a.4b.5b.6f, | 1f.2e.3a.4b.5c.6a, | 1f.2e.3a.4b.5c.6b, |
| 1f.2e.3a.4b.5c.6c, | 1f.2e.3a.4b.5c.6d, | 1f.2e.3a.4b.5c.6e, | 1f.2e.3a.4b.5c.6f, | 1f.2e.3a.4b.5d.6a, |
| 1f.2e.3a.4b.5d.6b, | 1f.2e.3a.4b.5d.6c, | 1f.2e.3a.4b.5d.6d, | 1f.2e.3a.4b.5d.6e, | |
| 1f.2e.3a.4b.5d.6f, | 1f.2e.3a.4b.5e.6a, | 1f.2e.3a.4b.5e.6b, | 1f.2e.3a.4b.5e.6c, | 1f.2e.3a.4b.5e.6d, |
| 1f.2e.3a.4b.5e.6e, | 1f.2e.3a.4b.5e.6f, | 1f.2e.3a.4b.5f.6a, | 1f.2e.3a.4b.5f.6b, | 1f.2e.3a.4b.5f.6c, |
| 1f.2e.3a.4b.5f.6d, | 1f.2e.3a.4b.5f.6e, | 1f.2e.3a.4b.5f.6f, | 1f.2e.3a.4c.5a.6a, | 1f.2e.3a.4c.5a.6b, |
| 1f.2e.3a.4c.5a.6c, | 1f.2e.3a.4c.5a.6d, | 1f.2e.3a.4c.5a.6e, | 1f.2e.3a.4c.5a.6f, | 1f.2e.3a.4c.5b.6a, |
| 1f.2e.3a.4c.5b.6b, | 1f.2e.3a.4c.5b.6c, | 1f.2e.3a.4c.5b.6d, | 1f.2e.3a.4c.5b.6e, | 1f.2e.3a.4c.5b.6f, |
| 1f.2e.3a.4c.5c.6a, | 1f.2e.3a.4c.5c.6b, | 1f.2e.3a.4c.5c.6c, | 1f.2e.3a.4c.5c.6d, | 1f.2e.3a.4c.5c.6e, |
| 1f.2e.3a.4c.5c.6f, | 1f.2e.3a.4c.5d.6a, | 1f.2e.3a.4c.5d.6b, | 1f.2e.3a.4c.5d.6c, | 1f.2e.3a.4c.5d.6d, |
| 1f.2e.3a.4c.5d.6e, | 1f.2e.3a.4c.5d.6f, | 1f.2e.3a.4c.5e.6a, | 1f.2e.3a.4c.5e.6b, | 1f.2e.3a.4c.5e.6c, |
| 1f.2e.3a.4c.5e.6d, | 1f.2e.3a.4c.5e.6e, | 1f.2e.3a.4c.5e.6f, | 1f.2e.3a.4c.5f.6a, | 1f.2e.3a.4c.5f.6b, |
| 1f.2e.3a.4c.5f.6c, | 1f.2e.3a.4c.5f.6d, | 1f.2e.3a.4c.5f.6e, | 1f.2e.3a.4c.5f.6f, | 1f.2e.3a.4d.5a.6a, |
| 1f.2e.3a.4d.5a.6b, | 1f.2e.3a.4d.5a.6c, | 1f.2e.3a.4d.5a.6d, | 1f.2e.3a.4d.5a.6e, | |
| 1f.2e.3a.4d.5a.6f, | 1f.2e.3a.4d.5b.6a, | 1f.2e.3a.4d.5b.6b, | 1f.2e.3a.4d.5b.6c, | |
| 1f.2e.3a.4d.5b.6d, | 1f.2e.3a.4d.5b.6e, | 1f.2e.3a.4d.5b.6f, | 1f.2e.3a.4d.5c.6a, | |
| 1f.2e.3a.4d.5c.6b, | 1f.2e.3a.4d.5c.6c, | 1f.2e.3a.4d.5c.6d, | 1f.2e.3a.4d.5c.6e, | 1f.2e.3a.4d.5c.6f, |
| 1f.2e.3a.4d.5d.6a, | 1f.2e.3a.4d.5d.6b, | 1f.2e.3a.4d.5d.6c, | 1f.2e.3a.4d.5d.6d, | |
| 1f.2e.3a.4d.5d.6e, | 1f.2e.3a.4d.5d.6f, | 1f.2e.3a.4d.5e.6a, | 1f.2e.3a.4d.5e.6b, | |
| 1f.2e.3a.4d.5e.6c, | 1f.2e.3a.4d.5e.6d, | 1f.2e.3a.4d.5e.6e, | 1f.2e.3a.4d.5e.6f, | 1f.2e.3a.4d.5f.6a, |
| 1f.2e.3a.4d.5f.6b, | 1f.2e.3a.4d.5f.6c, | 1f.2e.3a.4d.5f.6d, | 1f.2e.3a.4d.5f.6e, | 1f.2e.3a.4d.5f.6f, |
| 1f.2e.3a.4e.5a.6a, | 1f.2e.3a.4e.5a.6b, | 1f.2e.3a.4e.5a.6c, | 1f.2e.3a.4e.5a.6d, | 1f.2e.3a.4e.5a.6e, |
| 1f.2e.3a.4e.5a.6f, | 1f.2e.3a.4e.5b.6a, | 1f.2e.3a.4e.5b.6b, | 1f.2e.3a.4e.5b.6c, | 1f.2e.3a.4e.5b.6d, |
| 1f.2e.3a.4e.5b.6e, | 1f.2e.3a.4e.5b.6f, | 1f.2e.3a.4e.5c.6a, | 1f.2e.3a.4e.5c.6b, | 1f.2e.3a.4e.5c.6c, |
| 1f.2e.3a.4e.5c.6d, | 1f.2e.3a.4e.5c.6e, | 1f.2e.3a.4e.5c.6f, | 1f.2e.3a.4e.5d.6a, | 1f.2e.3a.4e.5d.6b, |
| 1f.2e.3a.4e.5d.6c, | 1f.2e.3a.4e.5d.6d, | 1f.2e.3a.4e.5d.6e, | 1f.2e.3a.4e.5d.6f, | 1f.2e.3a.4e.5e.6a, |
| 1f.2e.3a.4e.5e.6b, | 1f.2e.3a.4e.5e.6c, | 1f.2e.3a.4e.5e.6d, | 1f.2e.3a.4e.5e.6e, | 1f.2e.3a.4e.5e.6f, |
| 1f.2e.3a.4e.5f.6a, | 1f.2e.3a.4e.5f.6b, | 1f.2e.3a.4e.5f.6c, | 1f.2e.3a.4e.5f.6d, | 1f.2e.3a.4e.5f.6e, |
| 1f.2e.3a.4e.5f.6f, | 1f.2e.3a.4f.5a.6a, | 1f.2e.3a.4f.5a.6b, | 1f.2e.3a.4f.5a.6c, | 1f.2e.3a.4f.5a.6d, |
| 1f.2e.3a.4f.5a.6e, | 1f.2e.3a.4f.5a.6f, | 1f.2e.3a.4f.5b.6a, | 1f.2e.3a.4f.5b.6b, | 1f.2e.3a.4f.5b.6c, |
| 1f.2e.3a.4f.5b.6d, | 1f.2e.3a.4f.5b.6e, | 1f.2e.3a.4f.5b.6f, | 1f.2e.3a.4f.5c.6a, | 1f.2e.3a.4f.5c.6b, |
| 1f.2e.3a.4f.5c.6c, | 1f.2e.3a.4f.5c.6d, | 1f.2e.3a.4f.5c.6e, | 1f.2e.3a.4f.5c.6f, | 1f.2e.3a.4f.5d.6a, |
| 1f.2e.3a.4f.5d.6b, | 1f.2e.3a.4f.5d.6c, | 1f.2e.3a.4f.5d.6d, | 1f.2e.3a.4f.5d.6e, | 1f.2e.3a.4f.5d.6f, |
| 1f.2e.3a.4f.5e.6a, | 1f.2e.3a.4f.5e.6b, | 1f.2e.3a.4f.5e.6c, | 1f.2e.3a.4f.5e.6d, | 1f.2e.3a.4f.5e.6e, |
| 1f.2e.3a.4f.5e.6f, | 1f.2e.3a.4f.5f.6a, | 1f.2e.3a.4f.5f.6b, | 1f.2e.3a.4f.5f.6c, | 1f.2e.3a.4f.5f.6d, |
| 1f.2e.3a.4f.5f.6e, | 1f.2e.3a.4f.5f.6f, | 1f.2e.3b.4a.5a.6a, | 1f.2e.3b.4a.5a.6b, | 1f.2e.3b.4a.5a.6c, |
| 1f.2e.3b.4a.5a.6d, | 1f.2e.3b.4a.5a.6e, | 1f.2e.3b.4a.5a.6f, | 1f.2e.3b.4a.5b.6a, | |
| 1f.2e.3b.4a.5b.6b, | 1f.2e.3b.4a.5b.6c, | 1f.2e.3b.4a.5b.6d, | 1f.2e.3b.4a.5b.6e, | |
| 1f.2e.3b.4a.5b.6f, | 1f.2e.3b.4a.5c.6a, | 1f.2e.3b.4a.5c.6b, | 1f.2e.3b.4a.5c.6c, | 1f.2e.3b.4a.5c.6d, |
| 1f.2e.3b.4a.5c.6e, | 1f.2e.3b.4a.5c.6f, | 1f.2e.3b.4a.5d.6a, | 1f.2e.3b.4a.5d.6b, | 1f.2e.3b.4a.5d.6c, |
| 1f.2e.3b.4a.5d.6d, | 1f.2e.3b.4a.5d.6e, | 1f.2e.3b.4a.5d.6f, | 1f.2e.3b.4a.5e.6a, | |
| 1f.2e.3b.4a.5e.6b, | 1f.2e.3b.4a.5e.6c, | 1f.2e.3b.4a.5e.6d, | 1f.2e.3b.4a.5e.6e, | 1f.2e.3b.4a.5e.6f, |
| 1f.2e.3b.4a.5f.6a, | 1f.2e.3b.4a.5f.6b, | 1f.2e.3b.4a.5f.6c, | 1f.2e.3b.4a.5f.6d, | 1f.2e.3b.4a.5f.6e, |
| 1f.2e.3b.4a.5f.6f, | 1f.2e.3b.4b.5a.6a, | 1f.2e.3b.4b.5a.6b, | 1f.2e.3b.4b.5a.6c, | 1f.2e.3b.4b.5a.6d, |
| 1f.2e.3b.4b.5a.6e, | 1f.2e.3b.4b.5a.6f, | 1f.2e.3b.4b.5b.6a, | 1f.2e.3b.4b.5b.6b, | |
| 1f.2e.3b.4b.5b.6c, | 1f.2e.3b.4b.5b.6d, | 1f.2e.3b.4b.5b.6e, | 1f.2e.3b.4b.5b.6f, | |
| 1f.2e.3b.4b.5c.6a, | 1f.2e.3b.4b.5c.6b, | 1f.2e.3b.4b.5c.6c, | 1f.2e.3b.4b.5c.6d, | |
| 1f.2e.3b.4b.5c.6e, | 1f.2e.3b.4b.5c.6f, | 1f.2e.3b.4b.5d.6a, | 1f.2e.3b.4b.5d.6b, | |
| 1f.2e.3b.4b.5d.6c, | 1f.2e.3b.4b.5d.6d, | 1f.2e.3b.4b.5d.6e, | 1f.2e.3b.4b.5d.6f, | |
| 1f.2e.3b.4b.5e.6a, | 1f.2e.3b.4b.5e.6b, | 1f.2e.3b.4b.5e.6c, | 1f.2e.3b.4b.5e.6d, | |
| 1f.2e.3b.4b.5e.6e, | 1f.2e.3b.4b.5e.6f, | 1f.2e.3b.4b.5f.6a, | 1f.2e.3b.4b.5f.6b, | 1f.2e.3b.4b.5f.6c, |
| 1f.2e.3b.4b.5f.6d, | 1f.2e.3b.4b.5f.6e, | 1f.2e.3b.4b.5f.6f, | 1f.2e.3b.4c.5a.6a, | 1f.2e.3b.4c.5a.6b, |
| 1f.2e.3b.4c.5a.6c, | 1f.2e.3b.4c.5a.6d, | 1f.2e.3b.4c.5a.6e, | 1f.2e.3b.4c.5a.6f, | 1f.2e.3b.4c.5b.6a, |
| 1f.2e.3b.4c.5b.6b, | 1f.2e.3b.4c.5b.6c, | 1f.2e.3b.4c.5b.6d, | 1f.2e.3b.4c.5b.6e, | 1f.2e.3b.4c.5b.6f, |
| 1f.2e.3b.4c.5c.6a, | 1f.2e.3b.4c.5c.6b, | 1f.2e.3b.4c.5c.6c, | 1f.2e.3b.4c.5c.6d, | 1f.2e.3b.4c.5c.6e, |
| 1f.2e.3b.4c.5c.6f, | 1f.2e.3b.4c.5d.6a, | 1f.2e.3b.4c.5d.6b, | 1f.2e.3b.4c.5d.6c, | |
| 1f.2e.3b.4c.5d.6d, | 1f.2e.3b.4c.5d.6e, | 1f.2e.3b.4c.5d.6f, | 1f.2e.3b.4c.5e.6a, | 1f.2e.3b.4c.5e.6b, |
| 1f.2e.3b.4c.5e.6c, | 1f.2e.3b.4c.5e.6d, | 1f.2e.3b.4c.5e.6e, | 1f.2e.3b.4c.5e.6f, | 1f.2e.3b.4c.5f.6a, |
| 1f.2e.3b.4c.5f.6b, | 1f.2e.3b.4c.5f.6c, | 1f.2e.3b.4c.5f.6d, | 1f.2e.3b.4c.5f.6e, | 1f.2e.3b.4c.5f.6f, |
| 1f.2e.3b.4d.5a.6a, | 1f.2e.3b.4d.5a.6b, | 1f.2e.3b.4d.5a.6c, | 1f.2e.3b.4d.5a.6d, | |
| 1f.2e.3b.4d.5a.6e, | 1f.2e.3b.4d.5a.6f, | 1f.2e.3b.4d.5b.6a, | 1f.2e.3b.4d.5b.6b, | |
| 1f.2e.3b.4d.5b.6c, | 1f.2e.3b.4d.5b.6d, | 1f.2e.3b.4d.5b.6e, | 1f.2e.3b.4d.5b.6f, | |
| 1f.2e.3b.4d.5c.6a, | 1f.2e.3b.4d.5c.6b, | 1f.2e.3b.4d.5c.6c, | 1f.2e.3b.4d.5c.6d, | |
| 1f.2e.3b.4d.5c.6e, | 1f.2e.3b.4d.5c.6f, | 1f.2e.3b.4d.5d.6a, | 1f.2e.3b.4d.5d.6b, | |

TABLE 7-continued

List of Compounds of Formula (II)

| | | | |
|---|---|---|---|
| 1f.2e.3b.4d.5d.6c, | 1f.2e.3b.4d.5d.6d, | 1f.2e.3b.4d.5d.6e, | 1f.2e.3b.4d.5d.6f, |
| 1f2e.3b.4d.5e.6a, | 1f.2e.3b.4d.5e.6b, | 1f.2e.3b.4d.5e.6c, | 1f.2e.3b.4d.5e.6d, |
| 1f.2e.3b.4d.5e.6e, | 1f.2e.3b.4d.5e.6f, | 1f.2e.3b.4d.5f.6a, | 1f.2e.3b.4d.5f.6b, | 1f.2e.3b.4d.5f.6c, |
| 1f.2e.3b.4d.5f.6d, | 1f.2e.3b.4d.5f.6e, | 1f.2e.3b.4d.5f.6f, | 1f.2e.3b.4e.5a.6a, | 1f.2e.3b.4e.5a.6b, |
| 1f.2e.3b.4e.5a.6c, | 1f.2e.3b.4e.5a.6d, | 1f.2e.3b.4e.5a.6e, | 1f.2e.3b.4e.5a.6f, | 1f.2e.3b.4e.5b.6a, |
| 1f.2e.3b.4e.5b.6b, | 1f.2e.3b.4e.5b.6c, | 1f.2e.3b.4e.5b.6d, | 1f.2e.3b.4e.5b.6e, |
| 1f.2e.3b.4e.5b.6f, | 1f.2e.3b.4e.5c.6a, | 1f.2e.3b.4e.5c.6b, | 1f.2e.3b.4e.5c.6c, | 1f.2e.3b.4e.5c.6d, |
| 1f.2e.3b.4e.5c.6e, | 1f.2e.3b.4e.5c.6f, | 1f.2e.3b.4e.5d.6a, | 1f.2e.3b.4e.5d.6b, | 1f.2e.3b.4e.5d.6c, |
| 1f.2e.3b.4e.5d.6d, | 1f.2e.3b.4e.5d.6e, | 1f.2e.3b.4e.5d.6f, | 1f.2e.3b.4e.5e.6a, |
| 1f.2e.3b.4e.5e.6b, | 1f.2e.3b.4e.5e.6c, | 1f.2e.3b.4e.5e.6d, | 1f.2e.3b.4e.5e.6e, | 1f.2e.3b.4e.5e.6f, |
| 1f.2e.3b.4e.5f.6a, | 1f.2e.3b.4e.5f.6b, | 1f.2e.3b.4e.5f.6c, | 1f.2e.3b.4e.5f.6d, | 1f.2e.3b.4e.5f.6e, |
| 1f.2e.3b.4e.5f.6f, | 1f.2e.3b.4f.5a.6a, | 1f.2e.3b.4f.5a.6b, | 1f.2e.3b.4f.5a.6c, | 1f.2e.3b.4f.5a.6d, |
| 1f.2e.3b.4f.5a.6e, | 1f.2e.3b.4f.5a.6f, | 1f.2e.3b.4f.5b.6a, | 1f.2e.3b.4f.5b.6b, | 1f.2e.3b.4f.5b.6c, |
| 1f.2e.3b.4f.5b.6d, | 1f.2e.3b.4f.5b.6e, | 1f.2e.3b.4f.5b.6f, | 1f.2e.3b.4f.5c.6a, | 1f.2e.3b.4f.5c.6b, |
| 1f.2e.3b.4f.5c.6c, | 1f.2e.3b.4f.5c.6d, | 1f.2e.3b.4f.5c.6e, | 1f.2e.3b.4f.5c.6f, | 1f.2e.3b.4f.5d.6a, |
| 1f.2e.3b.4f.5d.6b, | 1f.2e.3b.4f.5d.6c, | 1f.2e.3b.4f.5d.6d, | 1f.2e.3b.4f.5d.6e, | 1f.2e.3b.4f.5d.6f, |
| 1f.2e.3b.4f.5e.6a, | 1f.2e.3b.4f.5e.6b, | 1f.2e.3b.4f.5e.6c, | 1f.2e.3b.4f.5e.6d, | 1f.2e.3b.4f.5e.6e, |
| 1f.2e.3b.4f.5e.6f, | 1f.2e.3b.4f.5f.6a, | 1f.2e.3b.4f.5f.6b, | 1f.2e.3b.4f.5f.6c, | 1f.2e.3b.4f.5f.6d, |
| 1f.2e.3b.4f.5f.6e, | 1f.2e.3b.4f.5f.6f, | 1f.2e.3c.4a.5a.6a, | 1f.2e.3c.4a.5a.6b, | 1f.2e.3c.4a.5a.6c, |
| 1f.2e.3c.4a.5a.6d, | 1f.2e.3c.4a.5a.6e, | 1f.2e.3c.4a.5a.6f, | 1f.2e.3c.4a.5b.6a, | 1f.2e.3c.4a.5b.6b, |
| 1f.2e.3c.4a.5b.6c, | 1f.2e.3c.4a.5b.6d, | 1f.2e.3c.4a.5b.6e, | 1f.2e.3c.4a.5b.6f, | 1f.2e.3c.4a.5c.6a, |
| 1f.2e.3c.4a.5c.6b, | 1f.2e.3c.4a.5c.6c, | 1f.2e.3c.4a.5c.6d, | 1f.2e.3c.4a.5c.6e, | 1f.2e.3c.4a.5c.6f, |
| 1f.2e.3c.4a.5d.6a, | 1f.2e.3c.4a.5d.6b, | 1f.2e.3c.4a.5d.6c, | 1f.2e.3c.4a.5d.6d, |
| 1f.2e.3c.4a.5d.6e, | 1f.2e.3c.4a.5d.6f, | 1f.2e.3c.4a.5e.6a, | 1f.2e.3c.4a.5e.6b, | 1f.2e.3c.4a.5e.6c, |
| 1f.2e.3c.4a.5e.6d, | 1f.2e.3c.4a.5e.6e, | 1f.2e.3c.4a.5e.6f, | 1f.2e.3c.4a.5f.6a, | 1f.2e.3c.4a.5f.6b, |
| 1f.2e.3c.4a.5f.6c, | 1f.2e.3c.4a.5f.6d, | 1f.2e.3c.4a.5f.6e, | 1f.2e.3c.4a.5f.6f, | 1f.2e.3c.4b.5a.6a, |
| 1f.2e.3c.4b.5a.6b, | 1f.2e.3c.4b.5a.6c, | 1f.2e.3c.4b.5a.6d, | 1f.2e.3c.4b.5a.6e, | 1f.2e.3c.4b.5a.6f, |
| 1f.2e.3c.4b.5b.6a, | 1f.2e.3c.4b.5b.6b, | 1f.2e.3c.4b.5b.6c, | 1f.2e.3c.4b.5b.6d, |
| 1f.2e.3c.4b.5b.6e, | 1f.2e.3c.4b.5b.6f, | 1f.2e.3c.4b.5c.6a, | 1f.2e.3c.4b.5c.6b, | 1f.2e.3c.4b.5c.6c, |
| 1f.2e.3c.4b.5c.6d, | 1f.2e.3c.4b.5c.6e, | 1f.2e.3c.4b.5c.6f, | 1f.2e.3c.4b.5d.6a, | 1f.2e.3c.4b.5d.6b, |
| 1f.2e.3c.4b.5d.6c, | 1f.2e.3c.4b.5d.6d, | 1f.2e.3c.4b.5d.6e, | 1f.2e.3c.4b.5d.6f, | 1f.2e.3c.4b.5e.6a, |
| 1f.2e.3c.4b.5e.6b, | 1f.2e.3c.4b.5e.6c, | 1f.2e.3c.4b.5e.6d, | 1f.2e.3c.4b.5e.6e, | 1f.2e.3c.4b.5e.6f, |
| 1f.2e.3c.4b.5f.6a, | 1f.2e.3c.4b.5f.6b, | 1f.2e.3c.4b.5f.6c, | 1f.2e.3c.4b.5f.6d, | 1f.2e.3c.4b.5f.6e, |
| 1f.2e.3c.4b.5f.6f, | 1f.2e.3c.4c.5a.6a, | 1f.2e.3c.4c.5a.6b, | 1f.2e.3c.4c.5a.6c, | 1f.2e.3c.4c.5a.6d, |
| 1f.2e.3c.4c.5a.6e, | 1f.2e.3c.4c.5a.6f, | 1f.2e.3c.4c.5b.6a, | 1f.2e.3c.4c.5b.6b, | 1f.2e.3c.4c.5b.6c, |
| 1f.2e.3c.4c.5b.6d, | 1f.2e.3c.4c.5b.6e, | 1f.2e.3c.4c.5b.6f, | 1f.2e.3c.4c.5c.6a, | 1f.2e.3c.4c.5c.6b, |
| 1f.2e.3c.4c.5c.6c, | 1f.2e.3c.4c.5c.6d, | 1f.2e.3c.4c.5c.6e, | 1f.2e.3c.4c.5c.6f, | 1f.2e.3c.4c.5d.6a, |
| 1f.2e.3c.4c.5d.6b, | 1f.2e.3c.4c.5d.6c, | 1f.2e.3c.4c.5d.6d, | 1f.2e.3c.4c.5d.6e, | 1f.2e.3c.4c.5d.6f, |
| 1f.2e.3c.4c.5e.6a, | 1f.2e.3c.4c.5e.6b, | 1f.2e.3c.4c.5e.6c, | 1f.2e.3c.4c.5e.6d, | 1f.2e.3c.4c.5e.6e, |
| 1f.2e.3c.4c.5e.6f, | 1f.2e.3c.4c.5f.6a, | 1f.2e.3c.4c.5f.6b, | 1f.2e.3c.4c.5f.6c, | 1f.2e.3c.4c.5f.6d, |
| 1f.2e.3c.4c.5f.6e, | 1f.2e.3c.4c.5f.6f, | 1f.2e.3c.4d.5a.6a, | 1f.2e.3c.4d.5a.6b, | 1f.2e.3c.4d.5a.6c, |
| 1f.2e.3c.4d.5a.6d, | 1f.2e.3c.4d.5a.6e, | 1f.2e.3c.4d.5a.6f, | 1f.2e.3c.4d.5b.6a, |
| 1f.2e.3c.4d.5b.6b, | 1f.2e.3c.4d.5b.6c, | 1f.2e.3c.4d.5b.6d, | 1f.2e.3c.4d.5b.6e, |
| 1f.2e.3c.4d.5b.6f, | 1f.2e.3c.4d.5c.6a, | 1f.2e.3c.4d.5c.6b, | 1f.2e.3c.4d.5c.6c, | 1f.2e.3c.4d.5c.6d, |
| 1f.2e.3c.4d.5c.6e, | 1f.2e.3c.4d.5c.6f, | 1f.2e.3c.4d.5d.6a, | 1f.2e.3c.4d.5d.6b, | 1f.2e.3c.4d.5d.6c, |
| 1f.2e.3c.4d.5d.6d, | 1f.2e.3c.4d.5d.6e, | 1f.2e.3c.4d.5d.6f, | 1f.2e.3c.4d.5e.6a, |
| 1f.2e.3c.4d.5e.6b, | 1f.2e.3c.4d.5e.6c, | 1f.2e.3c.4d.5e.6d, | 1f.2e.3c.4d.5e.6e, | 1f.2e.3c.4d.5e.6f, |
| 1f.2e.3c.4d.5f.6a, | 1f.2e.3c.4d.5f.6b, | 1f.2e.3c.4d.5f.6c, | 1f.2e.3c.4d.5f.6d, | 1f.2e.3c.4d.5f.6e, |
| 1f.2e.3c.4d.5f.6f, | 1f.2e.3c.4e.5a.6a, | 1f.2e.3c.4e.5a.6b, | 1f.2e.3c.4e.5a.6c, | 1f.2e.3c.4e.5a.6d, |
| 1f.2e.3c.4e.5a.6e, | 1f.2e.3c.4e.5a.6f, | 1f.2e.3c.4e.5b.6a, | 1f.2e.3c.4e.5b.6b, | 1f.2e.3c.4e.5b.6c, |
| 1f.2e.3c.4e.5b.6d, | 1f.2e.3c.4e.5b.6e, | 1f.2e.3c.4e.5b.6f, | 1f.2e.3c.4e.5c.6a, | 1f.2e.3c.4e.5c.6b, |
| 1f.2e.3c.4e.5c.6c, | 1f.2e.3c.4e.5c.6d, | 1f.2e.3c.4e.5c.6e, | 1f.2e.3c.4e.5c.6f, | 1f.2e.3c.4e.5d.6a, |
| 1f.2e.3c.4e.5d.6b, | 1f.2e.3c.4e.5d.6c, | 1f.2e.3c.4e.5d.6d, | 1f.2e.3c.4e.5d.6e, | 1f.2e.3c.4e.5d.6f, |
| 1f.2e.3c.4e.5e.6a, | 1f.2e.3c.4e.5e.6b, | 1f.2e.3c.4e.5e.6c, | 1f.2e.3c.4e.5e.6d, | 1f.2e.3c.4e.5e.6e, |
| 1f.2e.3c.4e.5e.6f, | 1f.2e.3c.4e.5f.6a, | 1f.2e.3c.4e.5f.6b, | 1f.2e.3c.4e.5f.6c, | 1f.2e.3c.4e.5f.6d, |
| 1f.2e.3c.4e.5f.6e, | 1f.2e.3c.4e.5f.6f, | 1f.2e.3c.4f.5a.6a, | 1f.2e.3c.4f.5a.6b, | 1f.2e.3c.4f.5a.6c, |
| 1f.2e.3c.4f.5a.6d, | 1f.2e.3c.4f.5a.6e, | 1f.2e.3c.4f.5a.6f, | 1f.2e.3c.4f.5b.6a, | 1f.2e.3c.4f.5b.6b, |
| 1f.2e.3c.4f.5b.6c, | 1f.2e.3c.4f.5b.6d, | 1f.2e.3c.4f.5b.6e, | 1f.2e.3c.4f.5b.6f, | 1f.2e.3c.4f.5c.6a, |
| 1f.2e.3c.4f.5c.6b, | 1f.2e.3c.4f.5c.6c, | 1f.2e.3c.4f.5c.6d, | 1f.2e.3c.4f.5c.6e, | 1f.2e.3c.4f.5c.6f, |
| 1f.2e.3c.4f.5d.6a, | 1f.2e.3c.4f.5d.6b, | 1f.2e.3c.4f.5d.6c, | 1f.2e.3c.4f.5d.6d, | 1f.2e.3c.4f.5d.6e, |
| 1f.2e.3c.4f.5d.6f, | 1f.2e.3c.4f.5e.6a, | 1f.2e.3c.4f.5e.6b, | 1f.2e.3c.4f.5e.6c, | 1f.2e.3c.4f.5e.6d, |
| 1f.2e.3c.4f.5e.6e, | 1f.2e.3c.4f.5e.6f, | 1f.2e.3c.4f.5f.6a, | 1f.2e.3c.4f.5f.6b, | 1f.2e.3c.4f.5f.6c, |
| 1f.2e.3c.4f.5f.6d, | 1f.2e.3c.4f.5f.6e, | 1f.2e.3c.4f.5f.6f, | 1f.2e.3d.4a.5a.6a, | 1f.2e.3d.4a.5a.6b, |
| 1f.2e.3d.4a.5a.6c, | 1f.2e.3d.4a.5a.6d, | 1f.2e.3d.4a.5a.6e, | 1f.2e.3d.4a.5a.6f, |
| 1f.2e.3d.4a.5b.6a, | 1f.2e.3d.4a.5b.6b, | 1f.2e.3d.4a.5b.6c, | 1f.2e.3d.4a.5b.6d, |
| 1f.2e.3d.4a.5b.6e, | 1f.2e.3d.4a.5b.6f, | 1f.2e.3d.4a.5c.6a, | 1f.2e.3d.4a.5c.6b, | 1f.2e.3d.4a.5c.6c, |
| 1f.2e.3d.4a.5c.6d, | 1f.2e.3d.4a.5c.6e, | 1f.2e.3d.4a.5c.6f, | 1f.2e.3d.4a.5d.6a, |
| 1f.2e.3d.4a.5d.6b, | 1f.2e.3d.4a.5d.6c, | 1f.2e.3d.4a.5d.6d, | 1f.2e.3d.4a.5d.6e, |
| 1f.2e.3d.4a.5d.6f, | 1f.2e.3d.4a.5e.6a, | 1f.2e.3d.4a.5e.6b, | 1f.2e.3d.4a.5e.6c, |
| 1f.2e.3d.4a.5e.6d, | 1f.2e.3d.4a.5e.6e, | 1f.2e.3d.4a.5e.6f, | 1f.2e.3d.4a.5f.6a, | 1f.2e.3d.4a.5f.6b, |
| 1f.2e.3d.4a.5f.6c, | 1f.2e.3d.4a.5f.6d, | 1f.2e.3d.4a.5f.6e, | 1f.2e.3d.4a.5f.6f, | 1f.2e.3d.4b.5a.6a, |
| 1f.2e.3d.4b.5a.6b, | 1f.2e.3d.4b.5a.6c, | 1f.2e.3d.4b.5a.6d, | 1f.2e.3d.4b.5a.6e, |
| 1f.2e.3d.4b.5a.6f, | 1f.2e.3d.4b.5b.6a, | 1f.2e.3d.4b.5b.6b, | 1f.2e.3d.4b.5b.6c, |
| 1f.2e.3d.4b.5b.6d, | 1f.2e.3d.4b.5b.6e, | 1f.2e.3d.4b.5b.6f, | 1f.2e.3d.4b.5c.6a, |
| 1f.2e.3d.4b.5c.6b, | 1f.2e.3d.4b.5c.6c, | 1f.2e.3d.4b.5c.6d, | 1f.2e.3d.4b.5c.6e, |
| 1f.2e.3d.4b.5c.6f, | 1f.2e.3d.4b.5d.6a, | 1f.2e.3d.4b.5d.6b, | 1f.2e.3d.4b.5d.6c, |
| 1f.2e.3d.4b.5d.6d, | 1f.2e.3d.4b.5d.6e, | 1f.2e.3d.4b.5d.6f, | 1f.2e.3d.4b.5e.6a, |
| 1f.2e.3d.4b.5e.6b, | 1f.2e.3d.4b.5e.6c, | 1f.2e.3d.4b.5e.6d, | 1f.2e.3d.4b.5e.6e, |

TABLE 7-continued

List of Compounds of Formula (II)

| | | | | |
|---|---|---|---|---|
| 112e.3d.4b.5e.6f, | 1f.2e.3d.4b.5f.6a, | 1f.2e.3d.4b.5f.6b, | 1f.2e.3d.4b.5f.6c, | 1f.2e.3d.4b.5f.6d, |
| 1f.2e.3d.4b.5f.6e, | 1f.2e.3d.4b.5f.6f, | 1f.2e.3d.4c.5a.6a, | 1f.2e.3d.4c.5a.6b, | 1f.2e.3d.4c.5a.6c, |
| 1f.2e.3d.4c.5a.6d, | 1f.2e.3d.4c.5a.6e, | 1f.2e.3d.4c.5a.6f, | 1f.2e.3d.4c.5b.6a, | |
| 1f.2e.3d.4c.5b.6b, | 1f.2e.3d.4c.5b.6c, | 1f.2e.3d.4c.5b.6d, | 1f.2e.3d.4c.5b.6e, | |
| 1f.2e.3d.4c.5b.6f, | 1f.2e.3d.4c.5c.6a, | 1f.2e.3d.4c.5c.6b, | 1f.2e.3d.4c.5c.6c, | 1f.2e.3d.4c.5c.6d, |
| 1f.2e.3d.4c.5c.6e, | 1f.2e.3d.4c.5c.6f, | 1f.2e.3d.4c.5d.6a, | 1f.2e.3d.4c.5d.6b, | 1f.2e.3d.4c.5d.6c, |
| 1f.2e.3d.4c.5d.6d, | 1f.2e.3d.4c.5d.6e, | 1f.2e.3d.4c.5d.6f, | 1f.2e.3d.4c.5e.6a, | |
| 1f.2e.3d.4c.5e.6b, | 1f.2e.3d.4c.5e.6c, | 1f.2e.3d.4c.5e.6d, | 1f.2e.3d.4c.5e.6e, | 1f.2e.3d.4c.5e.6f, |
| 1f.2e.3d.4c.5f.6a, | 1f.2e.3d.4c.5f.6b, | 1f.2e.3d.4c.5f.6c, | 1f.2e.3d.4c.5f.6d, | 1f.2e.3d.4c.5f.6e, |
| 1f.2e.3d.4c.5f.6f, | 1f.2e.3d.4d.5a.6a, | 1f.2e.3d.4d.5a.6b, | 1f.2e.3d.4d.5a.6c, | |
| 1f.2e.3d.4d.5a.6d, | 1f.2e.3d.4d.5a.6e, | 1f.2e.3d.4d.5a.6f, | 1f.2e.3d.4d.5b.6a, | |
| 1f.2e.3d.4d.5b.6b, | 1f.2e.3d.4d.5b.6c, | 1f.2e.3d.4d.5b.6d, | 1f.2e.3d.4d.5b.6e, | |
| 1f.2e.3d.4d.5b.6f, | 1f.2e.3d.4d.5c.6a, | 1f.2e.3d.4d.5c.6b, | 1f.2e.3d.4d.5c.6c, | |
| 1f.2e.3d.4d.5c.6d, | 1f.2e.3d.4d.5c.6e, | 1f.2e.3d.4d.5c.6f, | 1f.2e.3d.4d.5d.6a, | |
| 1f.2e.3d.4d.5d.6b, | 1f.2e.3d.4d.5d.6c, | 1f.2e.3d.4d.5d.6d, | 1f.2e.3d.4d.5d.6e, | |
| 1f.2e.3d.4d.5d.6f, | 1f.2e.3d.4d.5e.6a, | 1f.2e.3d.4d.5e.6b, | 1f.2e.3d.4d.5e.6c, | |
| 1f.2e.3d.4d.5e.6d, | 1f.2e.3d.4d.5e.6e, | 1f.2e.3d.4d.5e.6f, | 1f.2e.3d.4d.5f.6a, | |
| 1f.2e.3d.4d.5f.6b, | 1f.2e.3d.4d.5f.6c, | 1f.2e.3d.4d.5f.6d, | 1f.2e.3d.4d.5f.6e, | 1f.2e.3d.4d.5f.6f, |
| 1f.2e.3d.4e.5a.6a, | 1f.2e.3d.4e.5a.6b, | 1f.2e.3d.4e.5a.6c, | 1f.2e.3d.4e.5a.6d, | |
| 1f.2e.3d.4e.5a.6e, | 1f.2e.3d.4e.5a.6f, | 1f.2e.3d.4e.5b.6a, | 1f.2e.3d.4e.5b.6b, | |
| 1f.2e.3d.4e.5b.6c, | 1f.2e.3d.4e.5b.6d, | 1f.2e.3d.4e.5b.6e, | 1f.2e.3d.4e.5b.6f, | |
| 1f.2e.3d.4e.5c.6a, | 1f.2e.3d.4e.5c.6b, | 1f.2e.3d.4e.5c.6c, | 1f.2e.3d.4e.5c.6d, | 1f.2e.3d.4e.5c.6e, |
| 1f.2e.3d.4e.5c.6f, | 1f.2e.3d.4e.5d.6a, | 1f.2e.3d.4e.5d.6b, | 1f.2e.3d.4e.5d.6c, | |
| 1f.2e.3d.4e.5d.6d, | 1f.2e.3d.4e.5d.6e, | 1f.2e.3d.4e.5d.6f, | 1f.2e.3d.4e.5e.6a, | |
| 1f.2e.3d.4e.5e.6b, | 1f.2e.3d.4e.5e.6c, | 1f.2e.3d.4e.5e.6d, | 1f.2e.3d.4e.5e.6e, | 1f.2e.3d.4e.5e.6f, |
| 1f.2e.3d.4e.5f.6a, | 1f.2e.3d.4e.5f.6b, | 1f.2e.3d.4e.5f.6c, | 1f.2e.3d.4e.5f.6d, | 1f.2e.3d.4e.5f.6e, |
| 1f.2e.3d.4e.5f.6f, | 1f.2e.3d.4f.5a.6a, | 1f.2e.3d.4f.5a.6b, | 1f.2e.3d.4f.5a.6c, | 1f.2e.3d.4f.5a.6d, |
| 1f.2e.3d.4f.5a.6e, | 1f.2e.3d.4f.5a.6f, | 1f.2e.3d.4f.5b.6a, | 1f.2e.3d.4f.5b.6b, | 1f.2e.3d.4f.5b.6c, |
| 1f.2e.3d.4f.5b.6d, | 1f.2e.3d.4f.5b.6e, | 1f.2e.3d.4f.5b.6f, | 1f.2e.3d.4f.5c.6a, | 1f.2e.3d.4f.5c.6b, |
| 1f.2e.3d.4f.5c.6c, | 1f.2e.3d.4f.5c.6d, | 1f.2e.3d.4f.5c.6e, | 1f.2e.3d.4f.5c.6f, | 1f.2e.3d.4f.5d.6a, |
| 1f.2e.3d.4f.5d.6b, | 1f.2e.3d.4f.5d.6c, | 1f.2e.3d.4f.5d.6d, | 1f.2e.3d.4f.5d.6e, | 1f.2e.3d.4f.5d.6f, |
| 1f.2e.3d.4f.5e.6a, | 1f.2e.3d.4f.5e.6b, | 1f.2e.3d.4f.5e.6c, | 1f.2e.3d.4f.5e.6d, | 1f.2e.3d.4f.5e.6e, |
| 1f.2e.3d.4f.5e.6f, | 1f.2e.3d.4f.5f.6a, | 1f.2e.3d.4f.5f.6b, | 1f.2e.3d.4f.5f.6c, | 1f.2e.3d.4f.5f.6d, |
| 1f.2e.3d.4f.5f.6e, | 1f.2e.3d.4f.5f.6f, | 1f.2e.3e.4a.5a.6a, | 1f.2e.3e.4a.5a.6b, | 1f.2e.3e.4a.5a.6c, |
| 1f.2e.3e.4a.5a.6d, | 1f.2e.3e.4a.5a.6e, | 1f.2e.3e.4a.5a.6f, | 1f.2e.3e.4a.5b.6a, | 1f.2e.3e.4a.5b.6b, |
| 1f.2e.3e.4a.5b.6c, | 1f.2e.3e.4a.5b.6d, | 1f.2e.3e.4a.5b.6e, | 1f.2e.3e.4a.5b.6f, | 1f.2e.3e.4a.5c.6a, |
| 1f.2e.3e.4a.5c.6b, | 1f.2e.3e.4a.5c.6c, | 1f.2e.3e.4a.5c.6d, | 1f.2e.3e.4a.5c.6e, | 1f.2e.3e.4a.5c.6f, |
| 1f.2e.3e.4a.5d.6a, | 1f.2e.3e.4a.5d.6b, | 1f.2e.3e.4a.5d.6c, | 1f.2e.3e.4a.5d.6d, | |
| 1f.2e.3e.4a.5d.6e, | 1f.2e.3e.4a.5d.6f, | 1f.2e.3e.4a.5e.6a, | 1f.2e.3e.4a.5e.6b, | 1f.2e.3e.4a.5e.6c, |
| 1f.2e.3e.4a.5e.6d, | 1f.2e.3e.4a.5e.6e, | 1f.2e.3e.4a.5e.6f, | 1f.2e.3e.4a.5f.6a, | 1f.2e.3e.4a.5f.6b, |
| 1f.2e.3e.4a.5f.6c, | 1f.2e.3e.4a.5f.6d, | 1f.2e.3e.4a.5f.6e, | 1f.2e.3e.4a.5f.6f, | 1f.2e.3e.4b.5a.6a, |
| 1f.2e.3e.4b.5a.6b, | 1f.2e.3e.4b.5a.6c, | 1f.2e.3e.4b.5a.6d, | 1f.2e.3e.4b.5a.6e, | 1f.2e.3e.4b.5a.6f, |
| 1f.2e.3e.4b.5b.6a, | 1f.2e.3e.4b.5b.6b, | 1f.2e.3e.4b.5b.6c, | 1f.2e.3e.4b.5b.6d, | |
| 1f.2e.3e.4b.5b.6e, | 1f.2e.3e.4b.5b.6f, | 1f.2e.3e.4b.5c.6a, | 1f.2e.3e.4b.5c.6b, | 1f.2e.3e.4b.5c.6c, |
| 1f.2e.3e.4b.5c.6d, | 1f.2e.3e.4b.5c.6e, | 1f.2e.3e.4b.5c.6f, | 1f.2e.3e.4b.5d.6a, | 1f.2e.3e.4b.5d.6b, |
| 1f.2e.3e.4b.5d.6c, | 1f.2e.3e.4b.5d.6d, | 1f.2e.3e.4b.5d.6e, | 1f.2e.3e.4b.5d.6f, | |
| 1f.2e.3e.4b.5e.6a, | 1f.2e.3e.4b.5e.6b, | 1f.2e.3e.4b.5e.6c, | 1f.2e.3e.4b.5e.6d, | 1f.2e.3e.4b.5e.6e, |
| 1f.2e.3e.4b.5e.6f, | 1f.2e.3e.4b.5f.6a, | 1f.2e.3e.4b.5f.6b, | 1f.2e.3e.4b.5f.6c, | 1f.2e.3e.4b.5f.6d, |
| 1f.2e.3e.4b.5f.6e, | 1f.2e.3e.4b.5f.6f, | 1f.2e.3e.4c.5a.6a, | 1f.2e.3e.4c.5a.6b, | 1f.2e.3e.4c.5a.6c, |
| 1f.2e.3e.4c.5a.6d, | 1f.2e.3e.4c.5a.6e, | 1f.2e.3e.4c.5a.6f, | 1f.2e.3e.4c.5b.6a, | 1f.2e.3e.4c.5b.6b, |
| 1f.2e.3e.4c.5b.6c, | 1f.2e.3e.4c.5b.6d, | 1f.2e.3e.4c.5b.6e, | 1f.2e.3e.4c.5b.6f, | 1f.2e.3e.4c.5c.6a, |
| 1f.2e.3e.4c.5c.6b, | 1f.2e.3e.4c.5c.6c, | 1f.2e.3e.4c.5c.6d, | 1f.2e.3e.4c.5c.6e, | 1f.2e.3e.4c.5c.6f, |
| 1f.2e.3e.4c.5d.6a, | 1f.2e.3e.4c.5d.6b, | 1f.2e.3e.4c.5d.6c, | 1f.2e.3e.4c.5d.6d, | 1f.2e.3e.4c.5d.6e, |
| 1f.2e.3e.4c.5d.6f, | 1f.2e.3e.4c.5e.6a, | 1f.2e.3e.4c.5e.6b, | 1f.2e.3e.4c.5e.6c, | 1f.2e.3e.4c.5e.6d, |
| 1f.2e.3e.4c.5e.6e, | 1f.2e.3e.4c.5e.6f, | 1f.2e.3e.4c.5f.6a, | 1f.2e.3e.4c.5f.6b, | 1f.2e.3e.4c.5f.6c, |
| 1f.2e.3e.4c.5f.6d, | 1f.2e.3e.4c.5f.6e, | 1f.2e.3e.4c.5f.6f, | 1f.2e.3e.4d.5a.6a, | 1f.2e.3e.4d.5a.6b, |
| 1f.2e.3e.4d.5a.6c, | 1f.2e.3e.4d.5a.6d, | 1f.2e.3e.4d.5a.6e, | 1f.2e.3e.4d.5a.6f, | |
| 1f.2e.3e.4d.5b.6a, | 1f.2e.3e.4d.5b.6b, | 1f.2e.3e.4d.5b.6c, | 1f.2e.3e.4d.5b.6d, | |
| 1f.2e.3e.4d.5b.6e, | 1f.2e.3e.4d.5b.6f, | 1f.2e.3e.4d.5c.6a, | 1f.2e.3e.4d.5c.6b, | 1f.2e.3e.4d.5c.6c, |
| 1f.2e.3e.4d.5c.6d, | 1f.2e.3e.4d.5c.6e, | 1f.2e.3e.4d.5c.6f, | 1f.2e.3e.4d.5d.6a, | |
| 1f.2e.3e.4d.5d.6b, | 1f.2e.3e.4d.5d.6c, | 1f.2e.3e.4d.5d.6d, | 1f.2e.3e.4d.5d.6e, | |
| 1f.2e.3e.4d.5d.6f, | 1f.2e.3e.4d.5e.6a, | 1f.2e.3e.4d.5e.6b, | 1f.2e.3e.4d.5e.6c, | |
| 1f.2e.3e.4d.5e.6d, | 1f.2e.3e.4d.5e.6e, | 1f.2e.3e.4d.5e.6f, | 1f.2e.3e.4d.5f.6a, | 1f.2e.3e.4d.5f.6b, |
| 1f.2e.3e.4d.5f.6c, | 1f.2e.3e.4d.5f.6d, | 1f.2e.3e.4d.5f.6e, | 1f.2e.3e.4d.5f.6f, | 1f.2e.3e.4e.5a.6a, |
| 1f.2e.3e.4e.5a.6b, | 1f.2e.3e.4e.5a.6c, | 1f.2e.3e.4e.5a.6d, | 1f.2e.3e.4e.5a.6e, | 1f.2e.3e.4e.5a.6f, |
| 1f.2e.3e.4e.5b.6a, | 1f.2e.3e.4e.5b.6b, | 1f.2e.3e.4e.5b.6c, | 1f.2e.3e.4e.5b.6d, | 1f.2e.3e.4e.5b.6e, |
| 1f.2e.3e.4e.5b.6f, | 1f.2e.3e.4e.5c.6a, | 1f.2e.3e.4e.5c.6b, | 1f.2e.3e.4e.5c.6c, | 1f.2e.3e.4e.5c.6d, |
| 1f.2e.3e.4e.5c.6e, | 1f.2e.3e.4e.5c.6f, | 1f.2e.3e.4e.5d.6a, | 1f.2e.3e.4e.5d.6b, | 1f.2e.3e.4e.5d.6c, |
| 1f.2e.3e.4e.5d.6d, | 1f.2e.3e.4e.5d.6e, | 1f.2e.3e.4e.5d.6f, | 1f.2e.3e.4e.5e.6a, | 1f.2e.3e.4e.5e.6b, |
| 1f.2e.3e.4e.5e.6c, | 1f.2e.3e.4e.5e.6d, | 1f.2e.3e.4e.5e.6e, | 1f.2e.3e.4e.5e.6f, | 1f.2e.3e.4e.5f.6a, |
| 1f.2e.3e.4e.5f.6b, | 1f.2e.3e.4e.5f.6c, | 1f.2e.3e.4e.5f.6d, | 1f.2e.3e.4e.5f.6e, | 1f.2e.3e.4e.5f.6f, |
| 1f.2e.3e.4f.5a.6a, | 1f.2e.3e.4f.5a.6b, | 1f.2e.3e.4f.5a.6c, | 1f.2e.3e.4f.5a.6d, | 1f.2e.3e.4f.5a.6e, |
| 1f.2e.3e.4f.5a.6f, | 1f.2e.3e.4f.5b.6a, | 1f.2e.3e.4f.5b.6b, | 1f.2e.3e.4f.5b.6c, | 1f.2e.3e.4f.5b.6d, |
| 1f.2e.3e.4f.5b.6e, | 1f.2e.3e.4f.5b.6f, | 1f.2e.3e.4f.5c.6a, | 1f.2e.3e.4f.5c.6b, | 1f.2e.3e.4f.5c.6c, |
| 1f.2e.3e.4f.5c.6d, | 1f.2e.3e.4f.5c.6e, | 1f.2e.3e.4f.5c.6f, | 1f.2e.3e.4f.5d.6a, | 1f.2e.3e.4f.5d.6b, |
| 1f.2e.3e.4f.5d.6c, | 1f.2e.3e.4f.5d.6d, | 1f.2e.3e.4f.5d.6e, | 1f.2e.3e.4f.5d.6f, | 1f.2e.3e.4f.5e.6a, |
| 1f.2e.3e.4f.5e.6b, | 1f.2e.3e.4f.5e.6c, | 1f.2e.3e.4f.5e.6d, | 1f.2e.3e.4f.5e.6e, | 1f.2e.3e.4f.5e.6f, |
| 1f.2e.3e.4f.5f.6a, | 1f.2e.3e.4f.5f.6b, | 1f.2e.3e.4f.5f.6c, | 1f.2e.3e.4f.5f.6d, | 1f.2e.3e.4f.5f.6e, |

TABLE 7-continued

List of Compounds of Formula (II)

| | | | | |
|---|---|---|---|---|
| 1f.2e.3e.4f.5f.6f, | 1f.2e.3f.4a.5a.6a, | 1f.2e.3f.4a.5a.6b, | 1f.2e.3f.4a.5a.6c, | 1f.2e.3f.4a.5a.6d, |
| 1f.2e.3f.4a.5a.6e, | 1f.2e.3f.4a.5a.6f, | 1f.2e.3f.4a.5b.6a, | 1f.2e.3f.4a.5b.6b, | 1f.2e.3f.4a.5b.6c, |
| 1f.2e.3f.4a.5b.6d, | 1f.2e.3f.4a.5b.6e, | 1f.2e.3f.4a.5b.6f, | 1f.2e.3f.4a.5c.6a, | 1f.2e.3f.4a.5c.6b, |
| 1f.2e.3f.4a.5c.6c, | 1f.2e.3f.4a.5c.6d, | 1f.2e.3f.4a.5c.6e, | 1f.2e.3f.4a.5c.6f, | 1f.2e.3f.4a.5d.6a, |
| 1f.2e.3f.4a.5d.6b, | 1f.2e.3f.4a.5d.6c, | 1f.2e.3f.4a.5d.6d, | 1f.2e.3f.4a.5d.6e, | 1f.2e.3f.4a.5d.6f, |
| 1f.2e.3f.4a.5e.6a, | 1f.2e.3f.4a.5e.6b, | 1f.2e.3f.4a.5e.6c, | 1f.2e.3f.4a.5e.6d, | 1f.2e.3f.4a.5e.6e, |
| 1f.2e.3f.4a.5e.6f, | 1f.2e.3f.4a.5f.6a, | 1f.2e.3f.4a.5f.6b, | 1f.2e.3f.4a.5f.6c, | 1f.2e.3f.4a.5f.6d, |
| 1f.2e.3f.4a.5f.6e, | 1f.2e.3f.4a.5f.6f, | 1f.2e.3f.4b.5a.6a, | 1f.2e.3f.4b.5a.6b, | 1f.2e.3f.4b.5a.6c, |
| 1f.2e.3f.4b.5a.6d, | 1f.2e.3f.4b.5a.6e, | 1f.2e.3f.4b.5a.6f, | 1f.2e.3f.4b.5b.6a, | 1f.2e.3f.4b.5b.6b, |
| 1f.2e.3f.4b.5b.6c, | 1f.2e.3f.4b.5b.6d, | 1f.2e.3f.4b.5b.6e, | 1f.2e.3f.4b.5b.6f, | 1f.2e.3f.4b.5c.6a, |
| 1f.2e.3f.4b.5c.6b, | 1f.2e.3f.4b.5c.6c, | 1f.2e.3f.4b.5c.6d, | 1f.2e.3f.4b.5c.6e, | 1f.2e.314b.5c.6f, |
| 1f.2e.3f.4b.5d.6a, | 1f.2e.3f.4b.5d.6b, | 1f.2e.3f.4b.5d.6c, | 1f.2e.3f.4b.5d.6d, | 1f.2e.3f.4b.5d.6e, |
| 1f.2e.3f.4b.5d.6f, | 1f.2e.3f.4b.5e.6a, | 1f.2e.3f.4b.5e.6b, | 1f.2e.3f.4b.5e.6c, | 1f.2e.314b.5e.6d, |
| 1f.2e.3f.4b.5e.6e, | 1f.2e.3f.4b.5e.6f, | 1f.2e.3f.4b.5f.6a, | 1f.2e.3f.4b.5f.6b, | 1f.2e.3f.4b.5f.6c, |
| 1f.2e.3f.4b.5f.6d, | 1f.2e.3f.4b.5f.6e, | 1f.2e.3f.4b.5f.6f, | 1f.2e.3f.4c.5a.6a, | 1f.2e.3f.4c.5a.6b, |
| 1f.2e.3f.4c.5a.6c, | 1f.2e.3f.4c.5a.6d, | 1f.2e.3f.4c.5a.6e, | 1f.2e.3f.4c.5a.6f, | 1f.2e.3f.4c.5b.6a, |
| 1f.2e.3f.4c.5b.6b, | 1f.2e.3f.4c.5b.6c, | 1f.2e.3f.4c.5b.6d, | 1f.2e.3f.4c.5b.6e, | 1f.2e.3f.4c.5b.6f, |
| 1f.2e.3f.4c.5c.6a, | 1f.2e.3f.4c.5c.6b, | 1f.2e.3f.4c.5c.6c, | 1f.2e.3f.4c.5c.6d, | 1f.2e.3f.4c.5c.6e, |
| 1f.2e.3f.4c.5c.6f, | 1f.2e.3f.4c.5d.6a, | 1f.2e.3f.4c.5d.6b, | 1f.2e.3f.4c.5d.6c, | 1f.2e.3f.4c.5d.6d, |
| 1f.2e.3f.4c.5d.6e, | 1f.2e.3f.4c.5d.6f, | 1f.2e.3f.4c.5e.6a, | 1f.2e.3f.4c.5e.6b, | 1f.2e.3f.4c.5e.6c, |
| 1f.2e.3f.4c.5e.6d, | 1f.2e.3f.4c.5e.6e, | 1f.2e.3f.4c.5e.6f, | 1f.2e.3f.4c.5f.6a, | 1f.2e.3f.4c.5f.6b, |
| 1f.2e.3f.4c.5f.6c, | 1f.2e.3f.4c.5f.6d, | 1f.2e.3f.4c.5f.6e, | 1f.2e.3f.4c.5f.6f, | 1f.2e.3f.4d.5a.6a, |
| 1f.2e.3f.4d.5a.6b, | 1f.2e.3f.4d.5a.6c, | 1f.2e.3f.4d.5a.6d, | 1f.2e.3f.4d.5a.6e, | 1f.2e.3f.4d.5a.6f, |
| 1f.2e.3f.4d.5b.6a, | 1f.2e.3f.4d.5b.6b, | 1f.2e.3f.4d.5b.6c, | 1f.2e.3f.4d.5b.6d, | 1f.2e.3f.4d.5b.6e, |
| 1f.2e.3f.4d.5b.6f, | 1f.2e.3f.4d.5c.6a, | 1f.2e.3f.4d.5c.6b, | 1f.2e.3f.4d.5c.6c, | 1f.2e.3f.4d.5c.6d, |
| 1f.2e.3f.4d.5c.6e, | 1f.2e.3f.4d.5c.6f, | 1f.2e.3f.4d.5d.6a, | 1f.2e.3f.4d.5d.6b, | 1f.2e.3f.4d.5d.6c, |
| 1f.2e.3f.4d.5d.6d, | 1f.2e.3f.4d.5d.6e, | 1f.2e.3f.4d.5d.6f, | 1f.2e.3f.4d.5e.6a, | 1f.2e.3f.4d.5e.6b, |
| 1f.2e.3f.4d.5e.6c, | 1f.2e.3f.4d.5e.6d, | 1f.2e.3f.4d.5e.6e, | 1f.2e.3f.4d.5e.6f, | 1f.2e.3f.4d.5f.6a, |
| 1f.2e.3f.4d.5f.6b, | 1f.2e.3f.4d.5f.6c, | 1f.2e.3f.4d.5f.6d, | 1f.2e.3f.4d.5f.6e, | 1f.2e.3f.4d.5f.6f, |
| 1f.2e.3f.4e.5a.6a, | 1f.2e.3f.4e.5a.6b, | 1f.2e.3f.4e.5a.6c, | 1f.2e.3f.4e.5a.6d, | 1f.2e.3f.4e.5a.6e, |
| 1f.2e.3f.4e.5a.6f, | 1f.2e.3f.4e.5b.6a, | 1f.2e.3f.4e.5b.6b, | 1f.2e.3f.4e.5b.6c, | 1f.2e.3f.4e.5b.6d, |
| 1f.2e.3f.4e.5b.6e, | 1f.2e.3f.4e.5b.6f, | 1f.2e.3f.4e.5c.6a, | 1f.2e.3f.4e.5c.6b, | 1f.2e.3f.4e.5c.6c, |
| 1f.2e.3f.4e.5c.6d, | 1f.2e.3f.4e.5c.6e, | 1f.2e.3f.4e.5c.6f, | 1f.2e.3f.4e.5d.6a, | 1f.2e.3f.4e.5d.6b, |
| 1f.2e.3f.4e.5d.6c, | 1f.2e.3f.4e.5d.6d, | 1f.2e.3f.4e.5d.6e, | 1f.2e.3f.4e.5d.6f, | 1f.2e.3f.4e.5e.6a, |
| 1f.2e.3f.4e.5e.6b, | 1f.2e.3f.4e.5e.6c, | 1f.2e.3f.4e.5e.6d, | 1f.2e.3f.4e.5e.6e, | 1f.2e.3f.4e.5e.6f, |
| 1f.2e.3f.4e.5f.6a, | 1f.2e.3f.4e.5f.6b, | 1f.2e.3f.4e.5f.6c, | 1f.2e.3f.4e.5f.6d, | 1f.2e.3f.4e.5f.6e, |
| 1f.2e.3f.4e.5f.6f, | 1f.2e.3f.4f.5a.6a, | 1f.2e.3f.4f.5a.6b, | 1f.2e.3f.4f.5a.6c, | 1f.2e.3f.4f.5a.6d, |
| 1f.2e.3f.4f.5a.6e, | 1f.2e.3f.4f.5a.6f, | 1f.2e.3f.4f.5b.6a, | 1f.2e.3f.4f.5b.6b, | 1f.2e.3f.4f.5b.6c, |
| 1f.2e.3f.4f.5b.6d, | 1f.2e.3f.4f.5b.6e, | 1f.2e.3f.4f.5b.6f, | 1f.2e.3f.4f.5c.6a, | 1f.2e.3f.4f.5c.6b, |
| 1f.2e.3f.4f.5c.6c, | 1f.2e.3f.4f.5c.6d, | 1f.2e.3f.4f.5c.6e, | 1f.2e.3f.4f.5c.6f, | 1f.2e.3f.4f.5d.6a, |
| 1f.2e.3f.4f.5d.6b, | 1f.2e.3f.4f.5d.6c, | 1f.2e.3f.4f.5d.6d, | 1f.2e.3f.4f.5d.6e, | 1f.2e.3f.4f.5d.6f, |
| 1f.2e.3f.4f.5e.6a, | 1f.2e.3f.4f.5e.6b, | 1f.2e.3f.4f.5e.6c, | 1f.2e.3f.4f.5e.6d, | 1f.2e.3f.4f.5e.6e, |
| 1f.2e.3f.4f.5e.6f, | 1f.2e.3f.4f.5f.6a, | 1f.2e.3f.4f.5f.6b, | 1f.2e.3f.4f.5f.6c, | 1f.2e.3f.4f.5f.6d, |
| 1f.2e.3f.4f.5f.6e, | 1f.2e.3f.4f.5f.6f, | 1f.2f.3a.4a.5a.6a, | 1f.2f.3a.4a.5a.6b, | 1f.2f.3a.4a.5a.6c, |
| 1f.2f.3a.4a.5a.6d, | 1f.2f.3a.4a.5a.6e, | 1f.2f.3a.4a.5a.6f, | 1f.2f.3a.4a.5b.6a, | 1f.2f.3a.4a.5b.6b, |
| 1f.2f.3a.4a.5b.6c, | 1f.2f.3a.4a.5b.6d, | 1f.2f.3a.4a.5b.6e, | 1f.2f.3a.4a.5b.6f, | 1f.2f.3a.4a.5c.6a, |
| 1f.2f.3a.4a.5c.6b, | 1f.2f.3a.4a.5c.6c, | 1f.2f.3a.4a.5c.6d, | 1f.2f.3a.4a.5c.6e, | 1f.2f.3a.4a.5c.6f, |
| 1f.2f.3a.4a.5d.6a, | 1f.2f.3a.4a.5d.6b, | 1f.2f.3a.4a.5d.6c, | 1f.2f.3a.4a.5d.6d, | 1f.2f.3a.4a.5d.6e, |
| 1f.2f.3a.4a.5d.6f, | 1f.2f.3a.4a.5e.6a, | 1f.2f.3a.4a.5e.6b, | 1f.2f.3a.4a.5e.6c, | 1f.2f.3a.4a.5e.6d, |
| 1f.2f.3a.4a.5e.6e, | 1f.2f.3a.4a.5e.6f, | 1f.2f.3a.4a.5f.6a, | 1f.2f.3a.4a.5f.6b, | 1f.2f.3a.4a.5f.6c, |
| 1f.2f.3a.4a.5f.6d, | 1f.2f.3a.4a.5f.6e, | 1f.2f.3a.4a.5f.6f, | 1f.2f.3a.4b.5a.6a, | 1f.2f.3a.4b.5a.6b, |
| 1f.2f.3a.4b.5a.6c, | 1f.2f.3a.4b.5a.6d, | 1f.2f.3a.4b.5a.6e, | 1f.2f.3a.4b.5a.6f, | 1f.2f.3a.4b.5b.6a, |
| 1f.2f.3a.4b.5b.6b, | 1f.2f.3a.4b.5b.6c, | 1f.2f.3a.4b.5b.6d, | 1f.2f.3a.4b.5b.6e, | 1f.2f.3a.4b.5b.6f, |
| 1f.2f.3a.4b.5c.6a, | 1f.2f.3a.4b.5c.6b, | 1f.2f.3a.4b.5c.6c, | 1f.2f.3a.4b.5c.6d, | 1f.2f.3a.4b.5c.6e, |
| 1f.2f.3a.4b.5c.6f, | 1f.2f.3a.4b.5d.6a, | 1f.2f.3a.4b.5d.6b, | 1f.2f.3a.4b.5d.6c, | 1f.2f.3a.4b.5d.6d, |
| 1f.2f.3a.4b.5d.6e, | 1f.2f.3a.4b.5d.6f, | 1f.2f.3a.4b.5e.6a, | 1f.2f.3a.4b.5e.6b, | 1f.2f.3a.4b.5e.6c, |
| 1f.2f.3a.4b.5e.6d, | 1f.2f.3a.4b.5e.6e, | 1f.2f.3a.4b.5e.6f, | 1f.2f.3a.4b.5f.6a, | 1f.2f.3a.4b.5f.6b, |
| 1f.2f.3a.4b.5f.6c, | 1f.2f.3a.4b.5f.6d, | 1f.2f.3a.4b.5f.6e, | 1f.2f.3a.4b.5f.6f, | 1f.2f.3a.4c.5a.6a, |
| 1f.2f.3a.4c.5a.6b, | 1f.2f.3a.4c.5a.6c, | 1f.2f.3a.4c.5a.6d, | 1f.2f.3a.4c.5a.6e, | 1f.2f.3a.4c.5a.6f, |
| 1f.2f.3a.4c.5b.6a, | 1f.2f.3a.4c.5b.6b, | 1f.2f.3a.4c.5b.6c, | 1f.2f.3a.4c.5b.6d, | 1f.2f.3a.4c.5b.6e, |
| 1f.2f.3a.4c.5b.6f, | 1f.2f.3a.4c.5c.6a, | 1f.2f.3a.4c.5c.6b, | 1f.2f.3a.4c.5c.6c, | 1f.2f.3a.4c.5c.6d, |
| 1f.2f.3a.4c.5c.6e, | 1f.2f.3a.4c.5c.6f, | 1f.2f.3a.4c.5d.6a, | 1f.2f.3a.4c.5d.6b, | 1f.2f.3a.4c.5d.6c, |
| 1f.2f.3a.4c.5d.6d, | 1f.2f.3a.4c.5d.6e, | 1f.2f.3a.4c.5d.6f, | 1f.2f.3a.4c.5e.6a, | 1f.2f.3a.4c.5e.6b, |
| 1f.2f.3a.4c.5e.6c, | 1f.2f.3a.4c.5e.6d, | 1f.2f.3a.4c.5e.6e, | 1f.2f.3a.4c.5e.6f, | 1f.2f.3a.4c.5f.6a, |
| 1f.2f.3a.4c.5f.6b, | 1f.2f.3a.4c.5f.6c, | 1f.2f.3a.4c.5f.6d, | 1f.2f.3a.4c.5f.6e, | 1f.2f.3a.4c.5f.6f, |
| 1f.2f.3a.4d.5a.6a, | 1f.2f.3a.4d.5a.6b, | 1f.2f.3a.4d.5a.6c, | 1f.2f.3a.4d.5a.6d, | 1f.2f.3a.4d.5a.6e, |
| 1f.2f.3a.4d.5a.6f, | 1f.2f.3a.4d.5b.6a, | 1f.2f.3a.4d.5b.6b, | 1f.2f.3a.4d.5b.6c, | 1f.2f.3a.4d.5b.6d, |
| 1f.2f.3a.4d.5b.6e, | 1f.2f.3a.4d.5b.6f, | 1f.2f.3a.4d.5c.6a, | 1f.2f.3a.4d.5c.6b, | 1f.2f.3a.4d.5c.6c, |
| 1f.2f.3a.4d.5c.6d, | 1f.2f.3a.4d.5c.6e, | 1f.2f.3a.4d.5c.6f, | 1f.2f.3a.4d.5d.6a, | 1f.2f.3a.4d.5d.6b, |
| 1f.2f.3a.4d.5d.6c, | 1f.2f.3a.4d.5d.6d, | 1f.2f.3a.4d.5d.6e, | 1f.2f.3a.4d.5d.6f, | 1f.2f.3a.4d.5e.6a, |
| 1f.2f.3a.4d.5e.6b, | 1f.2f.3a.4d.5e.6c, | 1f.2f.3a.4d.5e.6d, | 1f.2f.3a.4d.5e.6e, | 1f.2f.3a.4d.5e.6f, |
| 1f.2f.3a.4d.5f.6a, | 1f.2f.3a.4d.5f.6b, | 1f.2f.3a.4d.5f.6c, | 1f.2f.3a.4d.5f.6d, | 1f.2f.3a.4d.5f.6e, |
| 1f.2f.3a.4d.5f.6f, | 1f.2f.3a.4e.5a.6a, | 1f.2f.3a.4e.5a.6b, | 1f.2f.3a.4e.5a.6c, | 1f.2f.3a.4e.5a.6d, |
| 1f.2f.3a.4e.5a.6e, | 1f.2f.3a.4e.5a.6f, | 1f.2f.3a.4e.5b.6a, | 1f.2f.3a.4e.5b.6b, | 1f.2f.3a.4e.5b.6c, |
| 1f.2f.3a.4e.5b.6d, | 1f.2f.3a.4e.5b.6e, | 1f.2f.3a.4e.5b.6f, | 1f.2f.3a.4e.5c.6a, | 1f.2f.3a.4e.5c.6b, |
| 1f.2f.3a.4e.5c.6c, | 1f.2f.3a.4e.5c.6d, | 1f.2f.3a.4e.5c.6e, | 1f.2f.3a.4e.5c.6f, | 1f.2f.3a.4e.5d.6a, |
| 1f.2f.3a.4e.5d.6b, | 1f.2f.3a.4e.5d.6c, | 1f.2f.3a.4e.5d.6d, | 1f.2f.3a.4e.5d.6e, | 1f.2f.3a.4e.5d.6f, |
| 1f.2f.3a.4e.5e.6a, | 1f.2f.3a.4e.5e.6b, | 1f.2f.3a.4e.5e.6c, | 1f.2f.3a.4e.5e.6d, | 1f.2f.3a.4e.5e.6e, |

TABLE 7-continued

List of Compounds of Formula (II)

| | | | | |
|---|---|---|---|---|
| 1f.2f.3a.4e.5e.6f, | 1f.2f.3a.4e.5f.6a, | 1f.2f.3a.4e.5f.6b, | 1f.2f.3a.4e.5f.6c, | 1f.2f.3a.4e.5f.6d, |
| 1f.2f.3a.4e.5f.6e, | 1f.2f.3a.4e.5f.6f, | 1f.2f.3a.4f.5a.6a, | 1f.2f.3a.4f.5a.6b, | 1f.2f.3a.4f.5a.6c, |
| 1f.2f.3a.4f.5a.6d, | 1f.2f.3a.4f.5a.6e, | 1f.2f.3a.4f.5a.6f, | 1f.2f.3a.4f.5b.6a, | 1f.2f.3a.4f.5b.6b, |
| 1f.2f.3a.4f.5b.6c, | 1f.2f.3a.4f.5b.6d, | 1f.2f.3a.4f.5b.6e, | 1f.2f.3a.4f.5b.6f, | 1f.2f.3a.4f.5c.6a, |
| 1f.2f.3a.4f.5c.6b, | 1f.2f.3a.4f.5c.6c, | 1f.2f.3a.4f.5c.6d, | 1f.2f.3a.4f.5c.6e, | 1f.2f.3a.4f.5c.6f, |
| 1f.2f.3a.4f.5d.6a, | 1f.2f.3a.4f.5d.6b, | 1f.2f.3a.4f.5d.6c, | 1f.2f.3a.4f.5d.6d, | 1f.2f.3a.4f.5d.6e, |
| 1f.2f.3a.4f.5d.6f, | 1f.2f.3a.4f.5e.6a, | 1f.2f.3a.4f.5e.6b, | 1f.2f.3a.4f.5e.6c, | 1f.2f.3a.4f.5e.6d, |
| 1f.2f.3a.4f.5e.6e, | 1f.2f.3a.4f.5e.6f, | 1f.2f.3a.4f.5f.6a, | 1f.2f.3a.4f.5f.6b, | 1f.2f.3a.4f.5f.6c, |
| 1f.2f.3a.4f.5f.6d, | 1f.2f.3a.4f.5f.6e, | 1f.2f.3a.4f.5f.6f, | 1f.2f.3b.4a.5a.6a, | 1f.2f.3b.4a.5a.6b, |
| 1f.2f.3b.4a.5a.6c, | 1f.2f.3b.4a.5a.6d, | 1f.2f.3b.4a.5a.6e, | 1f.2f.3b.4a.5a.6f, | 1f.2f.3b.4a.5b.6a, |
| 1f.2f.3b.4a.5b.6b, | 1f.2f.3b.4a.5b.6c, | 1f.2f.3b.4a.5b.6d, | 1f.2f.3b.4a.5b.6e, | 1f.2f.3b.4a.5b.6f, |
| 1f.2f.3b.4a.5c.6a, | 1f.2f.3b.4a.5c.6b, | 1f.2f.3b.4a.5c.6c, | 1f.2f.3b.4a.5c.6d, | 1f.2f.3b.4a.5c.6e, |
| 1f.2f.3b.4a.5c.6f, | 1f.2f.3b.4a.5d.6a, | 1f.2f.3b.4a.5d.6b, | 1f.2f.3b.4a.5d.6c, | 1f.2f.3b.4a.5d.6d, |
| 1f.2f.3b.4a.5d.6e, | 1f.2f.3b.4a.5d.6f, | 1f.2f.3b.4a.5e.6a, | 1f.2f.3b.4a.5e.6b, | 1f.2f.3b.4a.5e.6c, |
| 1f.2f.3b.4a.5e.6d, | 1f.2f.3b.4a.5e.6e, | 1f.2f.3b.4a.5e.6f, | 1f.2f.3b.4a.5f.6a, | 1f.2f.3b.4a.5f.6b, |
| 1f.2f.3b.4a.5f.6c, | 1f.2f.3b.4a.5f.6d, | 1f.2f.3b.4a.5f.6e, | 1f.2f.3b.4a.5f.6f, | 1f.2f.3b.4b.5a.6a, |
| 1f.2f.3b.4b.5a.6b, | 1f.2f.3b.4b.5a.6c, | 1f.2f.3b.4b.5a.6d, | 1f.2f.3b.4b.5a.6e, | 1f.2f.3b.4b.5a.6f, |
| 1f.2f.3b.4b.5b.6a, | 1f.2f.3b.4b.5b.6b, | 1f.2f.3b.4b.5b.6c, | 1f.2f.3b.4b.5b.6d, | 1f.2f.3b.4b.5b.6e, |
| 1f.2f.3b.4b.5b.6f, | 1f.2f.3b.4b.5c.6a, | 1f.2f.3b.4b.5c.6b, | 1f.2f.3b.4b.5c.6c, | 1f.2f.3b.4b.5c.6d, |
| 1f.2f.3b.4b.5c.6e, | 1f.2f.3b.4b.5c.6f, | 1f.2f.3b.4b.5d.6a, | 1f.2f.3b.4b.5d.6b, | 1f.2f.3b.4b.5d.6c, |
| 1f.2f.3b.4b.5d.6d, | 1f.2f.3b.4b.5d.6e, | 1f.2f.3b.4b.5d.6f, | 1f.2f.3b.4b.5e.6a, | 1f.2f.3b.4b.5e.6b, |
| 1f.2f.3b.4b.5e.6c, | 1f.2f.3b.4b.5e.6d, | 1f.2f.3b.4b.5e.6e, | 1f.2f.3b.4b.5e.6f, | 1f.2f.3b.4b.5f.6a, |
| 1f.2f.3b.4b.5f.6b, | 1f.2f.3b.4b.5f.6c, | 1f.2f.3b.4b.5f.6d, | 1f.2f.3b.4b.5f.6e, | 1f.2f.3b.4b.5f.6f, |
| 1f.2f.3b.4c.5a.6a, | 1f.2f.3b.4c.5a.6b, | 1f.2f.3b.4c.5a.6c, | 1f.2f.3b.4c.5a.6d, | 1f.2f.3b.4c.5a.6e, |
| 1f.2f.3b.4c.5a.6f, | 1f.2f.3b.4c.5b.6a, | 1f.2f.3b.4c.5b.6b, | 1f.2f.3b.4c.5b.6c, | 1f.2f.3b.4c.5b.6d, |
| 1f.2f.3b.4c.5b.6e, | 1f.2f.3b.4c.5b.6f, | 1f.2f.3b.4c.5c.6a, | 1f.2f.3b.4c.5c.6b, | 1f.2f.3b.4c.5c.6c, |
| 1f.2f.3b.4c.5c.6d, | 1f.2f.3b.4c.5c.6e, | 1f.2f.3b.4c.5c.6f, | 1f.2f.3b.4c.5d.6a, | 1f.2f.3b.4c.5d.6b, |
| 1f.2f.3b.4c.5d.6c, | 1f.2f.3b.4c.5d.6d, | 1f.2f.3b.4c.5d.6e, | 1f.2f.3b.4c.5d.6f, | 1f.2f.3b.4c.5e.6a, |
| 1f.2f.3b.4c.5e.6b, | 1f.2f.3b.4c.5e.6c, | 1f.2f.3b.4c.5e.6d, | 1f.2f.3b.4c.5e.6e, | 1f.2f.3b.4c.5e.6f, |
| 1f.2f.3b.4c.5f.6a, | 1f.2f.3b.4c.5f.6b, | 1f.2f.3b.4c.5f.6c, | 1f.2f.3b.4c.5f.6d, | 1f.2f.3b.4c.5f.6e, |
| 1f.2f.3b.4c.5f.6f, | 1f.2f.3b.4d.5a.6a, | 1f.2f.3b.4d.5a.6b, | 1f.2f.3b.4d.5a.6c, | 1f.2f.3b.4d.5a.6d, |
| 1f.2f.3b.4d.5a.6e, | 1f.2f.3b.4d.5a.6f, | 1f.2f.3b.4d.5b.6a, | 1f.2f.3b.4d.5b.6b, | 1f.2f.3b.4d.5b.6c, |
| 1f.2f.3b.4d.5b.6d, | 1f.2f.3b.4d.5b.6e, | 1f.2f.3b.4d.5b.6f, | 1f.2f.3b.4d.5c.6a, | 1f.2f.3b.4d.5c.6b, |
| 1f.2f.3b.4d.5c.6c, | 1f.2f.3b.4d.5c.6d, | 1f.2f.3b.4d.5c.6e, | 1f.2f.3b.4d.5c.6f, | 1f.2f.3b.4d.5d.6a, |
| 1f.2f.3b.4d.5d.6b, | 1f.2f.3b.4d.5d.6c, | 1f.2f.3b.4d.5d.6d, | 1f.2f.3b.4d.5d.6e, | |
| 1f.2f.3b.4d.5d.6f, | 1f.2f.3b.4d.5e.6a, | 1f.2f.3b.4d.5e.6b, | 1f.2f.3b.4d.5e.6c, | 1f.2f.3b.4d.5e.6d, |
| 1f.2f.3b.4d.5e.6e, | 1f.2f.3b.4d.5e.6f, | 1f.2f.3b.4d.5f.6a, | 1f.2f.3b.4d.5f.6b, | 1f.2f.3b.4d.5f.6c, |
| 1f.2f.3b.4d.5f.6d, | 1f.2f.3b.4d.5f.6e, | 1f.2f.3b.4d.5f.6f, | 1f.2f.3b.4e.5a.6a, | 1f.2f.3b.4e.5a.6b, |
| 1f.2f.3b.4e.5a.6c, | 1f.2f.3b.4e.5a.6d, | 1f.2f.3b.4e.5a.6e, | 1f.2f.3b.4e.5a.6f, | 1f.2f.3b.4e.5b.6a, |
| 1f.2f.3b.4e.5b.6b, | 1f.2f.3b.4e.5b.6c, | 1f.2f.3b.4e.5b.6d, | 1f.2f.3b.4e.5b.6e, | 1f.2f.3b.4e.5b.6f, |
| 1f.2f.3b.4e.5c.6a, | 1f.2f.3b.4e.5c.6b, | 1f.2f.3b.4e.5c.6c, | 1f.2f.3b.4e.5c.6d, | 1f.2f.3b.4e.5c.6e, |
| 1f.2f.3b.4e.5c.6f, | 1f.2f.3b.4e.5d.6a, | 1f.2f.3b.4e.5d.6b, | 1f.2f.3b.4e.5d.6c, | 1f.2f.3b.4e.5d.6d, |
| 1f.2f.3b.4e.5d.6e, | 1f.2f.3b.4e.5d.6f, | 1f.2f.3b.4e.5e.6a, | 1f.2f.3b.4e.5e.6b, | 1f.2f.3b.4e.5e.6c, |
| 1f.2f.3b.4e.5e.6d, | 1f.2f.3b.4e.5e.6e, | 1f.2f.3b.4e.5e.6f, | 1f.2f.3b.4e.5f.6a, | 1f.2f.3b.4e.5f.6b, |
| 1f.2f.3b.4e.5f.6c, | 1f.2f.3b.4e.5f.6d, | 1f.2f.3b.4e.5f.6e, | 1f.2f.3b.4e.5f.6f, | 1f.2f.3b.4f.5a.6a, |
| 1f.2f.3b.4f.5a.6b, | 1f.2f.3b.4f.5a.6c, | 1f.2f.3b.4f.5a.6d, | 1f.2f.3b.4f.5a.6e, | 1f.2f.3b.4f.5a.6f, |
| 1f.2f.3b.4f.5b.6a, | 1f.2f.3b.4f.5b.6b, | 1f.2f.3b.4f.5b.6c, | 1f.2f.3b.4f.5b.6d, | 1f.2f.3b.4f.5b.6e, |
| 1f.2f.3b.4f.5b.6f, | 1f.2f.3b.4f.5c.6a, | 1f.2f.3b.4f.5c.6b, | 1f.2f.3b.4f.5c.6c, | 1f.2f.3b.4f.5c.6d, |
| 1f.2f.3b.4f.5c.6e, | 1f.2f.3b.4f.5c.6f, | 1f.2f.3b.4f.5d.6a, | 1f.2f.3b.4f.5d.6b, | 1f.2f.3b.4f.5d.6c, |
| 1f.2f.3b.4f.5d.6d, | 1f.2f.3b.4f.5d.6e, | 1f.2f.3b.4f.5d.6f, | 1f.2f.3b.4f.5e.6a, | 1f.2f.3b.4f.5e.6b, |
| 1f.2f.3b.4f.5e.6c, | 1f.2f.3b.4f.5e.6d, | 1f.2f.3b.4f.5e.6e, | 1f.2f.3b.4f.5e.6f, | 1f.2f.3b.4f.5f.6a, |
| 1f.2f.3b.4f.5f.6b, | 1f.2f.3b.4f.5f.6c, | 1f.2f.3b.4f.5f.6d, | 1f.2f.3b.4f.5f.6e, | 1f.2f.3b.4f.5f.6f, |
| 1f.2f.3c.4a.5a.6a, | 1f.2f.3c.4a.5a.6b, | 1f.2f.3c.4a.5a.6c, | 1f.2f.3c.4a.5a.6d, | 1f.2f.3c.4a.5a.6e, |
| 1f.2f.3c.4a.5a.6f, | 1f.2f.3c.4a.5b.6a, | 1f.2f.3c.4a.5b.6b, | 1f.2f.3c.4a.5b.6c, | 1f.2f.3c.4a.5b.6d, |
| 1f.2f.3c.4a.5b.6e, | 1f.2f.3c.4a.5b.6f, | 1f.2f.3c.4a.5c.6a, | 1f.2f.3c.4a.5c.6b, | 1f.2f.3c.4a.5c.6c, |
| 1f.2f.3c.4a.5c.6d, | 1f.2f.3c.4a.5c.6e, | 1f.2f.3c.4a.5c.6f, | 1f.2f.3c.4a.5d.6a, | 1f.2f.3c.4a.5d.6b, |
| 1f.2f.3c.4a.5d.6c, | 1f.2f.3c.4a.5d.6d, | 1f.2f.3c.4a.5d.6e, | 1f.2f.3c.4a.5d.6f, | 1f.2f.3c.4a.5e.6a, |
| 1f.2f.3c.4a.5e.6b, | 1f.2f.3c.4a.5e.6c, | 1f.2f.3c.4a.5e.6d, | 1f.2f.3c.4a.5e.6e, | 1f.2f.3c.4a.5e.6f, |
| 1f.2f.3c.4a.5f.6a, | 1f.2f.3c.4a.5f.6b, | 1f.2f.3c.4a.5f.6c, | 1f.2f.3c.4a.5f.6d, | 1f.2f.3c.4a.5f.6e, |
| 1f.2f.3c.4a.5f.6f, | 1f.2f.3c.4b.5a.6a, | 1f.2f.3c.4b.5a.6b, | 1f.2f.3c.4b.5a.6c, | 1f.2f.3c.4b.5a.6d, |
| 1f.2f.3c.4b.5a.6e, | 1f.2f.3c.4b.5a.6f, | 1f.2f.3c.4b.5b.6a, | 1f.2f.3c.4b.5b.6b, | 1f.2f.3c.4b.5b.6c, |
| 1f.2f.3c.4b.5b.6d, | 1f.2f.3c.4b.5b.6e, | 1f.2f.3c.4b.5b.6f, | 1f.2f.3c.4b.5c.6a, | 1f.2f.3c.4b.5c.6b, |
| 1f.2f.3c.4b.5c.6c, | 1f.2f.3c.4b.5c.6d, | 1f.2f.3c.4b.5c.6e, | 1f.2f.3c.4b.5c.6f, | 1f.2f.3c.4b.5d.6a, |
| 1f.2f.3c.4b.5d.6b, | 1f.2f.3c.4b.5d.6c, | 1f.2f.3c.4b.5d.6d, | 1f.2f.3c.4b.5d.6e, | 1f.2f.3c.4b.5d.6f, |
| 1f.2f.3c.4b.5e.6a, | 1f.2f.3c.4b.5e.6b, | 1f.2f.3c.4b.5e.6c, | 1f.2f.3c.4b.5e.6d, | 1f.2f.3c.4b.5e.6e, |
| 1f.2f.3c.4b.5e.6f, | 1f.2f.3c.4b.5f.6a, | 1f.2f.3c.4b.5f.6b, | 1f.2f.3c.4b.5f.6c, | 1f.2f.3c.4b.5f.6d, |
| 1f.2f.3c.4b.5f.6e, | 1f.2f.3c.4b.5f.6f, | 1f.2f.3c.4c.5a.6a, | 1f.2f.3c.4c.5a.6b, | 1f.2f.3c.4c.5a.6c, |
| 1f.2f.3c.4c.5a.6d, | 1f.2f.3c.4c.5a.6e, | 1f.2f.3c.4c.5a.6f, | 1f.2f.3c.4c.5b.6a, | 1f.2f.3c.4c.5b.6b, |
| 1f.2f.3c.4c.5b.6c, | 1f.2f.3c.4c.5b.6d, | 1f.2f.3c.4c.5b.6e, | 1f.2f.3c.4c.5b.6f, | 1f.2f.3c.4c.5c.6a, |
| 1f.2f.3c.4c.5c.6b, | 1f.2f.3c.4c.5c.6c, | 1f.2f.3c.4c.5c.6d, | 1f.2f.3c.4c.5c.6e, | 1f.2f.3c.4c.5c.6f, |
| 1f.2f.3c.4c.5d.6a, | 1f.2f.3c.4c.5d.6b, | 1f.2f.3c.4c.5d.6c, | 1f.2f.3c.4c.5d.6d, | 1f.2f.3c.4c.5d.6e, |
| 1f.2f.3c.4c.5d.6f, | 1f.2f.3c.4c.5e.6a, | 1f.2f.3c.4c.5e.6b, | 1f.2f.3c.4c.5e.6c, | 1f.2f.3c.4c.5e.6d, |
| 1f.2f.3c.4c.5e.6e, | 1f.2f.3c.4c.5e.6f, | 1f.2f.3c.4c.5f.6a, | 1f.2f.3c.4c.5f.6b, | 1f.2f.3c.4c.5f.6c, |
| 1f.2f.3c.4c.5f.6d, | 1f.2f.3c.4c.5f.6e, | 1f.2f.3c.4c.5f.6f, | 1f.2f.3c.4d.5a.6a, | 1f.2f.3c.4d.5a.6b, |
| 1f.2f.3c.4d.5a.6c, | 1f.2f.3c.4d.5a.6d, | 1f.2f.3c.4d.5a.6e, | 1f.2f.3c.4d.5a.6f, | 1f.2f.3c.4d.5b.6a, |
| 1f.2f.3c.4d.5b.6b, | 1f.2f.3c.4d.5b.6c, | 1f.2f.3c.4d.5b.6d, | 1f.2f.3c.4d.5b.6e, | 1f.2f.3c.4d.5b.6f, |
| 1f.2f.3c.4d.5c.6a, | 1f.2f.3c.4d.5c.6b, | 1f.2f.3c.4d.5c.6c, | 1f.2f.3c.4d.5c.6d, | 1f.2f.3c.4d.5c.6e, |
| 1f.2f.3c.4d.5c.6f, | 1f.2f.3c.4d.5d.6a, | 1f.2f.3c.4d.5d.6b, | 1f.2f.3c.4d.5d.6c, | 1f.2f.3c.4d.5d.6d, |

TABLE 7-continued

List of Compounds of Formula (II)

| | | | | |
|---|---|---|---|---|
| 1f.2f.3c.4d.5d.6e, | 1f.2f.3c.4d.5d.6f, | 1f.2f.3c.4d.5e.6a, | 1f.2f.3c.4d.5e.6b, | 1f.2f.3c.4d.5e.6c, |
| 1f.2f.3c.4d.5e.6d, | 1f.2f.3c.4d.5e.6e, | 1f.2f.3c.4d.5e.6f, | 1f.2f.3c.4d.5f.6a, | 1f.2f.3c.4d.5f.6b, |
| 1f.2f.3c.4d.5f.6c, | 1f.2f.3c.4d.5f.6d, | 1f.2f.3c.4d.5f.6e, | 1f.2f.3c.4d.5f.6f, | 1f.2f.3c.4e.5a.6a, |
| 1f.2f.3c.4e.5a.6b, | 1f.2f.3c.4e.5a.6c, | 1f.2f.3c.4e.5a.6d, | 1f.2f.3c.4e.5a.6e, | 1f.2f.3c.4e.5a.6f, |
| 1f.2f.3c.4e.5b.6a, | 1f.2f.3c.4e.5b.6b, | 1f.2f.3c.4e.5b.6c, | 1f.2f.3c.4e.5b.6d, | 1f.2f.3c.4e.5b.6e, |
| 1f.2f.3c.4e.5b.6f, | 1f.2f.3c.4e.5c.6a, | 1f.2f.3c.4e.5c.6b, | 1f.2f.3c.4e.5c.6c, | 1f.2f.3c.4e.5c.6d, |
| 1f.2f.3c.4e.5c.6e, | 1f.2f.3c.4e.5c.6f, | 1f.2f.3c.4e.5d.6a, | 1f.2f.3c.4e.5d.6b, | 1f.2f.3c.4e.5d.6c, |
| 1f.2f.3c.4e.5d.6d, | 1f.2f.3c.4e.5d.6e, | 1f.2f.3c.4e.5d.6f, | 1f.2f.3c.4e.5e.6a, | 1f.2f.3c.4e.5e.6b, |
| 1f.2f.3c.4e.5e.6c, | 1f.2f.3c.4e.5e.6d, | 1f.2f.3c.4e.5e.6e, | 1f.2f.3c.4e.5e.6f, | 1f.2f.3c.4e.5f.6a, |
| 1f.2f.3c.4e.5f.6b, | 1f.2f.3c.4e.5f.6c, | 1f.2f.3c.4e.5f.6d, | 1f.2f.3c.4e.5f.6e, | 1f.2f.3c.4e.5f.6f, |
| 1f.2f.3c.4f.5a.6a, | 1f.2f.3c.4f.5a.6b, | 1f.2f.3c.4f.5a.6c, | 1f.2f.3c.4f.5a.6d, | 1f.2f.3c.4f.5a.6e, |
| 1f.2f.3c.4f.5a.6f, | 1f.2f.3c.4f.5b.6a, | 1f.2f.3c.4f.5b.6b, | 1f.2f.3c.4f.5b.6c, | 1f.2f.3c.4f.5b.6d, |
| 1f.2f.3c.4f.5b.6e, | 1f.2f.3c.4f.5b.6f, | 1f.2f.3c.4f.5c.6a, | 1f.2f.3c.4f.5c.6b, | 1f.2f.3c.4f.5c.6c, |
| 1f.2f.3c.4f.5c.6d, | 1f.2f.3c.4f.5c.6e, | 1f.2f.3c.4f.5c.6f, | 1f.2f.3c.4f.5d.6a, | 1f.2f.3c.4f.5d.6b, |
| 1f.2f.3c.4f.5d.6c, | 1f.2f.3c.4f.5d.6d, | 1f.2f.3c.4f.5d.6e, | 1f.2f.3c.4f.5d.6f, | 1f.2f.3c.4f.5e.6a, |
| 1f.2f.3c.4f.5e.6b, | 1f.2f.3c.4f.5e.6c, | 1f.2f.3c.4f.5e.6d, | 1f.2f.3c.4f.5e.6e, | 1f.2f.3c.4f.5e.6f, |
| 1f.2f.3c.4f.5f.6a, | 1f.2f.3c.4f.5f.6b, | 1f.2f.3c.4f.5f.6c, | 1f.2f.3c.4f.5f.6d, | 1f.2f.3c.4f.5f.6e, |
| 1f.2f.3c.4f.5f.6f, | 1f.2f.3d.4a.5a.6a, | 1f.2f.3d.4a.5a.6b, | 1f.2f.3d.4a.5a.6c, | 1f.2f.3d.4a.5a.6d, |
| 1f.2f.3d.4a.5a.6e, | 1f.2f.3d.4a.5a.6f, | 1f.2f.3d.4a.5b.6a, | 1f.2f.3d.4a.5b.6b, | 1f.2f.3d.4a.5b.6c, |
| 1f.2f.3d.4a.5b.6d, | 1f.2f.3d.4a.5b.6e, | 1f.2f.3d.4a.5b.6f, | 1f.2f.3d.4a.5c.6a, | 1f.2f.3d.4a.5c.6b, |
| 1f.2f.3d.4a.5c.6c, | 1f.2f.3d.4a.5c.6d, | 1f.2f.3d.4a.5c.6e, | 1f.2f.3d.4a.5c.6f, | 1f.2f.3d.4a.5d.6a, |
| 1f.2f.3d.4a.5d.6b, | 1f.2f.3d.4a.5d.6c, | 1f.2f.3d.4a.5d.6d, | 1f.2f.3d.4a.5d.6e, | 1f.2f.3d.4a.5d.6f, |
| 1f.2f.3d.4a.5e.6a, | 1f.2f.3d.4a.5e.6b, | 1f.2f.3d.4a.5e.6c, | 1f.2f.3d.4a.5e.6d, | 1f.2f.3d.4a.5e.6e, |
| 1f.2f.3d.4a.5e.6f, | 1f.2f.3d.4a.5f.6a, | 1f.2f.3d.4a.5f.6b, | 1f.2f.3d.4a.5f.6c, | 1f.2f.3d.4a.5f.6d, |
| 1f.2f.3d.4a.5f.6e, | 1f.2f.3d.4a.5f.6f, | 1f.2f.3d.4b.5a.6a, | 1f.2f.3d.4b.5a.6b, | 1f.2f.3d.4b.5a.6c, |
| 1f.2f.3d.4b.5a.6d, | 1f.2f.3d.4b.5a.6e, | 1f.2f.3d.4b.5a.6f, | 1f.2f.3d.4b.5b.6a, | 1f.2f.3d.4b.5b.6b, |
| 1f.2f.3d.4b.5b.6c, | 1f.2f.3d.4b.5b.6d, | 1f.2f.3d.4b.5b.6e, | 1f.2f.3d.4b.5b.6f, | 1f.2f.3d.4b.5c.6a, |
| 1f.2f.3d.4b.5c.6b, | 1f.2f.3d.4b.5c.6c, | 1f.2f.3d.4b.5c.6d, | 1f.2f.3d.4b.5c.6e, | 1f.2f.3d.4b.5c.6f, |
| 1f.2f.3d.4b.5d.6a, | 1f.2f.3d.4b.5d.6b, | 1f.2f.3d.4b.5d.6c, | 1f.2f.3d.4b.5d.6d, | |
| 1f.2f.3d.4b.5d.6e, | 1f.2f.3d.4b.5d.6f, | 1f.2f.3d.4b.5e.6a, | 1f.2f.3d.4b.5e.6b, | 1f.2f.3d.4b.5e.6c, |
| 1f.2f.3d.4b.5e.6d, | 1f.2f.3d.4b.5e.6e, | 1f.2f.3d.4b.5e.6f, | 1f.2f.3d.4b.5f.6a, | 1f.2f.3d.4b.5f.6b, |
| 1f.2f.3d.4b.5f.6c, | 1f.2f.3d.4b.5f.6d, | 1f.2f.3d.4b.5f.6e, | 1f.2f.3d.4b.5f.6f, | 1f.2f.3d.4c.5a.6a, |
| 1f.2f.3d.4c.5a.6b, | 1f.2f.3d.4c.5a.6c, | 1f.2f.3d.4c.5a.6d, | 1f.2f.3d.4c.5a.6e, | 1f.2f.3d.4c.5a.6f, |
| 1f.2f.3d.4c.5b.6a, | 1f.2f.3d.4c.5b.6b, | 1f.2f.3d.4c.5b.6c, | 1f.2f.3d.4c.5b.6d, | 1f.2f.3d.4c.5b.6e, |
| 1f.2f.3d.4c.5b.6f, | 1f.2f.3d.4c.5c.6a, | 1f.2f.3d.4c.5c.6b, | 1f.2f.3d.4c.5c.6c, | 1f.2f.3d.4c.5c.6d, |
| 1f.2f.3d.4c.5c.6e, | 1f.2f.3d.4c.5c.6f, | 1f.2f.3d.4c.5d.6a, | 1f.2f.3d.4c.5d.6b, | 1f.2f.3d.4c.5d.6c, |
| 1f.2f.3d.4c.5d.6d, | 1f.2f.3d.4c.5d.6e, | 1f.2f.3d.4c.5d.6f, | 1f.2f.3d.4c.5e.6a, | 1f.2f.3d.4c.5e.6b, |
| 1f.2f.3d.4c.5e.6c, | 1f.2f.3d.4c.5e.6d, | 1f.2f.3d.4c.5e.6e, | 1f.2f.3d.4c.5e.6f, | 1f.2f.3d.4c.5f.6a, |
| 1f.2f.3d.4c.5f.6b, | 1f.2f.3d.4c.5f.6c, | 1f.2f.3d.4c.5f.6d, | 1f.2f.3d.4c.5f.6e, | 1f.2f.3d.4c.5f.6f, |
| 1f.2f.3d.4d.5a.6a, | 1f.2f.3d.4d.5a.6b, | 1f.2f.3d.4d.5a.6c, | 1f.2f.3d.4d.5a.6d, | |
| 1f.2f.3d.4d.5a.6e, | 1f.2f.3d.4d.5a.6f, | 1f.2f.3d.4d.5b.6a, | 1f.2f.3d.4d.5b.6b, | |
| 1f.2f.3d.4d.5b.6c, | 1f.2f.3d.4d.5b.6d, | 1f.2f.3d.4d.5b.6e, | 1f.2f.3d.4d.5b.6f, | |
| 1f.2f.3d.4d.5c.6a, | 1f.2f.3d.4d.5c.6b, | 1f.2f.3d.4d.5c.6c, | 1f.2f.3d.4d.5c.6d, | 1f.2f.3d.4d.5c.6e, |
| 1f.2f.3d.4d.5c.6f, | 1f.2f.3d.4d.5d.6a, | 1f.2f.3d.4d.5d.6b, | 1f.2f.3d.4d.5d.6c, | |
| 1f.2f.3d.4d.5d.6d, | 1f.2f.3d.4d.5d.6e, | 1f.2f.3d.4d.5d.6f, | 1f.2f.3d.4d.5e.6a, | |
| 1f.2f.3d.4d.5e.6b, | 1f.2f.3d.4d.5e.6c, | 1f.2f.3d.4d.5e.6d, | 1f.2f.3d.4d.5e.6e, | 1f.2f.3d.4d.5e.6f, |
| 1f.2f.3d.4d.5f.6a, | 1f.2f.3d.4d.5f.6b, | 1f.2f.3d.4d.5f.6c, | 1f.2f.3d.4d.5f.6d, | 1f.2f.3d.4d.5f.6e, |
| 1f.2f.3d.4d.5f.6f, | 1f.2f.3d.4e.5a.6a, | 1f.2f.3d.4e.5a.6b, | 1f.2f.3d.4e.5a.6c, | 1f.2f.3d.4e.5a.6d, |
| 1f.2f.3d.4e.5a.6e, | 1f.2f.3d.4e.5a.6f, | 1f.2f.3d.4e.5b.6a, | 1f.2f.3d.4e.5b.6b, | 1f.2f.3d.4e.5b.6c, |
| 1f.2f.3d.4e.5b.6d, | 1f.2f.3d.4e.5b.6e, | 1f.2f.3d.4e.5b.6f, | 1f.2f.3d.4e.5c.6a, | 1f.2f.3d.4e.5c.6b, |
| 1f.2f.3d.4e.5c.6c, | 1f.2f.3d.4e.5c.6d, | 1f.2f.3d.4e.5c.6e, | 1f.2f.3d.4e.5c.6f, | 1f.2f.3d.4e.5d.6a, |
| 1f.2f.3d.4e.5d.6b, | 1f.2f.3d.4e.5d.6c, | 1f.2f.3d.4e.5d.6d, | 1f.2f.3d.4e.5d.6e, | 1f.2f.3d.4e.5d.6f, |
| 1f.2f.3d.4e.5e.6a, | 1f.2f.3d.4e.5e.6b, | 1f.2f.3d.4e.5e.6c, | 1f.2f.3d.4e.5e.6d, | 1f.2f.3d.4e.5e.6e, |
| 1f.2f.3d.4e.5e.6f, | 1f.2f.3d.4e.5f.6a, | 1f.2f.3d.4e.5f.6b, | 1f.2f.3d.4e.5f.6c, | 1f.2f.3d.4e.5f.6d, |
| 1f.2f.3d.4e.5f.6e, | 1f.2f.3d.4e.5f.6f, | 1f.2f.3d.4f.5a.6a, | 1f.2f.3d.4f.5a.6b, | 1f.2f.3d.4f.5a.6c, |
| 1f.2f.3d.4f.5a.6d, | 1f.2f.3d.4f.5a.6e, | 1f.2f.3d.4f.5a.6f, | 1f.2f.3d.4f.5b.6a, | 1f.2f.3d.4f.5b.6b, |
| 1f.2f.3d.4f.5b.6c, | 1f.2f.3d.4f.5b.6d, | 1f.2f.3d.4f.5b.6e, | 1f.2f.3d.4f.5b.6f, | 1f.2f.3d.4f.5c.6a, |
| 1f.2f.3d.4f.5c.6b, | 1f.2f.3d.4f.5c.6c, | 1f.2f.3d.4f.5c.6d, | 1f.2f.3d.4f.5c.6e, | 1f.2f.3d.4f.5c.6f, |
| 1f.2f.3d.4f.5d.6a, | 1f.2f.3d.4f.5d.6b, | 1f.2f.3d.4f.5d.6c, | 1f.2f.3d.4f.5d.6d, | 1f.2f.3d.4f.5d.6e, |
| 1f.2f.3d.4f.5d.6f, | 1f.2f.3d.4f.5e.6a, | 1f.2f.3d.4f.5e.6b, | 1f.2f.3d.4f.5e.6c, | 1f.2f.3d.4f.5e.6d, |
| 1f.2f.3d.4f.5e.6e, | 1f.2f.3d.4f.5e.6f, | 1f.2f.3d.4f.5f.6a, | 1f.2f.3d.4f.5f.6b, | 1f.2f.3d.4f.5f.6c, |
| 1f.2f.3d.4f.5f.6d, | 1f.2f.3d.4f.5f.6e, | 1f.2f.3d.4f.5f.6f, | 1f.2f.3e.4a.5a.6a, | 1f.2f.3e.4a.5a.6b, |
| 1f.2f.3e.4a.5a.6c, | 1f.2f.3e.4a.5a.6d, | 1f.2f.3e.4a.5a.6e, | 1f.2f.3e.4a.5a.6f, | 1f.2f.3e.4a.5b.6a, |
| 1f.2f.3e.4a.5b.6b, | 1f.2f.3e.4a.5b.6c, | 1f.2f.3e.4a.5b.6d, | 1f.2f.3e.4a.5b.6e, | 1f.2f.3e.4a.5b.6f, |
| 1f.2f.3e.4a.5c.6a, | 1f.2f.3e.4a.5c.6b, | 1f.2f.3e.4a.5c.6c, | 1f.2f.3e.4a.5c.6d, | 1f.2f.3e.4a.5c.6e, |
| 1f.2f.3e.4a.5c.6f, | 1f.2f.3e.4a.5d.6a, | 1f.2f.3e.4a.5d.6b, | 1f.2f.3e.4a.5d.6c, | 1f.2f.3e.4a.5d.6d, |
| 1f.2f.3e.4a.5d.6e, | 1f.2f.3e.4a.5d.6f, | 1f.2f.3e.4a.5e.6a, | 1f.2f.3e.4a.5e.6b, | 1f.2f.3e.4a.5e.6c, |
| 1f.2f.3e.4a.5e.6d, | 1f.2f.3e.4a.5e.6e, | 1f.2f.3e.4a.5e.6f, | 1f.2f.3e.4a.5f.6a, | 1f.2f.3e.4a.5f.6b, |
| 1f.2f.3e.4a.5f.6c, | 1f.2f.3e.4a.5f.6d, | 1f.2f.3e.4a.5f.6e, | 1f.2f.3e.4a.5f.6f, | 1f.2f.3e.4b.5a.6a, |
| 1f.2f.3e.4b.5a.6b, | 1f.2f.3e.4b.5a.6c, | 1f.2f.3e.4b.5a.6d, | 1f.2f.3e.4b.5a.6e, | 1f.2f.3e.4b.5a.6f, |
| 1f.2f.3e.4b.5b.6a, | 1f.2f.3e.4b.5b.6b, | 1f.2f.3e.4b.5b.6c, | 1f.2f.3e.4b.5b.6d, | 1f.2f.3e.4b.5b.6e, |
| 1f.2f.3e.4b.5b.6f, | 1f.2f.3e.4b.5c.6a, | 1f.2f.3e.4b.5c.6b, | 1f.2f.3e.4b.5c.6c, | 1f.2f.3e.4b.5c.6d, |
| 1f.2f.3e.4b.5c.6e, | 1f.2f.3e.4b.5c.6f, | 1f.2f.3e.4b.5d.6a, | 1f.2f.3e.4b.5d.6b, | 1f.2f.3e.4b.5d.6c, |
| 1f.2f.3e.4b.5d.6d, | 1f.2f.3e.4b.5d.6e, | 1f.2f.3e.4b.5d.6f, | 1f.2f.3e.4b.5e.6a, | 1f.2f.3e.4b.5e.6b, |
| 1f.2f.3e.4b.5e.6c, | 1f.2f.3e.4b.5e.6d, | 1f.2f.3e.4b.5e.6e, | 1f.2f.3e.4b.5e.6f, | 1f.2f.3e.4b.5f.6a, |
| 1f.2f.3e.4b.5f.6b, | 1f.2f.3e.4b.5f.6c, | 1f.2f.3e.4b.5f.6d, | 1f.2f.3e.4b.5f.6e, | 1f.2f.3e.4b.5f.6f, |
| 1f.2f.3e.4c.5a.6a, | 1f.2f.3e.4c.5a.6b, | 1f.2f.3e.4c.5a.6c, | 1f.2f.3e.4c.5a.6d, | 1f.2f.3e.4c.5a.6e, |
| 1f.2f.3e.4c.5a.6f, | 1f.2f.3e.4c.5b.6a, | 1f.2f.3e.4c.5b.6b, | 1f.2f.3e.4c.5b.6c, | 1f.2f.3e.4c.5b.6d, |

TABLE 7-continued

List of Compounds of Formula (II)

| | | | | |
|---|---|---|---|---|
| 1f.2f.3e.4c.5b.6e, | 1f.2f.3e.4c.5b.6f, | 1f.2f.3e.4c.5c.6a, | 1f.2f.3e.4c.5c.6b, | 1f.2f.3e.4c.5c.6c, |
| 1f.2f.3e.4c.5c.6d, | 1f.2f.3e.4c.5c.6e, | 1f.2f.3e.4c.5c.6f, | 1f.2f.3e.4c.5d.6a, | 1f.2f.3e.4c.5d.6b, |
| 1f.2f.3e.4c.5d.6c, | 1f.2f.3e.4c.5d.6d, | 1f.2f.3e.4c.5d.6e, | 1f.2f.3e.4c.5d.6f, | 1f.2f.3e.4c.5e.6a, |
| 1f.2f.3e.4c.5e.6b, | 1f.2f.3e.4c.5e.6c, | 1f.2f.3e.4c.5e.6d, | 1f.2f.3e.4c.5e.6e, | 1f.2f.3e.4c.5e.6f, |
| 1f.2f.3e.4c.5f.6a, | 1f.2f.3e.4c.5f.6b, | 1f.2f.3e.4c.5f.6c, | 1f.2f.3e.4c.5f.6d, | 1f.2f.3e.4c.5f.6e, |
| 1f.2f.3e.4c.5f.6f, | 1f.2f.3e.4d.5a.6a, | 1f.2f.3e.4d.5a.6b, | 1f.2f.3e.4d.5a.6c, | 1f.2f.3e.4d.5a.6d, |
| 1f.2f.3e.4d.5a.6e, | 1f.2f.3e.4d.5a.6f, | 1f.2f.3e.4d.5b.6a, | 1f.2f.3e.4d.5b.6b, | 1f.2f.3e.4d.5b.6c, |
| 1f.2f.3e.4d.5b.6d, | 1f.2f.3e.4d.5b.6e, | 1f.2f.3e.4d.5b.6f, | 1f.2f.3e.4d.5c.6a, | 1f.2f.3e.4d.5c.6b, |
| 1f.2f.3e.4d.5c.6c, | 1f.2f.3e.4d.5c.6d, | 1f.2f.3e.4d.5c.6e, | 1f.2f.3e.4d.5c.6f, | 1f.2f.3e.4d.5d.6a, |
| 1f.2f.3e.4d.5d.6b, | 1f.2f.3e.4d.5d.6c, | 1f.2f.3e.4d.5d.6d, | 1f.2f.3e.4d.5d.6e, | 1f.2f.3e.4d.5d.6f, |
| 1f.2f.3e.4d.5e.6a, | 1f.2f.3e.4d.5e.6b, | 1f.2f.3e.4d.5e.6c, | 1f.2f.3e.4d.5e.6d, | 1f.2f.3e.4d.5e.6e, |
| 1f.2f.3e.4d.5e.6f, | 1f.2f.3e.4d.5f.6a, | 1f.2f.3e.4d.5f.6b, | 1f.2f.3e.4d.5f.6c, | 1f.2f.3e.4d.5f.6d, |
| 1f.2f.3e.4d.5f.6e, | 1f.2f.3e.4d.5f.6f, | 1f.2f.3e.4e.5a.6a, | 1f.2f.3e.4e.5a.6b, | 1f.2f.3e.4e.5a.6c, |
| 1f.2f.3e.4e.5a.6d, | 1f.2f.3e.4e.5a.6e, | 1f.2f.3e.4e.5a.6f, | 1f.2f.3e.4e.5b.6a, | 1f.2f.3e.4e.5b.6b, |
| 1f.2f.3e.4e.5b.6c, | 1f.2f.3e.4e.5b.6d, | 1f.2f.3e.4e.5b.6e, | 1f.2f.3e.4e.5b.6f, | 1f.2f.3e.4e.5c.6a, |
| 1f.2f.3e.4e.5c.6b, | 1f.2f.3e.4e.5c.6c, | 1f.2f.3e.4e.5c.6d, | 1f.2f.3e.4e.5c.6e, | 1f.2f.3e.4e.5c.6f, |
| 1f.2f.3e.4e.5d.6a, | 1f.2f.3e.4e.5d.6b, | 1f.2f.3e.4e.5d.6c, | 1f.2f.3e.4e.5d.6d, | 1f.2f.3e.4e.5d.6e, |
| 1f.2f.3e.4e.5d.6f, | 1f.2f.3e.4e.5e.6a, | 1f.2f.3e.4e.5e.6b, | 1f.2f.3e.4e.5e.6c, | 1f.2f.3e.4e.5e.6d, |
| 1f.2f.3e.4e.5e.6e, | 1f.2f.3e.4e.5e.6f, | 1f.2f.3e.4e.5f.6a, | 1f.2f.3e.4e.5f.6b, | 1f.2f.3e.4e.5f.6c, |
| 1f.2f.3e.4e.5f.6d, | 1f.2f.3e.4e.5f.6e, | 1f.2f.3e.4e.5f.6f, | 1f.2f.3e.4f.5a.6a, | 1f.2f.3e.4f.5a.6b, |
| 1f.2f.3e.4f.5a.6c, | 1f.2f.3e.4f.5a.6d, | 1f.2f.3e.4f.5a.6e, | 1f.2f.3e.4f.5a.6f, | 1f.2f.3e.4f.5b.6a, |
| 1f.2f.3e.4f.5b.6b, | 1f.2f.3e.4f.5b.6c, | 1f.2f.3e.4f.5b.6d, | 1f.2f.3e.4f.5b.6e, | 1f.2f.3e.4f.5b.6f, |
| 1f.2f.3e.4f.5c.6a, | 1f.2f.3e.4f.5c.6b, | 1f.2f.3e.4f.5c.6c, | 1f.2f.3e.4f.5c.6d, | 1f.2f.3e.4f.5c.6e, |
| 1f.2f.3e.4f.5c.6f, | 1f.2f.3e.4f.5d.6a, | 1f.2f.3e.4f.5d.6b, | 1f.2f.3e.4f.5d.6c, | 1f.2f.3e.4f.5d.6d, |
| 1f.2f.3e.4f.5d.6e, | 1f.2f.3e.4f.5d.6f, | 1f.2f.3e.4f.5e.6a, | 1f.2f.3e.4f.5e.6b, | 1f.2f.3e.4f.5e.6c, |
| 1f.2f.3e.4f.5e.6d, | 1f.2f.3e.4f.5e.6e, | 1f.2f.3e.4f.5e.6f, | 1f.2f.3e.4f.5f.6a, | 1f.2f.3e.4f.5f.6b, |
| 1f.2f.3e.4f.5f.6c, | 1f.2f.3e.4f.5f.6d, | 1f.2f.3e.4f.5f.6e, | 1f.2f.3e.4f.5f.6f, | 1f.2f.3f.4a.5a.6a, |
| 1f.2f.3f.4a.5a.6b, | 1f.2f.3f.4a.5a.6c, | 1f.2f.3f.4a.5a.6d, | 1f.2f.3f.4a.5a.6e, | 1f.2f.3f.4a.5a.6f, |
| 1f.2f.3f.4a.5b.6a, | 1f.2f.3f.4a.5b.6b, | 1f.2f.3f.4a.5b.6c, | 1f.2f.3f.4a.5b.6d, | 1f.2f.3f.4a.5b.6e, |
| 1f.2f.3f.4a.5b.6f, | 1f.2f.3f.4a.5c.6a, | 1f.2f.3f.4a.5c.6b, | 1f.2f.3f.4a.5c.6c, | 1f.2f.3f.4a.5c.6d, |
| 1f.2f.3f.4a.5c.6e, | 1f.2f.3f.4a.5c.6f, | 1f.2f.3f.4a.5d.6a, | 1f.2f.3f.4a.5d.6b, | 1f.2f.3f.4a.5d.6c, |
| 1f.2f.3f.4a.5d.6d, | 1f.2f.3f.4a.5d.6e, | 1f.2f.3f.4a.5d.6f, | 1f.2f.3f.4a.5e.6a, | 1f.2f.3f.4a.5e.6b, |
| 1f.2f.3f.4a.5e.6c, | 1f.2f.3f.4a.5e.6d, | 1f.2f.3f.4a.5e.6e, | 1f.2f.3f.4a.5e.6f, | 1f.2f.3f.4a.5f.6a, |
| 1f.2f.3f.4a.5f.6b, | 1f.2f.3f.4a.5f.6c, | 1f.2f.3f.4a.5f.6d, | 1f.2f.3f.4a.5f.6e, | 1f.2f.3f.4a.5f.6f, |
| 1f.2f.3f.4b.5a.6a, | 1f.2f.3f.4b.5a.6b, | 1f.2f.3f.4b.5a.6c, | 1f.2f.3f.4b.5a.6d, | 1f.2f.3f.4b.5a.6e, |
| 1f.2f.3f.4b.5a.6f, | 1f.2f.3f.4b.5b.6a, | 1f.2f.3f.4b.5b.6b, | 1f.2f.3f.4b.5b.6c, | 1f.2f.3f.4b.5b.6d, |
| 1f.2f.3f.4b.5b.6e, | 1f.2f.3f.4b.5b.6f, | 1f.2f.3f.4b.5c.6a, | 1f.2f.3f.4b.5c.6b, | 1f.2f.3f.4b.5c.6c, |
| 1f.2f.3f.4b.5c.6d, | 1f.2f.3f.4b.5c.6e, | 1f.2f.3f.4b.5c.6f, | 1f.2f.3f.4b.5d.6a, | 1f.2f.3f.4b.5d.6b, |
| 1f.2f.3f.4b.5d.6c, | 1f.2f.3f.4b.5d.6d, | 1f.2f.3f.4b.5d.6e, | 1f.2f.3f.4b.5d.6f, | 1f.2f.3f.4b.5e.6a, |
| 1f.2f.3f.4b.5e.6b, | 1f.2f.3f.4b.5e.6c, | 1f.2f.3f.4b.5e.6d, | 1f.2f.3f.4b.5e.6e, | 1f.2f.3f.4b.5e.6f, |
| 1f.2f.3f.4b.5f.6a, | 1f.2f.3f.4b.5f.6b, | 1f.2f.3f.4b.5f.6c, | 1f.2f.3f.4b.5f.6d, | 1f.2f.3f.4b.5f.6e, |
| 1f.2f.3f.4b.5f.6f, | 1f.2f.3f.4c.5a.6a, | 1f.2f.3f.4c.5a.6b, | 1f.2f.3f.4c.5a.6c, | 1f.2f.3f.4c.5a.6d, |
| 1f.2f.3f.4c.5a.6e, | 1f.2f.3f.4c.5a.6f, | 1f.2f.3f.4c.5b.6a, | 1f.2f.3f.4c.5b.6b, | 1f.2f.3f.4c.5b.6c, |
| 1f.2f.3f.4c.5b.6d, | 1f.2f.3f.4c.5b.6e, | 1f.2f.3f.4c.5b.6f, | 1f.2f.3f.4c.5c.6a, | 1f.2f.3f.4c.5c.6b, |
| 1f.2f.3f.4c.5c.6c, | 1f.2f.3f.4c.5c.6d, | 1f.2f.3f.4c.5c.6e, | 1f.2f.3f.4c.5c.6f, | 1f.2f.3f.4c.5d.6a, |
| 1f.2f.3f.4c.5d.6b, | 1f.2f.3f.4c.5d.6c, | 1f.2f.3f.4c.5d.6d, | 1f.2f.3f.4c.5d.6e, | 1f.2f.3f.4c.5d.6f, |
| 1f.2f.3f.4c.5e.6a, | 1f.2f.3f.4c.5e.6b, | 1f.2f.3f.4c.5e.6c, | 1f.2f.3f.4c.5e.6d, | 1f.2f.3f.4c.5e.6e, |
| 1f.2f.3f.4c.5e.6f, | 1f.2f.3f.4c.5f.6a, | 1f.2f.3f.4c.5f.6b, | 1f.2f.3f.4c.5f.6c, | 1f.2f.3f.4c.5f.6d, |
| 1f.2f.3f.4c.5f.6e, | 1f.2f.3f.4c.5f.6f, | 1f.2f.3f.4d.5a.6a, | 1f.2f.3f.4d.5a.6b, | 1f.2f.3f.4d.5a.6c, |
| 1f.2f.3f.4d.5a.6d, | 1f.2f.3f.4d.5a.6e, | 1f.2f.3f.4d.5a.6f, | 1f.2f.3f.4d.5b.6a, | 1f.2f.3f.4d.5b.6b, |
| 1f.2f.3f.4d.5b.6c, | 1f.2f.3f.4d.5b.6d, | 1f.2f.3f.4d.5b.6e, | 1f.2f.3f.4d.5b.6f, | 1f.2f.3f.4d.5c.6a, |
| 1f.2f.3f.4d.5c.6b, | 1f.2f.3f.4d.5c.6c, | 1f.2f.3f.4d.5c.6d, | 1f.2f.3f.4d.5c.6e, | 1f.2f.3f.4d.5c.6f, |
| 1f.2f.3f.4d.5d.6a, | 1f.2f.3f.4d.5d.6b, | 1f.2f.3f.4d.5d.6c, | 1f.2f.3f.4d.5d.6d, | 1f.2f.3f.4d.5d.6e, |
| 1f.2f.3f.4d.5d.6f, | 1f.2f.3f.4d.5e.6a, | 1f.2f.3f.4d.5e.6b, | 1f.2f.3f.4d.5e.6c, | 1f.2f.3f.4d.5e.6d, |
| 1f.2f.3f.4d.5e.6e, | 1f.2f.3f.4d.5e.6f, | 1f.2f.3f.4d.5f.6a, | 1f.2f.3f.4d.5f.6b, | 1f.2f.3f.4d.5f.6c, |
| 1f.2f.3f.4d.5f.6d, | 1f.2f.3f.4d.5f.6e, | 1f.2f.3f.4d.5f.6f, | 1f.2f.3f.4e.5a.6a, | 1f.2f.3f.4e.5a.6b, |
| 1f.2f.3f.4e.5a.6c, | 1f.2f.3f.4e.5a.6d, | 1f.2f.3f.4e.5a.6e, | 1f.2f.3f.4e.5a.6f, | 1f.2f.3f.4e.5b.6a, |
| 1f.2f.3f.4e.5b.6b, | 1f.2f.3f.4e.5b.6c, | 1f.2f.3f.4e.5b.6d, | 1f.2f.3f.4e.5b.6e, | 1f.2f.3f.4e.5b.6f, |
| 1f.2f.3f.4e.5c.6a, | 1f.2f.3f.4e.5c.6b, | 1f.2f.3f.4e.5c.6c, | 1f.2f.3f.4e.5c.6d, | 1f.2f.3f.4e.5c.6e, |
| 1f.2f.3f.4e.5c.6f, | 1f.2f.3f.4e.5d.6a, | 1f.2f.3f.4e.5d.6b, | 1f.2f.3f.4e.5d.6c, | 1f.2f.3f.4e.5d.6d, |
| 1f.2f.3f.4e.5d.6e, | 1f.2f.3f.4e.5d.6f, | 1f.2f.3f.4e.5e.6a, | 1f.2f.3f.4e.5e.6b, | 1f.2f.3f.4e.5e.6c, |
| 1f.2f.3f.4e.5e.6d, | 1f.2f.3f.4e.5e.6e, | 1f.2f.3f.4e.5e.6f, | 1f.2f.3f.4e.5f.6a, | 1f.2f.3f.4e.5f.6b, |
| 1f.2f.3f.4e.5f.6c, | 1f.2f.3f.4e.5f.6d, | 1f.2f.3f.4e.5f.6e, | 1f.2f.3f.4e.5f.6f, | 1f.2f.3f.4f.5a.6a, |
| 1f.2f.3f.4f.5a.6b, | 1f.2f.3f.4f.5a.6c, | 1f.2f.3f.4f.5a.6d, | 1f.2f.3f.4f.5a.6e, | 1f.2f.3f.4f.5a.6f, |
| 1f.2f.3f.4f.5b.6a, | 1f.2f.3f.4f.5b.6b, | 1f.2f.3f.4f.5b.6c, | 1f.2f.3f.4f.5b.6d, | 1f.2f.3f.4f.5b.6e, |
| 1f.2f.3f.4f.5b.6f, | 1f.2f.3f.4f.5c.6a, | 1f.2f.3f.4f.5c.6b, | 1f.2f.3f.4f.5c.6c, | 1f.2f.3f.4f.5c.6d, |
| 1f.2f.3f.4f.5c.6e, | 1f.2f.3f.4f.5c.6f, | 1f.2f.3f.4f.5d.6a, | 1f.2f.3f.4f.5d.6b, | 1f.2f.3f.4f.5d.6c, |
| 1f.2f.3f.4f.5d.6d, | 1f.2f.3f.4f.5d.6e, | 1f.2f.3f.4f.5d.6f, | 1f.2f.3f.4f.5e.6a, | 1f.2f.3f.4f.5e.6b, |
| 1f.2f.3f.4f.5e.6c, | 1f.2f.3f.4f.5e.6d, | 1f.2f.3f.4f.5e.6e, | 1f.2f.3f.4f.5e.6f, | 1f.2f.3f.4f.5f.6a, |
| 1f.2f.3f.4f.5f.6b, | 1f.2f.3f.4f.5f.6c, | 1f.2f.3f.4f.5f.6d, | 1f.2f.3f.4f.5f.6e, | 1f.2f.3f.4f.5f.6f, |

EXAMPLES

Scheme 1

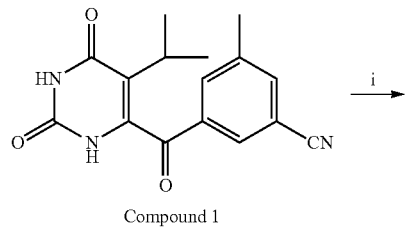

Compound 1

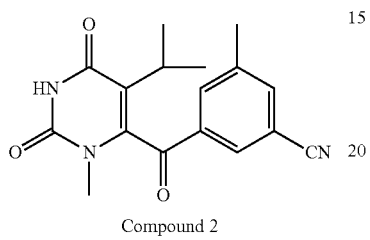

Compound 2

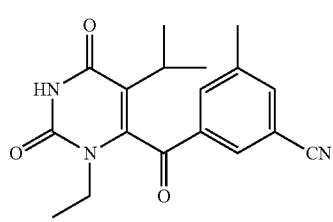

Compound 3

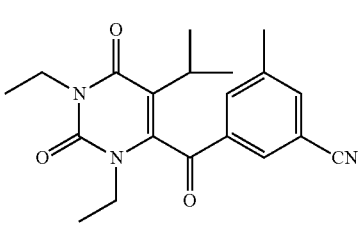

Compound 4

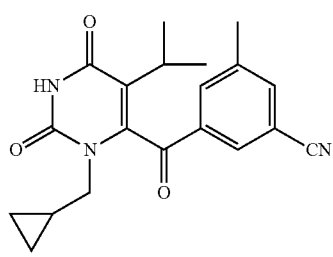

Compound 5

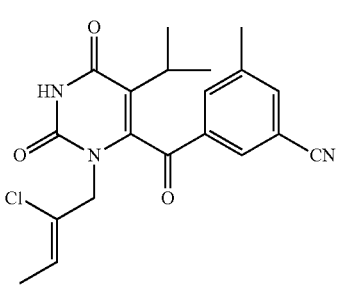

Compound 6

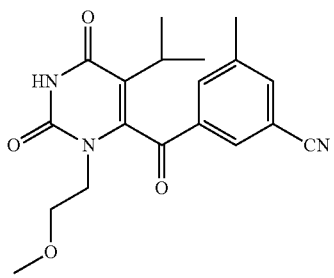

Compound 7

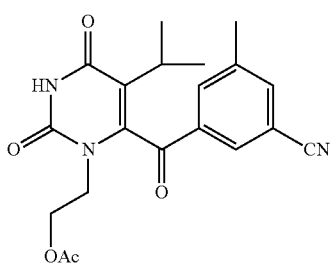

Compound 8

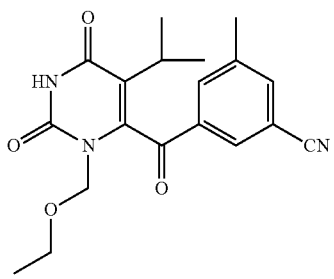

Compound 9

Reagents and conditions: i.alkyl halide, $K_2CO_3$, DMF or $CH_3CH_2OCH_2Cl$, $SnCl_4$, acetonitrile Compound 1: Compound 1 was prepared using the following general procedure:

5-Isopropyl barbtric acid (Lancaster) was reacted with phosphorus oxychloride to provide 2,4,6-trichloro-5-isopropylpyrimidine. The 2,4,6-trichloro-5-isopropylpyrimidine was then reacted with benzyl alkoxide to form 2,4-bis(benzyloxy)-6-chloro-5-isopropylpyrimidine. The 2,4-bis(benzyloxy)-6-chloro-5-isopropylpyrimidine was then reacted with 3-(cyanomethyl)-5-methylbenzonitrile to form 3-((2,6-bis(benzyloxy)-5-isopropylpyrimidin-4-yl)(cyano)methyl)-5-methylbenzonitrile. The 3-((2,6-bis(benzyloxy)-5-isopropylpyrimidin-4-yl)(cyano)methyl)-5-methylbenzonitrile was treated with NaH and $O_2$ to form ketone 3-(2,6-bis(benzyloxy)-5-isopropylpyrimidine-4-carbonyl)-5-methylbenzonitrile, which was then catalytically hydrogenated to form Compound 1.

The 3-(cyanomethyl)-5-methylbenzonitrile intermediate was prepared in multiple steps from 3,5-dimethylbenzoic acid by chlorinating 3,5-dimethylbenzoic acid with thionyl chloride to form the acid chloride, then forming the corresponding amide, 3,5-dimethylbenzamide, by reaction with ammonium hydroxide. The corresponding bromomethyl nitrile, 3-(bromomethyl)-5-methylbenzonitrile, was formed by reacting the 3,5-dimethylbenzamide with NBS and benzoyl peroxide under UV irradiation. The 3-(cyanomethyl)-5-methylbenzonitrile was then formed from 3-(bromomethyl)-5-methylbenzonitrile by reaction with KCN.)

Compound 2: To a mixture of lithium carbonate (13.2 mg, 0.178 mmol), 3-(5-isopropyl-2,6-dioxo-1,2,3,6-tetrahydropyrimidine-4-carbonyl)-5-methyl-benzonitrile (Compound 1, 52.9 mg, 0.178 mmol) in DMF (1.0 mL) was added iodomethane (11.1 μL, 0.178 mmol) and the reaction mixture was stirred for 72 h. The reaction mixture was then partioned between ethyl acetate and saturated ammonium chloride solution. The organic layer was removed, dried (MgSO$_4$), concentrated and purified by reverse phase HPLC (Phenomenex Synergi® column, 5 to 100% acetonitrile/H$_2$O) to give a white powder after lyophilization (17.4 mg, 31%). $^1$H NMR (300 MHz, CD$_3$OD): 8.23 (s, 1H), 8.14 (s, 1H), 7.93 (s, 1H), 3.03 (s, 3H), 2.47 (s, 3H), 2.3-2.1 (m, 1H), 1.15 (d, J=6.6 Hz, 3H), 1.08 (d, J=6.6 Hz, 3H). Mass spectrum: 312.2 (M+H), 310.0 (M−H).

Compound 3: To a mixture of potassium carbonate (0.67 g, 4.85 mmol), Compound 1 (1.44 g, 4.85 mmol, 1.0 eq.) in DMF (23 mL) at 0° C. was added iodoethane (0.326 mL, 4.04 mmol). The reaction mixture was warmed to room temperature overnight, then concentrated. The residue was partioned between ethyl acetate and saturated ammonium chloride solution. The organic layer was removed, dried (MgSO$_4$), concentrated and purified by flash column chromatography (20 to 50% ethyl acetate/hexane) to give 3-(3-ethyl-5-isopropyl-2,6-dioxo-1,2,3,6-tetrahydro-pyrimidine-4-carbonyl)-5-methyl-benzonitrile (0.900 g, 68%); $^1$H NMR (300 MHz, CDCl$_3$): δ 8.69 (br, 1H), 8.02 (s, 1H), 7.92 (s, 1H), 7.76 (s, 1H), 3.9-3.8 (m, 1H), 3.2-3.1 (m, 1H), 2.49 (s, 3H), 2.3-2.1 (m, 1H), 1.17 (d, J=6.9 Hz, 3H), 1.1-1.0 (m, 6H); Mass spectrum: 326.2 (M+H), 324.0 (M−H); and 3-(1,3-Diethyl-5-isopropyl-2,6-dioxo-1,2,3,6-tetrahydro-pyrimidine-4-carbonyl)-5-methyl-benzonitrile, Compound 4 (0.0899 g) $^1$H NMR (300 MHz, CD$_3$OD): δ 8.24 (s, 1H), 8.16 (s, 1H), 7.93 (s, 1H), 4.0-3.8 (m, 3H), 3.3-3.1 (m, 1H), 2.48 (s, 3H), 2.3-2.1 (m, 1H), 1.3-1.0 (m, 12H).

Compound 5: To a mixture of potassium carbonate (0.046 g, 0.336 mmol), Compound 1 (0.100 g, 0.336 mmol) in DMF (3.0 mL) at 0° C. was added (bromomethyl)cyclopropane (22 μL, 0.224 mmol). The reaction mixture was warmed to room temperature overnight, partioned between ethyl acetate and saturated ammonium chloride solution. The organic layer was removed, dried (MgSO$_4$), concentrated and purified by flash column chromatography (20 to 50% ethyl acetate/hexane) to give a white powder after lyophilization (0.0308 g, 39%); $^1$H NMR (300 MHz, CDCl$_3$): δ 9.62 (br, 1H), 8.02 (s, 1H), 7.91 (s, 1H), 7.74 (s, 1H), 3.56 (dd, J=14.7, 8.1 Hz, 1H), 3.19 (dd, J=14.7, 5.7 Hz, 1H), 2.47 (s, 3H), 2.3-2.1 (m, 1H), 1.18 (d, J=6.9 Hz, 3H), 1.07 (d, J=6.9 Hz, 3H), 0.9-0.7 (m, 1H), 0.4-0.2 (m, 4H); Mass spectrum: 352.1 (M+H), 350.0 (M−H).

Compound 6: A mixture of potassium carbonate (29 mg, 0.212 mmol, 1.2 eq.), Compound 1 (76 mg, 0.254 mmol, 1.0 eq.) and 1-bromo-2-chloro-but-2-ene (36 mg, 0.212 mmol, 1.0 eq, prepared according to Kuehne et al. *J. Org. Chem.* 1996, 61(22), 7873-7801) in DMF (2.0 mL) was stirred at 0° C., then warmed to room temperature over 3 h. The reaction mixture was partioned between ethyl acetate and saturated ammonium chloride solution. The organic layer was removed, dried (MgSO$_4$), concentrated and purified by reverse phase HPLC (Phenomenex Synergi® column, 5 to 100% acetonitrile/H$_2$O) to give a white powder after lyophilization (20.6 mg, 25%). $^1$H NMR (300 MHz, CDCl$_3$): δ 8.67 (br, 1H), 8.00 (s, 1H), 7.87 (s, 1H), 7.70 (s, 1H), 5.4-5.35 (m, 1H), 5.02 (d, J=14.4 Hz, 1H), 4.05 (d, J=16.2 Hz, 1H), 2.47 (s, 3H), 2.2-2.0 (m, 1H), 1.2-1.0 (m, 9H). Mass spectrum: 386.1, 388.1 (M+H).

Compound 7: Compound 1 (95 mg, 0.32 mmol, 1.2 eq.) was dissolved in 3 mL of DMF. Potassium carbonate (37 mg, 1 eq.) was added and the reaction mixture was stirred at room temperature for 10 minutes. 1-Bromo-2-methoxy-ethane (37 mg, 0.266 mmol, 1 eq.) and lithium iodide (36 mg, 1 eq.) were added. The reaction mixture was stirred at room temperature overnight. Ethyl acetate was added to the reaction mixture, followed by washing with brine. The organic layer was concentrated and purified (silica gel, 0-80% EtOAC/hexane) followed by reverse phase HPLC (Phenomenex Synergi® column, 5 to 100% acetonitrile/H$_2$O) to give a white powder after lyophilization (24.8 mg, 26%). LC-MS shows 356.1 (M+1). $^1$H NMR (300 MHz, CDCl$_3$): δ 9.10 (br, 1H), 8.10 (s, 1H), 8.01 (s, 1H), 7.77 (s, 1H), 3.78 (m, 2H), 3.59 (m, 1H), 3.36 (m, 1H), 3.03 (s, 3H), 2.48 (s, 3H), 2.2 (m, 1H), 1.20 (dd, 6H).

Compound 8: Compound 1 (62 mg, 0.208 mmol, 1.2 eq.) was dissolved in 2 mL DMF. Potassium carbonate (24 mg, 1 eq.) was added and the reaction mixture was stirred at room temperature for 10 minutes. Acetic acid 2-bromo-ethyl ester (29 mg, 0.174 mmol, 1 eq.) and lithium iodide (23 mg, 1 eq.) were added. The reaction mixture was stirred at room temperature for 3 days. Ethyl acetate was added to the reaction mixture, followed by washing with brine. The organic layer was concentrated and purified (silica gel, 0-80% EtOAC/hexane) followed by reverse phase HPLC (Phenomenex Synergi® column, 5 to 100% acetonitrile/H$_2$O) to give a white powder after lyophilization (15 mg, 22%). LC-MS shows 384.0 (M+1). 1H NMR (300 MHz, CDCl$_3$): δ 9.06 (br, 1H), 8.03 (s, 1H), 7.96 (s, 1H), 7.81 (s, 1H), 4.26 (m, 1H), 4.08 (m, 2H), 3.40 (m, 1H), 2.50 (s, 3H), 2.22 (m, 1H), 2.03 (s, 3H), 1.20 (dd, 6H).

Compound 9: To a mixture of Compound 1 (0.0953 g, 0.321 mmol.) chlorotrimethylsilane (2.0 μL, 0.016 mmol) and 1,1,1,3,3,3-hexamethyldisilazane (1.6 mL) was heated at 140° C. until a brown solution formed (4 h). Reaction mixture was cooled and concentrated. The resulting residue was dissolved in acetonitrile (1.6 mL) and chloromethyl ethyl ether (31 μL, 0.321 mmol) and tin tetrachloride (1M in CH$_2$Cl$_2$, 32 μL, 0.0321 mmol) were added. The reaction mixture was stirred overnight at room temperature, then quenched with saturated sodium bicarbonate solution for 1 h. The mixture was partioned between ethyl acetate and water. The organic layer was removed, dried (MgSO$_4$), concentrated and purified by flash column chromatography (10 to 40% ethyl acetate/hexane) to give a foam. Recrystallized from refluxing methanol provided a white solid (0.0639 g, 56%); $^1$H NMR (300 MHz, CD$_3$OD): δ 8.15 (s, 1H), 8.08 (s, 1H), 7.88 (s, 1H), 5.40 (d, J=10.5 Hz, 1H), 4.75 (d, J=10.5 Hz, 1H), 3.5-3.2 (m, 2H), 2.46 (s, 3H), 2.3-2.1 (m, 1H), 1.13 (d, J=6.9 Hz, 3H), 1.06 (d, J=6.9 Hz, 3H), 0.70 (t, J=6.9 Hz, 3H); Mass spectrum: 356.0 (M+H), 354.0 (M−H).

Scheme 2

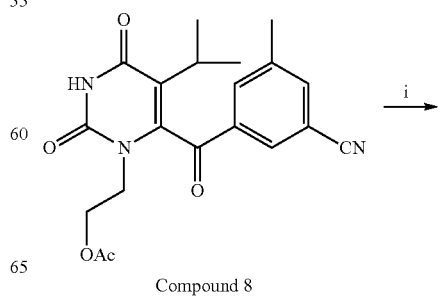

Compound 8

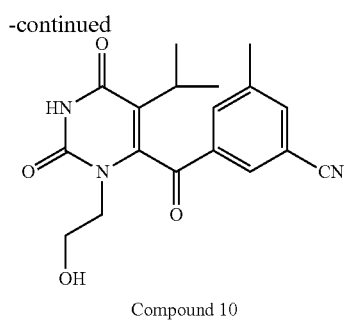

Compound 10

Reagents and conditions: i. K₂CO₃, MeOH.

Compound 10: Potassium carbonate (15 mg, 0.108 mmol, 2.8 eq) was added to Compound 8 (15 mg, 0.039 mmol) in 2 mL MeOH. The reaction mixture was stirred at room temperature for 2 hours. The reaction mixture was concentrated and purified by reverse phase HPLC (Phenomenex Synergi® column, 5 to 100% acetonitrile/H₂O) to give a white powder after lyophilization (6.1 mg, 46%). LC-MS shows 342.1 (M+1). ¹H NMR (300 MHz, CD₃OD) shows the major is desired, the minor is the cyclized form: δ 8.24 (s, 1H), 8.19 (s, 1H), 7.96 (s, 1H), 3.82 (m, 1H), 3.60 (m, 2H), 3.41 (m, 1H), 2.53 (s, 3H), 2.22 (m, 1H), 1.17 (dd, 6H).

Scheme 3

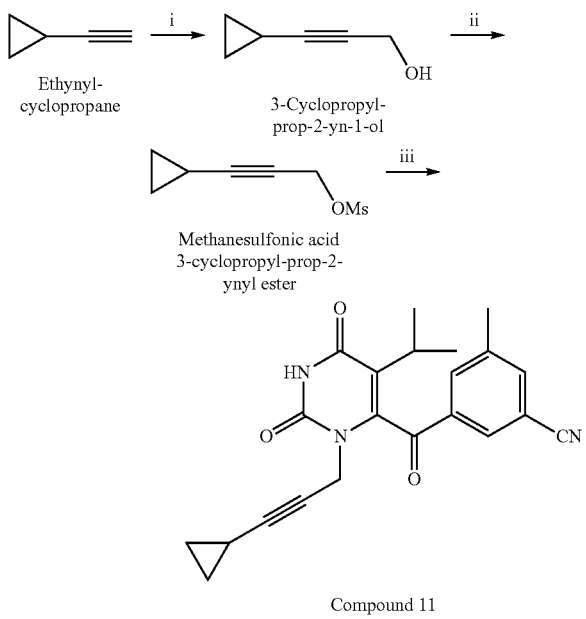

Compound 11

Reagents and conditions: i.n-BuLi, HCHO, THF, -78° C.; ii. MsCl, TEA, DCM, 0° C.; Compound 1, K₂CO₃, LiI, DMF.

3-Cyclopropyl-prop-2-yn-1-ol: At −78° C., n-butyl lithium (1.3 M in hexane, 14.3 mL, 18.57 mmol, 1.1 eq.) was added to ethynyl-cyclopropane (70% in toluene, 2 mL, 16.88 mmol) in 43 mL THF. The reaction mixture was stirred at 0° C. for 1 hour, then cooled to −78° C. Paraformaldehyde (633 mg, 21.1 mmol, 1.25 eq.) was added. The reaction mixture was then stirred at −78° C. and warmed to room temperature overnight. The reaction mixture was then concentrated, ethyl acetate was added, and the organic layer was washed with brine. The organic layer was concentrated and purified (silica gel, 0-20% EtOAc/hexane) to give a light yellow oil (900 mg, 56%). ¹H NMR (300 MHz, CDCl₃): δ 4.20 (s, 2H), 1.62 (s, 1H), 1.23 (m, 1H), 0.75 (m, 6H).

Methanesulfonic acid 3-cyclopropyl-prop-2-ynyl ester: At 0° C., TEA (140 μL, 1.0 mmol, 2.0 eq.) was added to 3-cyclopropyl-prop-2-yn-1-ol in 2 mL DCM solution, followed by MSCl (46 μL, 0.6 mmol, 1.2 eq.). The reaction mixture was stirred at 0° C. for 30 minutes. The reaction mixture was concentrated. Ethyl acetate was added and washed with saturated NaHCO₃ solution. The organic layer was concentrated after drying over anhydrous sodium sulfate to give a light yellow oil (59 mg, 68%) which was used directly in the next step.

Compound 11: Compound 1 (121 mg, 0.406 mmol, 1.2 eq.) was dissolved in 4 mL DMF. Potassium carbonate (59 mg, 0.338 mmol, 1 eq.) was added and the reaction mixture was stirred at room temperature for 10 minutes. Methanesulfonic acid 3-cyclopropyl-prop-2-ynyl ester (59 mg, 0.338 mmol, 1 eq.) and lithium iodide (45 mg, 1 eq.) were added. The reaction mixture was stirred at room temperature overnight. Ethyl acetate was added to the reaction mixture, followed by washing with brine. The organic layer was concentrated and purified (silica gel, 0-80% EtOAC/hexane) to give pale powder (88 mg, 69%). LC-MS shows 376.1 (M+1). ¹H NMR (300 MHz, CDCl₃): δ 8.81 (br, 1H), 8.17 (s, 1H), 8.03 (s, 1H), 7.81 (s, 1H), 4.91 (d, 1H), 3.98 (d, 1H), 2.52 (s, 3H), 2.22 (m, 1H), 1.20 (dd, 6H), 0.78 (m, 1H), 0.73 (m, 2H), 0.59 (m, 1H), 0.38 (m, 1H).

Scheme 4

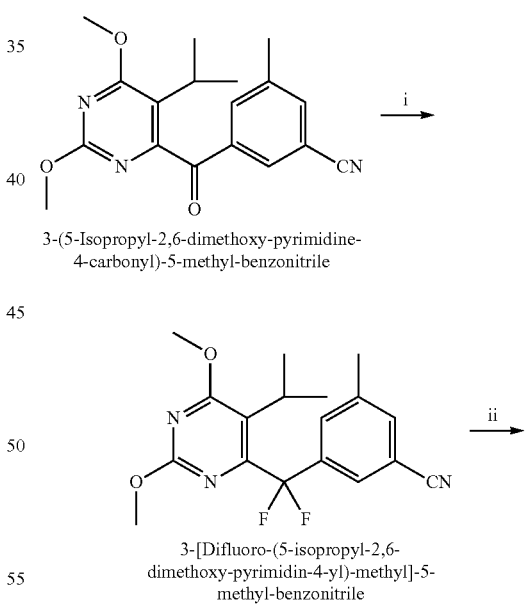

3-(5-Isopropyl-2,6-dimethoxy-pyrimidine-4-carbonyl)-5-methyl-benzonitrile

3-[Difluoro-(5-isopropyl-2,6-dimethoxy-pyrimidin-4-yl)-methyl]-5-methyl-benzonitrile

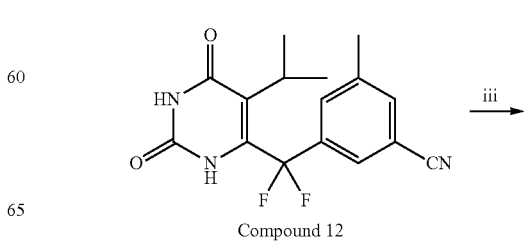

Compound 12

-continued

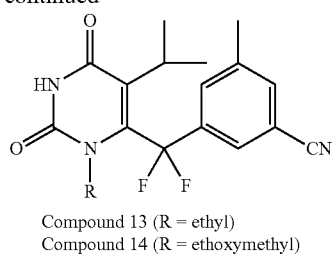

Compound 13 (R = ethyl)
Compound 14 (R = ethoxymethyl)

Reagents and conditions: i. Deoxoflouor, cat. EtOH, 110° C.; ii. AcBr, 60° C.; iii. K$_2$CO$_3$, EtI, DMF; or chloromethoxy-ethane, K$_2$CO$_3$, LiI DMF.

3-[Difluoro-(5-isopropyl-2,6-dimethoxy-pyrimidin-4-yl)-methyl]-5-methyl-benzonitrile: Deoxoflouor (3 mL, excess) was added to 3-(5-isopropyl-2,6-dimethoxy-pyrimidine-4-carbonyl)-5-methyl-benzonitrile (prepared in a manner similar to the procedure used to prepare the 3-(2,6-bis(benzyloxy)-5-isopropylpyrimidine-4-carbonyl)-5-methylbenzonitrile intermediate formed in the preparation of Compound 1, except that methoxide was used instead of benzyl alkoxide) (779 mg, 2.39 mmol), followed by a drop of ethanol (about 0.1 mL). The reaction mixture was heated to 110° C. under argon for 9 hours. The reaction mixture was then concentrated, ethyl acetate was added, and the mixture was washed with brine. The organic layer was concentrated and purified (silica gel, 0-80% EtOAC/hexane) to give a pale solid (500 mg, 73%). LC-MS shows 348.1 (M+1).

Compound 12: Acetyl bromide (2 mL, excess) was added to 3-[difluoro-(5-isopropyl-2,6-dimethoxy-pyrimidin-4-yl)-methyl]-5-methyl-benzonitrile (500 mg, 1.44 mmol). The reaction mixture was heated to 60° C. under argon overnight. The reaction mixture was then concentrated and purified (silica gel, 0-80% EtOAC/hexane) to give pale solid (390 mg, 85%). LC-MS shows 318.1 (M−1).

Compound 13: Compound 12 (92 mg, 0.288 mmol, 1.2 eq.) was dissolved in 1.4 mL DMF. Potassium carbonate (40 mg, 0.288 mmol, 1.2 eq.) was added and the reaction mixture was stirred at 0° C. for 10 minutes. Ethyl iodide (19.4 µL, 0.24 mmol, 1 eq.) was added. The reaction mixture was stirred at 0° C. and warmed to room temperature for 2 days. Ethyl acetate was added to the reaction mixture, followed by washing with brine. The organic layer was concentrated and purified (silica gel, 0-80% EtOAC/hexane) to give a pale powder (4.5 mg, 6%). LC-MS shows 348.1 (M+1). $^1$H NMR (300 MHz, CD$_3$OD): δ 7.95 (s, 1H), 7.82 (s, 2H), 3.58 (m, 2H), 2.50 (s, 3H), 1.22 (dd, 6H).

Compound 14: Compound 12 (80 mg, 0.25 mmol, 1.2 eq.) was dissolved in 2 mL DMF. Potassium carbonate (29 mg, 0.209 mmol, 1 eq.) was added and the reaction mixture was stirred at 0° C. for 10 minutes. Chloromethoxy-ethane (19.4 µL, 0.209 mmol, 1 eq.) was added, followed by lithium iodide (28 mg, 1 eq.). The reaction mixture was stirred at 0° C. and warmed to room temperature overnight. Ethyl acetate was added to the reaction mixture, followed by washing with brine. The organic layer was concentrated and purified (silica gel, 0-80% EtOAC/hexane) and prep TLC (2% MeOH/DCM) to give pale powder (8.3 mg, 11%). LC-MS shows 378.0 (M+1). $^1$H NMR (300 MHz, CDCl$_3$): δ 9.03 (br, 1H), 7.76 (s, 1H), 7.62 (s, 2H), 5.37 (s, 2H), 3.40 (m, 2H), 2.70 (m, 1H), 2.48 (s, 3H), 1.22 (dd, 6H), 1.00 (t, 3H). F NMR (300 MHz, CDCl$_3$): δ −77.43.

Compound 15 was also isolated as a byproduct of this reaction:

Compound 15

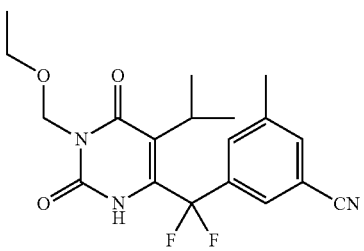

Scheme 5

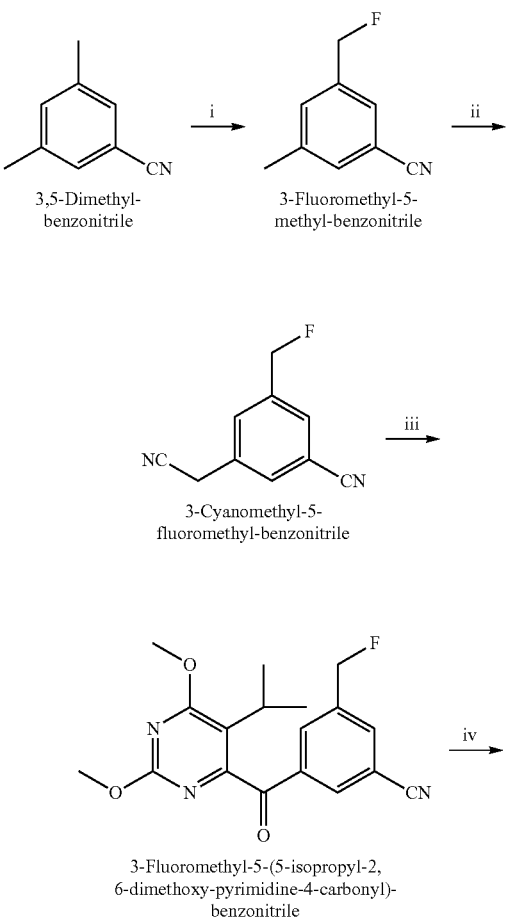

3,5-Dimethyl-benzonitrile

3-Fluoromethyl-5-methyl-benzonitrile

3-Cyanomethyl-5-fluoromethyl-benzonitrile

3-Fluoromethyl-5-(5-isopropyl-2,6-dimethoxy-pyrimidine-4-carbonyl)-benzonitrile

Compound 16

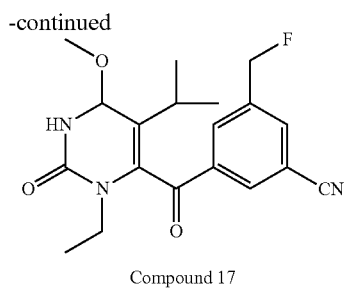

Compound 17

Reagents and condtions: i. a. NBS: CCl₄; b. KF, 18-cr-6, ACN; ii. a. NBS; CCl₄; b. KCN, EtOH/H₂O; iii. 4-chloro-5-isopropyl-2,6-dimethoxy-pyrimidine, NaH, DMF; b. NaH, O₂, DMF; iv. AcBr; v. EtI, K₂CO₃, DMF.

3-Fluoromethyl-5-methyl-benzonitrile: To a solution of 3,5-dimethylbenzonitrile (25 g, 190 mmol) in carbon tetrachloride (190 mL) was added N-bromosuccinimide (33.9 g, 190 mmol) and benzoyl peroxide (2.28 g, 9.4 mmol). The reaction mixture was refluxed under a UV lamp for 3 h, cooled to room temperature and filtered. The filtrate was concentrated and purified by silica gel chromatography (10% ethyl ether/hexanes) to give an impure product. The product was crystallized from refluxing ethyl ether (100 mL) and hexanes (400 mL) to give a white solid (19.11 g, 48%).

To a portion of the above material (3.04 g, 14.47 mmol) was added potassium fluoride (2.52 g, 43.41 mmol), 18-crown-6 (0.76 g, 2.89 mmol) and acetonitrile (20 mL) and the resulting yellow reaction mixture was refluxed for several days. The resulting white precipitate was removed by filtration and the filtrate was concentrated and purified by silica gel chromatography (0 to 20% ethyl acetate/hexanes) to give a white solid (1.27 g, 59%). ¹H NMR (300 MHz, CDCl₃): δ 7.41 (s, 2H), 7.37 (s, 1H), 5.33 (d, J=47 Hz, 2H), 2.37 (s, 3H).

3-Cyanomethyl-5-fluoromethyl-benzonitrile: To a solution of 3-fluoromethyl-5-methyl-benzonitrile (1.22 g, 8.18 mmol) in carbon tetrachloride (8 mL) was added N-bromosuccinimide (1.46 g, 8.18 mmol) and benzoyl peroxide (0.099 g, 0.41 mmol). The reaction mixture was refluxed under a UV lamp for 3.5 h, cooled to room temperature and filtered. The filtrate was concentrated and purified by silica gel chromatography (0 to 20% ethyl acetate/hexanes) to give a white solid (0.3561 g, 19%).

To the above material (0.3561 g, 1.56 mmol) was added potassium cyanide (0.187 g, 2.87 mmol), ethanol (1.5 mL) and water (0.5 mL). The reaction mixture was refluxed for 6 h, and cooled to room temperature. The product was extracted with ethyl acetate, washed with H₂O, and dried (MgSO₄), concentrated and purified by silica gel chromatography (0 to 40% ethyl acetate/hexanes) to give a white solid (0.1788 g, 66%). ¹H NMR (300 MHz, CDCl₃): δ 7.55 (s, 3H), 5.73 (d, J=47 Hz, 2H), 3.79 (s, 2H).

3-Fluoromethyl-5-(5-isopropyl-2,6-dimethoxy-pyrimidine-4-carbonyl)-benzonitrile: To a solution of 3-cyanomethyl-5-fluoromethyl-benzonitrile (0.1351 g, 0.776 mmol) and 4-chloro-5-isopropyl-2,6-dimethoxy-pyrimidine (0.176 g, 0.814 mmol) in DMF (5.0 mL) at 0° C. was added 60% sodium hydride (0.062 g, 1.552 mmol) over 30 min to give an orange solution. The reaction mixture was stirred for 1 h at 0° C., then 4 h at room temperature. The reaction mixture was quenched with 1N HCl solution and partioned between ethyl acetate and sat. NH₄Cl solution. The organic layer was washed with sat. NH₄Cl solution, dried (MgSO₄), concentrated and purified by silica gel chromatography (0 to 30% ethyl acetate/hexanes) to give a white solid (0.1714 g, 62%).

The above material was dissolved in DMF (5 mL) and cooled to 0° C. 60% Sodium hydride (0.027 g, 0.686 mmol) was added in portions, and the resulting yellow reaction mixture was stirred for 30 min at room temperature. Oxygen was bubbled into the reaction mixture with vigorous stirring for 4 h. The reaction mixture was quenched with 1N HCl solution and partioned between ethyl acetate and a sat. NH₄Cl solution. The organic layer was washed with H₂O, sat. NH₄Cl solution, dried (MgSO₄), concentrated and purified by silica gel chromatography (0 to 50% ethyl acetate/hexanes) to give a white solid (0.036 g, 22%). ¹H NMR (300 MHz, CDCl₃): δ 8.05 (s, 1H), 8.03 (s, 1H), 7.83 (s, 1H), 5.43 (d, J=47 Hz, 2H), 4.04 (s, 3H), 3.88 (s, 3H), 2.86-2.80 (m, 1H), 1.15 (d, J=6.9 Hz, 6H); Mass spectrum: 343.2 (M+H).

Compound 16: A solution of 3-fluoromethyl-5-(5-isopropyl-2,6-dimethoxy-pyrimidine-4-carbonyl)-benzonitrile (0.036 g, 0.105 mmol) in acetyl bromide (2.0 mL) was stirred for 6 h at 60° C. The reaction mixture was cooled to room temperature and coevaporated with acetonitrile (3×) to give an off-white film (0.016 g, 48%).

¹H NMR (300 MHz, CDCl₃): δ10.70 (br s, 1H), 10.30 (br s, 1H), 8.18 (s, 1H), 8.09 (s, 1H), 7.89 (s, 1H), 5.47 (d, J=47 Hz, 2H), 3.41 (s, 3H), 2.5-2.2 (m, 1H), 0.95 (d, J=6.6 Hz, 6H); Mass spectrum: 316.1 (M+H).

Compound 17: To a solution of Compound 16 (16 mg, 0.0507 mmol) in DMF (0.5 mL) at 0° C. were added iodoethane (4.1 μL, 0.0507 mmol) and potassium carbonate (7.0 mg, 0.0507 mmol). The reaction mixture was warmed to room temperature overnight, diluted with ethyl acetate and washed with brine, dried (MgSO₄), and concentrated. The crude product was purified by silica gel chromatography (20 to 50% ethyl acetate/hexanes) to give a white powder after lyophilization (4.6 mg, 26%). ¹H NMR (300 MHz, CD₃OD): δ 8.44 (s, 1H), 8.32 (s, 1H), 8.14 (s, 1H), 5.52 (d, J=47 Hz, 2H), 3.9-3.7 (m, 1H), 3.2-3.1 (m, 1H), 2.3-2.1 (m, 1H), 1.14 (d, J=6.9 Hz, 3H), 1.1-1.0 (m, 6H); Mass spectrum: 344.2 (M+H), 342.0 (M−H).

Scheme 6

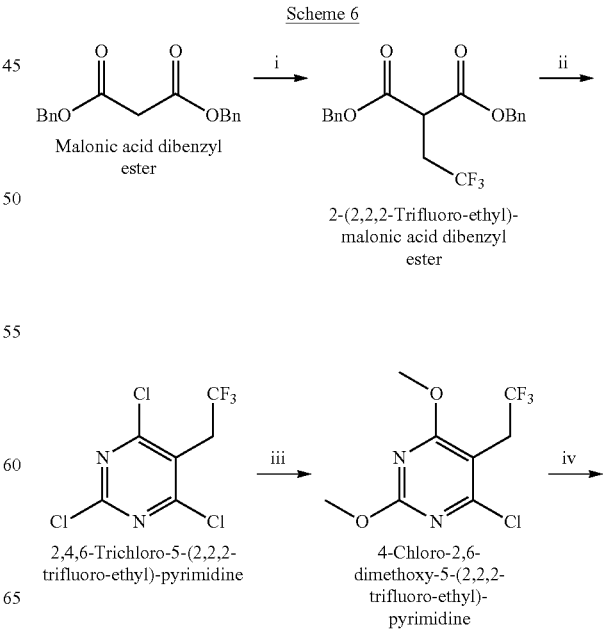

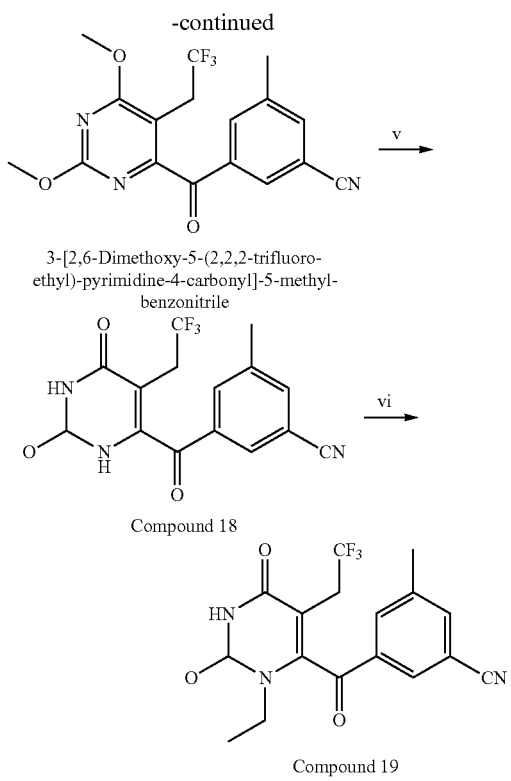

3-[2,6-Dimethoxy-5-(2,2,2-trifluoro-ethyl)-pyrimidine-4-carbonyl]-5-methyl-benzonitrile Compound 18

Compound 19

Reagents and condtions: i. Trifluoro-methanesulfonic acid 2,2,2-trifluoro-ethyl ester, NaH, THF; ii. a. urea, sodium ethoxide, ethanol; b. phosphorus oxychloride, 2,6-lutidine; iii. sodium methoxide, methanol; iv. a.3-Cyanomethyl-5-methyl-benzonitrile, NaH, DMF; b. O₂; v. AcBr; vi. EtI, Li₂CO₃, DMF.

2-(2,2,2-Trifluoro-ethyl)-malonic acid dibenzyl ester: To a suspension of 60% sodium hydride (0.678 g, 16.97 mmol) in THF (100 mL) at room temperature was added malonic acid dibenzyl ester (4.825 g, 16.97 mmol) to give a clear solution after 30 min. Trifluoro-methanesulfonic acid 2,2,2-trifluoro-ethyl ester (3.52 g, 15.43 mmol) was added and reaction mixture was stirred at 50° C. for 48 h. The reaction mixture was concentrated, partioned between ethyl ether and washed with saturated ammonium chloride solution and acidified with 1N HCl. The mixture was extracted with ethyl ether (2×), dried (MgSO₄), and concentrated. The resulting residue was purified by flash column chromatography (silica gel, 0 to 0% ethyl ether/hexanes) to give a colorless oil (3.844 g, 68%). $^1$H NMR (300 MHz, CDCl₃): δ 7.4-7.2 (m, 10H), 5.15 (s, 4H), 3.75 (t, J=6.9 Hz, 1H), 2.9-7.7 (m, 2H).

2,4,6-Trichloro-5-(2,2,2-trifluoro-ethyl)-pyrimidine: To a solution of 2-(2,2,2-trifluoro-ethyl)-malonic acid dibenzyl ester (3.40 g, 9.29 mmol) in ethanol (2.0 mL) at room temperature were added urea (0.558 g, 9.29 mmol) and sodium ethoxide (21 wt %, 8.0 mL, 21.4 mmol). The reaction mixture was stirred at 60° C. for 12 h. The reaction mixture was cooled to room temperature, diluted with ethyl ether (20 mL), and stirred for 1 h. The resulting solid was collected by filtration and dried under vacuum to give an off-white solid (1.228 g, 52%). This solid was suspended in phosphorus oxychloride (14 mL) and 2,6-lutidine (0.7 mL) was carefully added. The reaction mixture was stirred for 1 h at 140° C., then overnight at 105° C. The reaction mixture was cooled to room temperature, concentrated and coevaporated with toluene to give a brown oil. The residue was dissolved in ethyl ether and washed with saturated sodium bicarbonate solution. The organic layer was dried (MgSO₄), concentrated and purified by flash column chromatography (silica gel, 0 to 10% ethyl acetate/hexane) to give a white solid (0.6331 g, 49%). $^1$H NMR (300 MHz, CDCl₃): δ 3.75 (q, J=9.3 Hz, 2H).

4-Chloro-2,6-dimethoxy-5-(2,2,2-trifluoro-ethyl)-pyrimidine: To a solution of 2,4,6-trichloro-5-(2,2,2-trifluoro-ethyl)-pyrimidine (0.633 g, 2.39 mmol) in methanol (20 mL) at 0° C. was added sodium methoxide (25 wt %, 1.09 mL, 4.77 mmol). The reaction mixture was warmed to room temperature overnight. The reaction mixture was concentrated, dissolved in ethyl ether and washed with water. The organic layer was dried (MgSO₄), concentrated and purified by flash column chromatography (silica gel, 0 to 10% ethyl acetate/hexane) to give a colorless oil (0.5531 g, 90%). $^1$H NMR (300 MHz, CDCl₃): δ 3.87 (s, 3H), 3.83 (s, 3H), 3.32 (q, J=10.2 Hz, 2H); Mass spectrum: 257.1, 259.1 (M+H).

3-[2,6-Dimethoxy-5-(2,2,2-trifluoro-ethyl)-pyrimidine-4-carbonyl]-5-methyl-benzonitrile: To a solution of 3-cyanomethyl-5-fluoromethyl-benzonitrile (0.348 g, 2.23 mmol) and 4-chloro-2,6-dimethoxy-5-(2,2,2-trifluoro-ethyl)-pyrimidine (0.546 g, 2.13 mmol) in DMF (10.0 mL) at 0° C. was added 60% sodium hydride (0.170 g, 4.26 mmol) over 30 min to give an orange solution. The reaction mixture was stirred for 1 h at 0° C., then 3 h at room temperature. Oxygen was bubbled into reaction mixture with vigorous stirring for 24 h. The reaction mixture was quenched with 1N HCl solution and partioned between ethyl acetate and sat. NH₄Cl solution. The organic layer was washed with H₂O, sat. NH₄Cl solution, dried (MgSO₄), concentrated and purified by flash column chromatography (silica gel, 0 to 30% ethyl acetate/hexanes) to give a white solid (0.476 g, 61%). $^1$H NMR (300 MHz, CDCl₃): δ 7.92 (s, 2H), 7.63 (s, 1H), 4.06 (s, 3H), 3.93 (s, 3H), 3.60 (q, J=10.5 Hz, 2H), 2.41 (s, 3H); Mass spectrum: 366.2 (M+H).

Compound 18: A solution of 3-[2,6-dimethoxy-5-(2,2,2-trifluoro-ethyl)-pyrimidine-4-carbonyl]-5-methyl-benzonitrile (0.4638 g, 1.27 mmol) in acetyl bromide (13.0 mL) was stirred for 36 h at 60° C. The reaction mixture was cooled to room temperature and coevaporated with acetonitrile (3×). The residue was purified by flash column chromatography (silica gel, 0 to 5% methanol/dichloromethane) to give a brown solid (0.2179 g, 94%). $^1$H NMR (300 MHz, CD₃OD): δ 8.12 (s, 1H), 8.03 (s, 1H), 7.90 (s, 1H), 3.15 (q, J=10.5 Hz, 2H), 2.46 (s, 3H); Mass spectrum: 336.0 (M−H).

Compound 19: To a suspension of Compound 18 (0.147 g, 0.436 mmol) and lithium carbonate (0.016 g, 0.218 mmol) in DMF (1.0 mL) at room temperature was added iodoethane (17.6 μL, 0.218 mmol). The reaction mixture was stirred to room temperature for 72 h, then diluted with ethyl acetate, washed with saturated ammonium chloride solution, dried (MgSO₄), and concentrated. The residue was purified by reverse phase HPLC (Phenomenex Synergi® column, 5 to 100% acetonitrile/H₂O) to give a white powder after lyophilization (31.3 mg, 39%). $^1$H NMR (300 MHz, CD₃OD): δ 8.22 (s, 1H), 8.12 (s, 1H), 7.94 (s, 1H), 3.9-3.8 (m, 1H), 3.3-3.1 (m, 2H), 2.9-2.7 (m, 1H), 2.47 (s, 3H), 1.08 (t, J=6.6 Hz, 3H); Mass spectrum: 366.2 (M+H), 363.90 (M−H).

Scheme 7

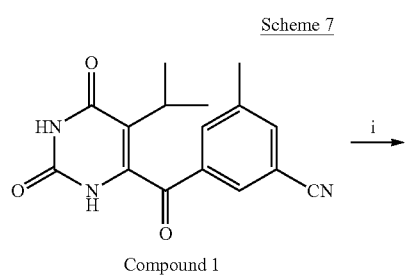

Compound 1

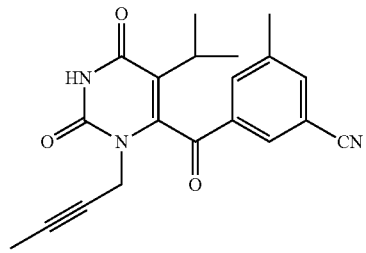

Compound 20

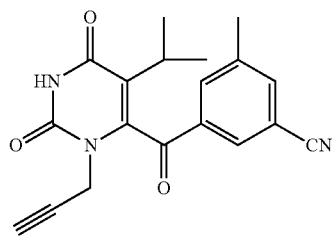

Compound 23

Compound 24

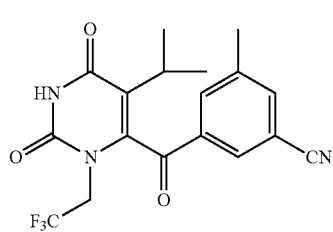

Compound 25

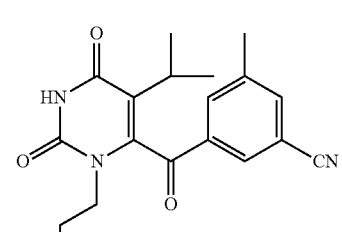

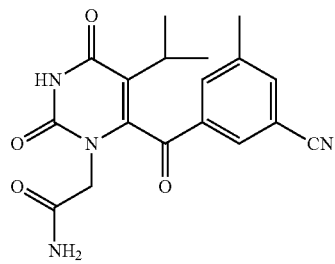

Compound 26

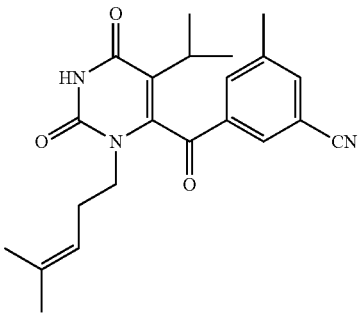

Compound 27

Reagents and conditions: i. alkyl halide, $K_2CO_3$, DMF.

Compound 22

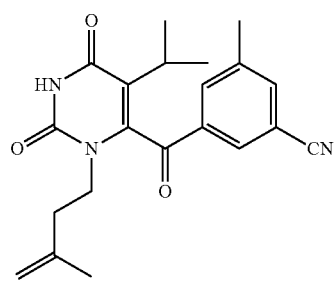

Compound 20: To a stirred solution of Compound 1 (297 mg, 1 mmol) and powdered anhydrous potassium carbonate (138 mg, 1 mmol) in DMF (5 mL) at room temperature, was added 3,3-dimethylallyl bromide (149 mg, 1 mmol). After stirring overnight, the mixture was evaporated in vacuo and the residue was purified by silica gel column chromatography (eluent, ethyl acetate:hexane (1:2)) to afford 254 mg (69%) of a white solid. m.p. 158-159° C. $^1$H-NMR (200 MHz, $CDCl_3$) δ1.10 (3H, d, J=6.8 Hz), 1.20 (3H, d, J=6.8 Hz), 1.33 (6H, d, J=4.6 Hz), 2.20 (1H, m), 2.51 (3H, s), 4.11 (1H, m), 4.32 (1H, m), 4.90 (1H, m), 7.76 (1H, s), 7.91 (1H, s), 8.02 (1H, s), 8.96 (1H, s).

A byproduct, Compound 21, was also isolated:

Compound 21

Compound 22: To a stirred solution of 2-butyn-1-ol (70 mg, 1 mmol) in chloroform (10 mL) cooled in an ice bath under nitrogen atmosphere, was added triethylamine (210 μL, 1.5 mmol) and methanesulfonyl chloride (90 μL, 1.2 mmol) was added dropwise. After stirring for 1.1 hr., the reaction mixture was washed with sat. aqueous sodium bicarbonate, dried with anhydrous magnesium sulfate, filtered, and evaporated in vacuo. The residue was further dried in high vacuo for approximately 20 min. and mixed with Compound 1 (297 mg, 1 mmol), powdered anhydrous potassium carbonate (138 mg, 1 mmol), and lithium iodide (134 mg, 1 mmol). DMF (5 mL) was then added to the mixture at room temperature and stirred overnight. After evaporation of DMF, the residue was dissolved in methanol-chloroform (1:9) and filtered through a celite pad. The filtrate was then evaporated in vacuo and the residue was purified by silica gel column chromatography (eluent, ethyl acetate:hexane (1:2)) to afford 110 mg (26%) of a white solid; m.p. 116-117° C.; $^1$H-NMR (200 MHz, CDCl$_3$) δ 1.14 (3H, d, J=7.0 Hz), 1.22 (3H, d, J=7.0 Hz), 1.44 (3H, t, J=2.4 Hz), 2.26 (1H, m), 2.56 (3H, s), 4.00 (1H, dd, J=2.4 Hz, 17.8 Hz), 4.86 (1H, dd, J=2.4 Hz, 17.8 Hz), 7.79 (1H, s), 8.09 (1H, s), 8.16 (1H, s), 8.89 (1H, s); m/z (EI) 349 [M$^+$]

Compound 23: To a stirred solution of Compound 1 (297 mg, 1 mmol) and powdered anhydrous potassium carbonate (138 mg, 1 mmol) in DMF (5 mL) at room temperature, was added 80 wt. % of propargyl bromide in toluene (112 μL, 1 mmol). After stirring overnight, the mixture was evaporated in vacuo and the residue was purified by silica gel column chromatography (eluent, ethyl acetate:hexane (1:2)) to afford 167 mg (50%) of a white solid; m.p. 209-210° C.; $^1$H-NMR (200 MHz, CDCl$_3$) δ 1.15 (3H, d, J=6.8 Hz), 1.23 (3H, d, J=6.8 Hz), 2.10 (1H, t, J=2.4 Hz), 2.29 (1H, m), 2.55 (3H, s), 4.16 (1H, d, J=16.0 Hz), 4.74 (1H, d, J=16.0 Hz), 7.83 (1H, s), 8.09 (1H, s), 8.17 (1H, s), 10.20 (1H, s); m/z (EI) 335 [M$^+$]

Compound 24: To a stirred solution of Compound 1 (297 mg, 1 mmol) and powdered anhydrous potassium carbonate (138 mg, 1 mmol) in DMF (5 mL) at room temperature, was added trifluoromethanesulfonic acid 2,2,2-trifluoroethyl ester (144 μL, 1 mmol). After stirring overnight, the mixture was evaporated in vacuo and the residue was purified by silica gel column chromatography (eluent, ethyl acetate:hexane (1:9)) to afford 48 mg (12%) as a white solid; m.p. 237-238° C.; $^1$H-NMR (200 MHz, CDCl$_3$) δ 1.17 (3H, d, J=5.4 Hz), 1.23 (3H, d, J=5.4 Hz), 2.23 (1H, m), 2.53 (3H, s), 4.14 (1H, m), 4.62 (1H, m), 7.80 (1H, s), 7.98 (1H, s), 8.07 (1H, s), 9.43 (1H, s); m/z (EI) 379 [M$^+$]

Compound 25: A mixture of Compound 1 (297 mg, 1 mmol) and powdered anhydrous potassium carbonate (138 mg, 1 mmol), lithium iodide (134 mg, 1 mmol), and 3-bromo-1-propanol (87 μL, 1 mmol) in DMF (5 mL) was stirred in an oil bath (90-110° C.) overnight. After cooling to room temperature, the mixture was evaporated in vacuo and the residue was purified by silica gel column chromatography (eluent, ethyl acetate:hexane (2:1)) to afford 138 mg (39%) of a white solid; m.p. 166-167° C.; $^1$H-NMR (200 MHz, DMSO-d$_6$) δ 1.00 (3H, d, J=7.0 Hz), 1.09 (3H, d, J=7.0 Hz), 1.53-1.63 (2H, m), 2.09 (1H, m), 2.47 (3H, s), 3.08 (1H, m), 3.20-3.28 (2H, m), 3.68 (1H, m), 4.38 (1H, t, J=5.4 Hz), 8.11 (1H, s), 8.24 (1H, s), 8.49 (1H, s), 11.45 (1H, s); m/z (EI) 355 [M$^+$]

Compound 26: To a stirred mixture of Compound 1 (836 mg, 2.81 mmol) and powdered anhydrous potassium carbonate (388 mg, 2.81 mmol), and lithium iodide (377 mg, 2.81 mmol) in DMF (5 mL) at room temperature, was added bromo acetamide (388 mg, 2.81 mmol). After stirring overnight, the mixture was evaporated in vacuo and the residue was purified by silica gel column chromatography (eluent, methanol:chloroform (5:95)) to afford 370 mg (37%) as a white solid; m.p. 275-276° C.; $^1$H-NMR (200 MHz, DMSO-d$_6$) δ 1.05 (3H, d, J=7.0 Hz), 1.11 (3H, d, J=7.0 Hz), 2.11 (1H, m), 2.45 (3H, s), 3.87 (1H, d, J=17.0 Hz), 4.02 (1H, d, J=17.0 Hz), 7.09 (1H, s), 7.34 (1H, s), 8.09 (1H, s), 8.19 (1H, s), 8.36 (1H, s) 11.56 (1H, s); m/z (EI) 354 [M$^+$]

Compound 27: To a stirred solution of 4-methyl-3-butene-1-ol (100 mg, 1 mmol) in chloroform (10 mL) cooled in an ice bath under nitrogen atmosphere, was added triethylamine (210 μL, 1.5 mmol) and methanesulfonyl chloride (90 μL, 1.2 mmol) was added dropwise. After stirring for 1.1 hr., the reaction mixture was washed with sat. aqueous sodium bicarbonate, dried with anhydrous magnesium sulfate, filtered, and evaporated in vacuo. The residue was further dried under high vacuum for approximately 20 min. and mixed with Compound 1 (297 mg, 1 mmol), powdered anhydrous potassium carbonate (138 mg, 1 mmol), and lithium iodide (134 mg, 1 mmol). DMF (5 mL) was then added to the mixture at room temperature and stirred overnight. After evaporation of DMF, the residue was dissolved in methanol-chloroform (1:9) and filtered through a celite pad. The filtrate was then evaporated in vacuo and the residue was purified by silica gel column chromatography (eluent, ethyl acetate:hexane (1:5)) to afford 118 mg (31%) as a white solid; m.p. 192-194° C.; $^1$H-NMR (200 MHz, CDCl$_3$) δ 1.13 (3H, d, J=7.0 Hz), 1.22 (3H, d, J=7.0 Hz), 1.49 (3H, s), 1.62 (3H, s), 2.17-2.27 (4H, m), 2.52 (3H, s), 2.95 (1H, m), 3.75 (1H, m), 4.90 (1H, m), 7.79 (1H, s), 7.94 (1H, s), 8.05 (1H, s), 8.88 (1H, s); m/z (EI) 379 (M$^+$)

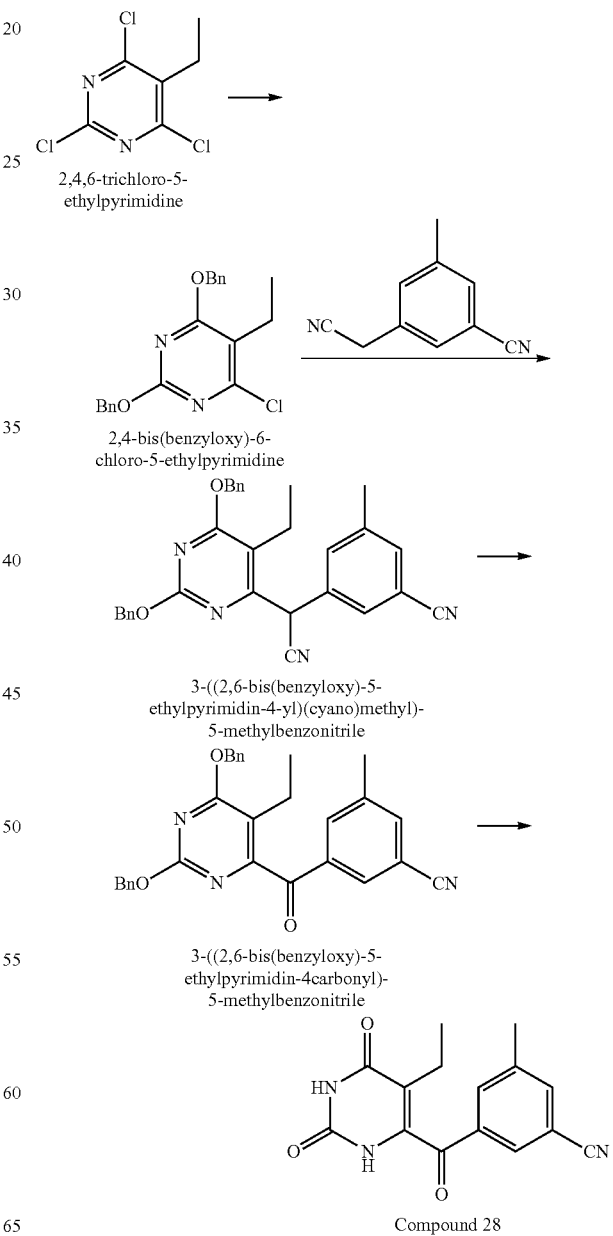

Scheme 8

2,4,6-trichloro-5-ethylpyrimidine 2,4-bis(benzyloxy)-6-chloro-5-ethylpyrimidine 3-((2,6-bis(benzyloxy)-5-ethylpyrimidin-4-yl)(cyano)methyl)-5-methylbenzonitrile 3-((2,6-bis(benzyloxy)-5-ethylpyrimidin-4carbonyl)-5-methylbenzonitrile Compound 28

2,4-Bis-benzyloxy-6-chloro-5-ethyl-pyrimidine: To a stirred solution of benzyl alcohol (80 mL) in water bath, was added sodium metal (2.17 g, 94.6 mmol) under nitrogen atmosphere. After complete reaction of sodium metal, the mixture was cooled in an ice bath and 2,4,6-trichloro-5-ethyl-pyrimidine (10.5 g, 49.6 mmol) was added in portions. After stirring for 30 min in an ice bath, the reaction mixture was stirred at room temperature for overnight. Excess benzyl alcohol was evaporated in vacuo and the residue was dissolved in ether, washed with water, dried with anhydrous magnesium sulfate, filtered, and evaporated in vacuo to give a pale yellow oil. The crude product was purified by silica gel column chromatography (eluent, ether:hexane (4:96)) to give 14 g (80%) of a white solid; m.p. 53-54° C.; $^1$H NMR (200 MHz, CDCl$_3$) δ: 1.14 (3H, t, J=7.4 Hz), 2.70 (2H, q, J=7.4 Hz), 5.41 (2H, s), 5.45 (2H, s), 7.34-7.53 (10H, m); m/z (EI): 354 (M$^+$).

3-[(2,6-Bis-benzyloxy-5-ethyl-pyrimidin-4-yl)-cyano-methyl]-5-methyl-benzonitrile: To a stirred mixture of 2,4-bis-benzyloxy-6-chloro-5-ethyl-pyrimidine (9.89 g, 27.87 mmol) and 3-cyanomethyl-5-methyl-benzonitrile (4.15 g, 26.55 mmol) in anhydrous DMF (50 mL) in an ice-water bath under an atmosphere of nitrogen, was portionwise added 60% sodium hydride (2.34 g, 58.4 mmol). After stirring for 1 hr, the mixture was stirred at room temperature for overnight. The mixture was neutralized with aqueous saturated ammonium chloride solution. The crude product was extracted with ether and recrystallized from dichloromethane-hexane to afford 10.3 g (82%) a pale yellow solid; m.p. 139-141° C.; $^1$H NMR (200 MHz, CDCl$_3$) δ: 1.00 (3H, t, J=7.6 Hz), 2.37 (3H, s), 2.52-2.58 (2H, m), 5.29 (1H, s), 5.49 (4H, s), 7.27-7.50 (10H, m); m/z (EI): 474 (M$^+$).

3-(2,6-Bis-benzyloxy-5-ethyl-pyrimidine-4-carbonyl)-5-methyl-benzonitrile: To a stirred solution of 3-[(2,6-Bis-benzyloxy-5-ethyl-pyrimidin-4-yl)-cyano-methyl]-5-methyl-benzonitrile (10 g, 21.1 mmol) in anhydrous DMF (80 mL) in a water bath under an atmosphere of nitrogen, was added 60%, in portions, sodium hydride (869 mg, 21.7 mmol). After 30 min, oxygen gas was bubbled into the reaction mixture for 5 hr. The mixture was neutralized with aqueous saturated ammonium chloride solution. The crude product was extracted with ether and recrystallized from dichloromethane-hexane to afford 8 g (80%) of a white solid; m.p. 123-124° C.; $^1$H NMR (200 MHz, CDCl$_3$) δ: 1.09 (3H, t, J=7.4 Hz), 2.43 (3H, s), 2.50 (2H, q, J=7.4 Hz), 5.35 (2H, s), 5.50 (2H, s), 7.27-7.46 (10H, m), 7.67 (1H, s), 7.87 (1H, s), 7.92 (1H, s); m/z (EI): 463 (M$^+$).

3-(5-Ethyl-2,6-dioxo-1,2,3,6-tetrahydro-pyrimidine-4-carbonyl)-5-methyl-benzonitrile (Compound 28): 3-(2,6-Bis-benzyloxy-5-ethyl-pyrimidine-4-carbonyl)-5-methyl-benzonitrile (4.5 g, 9.7 mmol) in anhydrous ethanol (30 mL) and THF (30 mL) was stirred with 10% palladium on carbon (250 mg) under an atmosphere of hydrogen. After 1.5 hr, the mixture was filtered through celite pad and the filtrate was evaporated in vacuo. The residue was purified by silica gel column chromatography (eluent, chloroform:methanol (95:5)) to afford 2.3 g (84%) of a white solid; m.p. 253-254° C.; $^1$H NMR (200 MHz, DMSO-d$_6$) δ: 0.84 (3H, t, J=7.0 Hz), 1.96 (2H, q, J=7.0 Hz), 2.45 (3H, s), 8.06 (1H, s), 8.11 (1H, s), 8.33 (1H, s), 11.05 (1H, s), 8.28 (1H, s); m/z (EI): 283 (M$^+$).

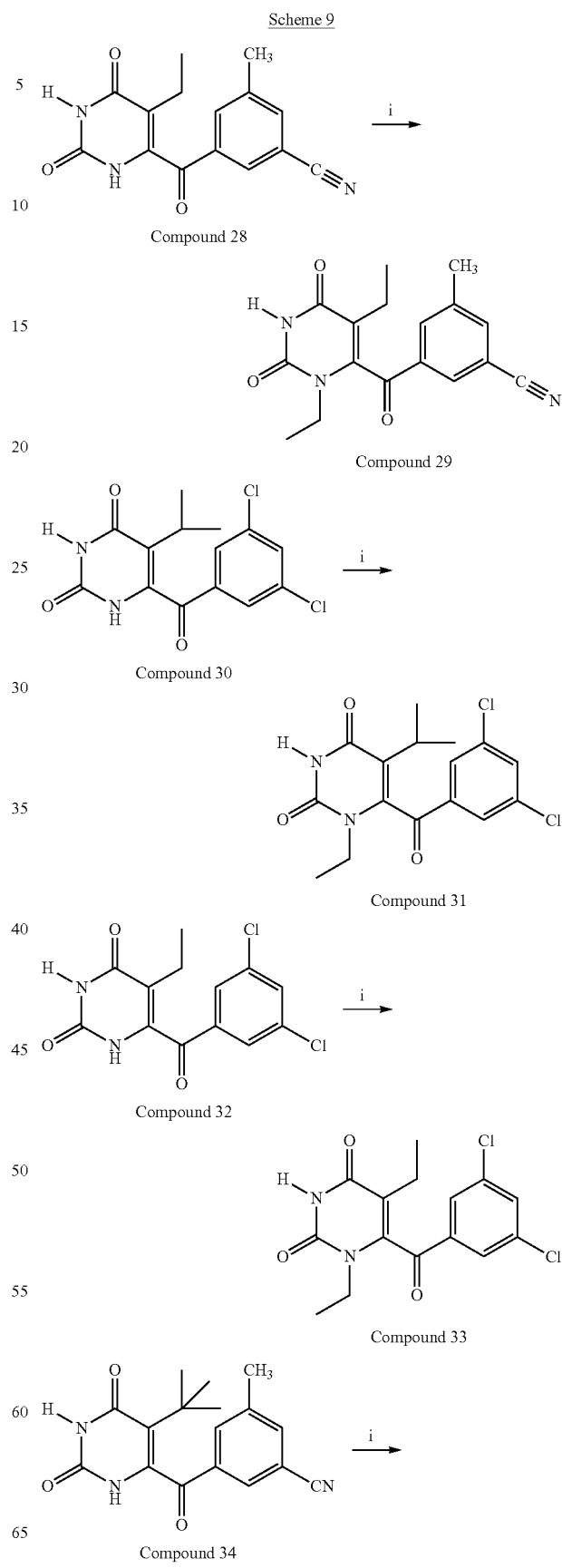

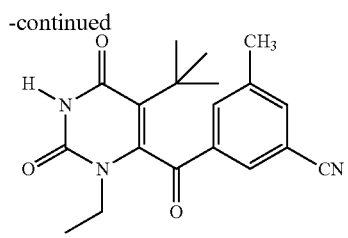

Compound 35

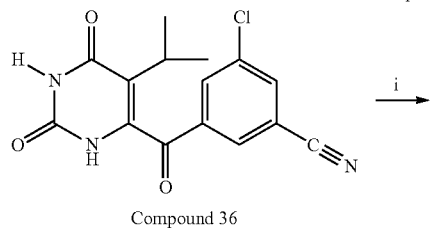

Compound 36

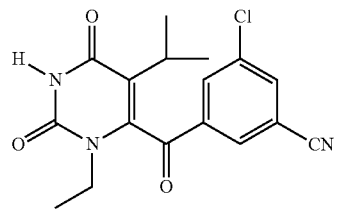

Compound 37

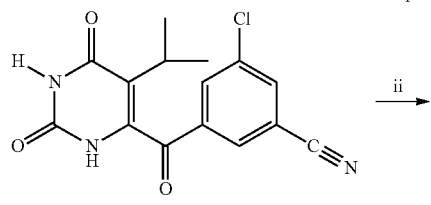

Compound 36

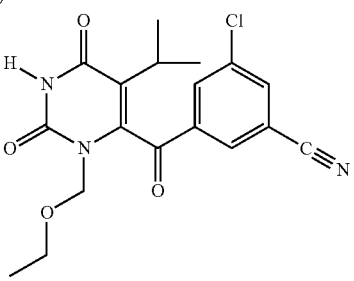

Compound 38

Reagents and conditions: i. alkyl halide or mesylate, K$_2$CO$_3$, DMF; ii. CH$_3$CH$_2$OCH$_2$Cl, SnCl$_4$, acetonitrile CH$_3$CH$_2$OCH$_2$Cl, SnCl$_4$, acetonitrile Compound 29: To a stirred solution of Compound 28 (297 mg, 1 mmol) and powdered anhydrous potassium carbonate (138 mg, 1 mmol) in DMF (5 mL) at room temperature, was added ethyl iodide (161 µL, 1 mmol). After stirring overnight, the mixture was evaporated in vacuo and the residue was purified by silica gel column chromatography (eluent, ethyl acetate:hexane (1:2)) to afford 134 mg (43%) as a white solid; m.p. 237-238° C.; $^1$H-NMR (200 MHz, CDCl$_3$) δ 0.97 (3H, t, J=7.4 Hz), 1.16 (3H, t, J=7.2 Hz), 1.95 (1H, m), 2.27 (1H, m), 2.53 (3H, s), 3.22 (1H, m), 3.92 (1H, m), 7.80 (1H, s), 7.95 (1H, s), 8.05 (1H, s), 9.06 (1H, s); m/z (EI) 311 [M$^+$]

Compound 31: To a stirred solution of Compound 30 (prepared using procedures similar to those described in U.S. Pat. No. 6,713,486, herein incorporated by reference in its entirety for all purposes) (327 mg, 1 mmol) and powdered anhydrous potassium carbonate (138 mg, 1 mmol) in DMF (5 mL) at room temperature, was added ethyl iodide (161 µL, 1 mmol). After stirring overnight, the mixture was evaporated in vacuo and the residue was purified by silica gel column chromatography (eluent, ethyl acetate:hexane (1:4)) to afford 149 mg (42%) as a white solid; m.p. 220-221° C.; $^1$H-NMR (200 MHz, CDCl$_3$) δ 1.12-1.21 (9H, m), 2.24 (1H, m), 3.20 (1H, m), 3.89 (1H, m), 7.71 (1H, t, J=1.8 Hz), 7.81 (2H, d, J=1.8 Hz), 8.95 (1H, s); m/z (EI) 354 [M$^+$]

Compound 33: To a stirred solution of Compound 32 (prepared using procedures similar to those described in U.S. Pat. No. 6,713,486) (313 mg, 1 mmol) and powdered anhydrous potassium carbonate (138 mg, 1 mmol) in DMF (5 mL) at room temperature, was added ethyl iodide (161 µL, 1 mmol). After stirring overnight, the mixture was evaporated in vacuo and the residue was purified by silica gel column chromatography (eluent, ethyl acetate:hexane (1:4)) to afford 204 mg (59%) as a white solid; m.p. 246-248° C.; $^1$H-NMR (200 MHz, CDCl$_3$) δ 0.98 (3H, t, J=7.4 Hz), 1.17 (3H, t, J=7.0 Hz), 1.97 (1H, m), 2.28 (1H, m), 3.24 (1H, m), 3.92 (1H, m), 7.11 (1H, t, J=2.0 Hz), 7.79 (2H, d, J=2.0 Hz), 9.12 (1H, s); m/z (EI) 340 [M$^+$]

Compound 35: To a stirred solution of Compound 34 (prepared using procedures similar to those described in U.S. Pat. No. 6,713,486) (311 mg, 1 mmol) and powdered anhydrous potassium carbonate (138 mg, 1 mmol) in DMF (5 mL) at room temperature, was added ethyl iodide (161 µL, 1 mmol). After stirring overnight, the mixture was evaporated in vacuo and the residue was purified by silica gel column chromatography (eluent, ethyl acetate:hexane (1:2)) to afford 106 mg (31%) as a white solid; m.p. 287-284° C.; $^1$H-NMR (200 MHz, CDCl$_3$) δ 1.10 (3H, t, J=7.0 Hz), 1.21 (9H, s), 2.53 (3H, s), 3.01 (1H, m), 3.94 (1H, m), 7.98 (1H, s), 8.04 (2H, br. s), 8.97 (1H, s); m/z (EI) 339 [M$^+$]

Compound 37: To a stirred solution of Compound 36 (prepared using procedures similar to those used to prepare Compound 28, except that 3-cyanomethyl-5-chloro-benzonitrile was used instead of 3-cyanomethyl-5-methyl-benzonitrile) (212 mg, 0.667 mmol) and powdered anhydrous potassium carbonate (92 mg, 0.667 mmol) in DMF (3.5 mL) at room temperature, was added ethyl iodide (54 µL, 0.667 mmol). After stirring overnight, the mixture was evaporated in vacuo and the residue was purified by silica gel column chromatography (eluent, ethyl acetate:hexane (1:2)) to afford 62 mg (27%) as a white solid; m.p. 248-249° C.; $^1$H-NMR (200 MHz, CDCl$_3$) δ 1.12-1.29 (9H, m), 2.20 (1H, m), 3.15 (1H, m), 3.91 (1H, m), 7.97 (1H, t, J=1.8 Hz), 8.12-8.15 (2H, m), 8.59 (1H, s); m/z (EI) 345 [M$^+$]

Compound 38: A mixture of Compound 36 (219 mg, 0.689 mmol), 1,1,1,3,3,3-hexamethyldisilazane (5 mL), and chloro trimethylsilane (0.2 mL) was refluxed for 4 hr. After cooling to room temperature, the mixture was evaporated in vacuo and the residue was dissolved in acetonitrile (5 mL). Chloromethylethyl ether (64 µL, 0.689 mmol) and 1M tin chloride in dichloromethane (40 µL, 0.04 mmol) were added with stirring. After stirring overnight, excess sodium bicarbonate was added and stirred for 1 hr. The mixture was evaporated in vacuo and the residue was purified by silica gel column chromatography (eluent, ethyl acetate:hexane (1:3)) to afford 206 mg (79%) of a white solid; m.p. 162-164° C.; $^1$H-NMR (200 MHz, CDCl$_3$) δ 0.79 (3H, t, J=7.0 Hz), 1.14 (2H, d, J=7.0 Hz), 1.22 (3H, d, J=7.0 Hz), 2.21 (1H, m), 3.21-3.50 (2H, m), 4.68 (1H, d, J=9.8 Hz), 5.56 (1H, d, J=9.8 Hz), 7.92 (1H, t, J=1.8 Hz), 8.11 (2H, d, J=1.8 Hz), 8.47 (1H, s); m/z (EI) 375 [M$^+$]

Scheme 10

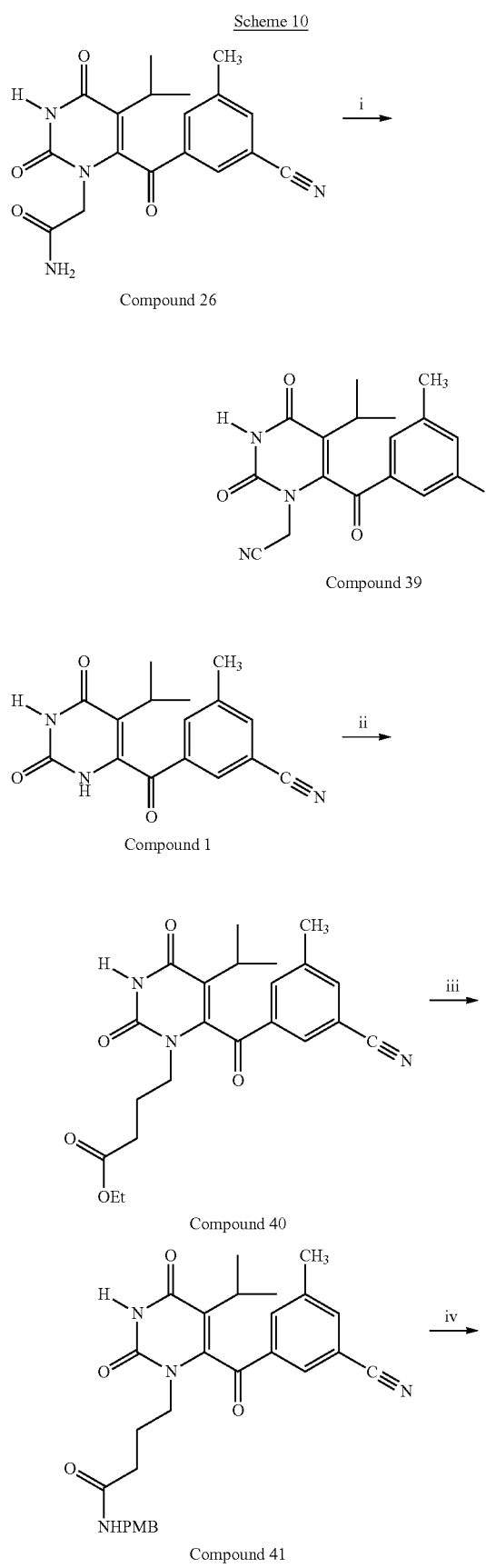

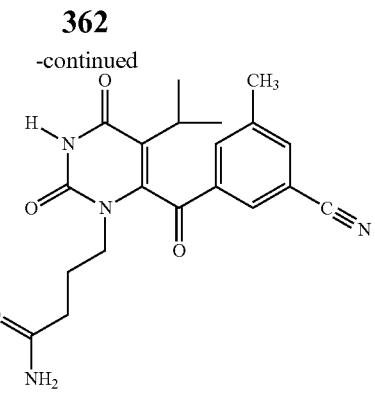

Reagents and conditions: i.thionyl chloride, benzene; ii.ethyl-4-bromobutyrate, LiI, K₂CO₃, DMF; iii. p-methoxybenzyl amine; iv. CAN, acetonitrile.

Compound 39: To a stirred solution of Compound 26 (120 mg, 0.338 mmol) in benzene (15 mL), was added thionyl chloride (1 mL) and DMF (1 drop). The mixture was then refluxed for 3 hr. After cooling to room temperature, the mixture was evaporated in vacuo and the residue was purified by silica gel column chromatography (eluent, ethyl acetate: hexane (1:1)) to afford 49 mg (43%) as a white solid; m.p. 270-271° C.; $^1$H-NMR (200 MHz, DMSO-$d_6$) δ 1.05 (6H, br. s), 2.14 (1H, m), 2.46 (3H, s), 4.48 (2H, br. d), 8.12 (1H, s), 8.27 (1H, s), 8.52 (1H, s), 11.80 (1H, s); m/z (EI) 336 [M$^+$]

Compound 40: A mixture of Compound 1 (891 mg, 3 mmol) and powdered anhydrous potassium carbonate (414 mg, 3 mmol), lithium iodide (402 mg, 3 mmol), and ethyl-4-bromobutyrate (432 μL, 3 mmol) in DMF (15 mL) was stirred in an oil bath (100-115° C.) overnight. After cooling to room temperature, the mixture was evaporated in vacuo and the residue was purified by silica gel column chromatography (eluent, ethyl acetate:hexane (1:2)) to afford 521 mg (42%) as a white syrup; $^1$H-NMR (200 MHz, CDCl$_3$) δ 1.12 (3H, d, J=7.0 Hz), 1.17-1.29 (8H, m), 1.85 (1H, m), 2.24 (2H, t, J=6.8 Hz), 2.51 (3H, s), 3.10 (1H, m), 3.86 (1H, m), 4.12 (2H, q, J=7.0 Hz), 7.79 (1H, s), 7.96 (1H, s), 8.06 (1H, s), 8.96 (1H, s).

Compound 41: Compound 40 (411 mg, 1 mmol) was stirred with p-methoxybenzyl amine (2 mL) in an oil bath (170° C.) for 4 hr. After cooling to room temperature, the mixture was purified by silica gel column chromatography (eluent, ethyl acetate:hexane (1:2)) to afford 218 mg (43%) as a pale yellow syrup; $^1$H-NMR (200 MHz, CDCl$_3$) δ 1.09 (3H, d, J=6.8 Hz), 1.20 (3H, d, J=6.8 Hz), 1.77-1.97 (2H, m), 2.17 (2H, t, J=6.8 Hz), 2.50 (3H, s), 3.23 (1H, m), 3.75 (3H, s), 3.82 (1H, m), 4.27 (2H, d, 5.4 Hz), 6.50 (1H, t, J=5.4 Hz), 6.78 (2H, d, J=7.5 Hz), 7.14 (2H, d, J=7.5 Hz), 7.72 (1H, s), 7.99 (1H, s), 8.06 (1H, s).

Compound 42: To a stirred solution of Compound 41 (218 mg, 0.43 mmol) in acetonitrile (4 mL) at room temperature, was added CAN (ceric ammonium nitrate) (475 mg, 0.86 mmol) followed by distilled water (2 mL). After 40 min., the mixture was diluted with ethyl acetate, washed with water, dried with anhydrous magnesium sulfate, filtered, and evaporated in vacuo to give a brown syrup. The crude product was purified by silica gel column chromatography (eluent, methanol:chloroform (3:97)) to afford 125 mg (75%) of a white solid; m.p. 261-262° C.; H-NMR (200 MHz, DMSO-$d_6$) δ 1.00 (3H, d, J=6.6 Hz), 1.08 (3H, d, J=6.6 Hz), 1.59-1.75 (2H, m), 1.87-2.12 (3H, m), 2.46 (3H, s), 3.03 (1H, m), 3.66 (1H, m), 6.66 (1H, s), 7.16 (1H, s), 8.10 (1H, s), 8.24 (1H, s), 8.47 (1H, s), 11.45 (1H, s); m/z (EI) 382 [M$^+$]

Scheme 11

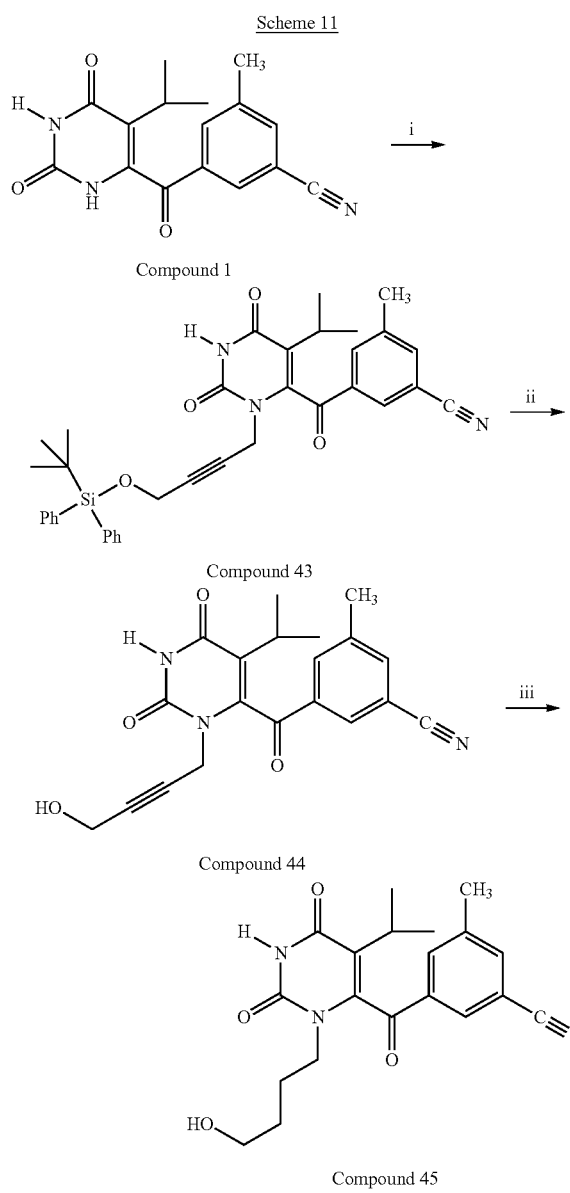

Reagents and conditions: i.Methanesulfonic acid 4-(tert-butyl-diphenyl-silanyloxy)-but-2-ynyl ester, LiI, K₂CO₃, DMF; ii. TBAF, THF; iii. H₂, Pd/C, ethanol/THF.

Compound 43: To a stirred solution of 4-tert-butyl-diphenylsilyloxy-2-butyn-1-ol (324 mg, 1 mmol) in chloroform (10 mL) cooled in an ice bath under nitrogen atmosphere, was added triethylamine (210 μL, 1.5 mmol) and methanesulfonyl chloride (90 μL, 1.2 mmol) was added dropwise. After stirring for 1.1 hr., the reaction mixture was washed with sat. aqueous sodium bicarbonate, dried with anhydrous magnesium sulfate, filtered, and evaporated in vacuo. The residue was further dried under high vacuum for about 20 min. and mixed with Compound 1 (297 mg, 1 mmol), powdered anhydrous potassium carbonate (138 mg, 1 mmol), and lithium iodide (134 mg, 1 mmol). DMF (5 mL) was then added to the mixture at room temperature and stirred for overnight. After evaporation of DMF, the residue was dissolved in methanol-chloroform (1:9) and filtered through celite pad. The filtrate was then evaporated in vacuo and the residue was purified by silica gel column chromatography (eluent, ethyl acetate:hexane (1:4)) to afford 370 mg (61%) of a colorless syrup; $^1$H-NMR (200 MHz, CDCl$_3$) δ 0.98 (9H, s), 1.10 (3H, d, J=6.8 Hz), 1.19 (3H, d, J=6.8 Hz), 2.22 (1H, m), 2.37 (3H, s), 3.87 (2H, s), 4.06 (1H, d, J=18.0 Hz), 4.83 (1H, d, J=18.0 Hz), 7.35-7.60 (11H, m), 7.96 (1H, s), 8.06 (1H, s), 8.39 (1H, s).

Compound 44: Compound 43 (370 mg, 0.61 mmol) was dissolved in THF (5 mL) and stirred with tetrabutylammonium fluoride (1M in THF; 0.8 mL, 0.8 mmol) at room temperature for 1 hr. The mixture was evaporated in vacuo and the residue was purified by silica gel column chromatography (eluent, ethyl acetate:hexane (1:1)) to afford 168 mg (75%) of a white solid; m.p. 181-182° C.; $^1$H-NMR (200 MHz, CDCl$_3$) δ 1.13 (3H, d, J=6.8 Hz), 1.22 (3H, d, J=6.8 Hz), 2.03 (1H, br. s), 2.26 (1H, m), 2.54 (3H, s), 3.90 (1H, d, J=16.6 Hz), 4.00 (1H, d, J=16.6 Hz), 4.12 (1H, d, J=18.2 Hz), 4.77 (1H, d, J=18.2 Hz), 7.80 (1H, s), 8.08 (1H, s), 8.19 (1H, s), 9.22 (1H, s); m/z (EI) 365 (M⁺)

Compound 45: Compound 44 (100 mg, 0.27 mmol) was stirred with 10% palladium on carbon (20 mg) in anhydrous ethanol (8 mL) and THF (5 mL) at room temperature under an atmosphere of hydrogen. After 6 hr., the reaction mixture was filtered through a celite pad and the pad was washed with ethanol and chloroform. The combined filtrate was evaporated in vacuo and the residue was purified by silica gel column chromatography (eluent, ethyl acetate:hexane (1:1)) to afford 57 mg (56%) of a colorless syrup. Recrystallization from chloroform/ether/hexane resulted a white solid; m.p. 119-120° C.; $^1$H-NMR (200 MHz, CDCl$_3$) δ 1.11 (3H, d, J=7.0 Hz), 1.22 (3H, d, J=7.0 Hz), 1.37-1.58 (2H, m), 1.61-1.69 (2H, m), 2.22 (1H, m), 2.53 (3H, s), 3.20 (1H, m), 3.53-3.59 (2H, m), 3.88 (1H, m), 7.81 (1H, s), 7.98 (1H, s), 8.09 (1H, s), 10.02 (1H, s); m/z (EI) 369 [M⁺]

Scheme 12

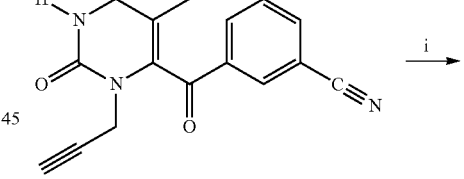

Compound 23

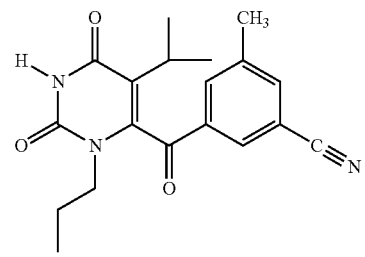

Compound 46

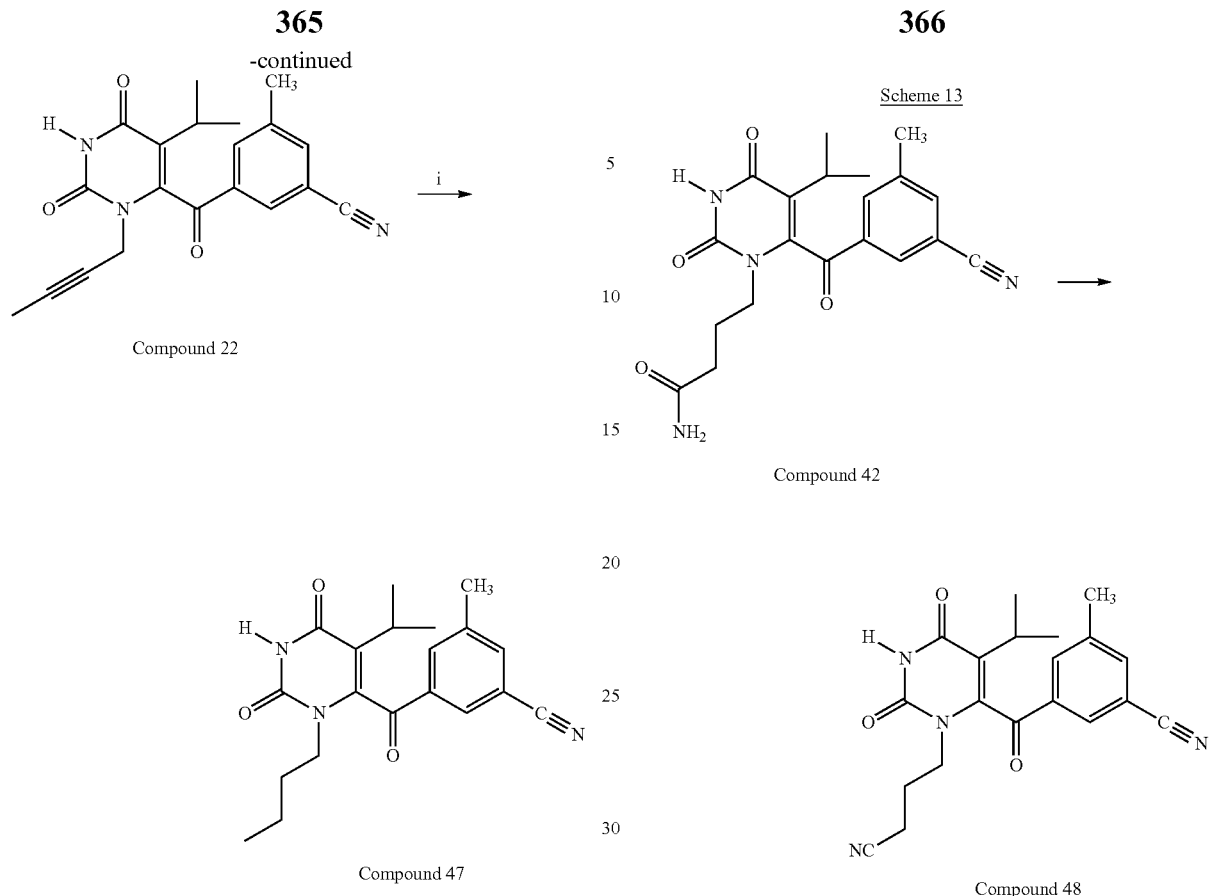

Compound 22

Compound 42

Compound 47

Compound 48

Reagents and conditions: i. H$_2$, Pd/C, ethanol/THF.

Compound 46: Compound 23 (100 mg, 0.298 mmol) was stirred with 10% palladium on carbon (20 mg) in anhydrous ethanol (10 mL) and THF (5 mL) at room temperature under an atmosphere of hydrogen. After 4.5 hr., the reaction mixture was filtered through A celite pad and the pad was washed with ethanol and chloroform. The combined filtrate was evaporated in vacuo and the residue was purified by silica gel column chromatography (eluent, ethyl acetate:hexane (1:3)) to afford 81 mg (80%) of a white solid; m.p. 202-203° C.; $^1$H-NMR (200 MHz, CDCl$_3$) δ 0.78 (3H, t, J=7.4 Hz), 1.13 (3H, d, J=7.0 Hz), 1.22 (3H, d, J=7.0 Hz), 1.54-1.64 (2H, m), 2.24 (1H, m), 2.54 (3H, s), 3.02 (1H, m), 3.81 (1H, m), 7.82 (1H, s), 7.97 (1H, s), 8.07 (1H, s), 9.76 (1H, s); m/z (EI) 339 [M$^+$]

Compound 47: Compound 22 (140 mg, 0.4 mmol) was stirred with 10% palladium on carbon (20 mg) in anhydrous ethanol (10 mL) at room temperature under an atmosphere of hydrogen. After 5 hr., the reaction mixture was filtered through a celite pad and the pad was washed with ethanol and chloroform. The combined filtrate was evaporated in vacuo and the residue was purified by silica gel column chromatography (eluent, ethyl acetate:hexane (1:2)) to afford 88 mg (62%) of a colorless syrup. Recrystallization from chloroform/ether/hexane resulted a white solid; m.p. 133-134° C.; $^1$H-NMR (200 MHz, DMSO-d$_6$) δ 0.71 (3H, t, J=6.6 Hz), 0.99-1.17 (8H, m), 1.35-1.39 (2H, m), 2.09 (1H, m), 2.46 (3H, s), 2.97 (1H, m), 3.65 (1H, m), 8.11 (1H, s), 8.24 (1H, s), 8.49 (1H, s), 11.44 (1H, s); m/z (EI) 353 [M$^+$]

Compound 48: To a stirred solution of Compound 42 (71 mg, 0.185 mmol) in benzene (24 mL), was added thionyl chloride (1 mL) and DMF (3 drops). The mixture was then refluxed for 3 hr. After cooling to room temperature, the mixture was evaporated in vacuo and the residue was purified by silica gel column chromatography (eluent, ethyl acetate: hexane (from 1:1 to 2:1) to afford 54 mg (80%) of Compound 48 as a white solid. m.p. 224-225° C.; $^1$H-NMR (200 MHz, DMSO-d$_6$) δ 1.14 (3H, d, J=7.0 Hz), 1.22 (3H, d, J=7.0 Hz), 1.84-2.02 (2H, m), 2.21-2.40 (3H, m), 2.54 (3H, s), 3.19 (1H, m), 4.03 (1H, m), 7.83 (1H, s), 8.03 (1H, s), 8.08 (1H, s), 9.58 (1H, s); m/z (EI) 364 (M$^+$)

Scheme 14

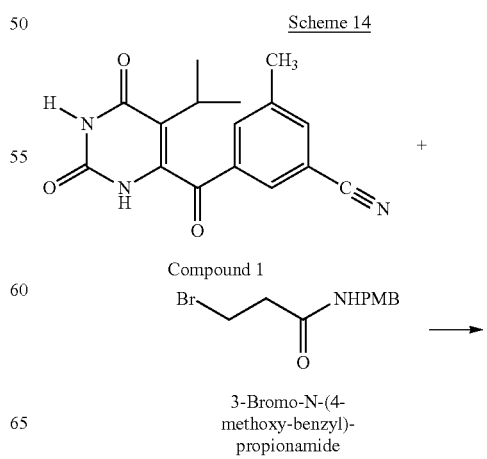

Compound 1

3-Bromo-N-(4-methoxy-benzyl)-propionamide

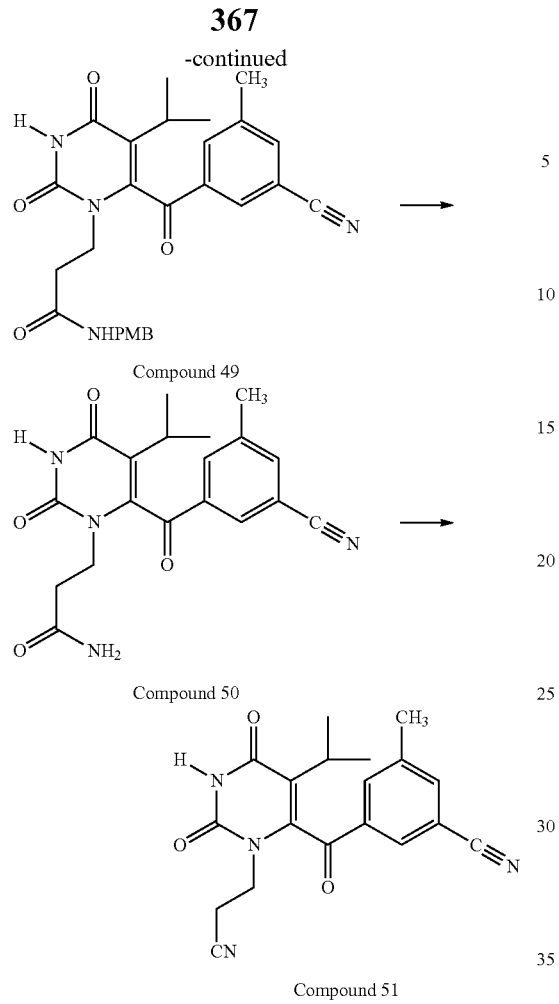

Compound 49

Compound 50

Compound 51

Compound 49: A mixture of Compound 1 (297 mg, 1 mmol) and powdered anhydrous potassium carbonate (138 mg, 1 mmol), lithium iodide (134 mg, 1 mmol), and 3-bromo-N-(4-methoxy-benzyl)-propionamide (272 mg, 1 mmol) in DMF (5 mL) was stirred in an oil bath (90-110° C.) for 17 hr. After cooling to room temperature, the mixture was evaporated in vacuo and the residue was purified by silica gel column chromatography (eluent, methanol:chloroform (3:97); $R_f$=0.15 fraction was collected.) to afford 73 mg (15%) of a white syrup. $^1$H-NMR (200 MHz, CDCl$_3$) δ 1.11 (3H, d, J=6.8 HzHz), 1.18 (3H, d, J=6.8 Hz), 2.22 (1H, m), 2.38-2.67 (5H, m), 3.42 (1H, m), 3.79 (3H, s), 4.17 (1H, m), 4.27 (2H, d, J=5.6 Hz), 5.96 (1H, t, J=5.6 Hz), 6.81-6.88 (2H, m), 7.14-7.225 (2H, m), 7.80 (1H, s), 8.01 (1H, s), 8.04 (1H, s), 8.83 (1H, s).

Compound 50: To a stirred solution of Compound 49 (73 mg, 0.149 mmol) in acetonitrile (2 mL) at room temperature, was added CAN (164 mg, 0.298 mmol) followed by distilled water (1 mL). After 1.5 hr., the mixture was diluted with ethyl acetate, washed with water, dried with anhydrous magnesium sulfate, filtered, and evaporated in vacuo to give a brown syrup. The crude product was purified by silica gel column chromatography (eluent, methanol:chloroform (5:95)) to afford 26 mg (47%) of Compound 50 as a white solid. m.p. 253-254° C.; $^1$H-NMR (200 MHz, CDCl$_3$) δ 1.10 (3H, d, J=6.6 Hz), 1.17 (3H, d, J=6.6 Hz), 2.20 (1H, m), 2.40-2.70 (5H, m), 3.40 (1H, m), 4.13 (1H, m), 6.12 (1H, s), 6.26 (1H, s), 7.80 (1H, s), 8.03 (1H, s), 8.11 (1H, s), 10.26 (1H, s); m/z (EI) 368 (M$^+$)

Compound 51: To a stirred solution of Compound 50 (45 mg, 0.122 mmol) in benzene (10 mL), was added thionyl chloride (1 mL) and DMF (3 drops). The mixture was then refluxed for 3 hr. After cooling to room temperature, the mixture was evaporated in vacuo and the residue was purified by silica gel column chromatography (eluent, ethyl acetate: hexane (2:1)) to afford 33 mg (76%) of Compound 51 as a white solid. m.p. 195-196° C.; $^1$H-NMR (200 MHz, CDCl$_3$) δ 1.13 (3H, d, J=6.6 Hz), 1.20 (3H, d, J=6.6 Hz), 2.23 (1H, m), 2.55 (3H, s), 2.65-2.86 (2H, m), 3.31 (1H, m), 4.20 (1H, m), 7.85 (1H, s), 8.02 (1H, s), 8.08 (1H, s), 9.14 (1H, s); m/z (EI) 350 (M$^+$)

Scheme 15

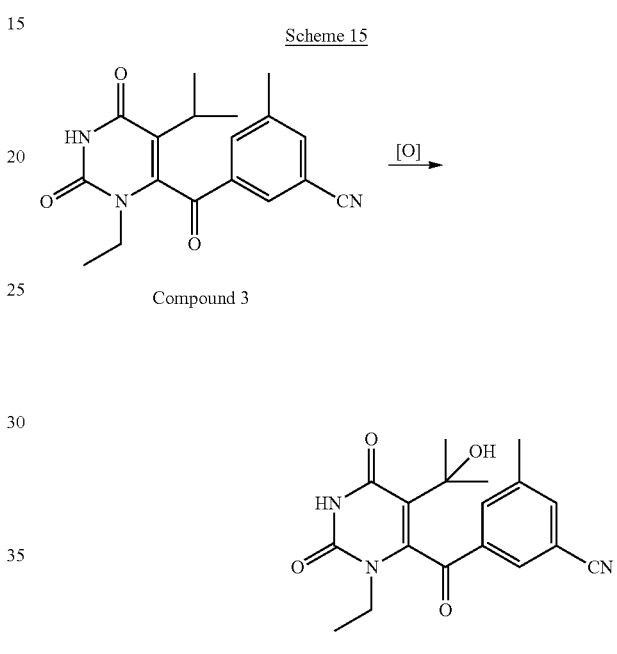

Compound 3

Compound 52

Compound 52: Compound 52 can be prepared by oxidizing Compound 3, e.g. by incubation in the presence of rat microsomes (In Vitro Technologies, MD) in phosphate buffer (50 mM, pH 7.4) and NADPH (Gentest).

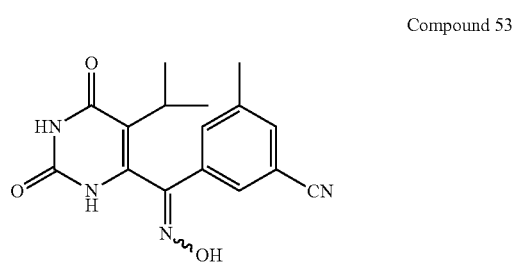

Compound 53

Compound 53: Hydroxylamine hydrochloride (262 mg, 3.77 mmol, 20 eq.) was added to Compound 1 (56 mg, 0.188 mmol) in 15 mL ethanol. The reaction mixture was heated to reflux for 3 days. The precipitate of the reaction crude was filtered off and the filtrate was concentrated down and purified by reversed phase HPLC (MeCN/water) to give white solid (19 mg, 32%). LC-MS shows 313.1 (M+1). $^1$H NMR (300 MHz, CD$_3$OD): δ 7.81 (s, 1H), 7.70 (s, 1H), 7.61 (s, 1H), 2.44 (s, 3H), 2.38 (m, 1H), 1.71 (d, 6H).

Compound 54

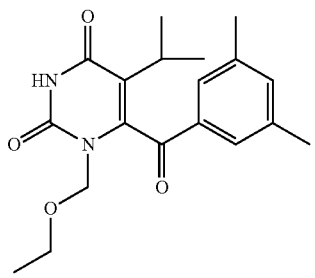

Compound 54, above, was prepared from 6-(3,5-dimethylbenzoyl)-5-isopropylpyrimidine-2,4(1H,3H)-dione using procedures described in U.S. Pat. No. 6,136,815, herein incorporated by reference in its entirety for all purposes.

Compound 56

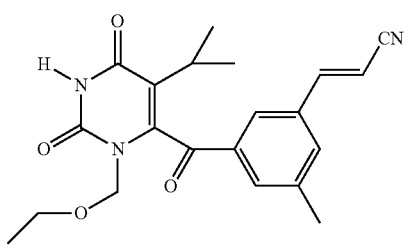

A mixture of 3-[3-(5-isopropyl-2,6-dioxo-1,2,3,6-tetrahydro-pyrimidine-4-carbonyl)-5-methyl-phenyl]acrylonitrile (55) (323 mg, 1 mmol), HMDS (5 mL), and trimethylsilyl chloride (10 µL) was refluxed for 4 hr. After cooling to room temperature, the mixture was evaporated in vacuo. The residue was then dissolved in acetonitrile (5 mL). The chloromethylethyl ether (93 µL, 1 mmol) was added to the stirred solution, followed by tin chloride (1 M) in dichloromethane (100 µL, 0.1 mmol). After stirring overnight, excess sodium bicarbonate was added to the reaction mixture. After stirring for 30 min., the mixture was evaporated in vacuo and the residue was purified by silica gel column chromatography (eluent, ethylacetate:hexanes (1:2)) to afford 170 mg (44%) of a colorless syrup. Recrystallization from ether/hexane resulted in a white solid. $^1$H NMR (200 MHz, CDCl$_3$) δ 0.75 (3H, t, J=7.0 Hz), 1.10 (3H, d, J=6.8 Hz), 1.21 (3H, d, J=6.8 Hz), 2.29 (1H, m), 2.47 (3H, s), 3.20-3.44 (2H, m), 4.77 (1H, d, J=10.0 Hz), 5.48 (1H, d, J=10.0 Hz), 5.99 (1H, d, J=16.6 Hz), 7.43 (1H, d, J=16.6 Hz), 7.55 (1H, s), 7.77 (1H, s), 7.86 (1H, s), 8.73 (1H, s). m/z (LC/Mass, EI) 382 (M+H+).

3-[3-(5-isopropyl-2,6-dioxo-1,2,3,6-tetrahydro-pyrimidine-4-carbonyl)-5-methyl-phenyl]-acrylonitrile (55) can be prepared by a variety of methods, as shown below in scheme 16.

Scheme 16

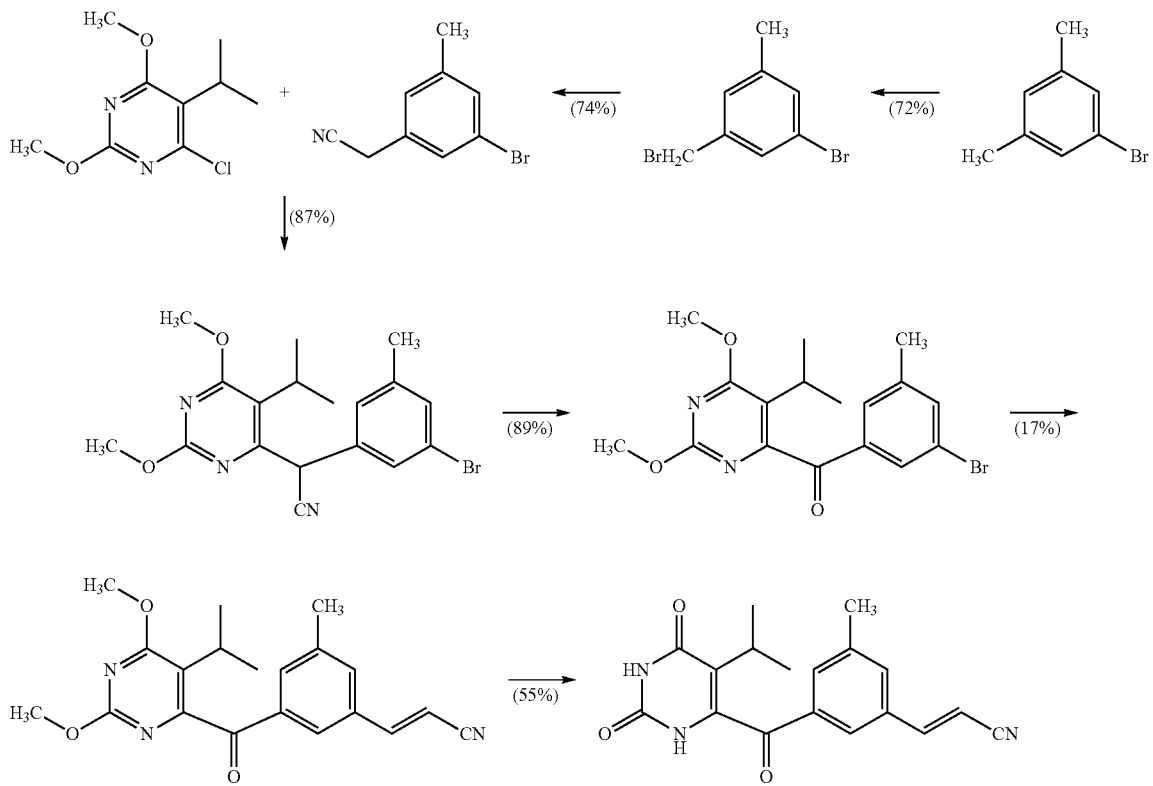

Compound 55

1-Bromo-3-bromomethyl-5-methyl-benzene: A mixture of 3,5-dimethylbromobenzene (80.25 g, 0.43M), NBS (77 g, 0.43 M), and benzoyl peroxide (5.2 g, 0.021 M) in carbon tetrachloride (400 mL) was refluxed for 3 hr. under a light of 500 W tungsten light. After cooling to room temperature, the mixture was filtered and the filtrate was evaporated in vacuo to give a white solid, which was purified by silica gel column chromatography (eluent: hexane) to afford 82 g (72%) of a white solid. m.p. 46-47° C.; $^1$H NMR (200 MHz, CDCl$_3$) δ 2.32 (3H, s), 4.38 (2H, s), 7.12 (1H, s), 7.25 (1H, s), 7.33 (1H, s).

(3-Bromo-5-methyl-phenyl)-acetonitrile: To a flask equipped with additional funnel, was placed potassium cyanide (29.6 g, 0.45 M) and distilled water (30 mL). The mixture, with stirring, was heated up to 70° C. in an oil bath and 1-bromo-3-bromomethyl-5-methyl-benzene (80 g, 0.3 M) in ethanol (150 mL) was dropwise added for 1 hr. through the addition funnel. After completion of addition, the mixture was refluxed for 2 hr. After cooling to room temperature, the mixture was evaporated in vacuo and the residue was partitioned between ether and water. The ether layer was taken, washed with water, dried with anhydrous magnesium sulfate, filtered, and evaporated in vacuo to give a brown residue, which was purified by silica gel column chromatography (eluent, ether:hexanes (1:3)) to afford 47 g (74%) of a light brown oil. $^1$H NMR (200 MHz, CDCl$_3$) δ 2.33 (3H, s), 3.68 (2H, s), 7.08 (1H, s), 7.28 (1H, s), 7.29 (1H, s).

(3-Bromo-5-methyl-phenyl)-(5-isopropyl-2,6-dimethoxy-pyrimidin-4-yl)-acetonitrile: To a stirred mixture of 4-chloro-5-isopropyl-2,6-dimethoxy-pyrimidine (47.63 g, 0.22 M) and (3-bromo-5-methyl-phenyl)-acetonitrile (42 g, 0.2 M) in anhydrous DMF (220 mL) in an ice-water bath under an atmosphere of nitrogen, was added 60% sodium hydride (16 g, 0.4 M) in portions. After stirring for 1 hr, the mixture was stirred at room temperature for overnight. The mixture was neutralized with aqueous saturated ammonium chloride solution. The crude product was extracted with ether and purified by silica gel column chromatography (eluent, ether:hexanes (1:7)) to afford 68 g (87%) of a white solid. m.p. 123-124° C.; $^1$H NMR (200 MHz, CDCl$_3$) δ 1.11 (3H, d, J=6.9 Hz), 1.15 (3H, D, J=6.9 Hz), 2.32 (3H, s), 2.97 (1H, m), 4.00 (3H, s), 4.01 (3H, s), 5.34 (1H, s), 7.14 (1H, s), 7.28 (1H, s), 7.31 (1H, s).

(3-Bromo-5-methyl-phenyl)-(5-isopropyl-2,6-dimethoxy-pyrimidin-4-yl)-methanone: To a stirred solution of (3-bromo-5-methyl-phenyl)-(5-isopropyl-2,6-dimethoxy-pyrimidin-4-yl)-acetonitrile (40 g, 0.1 M) in anhydrous DMF (300 mL) in a water bath under an atmosphere of nitrogen, was added 60% sodium hydride (4.92 g, 0.12 M) in portions. After 30 min, oxygen gas was bubbled into the reaction mixture for 2 hr. The mixture was neutralized with aqueous saturated ammonium chloride solution. The crude product was extracted with ether and purified by silica gel column chromatography (eluent, ether:hexanes (1:9)) to afford 34.6 g (89%) of a white solid. m.p. 122-123° C.; $^1$H NMR (200 MHz, CDCl$_3$) δ 1.17 (6H, d, J=7.1 Hz), 2.36 (3H, s), 2.77 (1H, m), 3.92 (3H, s), 4.05 (3H, s), 7.54-7.56 (2H, m), 7.75 (1H, m).

3-[3-(5-Isopropyl-2,6-dimethoxy-pyrimidine-4-carbonyl)-5-methyl-phenyl]-acrylonitrile: To a stirred solution of (3-bromo-5-methyl-phenyl)-(5-isopropyl-2,6-dimethoxy-pyrimidin-4-yl)-methanone (3.79 g, 10 mmol) in anhydrous DMF (10 mL), was added sodium acetate (902 mg, 11 mmol), palladium acetate (224 mg, 1 mmol), tetrakis(triphenylphosphine)palladium(0) (1.049 g, 4 mmol), and acrylonitrile in this order. The mixture was then stirred at 90-132° C. (oil bath) for about 23 hr. After cooling to room temperature, ether and ethyl acetate (2:1) was added to the reaction mixture. The mixture was then washed with aqueous saturated sodium bicarbonate solution, washed with water twice, dried with anhydrous magnesium sulfate, filtered, and evaporated in vacuo. The residue was purified by silica gel column chromatography (eluent, ethyl acetate:hexanes (1:4)) to afford 595 mg (17%) of a white solid. Z-isomer (275 mg, 8%) was also obtained as a white solid. m.p. 144-145° C.; $^1$H NMR (300 MHz, CDCl$_3$) δ 1.19 (6H, d, J=6.9 Hz), 2.42 (3H, s), 2.83 (1H, m), 3.94 (3H, s), 4.08 (3H, s), 5.92 (1H, d, J=16.8 Hz), 7.39 (1H, d, J=16.8 Hz), 7.49 (1H, s), 7.69 (1H, s), 7.75 (1H, s).

Z isomer: $^1$H NMR (300 MHz, CDCl$_3$) δ1.19 (6H, d, J=7.2 Hz), 2.45 (3H, s), 2.84 (1H, m), 3.93 (3H, s), 4.06 (3H, s), 5.49 (1H, d, J=12.0 Hz), 7.11 (1H, d, J=12.0 Hz), 7.75 (1H, s), 7.90 (1H, s), 7.97 (1H, s).

3-[3-(5-Isopropyl-2,6-dioxo-1,2,3,6-tetrahydro-pyrimidine-4-carbonyl)-5-methyl-phenyl]-acrylonitrile (Compound 55): To a stirred solution of 3-[3-(5-isopropyl-2,6-dimethoxy-pyrimidine-4-carbonyl)-5-methyl-phenyl]-acrylonitrile (5.36 g, 15.27 mmol) in anhydrous THF (50 mL), oxalyl chloride (25 mL) was added. The mixture was then refluxed with vigorous stirring for overnight. After cooling to room temperature, the mixture was evaporated in vacuo and the residue was purified by silica gel column chromatography (eluent, ethyl acetate:hexanes (from 1:1 to 4:1)) to afford 2.7 g (55%) of a white solid. m.p. 233-235° C.; $^1$H NMR (300 MHz, CD$_3$OD/CDCl$_3$) δ 1.16 (6H, d, J=6.9 Hz), 2.39-2.56 (4H, m), 6.12 (1H, d, J=16.6 Hz), 7.49 (1H, d, J=16.6 Hz), 7.66 (1H, s), 7.83 (1H, s), 7.87 (1H, s); m/z (LC/Mass, EI) 324 (M+H+).

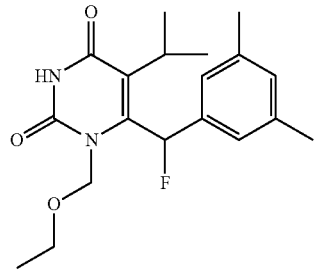

Compound 57

Compound 57: Compound 57 could be obtained by treatment of Compound 54 with sodium borohydride according to the method of Tanaka et al. *J. Med. Chem.* 1991, 34, 349-357, followed by treatment of the resulting intermediate with (diethylamino)sulfur trifluoride (available from Aldrich).

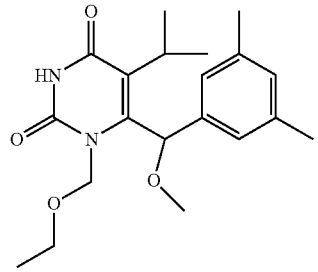

Compound 58

Compound 58: Compound 58 could be obtained by treatment of Compound 54 with sodium borohydride according to the method of Tanaka et al. *J. Med. Chem.* 1991, 34, 349-357, treatment of the resulting intermediate with methanesulfonyl chloride and refluxing in methanol with base.

Compound 59

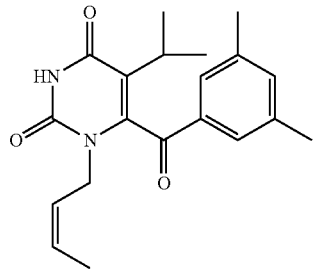

Compound 59, above, was prepared from 6-(3,5-dimethylbenzoyl)-5-isopropylpyrimidine-2,4(1H,3H)-dione using procedures similar to those described in U.S. Pat. No. 5,747,500, herein incorporated by reference in its entirety for all purposes.

Compound 60

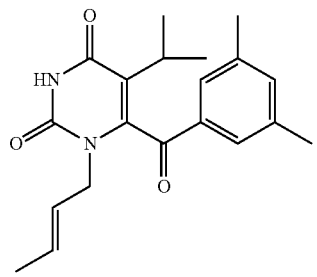

Compound 60, above, was prepared from 6-(3,5-dimethylbenzoyl)-5-isopropylpyrimidine-2,4(1H,3H)-dione using procedures similar to those described in U.S. Pat. No. 5,747,500.

Compound 61

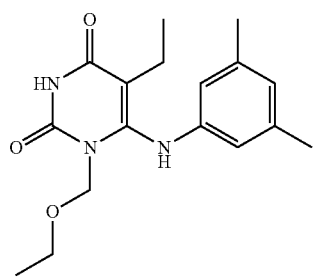

Compound 61, above, was prepared from 6-(3,5-dimethylphenylamine)-5-ethylpyrimidine-2,4(1H,3H)-dione using procedures similar to those described in U.S. Pat. No. 6,713,486, herein incorporated by reference in its entirety for all purposes.

Compound 62

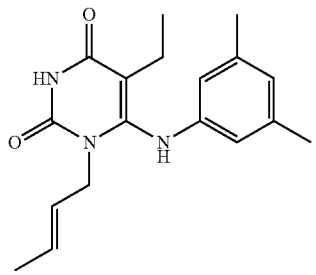

Compound 62, above, was prepared from 6-(3,5-dimethylphenylamine)-5-ethylpyrimidine-2,4(1H,3H)-dione using procedures similar to those described in U.S. Pat. No. 6,713,486.

Compound 63

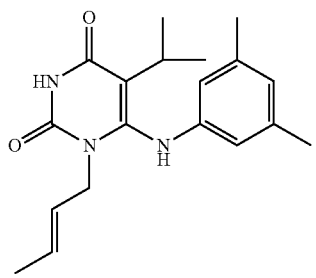

Compound 63, above, was prepared from 6-(3,5-dimethylphenylamine)-5-ethylpyrimidine-2,4(1H,3H)-dione using procedures similar to those described in U.S. Pat. No. 6,713,486.

Scheme 17

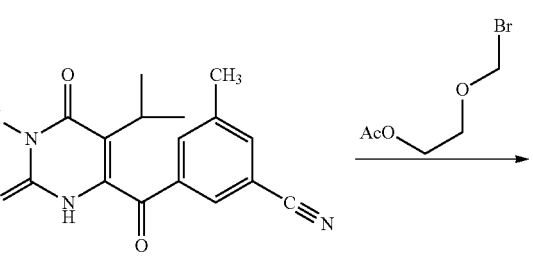

Compound 1

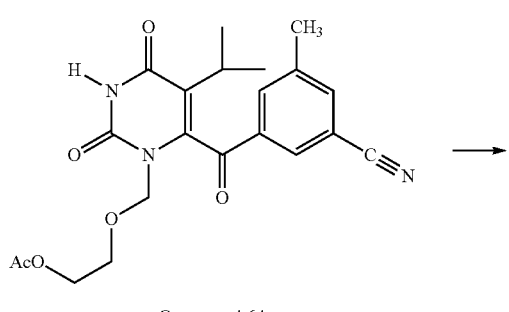

Compound 64

Compound 65

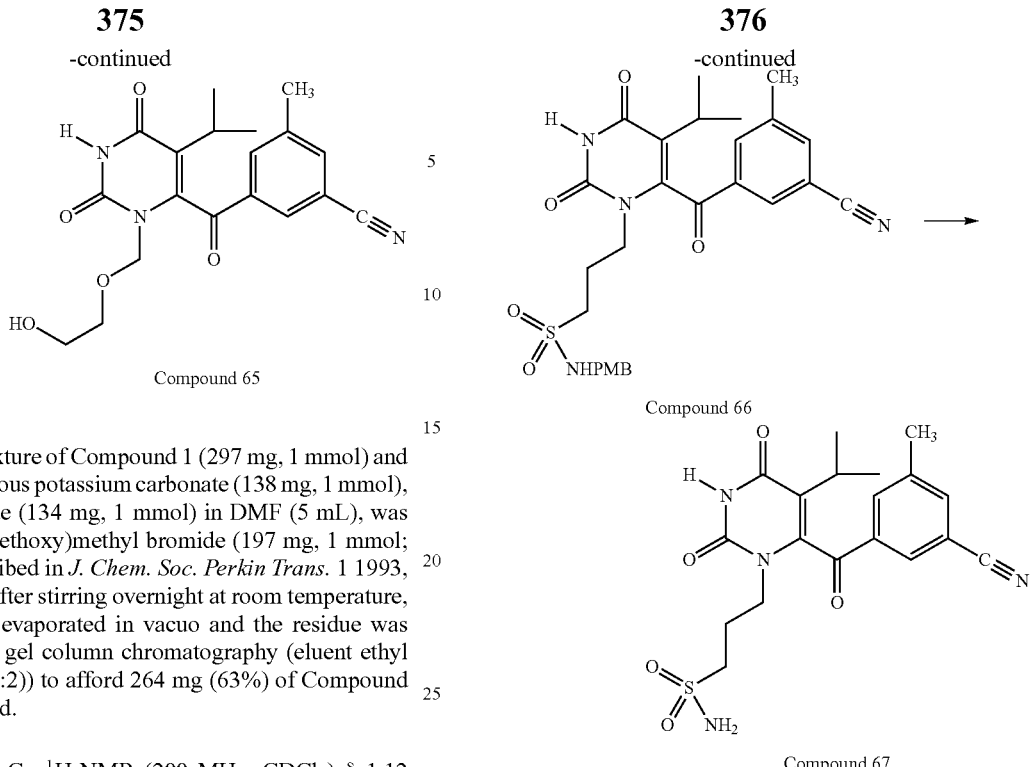

Compound 66

Compound 67

To a stirred mixture of Compound 1 (297 mg, 1 mmol) and powdered anhydrous potassium carbonate (138 mg, 1 mmol), and lithium iodide (134 mg, 1 mmol) in DMF (5 mL), was added (2-acetoxyethoxy)methyl bromide (197 mg, 1 mmol; prepared as described in *J. Chem. Soc. Perkin Trans.* 1 1993, pp. 1109-1111. After stirring overnight at room temperature, the mixture was evaporated in vacuo and the residue was purified by silica gel column chromatography (eluent ethyl acetate:hexane (1:2)) to afford 264 mg (63%) of Compound 64 as a white solid.

m.p. 178-179° C.; $^1$H-NMR (200 MHz, CDCl$_3$) δ 1.12 (3H, d, J=6.8 Hz), 1.21 (3H, d, J=6.8 Hz), 2.00 (3H, s), 2.25 (1H, m), 2.51 (3H, s), 3.51-3.58 (2H, m), 3.77-3.83 (2H, m), 4.85 (1H, d, J=10.4 Hz), 5.48 (1H, d, J=10.4 Hz), 7.77 (1H, s), 7.97 (1H, s), 8.04 (1H, s), 8.78 (1H, s).

Compound 64 (234 mg, 0.566 mmol) was stirred with ammonium hydroxide (2 mL) in THF (10 mL) and methanol (10 mL) overnight at room temperature. The mixture was then evaporated in vacuo and the residue was purified by silica gel column chromatography (eluent ethyl acetate:hexane (from 1:1 to 4:1)) to afford 180 mg (85%) of Compound 65 as a white foam. Recrystallization from chloroform/ether/hexane provided a white solid.

m.p. 149-150° C.; $^1$H-NMR (200 MHz, CDCl$_3$) δ 1.11 (3H, d, J=7.0 Hz), 1.20 (3H, d, J=7.0 Hz), 2.12 (1H, br. s), 2.25 (1H, m), 2.51 (1H, s), 3.44-3.59 (4H, m), 4.93 (1H, d, J=10.6 Hz), 5.42 (1H, d, J=10.6 Hz), 7.76 (1H, s), 8.03 (1H, s), 8.11 (1H, s), 9.31 (1H, s).

Scheme 18

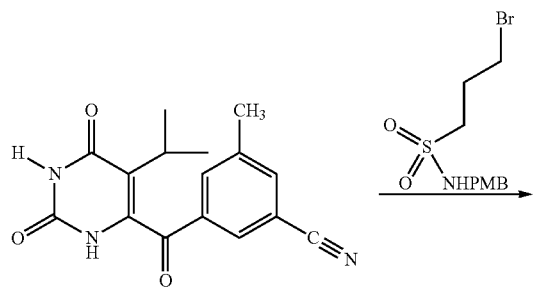

To a stirred mixture of Compound 1 (297 mg, 1 mmol) and powdered anhydrous potassium carbonate (138 mg, 1 mmol), and lithium iodide (134 mg, 1 mmol) in DMF (5 mL), was added 3-bromopropane-1-sulfonic acid p-methoxybenzylamide (322 mg, 1 mmol, prepared by the method of *J. Org. Chem.* 2006, 71, 6573-6578 (m.p. 105-106° C., $^1$H-NMR (200 MHz, DMSO-d$_6$) δ 2.06-2.20 (2H, m), 3.03 (2H, t, J=7.4 Hz), 3.55 (2H, t, J=6.6 Hz), 3.74 (3H, s), 4.08 (2H, d, J=6.2 Hz), 6.91 (2H, d, J=8.6 Hz), 7.26 (2H, d, J=8.6 Hz), 7.67 (1H, t, J=6.2 Hz). m/z (EI) 321 (M$^+$), 323 (M+2$^+$)). After stirring overnight at room temperature, the mixture was evaporated in vacuo and the residue was purified by silica gel column chromatography (eluent methanol:chloroform (3:97)) to afford 210 mg (39%) of Compound 66 as a white solid.

m.p. 170° C.; $^1$H-NMR (200 MHz, CDCl$_3$) δ 1.12 (3H, d, J=7.0 Hz), 1.20 (3H, d, J=7.0 Hz), 1.93-2.05 (2H, m), 2.22 (1H, m), 2.52 (3H, s), 2.81 (2H, t, J=6.8 Hz), 3.28 (1H, m), 3.80 (3H, s), 3.96 (1H, m), 4.21 (2H, d, J=5.8 Hz), 4.90 (1H, t, J=5.8 Hz), 6.89 (2H, d, J=7.0 Hz), 7.27 (2H, d, J=7.0 Hz), 7.79 (1H, s), 7.96 (1H, s), 8.03 (1H, s), 8.82 (1H, s).

To a stirred solution of Compound 66 (210 mg, 0.39 mmol) in acetonitrile (4 mL) at room temperature, was added CAN (427 mg, 0.78 mmol) followed by distilled water (2 mL). After 2 hr., the mixture was diluted with ethyl acetate, washed with water, dried with anhydrous magnesium sulfate, filtered, and evaporated in vacuo to give a brown syrup. The crude product was purified by silica gel column chromatography (eluent ethyl acetate:hexane (from 1:1 to 4:1)) to afford 120 mg (73%) of Compound 67 as a white solid.

m.p. 241-242° C.; $^1$H-NMR (200 MHz, DMSO-d$_6$) δ 0.99 (3H, d, J=6.2 Hz), 1.07 (3H, d, J=6.2 Hz), 1.80-1.87 (2H, m), 2.08 (1H, m), 2.45 (3H, s), 2.84-2.87 (2H, m), 3.14 (1H, m), 3.81 (1H, m), 6.71 (2H, s), 8.09 (1H, s), 8.24 (1H, s), 8.47 (1H, s), 11.50 (1H, s); m/z (EI) 418 (M$^+$).

Scheme 19

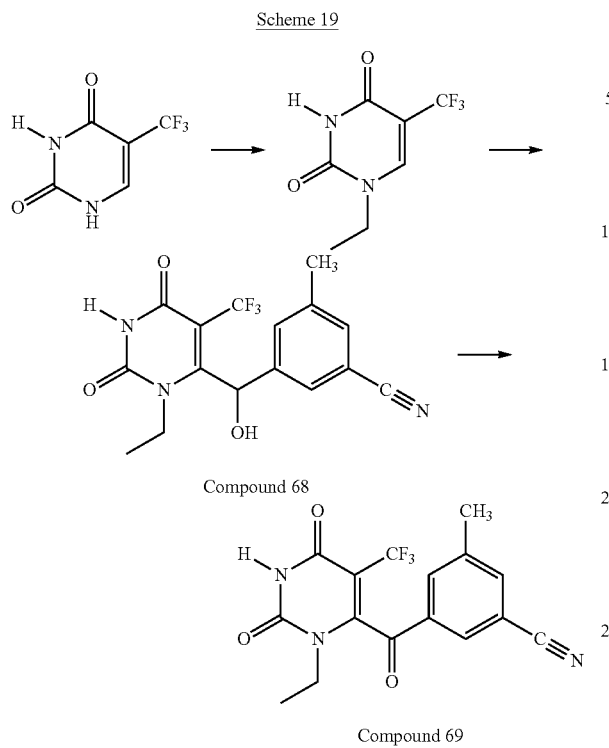

Compound 68

Compound 69

To a stirred mixture of 5-trifluoromethyl uracil (1.8 g, 10 mmol) and powdered anhydrous potassium carbonate (1.38 g, 10 mmol) in DMF (50 mL), was added iodoethane (0.8 mL, 10 mmol). After stirring overnight at room temperature, the mixture was evaporated in vacuo and the residue was purified by silica gel column chromatography (eluent ethyl acetate: hexane (1:1)) to afford 563 mg (27%) of 1-ethyl-5-trifluoromethyl uracil as a white solid. m.p. 259-260° C.; $^1$H-NMR (200 MHz, CDCl$_3$/CD$_3$OD) δ 1.35 (3H, d, J=7.2 Hz), 3.87 (2H, q, J=7.2 Hz), 7.94 (1H, s); m/z (EI) 208 (M$^+$).

To a solution of 1-ethyl-5-trifluoromethyl uracil (416 mg, 2 mmol) in THF (10 mL), was added 2M LDA in heptane/THF/benzene (2.2 mL, 4.4 mmol) under a nitrogen atmosphere at a rate such that the temperature did not exceed −70° C. After the mixture had been stirred for 1 hr, 3-cyano-5-methylbenzaldehyde (435 mg, 3 mmol) in THF (10 mL) was added, maintaining the temperature below −70° C. The mixture was stirred for 1 hr below −70° C. and allowed to warm to room temperature. The solution was neutralized with conc. HCl, diluted with water, and extracted with ethyl acetate. The organic layer was washed with sat. NaHCO$_3$ solution, dried over MgSO$_4$, filtered, and concentrated to dryness. The residue was purified by silica gel column chromatography (eluent methanol:chloroform (3:97)) to afford 552 mg (78%) of Compound 68 as a white solid. m.p. 260-262° C.; $^1$H-NMR (200 MHz, DMSO-d$_6$) δ 0.81 (3H, t, J=6.0 Hz), 2.37 (3H, s), 3.58-3.65 (2H, m), 6.10 (1H, d, J=5.2 Hz), 7.45 (1H, d, J=5.2 Hz), 7.59 (1H, s), 7.63 (1H, s), 7.66 (1H, s), 11.87 (1H, s); m/z (EI) 353 (M$^+$).

Compound 68 (200 mg, 0.566 mmol) was stirred with pyridinium dichromate (426 mg, 1.13 mmol) in DMF (4 mL) at room temperature. After 24 hr, the mixture was evaporated in vacuo and the residue was purified by silica gel column chromatography (eluent ethyl acetate:hexane (1:2)) to afford 173 mg (87%) of Compound 69 as a white solid.

m.p. 277-278° C.; $^1$H-NMR (200 MHz, DMSO-d$_6$) δ 1.00 (3H, d, J=6.8 Hz), 2.46 (3H, s), 3.13 (1H, m), 3.80 (1H, m), 8.13 (1H, s), 8.28 (1H, s), 8.54 (1H, s), 12.17 (1H, s); m/z (EI) 351 (M$^+$).

Scheme 20

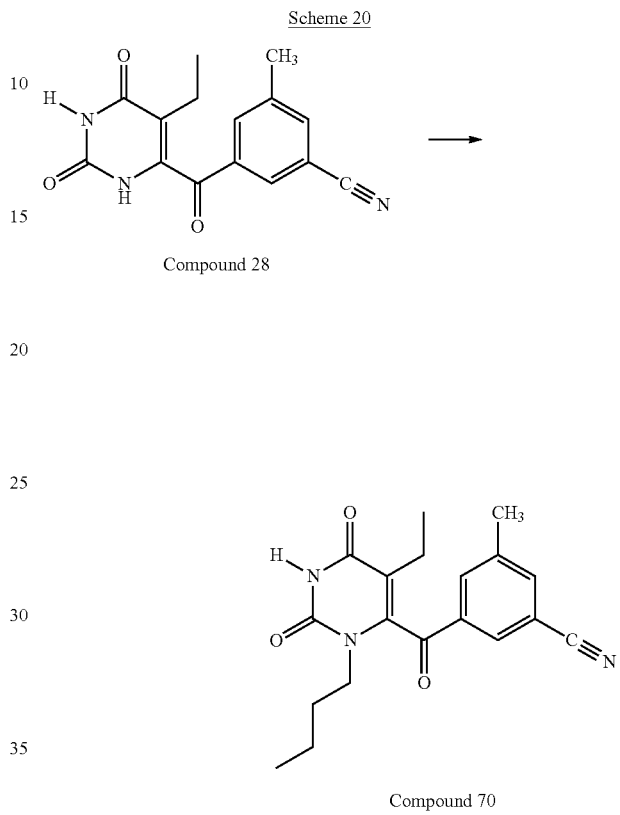

Compound 28

Compound 70

To a stirred mixture of Compound 28 (283 mg, 1 mmol) and powdered anhydrous potassium carbonate (138 mg, 1 mmol) in DMF (5 mL), was added 1-iodobutane (114 μL, 1 mmol). After stirring overnight at room temperature, the mixture was evaporated in vacuo and the residue was purified by silica gel column chromatography (eluent ethyl acetate:hexane (1:2)) to afford 145 mg (42%) of Compound 70 as a white solid.

m.p. 190-191° C.; $^1$H-NMR (200 MHz, CDCl$_3$) δ 0.80 (3H, t, J=7.4 Hz), 0.95 (3H, t, J=7.4 Hz), 1.08-1.28 (2H, m), 1.45-1.60 (2H, m), 1.93 (1H, m), 2.26 (1H, m), 2.52 (3H, s), 3.06 (1H, m), 3.81 (1H, m), 7.79 (1H, s), 7.93 (1H, s), 8.04 (1H, s), 9.56 (1H, s); m/z (EI) 339 (M$^+$).

Scheme 21

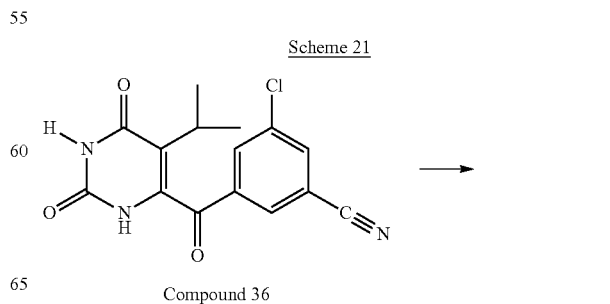

Compound 36

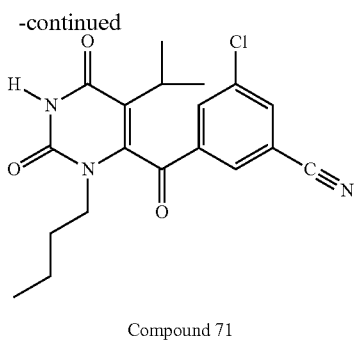

Compound 71

To a stirred mixture of Compound 36 (318 mg, 1 mmol) and powdered anhydrous potassium carbonate (138 mg, 1 mmol) in DMF (5 mL), was added 1-iodobutane (114 µL, 1 mmol). After stirring overnight at room temperature, the mixture was evaporated in vacuo and the residue was purified by silica gel column chromatography (eluent ethyl acetate:hexane (1:2)) to afford 96 mg (25%) of Compound 71 as a pale brown solid.

m.p. 183-184° C.; $^1$H-NMR (200 MHz, CDCl$_3$) δ 0.81 (3H, t, J=7.4 Hz), 1.07-1.28 (8H, m), 1.45-1.60 (2H, m), 2.20 (1H, m), 3.04 (1H, m), 3.81 (1H, m), 7.98 (1H, s), 8.13 (2H, s), 9.35 (1H, s); m/z (EI) 373 (M$^+$).

Scheme 22

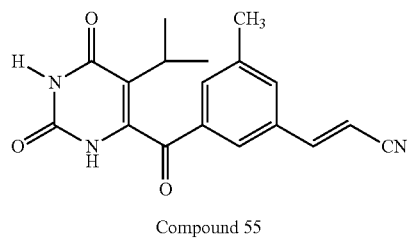

Compound 55

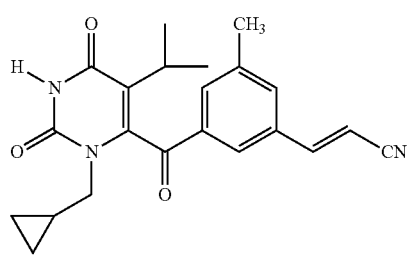

Compound 72

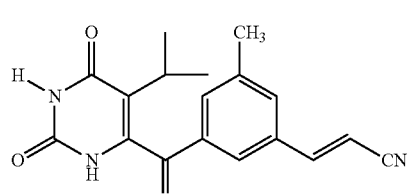

Compound 55

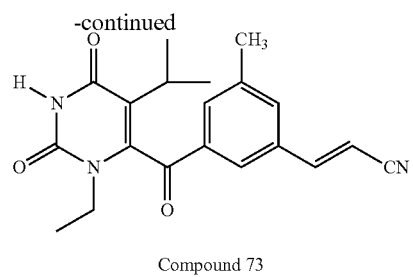

Compound 73

Compound 55

Compound 74

3-[3-(3-Cyclopropylmethyl-5-isopropyl-2,6-dioxo-1,2,3,6-tetrahydro-pyrimidine-4-carbonyl)-5-methyl-phenyl]-acrylonitrile (Compound 72): To a stirred solution of 3-[3-(5-isopropyl-2,6-dioxo-1,2,3,6-tetrahydro-pyrimidine-4-carbonyl)-5-methyl-phenyl]-acrylonitrile (Compound 55) (323 mg, 1 mmol), anhydrous powdered potassium carbonate (165 mg, 1.2 mmol), and lithium iodide (134 mg, 1 mmol) in DMF (5 mL) at room temperature, was added bromomethyl cyclopropane (97 µL, 1 mmol). After stirring overnight, the mixture was evaporated in vacuo and the residue was purified by silica gel column chromatography (eluent, ethyl acetate:hexane (1:2)) to give 320 mg (84%) of 3-[3-(3-cyclopropylmethyl-5-isopropyl-2,6-dioxo-1,2,3,6-tetrahydro-pyrimidine-4-carbonyl)-5-methyl-phenyl]-acrylonitrile (72) as a white solid. The product was recrystallized from chloroform-ether to afford a white solid. m.p. 225-226° C.; $^1$H-NMR (300 MHz, CDCl$_3$) δ 0.22-0.44 (4H, m), 0.93 (1H, m), 1.12 (3H, d, J=6.9 Hz), 1.24 (3H, d, J=6.9 Hz), 2.28 (1H, m), 2.50 (3H, s), 3.28 (1H, dd, J=6.0 Hz, J=15.0 Hz), 3.59 (1H, dd, J=6.0 Hz, J=15.0 Hz), 6.01 (1H, d, J=16.8 Hz), 7.44 (1H, d, J=16.8 Hz), 7.61 (1H, s), 7.77 (1H, s), 7.88 (1H, s), 9.00 (1H, s); m/z (EI) 377 (M$^+$).

3-[3-(3-Ethyl-5-isopropyl-2,6-dioxo-1,2,3,6-tetrahydro-pyrimidine-4-carbonyl)-5-methyl-phenyl]-acrylonitrile (Compound 73): To a stirred solution of 3-[3-(5-isopropyl-2,6-dioxo-1,2,3,6-tetrahydro-pyrimidine-4-carbonyl)-5-methyl-phenyl]-acrylonitrile (Compound 55) (323 mg, 1 mmol) and anhydrous powdered potassium carbonate (165 mg, 1.2 mmol) in DMF at room temperature, was added iodoethane (97 µL, 1.2 mmol). After stirring overnight, the mixture was evaporated in vacuo and the residue was purified by silica gel column chromatography (eluent, ethyl acetate:hexane (1:2)) to give 190 mg (54%) of 3-[3-(3-ethyl-5-isopropyl-2,6-dioxo-1,2,3,6-tetrahydro-pyrimidine-4-carbonyl)-5-methylphenyl]-acrylonitrile (73) as a white solid. The product was recrystallized from chloroform-ether. m.p. 174-176° C.; ¹H-NMR (200 MHz, CDCl₃) δ 1.12-1.30 (9H, m), 2.29 (1H, m), 2.51 (3H, s), 3.25 (1H, m), 3.90 (1H, m), 6.06 (1H, d, J=16.8 Hz), 7.47 (1H, d, J=16.8 Hz), 7.64 (1H, s), 7.80 (1H, s), 7.92 (1H, s), 10.08 (1H, s); m/z (EI) 351 (M⁺).

3-[3-(3-Butyl-5-isopropyl-2,6-dioxo-1,2,3,6-tetrahydro-pyrimidine-4-carbonyl)-5-methyl-phenyl]-acrylonitrile (Compound 74): To a stirred solution of 3-[3-(5-isopropyl-2,6-dioxo-1,2,3,6-tetrahydro-pyrimidine-4-carbonyl)-5-methyl-phenyl]-acrylonitrile (Compound 55) (323 mg, 1 mmol) and anhydrous powdered potassium carbonate (165 mg, 1.2 mmol) in DMF at room temperature, was added iodobuthane (136 µL, 1.2 mmol). After stirring overnight, the mixture was evaporated in vacuo and the residue was purified by silica gel column chromatography (eluent, ethyl acetate:hexane (1:2)) to give 170 mg (44%) of 3-[3-(3-butyl-5-isopropyl-2,6-dioxo-1,2,3,6-tetrahydro-pyrimidine-4-carbonyl)-5-methyl-phenyl]-acrylonitrile (74) as a white syrup. The product was recrystallized from ether-hexane to afford a white solid. m.p. 164-165° C.; ¹H-NMR (200 MHz, CDCl₃) δ 0.79 (3H, t, J=7.2 Hz), 1.11-1.29 (8H, m), 1.46-1.57 (2H, m), 2.27 (1H, m), 2.50 (3H, s), 3.09 (1H, m), 3.77 (1H, m), 6.00 (1H, d, J=16.8 Hz), 7.44 (1H, d, J=16.8 Hz), 7.61 (1H, s), 7.74 (1H, s), 7.86 (1H, s), 8.75 (1H, s); m/z (EI) 379 (M⁺).

Scheme 23

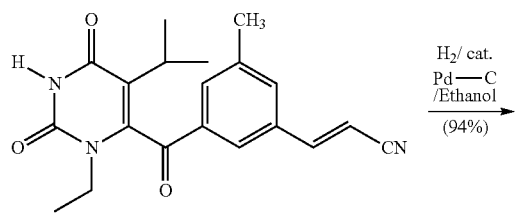

Compound 73

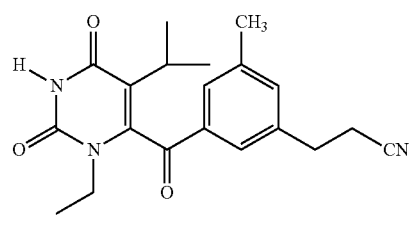

Compound 75

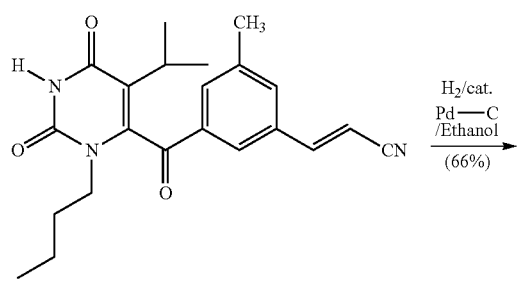

Compound 74

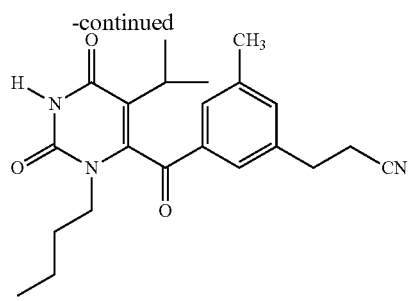

Compound 76

3-[3-(3-Ethyl-5-isopropyl-2,6-dioxo-1,2,3,6-tetrahydro-pyrimidine-4-carbonyl)-5-methyl-phenyl]-propionitrile (Compound 75): 3-[3-(3-Ethyl-5-isopropyl-2,6-dioxo-1,2,3,6-tetrahydro-pyrimidine-4-carbonyl)-5-methyl-phenyl]-acrylonitrile (Compound 73) (190 mg, 0.54 mmol) was stirred with 10% palladium on carbon (20 mg) in anhydrous ethanol (10 mL) at room temperature under an atmosphere of hydrogen. After 17 hr., the reaction mixture was filtered through a celite pad and the pad was washed with ethanol and chloroform. The combined filtrate was evaporated in vacuo and the residue was purified by silica gel column chromatography (eluent, ethyl acetate:hexane (1:2)) to afford 180 mg (94%) of 3-[3-(3-ethyl-5-isopropyl-2,6-dioxo-1,2,3,6-tetrahydro-pyrimidine-4-carbonyl)-5-methyl-phenyl]-propionitrile (75) as a white foam. Recrystallization from chloroform-ether resulted in a white solid. m.p. 173-174° C.; ¹H-NMR (300 MHz, CDCl₃) δ 1.13-1.18 (6H, m), 1.23 (3H, d, J=6.9 Hz), 2.31 (1H, m), 2.47 (3H, s), 2.70 (2H, t, J=6.9 Hz), 3.04 (2H, t, J=6.9 Hz), 3.25 (1H, m), 3.89 (1H, m), 7.45 (1H, s), 7.66 (2H, s), 9.17 (1H, s); m/z (EI) 353 (M⁺).

3-[3-(3-Butyl-5-isopropyl-2,6-dioxo-1,2,3,6-tetrahydro-pyrimidine-4-carbonyl)-5-methyl-phenyl]-propionitrile (Compound 76): 3-[3-(3-Butyl-5-isopropyl-2,6-dioxo-1,2,3,6-tetrahydro-pyrimidine-4-carbonyl)-5-methyl-phenyl]-acrylonitrile (Compound 74) (180 mg, 0.474 mmol) was stirred with 10% palladium on carbon (20 mg) in anhydrous ethanol (10 mL) at room temperature under an atmosphere of hydrogen. After 17 hr., the reaction mixture was filtered through a celite pad and the pad was washed with ethanol and chloroform. The combined filtrate was evaporated in vacuo and the residue was purified by silica gel column chromatography (eluent, ethyl acetate:hexane (1:2)) to afford 120 mg (66%) of 3-[3-(3-butyl-5-isopropyl-2,6-dioxo-1,2,3,6-tetrahydro-pyrimidine-4-carbonyl)-5-methyl-phenyl]-propionitrile (76) as a white foam. Recrystallization from ether-hexane resulted in a white solid. m.p. 172-173° C.; ¹H-NMR (300 MHz, CDCl₃) δ 0.79 (3H, t, J=7.5 Hz), 1.12-1.24 (8H, m), 1.45-1.59 (2H, m), 2.30 (1H, m), 2.46 (3H, s), 2.68 (2H, t, J=7.2 Hz), 3.00-3.15 (3H, m), 3.79 (1H, m), 7.44 (1H, s), 7.63 (2H, s), 8.89 (1H, s); m/z (EI) 381 (M⁺).

Scheme 24

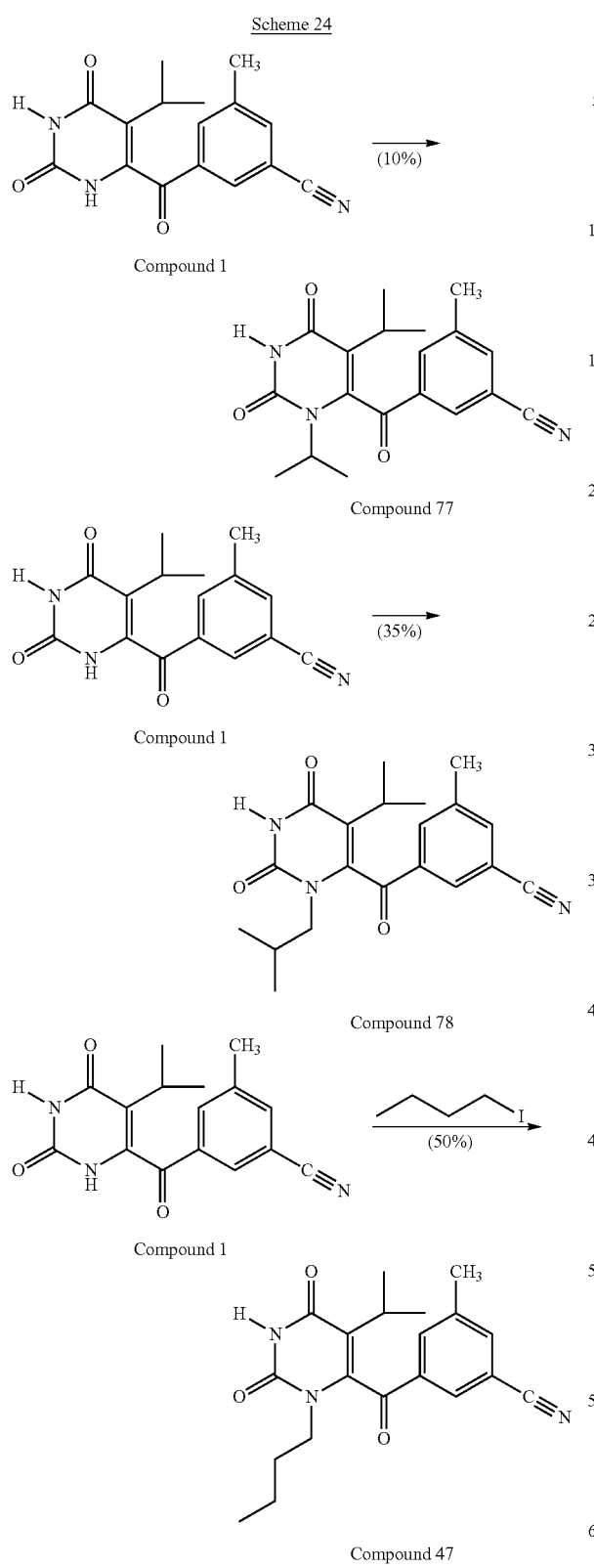

3-(3,5-Diisopropyl-2,6-dioxo-1,2,3,6-tetrahydro-pyrimidine-4-carbonyl)-5-methyl-benzonitrile (Compound 77): To a stirred mixture of 3-(5-isopropyl-2,6-dioxo-1,2,3,6-tetrahydro-pyrimidine-4-carbonyl)-5-methyl-benzonitrile (Compound 1) (5.94 g, 20 mmol) and powdered anhydrous potassium carbonate (3.31 g, 24 mmol) in DMF (40 mL), was added 2-iodopropane (2 mL, 20 mmol). The mixture was then stirred in an oil bath (50-60° C.) overnight and evaporated in vacuo. The residue was purified by silica gel column chromatography (eluent, ethyl acetate:hexane (1:2)) to afford 700 mg (10%) of 3-(3,5-diisopropyl-2,6-dioxo-1,2,3,6-tetrahydro-pyrimidine-4-carbonyl)-5-methyl-benzonitrile (77) as a white solid. m.p. 278-280° C.; $^1$H-NMR (200 MHz, CDCl$_3$) δ 1.11 (3H, d, J=7.0 Hz), 1.20 (3H, d, J=7.0 Hz), 1.37 (3H, d, J=6.6 Hz), 1.47 (3H, d, J=6.6 Hz), 2.19 (1H, m), 2.54 (3H, s), 3.55 (1H, m), 7.81 (1H, s), 7.98 (1H, s), 8.07 (1H, s), 9.09 (1H, s); m/z (EI) 339 (M$^+$).

3-(3-Isobutyl-5-isopropyl-2,6-dioxo-1,2,3,6-tetrahydro-pyrimidine-4-carbonyl)-5-methyl-benzonitrile (Compound 78): To a stirred mixture of 3-(5-isopropyl-2,6-dioxo-1,2,3,6-tetrahydro-pyrimidine-4-carbonyl)-5-methyl-benzonitrile (Compound 1) (1.19 g, 4 mmol) and powdered anhydrous potassium carbonate (662 mg, 4.8 mmol) in DMF (20 mL), was added 2-iodo-2-methylpropane (460 μL, 4 mmol). The mixture was then stirred in an oil bath (50-60° C.) for overnight and evaporated in vacuo. The residue was purified by silica gel column chromatography (eluent, ethyl acetate:hexane (1:2)) to afford 500 mg (35%) of 3-(3-isobutyl-5-isopropyl-2,6-dioxo-1,2,3,6-tetrahydro-pyrimidine-4-carbonyl)-5-methyl-benzonitrile (78) as a white solid. m.p. 200-201° C.; $^1$H-NMR (200 MHz, CDCl$_3$) δ 0.80 (3H, d, J=3.2 Hz), 0.83 (3H, d, J=3.2 Hz), 1.12 (3H, d, J=7.0 Hz), 1.23 (3H, d), J=7.0 Hz), 1.90 (1H, m), 2.25 (1H, m), 2.53 (3H, s), 2.93 (1H, dd, J=14.2 Hz, J=7.4 Hz), 3.75 (1H, dd, J=14.2 Hz, J=7.4 Hz), 7.80 (1H, s), 7.92 (1H, s), 8.03 (1H, s), 9.03 (1H, s); m/z (EI) 353 (M$^+$).

3-(3-Butyl-5-isopropyl-2,6-dioxo-1,2,3,6-tetrahydro-pyrimidine-4-carbonyl)-5-methyl-benzonitrile (Compound 47): To a stirred mixture of 3-(5-isopropyl-2,6-dioxo-1,2,3,6-tetrahydro-pyrimidine-4-carbonyl)-5-methyl-benzonitrile (Compound 1) (2.97 g, 10 mmol) and powdered anhydrous potassium carbonate (1.66 g, 12 mmol) in DMF (20 mL), was added iodobutane (1.37 mL, 12 mmol). The mixture was then stirred in an oil bath (50-60° C.) for 24 hr. and evaporated in vacuo. The residue was purified by silica gel column chromatography (eluent, ethyl acetate:hexane (1:2)) to afford 1.78 g (50%) of 3-(3-butyl-5-isopropyl-2,6-dioxo-1,2,3,6-tetrahydro-pyrimidine-4-carbonyl)-5-methyl-benzonitrile (47) as a white foam. $^1$H-NMR (200 MHz, CDCl$_3$) δ 0.80 (3H, d, J=3.2 Hz), 0.83 (3H, d, J=3.2 Hz), 1.12 (3H, d, J=7.0 Hz), 1.23 (3H, d, J=7.0 Hz), 1.90 (1H, m), 2.25 (1H, m), 2.53 (3H, s), 2.93 (1H, dd, J=14.2 Hz, J=7.4 Hz), 3.75 (1H, dd, J=14.2 Hz, J=7.4 Hz), 7.80 (1H, s), 7.92 (1H, s), 8.03 (1H, s), 9.03 (1H, s); m/z (EI) 353 (M$^+$).

Scheme 25

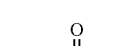

Compound 1

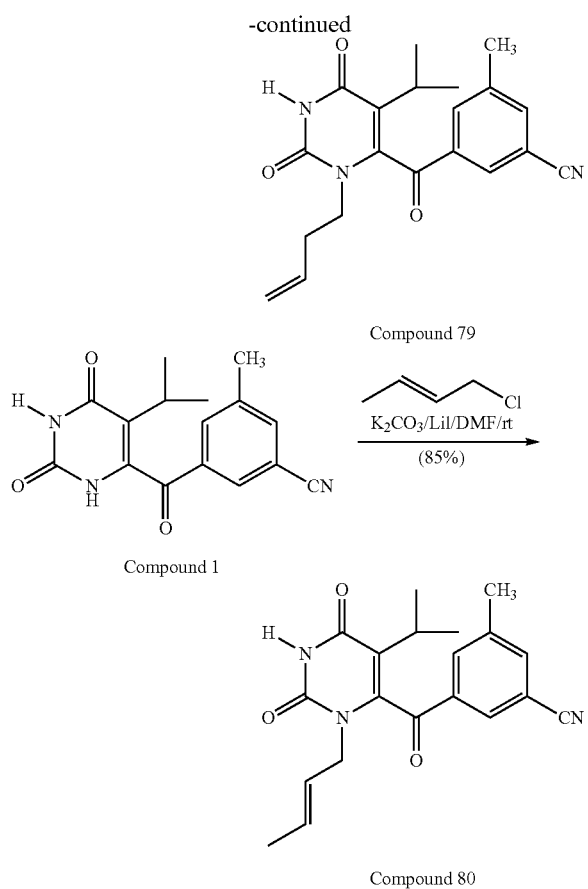

Compound 79

Compound 1

Compound 80

3-(3-But-3-enyl-5-isopropyl-2,6-dioxo-1,2,3,6-tetrahydro-pyrimidine-4-carbonyl)-5-methyl-benzonitrile (Compound 79): To a stirred solution of 3-butene-1-ol (216 mg, 3 mmol) in chloroform (20 mL) cooled in an ice bath under nitrogen atmosphere, was added triethylamine (630 μL, 4.5 mmol) and methanesulfonyl chloride (270 μL, 3.6 mmol) was added dropwise. After stirring for 1.1 hr., the reaction mixture was diluted with dichloromethane and washed with sat. aqueous sodium bicarbonate, dried with anhydrous magnesium sulfate, filtered, and evaporated in vacuo. The residue was further dried in high vacuum for ca. 20 min. and mixed with 3-(5-isopropyl-2,6-dioxo-1,2,3,6-tetrahydro-pyrimidine-4-carbonyl)-5-methyl-benzonitrile (Compound 1) (891 mg, 3 mmol), powdered anhydrous potassium carbonate (414 mg, 3.6 mmol), and lithium iodide (402 mg, 3 mmol). DMF (15 mL) was then added to the mixture and stirred for overnight in an oil bath (40-50° C.). After evaporation of DMF, the residue was dissolved in methanol-chloroform (1:9) and filtered through a celite pad. The filtrate was then evaporated in vacuo and the residue was purified by silica gel column chromatography (eluent, ethyl acetate:hexane (1:2)) to afford 320 mg (30%) of 3-(3-but-3-enyl-5-isopropyl-2,6-dioxo-1,2,3,6-tetrahydro-pyrimidine-4-carbonyl)-5-methyl-benzonitrile (79) as a white foam. Recrystallization from ether-hexane resulted a white solid. m.p. 133-134° C.; $^1$H-NMR (300 MHz, CDCl3) δ 1.13 (3H, d, J=6.9 Hz), 1.22 (3H, d, J=6.9 Hz), 2.19-2.34 (3H, m), 2.54 (3H, s), 3.15 (1H, m), 3.90 (1H, m), 4.94-5.02 (2H, m), 5.58 (1H, m), 7.82 (1H, s), 7.96 (1H, s), 8.06 (1H, s), 8.99 (1H, s); m/z (EI) 351 (M$^+$).

3-(3-But-2-enyl-5-isopropyl-2,6-dioxo-1,2,3,6-tetrahydro-pyrimidine-4-carbonyl)-5-methyl-benzonitrile (Compound 80): To a stirred solution of 3-(5-isopropyl-2,6-dioxo-1,2,3,6-tetrahydro-pyrimidine-4-carbonyl)-5-methyl-benzonitrile (Compound 1) (297 mg, 1 mmol), anhydrous powdered potassium carbonate (165 mg, 1.2 mmol), and lithium iodide (134 mg, 1 mmol) in DMF (5 mL) at room temperature, was added crotyl chloride (97 μL, 1 mmol). After stirring for overnight, the mixture was evaporated in vacuo and the residue was purified by silica gel column chromatography (eluent, ethyl acetate:hexane (1:2)) to give 300 mg (85%) of 3-(3-but-2-enyl-5-isopropyl-2,6-dioxo-1,2,3,6-tetrahydro-pyrimidine-4-carbonyl)-5-methyl-benzonitrile (80) as a white solid. The product was recrystallized from chloroform-ether-hexane to afford a white solid. m.p. 177-178° C.; $^1$H-NMR (300 MHz, CDCl$_3$) δ 1.12 (3H, d, J=6.6 Hz), 1.21 (3H, d, J=6.6 Hz), 1.44 (3H, d, J=5.1 Hz), 2.22 (1H, m), 2.53 (3H, s), 4.02-4.20 (2H, m), 5.19-5.43 (2H, m), 7.78 (1H, s), 7.93 (1H, s), 8.03 (1H, s), 8.95 (1H, s). m/z (EI) 351 (M$^+$).

Scheme 26

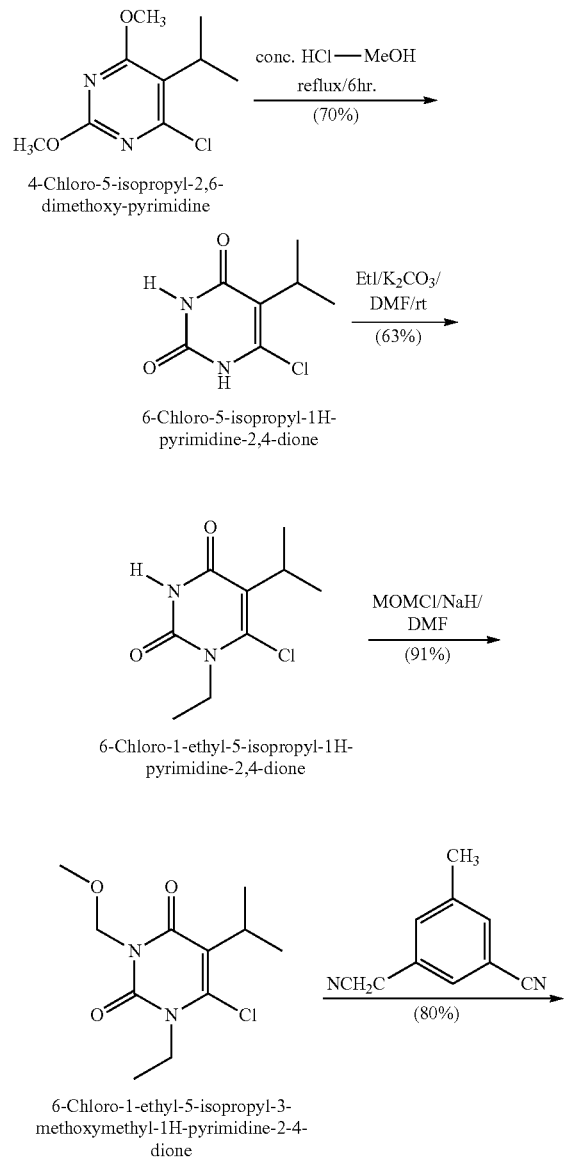

4-Chloro-5-isopropyl-2,6-dimethoxy-pyrimidine

6-Chloro-5-isopropyl-1H-pyrimidine-2,4-dione

6-Chloro-1-ethyl-5-isopropyl-1H-pyrimidine-2,4-dione

6-Chloro-1-ethyl-5-isopropyl-3-methoxymethyl-1H-pyrimidine-2-4-dione

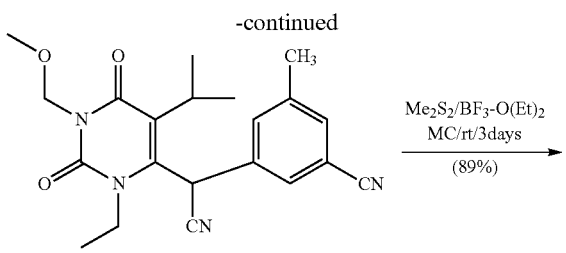

3-[Cyano-(3-ethyl-5-isopropyl-1-methoxymethyl-2,6-dioxo-1,2,3,6-tetrahydro-pyrimidin-4-yl)-methyl]-5-methyl-benzonitrile

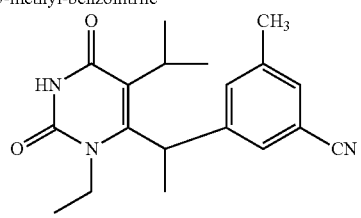

Compound 81

6-Chloro-5-isopropyl-1H-pyrimidine-2,4-dione: 4-Chloro-5-isopropyl-2,6-dimethoxy-pyrimidine (40 g, 18.47 mmol) was dissolved in 150 mL of conc. HCl-methanol (1:2) and refluxed for 6 hr. The mixture was evaporated in vacuo and the residue was purified by silica gel column chromatography (eluent, chloroform:methanol (from 95:5 to 90:10)) to give 24.4 g (70%) of 6-chloro-5-isopropyl-1H-pyrimidine-2,4-dione as a white solid. m.p. 250-251° C.; $^1$H-NMR (200 MHz, CDCl$_3$) δ 1.25 (6H, d, J=7.1 Hz), 3.13 (1H, m); m/z (EI) 188 (M$^+$).

6-Chloro-1-ethyl-5-isopropyl-1H-pyrimidine-2,4-dione: 6-Chloro-5-isopropyl-1H-pyrimidine-2,4-dione (18.8 g, 100 mmol) was stirred with anhydrous powdered potassium carbonate (16.56 g, 120 mmol) in DMF (200 mL) at room temperature. After 40 min., iodoethane (8 mL, 100 mmol) was added and the mixture was stirred overnight. The mixture was evaporated in vacuo and the residue was purified by silica gel column chromatography (eluent, ethyl acetate:hexane (from 1:4 to 1:2)) to give 13.8 g (63%) of 6-chloro-1-ethyl-5-isopropyl-1H-pyrimidine-2,4-dione as a white solid. m.p. 160-161° C.; $^1$H-NMR (200 MHz, CDCl$_3$) δ 1.28-1.35 (9H, m), 3.22 (1H, m), 4.15 (2H, q, J=7.2 Hz); m/z (EI) 216 (M$^+$).

6-Chloro-1-ethyl-5-isopropyl-3-methoxymethyl-1H-pyrimidine-2,4-dione: To a stirred solution of 6-chloro-1-ethyl-5-isopropyl-1H-pyrimidine-2,4-dione (11.5 g, 53 mmol) in DMF (100 mL) in a water bath, was added 60% NaH (3.18 g, 79.6 mmol). After stirring for 40 min., technical grade chloromethyl methyl ether (7.6 mL, 80 mmol) was added and the mixture was stirred at room temperature overnight. The mixture was evaporated in vacuo and the residue was purified by silica gel column chromatography (eluent, ethyl acetate:hexane (1:5)) to give 12.6 g (91%) of 6-chloro-1-ethyl-5-isopropyl-3-methoxymethyl-1H-pyrimidine-2,4-dione as a colorless oil. H-NMR (200 MHz, CDCl$_3$) δ 1.26-1.34 (9H, m), 3.24 (1H, m), 3.44 (3H, s), 4.16 (2H, q, J=7.0 Hz), 5.35 (2H, s); m/z (EI) 260 (M$^+$).

3-[Cyano-(3-ethyl-5-isopropyl-1-methoxymethyl-2,6-dioxo-1,2,3,6-tetrahydro-pyrimidin-4-yl)-methyl]-5-methyl-benzonitrile: To a stirred solution of 6-chloro-1-ethyl-5-isopropyl-3-methoxymethyl-1H-pyrimidine-2,4-dione (1.43 g, 5.48 mmol) and 3-cyano-5-methylbenzyl cyanide (857 mg, 5.48 mmol) in DMF (12 mL) in a water bath, was added 60% NaH (483 mg, 12 mmol). After 15 min., the mixture was stirred at room temperature for overnight. Excess ammonium chloride was added to the mixture and stirring was continued for 1 hr. The mixture was then evaporated in vacuo and the residue was purified by silica gel column chromatography (eluent, ethyl acetate:hexane (from 1:4 to 2:3)) to give 1.6 g (80%) of 3-[cyano-(3-ethyl-5-isopropyl-1-methoxymethyl-2,6-dioxo-1,2,3,6-tetrahydro-pyrimidin-4-yl)-methyl]-5-methyl-benzonitrile as a yellow solid. m.p. 202-205° C.; $^1$H-NMR (200 MHz, DMSO-d$_6$) δ 0.77 (3H, d, J=6.8 Hz), 1.10 (3H, t, J=6.8 Hz), 1.20 (3H, d, J=6.8 Hz), 2.40 (3H, s), 2.55 (1H, m), 3.71 (1H, m), 4.05 (1H, m), 5.21 (2H, dd, J=11.2 Hz, J=9.4 Hz), 6.26 (1H, s), 7.60 (1H, s), 7.69 (1H, s), 7.73 (1H, s); m/z (EI) 380 (M$^+$).

3-[Cyano-(3-ethyl-5-isopropyl-2,6-dioxo-1,2,3,6-tetrahydro-pyrimidin-4-yl)-methyl]-5-methyl-benzonitrile (Compound 85): To a stirred solution of 3-[cyano-(3-ethyl-5-isopropyl-1-methoxymethyl-2,6-dioxo-1,2,3,6-tetrahydro-pyrimidin-4-yl)-methyl]-5-methyl-benzonitrile (190 mg, 0.5 mmol) in dichloromethane (5 mL) at room temperature, were added dimethyl disulfide (804 μL, 10 mmol) and boron trifluoride-diethyl etherate (300 μL, 2.37 mmol). After stirring for 3 days, the mixture was evaporated in vacuo and the residue was purified by silica gel column chromatography (eluent, ethyl acetate:hexane (1:1)) to give 150 mg (89%) of 3-[cyano-(3-ethyl-5-isopropyl-2,6-dioxo-1,2,3,6-tetrahydro-pyrimidin-4-yl)-methyl]-5-methyl-benzonitrile as a white solid. The product was recrystallized from chloroform-methanol-ether. m.p. 260-261° C.; $^1$H-NMR (200 MHz, DMSO-d$_6$) δ 0.77 (3H, d, J=6.6 Hz), 1.07 (3H, t, J=7.0 Hz), 1.19 (3H, d, J=6.6 Hz), 2.41 (3H, s), 2.49 (1H, m), 3.68 (1H, m), 4.00 (1H, m), 6.22 (1H, s), 7.59 (1H, s), 7.71 (1H, s), 7.73 (1H, s), 11.45 (1H, s); m/z (EI) 336 (M$^+$).

Scheme 27

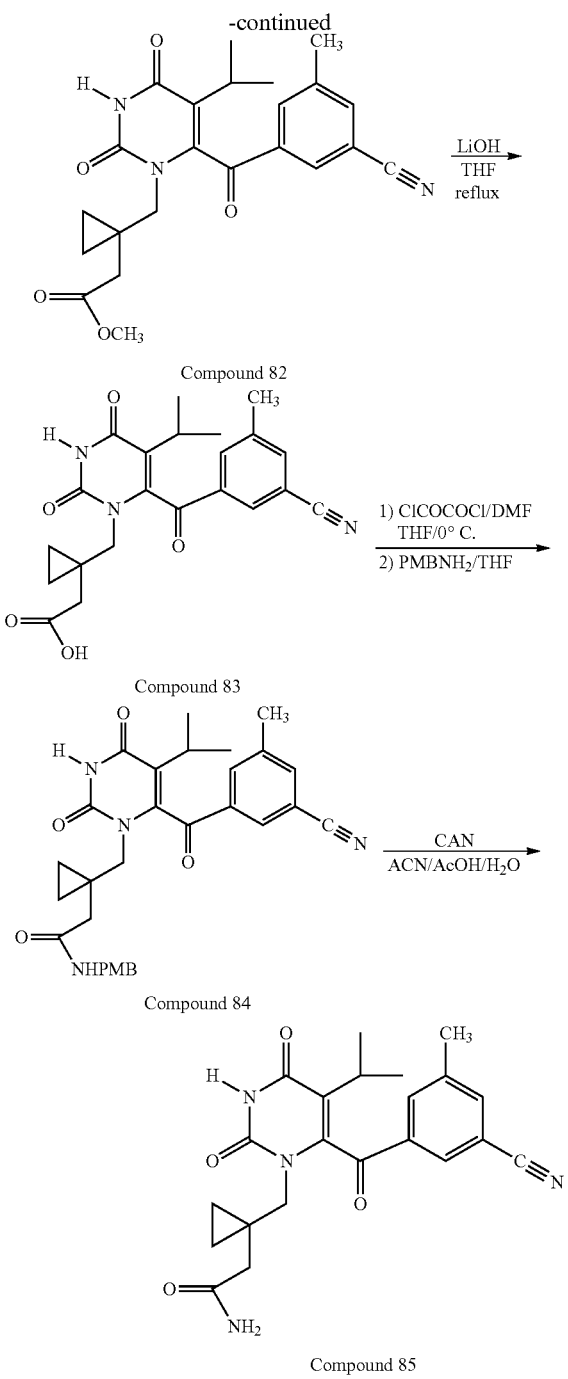

Compound 82

Compound 83

Compound 84

Compound 85

(1-Hydroxymethyl-cyclopropyl)-acetic acid methyl ester: To a stirred solution of crude 5-oxa-spiro[2.4]heptan-6-one (2.24 g, ca. 20 mmol; prepared according to the method of EP 0 678 515 A1 (herein incorporated by reference in its entirety for all purposes): impurity is N,N-dimethyl acetamide) in anhydrous methanol (40 mL) in water bath, was added sodium methoxide (1.296 g, 24 mmol). After 15 min, ammonium chloride (2 g) was added and the mixture was stirred at room temperature for 30 min. The mixture was evaporated in vacuo and the residue was purified by silica gel column chromatography (eluent, ethyl acetate:hexane (1:1)) to afford 5.8 g (47%) of (1-hydroxymethyl-cyclopropyl)-acetic acid methyl ester as a colorless oil. $^1$H-NMR (200 MHz, CDCl$_3$) δ 0.47-0.61 (4H, m), 2.44 (2H, s), 2.55 (1H, t, J=5.6 Hz), 3.48 (2H, d, J=5.6 Hz), 3.69 (3H, s).

(1-Methanesulfonyloxymethyl-cyclopropyl)-acetic acid methyl ester: To a stirred solution of (1-hydroxymethyl-cyclopropyl)-acetic acid methyl ester (600 mg, 4.16 mmol) in dichloromethane (10 mL) cooled in dry ice-acetone bath (−40° C.), was added methanesulfonyl chloride (483 μL, 6.24 mmol). The mixture was then cooled to −60° C. and triethylamine (928 μA, 6.66 mmol) was added. With stirring, the mixture was warmed up to 0° C. during 1 hr. After cooling the mixture to −15° C., cold 3 N HCl solution (0.6 mL), cold brine (2 mL), and dichloromethane (25 mL) were added in this order. The mixture was washed with cold brine (25 mL) twice, dried with MgSO$_4$, filtered, and evaporated in vacuo to give 962 mg (quantitative) of crude (1-methanesulfonyloxymethyl-cyclopropyl)-acetic acid methyl ester as a colorless oil. This crude product was used directly in the next reaction without further purification. $^1$H-NMR (200 MHz, CDCl$_3$) δ 0.62-0.72 (4H, m), 2.42 (2H, s), 3.02 (3H, s), 3.70 (3H, s), 4.17 (2H, s).

{1-[6-(3-Cyano-5-methyl-benzoyl)-5-isopropyl-2,4-dioxo-3,4-dihydro-2H-pyrimidin-1-ylmethyl]-cyclopropyl}-acetic acid methyl ester (Compound 82): To a mixture of 3-(5-isopropyl-2,6-dioxo-1,2,3,6-tetrahydro-pyrimidine-4-carbonyl)-5-methyl-benzonitrile (962 mg, 4.16 mmol), anhydrous powdered potassium carbonate (574 mg, 4.16 mmol), and lithium iodide (557 mg, 4.16 mmol), was added DMF (18 mL) at room temperature. After stirring for 30 min, crude (1-methanesulfonyloxymethyl-cyclopropyl)-acetic acid methyl ester (962 mg) in DMF (2 mL) was added. The mixture was then heated in an oil bath (70-80° C.) and stirred for ca. 19 hr. After cooling to room temperature, the mixture was evaporated in vacuo. The residue was dissolved in methanol-dichloromethane (5:95) and filtered through a celite pad. The filtrate was evaporated and the residue was purified by silica gel column chromatography (eluent, ethyl acetate:hexane (1:2)) to give 230 mg (13%) of {1-[6-(3-cyano-5-methyl-benzoyl)-5-isopropyl-2,4-dioxo-3,4-dihydro-2H-pyrimidin-1-ylmethyl]-cyclopropyl}-acetic acid methyl ester (82) as a white syrup. $^1$H-NMR (200 MHz, CDCl$_3$) δ 0.36-0.65 (4H, m), 1.12 (3H, d, J=7.0 Hz), 1.23 (3H, d, J=7.0 Hz), 2.17-2.32 (2H, m), 2.44-2.52 (4H, m), 3.58 (1H, d, J=15.2 Hz), 3.69 (3H, s), 3.76 (1H, d, J=15.2 Hz), 7.79 (1H, s), 7.95 (1H, s), 8.06 (1H, s), 9.36 (1H, s); m/z (EI) 423 (M$^+$).

{1-[6-(3-Cyano-5-methyl-benzoyl)-5-isopropyl-2,4-dioxo-3,4-dihydro-2H-pyrimidin-1-ylmethyl]-cyclopropyl}-acetic acid (Compound 83): To a stirred solution of {1-[6-(3-cyano-5-methyl-benzoyl)-5-isopropyl-2,4-dioxo-3,4-dihydro-2H-pyrimidin-1-ylmethyl]-cyclopropyl}-acetic acid methyl ester (170 mg, 0.4 mmol) in THF (4 mL), were added lithium hydroxide (20 mg, 0.8 mmol) and two drops of water. The mixture was then refluxed for 2 hr. After cooling to room temperature, the mixture was evaporated in vacuo and the residue was purified by silica gel column chromatography (eluent, from ethyl acetate to 20% methanol in ethyl acetate) to give 100 mg (62%) of {1-[6-(3-cyano-5-methyl-benzoyl)-5-isopropyl-2,4-dioxo-3,4-dihydro-2H-pyrimidin-1-ylmethyl]-cyclopropyl}-acetic acid (83) as a white solid. m.p. 244-245° C.; $^1$H-NMR (500 MHz, DMSO-d$_6$) δ 0.21-0.26 (2H, m), 0.34-0.36 (1H, m), 0.46-0.48 (1H, m), 0.98 (3H, d, J=6.8 Hz), 1.08 (3H, d, J=6.8 Hz), 2.06-2.12 (2H, m), 2.23 (1H, d, J=17.0 Hz), 2.44 (3H, s), 3.32 (1H, d, J=15.0 Hz), 3.74 (1H, d, J=15.0 Hz), 8.08 (1H, s), 8.19 (1H, s), 8.43 (1H, s), 11.45 (1H, s), 12.02 (1H, br. s); m/z (EI) 409 (M$^+$).

2-{1-[6-(3-Cyano-5-methyl-benzoyl)-5-isopropyl-2,4-dioxo-3,4-dihydro-2H-pyrimidin-1-ylmethyl]-cyclopropyl}-N-(4-methoxy-benzyl)-acetamide (Compound 84): To a stirred solution of {1-[6-(3-cyano-5-methyl-benzoyl)-5-isopropyl-2,4-dioxo-3,4-dihydro-2H-pyrimidin-1-ylmethyl]-cyclopropyl}-acetic acid (90 mg, 0.22 mmol) in THF (5 mL) cooled in an ice bath, were added oxalyl chloride (38 μL, 0.44 mmol) and one drop of DMF. After stirring for 1 hr., the mixture was evaporated in vacuo. The residue was dissolved in THF (8 mL) and p-methoxy benzylamine (261 μL, 2 mmol) was added. After stirring for 1 hr., the mixture was evaporated in vacuo and the residue was purified by silica gel column chromatography (eluent, ethyl acetate:hexane (2:1): Rf=0.25 fraction was collected) to give 97 mg (83%) of 2-{1-[6-(3-cyano-5-methyl-benzoyl)-5-isopropyl-2,4-dioxo-3,4-dihydro-2H-pyrimidin-1-ylmethyl]-cyclopropyl}-N-(4-methoxy-benzyl)-acetamide (84) as a white solid. $^1$H-NMR (200 MHz, CDCl$_3$) δ 0.40-0.46 (4H, m), 1.12 (3H, d, J=6.6 Hz), 1.23 (3H, d, J=6.6 Hz), 2.00 (1H, d, J=15.4 Hz), 2.25 (1H, m), 2.48-2.55 (4H, m), 3.45 (1H., d, J=15.4 Hz), 3.80 (3H, s), 3.90 (1H, d, J=15.4 Hz), 4.34-4.39 (2H, m), 6.69 (1H, m), 6.83-6.90 (2H, m), 7.22-7.30 (2H, m), 7.81 (1H, s), 8.01 (1H, s), 8.07 (1H, s), 9.81 (1H, s).

2-{1-[6-(3-Cyano-5-methyl-benzoyl)-5-isopropyl-2,4-dioxo-3,4-dihydro-2H-pyrimidin-1-ylmethyl]-cyclopropyl}-acetamide (Compound 85): To a stirred solution of 2-{1-[6-(3-cyano-5-methyl-benzoyl)-5-isopropyl-2,4-dioxo-3,4-dihydro-2H-pyrimidin-1-ylmethyl]-cyclopropyl}-N-(4-methoxy-benzyl)-acetamide (97 mg, 0.18 mmol) in acetonitrile (4 mL) and glacial acetic acid (1 mL) at room temperature, were added ceric ammonium nitrate (201 mg, 0.36 mmol) and water (2 mL) in this order. After stirring for 20 min., the mixture was diluted with ethyl acetate, washed with water twice, dried with MgSO$_4$, filtered, and evaporated in vacuo. The residue was purified by silica gel column chromatography (eluent, from ethyl acetate to 10% methanol in ethyl acetate) to give 59 mg (78%) of 2-{1-[6-(3-cyano-5-methyl-benzoyl)-5-isopropyl-2,4-dioxo-3,4-dihydro-2H-pyrimidin-1-ylmethyl]-cyclopropyl}-acetamide (85) as a white solid. m.p. 283-285° C.; $^1$H-NMR (500 MHz, DMSO-d$_6$) δ 0.20-0.27 (2H, m), 0.31-0.36 (1H, m), 0.43-0.47 (1H, m), 0.99 (3H, d, J=6.8 Hz), 1.08 (3H, d, J=6.8 Hz), 2.02-2.13 (2H, m), 2.17 (1H, d, J=16.5 Hz), 2.44 (3H, s), 3.32 (1H, d, J=15.1 Hz), 3.39-3.41 (1H, m), 3.46-3.51 (1H, m), 3.79 (1H, d, J=15.1 Hz), 8.08 (1H, s), 8.19 (1H, s), 8.42 (1H, s), 11.45 (1H, s); m/z (EI) 408 (M$^+$).

Scheme 28

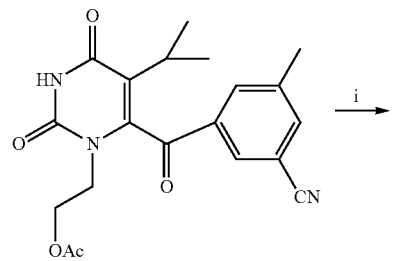

Compound 8

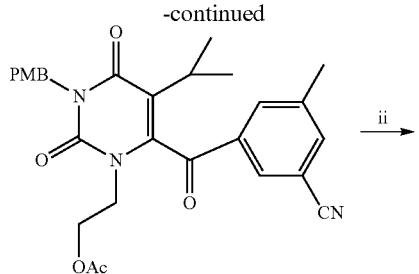

Acetic acid 2-[6-(3-cyano-5-methyl-benzoyl)-5-isopropyl-3-(4-methoxy-benzyl)-2,4-dioxo-3,4-dihydro-2H-pyrimidin-1-yl]-ethyl ester

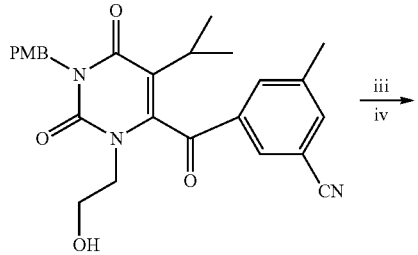

3-[3-(2-Hydroxy-ethyl)-5-isopropyl-1-(4-methoxy-benzyl)-2,6-dioxo-1,2,3,6-tetrahydro-pyrimidine-4-carbonyl]-5-methyl-benzonitrile

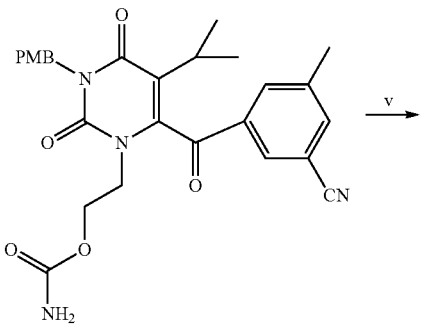

Carbamic acid 2-[6-(3-cyano-5-methyl-benzoyl)-5-isopropyl-3-(4-methoxy-benzyl)-2,4-dioxo-3,4-dihydro-2H-pyrimidin-1-yl]-ethyl ester

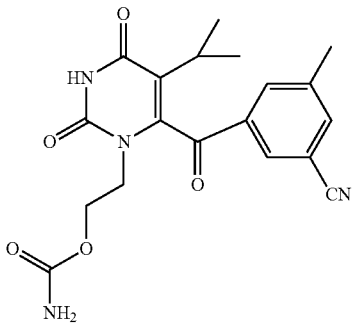

Compound 86

Reagents and conditions: 1. 1-bromomethyl-4-methoxy-benzene, K$_2$CO$_3$, LiI, DMF; ii. K$_2$CO$_3$, MeOH; iii. trichloro-isocyanato-methane, DCM; iv. sat. ammonia in DCM; CAN, acetic acid, MeCN/water.

Acetic acid 2-[6-(3-cyano-5-methyl-benzoyl)-5-isopropyl-3-(4-methoxy-benzyl)-2,4-dioxo-3,4-dihydro-2H-pyrimidin-1-yl]-ethyl ester: Acetic acid 2-[6-(3-cyano-5-methylbenzoyl)-5-isopropyl-2,4-dioxo-3,4-dihydro-2H-pyrimidin-1-yl]-ethyl ester (Compound 8) (126 mg, 0.328 mmol, 1.0 eq.) was dissolved in 1.5 mL of DMF. Potassium carbonate (45 mg, 1 eq.) was added and the reaction mixture was stirred at room temperature for 10 minutes. 1-Bromomethyl-4-methoxy-benzene (47 μL, 0.328 mmol, 1 eq.) and lithium iodide (44 mg, 1 eq.) were added. The reaction mixture was stirred at room temperature overnight. Ethyl acetate was added to the reaction mixture, followed by washing with brine. The organic layer was concentrated down and purified (silica gel, 0-80% EtOAC/hexane) to give a white powder (88 mg, 0.175 mmol, 53%). LC-MS shows 504.1 (M+1).

3-[3-(2-Hydroxy-ethyl)-5-isopropyl-1-(4-methoxy-benzyl)-2,6-dioxo-1,2,3,6-tetrahydro-pyrimidine-4-carbonyl]-5-methyl-benzonitrile: Acetic acid 2-[6-(3-cyano-5-methyl-benzoyl)-5-isopropyl-3-(4-methoxy-benzyl)-2,4-dioxo-3,4-dihydro-2H-pyrimidin-1-yl]-ethyl ester (88 mg, 0.175 mmol, 1.2 eq.) was dissolved in 1.5 mL MeOH. Potassium carbonate (48 mg, 0.349 mmol, 2 eq.) was added and the reaction mixture was stirred at room temperature for 20 minutes. The reaction mixture was concentrated down and purified (silica gel, 0-10% MeOH/DCM) to give a white powder (76 mg, 94%). LC-MS shows 462.1 (M+1).

Carbamic acid 2-[6-(3-cyano-5-methyl-benzoyl)-5-isopropyl-3-(4-methoxy-benzyl)-2,4-dioxo-3,4-dihydro-2H-pyrimidin-1-yl]-ethyl ester: Trichloro-isocyanato-methane (39 uL, 0.33 mmol, 2.0 eq) was added to 3-[3-(2-hydroxy-ethyl)-5-isopropyl-1-(4-methoxy-benzyl)-2,6-dioxo-1,2,3,6-tetrahydro-pyrimidine-4-carbonyl]-5-methyl-benzonitrile (76 mg, 0.165 mmol) in 2 mL of DCM. The reaction mixture was stirred at room temperature for 10 minutes. HPLC and LC-MS showed complete reaction of the starting materials. Ammonia gas was bubbled into 3 mL DCM in a test tube (keep bubbling for 5 minutes). The ammonia solution was added to the above reaction mixture. The reaction mixture was stirred at room temperature for 2 hours. The reaction mixture was filtered and concentrated down and purified (silica gel, 0-80% EtOAC/hexane) to give a white powder (42 mg, 51%). LC-MS shows 505.0 (M+1).

Carbamic acid 2-[6-(3-cyano-5-methyl-benzoyl)-5-isopropyl-2,4-dioxo-3,4-dihydro-2H-pyrimidin-1-yl]-ethyl ester (Compound 86): Ceric ammonium nitrate (156 mg, 0.189 mmol, 3 eq.) was added to carbamic acid 2-[6-(3-cyano-5-methyl-benzoyl)-5-isopropyl-3-(4-methoxy-benzyl)-2,4-dioxo-3,4-dihydro-2H-pyrimidin-1-yl]-ethyl ester (32 mg, 0.063 mmol, 1.0 eq.) in a mixture of MeCN (1 mL), acetic acid (0.4 mL) and water (0.2 mL). The reaction mixture was stirred at room temperature for 10 minutes. The reaction mixture concentrated down. Ethyl acetate was added and the mixture was washed with brine. The organic layer was concentrated down and purified (silica gel, 20-80% EtOAc /hexane) to give a white solid (13.6 mg, 56%). $^1$H NMR (300 MHz, d$^6$ DMSO): δ 11.52 (s, 1H), 8.43 (s, 1H), 8.22 (s, 1H), 8.09 (s, 1H), 3.92 (m, 1H), 3.81 (m, 2H), 3.22 (m, 1H), 2.44 (s, 3H), 2.08 (m, 1H), 1.04 (dd, 6H).

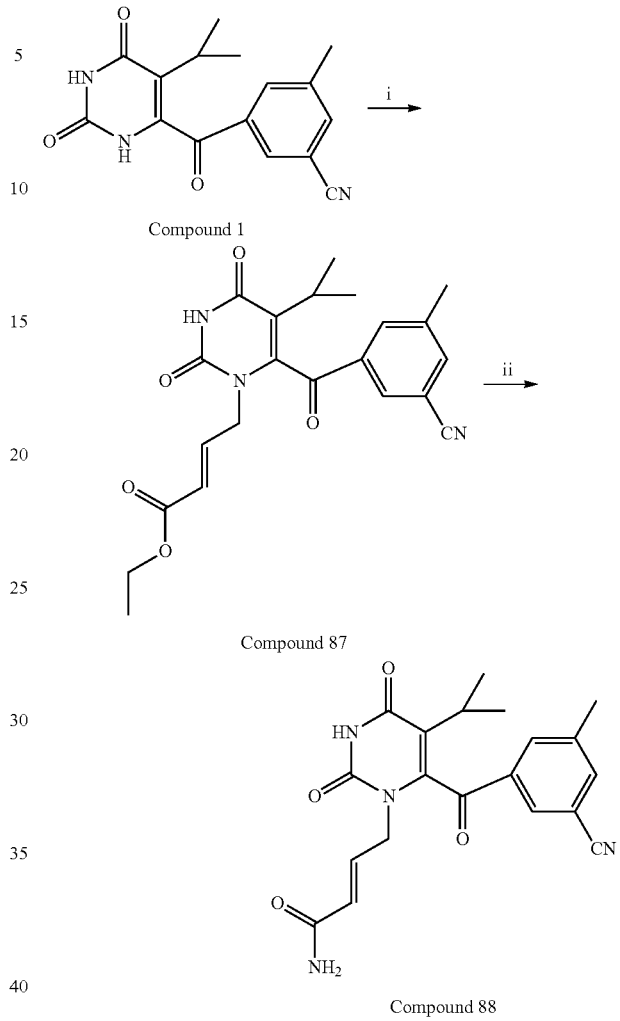

Scheme 29

Compound 1

Compound 87

Compound 88

Reagents and conditions: i. 4-Bromo-but-2-enoic acid ethyl ester, K$_2$CO$_3$, LiI, DMF; ii. NH$_4$OH in water, MeOH, microwave 120° C.

4-[6-(3-Cyano-5-methyl-benzoyl)-5-isopropyl-2,4-dioxo-3,4-dihydro-2H-pyrimidin-1-yl]-but-2-enoic acid ethyl ester (Compound 87): 3-(5-Isopropyl-2,6-dioxo-1,2,3,6-tetrahydro-pyrimidine-4-carbonyl)-5-methyl-benzonitrile (Compound 1) (412 mg, 1.386 mmol, 1.0 eq.) was dissolved in 8 mL DMF. Potassium carbonate (191 mg, 1 eq.) was added and the reaction mixture was stirred at room temperature for 10 minutes. 4-Bromo-but-2-enoic acid ethyl ester (0.24 mL, 1 eq.) and lithium iodide (186 mg, 1 eq.) were added. The reaction mixture was stirred at room temperature overnight. Ethyl acetate was added to the reaction mixture, followed by washing with brine. The organic layer was concentrated down and purified (silica gel, 0-80% EtOAC/hexane) to give a light yellow foam (384 mg, 68%). LC-MS shows 410.4 (M+1).

4-[6-(3-Cyano-5-methyl-benzoyl)-5-isopropyl-2,4-dioxo-3,4-dihydro-2H-pyrimidin-1-yl]-but-2-enoic acid amide (Compound 88): In a 5 mL microwave reaction tube, 4-[6-(3-cyano-5-methyl-benzoyl)-5-isopropyl-2,4-dioxo-3,4-dihydro-2H-pyrimidin-1-yl]-but-2-enoic acid ethyl ester (69 mg, 0.168 mmol) and 0.5 mL MeOH was added, followed by 0.7 mL NH$_4$OH (30% in water, excess). The reaction mixture was heated in the microwave at 120° C. for 30 minutes. The reaction mixture concentrated down and purified by reverse phase prep HPLC (MeCN/water) to give a white powder (4.2 mg, 6.6%). $^1$H NMR (300 MHz, CD$_3$OD): δ 8.8 (d, 1H), 7.64 (m, 2H), 7.4-7.28 (m, 2H), 3.19 (dd, 1H), 2.52 (m, 1H), 0.95 (d, 3H), 0.65 (dd, 3H). LC-MS shows 381.0 (M+1).

Scheme 30

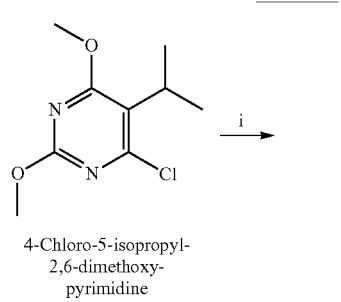

4-Chloro-5-isopropyl-
2,6-dimethoxy-
pyrimidine

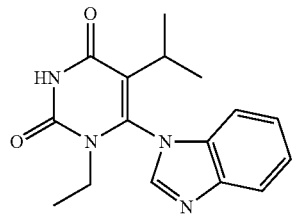

Compound 91

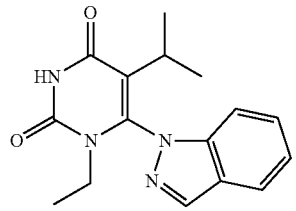

Compound 92

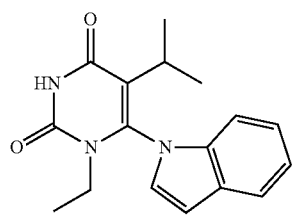

Compound 93

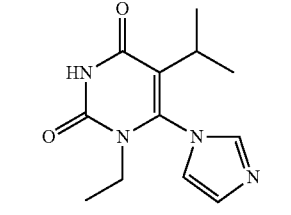

Compound 94

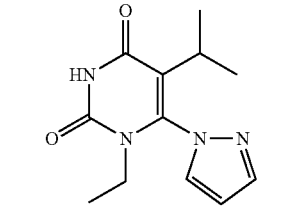

Compound 95

1-(5-Isopropyl-2,6-
dimethoxy-pyrimidin-
4-yl)-6-methyl-1H-
indole-4-carbonitrile Compound 89

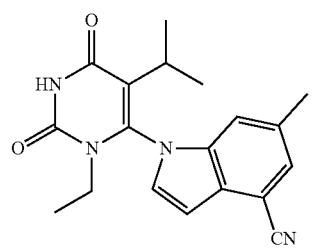

Compound 90

Reagents and conditions: i. 6-Methyl-1H-indole-4-carbonitrile, NaH, DMF, heat; ii. AcBr, heat; iii. EtI, K$_2$CO$_3$, DMF.

1-(5-Isopropyl-2,6-dimethoxy-pyrimidin-4-yl)-6-methyl-1H-indole-4-carbonitrile

NaH (148 mg, 1.1 eq.) was added to 6-methyl-1H-indole-4-carbonitrile (526 mg, 3.37 mmol) in 20 mL of DMF. After 5 minutes, 4-chloro-5-isopropyl-2,6-dimethoxy-pyrimidine was added to the reaction mixture. The reaction mixture was heated at 50° C. for 5 hours. The reaction mixture was diluted with EtOAc and washed with brine. The organic layer was concentrated and purified (silica gel, 0-80% EtOAC/hexane) to give a white solid (470 mg, 42%). LC-MS shows 337.2 (M+1).

1-(5-Isopropyl-2,6-dioxo-1,2,3,6-tetrahydro-pyrimidin-4-yl)-6-methyl-1H-indole-4-carbonitrile (Compound 89)

AcBr (3 mL) was added to 6-methyl-1-(5-isopropyl-2,6-dimethoxy-pyrimidin-4-yl)-1H-indole-4-carbonitrile (470 mg, 1.40 mmol). The reaction mixture was heated at 70° C.

for 6 hours. The reaction mixture was then cooled to room temperature and concentrated. The crude reaction product was purified (silica gel, 0-80% EtOAc/hexane) to give a white solid (280 mg, 65%). LC-MS shows 307.1 (M−1).

1-(3-Ethyl-5-isopropyl-2,6-dioxo-1,2,3,6-tetrahydro-pyrimidin-4-yl)-6-methyl-1H-indole-4-carbonitrile (Compound 90)

6-Chloro-1-(5-isopropyl-2,6-dioxo-1,2,3,6-tetrahydro-pyrimidin-4-yl)-1H-indole-4-carbonitrile (35 mg, 0.113 mmol, 1.0 eq.) was dissolved in 0.5 mL DMF. Potassium carbonate (16 mg, 1 eq.) was added and the reaction mixture was stirred at room temperature for 10 minutes. EtI (9.1 μL, 1 eq.) was added. The reaction mixture was stirred at room temperature for 2 hours. Ethyl acetate was added to the reaction mixture, followed by washing with brine. The organic layer was concentrated and purified (silica gel, 0-80% EtOAC/hexane) to give a white powder (14 mg, 37%). LC-MS shows 335.0 (M−1). $^1$H NMR (300 MHz, CDCl$_3$): δ 9.37 (br, 1 H), 8.05 (s, 1H), 7.08 (m, 2H), 6.80 (d, 1H), 3.58 (m, 1H), 3.17 (m, 1H), 2.62 (s, 3H), 1.88 (m, 1H), 1.17 (dd, 6H), 1.02 (t, 3H).

6-Benzoimidazol-1-yl-1-ethyl-5-isopropyl-1H-pyrimidine-2,4-dione (Compound 91): This compound was made by a procedure similar to that used to prepare 6-chloro-1-(3-ethyl-5-isopropyl-2,6-dioxo-1,2,3,6-tetrahydro-pyrimidin-4-yl)-1H-indole-4-carbonitrile (90), except that benzoimidazole was used instead of 6-chloro-1H-indole-4-carbonitrile. LC-MS shows 299.1 (M+1). $^1$H NMR (300 MHz, CDCl$_3$): δ 9.32 (br, 1H), 7.97 (m, 2H), 7.43 (m, 2H), 7.30 (m, 1H), 3.60 (m, 1H), 3.20 (m, 1H), 1.98 (m, 1H), 1.10 (m, 9H).

1-Ethyl-6-indazol-1-yl-5-isopropyl-1H-pyrimidine-2,4-dione (Compound 92): This compound was made by a procedure similar to that used to prepare 6-chloro-1-(3-ethyl-5-isopropyl-2,6-dioxo-1,2,3,6-tetrahydro-pyrimidin-4-yl)-1H-indole-4-carbonitrile (90), except that 1H-indazole was used instead of 6-chloro-1H-indole-4-carbonitrile. LC-MS shows 299.1 (M+1). $^1$H NMR (300 MHz, CDCl$_3$): δ 8.97 (br, 1H), 8.31 (s, 1H), 7.83 (d, 2H), 7.54 (m, 1H), 7.36 (m, 2H), 3.42 (m, 1H), 3.20 (m, 1H), 1.90 (m, 1H), 1.15 (dd, 6H), 1.00 (t, 3H).

1-Ethyl-6-indol-1-yl-5-isopropyl-1H-pyrimidine-2,4-dione (Compound 93): This compound was made by a procedure similar to that used to prepare 6-chloro-1-(3-ethyl-5-isopropyl-2,6-dioxo-1,2,3,6-tetrahydro-pyrimidin-4-yl)-1H-indole-4-carbonitrile (90), except that 1H-indole was used instead of 6-chloro-1H-indole-4-carbonitrile. LC-MS shows 298.2 (M+1). $^1$H NMR (300 MHz, CDCl$_3$): δ 8.32 (br, 1H), 7.72 (d, 1H), 7.25 (m, 2H), 7.19 (m, 1H), 6.80 (m, 1H), 3.50 (m, 1H), 3.18 (m, 1H), 1.97 (m, 1H), 1.17 (dd, 6H), 1.03 (t, 3H).

1-Ethyl-6-imidazol-1-yl-5-isopropyl-1H-pyrimidine-2,4-dione (Compound 94): This compound was made by a procedure similar to that used to prepare 6-chloro-1-(3-ethyl-5-isopropyl-2,6-dioxo-1,2,3,6-tetrahydro-pyrimidin-4-yl)-1H-indole-4-carbonitrile (90), except that imidazole was used instead of 6-chloro-1H-indole-4-carbonitrile. LC-MS shows 249.1 (M+1). $^1$H NMR (300 MHz, CDCl$_3$): δ 9.03 (br, 1H), 7.60 (m, 1H), 7.32 (m, 1H), 7.00 (m, 1H), 3.40 (m, 2H), 2.08 (m, 1H), 1.19 (m, 9H).

1-Ethyl-5-isopropyl-6-pyrazol-1-yl-1H-pyrimidine-2,4-dione (Compound 95): This compound was made using a procedure similar to that used to prepare 6-chloro-1-(3-ethyl-5-isopropyl-2,6-dioxo-1,2,3,6-tetrahydro-pyrimidin-4-yl)-1H-indole-4-carbonitrile (90), except that pyrazole was used instead of 6-chloro-1H-indole-4-carbonitrile. LC-MS shows 249.1 (M+1). $^1$H NMR (300 MHz, CDCl$_3$): δ 9.36 (br, 1H), 7.81 (m, 1H), 7.58 (m, 1H), 6.54 (m, 1H), 3.38 (m, 2H), 2.04 (m, 1H), 1.17 (m, 9H).

Scheme 31

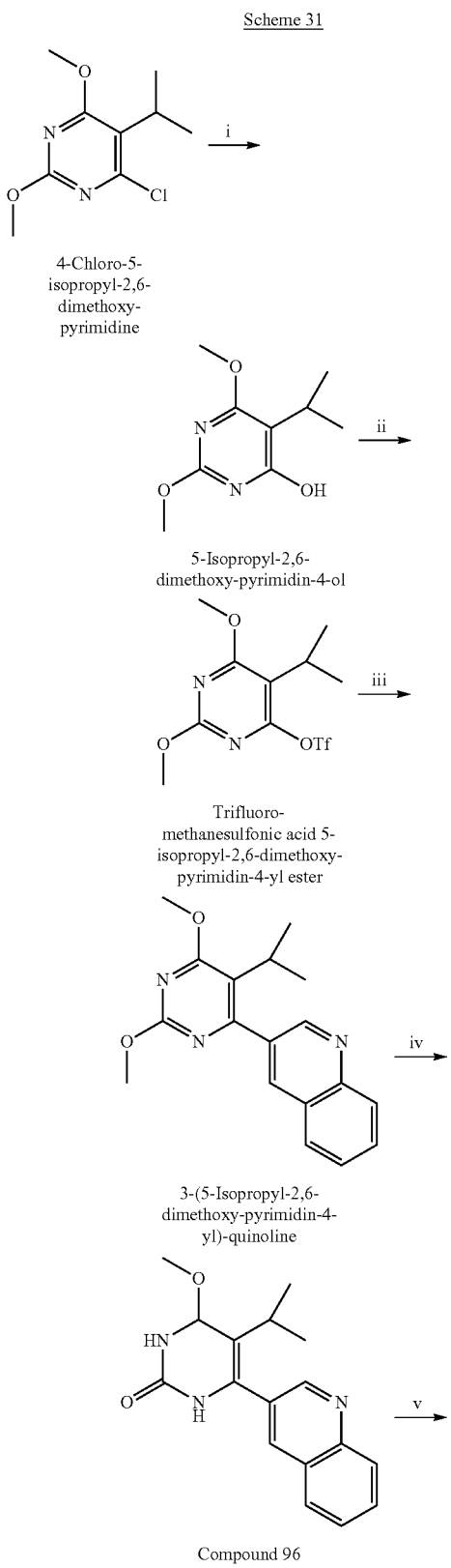

4-Chloro-5-isopropyl-2,6-dimethoxy-pyrimidine

5-Isopropyl-2,6-dimethoxy-pyrimidin-4-ol

Trifluoro-methanesulfonic acid 5-isopropyl-2,6-dimethoxy-pyrimidin-4-yl ester 3-(5-Isopropyl-2,6-dimethoxy-pyrimidin-4-yl)-quinoline Compound 96

399

-continued

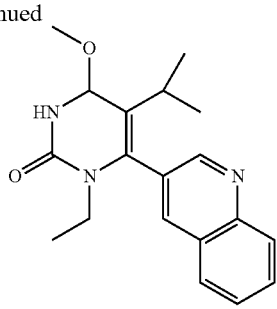

Compound 97

Reagents and conditions: i. a) BnOH, NaH, DMF; b) H$_2$, 10% Pd/C;
ii. N-phenyltrifluromethane sulfonimide, Cs$_2$CO$_3$, DCM.
iii. 3-quinoline boronic acid, Pd(dppf)$_2$Cl$_2$, 2M aq. Na$_2$CO$_3$, DME, microwave;
iv. AcBr, heat; v. EtI, K$_2$CO$_3$, DMF.

5-Isopropyl-2,6-dimethoxy-pyrimidin-4-ol: To a mixture of 4-chloro-5-isopropyl-2,6-dimethoxy-pyrimidine (1.4 g, 6.51 mmol, 1 eq) and benzyl alcohol (704 mg, 1.0 eq.) in 10 mL DMF, NaH (60% in mineral oil, 273 mg, 1.05 eq.) was added at 0° C. The reaction mixture was stirred at 0° C. then warmed up to room temperature. LC-MS showed that the desired product formed. The reaction mixture was then diluted with ethyl acetate, washed with water twice, dried with anhydrous magnesium sulfate, filtered, and evaporated in vacuo to give the crude product.

To the mixture of the above crude product (around 1.7 g) in 9 mL of EtOH and 36 mL of EtOAc, 10% Pd on carbon (340 mg) was added, and a hydrogen balloon was applied. The reaction mixture was stirred at room temperature for 1 hour. The mixture was filtered through celite and concentrated down. The crude product was purified by silica gel column chromatography (eluent: EtOAc/hexane (20-80%)) to afford 440 mg of 5-isopropyl-2,6-dimethoxy-pyrimidin-4-ol (34% for the two steps) of a white solid. $^1$H NMR (300 MHz, CDCl$_3$) 1.20 (6H, d), 3.25 (1H, m), 3.95 (6H, d), 12.9 (1H, br). LC-MS (M+1: 199.1, M−1: 197.0).

Trifluoro-methanesulfonic acid 5-isopropyl-2,6-dimethoxy-pyrimidin-4-yl ester: To a mixture of 5-isopropyl-2,6-dimethoxy-pyrimidin-4-ol (64 mg, 0.322 mmol) and N-phenyltrifluoromethane sulfonamide (127 mg, 1.1 eq.) in 3 mL of DCM, Cs$_2$CO$_3$ (116 mg, 1.1 eq.) was added. The reaction mixture was stirred at room temperature for 90 minutes. The reaction mixture was concentrated down and purified (silica gel, 0-80% EtOAC/hexane) to give white solid (74 mg, 69%). LC-MS shows 330.9 (M+1).

3-(5-Isopropyl-2,6-dimethoxy-pyrimidin-4-yl)-quinoline: In a 5 mL microwave reaction tube, trifluoro-methanesulfonic acid 5-isopropyl-2,6-dimethoxy-pyrimidin-4-yl ester (30 mg, 0.091 mmol), 3-quinoline boronic acid (19 mg, 1.2 eq.) and Pd(dppf)$_2$Cl$_2$ (7.4 mg, 10%) were mixed with 2 mL DME and 0.18 mL 2M aqueous Na$_2$CO$_3$ (4 eq.). The reaction mixture was heated in microwave at 130° C. for 40 minutes. The reaction mixture was concentrated down and purified by reverse phase prep HPLC (MeCN/water) to give a white powder (14 mg, 50%). LC-MS shows 310.2 (M+1).

5-Isopropyl-6-quinolin-3-yl-1H-pyrimidine-2,4-dione (Compound 96): In a 10 mL round bottom flask, 1 mL AcBr was added to 3-(5-Isopropyl-2,6-dimethoxy-pyrimidin-4-yl)-quinoline (14 mg, 0.045 mmol). The reaction mixture was heated at 70° C. for 2 hours. The reaction mixture was concentrated down and purified by reverse phase prep HPLC (MeCN/water) to give a white powder (6 mg, 47%). LC-MS shows 280.3 (M−1).

400

1-Ethyl-5-isopropyl-6-quinolin-3-yl-1H-pyrimidine-2,4-dione (Compound 97): 5-Isopropyl-6-quinolin-3-yl-1H-pyrimidine-2,4-dione (6 mg, 0.021 mmol, 1.0 eq.) was dissolved in 0.5 mL DMF. Potassium carbonate (3 mg, 1 eq.) was added and the reaction mixture was stirred at room temperature for 10 minutes. EdI (1.7 µL, 1 eq.) was added. The reaction mixture was stirred at room temperature overnight. No reaction was observed. More potassium carbonate (6 mg) was added. The reaction mixture was complete after 2 hours. The reaction crude was filtered and purified by reverse phase HPLC to give a white powder (1.5 mg, 23%). LC-MS shows 310.2 (M+1). $^1$H-NMR (300 MHz, CDCl$_3$): δ 8.83 (s, 1H), 8.40 (m, 1H), 8.22 (m, 1H), 7.96 (m, 2H), 7.78 (m, 1H), 3.58 (m, 2H), 2.10 (m, 1H), 1.90 (dd, 6H), 1.04 (t, 3H).

Scheme 32

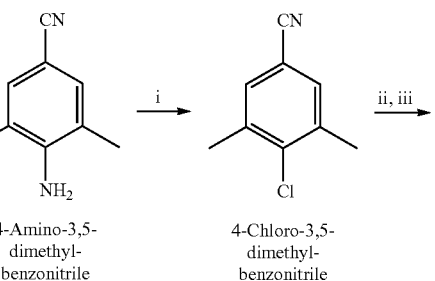

4-Amino-3,5-dimethyl-benzonitrile

4-Chloro-3,5-dimethyl-benzonitrile

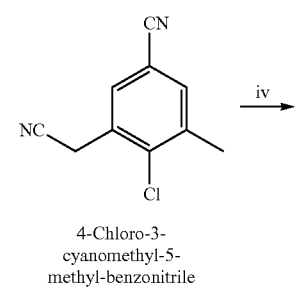

4-Chloro-3-cyanomethyl-5-methyl-benzonitrile

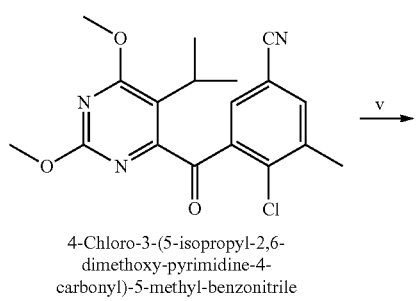

4-Chloro-3-(5-isopropyl-2,6-dimethoxy-pyrimidine-4-carbonyl)-5-methyl-benzonitrile

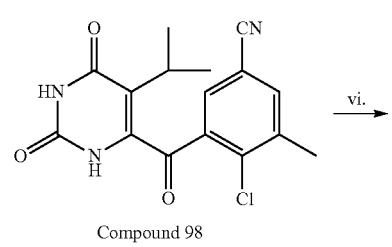

Compound 98

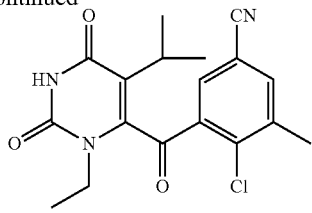

Compound 99

Reagents and conditions: i. tBuNO₂, CuCl₂, ACN, 89%; ii. NBS, CCl₄, 68%; iii. KCN, EtOH/H₂O, 39%; iv. a. 4-Chloro-5-isopropyl-2,6-dimethoxy-pyrimidine, NaH, DMF; b. O₂, 11% (2 steps); v. AcBr, 95%; vi. iodoethane, K₂CO₃, DMF, 30%.

4-Chloro-3,5-dimethyl-benzonitrile: To a mixture of copper (II) chloride (1.10 g, 8.21 mmol) in acetonitrile (27 mL) at 0° C. was added tert-butyl nitrite (1.35 g, 110.26 mmol). To this brown mixture was added 4-Amino-3,5-dimethyl-benzonitrile (1.0 g, 6.84 mmol) in portions over 5 minutes and reaction mixture stirred for 18 hr at room temperature. The reaction mixture was concentrated, diluted with 1N HCl and extracted with ethyl ether. The organic layer was dried (MgSO₄), concentrated and purified by flash column chromatography (silica gel, 0 to 20% ethyl acetate/hexane) to give a white solid (1.011 g, 89%). $^1$H NMR (300 MHz, CDCl₃): 7.30 (s, 2H), 2.33 (s, 6H); $^{13}$C NMR (75 MHz, CDCl₃): 139.9, 137.8, 131.5, 118.3, 109.9, 20.6.

4-Chloro-3-cyanomethyl-5-methyl-benzonitrile: A mixture of 4-chloro-3,5-dimethyl-benzonitrile (1.011 g, 6.10 mmol), N-bromosuccinimide (1.087 g, 6.10 mmol) and benzoyl peroxide (0.074 g, 0.305 mmol) in carbon tetrachloride (30 mL) was heated to reflux for 4 hr. The reaction mixture was cooled to room temperature and filtered. The filtrate was purified by flash column chromatography (silica gel, 0 to 30% ethyl acetate/hexane) to give 3-bromomethyl-4-chloro-5-methyl-benzonitrile as an impure white solid (0.9938 g, 66%), which was used in the next step without further purification.

3-Bromomethyl-4-chloro-5-methyl-benzonitrile (0.9938 g, 4.06 mmol), potassium cyanide (0.529 g, 8.12 mmol) in ethanol (5.0 mL) and H₂O (2.5 mL) was heated at 85° C. for 3 hr. The reaction mixture was cooled, diluted with ethyl acetate, washed with brine, dried (MgSO₄), concentrated and purified by flash column chromatography (silica gel, 0 to 30% ethyl acetate/hexane) to give 4-chloro-3-cyanomethyl-5-methyl-benzonitrile as a white solid (0.3707 g, 48%). $^1$H NMR (300 MHz, CDCl₃): 7.61 (s, 1H), 7.51 (s, 1H), 3.83 (s, 2H), 2.40 (s, 3H).

4-Chloro-3-(5-isopropyl-2,6-dimethoxy-pyrimidine-4-carbonyl)-5-methyl-benzonitrile: To a solution of 4-chloro-5-isopropyl-2,6-dimethoxy-pyrimidine (0.442 g, 2.04 mmol) and 4-chloro-3-cyanomethyl-5-methyl-benzonitrile (0.3707 g, 1.94 mmol) in DMF at 0° C. was added NaH portionwise over 15 minutes to give an orange-red reaction mixture. After stirring for 24 hr, O₂ was bubbled into the reaction mixture for 36 hr. The reaction mixture was quenched with saturated ammonium chloride solution and methanol, and diluted with ethyl acetate. The organic layer was washed with saturated ammonium chloride solution, H₂O, saturated ammonium chloride solution and dried (MgSO₄), then concentrated and purified by flash column chromatography (silica gel, 5 to 50% ethyl acetate/hexane) to give title compound (0.0767 g, 11%). $^1$H NMR (300 MHz, CDCl₃): 7.67 (s, 1H), 7.59 (s, 1H), 4.00 (s, 3H), 3.75 (s, 3H), 3.3-3.2 (m, 1H), 2.37 (s, 3H), 1.25 (s, 3H), 1.23 (s, 3H); $^{13}$C NMR (75 MHz, CDCl₃): 192.8, 171.1, 162.2, 160.2, 139.1, 138.9, 137.3, 135.9, 132.3, 119.9, 117.4, 110.8, 54.7, 54.2, 26.5, 20.2, 20.2; Mass Spectrum: 360.2, 362.1 (M+H).

4-Chloro-3-(5-isopropyl-2,6-dioxo-1,2,3,6-tetrahydro-pyrimidine-4-carbonyl)-5-methyl-benzonitrile (Compound 98): A solution of 4-chloro-3-(5-isopropyl-2,6-dimethoxy-pyrimidine-4-carbonyl)-5-methyl-benzonitrile (0.0767 g, 0.213 mmol) in acetyl bromide (3.5 mL) was heated at 65° C. for 18 hr, cooled to room temperature and concentrated. The resulting residue was purified by flash column chromatography (silica gel, 20 to 100% ethyl acetate/hexane) to give Compound 102 as an off-white solid (0.067 g, 95%). $^1$H NMR (300 MHz, CD₃OD): 8.05 (s, 1H), 7.96 (s, 1H), 2.47 (s, 3H), 2.5-2.4 (m, 1H), 1.09 (s, 3H), 1.07 (s, 3H); Mass Spectrum: 332.2 (M+H).

4-Chloro-3-(3-ethyl-5-isopropyl-2,6-dioxo-1,2,3,6-tetrahydro-pyrimidine-4-carbonyl)-5-methyl-benzonitrile (Compound 99): To a mixture of Compound 98 (0.067 g, 0.202 mmol) and potassium carbonate (0.0279 g, 0.202 mmol) in DMF (1.0 mL) was added iodoethane (14 μL, 0.168 mmol) and reaction mixture was stirred overnight at room temperature. The reaction mixture was quenched with saturated ammonium chloride solution and extracted with ethyl acetate, dried (MgSO₄) and concentrated. The resulting residue was purified by reverse phase HPLC (Phenomenex Synergi® column, 5 to 100% acetonitrile/H₂O) to give a white powder after lyophilization (20.5 mg, 28%). $^1$H NMR (300 MHz, CD₃CN): 9.15 (s, 1H), 8.16 (s, 1H), 7.96 (s, 1H), 3.52 (br s, 2H), 2.47 (s, 3H), 2.3-2.2 (m, 1H), 1.1-1.0 (s, 9H); Mass Spectrum: 360.2, 362.2 (M+H).

Scheme 33

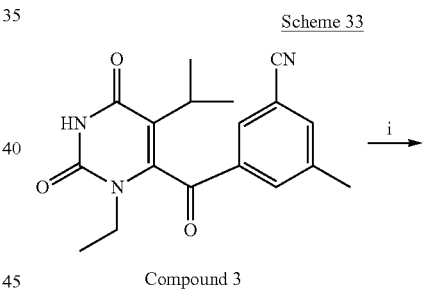

Compound 3

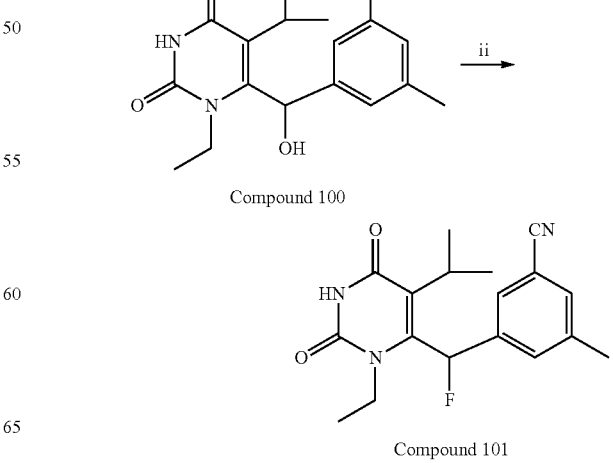

Compound 100

Compound 101

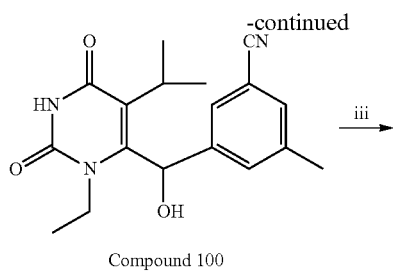

Compound 100

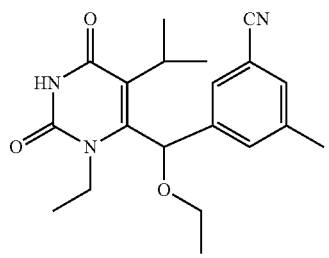

Compound 102

Reagents and conditions: i. NaBH₄, EtOH, 44%; ii. DAST, 68%; iii. a. MsCl, Et₃N, THF; b. KCN, EtOH/H₂O, 39%.

3-[(3-Ethyl-5-isopropyl-2,6-dioxo-1,2,3,6-tetrahydro-pyrimidin-4-yl)-hydroxy-methyl]-5-methyl-benzonitrile (Compound 100): To a solution of 3-(3-ethyl-5-isopropyl-2,6-dioxo-1,2,3,6-tetrahydro-pyrimidine-4-carbonyl)-5-methyl-benzonitrile (3) (0.700 g, 2.15 mmol) in ethanol (61 mL) at 0° C. was added sodium borohydride (0.081 g, 2.15 mmol) and the reaction mixture was stirred at 0° C. for 2 h, then at room temperature overnight. More sodium borohydride (0.081 g, 2.15 mmol). was then added, and the mixture was stirred for 24 h. More sodium borohydride (0.081 g, 2.15 mmol) was again added, and stirring was continued for 6 h. The reaction mixture was concentrated and quenched with saturated NH₄Cl solution, acidified with 1N HCl and then extracted with ethyl acetate (2×). The combined organic layer dried (MgSO₄), concentrated and purified by flash column chromatography (silica gel, 30 to 60% ethyl acetate/hexane) to give impure product. The impure product was purified again by flash column chromatography (silica gel, 0 to 5% methanol/dichloromethane), followed by purified by flash column chromatography (silica gel, 40 to 60% ethyl acetate/hexane) to give a white solid (0.31 g, 44%). ¹H NMR (300 MHz, CD₃OD): 7.55 (s, 1H), 7.47 (s, 1H), 7.43 (s, 1 H), 6.18 (s, 1H), 3.73 (q, J=6.9 Hz, 2H), 3.12-3.07 (m, 1H), 2.37 (s, 3H), 1.30 (d, J=7.2 Hz, 3H), 1.11 (d, J=6.6 Hz, 3H), 0.92-0.84 (m, 3H); Mass Spectrum: 328.1 (M+H).

3-[(3-Ethyl-5-isopropyl-2,6-dioxo-1,2,3,6-tetrahydro-pyrimidin-4-yl)-fluoro-methyl]-5-methyl-benzonitrile (Compound 101): To a solution of 3-[(3-Ethyl-5-isopropyl-2,6-dioxo-1,2,3,6-tetrahydro-pyrimidin-4-yl)-hydroxy-methyl]-5-methyl-benzonitrile (100) (55.7 mg, 0.17 mmol) in dichloromethane (2.0 mL) at 0° C. was added (diethylamino)sulfur trifluoride (33 µL, 0.255 mmol) and reaction mixture stirred for 1 h. The reaction mixture was quenched with saturated NaHCO₃ solution and extracted with ethyl acetate (2×). The combined organic layer was dried (MgSO4), concentrated and purified by reverse phase HPLC (Phenomenex Synergi® column, 5 to 100% acetonitrile/H₂O) to give a white powder after lyophilization (45 mg, 80%). ¹H NMR (300 MHz, CD₃OD): 7.60 (s, 1H), 7.55 (s, 1H), 7.46 (s, 1H), 7.04 (d, J=45.9 Hz, 1H), 3.75-3.57 (m, 2H), 2.94-2.89 (m, 1H), 2.40 (s, 3H), 1.24 (d, J=6.9 Hz, 3H), 1.1-1.0 (s, 6H); %). ¹⁹F NMR (CD₃OD): −180.5; Mass Spectrum: 330.1 (M+H).

3-[Ethoxy-(3-ethyl-5-isopropyl-2,6-dioxo-1,2,3,6-tetrahydro-pyrimidin-4-yl)-methyl]-5-methyl-benzonitrile (Compound 102): To a solution of 3-[(3-ethyl-5-isopropyl-2,6-dioxo-1,2,3,6-tetrahydro-pyrimidin-4-yl)-hydroxy-methyl]-5-methyl-benzonitrile (100) (69 mg, 0.211 mmol) and triethylamine (353 µL, 2.53 mmol) in THF (4.0 mL) was added methane sulfonyl chloride (166 µL, 2.11 mmol). The reaction mixture was stirred for 2 h at 0° C. then at room temperature for 48 h. The reaction mixture was diluted with ethyl acetate and washed with 1N HCl, saturated NaHCO₃ solution, dried (MgSO₄), concentrated and purified to give impure product (80 mg). The resulting residue was dissolved in ethanol (1.5 mL) and water (0.5 mL) and potassium cyanide was added (21 mg, 0.32 mmol). The reaction mixture was refluxed for 2 h, cooled and diluted with ethyl acetate and washed with saturated ammonium chloride solution, dried (MgSO₄) and concentrated. The resulting residue was purified by reverse phase HPLC (Phenomenex Synergi® column, 5 to 100% acetonitrile/H₂O) to give a white powder after lyophilization (14 mg, 22%). ¹H NMR (300 MHz, CD₃OD): 7.52 (s, 1H), 7.50 (s, 1H), 7.39 (s, 1H), 5.98 (s, 1H), 3.75-3.57 (m, 4H), 3.12-3.07 (m, 1H), 2.37 (s, 3H), 1.37-1.30 (m, 6H), 1.15 (d, J=6.3 Hz, 3H), 0.92-0.87 (m, 3H); Mass Spectrum: 356.2 (M+H).

Scheme 34

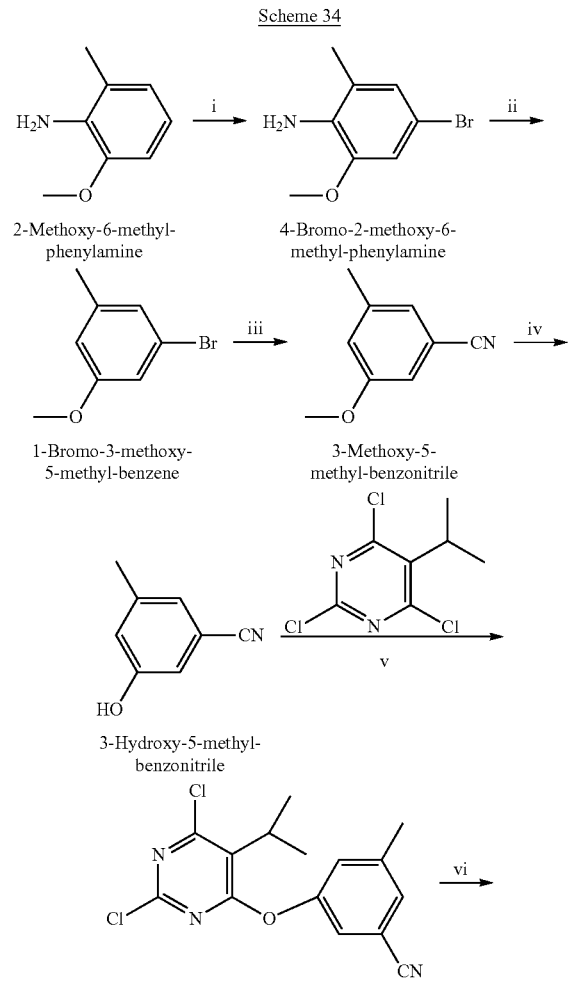

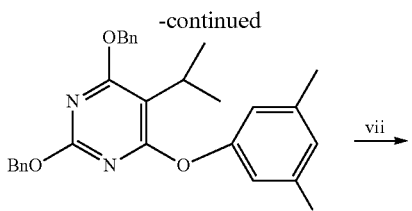

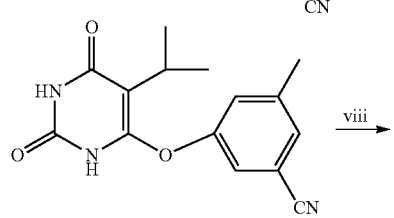

Compound 103

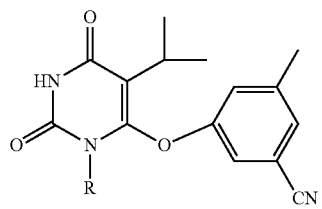

Compound 104 R = Et,
Compound 105 R = n-Bu

Reagents and conditions: i. Br, AcOH, MeOH, 0° C. -> r.t.; ii. NaNO$_2$, AcOH, HCl, H$_2$O, H$_3$PO$_2$, 0° C. -> r.t.; iii. Zn(CN)$_2$, Pd(PPh$_3$)$_4$, DMF, 90° C.; iv. BCl$_3$, Bu$_4$NI, DCM, -78° C. -> r.t.; v. NaH, DMF; vi. BnOH, NaH, DMF; vii. K$_2$CO$_3$, DMF, R-I.

4-Bromo-2-methoxy-6-methyl-phenylamine: In a 100 mL round bottom flask, 2-methoxy-6-methyl-phenylamine (4.54 g, 33.16 mmol) was dissolved in 15 mL MeOH and 5 mL acetic acid. The flask was cooled to 0° C. Bromine (1.7 mL, 33.16 mmol) in 5 mL acetic acid was added to the reaction dropwise (over 30 minutes). The reaction mixture was stirred at 0° C. for 2 hours, then was warmed up to room temperature for 1 hour. The reaction mixture was concentrated down. 1N NaOH was added to neutralize the reaction at 0° C. Ethyl acetate was added to extract the reaction mixture. The organic layer was concentrated after drying over anhydrous sodium sulfate to give a dark brown solid (5.8 g, 81%). LC-MS shows 218.0 (M+1). $^1$H NMR (300 MHz, CDCl$_3$): δ 6.88 (s, 1H), 6.81 (s, 1H), 3.84 (s, 3H), 2.11 (s, 3H).

1-Bromo-3-methoxy-5-methyl-benzene: In a 250 mL round bottom flask, 4-bromo-2-methoxy-6-methyl-phenylamine (5.8 g, 26.84 mmol) was charged with acetic acid (49 mL) and concentrated HCl (5.6 mL). Sodium nitrite (2.19 g, 31.78 mmol) in 7 mL water was added to the mixture dropwise at 0° C. The reaction mixture was stirred at 0° C. for 30 minutes. 50% Hypophosphorous acid (56.5 mL) was added at 0° C. The reaction mixture was stirred at 0° C., and warmed up to room temperature overnight. Ethyl acetate was then added, followed by washing with saturated NaHCO$_3$ solution. The organic layer was concentrated and purified (silica gel, 100% hexane) to give a pale liquid (5.12 g, 95%). $^1$H NMR (300 MHz, CDCl$_3$): δ 6.97 (s, 1H), 6.87 (s, 1H), 6.64 (s, 1H), 3.80 (s, 3H), 2.36 (s, 3H).

3-Methoxy-5-methyl-benzonitrile: In a 100 mL round bottom flask, 1-bromo-3-methoxy-5-methyl-benzene (2.17 g, 10.79 mmol), Zn(CN)$_2$ (1.9 g, 16.19 mmol, 1.5 eq.) and Pd(PPh$_3$)$_4$ (1.24 g, 1.08 mmol, 0.1 eq.) was charged with DMF (20 mL). The reaction mixture was heated at 90° C. under Ar for 7 hours. Ethyl acetate was added, followed by washing with brine. The organic layer was concentrated and purified (silica gel, 0-50% EtOAC/hexane) to give a white solid (1.31 g, 83%). $^1$H NMR (300 MHz, CDCl$_3$): δ 7.05 (s, 1H), 6.97 (s, 2H), 3.81 (s, 3H), 2.39 (s, 3H).

3-Hydroxy-5-methyl-benzonitrile: In a 100 mL round bottom flask, 3-methoxy-5-methyl-benzonitrile (500 mg, 3.39 mmol) was dissolved in 15 mL dry DCM, and tetrabutylammonium iodide (1.38 g, 3.73 mmol, 3.5 eq.) was added. The flask was cooled to -78° C. BCl$_3$ (1 M in DCM, 11.87 mL, 33.16 mmol) was added to the reaction dropwise. The reaction mixture was stirred at -78° C. and warmed up to room temperature overnight. The reaction mixture was quenched with ice and neutralized with saturated NaHCO$_3$ solution. DCM was added to extract the reaction mixture. The organic layer was concentrated down and purified (silica gel, 0-10% MeOH/DCM) to give a light yellow solid (408 g, 90%). LC-MS shows 132.0 (M-1). $^1$H NMR (300 MHz, CDCl$_3$): δ 7.20 (s, 1H), 6.96 (s, 1H), 6.91 (s, 1H), 2.37 (s, 3H).

3-(2,6-Dichloro-5-isopropyl-pyrimidin-4-yloxy)-5-methyl-benzonitrile: At 0° C., NaH (60%, 125 mg, 3.06 mmol, 1.0 eq.) was added to 3-hydroxy-5-methyl-benzonitrile (408 mg, 3.06 mmol) in 10 mL of DMF solution. The reaction mixture was stirred at 0° C. for 5 minutes. 2,4,6-Trichloro-5-isopropyl-pyrimidine (691 mg, 3.06 mmol) was then added. The reaction mixture was stirred at 0° C. for 30 minutes. Ethyl acetate was added to the reaction mixture, which was then washed with brine. The organic layer was concentrated and purified (silica gel, 0-50% EtOAc/hexane) to give a white solid (868 mg, 88%). LC-MS shows 322.1 (M+1). $^1$H NMR (300 MHz, CDCl$_3$): δ 7.41 (s, 1H), 7.26 (s, 1H), 7.19 (s, 1H), 3.60 (m, 1H), 2.42 (s, 3H), 1.42 (d, 6H).

3-(2,6-Bis-benzyloxy-5-isopropyl-pyrimidin-4-yloxy)-5-methyl-benzonitrile: At 0° C., NaH (60%, 118 mg, 2.88 mmol, 2.2 eq.) was added to benzyl alcohol (298 µL, 2.88 mmol) in 5 mL of THF solution. The reaction mixture was stirred at 0° C. for 5 minutes. 3-(2,6-Dichloro-5-isopropyl-pyrimidin-4-yloxy)-5-methyl-benzonitrile (422 mg, 1.31 mmol) was added. The reaction mixture was stirred at 0° C. for 15 minutes, then warmed to room temperature for 90 minutes. Ethyl acetate was added to the reaction mixture, which was then washed with brine. The organic layer was concentrated and purified (silica gel, 0-50% EtOAc/hexane) to give a white solid (372 mg, 65% pure by HPLC, 40%). LC-MS shows 466.1 (M+1).

3-(5-Isopropyl-2,6-dioxo-1,2,3,6-tetrahydro-pyrimidin-4-yloxy)-5-methyl-benzonitrile (Compound 103): 3-(2,6-Bis-benzyloxy-5-isopropyl-pyrimidin-4-yloxy)-5-methyl-benzonitrile (372 mg, 65% pure, 0.52 mmol) was dissolved in 20 mL of EtOAc and 5 mL of EtOH. 10% Pd/C (75 mg) was added and a hydrogen balloon was applied. The reaction mixture was stirred at room temperature for 1 hour. The Pd/C was filtered through celite, and the filtrate was concentrated and purified using silica gel (EtOAc/hexane) to give a white solid (100 mg, 29%). LC-MS shows 286.0 (M+1).

3-(3-Ethyl-5-isopropyl-2,6-dioxo-1,2,3,6-tetrahydro-pyrimidin-4-yloxy)-5-methyl-benzonitrile (Compound 104): Potassium carbonate (24 mg, 0.172 mmol, 1.0 eq.) was added to 3-(5-isopropyl-2,6-dioxo-1,2,3,6-tetrahydro-pyrimidin-4-yloxy)-5-methyl-benzonitrile (103) (59 mg, 0.207 mmol, 1.2 eq.) in 2.0 mL DMF. The reaction mixture was stirred at room temperature for 10 minutes, then ethyl iodide (14 µL, 0.172 mmol) was added. The reaction mixture was stirred at room temperature overnight. Ethyl acetate was added to the reaction mixture, which was then washed with brine. The organic layer was concentrated and purified (silica gel, 20-80% EtOAc/hexane), followed by reverse phase HPLC (MeCN/water) to give a white powder (15 mg, 28%). LC-MS shows 314.1 (M+1). $^1$H NMR (300 MHz, CDCl$_3$): δ 9.17 (br, 1H), 7.25 (s, 1H), 7.08 (s, 1H), 7.00 (s, 1H), 3.77 (t, 2H), 2.69 (m, 1H), 2.42 (s, 3H), 1.2 (m, 9H).

3-(3-Butyl-5-isopropyl-2,6-dioxo-1,2,3,6-tetrahydro-pyrimidin-4-yloxy)-5-methyl-benzonitrile (Compound 105): Potassium carbonate (9.3 mg, 0.0067 mmol, 1.0 eq.) was added to 3-(5-isopropyl-2,6-dioxo-1,2,3,6-tetrahydro-pyrimidin-4-yloxy)-5-methyl-benzonitrile (103) (23 mg, 0.0.08 mmol, 1.2 eq.) in 1.0 mL DMF. The reaction mixture was stirred at room temperature for 10 minutes, and n-butyl iodide (7.6 µL, 0.0.067 mmol) was added. The reaction mixture was filtered and purified by reverse phase HPLC (MeCN/water) to give a white powder (3.8 mg, 17%). LC-MS shows 342.1 (M+1). $^1$H NMR (300 MHz, CDCl$_3$): δ 8.37 (br, 1H), 7.28 (s, 1H), 7.08 (s, 1H), 6.98 (s, 1H), 3.42 (t, 2H), 2.71 (m, 1H), 2.42 (s, 3H), 1.60 (m, 2H), 1.28 (m, 2H), 1.17 (d, 6H), 0.88 (t, 3H).

tography (eluent, ethyl acetate:hexane (1:1)) to afford 382 mg (54%) of a white solid. m.p. 103-105° C.; m/z (EI) 369(M$^+$).

1-But-2-enyl-6-(3,5-dimethyl-phenylamino)-5-isopropyl-1H-pyrimidine-2,4-dione (Compound 108): To a stirred solution of N-(3-but-2-enyl-5-isopropyl-2,6-dioxo-1,2,3,6-tetrahydro-pyrimidin-4-yl)-N-(3,5-dimethyl-phenyl)-acetamide (107) (100 mg, 0.27 mmol) in methanol (3 mL), was added sodium methoxide (73 mg, 1.35 mmol). After 4 hr., the mixture was neutralized with excess NH$_4$Cl and evaporated in vacuo. The residue was purified by silica gel column chromatography (eluent, ethyl acetate:hexane (1:2)) to afford 62 mg (70%) of a white solid. m.p. 186-187° C.; $^1$H-NMR (200 MHz, CDCl$_3$) δ 1.17 (6H, d, J=6.9 Hz), 1.64-1.67 (3H, m), 2.24 (6H, s), 2.86 (1H, m), 4.25-4.30 (2H, m), 5.33 (1H, s), 5.48-5.54 (2H, m), 6.32 (2H, s), 6.60 (1H, s), 8.42 (1H, s); m/z (EI) 327 (M$^+$).

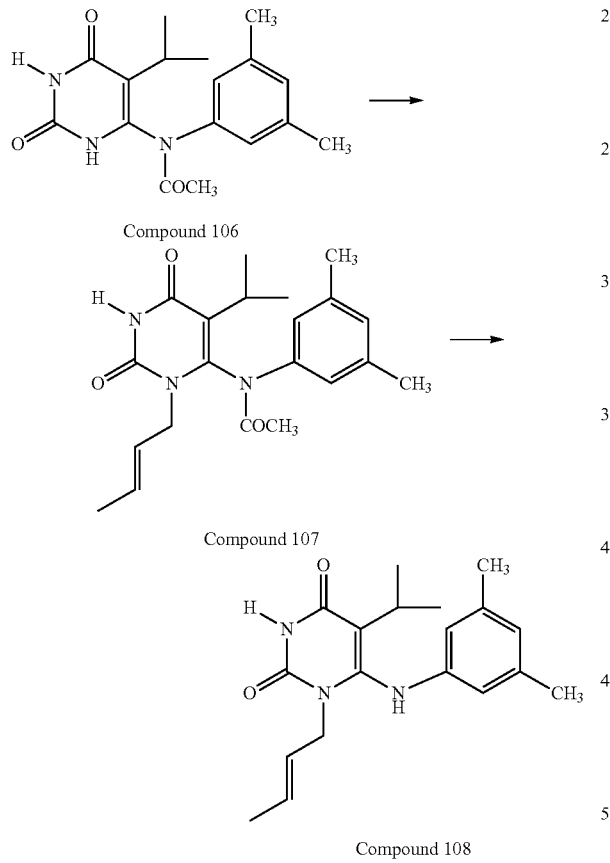

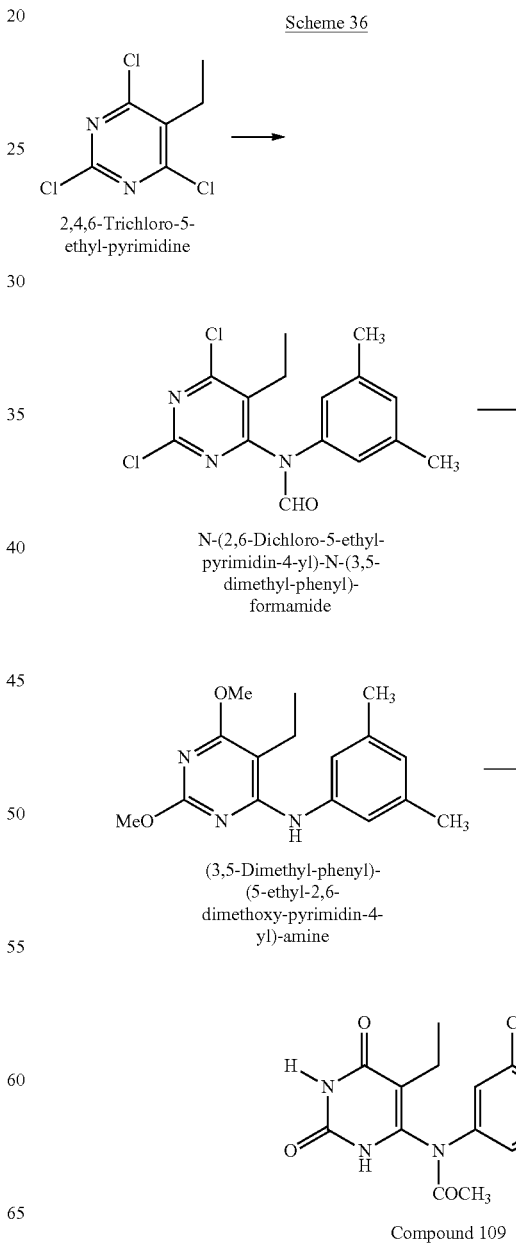

N-(3-But-2-enyl-5-isopropyl-2,6-dioxo-1,2,3,6-tetrahydro-pyrimidin-4-yl)-N-(3,5-dimethyl-phenyl)-acetamide (Compound 107): To a stirred solution of N-(3,5-dimethyl-phenyl)-N-(5-isopropyl-2,6-dioxo-1,2,3,6-tetrahydro-pyrimidin-4-yl)-acetamide (106) (prepared similarly to compound 109 in Scheme 36, below, except that 2,4,6-trichloro-5-isopropyl-pyrimidine was used instead of 2,4,6-trichloro-5-ethyl-pyrimidine) (600 mg, 1.9 mmol) anhydrous powdered K$_2$CO$_3$ (262 mg, 1.9 mmol), and lithium iodide (254 mg, 1.9 mmol) in DMF (7 mL), was added 1-methanesulfonyl-trans-2-butene (269 µL, 2.28 mmol). After stirring for 13 hr., the reaction mixture was diluted with ether, washed with water, dried with MgSO$_4$, filtered, and evaporated in vacuo. The residue was purified by silica gel column chroma-

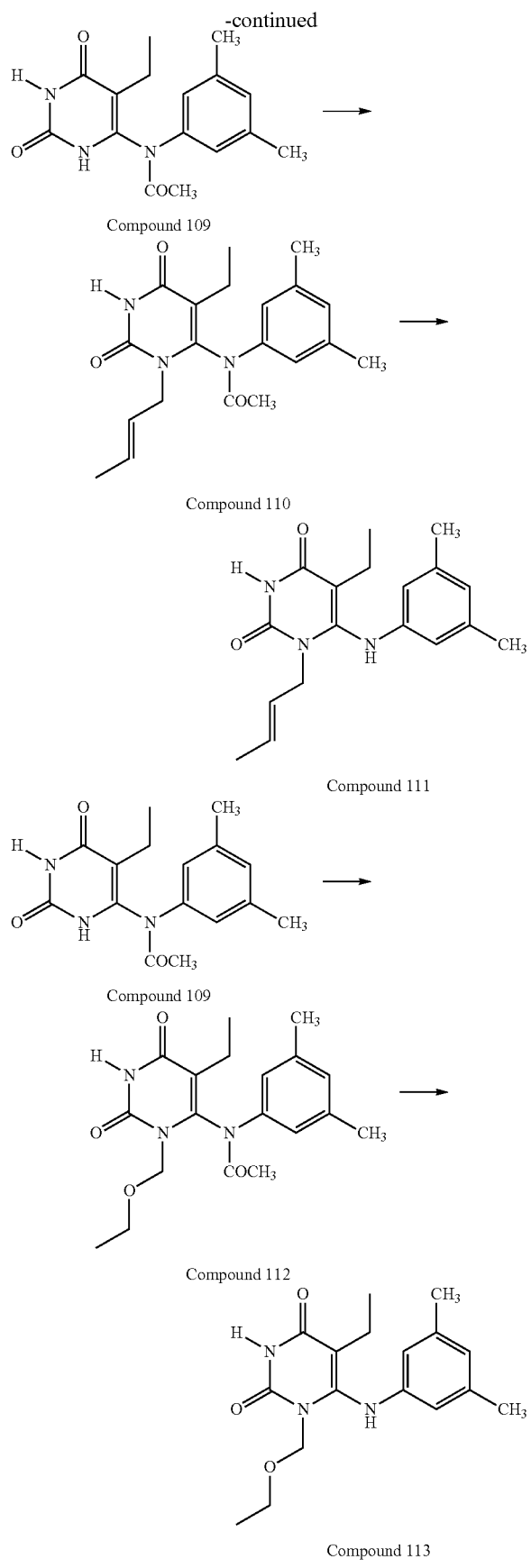

N-(2,6-Dichloro-5-ethyl-pyrimidin-4-yl)-N-(3,5-dimethyl-phenyl)-formamide: To a stirred solution of N-(3,5-dimethylphenyl)formaniline (8.94 g, 60 mmol) in DMF (60 mL) cooled in an ice bath under nitrogen, was portionwise added 60% sodium hydride (2.88 g, 72 mmol). After 10 min., 2,4,6-trichloro-5-ethyl-pyrimidine (15.2 g, 72 mmol) was added. After stirring for 10 min., the mixture was stirred at room temperature for 24 hr. The mixture was diluted with ether, washed with water three times, dried with MgSO$_4$, filtered, and evaporated in vacuo. The residue was purified by silica gel column chromatography (eluent, ether:hexane (1:10)) to afford 8.6 g (44%) of a white solid. m.p. 124-125° C.; m/z (EI) 323 (M$^+$).

(3,5-Dimethyl-phenyl)-(5-ethyl-2,6-dimethoxy-pyrimidin-4-yl)-amine: Sodium metal (2.3 g, 0.1 M) was reacted with methanol (80 mL) at room temperature. N-(2,6-Dichloro-5-ethyl-pyrimidin-4-yl)-N-(3,5-dimethyl-phenyl)-formamide (6.48 g, 20 mmol) was then added and the mixture was refluxed for 4 hr. After cooling to room temperature, the reaction mixture was neutralized with excess NH$_4$Cl. The mixture was evaporated in vacuo and the residue was purified by silica gel column chromatography (eluent, ethyl acetate:hexane (1:15)) to afford 5 g (88%) of a white solid. m.p. 113-114° C.; $^1$H-NMR (200 MHz, CDCl$_3$) δ 1.12 (3H, t, J=7.5 Hz), 2.31 (6H, s), 2.38 (2H, q, J=7.5 Hz), 3.94 (6H, s), 6.32 (1H, s), 6.70 (1H, s), 7.25 (2H, s); m/z (EI) 287(M$^+$).

N-(3,5-Dimethyl-phenyl)-N-(5-ethyl-2,6-dioxo-1,2,3,6-tetrahydro-pyrimidin-4-yl)-acetamide (Compound 109): (3,5-Dimethyl-phenyl)-(5-ethyl-2,6-dimethoxy-pyrimidin-4-yl)-amine (5 g, 17.4 mmol) was refluxed with acetyl bromide (50 mL) for 18 hr. After cooling to room temperature, the mixture was evaporated in vacuo and the residue was purified by silica gel column chromatography (eluent, ethyl acetate:hexane (2:1)) to afford 4.5 g (86%) of a white solid. m.p. 238-239° C.; $^1$H-NMR (200 MHz, CDCl$_3$) δ 0.93 (3H, t, J=7.5 Hz), 2.05-2.15 (3H, m), 2.24-2.40 (8H, m), 6.94-6.99 (3H, m); m/z (EI) 301(M$^+$).

N-(3-But-2-enyl-5-ethyl-2,6-dioxo-1,2,3,6-tetrahydro-pyrimidin-4-yl)-N-(3,5-dimethyl-phenyl)-acetamide (Compound 110): To a stirred solution of N-(3,5-dimethyl-phenyl)-N-(5-ethyl-2,6-dioxo-1,2,3,6-tetrahydro-pyrimidin-4-yl)-acetamide (109) (602 mg, 2 mmol) anhydrous powdered K$_2$CO$_3$ (276 mg, 2 mmol), and lithium iodide (268 mg, 2 mmol) in DMF (6 mL), was added 1-methanesulfonyl-trans-2-butene (283 μL, 2.4 mmol). After stirring for 13 hr., the reaction mixture was diluted with ether, washed with water, dried with MgSO$_4$, filtered, and evaporated in vacuo. The residue was purified by silica gel column chromatography (eluent, ethyl acetate:hexane (1:1)) to afford 291 mg (40%) of a white solid. m.p. 218-220° C.; m/z (EI) 355(M$^+$).

1-But-2-enyl-6-(3,5-dimethyl-phenylamino)-5-ethyl-1H-pyrimidine-2,4-dione (Compound III): To a stirred solution of N-(3-but-2-enyl-5-ethyl-2,6-dioxo-1,2,3,6-tetrahydro-pyrimidin-4-yl)-N-(3,5-dimethyl-phenyl)-acetamide (110) (90 mg, 0.25 mmol) in methanol (3 mL), was added sodium methoxide (73 mg, 1.35 mmol). After 4 hr., the mixture was neutralized with excess. NH$_4$Cl and evaporated in vacuo. The residue was purified by silica gel column chromatography (eluent, ethyl acetate:hexane (1:1)) to afford 57 mg (72%) of a white solid. m.p. 190-192° C.; $^1$H-NMR (200 MHz, CDCl$_3$) δ 1.00 (3H, t, J=7.5 Hz), 1.68-1.70 (3H, m), 2.28-2.37 (8H, m), 4.31-4.33 (2H, m), 5.44 (1H, s), 5.51-5.58 (2H, m), 6.39 (2H, s), 6.66 (1H, s), 8.72 (1H, s); m/z (EI) 313 (M$^+$).

N-(3,5-Dimethyl-phenyl)-N-(3-ethoxymethyl-5-ethyl-2,6-dioxo-1,2,3,6-tetrahydro-pyrimidin-4-yl)-acetamide (Compound 112): A mixture of N-(3,5-dimethyl-phenyl)-N-(5-ethyl-2,6-dioxo-1,2,3,6-tetrahydro-pyrimidin-4-yl)-acetamide (109) (301 mg, 1 mmol), hexamethyldisilazane (5 mL), and chlorotrimethylsilane (5 drops) was refluxed for 4 hr. After cooling to room temperature, the mixture was evaporated in vacuo. The residue was dissolved in acetonitrile (5 mL). Chloromethyl ethyl ether (110 µL, 1.2 mmol) and SnCl$_4$ (1 M in dichloromethane, 100 µL, 0.1 mmol) were added. The mixture was stirred at room temperature for 16 hrs. Excess sodium bicarbonate was then added and the mixture was stirred for 1 hr. The mixture was evaporated in vacuo and the residue was purified by silica gel column chromatography (eluent, ethyl acetate:hexane (1:1)) to afford 162 mg (45%) of a white solid. m.p. 182-183° C.; HRMS (EI) Calcd. 359.184507. Found 359.183174.

6-(3,5-Dimethyl-phenylamino)-1-ethoxymethyl-5-ethyl-1H-pyrimidine-2,4-dione (Compound 113): To a stirred solution of N-(3,5-dimethyl-phenyl)-N-(3-ethoxymethyl-5-ethyl-2,6-dioxo-1,2,3,6-tetrahydro-pyrimidin-4-yl)-acetamide (112) (93 mg, 0.26 mmol) in methanol (5 mL), was added sodium methoxide (73 mg, 1.35 mmol). After 4 hrs., the mixture was neutralized with excess NH$_4$Cl and evaporated in vacuo. The residue was purified by silica gel column chromatography (eluent, ethyl acetate:hexane (1:2)) to afford 58 mg (70%) of a white solid. m.p. 175-176° C.; $^1$H-NMR (200 MHz, CDCl$_3$) δ 0.93 (3H, t, J=7.5 Hz), 1.26 (3H, t, J=7.1 Hz), 2.19 (2H, q, J=7.5 Hz), 2.27 (6H, s), 3.70 (2H, q, J=7.1 Hz), 5.34 (2H, s), 6.42 (1H, s), 6.46 (2H, s), 6.65 (1H, s), 8.64 (1H, s); m/z (EI) 317 (M$^+$).

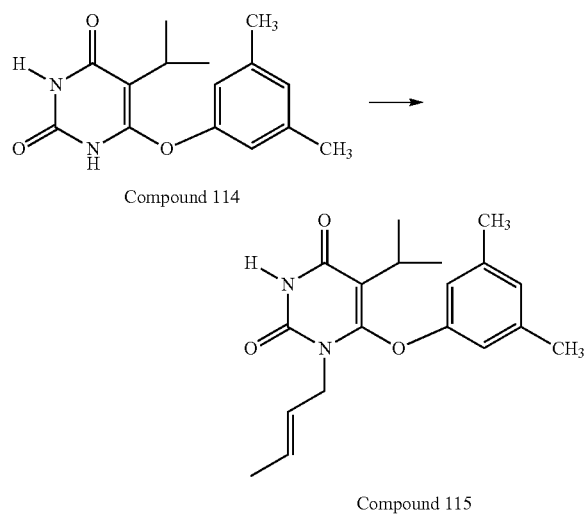

Scheme 37

Compound 114

Compound 115

1-But-2-enyl-6-(3,5-dimethyl-phenoxy)-5-isopropyl-1H-pyrimidine-2,4-dione (Compound 115): To a stirred solution of 6-(3,5-dimethyl-phenoxy)-5-isopropyl-1H-pyrimidine-2,4-dione (114) (prepared using the methods of WO9518109, herein incorporated by reference in its entirety for all purposes; 274 mg, 1 mmol) anhydrous powdered K$_2$CO$_3$ (138 mg, 1 mmol), and lithium iodide (134 mg, 1 mmol) in DMF (5 mL), was added 1-methanesulfonyl-trans-2-butene (141 µL, 1.2 mmol). After stirring for 15 hrs., the reaction mixture was diluted with ether, washed with water, dried with MgSO$_4$, filtered, and evaporated in vacuo. The residue was purified by silica gel column chromatography (eluent, ether:dichloromethane:hexane (1:1:2)) to afford 247 mg (75%) of a white solid. m.p. 141-143° C.; $^1$H-NMR (200 MHz, CDCl$_3$) δ1.13 (6H, d, J=7.0 Hz), 1.59 (3H, d, J=6.0 Hz), 2.29 (6H, s), 2.72 (1H, m), 4.20 (2H, d, J=5.5 Hz), 5.34-5.61 (2H, m), 6.51 (2H, s), 6.75 (1H, s), 9.00 (1H, s); m/z (EI) 328(M$^+$).

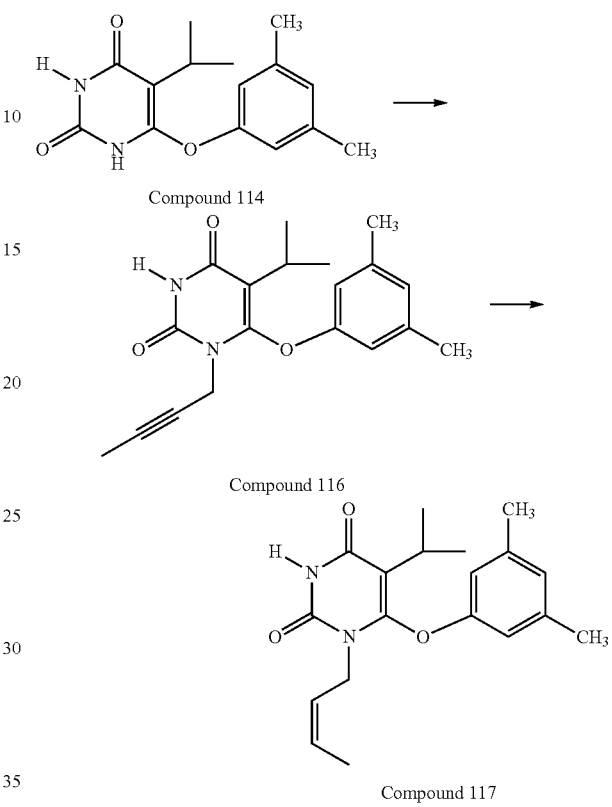

Scheme 38

Compound 114

Compound 116

Compound 117

1-But-2-ynyl-6-(3,5-dimethyl-phenoxy)-5-isopropyl-1H-pyrimidine-2,4-dione (Compound 116): To a stirred solution of 6-(3,5-dimethyl-phenoxy)-5-isopropyl-1H-pyrimidine-2,4-dione (114) (548 mg, 2 mmol) anhydrous powdered K$_2$CO$_3$ (276 mg, 2 mmol), and lithium iodide (268 mg, 2 mmol) in DMF (10 mL), was added 1-methanesulfonyl-2-propyne (247 µL, 2.1 mmol). After stirring for 17 hrs., the reaction mixture was diluted with ether, washed with water, dried with MgSO$_4$, filtered, and evaporated in vacuo. The residue was purified by silica gel column chromatography (eluent, ethyl acetate:hexane (1:2)) to afford 546 mg (84%) of a white solid. m.p. 158-160° C.; $^1$H-NMR (200 MHz, CDCl$_3$) δ1.15 (6H, d, J=7.0 Hz), 1.69 (3H, t, J=2.2 Hz), 2.32 (6H, s), 2.80 (1H, m), 4.43 (2H, q, J=2.2 Hz), 6.60 (2H, s), 6.78 (1H, s), 8.55 (1H, s); m/z (EI) 326(M$^+$).

1-But-2-enyl-6-(3,5-dimethyl-phenoxy)-5-isopropyl-1H-pyrimidine-2,4-dione (Compound 117): 1-But-2-ynyl-6-(3,5-dimethyl-phenoxy)-5-isopropyl-1H-pyrimidine-2,4-dione (116) (50 mg, 0.15 mmol) was stirred in the presence of palladium on barium sulfate (15 mg) in methanol (5 mL) under a hydrogen atmosphere. After 15 min., the mixture was filtered through a plug of celite and the filtrate was evaporated in vacuo. The residue was purified by silica gel column chromatography (eluent, ethyl acetate:hexane (1:2)) to afford 50 mg (100%) of a white solid. m.p. 141-142° C.; $^1$H-NMR (200 MHz, CDCl$_3$) δ 1.13 (6H, d, J=7.0 Hz), 1.61 (3H, dd, J=6.9 Hz, 1.4 Hz), 2.31 (6H, s), 2.79 (1H, m), 4.35 (2H, d, J=6.8 Hz), 5.38 (1H, m), 5.60 (1H, m), 6.54 (2H, s), 6.77 (1H, s); m/z (EI) 328(M$^+$).

Antiviral and Cytotoxicity Assays in MT2 and MT4 Cells.

For the antiviral assay utilizing MT-2 cells, 50 μL of 2× test concentration of 5-fold serially diluted compound in culture medium with 10% FBS was added to each well of a 96-well plate (9 concentrations) in triplicate. MT-2 cells were infected with HIV-IIIb at a multiplicity of infection (m.o.i) of 0.01 for 3 hours. Fifty microliters of infected cell suspension in culture medium with 10% FBS (~1.5×10$^4$ cells) was then added to each well containing 50 μA of diluted compound. The plates were then incubated at 37° C. for 5 days. For the antiviral assay utilizing MT-4 cells, 20 μL of 2× test concentration of 5-fold serially diluted compound in culture medium with 10% FBS was added to each well of a 384-well plate (7 concentrations) in triplicate. MT-4 cells were next mixed with HIV-IIIb at an m.o.i. of 0.1 and 20 μl of virus/cell mixture (2000 cells) was immediately added to each well containing 200 μL of diluted compound. The plates were then incubated at 37° C. for 5 days. After 5 days of incubation, 100 μL of CellTiter-Glo™ Reagent (catalog #G7571, Promega Biosciences, Inc., Madison, Wis.) was added to each well containing MT-2 cells and 40 μL to each well containing MT-4 cells. Cell lysis was carried out by incubation at room temperature for 10 min and chemiluminescence was read.

For compound cytotoxicity assessment in MT-2 cells, the protocol was identical to that of the antiviral assay in MT-2 cells, except that uninfected cells and a 3-fold serial dilution of compounds were used. For cytotoxicity assessment in MT-4 cells, the protocol is identical to that of the antiviral assay in MT-4 cells, except that no virus was added.

The compounds of the present invention have antiviral EC50 values (nM) in the range of about 0.1 to about 1000, or about 0.1 to about 500, or about 0.1 to about 300, or about 0.1 to about 200, or about 0.1 to about 100, or about 0.1 to about 50, or less than about 500, or less than about 400, or less than about 300, or less than about 200, or less than about 100, or less than about 50, or less than about 20, or less than about 10. Compounds 3, 5, 6, 9, 13, 14, 17, 25, 38, 46, 47, 54, 56, 57, 60, 70, 72, 73, 74, 76, 80, 86, and 115 have EC50 values of less than about 10.

What is claimed:

1. The compound 3-(3-ethyl-5-isopropyl-2,6-dioxo-1,2,3,6-tetrahydro-pyrimidine-4-carbonyl)-5-methylbenzonitrile, or a pharmaceutically acceptable salt and/or ester thereof.

2. A pharmaceutical composition comprising a therapeutically effective amount of 3-(3-Ethyl-5-isopropyl-2,6-dioxo-1,2,3,6-tetrahydro-pyrimidine-4-carbonyl)-5-methyl-benzonitrile, or a pharmaceutically acceptable salt and/or ester thereof, and a pharmaceutically acceptable carrier.

* * * * *